US011814642B2

(12) United States Patent
Hebben et al.

(10) Patent No.: US 11,814,642 B2
(45) Date of Patent: Nov. 14, 2023

(54) MANUFACTURING AND USE OF RECOMBINANT AAV VECTORS

(71) Applicant: LogicBio Therapeutics, Inc., Lexington, MA (US)

(72) Inventors: Matthias Charles Jerome Hebben, Lexington, MA (US); Jing Liao, Lexington, MA (US); Carmen Wu, Cambridge, MA (US); Wilhad Hans Reuter, Chestnut Hill, MA (US); Thomas Matthew Edwards, Littleton, MA (US)

(73) Assignee: LogicBio Therapeutics, Inc., Lexington, MA (US)

( * ) Notice: Subject to any disclaimer, the term of this patent is extended or adjusted under 35 U.S.C. 154(b) by 0 days.

(21) Appl. No.: 17/848,307

(22) Filed: Jun. 23, 2022

(65) Prior Publication Data

US 2023/0111556 A1 Apr. 13, 2023

Related U.S. Application Data

(63) Continuation of application No. PCT/US2022/017901, filed on Feb. 25, 2022.

(60) Provisional application No. 63/257,036, filed on Oct. 18, 2021, provisional application No. 63/234,610, filed on Aug. 18, 2021, provisional application No. 63/154,474, filed on Feb. 26, 2021.

(51) Int. Cl.

| | |
|---|---|
| ***C12N 15/864*** | (2006.01) |
| ***C12N 15/66*** | (2006.01) |
| ***C12N 15/11*** | (2006.01) |
| ***C12N 15/35*** | (2006.01) |
| ***A61K 48/00*** | (2006.01) |
| ***A61K 35/76*** | (2015.01) |
| ***C12N 15/86*** | (2006.01) |

(52) U.S. Cl.
CPC .... *C12N 15/86* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | | | |
|---|---|---|---|---|
| 2009/0191597 | A1* | 7/2009 | Samulski | C12N 7/00 435/325 |
| 2017/0218395 | A1 | 8/2017 | Byrne et al. | |
| 2019/0203227 | A1* | 7/2019 | Ho | C12N 15/52 |
| 2020/0061209 | A1 | 2/2020 | Bennett et al. | |
| 2023/0033268 | A1* | 2/2023 | Colella | A61P 3/00 |

FOREIGN PATENT DOCUMENTS

| | | | |
|---|---|---|---|
| WO | WO-2020/208379 A1 | | 10/2020 |
| WO | WO 2022232545 | * | 11/2022 |

OTHER PUBLICATIONS

Pogson et al, Synthetic plasmid oUC57(kan), Accession KX431576. 1, 2016, pp. 1-3.*
Pereira et al, The adeno-associated virus (AAV) Rep protein acts as both a repressor and an activator to regulate AAV transcription during a productive infection, J Virology, 1997, pp. 1079-1088.*
Chandler, R. J. et al., 48. Treatment of Methylmalonic Acidemia by Promoterless Gene-Targeting Using Adeno-Associated Viral (AAV) Mediated Homologous Recombination, Molecular Therapy, 24:S21-S22, Abstract, XP055909807, (2016).
International Search Report for PCT/US22/17901, 4 pages (dated Jun. 29, 2022).
Karnan, S. et al., Improved methods of AAV-mediated gene targeting for human cell lines using ribosome-skipping 2A peptide, Nucleic Acids Research, 44(6)e54:1-14, (2016).
Kattenhorn, L. M. et al., Adeno-Associated Virus Gene Therapy for Liver Disease, Human Gene Therapy, 27(12):947-961, (2016).
Written Opinion for PCT/US22/17901, 4 pages (dated Jun. 29, 2022).
Xiao, X. et al., Production of High-Titer Recombinant Adeno-Associated VIrus Vectors in the Absence of Helper Adenovirus, Amer. Soc. Microbio., 72(3):2224-2232 (1998).
Yang, H. et al., Anion-Exchange Chromatography for Determining Empty and Full Capsid Contents in Adeno-Associated Virus, Waters, 1-7 (2020).
Logic Bio Therapeutics, Late Stage AAV Purification Process Optimization in Preparation for Pivotal Clinical Trials, Presentation, 36 pages, (2022).

* cited by examiner

*Primary Examiner* — Maria Marvich
(74) *Attorney, Agent, or Firm* — Clark & Elbing LLP

(57) ABSTRACT

Presented herein are technologies and methods for improved production of AAV vectors.

13 Claims, 453 Drawing Sheets

Specification includes a Sequence Listing.

(B)

(B)

(A)

(A)

(B)

(C)

(D)

(A)

(B)

(C)

(D)

(A)

(B)

| First Expression Construct (SEQ ID NO) | Second Expression Construct | | | | Exemplary Viral Vector Product |
|---|---|---|---|---|---|
| | Capsid | | Transgene | | |
| | Capsid name | Gene ID No. | Gene Name | Gene ID No. | |
| 1 | AAV1 | 1450374 | ACADM | 34 | Payload comprising a ACADM gene or variant thereof packaged within a AAV1 capsid. |
| 1 | AAV2 | | ACADM | 34 | Payload comprising a ACADM gene or variant thereof packaged within a AAV2 capsid. |
| 1 | AAV3 | | ACADM | 34 | Payload comprising a ACADM gene or variant thereof packaged within a AAV3 capsid. |
| 1 | AAV4 | 1446389 | ACADM | 34 | Payload comprising a ACADM gene or variant thereof packaged within a AAV4 capsid. |
| 1 | AAV5 | | ACADM | 34 | Payload comprising a ACADM gene or variant thereof packaged within a AAV5 capsid. |
| 1 | AAV6 | | ACADM | 34 | Payload comprising a ACADM gene or variant thereof packaged within a AAV6 capsid. |
| 1 | AAV7 | | ACADM | 34 | Payload comprising a ACADM gene or variant thereof packaged within a AAV7 capsid. |
| 1 | AAV8 | 5075992 | ACADM | 34 | Payload comprising a ACADM gene or variant thereof packaged within a AAV8 capsid. |
| 1 | AAV9 | | ACADM | 34 | Payload comprising a ACADM gene or variant thereof packaged within a AAV9 capsid. |
| 1 | AAV10 | | ACADM | 34 | Payload comprising a ACADM gene or variant thereof packaged within a AAV10 capsid. |
| 1 | AAV11 | | ACADM | 34 | Payload comprising a ACADM gene or variant thereof packaged within a AAV11 capsid. |
| 1 | AAVC11.01 | | ACADM | 34 | Payload comprising a ACADM gene or variant thereof packaged within a AAVC11.01 capsid. |

FIG. 29

| | | | | | |
|---|---|---|---|---|---|
| 1 | AAVC11.02 | | ACADM | 34 | Payload comprising a ACADM gene or variant thereof packaged within a AAVC11.02 capsid. |
| 1 | AAVC11.03 | | ACADM | 34 | Payload comprising a ACADM gene or variant thereof packaged within a AAVC11.03 capsid. |
| 1 | AAVC11.04 | | ACADM | 34 | Payload comprising a ACADM gene or variant thereof packaged within a AAVC11.04 capsid. |
| 1 | AAVC11.05 | | ACADM | 34 | Payload comprising a ACADM gene or variant thereof packaged within a AAVC11.05 capsid. |
| 1 | AAVC11.06 | | ACADM | 34 | Payload comprising a ACADM gene or variant thereof packaged within a AAVC11.06 capsid. |
| 1 | AAVC11.07 | | ACADM | 34 | Payload comprising a ACADM gene or variant thereof packaged within a AAVC11.07 capsid. |
| 1 | AAVC11.08 | | ACADM | 34 | Payload comprising a ACADM gene or variant thereof packaged within a AAVC11.08 capsid. |
| 1 | AAVC11.09 | | ACADM | 34 | Payload comprising a ACADM gene or variant thereof packaged within a AAVC11.09 capsid. |
| 1 | AAVC11.10 | | ACADM | 34 | Payload comprising a ACADM gene or variant thereof packaged within a AAVC11.10 capsid. |
| 1 | AAVC11.11 | | ACADM | 34 | Payload comprising a ACADM gene or variant thereof packaged within a AAVC11.11 capsid. |
| 1 | AAVC11.12 | | ACADM | 34 | Payload comprising a ACADM gene or variant thereof packaged within a AAVC11.12 capsid. |
| 1 | AAVC11.13 | | ACADM | 34 | Payload comprising a ACADM gene or variant thereof packaged within a AAVC11.13 capsid. |
| 1 | AAVC11.14 | | ACADM | 34 | Payload comprising a ACADM gene or variant thereof packaged within a AAVC11.14 capsid. |
| 1 | AAVC11.15 | | ACADM | 34 | Payload comprising a ACADM gene or variant thereof packaged within a AAVC11.15 capsid. |
| 1 | AAVC11.16 | | ACADM | 34 | Payload comprising a ACADM gene or variant thereof packaged within a AAVC11.16 capsid. |
| 1 | AAVC11.17 | | ACADM | 34 | Payload comprising a ACADM gene or variant thereof packaged within a AAVC11.17 capsid. |
| 1 | AAVC11.18 | | ACADM | 34 | Payload comprising a ACADM gene or variant thereof packaged within a AAVC11.18 capsid. |

FIG. 29 (Continued)

| | | | | | |
|---|---|---|---|---|---|
| 1 | AAVC11.19 | | ACADM | 34 | Payload comprising a ACADM gene or variant thereof packaged within a AAVC11.19 capsid. |
| 1 | AAV12 | | ACADM | 34 | Payload comprising a ACADM gene or variant thereof packaged within a AAV12 capsid. |
| 1 | AAV13 | | ACADM | 34 | Payload comprising a ACADM gene or variant thereof packaged within a AAV13 capsid. |
| 1 | AAV-DJ | | ACADM | 34 | Payload comprising a ACADM gene or variant thereof packaged within a AAV-DJ capsid. |
| 1 | AAV-LK03 | | ACADM | 34 | Payload comprising a ACADM gene or variant thereof packaged within a AAV-LK03 capsid. |
| 1 | AAV-LK19 | | ACADM | 34 | Payload comprising a ACADM gene or variant thereof packaged within a AAV-LK19 capsid. |
| 1 | AAVrh.74 | | ACADM | 34 | Payload comprising a ACADM gene or variant thereof packaged within a AAVrh.74 capsid. |
| 1 | AAVrh.10 | | ACADM | 34 | Payload comprising a ACADM gene or variant thereof packaged within a AAVrh.10 capsid. |
| 1 | AAVhu.37 | | ACADM | 34 | Payload comprising a ACADM gene or variant thereof packaged within a AAVhu.37 capsid. |
| 1 | AAVrh.K | | ACADM | 34 | Payload comprising a ACADM gene or variant thereof packaged within a AAVrh.K capsid. |
| 1 | AAVrh.39 | | ACADM | 34 | Payload comprising a ACADM gene or variant thereof packaged within a AAVrh.39 capsid. |
| 1 | AAVrh.9 | | ACADM | 34 | Payload comprising a ACADM gene or variant thereof packaged within a AAVrh.9 capsid. |
| 1 | avian AAV | | ACADM | 34 | Payload comprising a ACADM gene or variant thereof packaged within a avian capsid. |

FIG. 29 (Continued)

| | | | | | |
|---|---|---|---|---|---|
| 1 | bovine AAV | | ACADM | 34 | Payload comprising a ACADM gene or variant thereof packaged within a bovine capsid. |
| 1 | canine AAV | | ACADM | 34 | Payload comprising a ACADM gene or variant thereof packaged within a canine capsid. |
| 1 | equine AAV | | ACADM | 34 | Payload comprising a ACADM gene or variant thereof packaged within a equine capsid. |
| 1 | primate AAV | | ACADM | 34 | Payload comprising a ACADM gene or variant thereof packaged within a primate capsid. |
| 1 | non-primate AAV | | ACADM | 34 | Payload comprising a ACADM gene or variant thereof packaged within a non-primate capsid. |
| 1 | ovine AAV | | ACADM | 34 | Payload comprising a ACADM gene or variant thereof packaged within a ovine capsid. |
| 1 | hybrid AAV | | ACADM | 34 | Payload comprising a ACADM gene or variant thereof packaged within a hybrid capsid. |
| 1 | chimeric AAV | | ACADM | 34 | Payload comprising a ACADM gene or variant thereof packaged within a chimeric capsid. |
| 2 | AAV1 | 1450374 | ACADM | 34 | Payload comprising a ACADM gene or variant thereof packaged within a AAV1 capsid. |
| 2 | AAV2 | | ACADM | 34 | Payload comprising a ACADM gene or variant thereof packaged within a AAV2 capsid. |
| 2 | AAV3 | | ACADM | 34 | Payload comprising a ACADM gene or variant thereof packaged within a AAV3 capsid. |
| 2 | AAV4 | 1446389 | ACADM | 34 | Payload comprising a ACADM gene or variant thereof packaged within a AAV4 capsid. |
| 2 | AAV5 | | ACADM | 34 | Payload comprising a ACADM gene or variant thereof packaged within a AAV5 capsid. |
| 2 | AAV6 | | ACADM | 34 | Payload comprising a ACADM gene or variant thereof packaged within a AAV6 capsid. |
| 2 | AAV7 | | ACADM | 34 | Payload comprising a ACADM gene or variant thereof packaged within a AAV7 capsid. |
| 2 | AAV8 | 5075992 | ACADM | 34 | Payload comprising a ACADM gene or variant thereof packaged within a AAV8 capsid. |
| 2 | AAV9 | | ACADM | 34 | Payload comprising a ACADM gene or variant thereof packaged within a AAV9 capsid. |

Fig. 29 (Continued)

| | | | | | |
|---|---|---|---|---|---|
| 2 | AAV10 | | ACADM | 34 | Payload comprising a ACADM gene or variant thereof packaged within a AAV10 capsid. |
| 2 | AAV11 | | ACADM | 34 | Payload comprising a ACADM gene or variant thereof packaged within a AAV11 capsid. |
| 2 | AAVC11.01 | | ACADM | 34 | Payload comprising a ACADM gene or variant thereof packaged within a AAVC11.01 capsid. |
| 2 | AAVC11.02 | | ACADM | 34 | Payload comprising a ACADM gene or variant thereof packaged within a AAVC11.02 capsid. |
| 2 | AAVC11.03 | | ACADM | 34 | Payload comprising a ACADM gene or variant thereof packaged within a AAVC11.03 capsid. |
| 2 | AAVC11.04 | | ACADM | 34 | Payload comprising a ACADM gene or variant thereof packaged within a AAVC11.04 capsid. |
| 2 | AAVC11.05 | | ACADM | 34 | Payload comprising a ACADM gene or variant thereof packaged within a AAVC11.05 capsid. |
| 2 | AAVC11.06 | | ACADM | 34 | Payload comprising a ACADM gene or variant thereof packaged within a AAVC11.06 capsid. |
| 2 | AAVC11.07 | | ACADM | 34 | Payload comprising a ACADM gene or variant thereof packaged within a AAVC11.07 capsid. |
| 2 | AAVC11.08 | | ACADM | 34 | Payload comprising a ACADM gene or variant thereof packaged within a AAVC11.08 capsid. |
| 2 | AAVC11.09 | | ACADM | 34 | Payload comprising a ACADM gene or variant thereof packaged within a AAVC11.09 capsid. |
| 2 | AAVC11.10 | | ACADM | 34 | Payload comprising a ACADM gene or variant thereof packaged within a AAVC11.10 capsid. |
| 2 | AAVC11.11 | | ACADM | 34 | Payload comprising a ACADM gene or variant thereof packaged within a AAVC11.11 capsid. |
| 2 | AAVC11.12 | | ACADM | 34 | Payload comprising a ACADM gene or variant thereof packaged within a AAVC11.12 capsid. |
| 2 | AAVC11.13 | | ACADM | 34 | Payload comprising a ACADM gene or variant thereof packaged within a AAVC11.13 capsid. |
| 2 | AAVC11.14 | | ACADM | 34 | Payload comprising a ACADM gene or variant thereof packaged within a AAVC11.14 capsid. |
| 2 | AAVC11.15 | | ACADM | 34 | Payload comprising a ACADM gene or variant thereof packaged within a AAVC11.15 capsid. |

Fig. 29 (Continued)

| | | | | | |
|---|---|---|---|---|---|
| 2 | AAVC11.16 | | ACADM | 34 | Payload comprising a ACADM gene or variant thereof packaged within a AAVC11.16 capsid. |
| 2 | AAVC11.17 | | ACADM | 34 | Payload comprising a ACADM gene or variant thereof packaged within a AAVC11.17 capsid. |
| 2 | AAVC11.18 | | ACADM | 34 | Payload comprising a ACADM gene or variant thereof packaged within a AAVC11.18 capsid. |
| 2 | AAVC11.19 | | ACADM | 34 | Payload comprising a ACADM gene or variant thereof packaged within a AAVC11.19 capsid. |
| 2 | AAV12 | | ACADM | 34 | Payload comprising a ACADM gene or variant thereof packaged within a AAV12 capsid. |
| 2 | AAV13 | | ACADM | 34 | Payload comprising a ACADM gene or variant thereof packaged within a AAV13 capsid. |
| 2 | AAV-DJ | | ACADM | 34 | Payload comprising a ACADM gene or variant thereof packaged within a AAV-DJ capsid. |
| 2 | AAV-LK03 | | ACADM | 34 | Payload comprising a ACADM gene or variant thereof packaged within a AAV-LK03 capsid. |
| 2 | AAV-LK19 | | ACADM | 34 | Payload comprising a ACADM gene or variant thereof packaged within a AAV-LK19 capsid. |
| 2 | AAVrh.74 | | ACADM | 34 | Payload comprising a ACADM gene or variant thereof packaged within a AAVrh.74 capsid. |
| 2 | AAVrh.10 | | ACADM | 34 | Payload comprising a ACADM gene or variant thereof packaged within a AAVrh.10 capsid. |
| 2 | AAVhu.37 | | ACADM | 34 | Payload comprising a ACADM gene or variant thereof packaged within a AAVhu.37 capsid. |
| 2 | AAVrh.K | | ACADM | 34 | Payload comprising a ACADM gene or variant thereof packaged within a AAVrh.K capsid. |
| 2 | AAVrh.39 | | ACADM | 34 | Payload comprising a ACADM gene or variant thereof packaged within a AAVrh.39 capsid. |
| 2 | AAVrh.9 | | ACADM | 34 | Payload comprising a ACADM gene or variant thereof packaged within a AAVrh.9 capsid. |
| 2 | avian AAV | | ACADM | 34 | Payload comprising a ACADM gene or variant thereof packaged within a avian capsid. |

Fig. 29 (Continued)

| | | | | | |
|---|---|---|---|---|---|
| 2 | bovine AAV | | ACADM | 34 | Payload comprising a ACADM gene or variant thereof packaged within a bovine capsid. |
| 2 | canine AAV | | ACADM | 34 | Payload comprising a ACADM gene or variant thereof packaged within a canine capsid. |
| 2 | equine AAV | | ACADM | 34 | Payload comprising a ACADM gene or variant thereof packaged within a equine capsid. |
| 2 | primate AAV | | ACADM | 34 | Payload comprising a ACADM gene or variant thereof packaged within a primate capsid. |
| 2 | non-primate AAV | | ACADM | 34 | Payload comprising a ACADM gene or variant thereof packaged within a non-primate capsid. |
| 2 | ovine AAV | | ACADM | 34 | Payload comprising a ACADM gene or variant thereof packaged within a ovine capsid. |
| 2 | hybrid AAV | | ACADM | 34 | Payload comprising a ACADM gene or variant thereof packaged within a hybrid capsid. |
| 2 | chimeric AAV | | ACADM | 34 | Payload comprising a ACADM gene or variant thereof packaged within a chimeric capsid. |
| 1 | AAV1 | 1450374 | ACADVL | 37 | Payload comprising a ACADVL gene or variant thereof packaged within a AAV1 capsid. |
| 1 | AAV2 | | ACADVL | 38 | Payload comprising a ACADVL gene or variant thereof packaged within a AAV2 capsid. |
| 1 | AAV3 | | ACADVL | 39 | Payload comprising a ACADVL gene or variant thereof packaged within a AAV3 capsid. |
| 1 | AAV4 | 1446389 | ACADVL | 40 | Payload comprising a ACADVL gene or variant thereof packaged within a AAV4 capsid. |
| 1 | AAV5 | | ACADVL | 41 | Payload comprising a ACADVL gene or variant thereof packaged within a AAV5 capsid. |
| 1 | AAV6 | | ACADVL | 42 | Payload comprising a ACADVL gene or variant thereof packaged within a AAV6 capsid. |
| 1 | AAV7 | | ACADVL | 43 | Payload comprising a ACADVL gene or variant thereof packaged within a AAV7 capsid. |
| 1 | AAV8 | 5075992 | ACADVL | 44 | Payload comprising a ACADVL gene or variant thereof packaged within a AAV8 capsid. |
| 1 | AAV9 | | ACADVL | 45 | Payload comprising a ACADVL gene or variant thereof packaged within a AAV9 capsid. |

Fig. 29 (Continued)

| | | | | | |
|---|---|---|---|---|---|
| 1 | AAV10 | | ACADVL | 46 | Payload comprising a ACADVL gene or variant thereof packaged within a AAV10 capsid. |
| 1 | AAV11 | | ACADVL | 47 | Payload comprising a ACADVL gene or variant thereof packaged within a AAV11 capsid. |
| 1 | AAVC11.01 | | ACADVL | 48 | Payload comprising a ACADVL gene or variant thereof packaged within a AAVC11.01 capsid. |
| 1 | AAVC11.02 | | ACADVL | 49 | Payload comprising a ACADVL gene or variant thereof packaged within a AAVC11.02 capsid. |
| 1 | AAVC11.03 | | ACADVL | 50 | Payload comprising a ACADVL gene or variant thereof packaged within a AAVC11.03 capsid. |
| 1 | AAVC11.04 | | ACADVL | 51 | Payload comprising a ACADVL gene or variant thereof packaged within a AAVC11.04 capsid. |
| 1 | AAVC11.05 | | ACADVL | 52 | Payload comprising a ACADVL gene or variant thereof packaged within a AAVC11.05 capsid. |
| 1 | AAVC11.06 | | ACADVL | 53 | Payload comprising a ACADVL gene or variant thereof packaged within a AAVC11.06 capsid. |
| 1 | AAVC11.07 | | ACADVL | 54 | Payload comprising a ACADVL gene or variant thereof packaged within a AAVC11.07 capsid. |
| 1 | AAVC11.08 | | ACADVL | 55 | Payload comprising a ACADVL gene or variant thereof packaged within a AAVC11.08 capsid. |
| 1 | AAVC11.09 | | ACADVL | 56 | Payload comprising a ACADVL gene or variant thereof packaged within a AAVC11.09 capsid. |
| 1 | AAVC11.10 | | ACADVL | 57 | Payload comprising a ACADVL gene or variant thereof packaged within a AAVC11.10 capsid. |
| 1 | AAVC11.11 | | ACADVL | 58 | Payload comprising a ACADVL gene or variant thereof packaged within a AAVC11.11 capsid. |
| 1 | AAVC11.12 | | ACADVL | 59 | Payload comprising a ACADVL gene or variant thereof packaged within a AAVC11.12 capsid. |
| 1 | AAVC11.13 | | ACADVL | 60 | Payload comprising a ACADVL gene or variant thereof packaged within a AAVC11.13 capsid. |
| 1 | AAVC11.14 | | ACADVL | 61 | Payload comprising a ACADVL gene or variant thereof packaged within a AAVC11.14 capsid. |
| 1 | AAVC11.15 | | ACADVL | 62 | Payload comprising a ACADVL gene or variant thereof packaged within a AAVC11.15 capsid. |

Fig. 29 (Continued)

| | | | | | |
|---|---|---|---|---|---|
| 1 | AAVC11.16 | | ACADVL | 63 | Payload comprising a ACADVL gene or variant thereof packaged within a AAVC11.16 capsid. |
| 1 | AAVC11.17 | | ACADVL | 64 | Payload comprising a ACADVL gene or variant thereof packaged within a AAVC11.17 capsid. |
| 1 | AAVC11.18 | | ACADVL | 65 | Payload comprising a ACADVL gene or variant thereof packaged within a AAVC11.18 capsid. |
| 1 | AAVC11.19 | | ACADVL | 66 | Payload comprising a ACADVL gene or variant thereof packaged within a AAVC11.19 capsid. |
| 1 | AAV12 | | ACADVL | 67 | Payload comprising a ACADVL gene or variant thereof packaged within a AAV12 capsid. |
| 1 | AAV13 | | ACADVL | 68 | Payload comprising a ACADVL gene or variant thereof packaged within a AAV13 capsid. |
| 1 | AAV-DJ | | ACADVL | 69 | Payload comprising a ACADVL gene or variant thereof packaged within a AAV-DJ capsid. |
| 1 | AAV-LK03 | | ACADVL | 70 | Payload comprising a ACADVL gene or variant thereof packaged within a AAV-LK03 capsid. |
| 1 | AAV-LK19 | | ACADVL | 71 | Payload comprising a ACADVL gene or variant thereof packaged within a AAV-LK19 capsid. |
| 1 | AAVrh.74 | | ACADVL | 72 | Payload comprising a ACADVL gene or variant thereof packaged within a AAVrh.74 capsid. |
| 1 | AAVrh.10 | | ACADVL | 73 | Payload comprising a ACADVL gene or variant thereof packaged within a AAVrh.10 capsid. |
| 1 | AAVhu.37 | | ACADVL | 74 | Payload comprising a ACADVL gene or variant thereof packaged within a AAVhu.37 capsid. |
| 1 | AAVrh.K | | ACADVL | 75 | Payload comprising a ACADVL gene or variant thereof packaged within a AAVrh.K capsid. |
| 1 | AAVrh.39 | | ACADVL | 76 | Payload comprising a ACADVL gene or variant thereof packaged within a AAVrh.39 capsid. |
| 1 | AAVrh.9 | | ACADVL | 77 | Payload comprising a ACADVL gene or variant thereof packaged within a AAVrh.9 capsid. |
| 1 | avian AAV | | ACADVL | 78 | Payload comprising a ACADVL gene or variant thereof packaged within a avian capsid. |

Fig. 29 (Continued)

| | | | | | |
|---|---|---|---|---|---|
| 1 | bovine AAV | | ACADVL | 79 | Payload comprising a ACADVL gene or variant thereof packaged within a bovine capsid. |
| 1 | canine AAV | | ACADVL | 80 | Payload comprising a ACADVL gene or variant thereof packaged within a canine capsid. |
| 1 | equine AAV | | ACADVL | 81 | Payload comprising a ACADVL gene or variant thereof packaged within a equine capsid. |
| 1 | primate AAV | | ACADVL | 82 | Payload comprising a ACADVL gene or variant thereof packaged within a primate capsid. |
| 1 | non-primate AAV | | ACADVL | 83 | Payload comprising a ACADVL gene or variant thereof packaged within a non-primate capsid. |
| 1 | ovine AAV | | ACADVL | 84 | Payload comprising a ACADVL gene or variant thereof packaged within a ovine capsid. |
| 1 | hybrid AAV | | ACADVL | 85 | Payload comprising a ACADVL gene or variant thereof packaged within a hybrid capsid. |
| 1 | chimeric AAV | | ACADVL | 86 | Payload comprising a ACADVL gene or variant thereof packaged within a chimeric capsid. |
| 2 | AAV1 | 1450374 | ACADVL | 87 | Payload comprising a ACADVL gene or variant thereof packaged within a AAV1 capsid. |
| 2 | AAV2 | | ACADVL | 88 | Payload comprising a ACADVL gene or variant thereof packaged within a AAV2 capsid. |
| 2 | AAV3 | | ACADVL | 89 | Payload comprising a ACADVL gene or variant thereof packaged within a AAV3 capsid. |
| 2 | AAV4 | 1446389 | ACADVL | 90 | Payload comprising a ACADVL gene or variant thereof packaged within a AAV4 capsid. |
| 2 | AAV5 | | ACADVL | 91 | Payload comprising a ACADVL gene or variant thereof packaged within a AAV5 capsid. |
| 2 | AAV6 | | ACADVL | 92 | Payload comprising a ACADVL gene or variant thereof packaged within a AAV6 capsid. |
| 2 | AAV7 | | ACADVL | 93 | Payload comprising a ACADVL gene or variant thereof packaged within a AAV7 capsid. |
| 2 | AAV8 | 5075992 | ACADVL | 94 | Payload comprising a ACADVL gene or variant thereof packaged within a AAV8 capsid. |
| 2 | AAV9 | | ACADVL | 95 | Payload comprising a ACADVL gene or variant thereof packaged within a AAV9 capsid. |

Fig. 29 (Continued)

| | | | | | |
|---|---|---|---|---|---|
| 2 | AAV10 | | ACADVL | 96 | Payload comprising a ACADVL gene or variant thereof packaged within a AAV10 capsid. |
| 2 | AAV11 | | ACADVL | 97 | Payload comprising a ACADVL gene or variant thereof packaged within a AAV11 capsid. |
| 2 | AAVC11.01 | | ACADVL | 98 | Payload comprising a ACADVL gene or variant thereof packaged within a AAVC11.01 capsid. |
| 2 | AAVC11.02 | | ACADVL | 99 | Payload comprising a ACADVL gene or variant thereof packaged within a AAVC11.02 capsid. |
| 2 | AAVC11.03 | | ACADVL | 100 | Payload comprising a ACADVL gene or variant thereof packaged within a AAVC11.03 capsid. |
| 2 | AAVC11.04 | | ACADVL | 101 | Payload comprising a ACADVL gene or variant thereof packaged within a AAVC11.04 capsid. |
| 2 | AAVC11.05 | | ACADVL | 102 | Payload comprising a ACADVL gene or variant thereof packaged within a AAVC11.05 capsid. |
| 2 | AAVC11.06 | | ACADVL | 103 | Payload comprising a ACADVL gene or variant thereof packaged within a AAVC11.06 capsid. |
| 2 | AAVC11.07 | | ACADVL | 104 | Payload comprising a ACADVL gene or variant thereof packaged within a AAVC11.07 capsid. |
| 2 | AAVC11.08 | | ACADVL | 105 | Payload comprising a ACADVL gene or variant thereof packaged within a AAVC11.08 capsid. |
| 2 | AAVC11.09 | | ACADVL | 106 | Payload comprising a ACADVL gene or variant thereof packaged within a AAVC11.09 capsid. |
| 2 | AAVC11.10 | | ACADVL | 107 | Payload comprising a ACADVL gene or variant thereof packaged within a AAVC11.10 capsid. |
| 2 | AAVC11.11 | | ACADVL | 108 | Payload comprising a ACADVL gene or variant thereof packaged within a AAVC11.11 capsid. |
| 2 | AAVC11.12 | | ACADVL | 109 | Payload comprising a ACADVL gene or variant thereof packaged within a AAVC11.12 capsid. |
| 2 | AAVC11.13 | | ACADVL | 110 | Payload comprising a ACADVL gene or variant thereof packaged within a AAVC11.13 capsid. |
| 2 | AAVC11.14 | | ACADVL | 111 | Payload comprising a ACADVL gene or variant thereof packaged within a AAVC11.14 capsid. |
| 2 | AAVC11.15 | | ACADVL | 112 | Payload comprising a ACADVL gene or variant thereof packaged within a AAVC11.15 capsid. |

Fig. 29 (Continued)

| | | | | | |
|---|---|---|---|---|---|
| 2 | AAVC11.16 | | ACADVL | 113 | Payload comprising a ACADVL gene or variant thereof packaged within a AAVC11.16 capsid. |
| 2 | AAVC11.17 | | ACADVL | 114 | Payload comprising a ACADVL gene or variant thereof packaged within a AAVC11.17 capsid. |
| 2 | AAVC11.18 | | ACADVL | 115 | Payload comprising a ACADVL gene or variant thereof packaged within a AAVC11.18 capsid. |
| 2 | AAVC11.19 | | ACADVL | 116 | Payload comprising a ACADVL gene or variant thereof packaged within a AAVC11.19 capsid. |
| 2 | AAV12 | | ACADVL | 117 | Payload comprising a ACADVL gene or variant thereof packaged within a AAV12 capsid. |
| 2 | AAV13 | | ACADVL | 118 | Payload comprising a ACADVL gene or variant thereof packaged within a AAV13 capsid. |
| 2 | AAV-DJ | | ACADVL | 119 | Payload comprising a ACADVL gene or variant thereof packaged within a AAV-DJ capsid. |
| 2 | AAV-LK03 | | ACADVL | 120 | Payload comprising a ACADVL gene or variant thereof packaged within a AAV-LK03 capsid. |
| 2 | AAV-LK19 | | ACADVL | 121 | Payload comprising a ACADVL gene or variant thereof packaged within a AAV-LK19 capsid. |
| 2 | AAVrh.74 | | ACADVL | 122 | Payload comprising a ACADVL gene or variant thereof packaged within a AAVrh.74 capsid. |
| 2 | AAVrh.10 | | ACADVL | 123 | Payload comprising a ACADVL gene or variant thereof packaged within a AAVrh.10 capsid. |
| 2 | AAVhu.37 | | ACADVL | 124 | Payload comprising a ACADVL gene or variant thereof packaged within a AAVhu.37 capsid. |
| 2 | AAVrh.K | | ACADVL | 125 | Payload comprising a ACADVL gene or variant thereof packaged within a AAVrh.K capsid. |
| 2 | AAVrh.39 | | ACADVL | 126 | Payload comprising a ACADVL gene or variant thereof packaged within a AAVrh.39 capsid. |
| 2 | AAVrh.9 | | ACADVL | 127 | Payload comprising a ACADVL gene or variant thereof packaged within a AAVrh.9 capsid. |
| 2 | avian AAV | | ACADVL | 128 | Payload comprising a ACADVL gene or variant thereof packaged within a avian capsid. |

Fig. 29 (Continued)

| | | | | | |
|---|---|---|---|---|---|
| 2 | bovine AAV | | ACADVL | 129 | Payload comprising a ACADVL gene or variant thereof packaged within a bovine capsid. |
| 2 | canine AAV | | ACADVL | 130 | Payload comprising a ACADVL gene or variant thereof packaged within a canine capsid. |
| 2 | equine AAV | | ACADVL | 131 | Payload comprising a ACADVL gene or variant thereof packaged within a equine capsid. |
| 2 | primate AAV | | ACADVL | 132 | Payload comprising a ACADVL gene or variant thereof packaged within a primate capsid. |
| 2 | non-primate AAV | | ACADVL | 133 | Payload comprising a ACADVL gene or variant thereof packaged within a non-primate capsid. |
| 2 | ovine AAV | | ACADVL | 134 | Payload comprising a ACADVL gene or variant thereof packaged within a ovine capsid. |
| 2 | hybrid AAV | | ACADVL | 135 | Payload comprising a ACADVL gene or variant thereof packaged within a hybrid capsid. |
| 2 | chimeric AAV | | ACADVL | 136 | Payload comprising a ACADVL gene or variant thereof packaged within a chimeric capsid. |
| 1 | AAV1 | 1450374 | AGL | 178 | Payload comprising a AGL gene or variant thereof packaged within a AAV1 capsid. |
| 1 | AAV2 | | AGL | 178 | Payload comprising a AGL gene or variant thereof packaged within a AAV2 capsid. |
| 1 | AAV3 | | AGL | 178 | Payload comprising a AGL gene or variant thereof packaged within a AAV3 capsid. |
| 1 | AAV4 | 1446389 | AGL | 178 | Payload comprising a AGL gene or variant thereof packaged within a AAV4 capsid. |
| 1 | AAV5 | | AGL | 178 | Payload comprising a AGL gene or variant thereof packaged within a AAV5 capsid. |
| 1 | AAV6 | | AGL | 178 | Payload comprising a AGL gene or variant thereof packaged within a AAV6 capsid. |
| 1 | AAV7 | | AGL | 178 | Payload comprising a AGL gene or variant thereof packaged within a AAV7 capsid. |
| 1 | AAV8 | 5075992 | AGL | 178 | Payload comprising a AGL gene or variant thereof packaged within a AAV8 capsid. |
| 1 | AAV9 | | AGL | 178 | Payload comprising a AGL gene or variant thereof packaged within a AAV9 capsid. |

Fig. 29 (Continued)

| | | | | | |
|---|---|---|---|---|---|
| 1 | AAV10 | | AGL | 178 | Payload comprising a AGL gene or variant thereof packaged within a AAV10 capsid. |
| 1 | AAV11 | | AGL | 178 | Payload comprising a AGL gene or variant thereof packaged within a AAV11 capsid. |
| 1 | AAVC11.01 | | AGL | 178 | Payload comprising a AGL gene or variant thereof packaged within a AAVC11.01 capsid. |
| 1 | AAVC11.02 | | AGL | 178 | Payload comprising a AGL gene or variant thereof packaged within a AAVC11.02 capsid. |
| 1 | AAVC11.03 | | AGL | 178 | Payload comprising a AGL gene or variant thereof packaged within a AAVC11.03 capsid. |
| 1 | AAVC11.04 | | AGL | 178 | Payload comprising a AGL gene or variant thereof packaged within a AAVC11.04 capsid. |
| 1 | AAVC11.05 | | AGL | 178 | Payload comprising a AGL gene or variant thereof packaged within a AAVC11.05 capsid. |
| 1 | AAVC11.06 | | AGL | 178 | Payload comprising a AGL gene or variant thereof packaged within a AAVC11.06 capsid. |
| 1 | AAVC11.07 | | AGL | 178 | Payload comprising a AGL gene or variant thereof packaged within a AAVC11.07 capsid. |
| 1 | AAVC11.08 | | AGL | 178 | Payload comprising a AGL gene or variant thereof packaged within a AAVC11.08 capsid. |
| 1 | AAVC11.09 | | AGL | 178 | Payload comprising a AGL gene or variant thereof packaged within a AAVC11.09 capsid. |
| 1 | AAVC11.10 | | AGL | 178 | Payload comprising a AGL gene or variant thereof packaged within a AAVC11.10 capsid. |
| 1 | AAVC11.11 | | AGL | 178 | Payload comprising a AGL gene or variant thereof packaged within a AAVC11.11 capsid. |
| 1 | AAVC11.12 | | AGL | 178 | Payload comprising a AGL gene or variant thereof packaged within a AAVC11.12 capsid. |
| 1 | AAVC11.13 | | AGL | 178 | Payload comprising a AGL gene or variant thereof packaged within a AAVC11.13 capsid. |
| 1 | AAVC11.14 | | AGL | 178 | Payload comprising a AGL gene or variant thereof packaged within a AAVC11.14 capsid. |
| 1 | AAVC11.15 | | AGL | 178 | Payload comprising a AGL gene or variant thereof packaged within a AAVC11.15 capsid. |

Fig. 29 (Continued)

| | | | | | |
|---|---|---|---|---|---|
| 1 | AAVC11.16 | | AGL | 178 | Payload comprising a AGL gene or variant thereof packaged within a AAVC11.16 capsid. |
| 1 | AAVC11.17 | | AGL | 178 | Payload comprising a AGL gene or variant thereof packaged within a AAVC11.17 capsid. |
| 1 | AAVC11.18 | | AGL | 178 | Payload comprising a AGL gene or variant thereof packaged within a AAVC11.18 capsid. |
| 1 | AAVC11.19 | | AGL | 178 | Payload comprising a AGL gene or variant thereof packaged within a AAVC11.19 capsid. |
| 1 | AAV12 | | AGL | 178 | Payload comprising a AGL gene or variant thereof packaged within a AAV12 capsid. |
| 1 | AAV13 | | AGL | 178 | Payload comprising a AGL gene or variant thereof packaged within a AAV13 capsid. |
| 1 | AAV-DJ | | AGL | 178 | Payload comprising a AGL gene or variant thereof packaged within a AAV-DJ capsid. |
| 1 | AAV-LK03 | | AGL | 178 | Payload comprising a AGL gene or variant thereof packaged within a AAV-LK03 capsid. |
| 1 | AAV-LK19 | | AGL | 178 | Payload comprising a AGL gene or variant thereof packaged within a AAV-LK19 capsid. |
| 1 | AAVrh.74 | | AGL | 178 | Payload comprising a AGL gene or variant thereof packaged within a AAVrh.74 capsid. |
| 1 | AAVrh.10 | | AGL | 178 | Payload comprising a AGL gene or variant thereof packaged within a AAVrh.10 capsid. |
| 1 | AAVhu.37 | | AGL | 178 | Payload comprising a AGL gene or variant thereof packaged within a AAVhu.37 capsid. |
| 1 | AAVrh.K | | AGL | 178 | Payload comprising a AGL gene or variant thereof packaged within a AAVrh.K capsid. |
| 1 | AAVrh.39 | | AGL | 178 | Payload comprising a AGL gene or variant thereof packaged within a AAVrh.39 capsid. |
| 1 | AAVrh.9 | | AGL | 178 | Payload comprising a AGL gene or variant thereof packaged within a AAVrh.9 capsid. |
| 1 | avian AAV | | AGL | 178 | Payload comprising a AGL gene or variant thereof packaged within a avian capsid. |

Fig. 29 (Continued)

| | | | | | |
|---|---|---|---|---|---|
| 1 | bovine AAV | | AGL | 178 | Payload comprising a AGL gene or variant thereof packaged within a bovine capsid. |
| 1 | canine AAV | | AGL | 178 | Payload comprising a AGL gene or variant thereof packaged within a canine capsid. |
| 1 | equine AAV | | AGL | 178 | Payload comprising a AGL gene or variant thereof packaged within a equine capsid. |
| 1 | primate AAV | | AGL | 178 | Payload comprising a AGL gene or variant thereof packaged within a primate capsid. |
| 1 | non-primate AAV | | AGL | 178 | Payload comprising a AGL gene or variant thereof packaged within a non-primate capsid. |
| 1 | ovine AAV | | AGL | 178 | Payload comprising a AGL gene or variant thereof packaged within a ovine capsid. |
| 1 | hybrid AAV | | AGL | 178 | Payload comprising a AGL gene or variant thereof packaged within a hybrid capsid. |
| 1 | chimeric AAV | | AGL | 178 | Payload comprising a AGL gene or variant thereof packaged within a chimeric capsid. |
| 2 | AAV1 | 1450374 | AGL | 178 | Payload comprising a AGL gene or variant thereof packaged within a AAV1 capsid. |
| 2 | AAV2 | | AGL | 178 | Payload comprising a AGL gene or variant thereof packaged within a AAV2 capsid. |
| 2 | AAV3 | | AGL | 178 | Payload comprising a AGL gene or variant thereof packaged within a AAV3 capsid. |
| 2 | AAV4 | 1446389 | AGL | 178 | Payload comprising a AGL gene or variant thereof packaged within a AAV4 capsid. |
| 2 | AAV5 | | AGL | 178 | Payload comprising a AGL gene or variant thereof packaged within a AAV5 capsid. |
| 2 | AAV6 | | AGL | 178 | Payload comprising a AGL gene or variant thereof packaged within a AAV6 capsid. |
| 2 | AAV7 | | AGL | 178 | Payload comprising a AGL gene or variant thereof packaged within a AAV7 capsid. |
| 2 | AAV8 | 5075992 | AGL | 178 | Payload comprising a AGL gene or variant thereof packaged within a AAV8 capsid. |
| 2 | AAV9 | | AGL | 178 | Payload comprising a AGL gene or variant thereof packaged within a AAV9 capsid. |

Fig. 29 (Continued)

| | | | | | |
|---|---|---|---|---|---|
| 2 | AAV10 | | AGL | 178 | Payload comprising a AGL gene or variant thereof packaged within a AAV10 capsid. |
| 2 | AAV11 | | AGL | 178 | Payload comprising a AGL gene or variant thereof packaged within a AAV11 capsid. |
| 2 | AAVC11.01 | | AGL | 178 | Payload comprising a AGL gene or variant thereof packaged within a AAVC11.01 capsid. |
| 2 | AAVC11.02 | | AGL | 178 | Payload comprising a AGL gene or variant thereof packaged within a AAVC11.02 capsid. |
| 2 | AAVC11.03 | | AGL | 178 | Payload comprising a AGL gene or variant thereof packaged within a AAVC11.03 capsid. |
| 2 | AAVC11.04 | | AGL | 178 | Payload comprising a AGL gene or variant thereof packaged within a AAVC11.04 capsid. |
| 2 | AAVC11.05 | | AGL | 178 | Payload comprising a AGL gene or variant thereof packaged within a AAVC11.05 capsid. |
| 2 | AAVC11.06 | | AGL | 178 | Payload comprising a AGL gene or variant thereof packaged within a AAVC11.06 capsid. |
| 2 | AAVC11.07 | | AGL | 178 | Payload comprising a AGL gene or variant thereof packaged within a AAVC11.07 capsid. |
| 2 | AAVC11.08 | | AGL | 178 | Payload comprising a AGL gene or variant thereof packaged within a AAVC11.08 capsid. |
| 2 | AAVC11.09 | | AGL | 178 | Payload comprising a AGL gene or variant thereof packaged within a AAVC11.09 capsid. |
| 2 | AAVC11.10 | | AGL | 178 | Payload comprising a AGL gene or variant thereof packaged within a AAVC11.10 capsid. |
| 2 | AAVC11.11 | | AGL | 178 | Payload comprising a AGL gene or variant thereof packaged within a AAVC11.11 capsid. |
| 2 | AAVC11.12 | | AGL | 178 | Payload comprising a AGL gene or variant thereof packaged within a AAVC11.12 capsid. |
| 2 | AAVC11.13 | | AGL | 178 | Payload comprising a AGL gene or variant thereof packaged within a AAVC11.13 capsid. |
| 2 | AAVC11.14 | | AGL | 178 | Payload comprising a AGL gene or variant thereof packaged within a AAVC11.14 capsid. |
| 2 | AAVC11.15 | | AGL | 178 | Payload comprising a AGL gene or variant thereof packaged within a AAVC11.15 capsid. |

Fig. 29 (Continued)

| | | | | | |
|---|---|---|---|---|---|
| 2 | AAVC11.16 | | AGL | 178 | Payload comprising a AGL gene or variant thereof packaged within a AAVC11.16 capsid. |
| 2 | AAVC11.17 | | AGL | 178 | Payload comprising a AGL gene or variant thereof packaged within a AAVC11.17 capsid. |
| 2 | AAVC11.18 | | AGL | 178 | Payload comprising a AGL gene or variant thereof packaged within a AAVC11.18 capsid. |
| 2 | AAVC11.19 | | AGL | 178 | Payload comprising a AGL gene or variant thereof packaged within a AAVC11.19 capsid. |
| 2 | AAV12 | | AGL | 178 | Payload comprising a AGL gene or variant thereof packaged within a AAV12 capsid. |
| 2 | AAV13 | | AGL | 178 | Payload comprising a AGL gene or variant thereof packaged within a AAV13 capsid. |
| 2 | AAV-DJ | | AGL | 178 | Payload comprising a AGL gene or variant thereof packaged within a AAV-DJ capsid. |
| 2 | AAV-LK03 | | AGL | 178 | Payload comprising a AGL gene or variant thereof packaged within a AAV-LK03 capsid. |
| 2 | AAV-LK19 | | AGL | 178 | Payload comprising a AGL gene or variant thereof packaged within a AAV-LK19 capsid. |
| 2 | AAVrh.74 | | AGL | 178 | Payload comprising a AGL gene or variant thereof packaged within a AAVrh.74 capsid. |
| 2 | AAVrh.10 | | AGL | 178 | Payload comprising a AGL gene or variant thereof packaged within a AAVrh.10 capsid. |
| 2 | AAVhu.37 | | AGL | 178 | Payload comprising a AGL gene or variant thereof packaged within a AAVhu.37 capsid. |
| 2 | AAVrh.K | | AGL | 178 | Payload comprising a AGL gene or variant thereof packaged within a AAVrh.K capsid. |
| 2 | AAVrh.39 | | AGL | 178 | Payload comprising a AGL gene or variant thereof packaged within a AAVrh.39 capsid. |
| 2 | AAVrh.9 | | AGL | 178 | Payload comprising a AGL gene or variant thereof packaged within a AAVrh.9 capsid. |
| 2 | avian AAV | | AGL | 178 | Payload comprising a AGL gene or variant thereof packaged within a avian capsid. |

Fig. 29 (Continued)

| | | | | | |
|---|---|---|---|---|---|
| 2 | bovine AAV | | AGL | 178 | Payload comprising a AGL gene or variant thereof packaged within a bovine capsid. |
| 2 | canine AAV | | AGL | 178 | Payload comprising a AGL gene or variant thereof packaged within a canine capsid. |
| 2 | equine AAV | | AGL | 178 | Payload comprising a AGL gene or variant thereof packaged within a equine capsid. |
| 2 | primate AAV | | AGL | 178 | Payload comprising a AGL gene or variant thereof packaged within a primate capsid. |
| 2 | non-primate AAV | | AGL | 178 | Payload comprising a AGL gene or variant thereof packaged within a non-primate capsid. |
| 2 | ovine AAV | | AGL | 178 | Payload comprising a AGL gene or variant thereof packaged within a ovine capsid. |
| 2 | hybrid AAV | | AGL | 178 | Payload comprising a AGL gene or variant thereof packaged within a hybrid capsid. |
| 2 | chimeric AAV | | AGL | 178 | Payload comprising a AGL gene or variant thereof packaged within a chimeric capsid. |
| 1 | AAV1 | 1450374 | ANO5 | 203859 | Payload comprising a ANO5 gene or variant thereof packaged within a AAV1 capsid. |
| 1 | AAV2 | | ANO5 | 203859 | Payload comprising a ANO5 gene or variant thereof packaged within a AAV2 capsid. |
| 1 | AAV3 | | ANO5 | 203859 | Payload comprising a ANO5 gene or variant thereof packaged within a AAV3 capsid. |
| 1 | AAV4 | 1446389 | ANO5 | 203859 | Payload comprising a ANO5 gene or variant thereof packaged within a AAV4 capsid. |
| 1 | AAV5 | | ANO5 | 203859 | Payload comprising a ANO5 gene or variant thereof packaged within a AAV5 capsid. |
| 1 | AAV6 | | ANO5 | 203859 | Payload comprising a ANO5 gene or variant thereof packaged within a AAV6 capsid. |
| 1 | AAV7 | | ANO5 | 203859 | Payload comprising a ANO5 gene or variant thereof packaged within a AAV7 capsid. |
| 1 | AAV8 | 5075992 | ANO5 | 203859 | Payload comprising a ANO5 gene or variant thereof packaged within a AAV8 capsid. |
| 1 | AAV9 | | ANO5 | 203859 | Payload comprising a ANO5 gene or variant thereof packaged within a AAV9 capsid. |

Fig. 29 (Continued)

| | | | | | |
|---|---|---|---|---|---|
| 1 | AAV10 | | ANO5 | 203859 | Payload comprising a ANO5 gene or variant thereof packaged within a AAV10 capsid. |
| 1 | AAV11 | | ANO5 | 203859 | Payload comprising a ANO5 gene or variant thereof packaged within a AAV11 capsid. |
| 1 | AAVC11.01 | | ANO5 | 203859 | Payload comprising a ANO5 gene or variant thereof packaged within a AAVC11.01 capsid. |
| 1 | AAVC11.02 | | ANO5 | 203859 | Payload comprising a ANO5 gene or variant thereof packaged within a AAVC11.02 capsid. |
| 1 | AAVC11.03 | | ANO5 | 203859 | Payload comprising a ANO5 gene or variant thereof packaged within a AAVC11.03 capsid. |
| 1 | AAVC11.04 | | ANO5 | 203859 | Payload comprising a ANO5 gene or variant thereof packaged within a AAVC11.04 capsid. |
| 1 | AAVC11.05 | | ANO5 | 203859 | Payload comprising a ANO5 gene or variant thereof packaged within a AAVC11.05 capsid. |
| 1 | AAVC11.06 | | ANO5 | 203859 | Payload comprising a ANO5 gene or variant thereof packaged within a AAVC11.06 capsid. |
| 1 | AAVC11.07 | | ANO5 | 203859 | Payload comprising a ANO5 gene or variant thereof packaged within a AAVC11.07 capsid. |
| 1 | AAVC11.08 | | ANO5 | 203859 | Payload comprising a ANO5 gene or variant thereof packaged within a AAVC11.08 capsid. |
| 1 | AAVC11.09 | | ANO5 | 203859 | Payload comprising a ANO5 gene or variant thereof packaged within a AAVC11.09 capsid. |
| 1 | AAVC11.10 | | ANO5 | 203859 | Payload comprising a ANO5 gene or variant thereof packaged within a AAVC11.10 capsid. |
| 1 | AAVC11.11 | | ANO5 | 203859 | Payload comprising a ANO5 gene or variant thereof packaged within a AAVC11.11 capsid. |
| 1 | AAVC11.12 | | ANO5 | 203859 | Payload comprising a ANO5 gene or variant thereof packaged within a AAVC11.12 capsid. |
| 1 | AAVC11.13 | | ANO5 | 203859 | Payload comprising a ANO5 gene or variant thereof packaged within a AAVC11.13 capsid. |
| 1 | AAVC11.14 | | ANO5 | 203859 | Payload comprising a ANO5 gene or variant thereof packaged within a AAVC11.14 capsid. |
| 1 | AAVC11.15 | | ANO5 | 203859 | Payload comprising a ANO5 gene or variant thereof packaged within a AAVC11.15 capsid. |

Fig. 29 (Continued)

| | | | | | |
|---|---|---|---|---|---|
| 1 | AAVC11.16 | | ANO5 | 203859 | Payload comprising a ANO5 gene or variant thereof packaged within a AAVC11.16 capsid. |
| 1 | AAVC11.17 | | ANO5 | 203859 | Payload comprising a ANO5 gene or variant thereof packaged within a AAVC11.17 capsid. |
| 1 | AAVC11.18 | | ANO5 | 203859 | Payload comprising a ANO5 gene or variant thereof packaged within a AAVC11.18 capsid. |
| 1 | AAVC11.19 | | ANO5 | 203859 | Payload comprising a ANO5 gene or variant thereof packaged within a AAVC11.19 capsid. |
| 1 | AAV12 | | ANO5 | 203859 | Payload comprising a ANO5 gene or variant thereof packaged within a AAV12 capsid. |
| 1 | AAV13 | | ANO5 | 203859 | Payload comprising a ANO5 gene or variant thereof packaged within a AAV13 capsid. |
| 1 | AAV-DJ | | ANO5 | 203859 | Payload comprising a ANO5 gene or variant thereof packaged within a AAV-DJ capsid. |
| 1 | AAV-LK03 | | ANO5 | 203859 | Payload comprising a ANO5 gene or variant thereof packaged within a AAV-LK03 capsid. |
| 1 | AAV-LK19 | | ANO5 | 203859 | Payload comprising a ANO5 gene or variant thereof packaged within a AAV-LK19 capsid. |
| 1 | AAVrh.74 | | ANO5 | 203859 | Payload comprising a ANO5 gene or variant thereof packaged within a AAVrh.74 capsid. |
| 1 | AAVrh.10 | | ANO5 | 203859 | Payload comprising a ANO5 gene or variant thereof packaged within a AAVrh.10 capsid. |
| 1 | AAVhu.37 | | ANO5 | 203859 | Payload comprising a ANO5 gene or variant thereof packaged within a AAVhu.37 capsid. |
| 1 | AAVrh.K | | ANO5 | 203859 | Payload comprising a ANO5 gene or variant thereof packaged within a AAVrh.K capsid. |
| 1 | AAVrh.39 | | ANO5 | 203859 | Payload comprising a ANO5 gene or variant thereof packaged within a AAVrh.39 capsid. |
| 1 | AAVrh.9 | | ANO5 | 203859 | Payload comprising a ANO5 gene or variant thereof packaged within a AAVrh.9 capsid. |
| 1 | avian AAV | | ANO5 | 203859 | Payload comprising a ANO5 gene or variant thereof packaged within a avian capsid. |

Fig. 29 (Continued)

| | | | | | |
|---|---|---|---|---|---|
| 1 | bovine AAV | | ANO5 | 203859 | Payload comprising a ANO5 gene or variant thereof packaged within a bovine capsid. |
| 1 | canine AAV | | ANO5 | 203859 | Payload comprising a ANO5 gene or variant thereof packaged within a canine capsid. |
| 1 | equine AAV | | ANO5 | 203859 | Payload comprising a ANO5 gene or variant thereof packaged within a equine capsid. |
| 1 | primate AAV | | ANO5 | 203859 | Payload comprising a ANO5 gene or variant thereof packaged within a primate capsid. |
| 1 | non-primate AAV | | ANO5 | 203859 | Payload comprising a ANO5 gene or variant thereof packaged within a non-primate capsid. |
| 1 | ovine AAV | | ANO5 | 203859 | Payload comprising a ANO5 gene or variant thereof packaged within a ovine capsid. |
| 1 | hybrid AAV | | ANO5 | 203859 | Payload comprising a ANO5 gene or variant thereof packaged within a hybrid capsid. |
| 1 | chimeric AAV | | ANO5 | 203859 | Payload comprising a ANO5 gene or variant thereof packaged within a chimeric capsid. |
| 2 | AAV1 | 1450374 | ANO5 | 203859 | Payload comprising a ANO5 gene or variant thereof packaged within a AAV1 capsid. |
| 2 | AAV2 | | ANO5 | 203859 | Payload comprising a ANO5 gene or variant thereof packaged within a AAV2 capsid. |
| 2 | AAV3 | | ANO5 | 203859 | Payload comprising a ANO5 gene or variant thereof packaged within a AAV3 capsid. |
| 2 | AAV4 | 1446389 | ANO5 | 203859 | Payload comprising a ANO5 gene or variant thereof packaged within a AAV4 capsid. |
| 2 | AAV5 | | ANO5 | 203859 | Payload comprising a ANO5 gene or variant thereof packaged within a AAV5 capsid. |
| 2 | AAV6 | | ANO5 | 203859 | Payload comprising a ANO5 gene or variant thereof packaged within a AAV6 capsid. |
| 2 | AAV7 | | ANO5 | 203859 | Payload comprising a ANO5 gene or variant thereof packaged within a AAV7 capsid. |
| 2 | AAV8 | 5075992 | ANO5 | 203859 | Payload comprising a ANO5 gene or variant thereof packaged within a AAV8 capsid. |
| 2 | AAV9 | | ANO5 | 203859 | Payload comprising a ANO5 gene or variant thereof packaged within a AAV9 capsid. |

Fig. 29 (Continued)

| | | | | | |
|---|---|---|---|---|---|
| 2 | AAV10 | | ANO5 | 203859 | Payload comprising a ANO5 gene or variant thereof packaged within a AAV10 capsid. |
| 2 | AAV11 | | ANO5 | 203859 | Payload comprising a ANO5 gene or variant thereof packaged within a AAV11 capsid. |
| 2 | AAVC11.01 | | ANO5 | 203859 | Payload comprising a ANO5 gene or variant thereof packaged within a AAVC11.01 capsid. |
| 2 | AAVC11.02 | | ANO5 | 203859 | Payload comprising a ANO5 gene or variant thereof packaged within a AAVC11.02 capsid. |
| 2 | AAVC11.03 | | ANO5 | 203859 | Payload comprising a ANO5 gene or variant thereof packaged within a AAVC11.03 capsid. |
| 2 | AAVC11.04 | | ANO5 | 203859 | Payload comprising a ANO5 gene or variant thereof packaged within a AAVC11.04 capsid. |
| 2 | AAVC11.05 | | ANO5 | 203859 | Payload comprising a ANO5 gene or variant thereof packaged within a AAVC11.05 capsid. |
| 2 | AAVC11.06 | | ANO5 | 203859 | Payload comprising a ANO5 gene or variant thereof packaged within a AAVC11.06 capsid. |
| 2 | AAVC11.07 | | ANO5 | 203859 | Payload comprising a ANO5 gene or variant thereof packaged within a AAVC11.07 capsid. |
| 2 | AAVC11.08 | | ANO5 | 203859 | Payload comprising a ANO5 gene or variant thereof packaged within a AAVC11.08 capsid. |
| 2 | AAVC11.09 | | ANO5 | 203859 | Payload comprising a ANO5 gene or variant thereof packaged within a AAVC11.09 capsid. |
| 2 | AAVC11.10 | | ANO5 | 203859 | Payload comprising a ANO5 gene or variant thereof packaged within a AAVC11.10 capsid. |
| 2 | AAVC11.11 | | ANO5 | 203859 | Payload comprising a ANO5 gene or variant thereof packaged within a AAVC11.11 capsid. |
| 2 | AAVC11.12 | | ANO5 | 203859 | Payload comprising a ANO5 gene or variant thereof packaged within a AAVC11.12 capsid. |
| 2 | AAVC11.13 | | ANO5 | 203859 | Payload comprising a ANO5 gene or variant thereof packaged within a AAVC11.13 capsid. |
| 2 | AAVC11.14 | | ANO5 | 203859 | Payload comprising a ANO5 gene or variant thereof packaged within a AAVC11.14 capsid. |
| 2 | AAVC11.15 | | ANO5 | 203859 | Payload comprising a ANO5 gene or variant thereof packaged within a AAVC11.15 capsid. |

Fig. 29 (Continued)

| | | | | | |
|---|---|---|---|---|---|
| 2 | AAVC11.16 | | ANO5 | 203859 | Payload comprising a ANO5 gene or variant thereof packaged within a AAVC11.16 capsid. |
| 2 | AAVC11.17 | | ANO5 | 203859 | Payload comprising a ANO5 gene or variant thereof packaged within a AAVC11.17 capsid. |
| 2 | AAVC11.18 | | ANO5 | 203859 | Payload comprising a ANO5 gene or variant thereof packaged within a AAVC11.18 capsid. |
| 2 | AAVC11.19 | | ANO5 | 203859 | Payload comprising a ANO5 gene or variant thereof packaged within a AAVC11.19 capsid. |
| 2 | AAV12 | | ANO5 | 203859 | Payload comprising a ANO5 gene or variant thereof packaged within a AAV12 capsid. |
| 2 | AAV13 | | ANO5 | 203859 | Payload comprising a ANO5 gene or variant thereof packaged within a AAV13 capsid. |
| 2 | AAV-DJ | | ANO5 | 203859 | Payload comprising a ANO5 gene or variant thereof packaged within a AAV-DJ capsid. |
| 2 | AAV-LK03 | | ANO5 | 203859 | Payload comprising a ANO5 gene or variant thereof packaged within a AAV-LK03 capsid. |
| 2 | AAV-LK19 | | ANO5 | 203859 | Payload comprising a ANO5 gene or variant thereof packaged within a AAV-LK19 capsid. |
| 2 | AAVrh.74 | | ANO5 | 203859 | Payload comprising a ANO5 gene or variant thereof packaged within a AAVrh.74 capsid. |
| 2 | AAVrh.10 | | ANO5 | 203859 | Payload comprising a ANO5 gene or variant thereof packaged within a AAVrh.10 capsid. |
| 2 | AAVhu.37 | | ANO5 | 203859 | Payload comprising a ANO5 gene or variant thereof packaged within a AAVhu.37 capsid. |
| 2 | AAVrh.K | | ANO5 | 203859 | Payload comprising a ANO5 gene or variant thereof packaged within a AAVrh.K capsid. |
| 2 | AAVrh.39 | | ANO5 | 203859 | Payload comprising a ANO5 gene or variant thereof packaged within a AAVrh.39 capsid. |
| 2 | AAVrh.9 | | ANO5 | 203859 | Payload comprising a ANO5 gene or variant thereof packaged within a AAVrh.9 capsid. |
| 2 | avian AAV | | ANO5 | 203859 | Payload comprising a ANO5 gene or variant thereof packaged within a avian capsid. |

Fig. 29 (Continued)

| | | | | | |
|---|---|---|---|---|---|
| 2 | bovine AAV | | ANO5 | 203859 | Payload comprising a ANO5 gene or variant thereof packaged within a bovine capsid. |
| 2 | canine AAV | | ANO5 | 203859 | Payload comprising a ANO5 gene or variant thereof packaged within a canine capsid. |
| 2 | equine AAV | | ANO5 | 203859 | Payload comprising a ANO5 gene or variant thereof packaged within a equine capsid. |
| 2 | primate AAV | | ANO5 | 203859 | Payload comprising a ANO5 gene or variant thereof packaged within a primate capsid. |
| 2 | non-primate AAV | | ANO5 | 203859 | Payload comprising a ANO5 gene or variant thereof packaged within a non-primate capsid. |
| 2 | ovine AAV | | ANO5 | 203859 | Payload comprising a ANO5 gene or variant thereof packaged within a ovine capsid. |
| 2 | hybrid AAV | | ANO5 | 203859 | Payload comprising a ANO5 gene or variant thereof packaged within a hybrid capsid. |
| 2 | chimeric AAV | | ANO5 | 203859 | Payload comprising a ANO5 gene or variant thereof packaged within a chimeric capsid. |
| 1 | AAV1 | 1450374 | ARG1 | 383 | Payload comprising a ARG1 gene or variant thereof packaged within a AAV1 capsid. |
| 1 | AAV2 | | ARG1 | 383 | Payload comprising a ARG1 gene or variant thereof packaged within a AAV2 capsid. |
| 1 | AAV3 | | ARG1 | 383 | Payload comprising a ARG1 gene or variant thereof packaged within a AAV3 capsid. |
| 1 | AAV4 | 1446389 | ARG1 | 383 | Payload comprising a ARG1 gene or variant thereof packaged within a AAV4 capsid. |
| 1 | AAV5 | | ARG1 | 383 | Payload comprising a ARG1 gene or variant thereof packaged within a AAV5 capsid. |
| 1 | AAV6 | | ARG1 | 383 | Payload comprising a ARG1 gene or variant thereof packaged within a AAV6 capsid. |
| 1 | AAV7 | | ARG1 | 383 | Payload comprising a ARG1 gene or variant thereof packaged within a AAV7 capsid. |
| 1 | AAV8 | 5075992 | ARG1 | 383 | Payload comprising a ARG1 gene or variant thereof packaged within a AAV8 capsid. |
| 1 | AAV9 | | ARG1 | 383 | Payload comprising a ARG1 gene or variant thereof packaged within a AAV9 capsid. |

Fig. 29 (Continued)

| | | | | | |
|---|---|---|---|---|---|
| 1 | AAV10 | | ARG1 | 383 | Payload comprising a ARG1 gene or variant thereof packaged within a AAV10 capsid. |
| 1 | AAV11 | | ARG1 | 383 | Payload comprising a ARG1 gene or variant thereof packaged within a AAV11 capsid. |
| 1 | AAVC11.01 | | ARG1 | 383 | Payload comprising a ARG1 gene or variant thereof packaged within a AAVC11.01 capsid. |
| 1 | AAVC11.02 | | ARG1 | 383 | Payload comprising a ARG1 gene or variant thereof packaged within a AAVC11.02 capsid. |
| 1 | AAVC11.03 | | ARG1 | 383 | Payload comprising a ARG1 gene or variant thereof packaged within a AAVC11.03 capsid. |
| 1 | AAVC11.04 | | ARG1 | 383 | Payload comprising a ARG1 gene or variant thereof packaged within a AAVC11.04 capsid. |
| 1 | AAVC11.05 | | ARG1 | 383 | Payload comprising a ARG1 gene or variant thereof packaged within a AAVC11.05 capsid. |
| 1 | AAVC11.06 | | ARG1 | 383 | Payload comprising a ARG1 gene or variant thereof packaged within a AAVC11.06 capsid. |
| 1 | AAVC11.07 | | ARG1 | 383 | Payload comprising a ARG1 gene or variant thereof packaged within a AAVC11.07 capsid. |
| 1 | AAVC11.08 | | ARG1 | 383 | Payload comprising a ARG1 gene or variant thereof packaged within a AAVC11.08 capsid. |
| 1 | AAVC11.09 | | ARG1 | 383 | Payload comprising a ARG1 gene or variant thereof packaged within a AAVC11.09 capsid. |
| 1 | AAVC11.10 | | ARG1 | 383 | Payload comprising a ARG1 gene or variant thereof packaged within a AAVC11.10 capsid. |
| 1 | AAVC11.11 | | ARG1 | 383 | Payload comprising a ARG1 gene or variant thereof packaged within a AAVC11.11 capsid. |
| 1 | AAVC11.12 | | ARG1 | 383 | Payload comprising a ARG1 gene or variant thereof packaged within a AAVC11.12 capsid. |
| 1 | AAVC11.13 | | ARG1 | 383 | Payload comprising a ARG1 gene or variant thereof packaged within a AAVC11.13 capsid. |
| 1 | AAVC11.14 | | ARG1 | 383 | Payload comprising a ARG1 gene or variant thereof packaged within a AAVC11.14 capsid. |
| 1 | AAVC11.15 | | ARG1 | 383 | Payload comprising a ARG1 gene or variant thereof packaged within a AAVC11.15 capsid. |

Fig. 29 (Continued)

| | | | | | |
|---|---|---|---|---|---|
| 1 | AAVC11.16 | | ARG1 | 383 | Payload comprising a ARG1 gene or variant thereof packaged within a AAVC11.16 capsid. |
| 1 | AAVC11.17 | | ARG1 | 383 | Payload comprising a ARG1 gene or variant thereof packaged within a AAVC11.17 capsid. |
| 1 | AAVC11.18 | | ARG1 | 383 | Payload comprising a ARG1 gene or variant thereof packaged within a AAVC11.18 capsid. |
| 1 | AAVC11.19 | | ARG1 | 383 | Payload comprising a ARG1 gene or variant thereof packaged within a AAVC11.19 capsid. |
| 1 | AAV12 | | ARG1 | 383 | Payload comprising a ARG1 gene or variant thereof packaged within a AAV12 capsid. |
| 1 | AAV13 | | ARG1 | 383 | Payload comprising a ARG1 gene or variant thereof packaged within a AAV13 capsid. |
| 1 | AAV-DJ | | ARG1 | 383 | Payload comprising a ARG1 gene or variant thereof packaged within a AAV-DJ capsid. |
| 1 | AAV-LK03 | | ARG1 | 383 | Payload comprising a ARG1 gene or variant thereof packaged within a AAV-LK03 capsid. |
| 1 | AAV-LK19 | | ARG1 | 383 | Payload comprising a ARG1 gene or variant thereof packaged within a AAV-LK19 capsid. |
| 1 | AAVrh.74 | | ARG1 | 383 | Payload comprising a ARG1 gene or variant thereof packaged within a AAVrh.74 capsid. |
| 1 | AAVrh.10 | | ARG1 | 383 | Payload comprising a ARG1 gene or variant thereof packaged within a AAVrh.10 capsid. |
| 1 | AAVhu.37 | | ARG1 | 383 | Payload comprising a ARG1 gene or variant thereof packaged within a AAVhu.37 capsid. |
| 1 | AAVrh.K | | ARG1 | 383 | Payload comprising a ARG1 gene or variant thereof packaged within a AAVrh.K capsid. |
| 1 | AAVrh.39 | | ARG1 | 383 | Payload comprising a ARG1 gene or variant thereof packaged within a AAVrh.39 capsid. |
| 1 | AAVrh.9 | | ARG1 | 383 | Payload comprising a ARG1 gene or variant thereof packaged within a AAVrh.9 capsid. |
| 1 | avian AAV | | ARG1 | 383 | Payload comprising a ARG1 gene or variant thereof packaged within a avian capsid. |

Fig. 29 (Continued)

| | | | | | |
|---|---|---|---|---|---|
| 1 | bovine AAV | | ARG1 | 383 | Payload comprising a ARG1 gene or variant thereof packaged within a bovine capsid. |
| 1 | canine AAV | | ARG1 | 383 | Payload comprising a ARG1 gene or variant thereof packaged within a canine capsid. |
| 1 | equine AAV | | ARG1 | 383 | Payload comprising a ARG1 gene or variant thereof packaged within a equine capsid. |
| 1 | primate AAV | | ARG1 | 383 | Payload comprising a ARG1 gene or variant thereof packaged within a primate capsid. |
| 1 | non-primate AAV | | ARG1 | 383 | Payload comprising a ARG1 gene or variant thereof packaged within a non-primate capsid. |
| 1 | ovine AAV | | ARG1 | 383 | Payload comprising a ARG1 gene or variant thereof packaged within a ovine capsid. |
| 1 | hybrid AAV | | ARG1 | 383 | Payload comprising a ARG1 gene or variant thereof packaged within a hybrid capsid. |
| 1 | chimeric AAV | | ARG1 | 383 | Payload comprising a ARG1 gene or variant thereof packaged within a chimeric capsid. |
| 2 | AAV1 | 1450374 | ARG1 | 383 | Payload comprising a ARG1 gene or variant thereof packaged within a AAV1 capsid. |
| 2 | AAV2 | | ARG1 | 383 | Payload comprising a ARG1 gene or variant thereof packaged within a AAV2 capsid. |
| 2 | AAV3 | | ARG1 | 383 | Payload comprising a ARG1 gene or variant thereof packaged within a AAV3 capsid. |
| 2 | AAV4 | 1446389 | ARG1 | 383 | Payload comprising a ARG1 gene or variant thereof packaged within a AAV4 capsid. |
| 2 | AAV5 | | ARG1 | 383 | Payload comprising a ARG1 gene or variant thereof packaged within a AAV5 capsid. |
| 2 | AAV6 | | ARG1 | 383 | Payload comprising a ARG1 gene or variant thereof packaged within a AAV6 capsid. |
| 2 | AAV7 | | ARG1 | 383 | Payload comprising a ARG1 gene or variant thereof packaged within a AAV7 capsid. |
| 2 | AAV8 | 5075992 | ARG1 | 383 | Payload comprising a ARG1 gene or variant thereof packaged within a AAV8 capsid. |
| 2 | AAV9 | | ARG1 | 383 | Payload comprising a ARG1 gene or variant thereof packaged within a AAV9 capsid. |

Fig. 29 (Continued)

| | | | | | |
|---|---|---|---|---|---|
| 2 | AAV10 | | ARG1 | 383 | Payload comprising a ARG1 gene or variant thereof packaged within a AAV10 capsid. |
| 2 | AAV11 | | ARG1 | 383 | Payload comprising a ARG1 gene or variant thereof packaged within a AAV11 capsid. |
| 2 | AAVC11.01 | | ARG1 | 383 | Payload comprising a ARG1 gene or variant thereof packaged within a AAVC11.01 capsid. |
| 2 | AAVC11.02 | | ARG1 | 383 | Payload comprising a ARG1 gene or variant thereof packaged within a AAVC11.02 capsid. |
| 2 | AAVC11.03 | | ARG1 | 383 | Payload comprising a ARG1 gene or variant thereof packaged within a AAVC11.03 capsid. |
| 2 | AAVC11.04 | | ARG1 | 383 | Payload comprising a ARG1 gene or variant thereof packaged within a AAVC11.04 capsid. |
| 2 | AAVC11.05 | | ARG1 | 383 | Payload comprising a ARG1 gene or variant thereof packaged within a AAVC11.05 capsid. |
| 2 | AAVC11.06 | | ARG1 | 383 | Payload comprising a ARG1 gene or variant thereof packaged within a AAVC11.06 capsid. |
| 2 | AAVC11.07 | | ARG1 | 383 | Payload comprising a ARG1 gene or variant thereof packaged within a AAVC11.07 capsid. |
| 2 | AAVC11.08 | | ARG1 | 383 | Payload comprising a ARG1 gene or variant thereof packaged within a AAVC11.08 capsid. |
| 2 | AAVC11.09 | | ARG1 | 383 | Payload comprising a ARG1 gene or variant thereof packaged within a AAVC11.09 capsid. |
| 2 | AAVC11.10 | | ARG1 | 383 | Payload comprising a ARG1 gene or variant thereof packaged within a AAVC11.10 capsid. |
| 2 | AAVC11.11 | | ARG1 | 383 | Payload comprising a ARG1 gene or variant thereof packaged within a AAVC11.11 capsid. |
| 2 | AAVC11.12 | | ARG1 | 383 | Payload comprising a ARG1 gene or variant thereof packaged within a AAVC11.12 capsid. |
| 2 | AAVC11.13 | | ARG1 | 383 | Payload comprising a ARG1 gene or variant thereof packaged within a AAVC11.13 capsid. |
| 2 | AAVC11.14 | | ARG1 | 383 | Payload comprising a ARG1 gene or variant thereof packaged within a AAVC11.14 capsid. |
| 2 | AAVC11.15 | | ARG1 | 383 | Payload comprising a ARG1 gene or variant thereof packaged within a AAVC11.15 capsid. |

Fig. 29 (Continued)

| | | | | | |
|---|---|---|---|---|---|
| 2 | AAVC11.16 | | ARG1 | 383 | Payload comprising a ARG1 gene or variant thereof packaged within a AAVC11.16 capsid. |
| 2 | AAVC11.17 | | ARG1 | 383 | Payload comprising a ARG1 gene or variant thereof packaged within a AAVC11.17 capsid. |
| 2 | AAVC11.18 | | ARG1 | 383 | Payload comprising a ARG1 gene or variant thereof packaged within a AAVC11.18 capsid. |
| 2 | AAVC11.19 | | ARG1 | 383 | Payload comprising a ARG1 gene or variant thereof packaged within a AAVC11.19 capsid. |
| 2 | AAV12 | | ARG1 | 383 | Payload comprising a ARG1 gene or variant thereof packaged within a AAV12 capsid. |
| 2 | AAV13 | | ARG1 | 383 | Payload comprising a ARG1 gene or variant thereof packaged within a AAV13 capsid. |
| 2 | AAV-DJ | | ARG1 | 383 | Payload comprising a ARG1 gene or variant thereof packaged within a AAV-DJ capsid. |
| 2 | AAV-LK03 | | ARG1 | 383 | Payload comprising a ARG1 gene or variant thereof packaged within a AAV-LK03 capsid. |
| 2 | AAV-LK19 | | ARG1 | 383 | Payload comprising a ARG1 gene or variant thereof packaged within a AAV-LK19 capsid. |
| 2 | AAVrh.74 | | ARG1 | 383 | Payload comprising a ARG1 gene or variant thereof packaged within a AAVrh.74 capsid. |
| 2 | AAVrh.10 | | ARG1 | 383 | Payload comprising a ARG1 gene or variant thereof packaged within a AAVrh.10 capsid. |
| 2 | AAVhu.37 | | ARG1 | 383 | Payload comprising a ARG1 gene or variant thereof packaged within a AAVhu.37 capsid. |
| 2 | AAVrh.K | | ARG1 | 383 | Payload comprising a ARG1 gene or variant thereof packaged within a AAVrh.K capsid. |
| 2 | AAVrh.39 | | ARG1 | 383 | Payload comprising a ARG1 gene or variant thereof packaged within a AAVrh.39 capsid. |
| 2 | AAVrh.9 | | ARG1 | 383 | Payload comprising a ARG1 gene or variant thereof packaged within a AAVrh.9 capsid. |
| 2 | avian AAV | | ARG1 | 383 | Payload comprising a ARG1 gene or variant thereof packaged within a avian capsid. |

Fig. 29 (Continued)

| | | | | | |
|---|---|---|---|---|---|
| 2 | bovine AAV | | ARG1 | 383 | Payload comprising a ARG1 gene or variant thereof packaged within a bovine capsid. |
| 2 | canine AAV | | ARG1 | 383 | Payload comprising a ARG1 gene or variant thereof packaged within a canine capsid. |
| 2 | equine AAV | | ARG1 | 383 | Payload comprising a ARG1 gene or variant thereof packaged within a equine capsid. |
| 2 | primate AAV | | ARG1 | 383 | Payload comprising a ARG1 gene or variant thereof packaged within a primate capsid. |
| 2 | non-primate AAV | | ARG1 | 383 | Payload comprising a ARG1 gene or variant thereof packaged within a non-primate capsid. |
| 2 | ovine AAV | | ARG1 | 383 | Payload comprising a ARG1 gene or variant thereof packaged within a ovine capsid. |
| 2 | hybrid AAV | | ARG1 | 383 | Payload comprising a ARG1 gene or variant thereof packaged within a hybrid capsid. |
| 2 | chimeric AAV | | ARG1 | 383 | Payload comprising a ARG1 gene or variant thereof packaged within a chimeric capsid. |
| 1 | AAV1 | 1450374 | ARSB | 411 | Payload comprising a ARSB gene or variant thereof packaged within a AAV1 capsid. |
| 1 | AAV2 | | ARSB | 411 | Payload comprising a ARSB gene or variant thereof packaged within a AAV2 capsid. |
| 1 | AAV3 | | ARSB | 411 | Payload comprising a ARSB gene or variant thereof packaged within a AAV3 capsid. |
| 1 | AAV4 | 1446389 | ARSB | 411 | Payload comprising a ARSB gene or variant thereof packaged within a AAV4 capsid. |
| 1 | AAV5 | | ARSB | 411 | Payload comprising a ARSB gene or variant thereof packaged within a AAV5 capsid. |
| 1 | AAV6 | | ARSB | 411 | Payload comprising a ARSB gene or variant thereof packaged within a AAV6 capsid. |
| 1 | AAV7 | | ARSB | 411 | Payload comprising a ARSB gene or variant thereof packaged within a AAV7 capsid. |
| 1 | AAV8 | 5075992 | ARSB | 411 | Payload comprising a ARSB gene or variant thereof packaged within a AAV8 capsid. |
| 1 | AAV9 | | ARSB | 411 | Payload comprising a ARSB gene or variant thereof packaged within a AAV9 capsid. |

Fig. 29 (Continued)

| | | | | | |
|---|---|---|---|---|---|
| 1 | AAV10 | | ARSB | 411 | Payload comprising a ARSB gene or variant thereof packaged within a AAV10 capsid. |
| 1 | AAV11 | | ARSB | 411 | Payload comprising a ARSB gene or variant thereof packaged within a AAV11 capsid. |
| 1 | AAVC11.01 | | ARSB | 411 | Payload comprising a ARSB gene or variant thereof packaged within a AAVC11.01 capsid. |
| 1 | AAVC11.02 | | ARSB | 411 | Payload comprising a ARSB gene or variant thereof packaged within a AAVC11.02 capsid. |
| 1 | AAVC11.03 | | ARSB | 411 | Payload comprising a ARSB gene or variant thereof packaged within a AAVC11.03 capsid. |
| 1 | AAVC11.04 | | ARSB | 411 | Payload comprising a ARSB gene or variant thereof packaged within a AAVC11.04 capsid. |
| 1 | AAVC11.05 | | ARSB | 411 | Payload comprising a ARSB gene or variant thereof packaged within a AAVC11.05 capsid. |
| 1 | AAVC11.06 | | ARSB | 411 | Payload comprising a ARSB gene or variant thereof packaged within a AAVC11.06 capsid. |
| 1 | AAVC11.07 | | ARSB | 411 | Payload comprising a ARSB gene or variant thereof packaged within a AAVC11.07 capsid. |
| 1 | AAVC11.08 | | ARSB | 411 | Payload comprising a ARSB gene or variant thereof packaged within a AAVC11.08 capsid. |
| 1 | AAVC11.09 | | ARSB | 411 | Payload comprising a ARSB gene or variant thereof packaged within a AAVC11.09 capsid. |
| 1 | AAVC11.10 | | ARSB | 411 | Payload comprising a ARSB gene or variant thereof packaged within a AAVC11.10 capsid. |
| 1 | AAVC11.11 | | ARSB | 411 | Payload comprising a ARSB gene or variant thereof packaged within a AAVC11.11 capsid. |
| 1 | AAVC11.12 | | ARSB | 411 | Payload comprising a ARSB gene or variant thereof packaged within a AAVC11.12 capsid. |
| 1 | AAVC11.13 | | ARSB | 411 | Payload comprising a ARSB gene or variant thereof packaged within a AAVC11.13 capsid. |
| 1 | AAVC11.14 | | ARSB | 411 | Payload comprising a ARSB gene or variant thereof packaged within a AAVC11.14 capsid. |
| 1 | AAVC11.15 | | ARSB | 411 | Payload comprising a ARSB gene or variant thereof packaged within a AAVC11.15 capsid. |

Fig. 29 (Continued)

| | | | | | |
|---|---|---|---|---|---|
| 1 | AAVC11.16 | | ARSB | 411 | Payload comprising a ARSB gene or variant thereof packaged within a AAVC11.16 capsid. |
| 1 | AAVC11.17 | | ARSB | 411 | Payload comprising a ARSB gene or variant thereof packaged within a AAVC11.17 capsid. |
| 1 | AAVC11.18 | | ARSB | 411 | Payload comprising a ARSB gene or variant thereof packaged within a AAVC11.18 capsid. |
| 1 | AAVC11.19 | | ARSB | 411 | Payload comprising a ARSB gene or variant thereof packaged within a AAVC11.19 capsid. |
| 1 | AAV12 | | ARSB | 411 | Payload comprising a ARSB gene or variant thereof packaged within a AAV12 capsid. |
| 1 | AAV13 | | ARSB | 411 | Payload comprising a ARSB gene or variant thereof packaged within a AAV13 capsid. |
| 1 | AAV-DJ | | ARSB | 411 | Payload comprising a ARSB gene or variant thereof packaged within a AAV-DJ capsid. |
| 1 | AAV-LK03 | | ARSB | 411 | Payload comprising a ARSB gene or variant thereof packaged within a AAV-LK03 capsid. |
| 1 | AAV-LK19 | | ARSB | 411 | Payload comprising a ARSB gene or variant thereof packaged within a AAV-LK19 capsid. |
| 1 | AAVrh.74 | | ARSB | 411 | Payload comprising a ARSB gene or variant thereof packaged within a AAVrh.74 capsid. |
| 1 | AAVrh.10 | | ARSB | 411 | Payload comprising a ARSB gene or variant thereof packaged within a AAVrh.10 capsid. |
| 1 | AAVhu.37 | | ARSB | 411 | Payload comprising a ARSB gene or variant thereof packaged within a AAVhu.37 capsid. |
| 1 | AAVrh.K | | ARSB | 411 | Payload comprising a ARSB gene or variant thereof packaged within a AAVrh.K capsid. |
| 1 | AAVrh.39 | | ARSB | 411 | Payload comprising a ARSB gene or variant thereof packaged within a AAVrh.39 capsid. |
| 1 | AAVrh.9 | | ARSB | 411 | Payload comprising a ARSB gene or variant thereof packaged within a AAVrh.9 capsid. |
| 1 | avian AAV | | ARSB | 411 | Payload comprising a ARSB gene or variant thereof packaged within a avian capsid. |

Fig. 29 (Continued)

| | | | | | |
|---|---|---|---|---|---|
| 1 | bovine AAV | | ARSB | 411 | Payload comprising a ARSB gene or variant thereof packaged within a bovine capsid. |
| 1 | canine AAV | | ARSB | 411 | Payload comprising a ARSB gene or variant thereof packaged within a canine capsid. |
| 1 | equine AAV | | ARSB | 411 | Payload comprising a ARSB gene or variant thereof packaged within a equine capsid. |
| 1 | primate AAV | | ARSB | 411 | Payload comprising a ARSB gene or variant thereof packaged within a primate capsid. |
| 1 | non-primate AAV | | ARSB | 411 | Payload comprising a ARSB gene or variant thereof packaged within a non-primate capsid. |
| 1 | ovine AAV | | ARSB | 411 | Payload comprising a ARSB gene or variant thereof packaged within a ovine capsid. |
| 1 | hybrid AAV | | ARSB | 411 | Payload comprising a ARSB gene or variant thereof packaged within a hybrid capsid. |
| 1 | chimeric AAV | | ARSB | 411 | Payload comprising a ARSB gene or variant thereof packaged within a chimeric capsid. |
| 2 | AAV1 | 1450374 | ARSB | 411 | Payload comprising a ARSB gene or variant thereof packaged within a AAV1 capsid. |
| 2 | AAV2 | | ARSB | 411 | Payload comprising a ARSB gene or variant thereof packaged within a AAV2 capsid. |
| 2 | AAV3 | | ARSB | 411 | Payload comprising a ARSB gene or variant thereof packaged within a AAV3 capsid. |
| 2 | AAV4 | 1446389 | ARSB | 411 | Payload comprising a ARSB gene or variant thereof packaged within a AAV4 capsid. |
| 2 | AAV5 | | ARSB | 411 | Payload comprising a ARSB gene or variant thereof packaged within a AAV5 capsid. |
| 2 | AAV6 | | ARSB | 411 | Payload comprising a ARSB gene or variant thereof packaged within a AAV6 capsid. |
| 2 | AAV7 | | ARSB | 411 | Payload comprising a ARSB gene or variant thereof packaged within a AAV7 capsid. |
| 2 | AAV8 | 5075992 | ARSB | 411 | Payload comprising a ARSB gene or variant thereof packaged within a AAV8 capsid. |
| 2 | AAV9 | | ARSB | 411 | Payload comprising a ARSB gene or variant thereof packaged within a AAV9 capsid. |

Fig. 29 (Continued)

| | | | | | |
|---|---|---|---|---|---|
| 2 | AAV10 | | ARSB | 411 | Payload comprising a ARSB gene or variant thereof packaged within a AAV10 capsid. |
| 2 | AAV11 | | ARSB | 411 | Payload comprising a ARSB gene or variant thereof packaged within a AAV11 capsid. |
| 2 | AAVC11.01 | | ARSB | 411 | Payload comprising a ARSB gene or variant thereof packaged within a AAVC11.01 capsid. |
| 2 | AAVC11.02 | | ARSB | 411 | Payload comprising a ARSB gene or variant thereof packaged within a AAVC11.02 capsid. |
| 2 | AAVC11.03 | | ARSB | 411 | Payload comprising a ARSB gene or variant thereof packaged within a AAVC11.03 capsid. |
| 2 | AAVC11.04 | | ARSB | 411 | Payload comprising a ARSB gene or variant thereof packaged within a AAVC11.04 capsid. |
| 2 | AAVC11.05 | | ARSB | 411 | Payload comprising a ARSB gene or variant thereof packaged within a AAVC11.05 capsid. |
| 2 | AAVC11.06 | | ARSB | 411 | Payload comprising a ARSB gene or variant thereof packaged within a AAVC11.06 capsid. |
| 2 | AAVC11.07 | | ARSB | 411 | Payload comprising a ARSB gene or variant thereof packaged within a AAVC11.07 capsid. |
| 2 | AAVC11.08 | | ARSB | 411 | Payload comprising a ARSB gene or variant thereof packaged within a AAVC11.08 capsid. |
| 2 | AAVC11.09 | | ARSB | 411 | Payload comprising a ARSB gene or variant thereof packaged within a AAVC11.09 capsid. |
| 2 | AAVC11.10 | | ARSB | 411 | Payload comprising a ARSB gene or variant thereof packaged within a AAVC11.10 capsid. |
| 2 | AAVC11.11 | | ARSB | 411 | Payload comprising a ARSB gene or variant thereof packaged within a AAVC11.11 capsid. |
| 2 | AAVC11.12 | | ARSB | 411 | Payload comprising a ARSB gene or variant thereof packaged within a AAVC11.12 capsid. |
| 2 | AAVC11.13 | | ARSB | 411 | Payload comprising a ARSB gene or variant thereof packaged within a AAVC11.13 capsid. |
| 2 | AAVC11.14 | | ARSB | 411 | Payload comprising a ARSB gene or variant thereof packaged within a AAVC11.14 capsid. |
| 2 | AAVC11.15 | | ARSB | 411 | Payload comprising a ARSB gene or variant thereof packaged within a AAVC11.15 capsid. |

Fig. 29 (Continued)

| | | | | | |
|---|---|---|---|---|---|
| 2 | AAVC11.16 | | ARSB | 411 | Payload comprising a ARSB gene or variant thereof packaged within a AAVC11.16 capsid. |
| 2 | AAVC11.17 | | ARSB | 411 | Payload comprising a ARSB gene or variant thereof packaged within a AAVC11.17 capsid. |
| 2 | AAVC11.18 | | ARSB | 411 | Payload comprising a ARSB gene or variant thereof packaged within a AAVC11.18 capsid. |
| 2 | AAVC11.19 | | ARSB | 411 | Payload comprising a ARSB gene or variant thereof packaged within a AAVC11.19 capsid. |
| 2 | AAV12 | | ARSB | 411 | Payload comprising a ARSB gene or variant thereof packaged within a AAV12 capsid. |
| 2 | AAV13 | | ARSB | 411 | Payload comprising a ARSB gene or variant thereof packaged within a AAV13 capsid. |
| 2 | AAV-DJ | | ARSB | 411 | Payload comprising a ARSB gene or variant thereof packaged within a AAV-DJ capsid. |
| 2 | AAV-LK03 | | ARSB | 411 | Payload comprising a ARSB gene or variant thereof packaged within a AAV-LK03 capsid. |
| 2 | AAV-LK19 | | ARSB | 411 | Payload comprising a ARSB gene or variant thereof packaged within a AAV-LK19 capsid. |
| 2 | AAVrh.74 | | ARSB | 411 | Payload comprising a ARSB gene or variant thereof packaged within a AAVrh.74 capsid. |
| 2 | AAVrh.10 | | ARSB | 411 | Payload comprising a ARSB gene or variant thereof packaged within a AAVrh.10 capsid. |
| 2 | AAVhu.37 | | ARSB | 411 | Payload comprising a ARSB gene or variant thereof packaged within a AAVhu.37 capsid. |
| 2 | AAVrh.K | | ARSB | 411 | Payload comprising a ARSB gene or variant thereof packaged within a AAVrh.K capsid. |
| 2 | AAVrh.39 | | ARSB | 411 | Payload comprising a ARSB gene or variant thereof packaged within a AAVrh.39 capsid. |
| 2 | AAVrh.9 | | ARSB | 411 | Payload comprising a ARSB gene or variant thereof packaged within a AAVrh.9 capsid. |
| 2 | avian AAV | | ARSB | 411 | Payload comprising a ARSB gene or variant thereof packaged within a avian capsid. |

Fig. 29 (Continued)

| | | | | | |
|---|---|---|---|---|---|
| 2 | bovine AAV | | ARSB | 411 | Payload comprising a ARSB gene or variant thereof packaged within a bovine capsid. |
| 2 | canine AAV | | ARSB | 411 | Payload comprising a ARSB gene or variant thereof packaged within a canine capsid. |
| 2 | equine AAV | | ARSB | 411 | Payload comprising a ARSB gene or variant thereof packaged within a equine capsid. |
| 2 | primate AAV | | ARSB | 411 | Payload comprising a ARSB gene or variant thereof packaged within a primate capsid. |
| 2 | non-primate AAV | | ARSB | 411 | Payload comprising a ARSB gene or variant thereof packaged within a non-primate capsid. |
| 2 | ovine AAV | | ARSB | 411 | Payload comprising a ARSB gene or variant thereof packaged within a ovine capsid. |
| 2 | hybrid AAV | | ARSB | 411 | Payload comprising a ARSB gene or variant thereof packaged within a hybrid capsid. |
| 2 | chimeric AAV | | ARSB | 411 | Payload comprising a ARSB gene or variant thereof packaged within a chimeric capsid. |
| 1 | AAV1 | 1450374 | ARSB | 411 | Payload comprising a ASL gene or variant thereof packaged within a AAV1 capsid. |
| 1 | AAV2 | | ARSB | 411 | Payload comprising a ASL gene or variant thereof packaged within a AAV2 capsid. |
| 1 | AAV3 | | ARSB | 411 | Payload comprising a ASL gene or variant thereof packaged within a AAV3 capsid. |
| 1 | AAV4 | 1446389 | ARSB | 411 | Payload comprising a ASL gene or variant thereof packaged within a AAV4 capsid. |
| 1 | AAV5 | | ARSB | 411 | Payload comprising a ASL gene or variant thereof packaged within a AAV5 capsid. |
| 1 | AAV6 | | ARSB | 411 | Payload comprising a ASL gene or variant thereof packaged within a AAV6 capsid. |
| 1 | AAV7 | | ARSB | 411 | Payload comprising a ASL gene or variant thereof packaged within a AAV7 capsid. |
| 1 | AAV8 | 5075992 | ARSB | 411 | Payload comprising a ASL gene or variant thereof packaged within a AAV8 capsid. |
| 1 | AAV9 | | ARSB | 411 | Payload comprising a ASL gene or variant thereof packaged within a AAV9 capsid. |

Fig. 29 (Continued)

| | | | | | |
|---|---|---|---|---|---|
| 1 | AAV10 | | ARSB | 411 | Payload comprising a ASL gene or variant thereof packaged within a AAV10 capsid. |
| 1 | AAV11 | | ARSB | 411 | Payload comprising a ASL gene or variant thereof packaged within a AAV11 capsid. |
| 1 | AAVC11.01 | | ARSB | 411 | Payload comprising a ASL gene or variant thereof packaged within a AAVC11.01 capsid. |
| 1 | AAVC11.02 | | ARSB | 411 | Payload comprising a ASL gene or variant thereof packaged within a AAVC11.02 capsid. |
| 1 | AAVC11.03 | | ARSB | 411 | Payload comprising a ASL gene or variant thereof packaged within a AAVC11.03 capsid. |
| 1 | AAVC11.04 | | ARSB | 411 | Payload comprising a ASL gene or variant thereof packaged within a AAVC11.04 capsid. |
| 1 | AAVC11.05 | | ARSB | 411 | Payload comprising a ASL gene or variant thereof packaged within a AAVC11.05 capsid. |
| 1 | AAVC11.06 | | ARSB | 411 | Payload comprising a ASL gene or variant thereof packaged within a AAVC11.06 capsid. |
| 1 | AAVC11.07 | | ARSB | 411 | Payload comprising a ASL gene or variant thereof packaged within a AAVC11.07 capsid. |
| 1 | AAVC11.08 | | ARSB | 411 | Payload comprising a ASL gene or variant thereof packaged within a AAVC11.08 capsid. |
| 1 | AAVC11.09 | | ARSB | 411 | Payload comprising a ASL gene or variant thereof packaged within a AAVC11.09 capsid. |
| 1 | AAVC11.10 | | ARSB | 411 | Payload comprising a ASL gene or variant thereof packaged within a AAVC11.10 capsid. |
| 1 | AAVC11.11 | | ARSB | 411 | Payload comprising a ASL gene or variant thereof packaged within a AAVC11.11 capsid. |
| 1 | AAVC11.12 | | ARSB | 411 | Payload comprising a ASL gene or variant thereof packaged within a AAVC11.12 capsid. |
| 1 | AAVC11.13 | | ARSB | 411 | Payload comprising a ASL gene or variant thereof packaged within a AAVC11.13 capsid. |
| 1 | AAVC11.14 | | ARSB | 411 | Payload comprising a ASL gene or variant thereof packaged within a AAVC11.14 capsid. |
| 1 | AAVC11.15 | | ARSB | 411 | Payload comprising a ASL gene or variant thereof packaged within a AAVC11.15 capsid. |

Fig. 29 (Continued)

| | | | | | |
|---|---|---|---|---|---|
| 1 | AAVC11.16 | | ARSB | 411 | Payload comprising a ASL gene or variant thereof packaged within a AAVC11.16 capsid. |
| 1 | AAVC11.17 | | ARSB | 411 | Payload comprising a ASL gene or variant thereof packaged within a AAVC11.17 capsid. |
| 1 | AAVC11.18 | | ARSB | 411 | Payload comprising a ASL gene or variant thereof packaged within a AAVC11.18 capsid. |
| 1 | AAVC11.19 | | ARSB | 411 | Payload comprising a ASL gene or variant thereof packaged within a AAVC11.19 capsid. |
| 1 | AAV12 | | ARSB | 411 | Payload comprising a ASL gene or variant thereof packaged within a AAV12 capsid. |
| 1 | AAV13 | | ARSB | 411 | Payload comprising a ASL gene or variant thereof packaged within a AAV13 capsid. |
| 1 | AAV-DJ | | ARSB | 411 | Payload comprising a ASL gene or variant thereof packaged within a AAV-DJ capsid. |
| 1 | AAV-LK03 | | ARSB | 411 | Payload comprising a ASL gene or variant thereof packaged within a AAV-LK03 capsid. |
| 1 | AAV-LK19 | | ARSB | 411 | Payload comprising a ASL gene or variant thereof packaged within a AAV-LK19 capsid. |
| 1 | AAVrh.74 | | ARSB | 411 | Payload comprising a ASL gene or variant thereof packaged within a AAVrh.74 capsid. |
| 1 | AAVrh.10 | | ARSB | 411 | Payload comprising a ASL gene or variant thereof packaged within a AAVrh.10 capsid. |
| 1 | AAVhu.37 | | ARSB | 411 | Payload comprising a ASL gene or variant thereof packaged within a AAVhu.37 capsid. |
| 1 | AAVrh.K | | ARSB | 411 | Payload comprising a ASL gene or variant thereof packaged within a AAVrh.K capsid. |
| 1 | AAVrh.39 | | ARSB | 411 | Payload comprising a ASL gene or variant thereof packaged within a AAVrh.39 capsid. |
| 1 | AAVrh.9 | | ARSB | 411 | Payload comprising a ASL gene or variant thereof packaged within a AAVrh.9 capsid. |
| 1 | avian AAV | | ARSB | 411 | Payload comprising a ASL gene or variant thereof packaged within a avian capsid. |

Fig. 29 (Continued)

| | | | | | |
|---|---|---|---|---|---|
| 1 | bovine AAV | | ARSB | 411 | Payload comprising a ASL gene or variant thereof packaged within a bovine capsid. |
| 1 | canine AAV | | ARSB | 411 | Payload comprising a ASL gene or variant thereof packaged within a canine capsid. |
| 1 | equine AAV | | ARSB | 411 | Payload comprising a ASL gene or variant thereof packaged within a equine capsid. |
| 1 | primate AAV | | ARSB | 411 | Payload comprising a ASL gene or variant thereof packaged within a primate capsid. |
| 1 | non-primate AAV | | ARSB | 411 | Payload comprising a ASL gene or variant thereof packaged within a non-primate capsid. |
| 1 | ovine AAV | | ARSB | 411 | Payload comprising a ASL gene or variant thereof packaged within a ovine capsid. |
| 1 | hybrid AAV | | ARSB | 411 | Payload comprising a ASL gene or variant thereof packaged within a hybrid capsid. |
| 1 | chimeric AAV | | ARSB | 411 | Payload comprising a ASL gene or variant thereof packaged within a chimeric capsid. |
| 2 | AAV1 | 1450374 | ARSB | 411 | Payload comprising a ASL gene or variant thereof packaged within a AAV1 capsid. |
| 2 | AAV2 | | ARSB | 411 | Payload comprising a ASL gene or variant thereof packaged within a AAV2 capsid. |
| 2 | AAV3 | | ARSB | 411 | Payload comprising a ASL gene or variant thereof packaged within a AAV3 capsid. |
| 2 | AAV4 | 1446389 | ARSB | 411 | Payload comprising a ASL gene or variant thereof packaged within a AAV4 capsid. |
| 2 | AAV5 | | ARSB | 411 | Payload comprising a ASL gene or variant thereof packaged within a AAV5 capsid. |
| 2 | AAV6 | | ARSB | 411 | Payload comprising a ASL gene or variant thereof packaged within a AAV6 capsid. |
| 2 | AAV7 | | ARSB | 411 | Payload comprising a ASL gene or variant thereof packaged within a AAV7 capsid. |
| 2 | AAV8 | 5075992 | ARSB | 411 | Payload comprising a ASL gene or variant thereof packaged within a AAV8 capsid. |
| 2 | AAV9 | | ARSB | 411 | Payload comprising a ASL gene or variant thereof packaged within a AAV9 capsid. |

Fig. 29 (Continued)

| | | | | | |
|---|---|---|---|---|---|
| 2 | AAV10 | | ARSB | 411 | Payload comprising a ASL gene or variant thereof packaged within a AAV10 capsid. |
| 2 | AAV11 | | ARSB | 411 | Payload comprising a ASL gene or variant thereof packaged within a AAV11 capsid. |
| 2 | AAVC11.01 | | ARSB | 411 | Payload comprising a ASL gene or variant thereof packaged within a AAVC11.01 capsid. |
| 2 | AAVC11.02 | | ARSB | 411 | Payload comprising a ASL gene or variant thereof packaged within a AAVC11.02 capsid. |
| 2 | AAVC11.03 | | ARSB | 411 | Payload comprising a ASL gene or variant thereof packaged within a AAVC11.03 capsid. |
| 2 | AAVC11.04 | | ARSB | 411 | Payload comprising a ASL gene or variant thereof packaged within a AAVC11.04 capsid. |
| 2 | AAVC11.05 | | ARSB | 411 | Payload comprising a ASL gene or variant thereof packaged within a AAVC11.05 capsid. |
| 2 | AAVC11.06 | | ARSB | 411 | Payload comprising a ASL gene or variant thereof packaged within a AAVC11.06 capsid. |
| 2 | AAVC11.07 | | ARSB | 411 | Payload comprising a ASL gene or variant thereof packaged within a AAVC11.07 capsid. |
| 2 | AAVC11.08 | | ARSB | 411 | Payload comprising a ASL gene or variant thereof packaged within a AAVC11.08 capsid. |
| 2 | AAVC11.09 | | ARSB | 411 | Payload comprising a ASL gene or variant thereof packaged within a AAVC11.09 capsid. |
| 2 | AAVC11.10 | | ARSB | 411 | Payload comprising a ASL gene or variant thereof packaged within a AAVC11.10 capsid. |
| 2 | AAVC11.11 | | ARSB | 411 | Payload comprising a ASL gene or variant thereof packaged within a AAVC11.11 capsid. |
| 2 | AAVC11.12 | | ARSB | 411 | Payload comprising a ASL gene or variant thereof packaged within a AAVC11.12 capsid. |
| 2 | AAVC11.13 | | ARSB | 411 | Payload comprising a ASL gene or variant thereof packaged within a AAVC11.13 capsid. |
| 2 | AAVC11.14 | | ARSB | 411 | Payload comprising a ASL gene or variant thereof packaged within a AAVC11.14 capsid. |
| 2 | AAVC11.15 | | ARSB | 411 | Payload comprising a ASL gene or variant thereof packaged within a AAVC11.15 capsid. |

Fig. 29 (Continued)

| | | | | | |
|---|---|---|---|---|---|
| 2 | AAVC11.16 | | ARSB | 411 | Payload comprising a ASL gene or variant thereof packaged within a AAVC11.16 capsid. |
| 2 | AAVC11.17 | | ARSB | 411 | Payload comprising a ASL gene or variant thereof packaged within a AAVC11.17 capsid. |
| 2 | AAVC11.18 | | ARSB | 411 | Payload comprising a ASL gene or variant thereof packaged within a AAVC11.18 capsid. |
| 2 | AAVC11.19 | | ARSB | 411 | Payload comprising a ASL gene or variant thereof packaged within a AAVC11.19 capsid. |
| 2 | AAV12 | | ARSB | 411 | Payload comprising a ASL gene or variant thereof packaged within a AAV12 capsid. |
| 2 | AAV13 | | ARSB | 411 | Payload comprising a ASL gene or variant thereof packaged within a AAV13 capsid. |
| 2 | AAV-DJ | | ARSB | 411 | Payload comprising a ASL gene or variant thereof packaged within a AAV-DJ capsid. |
| 2 | AAV-LK03 | | ARSB | 411 | Payload comprising a ASL gene or variant thereof packaged within a AAV-LK03 capsid. |
| 2 | AAV-LK19 | | ARSB | 411 | Payload comprising a ASL gene or variant thereof packaged within a AAV-LK19 capsid. |
| 2 | AAVrh.74 | | ARSB | 411 | Payload comprising a ASL gene or variant thereof packaged within a AAVrh.74 capsid. |
| 2 | AAVrh.10 | | ARSB | 411 | Payload comprising a ASL gene or variant thereof packaged within a AAVrh.10 capsid. |
| 2 | AAVhu.37 | | ARSB | 411 | Payload comprising a ASL gene or variant thereof packaged within a AAVhu.37 capsid. |
| 2 | AAVrh.K | | ARSB | 411 | Payload comprising a ASL gene or variant thereof packaged within a AAVrh.K capsid. |
| 2 | AAVrh.39 | | ARSB | 411 | Payload comprising a ASL gene or variant thereof packaged within a AAVrh.39 capsid. |
| 2 | AAVrh.9 | | ARSB | 411 | Payload comprising a ASL gene or variant thereof packaged within a AAVrh.9 capsid. |
| 2 | avian AAV | | ARSB | 411 | Payload comprising a ASL gene or variant thereof packaged within a avian capsid. |

Fig. 29 (Continued)

| | | | | | |
|---|---|---|---|---|---|
| 2 | bovine AAV | | ARSB | 411 | Payload comprising a ASL gene or variant thereof packaged within a bovine capsid. |
| 2 | canine AAV | | ARSB | 411 | Payload comprising a ASL gene or variant thereof packaged within a canine capsid. |
| 2 | equine AAV | | ARSB | 411 | Payload comprising a ASL gene or variant thereof packaged within a equine capsid. |
| 2 | primate AAV | | ARSB | 411 | Payload comprising a ASL gene or variant thereof packaged within a primate capsid. |
| 2 | non-primate AAV | | ARSB | 411 | Payload comprising a ASL gene or variant thereof packaged within a non-primate capsid. |
| 2 | ovine AAV | | ARSB | 411 | Payload comprising a ASL gene or variant thereof packaged within a ovine capsid. |
| 2 | hybrid AAV | | ARSB | 411 | Payload comprising a ASL gene or variant thereof packaged within a hybrid capsid. |
| 2 | chimeric AAV | | ARSB | 411 | Payload comprising a ASL gene or variant thereof packaged within a chimeric capsid. |
| 1 | AAV1 | 1450374 | ATP7B | 540 | Payload comprising a ATP7B gene or variant thereof packaged within a AAV1 capsid. |
| 1 | AAV2 | | ATP7B | 540 | Payload comprising a ATP7B gene or variant thereof packaged within a AAV2 capsid. |
| 1 | AAV3 | | ATP7B | 540 | Payload comprising a ATP7B gene or variant thereof packaged within a AAV3 capsid. |
| 1 | AAV4 | 1446389 | ATP7B | 540 | Payload comprising a ATP7B gene or variant thereof packaged within a AAV4 capsid. |
| 1 | AAV5 | | ATP7B | 540 | Payload comprising a ATP7B gene or variant thereof packaged within a AAV5 capsid. |
| 1 | AAV6 | | ATP7B | 540 | Payload comprising a ATP7B gene or variant thereof packaged within a AAV6 capsid. |
| 1 | AAV7 | | ATP7B | 540 | Payload comprising a ATP7B gene or variant thereof packaged within a AAV7 capsid. |
| 1 | AAV8 | 5075992 | ATP7B | 540 | Payload comprising a ATP7B gene or variant thereof packaged within a AAV8 capsid. |
| 1 | AAV9 | | ATP7B | 540 | Payload comprising a ATP7B gene or variant thereof packaged within a AAV9 capsid. |

Fig. 29 (Continued)

| | | | | | |
|---|---|---|---|---|---|
| 1 | AAV10 | | ATP7B | 540 | Payload comprising a ATP7B gene or variant thereof packaged within a AAV10 capsid. |
| 1 | AAV11 | | ATP7B | 540 | Payload comprising a ATP7B gene or variant thereof packaged within a AAV11 capsid. |
| 1 | AAVC11.01 | | ATP7B | 540 | Payload comprising a ATP7B gene or variant thereof packaged within a AAVC11.01 capsid. |
| 1 | AAVC11.02 | | ATP7B | 540 | Payload comprising a ATP7B gene or variant thereof packaged within a AAVC11.02 capsid. |
| 1 | AAVC11.03 | | ATP7B | 540 | Payload comprising a ATP7B gene or variant thereof packaged within a AAVC11.03 capsid. |
| 1 | AAVC11.04 | | ATP7B | 540 | Payload comprising a ATP7B gene or variant thereof packaged within a AAVC11.04 capsid. |
| 1 | AAVC11.05 | | ATP7B | 540 | Payload comprising a ATP7B gene or variant thereof packaged within a AAVC11.05 capsid. |
| 1 | AAVC11.06 | | ATP7B | 540 | Payload comprising a ATP7B gene or variant thereof packaged within a AAVC11.06 capsid. |
| 1 | AAVC11.07 | | ATP7B | 540 | Payload comprising a ATP7B gene or variant thereof packaged within a AAVC11.07 capsid. |
| 1 | AAVC11.08 | | ATP7B | 540 | Payload comprising a ATP7B gene or variant thereof packaged within a AAVC11.08 capsid. |
| 1 | AAVC11.09 | | ATP7B | 540 | Payload comprising a ATP7B gene or variant thereof packaged within a AAVC11.09 capsid. |
| 1 | AAVC11.10 | | ATP7B | 540 | Payload comprising a ATP7B gene or variant thereof packaged within a AAVC11.10 capsid. |
| 1 | AAVC11.11 | | ATP7B | 540 | Payload comprising a ATP7B gene or variant thereof packaged within a AAVC11.11 capsid. |
| 1 | AAVC11.12 | | ATP7B | 540 | Payload comprising a ATP7B gene or variant thereof packaged within a AAVC11.12 capsid. |
| 1 | AAVC11.13 | | ATP7B | 540 | Payload comprising a ATP7B gene or variant thereof packaged within a AAVC11.13 capsid. |
| 1 | AAVC11.14 | | ATP7B | 540 | Payload comprising a ATP7B gene or variant thereof packaged within a AAVC11.14 capsid. |
| 1 | AAVC11.15 | | ATP7B | 540 | Payload comprising a ATP7B gene or variant thereof packaged within a AAVC11.15 capsid. |

Fig. 29 (Continued)

| | | | | | |
|---|---|---|---|---|---|
| 1 | AAVC11.16 | | ATP7B | 540 | Payload comprising a ATP7B gene or variant thereof packaged within a AAVC11.16 capsid. |
| 1 | AAVC11.17 | | ATP7B | 540 | Payload comprising a ATP7B gene or variant thereof packaged within a AAVC11.17 capsid. |
| 1 | AAVC11.18 | | ATP7B | 540 | Payload comprising a ATP7B gene or variant thereof packaged within a AAVC11.18 capsid. |
| 1 | AAVC11.19 | | ATP7B | 540 | Payload comprising a ATP7B gene or variant thereof packaged within a AAVC11.19 capsid. |
| 1 | AAV12 | | ATP7B | 540 | Payload comprising a ATP7B gene or variant thereof packaged within a AAV12 capsid. |
| 1 | AAV13 | | ATP7B | 540 | Payload comprising a ATP7B gene or variant thereof packaged within a AAV13 capsid. |
| 1 | AAV-DJ | | ATP7B | 540 | Payload comprising a ATP7B gene or variant thereof packaged within a AAV-DJ capsid. |
| 1 | AAV-LK03 | | ATP7B | 540 | Payload comprising a ATP7B gene or variant thereof packaged within a AAV-LK03 capsid. |
| 1 | AAV-LK19 | | ATP7B | 540 | Payload comprising a ATP7B gene or variant thereof packaged within a AAV-LK19 capsid. |
| 1 | AAVrh.74 | | ATP7B | 540 | Payload comprising a ATP7B gene or variant thereof packaged within a AAVrh.74 capsid. |
| 1 | AAVrh.10 | | ATP7B | 540 | Payload comprising a ATP7B gene or variant thereof packaged within a AAVrh.10 capsid. |
| 1 | AAVhu.37 | | ATP7B | 540 | Payload comprising a ATP7B gene or variant thereof packaged within a AAVhu.37 capsid. |
| 1 | AAVrh.K | | ATP7B | 540 | Payload comprising a ATP7B gene or variant thereof packaged within a AAVrh.K capsid. |
| 1 | AAVrh.39 | | ATP7B | 540 | Payload comprising a ATP7B gene or variant thereof packaged within a AAVrh.39 capsid. |
| 1 | AAVrh.9 | | ATP7B | 540 | Payload comprising a ATP7B gene or variant thereof packaged within a AAVrh.9 capsid. |
| 1 | avian AAV | | ATP7B | 540 | Payload comprising a ATP7B gene or variant thereof packaged within a avian capsid. |

Fig. 29 (Continued)

| | | | | | |
|---|---|---|---|---|---|
| 1 | bovine AAV | | ATP7B | 540 | Payload comprising a ATP7B gene or variant thereof packaged within a bovine capsid. |
| 1 | canine AAV | | ATP7B | 540 | Payload comprising a ATP7B gene or variant thereof packaged within a canine capsid. |
| 1 | equine AAV | | ATP7B | 540 | Payload comprising a ATP7B gene or variant thereof packaged within a equine capsid. |
| 1 | primate AAV | | ATP7B | 540 | Payload comprising a ATP7B gene or variant thereof packaged within a primate capsid. |
| 1 | non-primate AAV | | ATP7B | 540 | Payload comprising a ATP7B gene or variant thereof packaged within a non-primate capsid. |
| 1 | ovine AAV | | ATP7B | 540 | Payload comprising a ATP7B gene or variant thereof packaged within a ovine capsid. |
| 1 | hybrid AAV | | ATP7B | 540 | Payload comprising a ATP7B gene or variant thereof packaged within a hybrid capsid. |
| 1 | chimeric AAV | | ATP7B | 540 | Payload comprising a ATP7B gene or variant thereof packaged within a chimeric capsid. |
| 2 | AAV1 | 1450374 | ATP7B | 540 | Payload comprising a ATP7B gene or variant thereof packaged within a AAV1 capsid. |
| 2 | AAV2 | | ATP7B | 540 | Payload comprising a ATP7B gene or variant thereof packaged within a AAV2 capsid. |
| 2 | AAV3 | | ATP7B | 540 | Payload comprising a ATP7B gene or variant thereof packaged within a AAV3 capsid. |
| 2 | AAV4 | 1446389 | ATP7B | 540 | Payload comprising a ATP7B gene or variant thereof packaged within a AAV4 capsid. |
| 2 | AAV5 | | ATP7B | 540 | Payload comprising a ATP7B gene or variant thereof packaged within a AAV5 capsid. |
| 2 | AAV6 | | ATP7B | 540 | Payload comprising a ATP7B gene or variant thereof packaged within a AAV6 capsid. |
| 2 | AAV7 | | ATP7B | 540 | Payload comprising a ATP7B gene or variant thereof packaged within a AAV7 capsid. |
| 2 | AAV8 | 5075992 | ATP7B | 540 | Payload comprising a ATP7B gene or variant thereof packaged within a AAV8 capsid. |
| 2 | AAV9 | | ATP7B | 540 | Payload comprising a ATP7B gene or variant thereof packaged within a AAV9 capsid. |

Fig. 29 (Continued)

| | | | | | |
|---|---|---|---|---|---|
| 2 | AAV10 | | ATP7B | 540 | Payload comprising a ATP7B gene or variant thereof packaged within a AAV10 capsid. |
| 2 | AAV11 | | ATP7B | 540 | Payload comprising a ATP7B gene or variant thereof packaged within a AAV11 capsid. |
| 2 | AAVC11.01 | | ATP7B | 540 | Payload comprising a ATP7B gene or variant thereof packaged within a AAVC11.01 capsid. |
| 2 | AAVC11.02 | | ATP7B | 540 | Payload comprising a ATP7B gene or variant thereof packaged within a AAVC11.02 capsid. |
| 2 | AAVC11.03 | | ATP7B | 540 | Payload comprising a ATP7B gene or variant thereof packaged within a AAVC11.03 capsid. |
| 2 | AAVC11.04 | | ATP7B | 540 | Payload comprising a ATP7B gene or variant thereof packaged within a AAVC11.04 capsid. |
| 2 | AAVC11.05 | | ATP7B | 540 | Payload comprising a ATP7B gene or variant thereof packaged within a AAVC11.05 capsid. |
| 2 | AAVC11.06 | | ATP7B | 540 | Payload comprising a ATP7B gene or variant thereof packaged within a AAVC11.06 capsid. |
| 2 | AAVC11.07 | | ATP7B | 540 | Payload comprising a ATP7B gene or variant thereof packaged within a AAVC11.07 capsid. |
| 2 | AAVC11.08 | | ATP7B | 540 | Payload comprising a ATP7B gene or variant thereof packaged within a AAVC11.08 capsid. |
| 2 | AAVC11.09 | | ATP7B | 540 | Payload comprising a ATP7B gene or variant thereof packaged within a AAVC11.09 capsid. |
| 2 | AAVC11.10 | | ATP7B | 540 | Payload comprising a ATP7B gene or variant thereof packaged within a AAVC11.10 capsid. |
| 2 | AAVC11.11 | | ATP7B | 540 | Payload comprising a ATP7B gene or variant thereof packaged within a AAVC11.11 capsid. |
| 2 | AAVC11.12 | | ATP7B | 540 | Payload comprising a ATP7B gene or variant thereof packaged within a AAVC11.12 capsid. |
| 2 | AAVC11.13 | | ATP7B | 540 | Payload comprising a ATP7B gene or variant thereof packaged within a AAVC11.13 capsid. |
| 2 | AAVC11.14 | | ATP7B | 540 | Payload comprising a ATP7B gene or variant thereof packaged within a AAVC11.14 capsid. |
| 2 | AAVC11.15 | | ATP7B | 540 | Payload comprising a ATP7B gene or variant thereof packaged within a AAVC11.15 capsid. |

Fig. 29 (Continued)

| | | | | | |
|---|---|---|---|---|---|
| 2 | AAVC11.16 | | ATP7B | 540 | Payload comprising a ATP7B gene or variant thereof packaged within a AAVC11.16 capsid. |
| 2 | AAVC11.17 | | ATP7B | 540 | Payload comprising a ATP7B gene or variant thereof packaged within a AAVC11.17 capsid. |
| 2 | AAVC11.18 | | ATP7B | 540 | Payload comprising a ATP7B gene or variant thereof packaged within a AAVC11.18 capsid. |
| 2 | AAVC11.19 | | ATP7B | 540 | Payload comprising a ATP7B gene or variant thereof packaged within a AAVC11.19 capsid. |
| 2 | AAV12 | | ATP7B | 540 | Payload comprising a ATP7B gene or variant thereof packaged within a AAV12 capsid. |
| 2 | AAV13 | | ATP7B | 540 | Payload comprising a ATP7B gene or variant thereof packaged within a AAV13 capsid. |
| 2 | AAV-DJ | | ATP7B | 540 | Payload comprising a ATP7B gene or variant thereof packaged within a AAV-DJ capsid. |
| 2 | AAV-LK03 | | ATP7B | 540 | Payload comprising a ATP7B gene or variant thereof packaged within a AAV-LK03 capsid. |
| 2 | AAV-LK19 | | ATP7B | 540 | Payload comprising a ATP7B gene or variant thereof packaged within a AAV-LK19 capsid. |
| 2 | AAVrh.74 | | ATP7B | 540 | Payload comprising a ATP7B gene or variant thereof packaged within a AAVrh.74 capsid. |
| 2 | AAVrh.10 | | ATP7B | 540 | Payload comprising a ATP7B gene or variant thereof packaged within a AAVrh.10 capsid. |
| 2 | AAVhu.37 | | ATP7B | 540 | Payload comprising a ATP7B gene or variant thereof packaged within a AAVhu.37 capsid. |
| 2 | AAVrh.K | | ATP7B | 540 | Payload comprising a ATP7B gene or variant thereof packaged within a AAVrh.K capsid. |
| 2 | AAVrh.39 | | ATP7B | 540 | Payload comprising a ATP7B gene or variant thereof packaged within a AAVrh.39 capsid. |
| 2 | AAVrh.9 | | ATP7B | 540 | Payload comprising a ATP7B gene or variant thereof packaged within a AAVrh.9 capsid. |
| 2 | avian AAV | | ATP7B | 540 | Payload comprising a ATP7B gene or variant thereof packaged within a avian capsid. |

Fig. 29 (Continued)

| | | | | | |
|---|---|---|---|---|---|
| 2 | bovine AAV | | ATP7B | 540 | Payload comprising a ATP7B gene or variant thereof packaged within a bovine capsid. |
| 2 | canine AAV | | ATP7B | 540 | Payload comprising a ATP7B gene or variant thereof packaged within a canine capsid. |
| 2 | equine AAV | | ATP7B | 540 | Payload comprising a ATP7B gene or variant thereof packaged within a equine capsid. |
| 2 | primate AAV | | ATP7B | 540 | Payload comprising a ATP7B gene or variant thereof packaged within a primate capsid. |
| 2 | non-primate AAV | | ATP7B | 540 | Payload comprising a ATP7B gene or variant thereof packaged within a non-primate capsid. |
| 2 | ovine AAV | | ATP7B | 540 | Payload comprising a ATP7B gene or variant thereof packaged within a ovine capsid. |
| 2 | hybrid AAV | | ATP7B | 540 | Payload comprising a ATP7B gene or variant thereof packaged within a hybrid capsid. |
| 2 | chimeric AAV | | ATP7B | 540 | Payload comprising a ATP7B gene or variant thereof packaged within a chimeric capsid. |
| 1 | AAV1 | 1450374 | BCKDA | 593 | Payload comprising a BCKDA gene or variant thereof packaged within a AAV1 capsid. |
| 1 | AAV2 | | BCKDA | 593 | Payload comprising a BCKDA gene or variant thereof packaged within a AAV2 capsid. |
| 1 | AAV3 | | BCKDA | 593 | Payload comprising a BCKDA gene or variant thereof packaged within a AAV3 capsid. |
| 1 | AAV4 | 1446389 | BCKDA | 593 | Payload comprising a BCKDA gene or variant thereof packaged within a AAV4 capsid. |
| 1 | AAV5 | | BCKDA | 593 | Payload comprising a BCKDA gene or variant thereof packaged within a AAV5 capsid. |
| 1 | AAV6 | | BCKDA | 593 | Payload comprising a BCKDA gene or variant thereof packaged within a AAV6 capsid. |
| 1 | AAV7 | | BCKDA | 593 | Payload comprising a BCKDA gene or variant thereof packaged within a AAV7 capsid. |
| 1 | AAV8 | 5075992 | BCKDA | 593 | Payload comprising a BCKDA gene or variant thereof packaged within a AAV8 capsid. |
| 1 | AAV9 | | BCKDA | 593 | Payload comprising a BCKDA gene or variant thereof packaged within a AAV9 capsid. |

Fig. 29 (Continued)

| | | | | | |
|---|---|---|---|---|---|
| 1 | AAV10 | | BCKDA | 593 | Payload comprising a BCKDA gene or variant thereof packaged within a AAV10 capsid. |
| 1 | AAV11 | | BCKDA | 593 | Payload comprising a BCKDA gene or variant thereof packaged within a AAV11 capsid. |
| 1 | AAVC11.01 | | BCKDA | 593 | Payload comprising a BCKDA gene or variant thereof packaged within a AAVC11.01 capsid. |
| 1 | AAVC11.02 | | BCKDA | 593 | Payload comprising a BCKDA gene or variant thereof packaged within a AAVC11.02 capsid. |
| 1 | AAVC11.03 | | BCKDA | 593 | Payload comprising a BCKDA gene or variant thereof packaged within a AAVC11.03 capsid. |
| 1 | AAVC11.04 | | BCKDA | 593 | Payload comprising a BCKDA gene or variant thereof packaged within a AAVC11.04 capsid. |
| 1 | AAVC11.05 | | BCKDA | 593 | Payload comprising a BCKDA gene or variant thereof packaged within a AAVC11.05 capsid. |
| 1 | AAVC11.06 | | BCKDA | 593 | Payload comprising a BCKDA gene or variant thereof packaged within a AAVC11.06 capsid. |
| 1 | AAVC11.07 | | BCKDA | 593 | Payload comprising a BCKDA gene or variant thereof packaged within a AAVC11.07 capsid. |
| 1 | AAVC11.08 | | BCKDA | 593 | Payload comprising a BCKDA gene or variant thereof packaged within a AAVC11.08 capsid. |
| 1 | AAVC11.09 | | BCKDA | 593 | Payload comprising a BCKDA gene or variant thereof packaged within a AAVC11.09 capsid. |
| 1 | AAVC11.10 | | BCKDA | 593 | Payload comprising a BCKDA gene or variant thereof packaged within a AAVC11.10 capsid. |
| 1 | AAVC11.11 | | BCKDA | 593 | Payload comprising a BCKDA gene or variant thereof packaged within a AAVC11.11 capsid. |
| 1 | AAVC11.12 | | BCKDA | 593 | Payload comprising a BCKDA gene or variant thereof packaged within a AAVC11.12 capsid. |
| 1 | AAVC11.13 | | BCKDA | 593 | Payload comprising a BCKDA gene or variant thereof packaged within a AAVC11.13 capsid. |
| 1 | AAVC11.14 | | BCKDA | 593 | Payload comprising a BCKDA gene or variant thereof packaged within a AAVC11.14 capsid. |
| 1 | AAVC11.15 | | BCKDA | 593 | Payload comprising a BCKDA gene or variant thereof packaged within a AAVC11.15 capsid. |

Fig. 29 (Continued)

| | | | | | |
|---|---|---|---|---|---|
| 1 | AAVC11.16 | | BCKDA | 593 | Payload comprising a BCKDA gene or variant thereof packaged within a AAVC11.16 capsid. |
| 1 | AAVC11.17 | | BCKDA | 593 | Payload comprising a BCKDA gene or variant thereof packaged within a AAVC11.17 capsid. |
| 1 | AAVC11.18 | | BCKDA | 593 | Payload comprising a BCKDA gene or variant thereof packaged within a AAVC11.18 capsid. |
| 1 | AAVC11.19 | | BCKDA | 593 | Payload comprising a BCKDA gene or variant thereof packaged within a AAVC11.19 capsid. |
| 1 | AAV12 | | BCKDA | 593 | Payload comprising a BCKDA gene or variant thereof packaged within a AAV12 capsid. |
| 1 | AAV13 | | BCKDA | 593 | Payload comprising a BCKDA gene or variant thereof packaged within a AAV13 capsid. |
| 1 | AAV-DJ | | BCKDA | 593 | Payload comprising a BCKDA gene or variant thereof packaged within a AAV-DJ capsid. |
| 1 | AAV-LK03 | | BCKDA | 593 | Payload comprising a BCKDA gene or variant thereof packaged within a AAV-LK03 capsid. |
| 1 | AAV-LK19 | | BCKDA | 593 | Payload comprising a BCKDA gene or variant thereof packaged within a AAV-LK19 capsid. |
| 1 | AAVrh.74 | | BCKDA | 593 | Payload comprising a BCKDA gene or variant thereof packaged within a AAVrh.74 capsid. |
| 1 | AAVrh.10 | | BCKDA | 593 | Payload comprising a BCKDA gene or variant thereof packaged within a AAVrh.10 capsid. |
| 1 | AAVhu.37 | | BCKDA | 593 | Payload comprising a BCKDA gene or variant thereof packaged within a AAVhu.37 capsid. |
| 1 | AAVrh.K | | BCKDA | 593 | Payload comprising a BCKDA gene or variant thereof packaged within a AAVrh.K capsid. |
| 1 | AAVrh.39 | | BCKDA | 593 | Payload comprising a BCKDA gene or variant thereof packaged within a AAVrh.39 capsid. |
| 1 | AAVrh.9 | | BCKDA | 593 | Payload comprising a BCKDA gene or variant thereof packaged within a AAVrh.9 capsid. |
| 1 | avian AAV | | BCKDA | 593 | Payload comprising a BCKDA gene or variant thereof packaged within a avian capsid. |

Fig. 29 (Continued)

| | | | | | |
|---|---|---|---|---|---|
| 1 | bovine AAV | | BCKDA | 593 | Payload comprising a BCKDA gene or variant thereof packaged within a bovine capsid. |
| 1 | canine AAV | | BCKDA | 593 | Payload comprising a BCKDA gene or variant thereof packaged within a canine capsid. |
| 1 | equine AAV | | BCKDA | 593 | Payload comprising a BCKDA gene or variant thereof packaged within a equine capsid. |
| 1 | primate AAV | | BCKDA | 593 | Payload comprising a BCKDA gene or variant thereof packaged within a primate capsid. |
| 1 | non-primate AAV | | BCKDA | 593 | Payload comprising a BCKDA gene or variant thereof packaged within a non-primate capsid. |
| 1 | ovine AAV | | BCKDA | 593 | Payload comprising a BCKDA gene or variant thereof packaged within a ovine capsid. |
| 1 | hybrid AAV | | BCKDA | 593 | Payload comprising a BCKDA gene or variant thereof packaged within a hybrid capsid. |
| 1 | chimeric AAV | | BCKDA | 593 | Payload comprising a BCKDA gene or variant thereof packaged within a chimeric capsid. |
| 2 | AAV1 | 1450374 | BCKDA | 593 | Payload comprising a BCKDA gene or variant thereof packaged within a AAV1 capsid. |
| 2 | AAV2 | | BCKDA | 593 | Payload comprising a BCKDA gene or variant thereof packaged within a AAV2 capsid. |
| 2 | AAV3 | | BCKDA | 593 | Payload comprising a BCKDA gene or variant thereof packaged within a AAV3 capsid. |
| 2 | AAV4 | 1446389 | BCKDA | 593 | Payload comprising a BCKDA gene or variant thereof packaged within a AAV4 capsid. |
| 2 | AAV5 | | BCKDA | 593 | Payload comprising a BCKDA gene or variant thereof packaged within a AAV5 capsid. |
| 2 | AAV6 | | BCKDA | 593 | Payload comprising a BCKDA gene or variant thereof packaged within a AAV6 capsid. |
| 2 | AAV7 | | BCKDA | 593 | Payload comprising a BCKDA gene or variant thereof packaged within a AAV7 capsid. |
| 2 | AAV8 | 5075992 | BCKDA | 593 | Payload comprising a BCKDA gene or variant thereof packaged within a AAV8 capsid. |
| 2 | AAV9 | | BCKDA | 593 | Payload comprising a BCKDA gene or variant thereof packaged within a AAV9 capsid. |

Fig. 29 (Continued)

| | | | | | |
|---|---|---|---|---|---|
| 2 | AAV10 | | BCKDA | 593 | Payload comprising a BCKDA gene or variant thereof packaged within a AAV10 capsid. |
| 2 | AAV11 | | BCKDA | 593 | Payload comprising a BCKDA gene or variant thereof packaged within a AAV11 capsid. |
| 2 | AAVC11.01 | | BCKDA | 593 | Payload comprising a BCKDA gene or variant thereof packaged within a AAVC11.01 capsid. |
| 2 | AAVC11.02 | | BCKDA | 593 | Payload comprising a BCKDA gene or variant thereof packaged within a AAVC11.02 capsid. |
| 2 | AAVC11.03 | | BCKDA | 593 | Payload comprising a BCKDA gene or variant thereof packaged within a AAVC11.03 capsid. |
| 2 | AAVC11.04 | | BCKDA | 593 | Payload comprising a BCKDA gene or variant thereof packaged within a AAVC11.04 capsid. |
| 2 | AAVC11.05 | | BCKDA | 593 | Payload comprising a BCKDA gene or variant thereof packaged within a AAVC11.05 capsid. |
| 2 | AAVC11.06 | | BCKDA | 593 | Payload comprising a BCKDA gene or variant thereof packaged within a AAVC11.06 capsid. |
| 2 | AAVC11.07 | | BCKDA | 593 | Payload comprising a BCKDA gene or variant thereof packaged within a AAVC11.07 capsid. |
| 2 | AAVC11.08 | | BCKDA | 593 | Payload comprising a BCKDA gene or variant thereof packaged within a AAVC11.08 capsid. |
| 2 | AAVC11.09 | | BCKDA | 593 | Payload comprising a BCKDA gene or variant thereof packaged within a AAVC11.09 capsid. |
| 2 | AAVC11.10 | | BCKDA | 593 | Payload comprising a BCKDA gene or variant thereof packaged within a AAVC11.10 capsid. |
| 2 | AAVC11.11 | | BCKDA | 593 | Payload comprising a BCKDA gene or variant thereof packaged within a AAVC11.11 capsid. |
| 2 | AAVC11.12 | | BCKDA | 593 | Payload comprising a BCKDA gene or variant thereof packaged within a AAVC11.12 capsid. |
| 2 | AAVC11.13 | | BCKDA | 593 | Payload comprising a BCKDA gene or variant thereof packaged within a AAVC11.13 capsid. |
| 2 | AAVC11.14 | | BCKDA | 593 | Payload comprising a BCKDA gene or variant thereof packaged within a AAVC11.14 capsid. |
| 2 | AAVC11.15 | | BCKDA | 593 | Payload comprising a BCKDA gene or variant thereof packaged within a AAVC11.15 capsid. |

Fig. 29 (Continued)

| | | | | | |
|---|---|---|---|---|---|
| 2 | AAVC11.16 | | BCKDA | 593 | Payload comprising a BCKDA gene or variant thereof packaged within a AAVC11.16 capsid. |
| 2 | AAVC11.17 | | BCKDA | 593 | Payload comprising a BCKDA gene or variant thereof packaged within a AAVC11.17 capsid. |
| 2 | AAVC11.18 | | BCKDA | 593 | Payload comprising a BCKDA gene or variant thereof packaged within a AAVC11.18 capsid. |
| 2 | AAVC11.19 | | BCKDA | 593 | Payload comprising a BCKDA gene or variant thereof packaged within a AAVC11.19 capsid. |
| 2 | AAV12 | | BCKDA | 593 | Payload comprising a BCKDA gene or variant thereof packaged within a AAV12 capsid. |
| 2 | AAV13 | | BCKDA | 593 | Payload comprising a BCKDA gene or variant thereof packaged within a AAV13 capsid. |
| 2 | AAV-DJ | | BCKDA | 593 | Payload comprising a BCKDA gene or variant thereof packaged within a AAV-DJ capsid. |
| 2 | AAV-LK03 | | BCKDA | 593 | Payload comprising a BCKDA gene or variant thereof packaged within a AAV-LK03 capsid. |
| 2 | AAV-LK19 | | BCKDA | 593 | Payload comprising a BCKDA gene or variant thereof packaged within a AAV-LK19 capsid. |
| 2 | AAVrh.74 | | BCKDA | 593 | Payload comprising a BCKDA gene or variant thereof packaged within a AAVrh.74 capsid. |
| 2 | AAVrh.10 | | BCKDA | 593 | Payload comprising a BCKDA gene or variant thereof packaged within a AAVrh.10 capsid. |
| 2 | AAVhu.37 | | BCKDA | 593 | Payload comprising a BCKDA gene or variant thereof packaged within a AAVhu.37 capsid. |
| 2 | AAVrh.K | | BCKDA | 593 | Payload comprising a BCKDA gene or variant thereof packaged within a AAVrh.K capsid. |
| 2 | AAVrh.39 | | BCKDA | 593 | Payload comprising a BCKDA gene or variant thereof packaged within a AAVrh.39 capsid. |
| 2 | AAVrh.9 | | BCKDA | 593 | Payload comprising a BCKDA gene or variant thereof packaged within a AAVrh.9 capsid. |
| 2 | avian AAV | | BCKDA | 593 | Payload comprising a BCKDA gene or variant thereof packaged within a avian capsid. |

Fig. 29 (Continued)

| | | | | | |
|---|---|---|---|---|---|
| 2 | bovine AAV | | BCKDA | 593 | Payload comprising a BCKDA gene or variant thereof packaged within a bovine capsid. |
| 2 | canine AAV | | BCKDA | 593 | Payload comprising a BCKDA gene or variant thereof packaged within a canine capsid. |
| 2 | equine AAV | | BCKDA | 593 | Payload comprising a BCKDA gene or variant thereof packaged within a equine capsid. |
| 2 | primate AAV | | BCKDA | 593 | Payload comprising a BCKDA gene or variant thereof packaged within a primate capsid. |
| 2 | non-primate AAV | | BCKDA | 593 | Payload comprising a BCKDA gene or variant thereof packaged within a non-primate capsid. |
| 2 | ovine AAV | | BCKDA | 593 | Payload comprising a BCKDA gene or variant thereof packaged within a ovine capsid. |
| 2 | hybrid AAV | | BCKDA | 593 | Payload comprising a BCKDA gene or variant thereof packaged within a hybrid capsid. |
| 2 | chimeric AAV | | BCKDA | 593 | Payload comprising a BCKDA gene or variant thereof packaged within a chimeric capsid. |
| 1 | AAV1 | 1450374 | BCKDB | 594 | Payload comprising a BCKDB gene or variant thereof packaged within a AAV1 capsid. |
| 1 | AAV2 | | BCKDB | 594 | Payload comprising a BCKDB gene or variant thereof packaged within a AAV2 capsid. |
| 1 | AAV3 | | BCKDB | 594 | Payload comprising a BCKDB gene or variant thereof packaged within a AAV3 capsid. |
| 1 | AAV4 | 1446389 | BCKDB | 594 | Payload comprising a BCKDB gene or variant thereof packaged within a AAV4 capsid. |
| 1 | AAV5 | | BCKDB | 594 | Payload comprising a BCKDB gene or variant thereof packaged within a AAV5 capsid. |
| 1 | AAV6 | | BCKDB | 594 | Payload comprising a BCKDB gene or variant thereof packaged within a AAV6 capsid. |
| 1 | AAV7 | | BCKDB | 594 | Payload comprising a BCKDB gene or variant thereof packaged within a AAV7 capsid. |
| 1 | AAV8 | 5075992 | BCKDB | 594 | Payload comprising a BCKDB gene or variant thereof packaged within a AAV8 capsid. |
| 1 | AAV9 | | BCKDB | 594 | Payload comprising a BCKDB gene or variant thereof packaged within a AAV9 capsid. |

Fig. 29 (Continued)

| | | | | | |
|---|---|---|---|---|---|
| 1 | AAV10 | | BCKDB | 594 | Payload comprising a BCKDB gene or variant thereof packaged within a AAV10 capsid. |
| 1 | AAV11 | | BCKDB | 594 | Payload comprising a BCKDB gene or variant thereof packaged within a AAV11 capsid. |
| 1 | AAVC11.01 | | BCKDB | 594 | Payload comprising a BCKDB gene or variant thereof packaged within a AAVC11.01 capsid. |
| 1 | AAVC11.02 | | BCKDB | 594 | Payload comprising a BCKDB gene or variant thereof packaged within a AAVC11.02 capsid. |
| 1 | AAVC11.03 | | BCKDB | 594 | Payload comprising a BCKDB gene or variant thereof packaged within a AAVC11.03 capsid. |
| 1 | AAVC11.04 | | BCKDB | 594 | Payload comprising a BCKDB gene or variant thereof packaged within a AAVC11.04 capsid. |
| 1 | AAVC11.05 | | BCKDB | 594 | Payload comprising a BCKDB gene or variant thereof packaged within a AAVC11.05 capsid. |
| 1 | AAVC11.06 | | BCKDB | 594 | Payload comprising a BCKDB gene or variant thereof packaged within a AAVC11.06 capsid. |
| 1 | AAVC11.07 | | BCKDB | 594 | Payload comprising a BCKDB gene or variant thereof packaged within a AAVC11.07 capsid. |
| 1 | AAVC11.08 | | BCKDB | 594 | Payload comprising a BCKDB gene or variant thereof packaged within a AAVC11.08 capsid. |
| 1 | AAVC11.09 | | BCKDB | 594 | Payload comprising a BCKDB gene or variant thereof packaged within a AAVC11.09 capsid. |
| 1 | AAVC11.10 | | BCKDB | 594 | Payload comprising a BCKDB gene or variant thereof packaged within a AAVC11.10 capsid. |
| 1 | AAVC11.11 | | BCKDB | 594 | Payload comprising a BCKDB gene or variant thereof packaged within a AAVC11.11 capsid. |
| 1 | AAVC11.12 | | BCKDB | 594 | Payload comprising a BCKDB gene or variant thereof packaged within a AAVC11.12 capsid. |
| 1 | AAVC11.13 | | BCKDB | 594 | Payload comprising a BCKDB gene or variant thereof packaged within a AAVC11.13 capsid. |
| 1 | AAVC11.14 | | BCKDB | 594 | Payload comprising a BCKDB gene or variant thereof packaged within a AAVC11.14 capsid. |
| 1 | AAVC11.15 | | BCKDB | 594 | Payload comprising a BCKDB gene or variant thereof packaged within a AAVC11.15 capsid. |

Fig. 29 (Continued)

| | | | | | |
|---|---|---|---|---|---|
| 1 | AAVC11.16 | | BCKDB | 594 | Payload comprising a BCKDB gene or variant thereof packaged within a AAVC11.16 capsid. |
| 1 | AAVC11.17 | | BCKDB | 594 | Payload comprising a BCKDB gene or variant thereof packaged within a AAVC11.17 capsid. |
| 1 | AAVC11.18 | | BCKDB | 594 | Payload comprising a BCKDB gene or variant thereof packaged within a AAVC11.18 capsid. |
| 1 | AAVC11.19 | | BCKDB | 594 | Payload comprising a BCKDB gene or variant thereof packaged within a AAVC11.19 capsid. |
| 1 | AAV12 | | BCKDB | 594 | Payload comprising a BCKDB gene or variant thereof packaged within a AAV12 capsid. |
| 1 | AAV13 | | BCKDB | 594 | Payload comprising a BCKDB gene or variant thereof packaged within a AAV13 capsid. |
| 1 | AAV-DJ | | BCKDB | 594 | Payload comprising a BCKDB gene or variant thereof packaged within a AAV-DJ capsid. |
| 1 | AAV-LK03 | | BCKDB | 594 | Payload comprising a BCKDB gene or variant thereof packaged within a AAV-LK03 capsid. |
| 1 | AAV-LK19 | | BCKDB | 594 | Payload comprising a BCKDB gene or variant thereof packaged within a AAV-LK19 capsid. |
| 1 | AAVrh.74 | | BCKDB | 594 | Payload comprising a BCKDB gene or variant thereof packaged within a AAVrh.74 capsid. |
| 1 | AAVrh.10 | | BCKDB | 594 | Payload comprising a BCKDB gene or variant thereof packaged within a AAVrh.10 capsid. |
| 1 | AAVhu.37 | | BCKDB | 594 | Payload comprising a BCKDB gene or variant thereof packaged within a AAVhu.37 capsid. |
| 1 | AAVrh.K | | BCKDB | 594 | Payload comprising a BCKDB gene or variant thereof packaged within a AAVrh.K capsid. |
| 1 | AAVrh.39 | | BCKDB | 594 | Payload comprising a BCKDB gene or variant thereof packaged within a AAVrh.39 capsid. |
| 1 | AAVrh.9 | | BCKDB | 594 | Payload comprising a BCKDB gene or variant thereof packaged within a AAVrh.9 capsid. |
| 1 | avian AAV | | BCKDB | 594 | Payload comprising a BCKDB gene or variant thereof packaged within a avian capsid. |

Fig. 29 (Continued)

| | | | | | |
|---|---|---|---|---|---|
| 1 | bovine AAV | | BCKDB | 594 | Payload comprising a BCKDB gene or variant thereof packaged within a bovine capsid. |
| 1 | canine AAV | | BCKDB | 594 | Payload comprising a BCKDB gene or variant thereof packaged within a canine capsid. |
| 1 | equine AAV | | BCKDB | 594 | Payload comprising a BCKDB gene or variant thereof packaged within a equine capsid. |
| 1 | primate AAV | | BCKDB | 594 | Payload comprising a BCKDB gene or variant thereof packaged within a primate capsid. |
| 1 | non-primate AAV | | BCKDB | 594 | Payload comprising a BCKDB gene or variant thereof packaged within a non-primate capsid. |
| 1 | ovine AAV | | BCKDB | 594 | Payload comprising a BCKDB gene or variant thereof packaged within a ovine capsid. |
| 1 | hybrid AAV | | BCKDB | 594 | Payload comprising a BCKDB gene or variant thereof packaged within a hybrid capsid. |
| 1 | chimeric AAV | | BCKDB | 594 | Payload comprising a BCKDB gene or variant thereof packaged within a chimeric capsid. |
| 2 | AAV1 | 1450374 | BCKDB | 594 | Payload comprising a BCKDB gene or variant thereof packaged within a AAV1 capsid. |
| 2 | AAV2 | | BCKDB | 594 | Payload comprising a BCKDB gene or variant thereof packaged within a AAV2 capsid. |
| 2 | AAV3 | | BCKDB | 594 | Payload comprising a BCKDB gene or variant thereof packaged within a AAV3 capsid. |
| 2 | AAV4 | 1446389 | BCKDB | 594 | Payload comprising a BCKDB gene or variant thereof packaged within a AAV4 capsid. |
| 2 | AAV5 | | BCKDB | 594 | Payload comprising a BCKDB gene or variant thereof packaged within a AAV5 capsid. |
| 2 | AAV6 | | BCKDB | 594 | Payload comprising a BCKDB gene or variant thereof packaged within a AAV6 capsid. |
| 2 | AAV7 | | BCKDB | 594 | Payload comprising a BCKDB gene or variant thereof packaged within a AAV7 capsid. |
| 2 | AAV8 | 5075992 | BCKDB | 594 | Payload comprising a BCKDB gene or variant thereof packaged within a AAV8 capsid. |
| 2 | AAV9 | | BCKDB | 594 | Payload comprising a BCKDB gene or variant thereof packaged within a AAV9 capsid. |

Fig. 29 (Continued)

| | | | | | |
|---|---|---|---|---|---|
| 2 | AAV10 | | BCKDB | 594 | Payload comprising a BCKDB gene or variant thereof packaged within a AAV10 capsid. |
| 2 | AAV11 | | BCKDB | 594 | Payload comprising a BCKDB gene or variant thereof packaged within a AAV11 capsid. |
| 2 | AAVC11.01 | | BCKDB | 594 | Payload comprising a BCKDB gene or variant thereof packaged within a AAVC11.01 capsid. |
| 2 | AAVC11.02 | | BCKDB | 594 | Payload comprising a BCKDB gene or variant thereof packaged within a AAVC11.02 capsid. |
| 2 | AAVC11.03 | | BCKDB | 594 | Payload comprising a BCKDB gene or variant thereof packaged within a AAVC11.03 capsid. |
| 2 | AAVC11.04 | | BCKDB | 594 | Payload comprising a BCKDB gene or variant thereof packaged within a AAVC11.04 capsid. |
| 2 | AAVC11.05 | | BCKDB | 594 | Payload comprising a BCKDB gene or variant thereof packaged within a AAVC11.05 capsid. |
| 2 | AAVC11.06 | | BCKDB | 594 | Payload comprising a BCKDB gene or variant thereof packaged within a AAVC11.06 capsid. |
| 2 | AAVC11.07 | | BCKDB | 594 | Payload comprising a BCKDB gene or variant thereof packaged within a AAVC11.07 capsid. |
| 2 | AAVC11.08 | | BCKDB | 594 | Payload comprising a BCKDB gene or variant thereof packaged within a AAVC11.08 capsid. |
| 2 | AAVC11.09 | | BCKDB | 594 | Payload comprising a BCKDB gene or variant thereof packaged within a AAVC11.09 capsid. |
| 2 | AAVC11.10 | | BCKDB | 594 | Payload comprising a BCKDB gene or variant thereof packaged within a AAVC11.10 capsid. |
| 2 | AAVC11.11 | | BCKDB | 594 | Payload comprising a BCKDB gene or variant thereof packaged within a AAVC11.11 capsid. |
| 2 | AAVC11.12 | | BCKDB | 594 | Payload comprising a BCKDB gene or variant thereof packaged within a AAVC11.12 capsid. |
| 2 | AAVC11.13 | | BCKDB | 594 | Payload comprising a BCKDB gene or variant thereof packaged within a AAVC11.13 capsid. |
| 2 | AAVC11.14 | | BCKDB | 594 | Payload comprising a BCKDB gene or variant thereof packaged within a AAVC11.14 capsid. |
| 2 | AAVC11.15 | | BCKDB | 594 | Payload comprising a BCKDB gene or variant thereof packaged within a AAVC11.15 capsid. |

Fig. 29 (Continued)

| | | | | | |
|---|---|---|---|---|---|
| 2 | AAVC11.16 | | BCKDB | 594 | Payload comprising a BCKDB gene or variant thereof packaged within a AAVC11.16 capsid. |
| 2 | AAVC11.17 | | BCKDB | 594 | Payload comprising a BCKDB gene or variant thereof packaged within a AAVC11.17 capsid. |
| 2 | AAVC11.18 | | BCKDB | 594 | Payload comprising a BCKDB gene or variant thereof packaged within a AAVC11.18 capsid. |
| 2 | AAVC11.19 | | BCKDB | 594 | Payload comprising a BCKDB gene or variant thereof packaged within a AAVC11.19 capsid. |
| 2 | AAV12 | | BCKDB | 594 | Payload comprising a BCKDB gene or variant thereof packaged within a AAV12 capsid. |
| 2 | AAV13 | | BCKDB | 594 | Payload comprising a BCKDB gene or variant thereof packaged within a AAV13 capsid. |
| 2 | AAV-DJ | | BCKDB | 594 | Payload comprising a BCKDB gene or variant thereof packaged within a AAV-DJ capsid. |
| 2 | AAV-LK03 | | BCKDB | 594 | Payload comprising a BCKDB gene or variant thereof packaged within a AAV-LK03 capsid. |
| 2 | AAV-LK19 | | BCKDB | 594 | Payload comprising a BCKDB gene or variant thereof packaged within a AAV-LK19 capsid. |
| 2 | AAVrh.74 | | BCKDB | 594 | Payload comprising a BCKDB gene or variant thereof packaged within a AAVrh.74 capsid. |
| 2 | AAVrh.10 | | BCKDB | 594 | Payload comprising a BCKDB gene or variant thereof packaged within a AAVrh.10 capsid. |
| 2 | AAVhu.37 | | BCKDB | 594 | Payload comprising a BCKDB gene or variant thereof packaged within a AAVhu.37 capsid. |
| 2 | AAVrh.K | | BCKDB | 594 | Payload comprising a BCKDB gene or variant thereof packaged within a AAVrh.K capsid. |
| 2 | AAVrh.39 | | BCKDB | 594 | Payload comprising a BCKDB gene or variant thereof packaged within a AAVrh.39 capsid. |
| 2 | AAVrh.9 | | BCKDB | 594 | Payload comprising a BCKDB gene or variant thereof packaged within a AAVrh.9 capsid. |
| 2 | avian AAV | | BCKDB | 594 | Payload comprising a BCKDB gene or variant thereof packaged within a avian capsid. |

Fig. 29 (Continued)

| | | | | | |
|---|---|---|---|---|---|
| 2 | bovine AAV | | BCKDB | 594 | Payload comprising a BCKDB gene or variant thereof packaged within a bovine capsid. |
| 2 | canine AAV | | BCKDB | 594 | Payload comprising a BCKDB gene or variant thereof packaged within a canine capsid. |
| 2 | equine AAV | | BCKDB | 594 | Payload comprising a BCKDB gene or variant thereof packaged within a equine capsid. |
| 2 | primate AAV | | BCKDB | 594 | Payload comprising a BCKDB gene or variant thereof packaged within a primate capsid. |
| 2 | non-primate AAV | | BCKDB | 594 | Payload comprising a BCKDB gene or variant thereof packaged within a non-primate capsid. |
| 2 | ovine AAV | | BCKDB | 594 | Payload comprising a BCKDB gene or variant thereof packaged within a ovine capsid. |
| 2 | hybrid AAV | | BCKDB | 594 | Payload comprising a BCKDB gene or variant thereof packaged within a hybrid capsid. |
| 2 | chimeric AAV | | BCKDB | 594 | Payload comprising a BCKDB gene or variant thereof packaged within a chimeric capsid. |
| 1 | AAV1 | 1450374 | C1INH | 710 | Payload comprising a C1INH gene or variant thereof packaged within a AAV1 capsid. |
| 1 | AAV2 | | C1INH | 710 | Payload comprising a C1INH gene or variant thereof packaged within a AAV2 capsid. |
| 1 | AAV3 | | C1INH | 710 | Payload comprising a C1INH gene or variant thereof packaged within a AAV3 capsid. |
| 1 | AAV4 | 1446389 | C1INH | 710 | Payload comprising a C1INH gene or variant thereof packaged within a AAV4 capsid. |
| 1 | AAV5 | | C1INH | 710 | Payload comprising a C1INH gene or variant thereof packaged within a AAV5 capsid. |
| 1 | AAV6 | | C1INH | 710 | Payload comprising a C1INH gene or variant thereof packaged within a AAV6 capsid. |
| 1 | AAV7 | | C1INH | 710 | Payload comprising a C1INH gene or variant thereof packaged within a AAV7 capsid. |
| 1 | AAV8 | 5075992 | C1INH | 710 | Payload comprising a C1INH gene or variant thereof packaged within a AAV8 capsid. |
| 1 | AAV9 | | C1INH | 710 | Payload comprising a C1INH gene or variant thereof packaged within a AAV9 capsid. |

Fig. 29 (Continued)

| | | | | | |
|---|---|---|---|---|---|
| 1 | AAV10 | | C1INH | 710 | Payload comprising a C1INH gene or variant thereof packaged within a AAV10 capsid. |
| 1 | AAV11 | | C1INH | 710 | Payload comprising a C1INH gene or variant thereof packaged within a AAV11 capsid. |
| 1 | AAVC11.01 | | C1INH | 710 | Payload comprising a C1INH gene or variant thereof packaged within a AAVC11.01 capsid. |
| 1 | AAVC11.02 | | C1INH | 710 | Payload comprising a C1INH gene or variant thereof packaged within a AAVC11.02 capsid. |
| 1 | AAVC11.03 | | C1INH | 710 | Payload comprising a C1INH gene or variant thereof packaged within a AAVC11.03 capsid. |
| 1 | AAVC11.04 | | C1INH | 710 | Payload comprising a C1INH gene or variant thereof packaged within a AAVC11.04 capsid. |
| 1 | AAVC11.05 | | C1INH | 710 | Payload comprising a C1INH gene or variant thereof packaged within a AAVC11.05 capsid. |
| 1 | AAVC11.06 | | C1INH | 710 | Payload comprising a C1INH gene or variant thereof packaged within a AAVC11.06 capsid. |
| 1 | AAVC11.07 | | C1INH | 710 | Payload comprising a C1INH gene or variant thereof packaged within a AAVC11.07 capsid. |
| 1 | AAVC11.08 | | C1INH | 710 | Payload comprising a C1INH gene or variant thereof packaged within a AAVC11.08 capsid. |
| 1 | AAVC11.09 | | C1INH | 710 | Payload comprising a C1INH gene or variant thereof packaged within a AAVC11.09 capsid. |
| 1 | AAVC11.10 | | C1INH | 710 | Payload comprising a C1INH gene or variant thereof packaged within a AAVC11.10 capsid. |
| 1 | AAVC11.11 | | C1INH | 710 | Payload comprising a C1INH gene or variant thereof packaged within a AAVC11.11 capsid. |
| 1 | AAVC11.12 | | C1INH | 710 | Payload comprising a C1INH gene or variant thereof packaged within a AAVC11.12 capsid. |
| 1 | AAVC11.13 | | C1INH | 710 | Payload comprising a C1INH gene or variant thereof packaged within a AAVC11.13 capsid. |
| 1 | AAVC11.14 | | C1INH | 710 | Payload comprising a C1INH gene or variant thereof packaged within a AAVC11.14 capsid. |
| 1 | AAVC11.15 | | C1INH | 710 | Payload comprising a C1INH gene or variant thereof packaged within a AAVC11.15 capsid. |

Fig. 29 (Continued)

| | | | | | |
|---|---|---|---|---|---|
| 1 | AAVC11.16 | | C1INH | 710 | Payload comprising a C1INH gene or variant thereof packaged within a AAVC11.16 capsid. |
| 1 | AAVC11.17 | | C1INH | 710 | Payload comprising a C1INH gene or variant thereof packaged within a AAVC11.17 capsid. |
| 1 | AAVC11.18 | | C1INH | 710 | Payload comprising a C1INH gene or variant thereof packaged within a AAVC11.18 capsid. |
| 1 | AAVC11.19 | | C1INH | 710 | Payload comprising a C1INH gene or variant thereof packaged within a AAVC11.19 capsid. |
| 1 | AAV12 | | C1INH | 710 | Payload comprising a C1INH gene or variant thereof packaged within a AAV12 capsid. |
| 1 | AAV13 | | C1INH | 710 | Payload comprising a C1INH gene or variant thereof packaged within a AAV13 capsid. |
| 1 | AAV-DJ | | C1INH | 710 | Payload comprising a C1INH gene or variant thereof packaged within a AAV-DJ capsid. |
| 1 | AAV-LK03 | | C1INH | 710 | Payload comprising a C1INH gene or variant thereof packaged within a AAV-LK03 capsid. |
| 1 | AAV-LK19 | | C1INH | 710 | Payload comprising a C1INH gene or variant thereof packaged within a AAV-LK19 capsid. |
| 1 | AAVrh.74 | | C1INH | 710 | Payload comprising a C1INH gene or variant thereof packaged within a AAVrh.74 capsid. |
| 1 | AAVrh.10 | | C1INH | 710 | Payload comprising a C1INH gene or variant thereof packaged within a AAVrh.10 capsid. |
| 1 | AAVhu.37 | | C1INH | 710 | Payload comprising a C1INH gene or variant thereof packaged within a AAVhu.37 capsid. |
| 1 | AAVrh.K | | C1INH | 710 | Payload comprising a C1INH gene or variant thereof packaged within a AAVrh.K capsid. |
| 1 | AAVrh.39 | | C1INH | 710 | Payload comprising a C1INH gene or variant thereof packaged within a AAVrh.39 capsid. |
| 1 | AAVrh.9 | | C1INH | 710 | Payload comprising a C1INH gene or variant thereof packaged within a AAVrh.9 capsid. |
| 1 | avian AAV | | C1INH | 710 | Payload comprising a C1INH gene or variant thereof packaged within a avian capsid. |

Fig. 29 (Continued)

| | | | | | |
|---|---|---|---|---|---|
| 1 | bovine AAV | | C1INH | 710 | Payload comprising a C1INH gene or variant thereof packaged within a bovine capsid. |
| 1 | canine AAV | | C1INH | 710 | Payload comprising a C1INH gene or variant thereof packaged within a canine capsid. |
| 1 | equine AAV | | C1INH | 710 | Payload comprising a C1INH gene or variant thereof packaged within a equine capsid. |
| 1 | primate AAV | | C1INH | 710 | Payload comprising a C1INH gene or variant thereof packaged within a primate capsid. |
| 1 | non-primate AAV | | C1INH | 710 | Payload comprising a C1INH gene or variant thereof packaged within a non-primate capsid. |
| 1 | ovine AAV | | C1INH | 710 | Payload comprising a C1INH gene or variant thereof packaged within a ovine capsid. |
| 1 | hybrid AAV | | C1INH | 710 | Payload comprising a C1INH gene or variant thereof packaged within a hybrid capsid. |
| 1 | chimeric AAV | | C1INH | 710 | Payload comprising a C1INH gene or variant thereof packaged within a chimeric capsid. |
| 2 | AAV1 | 1450374 | C1INH | 710 | Payload comprising a C1INH gene or variant thereof packaged within a AAV1 capsid. |
| 2 | AAV2 | | C1INH | 710 | Payload comprising a C1INH gene or variant thereof packaged within a AAV2 capsid. |
| 2 | AAV3 | | C1INH | 710 | Payload comprising a C1INH gene or variant thereof packaged within a AAV3 capsid. |
| 2 | AAV4 | 1446389 | C1INH | 710 | Payload comprising a C1INH gene or variant thereof packaged within a AAV4 capsid. |
| 2 | AAV5 | | C1INH | 710 | Payload comprising a C1INH gene or variant thereof packaged within a AAV5 capsid. |
| 2 | AAV6 | | C1INH | 710 | Payload comprising a C1INH gene or variant thereof packaged within a AAV6 capsid. |
| 2 | AAV7 | | C1INH | 710 | Payload comprising a C1INH gene or variant thereof packaged within a AAV7 capsid. |
| 2 | AAV8 | 5075992 | C1INH | 710 | Payload comprising a C1INH gene or variant thereof packaged within a AAV8 capsid. |
| 2 | AAV9 | | C1INH | 710 | Payload comprising a C1INH gene or variant thereof packaged within a AAV9 capsid. |

Fig. 29 (Continued)

| | | | | | |
|---|---|---|---|---|---|
| 2 | AAV10 | | C1INH | 710 | Payload comprising a C1INH gene or variant thereof packaged within a AAV10 capsid. |
| 2 | AAV11 | | C1INH | 710 | Payload comprising a C1INH gene or variant thereof packaged within a AAV11 capsid. |
| 2 | AAVC11.01 | | C1INH | 710 | Payload comprising a C1INH gene or variant thereof packaged within a AAVC11.01 capsid. |
| 2 | AAVC11.02 | | C1INH | 710 | Payload comprising a C1INH gene or variant thereof packaged within a AAVC11.02 capsid. |
| 2 | AAVC11.03 | | C1INH | 710 | Payload comprising a C1INH gene or variant thereof packaged within a AAVC11.03 capsid. |
| 2 | AAVC11.04 | | C1INH | 710 | Payload comprising a C1INH gene or variant thereof packaged within a AAVC11.04 capsid. |
| 2 | AAVC11.05 | | C1INH | 710 | Payload comprising a C1INH gene or variant thereof packaged within a AAVC11.05 capsid. |
| 2 | AAVC11.06 | | C1INH | 710 | Payload comprising a C1INH gene or variant thereof packaged within a AAVC11.06 capsid. |
| 2 | AAVC11.07 | | C1INH | 710 | Payload comprising a C1INH gene or variant thereof packaged within a AAVC11.07 capsid. |
| 2 | AAVC11.08 | | C1INH | 710 | Payload comprising a C1INH gene or variant thereof packaged within a AAVC11.08 capsid. |
| 2 | AAVC11.09 | | C1INH | 710 | Payload comprising a C1INH gene or variant thereof packaged within a AAVC11.09 capsid. |
| 2 | AAVC11.10 | | C1INH | 710 | Payload comprising a C1INH gene or variant thereof packaged within a AAVC11.10 capsid. |
| 2 | AAVC11.11 | | C1INH | 710 | Payload comprising a C1INH gene or variant thereof packaged within a AAVC11.11 capsid. |
| 2 | AAVC11.12 | | C1INH | 710 | Payload comprising a C1INH gene or variant thereof packaged within a AAVC11.12 capsid. |
| 2 | AAVC11.13 | | C1INH | 710 | Payload comprising a C1INH gene or variant thereof packaged within a AAVC11.13 capsid. |
| 2 | AAVC11.14 | | C1INH | 710 | Payload comprising a C1INH gene or variant thereof packaged within a AAVC11.14 capsid. |
| 2 | AAVC11.15 | | C1INH | 710 | Payload comprising a C1INH gene or variant thereof packaged within a AAVC11.15 capsid. |

Fig. 29 (Continued)

| | | | | | |
|---|---|---|---|---|---|
| 2 | AAVC11.16 | | C1INH | 710 | Payload comprising a C1INH gene or variant thereof packaged within a AAVC11.16 capsid. |
| 2 | AAVC11.17 | | C1INH | 710 | Payload comprising a C1INH gene or variant thereof packaged within a AAVC11.17 capsid. |
| 2 | AAVC11.18 | | C1INH | 710 | Payload comprising a C1INH gene or variant thereof packaged within a AAVC11.18 capsid. |
| 2 | AAVC11.19 | | C1INH | 710 | Payload comprising a C1INH gene or variant thereof packaged within a AAVC11.19 capsid. |
| 2 | AAV12 | | C1INH | 710 | Payload comprising a C1INH gene or variant thereof packaged within a AAV12 capsid. |
| 2 | AAV13 | | C1INH | 710 | Payload comprising a C1INH gene or variant thereof packaged within a AAV13 capsid. |
| 2 | AAV-DJ | | C1INH | 710 | Payload comprising a C1INH gene or variant thereof packaged within a AAV-DJ capsid. |
| 2 | AAV-LK03 | | C1INH | 710 | Payload comprising a C1INH gene or variant thereof packaged within a AAV-LK03 capsid. |
| 2 | AAV-LK19 | | C1INH | 710 | Payload comprising a C1INH gene or variant thereof packaged within a AAV-LK19 capsid. |
| 2 | AAVrh.74 | | C1INH | 710 | Payload comprising a C1INH gene or variant thereof packaged within a AAVrh.74 capsid. |
| 2 | AAVrh.10 | | C1INH | 710 | Payload comprising a C1INH gene or variant thereof packaged within a AAVrh.10 capsid. |
| 2 | AAVhu.37 | | C1INH | 710 | Payload comprising a C1INH gene or variant thereof packaged within a AAVhu.37 capsid. |
| 2 | AAVrh.K | | C1INH | 710 | Payload comprising a C1INH gene or variant thereof packaged within a AAVrh.K capsid. |
| 2 | AAVrh.39 | | C1INH | 710 | Payload comprising a C1INH gene or variant thereof packaged within a AAVrh.39 capsid. |
| 2 | AAVrh.9 | | C1INH | 710 | Payload comprising a C1INH gene or variant thereof packaged within a AAVrh.9 capsid. |
| 2 | avian AAV | | C1INH | 710 | Payload comprising a C1INH gene or variant thereof packaged within a avian capsid. |

Fig. 29 (Continued)

| | | | | | |
|---|---|---|---|---|---|
| 2 | bovine AAV | | C1INH | 710 | Payload comprising a C1INH gene or variant thereof packaged within a bovine capsid. |
| 2 | canine AAV | | C1INH | 710 | Payload comprising a C1INH gene or variant thereof packaged within a canine capsid. |
| 2 | equine AAV | | C1INH | 710 | Payload comprising a C1INH gene or variant thereof packaged within a equine capsid. |
| 2 | primate AAV | | C1INH | 710 | Payload comprising a C1INH gene or variant thereof packaged within a primate capsid. |
| 2 | non-primate AAV | | C1INH | 710 | Payload comprising a C1INH gene or variant thereof packaged within a non-primate capsid. |
| 2 | ovine AAV | | C1INH | 710 | Payload comprising a C1INH gene or variant thereof packaged within a ovine capsid. |
| 2 | hybrid AAV | | C1INH | 710 | Payload comprising a C1INH gene or variant thereof packaged within a hybrid capsid. |
| 2 | chimeric AAV | | C1INH | 710 | Payload comprising a C1INH gene or variant thereof packaged within a chimeric capsid. |
| 1 | AAV1 | 1450374 | CACT | 788 | Payload comprising a CACT gene or variant thereof packaged within a AAV1 capsid. |
| 1 | AAV2 | | CACT | 788 | Payload comprising a CACT gene or variant thereof packaged within a AAV2 capsid. |
| 1 | AAV3 | | CACT | 788 | Payload comprising a CACT gene or variant thereof packaged within a AAV3 capsid. |
| 1 | AAV4 | 1446389 | CACT | 788 | Payload comprising a CACT gene or variant thereof packaged within a AAV4 capsid. |
| 1 | AAV5 | | CACT | 788 | Payload comprising a CACT gene or variant thereof packaged within a AAV5 capsid. |
| 1 | AAV6 | | CACT | 788 | Payload comprising a CACT gene or variant thereof packaged within a AAV6 capsid. |
| 1 | AAV7 | | CACT | 788 | Payload comprising a CACT gene or variant thereof packaged within a AAV7 capsid. |
| 1 | AAV8 | 5075992 | CACT | 788 | Payload comprising a CACT gene or variant thereof packaged within a AAV8 capsid. |
| 1 | AAV9 | | CACT | 788 | Payload comprising a CACT gene or variant thereof packaged within a AAV9 capsid. |

Fig. 29 (Continued)

| | | | | | |
|---|---|---|---|---|---|
| 1 | AAV10 | | CACT | 788 | Payload comprising a CACT gene or variant thereof packaged within a AAV10 capsid. |
| 1 | AAV11 | | CACT | 788 | Payload comprising a CACT gene or variant thereof packaged within a AAV11 capsid. |
| 1 | AAVC11.01 | | CACT | 788 | Payload comprising a CACT gene or variant thereof packaged within a AAVC11.01 capsid. |
| 1 | AAVC11.02 | | CACT | 788 | Payload comprising a CACT gene or variant thereof packaged within a AAVC11.02 capsid. |
| 1 | AAVC11.03 | | CACT | 788 | Payload comprising a CACT gene or variant thereof packaged within a AAVC11.03 capsid. |
| 1 | AAVC11.04 | | CACT | 788 | Payload comprising a CACT gene or variant thereof packaged within a AAVC11.04 capsid. |
| 1 | AAVC11.05 | | CACT | 788 | Payload comprising a CACT gene or variant thereof packaged within a AAVC11.05 capsid. |
| 1 | AAVC11.06 | | CACT | 788 | Payload comprising a CACT gene or variant thereof packaged within a AAVC11.06 capsid. |
| 1 | AAVC11.07 | | CACT | 788 | Payload comprising a CACT gene or variant thereof packaged within a AAVC11.07 capsid. |
| 1 | AAVC11.08 | | CACT | 788 | Payload comprising a CACT gene or variant thereof packaged within a AAVC11.08 capsid. |
| 1 | AAVC11.09 | | CACT | 788 | Payload comprising a CACT gene or variant thereof packaged within a AAVC11.09 capsid. |
| 1 | AAVC11.10 | | CACT | 788 | Payload comprising a CACT gene or variant thereof packaged within a AAVC11.10 capsid. |
| 1 | AAVC11.11 | | CACT | 788 | Payload comprising a CACT gene or variant thereof packaged within a AAVC11.11 capsid. |
| 1 | AAVC11.12 | | CACT | 788 | Payload comprising a CACT gene or variant thereof packaged within a AAVC11.12 capsid. |
| 1 | AAVC11.13 | | CACT | 788 | Payload comprising a CACT gene or variant thereof packaged within a AAVC11.13 capsid. |
| 1 | AAVC11.14 | | CACT | 788 | Payload comprising a CACT gene or variant thereof packaged within a AAVC11.14 capsid. |
| 1 | AAVC11.15 | | CACT | 788 | Payload comprising a CACT gene or variant thereof packaged within a AAVC11.15 capsid. |

Fig. 29 (Continued)

| | | | | | |
|---|---|---|---|---|---|
| 1 | AAVC11.16 | | CACT | 788 | Payload comprising a CACT gene or variant thereof packaged within a AAVC11.16 capsid. |
| 1 | AAVC11.17 | | CACT | 788 | Payload comprising a CACT gene or variant thereof packaged within a AAVC11.17 capsid. |
| 1 | AAVC11.18 | | CACT | 788 | Payload comprising a CACT gene or variant thereof packaged within a AAVC11.18 capsid. |
| 1 | AAVC11.19 | | CACT | 788 | Payload comprising a CACT gene or variant thereof packaged within a AAVC11.19 capsid. |
| 1 | AAV12 | | CACT | 788 | Payload comprising a CACT gene or variant thereof packaged within a AAV12 capsid. |
| 1 | AAV13 | | CACT | 788 | Payload comprising a CACT gene or variant thereof packaged within a AAV13 capsid. |
| 1 | AAV-DJ | | CACT | 788 | Payload comprising a CACT gene or variant thereof packaged within a AAV-DJ capsid. |
| 1 | AAV-LK03 | | CACT | 788 | Payload comprising a CACT gene or variant thereof packaged within a AAV-LK03 capsid. |
| 1 | AAV-LK19 | | CACT | 788 | Payload comprising a CACT gene or variant thereof packaged within a AAV-LK19 capsid. |
| 1 | AAVrh.74 | | CACT | 788 | Payload comprising a CACT gene or variant thereof packaged within a AAVrh.74 capsid. |
| 1 | AAVrh.10 | | CACT | 788 | Payload comprising a CACT gene or variant thereof packaged within a AAVrh.10 capsid. |
| 1 | AAVhu.37 | | CACT | 788 | Payload comprising a CACT gene or variant thereof packaged within a AAVhu.37 capsid. |
| 1 | AAVrh.K | | CACT | 788 | Payload comprising a CACT gene or variant thereof packaged within a AAVrh.K capsid. |
| 1 | AAVrh.39 | | CACT | 788 | Payload comprising a CACT gene or variant thereof packaged within a AAVrh.39 capsid. |
| 1 | AAVrh.9 | | CACT | 788 | Payload comprising a CACT gene or variant thereof packaged within a AAVrh.9 capsid. |
| 1 | avian AAV | | CACT | 788 | Payload comprising a CACT gene or variant thereof packaged within a avian capsid. |

Fig. 29 (Continued)

| | | | | | |
|---|---|---|---|---|---|
| 1 | bovine AAV | | CACT | 788 | Payload comprising a CACT gene or variant thereof packaged within a bovine capsid. |
| 1 | canine AAV | | CACT | 788 | Payload comprising a CACT gene or variant thereof packaged within a canine capsid. |
| 1 | equine AAV | | CACT | 788 | Payload comprising a CACT gene or variant thereof packaged within a equine capsid. |
| 1 | primate AAV | | CACT | 788 | Payload comprising a CACT gene or variant thereof packaged within a primate capsid. |
| 1 | non-primate AAV | | CACT | 788 | Payload comprising a CACT gene or variant thereof packaged within a non-primate capsid. |
| 1 | ovine AAV | | CACT | 788 | Payload comprising a CACT gene or variant thereof packaged within a ovine capsid. |
| 1 | hybrid AAV | | CACT | 788 | Payload comprising a CACT gene or variant thereof packaged within a hybrid capsid. |
| 1 | chimeric AAV | | CACT | 788 | Payload comprising a CACT gene or variant thereof packaged within a chimeric capsid. |
| 2 | AAV1 | 1450374 | CACT | 788 | Payload comprising a CACT gene or variant thereof packaged within a AAV1 capsid. |
| 2 | AAV2 | | CACT | 788 | Payload comprising a CACT gene or variant thereof packaged within a AAV2 capsid. |
| 2 | AAV3 | | CACT | 788 | Payload comprising a CACT gene or variant thereof packaged within a AAV3 capsid. |
| 2 | AAV4 | 1446389 | CACT | 788 | Payload comprising a CACT gene or variant thereof packaged within a AAV4 capsid. |
| 2 | AAV5 | | CACT | 788 | Payload comprising a CACT gene or variant thereof packaged within a AAV5 capsid. |
| 2 | AAV6 | | CACT | 788 | Payload comprising a CACT gene or variant thereof packaged within a AAV6 capsid. |
| 2 | AAV7 | | CACT | 788 | Payload comprising a CACT gene or variant thereof packaged within a AAV7 capsid. |
| 2 | AAV8 | 5075992 | CACT | 788 | Payload comprising a CACT gene or variant thereof packaged within a AAV8 capsid. |
| 2 | AAV9 | | CACT | 788 | Payload comprising a CACT gene or variant thereof packaged within a AAV9 capsid. |

Fig. 29 (Continued)

| | | | | | |
|---|---|---|---|---|---|
| 2 | AAV10 | | CACT | 788 | Payload comprising a CACT gene or variant thereof packaged within a AAV10 capsid. |
| 2 | AAV11 | | CACT | 788 | Payload comprising a CACT gene or variant thereof packaged within a AAV11 capsid. |
| 2 | AAVC11.01 | | CACT | 788 | Payload comprising a CACT gene or variant thereof packaged within a AAVC11.01 capsid. |
| 2 | AAVC11.02 | | CACT | 788 | Payload comprising a CACT gene or variant thereof packaged within a AAVC11.02 capsid. |
| 2 | AAVC11.03 | | CACT | 788 | Payload comprising a CACT gene or variant thereof packaged within a AAVC11.03 capsid. |
| 2 | AAVC11.04 | | CACT | 788 | Payload comprising a CACT gene or variant thereof packaged within a AAVC11.04 capsid. |
| 2 | AAVC11.05 | | CACT | 788 | Payload comprising a CACT gene or variant thereof packaged within a AAVC11.05 capsid. |
| 2 | AAVC11.06 | | CACT | 788 | Payload comprising a CACT gene or variant thereof packaged within a AAVC11.06 capsid. |
| 2 | AAVC11.07 | | CACT | 788 | Payload comprising a CACT gene or variant thereof packaged within a AAVC11.07 capsid. |
| 2 | AAVC11.08 | | CACT | 788 | Payload comprising a CACT gene or variant thereof packaged within a AAVC11.08 capsid. |
| 2 | AAVC11.09 | | CACT | 788 | Payload comprising a CACT gene or variant thereof packaged within a AAVC11.09 capsid. |
| 2 | AAVC11.10 | | CACT | 788 | Payload comprising a CACT gene or variant thereof packaged within a AAVC11.10 capsid. |
| 2 | AAVC11.11 | | CACT | 788 | Payload comprising a CACT gene or variant thereof packaged within a AAVC11.11 capsid. |
| 2 | AAVC11.12 | | CACT | 788 | Payload comprising a CACT gene or variant thereof packaged within a AAVC11.12 capsid. |
| 2 | AAVC11.13 | | CACT | 788 | Payload comprising a CACT gene or variant thereof packaged within a AAVC11.13 capsid. |
| 2 | AAVC11.14 | | CACT | 788 | Payload comprising a CACT gene or variant thereof packaged within a AAVC11.14 capsid. |
| 2 | AAVC11.15 | | CACT | 788 | Payload comprising a CACT gene or variant thereof packaged within a AAVC11.15 capsid. |

Fig. 29 (Continued)

| | | | | | |
|---|---|---|---|---|---|
| 2 | AAVC11.16 | | CACT | 788 | Payload comprising a CACT gene or variant thereof packaged within a AAVC11.16 capsid. |
| 2 | AAVC11.17 | | CACT | 788 | Payload comprising a CACT gene or variant thereof packaged within a AAVC11.17 capsid. |
| 2 | AAVC11.18 | | CACT | 788 | Payload comprising a CACT gene or variant thereof packaged within a AAVC11.18 capsid. |
| 2 | AAVC11.19 | | CACT | 788 | Payload comprising a CACT gene or variant thereof packaged within a AAVC11.19 capsid. |
| 2 | AAV12 | | CACT | 788 | Payload comprising a CACT gene or variant thereof packaged within a AAV12 capsid. |
| 2 | AAV13 | | CACT | 788 | Payload comprising a CACT gene or variant thereof packaged within a AAV13 capsid. |
| 2 | AAV-DJ | | CACT | 788 | Payload comprising a CACT gene or variant thereof packaged within a AAV-DJ capsid. |
| 2 | AAV-LK03 | | CACT | 788 | Payload comprising a CACT gene or variant thereof packaged within a AAV-LK03 capsid. |
| 2 | AAV-LK19 | | CACT | 788 | Payload comprising a CACT gene or variant thereof packaged within a AAV-LK19 capsid. |
| 2 | AAVrh.74 | | CACT | 788 | Payload comprising a CACT gene or variant thereof packaged within a AAVrh.74 capsid. |
| 2 | AAVrh.10 | | CACT | 788 | Payload comprising a CACT gene or variant thereof packaged within a AAVrh.10 capsid. |
| 2 | AAVhu.37 | | CACT | 788 | Payload comprising a CACT gene or variant thereof packaged within a AAVhu.37 capsid. |
| 2 | AAVrh.K | | CACT | 788 | Payload comprising a CACT gene or variant thereof packaged within a AAVrh.K capsid. |
| 2 | AAVrh.39 | | CACT | 788 | Payload comprising a CACT gene or variant thereof packaged within a AAVrh.39 capsid. |
| 2 | AAVrh.9 | | CACT | 788 | Payload comprising a CACT gene or variant thereof packaged within a AAVrh.9 capsid. |
| 2 | avian AAV | | CACT | 788 | Payload comprising a CACT gene or variant thereof packaged within a avian capsid. |

Fig. 29 (Continued)

| | | | | | |
|---|---|---|---|---|---|
| 2 | bovine AAV | | CACT | 788 | Payload comprising a CACT gene or variant thereof packaged within a bovine capsid. |
| 2 | canine AAV | | CACT | 788 | Payload comprising a CACT gene or variant thereof packaged within a canine capsid. |
| 2 | equine AAV | | CACT | 788 | Payload comprising a CACT gene or variant thereof packaged within a equine capsid. |
| 2 | primate AAV | | CACT | 788 | Payload comprising a CACT gene or variant thereof packaged within a primate capsid. |
| 2 | non-primate AAV | | CACT | 788 | Payload comprising a CACT gene or variant thereof packaged within a non-primate capsid. |
| 2 | ovine AAV | | CACT | 788 | Payload comprising a CACT gene or variant thereof packaged within a ovine capsid. |
| 2 | hybrid AAV | | CACT | 788 | Payload comprising a CACT gene or variant thereof packaged within a hybrid capsid. |
| 2 | chimeric AAV | | CACT | 788 | Payload comprising a CACT gene or variant thereof packaged within a chimeric capsid. |
| 1 | AAV1 | 1450374 | CAPN3 | 825 | Payload comprising a CAPN3 gene or variant thereof packaged within a AAV1 capsid. |
| 1 | AAV2 | | CAPN3 | 825 | Payload comprising a CAPN3 gene or variant thereof packaged within a AAV2 capsid. |
| 1 | AAV3 | | CAPN3 | 825 | Payload comprising a CAPN3 gene or variant thereof packaged within a AAV3 capsid. |
| 1 | AAV4 | 1446389 | CAPN3 | 825 | Payload comprising a CAPN3 gene or variant thereof packaged within a AAV4 capsid. |
| 1 | AAV5 | | CAPN3 | 825 | Payload comprising a CAPN3 gene or variant thereof packaged within a AAV5 capsid. |
| 1 | AAV6 | | CAPN3 | 825 | Payload comprising a CAPN3 gene or variant thereof packaged within a AAV6 capsid. |
| 1 | AAV7 | | CAPN3 | 825 | Payload comprising a CAPN3 gene or variant thereof packaged within a AAV7 capsid. |
| 1 | AAV8 | 5075992 | CAPN3 | 825 | Payload comprising a CAPN3 gene or variant thereof packaged within a AAV8 capsid. |
| 1 | AAV9 | | CAPN3 | 825 | Payload comprising a CAPN3 gene or variant thereof packaged within a AAV9 capsid. |

Fig. 29 (Continued)

| | | | | | |
|---|---|---|---|---|---|
| 1 | AAV10 | | CAPN3 | 825 | Payload comprising a CAPN3 gene or variant thereof packaged within a AAV10 capsid. |
| 1 | AAV11 | | CAPN3 | 825 | Payload comprising a CAPN3 gene or variant thereof packaged within a AAV11 capsid. |
| 1 | AAVC11.01 | | CAPN3 | 825 | Payload comprising a CAPN3 gene or variant thereof packaged within a AAVC11.01 capsid. |
| 1 | AAVC11.02 | | CAPN3 | 825 | Payload comprising a CAPN3 gene or variant thereof packaged within a AAVC11.02 capsid. |
| 1 | AAVC11.03 | | CAPN3 | 825 | Payload comprising a CAPN3 gene or variant thereof packaged within a AAVC11.03 capsid. |
| 1 | AAVC11.04 | | CAPN3 | 825 | Payload comprising a CAPN3 gene or variant thereof packaged within a AAVC11.04 capsid. |
| 1 | AAVC11.05 | | CAPN3 | 825 | Payload comprising a CAPN3 gene or variant thereof packaged within a AAVC11.05 capsid. |
| 1 | AAVC11.06 | | CAPN3 | 825 | Payload comprising a CAPN3 gene or variant thereof packaged within a AAVC11.06 capsid. |
| 1 | AAVC11.07 | | CAPN3 | 825 | Payload comprising a CAPN3 gene or variant thereof packaged within a AAVC11.07 capsid. |
| 1 | AAVC11.08 | | CAPN3 | 825 | Payload comprising a CAPN3 gene or variant thereof packaged within a AAVC11.08 capsid. |
| 1 | AAVC11.09 | | CAPN3 | 825 | Payload comprising a CAPN3 gene or variant thereof packaged within a AAVC11.09 capsid. |
| 1 | AAVC11.10 | | CAPN3 | 825 | Payload comprising a CAPN3 gene or variant thereof packaged within a AAVC11.10 capsid. |
| 1 | AAVC11.11 | | CAPN3 | 825 | Payload comprising a CAPN3 gene or variant thereof packaged within a AAVC11.11 capsid. |
| 1 | AAVC11.12 | | CAPN3 | 825 | Payload comprising a CAPN3 gene or variant thereof packaged within a AAVC11.12 capsid. |
| 1 | AAVC11.13 | | CAPN3 | 825 | Payload comprising a CAPN3 gene or variant thereof packaged within a AAVC11.13 capsid. |
| 1 | AAVC11.14 | | CAPN3 | 825 | Payload comprising a CAPN3 gene or variant thereof packaged within a AAVC11.14 capsid. |
| 1 | AAVC11.15 | | CAPN3 | 825 | Payload comprising a CAPN3 gene or variant thereof packaged within a AAVC11.15 capsid. |

Fig. 29 (Continued)

| | | | | | |
|---|---|---|---|---|---|
| 1 | AAVC11.16 | | CAPN3 | 825 | Payload comprising a CAPN3 gene or variant thereof packaged within a AAVC11.16 capsid. |
| 1 | AAVC11.17 | | CAPN3 | 825 | Payload comprising a CAPN3 gene or variant thereof packaged within a AAVC11.17 capsid. |
| 1 | AAVC11.18 | | CAPN3 | 825 | Payload comprising a CAPN3 gene or variant thereof packaged within a AAVC11.18 capsid. |
| 1 | AAVC11.19 | | CAPN3 | 825 | Payload comprising a CAPN3 gene or variant thereof packaged within a AAVC11.19 capsid. |
| 1 | AAV12 | | CAPN3 | 825 | Payload comprising a CAPN3 gene or variant thereof packaged within a AAV12 capsid. |
| 1 | AAV13 | | CAPN3 | 825 | Payload comprising a CAPN3 gene or variant thereof packaged within a AAV13 capsid. |
| 1 | AAV-DJ | | CAPN3 | 825 | Payload comprising a CAPN3 gene or variant thereof packaged within a AAV-DJ capsid. |
| 1 | AAV-LK03 | | CAPN3 | 825 | Payload comprising a CAPN3 gene or variant thereof packaged within a AAV-LK03 capsid. |
| 1 | AAV-LK19 | | CAPN3 | 825 | Payload comprising a CAPN3 gene or variant thereof packaged within a AAV-LK19 capsid. |
| 1 | AAVrh.74 | | CAPN3 | 825 | Payload comprising a CAPN3 gene or variant thereof packaged within a AAVrh.74 capsid. |
| 1 | AAVrh.10 | | CAPN3 | 825 | Payload comprising a CAPN3 gene or variant thereof packaged within a AAVrh.10 capsid. |
| 1 | AAVhu.37 | | CAPN3 | 825 | Payload comprising a CAPN3 gene or variant thereof packaged within a AAVhu.37 capsid. |
| 1 | AAVrh.K | | CAPN3 | 825 | Payload comprising a CAPN3 gene or variant thereof packaged within a AAVrh.K capsid. |
| 1 | AAVrh.39 | | CAPN3 | 825 | Payload comprising a CAPN3 gene or variant thereof packaged within a AAVrh.39 capsid. |
| 1 | AAVrh.9 | | CAPN3 | 825 | Payload comprising a CAPN3 gene or variant thereof packaged within a AAVrh.9 capsid. |
| 1 | avian AAV | | CAPN3 | 825 | Payload comprising a CAPN3 gene or variant thereof packaged within a avian capsid. |

Fig. 29 (Continued)

| | | | | | |
|---|---|---|---|---|---|
| 1 | bovine AAV | | CAPN3 | 825 | Payload comprising a CAPN3 gene or variant thereof packaged within a bovine capsid. |
| 1 | canine AAV | | CAPN3 | 825 | Payload comprising a CAPN3 gene or variant thereof packaged within a canine capsid. |
| 1 | equine AAV | | CAPN3 | 825 | Payload comprising a CAPN3 gene or variant thereof packaged within a equine capsid. |
| 1 | primate AAV | | CAPN3 | 825 | Payload comprising a CAPN3 gene or variant thereof packaged within a primate capsid. |
| 1 | non-primate AAV | | CAPN3 | 825 | Payload comprising a CAPN3 gene or variant thereof packaged within a non-primate capsid. |
| 1 | ovine AAV | | CAPN3 | 825 | Payload comprising a CAPN3 gene or variant thereof packaged within a ovine capsid. |
| 1 | hybrid AAV | | CAPN3 | 825 | Payload comprising a CAPN3 gene or variant thereof packaged within a hybrid capsid. |
| 1 | chimeric AAV | | CAPN3 | 825 | Payload comprising a CAPN3 gene or variant thereof packaged within a chimeric capsid. |
| 2 | AAV1 | 1450374 | CAPN3 | 825 | Payload comprising a CAPN3 gene or variant thereof packaged within a AAV1 capsid. |
| 2 | AAV2 | | CAPN3 | 825 | Payload comprising a CAPN3 gene or variant thereof packaged within a AAV2 capsid. |
| 2 | AAV3 | | CAPN3 | 825 | Payload comprising a CAPN3 gene or variant thereof packaged within a AAV3 capsid. |
| 2 | AAV4 | 1446389 | CAPN3 | 825 | Payload comprising a CAPN3 gene or variant thereof packaged within a AAV4 capsid. |
| 2 | AAV5 | | CAPN3 | 825 | Payload comprising a CAPN3 gene or variant thereof packaged within a AAV5 capsid. |
| 2 | AAV6 | | CAPN3 | 825 | Payload comprising a CAPN3 gene or variant thereof packaged within a AAV6 capsid. |
| 2 | AAV7 | | CAPN3 | 825 | Payload comprising a CAPN3 gene or variant thereof packaged within a AAV7 capsid. |
| 2 | AAV8 | 5075992 | CAPN3 | 825 | Payload comprising a CAPN3 gene or variant thereof packaged within a AAV8 capsid. |
| 2 | AAV9 | | CAPN3 | 825 | Payload comprising a CAPN3 gene or variant thereof packaged within a AAV9 capsid. |

Fig. 29 (Continued)

| | | | | | |
|---|---|---|---|---|---|
| 2 | AAV10 | | CAPN3 | 825 | Payload comprising a CAPN3 gene or variant thereof packaged within a AAV10 capsid. |
| 2 | AAV11 | | CAPN3 | 825 | Payload comprising a CAPN3 gene or variant thereof packaged within a AAV11 capsid. |
| 2 | AAVC11.01 | | CAPN3 | 825 | Payload comprising a CAPN3 gene or variant thereof packaged within a AAVC11.01 capsid. |
| 2 | AAVC11.02 | | CAPN3 | 825 | Payload comprising a CAPN3 gene or variant thereof packaged within a AAVC11.02 capsid. |
| 2 | AAVC11.03 | | CAPN3 | 825 | Payload comprising a CAPN3 gene or variant thereof packaged within a AAVC11.03 capsid. |
| 2 | AAVC11.04 | | CAPN3 | 825 | Payload comprising a CAPN3 gene or variant thereof packaged within a AAVC11.04 capsid. |
| 2 | AAVC11.05 | | CAPN3 | 825 | Payload comprising a CAPN3 gene or variant thereof packaged within a AAVC11.05 capsid. |
| 2 | AAVC11.06 | | CAPN3 | 825 | Payload comprising a CAPN3 gene or variant thereof packaged within a AAVC11.06 capsid. |
| 2 | AAVC11.07 | | CAPN3 | 825 | Payload comprising a CAPN3 gene or variant thereof packaged within a AAVC11.07 capsid. |
| 2 | AAVC11.08 | | CAPN3 | 825 | Payload comprising a CAPN3 gene or variant thereof packaged within a AAVC11.08 capsid. |
| 2 | AAVC11.09 | | CAPN3 | 825 | Payload comprising a CAPN3 gene or variant thereof packaged within a AAVC11.09 capsid. |
| 2 | AAVC11.10 | | CAPN3 | 825 | Payload comprising a CAPN3 gene or variant thereof packaged within a AAVC11.10 capsid. |
| 2 | AAVC11.11 | | CAPN3 | 825 | Payload comprising a CAPN3 gene or variant thereof packaged within a AAVC11.11 capsid. |
| 2 | AAVC11.12 | | CAPN3 | 825 | Payload comprising a CAPN3 gene or variant thereof packaged within a AAVC11.12 capsid. |
| 2 | AAVC11.13 | | CAPN3 | 825 | Payload comprising a CAPN3 gene or variant thereof packaged within a AAVC11.13 capsid. |
| 2 | AAVC11.14 | | CAPN3 | 825 | Payload comprising a CAPN3 gene or variant thereof packaged within a AAVC11.14 capsid. |
| 2 | AAVC11.15 | | CAPN3 | 825 | Payload comprising a CAPN3 gene or variant thereof packaged within a AAVC11.15 capsid. |

Fig. 29 (Continued)

| | | | | | |
|---|---|---|---|---|---|
| 2 | AAVC11.16 | | CAPN3 | 825 | Payload comprising a CAPN3 gene or variant thereof packaged within a AAVC11.16 capsid. |
| 2 | AAVC11.17 | | CAPN3 | 825 | Payload comprising a CAPN3 gene or variant thereof packaged within a AAVC11.17 capsid. |
| 2 | AAVC11.18 | | CAPN3 | 825 | Payload comprising a CAPN3 gene or variant thereof packaged within a AAVC11.18 capsid. |
| 2 | AAVC11.19 | | CAPN3 | 825 | Payload comprising a CAPN3 gene or variant thereof packaged within a AAVC11.19 capsid. |
| 2 | AAV12 | | CAPN3 | 825 | Payload comprising a CAPN3 gene or variant thereof packaged within a AAV12 capsid. |
| 2 | AAV13 | | CAPN3 | 825 | Payload comprising a CAPN3 gene or variant thereof packaged within a AAV13 capsid. |
| 2 | AAV-DJ | | CAPN3 | 825 | Payload comprising a CAPN3 gene or variant thereof packaged within a AAV-DJ capsid. |
| 2 | AAV-LK03 | | CAPN3 | 825 | Payload comprising a CAPN3 gene or variant thereof packaged within a AAV-LK03 capsid. |
| 2 | AAV-LK19 | | CAPN3 | 825 | Payload comprising a CAPN3 gene or variant thereof packaged within a AAV-LK19 capsid. |
| 2 | AAVrh.74 | | CAPN3 | 825 | Payload comprising a CAPN3 gene or variant thereof packaged within a AAVrh.74 capsid. |
| 2 | AAVrh.10 | | CAPN3 | 825 | Payload comprising a CAPN3 gene or variant thereof packaged within a AAVrh.10 capsid. |
| 2 | AAVhu.37 | | CAPN3 | 825 | Payload comprising a CAPN3 gene or variant thereof packaged within a AAVhu.37 capsid. |
| 2 | AAVrh.K | | CAPN3 | 825 | Payload comprising a CAPN3 gene or variant thereof packaged within a AAVrh.K capsid. |
| 2 | AAVrh.39 | | CAPN3 | 825 | Payload comprising a CAPN3 gene or variant thereof packaged within a AAVrh.39 capsid. |
| 2 | AAVrh.9 | | CAPN3 | 825 | Payload comprising a CAPN3 gene or variant thereof packaged within a AAVrh.9 capsid. |
| 2 | avian AAV | | CAPN3 | 825 | Payload comprising a CAPN3 gene or variant thereof packaged within a avian capsid. |

Fig. 29 (Continued)

| | | | | | |
|---|---|---|---|---|---|
| 2 | bovine AAV | | CAPN3 | 825 | Payload comprising a CAPN3 gene or variant thereof packaged within a bovine capsid. |
| 2 | canine AAV | | CAPN3 | 825 | Payload comprising a CAPN3 gene or variant thereof packaged within a canine capsid. |
| 2 | equine AAV | | CAPN3 | 825 | Payload comprising a CAPN3 gene or variant thereof packaged within a equine capsid. |
| 2 | primate AAV | | CAPN3 | 825 | Payload comprising a CAPN3 gene or variant thereof packaged within a primate capsid. |
| 2 | non-primate AAV | | CAPN3 | 825 | Payload comprising a CAPN3 gene or variant thereof packaged within a non-primate capsid. |
| 2 | ovine AAV | | CAPN3 | 825 | Payload comprising a CAPN3 gene or variant thereof packaged within a ovine capsid. |
| 2 | hybrid AAV | | CAPN3 | 825 | Payload comprising a CAPN3 gene or variant thereof packaged within a hybrid capsid. |
| 2 | chimeric AAV | | CAPN3 | 875 | Payload comprising a CAPN3 gene or variant thereof packaged within a chimeric capsid. |
| 1 | AAV1 | 1450374 | CBS | 875 | Payload comprising a CBS gene or variant thereof packaged within a AAV1 capsid. |
| 1 | AAV2 | | CBS | 875 | Payload comprising a CBS gene or variant thereof packaged within a AAV2 capsid. |
| 1 | AAV3 | | CBS | 875 | Payload comprising a CBS gene or variant thereof packaged within a AAV3 capsid. |
| 1 | AAV4 | 1446389 | CBS | 875 | Payload comprising a CBS gene or variant thereof packaged within a AAV4 capsid. |
| 1 | AAV5 | | CBS | 875 | Payload comprising a CBS gene or variant thereof packaged within a AAV5 capsid. |
| 1 | AAV6 | | CBS | 875 | Payload comprising a CBS gene or variant thereof packaged within a AAV6 capsid. |
| 1 | AAV7 | | CBS | 875 | Payload comprising a CBS gene or variant thereof packaged within a AAV7 capsid. |
| 1 | AAV8 | 5075992 | CBS | 875 | Payload comprising a CBS gene or variant thereof packaged within a AAV8 capsid. |
| 1 | AAV9 | | CBS | 875 | Payload comprising a CBS gene or variant thereof packaged within a AAV9 capsid. |

Fig. 29 (Continued)

| | | | | | |
|---|---|---|---|---|---|
| 1 | AAV10 | | CBS | 875 | Payload comprising a CBS gene or variant thereof packaged within a AAV10 capsid. |
| 1 | AAV11 | | CBS | 875 | Payload comprising a CBS gene or variant thereof packaged within a AAV11 capsid. |
| 1 | AAVC11.01 | | CBS | 875 | Payload comprising a CBS gene or variant thereof packaged within a AAVC11.01 capsid. |
| 1 | AAVC11.02 | | CBS | 875 | Payload comprising a CBS gene or variant thereof packaged within a AAVC11.02 capsid. |
| 1 | AAVC11.03 | | CBS | 875 | Payload comprising a CBS gene or variant thereof packaged within a AAVC11.03 capsid. |
| 1 | AAVC11.04 | | CBS | 875 | Payload comprising a CBS gene or variant thereof packaged within a AAVC11.04 capsid. |
| 1 | AAVC11.05 | | CBS | 875 | Payload comprising a CBS gene or variant thereof packaged within a AAVC11.05 capsid. |
| 1 | AAVC11.06 | | CBS | 875 | Payload comprising a CBS gene or variant thereof packaged within a AAVC11.06 capsid. |
| 1 | AAVC11.07 | | CBS | 875 | Payload comprising a CBS gene or variant thereof packaged within a AAVC11.07 capsid. |
| 1 | AAVC11.08 | | CBS | 875 | Payload comprising a CBS gene or variant thereof packaged within a AAVC11.08 capsid. |
| 1 | AAVC11.09 | | CBS | 875 | Payload comprising a CBS gene or variant thereof packaged within a AAVC11.09 capsid. |
| 1 | AAVC11.10 | | CBS | 875 | Payload comprising a CBS gene or variant thereof packaged within a AAVC11.10 capsid. |
| 1 | AAVC11.11 | | CBS | 875 | Payload comprising a CBS gene or variant thereof packaged within a AAVC11.11 capsid. |
| 1 | AAVC11.12 | | CBS | 875 | Payload comprising a CBS gene or variant thereof packaged within a AAVC11.12 capsid. |
| 1 | AAVC11.13 | | CBS | 875 | Payload comprising a CBS gene or variant thereof packaged within a AAVC11.13 capsid. |
| 1 | AAVC11.14 | | CBS | 875 | Payload comprising a CBS gene or variant thereof packaged within a AAVC11.14 capsid. |
| 1 | AAVC11.15 | | CBS | 875 | Payload comprising a CBS gene or variant thereof packaged within a AAVC11.15 capsid. |

Fig. 29 (Continued)

| | | | | | |
|---|---|---|---|---|---|
| 1 | AAVC11.16 | | CBS | 875 | Payload comprising a CBS gene or variant thereof packaged within a AAVC11.16 capsid. |
| 1 | AAVC11.17 | | CBS | 875 | Payload comprising a CBS gene or variant thereof packaged within a AAVC11.17 capsid. |
| 1 | AAVC11.18 | | CBS | 875 | Payload comprising a CBS gene or variant thereof packaged within a AAVC11.18 capsid. |
| 1 | AAVC11.19 | | CBS | 875 | Payload comprising a CBS gene or variant thereof packaged within a AAVC11.19 capsid. |
| 1 | AAV12 | | CBS | 875 | Payload comprising a CBS gene or variant thereof packaged within a AAV12 capsid. |
| 1 | AAV13 | | CBS | 875 | Payload comprising a CBS gene or variant thereof packaged within a AAV13 capsid. |
| 1 | AAV-DJ | | CBS | 875 | Payload comprising a CBS gene or variant thereof packaged within a AAV-DJ capsid. |
| 1 | AAV-LK03 | | CBS | 875 | Payload comprising a CBS gene or variant thereof packaged within a AAV-LK03 capsid. |
| 1 | AAV-LK19 | | CBS | 875 | Payload comprising a CBS gene or variant thereof packaged within a AAV-LK19 capsid. |
| 1 | AAVrh.74 | | CBS | 875 | Payload comprising a CBS gene or variant thereof packaged within a AAVrh.74 capsid. |
| 1 | AAVrh.10 | | CBS | 875 | Payload comprising a CBS gene or variant thereof packaged within a AAVrh.10 capsid. |
| 1 | AAVhu.37 | | CBS | 875 | Payload comprising a CBS gene or variant thereof packaged within a AAVhu.37 capsid. |
| 1 | AAVrh.K | | CBS | 875 | Payload comprising a CBS gene or variant thereof packaged within a AAVrh.K capsid. |
| 1 | AAVrh.39 | | CBS | 875 | Payload comprising a CBS gene or variant thereof packaged within a AAVrh.39 capsid. |
| 1 | AAVrh.9 | | CBS | 875 | Payload comprising a CBS gene or variant thereof packaged within a AAVrh.9 capsid. |
| 1 | avian AAV | | CBS | 875 | Payload comprising a CBS gene or variant thereof packaged within a avian capsid. |

Fig. 29 (Continued)

| | | | | | |
|---|---|---|---|---|---|
| 1 | bovine AAV | | CBS | 875 | Payload comprising a CBS gene or variant thereof packaged within a bovine capsid. |
| 1 | canine AAV | | CBS | 875 | Payload comprising a CBS gene or variant thereof packaged within a canine capsid. |
| 1 | equine AAV | | CBS | 875 | Payload comprising a CBS gene or variant thereof packaged within a equine capsid. |
| 1 | primate AAV | | CBS | 875 | Payload comprising a CBS gene or variant thereof packaged within a primate capsid. |
| 1 | non-primate AAV | | CBS | 875 | Payload comprising a CBS gene or variant thereof packaged within a non-primate capsid. |
| 1 | ovine AAV | | CBS | 875 | Payload comprising a CBS gene or variant thereof packaged within a ovine capsid. |
| 1 | hybrid AAV | | CBS | 875 | Payload comprising a CBS gene or variant thereof packaged within a hybrid capsid. |
| 1 | chimeric AAV | | CBS | 875 | Payload comprising a CBS gene or variant thereof packaged within a chimeric capsid. |
| 2 | AAV1 | 1450374 | CBS | 875 | Payload comprising a CBS gene or variant thereof packaged within a AAV1 capsid. |
| 2 | AAV2 | | CBS | 875 | Payload comprising a CBS gene or variant thereof packaged within a AAV2 capsid. |
| 2 | AAV3 | | CBS | 875 | Payload comprising a CBS gene or variant thereof packaged within a AAV3 capsid. |
| 2 | AAV4 | 1446389 | CBS | 875 | Payload comprising a CBS gene or variant thereof packaged within a AAV4 capsid. |
| 2 | AAV5 | | CBS | 875 | Payload comprising a CBS gene or variant thereof packaged within a AAV5 capsid. |
| 2 | AAV6 | | CBS | 875 | Payload comprising a CBS gene or variant thereof packaged within a AAV6 capsid. |
| 2 | AAV7 | | CBS | 875 | Payload comprising a CBS gene or variant thereof packaged within a AAV7 capsid. |
| 2 | AAV8 | 5075992 | CBS | 875 | Payload comprising a CBS gene or variant thereof packaged within a AAV8 capsid. |
| 2 | AAV9 | | CBS | 875 | Payload comprising a CBS gene or variant thereof packaged within a AAV9 capsid. |

Fig. 29 (Continued)

| | | | | | |
|---|---|---|---|---|---|
| 2 | AAV10 | | CBS | 875 | Payload comprising a CBS gene or variant thereof packaged within a AAV10 capsid. |
| 2 | AAV11 | | CBS | 875 | Payload comprising a CBS gene or variant thereof packaged within a AAV11 capsid. |
| 2 | AAVC11.01 | | CBS | 875 | Payload comprising a CBS gene or variant thereof packaged within a AAVC11.01 capsid. |
| 2 | AAVC11.02 | | CBS | 875 | Payload comprising a CBS gene or variant thereof packaged within a AAVC11.02 capsid. |
| 2 | AAVC11.03 | | CBS | 875 | Payload comprising a CBS gene or variant thereof packaged within a AAVC11.03 capsid. |
| 2 | AAVC11.04 | | CBS | 875 | Payload comprising a CBS gene or variant thereof packaged within a AAVC11.04 capsid. |
| 2 | AAVC11.05 | | CBS | 875 | Payload comprising a CBS gene or variant thereof packaged within a AAVC11.05 capsid. |
| 2 | AAVC11.06 | | CBS | 875 | Payload comprising a CBS gene or variant thereof packaged within a AAVC11.06 capsid. |
| 2 | AAVC11.07 | | CBS | 875 | Payload comprising a CBS gene or variant thereof packaged within a AAVC11.07 capsid. |
| 2 | AAVC11.08 | | CBS | 875 | Payload comprising a CBS gene or variant thereof packaged within a AAVC11.08 capsid. |
| 2 | AAVC11.09 | | CBS | 875 | Payload comprising a CBS gene or variant thereof packaged within a AAVC11.09 capsid. |
| 2 | AAVC11.10 | | CBS | 875 | Payload comprising a CBS gene or variant thereof packaged within a AAVC11.10 capsid. |
| 2 | AAVC11.11 | | CBS | 875 | Payload comprising a CBS gene or variant thereof packaged within a AAVC11.11 capsid. |
| 2 | AAVC11.12 | | CBS | 875 | Payload comprising a CBS gene or variant thereof packaged within a AAVC11.12 capsid. |
| 2 | AAVC11.13 | | CBS | 875 | Payload comprising a CBS gene or variant thereof packaged within a AAVC11.13 capsid. |
| 2 | AAVC11.14 | | CBS | 875 | Payload comprising a CBS gene or variant thereof packaged within a AAVC11.14 capsid. |
| 2 | AAVC11.15 | | CBS | 875 | Payload comprising a CBS gene or variant thereof packaged within a AAVC11.15 capsid. |

Fig. 29 (Continued)

| | | | | | |
|---|---|---|---|---|---|
| 2 | AAVC11.16 | | CBS | 875 | Payload comprising a CBS gene or variant thereof packaged within a AAVC11.16 capsid. |
| 2 | AAVC11.17 | | CBS | 875 | Payload comprising a CBS gene or variant thereof packaged within a AAVC11.17 capsid. |
| 2 | AAVC11.18 | | CBS | 875 | Payload comprising a CBS gene or variant thereof packaged within a AAVC11.18 capsid. |
| 2 | AAVC11.19 | | CBS | 875 | Payload comprising a CBS gene or variant thereof packaged within a AAVC11.19 capsid. |
| 2 | AAV12 | | CBS | 875 | Payload comprising a CBS gene or variant thereof packaged within a AAV12 capsid. |
| 2 | AAV13 | | CBS | 875 | Payload comprising a CBS gene or variant thereof packaged within a AAV13 capsid. |
| 2 | AAV-DJ | | CBS | 875 | Payload comprising a CBS gene or variant thereof packaged within a AAV-DJ capsid. |
| 2 | AAV-LK03 | | CBS | 875 | Payload comprising a CBS gene or variant thereof packaged within a AAV-LK03 capsid. |
| 2 | AAV-LK19 | | CBS | 875 | Payload comprising a CBS gene or variant thereof packaged within a AAV-LK19 capsid. |
| 2 | AAVrh.74 | | CBS | 875 | Payload comprising a CBS gene or variant thereof packaged within a AAVrh.74 capsid. |
| 2 | AAVrh.10 | | CBS | 875 | Payload comprising a CBS gene or variant thereof packaged within a AAVrh.10 capsid. |
| 2 | AAVhu.37 | | CBS | 875 | Payload comprising a CBS gene or variant thereof packaged within a AAVhu.37 capsid. |
| 2 | AAVrh.K | | CBS | 875 | Payload comprising a CBS gene or variant thereof packaged within a AAVrh.K capsid. |
| 2 | AAVrh.39 | | CBS | 875 | Payload comprising a CBS gene or variant thereof packaged within a AAVrh.39 capsid. |
| 2 | AAVrh.9 | | CBS | 875 | Payload comprising a CBS gene or variant thereof packaged within a AAVrh.9 capsid. |
| 2 | avian AAV | | CBS | 875 | Payload comprising a CBS gene or variant thereof packaged within a avian capsid. |

Fig. 29 (Continued)

| | | | | | |
|---|---|---|---|---|---|
| 2 | bovine AAV | | CBS | 875 | Payload comprising a CBS gene or variant thereof packaged within a bovine capsid. |
| 2 | canine AAV | | CBS | 875 | Payload comprising a CBS gene or variant thereof packaged within a canine capsid. |
| 2 | equine AAV | | CBS | 875 | Payload comprising a CBS gene or variant thereof packaged within a equine capsid. |
| 2 | primate AAV | | CBS | 875 | Payload comprising a CBS gene or variant thereof packaged within a primate capsid. |
| 2 | non-primate AAV | | CBS | 875 | Payload comprising a CBS gene or variant thereof packaged within a non-primate capsid. |
| 2 | ovine AAV | | CBS | 875 | Payload comprising a CBS gene or variant thereof packaged within a ovine capsid. |
| 2 | hybrid AAV | | CBS | 875 | Payload comprising a CBS gene or variant thereof packaged within a hybrid capsid. |
| 2 | chimeric AAV | | CBS | 875 | Payload comprising a CBS gene or variant thereof packaged within a chimeric capsid. |
| 1 | AAV1 | 1450374 | COL17A1 | 1308 | Payload comprising a COL17A1 gene or variant thereof packaged within a AAV1 capsid. |
| 1 | AAV2 | | COL17A1 | 1308 | Payload comprising a COL17A1 gene or variant thereof packaged within a AAV2 capsid. |
| 1 | AAV3 | | COL17A1 | 1308 | Payload comprising a COL17A1 gene or variant thereof packaged within a AAV3 capsid. |
| 1 | AAV4 | 1446389 | COL17A1 | 1308 | Payload comprising a COL17A1 gene or variant thereof packaged within a AAV4 capsid. |
| 1 | AAV5 | | COL17A1 | 1308 | Payload comprising a COL17A1 gene or variant thereof packaged within a AAV5 capsid. |
| 1 | AAV6 | | COL17A1 | 1308 | Payload comprising a COL17A1 gene or variant thereof packaged within a AAV6 capsid. |
| 1 | AAV7 | | COL17A1 | 1308 | Payload comprising a COL17A1 gene or variant thereof packaged within a AAV7 capsid. |
| 1 | AAV8 | 5075992 | COL17A1 | 1308 | Payload comprising a COL17A1 gene or variant thereof packaged within a AAV8 capsid. |
| 1 | AAV9 | | COL17A1 | 1308 | Payload comprising a COL17A1 gene or variant thereof packaged within a AAV9 capsid. |

Fig. 29 (Continued)

| | | | | | |
|---|---|---|---|---|---|
| 1 | AAV10 | | COL17A1 | 1308 | Payload comprising a COL17A1 gene or variant thereof packaged within a AAV10 capsid. |
| 1 | AAV11 | | COL17A1 | 1308 | Payload comprising a COL17A1 gene or variant thereof packaged within a AAV11 capsid. |
| 1 | AAVC11.01 | | COL17A1 | 1308 | Payload comprising a COL17A1 gene or variant thereof packaged within a AAVC11.01 capsid. |
| 1 | AAVC11.02 | | COL17A1 | 1308 | Payload comprising a COL17A1 gene or variant thereof packaged within a AAVC11.02 capsid. |
| 1 | AAVC11.03 | | COL17A1 | 1308 | Payload comprising a COL17A1 gene or variant thereof packaged within a AAVC11.03 capsid. |
| 1 | AAVC11.04 | | COL17A1 | 1308 | Payload comprising a COL17A1 gene or variant thereof packaged within a AAVC11.04 capsid. |
| 1 | AAVC11.05 | | COL17A1 | 1308 | Payload comprising a COL17A1 gene or variant thereof packaged within a AAVC11.05 capsid. |
| 1 | AAVC11.06 | | COL17A1 | 1308 | Payload comprising a COL17A1 gene or variant thereof packaged within a AAVC11.06 capsid. |
| 1 | AAVC11.07 | | COL17A1 | 1308 | Payload comprising a COL17A1 gene or variant thereof packaged within a AAVC11.07 capsid. |
| 1 | AAVC11.08 | | COL17A1 | 1308 | Payload comprising a COL17A1 gene or variant thereof packaged within a AAVC11.08 capsid. |
| 1 | AAVC11.09 | | COL17A1 | 1308 | Payload comprising a COL17A1 gene or variant thereof packaged within a AAVC11.09 capsid. |
| 1 | AAVC11.10 | | COL17A1 | 1308 | Payload comprising a COL17A1 gene or variant thereof packaged within a AAVC11.10 capsid. |
| 1 | AAVC11.11 | | COL17A1 | 1308 | Payload comprising a COL17A1 gene or variant thereof packaged within a AAVC11.11 capsid. |
| 1 | AAVC11.12 | | COL17A1 | 1308 | Payload comprising a COL17A1 gene or variant thereof packaged within a AAVC11.12 capsid. |
| 1 | AAVC11.13 | | COL17A1 | 1308 | Payload comprising a COL17A1 gene or variant thereof packaged within a AAVC11.13 capsid. |
| 1 | AAVC11.14 | | COL17A1 | 1308 | Payload comprising a COL17A1 gene or variant thereof packaged within a AAVC11.14 capsid. |
| 1 | AAVC11.15 | | COL17A1 | 1308 | Payload comprising a COL17A1 gene or variant thereof packaged within a AAVC11.15 capsid. |

Fig. 29 (Continued)

| | | | | | |
|---|---|---|---|---|---|
| 1 | AAVC11.16 | | COL17A1 | 1308 | Payload comprising a COL17A1 gene or variant thereof packaged within a AAVC11.16 capsid. |
| 1 | AAVC11.17 | | COL17A1 | 1308 | Payload comprising a COL17A1 gene or variant thereof packaged within a AAVC11.17 capsid. |
| 1 | AAVC11.18 | | COL17A1 | 1308 | Payload comprising a COL17A1 gene or variant thereof packaged within a AAVC11.18 capsid. |
| 1 | AAVC11.19 | | COL17A1 | 1308 | Payload comprising a COL17A1 gene or variant thereof packaged within a AAVC11.19 capsid. |
| 1 | AAV12 | | COL17A1 | 1308 | Payload comprising a COL17A1 gene or variant thereof packaged within a AAV12 capsid. |
| 1 | AAV13 | | COL17A1 | 1308 | Payload comprising a COL17A1 gene or variant thereof packaged within a AAV13 capsid. |
| 1 | AAV-DJ | | COL17A1 | 1308 | Payload comprising a COL17A1 gene or variant thereof packaged within a AAV-DJ capsid. |
| 1 | AAV-LK03 | | COL17A1 | 1308 | Payload comprising a COL17A1 gene or variant thereof packaged within a AAV-LK03 capsid. |
| 1 | AAV-LK19 | | COL17A1 | 1308 | Payload comprising a COL17A1 gene or variant thereof packaged within a AAV-LK19 capsid. |
| 1 | AAVrh.74 | | COL17A1 | 1308 | Payload comprising a COL17A1 gene or variant thereof packaged within a AAVrh.74 capsid. |
| 1 | AAVrh.10 | | COL17A1 | 1308 | Payload comprising a COL17A1 gene or variant thereof packaged within a AAVrh.10 capsid. |
| 1 | AAVhu.37 | | COL17A1 | 1308 | Payload comprising a COL17A1 gene or variant thereof packaged within a AAVhu.37 capsid. |
| 1 | AAVrh.K | | COL17A1 | 1308 | Payload comprising a COL17A1 gene or variant thereof packaged within a AAVrh.K capsid. |
| 1 | AAVrh.39 | | COL17A1 | 1308 | Payload comprising a COL17A1 gene or variant thereof packaged within a AAVrh.39 capsid. |
| 1 | AAVrh.9 | | COL17A1 | 1308 | Payload comprising a COL17A1 gene or variant thereof packaged within a AAVrh.9 capsid. |
| 1 | avian AAV | | COL17A1 | 1308 | Payload comprising a COL17A1 gene or variant thereof packaged within a avian capsid. |

Fig. 29 (Continued)

| | | | | | |
|---|---|---|---|---|---|
| 1 | bovine AAV | | COL17A1 | 1308 | Payload comprising a COL17A1 gene or variant thereof packaged within a bovine capsid. |
| 1 | canine AAV | | COL17A1 | 1308 | Payload comprising a COL17A1 gene or variant thereof packaged within a canine capsid. |
| 1 | equine AAV | | COL17A1 | 1308 | Payload comprising a COL17A1 gene or variant thereof packaged within a equine capsid. |
| 1 | primate AAV | | COL17A1 | 1308 | Payload comprising a COL17A1 gene or variant thereof packaged within a primate capsid. |
| 1 | non-primate AAV | | COL17A1 | 1308 | Payload comprising a COL17A1 gene or variant thereof packaged within a non-primate capsid. |
| 1 | ovine AAV | | COL17A1 | 1308 | Payload comprising a COL17A1 gene or variant thereof packaged within a ovine capsid. |
| 1 | hybrid AAV | | COL17A1 | 1308 | Payload comprising a COL17A1 gene or variant thereof packaged within a hybrid capsid. |
| 1 | chimeric AAV | | COL17A1 | 1308 | Payload comprising a COL17A1 gene or variant thereof packaged within a chimeric capsid. |
| 2 | AAV1 | 1450374 | COL17A1 | 1308 | Payload comprising a COL17A1 gene or variant thereof packaged within a AAV1 capsid. |
| 2 | AAV2 | | COL17A1 | 1308 | Payload comprising a COL17A1 gene or variant thereof packaged within a AAV2 capsid. |
| 2 | AAV3 | | COL17A1 | 1308 | Payload comprising a COL17A1 gene or variant thereof packaged within a AAV3 capsid. |
| 2 | AAV4 | 1446389 | COL17A1 | 1308 | Payload comprising a COL17A1 gene or variant thereof packaged within a AAV4 capsid. |
| 2 | AAV5 | | COL17A1 | 1308 | Payload comprising a COL17A1 gene or variant thereof packaged within a AAV5 capsid. |
| 2 | AAV6 | | COL17A1 | 1308 | Payload comprising a COL17A1 gene or variant thereof packaged within a AAV6 capsid. |
| 2 | AAV7 | | COL17A1 | 1308 | Payload comprising a COL17A1 gene or variant thereof packaged within a AAV7 capsid. |
| 2 | AAV8 | 5075992 | COL17A1 | 1308 | Payload comprising a COL17A1 gene or variant thereof packaged within a AAV8 capsid. |
| 2 | AAV9 | | COL17A1 | 1308 | Payload comprising a COL17A1 gene or variant thereof packaged within a AAV9 capsid. |

Fig. 29 (Continued)

| | | | | | |
|---|---|---|---|---|---|
| 2 | AAV10 | | COL17A1 | 1308 | Payload comprising a COL17A1 gene or variant thereof packaged within a AAV10 capsid. |
| 2 | AAV11 | | COL17A1 | 1308 | Payload comprising a COL17A1 gene or variant thereof packaged within a AAV11 capsid. |
| 2 | AAVC11.01 | | COL17A1 | 1308 | Payload comprising a COL17A1 gene or variant thereof packaged within a AAVC11.01 capsid. |
| 2 | AAVC11.02 | | COL17A1 | 1308 | Payload comprising a COL17A1 gene or variant thereof packaged within a AAVC11.02 capsid. |
| 2 | AAVC11.03 | | COL17A1 | 1308 | Payload comprising a COL17A1 gene or variant thereof packaged within a AAVC11.03 capsid. |
| 2 | AAVC11.04 | | COL17A1 | 1308 | Payload comprising a COL17A1 gene or variant thereof packaged within a AAVC11.04 capsid. |
| 2 | AAVC11.05 | | COL17A1 | 1308 | Payload comprising a COL17A1 gene or variant thereof packaged within a AAVC11.05 capsid. |
| 2 | AAVC11.06 | | COL17A1 | 1308 | Payload comprising a COL17A1 gene or variant thereof packaged within a AAVC11.06 capsid. |
| 2 | AAVC11.07 | | COL17A1 | 1308 | Payload comprising a COL17A1 gene or variant thereof packaged within a AAVC11.07 capsid. |
| 2 | AAVC11.08 | | COL17A1 | 1308 | Payload comprising a COL17A1 gene or variant thereof packaged within a AAVC11.08 capsid. |
| 2 | AAVC11.09 | | COL17A1 | 1308 | Payload comprising a COL17A1 gene or variant thereof packaged within a AAVC11.09 capsid. |
| 2 | AAVC11.10 | | COL17A1 | 1308 | Payload comprising a COL17A1 gene or variant thereof packaged within a AAVC11.10 capsid. |
| 2 | AAVC11.11 | | COL17A1 | 1308 | Payload comprising a COL17A1 gene or variant thereof packaged within a AAVC11.11 capsid. |
| 2 | AAVC11.12 | | COL17A1 | 1308 | Payload comprising a COL17A1 gene or variant thereof packaged within a AAVC11.12 capsid. |
| 2 | AAVC11.13 | | COL17A1 | 1308 | Payload comprising a COL17A1 gene or variant thereof packaged within a AAVC11.13 capsid. |
| 2 | AAVC11.14 | | COL17A1 | 1308 | Payload comprising a COL17A1 gene or variant thereof packaged within a AAVC11.14 capsid. |
| 2 | AAVC11.15 | | COL17A1 | 1308 | Payload comprising a COL17A1 gene or variant thereof packaged within a AAVC11.15 capsid. |

Fig. 29 (Continued)

| | | | | | |
|---|---|---|---|---|---|
| 2 | AAVC11.16 | | COL17A1 | 1308 | Payload comprising a COL17A1 gene or variant thereof packaged within a AAVC11.16 capsid. |
| 2 | AAVC11.17 | | COL17A1 | 1308 | Payload comprising a COL17A1 gene or variant thereof packaged within a AAVC11.17 capsid. |
| 2 | AAVC11.18 | | COL17A1 | 1308 | Payload comprising a COL17A1 gene or variant thereof packaged within a AAVC11.18 capsid. |
| 2 | AAVC11.19 | | COL17A1 | 1308 | Payload comprising a COL17A1 gene or variant thereof packaged within a AAVC11.19 capsid. |
| 2 | AAV12 | | COL17A1 | 1308 | Payload comprising a COL17A1 gene or variant thereof packaged within a AAV12 capsid. |
| 2 | AAV13 | | COL17A1 | 1308 | Payload comprising a COL17A1 gene or variant thereof packaged within a AAV13 capsid. |
| 2 | AAV-DJ | | COL17A1 | 1308 | Payload comprising a COL17A1 gene or variant thereof packaged within a AAV-DJ capsid. |
| 2 | AAV-LK03 | | COL17A1 | 1308 | Payload comprising a COL17A1 gene or variant thereof packaged within a AAV-LK03 capsid. |
| 2 | AAV-LK19 | | COL17A1 | 1308 | Payload comprising a COL17A1 gene or variant thereof packaged within a AAV-LK19 capsid. |
| 2 | AAVrh.74 | | COL17A1 | 1308 | Payload comprising a COL17A1 gene or variant thereof packaged within a AAVrh.74 capsid. |
| 2 | AAVrh.10 | | COL17A1 | 1308 | Payload comprising a COL17A1 gene or variant thereof packaged within a AAVrh.10 capsid. |
| 2 | AAVhu.37 | | COL17A1 | 1308 | Payload comprising a COL17A1 gene or variant thereof packaged within a AAVhu.37 capsid. |
| 2 | AAVrh.K | | COL17A1 | 1308 | Payload comprising a COL17A1 gene or variant thereof packaged within a AAVrh.K capsid. |
| 2 | AAVrh.39 | | COL17A1 | 1308 | Payload comprising a COL17A1 gene or variant thereof packaged within a AAVrh.39 capsid. |
| 2 | AAVrh.9 | | COL17A1 | 1308 | Payload comprising a COL17A1 gene or variant thereof packaged within a AAVrh.9 capsid. |
| 2 | avian AAV | | COL17A1 | 1308 | Payload comprising a COL17A1 gene or variant thereof packaged within a avian capsid. |

Fig. 29 (Continued)

| | | | | | |
|---|---|---|---|---|---|
| 2 | bovine AAV | | COL17A1 | 1308 | Payload comprising a COL17A1 gene or variant thereof packaged within a bovine capsid. |
| 2 | canine AAV | | COL17A1 | 1308 | Payload comprising a COL17A1 gene or variant thereof packaged within a canine capsid. |
| 2 | equine AAV | | COL17A1 | 1308 | Payload comprising a COL17A1 gene or variant thereof packaged within a equine capsid. |
| 2 | primate AAV | | COL17A1 | 1308 | Payload comprising a COL17A1 gene or variant thereof packaged within a primate capsid. |
| 2 | non-primate AAV | | COL17A1 | 1308 | Payload comprising a COL17A1 gene or variant thereof packaged within a non-primate capsid. |
| 2 | ovine AAV | | COL17A1 | 1308 | Payload comprising a COL17A1 gene or variant thereof packaged within a ovine capsid. |
| 2 | hybrid AAV | | COL17A1 | 1308 | Payload comprising a COL17A1 gene or variant thereof packaged within a hybrid capsid. |
| 2 | chimeric AAV | | COL17A1 | 1308 | Payload comprising a COL17A1 gene or variant thereof packaged within a chimeric capsid. |
| 1 | AAV1 | 1450374 | COL7A1 | 1294 | Payload comprising a COL7A1 gene or variant thereof packaged within a AAV1 capsid. |
| 1 | AAV2 | | COL7A1 | 1294 | Payload comprising a COL7A1 gene or variant thereof packaged within a AAV2 capsid. |
| 1 | AAV3 | | COL7A1 | 1294 | Payload comprising a COL7A1 gene or variant thereof packaged within a AAV3 capsid. |
| 1 | AAV4 | 1446389 | COL7A1 | 1294 | Payload comprising a COL7A1 gene or variant thereof packaged within a AAV4 capsid. |
| 1 | AAV5 | | COL7A1 | 1294 | Payload comprising a COL7A1 gene or variant thereof packaged within a AAV5 capsid. |
| 1 | AAV6 | | COL7A1 | 1294 | Payload comprising a COL7A1 gene or variant thereof packaged within a AAV6 capsid. |
| 1 | AAV7 | | COL7A1 | 1294 | Payload comprising a COL7A1 gene or variant thereof packaged within a AAV7 capsid. |
| 1 | AAV8 | 5075992 | COL7A1 | 1294 | Payload comprising a COL7A1 gene or variant thereof packaged within a AAV8 capsid. |
| 1 | AAV9 | | COL7A1 | 1294 | Payload comprising a COL7A1 gene or variant thereof packaged within a AAV9 capsid. |

Fig. 29 (Continued)

| | | | | | |
|---|---|---|---|---|---|
| 1 | AAV10 | | COL7A1 | 1294 | Payload comprising a COL7A1 gene or variant thereof packaged within a AAV10 capsid. |
| 1 | AAV11 | | COL7A1 | 1294 | Payload comprising a COL7A1 gene or variant thereof packaged within a AAV11 capsid. |
| 1 | AAVC11.01 | | COL7A1 | 1294 | Payload comprising a COL7A1 gene or variant thereof packaged within a AAVC11.01 capsid. |
| 1 | AAVC11.02 | | COL7A1 | 1294 | Payload comprising a COL7A1 gene or variant thereof packaged within a AAVC11.02 capsid. |
| 1 | AAVC11.03 | | COL7A1 | 1294 | Payload comprising a COL7A1 gene or variant thereof packaged within a AAVC11.03 capsid. |
| 1 | AAVC11.04 | | COL7A1 | 1294 | Payload comprising a COL7A1 gene or variant thereof packaged within a AAVC11.04 capsid. |
| 1 | AAVC11.05 | | COL7A1 | 1294 | Payload comprising a COL7A1 gene or variant thereof packaged within a AAVC11.05 capsid. |
| 1 | AAVC11.06 | | COL7A1 | 1294 | Payload comprising a COL7A1 gene or variant thereof packaged within a AAVC11.06 capsid. |
| 1 | AAVC11.07 | | COL7A1 | 1294 | Payload comprising a COL7A1 gene or variant thereof packaged within a AAVC11.07 capsid. |
| 1 | AAVC11.08 | | COL7A1 | 1294 | Payload comprising a COL7A1 gene or variant thereof packaged within a AAVC11.08 capsid. |
| 1 | AAVC11.09 | | COL7A1 | 1294 | Payload comprising a COL7A1 gene or variant thereof packaged within a AAVC11.09 capsid. |
| 1 | AAVC11.10 | | COL7A1 | 1294 | Payload comprising a COL7A1 gene or variant thereof packaged within a AAVC11.10 capsid. |
| 1 | AAVC11.11 | | COL7A1 | 1294 | Payload comprising a COL7A1 gene or variant thereof packaged within a AAVC11.11 capsid. |
| 1 | AAVC11.12 | | COL7A1 | 1294 | Payload comprising a COL7A1 gene or variant thereof packaged within a AAVC11.12 capsid. |
| 1 | AAVC11.13 | | COL7A1 | 1294 | Payload comprising a COL7A1 gene or variant thereof packaged within a AAVC11.13 capsid. |
| 1 | AAVC11.14 | | COL7A1 | 1294 | Payload comprising a COL7A1 gene or variant thereof packaged within a AAVC11.14 capsid. |
| 1 | AAVC11.15 | | COL7A1 | 1294 | Payload comprising a COL7A1 gene or variant thereof packaged within a AAVC11.15 capsid. |

Fig. 29 (Continued)

| | | | | | |
|---|---|---|---|---|---|
| 1 | AAVC11.16 | | COL7A1 | 1294 | Payload comprising a COL7A1 gene or variant thereof packaged within a AAVC11.16 capsid. |
| 1 | AAVC11.17 | | COL7A1 | 1294 | Payload comprising a COL7A1 gene or variant thereof packaged within a AAVC11.17 capsid. |
| 1 | AAVC11.18 | | COL7A1 | 1294 | Payload comprising a COL7A1 gene or variant thereof packaged within a AAVC11.18 capsid. |
| 1 | AAVC11.19 | | COL7A1 | 1294 | Payload comprising a COL7A1 gene or variant thereof packaged within a AAVC11.19 capsid. |
| 1 | AAV12 | | COL7A1 | 1294 | Payload comprising a COL7A1 gene or variant thereof packaged within a AAV12 capsid. |
| 1 | AAV13 | | COL7A1 | 1294 | Payload comprising a COL7A1 gene or variant thereof packaged within a AAV13 capsid. |
| 1 | AAV-DJ | | COL7A1 | 1294 | Payload comprising a COL7A1 gene or variant thereof packaged within a AAV-DJ capsid. |
| 1 | AAV-LK03 | | COL7A1 | 1294 | Payload comprising a COL7A1 gene or variant thereof packaged within a AAV-LK03 capsid. |
| 1 | AAV-LK19 | | COL7A1 | 1294 | Payload comprising a COL7A1 gene or variant thereof packaged within a AAV-LK19 capsid. |
| 1 | AAVrh.74 | | COL7A1 | 1294 | Payload comprising a COL7A1 gene or variant thereof packaged within a AAVrh.74 capsid. |
| 1 | AAVrh.10 | | COL7A1 | 1294 | Payload comprising a COL7A1 gene or variant thereof packaged within a AAVrh.10 capsid. |
| 1 | AAVhu.37 | | COL7A1 | 1294 | Payload comprising a COL7A1 gene or variant thereof packaged within a AAVhu.37 capsid. |
| 1 | AAVrh.K | | COL7A1 | 1294 | Payload comprising a COL7A1 gene or variant thereof packaged within a AAVrh.K capsid. |
| 1 | AAVrh.39 | | COL7A1 | 1294 | Payload comprising a COL7A1 gene or variant thereof packaged within a AAVrh.39 capsid. |
| 1 | AAVrh.9 | | COL7A1 | 1294 | Payload comprising a COL7A1 gene or variant thereof packaged within a AAVrh.9 capsid. |
| 1 | avian AAV | | COL7A1 | 1294 | Payload comprising a COL7A1 gene or variant thereof packaged within a avian capsid. |

Fig. 29 (Continued)

| | | | | | |
|---|---|---|---|---|---|
| 1 | bovine AAV | | COL7A1 | 1294 | Payload comprising a COL7A1 gene or variant thereof packaged within a bovine capsid. |
| 1 | canine AAV | | COL7A1 | 1294 | Payload comprising a COL7A1 gene or variant thereof packaged within a canine capsid. |
| 1 | equine AAV | | COL7A1 | 1294 | Payload comprising a COL7A1 gene or variant thereof packaged within a equine capsid. |
| 1 | primate AAV | | COL7A1 | 1294 | Payload comprising a COL7A1 gene or variant thereof packaged within a primate capsid. |
| 1 | non-primate AAV | | COL7A1 | 1294 | Payload comprising a COL7A1 gene or variant thereof packaged within a non-primate capsid. |
| 1 | ovine AAV | | COL7A1 | 1294 | Payload comprising a COL7A1 gene or variant thereof packaged within a ovine capsid. |
| 1 | hybrid AAV | | COL7A1 | 1294 | Payload comprising a COL7A1 gene or variant thereof packaged within a hybrid capsid. |
| 1 | chimeric AAV | | COL7A1 | 1294 | Payload comprising a COL7A1 gene or variant thereof packaged within a chimeric capsid. |
| 2 | AAV1 | 1450374 | COL7A1 | 1294 | Payload comprising a COL7A1 gene or variant thereof packaged within a AAV1 capsid. |
| 2 | AAV2 | | COL7A1 | 1294 | Payload comprising a COL7A1 gene or variant thereof packaged within a AAV2 capsid. |
| 2 | AAV3 | | COL7A1 | 1294 | Payload comprising a COL7A1 gene or variant thereof packaged within a AAV3 capsid. |
| 2 | AAV4 | 1446389 | COL7A1 | 1294 | Payload comprising a COL7A1 gene or variant thereof packaged within a AAV4 capsid. |
| 2 | AAV5 | | COL7A1 | 1294 | Payload comprising a COL7A1 gene or variant thereof packaged within a AAV5 capsid. |
| 2 | AAV6 | | COL7A1 | 1294 | Payload comprising a COL7A1 gene or variant thereof packaged within a AAV6 capsid. |
| 2 | AAV7 | | COL7A1 | 1294 | Payload comprising a COL7A1 gene or variant thereof packaged within a AAV7 capsid. |
| 2 | AAV8 | 5075992 | COL7A1 | 1294 | Payload comprising a COL7A1 gene or variant thereof packaged within a AAV8 capsid. |
| 2 | AAV9 | | COL7A1 | 1294 | Payload comprising a COL7A1 gene or variant thereof packaged within a AAV9 capsid. |

Fig. 29 (Continued)

| | | | | | |
|---|---|---|---|---|---|
| 2 | AAV10 | | COL7A1 | 1294 | Payload comprising a COL7A1 gene or variant thereof packaged within a AAV10 capsid. |
| 2 | AAV11 | | COL7A1 | 1294 | Payload comprising a COL7A1 gene or variant thereof packaged within a AAV11 capsid. |
| 2 | AAVC11.01 | | COL7A1 | 1294 | Payload comprising a COL7A1 gene or variant thereof packaged within a AAVC11.01 capsid. |
| 2 | AAVC11.02 | | COL7A1 | 1294 | Payload comprising a COL7A1 gene or variant thereof packaged within a AAVC11.02 capsid. |
| 2 | AAVC11.03 | | COL7A1 | 1294 | Payload comprising a COL7A1 gene or variant thereof packaged within a AAVC11.03 capsid. |
| 2 | AAVC11.04 | | COL7A1 | 1294 | Payload comprising a COL7A1 gene or variant thereof packaged within a AAVC11.04 capsid. |
| 2 | AAVC11.05 | | COL7A1 | 1294 | Payload comprising a COL7A1 gene or variant thereof packaged within a AAVC11.05 capsid. |
| 2 | AAVC11.06 | | COL7A1 | 1294 | Payload comprising a COL7A1 gene or variant thereof packaged within a AAVC11.06 capsid. |
| 2 | AAVC11.07 | | COL7A1 | 1294 | Payload comprising a COL7A1 gene or variant thereof packaged within a AAVC11.07 capsid. |
| 2 | AAVC11.08 | | COL7A1 | 1294 | Payload comprising a COL7A1 gene or variant thereof packaged within a AAVC11.08 capsid. |
| 2 | AAVC11.09 | | COL7A1 | 1294 | Payload comprising a COL7A1 gene or variant thereof packaged within a AAVC11.09 capsid. |
| 2 | AAVC11.10 | | COL7A1 | 1294 | Payload comprising a COL7A1 gene or variant thereof packaged within a AAVC11.10 capsid. |
| 2 | AAVC11.11 | | COL7A1 | 1294 | Payload comprising a COL7A1 gene or variant thereof packaged within a AAVC11.11 capsid. |
| 2 | AAVC11.12 | | COL7A1 | 1294 | Payload comprising a COL7A1 gene or variant thereof packaged within a AAVC11.12 capsid. |
| 2 | AAVC11.13 | | COL7A1 | 1294 | Payload comprising a COL7A1 gene or variant thereof packaged within a AAVC11.13 capsid. |
| 2 | AAVC11.14 | | COL7A1 | 1294 | Payload comprising a COL7A1 gene or variant thereof packaged within a AAVC11.14 capsid. |
| 2 | AAVC11.15 | | COL7A1 | 1294 | Payload comprising a COL7A1 gene or variant thereof packaged within a AAVC11.15 capsid. |

Fig. 29 (Continued)

| | | | | | |
|---|---|---|---|---|---|
| 2 | AAVC11.16 | | COL7A1 | 1294 | Payload comprising a COL7A1 gene or variant thereof packaged within a AAVC11.16 capsid. |
| 2 | AAVC11.17 | | COL7A1 | 1294 | Payload comprising a COL7A1 gene or variant thereof packaged within a AAVC11.17 capsid. |
| 2 | AAVC11.18 | | COL7A1 | 1294 | Payload comprising a COL7A1 gene or variant thereof packaged within a AAVC11.18 capsid. |
| 2 | AAVC11.19 | | COL7A1 | 1294 | Payload comprising a COL7A1 gene or variant thereof packaged within a AAVC11.19 capsid. |
| 2 | AAV12 | | COL7A1 | 1294 | Payload comprising a COL7A1 gene or variant thereof packaged within a AAV12 capsid. |
| 2 | AAV13 | | COL7A1 | 1294 | Payload comprising a COL7A1 gene or variant thereof packaged within a AAV13 capsid. |
| 2 | AAV-DJ | | COL7A1 | 1294 | Payload comprising a COL7A1 gene or variant thereof packaged within a AAV-DJ capsid. |
| 2 | AAV-LK03 | | COL7A1 | 1294 | Payload comprising a COL7A1 gene or variant thereof packaged within a AAV-LK03 capsid. |
| 2 | AAV-LK19 | | COL7A1 | 1294 | Payload comprising a COL7A1 gene or variant thereof packaged within a AAV-LK19 capsid. |
| 2 | AAVrh.74 | | COL7A1 | 1294 | Payload comprising a COL7A1 gene or variant thereof packaged within a AAVrh.74 capsid. |
| 2 | AAVrh.10 | | COL7A1 | 1294 | Payload comprising a COL7A1 gene or variant thereof packaged within a AAVrh.10 capsid. |
| 2 | AAVhu.37 | | COL7A1 | 1294 | Payload comprising a COL7A1 gene or variant thereof packaged within a AAVhu.37 capsid. |
| 2 | AAVrh.K | | COL7A1 | 1294 | Payload comprising a COL7A1 gene or variant thereof packaged within a AAVrh.K capsid. |
| 2 | AAVrh.39 | | COL7A1 | 1294 | Payload comprising a COL7A1 gene or variant thereof packaged within a AAVrh.39 capsid. |
| 2 | AAVrh.9 | | COL7A1 | 1294 | Payload comprising a COL7A1 gene or variant thereof packaged within a AAVrh.9 capsid. |
| 2 | avian AAV | | COL7A1 | 1294 | Payload comprising a COL7A1 gene or variant thereof packaged within a avian capsid. |

Fig. 29 (Continued)

| | | | | | |
|---|---|---|---|---|---|
| 2 | bovine AAV | | COL7A1 | 1294 | Payload comprising a COL7A1 gene or variant thereof packaged within a bovine capsid. |
| 2 | canine AAV | | COL7A1 | 1294 | Payload comprising a COL7A1 gene or variant thereof packaged within a canine capsid. |
| 2 | equine AAV | | COL7A1 | 1294 | Payload comprising a COL7A1 gene or variant thereof packaged within a equine capsid. |
| 2 | primate AAV | | COL7A1 | 1294 | Payload comprising a COL7A1 gene or variant thereof packaged within a primate capsid. |
| 2 | non-primate AAV | | COL7A1 | 1294 | Payload comprising a COL7A1 gene or variant thereof packaged within a non-primate capsid. |
| 2 | ovine AAV | | COL7A1 | 1294 | Payload comprising a COL7A1 gene or variant thereof packaged within a ovine capsid. |
| 2 | hybrid AAV | | COL7A1 | 1294 | Payload comprising a COL7A1 gene or variant thereof packaged within a hybrid capsid. |
| 2 | chimeric AAV | | COL7A1 | 1294 | Payload comprising a COL7A1 gene or variant thereof packaged within a chimeric capsid. |
| 1 | AAV1 | 1450374 | CPS1 | 1373 | Payload comprising a CPS1 gene or variant thereof packaged within a AAV1 capsid. |
| 1 | AAV2 | | CPS1 | 1373 | Payload comprising a CPS1 gene or variant thereof packaged within a AAV2 capsid. |
| 1 | AAV3 | | CPS1 | 1373 | Payload comprising a CPS1 gene or variant thereof packaged within a AAV3 capsid. |
| 1 | AAV4 | 1446389 | CPS1 | 1373 | Payload comprising a CPS1 gene or variant thereof packaged within a AAV4 capsid. |
| 1 | AAV5 | | CPS1 | 1373 | Payload comprising a CPS1 gene or variant thereof packaged within a AAV5 capsid. |
| 1 | AAV6 | | CPS1 | 1373 | Payload comprising a CPS1 gene or variant thereof packaged within a AAV6 capsid. |
| 1 | AAV7 | | CPS1 | 1373 | Payload comprising a CPS1 gene or variant thereof packaged within a AAV7 capsid. |
| 1 | AAV8 | 5075992 | CPS1 | 1373 | Payload comprising a CPS1 gene or variant thereof packaged within a AAV8 capsid. |
| 1 | AAV9 | | CPS1 | 1373 | Payload comprising a CPS1 gene or variant thereof packaged within a AAV9 capsid. |

Fig. 29 (Continued)

| | | | | | |
|---|---|---|---|---|---|
| 1 | AAV10 | | CPS1 | 1373 | Payload comprising a CPS1 gene or variant thereof packaged within a AAV10 capsid. |
| 1 | AAV11 | | CPS1 | 1373 | Payload comprising a CPS1 gene or variant thereof packaged within a AAV11 capsid. |
| 1 | AAVC11.01 | | CPS1 | 1373 | Payload comprising a CPS1 gene or variant thereof packaged within a AAVC11.01 capsid. |
| 1 | AAVC11.02 | | CPS1 | 1373 | Payload comprising a CPS1 gene or variant thereof packaged within a AAVC11.02 capsid. |
| 1 | AAVC11.03 | | CPS1 | 1373 | Payload comprising a CPS1 gene or variant thereof packaged within a AAVC11.03 capsid. |
| 1 | AAVC11.04 | | CPS1 | 1373 | Payload comprising a CPS1 gene or variant thereof packaged within a AAVC11.04 capsid. |
| 1 | AAVC11.05 | | CPS1 | 1373 | Payload comprising a CPS1 gene or variant thereof packaged within a AAVC11.05 capsid. |
| 1 | AAVC11.06 | | CPS1 | 1373 | Payload comprising a CPS1 gene or variant thereof packaged within a AAVC11.06 capsid. |
| 1 | AAVC11.07 | | CPS1 | 1373 | Payload comprising a CPS1 gene or variant thereof packaged within a AAVC11.07 capsid. |
| 1 | AAVC11.08 | | CPS1 | 1373 | Payload comprising a CPS1 gene or variant thereof packaged within a AAVC11.08 capsid. |
| 1 | AAVC11.09 | | CPS1 | 1373 | Payload comprising a CPS1 gene or variant thereof packaged within a AAVC11.09 capsid. |
| 1 | AAVC11.10 | | CPS1 | 1373 | Payload comprising a CPS1 gene or variant thereof packaged within a AAVC11.10 capsid. |
| 1 | AAVC11.11 | | CPS1 | 1373 | Payload comprising a CPS1 gene or variant thereof packaged within a AAVC11.11 capsid. |
| 1 | AAVC11.12 | | CPS1 | 1373 | Payload comprising a CPS1 gene or variant thereof packaged within a AAVC11.12 capsid. |
| 1 | AAVC11.13 | | CPS1 | 1373 | Payload comprising a CPS1 gene or variant thereof packaged within a AAVC11.13 capsid. |
| 1 | AAVC11.14 | | CPS1 | 1373 | Payload comprising a CPS1 gene or variant thereof packaged within a AAVC11.14 capsid. |
| 1 | AAVC11.15 | | CPS1 | 1373 | Payload comprising a CPS1 gene or variant thereof packaged within a AAVC11.15 capsid. |

Fig. 29 (Continued)

| | | | | | |
|---|---|---|---|---|---|
| 1 | AAVC11.16 | | CPS1 | 1373 | Payload comprising a CPS1 gene or variant thereof packaged within a AAVC11.16 capsid. |
| 1 | AAVC11.17 | | CPS1 | 1373 | Payload comprising a CPS1 gene or variant thereof packaged within a AAVC11.17 capsid. |
| 1 | AAVC11.18 | | CPS1 | 1373 | Payload comprising a CPS1 gene or variant thereof packaged within a AAVC11.18 capsid. |
| 1 | AAVC11.19 | | CPS1 | 1373 | Payload comprising a CPS1 gene or variant thereof packaged within a AAVC11.19 capsid. |
| 1 | AAV12 | | CPS1 | 1373 | Payload comprising a CPS1 gene or variant thereof packaged within a AAV12 capsid. |
| 1 | AAV13 | | CPS1 | 1373 | Payload comprising a CPS1 gene or variant thereof packaged within a AAV13 capsid. |
| 1 | AAV-DJ | | CPS1 | 1373 | Payload comprising a CPS1 gene or variant thereof packaged within a AAV-DJ capsid. |
| 1 | AAV-LK03 | | CPS1 | 1373 | Payload comprising a CPS1 gene or variant thereof packaged within a AAV-LK03 capsid. |
| 1 | AAV-LK19 | | CPS1 | 1373 | Payload comprising a CPS1 gene or variant thereof packaged within a AAV-LK19 capsid. |
| 1 | AAVrh.74 | | CPS1 | 1373 | Payload comprising a CPS1 gene or variant thereof packaged within a AAVrh.74 capsid. |
| 1 | AAVrh.10 | | CPS1 | 1373 | Payload comprising a CPS1 gene or variant thereof packaged within a AAVrh.10 capsid. |
| 1 | AAVhu.37 | | CPS1 | 1373 | Payload comprising a CPS1 gene or variant thereof packaged within a AAVhu.37 capsid. |
| 1 | AAVrh.K | | CPS1 | 1373 | Payload comprising a CPS1 gene or variant thereof packaged within a AAVrh.K capsid. |
| 1 | AAVrh.39 | | CPS1 | 1373 | Payload comprising a CPS1 gene or variant thereof packaged within a AAVrh.39 capsid. |
| 1 | AAVrh.9 | | CPS1 | 1373 | Payload comprising a CPS1 gene or variant thereof packaged within a AAVrh.9 capsid. |
| 1 | avian AAV | | CPS1 | 1373 | Payload comprising a CPS1 gene or variant thereof packaged within a avian capsid. |

Fig. 29 (Continued)

| | | | | | |
|---|---|---|---|---|---|
| 1 | bovine AAV | | CPS1 | 1373 | Payload comprising a CPS1 gene or variant thereof packaged within a bovine capsid. |
| 1 | canine AAV | | CPS1 | 1373 | Payload comprising a CPS1 gene or variant thereof packaged within a canine capsid. |
| 1 | equine AAV | | CPS1 | 1373 | Payload comprising a CPS1 gene or variant thereof packaged within a equine capsid. |
| 1 | primate AAV | | CPS1 | 1373 | Payload comprising a CPS1 gene or variant thereof packaged within a primate capsid. |
| 1 | non-primate AAV | | CPS1 | 1373 | Payload comprising a CPS1 gene or variant thereof packaged within a non-primate capsid. |
| 1 | ovine AAV | | CPS1 | 1373 | Payload comprising a CPS1 gene or variant thereof packaged within a ovine capsid. |
| 1 | hybrid AAV | | CPS1 | 1373 | Payload comprising a CPS1 gene or variant thereof packaged within a hybrid capsid. |
| 1 | chimeric AAV | | CPS1 | 1373 | Payload comprising a CPS1 gene or variant thereof packaged within a chimeric capsid. |
| 2 | AAV1 | 1450374 | CPS1 | 1373 | Payload comprising a CPS1 gene or variant thereof packaged within a AAV1 capsid. |
| 2 | AAV2 | | CPS1 | 1373 | Payload comprising a CPS1 gene or variant thereof packaged within a AAV2 capsid. |
| 2 | AAV3 | | CPS1 | 1373 | Payload comprising a CPS1 gene or variant thereof packaged within a AAV3 capsid. |
| 2 | AAV4 | 1446389 | CPS1 | 1373 | Payload comprising a CPS1 gene or variant thereof packaged within a AAV4 capsid. |
| 2 | AAV5 | | CPS1 | 1373 | Payload comprising a CPS1 gene or variant thereof packaged within a AAV5 capsid. |
| 2 | AAV6 | | CPS1 | 1373 | Payload comprising a CPS1 gene or variant thereof packaged within a AAV6 capsid. |
| 2 | AAV7 | | CPS1 | 1373 | Payload comprising a CPS1 gene or variant thereof packaged within a AAV7 capsid. |
| 2 | AAV8 | 5075992 | CPS1 | 1373 | Payload comprising a CPS1 gene or variant thereof packaged within a AAV8 capsid. |
| 2 | AAV9 | | CPS1 | 1373 | Payload comprising a CPS1 gene or variant thereof packaged within a AAV9 capsid. |

Fig. 29 (Continued)

| | | | | | |
|---|---|---|---|---|---|
| 2 | AAV10 | | CPS1 | 1373 | Payload comprising a CPS1 gene or variant thereof packaged within a AAV10 capsid. |
| 2 | AAV11 | | CPS1 | 1373 | Payload comprising a CPS1 gene or variant thereof packaged within a AAV11 capsid. |
| 2 | AAVC11.01 | | CPS1 | 1373 | Payload comprising a CPS1 gene or variant thereof packaged within a AAVC11.01 capsid. |
| 2 | AAVC11.02 | | CPS1 | 1373 | Payload comprising a CPS1 gene or variant thereof packaged within a AAVC11.02 capsid. |
| 2 | AAVC11.03 | | CPS1 | 1373 | Payload comprising a CPS1 gene or variant thereof packaged within a AAVC11.03 capsid. |
| 2 | AAVC11.04 | | CPS1 | 1373 | Payload comprising a CPS1 gene or variant thereof packaged within a AAVC11.04 capsid. |
| 2 | AAVC11.05 | | CPS1 | 1373 | Payload comprising a CPS1 gene or variant thereof packaged within a AAVC11.05 capsid. |
| 2 | AAVC11.06 | | CPS1 | 1373 | Payload comprising a CPS1 gene or variant thereof packaged within a AAVC11.06 capsid. |
| 2 | AAVC11.07 | | CPS1 | 1373 | Payload comprising a CPS1 gene or variant thereof packaged within a AAVC11.07 capsid. |
| 2 | AAVC11.08 | | CPS1 | 1373 | Payload comprising a CPS1 gene or variant thereof packaged within a AAVC11.08 capsid. |
| 2 | AAVC11.09 | | CPS1 | 1373 | Payload comprising a CPS1 gene or variant thereof packaged within a AAVC11.09 capsid. |
| 2 | AAVC11.10 | | CPS1 | 1373 | Payload comprising a CPS1 gene or variant thereof packaged within a AAVC11.10 capsid. |
| 2 | AAVC11.11 | | CPS1 | 1373 | Payload comprising a CPS1 gene or variant thereof packaged within a AAVC11.11 capsid. |
| 2 | AAVC11.12 | | CPS1 | 1373 | Payload comprising a CPS1 gene or variant thereof packaged within a AAVC11.12 capsid. |
| 2 | AAVC11.13 | | CPS1 | 1373 | Payload comprising a CPS1 gene or variant thereof packaged within a AAVC11.13 capsid. |
| 2 | AAVC11.14 | | CPS1 | 1373 | Payload comprising a CPS1 gene or variant thereof packaged within a AAVC11.14 capsid. |
| 2 | AAVC11.15 | | CPS1 | 1373 | Payload comprising a CPS1 gene or variant thereof packaged within a AAVC11.15 capsid. |

Fig. 29 (Continued)

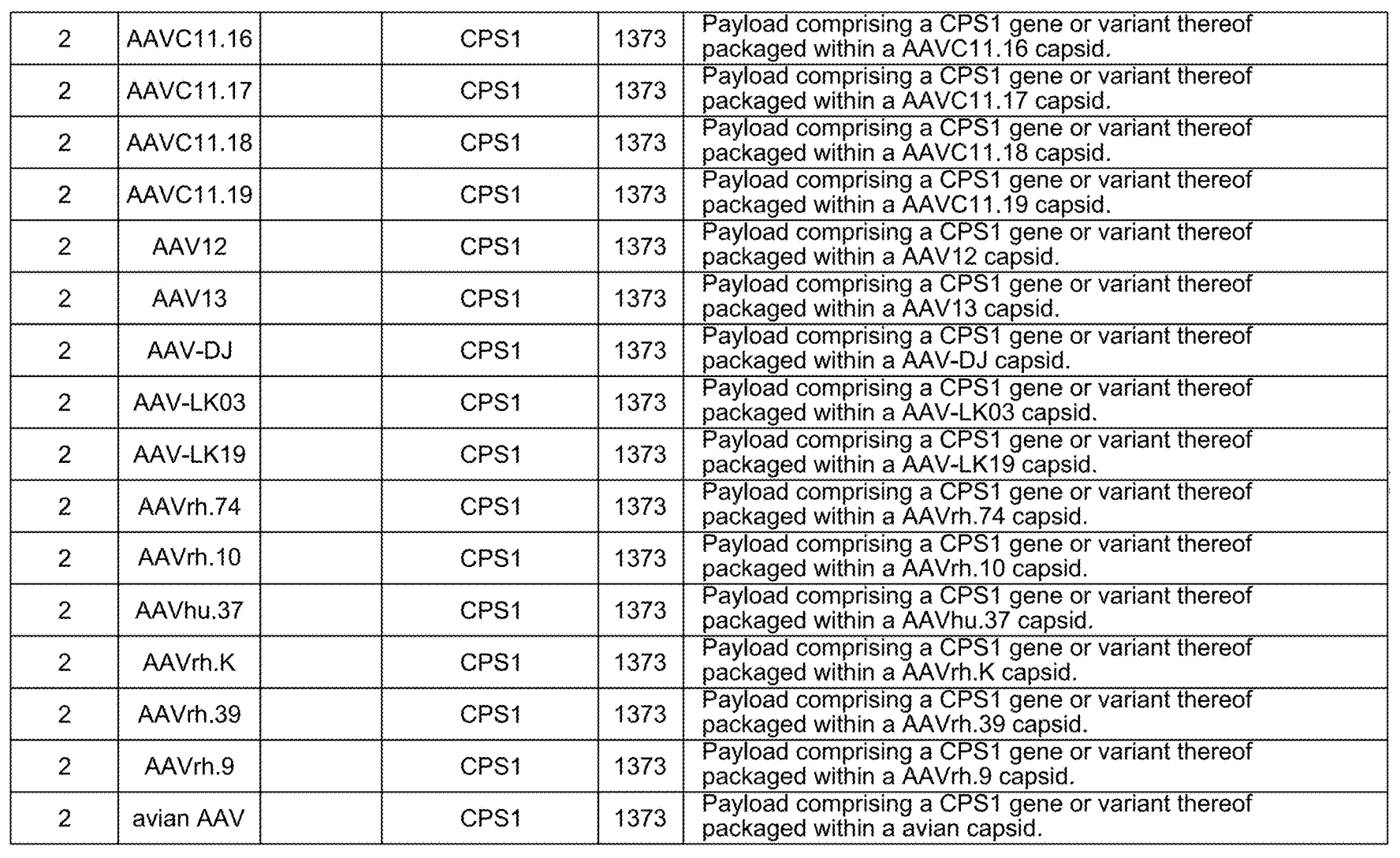

| | | | | | |
|---|---|---|---|---|---|
| 2 | AAVC11.16 | | CPS1 | 1373 | Payload comprising a CPS1 gene or variant thereof packaged within a AAVC11.16 capsid. |
| 2 | AAVC11.17 | | CPS1 | 1373 | Payload comprising a CPS1 gene or variant thereof packaged within a AAVC11.17 capsid. |
| 2 | AAVC11.18 | | CPS1 | 1373 | Payload comprising a CPS1 gene or variant thereof packaged within a AAVC11.18 capsid. |
| 2 | AAVC11.19 | | CPS1 | 1373 | Payload comprising a CPS1 gene or variant thereof packaged within a AAVC11.19 capsid. |
| 2 | AAV12 | | CPS1 | 1373 | Payload comprising a CPS1 gene or variant thereof packaged within a AAV12 capsid. |
| 2 | AAV13 | | CPS1 | 1373 | Payload comprising a CPS1 gene or variant thereof packaged within a AAV13 capsid. |
| 2 | AAV-DJ | | CPS1 | 1373 | Payload comprising a CPS1 gene or variant thereof packaged within a AAV-DJ capsid. |
| 2 | AAV-LK03 | | CPS1 | 1373 | Payload comprising a CPS1 gene or variant thereof packaged within a AAV-LK03 capsid. |
| 2 | AAV-LK19 | | CPS1 | 1373 | Payload comprising a CPS1 gene or variant thereof packaged within a AAV-LK19 capsid. |
| 2 | AAVrh.74 | | CPS1 | 1373 | Payload comprising a CPS1 gene or variant thereof packaged within a AAVrh.74 capsid. |
| 2 | AAVrh.10 | | CPS1 | 1373 | Payload comprising a CPS1 gene or variant thereof packaged within a AAVrh.10 capsid. |
| 2 | AAVhu.37 | | CPS1 | 1373 | Payload comprising a CPS1 gene or variant thereof packaged within a AAVhu.37 capsid. |
| 2 | AAVrh.K | | CPS1 | 1373 | Payload comprising a CPS1 gene or variant thereof packaged within a AAVrh.K capsid. |
| 2 | AAVrh.39 | | CPS1 | 1373 | Payload comprising a CPS1 gene or variant thereof packaged within a AAVrh.39 capsid. |
| 2 | AAVrh.9 | | CPS1 | 1373 | Payload comprising a CPS1 gene or variant thereof packaged within a AAVrh.9 capsid. |
| 2 | avian AAV | | CPS1 | 1373 | Payload comprising a CPS1 gene or variant thereof packaged within a avian capsid. |

Fig. 29 (Continued)

| | | | | | |
|---|---|---|---|---|---|
| 2 | bovine AAV | | CPS1 | 1373 | Payload comprising a CPS1 gene or variant thereof packaged within a bovine capsid. |
| 2 | canine AAV | | CPS1 | 1373 | Payload comprising a CPS1 gene or variant thereof packaged within a canine capsid. |
| 2 | equine AAV | | CPS1 | 1373 | Payload comprising a CPS1 gene or variant thereof packaged within a equine capsid. |
| 2 | primate AAV | | CPS1 | 1373 | Payload comprising a CPS1 gene or variant thereof packaged within a primate capsid. |
| 2 | non-primate AAV | | CPS1 | 1373 | Payload comprising a CPS1 gene or variant thereof packaged within a non-primate capsid. |
| 2 | ovine AAV | | CPS1 | 1373 | Payload comprising a CPS1 gene or variant thereof packaged within a ovine capsid. |
| 2 | hybrid AAV | | CPS1 | 1373 | Payload comprising a CPS1 gene or variant thereof packaged within a hybrid capsid. |
| 2 | chimeric AAV | | CPS1 | 1373 | Payload comprising a CPS1 gene or variant thereof packaged within a chimeric capsid. |
| 1 | AAV1 | 1450374 | CPT1 | 1374 | Payload comprising a CPT1 gene or variant thereof packaged within a AAV1 capsid. |
| 1 | AAV2 | | CPT1 | 1374 | Payload comprising a CPT1 gene or variant thereof packaged within a AAV2 capsid. |
| 1 | AAV3 | | CPT1 | 1374 | Payload comprising a CPT1 gene or variant thereof packaged within a AAV3 capsid. |
| 1 | AAV4 | 1446389 | CPT1 | 1374 | Payload comprising a CPT1 gene or variant thereof packaged within a AAV4 capsid. |
| 1 | AAV5 | | CPT1 | 1374 | Payload comprising a CPT1 gene or variant thereof packaged within a AAV5 capsid. |
| 1 | AAV6 | | CPT1 | 1374 | Payload comprising a CPT1 gene or variant thereof packaged within a AAV6 capsid. |
| 1 | AAV7 | | CPT1 | 1374 | Payload comprising a CPT1 gene or variant thereof packaged within a AAV7 capsid. |
| 1 | AAV8 | 5075992 | CPT1 | 1374 | Payload comprising a CPT1 gene or variant thereof packaged within a AAV8 capsid. |
| 1 | AAV9 | | CPT1 | 1374 | Payload comprising a CPT1 gene or variant thereof packaged within a AAV9 capsid. |

Fig. 29 (Continued)

| | | | | | |
|---|---|---|---|---|---|
| 1 | AAV10 | | CPT1 | 1374 | Payload comprising a CPT1 gene or variant thereof packaged within a AAV10 capsid. |
| 1 | AAV11 | | CPT1 | 1374 | Payload comprising a CPT1 gene or variant thereof packaged within a AAV11 capsid. |
| 1 | AAVC11.01 | | CPT1 | 1374 | Payload comprising a CPT1 gene or variant thereof packaged within a AAVC11.01 capsid. |
| 1 | AAVC11.02 | | CPT1 | 1374 | Payload comprising a CPT1 gene or variant thereof packaged within a AAVC11.02 capsid. |
| 1 | AAVC11.03 | | CPT1 | 1374 | Payload comprising a CPT1 gene or variant thereof packaged within a AAVC11.03 capsid. |
| 1 | AAVC11.04 | | CPT1 | 1374 | Payload comprising a CPT1 gene or variant thereof packaged within a AAVC11.04 capsid. |
| 1 | AAVC11.05 | | CPT1 | 1374 | Payload comprising a CPT1 gene or variant thereof packaged within a AAVC11.05 capsid. |
| 1 | AAVC11.06 | | CPT1 | 1374 | Payload comprising a CPT1 gene or variant thereof packaged within a AAVC11.06 capsid. |
| 1 | AAVC11.07 | | CPT1 | 1374 | Payload comprising a CPT1 gene or variant thereof packaged within a AAVC11.07 capsid. |
| 1 | AAVC11.08 | | CPT1 | 1374 | Payload comprising a CPT1 gene or variant thereof packaged within a AAVC11.08 capsid. |
| 1 | AAVC11.09 | | CPT1 | 1374 | Payload comprising a CPT1 gene or variant thereof packaged within a AAVC11.09 capsid. |
| 1 | AAVC11.10 | | CPT1 | 1374 | Payload comprising a CPT1 gene or variant thereof packaged within a AAVC11.10 capsid. |
| 1 | AAVC11.11 | | CPT1 | 1374 | Payload comprising a CPT1 gene or variant thereof packaged within a AAVC11.11 capsid. |
| 1 | AAVC11.12 | | CPT1 | 1374 | Payload comprising a CPT1 gene or variant thereof packaged within a AAVC11.12 capsid. |
| 1 | AAVC11.13 | | CPT1 | 1374 | Payload comprising a CPT1 gene or variant thereof packaged within a AAVC11.13 capsid. |
| 1 | AAVC11.14 | | CPT1 | 1374 | Payload comprising a CPT1 gene or variant thereof packaged within a AAVC11.14 capsid. |
| 1 | AAVC11.15 | | CPT1 | 1374 | Payload comprising a CPT1 gene or variant thereof packaged within a AAVC11.15 capsid. |

Fig. 29 (Continued)

| | | | | | |
|---|---|---|---|---|---|
| 1 | AAVC11.16 | | CPT1 | 1374 | Payload comprising a CPT1 gene or variant thereof packaged within a AAVC11.16 capsid. |
| 1 | AAVC11.17 | | CPT1 | 1374 | Payload comprising a CPT1 gene or variant thereof packaged within a AAVC11.17 capsid. |
| 1 | AAVC11.18 | | CPT1 | 1374 | Payload comprising a CPT1 gene or variant thereof packaged within a AAVC11.18 capsid. |
| 1 | AAVC11.19 | | CPT1 | 1374 | Payload comprising a CPT1 gene or variant thereof packaged within a AAVC11.19 capsid. |
| 1 | AAV12 | | CPT1 | 1374 | Payload comprising a CPT1 gene or variant thereof packaged within a AAV12 capsid. |
| 1 | AAV13 | | CPT1 | 1374 | Payload comprising a CPT1 gene or variant thereof packaged within a AAV13 capsid. |
| 1 | AAV-DJ | | CPT1 | 1374 | Payload comprising a CPT1 gene or variant thereof packaged within a AAV-DJ capsid. |
| 1 | AAV-LK03 | | CPT1 | 1374 | Payload comprising a CPT1 gene or variant thereof packaged within a AAV-LK03 capsid. |
| 1 | AAV-LK19 | | CPT1 | 1374 | Payload comprising a CPT1 gene or variant thereof packaged within a AAV-LK19 capsid. |
| 1 | AAVrh.74 | | CPT1 | 1374 | Payload comprising a CPT1 gene or variant thereof packaged within a AAVrh.74 capsid. |
| 1 | AAVrh.10 | | CPT1 | 1374 | Payload comprising a CPT1 gene or variant thereof packaged within a AAVrh.10 capsid. |
| 1 | AAVhu.37 | | CPT1 | 1374 | Payload comprising a CPT1 gene or variant thereof packaged within a AAVhu.37 capsid. |
| 1 | AAVrh.K | | CPT1 | 1374 | Payload comprising a CPT1 gene or variant thereof packaged within a AAVrh.K capsid. |
| 1 | AAVrh.39 | | CPT1 | 1374 | Payload comprising a CPT1 gene or variant thereof packaged within a AAVrh.39 capsid. |
| 1 | AAVrh.9 | | CPT1 | 1374 | Payload comprising a CPT1 gene or variant thereof packaged within a AAVrh.9 capsid. |
| 1 | avian AAV | | CPT1 | 1374 | Payload comprising a CPT1 gene or variant thereof packaged within a avian capsid. |

Fig. 29 (Continued)

| | | | | | |
|---|---|---|---|---|---|
| 1 | bovine AAV | | CPT1 | 1374 | Payload comprising a CPT1 gene or variant thereof packaged within a bovine capsid. |
| 1 | canine AAV | | CPT1 | 1374 | Payload comprising a CPT1 gene or variant thereof packaged within a canine capsid. |
| 1 | equine AAV | | CPT1 | 1374 | Payload comprising a CPT1 gene or variant thereof packaged within a equine capsid. |
| 1 | primate AAV | | CPT1 | 1374 | Payload comprising a CPT1 gene or variant thereof packaged within a primate capsid. |
| 1 | non-primate AAV | | CPT1 | 1374 | Payload comprising a CPT1 gene or variant thereof packaged within a non-primate capsid. |
| 1 | ovine AAV | | CPT1 | 1374 | Payload comprising a CPT1 gene or variant thereof packaged within a ovine capsid. |
| 1 | hybrid AAV | | CPT1 | 1374 | Payload comprising a CPT1 gene or variant thereof packaged within a hybrid capsid. |
| 1 | chimeric AAV | | CPT1 | 1374 | Payload comprising a CPT1 gene or variant thereof packaged within a chimeric capsid. |
| 2 | AAV1 | 1450374 | CPT1 | 1374 | Payload comprising a CPT1 gene or variant thereof packaged within a AAV1 capsid. |
| 2 | AAV2 | | CPT1 | 1374 | Payload comprising a CPT1 gene or variant thereof packaged within a AAV2 capsid. |
| 2 | AAV3 | | CPT1 | 1374 | Payload comprising a CPT1 gene or variant thereof packaged within a AAV3 capsid. |
| 2 | AAV4 | 1446389 | CPT1 | 1374 | Payload comprising a CPT1 gene or variant thereof packaged within a AAV4 capsid. |
| 2 | AAV5 | | CPT1 | 1374 | Payload comprising a CPT1 gene or variant thereof packaged within a AAV5 capsid. |
| 2 | AAV6 | | CPT1 | 1374 | Payload comprising a CPT1 gene or variant thereof packaged within a AAV6 capsid. |
| 2 | AAV7 | | CPT1 | 1374 | Payload comprising a CPT1 gene or variant thereof packaged within a AAV7 capsid. |
| 2 | AAV8 | 5075992 | CPT1 | 1374 | Payload comprising a CPT1 gene or variant thereof packaged within a AAV8 capsid. |
| 2 | AAV9 | | CPT1 | 1374 | Payload comprising a CPT1 gene or variant thereof packaged within a AAV9 capsid. |

Fig. 29 (Continued)

| | | | | | |
|---|---|---|---|---|---|
| 2 | AAV10 | | CPT1 | 1374 | Payload comprising a CPT1 gene or variant thereof packaged within a AAV10 capsid. |
| 2 | AAV11 | | CPT1 | 1374 | Payload comprising a CPT1 gene or variant thereof packaged within a AAV11 capsid. |
| 2 | AAVC11.01 | | CPT1 | 1374 | Payload comprising a CPT1 gene or variant thereof packaged within a AAVC11.01 capsid. |
| 2 | AAVC11.02 | | CPT1 | 1374 | Payload comprising a CPT1 gene or variant thereof packaged within a AAVC11.02 capsid. |
| 2 | AAVC11.03 | | CPT1 | 1374 | Payload comprising a CPT1 gene or variant thereof packaged within a AAVC11.03 capsid. |
| 2 | AAVC11.04 | | CPT1 | 1374 | Payload comprising a CPT1 gene or variant thereof packaged within a AAVC11.04 capsid. |
| 2 | AAVC11.05 | | CPT1 | 1374 | Payload comprising a CPT1 gene or variant thereof packaged within a AAVC11.05 capsid. |
| 2 | AAVC11.06 | | CPT1 | 1374 | Payload comprising a CPT1 gene or variant thereof packaged within a AAVC11.06 capsid. |
| 2 | AAVC11.07 | | CPT1 | 1374 | Payload comprising a CPT1 gene or variant thereof packaged within a AAVC11.07 capsid. |
| 2 | AAVC11.08 | | CPT1 | 1374 | Payload comprising a CPT1 gene or variant thereof packaged within a AAVC11.08 capsid. |
| 2 | AAVC11.09 | | CPT1 | 1374 | Payload comprising a CPT1 gene or variant thereof packaged within a AAVC11.09 capsid. |
| 2 | AAVC11.10 | | CPT1 | 1374 | Payload comprising a CPT1 gene or variant thereof packaged within a AAVC11.10 capsid. |
| 2 | AAVC11.11 | | CPT1 | 1374 | Payload comprising a CPT1 gene or variant thereof packaged within a AAVC11.11 capsid. |
| 2 | AAVC11.12 | | CPT1 | 1374 | Payload comprising a CPT1 gene or variant thereof packaged within a AAVC11.12 capsid. |
| 2 | AAVC11.13 | | CPT1 | 1374 | Payload comprising a CPT1 gene or variant thereof packaged within a AAVC11.13 capsid. |
| 2 | AAVC11.14 | | CPT1 | 1374 | Payload comprising a CPT1 gene or variant thereof packaged within a AAVC11.14 capsid. |
| 2 | AAVC11.15 | | CPT1 | 1374 | Payload comprising a CPT1 gene or variant thereof packaged within a AAVC11.15 capsid. |

Fig. 29 (Continued)

| | | | | | |
|---|---|---|---|---|---|
| 2 | AAVC11.16 | | CPT1 | 1374 | Payload comprising a CPT1 gene or variant thereof packaged within a AAVC11.16 capsid. |
| 2 | AAVC11.17 | | CPT1 | 1374 | Payload comprising a CPT1 gene or variant thereof packaged within a AAVC11.17 capsid. |
| 2 | AAVC11.18 | | CPT1 | 1374 | Payload comprising a CPT1 gene or variant thereof packaged within a AAVC11.18 capsid. |
| 2 | AAVC11.19 | | CPT1 | 1374 | Payload comprising a CPT1 gene or variant thereof packaged within a AAVC11.19 capsid. |
| 2 | AAV12 | | CPT1 | 1374 | Payload comprising a CPT1 gene or variant thereof packaged within a AAV12 capsid. |
| 2 | AAV13 | | CPT1 | 1374 | Payload comprising a CPT1 gene or variant thereof packaged within a AAV13 capsid. |
| 2 | AAV-DJ | | CPT1 | 1374 | Payload comprising a CPT1 gene or variant thereof packaged within a AAV-DJ capsid. |
| 2 | AAV-LK03 | | CPT1 | 1374 | Payload comprising a CPT1 gene or variant thereof packaged within a AAV-LK03 capsid. |
| 2 | AAV-LK19 | | CPT1 | 1374 | Payload comprising a CPT1 gene or variant thereof packaged within a AAV-LK19 capsid. |
| 2 | AAVrh.74 | | CPT1 | 1374 | Payload comprising a CPT1 gene or variant thereof packaged within a AAVrh.74 capsid. |
| 2 | AAVrh.10 | | CPT1 | 1374 | Payload comprising a CPT1 gene or variant thereof packaged within a AAVrh.10 capsid. |
| 2 | AAVhu.37 | | CPT1 | 1374 | Payload comprising a CPT1 gene or variant thereof packaged within a AAVhu.37 capsid. |
| 2 | AAVrh.K | | CPT1 | 1374 | Payload comprising a CPT1 gene or variant thereof packaged within a AAVrh.K capsid. |
| 2 | AAVrh.39 | | CPT1 | 1374 | Payload comprising a CPT1 gene or variant thereof packaged within a AAVrh.39 capsid. |
| 2 | AAVrh.9 | | CPT1 | 1374 | Payload comprising a CPT1 gene or variant thereof packaged within a AAVrh.9 capsid. |
| 2 | avian AAV | | CPT1 | 1374 | Payload comprising a CPT1 gene or variant thereof packaged within a avian capsid. |

Fig. 29 (Continued)

| | | | | | |
|---|---|---|---|---|---|
| 2 | bovine AAV | | CPT1 | 1374 | Payload comprising a CPT1 gene or variant thereof packaged within a bovine capsid. |
| 2 | canine AAV | | CPT1 | 1374 | Payload comprising a CPT1 gene or variant thereof packaged within a canine capsid. |
| 2 | equine AAV | | CPT1 | 1374 | Payload comprising a CPT1 gene or variant thereof packaged within a equine capsid. |
| 2 | primate AAV | | CPT1 | 1374 | Payload comprising a CPT1 gene or variant thereof packaged within a primate capsid. |
| 2 | non-primate AAV | | CPT1 | 1374 | Payload comprising a CPT1 gene or variant thereof packaged within a non-primate capsid. |
| 2 | ovine AAV | | CPT1 | 1374 | Payload comprising a CPT1 gene or variant thereof packaged within a ovine capsid. |
| 2 | hybrid AAV | | CPT1 | 1374 | Payload comprising a CPT1 gene or variant thereof packaged within a hybrid capsid. |
| 2 | chimeric AAV | | CPT1 | 1374 | Payload comprising a CPT1 gene or variant thereof packaged within a chimeric capsid. |
| 1 | AAV1 | 1450374 | CPT2 | 1376 | Payload comprising a CPT2 gene or variant thereof packaged within a AAV1 capsid. |
| 1 | AAV2 | | CPT2 | 1376 | Payload comprising a CPT2 gene or variant thereof packaged within a AAV2 capsid. |
| 1 | AAV3 | | CPT2 | 1376 | Payload comprising a CPT2 gene or variant thereof packaged within a AAV3 capsid. |
| 1 | AAV4 | 1446389 | CPT2 | 1376 | Payload comprising a CPT2 gene or variant thereof packaged within a AAV4 capsid. |
| 1 | AAV5 | | CPT2 | 1376 | Payload comprising a CPT2 gene or variant thereof packaged within a AAV5 capsid. |
| 1 | AAV6 | | CPT2 | 1376 | Payload comprising a CPT2 gene or variant thereof packaged within a AAV6 capsid. |
| 1 | AAV7 | | CPT2 | 1376 | Payload comprising a CPT2 gene or variant thereof packaged within a AAV7 capsid. |
| 1 | AAV8 | 5075992 | CPT2 | 1376 | Payload comprising a CPT2 gene or variant thereof packaged within a AAV8 capsid. |
| 1 | AAV9 | | CPT2 | 1376 | Payload comprising a CPT2 gene or variant thereof packaged within a AAV9 capsid. |

Fig. 29 (Continued)

| | | | | | |
|---|---|---|---|---|---|
| 1 | AAV10 | | CPT2 | 1376 | Payload comprising a CPT2 gene or variant thereof packaged within a AAV10 capsid. |
| 1 | AAV11 | | CPT2 | 1376 | Payload comprising a CPT2 gene or variant thereof packaged within a AAV11 capsid. |
| 1 | AAVC11.01 | | CPT2 | 1376 | Payload comprising a CPT2 gene or variant thereof packaged within a AAVC11.01 capsid. |
| 1 | AAVC11.02 | | CPT2 | 1376 | Payload comprising a CPT2 gene or variant thereof packaged within a AAVC11.02 capsid. |
| 1 | AAVC11.03 | | CPT2 | 1376 | Payload comprising a CPT2 gene or variant thereof packaged within a AAVC11.03 capsid. |
| 1 | AAVC11.04 | | CPT2 | 1376 | Payload comprising a CPT2 gene or variant thereof packaged within a AAVC11.04 capsid. |
| 1 | AAVC11.05 | | CPT2 | 1376 | Payload comprising a CPT2 gene or variant thereof packaged within a AAVC11.05 capsid. |
| 1 | AAVC11.06 | | CPT2 | 1376 | Payload comprising a CPT2 gene or variant thereof packaged within a AAVC11.06 capsid. |
| 1 | AAVC11.07 | | CPT2 | 1376 | Payload comprising a CPT2 gene or variant thereof packaged within a AAVC11.07 capsid. |
| 1 | AAVC11.08 | | CPT2 | 1376 | Payload comprising a CPT2 gene or variant thereof packaged within a AAVC11.08 capsid. |
| 1 | AAVC11.09 | | CPT2 | 1376 | Payload comprising a CPT2 gene or variant thereof packaged within a AAVC11.09 capsid. |
| 1 | AAVC11.10 | | CPT2 | 1376 | Payload comprising a CPT2 gene or variant thereof packaged within a AAVC11.10 capsid. |
| 1 | AAVC11.11 | | CPT2 | 1376 | Payload comprising a CPT2 gene or variant thereof packaged within a AAVC11.11 capsid. |
| 1 | AAVC11.12 | | CPT2 | 1376 | Payload comprising a CPT2 gene or variant thereof packaged within a AAVC11.12 capsid. |
| 1 | AAVC11.13 | | CPT2 | 1376 | Payload comprising a CPT2 gene or variant thereof packaged within a AAVC11.13 capsid. |
| 1 | AAVC11.14 | | CPT2 | 1376 | Payload comprising a CPT2 gene or variant thereof packaged within a AAVC11.14 capsid. |
| 1 | AAVC11.15 | | CPT2 | 1376 | Payload comprising a CPT2 gene or variant thereof packaged within a AAVC11.15 capsid. |

Fig. 29 (Continued)

| | | | | | |
|---|---|---|---|---|---|
| 1 | AAVC11.16 | | CPT2 | 1376 | Payload comprising a CPT2 gene or variant thereof packaged within a AAVC11.16 capsid. |
| 1 | AAVC11.17 | | CPT2 | 1376 | Payload comprising a CPT2 gene or variant thereof packaged within a AAVC11.17 capsid. |
| 1 | AAVC11.18 | | CPT2 | 1376 | Payload comprising a CPT2 gene or variant thereof packaged within a AAVC11.18 capsid. |
| 1 | AAVC11.19 | | CPT2 | 1376 | Payload comprising a CPT2 gene or variant thereof packaged within a AAVC11.19 capsid. |
| 1 | AAV12 | | CPT2 | 1376 | Payload comprising a CPT2 gene or variant thereof packaged within a AAV12 capsid. |
| 1 | AAV13 | | CPT2 | 1376 | Payload comprising a CPT2 gene or variant thereof packaged within a AAV13 capsid. |
| 1 | AAV-DJ | | CPT2 | 1376 | Payload comprising a CPT2 gene or variant thereof packaged within a AAV-DJ capsid. |
| 1 | AAV-LK03 | | CPT2 | 1376 | Payload comprising a CPT2 gene or variant thereof packaged within a AAV-LK03 capsid. |
| 1 | AAV-LK19 | | CPT2 | 1376 | Payload comprising a CPT2 gene or variant thereof packaged within a AAV-LK19 capsid. |
| 1 | AAVrh.74 | | CPT2 | 1376 | Payload comprising a CPT2 gene or variant thereof packaged within a AAVrh.74 capsid. |
| 1 | AAVrh.10 | | CPT2 | 1376 | Payload comprising a CPT2 gene or variant thereof packaged within a AAVrh.10 capsid. |
| 1 | AAVhu.37 | | CPT2 | 1376 | Payload comprising a CPT2 gene or variant thereof packaged within a AAVhu.37 capsid. |
| 1 | AAVrh.K | | CPT2 | 1376 | Payload comprising a CPT2 gene or variant thereof packaged within a AAVrh.K capsid. |
| 1 | AAVrh.39 | | CPT2 | 1376 | Payload comprising a CPT2 gene or variant thereof packaged within a AAVrh.39 capsid. |
| 1 | AAVrh.9 | | CPT2 | 1376 | Payload comprising a CPT2 gene or variant thereof packaged within a AAVrh.9 capsid. |
| 1 | avian AAV | | CPT2 | 1376 | Payload comprising a CPT2 gene or variant thereof packaged within a avian capsid. |

Fig. 29 (Continued)

| | | | | | |
|---|---|---|---|---|---|
| 1 | bovine AAV | | CPT2 | 1376 | Payload comprising a CPT2 gene or variant thereof packaged within a bovine capsid. |
| 1 | canine AAV | | CPT2 | 1376 | Payload comprising a CPT2 gene or variant thereof packaged within a canine capsid. |
| 1 | equine AAV | | CPT2 | 1376 | Payload comprising a CPT2 gene or variant thereof packaged within a equine capsid. |
| 1 | primate AAV | | CPT2 | 1376 | Payload comprising a CPT2 gene or variant thereof packaged within a primate capsid. |
| 1 | non-primate AAV | | CPT2 | 1376 | Payload comprising a CPT2 gene or variant thereof packaged within a non-primate capsid. |
| 1 | ovine AAV | | CPT2 | 1376 | Payload comprising a CPT2 gene or variant thereof packaged within a ovine capsid. |
| 1 | hybrid AAV | | CPT2 | 1376 | Payload comprising a CPT2 gene or variant thereof packaged within a hybrid capsid. |
| 1 | chimeric AAV | | CPT2 | 1376 | Payload comprising a CPT2 gene or variant thereof packaged within a chimeric capsid. |
| 2 | AAV1 | 1450374 | CPT2 | 1376 | Payload comprising a CPT2 gene or variant thereof packaged within a AAV1 capsid. |
| 2 | AAV2 | | CPT2 | 1376 | Payload comprising a CPT2 gene or variant thereof packaged within a AAV2 capsid. |
| 2 | AAV3 | | CPT2 | 1376 | Payload comprising a CPT2 gene or variant thereof packaged within a AAV3 capsid. |
| 2 | AAV4 | 1446389 | CPT2 | 1376 | Payload comprising a CPT2 gene or variant thereof packaged within a AAV4 capsid. |
| 2 | AAV5 | | CPT2 | 1376 | Payload comprising a CPT2 gene or variant thereof packaged within a AAV5 capsid. |
| 2 | AAV6 | | CPT2 | 1376 | Payload comprising a CPT2 gene or variant thereof packaged within a AAV6 capsid. |
| 2 | AAV7 | | CPT2 | 1376 | Payload comprising a CPT2 gene or variant thereof packaged within a AAV7 capsid. |
| 2 | AAV8 | 5075992 | CPT2 | 1376 | Payload comprising a CPT2 gene or variant thereof packaged within a AAV8 capsid. |
| 2 | AAV9 | | CPT2 | 1376 | Payload comprising a CPT2 gene or variant thereof packaged within a AAV9 capsid. |

Fig. 29 (Continued)

| | | | | | |
|---|---|---|---|---|---|
| 2 | AAV10 | | CPT2 | 1376 | Payload comprising a CPT2 gene or variant thereof packaged within a AAV10 capsid. |
| 2 | AAV11 | | CPT2 | 1376 | Payload comprising a CPT2 gene or variant thereof packaged within a AAV11 capsid. |
| 2 | AAVC11.01 | | CPT2 | 1376 | Payload comprising a CPT2 gene or variant thereof packaged within a AAVC11.01 capsid. |
| 2 | AAVC11.02 | | CPT2 | 1376 | Payload comprising a CPT2 gene or variant thereof packaged within a AAVC11.02 capsid. |
| 2 | AAVC11.03 | | CPT2 | 1376 | Payload comprising a CPT2 gene or variant thereof packaged within a AAVC11.03 capsid. |
| 2 | AAVC11.04 | | CPT2 | 1376 | Payload comprising a CPT2 gene or variant thereof packaged within a AAVC11.04 capsid. |
| 2 | AAVC11.05 | | CPT2 | 1376 | Payload comprising a CPT2 gene or variant thereof packaged within a AAVC11.05 capsid. |
| 2 | AAVC11.06 | | CPT2 | 1376 | Payload comprising a CPT2 gene or variant thereof packaged within a AAVC11.06 capsid. |
| 2 | AAVC11.07 | | CPT2 | 1376 | Payload comprising a CPT2 gene or variant thereof packaged within a AAVC11.07 capsid. |
| 2 | AAVC11.08 | | CPT2 | 1376 | Payload comprising a CPT2 gene or variant thereof packaged within a AAVC11.08 capsid. |
| 2 | AAVC11.09 | | CPT2 | 1376 | Payload comprising a CPT2 gene or variant thereof packaged within a AAVC11.09 capsid. |
| 2 | AAVC11.10 | | CPT2 | 1376 | Payload comprising a CPT2 gene or variant thereof packaged within a AAVC11.10 capsid. |
| 2 | AAVC11.11 | | CPT2 | 1376 | Payload comprising a CPT2 gene or variant thereof packaged within a AAVC11.11 capsid. |
| 2 | AAVC11.12 | | CPT2 | 1376 | Payload comprising a CPT2 gene or variant thereof packaged within a AAVC11.12 capsid. |
| 2 | AAVC11.13 | | CPT2 | 1376 | Payload comprising a CPT2 gene or variant thereof packaged within a AAVC11.13 capsid. |
| 2 | AAVC11.14 | | CPT2 | 1376 | Payload comprising a CPT2 gene or variant thereof packaged within a AAVC11.14 capsid. |
| 2 | AAVC11.15 | | CPT2 | 1376 | Payload comprising a CPT2 gene or variant thereof packaged within a AAVC11.15 capsid. |

Fig. 29 (Continued)

| | | | | | |
|---|---|---|---|---|---|
| 2 | AAVC11.16 | | CPT2 | 1376 | Payload comprising a CPT2 gene or variant thereof packaged within a AAVC11.16 capsid. |
| 2 | AAVC11.17 | | CPT2 | 1376 | Payload comprising a CPT2 gene or variant thereof packaged within a AAVC11.17 capsid. |
| 2 | AAVC11.18 | | CPT2 | 1376 | Payload comprising a CPT2 gene or variant thereof packaged within a AAVC11.18 capsid. |
| 2 | AAVC11.19 | | CPT2 | 1376 | Payload comprising a CPT2 gene or variant thereof packaged within a AAVC11.19 capsid. |
| 2 | AAV12 | | CPT2 | 1376 | Payload comprising a CPT2 gene or variant thereof packaged within a AAV12 capsid. |
| 2 | AAV13 | | CPT2 | 1376 | Payload comprising a CPT2 gene or variant thereof packaged within a AAV13 capsid. |
| 2 | AAV-DJ | | CPT2 | 1376 | Payload comprising a CPT2 gene or variant thereof packaged within a AAV-DJ capsid. |
| 2 | AAV-LK03 | | CPT2 | 1376 | Payload comprising a CPT2 gene or variant thereof packaged within a AAV-LK03 capsid. |
| 2 | AAV-LK19 | | CPT2 | 1376 | Payload comprising a CPT2 gene or variant thereof packaged within a AAV-LK19 capsid. |
| 2 | AAVrh.74 | | CPT2 | 1376 | Payload comprising a CPT2 gene or variant thereof packaged within a AAVrh.74 capsid. |
| 2 | AAVrh.10 | | CPT2 | 1376 | Payload comprising a CPT2 gene or variant thereof packaged within a AAVrh.10 capsid. |
| 2 | AAVhu.37 | | CPT2 | 1376 | Payload comprising a CPT2 gene or variant thereof packaged within a AAVhu.37 capsid. |
| 2 | AAVrh.K | | CPT2 | 1376 | Payload comprising a CPT2 gene or variant thereof packaged within a AAVrh.K capsid. |
| 2 | AAVrh.39 | | CPT2 | 1376 | Payload comprising a CPT2 gene or variant thereof packaged within a AAVrh.39 capsid. |
| 2 | AAVrh.9 | | CPT2 | 1376 | Payload comprising a CPT2 gene or variant thereof packaged within a AAVrh.9 capsid. |
| 2 | avian AAV | | CPT2 | 1376 | Payload comprising a CPT2 gene or variant thereof packaged within a avian capsid. |

Fig. 29 (Continued)

| | | | | | |
|---|---|---|---|---|---|
| 2 | bovine AAV | | CPT2 | 1376 | Payload comprising a CPT2 gene or variant thereof packaged within a bovine capsid. |
| 2 | canine AAV | | CPT2 | 1376 | Payload comprising a CPT2 gene or variant thereof packaged within a canine capsid. |
| 2 | equine AAV | | CPT2 | 1376 | Payload comprising a CPT2 gene or variant thereof packaged within a equine capsid. |
| 2 | primate AAV | | CPT2 | 1376 | Payload comprising a CPT2 gene or variant thereof packaged within a primate capsid. |
| 2 | non-primate AAV | | CPT2 | 1376 | Payload comprising a CPT2 gene or variant thereof packaged within a non-primate capsid. |
| 2 | ovine AAV | | CPT2 | 1376 | Payload comprising a CPT2 gene or variant thereof packaged within a ovine capsid. |
| 2 | hybrid AAV | | CPT2 | 1376 | Payload comprising a CPT2 gene or variant thereof packaged within a hybrid capsid. |
| 2 | chimeric AAV | | CPT2 | 1376 | Payload comprising a CPT2 gene or variant thereof packaged within a chimeric capsid. |
| 1 | AAV1 | 1450374 | DDC | 1644 | Payload comprising a DDC gene or variant thereof packaged within a AAV1 capsid. |
| 1 | AAV2 | | DDC | 1644 | Payload comprising a DDC gene or variant thereof packaged within a AAV2 capsid. |
| 1 | AAV3 | | DDC | 1644 | Payload comprising a DDC gene or variant thereof packaged within a AAV3 capsid. |
| 1 | AAV4 | 1446389 | DDC | 1644 | Payload comprising a DDC gene or variant thereof packaged within a AAV4 capsid. |
| 1 | AAV5 | | DDC | 1644 | Payload comprising a DDC gene or variant thereof packaged within a AAV5 capsid. |
| 1 | AAV6 | | DDC | 1644 | Payload comprising a DDC gene or variant thereof packaged within a AAV6 capsid. |
| 1 | AAV7 | | DDC | 1644 | Payload comprising a DDC gene or variant thereof packaged within a AAV7 capsid. |
| 1 | AAV8 | 5075992 | DDC | 1644 | Payload comprising a DDC gene or variant thereof packaged within a AAV8 capsid. |
| 1 | AAV9 | | DDC | 1644 | Payload comprising a DDC gene or variant thereof packaged within a AAV9 capsid. |

Fig. 29 (Continued)

| | | | | | |
|---|---|---|---|---|---|
| 1 | AAV10 | | DDC | 1644 | Payload comprising a DDC gene or variant thereof packaged within a AAV10 capsid. |
| 1 | AAV11 | | DDC | 1644 | Payload comprising a DDC gene or variant thereof packaged within a AAV11 capsid. |
| 1 | AAVC11.01 | | DDC | 1644 | Payload comprising a DDC gene or variant thereof packaged within a AAVC11.01 capsid. |
| 1 | AAVC11.02 | | DDC | 1644 | Payload comprising a DDC gene or variant thereof packaged within a AAVC11.02 capsid. |
| 1 | AAVC11.03 | | DDC | 1644 | Payload comprising a DDC gene or variant thereof packaged within a AAVC11.03 capsid. |
| 1 | AAVC11.04 | | DDC | 1644 | Payload comprising a DDC gene or variant thereof packaged within a AAVC11.04 capsid. |
| 1 | AAVC11.05 | | DDC | 1644 | Payload comprising a DDC gene or variant thereof packaged within a AAVC11.05 capsid. |
| 1 | AAVC11.06 | | DDC | 1644 | Payload comprising a DDC gene or variant thereof packaged within a AAVC11.06 capsid. |
| 1 | AAVC11.07 | | DDC | 1644 | Payload comprising a DDC gene or variant thereof packaged within a AAVC11.07 capsid. |
| 1 | AAVC11.08 | | DDC | 1644 | Payload comprising a DDC gene or variant thereof packaged within a AAVC11.08 capsid. |
| 1 | AAVC11.09 | | DDC | 1644 | Payload comprising a DDC gene or variant thereof packaged within a AAVC11.09 capsid. |
| 1 | AAVC11.10 | | DDC | 1644 | Payload comprising a DDC gene or variant thereof packaged within a AAVC11.10 capsid. |
| 1 | AAVC11.11 | | DDC | 1644 | Payload comprising a DDC gene or variant thereof packaged within a AAVC11.11 capsid. |
| 1 | AAVC11.12 | | DDC | 1644 | Payload comprising a DDC gene or variant thereof packaged within a AAVC11.12 capsid. |
| 1 | AAVC11.13 | | DDC | 1644 | Payload comprising a DDC gene or variant thereof packaged within a AAVC11.13 capsid. |
| 1 | AAVC11.14 | | DDC | 1644 | Payload comprising a DDC gene or variant thereof packaged within a AAVC11.14 capsid. |
| 1 | AAVC11.15 | | DDC | 1644 | Payload comprising a DDC gene or variant thereof packaged within a AAVC11.15 capsid. |

Fig. 29 (Continued)

| | | | | | |
|---|---|---|---|---|---|
| 1 | AAVC11.16 | | DDC | 1644 | Payload comprising a DDC gene or variant thereof packaged within a AAVC11.16 capsid. |
| 1 | AAVC11.17 | | DDC | 1644 | Payload comprising a DDC gene or variant thereof packaged within a AAVC11.17 capsid. |
| 1 | AAVC11.18 | | DDC | 1644 | Payload comprising a DDC gene or variant thereof packaged within a AAVC11.18 capsid. |
| 1 | AAVC11.19 | | DDC | 1644 | Payload comprising a DDC gene or variant thereof packaged within a AAVC11.19 capsid. |
| 1 | AAV12 | | DDC | 1644 | Payload comprising a DDC gene or variant thereof packaged within a AAV12 capsid. |
| 1 | AAV13 | | DDC | 1644 | Payload comprising a DDC gene or variant thereof packaged within a AAV13 capsid. |
| 1 | AAV-DJ | | DDC | 1644 | Payload comprising a DDC gene or variant thereof packaged within a AAV-DJ capsid. |
| 1 | AAV-LK03 | | DDC | 1644 | Payload comprising a DDC gene or variant thereof packaged within a AAV-LK03 capsid. |
| 1 | AAV-LK19 | | DDC | 1644 | Payload comprising a DDC gene or variant thereof packaged within a AAV-LK19 capsid. |
| 1 | AAVrh.74 | | DDC | 1644 | Payload comprising a DDC gene or variant thereof packaged within a AAVrh.74 capsid. |
| 1 | AAVrh.10 | | DDC | 1644 | Payload comprising a DDC gene or variant thereof packaged within a AAVrh.10 capsid. |
| 1 | AAVhu.37 | | DDC | 1644 | Payload comprising a DDC gene or variant thereof packaged within a AAVhu.37 capsid. |
| 1 | AAVrh.K | | DDC | 1644 | Payload comprising a DDC gene or variant thereof packaged within a AAVrh.K capsid. |
| 1 | AAVrh.39 | | DDC | 1644 | Payload comprising a DDC gene or variant thereof packaged within a AAVrh.39 capsid. |
| 1 | AAVrh.9 | | DDC | 1644 | Payload comprising a DDC gene or variant thereof packaged within a AAVrh.9 capsid. |
| 1 | avian AAV | | DDC | 1644 | Payload comprising a DDC gene or variant thereof packaged within a avian capsid. |

Fig. 29 (Continued)

| | | | | | |
|---|---|---|---|---|---|
| 1 | bovine AAV | | DDC | 1644 | Payload comprising a DDC gene or variant thereof packaged within a bovine capsid. |
| 1 | canine AAV | | DDC | 1644 | Payload comprising a DDC gene or variant thereof packaged within a canine capsid. |
| 1 | equine AAV | | DDC | 1644 | Payload comprising a DDC gene or variant thereof packaged within a equine capsid. |
| 1 | primate AAV | | DDC | 1644 | Payload comprising a DDC gene or variant thereof packaged within a primate capsid. |
| 1 | non-primate AAV | | DDC | 1644 | Payload comprising a DDC gene or variant thereof packaged within a non-primate capsid. |
| 1 | ovine AAV | | DDC | 1644 | Payload comprising a DDC gene or variant thereof packaged within a ovine capsid. |
| 1 | hybrid AAV | | DDC | 1644 | Payload comprising a DDC gene or variant thereof packaged within a hybrid capsid. |
| 1 | chimeric AAV | | DDC | 1644 | Payload comprising a DDC gene or variant thereof packaged within a chimeric capsid. |
| 2 | AAV1 | 1450374 | DDC | 1644 | Payload comprising a DDC gene or variant thereof packaged within a AAV1 capsid. |
| 2 | AAV2 | | DDC | 1644 | Payload comprising a DDC gene or variant thereof packaged within a AAV2 capsid. |
| 2 | AAV3 | | DDC | 1644 | Payload comprising a DDC gene or variant thereof packaged within a AAV3 capsid. |
| 2 | AAV4 | 1446389 | DDC | 1644 | Payload comprising a DDC gene or variant thereof packaged within a AAV4 capsid. |
| 2 | AAV5 | | DDC | 1644 | Payload comprising a DDC gene or variant thereof packaged within a AAV5 capsid. |
| 2 | AAV6 | | DDC | 1644 | Payload comprising a DDC gene or variant thereof packaged within a AAV6 capsid. |
| 2 | AAV7 | | DDC | 1644 | Payload comprising a DDC gene or variant thereof packaged within a AAV7 capsid. |
| 2 | AAV8 | 5075992 | DDC | 1644 | Payload comprising a DDC gene or variant thereof packaged within a AAV8 capsid. |
| 2 | AAV9 | | DDC | 1644 | Payload comprising a DDC gene or variant thereof packaged within a AAV9 capsid. |

Fig. 29 (Continued)

| | | | | | |
|---|---|---|---|---|---|
| 2 | AAV10 | | DDC | 1644 | Payload comprising a DDC gene or variant thereof packaged within a AAV10 capsid. |
| 2 | AAV11 | | DDC | 1644 | Payload comprising a DDC gene or variant thereof packaged within a AAV11 capsid. |
| 2 | AAVC11.01 | | DDC | 1644 | Payload comprising a DDC gene or variant thereof packaged within a AAVC11.01 capsid. |
| 2 | AAVC11.02 | | DDC | 1644 | Payload comprising a DDC gene or variant thereof packaged within a AAVC11.02 capsid. |
| 2 | AAVC11.03 | | DDC | 1644 | Payload comprising a DDC gene or variant thereof packaged within a AAVC11.03 capsid. |
| 2 | AAVC11.04 | | DDC | 1644 | Payload comprising a DDC gene or variant thereof packaged within a AAVC11.04 capsid. |
| 2 | AAVC11.05 | | DDC | 1644 | Payload comprising a DDC gene or variant thereof packaged within a AAVC11.05 capsid. |
| 2 | AAVC11.06 | | DDC | 1644 | Payload comprising a DDC gene or variant thereof packaged within a AAVC11.06 capsid. |
| 2 | AAVC11.07 | | DDC | 1644 | Payload comprising a DDC gene or variant thereof packaged within a AAVC11.07 capsid. |
| 2 | AAVC11.08 | | DDC | 1644 | Payload comprising a DDC gene or variant thereof packaged within a AAVC11.08 capsid. |
| 2 | AAVC11.09 | | DDC | 1644 | Payload comprising a DDC gene or variant thereof packaged within a AAVC11.09 capsid. |
| 2 | AAVC11.10 | | DDC | 1644 | Payload comprising a DDC gene or variant thereof packaged within a AAVC11.10 capsid. |
| 2 | AAVC11.11 | | DDC | 1644 | Payload comprising a DDC gene or variant thereof packaged within a AAVC11.11 capsid. |
| 2 | AAVC11.12 | | DDC | 1644 | Payload comprising a DDC gene or variant thereof packaged within a AAVC11.12 capsid. |
| 2 | AAVC11.13 | | DDC | 1644 | Payload comprising a DDC gene or variant thereof packaged within a AAVC11.13 capsid. |
| 2 | AAVC11.14 | | DDC | 1644 | Payload comprising a DDC gene or variant thereof packaged within a AAVC11.14 capsid. |
| 2 | AAVC11.15 | | DDC | 1644 | Payload comprising a DDC gene or variant thereof packaged within a AAVC11.15 capsid. |

Fig. 29 (Continued)

| | | | | | |
|---|---|---|---|---|---|
| 2 | AAVC11.16 | | DDC | 1644 | Payload comprising a DDC gene or variant thereof packaged within a AAVC11.16 capsid. |
| 2 | AAVC11.17 | | DDC | 1644 | Payload comprising a DDC gene or variant thereof packaged within a AAVC11.17 capsid. |
| 2 | AAVC11.18 | | DDC | 1644 | Payload comprising a DDC gene or variant thereof packaged within a AAVC11.18 capsid. |
| 2 | AAVC11.19 | | DDC | 1644 | Payload comprising a DDC gene or variant thereof packaged within a AAVC11.19 capsid. |
| 2 | AAV12 | | DDC | 1644 | Payload comprising a DDC gene or variant thereof packaged within a AAV12 capsid. |
| 2 | AAV13 | | DDC | 1644 | Payload comprising a DDC gene or variant thereof packaged within a AAV13 capsid. |
| 2 | AAV-DJ | | DDC | 1644 | Payload comprising a DDC gene or variant thereof packaged within a AAV-DJ capsid. |
| 2 | AAV-LK03 | | DDC | 1644 | Payload comprising a DDC gene or variant thereof packaged within a AAV-LK03 capsid. |
| 2 | AAV-LK19 | | DDC | 1644 | Payload comprising a DDC gene or variant thereof packaged within a AAV-LK19 capsid. |
| 2 | AAVrh.74 | | DDC | 1644 | Payload comprising a DDC gene or variant thereof packaged within a AAVrh.74 capsid. |
| 2 | AAVrh.10 | | DDC | 1644 | Payload comprising a DDC gene or variant thereof packaged within a AAVrh.10 capsid. |
| 2 | AAVhu.37 | | DDC | 1644 | Payload comprising a DDC gene or variant thereof packaged within a AAVhu.37 capsid. |
| 2 | AAVrh.K | | DDC | 1644 | Payload comprising a DDC gene or variant thereof packaged within a AAVrh.K capsid. |
| 2 | AAVrh.39 | | DDC | 1644 | Payload comprising a DDC gene or variant thereof packaged within a AAVrh.39 capsid. |
| 2 | AAVrh.9 | | DDC | 1644 | Payload comprising a DDC gene or variant thereof packaged within a AAVrh.9 capsid. |
| 2 | avian AAV | | DDC | 1644 | Payload comprising a DDC gene or variant thereof packaged within a avian capsid. |

Fig. 29 (Continued)

| | | | | | |
|---|---|---|---|---|---|
| 2 | bovine AAV | | DDC | 1644 | Payload comprising a DDC gene or variant thereof packaged within a bovine capsid. |
| 2 | canine AAV | | DDC | 1644 | Payload comprising a DDC gene or variant thereof packaged within a canine capsid. |
| 2 | equine AAV | | DDC | 1644 | Payload comprising a DDC gene or variant thereof packaged within a equine capsid. |
| 2 | primate AAV | | DDC | 1644 | Payload comprising a DDC gene or variant thereof packaged within a primate capsid. |
| 2 | non-primate AAV | | DDC | 1644 | Payload comprising a DDC gene or variant thereof packaged within a non-primate capsid. |
| 2 | ovine AAV | | DDC | 1644 | Payload comprising a DDC gene or variant thereof packaged within a ovine capsid. |
| 2 | hybrid AAV | | DDC | 1644 | Payload comprising a DDC gene or variant thereof packaged within a hybrid capsid. |
| 2 | chimeric AAV | | DDC | 1644 | Payload comprising a DDC gene or variant thereof packaged within a chimeric capsid. |
| 1 | AAV1 | 1450374 | DMD | 1756 | Payload comprising a DMD gene or variant thereof packaged within a AAV1 capsid. |
| 1 | AAV2 | | DMD | 1756 | Payload comprising a DMD gene or variant thereof packaged within a AAV2 capsid. |
| 1 | AAV3 | | DMD | 1756 | Payload comprising a DMD gene or variant thereof packaged within a AAV3 capsid. |
| 1 | AAV4 | 1446389 | DMD | 1756 | Payload comprising a DMD gene or variant thereof packaged within a AAV4 capsid. |
| 1 | AAV5 | | DMD | 1756 | Payload comprising a DMD gene or variant thereof packaged within a AAV5 capsid. |
| 1 | AAV6 | | DMD | 1756 | Payload comprising a DMD gene or variant thereof packaged within a AAV6 capsid. |
| 1 | AAV7 | | DMD | 1756 | Payload comprising a DMD gene or variant thereof packaged within a AAV7 capsid. |
| 1 | AAV8 | 5075992 | DMD | 1756 | Payload comprising a DMD gene or variant thereof packaged within a AAV8 capsid. |
| 1 | AAV9 | | DMD | 1756 | Payload comprising a DMD gene or variant thereof packaged within a AAV9 capsid. |

Fig. 29 (Continued)

| | | | | | |
|---|---|---|---|---|---|
| 1 | AAV10 | | DMD | 1756 | Payload comprising a DMD gene or variant thereof packaged within a AAV10 capsid. |
| 1 | AAV11 | | DMD | 1756 | Payload comprising a DMD gene or variant thereof packaged within a AAV11 capsid. |
| 1 | AAVC11.01 | | DMD | 1756 | Payload comprising a DMD gene or variant thereof packaged within a AAVC11.01 capsid. |
| 1 | AAVC11.02 | | DMD | 1756 | Payload comprising a DMD gene or variant thereof packaged within a AAVC11.02 capsid. |
| 1 | AAVC11.03 | | DMD | 1756 | Payload comprising a DMD gene or variant thereof packaged within a AAVC11.03 capsid. |
| 1 | AAVC11.04 | | DMD | 1756 | Payload comprising a DMD gene or variant thereof packaged within a AAVC11.04 capsid. |
| 1 | AAVC11.05 | | DMD | 1756 | Payload comprising a DMD gene or variant thereof packaged within a AAVC11.05 capsid. |
| 1 | AAVC11.06 | | DMD | 1756 | Payload comprising a DMD gene or variant thereof packaged within a AAVC11.06 capsid. |
| 1 | AAVC11.07 | | DMD | 1756 | Payload comprising a DMD gene or variant thereof packaged within a AAVC11.07 capsid. |
| 1 | AAVC11.08 | | DMD | 1756 | Payload comprising a DMD gene or variant thereof packaged within a AAVC11.08 capsid. |
| 1 | AAVC11.09 | | DMD | 1756 | Payload comprising a DMD gene or variant thereof packaged within a AAVC11.09 capsid. |
| 1 | AAVC11.10 | | DMD | 1756 | Payload comprising a DMD gene or variant thereof packaged within a AAVC11.10 capsid. |
| 1 | AAVC11.11 | | DMD | 1756 | Payload comprising a DMD gene or variant thereof packaged within a AAVC11.11 capsid. |
| 1 | AAVC11.12 | | DMD | 1756 | Payload comprising a DMD gene or variant thereof packaged within a AAVC11.12 capsid. |
| 1 | AAVC11.13 | | DMD | 1756 | Payload comprising a DMD gene or variant thereof packaged within a AAVC11.13 capsid. |
| 1 | AAVC11.14 | | DMD | 1756 | Payload comprising a DMD gene or variant thereof packaged within a AAVC11.14 capsid. |
| 1 | AAVC11.15 | | DMD | 1756 | Payload comprising a DMD gene or variant thereof packaged within a AAVC11.15 capsid. |

Fig. 29 (Continued)

| | | | | | |
|---|---|---|---|---|---|
| 1 | AAVC11.16 | | DMD | 1756 | Payload comprising a DMD gene or variant thereof packaged within a AAVC11.16 capsid. |
| 1 | AAVC11.17 | | DMD | 1756 | Payload comprising a DMD gene or variant thereof packaged within a AAVC11.17 capsid. |
| 1 | AAVC11.18 | | DMD | 1756 | Payload comprising a DMD gene or variant thereof packaged within a AAVC11.18 capsid. |
| 1 | AAVC11.19 | | DMD | 1756 | Payload comprising a DMD gene or variant thereof packaged within a AAVC11.19 capsid. |
| 1 | AAV12 | | DMD | 1756 | Payload comprising a DMD gene or variant thereof packaged within a AAV12 capsid. |
| 1 | AAV13 | | DMD | 1756 | Payload comprising a DMD gene or variant thereof packaged within a AAV13 capsid. |
| 1 | AAV-DJ | | DMD | 1756 | Payload comprising a DMD gene or variant thereof packaged within a AAV-DJ capsid. |
| 1 | AAV-LK03 | | DMD | 1756 | Payload comprising a DMD gene or variant thereof packaged within a AAV-LK03 capsid. |
| 1 | AAV-LK19 | | DMD | 1756 | Payload comprising a DMD gene or variant thereof packaged within a AAV-LK19 capsid. |
| 1 | AAVrh.74 | | DMD | 1756 | Payload comprising a DMD gene or variant thereof packaged within a AAVrh.74 capsid. |
| 1 | AAVrh.10 | | DMD | 1756 | Payload comprising a DMD gene or variant thereof packaged within a AAVrh.10 capsid. |
| 1 | AAVhu.37 | | DMD | 1756 | Payload comprising a DMD gene or variant thereof packaged within a AAVhu.37 capsid. |
| 1 | AAVrh.K | | DMD | 1756 | Payload comprising a DMD gene or variant thereof packaged within a AAVrh.K capsid. |
| 1 | AAVrh.39 | | DMD | 1756 | Payload comprising a DMD gene or variant thereof packaged within a AAVrh.39 capsid. |
| 1 | AAVrh.9 | | DMD | 1756 | Payload comprising a DMD gene or variant thereof packaged within a AAVrh.9 capsid. |
| 1 | avian AAV | | DMD | 1756 | Payload comprising a DMD gene or variant thereof packaged within a avian capsid. |

Fig. 29 (Continued)

| | | | | | |
|---|---|---|---|---|---|
| 1 | bovine AAV | | DMD | 1756 | Payload comprising a DMD gene or variant thereof packaged within a bovine capsid. |
| 1 | canine AAV | | DMD | 1756 | Payload comprising a DMD gene or variant thereof packaged within a canine capsid. |
| 1 | equine AAV | | DMD | 1756 | Payload comprising a DMD gene or variant thereof packaged within a equine capsid. |
| 1 | primate AAV | | DMD | 1756 | Payload comprising a DMD gene or variant thereof packaged within a primate capsid. |
| 1 | non-primate AAV | | DMD | 1756 | Payload comprising a DMD gene or variant thereof packaged within a non-primate capsid. |
| 1 | ovine AAV | | DMD | 1756 | Payload comprising a DMD gene or variant thereof packaged within a ovine capsid. |
| 1 | hybrid AAV | | DMD | 1756 | Payload comprising a DMD gene or variant thereof packaged within a hybrid capsid. |
| 1 | chimeric AAV | | DMD | 1756 | Payload comprising a DMD gene or variant thereof packaged within a chimeric capsid. |
| 2 | AAV1 | 1450374 | DMD | 1756 | Payload comprising a DMD gene or variant thereof packaged within a AAV1 capsid. |
| 2 | AAV2 | | DMD | 1756 | Payload comprising a DMD gene or variant thereof packaged within a AAV2 capsid. |
| 2 | AAV3 | | DMD | 1756 | Payload comprising a DMD gene or variant thereof packaged within a AAV3 capsid. |
| 2 | AAV4 | 1446389 | DMD | 1756 | Payload comprising a DMD gene or variant thereof packaged within a AAV4 capsid. |
| 2 | AAV5 | | DMD | 1756 | Payload comprising a DMD gene or variant thereof packaged within a AAV5 capsid. |
| 2 | AAV6 | | DMD | 1756 | Payload comprising a DMD gene or variant thereof packaged within a AAV6 capsid. |
| 2 | AAV7 | | DMD | 1756 | Payload comprising a DMD gene or variant thereof packaged within a AAV7 capsid. |
| 2 | AAV8 | 5075992 | DMD | 1756 | Payload comprising a DMD gene or variant thereof packaged within a AAV8 capsid. |
| 2 | AAV9 | | DMD | 1756 | Payload comprising a DMD gene or variant thereof packaged within a AAV9 capsid. |

Fig. 29 (Continued)

| | | | | | |
|---|---|---|---|---|---|
| 2 | AAV10 | | DMD | 1756 | Payload comprising a DMD gene or variant thereof packaged within a AAV10 capsid. |
| 2 | AAV11 | | DMD | 1756 | Payload comprising a DMD gene or variant thereof packaged within a AAV11 capsid. |
| 2 | AAVC11.01 | | DMD | 1756 | Payload comprising a DMD gene or variant thereof packaged within a AAVC11.01 capsid. |
| 2 | AAVC11.02 | | DMD | 1756 | Payload comprising a DMD gene or variant thereof packaged within a AAVC11.02 capsid. |
| 2 | AAVC11.03 | | DMD | 1756 | Payload comprising a DMD gene or variant thereof packaged within a AAVC11.03 capsid. |
| 2 | AAVC11.04 | | DMD | 1756 | Payload comprising a DMD gene or variant thereof packaged within a AAVC11.04 capsid. |
| 2 | AAVC11.05 | | DMD | 1756 | Payload comprising a DMD gene or variant thereof packaged within a AAVC11.05 capsid. |
| 2 | AAVC11.06 | | DMD | 1756 | Payload comprising a DMD gene or variant thereof packaged within a AAVC11.06 capsid. |
| 2 | AAVC11.07 | | DMD | 1756 | Payload comprising a DMD gene or variant thereof packaged within a AAVC11.07 capsid. |
| 2 | AAVC11.08 | | DMD | 1756 | Payload comprising a DMD gene or variant thereof packaged within a AAVC11.08 capsid. |
| 2 | AAVC11.09 | | DMD | 1756 | Payload comprising a DMD gene or variant thereof packaged within a AAVC11.09 capsid. |
| 2 | AAVC11.10 | | DMD | 1756 | Payload comprising a DMD gene or variant thereof packaged within a AAVC11.10 capsid. |
| 2 | AAVC11.11 | | DMD | 1756 | Payload comprising a DMD gene or variant thereof packaged within a AAVC11.11 capsid. |
| 2 | AAVC11.12 | | DMD | 1756 | Payload comprising a DMD gene or variant thereof packaged within a AAVC11.12 capsid. |
| 2 | AAVC11.13 | | DMD | 1756 | Payload comprising a DMD gene or variant thereof packaged within a AAVC11.13 capsid. |
| 2 | AAVC11.14 | | DMD | 1756 | Payload comprising a DMD gene or variant thereof packaged within a AAVC11.14 capsid. |
| 2 | AAVC11.15 | | DMD | 1756 | Payload comprising a DMD gene or variant thereof packaged within a AAVC11.15 capsid. |

Fig. 29 (Continued)

| | | | | | |
|---|---|---|---|---|---|
| 2 | AAVC11.16 | | DMD | 1756 | Payload comprising a DMD gene or variant thereof packaged within a AAVC11.16 capsid. |
| 2 | AAVC11.17 | | DMD | 1756 | Payload comprising a DMD gene or variant thereof packaged within a AAVC11.17 capsid. |
| 2 | AAVC11.18 | | DMD | 1756 | Payload comprising a DMD gene or variant thereof packaged within a AAVC11.18 capsid. |
| 2 | AAVC11.19 | | DMD | 1756 | Payload comprising a DMD gene or variant thereof packaged within a AAVC11.19 capsid. |
| 2 | AAV12 | | DMD | 1756 | Payload comprising a DMD gene or variant thereof packaged within a AAV12 capsid. |
| 2 | AAV13 | | DMD | 1756 | Payload comprising a DMD gene or variant thereof packaged within a AAV13 capsid. |
| 2 | AAV-DJ | | DMD | 1756 | Payload comprising a DMD gene or variant thereof packaged within a AAV-DJ capsid. |
| 2 | AAV-LK03 | | DMD | 1756 | Payload comprising a DMD gene or variant thereof packaged within a AAV-LK03 capsid. |
| 2 | AAV-LK19 | | DMD | 1756 | Payload comprising a DMD gene or variant thereof packaged within a AAV-LK19 capsid. |
| 2 | AAVrh.74 | | DMD | 1756 | Payload comprising a DMD gene or variant thereof packaged within a AAVrh.74 capsid. |
| 2 | AAVrh.10 | | DMD | 1756 | Payload comprising a DMD gene or variant thereof packaged within a AAVrh.10 capsid. |
| 2 | AAVhu.37 | | DMD | 1756 | Payload comprising a DMD gene or variant thereof packaged within a AAVhu.37 capsid. |
| 2 | AAVrh.K | | DMD | 1756 | Payload comprising a DMD gene or variant thereof packaged within a AAVrh.K capsid. |
| 2 | AAVrh.39 | | DMD | 1756 | Payload comprising a DMD gene or variant thereof packaged within a AAVrh.39 capsid. |
| 2 | AAVrh.9 | | DMD | 1756 | Payload comprising a DMD gene or variant thereof packaged within a AAVrh.9 capsid. |
| 2 | avian AAV | | DMD | 1756 | Payload comprising a DMD gene or variant thereof packaged within a avian capsid. |

Fig. 29 (Continued)

| | | | | | |
|---|---|---|---|---|---|
| 2 | bovine AAV | | DMD | 1756 | Payload comprising a DMD gene or variant thereof packaged within a bovine capsid. |
| 2 | canine AAV | | DMD | 1756 | Payload comprising a DMD gene or variant thereof packaged within a canine capsid. |
| 2 | equine AAV | | DMD | 1756 | Payload comprising a DMD gene or variant thereof packaged within a equine capsid. |
| 2 | primate AAV | | DMD | 1756 | Payload comprising a DMD gene or variant thereof packaged within a primate capsid. |
| 2 | non-primate AAV | | DMD | 1756 | Payload comprising a DMD gene or variant thereof packaged within a non-primate capsid. |
| 2 | ovine AAV | | DMD | 1756 | Payload comprising a DMD gene or variant thereof packaged within a ovine capsid. |
| 2 | hybrid AAV | | DMD | 1756 | Payload comprising a DMD gene or variant thereof packaged within a hybrid capsid. |
| 2 | chimeric AAV | | DMD | 1756 | Payload comprising a DMD gene or variant thereof packaged within a chimeric capsid. |
| 1 | AAV1 | 1450374 | DYSF | 8291 | Payload comprising a DYSF gene or variant thereof packaged within a AAV1 capsid. |
| 1 | AAV2 | | DYSF | 8291 | Payload comprising a DYSF gene or variant thereof packaged within a AAV2 capsid. |
| 1 | AAV3 | | DYSF | 8291 | Payload comprising a DYSF gene or variant thereof packaged within a AAV3 capsid. |
| 1 | AAV4 | 1446389 | DYSF | 8291 | Payload comprising a DYSF gene or variant thereof packaged within a AAV4 capsid. |
| 1 | AAV5 | | DYSF | 8291 | Payload comprising a DYSF gene or variant thereof packaged within a AAV5 capsid. |
| 1 | AAV6 | | DYSF | 8291 | Payload comprising a DYSF gene or variant thereof packaged within a AAV6 capsid. |
| 1 | AAV7 | | DYSF | 8291 | Payload comprising a DYSF gene or variant thereof packaged within a AAV7 capsid. |
| 1 | AAV8 | 5075992 | DYSF | 8291 | Payload comprising a DYSF gene or variant thereof packaged within a AAV8 capsid. |
| 1 | AAV9 | | DYSF | 8291 | Payload comprising a DYSF gene or variant thereof packaged within a AAV9 capsid. |

Fig. 29 (Continued)

| | | | | | |
|---|---|---|---|---|---|
| 1 | AAV10 | | DYSF | 8291 | Payload comprising a DYSF gene or variant thereof packaged within a AAV10 capsid. |
| 1 | AAV11 | | DYSF | 8291 | Payload comprising a DYSF gene or variant thereof packaged within a AAV11 capsid. |
| 1 | AAVC11.01 | | DYSF | 8291 | Payload comprising a DYSF gene or variant thereof packaged within a AAVC11.01 capsid. |
| 1 | AAVC11.02 | | DYSF | 8291 | Payload comprising a DYSF gene or variant thereof packaged within a AAVC11.02 capsid. |
| 1 | AAVC11.03 | | DYSF | 8291 | Payload comprising a DYSF gene or variant thereof packaged within a AAVC11.03 capsid. |
| 1 | AAVC11.04 | | DYSF | 8291 | Payload comprising a DYSF gene or variant thereof packaged within a AAVC11.04 capsid. |
| 1 | AAVC11.05 | | DYSF | 8291 | Payload comprising a DYSF gene or variant thereof packaged within a AAVC11.05 capsid. |
| 1 | AAVC11.06 | | DYSF | 8291 | Payload comprising a DYSF gene or variant thereof packaged within a AAVC11.06 capsid. |
| 1 | AAVC11.07 | | DYSF | 8291 | Payload comprising a DYSF gene or variant thereof packaged within a AAVC11.07 capsid. |
| 1 | AAVC11.08 | | DYSF | 8291 | Payload comprising a DYSF gene or variant thereof packaged within a AAVC11.08 capsid. |
| 1 | AAVC11.09 | | DYSF | 8291 | Payload comprising a DYSF gene or variant thereof packaged within a AAVC11.09 capsid. |
| 1 | AAVC11.10 | | DYSF | 8291 | Payload comprising a DYSF gene or variant thereof packaged within a AAVC11.10 capsid. |
| 1 | AAVC11.11 | | DYSF | 8291 | Payload comprising a DYSF gene or variant thereof packaged within a AAVC11.11 capsid. |
| 1 | AAVC11.12 | | DYSF | 8291 | Payload comprising a DYSF gene or variant thereof packaged within a AAVC11.12 capsid. |
| 1 | AAVC11.13 | | DYSF | 8291 | Payload comprising a DYSF gene or variant thereof packaged within a AAVC11.13 capsid. |
| 1 | AAVC11.14 | | DYSF | 8291 | Payload comprising a DYSF gene or variant thereof packaged within a AAVC11.14 capsid. |
| 1 | AAVC11.15 | | DYSF | 8291 | Payload comprising a DYSF gene or variant thereof packaged within a AAVC11.15 capsid. |

Fig. 29 (Continued)

| | | | | | |
|---|---|---|---|---|---|
| 1 | AAVC11.16 | | DYSF | 8291 | Payload comprising a DYSF gene or variant thereof packaged within a AAVC11.16 capsid. |
| 1 | AAVC11.17 | | DYSF | 8291 | Payload comprising a DYSF gene or variant thereof packaged within a AAVC11.17 capsid. |
| 1 | AAVC11.18 | | DYSF | 8291 | Payload comprising a DYSF gene or variant thereof packaged within a AAVC11.18 capsid. |
| 1 | AAVC11.19 | | DYSF | 8291 | Payload comprising a DYSF gene or variant thereof packaged within a AAVC11.19 capsid. |
| 1 | AAV12 | | DYSF | 8291 | Payload comprising a DYSF gene or variant thereof packaged within a AAV12 capsid. |
| 1 | AAV13 | | DYSF | 8291 | Payload comprising a DYSF gene or variant thereof packaged within a AAV13 capsid. |
| 1 | AAV-DJ | | DYSF | 8291 | Payload comprising a DYSF gene or variant thereof packaged within a AAV-DJ capsid. |
| 1 | AAV-LK03 | | DYSF | 8291 | Payload comprising a DYSF gene or variant thereof packaged within a AAV-LK03 capsid. |
| 1 | AAV-LK19 | | DYSF | 8291 | Payload comprising a DYSF gene or variant thereof packaged within a AAV-LK19 capsid. |
| 1 | AAVrh.74 | | DYSF | 8291 | Payload comprising a DYSF gene or variant thereof packaged within a AAVrh.74 capsid. |
| 1 | AAVrh.10 | | DYSF | 8291 | Payload comprising a DYSF gene or variant thereof packaged within a AAVrh.10 capsid. |
| 1 | AAVhu.37 | | DYSF | 8291 | Payload comprising a DYSF gene or variant thereof packaged within a AAVhu.37 capsid. |
| 1 | AAVrh.K | | DYSF | 8291 | Payload comprising a DYSF gene or variant thereof packaged within a AAVrh.K capsid. |
| 1 | AAVrh.39 | | DYSF | 8291 | Payload comprising a DYSF gene or variant thereof packaged within a AAVrh.39 capsid. |
| 1 | AAVrh.9 | | DYSF | 8291 | Payload comprising a DYSF gene or variant thereof packaged within a AAVrh.9 capsid. |
| 1 | avian AAV | | DYSF | 8291 | Payload comprising a DYSF gene or variant thereof packaged within a avian capsid. |

Fig. 29 (Continued)

| | | | | | |
|---|---|---|---|---|---|
| 1 | bovine AAV | | DYSF | 8291 | Payload comprising a DYSF gene or variant thereof packaged within a bovine capsid. |
| 1 | canine AAV | | DYSF | 8291 | Payload comprising a DYSF gene or variant thereof packaged within a canine capsid. |
| 1 | equine AAV | | DYSF | 8291 | Payload comprising a DYSF gene or variant thereof packaged within a equine capsid. |
| 1 | primate AAV | | DYSF | 8291 | Payload comprising a DYSF gene or variant thereof packaged within a primate capsid. |
| 1 | non-primate AAV | | DYSF | 8291 | Payload comprising a DYSF gene or variant thereof packaged within a non-primate capsid. |
| 1 | ovine AAV | | DYSF | 8291 | Payload comprising a DYSF gene or variant thereof packaged within a ovine capsid. |
| 1 | hybrid AAV | | DYSF | 8291 | Payload comprising a DYSF gene or variant thereof packaged within a hybrid capsid. |
| 1 | chimeric AAV | | DYSF | 8291 | Payload comprising a DYSF gene or variant thereof packaged within a chimeric capsid. |
| 2 | AAV1 | 1450374 | DYSF | 8291 | Payload comprising a DYSF gene or variant thereof packaged within a AAV1 capsid. |
| 2 | AAV2 | | DYSF | 8291 | Payload comprising a DYSF gene or variant thereof packaged within a AAV2 capsid. |
| 2 | AAV3 | | DYSF | 8291 | Payload comprising a DYSF gene or variant thereof packaged within a AAV3 capsid. |
| 2 | AAV4 | 1446389 | DYSF | 8291 | Payload comprising a DYSF gene or variant thereof packaged within a AAV4 capsid. |
| 2 | AAV5 | | DYSF | 8291 | Payload comprising a DYSF gene or variant thereof packaged within a AAV5 capsid. |
| 2 | AAV6 | | DYSF | 8291 | Payload comprising a DYSF gene or variant thereof packaged within a AAV6 capsid. |
| 2 | AAV7 | | DYSF | 8291 | Payload comprising a DYSF gene or variant thereof packaged within a AAV7 capsid. |
| 2 | AAV8 | 5075992 | DYSF | 8291 | Payload comprising a DYSF gene or variant thereof packaged within a AAV8 capsid. |
| 2 | AAV9 | | DYSF | 8291 | Payload comprising a DYSF gene or variant thereof packaged within a AAV9 capsid. |

Fig. 29 (Continued)

| | | | | | |
|---|---|---|---|---|---|
| 2 | AAV10 | | DYSF | 8291 | Payload comprising a DYSF gene or variant thereof packaged within a AAV10 capsid. |
| 2 | AAV11 | | DYSF | 8291 | Payload comprising a DYSF gene or variant thereof packaged within a AAV11 capsid. |
| 2 | AAVC11.01 | | DYSF | 8291 | Payload comprising a DYSF gene or variant thereof packaged within a AAVC11.01 capsid. |
| 2 | AAVC11.02 | | DYSF | 8291 | Payload comprising a DYSF gene or variant thereof packaged within a AAVC11.02 capsid. |
| 2 | AAVC11.03 | | DYSF | 8291 | Payload comprising a DYSF gene or variant thereof packaged within a AAVC11.03 capsid. |
| 2 | AAVC11.04 | | DYSF | 8291 | Payload comprising a DYSF gene or variant thereof packaged within a AAVC11.04 capsid. |
| 2 | AAVC11.05 | | DYSF | 8291 | Payload comprising a DYSF gene or variant thereof packaged within a AAVC11.05 capsid. |
| 2 | AAVC11.06 | | DYSF | 8291 | Payload comprising a DYSF gene or variant thereof packaged within a AAVC11.06 capsid. |
| 2 | AAVC11.07 | | DYSF | 8291 | Payload comprising a DYSF gene or variant thereof packaged within a AAVC11.07 capsid. |
| 2 | AAVC11.08 | | DYSF | 8291 | Payload comprising a DYSF gene or variant thereof packaged within a AAVC11.08 capsid. |
| 2 | AAVC11.09 | | DYSF | 8291 | Payload comprising a DYSF gene or variant thereof packaged within a AAVC11.09 capsid. |
| 2 | AAVC11.10 | | DYSF | 8291 | Payload comprising a DYSF gene or variant thereof packaged within a AAVC11.10 capsid. |
| 2 | AAVC11.11 | | DYSF | 8291 | Payload comprising a DYSF gene or variant thereof packaged within a AAVC11.11 capsid. |
| 2 | AAVC11.12 | | DYSF | 8291 | Payload comprising a DYSF gene or variant thereof packaged within a AAVC11.12 capsid. |
| 2 | AAVC11.13 | | DYSF | 8291 | Payload comprising a DYSF gene or variant thereof packaged within a AAVC11.13 capsid. |
| 2 | AAVC11.14 | | DYSF | 8291 | Payload comprising a DYSF gene or variant thereof packaged within a AAVC11.14 capsid. |
| 2 | AAVC11.15 | | DYSF | 8291 | Payload comprising a DYSF gene or variant thereof packaged within a AAVC11.15 capsid. |

Fig. 29 (Continued)

| | | | | | |
|---|---|---|---|---|---|
| 2 | AAVC11.16 | | DYSF | 8291 | Payload comprising a DYSF gene or variant thereof packaged within a AAVC11.16 capsid. |
| 2 | AAVC11.17 | | DYSF | 8291 | Payload comprising a DYSF gene or variant thereof packaged within a AAVC11.17 capsid. |
| 2 | AAVC11.18 | | DYSF | 8291 | Payload comprising a DYSF gene or variant thereof packaged within a AAVC11.18 capsid. |
| 2 | AAVC11.19 | | DYSF | 8291 | Payload comprising a DYSF gene or variant thereof packaged within a AAVC11.19 capsid. |
| 2 | AAV12 | | DYSF | 8291 | Payload comprising a DYSF gene or variant thereof packaged within a AAV12 capsid. |
| 2 | AAV13 | | DYSF | 8291 | Payload comprising a DYSF gene or variant thereof packaged within a AAV13 capsid. |
| 2 | AAV-DJ | | DYSF | 8291 | Payload comprising a DYSF gene or variant thereof packaged within a AAV-DJ capsid. |
| 2 | AAV-LK03 | | DYSF | 8291 | Payload comprising a DYSF gene or variant thereof packaged within a AAV-LK03 capsid. |
| 2 | AAV-LK19 | | DYSF | 8291 | Payload comprising a DYSF gene or variant thereof packaged within a AAV-LK19 capsid. |
| 2 | AAVrh.74 | | DYSF | 8291 | Payload comprising a DYSF gene or variant thereof packaged within a AAVrh.74 capsid. |
| 2 | AAVrh.10 | | DYSF | 8291 | Payload comprising a DYSF gene or variant thereof packaged within a AAVrh.10 capsid. |
| 2 | AAVhu.37 | | DYSF | 8291 | Payload comprising a DYSF gene or variant thereof packaged within a AAVhu.37 capsid. |
| 2 | AAVrh.K | | DYSF | 8291 | Payload comprising a DYSF gene or variant thereof packaged within a AAVrh.K capsid. |
| 2 | AAVrh.39 | | DYSF | 8291 | Payload comprising a DYSF gene or variant thereof packaged within a AAVrh.39 capsid. |
| 2 | AAVrh.9 | | DYSF | 8291 | Payload comprising a DYSF gene or variant thereof packaged within a AAVrh.9 capsid. |
| 2 | avian AAV | | DYSF | 8291 | Payload comprising a DYSF gene or variant thereof packaged within a avian capsid. |

Fig. 29 (Continued)

| | | | | | |
|---|---|---|---|---|---|
| 2 | bovine AAV | | DYSF | 8291 | Payload comprising a DYSF gene or variant thereof packaged within a bovine capsid. |
| 2 | canine AAV | | DYSF | 8291 | Payload comprising a DYSF gene or variant thereof packaged within a canine capsid. |
| 2 | equine AAV | | DYSF | 8291 | Payload comprising a DYSF gene or variant thereof packaged within a equine capsid. |
| 2 | primate AAV | | DYSF | 8291 | Payload comprising a DYSF gene or variant thereof packaged within a primate capsid. |
| 2 | non-primate AAV | | DYSF | 8291 | Payload comprising a DYSF gene or variant thereof packaged within a non-primate capsid. |
| 2 | ovine AAV | | DYSF | 8291 | Payload comprising a DYSF gene or variant thereof packaged within a ovine capsid. |
| 2 | hybrid AAV | | DYSF | 8291 | Payload comprising a DYSF gene or variant thereof packaged within a hybrid capsid. |
| 2 | chimeric AAV | | DYSF | 8291 | Payload comprising a DYSF gene or variant thereof packaged within a chimeric capsid. |
| 1 | AAV1 | 1450374 | Factor IX (FIX) | 2158 | Payload comprising a Factor IX (FIX) gene or variant thereof packaged within a AAV1 capsid. |
| 1 | AAV2 | | Factor IX (FIX) | 2158 | Payload comprising a Factor IX (FIX) gene or variant thereof packaged within a AAV2 capsid. |
| 1 | AAV3 | | Factor IX (FIX) | 2158 | Payload comprising a Factor IX (FIX) gene or variant thereof packaged within a AAV3 capsid. |
| 1 | AAV4 | 1446389 | Factor IX (FIX) | 2158 | Payload comprising a Factor IX (FIX) gene or variant thereof packaged within a AAV4 capsid. |
| 1 | AAV5 | | Factor IX (FIX) | 2158 | Payload comprising a Factor IX (FIX) gene or variant thereof packaged within a AAV5 capsid. |
| 1 | AAV6 | | Factor IX (FIX) | 2158 | Payload comprising a Factor IX (FIX) gene or variant thereof packaged within a AAV6 capsid. |
| 1 | AAV7 | | Factor IX (FIX) | 2158 | Payload comprising a Factor IX (FIX) gene or variant thereof packaged within a AAV7 capsid. |
| 1 | AAV8 | 5075992 | Factor IX (FIX) | 2158 | Payload comprising a Factor IX (FIX) gene or variant thereof packaged within a AAV8 capsid. |
| 1 | AAV9 | | Factor IX (FIX) | 2158 | Payload comprising a Factor IX (FIX) gene or variant thereof packaged within a AAV9 capsid. |

Fig. 29 (Continued)

| | | | | | |
|---|---|---|---|---|---|
| 1 | AAV10 | | Factor IX (FIX) | 2158 | Payload comprising a Factor IX (FIX) gene or variant thereof packaged within a AAV10 capsid. |
| 1 | AAV11 | | Factor IX (FIX) | 2158 | Payload comprising a Factor IX (FIX) gene or variant thereof packaged within a AAV11 capsid. |
| 1 | AAVC11.01 | | Factor IX (FIX) | 2158 | Payload comprising a Factor IX (FIX) gene or variant thereof packaged within a AAVC11.01 capsid. |
| 1 | AAVC11.02 | | Factor IX (FIX) | 2158 | Payload comprising a Factor IX (FIX) gene or variant thereof packaged within a AAVC11.02 capsid. |
| 1 | AAVC11.03 | | Factor IX (FIX) | 2158 | Payload comprising a Factor IX (FIX) gene or variant thereof packaged within a AAVC11.03 capsid. |
| 1 | AAVC11.04 | | Factor IX (FIX) | 2158 | Payload comprising a Factor IX (FIX) gene or variant thereof packaged within a AAVC11.04 capsid. |
| 1 | AAVC11.05 | | Factor IX (FIX) | 2158 | Payload comprising a Factor IX (FIX) gene or variant thereof packaged within a AAVC11.05 capsid. |
| 1 | AAVC11.06 | | Factor IX (FIX) | 2158 | Payload comprising a Factor IX (FIX) gene or variant thereof packaged within a AAVC11.06 capsid. |
| 1 | AAVC11.07 | | Factor IX (FIX) | 2158 | Payload comprising a Factor IX (FIX) gene or variant thereof packaged within a AAVC11.07 capsid. |
| 1 | AAVC11.08 | | Factor IX (FIX) | 2158 | Payload comprising a Factor IX (FIX) gene or variant thereof packaged within a AAVC11.08 capsid. |
| 1 | AAVC11.09 | | Factor IX (FIX) | 2158 | Payload comprising a Factor IX (FIX) gene or variant thereof packaged within a AAVC11.09 capsid. |
| 1 | AAVC11.10 | | Factor IX (FIX) | 2158 | Payload comprising a Factor IX (FIX) gene or variant thereof packaged within a AAVC11.10 capsid. |
| 1 | AAVC11.11 | | Factor IX (FIX) | 2158 | Payload comprising a Factor IX (FIX) gene or variant thereof packaged within a AAVC11.11 capsid. |
| 1 | AAVC11.12 | | Factor IX (FIX) | 2158 | Payload comprising a Factor IX (FIX) gene or variant thereof packaged within a AAVC11.12 capsid. |
| 1 | AAVC11.13 | | Factor IX (FIX) | 2158 | Payload comprising a Factor IX (FIX) gene or variant thereof packaged within a AAVC11.13 capsid. |
| 1 | AAVC11.14 | | Factor IX (FIX) | 2158 | Payload comprising a Factor IX (FIX) gene or variant thereof packaged within a AAVC11.14 capsid. |
| 1 | AAVC11.15 | | Factor IX (FIX) | 2158 | Payload comprising a Factor IX (FIX) gene or variant thereof packaged within a AAVC11.15 capsid. |

Fig. 29 (Continued)

| | | | | | |
|---|---|---|---|---|---|
| 1 | AAVC11.16 | | Factor IX (FIX) | 2158 | Payload comprising a Factor IX (FIX) gene or variant thereof packaged within a AAVC11.16 capsid. |
| 1 | AAVC11.17 | | Factor IX (FIX) | 2158 | Payload comprising a Factor IX (FIX) gene or variant thereof packaged within a AAVC11.17 capsid. |
| 1 | AAVC11.18 | | Factor IX (FIX) | 2158 | Payload comprising a Factor IX (FIX) gene or variant thereof packaged within a AAVC11.18 capsid. |
| 1 | AAVC11.19 | | Factor IX (FIX) | 2158 | Payload comprising a Factor IX (FIX) gene or variant thereof packaged within a AAVC11.19 capsid. |
| 1 | AAV12 | | Factor IX (FIX) | 2158 | Payload comprising a Factor IX (FIX) gene or variant thereof packaged within a AAV12 capsid. |
| 1 | AAV13 | | Factor IX (FIX) | 2158 | Payload comprising a Factor IX (FIX) gene or variant thereof packaged within a AAV13 capsid. |
| 1 | AAV-DJ | | Factor IX (FIX) | 2158 | Payload comprising a Factor IX (FIX) gene or variant thereof packaged within a AAV-DJ capsid. |
| 1 | AAV-LK03 | | Factor IX (FIX) | 2158 | Payload comprising a Factor IX (FIX) gene or variant thereof packaged within a AAV-LK03 capsid. |
| 1 | AAV-LK19 | | Factor IX (FIX) | 2158 | Payload comprising a Factor IX (FIX) gene or variant thereof packaged within a AAV-LK19 capsid. |
| 1 | AAVrh.74 | | Factor IX (FIX) | 2158 | Payload comprising a Factor IX (FIX) gene or variant thereof packaged within a AAVrh.74 capsid. |
| 1 | AAVrh.10 | | Factor IX (FIX) | 2158 | Payload comprising a Factor IX (FIX) gene or variant thereof packaged within a AAVrh.10 capsid. |
| 1 | AAVhu.37 | | Factor IX (FIX) | 2158 | Payload comprising a Factor IX (FIX) gene or variant thereof packaged within a AAVhu.37 capsid. |
| 1 | AAVrh.K | | Factor IX (FIX) | 2158 | Payload comprising a Factor IX (FIX) gene or variant thereof packaged within a AAVrh.K capsid. |
| 1 | AAVrh.39 | | Factor IX (FIX) | 2158 | Payload comprising a Factor IX (FIX) gene or variant thereof packaged within a AAVrh.39 capsid. |
| 1 | AAVrh.9 | | Factor IX (FIX) | 2158 | Payload comprising a Factor IX (FIX) gene or variant thereof packaged within a AAVrh.9 capsid. |
| 1 | avian AAV | | Factor IX (FIX) | 2158 | Payload comprising a Factor IX (FIX) gene or variant thereof packaged within a avian capsid. |

Fig. 29 (Continued)

| | | | | | |
|---|---|---|---|---|---|
| 1 | bovine AAV | | Factor IX (FIX) | 2158 | Payload comprising a Factor IX (FIX) gene or variant thereof packaged within a bovine capsid. |
| 1 | canine AAV | | Factor IX (FIX) | 2158 | Payload comprising a Factor IX (FIX) gene or variant thereof packaged within a canine capsid. |
| 1 | equine AAV | | Factor IX (FIX) | 2158 | Payload comprising a Factor IX (FIX) gene or variant thereof packaged within a equine capsid. |
| 1 | primate AAV | | Factor IX (FIX) | 2158 | Payload comprising a Factor IX (FIX) gene or variant thereof packaged within a primate capsid. |
| 1 | non-primate AAV | | Factor IX (FIX) | 2158 | Payload comprising a Factor IX (FIX) gene or variant thereof packaged within a non-primate capsid. |
| 1 | ovine AAV | | Factor IX (FIX) | 2158 | Payload comprising a Factor IX (FIX) gene or variant thereof packaged within a ovine capsid. |
| 1 | hybrid AAV | | Factor IX (FIX) | 2158 | Payload comprising a Factor IX (FIX) gene or variant thereof packaged within a hybrid capsid. |
| 1 | chimeric AAV | | Factor IX (FIX) | 2158 | Payload comprising a Factor IX (FIX) gene or variant thereof packaged within a chimeric capsid. |
| 2 | AAV1 | 1450374 | Factor IX (FIX) | 2158 | Payload comprising a Factor IX (FIX) gene or variant thereof packaged within a AAV1 capsid. |
| 2 | AAV2 | | Factor IX (FIX) | 2158 | Payload comprising a Factor IX (FIX) gene or variant thereof packaged within a AAV2 capsid. |
| 2 | AAV3 | | Factor IX (FIX) | 2158 | Payload comprising a Factor IX (FIX) gene or variant thereof packaged within a AAV3 capsid. |
| 2 | AAV4 | 1446389 | Factor IX (FIX) | 2158 | Payload comprising a Factor IX (FIX) gene or variant thereof packaged within a AAV4 capsid. |
| 2 | AAV5 | | Factor IX (FIX) | 2158 | Payload comprising a Factor IX (FIX) gene or variant thereof packaged within a AAV5 capsid. |
| 2 | AAV6 | | Factor IX (FIX) | 2158 | Payload comprising a Factor IX (FIX) gene or variant thereof packaged within a AAV6 capsid. |
| 2 | AAV7 | | Factor IX (FIX) | 2158 | Payload comprising a Factor IX (FIX) gene or variant thereof packaged within a AAV7 capsid. |
| 2 | AAV8 | 5075992 | Factor IX (FIX) | 2158 | Payload comprising a Factor IX (FIX) gene or variant thereof packaged within a AAV8 capsid. |
| 2 | AAV9 | | Factor IX (FIX) | 2158 | Payload comprising a Factor IX (FIX) gene or variant thereof packaged within a AAV9 capsid. |

Fig. 29 (Continued)

| | | | | | |
|---|---|---|---|---|---|
| 2 | AAV10 | | Factor IX (FIX) | 2158 | Payload comprising a Factor IX (FIX) gene or variant thereof packaged within a AAV10 capsid. |
| 2 | AAV11 | | Factor IX (FIX) | 2158 | Payload comprising a Factor IX (FIX) gene or variant thereof packaged within a AAV11 capsid. |
| 2 | AAVC11.01 | | Factor IX (FIX) | 2158 | Payload comprising a Factor IX (FIX) gene or variant thereof packaged within a AAVC11.01 capsid. |
| 2 | AAVC11.02 | | Factor IX (FIX) | 2158 | Payload comprising a Factor IX (FIX) gene or variant thereof packaged within a AAVC11.02 capsid. |
| 2 | AAVC11.03 | | Factor IX (FIX) | 2158 | Payload comprising a Factor IX (FIX) gene or variant thereof packaged within a AAVC11.03 capsid. |
| 2 | AAVC11.04 | | Factor IX (FIX) | 2158 | Payload comprising a Factor IX (FIX) gene or variant thereof packaged within a AAVC11.04 capsid. |
| 2 | AAVC11.05 | | Factor IX (FIX) | 2158 | Payload comprising a Factor IX (FIX) gene or variant thereof packaged within a AAVC11.05 capsid. |
| 2 | AAVC11.06 | | Factor IX (FIX) | 2158 | Payload comprising a Factor IX (FIX) gene or variant thereof packaged within a AAVC11.06 capsid. |
| 2 | AAVC11.07 | | Factor IX (FIX) | 2158 | Payload comprising a Factor IX (FIX) gene or variant thereof packaged within a AAVC11.07 capsid. |
| 2 | AAVC11.08 | | Factor IX (FIX) | 2158 | Payload comprising a Factor IX (FIX) gene or variant thereof packaged within a AAVC11.08 capsid. |
| 2 | AAVC11.09 | | Factor IX (FIX) | 2158 | Payload comprising a Factor IX (FIX) gene or variant thereof packaged within a AAVC11.09 capsid. |
| 2 | AAVC11.10 | | Factor IX (FIX) | 2158 | Payload comprising a Factor IX (FIX) gene or variant thereof packaged within a AAVC11.10 capsid. |
| 2 | AAVC11.11 | | Factor IX (FIX) | 2158 | Payload comprising a Factor IX (FIX) gene or variant thereof packaged within a AAVC11.11 capsid. |
| 2 | AAVC11.12 | | Factor IX (FIX) | 2158 | Payload comprising a Factor IX (FIX) gene or variant thereof packaged within a AAVC11.12 capsid. |
| 2 | AAVC11.13 | | Factor IX (FIX) | 2158 | Payload comprising a Factor IX (FIX) gene or variant thereof packaged within a AAVC11.13 capsid. |
| 2 | AAVC11.14 | | Factor IX (FIX) | 2158 | Payload comprising a Factor IX (FIX) gene or variant thereof packaged within a AAVC11.14 capsid. |
| 2 | AAVC11.15 | | Factor IX (FIX) | 2158 | Payload comprising a Factor IX (FIX) gene or variant thereof packaged within a AAVC11.15 capsid. |

Fig. 29 (Continued)

| | | | | | |
|---|---|---|---|---|---|
| 2 | AAVC11.16 | | Factor IX (FIX) | 2158 | Payload comprising a Factor IX (FIX) gene or variant thereof packaged within a AAVC11.16 capsid. |
| 2 | AAVC11.17 | | Factor IX (FIX) | 2158 | Payload comprising a Factor IX (FIX) gene or variant thereof packaged within a AAVC11.17 capsid. |
| 2 | AAVC11.18 | | Factor IX (FIX) | 2158 | Payload comprising a Factor IX (FIX) gene or variant thereof packaged within a AAVC11.18 capsid. |
| 2 | AAVC11.19 | | Factor IX (FIX) | 2158 | Payload comprising a Factor IX (FIX) gene or variant thereof packaged within a AAVC11.19 capsid. |
| 2 | AAV12 | | Factor IX (FIX) | 2158 | Payload comprising a Factor IX (FIX) gene or variant thereof packaged within a AAV12 capsid. |
| 2 | AAV13 | | Factor IX (FIX) | 2158 | Payload comprising a Factor IX (FIX) gene or variant thereof packaged within a AAV13 capsid. |
| 2 | AAV-DJ | | Factor IX (FIX) | 2158 | Payload comprising a Factor IX (FIX) gene or variant thereof packaged within a AAV-DJ capsid. |
| 2 | AAV-LK03 | | Factor IX (FIX) | 2158 | Payload comprising a Factor IX (FIX) gene or variant thereof packaged within a AAV-LK03 capsid. |
| 2 | AAV-LK19 | | Factor IX (FIX) | 2158 | Payload comprising a Factor IX (FIX) gene or variant thereof packaged within a AAV-LK19 capsid. |
| 2 | AAVrh.74 | | Factor IX (FIX) | 2158 | Payload comprising a Factor IX (FIX) gene or variant thereof packaged within a AAVrh.74 capsid. |
| 2 | AAVrh.10 | | Factor IX (FIX) | 2158 | Payload comprising a Factor IX (FIX) gene or variant thereof packaged within a AAVrh.10 capsid. |
| 2 | AAVhu.37 | | Factor IX (FIX) | 2158 | Payload comprising a Factor IX (FIX) gene or variant thereof packaged within a AAVhu.37 capsid. |
| 2 | AAVrh.K | | Factor IX (FIX) | 2158 | Payload comprising a Factor IX (FIX) gene or variant thereof packaged within a AAVrh.K capsid. |
| 2 | AAVrh.39 | | Factor IX (FIX) | 2158 | Payload comprising a Factor IX (FIX) gene or variant thereof packaged within a AAVrh.39 capsid. |
| 2 | AAVrh.9 | | Factor IX (FIX) | 2158 | Payload comprising a Factor IX (FIX) gene or variant thereof packaged within a AAVrh.9 capsid. |
| 2 | avian AAV | | Factor IX (FIX) | 2158 | Payload comprising a Factor IX (FIX) gene or variant thereof packaged within a avian capsid. |

Fig. 29 (Continued)

| | | | | | |
|---|---|---|---|---|---|
| 2 | bovine AAV | | Factor IX (FIX) | 2158 | Payload comprising a Factor IX (FIX) gene or variant thereof packaged within a bovine capsid. |
| 2 | canine AAV | | Factor IX (FIX) | 2158 | Payload comprising a Factor IX (FIX) gene or variant thereof packaged within a canine capsid. |
| 2 | equine AAV | | Factor IX (FIX) | 2158 | Payload comprising a Factor IX (FIX) gene or variant thereof packaged within a equine capsid. |
| 2 | primate AAV | | Factor IX (FIX) | 2158 | Payload comprising a Factor IX (FIX) gene or variant thereof packaged within a primate capsid. |
| 2 | non-primate AAV | | Factor IX (FIX) | 2158 | Payload comprising a Factor IX (FIX) gene or variant thereof packaged within a non-primate capsid. |
| 2 | ovine AAV | | Factor IX (FIX) | 2158 | Payload comprising a Factor IX (FIX) gene or variant thereof packaged within a ovine capsid. |
| 2 | hybrid AAV | | Factor IX (FIX) | 2158 | Payload comprising a Factor IX (FIX) gene or variant thereof packaged within a hybrid capsid. |
| 2 | chimeric AAV | | Factor IX (FIX) | 2158 | Payload comprising a Factor IX (FIX) gene or variant thereof packaged within a chimeric capsid. |
| 1 | AAV1 | 1450374 | Factor VIII (FVIII) | 2157 | Payload comprising a Factor VIII (FVIII) gene or variant thereof packaged within a AAV1 capsid. |
| 1 | AAV2 | | Factor VIII (FVIII) | 2157 | Payload comprising a Factor VIII (FVIII) gene or variant thereof packaged within a AAV2 capsid. |
| 1 | AAV3 | | Factor VIII (FVIII) | 2157 | Payload comprising a Factor VIII (FVIII) gene or variant thereof packaged within a AAV3 capsid. |
| 1 | AAV4 | 1446389 | Factor VIII (FVIII) | 2157 | Payload comprising a Factor VIII (FVIII) gene or variant thereof packaged within a AAV4 capsid. |
| 1 | AAV5 | | Factor VIII (FVIII) | 2157 | Payload comprising a Factor VIII (FVIII) gene or variant thereof packaged within a AAV5 capsid. |
| 1 | AAV6 | | Factor VIII (FVIII) | 2157 | Payload comprising a Factor VIII (FVIII) gene or variant thereof packaged within a AAV6 capsid. |
| 1 | AAV7 | | Factor VIII (FVIII) | 2157 | Payload comprising a Factor VIII (FVIII) gene or variant thereof packaged within a AAV7 capsid. |
| 1 | AAV8 | 5075992 | Factor VIII (FVIII) | 2157 | Payload comprising a Factor VIII (FVIII) gene or variant thereof packaged within a AAV8 capsid. |
| 1 | AAV9 | | Factor VIII (FVIII) | 2157 | Payload comprising a Factor VIII (FVIII) gene or variant thereof packaged within a AAV9 capsid. |

Fig. 29 (Continued)

| | | | | | |
|---|---|---|---|---|---|
| 1 | AAV10 | | Factor VIII (FVIII) | 2157 | Payload comprising a Factor VIII (FVIII) gene or variant thereof packaged within a AAV10 capsid. |
| 1 | AAV11 | | Factor VIII (FVIII) | 2157 | Payload comprising a Factor VIII (FVIII) gene or variant thereof packaged within a AAV11 capsid. |
| 1 | AAVC11.01 | | Factor VIII (FVIII) | 2157 | Payload comprising a Factor VIII (FVIII) gene or variant thereof packaged within a AAVC11.01 capsid. |
| 1 | AAVC11.02 | | Factor VIII (FVIII) | 2157 | Payload comprising a Factor VIII (FVIII) gene or variant thereof packaged within a AAVC11.02 capsid. |
| 1 | AAVC11.03 | | Factor VIII (FVIII) | 2157 | Payload comprising a Factor VIII (FVIII) gene or variant thereof packaged within a AAVC11.03 capsid. |
| 1 | AAVC11.04 | | Factor VIII (FVIII) | 2157 | Payload comprising a Factor VIII (FVIII) gene or variant thereof packaged within a AAVC11.04 capsid. |
| 1 | AAVC11.05 | | Factor VIII (FVIII) | 2157 | Payload comprising a Factor VIII (FVIII) gene or variant thereof packaged within a AAVC11.05 capsid. |
| 1 | AAVC11.06 | | Factor VIII (FVIII) | 2157 | Payload comprising a Factor VIII (FVIII) gene or variant thereof packaged within a AAVC11.06 capsid. |
| 1 | AAVC11.07 | | Factor VIII (FVIII) | 2157 | Payload comprising a Factor VIII (FVIII) gene or variant thereof packaged within a AAVC11.07 capsid. |
| 1 | AAVC11.08 | | Factor VIII (FVIII) | 2157 | Payload comprising a Factor VIII (FVIII) gene or variant thereof packaged within a AAVC11.08 capsid. |
| 1 | AAVC11.09 | | Factor VIII (FVIII) | 2157 | Payload comprising a Factor VIII (FVIII) gene or variant thereof packaged within a AAVC11.09 capsid. |
| 1 | AAVC11.10 | | Factor VIII (FVIII) | 2157 | Payload comprising a Factor VIII (FVIII) gene or variant thereof packaged within a AAVC11.10 capsid. |
| 1 | AAVC11.11 | | Factor VIII (FVIII) | 2157 | Payload comprising a Factor VIII (FVIII) gene or variant thereof packaged within a AAVC11.11 capsid. |
| 1 | AAVC11.12 | | Factor VIII (FVIII) | 2157 | Payload comprising a Factor VIII (FVIII) gene or variant thereof packaged within a AAVC11.12 capsid. |
| 1 | AAVC11.13 | | Factor VIII (FVIII) | 2157 | Payload comprising a Factor VIII (FVIII) gene or variant thereof packaged within a AAVC11.13 capsid. |
| 1 | AAVC11.14 | | Factor VIII (FVIII) | 2157 | Payload comprising a Factor VIII (FVIII) gene or variant thereof packaged within a AAVC11.14 capsid. |
| 1 | AAVC11.15 | | Factor VIII (FVIII) | 2157 | Payload comprising a Factor VIII (FVIII) gene or variant thereof packaged within a AAVC11.15 capsid. |

Fig. 29 (Continued)

| | | | | | |
|---|---|---|---|---|---|
| 1 | AAVC11.16 | | Factor VIII (FVIII) | 2157 | Payload comprising a Factor VIII (FVIII) gene or variant thereof packaged within a AAVC11.16 capsid. |
| 1 | AAVC11.17 | | Factor VIII (FVIII) | 2157 | Payload comprising a Factor VIII (FVIII) gene or variant thereof packaged within a AAVC11.17 capsid. |
| 1 | AAVC11.18 | | Factor VIII (FVIII) | 2157 | Payload comprising a Factor VIII (FVIII) gene or variant thereof packaged within a AAVC11.18 capsid. |
| 1 | AAVC11.19 | | Factor VIII (FVIII) | 2157 | Payload comprising a Factor VIII (FVIII) gene or variant thereof packaged within a AAVC11.19 capsid. |
| 1 | AAV12 | | Factor VIII (FVIII) | 2157 | Payload comprising a Factor VIII (FVIII) gene or variant thereof packaged within a AAV12 capsid. |
| 1 | AAV13 | | Factor VIII (FVIII) | 2157 | Payload comprising a Factor VIII (FVIII) gene or variant thereof packaged within a AAV13 capsid. |
| 1 | AAV-DJ | | Factor VIII (FVIII) | 2157 | Payload comprising a Factor VIII (FVIII) gene or variant thereof packaged within a AAV-DJ capsid. |
| 1 | AAV-LK03 | | Factor VIII (FVIII) | 2157 | Payload comprising a Factor VIII (FVIII) gene or variant thereof packaged within a AAV-LK03 capsid. |
| 1 | AAV-LK19 | | Factor VIII (FVIII) | 2157 | Payload comprising a Factor VIII (FVIII) gene or variant thereof packaged within a AAV-LK19 capsid. |
| 1 | AAVrh.74 | | Factor VIII (FVIII) | 2157 | Payload comprising a Factor VIII (FVIII) gene or variant thereof packaged within a AAVrh.74 capsid. |
| 1 | AAVrh.10 | | Factor VIII (FVIII) | 2157 | Payload comprising a Factor VIII (FVIII) gene or variant thereof packaged within a AAVrh.10 capsid. |
| 1 | AAVhu.37 | | Factor VIII (FVIII) | 2157 | Payload comprising a Factor VIII (FVIII) gene or variant thereof packaged within a AAVhu.37 capsid. |
| 1 | AAVrh.K | | Factor VIII (FVIII) | 2157 | Payload comprising a Factor VIII (FVIII) gene or variant thereof packaged within a AAVrh.K capsid. |
| 1 | AAVrh.39 | | Factor VIII (FVIII) | 2157 | Payload comprising a Factor VIII (FVIII) gene or variant thereof packaged within a AAVrh.39 capsid. |
| 1 | AAVrh.9 | | Factor VIII (FVIII) | 2157 | Payload comprising a Factor VIII (FVIII) gene or variant thereof packaged within a AAVrh.9 capsid. |
| 1 | avian AAV | | Factor VIII (FVIII) | 2157 | Payload comprising a Factor VIII (FVIII) gene or variant thereof packaged within a avian capsid. |

Fig. 29 (Continued)

| | | | | | |
|---|---|---|---|---|---|
| 1 | bovine AAV | | Factor VIII (FVIII) | 2157 | Payload comprising a Factor VIII (FVIII) gene or variant thereof packaged within a bovine capsid. |
| 1 | canine AAV | | Factor VIII (FVIII) | 2157 | Payload comprising a Factor VIII (FVIII) gene or variant thereof packaged within a canine capsid. |
| 1 | equine AAV | | Factor VIII (FVIII) | 2157 | Payload comprising a Factor VIII (FVIII) gene or variant thereof packaged within a equine capsid. |
| 1 | primate AAV | | Factor VIII (FVIII) | 2157 | Payload comprising a Factor VIII (FVIII) gene or variant thereof packaged within a primate capsid. |
| 1 | non-primate AAV | | Factor VIII (FVIII) | 2157 | Payload comprising a Factor VIII (FVIII) gene or variant thereof packaged within a non-primate capsid. |
| 1 | ovine AAV | | Factor VIII (FVIII) | 2157 | Payload comprising a Factor VIII (FVIII) gene or variant thereof packaged within a ovine capsid. |
| 1 | hybrid AAV | | Factor VIII (FVIII) | 2157 | Payload comprising a Factor VIII (FVIII) gene or variant thereof packaged within a hybrid capsid. |
| 1 | chimeric AAV | | Factor VIII (FVIII) | 2157 | Payload comprising a Factor VIII (FVIII) gene or variant thereof packaged within a chimeric capsid. |
| 2 | AAV1 | 1450374 | Factor VIII (FVIII) | 2157 | Payload comprising a Factor VIII (FVIII) gene or variant thereof packaged within a AAV1 capsid. |
| 2 | AAV2 | | Factor VIII (FVIII) | 2157 | Payload comprising a Factor VIII (FVIII) gene or variant thereof packaged within a AAV2 capsid. |
| 2 | AAV3 | | Factor VIII (FVIII) | 2157 | Payload comprising a Factor VIII (FVIII) gene or variant thereof packaged within a AAV3 capsid. |
| 2 | AAV4 | 1446389 | Factor VIII (FVIII) | 2157 | Payload comprising a Factor VIII (FVIII) gene or variant thereof packaged within a AAV4 capsid. |
| 2 | AAV5 | | Factor VIII (FVIII) | 2157 | Payload comprising a Factor VIII (FVIII) gene or variant thereof packaged within a AAV5 capsid. |
| 2 | AAV6 | | Factor VIII (FVIII) | 2157 | Payload comprising a Factor VIII (FVIII) gene or variant thereof packaged within a AAV6 capsid. |
| 2 | AAV7 | | Factor VIII (FVIII) | 2157 | Payload comprising a Factor VIII (FVIII) gene or variant thereof packaged within a AAV7 capsid. |
| 2 | AAV8 | 5075992 | Factor VIII (FVIII) | 2157 | Payload comprising a Factor VIII (FVIII) gene or variant thereof packaged within a AAV8 capsid. |
| 2 | AAV9 | | Factor VIII (FVIII) | 2157 | Payload comprising a Factor VIII (FVIII) gene or variant thereof packaged within a AAV9 capsid. |

Fig. 29 (Continued)

| | | | | | |
|---|---|---|---|---|---|
| 2 | AAV10 | | Factor VIII (FVIII) | 2157 | Payload comprising a Factor VIII (FVIII) gene or variant thereof packaged within a AAV10 capsid. |
| 2 | AAV11 | | Factor VIII (FVIII) | 2157 | Payload comprising a Factor VIII (FVIII) gene or variant thereof packaged within a AAV11 capsid. |
| 2 | AAVC11.01 | | Factor VIII (FVIII) | 2157 | Payload comprising a Factor VIII (FVIII) gene or variant thereof packaged within a AAVC11.01 capsid. |
| 2 | AAVC11.02 | | Factor VIII (FVIII) | 2157 | Payload comprising a Factor VIII (FVIII) gene or variant thereof packaged within a AAVC11.02 capsid. |
| 2 | AAVC11.03 | | Factor VIII (FVIII) | 2157 | Payload comprising a Factor VIII (FVIII) gene or variant thereof packaged within a AAVC11.03 capsid. |
| 2 | AAVC11.04 | | Factor VIII (FVIII) | 2157 | Payload comprising a Factor VIII (FVIII) gene or variant thereof packaged within a AAVC11.04 capsid. |
| 2 | AAVC11.05 | | Factor VIII (FVIII) | 2157 | Payload comprising a Factor VIII (FVIII) gene or variant thereof packaged within a AAVC11.05 capsid. |
| 2 | AAVC11.06 | | Factor VIII (FVIII) | 2157 | Payload comprising a Factor VIII (FVIII) gene or variant thereof packaged within a AAVC11.06 capsid. |
| 2 | AAVC11.07 | | Factor VIII (FVIII) | 2157 | Payload comprising a Factor VIII (FVIII) gene or variant thereof packaged within a AAVC11.07 capsid. |
| 2 | AAVC11.08 | | Factor VIII (FVIII) | 2157 | Payload comprising a Factor VIII (FVIII) gene or variant thereof packaged within a AAVC11.08 capsid. |
| 2 | AAVC11.09 | | Factor VIII (FVIII) | 2157 | Payload comprising a Factor VIII (FVIII) gene or variant thereof packaged within a AAVC11.09 capsid. |
| 2 | AAVC11.10 | | Factor VIII (FVIII) | 2157 | Payload comprising a Factor VIII (FVIII) gene or variant thereof packaged within a AAVC11.10 capsid. |
| 2 | AAVC11.11 | | Factor VIII (FVIII) | 2157 | Payload comprising a Factor VIII (FVIII) gene or variant thereof packaged within a AAVC11.11 capsid. |
| 2 | AAVC11.12 | | Factor VIII (FVIII) | 2157 | Payload comprising a Factor VIII (FVIII) gene or variant thereof packaged within a AAVC11.12 capsid. |
| 2 | AAVC11.13 | | Factor VIII (FVIII) | 2157 | Payload comprising a Factor VIII (FVIII) gene or variant thereof packaged within a AAVC11.13 capsid. |
| 2 | AAVC11.14 | | Factor VIII (FVIII) | 2157 | Payload comprising a Factor VIII (FVIII) gene or variant thereof packaged within a AAVC11.14 capsid. |
| 2 | AAVC11.15 | | Factor VIII (FVIII) | 2157 | Payload comprising a Factor VIII (FVIII) gene or variant thereof packaged within a AAVC11.15 capsid. |

Fig. 29 (Continued)

| | | | | | |
|---|---|---|---|---|---|
| 2 | AAVC11.16 | | Factor VIII (FVIII) | 2157 | Payload comprising a Factor VIII (FVIII) gene or variant thereof packaged within a AAVC11.16 capsid. |
| 2 | AAVC11.17 | | Factor VIII (FVIII) | 2157 | Payload comprising a Factor VIII (FVIII) gene or variant thereof packaged within a AAVC11.17 capsid. |
| 2 | AAVC11.18 | | Factor VIII (FVIII) | 2157 | Payload comprising a Factor VIII (FVIII) gene or variant thereof packaged within a AAVC11.18 capsid. |
| 2 | AAVC11.19 | | Factor VIII (FVIII) | 2157 | Payload comprising a Factor VIII (FVIII) gene or variant thereof packaged within a AAVC11.19 capsid. |
| 2 | AAV12 | | Factor VIII (FVIII) | 2157 | Payload comprising a Factor VIII (FVIII) gene or variant thereof packaged within a AAV12 capsid. |
| 2 | AAV13 | | Factor VIII (FVIII) | 2157 | Payload comprising a Factor VIII (FVIII) gene or variant thereof packaged within a AAV13 capsid. |
| 2 | AAV-DJ | | Factor VIII (FVIII) | 2157 | Payload comprising a Factor VIII (FVIII) gene or variant thereof packaged within a AAV-DJ capsid. |
| 2 | AAV-LK03 | | Factor VIII (FVIII) | 2157 | Payload comprising a Factor VIII (FVIII) gene or variant thereof packaged within a AAV-LK03 capsid. |
| 2 | AAV-LK19 | | Factor VIII (FVIII) | 2157 | Payload comprising a Factor VIII (FVIII) gene or variant thereof packaged within a AAV-LK19 capsid. |
| 2 | AAVrh.74 | | Factor VIII (FVIII) | 2157 | Payload comprising a Factor VIII (FVIII) gene or variant thereof packaged within a AAVrh.74 capsid. |
| 2 | AAVrh.10 | | Factor VIII (FVIII) | 2157 | Payload comprising a Factor VIII (FVIII) gene or variant thereof packaged within a AAVrh.10 capsid. |
| 2 | AAVhu.37 | | Factor VIII (FVIII) | 2157 | Payload comprising a Factor VIII (FVIII) gene or variant thereof packaged within a AAVhu.37 capsid. |
| 2 | AAVrh.K | | Factor VIII (FVIII) | 2157 | Payload comprising a Factor VIII (FVIII) gene or variant thereof packaged within a AAVrh.K capsid. |
| 2 | AAVrh.39 | | Factor VIII (FVIII) | 2157 | Payload comprising a Factor VIII (FVIII) gene or variant thereof packaged within a AAVrh.39 capsid. |
| 2 | AAVrh.9 | | Factor VIII (FVIII) | 2157 | Payload comprising a Factor VIII (FVIII) gene or variant thereof packaged within a AAVrh.9 capsid. |
| 2 | avian AAV | | Factor VIII (FVIII) | 2157 | Payload comprising a Factor VIII (FVIII) gene or variant thereof packaged within a avian capsid. |

Fig. 29 (Continued)

| | | | | | |
|---|---|---|---|---|---|
| 2 | bovine AAV | | Factor VIII (FVIII) | 2157 | Payload comprising a Factor VIII (FVIII) gene or variant thereof packaged within a bovine capsid. |
| 2 | canine AAV | | Factor VIII (FVIII) | 2157 | Payload comprising a Factor VIII (FVIII) gene or variant thereof packaged within a canine capsid. |
| 2 | equine AAV | | Factor VIII (FVIII) | 2157 | Payload comprising a Factor VIII (FVIII) gene or variant thereof packaged within a equine capsid. |
| 2 | primate AAV | | Factor VIII (FVIII) | 2157 | Payload comprising a Factor VIII (FVIII) gene or variant thereof packaged within a primate capsid. |
| 2 | non-primate AAV | | Factor VIII (FVIII) | 2157 | Payload comprising a Factor VIII (FVIII) gene or variant thereof packaged within a non-primate capsid. |
| 2 | ovine AAV | | Factor VIII (FVIII) | 2157 | Payload comprising a Factor VIII (FVIII) gene or variant thereof packaged within a ovine capsid. |
| 2 | hybrid AAV | | Factor VIII (FVIII) | 2157 | Payload comprising a Factor VIII (FVIII) gene or variant thereof packaged within a hybrid capsid. |
| 2 | chimeric AAV | | Factor VIII (FVIII) | 2157 | Payload comprising a Factor VIII (FVIII) gene or variant thereof packaged within a chimeric capsid. |
| 1 | AAV1 | 1450374 | Factor XII (FXII) | 2161 | Payload comprising a Factor XII (FXII) gene or variant thereof packaged within a AAV1 capsid. |
| 1 | AAV2 | | Factor XII (FXII) | 2161 | Payload comprising a Factor XII (FXII) gene or variant thereof packaged within a AAV2 capsid. |
| 1 | AAV3 | | Factor XII (FXII) | 2161 | Payload comprising a Factor XII (FXII) gene or variant thereof packaged within a AAV3 capsid. |
| 1 | AAV4 | 1446389 | Factor XII (FXII) | 2161 | Payload comprising a Factor XII (FXII) gene or variant thereof packaged within a AAV4 capsid. |
| 1 | AAV5 | | Factor XII (FXII) | 2161 | Payload comprising a Factor XII (FXII) gene or variant thereof packaged within a AAV5 capsid. |
| 1 | AAV6 | | Factor XII (FXII) | 2161 | Payload comprising a Factor XII (FXII) gene or variant thereof packaged within a AAV6 capsid. |
| 1 | AAV7 | | Factor XII (FXII) | 2161 | Payload comprising a Factor XII (FXII) gene or variant thereof packaged within a AAV7 capsid. |
| 1 | AAV8 | 5075992 | Factor XII (FXII) | 2161 | Payload comprising a Factor XII (FXII) gene or variant thereof packaged within a AAV8 capsid. |
| 1 | AAV9 | | Factor XII (FXII) | 2161 | Payload comprising a Factor XII (FXII) gene or variant thereof packaged within a AAV9 capsid. |

Fig. 29 (Continued)

| | | | | | |
|---|---|---|---|---|---|
| 1 | AAV10 | | Factor XII (FXII) | 2161 | Payload comprising a Factor XII (FXII) gene or variant thereof packaged within a AAV10 capsid. |
| 1 | AAV11 | | Factor XII (FXII) | 2161 | Payload comprising a Factor XII (FXII) gene or variant thereof packaged within a AAV11 capsid. |
| 1 | AAVC11.01 | | Factor XII (FXII) | 2161 | Payload comprising a Factor XII (FXII) gene or variant thereof packaged within a AAVC11.01 capsid. |
| 1 | AAVC11.02 | | Factor XII (FXII) | 2161 | Payload comprising a Factor XII (FXII) gene or variant thereof packaged within a AAVC11.02 capsid. |
| 1 | AAVC11.03 | | Factor XII (FXII) | 2161 | Payload comprising a Factor XII (FXII) gene or variant thereof packaged within a AAVC11.03 capsid. |
| 1 | AAVC11.04 | | Factor XII (FXII) | 2161 | Payload comprising a Factor XII (FXII) gene or variant thereof packaged within a AAVC11.04 capsid. |
| 1 | AAVC11.05 | | Factor XII (FXII) | 2161 | Payload comprising a Factor XII (FXII) gene or variant thereof packaged within a AAVC11.05 capsid. |
| 1 | AAVC11.06 | | Factor XII (FXII) | 2161 | Payload comprising a Factor XII (FXII) gene or variant thereof packaged within a AAVC11.06 capsid. |
| 1 | AAVC11.07 | | Factor XII (FXII) | 2161 | Payload comprising a Factor XII (FXII) gene or variant thereof packaged within a AAVC11.07 capsid |
| 1 | AAVC11.08 | | Factor XII (FXII) | 2161 | Payload comprising a Factor XII (FXII) gene or variant thereof packaged within a AAVC11.08 capsid. |
| 1 | AAVC11.09 | | Factor XII (FXII) | 2161 | Payload comprising a Factor XII (FXII) gene or variant thereof packaged within a AAVC11.09 capsid. |
| 1 | AAVC11.10 | | Factor XII (FXII) | 2161 | Payload comprising a Factor XII (FXII) gene or variant thereof packaged within a AAVC11.10 capsid. |
| 1 | AAVC11.11 | | Factor XII (FXII) | 2161 | Payload comprising a Factor XII (FXII) gene or variant thereof packaged within a AAVC11.11 capsid. |
| 1 | AAVC11.12 | | Factor XII (FXII) | 2161 | Payload comprising a Factor XII (FXII) gene or variant thereof packaged within a AAVC11.12 capsid. |
| 1 | AAVC11.13 | | Factor XII (FXII) | 2161 | Payload comprising a Factor XII (FXII) gene or variant thereof packaged within a AAVC11.13 capsid. |
| 1 | AAVC11.14 | | Factor XII (FXII) | 2161 | Payload comprising a Factor XII (FXII) gene or variant thereof packaged within a AAVC11.14 capsid. |
| 1 | AAVC11.15 | | Factor XII (FXII) | 2161 | Payload comprising a Factor XII (FXII) gene or variant thereof packaged within a AAVC11.15 capsid. |

Fig. 29 (Continued)

| | | | | | |
|---|---|---|---|---|---|
| 1 | AAVC11.16 | | Factor XII (FXII) | 2161 | Payload comprising a Factor XII (FXII) gene or variant thereof packaged within a AAVC11.16 capsid. |
| 1 | AAVC11.17 | | Factor XII (FXII) | 2161 | Payload comprising a Factor XII (FXII) gene or variant thereof packaged within a AAVC11.17 capsid. |
| 1 | AAVC11.18 | | Factor XII (FXII) | 2161 | Payload comprising a Factor XII (FXII) gene or variant thereof packaged within a AAVC11.18 capsid |
| 1 | AAVC11.19 | | Factor XII (FXII) | 2161 | Payload comprising a Factor XII (FXII) gene or variant thereof packaged within a AAVC11.19 capsid. |
| 1 | AAV12 | | Factor XII (FXII) | 2161 | Payload comprising a Factor XII (FXII) gene or variant thereof packaged within a AAV12 capsid. |
| 1 | AAV13 | | Factor XII (FXII) | 2161 | Payload comprising a Factor XII (FXII) gene or variant thereof packaged within a AAV13 capsid. |
| 1 | AAV-DJ | | Factor XII (FXII) | 2161 | Payload comprising a Factor XII (FXII) gene or variant thereof packaged within a AAV-DJ capsid |
| 1 | AAV-LK03 | | Factor XII (FXII) | 2161 | Payload comprising a Factor XII (FXII) gene or variant thereof packaged within a AAV-LK03 capsid. |
| 1 | AAV-LK19 | | Factor XII (FXII) | 2161 | Payload comprising a Factor XII (FXII) gene or variant thereof packaged within a AAV-LK19 capsid. |
| 1 | AAVrh.74 | | Factor XII (FXII) | 2161 | Payload comprising a Factor XII (FXII) gene or variant thereof packaged within a AAVrh.74 capsid. |
| 1 | AAVrh.10 | | Factor XII (FXII) | 2161 | Payload comprising a Factor XII (FXII) gene or variant thereof packaged within a AAVrh.10 capsid. |
| 1 | AAVhu.37 | | Factor XII (FXII) | 2161 | Payload comprising a Factor XII (FXII) gene or variant thereof packaged within a AAVhu.37 capsid. |
| 1 | AAVrh.K | | Factor XII (FXII) | 2161 | Payload comprising a Factor XII (FXII) gene or variant thereof packaged within a AAVrh.K capsid. |
| 1 | AAVrh.39 | | Factor XII (FXII) | 2161 | Payload comprising a Factor XII (FXII) gene or variant thereof packaged within a AAVrh.39 capsid. |
| 1 | AAVrh.9 | | Factor XII (FXII) | 2161 | Payload comprising a Factor XII (FXII) gene or variant thereof packaged within a AAVrh.9 capsid. |
| 1 | avian AAV | | Factor XII (FXII) | 2161 | Payload comprising a Factor XII (FXII) gene or variant thereof packaged within a avian capsid. |

Fig. 29 (Continued)

| | | | | | |
|---|---|---|---|---|---|
| 1 | bovine AAV | | Factor XII (FXII) | 2161 | Payload comprising a Factor XII (FXII) gene or variant thereof packaged within a bovine capsid. |
| 1 | canine AAV | | Factor XII (FXII) | 2161 | Payload comprising a Factor XII (FXII) gene or variant thereof packaged within a canine capsid. |
| 1 | equine AAV | | Factor XII (FXII) | 2161 | Payload comprising a Factor XII (FXII) gene or variant thereof packaged within a equine capsid. |
| 1 | primate AAV | | Factor XII (FXII) | 2161 | Payload comprising a Factor XII (FXII) gene or variant thereof packaged within a primate capsid. |
| 1 | non-primate AAV | | Factor XII (FXII) | 2161 | Payload comprising a Factor XII (FXII) gene or variant thereof packaged within a non-primate capsid. |
| 1 | ovine AAV | | Factor XII (FXII) | 2161 | Payload comprising a Factor XII (FXII) gene or variant thereof packaged within a ovine capsid. |
| 1 | hybrid AAV | | Factor XII (FXII) | 2161 | Payload comprising a Factor XII (FXII) gene or variant thereof packaged within a hybrid capsid. |
| 1 | chimeric AAV | | Factor XII (FXII) | 2161 | Payload comprising a Factor XII (FXII) gene or variant thereof packaged within a chimeric capsid. |
| 2 | AAV1 | 1450374 | Factor XII (FXII) | 2161 | Payload comprising a Factor XII (FXII) gene or variant thereof packaged within a AAV1 capsid. |
| 2 | AAV2 | | Factor XII (FXII) | 2161 | Payload comprising a Factor XII (FXII) gene or variant thereof packaged within a AAV2 capsid. |
| 2 | AAV3 | | Factor XII (FXII) | 2161 | Payload comprising a Factor XII (FXII) gene or variant thereof packaged within a AAV3 capsid. |
| 2 | AAV4 | 1446389 | Factor XII (FXII) | 2161 | Payload comprising a Factor XII (FXII) gene or variant thereof packaged within a AAV4 capsid. |
| 2 | AAV5 | | Factor XII (FXII) | 2161 | Payload comprising a Factor XII (FXII) gene or variant thereof packaged within a AAV5 capsid. |
| 2 | AAV6 | | Factor XII (FXII) | 2161 | Payload comprising a Factor XII (FXII) gene or variant thereof packaged within a AAV6 capsid. |
| 2 | AAV7 | | Factor XII (FXII) | 2161 | Payload comprising a Factor XII (FXII) gene or variant thereof packaged within a AAV7 capsid. |
| 2 | AAV8 | 5075992 | Factor XII (FXII) | 2161 | Payload comprising a Factor XII (FXII) gene or variant thereof packaged within a AAV8 capsid. |
| 2 | AAV9 | | Factor XII (FXII) | 2161 | Payload comprising a Factor XII (FXII) gene or variant thereof packaged within a AAV9 capsid. |

Fig. 29 (Continued)

| | | | | | |
|---|---|---|---|---|---|
| 2 | AAV10 | | Factor XII (FXII) | 2161 | Payload comprising a Factor XII (FXII) gene or variant thereof packaged within a AAV10 capsid. |
| 2 | AAV11 | | Factor XII (FXII) | 2161 | Payload comprising a Factor XII (FXII) gene or variant thereof packaged within a AAV11 capsid. |
| 2 | AAVC11.01 | | Factor XII (FXII) | 2161 | Payload comprising a Factor XII (FXII) gene or variant thereof packaged within a AAVC11.01 capsid. |
| 2 | AAVC11.02 | | Factor XII (FXII) | 2161 | Payload comprising a Factor XII (FXII) gene or variant thereof packaged within a AAVC11.02 capsid. |
| 2 | AAVC11.03 | | Factor XII (FXII) | 2161 | Payload comprising a Factor XII (FXII) gene or variant thereof packaged within a AAVC11.03 capsid. |
| 2 | AAVC11.04 | | Factor XII (FXII) | 2161 | Payload comprising a Factor XII (FXII) gene or variant thereof packaged within a AAVC11.04 capsid. |
| 2 | AAVC11.05 | | Factor XII (FXII) | 2161 | Payload comprising a Factor XII (FXII) gene or variant thereof packaged within a AAVC11.05 capsid. |
| 2 | AAVC11.06 | | Factor XII (FXII) | 2161 | Payload comprising a Factor XII (FXII) gene or variant thereof packaged within a AAVC11.06 capsid. |
| 2 | AAVC11.07 | | Factor XII (FXII) | 2161 | Payload comprising a Factor XII (FXII) gene or variant thereof packaged within a AAVC11.07 capsid |
| 2 | AAVC11.08 | | Factor XII (FXII) | 2161 | Payload comprising a Factor XII (FXII) gene or variant thereof packaged within a AAVC11.08 capsid. |
| 2 | AAVC11.09 | | Factor XII (FXII) | 2161 | Payload comprising a Factor XII (FXII) gene or variant thereof packaged within a AAVC11.09 capsid. |
| 2 | AAVC11.10 | | Factor XII (FXII) | 2161 | Payload comprising a Factor XII (FXII) gene or variant thereof packaged within a AAVC11.10 capsid. |
| 2 | AAVC11.11 | | Factor XII (FXII) | 2161 | Payload comprising a Factor XII (FXII) gene or variant thereof packaged within a AAVC11.11 capsid. |
| 2 | AAVC11.12 | | Factor XII (FXII) | 2161 | Payload comprising a Factor XII (FXII) gene or variant thereof packaged within a AAVC11.12 capsid. |
| 2 | AAVC11.13 | | Factor XII (FXII) | 2161 | Payload comprising a Factor XII (FXII) gene or variant thereof packaged within a AAVC11.13 capsid. |
| 2 | AAVC11.14 | | Factor XII (FXII) | 2161 | Payload comprising a Factor XII (FXII) gene or variant thereof packaged within a AAVC11.14 capsid. |
| 2 | AAVC11.15 | | Factor XII (FXII) | 2161 | Payload comprising a Factor XII (FXII) gene or variant thereof packaged within a AAVC11.15 capsid. |

Fig. 29 (Continued)

| | | | | | |
|---|---|---|---|---|---|
| 2 | AAVC11.16 | | Factor XII (FXII) | 2161 | Payload comprising a Factor XII (FXII) gene or variant thereof packaged within a AAVC11.16 capsid. |
| 2 | AAVC11.17 | | Factor XII (FXII) | 2161 | Payload comprising a Factor XII (FXII) gene or variant thereof packaged within a AAVC11.17 capsid. |
| 2 | AAVC11.18 | | Factor XII (FXII) | 2161 | Payload comprising a Factor XII (FXII) gene or variant thereof packaged within a AAVC11.18 capsid |
| 2 | AAVC11.19 | | Factor XII (FXII) | 2161 | Payload comprising a Factor XII (FXII) gene or variant thereof packaged within a AAVC11.19 capsid. |
| 2 | AAV12 | | Factor XII (FXII) | 2161 | Payload comprising a Factor XII (FXII) gene or variant thereof packaged within a AAV12 capsid. |
| 2 | AAV13 | | Factor XII (FXII) | 2161 | Payload comprising a Factor XII (FXII) gene or variant thereof packaged within a AAV13 capsid. |
| 2 | AAV-DJ | | Factor XII (FXII) | 2161 | Payload comprising a Factor XII (FXII) gene or variant thereof packaged within a AAV-DJ capsid |
| 2 | AAV-LK03 | | Factor XII (FXII) | 2161 | Payload comprising a Factor XII (FXII) gene or variant thereof packaged within a AAV-LK03 capsid. |
| 2 | AAV-LK19 | | Factor XII (FXII) | 2161 | Payload comprising a Factor XII (FXII) gene or variant thereof packaged within a AAV-LK19 capsid. |
| 2 | AAVrh.74 | | Factor XII (FXII) | 2161 | Payload comprising a Factor XII (FXII) gene or variant thereof packaged within a AAVrh.74 capsid. |
| 2 | AAVrh.10 | | Factor XII (FXII) | 2161 | Payload comprising a Factor XII (FXII) gene or variant thereof packaged within a AAVrh.10 capsid. |
| 2 | AAVhu.37 | | Factor XII (FXII) | 2161 | Payload comprising a Factor XII (FXII) gene or variant thereof packaged within a AAVhu.37 capsid. |
| 2 | AAVrh.K | | Factor XII (FXII) | 2161 | Payload comprising a Factor XII (FXII) gene or variant thereof packaged within a AAVrh.K capsid. |
| 2 | AAVrh.39 | | Factor XII (FXII) | 2161 | Payload comprising a Factor XII (FXII) gene or variant thereof packaged within a AAVrh.39 capsid. |
| 2 | AAVrh.9 | | Factor XII (FXII) | 2161 | Payload comprising a Factor XII (FXII) gene or variant thereof packaged within a AAVrh.9 capsid. |
| 2 | avian AAV | | Factor XII (FXII) | 2161 | Payload comprising a Factor XII (FXII) gene or variant thereof packaged within a avian capsid. |

Fig. 29 (Continued)

| | | | | | |
|---|---|---|---|---|---|
| 2 | bovine AAV | | Factor XII (FXII) | 2161 | Payload comprising a Factor XII (FXII) gene or variant thereof packaged within a bovine capsid. |
| 2 | canine AAV | | Factor XII (FXII) | 2161 | Payload comprising a Factor XII (FXII) gene or variant thereof packaged within a canine capsid. |
| 2 | equine AAV | | Factor XII (FXII) | 2161 | Payload comprising a Factor XII (FXII) gene or variant thereof packaged within a equine capsid. |
| 2 | primate AAV | | Factor XII (FXII) | 2161 | Payload comprising a Factor XII (FXII) gene or variant thereof packaged within a primate capsid. |
| 2 | non-primate AAV | | Factor XII (FXII) | 2161 | Payload comprising a Factor XII (FXII) gene or variant thereof packaged within a non-primate capsid. |
| 2 | ovine AAV | | Factor XII (FXII) | 2161 | Payload comprising a Factor XII (FXII) gene or variant thereof packaged within a ovine capsid. |
| 2 | hybrid AAV | | Factor XII (FXII) | 2161 | Payload comprising a Factor XII (FXII) gene or variant thereof packaged within a hybrid capsid. |
| 2 | chimeric AAV | | Factor XII (FXII) | 2161 | Payload comprising a Factor XII (FXII) gene or variant thereof packaged within a chimeric capsid. |
| 1 | AAV1 | 1450374 | FAH | 2184 | Payload comprising a FAH gene or variant thereof packaged within a AAV1 capsid. |
| 1 | AAV2 | | FAH | 2184 | Payload comprising a FAH gene or variant thereof packaged within a AAV2 capsid. |
| 1 | AAV3 | | FAH | 2184 | Payload comprising a FAH gene or variant thereof packaged within a AAV3 capsid. |
| 1 | AAV4 | 1446389 | FAH | 2184 | Payload comprising a FAH gene or variant thereof packaged within a AAV4 capsid. |
| 1 | AAV5 | | FAH | 2184 | Payload comprising a FAH gene or variant thereof packaged within a AAV5 capsid. |
| 1 | AAV6 | | FAH | 2184 | Payload comprising a FAH gene or variant thereof packaged within a AAV6 capsid. |
| 1 | AAV7 | | FAH | 2184 | Payload comprising a FAH gene or variant thereof packaged within a AAV7 capsid. |
| 1 | AAV8 | 5075992 | FAH | 2184 | Payload comprising a FAH gene or variant thereof packaged within a AAV8 capsid. |
| 1 | AAV9 | | FAH | 2184 | Payload comprising a FAH gene or variant thereof packaged within a AAV9 capsid. |

Fig. 29 (Continued)

| | | | | | |
|---|---|---|---|---|---|
| 1 | AAV10 | | FAH | 2184 | Payload comprising a FAH gene or variant thereof packaged within a AAV10 capsid. |
| 1 | AAV11 | | FAH | 2184 | Payload comprising a FAH gene or variant thereof packaged within a AAV11 capsid. |
| 1 | AAVC11.01 | | FAH | 2184 | Payload comprising a FAH gene or variant thereof packaged within a AAVC11.01 capsid. |
| 1 | AAVC11.02 | | FAH | 2184 | Payload comprising a FAH gene or variant thereof packaged within a AAVC11.02 capsid. |
| 1 | AAVC11.03 | | FAH | 2184 | Payload comprising a FAH gene or variant thereof packaged within a AAVC11.03 capsid. |
| 1 | AAVC11.04 | | FAH | 2184 | Payload comprising a FAH gene or variant thereof packaged within a AAVC11.04 capsid. |
| 1 | AAVC11.05 | | FAH | 2184 | Payload comprising a FAH gene or variant thereof packaged within a AAVC11.05 capsid. |
| 1 | AAVC11.06 | | FAH | 2184 | Payload comprising a FAH gene or variant thereof packaged within a AAVC11.06 capsid. |
| 1 | AAVC11.07 | | FAH | 2184 | Payload comprising a FAH gene or variant thereof packaged within a AAVC11.07 capsid |
| 1 | AAVC11.08 | | FAH | 2184 | Payload comprising a FAH gene or variant thereof packaged within a AAVC11.08 capsid. |
| 1 | AAVC11.09 | | FAH | 2184 | Payload comprising a FAH gene or variant thereof packaged within a AAVC11.09 capsid. |
| 1 | AAVC11.10 | | FAH | 2184 | Payload comprising a FAH gene or variant thereof packaged within a AAVC11.10 capsid. |
| 1 | AAVC11.11 | | FAH | 2184 | Payload comprising a FAH gene or variant thereof packaged within a AAVC11.11 capsid. |
| 1 | AAVC11.12 | | FAH | 2184 | Payload comprising a FAH gene or variant thereof packaged within a AAVC11.12 capsid. |
| 1 | AAVC11.13 | | FAH | 2184 | Payload comprising a FAH gene or variant thereof packaged within a AAVC11.13 capsid. |
| 1 | AAVC11.14 | | FAH | 2184 | Payload comprising a FAH gene or variant thereof packaged within a AAVC11.14 capsid. |
| 1 | AAVC11.15 | | FAH | 2184 | Payload comprising a FAH gene or variant thereof packaged within a AAVC11.15 capsid. |

Fig. 29 (Continued)

| | | | | | |
|---|---|---|---|---|---|
| 1 | AAVC11.16 | | FAH | 2184 | Payload comprising a FAH gene or variant thereof packaged within a AAVC11.16 capsid. |
| 1 | AAVC11.17 | | FAH | 2184 | Payload comprising a FAH gene or variant thereof packaged within a AAVC11.17 capsid. |
| 1 | AAVC11.18 | | FAH | 2184 | Payload comprising a FAH gene or variant thereof packaged within a AAVC11.18 capsid |
| 1 | AAVC11.19 | | FAH | 2184 | Payload comprising a FAH gene or variant thereof packaged within a AAVC11.19 capsid. |
| 1 | AAV12 | | FAH | 2184 | Payload comprising a FAH gene or variant thereof packaged within a AAV12 capsid. |
| 1 | AAV13 | | FAH | 2184 | Payload comprising a FAH gene or variant thereof packaged within a AAV13 capsid. |
| 1 | AAV-DJ | | FAH | 2184 | Payload comprising a FAH gene or variant thereof packaged within a AAV-DJ capsid |
| 1 | AAV-LK03 | | FAH | 2184 | Payload comprising a FAH gene or variant thereof packaged within a AAV-LK03 capsid. |
| 1 | AAV-LK19 | | FAH | 2184 | Payload comprising a FAH gene or variant thereof packaged within a AAV-LK19 capsid. |
| 1 | AAVrh.74 | | FAH | 2184 | Payload comprising a FAH gene or variant thereof packaged within a AAVrh.74 capsid. |
| 1 | AAVrh.10 | | FAH | 2184 | Payload comprising a FAH gene or variant thereof packaged within a AAVrh.10 capsid. |
| 1 | AAVhu.37 | | FAH | 2184 | Payload comprising a FAH gene or variant thereof packaged within a AAVhu.37 capsid. |
| 1 | AAVrh.K | | FAH | 2184 | Payload comprising a FAH gene or variant thereof packaged within a AAVrh.K capsid. |
| 1 | AAVrh.39 | | FAH | 2184 | Payload comprising a FAH gene or variant thereof packaged within a AAVrh.39 capsid. |
| 1 | AAVrh.9 | | FAH | 2184 | Payload comprising a FAH gene or variant thereof packaged within a AAVrh.9 capsid. |
| 1 | avian AAV | | FAH | 2184 | Payload comprising a FAH gene or variant thereof packaged within a avian capsid. |

Fig. 29 (Continued)

| | | | | | |
|---|---|---|---|---|---|
| 1 | bovine AAV | | FAH | 2184 | Payload comprising a FAH gene or variant thereof packaged within a bovine capsid. |
| 1 | canine AAV | | FAH | 2184 | Payload comprising a FAH gene or variant thereof packaged within a canine capsid. |
| 1 | equine AAV | | FAH | 2184 | Payload comprising a FAH gene or variant thereof packaged within a equine capsid. |
| 1 | primate AAV | | FAH | 2184 | Payload comprising a FAH gene or variant thereof packaged within a primate capsid. |
| 1 | non-primate AAV | | FAH | 2184 | Payload comprising a FAH gene or variant thereof packaged within a non-primate capsid. |
| 1 | ovine AAV | | FAH | 2184 | Payload comprising a FAH gene or variant thereof packaged within a ovine capsid. |
| 1 | hybrid AAV | | FAH | 2184 | Payload comprising a FAH gene or variant thereof packaged within a hybrid capsid. |
| 1 | chimeric AAV | | FAH | 2184 | Payload comprising a FAH gene or variant thereof packaged within a chimeric capsid. |
| 2 | AAV1 | 1450374 | FAH | 2184 | Payload comprising a FAH gene or variant thereof packaged within a AAV1 capsid. |
| 2 | AAV2 | | FAH | 2184 | Payload comprising a FAH gene or variant thereof packaged within a AAV2 capsid. |
| 2 | AAV3 | | FAH | 2184 | Payload comprising a FAH gene or variant thereof packaged within a AAV3 capsid. |
| 2 | AAV4 | 1446389 | FAH | 2184 | Payload comprising a FAH gene or variant thereof packaged within a AAV4 capsid. |
| 2 | AAV5 | | FAH | 2184 | Payload comprising a FAH gene or variant thereof packaged within a AAV5 capsid. |
| 2 | AAV6 | | FAH | 2184 | Payload comprising a FAH gene or variant thereof packaged within a AAV6 capsid. |
| 2 | AAV7 | | FAH | 2184 | Payload comprising a FAH gene or variant thereof packaged within a AAV7 capsid. |
| 2 | AAV8 | 5075992 | FAH | 2184 | Payload comprising a FAH gene or variant thereof packaged within a AAV8 capsid. |
| 2 | AAV9 | | FAH | 2184 | Payload comprising a FAH gene or variant thereof packaged within a AAV9 capsid. |

Fig. 29 (Continued)

| | | | | | |
|---|---|---|---|---|---|
| 2 | AAV10 | | FAH | 2184 | Payload comprising a FAH gene or variant thereof packaged within a AAV10 capsid. |
| 2 | AAV11 | | FAH | 2184 | Payload comprising a FAH gene or variant thereof packaged within a AAV11 capsid. |
| 2 | AAVC11.01 | | FAH | 2184 | Payload comprising a FAH gene or variant thereof packaged within a AAVC11.01 capsid. |
| 2 | AAVC11.02 | | FAH | 2184 | Payload comprising a FAH gene or variant thereof packaged within a AAVC11.02 capsid. |
| 2 | AAVC11.03 | | FAH | 2184 | Payload comprising a FAH gene or variant thereof packaged within a AAVC11.03 capsid. |
| 2 | AAVC11.04 | | FAH | 2184 | Payload comprising a FAH gene or variant thereof packaged within a AAVC11.04 capsid. |
| 2 | AAVC11.05 | | FAH | 2184 | Payload comprising a FAH gene or variant thereof packaged within a AAVC11.05 capsid. |
| 2 | AAVC11.06 | | FAH | 2184 | Payload comprising a FAH gene or variant thereof packaged within a AAVC11.06 capsid. |
| 2 | AAVC11.07 | | FAH | 2184 | Payload comprising a FAH gene or variant thereof packaged within a AAVC11.07 capsid |
| 2 | AAVC11.08 | | FAH | 2184 | Payload comprising a FAH gene or variant thereof packaged within a AAVC11.08 capsid. |
| 2 | AAVC11.09 | | FAH | 2184 | Payload comprising a FAH gene or variant thereof packaged within a AAVC11.09 capsid. |
| 2 | AAVC11.10 | | FAH | 2184 | Payload comprising a FAH gene or variant thereof packaged within a AAVC11.10 capsid. |
| 2 | AAVC11.11 | | FAH | 2184 | Payload comprising a FAH gene or variant thereof packaged within a AAVC11.11 capsid. |
| 2 | AAVC11.12 | | FAH | 2184 | Payload comprising a FAH gene or variant thereof packaged within a AAVC11.12 capsid. |
| 2 | AAVC11.13 | | FAH | 2184 | Payload comprising a FAH gene or variant thereof packaged within a AAVC11.13 capsid. |
| 2 | AAVC11.14 | | FAH | 2184 | Payload comprising a FAH gene or variant thereof packaged within a AAVC11.14 capsid. |
| 2 | AAVC11.15 | | FAH | 2184 | Payload comprising a FAH gene or variant thereof packaged within a AAVC11.15 capsid. |

Fig. 29 (Continued)

| | | | | | |
|---|---|---|---|---|---|
| 2 | AAVC11.16 | | FAH | 2184 | Payload comprising a FAH gene or variant thereof packaged within a AAVC11.16 capsid. |
| 2 | AAVC11.17 | | FAH | 2184 | Payload comprising a FAH gene or variant thereof packaged within a AAVC11.17 capsid. |
| 2 | AAVC11.18 | | FAH | 2184 | Payload comprising a FAH gene or variant thereof packaged within a AAVC11.18 capsid |
| 2 | AAVC11.19 | | FAH | 2184 | Payload comprising a FAH gene or variant thereof packaged within a AAVC11.19 capsid. |
| 2 | AAV12 | | FAH | 2184 | Payload comprising a FAH gene or variant thereof packaged within a AAV12 capsid. |
| 2 | AAV13 | | FAH | 2184 | Payload comprising a FAH gene or variant thereof packaged within a AAV13 capsid. |
| 2 | AAV-DJ | | FAH | 2184 | Payload comprising a FAH gene or variant thereof packaged within a AAV-DJ capsid |
| 2 | AAV-LK03 | | FAH | 2184 | Payload comprising a FAH gene or variant thereof packaged within a AAV-LK03 capsid. |
| 2 | AAV-LK19 | | FAH | 2184 | Payload comprising a FAH gene or variant thereof packaged within a AAV-LK19 capsid. |
| 2 | AAVrh.74 | | FAH | 2184 | Payload comprising a FAH gene or variant thereof packaged within a AAVrh.74 capsid. |
| 2 | AAVrh.10 | | FAH | 2184 | Payload comprising a FAH gene or variant thereof packaged within a AAVrh.10 capsid. |
| 2 | AAVhu.37 | | FAH | 2184 | Payload comprising a FAH gene or variant thereof packaged within a AAVhu.37 capsid. |
| 2 | AAVrh.K | | FAH | 2184 | Payload comprising a FAH gene or variant thereof packaged within a AAVrh.K capsid. |
| 2 | AAVrh.39 | | FAH | 2184 | Payload comprising a FAH gene or variant thereof packaged within a AAVrh.39 capsid. |
| 2 | AAVrh.9 | | FAH | 2184 | Payload comprising a FAH gene or variant thereof packaged within a AAVrh.9 capsid. |
| 2 | avian AAV | | FAH | 2184 | Payload comprising a FAH gene or variant thereof packaged within a avian capsid. |

Fig. 29 (Continued)

| | | | | | |
|---|---|---|---|---|---|
| 2 | bovine AAV | | FAH | 2184 | Payload comprising a FAH gene or variant thereof packaged within a bovine capsid. |
| 2 | canine AAV | | FAH | 2184 | Payload comprising a FAH gene or variant thereof packaged within a canine capsid. |
| 2 | equine AAV | | FAH | 2184 | Payload comprising a FAH gene or variant thereof packaged within a equine capsid. |
| 2 | primate AAV | | FAH | 2184 | Payload comprising a FAH gene or variant thereof packaged within a primate capsid. |
| 2 | non-primate AAV | | FAH | 2184 | Payload comprising a FAH gene or variant thereof packaged within a non-primate capsid. |
| 2 | ovine AAV | | FAH | 2184 | Payload comprising a FAH gene or variant thereof packaged within a ovine capsid. |
| 2 | hybrid AAV | | FAH | 2184 | Payload comprising a FAH gene or variant thereof packaged within a hybrid capsid. |
| 2 | chimeric AAV | | FAH | 2184 | Payload comprising a FAH gene or variant thereof packaged within a chimeric capsid. |
| 1 | AAV1 | 1450374 | FHL1 | 2273 | Payload comprising a FHL1 gene or variant thereof packaged within a AAV1 capsid. |
| 1 | AAV2 | | FHL1 | 2273 | Payload comprising a FHL1 gene or variant thereof packaged within a AAV2 capsid. |
| 1 | AAV3 | | FHL1 | 2273 | Payload comprising a FHL1 gene or variant thereof packaged within a AAV3 capsid. |
| 1 | AAV4 | 1446389 | FHL1 | 2273 | Payload comprising a FHL1 gene or variant thereof packaged within a AAV4 capsid. |
| 1 | AAV5 | | FHL1 | 2273 | Payload comprising a FHL1 gene or variant thereof packaged within a AAV5 capsid. |
| 1 | AAV6 | | FHL1 | 2273 | Payload comprising a FHL1 gene or variant thereof packaged within a AAV6 capsid. |
| 1 | AAV7 | | FHL1 | 2273 | Payload comprising a FHL1 gene or variant thereof packaged within a AAV7 capsid. |
| 1 | AAV8 | 5075992 | FHL1 | 2273 | Payload comprising a FHL1 gene or variant thereof packaged within a AAV8 capsid. |
| 1 | AAV9 | | FHL1 | 2273 | Payload comprising a FHL1 gene or variant thereof packaged within a AAV9 capsid. |

Fig. 29 (Continued)

| | | | | | |
|---|---|---|---|---|---|
| 1 | AAV10 | | FHL1 | 2273 | Payload comprising a FHL1 gene or variant thereof packaged within a AAV10 capsid. |
| 1 | AAV11 | | FHL1 | 2273 | Payload comprising a FHL1 gene or variant thereof packaged within a AAV11 capsid. |
| 1 | AAVC11.01 | | FHL1 | 2273 | Payload comprising a FHL1 gene or variant thereof packaged within a AAVC11.01 capsid. |
| 1 | AAVC11.02 | | FHL1 | 2273 | Payload comprising a FHL1 gene or variant thereof packaged within a AAVC11.02 capsid. |
| 1 | AAVC11.03 | | FHL1 | 2273 | Payload comprising a FHL1 gene or variant thereof packaged within a AAVC11.03 capsid. |
| 1 | AAVC11.04 | | FHL1 | 2273 | Payload comprising a FHL1 gene or variant thereof packaged within a AAVC11.04 capsid. |
| 1 | AAVC11.05 | | FHL1 | 2273 | Payload comprising a FHL1 gene or variant thereof packaged within a AAVC11.05 capsid. |
| 1 | AAVC11.06 | | FHL1 | 2273 | Payload comprising a FHL1 gene or variant thereof packaged within a AAVC11.06 capsid. |
| 1 | AAVC11.07 | | FHL1 | 2273 | Payload comprising a FHL1 gene or variant thereof packaged within a AAVC11.07 capsid |
| 1 | AAVC11.08 | | FHL1 | 2273 | Payload comprising a FHL1 gene or variant thereof packaged within a AAVC11.08 capsid. |
| 1 | AAVC11.09 | | FHL1 | 2273 | Payload comprising a FHL1 gene or variant thereof packaged within a AAVC11.09 capsid. |
| 1 | AAVC11.10 | | FHL1 | 2273 | Payload comprising a FHL1 gene or variant thereof packaged within a AAVC11.10 capsid. |
| 1 | AAVC11.11 | | FHL1 | 2273 | Payload comprising a FHL1 gene or variant thereof packaged within a AAVC11.11 capsid. |
| 1 | AAVC11.12 | | FHL1 | 2273 | Payload comprising a FHL1 gene or variant thereof packaged within a AAVC11.12 capsid. |
| 1 | AAVC11.13 | | FHL1 | 2273 | Payload comprising a FHL1 gene or variant thereof packaged within a AAVC11.13 capsid. |
| 1 | AAVC11.14 | | FHL1 | 2273 | Payload comprising a FHL1 gene or variant thereof packaged within a AAVC11.14 capsid. |
| 1 | AAVC11.15 | | FHL1 | 2273 | Payload comprising a FHL1 gene or variant thereof packaged within a AAVC11.15 capsid. |

Fig. 29 (Continued)

| | | | | | |
|---|---|---|---|---|---|
| 1 | AAVC11.16 | | FHL1 | 2273 | Payload comprising a FHL1 gene or variant thereof packaged within a AAVC11.16 capsid. |
| 1 | AAVC11.17 | | FHL1 | 2273 | Payload comprising a FHL1 gene or variant thereof packaged within a AAVC11.17 capsid. |
| 1 | AAVC11.18 | | FHL1 | 2273 | Payload comprising a FHL1 gene or variant thereof packaged within a AAVC11.18 capsid |
| 1 | AAVC11.19 | | FHL1 | 2273 | Payload comprising a FHL1 gene or variant thereof packaged within a AAVC11.19 capsid. |
| 1 | AAV12 | | FHL1 | 2273 | Payload comprising a FHL1 gene or variant thereof packaged within a AAV12 capsid. |
| 1 | AAV13 | | FHL1 | 2273 | Payload comprising a FHL1 gene or variant thereof packaged within a AAV13 capsid. |
| 1 | AAV-DJ | | FHL1 | 2273 | Payload comprising a FHL1 gene or variant thereof packaged within a AAV-DJ capsid |
| 1 | AAV-LK03 | | FHL1 | 2273 | Payload comprising a FHL1 gene or variant thereof packaged within a AAV-LK03 capsid. |
| 1 | AAV-LK19 | | FHL1 | 2273 | Payload comprising a FHL1 gene or variant thereof packaged within a AAV-LK19 capsid. |
| 1 | AAVrh.74 | | FHL1 | 2273 | Payload comprising a FHL1 gene or variant thereof packaged within a AAVrh.74 capsid. |
| 1 | AAVrh.10 | | FHL1 | 2273 | Payload comprising a FHL1 gene or variant thereof packaged within a AAVrh.10 capsid. |
| 1 | AAVhu.37 | | FHL1 | 2273 | Payload comprising a FHL1 gene or variant thereof packaged within a AAVhu.37 capsid. |
| 1 | AAVrh.K | | FHL1 | 2273 | Payload comprising a FHL1 gene or variant thereof packaged within a AAVrh.K capsid. |
| 1 | AAVrh.39 | | FHL1 | 2273 | Payload comprising a FHL1 gene or variant thereof packaged within a AAVrh.39 capsid. |
| 1 | AAVrh.9 | | FHL1 | 2273 | Payload comprising a FHL1 gene or variant thereof packaged within a AAVrh.9 capsid. |
| 1 | avian AAV | | FHL1 | 2273 | Payload comprising a FHL1 gene or variant thereof packaged within a avian capsid. |

Fig. 29 (Continued)

| | | | | | |
|---|---|---|---|---|---|
| 1 | bovine AAV | | FHL1 | 2273 | Payload comprising a FHL1 gene or variant thereof packaged within a bovine capsid. |
| 1 | canine AAV | | FHL1 | 2273 | Payload comprising a FHL1 gene or variant thereof packaged within a canine capsid. |
| 1 | equine AAV | | FHL1 | 2273 | Payload comprising a FHL1 gene or variant thereof packaged within a equine capsid. |
| 1 | primate AAV | | FHL1 | 2273 | Payload comprising a FHL1 gene or variant thereof packaged within a primate capsid. |
| 1 | non-primate AAV | | FHL1 | 2273 | Payload comprising a FHL1 gene or variant thereof packaged within a non-primate capsid. |
| 1 | ovine AAV | | FHL1 | 2273 | Payload comprising a FHL1 gene or variant thereof packaged within a ovine capsid. |
| 1 | hybrid AAV | | FHL1 | 2273 | Payload comprising a FHL1 gene or variant thereof packaged within a hybrid capsid. |
| 1 | chimeric AAV | | FHL1 | 2273 | Payload comprising a FHL1 gene or variant thereof packaged within a chimeric capsid. |
| 2 | AAV1 | 1450374 | FHL1 | 2273 | Payload comprising a FHL1 gene or variant thereof packaged within a AAV1 capsid. |
| 2 | AAV2 | | FHL1 | 2273 | Payload comprising a FHL1 gene or variant thereof packaged within a AAV2 capsid. |
| 2 | AAV3 | | FHL1 | 2273 | Payload comprising a FHL1 gene or variant thereof packaged within a AAV3 capsid. |
| 2 | AAV4 | 1446389 | FHL1 | 2273 | Payload comprising a FHL1 gene or variant thereof packaged within a AAV4 capsid. |
| 2 | AAV5 | | FHL1 | 2273 | Payload comprising a FHL1 gene or variant thereof packaged within a AAV5 capsid. |
| 2 | AAV6 | | FHL1 | 2273 | Payload comprising a FHL1 gene or variant thereof packaged within a AAV6 capsid. |
| 2 | AAV7 | | FHL1 | 2273 | Payload comprising a FHL1 gene or variant thereof packaged within a AAV7 capsid. |
| 2 | AAV8 | 5075992 | FHL1 | 2273 | Payload comprising a FHL1 gene or variant thereof packaged within a AAV8 capsid. |
| 2 | AAV9 | | FHL1 | 2273 | Payload comprising a FHL1 gene or variant thereof packaged within a AAV9 capsid. |

Fig. 29 (Continued)

| | | | | | |
|---|---|---|---|---|---|
| 2 | AAV10 | | FHL1 | 2273 | Payload comprising a FHL1 gene or variant thereof packaged within a AAV10 capsid. |
| 2 | AAV11 | | FHL1 | 2273 | Payload comprising a FHL1 gene or variant thereof packaged within a AAV11 capsid. |
| 2 | AAVC11.01 | | FHL1 | 2273 | Payload comprising a FHL1 gene or variant thereof packaged within a AAVC11.01 capsid. |
| 2 | AAVC11.02 | | FHL1 | 2273 | Payload comprising a FHL1 gene or variant thereof packaged within a AAVC11.02 capsid. |
| 2 | AAVC11.03 | | FHL1 | 2273 | Payload comprising a FHL1 gene or variant thereof packaged within a AAVC11.03 capsid. |
| 2 | AAVC11.04 | | FHL1 | 2273 | Payload comprising a FHL1 gene or variant thereof packaged within a AAVC11.04 capsid. |
| 2 | AAVC11.05 | | FHL1 | 2273 | Payload comprising a FHL1 gene or variant thereof packaged within a AAVC11.05 capsid. |
| 2 | AAVC11.06 | | FHL1 | 2273 | Payload comprising a FHL1 gene or variant thereof packaged within a AAVC11.06 capsid. |
| 2 | AAVC11.07 | | FHL1 | 2273 | Payload comprising a FHL1 gene or variant thereof packaged within a AAVC11.07 capsid |
| 2 | AAVC11.08 | | FHL1 | 2273 | Payload comprising a FHL1 gene or variant thereof packaged within a AAVC11.08 capsid. |
| 2 | AAVC11.09 | | FHL1 | 2273 | Payload comprising a FHL1 gene or variant thereof packaged within a AAVC11.09 capsid. |
| 2 | AAVC11.10 | | FHL1 | 2273 | Payload comprising a FHL1 gene or variant thereof packaged within a AAVC11.10 capsid. |
| 2 | AAVC11.11 | | FHL1 | 2273 | Payload comprising a FHL1 gene or variant thereof packaged within a AAVC11.11 capsid. |
| 2 | AAVC11.12 | | FHL1 | 2273 | Payload comprising a FHL1 gene or variant thereof packaged within a AAVC11.12 capsid. |
| 2 | AAVC11.13 | | FHL1 | 2273 | Payload comprising a FHL1 gene or variant thereof packaged within a AAVC11.13 capsid. |
| 2 | AAVC11.14 | | FHL1 | 2273 | Payload comprising a FHL1 gene or variant thereof packaged within a AAVC11.14 capsid. |
| 2 | AAVC11.15 | | FHL1 | 2273 | Payload comprising a FHL1 gene or variant thereof packaged within a AAVC11.15 capsid. |

Fig. 29 (Continued)

| | | | | | |
|---|---|---|---|---|---|
| 2 | AAVC11.16 | | FHL1 | 2273 | Payload comprising a FHL1 gene or variant thereof packaged within a AAVC11.16 capsid. |
| 2 | AAVC11.17 | | FHL1 | 2273 | Payload comprising a FHL1 gene or variant thereof packaged within a AAVC11.17 capsid. |
| 2 | AAVC11.18 | | FHL1 | 2273 | Payload comprising a FHL1 gene or variant thereof packaged within a AAVC11.18 capsid |
| 2 | AAVC11.19 | | FHL1 | 2273 | Payload comprising a FHL1 gene or variant thereof packaged within a AAVC11.19 capsid. |
| 2 | AAV12 | | FHL1 | 2273 | Payload comprising a FHL1 gene or variant thereof packaged within a AAV12 capsid. |
| 2 | AAV13 | | FHL1 | 2273 | Payload comprising a FHL1 gene or variant thereof packaged within a AAV13 capsid. |
| 2 | AAV-DJ | | FHL1 | 2273 | Payload comprising a FHL1 gene or variant thereof packaged within a AAV-DJ capsid |
| 2 | AAV-LK03 | | FHL1 | 2273 | Payload comprising a FHL1 gene or variant thereof packaged within a AAV-LK03 capsid. |
| 2 | AAV-LK19 | | FHL1 | 2273 | Payload comprising a FHL1 gene or variant thereof packaged within a AAV-LK19 capsid. |
| 2 | AAVrh.74 | | FHL1 | 2273 | Payload comprising a FHL1 gene or variant thereof packaged within a AAVrh.74 capsid. |
| 2 | AAVrh.10 | | FHL1 | 2273 | Payload comprising a FHL1 gene or variant thereof packaged within a AAVrh.10 capsid. |
| 2 | AAVhu.37 | | FHL1 | 2273 | Payload comprising a FHL1 gene or variant thereof packaged within a AAVhu.37 capsid. |
| 2 | AAVrh.K | | FHL1 | 2273 | Payload comprising a FHL1 gene or variant thereof packaged within a AAVrh.K capsid. |
| 2 | AAVrh.39 | | FHL1 | 2273 | Payload comprising a FHL1 gene or variant thereof packaged within a AAVrh.39 capsid. |
| 2 | AAVrh.9 | | FHL1 | 2273 | Payload comprising a FHL1 gene or variant thereof packaged within a AAVrh.9 capsid. |
| 2 | avian AAV | | FHL1 | 2273 | Payload comprising a FHL1 gene or variant thereof packaged within a avian capsid. |

Fig. 29 (Continued)

| | | | | | |
|---|---|---|---|---|---|
| 2 | bovine AAV | | FHL1 | 2273 | Payload comprising a FHL1 gene or variant thereof packaged within a bovine capsid. |
| 2 | canine AAV | | FHL1 | 2273 | Payload comprising a FHL1 gene or variant thereof packaged within a canine capsid. |
| 2 | equine AAV | | FHL1 | 2273 | Payload comprising a FHL1 gene or variant thereof packaged within a equine capsid. |
| 2 | primate AAV | | FHL1 | 2273 | Payload comprising a FHL1 gene or variant thereof packaged within a primate capsid. |
| 2 | non-primate AAV | | FHL1 | 2273 | Payload comprising a FHL1 gene or variant thereof packaged within a non-primate capsid. |
| 2 | ovine AAV | | FHL1 | 2273 | Payload comprising a FHL1 gene or variant thereof packaged within a ovine capsid. |
| 2 | hybrid AAV | | FHL1 | 2273 | Payload comprising a FHL1 gene or variant thereof packaged within a hybrid capsid. |
| 2 | chimeric AAV | | FHL1 | 2273 | Payload comprising a FHL1 gene or variant thereof packaged within a chimeric capsid. |
| 1 | AAV1 | 1450374 | FKRP | 79147 | Payload comprising a FKRP gene or variant thereof packaged within a AAV1 capsid. |
| 1 | AAV2 | | FKRP | 79147 | Payload comprising a FKRP gene or variant thereof packaged within a AAV2 capsid. |
| 1 | AAV3 | | FKRP | 79147 | Payload comprising a FKRP gene or variant thereof packaged within a AAV3 capsid. |
| 1 | AAV4 | 1446389 | FKRP | 79147 | Payload comprising a FKRP gene or variant thereof packaged within a AAV4 capsid. |
| 1 | AAV5 | | FKRP | 79147 | Payload comprising a FKRP gene or variant thereof packaged within a AAV5 capsid. |
| 1 | AAV6 | | FKRP | 79147 | Payload comprising a FKRP gene or variant thereof packaged within a AAV6 capsid. |
| 1 | AAV7 | | FKRP | 79147 | Payload comprising a FKRP gene or variant thereof packaged within a AAV7 capsid. |
| 1 | AAV8 | 5075992 | FKRP | 79147 | Payload comprising a FKRP gene or variant thereof packaged within a AAV8 capsid. |
| 1 | AAV9 | | FKRP | 79147 | Payload comprising a FKRP gene or variant thereof packaged within a AAV9 capsid. |

Fig. 29 (Continued)

| | | | | | |
|---|---|---|---|---|---|
| 1 | AAV10 | | FKRP | 79147 | Payload comprising a FKRP gene or variant thereof packaged within a AAV10 capsid. |
| 1 | AAV11 | | FKRP | 79147 | Payload comprising a FKRP gene or variant thereof packaged within a AAV11 capsid. |
| 1 | AAVC11.01 | | FKRP | 79147 | Payload comprising a FKRP gene or variant thereof packaged within a AAVC11.01 capsid. |
| 1 | AAVC11.02 | | FKRP | 79147 | Payload comprising a FKRP gene or variant thereof packaged within a AAVC11.02 capsid. |
| 1 | AAVC11.03 | | FKRP | 79147 | Payload comprising a FKRP gene or variant thereof packaged within a AAVC11.03 capsid. |
| 1 | AAVC11.04 | | FKRP | 79147 | Payload comprising a FKRP gene or variant thereof packaged within a AAVC11.04 capsid. |
| 1 | AAVC11.05 | | FKRP | 79147 | Payload comprising a FKRP gene or variant thereof packaged within a AAVC11.05 capsid. |
| 1 | AAVC11.06 | | FKRP | 79147 | Payload comprising a FKRP gene or variant thereof packaged within a AAVC11.06 capsid. |
| 1 | AAVC11.07 | | FKRP | 79147 | Payload comprising a FKRP gene or variant thereof packaged within a AAVC11.07 capsid |
| 1 | AAVC11.08 | | FKRP | 79147 | Payload comprising a FKRP gene or variant thereof packaged within a AAVC11.08 capsid. |
| 1 | AAVC11.09 | | FKRP | 79147 | Payload comprising a FKRP gene or variant thereof packaged within a AAVC11.09 capsid. |
| 1 | AAVC11.10 | | FKRP | 79147 | Payload comprising a FKRP gene or variant thereof packaged within a AAVC11.10 capsid. |
| 1 | AAVC11.11 | | FKRP | 79147 | Payload comprising a FKRP gene or variant thereof packaged within a AAVC11.11 capsid. |
| 1 | AAVC11.12 | | FKRP | 79147 | Payload comprising a FKRP gene or variant thereof packaged within a AAVC11.12 capsid. |
| 1 | AAVC11.13 | | FKRP | 79147 | Payload comprising a FKRP gene or variant thereof packaged within a AAVC11.13 capsid. |
| 1 | AAVC11.14 | | FKRP | 79147 | Payload comprising a FKRP gene or variant thereof packaged within a AAVC11.14 capsid. |
| 1 | AAVC11.15 | | FKRP | 79147 | Payload comprising a FKRP gene or variant thereof packaged within a AAVC11.15 capsid. |

Fig. 29 (Continued)

| | | | | | |
|---|---|---|---|---|---|
| 1 | AAVC11.16 | | FKRP | 79147 | Payload comprising a FKRP gene or variant thereof packaged within a AAVC11.16 capsid. |
| 1 | AAVC11.17 | | FKRP | 79147 | Payload comprising a FKRP gene or variant thereof packaged within a AAVC11.17 capsid. |
| 1 | AAVC11.18 | | FKRP | 79147 | Payload comprising a FKRP gene or variant thereof packaged within a AAVC11.18 capsid |
| 1 | AAVC11.19 | | FKRP | 79147 | Payload comprising a FKRP gene or variant thereof packaged within a AAVC11.19 capsid. |
| 1 | AAV12 | | FKRP | 79147 | Payload comprising a FKRP gene or variant thereof packaged within a AAV12 capsid. |
| 1 | AAV13 | | FKRP | 79147 | Payload comprising a FKRP gene or variant thereof packaged within a AAV13 capsid. |
| 1 | AAV-DJ | | FKRP | 79147 | Payload comprising a FKRP gene or variant thereof packaged within a AAV-DJ capsid |
| 1 | AAV-LK03 | | FKRP | 79147 | Payload comprising a FKRP gene or variant thereof packaged within a AAV-LK03 capsid. |
| 1 | AAV-LK19 | | FKRP | 79147 | Payload comprising a FKRP gene or variant thereof packaged within a AAV-LK19 capsid. |
| 1 | AAVrh.74 | | FKRP | 79147 | Payload comprising a FKRP gene or variant thereof packaged within a AAVrh.74 capsid. |
| 1 | AAVrh.10 | | FKRP | 79147 | Payload comprising a FKRP gene or variant thereof packaged within a AAVrh.10 capsid. |
| 1 | AAVhu.37 | | FKRP | 79147 | Payload comprising a FKRP gene or variant thereof packaged within a AAVhu.37 capsid. |
| 1 | AAVrh.K | | FKRP | 79147 | Payload comprising a FKRP gene or variant thereof packaged within a AAVrh.K capsid. |
| 1 | AAVrh.39 | | FKRP | 79147 | Payload comprising a FKRP gene or variant thereof packaged within a AAVrh.39 capsid. |
| 1 | AAVrh.9 | | FKRP | 79147 | Payload comprising a FKRP gene or variant thereof packaged within a AAVrh.9 capsid. |
| 1 | avian AAV | | FKRP | 79147 | Payload comprising a FKRP gene or variant thereof packaged within a avian capsid. |

Fig. 29 (Continued)

| | | | | | |
|---|---|---|---|---|---|
| 1 | bovine AAV | | FKRP | 79147 | Payload comprising a FKRP gene or variant thereof packaged within a bovine capsid. |
| 1 | canine AAV | | FKRP | 79147 | Payload comprising a FKRP gene or variant thereof packaged within a canine capsid. |
| 1 | equine AAV | | FKRP | 79147 | Payload comprising a FKRP gene or variant thereof packaged within a equine capsid. |
| 1 | primate AAV | | FKRP | 79147 | Payload comprising a FKRP gene or variant thereof packaged within a primate capsid. |
| 1 | non-primate AAV | | FKRP | 79147 | Payload comprising a FKRP gene or variant thereof packaged within a non-primate capsid. |
| 1 | ovine AAV | | FKRP | 79147 | Payload comprising a FKRP gene or variant thereof packaged within a ovine capsid. |
| 1 | hybrid AAV | | FKRP | 79147 | Payload comprising a FKRP gene or variant thereof packaged within a hybrid capsid. |
| 1 | chimeric AAV | | FKRP | 79147 | Payload comprising a FKRP gene or variant thereof packaged within a chimeric capsid. |
| 2 | AAV1 | 1450374 | FKRP | 79147 | Payload comprising a FKRP gene or variant thereof packaged within a AAV1 capsid. |
| 2 | AAV2 | | FKRP | 79147 | Payload comprising a FKRP gene or variant thereof packaged within a AAV2 capsid. |
| 2 | AAV3 | | FKRP | 79147 | Payload comprising a FKRP gene or variant thereof packaged within a AAV3 capsid. |
| 2 | AAV4 | 1446389 | FKRP | 79147 | Payload comprising a FKRP gene or variant thereof packaged within a AAV4 capsid. |
| 2 | AAV5 | | FKRP | 79147 | Payload comprising a FKRP gene or variant thereof packaged within a AAV5 capsid. |
| 2 | AAV6 | | FKRP | 79147 | Payload comprising a FKRP gene or variant thereof packaged within a AAV6 capsid. |
| 2 | AAV7 | | FKRP | 79147 | Payload comprising a FKRP gene or variant thereof packaged within a AAV7 capsid. |
| 2 | AAV8 | 5075992 | FKRP | 79147 | Payload comprising a FKRP gene or variant thereof packaged within a AAV8 capsid. |
| 2 | AAV9 | | FKRP | 79147 | Payload comprising a FKRP gene or variant thereof packaged within a AAV9 capsid. |

Fig. 29 (Continued)

| | | | | | |
|---|---|---|---|---|---|
| 2 | AAV10 | | FKRP | 79147 | Payload comprising a FKRP gene or variant thereof packaged within a AAV10 capsid. |
| 2 | AAV11 | | FKRP | 79147 | Payload comprising a FKRP gene or variant thereof packaged within a AAV11 capsid. |
| 2 | AAVC11.01 | | FKRP | 79147 | Payload comprising a FKRP gene or variant thereof packaged within a AAVC11.01 capsid. |
| 2 | AAVC11.02 | | FKRP | 79147 | Payload comprising a FKRP gene or variant thereof packaged within a AAVC11.02 capsid. |
| 2 | AAVC11.03 | | FKRP | 79147 | Payload comprising a FKRP gene or variant thereof packaged within a AAVC11.03 capsid. |
| 2 | AAVC11.04 | | FKRP | 79147 | Payload comprising a FKRP gene or variant thereof packaged within a AAVC11.04 capsid. |
| 2 | AAVC11.05 | | FKRP | 79147 | Payload comprising a FKRP gene or variant thereof packaged within a AAVC11.05 capsid. |
| 2 | AAVC11.06 | | FKRP | 79147 | Payload comprising a FKRP gene or variant thereof packaged within a AAVC11.06 capsid. |
| 2 | AAVC11.07 | | FKRP | 79147 | Payload comprising a FKRP gene or variant thereof packaged within a AAVC11.07 capsid |
| 2 | AAVC11.08 | | FKRP | 79147 | Payload comprising a FKRP gene or variant thereof packaged within a AAVC11.08 capsid. |
| 2 | AAVC11.09 | | FKRP | 79147 | Payload comprising a FKRP gene or variant thereof packaged within a AAVC11.09 capsid. |
| 2 | AAVC11.10 | | FKRP | 79147 | Payload comprising a FKRP gene or variant thereof packaged within a AAVC11.10 capsid. |
| 2 | AAVC11.11 | | FKRP | 79147 | Payload comprising a FKRP gene or variant thereof packaged within a AAVC11.11 capsid. |
| 2 | AAVC11.12 | | FKRP | 79147 | Payload comprising a FKRP gene or variant thereof packaged within a AAVC11.12 capsid. |
| 2 | AAVC11.13 | | FKRP | 79147 | Payload comprising a FKRP gene or variant thereof packaged within a AAVC11.13 capsid. |
| 2 | AAVC11.14 | | FKRP | 79147 | Payload comprising a FKRP gene or variant thereof packaged within a AAVC11.14 capsid. |
| 2 | AAVC11.15 | | FKRP | 79147 | Payload comprising a FKRP gene or variant thereof packaged within a AAVC11.15 capsid. |

Fig. 29 (Continued)

| | | | | | |
|---|---|---|---|---|---|
| 2 | AAVC11.16 | | FKRP | 79147 | Payload comprising a FKRP gene or variant thereof packaged within a AAVC11.16 capsid. |
| 2 | AAVC11.17 | | FKRP | 79147 | Payload comprising a FKRP gene or variant thereof packaged within a AAVC11.17 capsid. |
| 2 | AAVC11.18 | | FKRP | 79147 | Payload comprising a FKRP gene or variant thereof packaged within a AAVC11.18 capsid |
| 2 | AAVC11.19 | | FKRP | 79147 | Payload comprising a FKRP gene or variant thereof packaged within a AAVC11.19 capsid. |
| 2 | AAV12 | | FKRP | 79147 | Payload comprising a FKRP gene or variant thereof packaged within a AAV12 capsid. |
| 2 | AAV13 | | FKRP | 79147 | Payload comprising a FKRP gene or variant thereof packaged within a AAV13 capsid. |
| 2 | AAV-DJ | | FKRP | 79147 | Payload comprising a FKRP gene or variant thereof packaged within a AAV-DJ capsid |
| 2 | AAV-LK03 | | FKRP | 79147 | Payload comprising a FKRP gene or variant thereof packaged within a AAV-LK03 capsid. |
| 2 | AAV-LK19 | | FKRP | 79147 | Payload comprising a FKRP gene or variant thereof packaged within a AAV-LK19 capsid. |
| 2 | AAVrh.74 | | FKRP | 79147 | Payload comprising a FKRP gene or variant thereof packaged within a AAVrh.74 capsid. |
| 2 | AAVrh.10 | | FKRP | 79147 | Payload comprising a FKRP gene or variant thereof packaged within a AAVrh.10 capsid. |
| 2 | AAVhu.37 | | FKRP | 79147 | Payload comprising a FKRP gene or variant thereof packaged within a AAVhu.37 capsid. |
| 2 | AAVrh.K | | FKRP | 79147 | Payload comprising a FKRP gene or variant thereof packaged within a AAVrh.K capsid. |
| 2 | AAVrh.39 | | FKRP | 79147 | Payload comprising a FKRP gene or variant thereof packaged within a AAVrh.39 capsid. |
| 2 | AAVrh.9 | | FKRP | 79147 | Payload comprising a FKRP gene or variant thereof packaged within a AAVrh.9 capsid. |
| 2 | avian AAV | | FKRP | 79147 | Payload comprising a FKRP gene or variant thereof packaged within a avian capsid. |

Fig. 29 (Continued)

| | | | | | |
|---|---|---|---|---|---|
| 2 | bovine AAV | | FKRP | 79147 | Payload comprising a FKRP gene or variant thereof packaged within a bovine capsid. |
| 2 | canine AAV | | FKRP | 79147 | Payload comprising a FKRP gene or variant thereof packaged within a canine capsid. |
| 2 | equine AAV | | FKRP | 79147 | Payload comprising a FKRP gene or variant thereof packaged within a equine capsid. |
| 2 | primate AAV | | FKRP | 79147 | Payload comprising a FKRP gene or variant thereof packaged within a primate capsid. |
| 2 | non-primate AAV | | FKRP | 79147 | Payload comprising a FKRP gene or variant thereof packaged within a non-primate capsid. |
| 2 | ovine AAV | | FKRP | 79147 | Payload comprising a FKRP gene or variant thereof packaged within a ovine capsid. |
| 2 | hybrid AAV | | FKRP | 79147 | Payload comprising a FKRP gene or variant thereof packaged within a hybrid capsid. |
| 2 | chimeric AAV | | FKRP | 79147 | Payload comprising a FKRP gene or variant thereof packaged within a chimeric capsid. |
| 1 | AAV1 | 1450374 | G6PC1 | 2538 | Payload comprising a G6PC1 gene or variant thereof packaged within a AAV1 capsid. |
| 1 | AAV2 | | G6PC1 | 2538 | Payload comprising a G6PC1 gene or variant thereof packaged within a AAV2 capsid. |
| 1 | AAV3 | | G6PC1 | 2538 | Payload comprising a G6PC1 gene or variant thereof packaged within a AAV3 capsid. |
| 1 | AAV4 | 1446389 | G6PC1 | 2538 | Payload comprising a G6PC1 gene or variant thereof packaged within a AAV4 capsid. |
| 1 | AAV5 | | G6PC1 | 2538 | Payload comprising a G6PC1 gene or variant thereof packaged within a AAV5 capsid. |
| 1 | AAV6 | | G6PC1 | 2538 | Payload comprising a G6PC1 gene or variant thereof packaged within a AAV6 capsid. |
| 1 | AAV7 | | G6PC1 | 2538 | Payload comprising a G6PC1 gene or variant thereof packaged within a AAV7 capsid. |
| 1 | AAV8 | 5075992 | G6PC1 | 2538 | Payload comprising a G6PC1 gene or variant thereof packaged within a AAV8 capsid. |
| 1 | AAV9 | | G6PC1 | 2538 | Payload comprising a G6PC1 gene or variant thereof packaged within a AAV9 capsid. |

Fig. 29 (Continued)

| | | | | | |
|---|---|---|---|---|---|
| 1 | AAV10 | | G6PC1 | 2538 | Payload comprising a G6PC1 gene or variant thereof packaged within a AAV10 capsid. |
| 1 | AAV11 | | G6PC1 | 2538 | Payload comprising a G6PC1 gene or variant thereof packaged within a AAV11 capsid. |
| 1 | AAVC11.01 | | G6PC1 | 2538 | Payload comprising a G6PC1 gene or variant thereof packaged within a AAVC11.01 capsid. |
| 1 | AAVC11.02 | | G6PC1 | 2538 | Payload comprising a G6PC1 gene or variant thereof packaged within a AAVC11.02 capsid. |
| 1 | AAVC11.03 | | G6PC1 | 2538 | Payload comprising a G6PC1 gene or variant thereof packaged within a AAVC11.03 capsid. |
| 1 | AAVC11.04 | | G6PC1 | 2538 | Payload comprising a G6PC1 gene or variant thereof packaged within a AAVC11.04 capsid. |
| 1 | AAVC11.05 | | G6PC1 | 2538 | Payload comprising a G6PC1 gene or variant thereof packaged within a AAVC11.05 capsid. |
| 1 | AAVC11.06 | | G6PC1 | 2538 | Payload comprising a G6PC1 gene or variant thereof packaged within a AAVC11.06 capsid. |
| 1 | AAVC11.07 | | G6PC1 | 2538 | Payload comprising a G6PC1 gene or variant thereof packaged within a AAVC11.07 capsid |
| 1 | AAVC11.08 | | G6PC1 | 2538 | Payload comprising a G6PC1 gene or variant thereof packaged within a AAVC11.08 capsid. |
| 1 | AAVC11.09 | | G6PC1 | 2538 | Payload comprising a G6PC1 gene or variant thereof packaged within a AAVC11.09 capsid. |
| 1 | AAVC11.10 | | G6PC1 | 2538 | Payload comprising a G6PC1 gene or variant thereof packaged within a AAVC11.10 capsid. |
| 1 | AAVC11.11 | | G6PC1 | 2538 | Payload comprising a G6PC1 gene or variant thereof packaged within a AAVC11.11 capsid. |
| 1 | AAVC11.12 | | G6PC1 | 2538 | Payload comprising a G6PC1 gene or variant thereof packaged within a AAVC11.12 capsid. |
| 1 | AAVC11.13 | | G6PC1 | 2538 | Payload comprising a G6PC1 gene or variant thereof packaged within a AAVC11.13 capsid. |
| 1 | AAVC11.14 | | G6PC1 | 2538 | Payload comprising a G6PC1 gene or variant thereof packaged within a AAVC11.14 capsid. |
| 1 | AAVC11.15 | | G6PC1 | 2538 | Payload comprising a G6PC1 gene or variant thereof packaged within a AAVC11.15 capsid. |

Fig. 29 (Continued)

| | | | | | |
|---|---|---|---|---|---|
| 1 | AAVC11.16 | | G6PC1 | 2538 | Payload comprising a G6PC1 gene or variant thereof packaged within a AAVC11.16 capsid. |
| 1 | AAVC11.17 | | G6PC1 | 2538 | Payload comprising a G6PC1 gene or variant thereof packaged within a AAVC11.17 capsid. |
| 1 | AAVC11.18 | | G6PC1 | 2538 | Payload comprising a G6PC1 gene or variant thereof packaged within a AAVC11.18 capsid |
| 1 | AAVC11.19 | | G6PC1 | 2538 | Payload comprising a G6PC1 gene or variant thereof packaged within a AAVC11.19 capsid. |
| 1 | AAV12 | | G6PC1 | 2538 | Payload comprising a G6PC1 gene or variant thereof packaged within a AAV12 capsid. |
| 1 | AAV13 | | G6PC1 | 2538 | Payload comprising a G6PC1 gene or variant thereof packaged within a AAV13 capsid. |
| 1 | AAV-DJ | | G6PC1 | 2538 | Payload comprising a G6PC1 gene or variant thereof packaged within a AAV-DJ capsid |
| 1 | AAV-LK03 | | G6PC1 | 2538 | Payload comprising a G6PC1 gene or variant thereof packaged within a AAV-LK03 capsid. |
| 1 | AAV-LK19 | | G6PC1 | 2538 | Payload comprising a G6PC1 gene or variant thereof packaged within a AAV-LK19 capsid. |
| 1 | AAVrh.74 | | G6PC1 | 2538 | Payload comprising a G6PC1 gene or variant thereof packaged within a AAVrh.74 capsid. |
| 1 | AAVrh.10 | | G6PC1 | 2538 | Payload comprising a G6PC1 gene or variant thereof packaged within a AAVrh.10 capsid. |
| 1 | AAVhu.37 | | G6PC1 | 2538 | Payload comprising a G6PC1 gene or variant thereof packaged within a AAVhu.37 capsid. |
| 1 | AAVrh.K | | G6PC1 | 2538 | Payload comprising a G6PC1 gene or variant thereof packaged within a AAVrh.K capsid. |
| 1 | AAVrh.39 | | G6PC1 | 2538 | Payload comprising a G6PC1 gene or variant thereof packaged within a AAVrh.39 capsid. |
| 1 | AAVrh.9 | | G6PC1 | 2538 | Payload comprising a G6PC1 gene or variant thereof packaged within a AAVrh.9 capsid. |
| 1 | avian AAV | | G6PC1 | 2538 | Payload comprising a G6PC1 gene or variant thereof packaged within a avian capsid. |

Fig. 29 (Continued)

| | | | | | |
|---|---|---|---|---|---|
| 1 | bovine AAV | | G6PC1 | 2538 | Payload comprising a G6PC1 gene or variant thereof packaged within a bovine capsid. |
| 1 | canine AAV | | G6PC1 | 2538 | Payload comprising a G6PC1 gene or variant thereof packaged within a canine capsid. |
| 1 | equine AAV | | G6PC1 | 2538 | Payload comprising a G6PC1 gene or variant thereof packaged within a equine capsid. |
| 1 | primate AAV | | G6PC1 | 2538 | Payload comprising a G6PC1 gene or variant thereof packaged within a primate capsid. |
| 1 | non-primate AAV | | G6PC1 | 2538 | Payload comprising a G6PC1 gene or variant thereof packaged within a non-primate capsid. |
| 1 | ovine AAV | | G6PC1 | 2538 | Payload comprising a G6PC1 gene or variant thereof packaged within a ovine capsid. |
| 1 | hybrid AAV | | G6PC1 | 2538 | Payload comprising a G6PC1 gene or variant thereof packaged within a hybrid capsid. |
| 1 | chimeric AAV | | G6PC1 | 2538 | Payload comprising a G6PC1 gene or variant thereof packaged within a chimeric capsid. |
| 2 | AAV1 | 1450374 | G6PC1 | 2538 | Payload comprising a G6PC1 gene or variant thereof packaged within a AAV1 capsid. |
| 2 | AAV2 | | G6PC1 | 2538 | Payload comprising a G6PC1 gene or variant thereof packaged within a AAV2 capsid. |
| 2 | AAV3 | | G6PC1 | 2538 | Payload comprising a G6PC1 gene or variant thereof packaged within a AAV3 capsid. |
| 2 | AAV4 | 1446389 | G6PC1 | 2538 | Payload comprising a G6PC1 gene or variant thereof packaged within a AAV4 capsid. |
| 2 | AAV5 | | G6PC1 | 2538 | Payload comprising a G6PC1 gene or variant thereof packaged within a AAV5 capsid. |
| 2 | AAV6 | | G6PC1 | 2538 | Payload comprising a G6PC1 gene or variant thereof packaged within a AAV6 capsid. |
| 2 | AAV7 | | G6PC1 | 2538 | Payload comprising a G6PC1 gene or variant thereof packaged within a AAV7 capsid. |
| 2 | AAV8 | 5075992 | G6PC1 | 2538 | Payload comprising a G6PC1 gene or variant thereof packaged within a AAV8 capsid. |
| 2 | AAV9 | | G6PC1 | 2538 | Payload comprising a G6PC1 gene or variant thereof packaged within a AAV9 capsid. |

Fig. 29 (Continued)

| | | | | | |
|---|---|---|---|---|---|
| 2 | AAV10 | | G6PC1 | 2538 | Payload comprising a G6PC1 gene or variant thereof packaged within a AAV10 capsid. |
| 2 | AAV11 | | G6PC1 | 2538 | Payload comprising a G6PC1 gene or variant thereof packaged within a AAV11 capsid. |
| 2 | AAVC11.01 | | G6PC1 | 2538 | Payload comprising a G6PC1 gene or variant thereof packaged within a AAVC11.01 capsid. |
| 2 | AAVC11.02 | | G6PC1 | 2538 | Payload comprising a G6PC1 gene or variant thereof packaged within a AAVC11.02 capsid. |
| 2 | AAVC11.03 | | G6PC1 | 2538 | Payload comprising a G6PC1 gene or variant thereof packaged within a AAVC11.03 capsid. |
| 2 | AAVC11.04 | | G6PC1 | 2538 | Payload comprising a G6PC1 gene or variant thereof packaged within a AAVC11.04 capsid. |
| 2 | AAVC11.05 | | G6PC1 | 2538 | Payload comprising a G6PC1 gene or variant thereof packaged within a AAVC11.05 capsid. |
| 2 | AAVC11.06 | | G6PC1 | 2538 | Payload comprising a G6PC1 gene or variant thereof packaged within a AAVC11.06 capsid. |
| 2 | AAVC11.07 | | G6PC1 | 2538 | Payload comprising a G6PC1 gene or variant thereof packaged within a AAVC11.07 capsid |
| 2 | AAVC11.08 | | G6PC1 | 2538 | Payload comprising a G6PC1 gene or variant thereof packaged within a AAVC11.08 capsid. |
| 2 | AAVC11.09 | | G6PC1 | 2538 | Payload comprising a G6PC1 gene or variant thereof packaged within a AAVC11.09 capsid. |
| 2 | AAVC11.10 | | G6PC1 | 2538 | Payload comprising a G6PC1 gene or variant thereof packaged within a AAVC11.10 capsid. |
| 2 | AAVC11.11 | | G6PC1 | 2538 | Payload comprising a G6PC1 gene or variant thereof packaged within a AAVC11.11 capsid. |
| 2 | AAVC11.12 | | G6PC1 | 2538 | Payload comprising a G6PC1 gene or variant thereof packaged within a AAVC11.12 capsid. |
| 2 | AAVC11.13 | | G6PC1 | 2538 | Payload comprising a G6PC1 gene or variant thereof packaged within a AAVC11.13 capsid. |
| 2 | AAVC11.14 | | G6PC1 | 2538 | Payload comprising a G6PC1 gene or variant thereof packaged within a AAVC11.14 capsid. |
| 2 | AAVC11.15 | | G6PC1 | 2538 | Payload comprising a G6PC1 gene or variant thereof packaged within a AAVC11.15 capsid. |

Fig. 29 (Continued)

| | | | | | |
|---|---|---|---|---|---|
| 2 | AAVC11.16 | | G6PC1 | 2538 | Payload comprising a G6PC1 gene or variant thereof packaged within a AAVC11.16 capsid. |
| 2 | AAVC11.17 | | G6PC1 | 2538 | Payload comprising a G6PC1 gene or variant thereof packaged within a AAVC11.17 capsid. |
| 2 | AAVC11.18 | | G6PC1 | 2538 | Payload comprising a G6PC1 gene or variant thereof packaged within a AAVC11.18 capsid |
| 2 | AAVC11.19 | | G6PC1 | 2538 | Payload comprising a G6PC1 gene or variant thereof packaged within a AAVC11.19 capsid. |
| 2 | AAV12 | | G6PC1 | 2538 | Payload comprising a G6PC1 gene or variant thereof packaged within a AAV12 capsid. |
| 2 | AAV13 | | G6PC1 | 2538 | Payload comprising a G6PC1 gene or variant thereof packaged within a AAV13 capsid. |
| 2 | AAV-DJ | | G6PC1 | 2538 | Payload comprising a G6PC1 gene or variant thereof packaged within a AAV-DJ capsid |
| 2 | AAV-LK03 | | G6PC1 | 2538 | Payload comprising a G6PC1 gene or variant thereof packaged within a AAV-LK03 capsid. |
| 2 | AAV-LK19 | | G6PC1 | 2538 | Payload comprising a G6PC1 gene or variant thereof packaged within a AAV-LK19 capsid. |
| 2 | AAVrh.74 | | G6PC1 | 2538 | Payload comprising a G6PC1 gene or variant thereof packaged within a AAVrh.74 capsid. |
| 2 | AAVrh.10 | | G6PC1 | 2538 | Payload comprising a G6PC1 gene or variant thereof packaged within a AAVrh.10 capsid. |
| 2 | AAVhu.37 | | G6PC1 | 2538 | Payload comprising a G6PC1 gene or variant thereof packaged within a AAVhu.37 capsid. |
| 2 | AAVrh.K | | G6PC1 | 2538 | Payload comprising a G6PC1 gene or variant thereof packaged within a AAVrh.K capsid. |
| 2 | AAVrh.39 | | G6PC1 | 2538 | Payload comprising a G6PC1 gene or variant thereof packaged within a AAVrh.39 capsid. |
| 2 | AAVrh.9 | | G6PC1 | 2538 | Payload comprising a G6PC1 gene or variant thereof packaged within a AAVrh.9 capsid. |
| 2 | avian AAV | | G6PC1 | 2538 | Payload comprising a G6PC1 gene or variant thereof packaged within a avian capsid. |

Fig. 29 (Continued)

| | | | | | |
|---|---|---|---|---|---|
| 2 | bovine AAV | | G6PC1 | 2538 | Payload comprising a G6PC1 gene or variant thereof packaged within a bovine capsid. |
| 2 | canine AAV | | G6PC1 | 2538 | Payload comprising a G6PC1 gene or variant thereof packaged within a canine capsid. |
| 2 | equine AAV | | G6PC1 | 2538 | Payload comprising a G6PC1 gene or variant thereof packaged within a equine capsid. |
| 2 | primate AAV | | G6PC1 | 2538 | Payload comprising a G6PC1 gene or variant thereof packaged within a primate capsid. |
| 2 | non-primate AAV | | G6PC1 | 2538 | Payload comprising a G6PC1 gene or variant thereof packaged within a non-primate capsid. |
| 2 | ovine AAV | | G6PC1 | 2538 | Payload comprising a G6PC1 gene or variant thereof packaged within a ovine capsid. |
| 2 | hybrid AAV | | G6PC1 | 2538 | Payload comprising a G6PC1 gene or variant thereof packaged within a hybrid capsid. |
| 2 | chimeric AAV | | G6PC1 | 2538 | Payload comprising a G6PC1 gene or variant thereof packaged within a chimeric capsid. |
| 1 | AAV1 | 1450374 | G6PC2 | 57818 | Payload comprising a G6PC2 gene or variant thereof packaged within a AAV1 capsid. |
| 1 | AAV2 | | G6PC2 | 57818 | Payload comprising a G6PC2 gene or variant thereof packaged within a AAV2 capsid. |
| 1 | AAV3 | | G6PC2 | 57818 | Payload comprising a G6PC2 gene or variant thereof packaged within a AAV3 capsid. |
| 1 | AAV4 | 1446389 | G6PC2 | 57818 | Payload comprising a G6PC2 gene or variant thereof packaged within a AAV4 capsid. |
| 1 | AAV5 | | G6PC2 | 57818 | Payload comprising a G6PC2 gene or variant thereof packaged within a AAV5 capsid. |
| 1 | AAV6 | | G6PC2 | 57818 | Payload comprising a G6PC2 gene or variant thereof packaged within a AAV6 capsid. |
| 1 | AAV7 | | G6PC2 | 57818 | Payload comprising a G6PC2 gene or variant thereof packaged within a AAV7 capsid. |
| 1 | AAV8 | 5075992 | G6PC2 | 57818 | Payload comprising a G6PC2 gene or variant thereof packaged within a AAV8 capsid. |
| 1 | AAV9 | | G6PC2 | 57818 | Payload comprising a G6PC2 gene or variant thereof packaged within a AAV9 capsid. |

Fig. 29 (Continued)

| | | | | | |
|---|---|---|---|---|---|
| 1 | AAV10 | | G6PC2 | 57818 | Payload comprising a G6PC2 gene or variant thereof packaged within a AAV10 capsid. |
| 1 | AAV11 | | G6PC2 | 57818 | Payload comprising a G6PC2 gene or variant thereof packaged within a AAV11 capsid. |
| 1 | AAVC11.01 | | G6PC2 | 57818 | Payload comprising a G6PC2 gene or variant thereof packaged within a AAVC11.01 capsid. |
| 1 | AAVC11.02 | | G6PC2 | 57818 | Payload comprising a G6PC2 gene or variant thereof packaged within a AAVC11.02 capsid. |
| 1 | AAVC11.03 | | G6PC2 | 57818 | Payload comprising a G6PC2 gene or variant thereof packaged within a AAVC11.03 capsid. |
| 1 | AAVC11.04 | | G6PC2 | 57818 | Payload comprising a G6PC2 gene or variant thereof packaged within a AAVC11.04 capsid. |
| 1 | AAVC11.05 | | G6PC2 | 57818 | Payload comprising a G6PC2 gene or variant thereof packaged within a AAVC11.05 capsid. |
| 1 | AAVC11.06 | | G6PC2 | 57818 | Payload comprising a G6PC2 gene or variant thereof packaged within a AAVC11.06 capsid. |
| 1 | AAVC11.07 | | G6PC2 | 57818 | Payload comprising a G6PC2 gene or variant thereof packaged within a AAVC11.07 capsid |
| 1 | AAVC11.08 | | G6PC2 | 57818 | Payload comprising a G6PC2 gene or variant thereof packaged within a AAVC11.08 capsid. |
| 1 | AAVC11.09 | | G6PC2 | 57818 | Payload comprising a G6PC2 gene or variant thereof packaged within a AAVC11.09 capsid. |
| 1 | AAVC11.10 | | G6PC2 | 57818 | Payload comprising a G6PC2 gene or variant thereof packaged within a AAVC11.10 capsid. |
| 1 | AAVC11.11 | | G6PC2 | 57818 | Payload comprising a G6PC2 gene or variant thereof packaged within a AAVC11.11 capsid. |
| 1 | AAVC11.12 | | G6PC2 | 57818 | Payload comprising a G6PC2 gene or variant thereof packaged within a AAVC11.12 capsid. |
| 1 | AAVC11.13 | | G6PC2 | 57818 | Payload comprising a G6PC2 gene or variant thereof packaged within a AAVC11.13 capsid. |
| 1 | AAVC11.14 | | G6PC2 | 57818 | Payload comprising a G6PC2 gene or variant thereof packaged within a AAVC11.14 capsid. |
| 1 | AAVC11.15 | | G6PC2 | 57818 | Payload comprising a G6PC2 gene or variant thereof packaged within a AAVC11.15 capsid. |

Fig. 29 (Continued)

| | | | | | |
|---|---|---|---|---|---|
| 1 | AAVC11.16 | | G6PC2 | 57818 | Payload comprising a G6PC2 gene or variant thereof packaged within a AAVC11.16 capsid. |
| 1 | AAVC11.17 | | G6PC2 | 57818 | Payload comprising a G6PC2 gene or variant thereof packaged within a AAVC11.17 capsid. |
| 1 | AAVC11.18 | | G6PC2 | 57818 | Payload comprising a G6PC2 gene or variant thereof packaged within a AAVC11.18 capsid |
| 1 | AAVC11.19 | | G6PC2 | 57818 | Payload comprising a G6PC2 gene or variant thereof packaged within a AAVC11.19 capsid. |
| 1 | AAV12 | | G6PC2 | 57818 | Payload comprising a G6PC2 gene or variant thereof packaged within a AAV12 capsid. |
| 1 | AAV13 | | G6PC2 | 57818 | Payload comprising a G6PC2 gene or variant thereof packaged within a AAV13 capsid. |
| 1 | AAV-DJ | | G6PC2 | 57818 | Payload comprising a G6PC2 gene or variant thereof packaged within a AAV-DJ capsid |
| 1 | AAV-LK03 | | G6PC2 | 57818 | Payload comprising a G6PC2 gene or variant thereof packaged within a AAV-LK03 capsid. |
| 1 | AAV-LK19 | | G6PC2 | 57818 | Payload comprising a G6PC2 gene or variant thereof packaged within a AAV-LK19 capsid. |
| 1 | AAVrh.74 | | G6PC2 | 57818 | Payload comprising a G6PC2 gene or variant thereof packaged within a AAVrh.74 capsid. |
| 1 | AAVrh.10 | | G6PC2 | 57818 | Payload comprising a G6PC2 gene or variant thereof packaged within a AAVrh.10 capsid. |
| 1 | AAVhu.37 | | G6PC2 | 57818 | Payload comprising a G6PC2 gene or variant thereof packaged within a AAVhu.37 capsid. |
| 1 | AAVrh.K | | G6PC2 | 57818 | Payload comprising a G6PC2 gene or variant thereof packaged within a AAVrh.K capsid. |
| 1 | AAVrh.39 | | G6PC2 | 57818 | Payload comprising a G6PC2 gene or variant thereof packaged within a AAVrh.39 capsid. |
| 1 | AAVrh.9 | | G6PC2 | 57818 | Payload comprising a G6PC2 gene or variant thereof packaged within a AAVrh.9 capsid. |
| 1 | avian AAV | | G6PC2 | 57818 | Payload comprising a G6PC2 gene or variant thereof packaged within a avian capsid. |

Fig. 29 (Continued)

| | | | | | |
|---|---|---|---|---|---|
| 1 | bovine AAV | | G6PC2 | 57818 | Payload comprising a G6PC2 gene or variant thereof packaged within a bovine capsid. |
| 1 | canine AAV | | G6PC2 | 57818 | Payload comprising a G6PC2 gene or variant thereof packaged within a canine capsid. |
| 1 | equine AAV | | G6PC2 | 57818 | Payload comprising a G6PC2 gene or variant thereof packaged within a equine capsid. |
| 1 | primate AAV | | G6PC2 | 57818 | Payload comprising a G6PC2 gene or variant thereof packaged within a primate capsid. |
| 1 | non-primate AAV | | G6PC2 | 57818 | Payload comprising a G6PC2 gene or variant thereof packaged within a non-primate capsid. |
| 1 | ovine AAV | | G6PC2 | 57818 | Payload comprising a G6PC2 gene or variant thereof packaged within a ovine capsid. |
| 1 | hybrid AAV | | G6PC2 | 57818 | Payload comprising a G6PC2 gene or variant thereof packaged within a hybrid capsid. |
| 1 | chimeric AAV | | G6PC2 | 57818 | Payload comprising a G6PC2 gene or variant thereof packaged within a chimeric capsid. |
| 2 | AAV1 | 1450374 | G6PC2 | 57818 | Payload comprising a G6PC2 gene or variant thereof packaged within a AAV1 capsid. |
| 2 | AAV2 | | G6PC2 | 57818 | Payload comprising a G6PC2 gene or variant thereof packaged within a AAV2 capsid. |
| 2 | AAV3 | | G6PC2 | 57818 | Payload comprising a G6PC2 gene or variant thereof packaged within a AAV3 capsid. |
| 2 | AAV4 | 1446389 | G6PC2 | 57818 | Payload comprising a G6PC2 gene or variant thereof packaged within a AAV4 capsid. |
| 2 | AAV5 | | G6PC2 | 57818 | Payload comprising a G6PC2 gene or variant thereof packaged within a AAV5 capsid. |
| 2 | AAV6 | | G6PC2 | 57818 | Payload comprising a G6PC2 gene or variant thereof packaged within a AAV6 capsid. |
| 2 | AAV7 | | G6PC2 | 57818 | Payload comprising a G6PC2 gene or variant thereof packaged within a AAV7 capsid. |
| 2 | AAV8 | 5075992 | G6PC2 | 57818 | Payload comprising a G6PC2 gene or variant thereof packaged within a AAV8 capsid. |
| 2 | AAV9 | | G6PC2 | 57818 | Payload comprising a G6PC2 gene or variant thereof packaged within a AAV9 capsid. |

Fig. 29 (Continued)

| | | | | | |
|---|---|---|---|---|---|
| 2 | AAV10 | | G6PC2 | 57818 | Payload comprising a G6PC2 gene or variant thereof packaged within a AAV10 capsid. |
| 2 | AAV11 | | G6PC2 | 57818 | Payload comprising a G6PC2 gene or variant thereof packaged within a AAV11 capsid. |
| 2 | AAVC11.01 | | G6PC2 | 57818 | Payload comprising a G6PC2 gene or variant thereof packaged within a AAVC11.01 capsid. |
| 2 | AAVC11.02 | | G6PC2 | 57818 | Payload comprising a G6PC2 gene or variant thereof packaged within a AAVC11.02 capsid. |
| 2 | AAVC11.03 | | G6PC2 | 57818 | Payload comprising a G6PC2 gene or variant thereof packaged within a AAVC11.03 capsid. |
| 2 | AAVC11.04 | | G6PC2 | 57818 | Payload comprising a G6PC2 gene or variant thereof packaged within a AAVC11.04 capsid. |
| 2 | AAVC11.05 | | G6PC2 | 57818 | Payload comprising a G6PC2 gene or variant thereof packaged within a AAVC11.05 capsid. |
| 2 | AAVC11.06 | | G6PC2 | 57818 | Payload comprising a G6PC2 gene or variant thereof packaged within a AAVC11.06 capsid. |
| 2 | AAVC11.07 | | G6PC2 | 57818 | Payload comprising a G6PC2 gene or variant thereof packaged within a AAVC11.07 capsid |
| 2 | AAVC11.08 | | G6PC2 | 57818 | Payload comprising a G6PC2 gene or variant thereof packaged within a AAVC11.08 capsid. |
| 2 | AAVC11.09 | | G6PC2 | 57818 | Payload comprising a G6PC2 gene or variant thereof packaged within a AAVC11.09 capsid. |
| 2 | AAVC11.10 | | G6PC2 | 57818 | Payload comprising a G6PC2 gene or variant thereof packaged within a AAVC11.10 capsid. |
| 2 | AAVC11.11 | | G6PC2 | 57818 | Payload comprising a G6PC2 gene or variant thereof packaged within a AAVC11.11 capsid. |
| 2 | AAVC11.12 | | G6PC2 | 57818 | Payload comprising a G6PC2 gene or variant thereof packaged within a AAVC11.12 capsid. |
| 2 | AAVC11.13 | | G6PC2 | 57818 | Payload comprising a G6PC2 gene or variant thereof packaged within a AAVC11.13 capsid. |
| 2 | AAVC11.14 | | G6PC2 | 57818 | Payload comprising a G6PC2 gene or variant thereof packaged within a AAVC11.14 capsid. |
| 2 | AAVC11.15 | | G6PC2 | 57818 | Payload comprising a G6PC2 gene or variant thereof packaged within a AAVC11.15 capsid. |

Fig. 29 (Continued)

| | | | | | |
|---|---|---|---|---|---|
| 2 | AAVC11.16 | | G6PC2 | 57818 | Payload comprising a G6PC2 gene or variant thereof packaged within a AAVC11.16 capsid. |
| 2 | AAVC11.17 | | G6PC2 | 57818 | Payload comprising a G6PC2 gene or variant thereof packaged within a AAVC11.17 capsid. |
| 2 | AAVC11.18 | | G6PC2 | 57818 | Payload comprising a G6PC2 gene or variant thereof packaged within a AAVC11.18 capsid |
| 2 | AAVC11.19 | | G6PC2 | 57818 | Payload comprising a G6PC2 gene or variant thereof packaged within a AAVC11.19 capsid. |
| 2 | AAV12 | | G6PC2 | 57818 | Payload comprising a G6PC2 gene or variant thereof packaged within a AAV12 capsid. |
| 2 | AAV13 | | G6PC2 | 57818 | Payload comprising a G6PC2 gene or variant thereof packaged within a AAV13 capsid. |
| 2 | AAV-DJ | | G6PC2 | 57818 | Payload comprising a G6PC2 gene or variant thereof packaged within a AAV-DJ capsid |
| 2 | AAV-LK03 | | G6PC2 | 57818 | Payload comprising a G6PC2 gene or variant thereof packaged within a AAV-LK03 capsid. |
| 2 | AAV-LK19 | | G6PC2 | 57818 | Payload comprising a G6PC2 gene or variant thereof packaged within a AAV-LK19 capsid. |
| 2 | AAVrh.74 | | G6PC2 | 57818 | Payload comprising a G6PC2 gene or variant thereof packaged within a AAVrh.74 capsid. |
| 2 | AAVrh.10 | | G6PC2 | 57818 | Payload comprising a G6PC2 gene or variant thereof packaged within a AAVrh.10 capsid. |
| 2 | AAVhu.37 | | G6PC2 | 57818 | Payload comprising a G6PC2 gene or variant thereof packaged within a AAVhu.37 capsid. |
| 2 | AAVrh.K | | G6PC2 | 57818 | Payload comprising a G6PC2 gene or variant thereof packaged within a AAVrh.K capsid. |
| 2 | AAVrh.39 | | G6PC2 | 57818 | Payload comprising a G6PC2 gene or variant thereof packaged within a AAVrh.39 capsid. |
| 2 | AAVrh.9 | | G6PC2 | 57818 | Payload comprising a G6PC2 gene or variant thereof packaged within a AAVrh.9 capsid. |
| 2 | avian AAV | | G6PC2 | 57818 | Payload comprising a G6PC2 gene or variant thereof packaged within a avian capsid. |

Fig. 29 (Continued)

| | | | | | |
|---|---|---|---|---|---|
| 2 | bovine AAV | | G6PC2 | 57818 | Payload comprising a G6PC2 gene or variant thereof packaged within a bovine capsid. |
| 2 | canine AAV | | G6PC2 | 57818 | Payload comprising a G6PC2 gene or variant thereof packaged within a canine capsid. |
| 2 | equine AAV | | G6PC2 | 57818 | Payload comprising a G6PC2 gene or variant thereof packaged within a equine capsid. |
| 2 | primate AAV | | G6PC2 | 57818 | Payload comprising a G6PC2 gene or variant thereof packaged within a primate capsid. |
| 2 | non-primate AAV | | G6PC2 | 57818 | Payload comprising a G6PC2 gene or variant thereof packaged within a non-primate capsid. |
| 2 | ovine AAV | | G6PC2 | 57818 | Payload comprising a G6PC2 gene or variant thereof packaged within a ovine capsid. |
| 2 | hybrid AAV | | G6PC2 | 57818 | Payload comprising a G6PC2 gene or variant thereof packaged within a hybrid capsid. |
| 2 | chimeric AAV | | G6PC2 | 57818 | Payload comprising a G6PC2 gene or variant thereof packaged within a chimeric capsid. |
| 1 | AAV1 | 1450374 | G6PC3 | 92579 | Payload comprising a G6PC3 gene or variant thereof packaged within a AAV1 capsid. |
| 1 | AAV2 | | G6PC3 | 92579 | Payload comprising a G6PC3 gene or variant thereof packaged within a AAV2 capsid. |
| 1 | AAV3 | | G6PC3 | 92579 | Payload comprising a G6PC3 gene or variant thereof packaged within a AAV3 capsid. |
| 1 | AAV4 | 1446389 | G6PC3 | 92579 | Payload comprising a G6PC3 gene or variant thereof packaged within a AAV4 capsid. |
| 1 | AAV5 | | G6PC3 | 92579 | Payload comprising a G6PC3 gene or variant thereof packaged within a AAV5 capsid. |
| 1 | AAV6 | | G6PC3 | 92579 | Payload comprising a G6PC3 gene or variant thereof packaged within a AAV6 capsid. |
| 1 | AAV7 | | G6PC3 | 92579 | Payload comprising a G6PC3 gene or variant thereof packaged within a AAV7 capsid. |
| 1 | AAV8 | 5075992 | G6PC3 | 92579 | Payload comprising a G6PC3 gene or variant thereof packaged within a AAV8 capsid. |
| 1 | AAV9 | | G6PC3 | 92579 | Payload comprising a G6PC3 gene or variant thereof packaged within a AAV9 capsid. |

Fig. 29 (Continued)

| | | | | | |
|---|---|---|---|---|---|
| 1 | AAV10 | | G6PC3 | 92579 | Payload comprising a G6PC3 gene or variant thereof packaged within a AAV10 capsid. |
| 1 | AAV11 | | G6PC3 | 92579 | Payload comprising a G6PC3 gene or variant thereof packaged within a AAV11 capsid. |
| 1 | AAVC11.01 | | G6PC3 | 92579 | Payload comprising a G6PC3 gene or variant thereof packaged within a AAVC11.01 capsid. |
| 1 | AAVC11.02 | | G6PC3 | 92579 | Payload comprising a G6PC3 gene or variant thereof packaged within a AAVC11.02 capsid. |
| 1 | AAVC11.03 | | G6PC3 | 92579 | Payload comprising a G6PC3 gene or variant thereof packaged within a AAVC11.03 capsid. |
| 1 | AAVC11.04 | | G6PC3 | 92579 | Payload comprising a G6PC3 gene or variant thereof packaged within a AAVC11.04 capsid. |
| 1 | AAVC11.05 | | G6PC3 | 92579 | Payload comprising a G6PC3 gene or variant thereof packaged within a AAVC11.05 capsid. |
| 1 | AAVC11.06 | | G6PC3 | 92579 | Payload comprising a G6PC3 gene or variant thereof packaged within a AAVC11.06 capsid. |
| 1 | AAVC11.07 | | G6PC3 | 92579 | Payload comprising a G6PC3 gene or variant thereof packaged within a AAVC11.07 capsid |
| 1 | AAVC11.08 | | G6PC3 | 92579 | Payload comprising a G6PC3 gene or variant thereof packaged within a AAVC11.08 capsid. |
| 1 | AAVC11.09 | | G6PC3 | 92579 | Payload comprising a G6PC3 gene or variant thereof packaged within a AAVC11.09 capsid. |
| 1 | AAVC11.10 | | G6PC3 | 92579 | Payload comprising a G6PC3 gene or variant thereof packaged within a AAVC11.10 capsid. |
| 1 | AAVC11.11 | | G6PC3 | 92579 | Payload comprising a G6PC3 gene or variant thereof packaged within a AAVC11.11 capsid. |
| 1 | AAVC11.12 | | G6PC3 | 92579 | Payload comprising a G6PC3 gene or variant thereof packaged within a AAVC11.12 capsid. |
| 1 | AAVC11.13 | | G6PC3 | 92579 | Payload comprising a G6PC3 gene or variant thereof packaged within a AAVC11.13 capsid. |
| 1 | AAVC11.14 | | G6PC3 | 92579 | Payload comprising a G6PC3 gene or variant thereof packaged within a AAVC11.14 capsid. |
| 1 | AAVC11.15 | | G6PC3 | 92579 | Payload comprising a G6PC3 gene or variant thereof packaged within a AAVC11.15 capsid. |

Fig. 29 (Continued)

| | | | | | |
|---|---|---|---|---|---|
| 1 | AAVC11.16 | | G6PC3 | 92579 | Payload comprising a G6PC3 gene or variant thereof packaged within a AAVC11.16 capsid. |
| 1 | AAVC11.17 | | G6PC3 | 92579 | Payload comprising a G6PC3 gene or variant thereof packaged within a AAVC11.17 capsid. |
| 1 | AAVC11.18 | | G6PC3 | 92579 | Payload comprising a G6PC3 gene or variant thereof packaged within a AAVC11.18 capsid |
| 1 | AAVC11.19 | | G6PC3 | 92579 | Payload comprising a G6PC3 gene or variant thereof packaged within a AAVC11.19 capsid. |
| 1 | AAV12 | | G6PC3 | 92579 | Payload comprising a G6PC3 gene or variant thereof packaged within a AAV12 capsid. |
| 1 | AAV13 | | G6PC3 | 92579 | Payload comprising a G6PC3 gene or variant thereof packaged within a AAV13 capsid. |
| 1 | AAV-DJ | | G6PC3 | 92579 | Payload comprising a G6PC3 gene or variant thereof packaged within a AAV-DJ capsid |
| 1 | AAV-LK03 | | G6PC3 | 92579 | Payload comprising a G6PC3 gene or variant thereof packaged within a AAV-LK03 capsid. |
| 1 | AAV-LK19 | | G6PC3 | 92579 | Payload comprising a G6PC3 gene or variant thereof packaged within a AAV-LK19 capsid. |
| 1 | AAVrh.74 | | G6PC3 | 92579 | Payload comprising a G6PC3 gene or variant thereof packaged within a AAVrh.74 capsid. |
| 1 | AAVrh.10 | | G6PC3 | 92579 | Payload comprising a G6PC3 gene or variant thereof packaged within a AAVrh.10 capsid. |
| 1 | AAVhu.37 | | G6PC3 | 92579 | Payload comprising a G6PC3 gene or variant thereof packaged within a AAVhu.37 capsid. |
| 1 | AAVrh.K | | G6PC3 | 92579 | Payload comprising a G6PC3 gene or variant thereof packaged within a AAVrh.K capsid. |
| 1 | AAVrh.39 | | G6PC3 | 92579 | Payload comprising a G6PC3 gene or variant thereof packaged within a AAVrh.39 capsid. |
| 1 | AAVrh.9 | | G6PC3 | 92579 | Payload comprising a G6PC3 gene or variant thereof packaged within a AAVrh.9 capsid. |
| 1 | avian AAV | | G6PC3 | 92579 | Payload comprising a G6PC3 gene or variant thereof packaged within a avian capsid. |

Fig. 29 (Continued)

| | | | | | |
|---|---|---|---|---|---|
| 1 | bovine AAV | | G6PC3 | 92579 | Payload comprising a G6PC3 gene or variant thereof packaged within a bovine capsid. |
| 1 | canine AAV | | G6PC3 | 92579 | Payload comprising a G6PC3 gene or variant thereof packaged within a canine capsid. |
| 1 | equine AAV | | G6PC3 | 92579 | Payload comprising a G6PC3 gene or variant thereof packaged within a equine capsid. |
| 1 | primate AAV | | G6PC3 | 92579 | Payload comprising a G6PC3 gene or variant thereof packaged within a primate capsid. |
| 1 | non-primate AAV | | G6PC3 | 92579 | Payload comprising a G6PC3 gene or variant thereof packaged within a non-primate capsid. |
| 1 | ovine AAV | | G6PC3 | 92579 | Payload comprising a G6PC3 gene or variant thereof packaged within a ovine capsid. |
| 1 | hybrid AAV | | G6PC3 | 92579 | Payload comprising a G6PC3 gene or variant thereof packaged within a hybrid capsid. |
| 1 | chimeric AAV | | G6PC3 | 92579 | Payload comprising a G6PC3 gene or variant thereof packaged within a chimeric capsid. |
| 2 | AAV1 | 1450374 | G6PC3 | 92579 | Payload comprising a G6PC3 gene or variant thereof packaged within a AAV1 capsid. |
| 2 | AAV2 | | G6PC3 | 92579 | Payload comprising a G6PC3 gene or variant thereof packaged within a AAV2 capsid. |
| 2 | AAV3 | | G6PC3 | 92579 | Payload comprising a G6PC3 gene or variant thereof packaged within a AAV3 capsid. |
| 2 | AAV4 | 1446389 | G6PC3 | 92579 | Payload comprising a G6PC3 gene or variant thereof packaged within a AAV4 capsid. |
| 2 | AAV5 | | G6PC3 | 92579 | Payload comprising a G6PC3 gene or variant thereof packaged within a AAV5 capsid. |
| 2 | AAV6 | | G6PC3 | 92579 | Payload comprising a G6PC3 gene or variant thereof packaged within a AAV6 capsid. |
| 2 | AAV7 | | G6PC3 | 92579 | Payload comprising a G6PC3 gene or variant thereof packaged within a AAV7 capsid. |
| 2 | AAV8 | 5075992 | G6PC3 | 92579 | Payload comprising a G6PC3 gene or variant thereof packaged within a AAV8 capsid. |
| 2 | AAV9 | | G6PC3 | 92579 | Payload comprising a G6PC3 gene or variant thereof packaged within a AAV9 capsid. |

Fig. 29 (Continued)

| | | | | | |
|---|---|---|---|---|---|
| 2 | AAV10 | | G6PC3 | 92579 | Payload comprising a G6PC3 gene or variant thereof packaged within a AAV10 capsid. |
| 2 | AAV11 | | G6PC3 | 92579 | Payload comprising a G6PC3 gene or variant thereof packaged within a AAV11 capsid. |
| 2 | AAVC11.01 | | G6PC3 | 92579 | Payload comprising a G6PC3 gene or variant thereof packaged within a AAVC11.01 capsid. |
| 2 | AAVC11.02 | | G6PC3 | 92579 | Payload comprising a G6PC3 gene or variant thereof packaged within a AAVC11.02 capsid. |
| 2 | AAVC11.03 | | G6PC3 | 92579 | Payload comprising a G6PC3 gene or variant thereof packaged within a AAVC11.03 capsid. |
| 2 | AAVC11.04 | | G6PC3 | 92579 | Payload comprising a G6PC3 gene or variant thereof packaged within a AAVC11.04 capsid. |
| 2 | AAVC11.05 | | G6PC3 | 92579 | Payload comprising a G6PC3 gene or variant thereof packaged within a AAVC11.05 capsid. |
| 2 | AAVC11.06 | | G6PC3 | 92579 | Payload comprising a G6PC3 gene or variant thereof packaged within a AAVC11.06 capsid. |
| 2 | AAVC11.07 | | G6PC3 | 92579 | Payload comprising a G6PC3 gene or variant thereof packaged within a AAVC11.07 capsid |
| 2 | AAVC11.08 | | G6PC3 | 92579 | Payload comprising a G6PC3 gene or variant thereof packaged within a AAVC11.08 capsid. |
| 2 | AAVC11.09 | | G6PC3 | 92579 | Payload comprising a G6PC3 gene or variant thereof packaged within a AAVC11.09 capsid. |
| 2 | AAVC11.10 | | G6PC3 | 92579 | Payload comprising a G6PC3 gene or variant thereof packaged within a AAVC11.10 capsid. |
| 2 | AAVC11.11 | | G6PC3 | 92579 | Payload comprising a G6PC3 gene or variant thereof packaged within a AAVC11.11 capsid. |
| 2 | AAVC11.12 | | G6PC3 | 92579 | Payload comprising a G6PC3 gene or variant thereof packaged within a AAVC11.12 capsid. |
| 2 | AAVC11.13 | | G6PC3 | 92579 | Payload comprising a G6PC3 gene or variant thereof packaged within a AAVC11.13 capsid. |
| 2 | AAVC11.14 | | G6PC3 | 92579 | Payload comprising a G6PC3 gene or variant thereof packaged within a AAVC11.14 capsid. |
| 2 | AAVC11.15 | | G6PC3 | 92579 | Payload comprising a G6PC3 gene or variant thereof packaged within a AAVC11.15 capsid. |

Fig. 29 (Continued)

| | | | | | |
|---|---|---|---|---|---|
| 2 | AAVC11.16 | | G6PC3 | 92579 | Payload comprising a G6PC3 gene or variant thereof packaged within a AAVC11.16 capsid. |
| 2 | AAVC11.17 | | G6PC3 | 92579 | Payload comprising a G6PC3 gene or variant thereof packaged within a AAVC11.17 capsid. |
| 2 | AAVC11.18 | | G6PC3 | 92579 | Payload comprising a G6PC3 gene or variant thereof packaged within a AAVC11.18 capsid |
| 2 | AAVC11.19 | | G6PC3 | 92579 | Payload comprising a G6PC3 gene or variant thereof packaged within a AAVC11.19 capsid. |
| 2 | AAV12 | | G6PC3 | 92579 | Payload comprising a G6PC3 gene or variant thereof packaged within a AAV12 capsid. |
| 2 | AAV13 | | G6PC3 | 92579 | Payload comprising a G6PC3 gene or variant thereof packaged within a AAV13 capsid. |
| 2 | AAV-DJ | | G6PC3 | 92579 | Payload comprising a G6PC3 gene or variant thereof packaged within a AAV-DJ capsid |
| 2 | AAV-LK03 | | G6PC3 | 92579 | Payload comprising a G6PC3 gene or variant thereof packaged within a AAV-LK03 capsid. |
| 2 | AAV-LK19 | | G6PC3 | 92579 | Payload comprising a G6PC3 gene or variant thereof packaged within a AAV-LK19 capsid. |
| 2 | AAVrh.74 | | G6PC3 | 92579 | Payload comprising a G6PC3 gene or variant thereof packaged within a AAVrh.74 capsid. |
| 2 | AAVrh.10 | | G6PC3 | 92579 | Payload comprising a G6PC3 gene or variant thereof packaged within a AAVrh.10 capsid. |
| 2 | AAVhu.37 | | G6PC3 | 92579 | Payload comprising a G6PC3 gene or variant thereof packaged within a AAVhu.37 capsid. |
| 2 | AAVrh.K | | G6PC3 | 92579 | Payload comprising a G6PC3 gene or variant thereof packaged within a AAVrh.K capsid. |
| 2 | AAVrh.39 | | G6PC3 | 92579 | Payload comprising a G6PC3 gene or variant thereof packaged within a AAVrh.39 capsid. |
| 2 | AAVrh.9 | | G6PC3 | 92579 | Payload comprising a G6PC3 gene or variant thereof packaged within a AAVrh.9 capsid. |
| 2 | avian AAV | | G6PC3 | 92579 | Payload comprising a G6PC3 gene or variant thereof packaged within a avian capsid. |

Fig. 29 (Continued)

| | | | | | |
|---|---|---|---|---|---|
| 2 | bovine AAV | | G6PC3 | 92579 | Payload comprising a G6PC3 gene or variant thereof packaged within a bovine capsid. |
| 2 | canine AAV | | G6PC3 | 92579 | Payload comprising a G6PC3 gene or variant thereof packaged within a canine capsid. |
| 2 | equine AAV | | G6PC3 | 92579 | Payload comprising a G6PC3 gene or variant thereof packaged within a equine capsid. |
| 2 | primate AAV | | G6PC3 | 92579 | Payload comprising a G6PC3 gene or variant thereof packaged within a primate capsid. |
| 2 | non-primate AAV | | G6PC3 | 92579 | Payload comprising a G6PC3 gene or variant thereof packaged within a non-primate capsid. |
| 2 | ovine AAV | | G6PC3 | 92579 | Payload comprising a G6PC3 gene or variant thereof packaged within a ovine capsid. |
| 2 | hybrid AAV | | G6PC3 | 92579 | Payload comprising a G6PC3 gene or variant thereof packaged within a hybrid capsid. |
| 2 | chimeric AAV | | G6PC3 | 2542 | Payload comprising a G6PC3 gene or variant thereof packaged within a chimeric capsid. |
| 1 | AAV1 | 1450374 | G6PT1 | 2542 | Payload comprising a G6PT1 gene or variant thereof packaged within a AAV1 capsid. |
| 1 | AAV2 | | G6PT1 | 2542 | Payload comprising a G6PT1 gene or variant thereof packaged within a AAV2 capsid. |
| 1 | AAV3 | | G6PT1 | 2542 | Payload comprising a G6PT1 gene or variant thereof packaged within a AAV3 capsid. |
| 1 | AAV4 | 1446389 | G6PT1 | 2542 | Payload comprising a G6PT1 gene or variant thereof packaged within a AAV4 capsid. |
| 1 | AAV5 | | G6PT1 | 2542 | Payload comprising a G6PT1 gene or variant thereof packaged within a AAV5 capsid. |
| 1 | AAV6 | | G6PT1 | 2542 | Payload comprising a G6PT1 gene or variant thereof packaged within a AAV6 capsid. |
| 1 | AAV7 | | G6PT1 | 2542 | Payload comprising a G6PT1 gene or variant thereof packaged within a AAV7 capsid. |
| 1 | AAV8 | 5075992 | G6PT1 | 2542 | Payload comprising a G6PT1 gene or variant thereof packaged within a AAV8 capsid. |
| 1 | AAV9 | | G6PT1 | 2542 | Payload comprising a G6PT1 gene or variant thereof packaged within a AAV9 capsid. |

Fig. 29 (Continued)

| | | | | | |
|---|---|---|---|---|---|
| 1 | AAV10 | | G6PT1 | 2542 | Payload comprising a G6PT1 gene or variant thereof packaged within a AAV10 capsid. |
| 1 | AAV11 | | G6PT1 | 2542 | Payload comprising a G6PT1 gene or variant thereof packaged within a AAV11 capsid. |
| 1 | AAVC11.01 | | G6PT1 | 2542 | Payload comprising a G6PT1 gene or variant thereof packaged within a AAVC11.01 capsid. |
| 1 | AAVC11.02 | | G6PT1 | 2542 | Payload comprising a G6PT1 gene or variant thereof packaged within a AAVC11.02 capsid. |
| 1 | AAVC11.03 | | G6PT1 | 2542 | Payload comprising a G6PT1 gene or variant thereof packaged within a AAVC11.03 capsid. |
| 1 | AAVC11.04 | | G6PT1 | 2542 | Payload comprising a G6PT1 gene or variant thereof packaged within a AAVC11.04 capsid. |
| 1 | AAVC11.05 | | G6PT1 | 2542 | Payload comprising a G6PT1 gene or variant thereof packaged within a AAVC11.05 capsid. |
| 1 | AAVC11.06 | | G6PT1 | 2542 | Payload comprising a G6PT1 gene or variant thereof packaged within a AAVC11.06 capsid. |
| 1 | AAVC11.07 | | G6PT1 | 2542 | Payload comprising a G6PT1 gene or variant thereof packaged within a AAVC11.07 capsid |
| 1 | AAVC11.08 | | G6PT1 | 2542 | Payload comprising a G6PT1 gene or variant thereof packaged within a AAVC11.08 capsid. |
| 1 | AAVC11.09 | | G6PT1 | 2542 | Payload comprising a G6PT1 gene or variant thereof packaged within a AAVC11.09 capsid. |
| 1 | AAVC11.10 | | G6PT1 | 2542 | Payload comprising a G6PT1 gene or variant thereof packaged within a AAVC11.10 capsid. |
| 1 | AAVC11.11 | | G6PT1 | 2542 | Payload comprising a G6PT1 gene or variant thereof packaged within a AAVC11.11 capsid. |
| 1 | AAVC11.12 | | G6PT1 | 2542 | Payload comprising a G6PT1 gene or variant thereof packaged within a AAVC11.12 capsid. |
| 1 | AAVC11.13 | | G6PT1 | 2542 | Payload comprising a G6PT1 gene or variant thereof packaged within a AAVC11.13 capsid. |
| 1 | AAVC11.14 | | G6PT1 | 2542 | Payload comprising a G6PT1 gene or variant thereof packaged within a AAVC11.14 capsid. |
| 1 | AAVC11.15 | | G6PT1 | 2542 | Payload comprising a G6PT1 gene or variant thereof packaged within a AAVC11.15 capsid. |

Fig. 29 (Continued)

| | | | | | |
|---|---|---|---|---|---|
| 1 | AAVC11.16 | | G6PT1 | 2542 | Payload comprising a G6PT1 gene or variant thereof packaged within a AAVC11.16 capsid. |
| 1 | AAVC11.17 | | G6PT1 | 2542 | Payload comprising a G6PT1 gene or variant thereof packaged within a AAVC11.17 capsid. |
| 1 | AAVC11.18 | | G6PT1 | 2542 | Payload comprising a G6PT1 gene or variant thereof packaged within a AAVC11.18 capsid |
| 1 | AAVC11.19 | | G6PT1 | 2542 | Payload comprising a G6PT1 gene or variant thereof packaged within a AAVC11.19 capsid. |
| 1 | AAV12 | | G6PT1 | 2542 | Payload comprising a G6PT1 gene or variant thereof packaged within a AAV12 capsid. |
| 1 | AAV13 | | G6PT1 | 2542 | Payload comprising a G6PT1 gene or variant thereof packaged within a AAV13 capsid. |
| 1 | AAV-DJ | | G6PT1 | 2542 | Payload comprising a G6PT1 gene or variant thereof packaged within a AAV-DJ capsid |
| 1 | AAV-LK03 | | G6PT1 | 2542 | Payload comprising a G6PT1 gene or variant thereof packaged within a AAV-LK03 capsid. |
| 1 | AAV-LK19 | | G6PT1 | 2542 | Payload comprising a G6PT1 gene or variant thereof packaged within a AAV-LK19 capsid. |
| 1 | AAVrh.74 | | G6PT1 | 2542 | Payload comprising a G6PT1 gene or variant thereof packaged within a AAVrh.74 capsid. |
| 1 | AAVrh.10 | | G6PT1 | 2542 | Payload comprising a G6PT1 gene or variant thereof packaged within a AAVrh.10 capsid. |
| 1 | AAVhu.37 | | G6PT1 | 2542 | Payload comprising a G6PT1 gene or variant thereof packaged within a AAVhu.37 capsid. |
| 1 | AAVrh.K | | G6PT1 | 2542 | Payload comprising a G6PT1 gene or variant thereof packaged within a AAVrh.K capsid. |
| 1 | AAVrh.39 | | G6PT1 | 2542 | Payload comprising a G6PT1 gene or variant thereof packaged within a AAVrh.39 capsid. |
| 1 | AAVrh.9 | | G6PT1 | 2542 | Payload comprising a G6PT1 gene or variant thereof packaged within a AAVrh.9 capsid. |
| 1 | avian AAV | | G6PT1 | 2542 | Payload comprising a G6PT1 gene or variant thereof packaged within a avian capsid. |

Fig. 29 (Continued)

| | | | | | |
|---|---|---|---|---|---|
| 1 | bovine AAV | | G6PT1 | 2542 | Payload comprising a G6PT1 gene or variant thereof packaged within a bovine capsid. |
| 1 | canine AAV | | G6PT1 | 2542 | Payload comprising a G6PT1 gene or variant thereof packaged within a canine capsid. |
| 1 | equine AAV | | G6PT1 | 2542 | Payload comprising a G6PT1 gene or variant thereof packaged within a equine capsid. |
| 1 | primate AAV | | G6PT1 | 2542 | Payload comprising a G6PT1 gene or variant thereof packaged within a primate capsid. |
| 1 | non-primate AAV | | G6PT1 | 2542 | Payload comprising a G6PT1 gene or variant thereof packaged within a non-primate capsid. |
| 1 | ovine AAV | | G6PT1 | 2542 | Payload comprising a G6PT1 gene or variant thereof packaged within a ovine capsid. |
| 1 | hybrid AAV | | G6PT1 | 2542 | Payload comprising a G6PT1 gene or variant thereof packaged within a hybrid capsid. |
| 1 | chimeric AAV | | G6PT1 | 2542 | Payload comprising a G6PT1 gene or variant thereof packaged within a chimeric capsid. |
| 2 | AAV1 | 1450374 | G6PT1 | 2542 | Payload comprising a G6PT1 gene or variant thereof packaged within a AAV1 capsid. |
| 2 | AAV2 | | G6PT1 | 2542 | Payload comprising a G6PT1 gene or variant thereof packaged within a AAV2 capsid. |
| 2 | AAV3 | | G6PT1 | 2542 | Payload comprising a G6PT1 gene or variant thereof packaged within a AAV3 capsid. |
| 2 | AAV4 | 1446389 | G6PT1 | 2542 | Payload comprising a G6PT1 gene or variant thereof packaged within a AAV4 capsid. |
| 2 | AAV5 | | G6PT1 | 2542 | Payload comprising a G6PT1 gene or variant thereof packaged within a AAV5 capsid. |
| 2 | AAV6 | | G6PT1 | 2542 | Payload comprising a G6PT1 gene or variant thereof packaged within a AAV6 capsid. |
| 2 | AAV7 | | G6PT1 | 2542 | Payload comprising a G6PT1 gene or variant thereof packaged within a AAV7 capsid. |
| 2 | AAV8 | 5075992 | G6PT1 | 2542 | Payload comprising a G6PT1 gene or variant thereof packaged within a AAV8 capsid. |
| 2 | AAV9 | | G6PT1 | 2542 | Payload comprising a G6PT1 gene or variant thereof packaged within a AAV9 capsid. |

Fig. 29 (Continued)

| | | | | | |
|---|---|---|---|---|---|
| 2 | AAV10 | | G6PT1 | 2542 | Payload comprising a G6PT1 gene or variant thereof packaged within a AAV10 capsid. |
| 2 | AAV11 | | G6PT1 | 2542 | Payload comprising a G6PT1 gene or variant thereof packaged within a AAV11 capsid. |
| 2 | AAVC11.01 | | G6PT1 | 2542 | Payload comprising a G6PT1 gene or variant thereof packaged within a AAVC11.01 capsid. |
| 2 | AAVC11.02 | | G6PT1 | 2542 | Payload comprising a G6PT1 gene or variant thereof packaged within a AAVC11.02 capsid. |
| 2 | AAVC11.03 | | G6PT1 | 2542 | Payload comprising a G6PT1 gene or variant thereof packaged within a AAVC11.03 capsid. |
| 2 | AAVC11.04 | | G6PT1 | 2542 | Payload comprising a G6PT1 gene or variant thereof packaged within a AAVC11.04 capsid. |
| 2 | AAVC11.05 | | G6PT1 | 2542 | Payload comprising a G6PT1 gene or variant thereof packaged within a AAVC11.05 capsid. |
| 2 | AAVC11.06 | | G6PT1 | 2542 | Payload comprising a G6PT1 gene or variant thereof packaged within a AAVC11.06 capsid. |
| 2 | AAVC11.07 | | G6PT1 | 2542 | Payload comprising a G6PT1 gene or variant thereof packaged within a AAVC11.07 capsid |
| 2 | AAVC11.08 | | G6PT1 | 2542 | Payload comprising a G6PT1 gene or variant thereof packaged within a AAVC11.08 capsid. |
| 2 | AAVC11.09 | | G6PT1 | 2542 | Payload comprising a G6PT1 gene or variant thereof packaged within a AAVC11.09 capsid. |
| 2 | AAVC11.10 | | G6PT1 | 2542 | Payload comprising a G6PT1 gene or variant thereof packaged within a AAVC11.10 capsid. |
| 2 | AAVC11.11 | | G6PT1 | 2542 | Payload comprising a G6PT1 gene or variant thereof packaged within a AAVC11.11 capsid. |
| 2 | AAVC11.12 | | G6PT1 | 2542 | Payload comprising a G6PT1 gene or variant thereof packaged within a AAVC11.12 capsid. |
| 2 | AAVC11.13 | | G6PT1 | 2542 | Payload comprising a G6PT1 gene or variant thereof packaged within a AAVC11.13 capsid. |
| 2 | AAVC11.14 | | G6PT1 | 2542 | Payload comprising a G6PT1 gene or variant thereof packaged within a AAVC11.14 capsid. |
| 2 | AAVC11.15 | | G6PT1 | 2542 | Payload comprising a G6PT1 gene or variant thereof packaged within a AAVC11.15 capsid. |

Fig. 29 (Continued)

| | | | | | |
|---|---|---|---|---|---|
| 2 | AAVC11.16 | | G6PT1 | 2542 | Payload comprising a G6PT1 gene or variant thereof packaged within a AAVC11.16 capsid. |
| 2 | AAVC11.17 | | G6PT1 | 2542 | Payload comprising a G6PT1 gene or variant thereof packaged within a AAVC11.17 capsid. |
| 2 | AAVC11.18 | | G6PT1 | 2542 | Payload comprising a G6PT1 gene or variant thereof packaged within a AAVC11.18 capsid |
| 2 | AAVC11.19 | | G6PT1 | 2542 | Payload comprising a G6PT1 gene or variant thereof packaged within a AAVC11.19 capsid. |
| 2 | AAV12 | | G6PT1 | 2542 | Payload comprising a G6PT1 gene or variant thereof packaged within a AAV12 capsid. |
| 2 | AAV13 | | G6PT1 | 2542 | Payload comprising a G6PT1 gene or variant thereof packaged within a AAV13 capsid. |
| 2 | AAV-DJ | | G6PT1 | 2542 | Payload comprising a G6PT1 gene or variant thereof packaged within a AAV-DJ capsid |
| 2 | AAV-LK03 | | G6PT1 | 2542 | Payload comprising a G6PT1 gene or variant thereof packaged within a AAV-LK03 capsid. |
| 2 | AAV-LK19 | | G6PT1 | 2542 | Payload comprising a G6PT1 gene or variant thereof packaged within a AAV-LK19 capsid. |
| 2 | AAVrh.74 | | G6PT1 | 2542 | Payload comprising a G6PT1 gene or variant thereof packaged within a AAVrh.74 capsid. |
| 2 | AAVrh.10 | | G6PT1 | 2542 | Payload comprising a G6PT1 gene or variant thereof packaged within a AAVrh.10 capsid. |
| 2 | AAVhu.37 | | G6PT1 | 2542 | Payload comprising a G6PT1 gene or variant thereof packaged within a AAVhu.37 capsid. |
| 2 | AAVrh.K | | G6PT1 | 2542 | Payload comprising a G6PT1 gene or variant thereof packaged within a AAVrh.K capsid. |
| 2 | AAVrh.39 | | G6PT1 | 2542 | Payload comprising a G6PT1 gene or variant thereof packaged within a AAVrh.39 capsid. |
| 2 | AAVrh.9 | | G6PT1 | 2542 | Payload comprising a G6PT1 gene or variant thereof packaged within a AAVrh.9 capsid. |
| 2 | avian AAV | | G6PT1 | 2542 | Payload comprising a G6PT1 gene or variant thereof packaged within a avian capsid. |

Fig. 29 (Continued)

| | | | | | |
|---|---|---|---|---|---|
| 2 | bovine AAV | | G6PT1 | 2542 | Payload comprising a G6PT1 gene or variant thereof packaged within a bovine capsid. |
| 2 | canine AAV | | G6PT1 | 2542 | Payload comprising a G6PT1 gene or variant thereof packaged within a canine capsid. |
| 2 | equine AAV | | G6PT1 | 2542 | Payload comprising a G6PT1 gene or variant thereof packaged within a equine capsid. |
| 2 | primate AAV | | G6PT1 | 2542 | Payload comprising a G6PT1 gene or variant thereof packaged within a primate capsid. |
| 2 | non-primate AAV | | G6PT1 | 2542 | Payload comprising a G6PT1 gene or variant thereof packaged within a non-primate capsid. |
| 2 | ovine AAV | | G6PT1 | 2542 | Payload comprising a G6PT1 gene or variant thereof packaged within a ovine capsid. |
| 2 | hybrid AAV | | G6PT1 | 2542 | Payload comprising a G6PT1 gene or variant thereof packaged within a hybrid capsid. |
| 2 | chimeric AAV | | G6PT1 | 2542 | Payload comprising a G6PT1 gene or variant thereof packaged within a chimeric capsid. |
| 1 | AAV1 | 1450374 | GAA | 2548 | Payload comprising a GAA gene or variant thereof packaged within a AAV1 capsid. |
| 1 | AAV2 | | GAA | 2548 | Payload comprising a GAA gene or variant thereof packaged within a AAV2 capsid. |
| 1 | AAV3 | | GAA | 2548 | Payload comprising a GAA gene or variant thereof packaged within a AAV3 capsid. |
| 1 | AAV4 | 1446389 | GAA | 2548 | Payload comprising a GAA gene or variant thereof packaged within a AAV4 capsid. |
| 1 | AAV5 | | GAA | 2548 | Payload comprising a GAA gene or variant thereof packaged within a AAV5 capsid. |
| 1 | AAV6 | | GAA | 2548 | Payload comprising a GAA gene or variant thereof packaged within a AAV6 capsid. |
| 1 | AAV7 | | GAA | 2548 | Payload comprising a GAA gene or variant thereof packaged within a AAV7 capsid. |
| 1 | AAV8 | 5075992 | GAA | 2548 | Payload comprising a GAA gene or variant thereof packaged within a AAV8 capsid. |
| 1 | AAV9 | | GAA | 2548 | Payload comprising a GAA gene or variant thereof packaged within a AAV9 capsid. |

Fig. 29 (Continued)

| | | | | | |
|---|---|---|---|---|---|
| 1 | AAV10 | | GAA | 2548 | Payload comprising a GAA gene or variant thereof packaged within a AAV10 capsid. |
| 1 | AAV11 | | GAA | 2548 | Payload comprising a GAA gene or variant thereof packaged within a AAV11 capsid. |
| 1 | AAVC11.01 | | GAA | 2548 | Payload comprising a GAA gene or variant thereof packaged within a AAVC11.01 capsid. |
| 1 | AAVC11.02 | | GAA | 2548 | Payload comprising a GAA gene or variant thereof packaged within a AAVC11.02 capsid. |
| 1 | AAVC11.03 | | GAA | 2548 | Payload comprising a GAA gene or variant thereof packaged within a AAVC11.03 capsid. |
| 1 | AAVC11.04 | | GAA | 2548 | Payload comprising a GAA gene or variant thereof packaged within a AAVC11.04 capsid. |
| 1 | AAVC11.05 | | GAA | 2548 | Payload comprising a GAA gene or variant thereof packaged within a AAVC11.05 capsid. |
| 1 | AAVC11.06 | | GAA | 2548 | Payload comprising a GAA gene or variant thereof packaged within a AAVC11.06 capsid. |
| 1 | AAVC11.07 | | GAA | 2548 | Payload comprising a GAA gene or variant thereof packaged within a AAVC11.07 capsid |
| 1 | AAVC11.08 | | GAA | 2548 | Payload comprising a GAA gene or variant thereof packaged within a AAVC11.08 capsid. |
| 1 | AAVC11.09 | | GAA | 2548 | Payload comprising a GAA gene or variant thereof packaged within a AAVC11.09 capsid. |
| 1 | AAVC11.10 | | GAA | 2548 | Payload comprising a GAA gene or variant thereof packaged within a AAVC11.10 capsid. |
| 1 | AAVC11.11 | | GAA | 2548 | Payload comprising a GAA gene or variant thereof packaged within a AAVC11.11 capsid. |
| 1 | AAVC11.12 | | GAA | 2548 | Payload comprising a GAA gene or variant thereof packaged within a AAVC11.12 capsid. |
| 1 | AAVC11.13 | | GAA | 2548 | Payload comprising a GAA gene or variant thereof packaged within a AAVC11.13 capsid. |
| 1 | AAVC11.14 | | GAA | 2548 | Payload comprising a GAA gene or variant thereof packaged within a AAVC11.14 capsid. |
| 1 | AAVC11.15 | | GAA | 2548 | Payload comprising a GAA gene or variant thereof packaged within a AAVC11.15 capsid. |

Fig. 29 (Continued)

| | | | | | |
|---|---|---|---|---|---|
| 1 | AAVC11.16 | | GAA | 2548 | Payload comprising a GAA gene or variant thereof packaged within a AAVC11.16 capsid. |
| 1 | AAVC11.17 | | GAA | 2548 | Payload comprising a GAA gene or variant thereof packaged within a AAVC11.17 capsid. |
| 1 | AAVC11.18 | | GAA | 2548 | Payload comprising a GAA gene or variant thereof packaged within a AAVC11.18 capsid |
| 1 | AAVC11.19 | | GAA | 2548 | Payload comprising a GAA gene or variant thereof packaged within a AAVC11.19 capsid. |
| 1 | AAV12 | | GAA | 2548 | Payload comprising a GAA gene or variant thereof packaged within a AAV12 capsid. |
| 1 | AAV13 | | GAA | 2548 | Payload comprising a GAA gene or variant thereof packaged within a AAV13 capsid. |
| 1 | AAV-DJ | | GAA | 2548 | Payload comprising a GAA gene or variant thereof packaged within a AAV-DJ capsid |
| 1 | AAV-LK03 | | GAA | 2548 | Payload comprising a GAA gene or variant thereof packaged within a AAV-LK03 capsid. |
| 1 | AAV-LK19 | | GAA | 2548 | Payload comprising a GAA gene or variant thereof packaged within a AAV-LK19 capsid. |
| 1 | AAVrh.74 | | GAA | 2548 | Payload comprising a GAA gene or variant thereof packaged within a AAVrh.74 capsid. |
| 1 | AAVrh.10 | | GAA | 2548 | Payload comprising a GAA gene or variant thereof packaged within a AAVrh.10 capsid. |
| 1 | AAVhu.37 | | GAA | 2548 | Payload comprising a GAA gene or variant thereof packaged within a AAVhu.37 capsid. |
| 1 | AAVrh.K | | GAA | 2548 | Payload comprising a GAA gene or variant thereof packaged within a AAVrh.K capsid. |
| 1 | AAVrh.39 | | GAA | 2548 | Payload comprising a GAA gene or variant thereof packaged within a AAVrh.39 capsid. |
| 1 | AAVrh.9 | | GAA | 2548 | Payload comprising a GAA gene or variant thereof packaged within a AAVrh.9 capsid. |
| 1 | avian AAV | | GAA | 2548 | Payload comprising a GAA gene or variant thereof packaged within a avian capsid. |

Fig. 29 (Continued)

| | | | | | |
|---|---|---|---|---|---|
| 1 | bovine AAV | | GAA | 2548 | Payload comprising a GAA gene or variant thereof packaged within a bovine capsid. |
| 1 | canine AAV | | GAA | 2548 | Payload comprising a GAA gene or variant thereof packaged within a canine capsid. |
| 1 | equine AAV | | GAA | 2548 | Payload comprising a GAA gene or variant thereof packaged within a equine capsid. |
| 1 | primate AAV | | GAA | 2548 | Payload comprising a GAA gene or variant thereof packaged within a primate capsid. |
| 1 | non-primate AAV | | GAA | 2548 | Payload comprising a GAA gene or variant thereof packaged within a non-primate capsid. |
| 1 | ovine AAV | | GAA | 2548 | Payload comprising a GAA gene or variant thereof packaged within a ovine capsid. |
| 1 | hybrid AAV | | GAA | 2548 | Payload comprising a GAA gene or variant thereof packaged within a hybrid capsid. |
| 1 | chimeric AAV | | GAA | 2548 | Payload comprising a GAA gene or variant thereof packaged within a chimeric capsid. |
| 2 | AAV1 | 1450374 | GAA | 2548 | Payload comprising a GAA gene or variant thereof packaged within a AAV1 capsid. |
| 2 | AAV2 | | GAA | 2548 | Payload comprising a GAA gene or variant thereof packaged within a AAV2 capsid. |
| 2 | AAV3 | | GAA | 2548 | Payload comprising a GAA gene or variant thereof packaged within a AAV3 capsid. |
| 2 | AAV4 | 1446389 | GAA | 2548 | Payload comprising a GAA gene or variant thereof packaged within a AAV4 capsid. |
| 2 | AAV5 | | GAA | 2548 | Payload comprising a GAA gene or variant thereof packaged within a AAV5 capsid. |
| 2 | AAV6 | | GAA | 2548 | Payload comprising a GAA gene or variant thereof packaged within a AAV6 capsid. |
| 2 | AAV7 | | GAA | 2548 | Payload comprising a GAA gene or variant thereof packaged within a AAV7 capsid. |
| 2 | AAV8 | 5075992 | GAA | 2548 | Payload comprising a GAA gene or variant thereof packaged within a AAV8 capsid. |
| 2 | AAV9 | | GAA | 2548 | Payload comprising a GAA gene or variant thereof packaged within a AAV9 capsid. |

Fig. 29 (Continued)

| | | | | | |
|---|---|---|---|---|---|
| 2 | AAV10 | | GAA | 2548 | Payload comprising a GAA gene or variant thereof packaged within a AAV10 capsid. |
| 2 | AAV11 | | GAA | 2548 | Payload comprising a GAA gene or variant thereof packaged within a AAV11 capsid. |
| 2 | AAVC11.01 | | GAA | 2548 | Payload comprising a GAA gene or variant thereof packaged within a AAVC11.01 capsid. |
| 2 | AAVC11.02 | | GAA | 2548 | Payload comprising a GAA gene or variant thereof packaged within a AAVC11.02 capsid. |
| 2 | AAVC11.03 | | GAA | 2548 | Payload comprising a GAA gene or variant thereof packaged within a AAVC11.03 capsid. |
| 2 | AAVC11.04 | | GAA | 2548 | Payload comprising a GAA gene or variant thereof packaged within a AAVC11.04 capsid. |
| 2 | AAVC11.05 | | GAA | 2548 | Payload comprising a GAA gene or variant thereof packaged within a AAVC11.05 capsid. |
| 2 | AAVC11.06 | | GAA | 2548 | Payload comprising a GAA gene or variant thereof packaged within a AAVC11.06 capsid. |
| 2 | AAVC11.07 | | GAA | 2548 | Payload comprising a GAA gene or variant thereof packaged within a AAVC11.07 capsid |
| 2 | AAVC11.08 | | GAA | 2548 | Payload comprising a GAA gene or variant thereof packaged within a AAVC11.08 capsid. |
| 2 | AAVC11.09 | | GAA | 2548 | Payload comprising a GAA gene or variant thereof packaged within a AAVC11.09 capsid. |
| 2 | AAVC11.10 | | GAA | 2548 | Payload comprising a GAA gene or variant thereof packaged within a AAVC11.10 capsid. |
| 2 | AAVC11.11 | | GAA | 2548 | Payload comprising a GAA gene or variant thereof packaged within a AAVC11.11 capsid. |
| 2 | AAVC11.12 | | GAA | 2548 | Payload comprising a GAA gene or variant thereof packaged within a AAVC11.12 capsid. |
| 2 | AAVC11.13 | | GAA | 2548 | Payload comprising a GAA gene or variant thereof packaged within a AAVC11.13 capsid. |
| 2 | AAVC11.14 | | GAA | 2548 | Payload comprising a GAA gene or variant thereof packaged within a AAVC11.14 capsid. |
| 2 | AAVC11.15 | | GAA | 2548 | Payload comprising a GAA gene or variant thereof packaged within a AAVC11.15 capsid. |

Fig. 29 (Continued)

| | | | | | |
|---|---|---|---|---|---|
| 2 | AAVC11.16 | | GAA | 2548 | Payload comprising a GAA gene or variant thereof packaged within a AAVC11.16 capsid. |
| 2 | AAVC11.17 | | GAA | 2548 | Payload comprising a GAA gene or variant thereof packaged within a AAVC11.17 capsid. |
| 2 | AAVC11.18 | | GAA | 2548 | Payload comprising a GAA gene or variant thereof packaged within a AAVC11.18 capsid |
| 2 | AAVC11.19 | | GAA | 2548 | Payload comprising a GAA gene or variant thereof packaged within a AAVC11.19 capsid. |
| 2 | AAV12 | | GAA | 2548 | Payload comprising a GAA gene or variant thereof packaged within a AAV12 capsid. |
| 2 | AAV13 | | GAA | 2548 | Payload comprising a GAA gene or variant thereof packaged within a AAV13 capsid. |
| 2 | AAV-DJ | | GAA | 2548 | Payload comprising a GAA gene or variant thereof packaged within a AAV-DJ capsid |
| 2 | AAV-LK03 | | GAA | 2548 | Payload comprising a GAA gene or variant thereof packaged within a AAV-LK03 capsid. |
| 2 | AAV-LK19 | | GAA | 2548 | Payload comprising a GAA gene or variant thereof packaged within a AAV-LK19 capsid. |
| 2 | AAVrh.74 | | GAA | 2548 | Payload comprising a GAA gene or variant thereof packaged within a AAVrh.74 capsid. |
| 2 | AAVrh.10 | | GAA | 2548 | Payload comprising a GAA gene or variant thereof packaged within a AAVrh.10 capsid. |
| 2 | AAVhu.37 | | GAA | 2548 | Payload comprising a GAA gene or variant thereof packaged within a AAVhu.37 capsid. |
| 2 | AAVrh.K | | GAA | 2548 | Payload comprising a GAA gene or variant thereof packaged within a AAVrh.K capsid. |
| 2 | AAVrh.39 | | GAA | 2548 | Payload comprising a GAA gene or variant thereof packaged within a AAVrh.39 capsid. |
| 2 | AAVrh.9 | | GAA | 2548 | Payload comprising a GAA gene or variant thereof packaged within a AAVrh.9 capsid. |
| 2 | avian AAV | | GAA | 2548 | Payload comprising a GAA gene or variant thereof packaged within a avian capsid. |

Fig. 29 (Continued)

| | | | | | |
|---|---|---|---|---|---|
| 2 | bovine AAV | | GAA | 2548 | Payload comprising a GAA gene or variant thereof packaged within a bovine capsid. |
| 2 | canine AAV | | GAA | 2548 | Payload comprising a GAA gene or variant thereof packaged within a canine capsid. |
| 2 | equine AAV | | GAA | 2548 | Payload comprising a GAA gene or variant thereof packaged within a equine capsid. |
| 2 | primate AAV | | GAA | 2548 | Payload comprising a GAA gene or variant thereof packaged within a primate capsid. |
| 2 | non-primate AAV | | GAA | 2548 | Payload comprising a GAA gene or variant thereof packaged within a non-primate capsid. |
| 2 | ovine AAV | | GAA | 2548 | Payload comprising a GAA gene or variant thereof packaged within a ovine capsid. |
| 2 | hybrid AAV | | GAA | 2548 | Payload comprising a GAA gene or variant thereof packaged within a hybrid capsid. |
| 2 | chimeric AAV | | GAA | 2548 | Payload comprising a GAA gene or variant thereof packaged within a chimeric capsid. |
| 1 | AAV1 | 1450374 | GALNS | 2588 | Payload comprising a GALNS gene or variant thereof packaged within a AAV1 capsid. |
| 1 | AAV2 | | GALNS | 2588 | Payload comprising a GALNS gene or variant thereof packaged within a AAV2 capsid. |
| 1 | AAV3 | | GALNS | 2588 | Payload comprising a GALNS gene or variant thereof packaged within a AAV3 capsid. |
| 1 | AAV4 | 1446389 | GALNS | 2588 | Payload comprising a GALNS gene or variant thereof packaged within a AAV4 capsid. |
| 1 | AAV5 | | GALNS | 2588 | Payload comprising a GALNS gene or variant thereof packaged within a AAV5 capsid. |
| 1 | AAV6 | | GALNS | 2588 | Payload comprising a GALNS gene or variant thereof packaged within a AAV6 capsid. |
| 1 | AAV7 | | GALNS | 2588 | Payload comprising a GALNS gene or variant thereof packaged within a AAV7 capsid. |
| 1 | AAV8 | 5075992 | GALNS | 2588 | Payload comprising a GALNS gene or variant thereof packaged within a AAV8 capsid. |
| 1 | AAV9 | | GALNS | 2588 | Payload comprising a GALNS gene or variant thereof packaged within a AAV9 capsid. |

Fig. 29 (Continued)

| | | | | | |
|---|---|---|---|---|---|
| 1 | AAV10 | | GALNS | 2588 | Payload comprising a GALNS gene or variant thereof packaged within a AAV10 capsid. |
| 1 | AAV11 | | GALNS | 2588 | Payload comprising a GALNS gene or variant thereof packaged within a AAV11 capsid. |
| 1 | AAVC11.01 | | GALNS | 2588 | Payload comprising a GALNS gene or variant thereof packaged within a AAVC11.01 capsid. |
| 1 | AAVC11.02 | | GALNS | 2588 | Payload comprising a GALNS gene or variant thereof packaged within a AAVC11.02 capsid. |
| 1 | AAVC11.03 | | GALNS | 2588 | Payload comprising a GALNS gene or variant thereof packaged within a AAVC11.03 capsid. |
| 1 | AAVC11.04 | | GALNS | 2588 | Payload comprising a GALNS gene or variant thereof packaged within a AAVC11.04 capsid. |
| 1 | AAVC11.05 | | GALNS | 2588 | Payload comprising a GALNS gene or variant thereof packaged within a AAVC11.05 capsid. |
| 1 | AAVC11.06 | | GALNS | 2588 | Payload comprising a GALNS gene or variant thereof packaged within a AAVC11.06 capsid. |
| 1 | AAVC11.07 | | GALNS | 2588 | Payload comprising a GALNS gene or variant thereof packaged within a AAVC11.07 capsid |
| 1 | AAVC11.08 | | GALNS | 2588 | Payload comprising a GALNS gene or variant thereof packaged within a AAVC11.08 capsid. |
| 1 | AAVC11.09 | | GALNS | 2588 | Payload comprising a GALNS gene or variant thereof packaged within a AAVC11.09 capsid. |
| 1 | AAVC11.10 | | GALNS | 2588 | Payload comprising a GALNS gene or variant thereof packaged within a AAVC11.10 capsid. |
| 1 | AAVC11.11 | | GALNS | 2588 | Payload comprising a GALNS gene or variant thereof packaged within a AAVC11.11 capsid. |
| 1 | AAVC11.12 | | GALNS | 2588 | Payload comprising a GALNS gene or variant thereof packaged within a AAVC11.12 capsid. |
| 1 | AAVC11.13 | | GALNS | 2588 | Payload comprising a GALNS gene or variant thereof packaged within a AAVC11.13 capsid. |
| 1 | AAVC11.14 | | GALNS | 2588 | Payload comprising a GALNS gene or variant thereof packaged within a AAVC11.14 capsid. |
| 1 | AAVC11.15 | | GALNS | 2588 | Payload comprising a GALNS gene or variant thereof packaged within a AAVC11.15 capsid. |

Fig. 29 (Continued)

| | | | | | |
|---|---|---|---|---|---|
| 1 | AAVC11.16 | | GALNS | 2588 | Payload comprising a GALNS gene or variant thereof packaged within a AAVC11.16 capsid. |
| 1 | AAVC11.17 | | GALNS | 2588 | Payload comprising a GALNS gene or variant thereof packaged within a AAVC11.17 capsid. |
| 1 | AAVC11.18 | | GALNS | 2588 | Payload comprising a GALNS gene or variant thereof packaged within a AAVC11.18 capsid |
| 1 | AAVC11.19 | | GALNS | 2588 | Payload comprising a GALNS gene or variant thereof packaged within a AAVC11.19 capsid. |
| 1 | AAV12 | | GALNS | 2588 | Payload comprising a GALNS gene or variant thereof packaged within a AAV12 capsid. |
| 1 | AAV13 | | GALNS | 2588 | Payload comprising a GALNS gene or variant thereof packaged within a AAV13 capsid. |
| 1 | AAV-DJ | | GALNS | 2588 | Payload comprising a GALNS gene or variant thereof packaged within a AAV-DJ capsid |
| 1 | AAV-LK03 | | GALNS | 2588 | Payload comprising a GALNS gene or variant thereof packaged within a AAV-LK03 capsid. |
| 1 | AAV-LK19 | | GALNS | 2588 | Payload comprising a GALNS gene or variant thereof packaged within a AAV-LK19 capsid. |
| 1 | AAVrh.74 | | GALNS | 2588 | Payload comprising a GALNS gene or variant thereof packaged within a AAVrh.74 capsid. |
| 1 | AAVrh.10 | | GALNS | 2588 | Payload comprising a GALNS gene or variant thereof packaged within a AAVrh.10 capsid. |
| 1 | AAVhu.37 | | GALNS | 2588 | Payload comprising a GALNS gene or variant thereof packaged within a AAVhu.37 capsid. |
| 1 | AAVrh.K | | GALNS | 2588 | Payload comprising a GALNS gene or variant thereof packaged within a AAVrh.K capsid. |
| 1 | AAVrh.39 | | GALNS | 2588 | Payload comprising a GALNS gene or variant thereof packaged within a AAVrh.39 capsid. |
| 1 | AAVrh.9 | | GALNS | 2588 | Payload comprising a GALNS gene or variant thereof packaged within a AAVrh.9 capsid. |
| 1 | avian AAV | | GALNS | 2588 | Payload comprising a GALNS gene or variant thereof packaged within a avian capsid. |

Fig. 29 (Continued)

| | | | | | |
|---|---|---|---|---|---|
| 1 | bovine AAV | | GALNS | 2588 | Payload comprising a GALNS gene or variant thereof packaged within a bovine capsid. |
| 1 | canine AAV | | GALNS | 2588 | Payload comprising a GALNS gene or variant thereof packaged within a canine capsid. |
| 1 | equine AAV | | GALNS | 2588 | Payload comprising a GALNS gene or variant thereof packaged within a equine capsid. |
| 1 | primate AAV | | GALNS | 2588 | Payload comprising a GALNS gene or variant thereof packaged within a primate capsid. |
| 1 | non-primate AAV | | GALNS | 2588 | Payload comprising a GALNS gene or variant thereof packaged within a non-primate capsid. |
| 1 | ovine AAV | | GALNS | 2588 | Payload comprising a GALNS gene or variant thereof packaged within a ovine capsid. |
| 1 | hybrid AAV | | GALNS | 2588 | Payload comprising a GALNS gene or variant thereof packaged within a hybrid capsid. |
| 1 | chimeric AAV | | GALNS | 2588 | Payload comprising a GALNS gene or variant thereof packaged within a chimeric capsid. |
| 2 | AAV1 | 1450374 | GALNS | 2588 | Payload comprising a GALNS gene or variant thereof packaged within a AAV1 capsid. |
| 2 | AAV2 | | GALNS | 2588 | Payload comprising a GALNS gene or variant thereof packaged within a AAV2 capsid. |
| 2 | AAV3 | | GALNS | 2588 | Payload comprising a GALNS gene or variant thereof packaged within a AAV3 capsid. |
| 2 | AAV4 | 1446389 | GALNS | 2588 | Payload comprising a GALNS gene or variant thereof packaged within a AAV4 capsid. |
| 2 | AAV5 | | GALNS | 2588 | Payload comprising a GALNS gene or variant thereof packaged within a AAV5 capsid. |
| 2 | AAV6 | | GALNS | 2588 | Payload comprising a GALNS gene or variant thereof packaged within a AAV6 capsid. |
| 2 | AAV7 | | GALNS | 2588 | Payload comprising a GALNS gene or variant thereof packaged within a AAV7 capsid. |
| 2 | AAV8 | 5075992 | GALNS | 2588 | Payload comprising a GALNS gene or variant thereof packaged within a AAV8 capsid. |
| 2 | AAV9 | | GALNS | 2588 | Payload comprising a GALNS gene or variant thereof packaged within a AAV9 capsid. |

Fig. 29 (Continued)

| | | | | | |
|---|---|---|---|---|---|
| 2 | AAV10 | | GALNS | 2588 | Payload comprising a GALNS gene or variant thereof packaged within a AAV10 capsid. |
| 2 | AAV11 | | GALNS | 2588 | Payload comprising a GALNS gene or variant thereof packaged within a AAV11 capsid. |
| 2 | AAVC11.01 | | GALNS | 2588 | Payload comprising a GALNS gene or variant thereof packaged within a AAVC11.01 capsid. |
| 2 | AAVC11.02 | | GALNS | 2588 | Payload comprising a GALNS gene or variant thereof packaged within a AAVC11.02 capsid. |
| 2 | AAVC11.03 | | GALNS | 2588 | Payload comprising a GALNS gene or variant thereof packaged within a AAVC11.03 capsid. |
| 2 | AAVC11.04 | | GALNS | 2588 | Payload comprising a GALNS gene or variant thereof packaged within a AAVC11.04 capsid. |
| 2 | AAVC11.05 | | GALNS | 2588 | Payload comprising a GALNS gene or variant thereof packaged within a AAVC11.05 capsid. |
| 2 | AAVC11.06 | | GALNS | 2588 | Payload comprising a GALNS gene or variant thereof packaged within a AAVC11.06 capsid. |
| 2 | AAVC11.07 | | GALNS | 2588 | Payload comprising a GALNS gene or variant thereof packaged within a AAVC11.07 capsid |
| 2 | AAVC11.08 | | GALNS | 2588 | Payload comprising a GALNS gene or variant thereof packaged within a AAVC11.08 capsid. |
| 2 | AAVC11.09 | | GALNS | 2588 | Payload comprising a GALNS gene or variant thereof packaged within a AAVC11.09 capsid. |
| 2 | AAVC11.10 | | GALNS | 2588 | Payload comprising a GALNS gene or variant thereof packaged within a AAVC11.10 capsid. |
| 2 | AAVC11.11 | | GALNS | 2588 | Payload comprising a GALNS gene or variant thereof packaged within a AAVC11.11 capsid. |
| 2 | AAVC11.12 | | GALNS | 2588 | Payload comprising a GALNS gene or variant thereof packaged within a AAVC11.12 capsid. |
| 2 | AAVC11.13 | | GALNS | 2588 | Payload comprising a GALNS gene or variant thereof packaged within a AAVC11.13 capsid. |
| 2 | AAVC11.14 | | GALNS | 2588 | Payload comprising a GALNS gene or variant thereof packaged within a AAVC11.14 capsid. |
| 2 | AAVC11.15 | | GALNS | 2588 | Payload comprising a GALNS gene or variant thereof packaged within a AAVC11.15 capsid. |

Fig. 29 (Continued)

| | | | | | |
|---|---|---|---|---|---|
| 2 | AAVC11.16 | | GALNS | 2588 | Payload comprising a GALNS gene or variant thereof packaged within a AAVC11.16 capsid. |
| 2 | AAVC11.17 | | GALNS | 2588 | Payload comprising a GALNS gene or variant thereof packaged within a AAVC11.17 capsid. |
| 2 | AAVC11.18 | | GALNS | 2588 | Payload comprising a GALNS gene or variant thereof packaged within a AAVC11.18 capsid |
| 2 | AAVC11.19 | | GALNS | 2588 | Payload comprising a GALNS gene or variant thereof packaged within a AAVC11.19 capsid. |
| 2 | AAV12 | | GALNS | 2588 | Payload comprising a GALNS gene or variant thereof packaged within a AAV12 capsid. |
| 2 | AAV13 | | GALNS | 2588 | Payload comprising a GALNS gene or variant thereof packaged within a AAV13 capsid. |
| 2 | AAV-DJ | | GALNS | 2588 | Payload comprising a GALNS gene or variant thereof packaged within a AAV-DJ capsid |
| 2 | AAV-LK03 | | GALNS | 2588 | Payload comprising a GALNS gene or variant thereof packaged within a AAV-LK03 capsid. |
| 2 | AAV-LK19 | | GALNS | 2588 | Payload comprising a GALNS gene or variant thereof packaged within a AAV-LK19 capsid. |
| 2 | AAVrh.74 | | GALNS | 2588 | Payload comprising a GALNS gene or variant thereof packaged within a AAVrh.74 capsid. |
| 2 | AAVrh.10 | | GALNS | 2588 | Payload comprising a GALNS gene or variant thereof packaged within a AAVrh.10 capsid. |
| 2 | AAVhu.37 | | GALNS | 2588 | Payload comprising a GALNS gene or variant thereof packaged within a AAVhu.37 capsid. |
| 2 | AAVrh.K | | GALNS | 2588 | Payload comprising a GALNS gene or variant thereof packaged within a AAVrh.K capsid. |
| 2 | AAVrh.39 | | GALNS | 2588 | Payload comprising a GALNS gene or variant thereof packaged within a AAVrh.39 capsid. |
| 2 | AAVrh.9 | | GALNS | 2588 | Payload comprising a GALNS gene or variant thereof packaged within a AAVrh.9 capsid. |
| 2 | avian AAV | | GALNS | 2588 | Payload comprising a GALNS gene or variant thereof packaged within a avian capsid. |

Fig. 29 (Continued)

| | | | | | |
|---|---|---|---|---|---|
| 2 | bovine AAV | | GALNS | 2588 | Payload comprising a GALNS gene or variant thereof packaged within a bovine capsid. |
| 2 | canine AAV | | GALNS | 2588 | Payload comprising a GALNS gene or variant thereof packaged within a canine capsid. |
| 2 | equine AAV | | GALNS | 2588 | Payload comprising a GALNS gene or variant thereof packaged within a equine capsid. |
| 2 | primate AAV | | GALNS | 2588 | Payload comprising a GALNS gene or variant thereof packaged within a primate capsid. |
| 2 | non-primate AAV | | GALNS | 2588 | Payload comprising a GALNS gene or variant thereof packaged within a non-primate capsid. |
| 2 | ovine AAV | | GALNS | 2588 | Payload comprising a GALNS gene or variant thereof packaged within a ovine capsid. |
| 2 | hybrid AAV | | GALNS | 2588 | Payload comprising a GALNS gene or variant thereof packaged within a hybrid capsid. |
| 2 | chimeric AAV | | GALNS | 2588 | Payload comprising a GALNS gene or variant thereof packaged within a chimeric capsid. |
| 1 | AAV1 | 1450374 | GLB1 | 2720 | Payload comprising a GLB1 gene or variant thereof packaged within a AAV1 capsid. |
| 1 | AAV2 | | GLB1 | 2720 | Payload comprising a GLB1 gene or variant thereof packaged within a AAV2 capsid. |
| 1 | AAV3 | | GLB1 | 2720 | Payload comprising a GLB1 gene or variant thereof packaged within a AAV3 capsid. |
| 1 | AAV4 | 1446389 | GLB1 | 2720 | Payload comprising a GLB1 gene or variant thereof packaged within a AAV4 capsid. |
| 1 | AAV5 | | GLB1 | 2720 | Payload comprising a GLB1 gene or variant thereof packaged within a AAV5 capsid. |
| 1 | AAV6 | | GLB1 | 2720 | Payload comprising a GLB1 gene or variant thereof packaged within a AAV6 capsid. |
| 1 | AAV7 | | GLB1 | 2720 | Payload comprising a GLB1 gene or variant thereof packaged within a AAV7 capsid. |
| 1 | AAV8 | 5075992 | GLB1 | 2720 | Payload comprising a GLB1 gene or variant thereof packaged within a AAV8 capsid. |
| 1 | AAV9 | | GLB1 | 2720 | Payload comprising a GLB1 gene or variant thereof packaged within a AAV9 capsid. |

Fig. 29 (Continued)

| | | | | | |
|---|---|---|---|---|---|
| 1 | AAV10 | | GLB1 | 2720 | Payload comprising a GLB1 gene or variant thereof packaged within a AAV10 capsid. |
| 1 | AAV11 | | GLB1 | 2720 | Payload comprising a GLB1 gene or variant thereof packaged within a AAV11 capsid. |
| 1 | AAVC11.01 | | GLB1 | 2720 | Payload comprising a GLB1 gene or variant thereof packaged within a AAVC11.01 capsid. |
| 1 | AAVC11.02 | | GLB1 | 2720 | Payload comprising a GLB1 gene or variant thereof packaged within a AAVC11.02 capsid. |
| 1 | AAVC11.03 | | GLB1 | 2720 | Payload comprising a GLB1 gene or variant thereof packaged within a AAVC11.03 capsid. |
| 1 | AAVC11.04 | | GLB1 | 2720 | Payload comprising a GLB1 gene or variant thereof packaged within a AAVC11.04 capsid. |
| 1 | AAVC11.05 | | GLB1 | 2720 | Payload comprising a GLB1 gene or variant thereof packaged within a AAVC11.05 capsid. |
| 1 | AAVC11.06 | | GLB1 | 2720 | Payload comprising a GLB1 gene or variant thereof packaged within a AAVC11.06 capsid. |
| 1 | AAVC11.07 | | GLB1 | 2720 | Payload comprising a GLB1 gene or variant thereof packaged within a AAVC11.07 capsid |
| 1 | AAVC11.08 | | GLB1 | 2720 | Payload comprising a GLB1 gene or variant thereof packaged within a AAVC11.08 capsid. |
| 1 | AAVC11.09 | | GLB1 | 2720 | Payload comprising a GLB1 gene or variant thereof packaged within a AAVC11.09 capsid. |
| 1 | AAVC11.10 | | GLB1 | 2720 | Payload comprising a GLB1 gene or variant thereof packaged within a AAVC11.10 capsid. |
| 1 | AAVC11.11 | | GLB1 | 2720 | Payload comprising a GLB1 gene or variant thereof packaged within a AAVC11.11 capsid. |
| 1 | AAVC11.12 | | GLB1 | 2720 | Payload comprising a GLB1 gene or variant thereof packaged within a AAVC11.12 capsid. |
| 1 | AAVC11.13 | | GLB1 | 2720 | Payload comprising a GLB1 gene or variant thereof packaged within a AAVC11.13 capsid. |
| 1 | AAVC11.14 | | GLB1 | 2720 | Payload comprising a GLB1 gene or variant thereof packaged within a AAVC11.14 capsid. |
| 1 | AAVC11.15 | | GLB1 | 2720 | Payload comprising a GLB1 gene or variant thereof packaged within a AAVC11.15 capsid. |

Fig. 29 (Continued)

| | | | | | |
|---|---|---|---|---|---|
| 1 | AAVC11.16 | | GLB1 | 2720 | Payload comprising a GLB1 gene or variant thereof packaged within a AAVC11.16 capsid. |
| 1 | AAVC11.17 | | GLB1 | 2720 | Payload comprising a GLB1 gene or variant thereof packaged within a AAVC11.17 capsid. |
| 1 | AAVC11.18 | | GLB1 | 2720 | Payload comprising a GLB1 gene or variant thereof packaged within a AAVC11.18 capsid |
| 1 | AAVC11.19 | | GLB1 | 2720 | Payload comprising a GLB1 gene or variant thereof packaged within a AAVC11.19 capsid. |
| 1 | AAV12 | | GLB1 | 2720 | Payload comprising a GLB1 gene or variant thereof packaged within a AAV12 capsid. |
| 1 | AAV13 | | GLB1 | 2720 | Payload comprising a GLB1 gene or variant thereof packaged within a AAV13 capsid. |
| 1 | AAV-DJ | | GLB1 | 2720 | Payload comprising a GLB1 gene or variant thereof packaged within a AAV-DJ capsid |
| 1 | AAV-LK03 | | GLB1 | 2720 | Payload comprising a GLB1 gene or variant thereof packaged within a AAV-LK03 capsid. |
| 1 | AAV-LK19 | | GLB1 | 2720 | Payload comprising a GLB1 gene or variant thereof packaged within a AAV-LK19 capsid. |
| 1 | AAVrh.74 | | GLB1 | 2720 | Payload comprising a GLB1 gene or variant thereof packaged within a AAVrh.74 capsid. |
| 1 | AAVrh.10 | | GLB1 | 2720 | Payload comprising a GLB1 gene or variant thereof packaged within a AAVrh.10 capsid. |
| 1 | AAVhu.37 | | GLB1 | 2720 | Payload comprising a GLB1 gene or variant thereof packaged within a AAVhu.37 capsid. |
| 1 | AAVrh.K | | GLB1 | 2720 | Payload comprising a GLB1 gene or variant thereof packaged within a AAVrh.K capsid. |
| 1 | AAVrh.39 | | GLB1 | 2720 | Payload comprising a GLB1 gene or variant thereof packaged within a AAVrh.39 capsid. |
| 1 | AAVrh.9 | | GLB1 | 2720 | Payload comprising a GLB1 gene or variant thereof packaged within a AAVrh.9 capsid. |
| 1 | avian AAV | | GLB1 | 2720 | Payload comprising a GLB1 gene or variant thereof packaged within a avian capsid. |

Fig. 29 (Continued)

| | | | | | |
|---|---|---|---|---|---|
| 1 | bovine AAV | | GLB1 | 2720 | Payload comprising a GLB1 gene or variant thereof packaged within a bovine capsid. |
| 1 | canine AAV | | GLB1 | 2720 | Payload comprising a GLB1 gene or variant thereof packaged within a canine capsid. |
| 1 | equine AAV | | GLB1 | 2720 | Payload comprising a GLB1 gene or variant thereof packaged within a equine capsid. |
| 1 | primate AAV | | GLB1 | 2720 | Payload comprising a GLB1 gene or variant thereof packaged within a primate capsid. |
| 1 | non-primate AAV | | GLB1 | 2720 | Payload comprising a GLB1 gene or variant thereof packaged within a non-primate capsid. |
| 1 | ovine AAV | | GLB1 | 2720 | Payload comprising a GLB1 gene or variant thereof packaged within a ovine capsid. |
| 1 | hybrid AAV | | GLB1 | 2720 | Payload comprising a GLB1 gene or variant thereof packaged within a hybrid capsid. |
| 1 | chimeric AAV | | GLB1 | 2720 | Payload comprising a GLB1 gene or variant thereof packaged within a chimeric capsid. |
| 2 | AAV1 | 1450374 | GLB1 | 2720 | Payload comprising a GLB1 gene or variant thereof packaged within a AAV1 capsid. |
| 2 | AAV2 | | GLB1 | 2720 | Payload comprising a GLB1 gene or variant thereof packaged within a AAV2 capsid. |
| 2 | AAV3 | | GLB1 | 2720 | Payload comprising a GLB1 gene or variant thereof packaged within a AAV3 capsid. |
| 2 | AAV4 | 1446389 | GLB1 | 2720 | Payload comprising a GLB1 gene or variant thereof packaged within a AAV4 capsid. |
| 2 | AAV5 | | GLB1 | 2720 | Payload comprising a GLB1 gene or variant thereof packaged within a AAV5 capsid. |
| 2 | AAV6 | | GLB1 | 2720 | Payload comprising a GLB1 gene or variant thereof packaged within a AAV6 capsid. |
| 2 | AAV7 | | GLB1 | 2720 | Payload comprising a GLB1 gene or variant thereof packaged within a AAV7 capsid. |
| 2 | AAV8 | 5075992 | GLB1 | 2720 | Payload comprising a GLB1 gene or variant thereof packaged within a AAV8 capsid. |
| 2 | AAV9 | | GLB1 | 2720 | Payload comprising a GLB1 gene or variant thereof packaged within a AAV9 capsid. |

Fig. 29 (Continued)

| | | | | | |
|---|---|---|---|---|---|
| 2 | AAV10 | | GLB1 | 2720 | Payload comprising a GLB1 gene or variant thereof packaged within a AAV10 capsid. |
| 2 | AAV11 | | GLB1 | 2720 | Payload comprising a GLB1 gene or variant thereof packaged within a AAV11 capsid. |
| 2 | AAVC11.01 | | GLB1 | 2720 | Payload comprising a GLB1 gene or variant thereof packaged within a AAVC11.01 capsid. |
| 2 | AAVC11.02 | | GLB1 | 2720 | Payload comprising a GLB1 gene or variant thereof packaged within a AAVC11.02 capsid. |
| 2 | AAVC11.03 | | GLB1 | 2720 | Payload comprising a GLB1 gene or variant thereof packaged within a AAVC11.03 capsid. |
| 2 | AAVC11.04 | | GLB1 | 2720 | Payload comprising a GLB1 gene or variant thereof packaged within a AAVC11.04 capsid. |
| 2 | AAVC11.05 | | GLB1 | 2720 | Payload comprising a GLB1 gene or variant thereof packaged within a AAVC11.05 capsid. |
| 2 | AAVC11.06 | | GLB1 | 2720 | Payload comprising a GLB1 gene or variant thereof packaged within a AAVC11.06 capsid. |
| 2 | AAVC11.07 | | GLB1 | 2720 | Payload comprising a GLB1 gene or variant thereof packaged within a AAVC11.07 capsid |
| 2 | AAVC11.08 | | GLB1 | 2720 | Payload comprising a GLB1 gene or variant thereof packaged within a AAVC11.08 capsid. |
| 2 | AAVC11.09 | | GLB1 | 2720 | Payload comprising a GLB1 gene or variant thereof packaged within a AAVC11.09 capsid. |
| 2 | AAVC11.10 | | GLB1 | 2720 | Payload comprising a GLB1 gene or variant thereof packaged within a AAVC11.10 capsid. |
| 2 | AAVC11.11 | | GLB1 | 2720 | Payload comprising a GLB1 gene or variant thereof packaged within a AAVC11.11 capsid. |
| 2 | AAVC11.12 | | GLB1 | 2720 | Payload comprising a GLB1 gene or variant thereof packaged within a AAVC11.12 capsid. |
| 2 | AAVC11.13 | | GLB1 | 2720 | Payload comprising a GLB1 gene or variant thereof packaged within a AAVC11.13 capsid. |
| 2 | AAVC11.14 | | GLB1 | 2720 | Payload comprising a GLB1 gene or variant thereof packaged within a AAVC11.14 capsid. |
| 2 | AAVC11.15 | | GLB1 | 2720 | Payload comprising a GLB1 gene or variant thereof packaged within a AAVC11.15 capsid. |

Fig. 29 (Continued)

| | | | | | |
|---|---|---|---|---|---|
| 2 | AAVC11.16 | | GLB1 | 2720 | Payload comprising a GLB1 gene or variant thereof packaged within a AAVC11.16 capsid. |
| 2 | AAVC11.17 | | GLB1 | 2720 | Payload comprising a GLB1 gene or variant thereof packaged within a AAVC11.17 capsid. |
| 2 | AAVC11.18 | | GLB1 | 2720 | Payload comprising a GLB1 gene or variant thereof packaged within a AAVC11.18 capsid |
| 2 | AAVC11.19 | | GLB1 | 2720 | Payload comprising a GLB1 gene or variant thereof packaged within a AAVC11.19 capsid. |
| 2 | AAV12 | | GLB1 | 2720 | Payload comprising a GLB1 gene or variant thereof packaged within a AAV12 capsid. |
| 2 | AAV13 | | GLB1 | 2720 | Payload comprising a GLB1 gene or variant thereof packaged within a AAV13 capsid. |
| 2 | AAV-DJ | | GLB1 | 2720 | Payload comprising a GLB1 gene or variant thereof packaged within a AAV-DJ capsid |
| 2 | AAV-LK03 | | GLB1 | 2720 | Payload comprising a GLB1 gene or variant thereof packaged within a AAV-LK03 capsid. |
| 2 | AAV-LK19 | | GLB1 | 2720 | Payload comprising a GLB1 gene or variant thereof packaged within a AAV-LK19 capsid. |
| 2 | AAVrh.74 | | GLB1 | 2720 | Payload comprising a GLB1 gene or variant thereof packaged within a AAVrh.74 capsid. |
| 2 | AAVrh.10 | | GLB1 | 2720 | Payload comprising a GLB1 gene or variant thereof packaged within a AAVrh.10 capsid. |
| 2 | AAVhu.37 | | GLB1 | 2720 | Payload comprising a GLB1 gene or variant thereof packaged within a AAVhu.37 capsid. |
| 2 | AAVrh.K | | GLB1 | 2720 | Payload comprising a GLB1 gene or variant thereof packaged within a AAVrh.K capsid. |
| 2 | AAVrh.39 | | GLB1 | 2720 | Payload comprising a GLB1 gene or variant thereof packaged within a AAVrh.39 capsid. |
| 2 | AAVrh.9 | | GLB1 | 2720 | Payload comprising a GLB1 gene or variant thereof packaged within a AAVrh.9 capsid. |
| 2 | avian AAV | | GLB1 | 2720 | Payload comprising a GLB1 gene or variant thereof packaged within a avian capsid. |

Fig. 29 (Continued)

| | | | | | |
|---|---|---|---|---|---|
| 2 | bovine AAV | | GLB1 | 2720 | Payload comprising a GLB1 gene or variant thereof packaged within a bovine capsid. |
| 2 | canine AAV | | GLB1 | 2720 | Payload comprising a GLB1 gene or variant thereof packaged within a canine capsid. |
| 2 | equine AAV | | GLB1 | 2720 | Payload comprising a GLB1 gene or variant thereof packaged within a equine capsid. |
| 2 | primate AAV | | GLB1 | 2720 | Payload comprising a GLB1 gene or variant thereof packaged within a primate capsid. |
| 2 | non-primate AAV | | GLB1 | 2720 | Payload comprising a GLB1 gene or variant thereof packaged within a non-primate capsid. |
| 2 | ovine AAV | | GLB1 | 2720 | Payload comprising a GLB1 gene or variant thereof packaged within a ovine capsid. |
| 2 | hybrid AAV | | GLB1 | 2720 | Payload comprising a GLB1 gene or variant thereof packaged within a hybrid capsid. |
| 2 | chimeric AAV | | GLB1 | 2720 | Payload comprising a GLB1 gene or variant thereof packaged within a chimeric capsid. |
| 1 | AAV1 | 1450374 | GNS | 2799 | Payload comprising a GNS gene or variant thereof packaged within a AAV1 capsid. |
| 1 | AAV2 | | GNS | 2799 | Payload comprising a GNS gene or variant thereof packaged within a AAV2 capsid. |
| 1 | AAV3 | | GNS | 2799 | Payload comprising a GNS gene or variant thereof packaged within a AAV3 capsid. |
| 1 | AAV4 | 1446389 | GNS | 2799 | Payload comprising a GNS gene or variant thereof packaged within a AAV4 capsid. |
| 1 | AAV5 | | GNS | 2799 | Payload comprising a GNS gene or variant thereof packaged within a AAV5 capsid. |
| 1 | AAV6 | | GNS | 2799 | Payload comprising a GNS gene or variant thereof packaged within a AAV6 capsid. |
| 1 | AAV7 | | GNS | 2799 | Payload comprising a GNS gene or variant thereof packaged within a AAV7 capsid. |
| 1 | AAV8 | 5075992 | GNS | 2799 | Payload comprising a GNS gene or variant thereof packaged within a AAV8 capsid. |
| 1 | AAV9 | | GNS | 2799 | Payload comprising a GNS gene or variant thereof packaged within a AAV9 capsid. |

Fig. 29 (Continued)

| | | | | | |
|---|---|---|---|---|---|
| 1 | AAV10 | | GNS | 2799 | Payload comprising a GNS gene or variant thereof packaged within a AAV10 capsid. |
| 1 | AAV11 | | GNS | 2799 | Payload comprising a GNS gene or variant thereof packaged within a AAV11 capsid. |
| 1 | AAVC11.01 | | GNS | 2799 | Payload comprising a GNS gene or variant thereof packaged within a AAVC11.01 capsid. |
| 1 | AAVC11.02 | | GNS | 2799 | Payload comprising a GNS gene or variant thereof packaged within a AAVC11.02 capsid. |
| 1 | AAVC11.03 | | GNS | 2799 | Payload comprising a GNS gene or variant thereof packaged within a AAVC11.03 capsid. |
| 1 | AAVC11.04 | | GNS | 2799 | Payload comprising a GNS gene or variant thereof packaged within a AAVC11.04 capsid. |
| 1 | AAVC11.05 | | GNS | 2799 | Payload comprising a GNS gene or variant thereof packaged within a AAVC11.05 capsid. |
| 1 | AAVC11.06 | | GNS | 2799 | Payload comprising a GNS gene or variant thereof packaged within a AAVC11.06 capsid. |
| 1 | AAVC11.07 | | GNS | 2799 | Payload comprising a GNS gene or variant thereof packaged within a AAVC11.07 capsid |
| 1 | AAVC11.08 | | GNS | 2799 | Payload comprising a GNS gene or variant thereof packaged within a AAVC11.08 capsid. |
| 1 | AAVC11.09 | | GNS | 2799 | Payload comprising a GNS gene or variant thereof packaged within a AAVC11.09 capsid. |
| 1 | AAVC11.10 | | GNS | 2799 | Payload comprising a GNS gene or variant thereof packaged within a AAVC11.10 capsid. |
| 1 | AAVC11.11 | | GNS | 2799 | Payload comprising a GNS gene or variant thereof packaged within a AAVC11.11 capsid. |
| 1 | AAVC11.12 | | GNS | 2799 | Payload comprising a GNS gene or variant thereof packaged within a AAVC11.12 capsid. |
| 1 | AAVC11.13 | | GNS | 2799 | Payload comprising a GNS gene or variant thereof packaged within a AAVC11.13 capsid. |
| 1 | AAVC11.14 | | GNS | 2799 | Payload comprising a GNS gene or variant thereof packaged within a AAVC11.14 capsid. |
| 1 | AAVC11.15 | | GNS | 2799 | Payload comprising a GNS gene or variant thereof packaged within a AAVC11.15 capsid. |

Fig. 29 (Continued)

| | | | | | |
|---|---|---|---|---|---|
| 1 | AAVC11.16 | | GNS | 2799 | Payload comprising a GNS gene or variant thereof packaged within a AAVC11.16 capsid. |
| 1 | AAVC11.17 | | GNS | 2799 | Payload comprising a GNS gene or variant thereof packaged within a AAVC11.17 capsid. |
| 1 | AAVC11.18 | | GNS | 2799 | Payload comprising a GNS gene or variant thereof packaged within a AAVC11.18 capsid |
| 1 | AAVC11.19 | | GNS | 2799 | Payload comprising a GNS gene or variant thereof packaged within a AAVC11.19 capsid. |
| 1 | AAV12 | | GNS | 2799 | Payload comprising a GNS gene or variant thereof packaged within a AAV12 capsid. |
| 1 | AAV13 | | GNS | 2799 | Payload comprising a GNS gene or variant thereof packaged within a AAV13 capsid. |
| 1 | AAV-DJ | | GNS | 2799 | Payload comprising a GNS gene or variant thereof packaged within a AAV-DJ capsid |
| 1 | AAV-LK03 | | GNS | 2799 | Payload comprising a GNS gene or variant thereof packaged within a AAV-LK03 capsid. |
| 1 | AAV-LK19 | | GNS | 2799 | Payload comprising a GNS gene or variant thereof packaged within a AAV-LK19 capsid. |
| 1 | AAVrh.74 | | GNS | 2799 | Payload comprising a GNS gene or variant thereof packaged within a AAVrh.74 capsid. |
| 1 | AAVrh.10 | | GNS | 2799 | Payload comprising a GNS gene or variant thereof packaged within a AAVrh.10 capsid. |
| 1 | AAVhu.37 | | GNS | 2799 | Payload comprising a GNS gene or variant thereof packaged within a AAVhu.37 capsid. |
| 1 | AAVrh.K | | GNS | 2799 | Payload comprising a GNS gene or variant thereof packaged within a AAVrh.K capsid. |
| 1 | AAVrh.39 | | GNS | 2799 | Payload comprising a GNS gene or variant thereof packaged within a AAVrh.39 capsid. |
| 1 | AAVrh.9 | | GNS | 2799 | Payload comprising a GNS gene or variant thereof packaged within a AAVrh.9 capsid. |
| 1 | avian AAV | | GNS | 2799 | Payload comprising a GNS gene or variant thereof packaged within a avian capsid. |

Fig. 29 (Continued)

| | | | | | |
|---|---|---|---|---|---|
| 1 | bovine AAV | | GNS | 2799 | Payload comprising a GNS gene or variant thereof packaged within a bovine capsid. |
| 1 | canine AAV | | GNS | 2799 | Payload comprising a GNS gene or variant thereof packaged within a canine capsid. |
| 1 | equine AAV | | GNS | 2799 | Payload comprising a GNS gene or variant thereof packaged within a equine capsid. |
| 1 | primate AAV | | GNS | 2799 | Payload comprising a GNS gene or variant thereof packaged within a primate capsid. |
| 1 | non-primate AAV | | GNS | 2799 | Payload comprising a GNS gene or variant thereof packaged within a non-primate capsid. |
| 1 | ovine AAV | | GNS | 2799 | Payload comprising a GNS gene or variant thereof packaged within a ovine capsid. |
| 1 | hybrid AAV | | GNS | 2799 | Payload comprising a GNS gene or variant thereof packaged within a hybrid capsid. |
| 1 | chimeric AAV | | GNS | 2799 | Payload comprising a GNS gene or variant thereof packaged within a chimeric capsid. |
| 2 | AAV1 | 1450374 | GNS | 2799 | Payload comprising a GNS gene or variant thereof packaged within a AAV1 capsid. |
| 2 | AAV2 | | GNS | 2799 | Payload comprising a GNS gene or variant thereof packaged within a AAV2 capsid. |
| 2 | AAV3 | | GNS | 2799 | Payload comprising a GNS gene or variant thereof packaged within a AAV3 capsid. |
| 2 | AAV4 | 1446389 | GNS | 2799 | Payload comprising a GNS gene or variant thereof packaged within a AAV4 capsid. |
| 2 | AAV5 | | GNS | 2799 | Payload comprising a GNS gene or variant thereof packaged within a AAV5 capsid. |
| 2 | AAV6 | | GNS | 2799 | Payload comprising a GNS gene or variant thereof packaged within a AAV6 capsid. |
| 2 | AAV7 | | GNS | 2799 | Payload comprising a GNS gene or variant thereof packaged within a AAV7 capsid. |
| 2 | AAV8 | 5075992 | GNS | 2799 | Payload comprising a GNS gene or variant thereof packaged within a AAV8 capsid. |
| 2 | AAV9 | | GNS | 2799 | Payload comprising a GNS gene or variant thereof packaged within a AAV9 capsid. |

Fig. 29 (Continued)

| | | | | | |
|---|---|---|---|---|---|
| 2 | AAV10 | | GNS | 2799 | Payload comprising a GNS gene or variant thereof packaged within a AAV10 capsid. |
| 2 | AAV11 | | GNS | 2799 | Payload comprising a GNS gene or variant thereof packaged within a AAV11 capsid. |
| 2 | AAVC11.01 | | GNS | 2799 | Payload comprising a GNS gene or variant thereof packaged within a AAVC11.01 capsid. |
| 2 | AAVC11.02 | | GNS | 2799 | Payload comprising a GNS gene or variant thereof packaged within a AAVC11.02 capsid. |
| 2 | AAVC11.03 | | GNS | 2799 | Payload comprising a GNS gene or variant thereof packaged within a AAVC11.03 capsid. |
| 2 | AAVC11.04 | | GNS | 2799 | Payload comprising a GNS gene or variant thereof packaged within a AAVC11.04 capsid. |
| 2 | AAVC11.05 | | GNS | 2799 | Payload comprising a GNS gene or variant thereof packaged within a AAVC11.05 capsid. |
| 2 | AAVC11.06 | | GNS | 2799 | Payload comprising a GNS gene or variant thereof packaged within a AAVC11.06 capsid. |
| 2 | AAVC11.07 | | GNS | 2799 | Payload comprising a GNS gene or variant thereof packaged within a AAVC11.07 capsid |
| 2 | AAVC11.08 | | GNS | 2799 | Payload comprising a GNS gene or variant thereof packaged within a AAVC11.08 capsid. |
| 2 | AAVC11.09 | | GNS | 2799 | Payload comprising a GNS gene or variant thereof packaged within a AAVC11.09 capsid. |
| 2 | AAVC11.10 | | GNS | 2799 | Payload comprising a GNS gene or variant thereof packaged within a AAVC11.10 capsid. |
| 2 | AAVC11.11 | | GNS | 2799 | Payload comprising a GNS gene or variant thereof packaged within a AAVC11.11 capsid. |
| 2 | AAVC11.12 | | GNS | 2799 | Payload comprising a GNS gene or variant thereof packaged within a AAVC11.12 capsid. |
| 2 | AAVC11.13 | | GNS | 2799 | Payload comprising a GNS gene or variant thereof packaged within a AAVC11.13 capsid. |
| 2 | AAVC11.14 | | GNS | 2799 | Payload comprising a GNS gene or variant thereof packaged within a AAVC11.14 capsid. |
| 2 | AAVC11.15 | | GNS | 2799 | Payload comprising a GNS gene or variant thereof packaged within a AAVC11.15 capsid. |

Fig. 29 (Continued)

| | | | | | |
|---|---|---|---|---|---|
| 2 | AAVC11.16 | | GNS | 2799 | Payload comprising a GNS gene or variant thereof packaged within a AAVC11.16 capsid. |
| 2 | AAVC11.17 | | GNS | 2799 | Payload comprising a GNS gene or variant thereof packaged within a AAVC11.17 capsid. |
| 2 | AAVC11.18 | | GNS | 2799 | Payload comprising a GNS gene or variant thereof packaged within a AAVC11.18 capsid |
| 2 | AAVC11.19 | | GNS | 2799 | Payload comprising a GNS gene or variant thereof packaged within a AAVC11.19 capsid. |
| 2 | AAV12 | | GNS | 2799 | Payload comprising a GNS gene or variant thereof packaged within a AAV12 capsid. |
| 2 | AAV13 | | GNS | 2799 | Payload comprising a GNS gene or variant thereof packaged within a AAV13 capsid. |
| 2 | AAV-DJ | | GNS | 2799 | Payload comprising a GNS gene or variant thereof packaged within a AAV-DJ capsid |
| 2 | AAV-LK03 | | GNS | 2799 | Payload comprising a GNS gene or variant thereof packaged within a AAV-LK03 capsid. |
| 2 | AAV-LK19 | | GNS | 2799 | Payload comprising a GNS gene or variant thereof packaged within a AAV-LK19 capsid. |
| 2 | AAVrh.74 | | GNS | 2799 | Payload comprising a GNS gene or variant thereof packaged within a AAVrh.74 capsid. |
| 2 | AAVrh.10 | | GNS | 2799 | Payload comprising a GNS gene or variant thereof packaged within a AAVrh.10 capsid. |
| 2 | AAVhu.37 | | GNS | 2799 | Payload comprising a GNS gene or variant thereof packaged within a AAVhu.37 capsid. |
| 2 | AAVrh.K | | GNS | 2799 | Payload comprising a GNS gene or variant thereof packaged within a AAVrh.K capsid. |
| 2 | AAVrh.39 | | GNS | 2799 | Payload comprising a GNS gene or variant thereof packaged within a AAVrh.39 capsid. |
| 2 | AAVrh.9 | | GNS | 2799 | Payload comprising a GNS gene or variant thereof packaged within a AAVrh.9 capsid. |
| 2 | avian AAV | | GNS | 2799 | Payload comprising a GNS gene or variant thereof packaged within a avian capsid. |

Fig. 29 (Continued)

| | | | | | |
|---|---|---|---|---|---|
| 2 | bovine AAV | | GNS | 2799 | Payload comprising a GNS gene or variant thereof packaged within a bovine capsid. |
| 2 | canine AAV | | GNS | 2799 | Payload comprising a GNS gene or variant thereof packaged within a canine capsid. |
| 2 | equine AAV | | GNS | 2799 | Payload comprising a GNS gene or variant thereof packaged within a equine capsid. |
| 2 | primate AAV | | GNS | 2799 | Payload comprising a GNS gene or variant thereof packaged within a primate capsid. |
| 2 | non-primate AAV | | GNS | 2799 | Payload comprising a GNS gene or variant thereof packaged within a non-primate capsid. |
| 2 | ovine AAV | | GNS | 2799 | Payload comprising a GNS gene or variant thereof packaged within a ovine capsid. |
| 2 | hybrid AAV | | GNS | 2799 | Payload comprising a GNS gene or variant thereof packaged within a hybrid capsid. |
| 2 | chimeric AAV | | GNS | 2799 | Payload comprising a GNS gene or variant thereof packaged within a chimeric capsid. |
| 1 | AAV1 | 1450374 | GUSB | 2990 | Payload comprising a GUSB gene or variant thereof packaged within a AAV1 capsid. |
| 1 | AAV2 | | GUSB | 2990 | Payload comprising a GUSB gene or variant thereof packaged within a AAV2 capsid. |
| 1 | AAV3 | | GUSB | 2990 | Payload comprising a GUSB gene or variant thereof packaged within a AAV3 capsid. |
| 1 | AAV4 | 1446389 | GUSB | 2990 | Payload comprising a GUSB gene or variant thereof packaged within a AAV4 capsid. |
| 1 | AAV5 | | GUSB | 2990 | Payload comprising a GUSB gene or variant thereof packaged within a AAV5 capsid. |
| 1 | AAV6 | | GUSB | 2990 | Payload comprising a GUSB gene or variant thereof packaged within a AAV6 capsid. |
| 1 | AAV7 | | GUSB | 2990 | Payload comprising a GUSB gene or variant thereof packaged within a AAV7 capsid. |
| 1 | AAV8 | 5075992 | GUSB | 2990 | Payload comprising a GUSB gene or variant thereof packaged within a AAV8 capsid. |
| 1 | AAV9 | | GUSB | 2990 | Payload comprising a GUSB gene or variant thereof packaged within a AAV9 capsid. |

Fig. 29 (Continued)

| | | | | | |
|---|---|---|---|---|---|
| 1 | AAV10 | | GUSB | 2990 | Payload comprising a GUSB gene or variant thereof packaged within a AAV10 capsid. |
| 1 | AAV11 | | GUSB | 2990 | Payload comprising a GUSB gene or variant thereof packaged within a AAV11 capsid. |
| 1 | AAVC11.01 | | GUSB | 2990 | Payload comprising a GUSB gene or variant thereof packaged within a AAVC11.01 capsid. |
| 1 | AAVC11.02 | | GUSB | 2990 | Payload comprising a GUSB gene or variant thereof packaged within a AAVC11.02 capsid. |
| 1 | AAVC11.03 | | GUSB | 2990 | Payload comprising a GUSB gene or variant thereof packaged within a AAVC11.03 capsid. |
| 1 | AAVC11.04 | | GUSB | 2990 | Payload comprising a GUSB gene or variant thereof packaged within a AAVC11.04 capsid. |
| 1 | AAVC11.05 | | GUSB | 2990 | Payload comprising a GUSB gene or variant thereof packaged within a AAVC11.05 capsid. |
| 1 | AAVC11.06 | | GUSB | 2990 | Payload comprising a GUSB gene or variant thereof packaged within a AAVC11.06 capsid. |
| 1 | AAVC11.07 | | GUSB | 2990 | Payload comprising a GUSB gene or variant thereof packaged within a AAVC11.07 capsid |
| 1 | AAVC11.08 | | GUSB | 2990 | Payload comprising a GUSB gene or variant thereof packaged within a AAVC11.08 capsid. |
| 1 | AAVC11.09 | | GUSB | 2990 | Payload comprising a GUSB gene or variant thereof packaged within a AAVC11.09 capsid. |
| 1 | AAVC11.10 | | GUSB | 2990 | Payload comprising a GUSB gene or variant thereof packaged within a AAVC11.10 capsid. |
| 1 | AAVC11.11 | | GUSB | 2990 | Payload comprising a GUSB gene or variant thereof packaged within a AAVC11.11 capsid. |
| 1 | AAVC11.12 | | GUSB | 2990 | Payload comprising a GUSB gene or variant thereof packaged within a AAVC11.12 capsid. |
| 1 | AAVC11.13 | | GUSB | 2990 | Payload comprising a GUSB gene or variant thereof packaged within a AAVC11.13 capsid. |
| 1 | AAVC11.14 | | GUSB | 2990 | Payload comprising a GUSB gene or variant thereof packaged within a AAVC11.14 capsid. |
| 1 | AAVC11.15 | | GUSB | 2990 | Payload comprising a GUSB gene or variant thereof packaged within a AAVC11.15 capsid. |

Fig. 29 (Continued)

| | | | | | |
|---|---|---|---|---|---|
| 1 | AAVC11.16 | | GUSB | 2990 | Payload comprising a GUSB gene or variant thereof packaged within a AAVC11.16 capsid. |
| 1 | AAVC11.17 | | GUSB | 2990 | Payload comprising a GUSB gene or variant thereof packaged within a AAVC11.17 capsid. |
| 1 | AAVC11.18 | | GUSB | 2990 | Payload comprising a GUSB gene or variant thereof packaged within a AAVC11.18 capsid |
| 1 | AAVC11.19 | | GUSB | 2990 | Payload comprising a GUSB gene or variant thereof packaged within a AAVC11.19 capsid. |
| 1 | AAV12 | | GUSB | 2990 | Payload comprising a GUSB gene or variant thereof packaged within a AAV12 capsid. |
| 1 | AAV13 | | GUSB | 2990 | Payload comprising a GUSB gene or variant thereof packaged within a AAV13 capsid. |
| 1 | AAV-DJ | | GUSB | 2990 | Payload comprising a GUSB gene or variant thereof packaged within a AAV-DJ capsid |
| 1 | AAV-LK03 | | GUSB | 2990 | Payload comprising a GUSB gene or variant thereof packaged within a AAV-LK03 capsid. |
| 1 | AAV-LK19 | | GUSB | 2990 | Payload comprising a GUSB gene or variant thereof packaged within a AAV-LK19 capsid. |
| 1 | AAVrh.74 | | GUSB | 2990 | Payload comprising a GUSB gene or variant thereof packaged within a AAVrh.74 capsid. |
| 1 | AAVrh.10 | | GUSB | 2990 | Payload comprising a GUSB gene or variant thereof packaged within a AAVrh.10 capsid. |
| 1 | AAVhu.37 | | GUSB | 2990 | Payload comprising a GUSB gene or variant thereof packaged within a AAVhu.37 capsid. |
| 1 | AAVrh.K | | GUSB | 2990 | Payload comprising a GUSB gene or variant thereof packaged within a AAVrh.K capsid. |
| 1 | AAVrh.39 | | GUSB | 2990 | Payload comprising a GUSB gene or variant thereof packaged within a AAVrh.39 capsid. |
| 1 | AAVrh.9 | | GUSB | 2990 | Payload comprising a GUSB gene or variant thereof packaged within a AAVrh.9 capsid. |
| 1 | avian AAV | | GUSB | 2990 | Payload comprising a GUSB gene or variant thereof packaged within a avian capsid. |

Fig. 29 (Continued)

| | | | | | |
|---|---|---|---|---|---|
| 1 | bovine AAV | | GUSB | 2990 | Payload comprising a GUSB gene or variant thereof packaged within a bovine capsid. |
| 1 | canine AAV | | GUSB | 2990 | Payload comprising a GUSB gene or variant thereof packaged within a canine capsid. |
| 1 | equine AAV | | GUSB | 2990 | Payload comprising a GUSB gene or variant thereof packaged within a equine capsid. |
| 1 | primate AAV | | GUSB | 2990 | Payload comprising a GUSB gene or variant thereof packaged within a primate capsid. |
| 1 | non-primate AAV | | GUSB | 2990 | Payload comprising a GUSB gene or variant thereof packaged within a non-primate capsid. |
| 1 | ovine AAV | | GUSB | 2990 | Payload comprising a GUSB gene or variant thereof packaged within a ovine capsid. |
| 1 | hybrid AAV | | GUSB | 2990 | Payload comprising a GUSB gene or variant thereof packaged within a hybrid capsid. |
| 1 | chimeric AAV | | GUSB | 2990 | Payload comprising a GUSB gene or variant thereof packaged within a chimeric capsid. |
| 2 | AAV1 | 1450374 | GUSB | 2990 | Payload comprising a GUSB gene or variant thereof packaged within a AAV1 capsid. |
| 2 | AAV2 | | GUSB | 2990 | Payload comprising a GUSB gene or variant thereof packaged within a AAV2 capsid. |
| 2 | AAV3 | | GUSB | 2990 | Payload comprising a GUSB gene or variant thereof packaged within a AAV3 capsid. |
| 2 | AAV4 | 1446389 | GUSB | 2990 | Payload comprising a GUSB gene or variant thereof packaged within a AAV4 capsid. |
| 2 | AAV5 | | GUSB | 2990 | Payload comprising a GUSB gene or variant thereof packaged within a AAV5 capsid. |
| 2 | AAV6 | | GUSB | 2990 | Payload comprising a GUSB gene or variant thereof packaged within a AAV6 capsid. |
| 2 | AAV7 | | GUSB | 2990 | Payload comprising a GUSB gene or variant thereof packaged within a AAV7 capsid. |
| 2 | AAV8 | 5075992 | GUSB | 2990 | Payload comprising a GUSB gene or variant thereof packaged within a AAV8 capsid. |
| 2 | AAV9 | | GUSB | 2990 | Payload comprising a GUSB gene or variant thereof packaged within a AAV9 capsid. |

Fig. 29 (Continued)

| | | | | | |
|---|---|---|---|---|---|
| 2 | AAV10 | | GUSB | 2990 | Payload comprising a GUSB gene or variant thereof packaged within a AAV10 capsid. |
| 2 | AAV11 | | GUSB | 2990 | Payload comprising a GUSB gene or variant thereof packaged within a AAV11 capsid. |
| 2 | AAVC11.01 | | GUSB | 2990 | Payload comprising a GUSB gene or variant thereof packaged within a AAVC11.01 capsid. |
| 2 | AAVC11.02 | | GUSB | 2990 | Payload comprising a GUSB gene or variant thereof packaged within a AAVC11.02 capsid. |
| 2 | AAVC11.03 | | GUSB | 2990 | Payload comprising a GUSB gene or variant thereof packaged within a AAVC11.03 capsid. |
| 2 | AAVC11.04 | | GUSB | 2990 | Payload comprising a GUSB gene or variant thereof packaged within a AAVC11.04 capsid. |
| 2 | AAVC11.05 | | GUSB | 2990 | Payload comprising a GUSB gene or variant thereof packaged within a AAVC11.05 capsid. |
| 2 | AAVC11.06 | | GUSB | 2990 | Payload comprising a GUSB gene or variant thereof packaged within a AAVC11.06 capsid. |
| 2 | AAVC11.07 | | GUSB | 2990 | Payload comprising a GUSB gene or variant thereof packaged within a AAVC11.07 capsid |
| 2 | AAVC11.08 | | GUSB | 2990 | Payload comprising a GUSB gene or variant thereof packaged within a AAVC11.08 capsid. |
| 2 | AAVC11.09 | | GUSB | 2990 | Payload comprising a GUSB gene or variant thereof packaged within a AAVC11.09 capsid. |
| 2 | AAVC11.10 | | GUSB | 2990 | Payload comprising a GUSB gene or variant thereof packaged within a AAVC11.10 capsid. |
| 2 | AAVC11.11 | | GUSB | 2990 | Payload comprising a GUSB gene or variant thereof packaged within a AAVC11.11 capsid. |
| 2 | AAVC11.12 | | GUSB | 2990 | Payload comprising a GUSB gene or variant thereof packaged within a AAVC11.12 capsid. |
| 2 | AAVC11.13 | | GUSB | 2990 | Payload comprising a GUSB gene or variant thereof packaged within a AAVC11.13 capsid. |
| 2 | AAVC11.14 | | GUSB | 2990 | Payload comprising a GUSB gene or variant thereof packaged within a AAVC11.14 capsid. |
| 2 | AAVC11.15 | | GUSB | 2990 | Payload comprising a GUSB gene or variant thereof packaged within a AAVC11.15 capsid. |

Fig. 29 (Continued)

| | | | | | |
|---|---|---|---|---|---|
| 2 | AAVC11.16 | | GUSB | 2990 | Payload comprising a GUSB gene or variant thereof packaged within a AAVC11.16 capsid. |
| 2 | AAVC11.17 | | GUSB | 2990 | Payload comprising a GUSB gene or variant thereof packaged within a AAVC11.17 capsid. |
| 2 | AAVC11.18 | | GUSB | 2990 | Payload comprising a GUSB gene or variant thereof packaged within a AAVC11.18 capsid |
| 2 | AAVC11.19 | | GUSB | 2990 | Payload comprising a GUSB gene or variant thereof packaged within a AAVC11.19 capsid. |
| 2 | AAV12 | | GUSB | 2990 | Payload comprising a GUSB gene or variant thereof packaged within a AAV12 capsid. |
| 2 | AAV13 | | GUSB | 2990 | Payload comprising a GUSB gene or variant thereof packaged within a AAV13 capsid. |
| 2 | AAV-DJ | | GUSB | 2990 | Payload comprising a GUSB gene or variant thereof packaged within a AAV-DJ capsid |
| 2 | AAV-LK03 | | GUSB | 2990 | Payload comprising a GUSB gene or variant thereof packaged within a AAV-LK03 capsid. |
| 2 | AAV-LK19 | | GUSB | 2990 | Payload comprising a GUSB gene or variant thereof packaged within a AAV-LK19 capsid. |
| 2 | AAVrh.74 | | GUSB | 2990 | Payload comprising a GUSB gene or variant thereof packaged within a AAVrh.74 capsid. |
| 2 | AAVrh.10 | | GUSB | 2990 | Payload comprising a GUSB gene or variant thereof packaged within a AAVrh.10 capsid. |
| 2 | AAVhu.37 | | GUSB | 2990 | Payload comprising a GUSB gene or variant thereof packaged within a AAVhu.37 capsid. |
| 2 | AAVrh.K | | GUSB | 2990 | Payload comprising a GUSB gene or variant thereof packaged within a AAVrh.K capsid. |
| 2 | AAVrh.39 | | GUSB | 2990 | Payload comprising a GUSB gene or variant thereof packaged within a AAVrh.39 capsid. |
| 2 | AAVrh.9 | | GUSB | 2990 | Payload comprising a GUSB gene or variant thereof packaged within a AAVrh.9 capsid. |
| 2 | avian AAV | | GUSB | 2990 | Payload comprising a GUSB gene or variant thereof packaged within a avian capsid. |

Fig. 29 (Continued)

| | | | | | |
|---|---|---|---|---|---|
| 2 | bovine AAV | | GUSB | 2990 | Payload comprising a GUSB gene or variant thereof packaged within a bovine capsid. |
| 2 | canine AAV | | GUSB | 2990 | Payload comprising a GUSB gene or variant thereof packaged within a canine capsid. |
| 2 | equine AAV | | GUSB | 2990 | Payload comprising a GUSB gene or variant thereof packaged within a equine capsid. |
| 2 | primate AAV | | GUSB | 2990 | Payload comprising a GUSB gene or variant thereof packaged within a primate capsid. |
| 2 | non-primate AAV | | GUSB | 2990 | Payload comprising a GUSB gene or variant thereof packaged within a non-primate capsid. |
| 2 | ovine AAV | | GUSB | 2990 | Payload comprising a GUSB gene or variant thereof packaged within a ovine capsid. |
| 2 | hybrid AAV | | GUSB | 2990 | Payload comprising a GUSB gene or variant thereof packaged within a hybrid capsid. |
| 2 | chimeric AAV | | GUSB | 2990 | Payload comprising a GUSB gene or variant thereof packaged within a chimeric capsid. |
| 1 | AAV1 | 1450374 | HADHA | 3030 | Payload comprising a HADHA gene or variant thereof packaged within a AAV1 capsid. |
| 1 | AAV2 | | HADHA | 3030 | Payload comprising a HADHA gene or variant thereof packaged within a AAV2 capsid. |
| 1 | AAV3 | | HADHA | 3030 | Payload comprising a HADHA gene or variant thereof packaged within a AAV3 capsid. |
| 1 | AAV4 | 1446389 | HADHA | 3030 | Payload comprising a HADHA gene or variant thereof packaged within a AAV4 capsid. |
| 1 | AAV5 | | HADHA | 3030 | Payload comprising a HADHA gene or variant thereof packaged within a AAV5 capsid. |
| 1 | AAV6 | | HADHA | 3030 | Payload comprising a HADHA gene or variant thereof packaged within a AAV6 capsid. |
| 1 | AAV7 | | HADHA | 3030 | Payload comprising a HADHA gene or variant thereof packaged within a AAV7 capsid. |
| 1 | AAV8 | 5075992 | HADHA | 3030 | Payload comprising a HADHA gene or variant thereof packaged within a AAV8 capsid. |
| 1 | AAV9 | | HADHA | 3030 | Payload comprising a HADHA gene or variant thereof packaged within a AAV9 capsid. |

Fig. 29 (Continued)

| | | | | | |
|---|---|---|---|---|---|
| 1 | AAV10 | | HADHA | 3030 | Payload comprising a HADHA gene or variant thereof packaged within a AAV10 capsid. |
| 1 | AAV11 | | HADHA | 3030 | Payload comprising a HADHA gene or variant thereof packaged within a AAV11 capsid. |
| 1 | AAVC11.01 | | HADHA | 3030 | Payload comprising a HADHA gene or variant thereof packaged within a AAVC11.01 capsid. |
| 1 | AAVC11.02 | | HADHA | 3030 | Payload comprising a HADHA gene or variant thereof packaged within a AAVC11.02 capsid. |
| 1 | AAVC11.03 | | HADHA | 3030 | Payload comprising a HADHA gene or variant thereof packaged within a AAVC11.03 capsid. |
| 1 | AAVC11.04 | | HADHA | 3030 | Payload comprising a HADHA gene or variant thereof packaged within a AAVC11.04 capsid. |
| 1 | AAVC11.05 | | HADHA | 3030 | Payload comprising a HADHA gene or variant thereof packaged within a AAVC11.05 capsid. |
| 1 | AAVC11.06 | | HADHA | 3030 | Payload comprising a HADHA gene or variant thereof packaged within a AAVC11.06 capsid. |
| 1 | AAVC11.07 | | HADHA | 3030 | Payload comprising a HADHA gene or variant thereof packaged within a AAVC11.07 capsid |
| 1 | AAVC11.08 | | HADHA | 3030 | Payload comprising a HADHA gene or variant thereof packaged within a AAVC11.08 capsid. |
| 1 | AAVC11.09 | | HADHA | 3030 | Payload comprising a HADHA gene or variant thereof packaged within a AAVC11.09 capsid. |
| 1 | AAVC11.10 | | HADHA | 3030 | Payload comprising a HADHA gene or variant thereof packaged within a AAVC11.10 capsid. |
| 1 | AAVC11.11 | | HADHA | 3030 | Payload comprising a HADHA gene or variant thereof packaged within a AAVC11.11 capsid. |
| 1 | AAVC11.12 | | HADHA | 3030 | Payload comprising a HADHA gene or variant thereof packaged within a AAVC11.12 capsid. |
| 1 | AAVC11.13 | | HADHA | 3030 | Payload comprising a HADHA gene or variant thereof packaged within a AAVC11.13 capsid. |
| 1 | AAVC11.14 | | HADHA | 3030 | Payload comprising a HADHA gene or variant thereof packaged within a AAVC11.14 capsid. |
| 1 | AAVC11.15 | | HADHA | 3030 | Payload comprising a HADHA gene or variant thereof packaged within a AAVC11.15 capsid. |

Fig. 29 (Continued)

| | | | | | |
|---|---|---|---|---|---|
| 1 | AAVC11.16 | | HADHA | 3030 | Payload comprising a HADHA gene or variant thereof packaged within a AAVC11.16 capsid. |
| 1 | AAVC11.17 | | HADHA | 3030 | Payload comprising a HADHA gene or variant thereof packaged within a AAVC11.17 capsid. |
| 1 | AAVC11.18 | | HADHA | 3030 | Payload comprising a HADHA gene or variant thereof packaged within a AAVC11.18 capsid |
| 1 | AAVC11.19 | | HADHA | 3030 | Payload comprising a HADHA gene or variant thereof packaged within a AAVC11.19 capsid. |
| 1 | AAV12 | | HADHA | 3030 | Payload comprising a HADHA gene or variant thereof packaged within a AAV12 capsid. |
| 1 | AAV13 | | HADHA | 3030 | Payload comprising a HADHA gene or variant thereof packaged within a AAV13 capsid. |
| 1 | AAV-DJ | | HADHA | 3030 | Payload comprising a HADHA gene or variant thereof packaged within a AAV-DJ capsid |
| 1 | AAV-LK03 | | HADHA | 3030 | Payload comprising a HADHA gene or variant thereof packaged within a AAV-LK03 capsid. |
| 1 | AAV-LK19 | | HADHA | 3030 | Payload comprising a HADHA gene or variant thereof packaged within a AAV-LK19 capsid. |
| 1 | AAVrh.74 | | HADHA | 3030 | Payload comprising a HADHA gene or variant thereof packaged within a AAVrh.74 capsid. |
| 1 | AAVrh.10 | | HADHA | 3030 | Payload comprising a HADHA gene or variant thereof packaged within a AAVrh.10 capsid. |
| 1 | AAVhu.37 | | HADHA | 3030 | Payload comprising a HADHA gene or variant thereof packaged within a AAVhu.37 capsid. |
| 1 | AAVrh.K | | HADHA | 3030 | Payload comprising a HADHA gene or variant thereof packaged within a AAVrh.K capsid. |
| 1 | AAVrh.39 | | HADHA | 3030 | Payload comprising a HADHA gene or variant thereof packaged within a AAVrh.39 capsid. |
| 1 | AAVrh.9 | | HADHA | 3030 | Payload comprising a HADHA gene or variant thereof packaged within a AAVrh.9 capsid. |
| 1 | avian AAV | | HADHA | 3030 | Payload comprising a HADHA gene or variant thereof packaged within a avian capsid. |

Fig. 29 (Continued)

| | | | | | |
|---|---|---|---|---|---|
| 1 | bovine AAV | | HADHA | 3030 | Payload comprising a HADHA gene or variant thereof packaged within a bovine capsid. |
| 1 | canine AAV | | HADHA | 3030 | Payload comprising a HADHA gene or variant thereof packaged within a canine capsid. |
| 1 | equine AAV | | HADHA | 3030 | Payload comprising a HADHA gene or variant thereof packaged within a equine capsid. |
| 1 | primate AAV | | HADHA | 3030 | Payload comprising a HADHA gene or variant thereof packaged within a primate capsid. |
| 1 | non-primate AAV | | HADHA | 3030 | Payload comprising a HADHA gene or variant thereof packaged within a non-primate capsid. |
| 1 | ovine AAV | | HADHA | 3030 | Payload comprising a HADHA gene or variant thereof packaged within a ovine capsid. |
| 1 | hybrid AAV | | HADHA | 3030 | Payload comprising a HADHA gene or variant thereof packaged within a hybrid capsid. |
| 1 | chimeric AAV | | HADHA | 3030 | Payload comprising a HADHA gene or variant thereof packaged within a chimeric capsid. |
| 2 | AAV1 | 1450374 | HADHA | 3030 | Payload comprising a HADHA gene or variant thereof packaged within a AAV1 capsid. |
| 2 | AAV2 | | HADHA | 3030 | Payload comprising a HADHA gene or variant thereof packaged within a AAV2 capsid. |
| 2 | AAV3 | | HADHA | 3030 | Payload comprising a HADHA gene or variant thereof packaged within a AAV3 capsid. |
| 2 | AAV4 | 1446389 | HADHA | 3030 | Payload comprising a HADHA gene or variant thereof packaged within a AAV4 capsid. |
| 2 | AAV5 | | HADHA | 3030 | Payload comprising a HADHA gene or variant thereof packaged within a AAV5 capsid. |
| 2 | AAV6 | | HADHA | 3030 | Payload comprising a HADHA gene or variant thereof packaged within a AAV6 capsid. |
| 2 | AAV7 | | HADHA | 3030 | Payload comprising a HADHA gene or variant thereof packaged within a AAV7 capsid. |
| 2 | AAV8 | 5075992 | HADHA | 3030 | Payload comprising a HADHA gene or variant thereof packaged within a AAV8 capsid. |
| 2 | AAV9 | | HADHA | 3030 | Payload comprising a HADHA gene or variant thereof packaged within a AAV9 capsid. |

Fig. 29 (Continued)

| | | | | | |
|---|---|---|---|---|---|
| 2 | AAV10 | | HADHA | 3030 | Payload comprising a HADHA gene or variant thereof packaged within a AAV10 capsid. |
| 2 | AAV11 | | HADHA | 3030 | Payload comprising a HADHA gene or variant thereof packaged within a AAV11 capsid. |
| 2 | AAVC11.01 | | HADHA | 3030 | Payload comprising a HADHA gene or variant thereof packaged within a AAVC11.01 capsid. |
| 2 | AAVC11.02 | | HADHA | 3030 | Payload comprising a HADHA gene or variant thereof packaged within a AAVC11.02 capsid. |
| 2 | AAVC11.03 | | HADHA | 3030 | Payload comprising a HADHA gene or variant thereof packaged within a AAVC11.03 capsid. |
| 2 | AAVC11.04 | | HADHA | 3030 | Payload comprising a HADHA gene or variant thereof packaged within a AAVC11.04 capsid. |
| 2 | AAVC11.05 | | HADHA | 3030 | Payload comprising a HADHA gene or variant thereof packaged within a AAVC11.05 capsid. |
| 2 | AAVC11.06 | | HADHA | 3030 | Payload comprising a HADHA gene or variant thereof packaged within a AAVC11.06 capsid. |
| 2 | AAVC11.07 | | HADHA | 3030 | Payload comprising a HADHA gene or variant thereof packaged within a AAVC11.07 capsid |
| 2 | AAVC11.08 | | HADHA | 3030 | Payload comprising a HADHA gene or variant thereof packaged within a AAVC11.08 capsid. |
| 2 | AAVC11.09 | | HADHA | 3030 | Payload comprising a HADHA gene or variant thereof packaged within a AAVC11.09 capsid. |
| 2 | AAVC11.10 | | HADHA | 3030 | Payload comprising a HADHA gene or variant thereof packaged within a AAVC11.10 capsid. |
| 2 | AAVC11.11 | | HADHA | 3030 | Payload comprising a HADHA gene or variant thereof packaged within a AAVC11.11 capsid. |
| 2 | AAVC11.12 | | HADHA | 3030 | Payload comprising a HADHA gene or variant thereof packaged within a AAVC11.12 capsid. |
| 2 | AAVC11.13 | | HADHA | 3030 | Payload comprising a HADHA gene or variant thereof packaged within a AAVC11.13 capsid. |
| 2 | AAVC11.14 | | HADHA | 3030 | Payload comprising a HADHA gene or variant thereof packaged within a AAVC11.14 capsid. |
| 2 | AAVC11.15 | | HADHA | 3030 | Payload comprising a HADHA gene or variant thereof packaged within a AAVC11.15 capsid. |

Fig. 29 (Continued)

| | | | | | |
|---|---|---|---|---|---|
| 2 | AAVC11.16 | | HADHA | 3030 | Payload comprising a HADHA gene or variant thereof packaged within a AAVC11.16 capsid. |
| 2 | AAVC11.17 | | HADHA | 3030 | Payload comprising a HADHA gene or variant thereof packaged within a AAVC11.17 capsid. |
| 2 | AAVC11.18 | | HADHA | 3030 | Payload comprising a HADHA gene or variant thereof packaged within a AAVC11.18 capsid |
| 2 | AAVC11.19 | | HADHA | 3030 | Payload comprising a HADHA gene or variant thereof packaged within a AAVC11.19 capsid. |
| 2 | AAV12 | | HADHA | 3030 | Payload comprising a HADHA gene or variant thereof packaged within a AAV12 capsid. |
| 2 | AAV13 | | HADHA | 3030 | Payload comprising a HADHA gene or variant thereof packaged within a AAV13 capsid. |
| 2 | AAV-DJ | | HADHA | 3030 | Payload comprising a HADHA gene or variant thereof packaged within a AAV-DJ capsid |
| 2 | AAV-LK03 | | HADHA | 3030 | Payload comprising a HADHA gene or variant thereof packaged within a AAV-LK03 capsid. |
| 2 | AAV-LK19 | | HADHA | 3030 | Payload comprising a HADHA gene or variant thereof packaged within a AAV-LK19 capsid. |
| 2 | AAVrh.74 | | HADHA | 3030 | Payload comprising a HADHA gene or variant thereof packaged within a AAVrh.74 capsid. |
| 2 | AAVrh.10 | | HADHA | 3030 | Payload comprising a HADHA gene or variant thereof packaged within a AAVrh.10 capsid. |
| 2 | AAVhu.37 | | HADHA | 3030 | Payload comprising a HADHA gene or variant thereof packaged within a AAVhu.37 capsid. |
| 2 | AAVrh.K | | HADHA | 3030 | Payload comprising a HADHA gene or variant thereof packaged within a AAVrh.K capsid. |
| 2 | AAVrh.39 | | HADHA | 3030 | Payload comprising a HADHA gene or variant thereof packaged within a AAVrh.39 capsid. |
| 2 | AAVrh.9 | | HADHA | 3030 | Payload comprising a HADHA gene or variant thereof packaged within a AAVrh.9 capsid. |
| 2 | avian AAV | | HADHA | 3030 | Payload comprising a HADHA gene or variant thereof packaged within a avian capsid. |

Fig. 29 (Continued)

| | | | | | |
|---|---|---|---|---|---|
| 2 | bovine AAV | | HADHA | 3030 | Payload comprising a HADHA gene or variant thereof packaged within a bovine capsid. |
| 2 | canine AAV | | HADHA | 3030 | Payload comprising a HADHA gene or variant thereof packaged within a canine capsid. |
| 2 | equine AAV | | HADHA | 3030 | Payload comprising a HADHA gene or variant thereof packaged within a equine capsid. |
| 2 | primate AAV | | HADHA | 3030 | Payload comprising a HADHA gene or variant thereof packaged within a primate capsid. |
| 2 | non-primate AAV | | HADHA | 3030 | Payload comprising a HADHA gene or variant thereof packaged within a non-primate capsid. |
| 2 | ovine AAV | | HADHA | 3030 | Payload comprising a HADHA gene or variant thereof packaged within a ovine capsid. |
| 2 | hybrid AAV | | HADHA | 3030 | Payload comprising a HADHA gene or variant thereof packaged within a hybrid capsid. |
| 2 | chimeric AAV | | HADHA | 3030 | Payload comprising a HADHA gene or variant thereof packaged within a chimeric capsid. |
| 1 | AAV1 | 1450374 | HADHB | 3032 | Payload comprising a HADHB gene or variant thereof packaged within a AAV1 capsid. |
| 1 | AAV2 | | HADHB | 3032 | Payload comprising a HADHB gene or variant thereof packaged within a AAV2 capsid. |
| 1 | AAV3 | | HADHB | 3032 | Payload comprising a HADHB gene or variant thereof packaged within a AAV3 capsid. |
| 1 | AAV4 | 1446389 | HADHB | 3032 | Payload comprising a HADHB gene or variant thereof packaged within a AAV4 capsid. |
| 1 | AAV5 | | HADHB | 3032 | Payload comprising a HADHB gene or variant thereof packaged within a AAV5 capsid. |
| 1 | AAV6 | | HADHB | 3032 | Payload comprising a HADHB gene or variant thereof packaged within a AAV6 capsid. |
| 1 | AAV7 | | HADHB | 3032 | Payload comprising a HADHB gene or variant thereof packaged within a AAV7 capsid. |
| 1 | AAV8 | 5075992 | HADHB | 3032 | Payload comprising a HADHB gene or variant thereof packaged within a AAV8 capsid. |
| 1 | AAV9 | | HADHB | 3032 | Payload comprising a HADHB gene or variant thereof packaged within a AAV9 capsid. |

Fig. 29 (Continued)

| | | | | | |
|---|---|---|---|---|---|
| 1 | AAV10 | | HADHB | 3032 | Payload comprising a HADHB gene or variant thereof packaged within a AAV10 capsid. |
| 1 | AAV11 | | HADHB | 3032 | Payload comprising a HADHB gene or variant thereof packaged within a AAV11 capsid. |
| 1 | AAVC11.01 | | HADHB | 3032 | Payload comprising a HADHB gene or variant thereof packaged within a AAVC11.01 capsid. |
| 1 | AAVC11.02 | | HADHB | 3032 | Payload comprising a HADHB gene or variant thereof packaged within a AAVC11.02 capsid. |
| 1 | AAVC11.03 | | HADHB | 3032 | Payload comprising a HADHB gene or variant thereof packaged within a AAVC11.03 capsid. |
| 1 | AAVC11.04 | | HADHB | 3032 | Payload comprising a HADHB gene or variant thereof packaged within a AAVC11.04 capsid. |
| 1 | AAVC11.05 | | HADHB | 3032 | Payload comprising a HADHB gene or variant thereof packaged within a AAVC11.05 capsid. |
| 1 | AAVC11.06 | | HADHB | 3032 | Payload comprising a HADHB gene or variant thereof packaged within a AAVC11.06 capsid. |
| 1 | AAVC11.07 | | HADHB | 3032 | Payload comprising a HADHB gene or variant thereof packaged within a AAVC11.07 capsid |
| 1 | AAVC11.08 | | HADHB | 3032 | Payload comprising a HADHB gene or variant thereof packaged within a AAVC11.08 capsid. |
| 1 | AAVC11.09 | | HADHB | 3032 | Payload comprising a HADHB gene or variant thereof packaged within a AAVC11.09 capsid. |
| 1 | AAVC11.10 | | HADHB | 3032 | Payload comprising a HADHB gene or variant thereof packaged within a AAVC11.10 capsid. |
| 1 | AAVC11.11 | | HADHB | 3032 | Payload comprising a HADHB gene or variant thereof packaged within a AAVC11.11 capsid. |
| 1 | AAVC11.12 | | HADHB | 3032 | Payload comprising a HADHB gene or variant thereof packaged within a AAVC11.12 capsid. |
| 1 | AAVC11.13 | | HADHB | 3032 | Payload comprising a HADHB gene or variant thereof packaged within a AAVC11.13 capsid. |
| 1 | AAVC11.14 | | HADHB | 3032 | Payload comprising a HADHB gene or variant thereof packaged within a AAVC11.14 capsid. |
| 1 | AAVC11.15 | | HADHB | 3032 | Payload comprising a HADHB gene or variant thereof packaged within a AAVC11.15 capsid. |

Fig. 29 (Continued)

| | | | | | |
|---|---|---|---|---|---|
| 1 | AAVC11.16 | | HADHB | 3032 | Payload comprising a HADHB gene or variant thereof packaged within a AAVC11.16 capsid. |
| 1 | AAVC11.17 | | HADHB | 3032 | Payload comprising a HADHB gene or variant thereof packaged within a AAVC11.17 capsid. |
| 1 | AAVC11.18 | | HADHB | 3032 | Payload comprising a HADHB gene or variant thereof packaged within a AAVC11.18 capsid |
| 1 | AAVC11.19 | | HADHB | 3032 | Payload comprising a HADHB gene or variant thereof packaged within a AAVC11.19 capsid. |
| 1 | AAV12 | | HADHB | 3032 | Payload comprising a HADHB gene or variant thereof packaged within a AAV12 capsid. |
| 1 | AAV13 | | HADHB | 3032 | Payload comprising a HADHB gene or variant thereof packaged within a AAV13 capsid. |
| 1 | AAV-DJ | | HADHB | 3032 | Payload comprising a HADHB gene or variant thereof packaged within a AAV-DJ capsid |
| 1 | AAV-LK03 | | HADHB | 3032 | Payload comprising a HADHB gene or variant thereof packaged within a AAV-LK03 capsid. |
| 1 | AAV-LK19 | | HADHB | 3032 | Payload comprising a HADHB gene or variant thereof packaged within a AAV-LK19 capsid. |
| 1 | AAVrh.74 | | HADHB | 3032 | Payload comprising a HADHB gene or variant thereof packaged within a AAVrh.74 capsid. |
| 1 | AAVrh.10 | | HADHB | 3032 | Payload comprising a HADHB gene or variant thereof packaged within a AAVrh.10 capsid. |
| 1 | AAVhu.37 | | HADHB | 3032 | Payload comprising a HADHB gene or variant thereof packaged within a AAVhu.37 capsid. |
| 1 | AAVrh.K | | HADHB | 3032 | Payload comprising a HADHB gene or variant thereof packaged within a AAVrh.K capsid. |
| 1 | AAVrh.39 | | HADHB | 3032 | Payload comprising a HADHB gene or variant thereof packaged within a AAVrh.39 capsid. |
| 1 | AAVrh.9 | | HADHB | 3032 | Payload comprising a HADHB gene or variant thereof packaged within a AAVrh.9 capsid. |
| 1 | avian AAV | | HADHB | 3032 | Payload comprising a HADHB gene or variant thereof packaged within a avian capsid. |

Fig. 29 (Continued)

| | | | | | |
|---|---|---|---|---|---|
| 1 | bovine AAV | | HADHB | 3032 | Payload comprising a HADHB gene or variant thereof packaged within a bovine capsid. |
| 1 | canine AAV | | HADHB | 3032 | Payload comprising a HADHB gene or variant thereof packaged within a canine capsid. |
| 1 | equine AAV | | HADHB | 3032 | Payload comprising a HADHB gene or variant thereof packaged within a equine capsid. |
| 1 | primate AAV | | HADHB | 3032 | Payload comprising a HADHB gene or variant thereof packaged within a primate capsid. |
| 1 | non-primate AAV | | HADHB | 3032 | Payload comprising a HADHB gene or variant thereof packaged within a non-primate capsid. |
| 1 | ovine AAV | | HADHB | 3032 | Payload comprising a HADHB gene or variant thereof packaged within a ovine capsid. |
| 1 | hybrid AAV | | HADHB | 3032 | Payload comprising a HADHB gene or variant thereof packaged within a hybrid capsid. |
| 1 | chimeric AAV | | HADHB | 3032 | Payload comprising a HADHB gene or variant thereof packaged within a chimeric capsid. |
| 2 | AAV1 | 1450374 | HADHB | 3032 | Payload comprising a HADHB gene or variant thereof packaged within a AAV1 capsid. |
| 2 | AAV2 | | HADHB | 3032 | Payload comprising a HADHB gene or variant thereof packaged within a AAV2 capsid. |
| 2 | AAV3 | | HADHB | 3032 | Payload comprising a HADHB gene or variant thereof packaged within a AAV3 capsid. |
| 2 | AAV4 | 1446389 | HADHB | 3032 | Payload comprising a HADHB gene or variant thereof packaged within a AAV4 capsid. |
| 2 | AAV5 | | HADHB | 3032 | Payload comprising a HADHB gene or variant thereof packaged within a AAV5 capsid. |
| 2 | AAV6 | | HADHB | 3032 | Payload comprising a HADHB gene or variant thereof packaged within a AAV6 capsid. |
| 2 | AAV7 | | HADHB | 3032 | Payload comprising a HADHB gene or variant thereof packaged within a AAV7 capsid. |
| 2 | AAV8 | 5075992 | HADHB | 3032 | Payload comprising a HADHB gene or variant thereof packaged within a AAV8 capsid. |
| 2 | AAV9 | | HADHB | 3032 | Payload comprising a HADHB gene or variant thereof packaged within a AAV9 capsid. |

Fig. 29 (Continued)

| | | | | | |
|---|---|---|---|---|---|
| 2 | AAV10 | | HADHB | 3032 | Payload comprising a HADHB gene or variant thereof packaged within a AAV10 capsid. |
| 2 | AAV11 | | HADHB | 3032 | Payload comprising a HADHB gene or variant thereof packaged within a AAV11 capsid. |
| 2 | AAVC11.01 | | HADHB | 3032 | Payload comprising a HADHB gene or variant thereof packaged within a AAVC11.01 capsid. |
| 2 | AAVC11.02 | | HADHB | 3032 | Payload comprising a HADHB gene or variant thereof packaged within a AAVC11.02 capsid. |
| 2 | AAVC11.03 | | HADHB | 3032 | Payload comprising a HADHB gene or variant thereof packaged within a AAVC11.03 capsid. |
| 2 | AAVC11.04 | | HADHB | 3032 | Payload comprising a HADHB gene or variant thereof packaged within a AAVC11.04 capsid. |
| 2 | AAVC11.05 | | HADHB | 3032 | Payload comprising a HADHB gene or variant thereof packaged within a AAVC11.05 capsid. |
| 2 | AAVC11.06 | | HADHB | 3032 | Payload comprising a HADHB gene or variant thereof packaged within a AAVC11.06 capsid. |
| 2 | AAVC11.07 | | HADHB | 3032 | Payload comprising a HADHB gene or variant thereof packaged within a AAVC11.07 capsid |
| 2 | AAVC11.08 | | HADHB | 3032 | Payload comprising a HADHB gene or variant thereof packaged within a AAVC11.08 capsid. |
| 2 | AAVC11.09 | | HADHB | 3032 | Payload comprising a HADHB gene or variant thereof packaged within a AAVC11.09 capsid. |
| 2 | AAVC11.10 | | HADHB | 3032 | Payload comprising a HADHB gene or variant thereof packaged within a AAVC11.10 capsid. |
| 2 | AAVC11.11 | | HADHB | 3032 | Payload comprising a HADHB gene or variant thereof packaged within a AAVC11.11 capsid. |
| 2 | AAVC11.12 | | HADHB | 3032 | Payload comprising a HADHB gene or variant thereof packaged within a AAVC11.12 capsid. |
| 2 | AAVC11.13 | | HADHB | 3032 | Payload comprising a HADHB gene or variant thereof packaged within a AAVC11.13 capsid. |
| 2 | AAVC11.14 | | HADHB | 3032 | Payload comprising a HADHB gene or variant thereof packaged within a AAVC11.14 capsid. |
| 2 | AAVC11.15 | | HADHB | 3032 | Payload comprising a HADHB gene or variant thereof packaged within a AAVC11.15 capsid. |

Fig. 29 (Continued)

| | | | | | |
|---|---|---|---|---|---|
| 2 | AAVC11.16 | | HADHB | 3032 | Payload comprising a HADHB gene or variant thereof packaged within a AAVC11.16 capsid. |
| 2 | AAVC11.17 | | HADHB | 3032 | Payload comprising a HADHB gene or variant thereof packaged within a AAVC11.17 capsid. |
| 2 | AAVC11.18 | | HADHB | 3032 | Payload comprising a HADHB gene or variant thereof packaged within a AAVC11.18 capsid |
| 2 | AAVC11.19 | | HADHB | 3032 | Payload comprising a HADHB gene or variant thereof packaged within a AAVC11.19 capsid. |
| 2 | AAV12 | | HADHB | 3032 | Payload comprising a HADHB gene or variant thereof packaged within a AAV12 capsid. |
| 2 | AAV13 | | HADHB | 3032 | Payload comprising a HADHB gene or variant thereof packaged within a AAV13 capsid. |
| 2 | AAV-DJ | | HADHB | 3032 | Payload comprising a HADHB gene or variant thereof packaged within a AAV-DJ capsid |
| 2 | AAV-LK03 | | HADHB | 3032 | Payload comprising a HADHB gene or variant thereof packaged within a AAV-LK03 capsid. |
| 2 | AAV-LK19 | | HADHB | 3032 | Payload comprising a HADHB gene or variant thereof packaged within a AAV-LK19 capsid. |
| 2 | AAVrh.74 | | HADHB | 3032 | Payload comprising a HADHB gene or variant thereof packaged within a AAVrh.74 capsid. |
| 2 | AAVrh.10 | | HADHB | 3032 | Payload comprising a HADHB gene or variant thereof packaged within a AAVrh.10 capsid. |
| 2 | AAVhu.37 | | HADHB | 3032 | Payload comprising a HADHB gene or variant thereof packaged within a AAVhu.37 capsid. |
| 2 | AAVrh.K | | HADHB | 3032 | Payload comprising a HADHB gene or variant thereof packaged within a AAVrh.K capsid. |
| 2 | AAVrh.39 | | HADHB | 3032 | Payload comprising a HADHB gene or variant thereof packaged within a AAVrh.39 capsid. |
| 2 | AAVrh.9 | | HADHB | 3032 | Payload comprising a HADHB gene or variant thereof packaged within a AAVrh.9 capsid. |
| 2 | avian AAV | | HADHB | 3032 | Payload comprising a HADHB gene or variant thereof packaged within a avian capsid. |

Fig. 29 (Continued)

| | | | | | |
|---|---|---|---|---|---|
| 2 | bovine AAV | | HADHB | 3032 | Payload comprising a HADHB gene or variant thereof packaged within a bovine capsid. |
| 2 | canine AAV | | HADHB | 3032 | Payload comprising a HADHB gene or variant thereof packaged within a canine capsid. |
| 2 | equine AAV | | HADHB | 3032 | Payload comprising a HADHB gene or variant thereof packaged within a equine capsid. |
| 2 | primate AAV | | HADHB | 3032 | Payload comprising a HADHB gene or variant thereof packaged within a primate capsid. |
| 2 | non-primate AAV | | HADHB | 3032 | Payload comprising a HADHB gene or variant thereof packaged within a non-primate capsid. |
| 2 | ovine AAV | | HADHB | 3032 | Payload comprising a HADHB gene or variant thereof packaged within a ovine capsid. |
| 2 | hybrid AAV | | HADHB | 3032 | Payload comprising a HADHB gene or variant thereof packaged within a hybrid capsid. |
| 2 | chimeric AAV | | HADHB | 3032 | Payload comprising a HADHB gene or variant thereof packaged within a chimeric capsid. |
| 1 | AAV1 | 1450374 | HGSNAT | 138050 | Payload comprising a HGSNAT gene or variant thereof packaged within a AAV1 capsid. |
| 1 | AAV2 | | HGSNAT | 138050 | Payload comprising a HGSNAT gene or variant thereof packaged within a AAV2 capsid. |
| 1 | AAV3 | | HGSNAT | 138050 | Payload comprising a HGSNAT gene or variant thereof packaged within a AAV3 capsid. |
| 1 | AAV4 | 1446389 | HGSNAT | 138050 | Payload comprising a HGSNAT gene or variant thereof packaged within a AAV4 capsid. |
| 1 | AAV5 | | HGSNAT | 138050 | Payload comprising a HGSNAT gene or variant thereof packaged within a AAV5 capsid. |
| 1 | AAV6 | | HGSNAT | 138050 | Payload comprising a HGSNAT gene or variant thereof packaged within a AAV6 capsid. |
| 1 | AAV7 | | HGSNAT | 138050 | Payload comprising a HGSNAT gene or variant thereof packaged within a AAV7 capsid. |
| 1 | AAV8 | 5075992 | HGSNAT | 138050 | Payload comprising a HGSNAT gene or variant thereof packaged within a AAV8 capsid. |
| 1 | AAV9 | | HGSNAT | 138050 | Payload comprising a HGSNAT gene or variant thereof packaged within a AAV9 capsid. |

Fig. 29 (Continued)

| | | | | | |
|---|---|---|---|---|---|
| 1 | AAV10 | | HGSNAT | 138050 | Payload comprising a HGSNAT gene or variant thereof packaged within a AAV10 capsid. |
| 1 | AAV11 | | HGSNAT | 138050 | Payload comprising a HGSNAT gene or variant thereof packaged within a AAV11 capsid. |
| 1 | AAVC11.01 | | HGSNAT | 138050 | Payload comprising a HGSNAT gene or variant thereof packaged within a AAVC11.01 capsid. |
| 1 | AAVC11.02 | | HGSNAT | 138050 | Payload comprising a HGSNAT gene or variant thereof packaged within a AAVC11.02 capsid. |
| 1 | AAVC11.03 | | HGSNAT | 138050 | Payload comprising a HGSNAT gene or variant thereof packaged within a AAVC11.03 capsid. |
| 1 | AAVC11.04 | | HGSNAT | 138050 | Payload comprising a HGSNAT gene or variant thereof packaged within a AAVC11.04 capsid. |
| 1 | AAVC11.05 | | HGSNAT | 138050 | Payload comprising a HGSNAT gene or variant thereof packaged within a AAVC11.05 capsid. |
| 1 | AAVC11.06 | | HGSNAT | 138050 | Payload comprising a HGSNAT gene or variant thereof packaged within a AAVC11.06 capsid. |
| 1 | AAVC11.07 | | HGSNAT | 138050 | Payload comprising a HGSNAT gene or variant thereof packaged within a AAVC11.07 capsid |
| 1 | AAVC11.08 | | HGSNAT | 138050 | Payload comprising a HGSNAT gene or variant thereof packaged within a AAVC11.08 capsid. |
| 1 | AAVC11.09 | | HGSNAT | 138050 | Payload comprising a HGSNAT gene or variant thereof packaged within a AAVC11.09 capsid. |
| 1 | AAVC11.10 | | HGSNAT | 138050 | Payload comprising a HGSNAT gene or variant thereof packaged within a AAVC11.10 capsid. |
| 1 | AAVC11.11 | | HGSNAT | 138050 | Payload comprising a HGSNAT gene or variant thereof packaged within a AAVC11.11 capsid. |
| 1 | AAVC11.12 | | HGSNAT | 138050 | Payload comprising a HGSNAT gene or variant thereof packaged within a AAVC11.12 capsid. |
| 1 | AAVC11.13 | | HGSNAT | 138050 | Payload comprising a HGSNAT gene or variant thereof packaged within a AAVC11.13 capsid. |
| 1 | AAVC11.14 | | HGSNAT | 138050 | Payload comprising a HGSNAT gene or variant thereof packaged within a AAVC11.14 capsid. |
| 1 | AAVC11.15 | | HGSNAT | 138050 | Payload comprising a HGSNAT gene or variant thereof packaged within a AAVC11.15 capsid. |

Fig. 29 (Continued)

| | | | | | |
|---|---|---|---|---|---|
| 1 | AAVC11.16 | | HGSNAT | 138050 | Payload comprising a HGSNAT gene or variant thereof packaged within a AAVC11.16 capsid. |
| 1 | AAVC11.17 | | HGSNAT | 138050 | Payload comprising a HGSNAT gene or variant thereof packaged within a AAVC11.17 capsid. |
| 1 | AAVC11.18 | | HGSNAT | 138050 | Payload comprising a HGSNAT gene or variant thereof packaged within a AAVC11.18 capsid |
| 1 | AAVC11.19 | | HGSNAT | 138050 | Payload comprising a HGSNAT gene or variant thereof packaged within a AAVC11.19 capsid. |
| 1 | AAV12 | | HGSNAT | 138050 | Payload comprising a HGSNAT gene or variant thereof packaged within a AAV12 capsid. |
| 1 | AAV13 | | HGSNAT | 138050 | Payload comprising a HGSNAT gene or variant thereof packaged within a AAV13 capsid. |
| 1 | AAV-DJ | | HGSNAT | 138050 | Payload comprising a HGSNAT gene or variant thereof packaged within a AAV-DJ capsid |
| 1 | AAV-LK03 | | HGSNAT | 138050 | Payload comprising a HGSNAT gene or variant thereof packaged within a AAV-LK03 capsid. |
| 1 | AAV-LK19 | | HGSNAT | 138050 | Payload comprising a HGSNAT gene or variant thereof packaged within a AAV-LK19 capsid. |
| 1 | AAVrh.74 | | HGSNAT | 138050 | Payload comprising a HGSNAT gene or variant thereof packaged within a AAVrh.74 capsid. |
| 1 | AAVrh.10 | | HGSNAT | 138050 | Payload comprising a HGSNAT gene or variant thereof packaged within a AAVrh.10 capsid. |
| 1 | AAVhu.37 | | HGSNAT | 138050 | Payload comprising a HGSNAT gene or variant thereof packaged within a AAVhu.37 capsid. |
| 1 | AAVrh.K | | HGSNAT | 138050 | Payload comprising a HGSNAT gene or variant thereof packaged within a AAVrh.K capsid. |
| 1 | AAVrh.39 | | HGSNAT | 138050 | Payload comprising a HGSNAT gene or variant thereof packaged within a AAVrh.39 capsid. |
| 1 | AAVrh.9 | | HGSNAT | 138050 | Payload comprising a HGSNAT gene or variant thereof packaged within a AAVrh.9 capsid. |
| 1 | avian AAV | | HGSNAT | 138050 | Payload comprising a HGSNAT gene or variant thereof packaged within a avian capsid. |

Fig. 29 (Continued)

| | | | | | |
|---|---|---|---|---|---|
| 1 | bovine AAV | | HGSNAT | 138050 | Payload comprising a HGSNAT gene or variant thereof packaged within a bovine capsid. |
| 1 | canine AAV | | HGSNAT | 138050 | Payload comprising a HGSNAT gene or variant thereof packaged within a canine capsid. |
| 1 | equine AAV | | HGSNAT | 138050 | Payload comprising a HGSNAT gene or variant thereof packaged within a equine capsid. |
| 1 | primate AAV | | HGSNAT | 138050 | Payload comprising a HGSNAT gene or variant thereof packaged within a primate capsid. |
| 1 | non-primate AAV | | HGSNAT | 138050 | Payload comprising a HGSNAT gene or variant thereof packaged within a non-primate capsid. |
| 1 | ovine AAV | | HGSNAT | 138050 | Payload comprising a HGSNAT gene or variant thereof packaged within a ovine capsid. |
| 1 | hybrid AAV | | HGSNAT | 138050 | Payload comprising a HGSNAT gene or variant thereof packaged within a hybrid capsid. |
| 1 | chimeric AAV | | HGSNAT | 138050 | Payload comprising a HGSNAT gene or variant thereof packaged within a chimeric capsid. |
| 2 | AAV1 | 1450374 | HGSNAT | 138050 | Payload comprising a HGSNAT gene or variant thereof packaged within a AAV1 capsid. |
| 2 | AAV2 | | HGSNAT | 138050 | Payload comprising a HGSNAT gene or variant thereof packaged within a AAV2 capsid. |
| 2 | AAV3 | | HGSNAT | 138050 | Payload comprising a HGSNAT gene or variant thereof packaged within a AAV3 capsid. |
| 2 | AAV4 | 1446389 | HGSNAT | 138050 | Payload comprising a HGSNAT gene or variant thereof packaged within a AAV4 capsid. |
| 2 | AAV5 | | HGSNAT | 138050 | Payload comprising a HGSNAT gene or variant thereof packaged within a AAV5 capsid. |
| 2 | AAV6 | | HGSNAT | 138050 | Payload comprising a HGSNAT gene or variant thereof packaged within a AAV6 capsid. |
| 2 | AAV7 | | HGSNAT | 138050 | Payload comprising a HGSNAT gene or variant thereof packaged within a AAV7 capsid. |
| 2 | AAV8 | 5075992 | HGSNAT | 138050 | Payload comprising a HGSNAT gene or variant thereof packaged within a AAV8 capsid. |
| 2 | AAV9 | | HGSNAT | 138050 | Payload comprising a HGSNAT gene or variant thereof packaged within a AAV9 capsid. |

Fig. 29 (Continued)

| | | | | | |
|---|---|---|---|---|---|
| 2 | AAV10 | | HGSNAT | 138050 | Payload comprising a HGSNAT gene or variant thereof packaged within a AAV10 capsid. |
| 2 | AAV11 | | HGSNAT | 138050 | Payload comprising a HGSNAT gene or variant thereof packaged within a AAV11 capsid. |
| 2 | AAVC11.01 | | HGSNAT | 138050 | Payload comprising a HGSNAT gene or variant thereof packaged within a AAVC11.01 capsid. |
| 2 | AAVC11.02 | | HGSNAT | 138050 | Payload comprising a HGSNAT gene or variant thereof packaged within a AAVC11.02 capsid. |
| 2 | AAVC11.03 | | HGSNAT | 138050 | Payload comprising a HGSNAT gene or variant thereof packaged within a AAVC11.03 capsid. |
| 2 | AAVC11.04 | | HGSNAT | 138050 | Payload comprising a HGSNAT gene or variant thereof packaged within a AAVC11.04 capsid. |
| 2 | AAVC11.05 | | HGSNAT | 138050 | Payload comprising a HGSNAT gene or variant thereof packaged within a AAVC11.05 capsid. |
| 2 | AAVC11.06 | | HGSNAT | 138050 | Payload comprising a HGSNAT gene or variant thereof packaged within a AAVC11.06 capsid. |
| 2 | AAVC11.07 | | HGSNAT | 138050 | Payload comprising a HGSNAT gene or variant thereof packaged within a AAVC11.07 capsid |
| 2 | AAVC11.08 | | HGSNAT | 138050 | Payload comprising a HGSNAT gene or variant thereof packaged within a AAVC11.08 capsid. |
| 2 | AAVC11.09 | | HGSNAT | 138050 | Payload comprising a HGSNAT gene or variant thereof packaged within a AAVC11.09 capsid. |
| 2 | AAVC11.10 | | HGSNAT | 138050 | Payload comprising a HGSNAT gene or variant thereof packaged within a AAVC11.10 capsid. |
| 2 | AAVC11.11 | | HGSNAT | 138050 | Payload comprising a HGSNAT gene or variant thereof packaged within a AAVC11.11 capsid. |
| 2 | AAVC11.12 | | HGSNAT | 138050 | Payload comprising a HGSNAT gene or variant thereof packaged within a AAVC11.12 capsid. |
| 2 | AAVC11.13 | | HGSNAT | 138050 | Payload comprising a HGSNAT gene or variant thereof packaged within a AAVC11.13 capsid. |
| 2 | AAVC11.14 | | HGSNAT | 138050 | Payload comprising a HGSNAT gene or variant thereof packaged within a AAVC11.14 capsid. |
| 2 | AAVC11.15 | | HGSNAT | 138050 | Payload comprising a HGSNAT gene or variant thereof packaged within a AAVC11.15 capsid. |

Fig. 29 (Continued)

| | | | | | |
|---|---|---|---|---|---|
| 2 | AAVC11.16 | | HGSNAT | 138050 | Payload comprising a HGSNAT gene or variant thereof packaged within a AAVC11.16 capsid. |
| 2 | AAVC11.17 | | HGSNAT | 138050 | Payload comprising a HGSNAT gene or variant thereof packaged within a AAVC11.17 capsid. |
| 2 | AAVC11.18 | | HGSNAT | 138050 | Payload comprising a HGSNAT gene or variant thereof packaged within a AAVC11.18 capsid |
| 2 | AAVC11.19 | | HGSNAT | 138050 | Payload comprising a HGSNAT gene or variant thereof packaged within a AAVC11.19 capsid. |
| 2 | AAV12 | | HGSNAT | 138050 | Payload comprising a HGSNAT gene or variant thereof packaged within a AAV12 capsid. |
| 2 | AAV13 | | HGSNAT | 138050 | Payload comprising a HGSNAT gene or variant thereof packaged within a AAV13 capsid. |
| 2 | AAV-DJ | | HGSNAT | 138050 | Payload comprising a HGSNAT gene or variant thereof packaged within a AAV-DJ capsid |
| 2 | AAV-LK03 | | HGSNAT | 138050 | Payload comprising a HGSNAT gene or variant thereof packaged within a AAV-LK03 capsid. |
| 2 | AAV-LK19 | | HGSNAT | 138050 | Payload comprising a HGSNAT gene or variant thereof packaged within a AAV-LK19 capsid. |
| 2 | AAVrh.74 | | HGSNAT | 138050 | Payload comprising a HGSNAT gene or variant thereof packaged within a AAVrh.74 capsid. |
| 2 | AAVrh.10 | | HGSNAT | 138050 | Payload comprising a HGSNAT gene or variant thereof packaged within a AAVrh.10 capsid. |
| 2 | AAVhu.37 | | HGSNAT | 138050 | Payload comprising a HGSNAT gene or variant thereof packaged within a AAVhu.37 capsid. |
| 2 | AAVrh.K | | HGSNAT | 138050 | Payload comprising a HGSNAT gene or variant thereof packaged within a AAVrh.K capsid. |
| 2 | AAVrh.39 | | HGSNAT | 138050 | Payload comprising a HGSNAT gene or variant thereof packaged within a AAVrh.39 capsid. |
| 2 | AAVrh.9 | | HGSNAT | 138050 | Payload comprising a HGSNAT gene or variant thereof packaged within a AAVrh.9 capsid. |
| 2 | avian AAV | | HGSNAT | 138050 | Payload comprising a HGSNAT gene or variant thereof packaged within a avian capsid. |

Fig. 29 (Continued)

| | | | | | |
|---|---|---|---|---|---|
| 2 | bovine AAV | | HGSNAT | 138050 | Payload comprising a HGSNAT gene or variant thereof packaged within a bovine capsid. |
| 2 | canine AAV | | HGSNAT | 138050 | Payload comprising a HGSNAT gene or variant thereof packaged within a canine capsid. |
| 2 | equine AAV | | HGSNAT | 138050 | Payload comprising a HGSNAT gene or variant thereof packaged within a equine capsid. |
| 2 | primate AAV | | HGSNAT | 138050 | Payload comprising a HGSNAT gene or variant thereof packaged within a primate capsid. |
| 2 | non-primate AAV | | HGSNAT | 138050 | Payload comprising a HGSNAT gene or variant thereof packaged within a non-primate capsid. |
| 2 | ovine AAV | | HGSNAT | 138050 | Payload comprising a HGSNAT gene or variant thereof packaged within a ovine capsid. |
| 2 | hybrid AAV | | HGSNAT | 138050 | Payload comprising a HGSNAT gene or variant thereof packaged within a hybrid capsid. |
| 2 | chimeric AAV | | HGSNAT | 138050 | Payload comprising a HGSNAT gene or variant thereof packaged within a chimeric capsid. |
| 1 | AAV1 | 1450374 | HYAL1 | 3373 | Payload comprising a HYAL1 gene or variant thereof packaged within a AAV1 capsid. |
| 1 | AAV2 | | HYAL1 | 3373 | Payload comprising a HYAL1 gene or variant thereof packaged within a AAV2 capsid. |
| 1 | AAV3 | | HYAL1 | 3373 | Payload comprising a HYAL1 gene or variant thereof packaged within a AAV3 capsid. |
| 1 | AAV4 | 1446389 | HYAL1 | 3373 | Payload comprising a HYAL1 gene or variant thereof packaged within a AAV4 capsid. |
| 1 | AAV5 | | HYAL1 | 3373 | Payload comprising a HYAL1 gene or variant thereof packaged within a AAV5 capsid. |
| 1 | AAV6 | | HYAL1 | 3373 | Payload comprising a HYAL1 gene or variant thereof packaged within a AAV6 capsid. |
| 1 | AAV7 | | HYAL1 | 3373 | Payload comprising a HYAL1 gene or variant thereof packaged within a AAV7 capsid. |
| 1 | AAV8 | 5075992 | HYAL1 | 3373 | Payload comprising a HYAL1 gene or variant thereof packaged within a AAV8 capsid. |
| 1 | AAV9 | | HYAL1 | 3373 | Payload comprising a HYAL1 gene or variant thereof packaged within a AAV9 capsid. |

Fig. 29 (Continued)

| | | | | | |
|---|---|---|---|---|---|
| 1 | AAV10 | | HYAL1 | 3373 | Payload comprising a HYAL1 gene or variant thereof packaged within a AAV10 capsid. |
| 1 | AAV11 | | HYAL1 | 3373 | Payload comprising a HYAL1 gene or variant thereof packaged within a AAV11 capsid. |
| 1 | AAVC11.01 | | HYAL1 | 3373 | Payload comprising a HYAL1 gene or variant thereof packaged within a AAVC11.01 capsid. |
| 1 | AAVC11.02 | | HYAL1 | 3373 | Payload comprising a HYAL1 gene or variant thereof packaged within a AAVC11.02 capsid. |
| 1 | AAVC11.03 | | HYAL1 | 3373 | Payload comprising a HYAL1 gene or variant thereof packaged within a AAVC11.03 capsid. |
| 1 | AAVC11.04 | | HYAL1 | 3373 | Payload comprising a HYAL1 gene or variant thereof packaged within a AAVC11.04 capsid. |
| 1 | AAVC11.05 | | HYAL1 | 3373 | Payload comprising a HYAL1 gene or variant thereof packaged within a AAVC11.05 capsid. |
| 1 | AAVC11.06 | | HYAL1 | 3373 | Payload comprising a HYAL1 gene or variant thereof packaged within a AAVC11.06 capsid. |
| 1 | AAVC11.07 | | HYAL1 | 3373 | Payload comprising a HYAL1 gene or variant thereof packaged within a AAVC11.07 capsid |
| 1 | AAVC11.08 | | HYAL1 | 3373 | Payload comprising a HYAL1 gene or variant thereof packaged within a AAVC11.08 capsid. |
| 1 | AAVC11.09 | | HYAL1 | 3373 | Payload comprising a HYAL1 gene or variant thereof packaged within a AAVC11.09 capsid. |
| 1 | AAVC11.10 | | HYAL1 | 3373 | Payload comprising a HYAL1 gene or variant thereof packaged within a AAVC11.10 capsid. |
| 1 | AAVC11.11 | | HYAL1 | 3373 | Payload comprising a HYAL1 gene or variant thereof packaged within a AAVC11.11 capsid. |
| 1 | AAVC11.12 | | HYAL1 | 3373 | Payload comprising a HYAL1 gene or variant thereof packaged within a AAVC11.12 capsid. |
| 1 | AAVC11.13 | | HYAL1 | 3373 | Payload comprising a HYAL1 gene or variant thereof packaged within a AAVC11.13 capsid. |
| 1 | AAVC11.14 | | HYAL1 | 3373 | Payload comprising a HYAL1 gene or variant thereof packaged within a AAVC11.14 capsid. |
| 1 | AAVC11.15 | | HYAL1 | 3373 | Payload comprising a HYAL1 gene or variant thereof packaged within a AAVC11.15 capsid. |

Fig. 29 (Continued)

| | | | | | |
|---|---|---|---|---|---|
| 1 | AAVC11.16 | | HYAL1 | 3373 | Payload comprising a HYAL1 gene or variant thereof packaged within a AAVC11.16 capsid. |
| 1 | AAVC11.17 | | HYAL1 | 3373 | Payload comprising a HYAL1 gene or variant thereof packaged within a AAVC11.17 capsid. |
| 1 | AAVC11.18 | | HYAL1 | 3373 | Payload comprising a HYAL1 gene or variant thereof packaged within a AAVC11.18 capsid |
| 1 | AAVC11.19 | | HYAL1 | 3373 | Payload comprising a HYAL1 gene or variant thereof packaged within a AAVC11.19 capsid. |
| 1 | AAV12 | | HYAL1 | 3373 | Payload comprising a HYAL1 gene or variant thereof packaged within a AAV12 capsid. |
| 1 | AAV13 | | HYAL1 | 3373 | Payload comprising a HYAL1 gene or variant thereof packaged within a AAV13 capsid. |
| 1 | AAV-DJ | | HYAL1 | 3373 | Payload comprising a HYAL1 gene or variant thereof packaged within a AAV-DJ capsid |
| 1 | AAV-LK03 | | HYAL1 | 3373 | Payload comprising a HYAL1 gene or variant thereof packaged within a AAV-LK03 capsid. |
| 1 | AAV-LK19 | | HYAL1 | 3373 | Payload comprising a HYAL1 gene or variant thereof packaged within a AAV-LK19 capsid. |
| 1 | AAVrh.74 | | HYAL1 | 3373 | Payload comprising a HYAL1 gene or variant thereof packaged within a AAVrh.74 capsid. |
| 1 | AAVrh.10 | | HYAL1 | 3373 | Payload comprising a HYAL1 gene or variant thereof packaged within a AAVrh.10 capsid. |
| 1 | AAVhu.37 | | HYAL1 | 3373 | Payload comprising a HYAL1 gene or variant thereof packaged within a AAVhu.37 capsid. |
| 1 | AAVrh.K | | HYAL1 | 3373 | Payload comprising a HYAL1 gene or variant thereof packaged within a AAVrh.K capsid. |
| 1 | AAVrh.39 | | HYAL1 | 3373 | Payload comprising a HYAL1 gene or variant thereof packaged within a AAVrh.39 capsid. |
| 1 | AAVrh.9 | | HYAL1 | 3373 | Payload comprising a HYAL1 gene or variant thereof packaged within a AAVrh.9 capsid. |
| 1 | avian AAV | | HYAL1 | 3373 | Payload comprising a HYAL1 gene or variant thereof packaged within a avian capsid. |

Fig. 29 (Continued)

| | | | | | |
|---|---|---|---|---|---|
| 1 | bovine AAV | | HYAL1 | 3373 | Payload comprising a HYAL1 gene or variant thereof packaged within a bovine capsid. |
| 1 | canine AAV | | HYAL1 | 3373 | Payload comprising a HYAL1 gene or variant thereof packaged within a canine capsid. |
| 1 | equine AAV | | HYAL1 | 3373 | Payload comprising a HYAL1 gene or variant thereof packaged within a equine capsid. |
| 1 | primate AAV | | HYAL1 | 3373 | Payload comprising a HYAL1 gene or variant thereof packaged within a primate capsid. |
| 1 | non-primate AAV | | HYAL1 | 3373 | Payload comprising a HYAL1 gene or variant thereof packaged within a non-primate capsid. |
| 1 | ovine AAV | | HYAL1 | 3373 | Payload comprising a HYAL1 gene or variant thereof packaged within a ovine capsid. |
| 1 | hybrid AAV | | HYAL1 | 3373 | Payload comprising a HYAL1 gene or variant thereof packaged within a hybrid capsid. |
| 1 | chimeric AAV | | HYAL1 | 3373 | Payload comprising a HYAL1 gene or variant thereof packaged within a chimeric capsid. |
| 2 | AAV1 | 1450374 | HYAL1 | 3373 | Payload comprising a HYAL1 gene or variant thereof packaged within a AAV1 capsid. |
| 2 | AAV2 | | HYAL1 | 3373 | Payload comprising a HYAL1 gene or variant thereof packaged within a AAV2 capsid. |
| 2 | AAV3 | | HYAL1 | 3373 | Payload comprising a HYAL1 gene or variant thereof packaged within a AAV3 capsid. |
| 2 | AAV4 | 1446389 | HYAL1 | 3373 | Payload comprising a HYAL1 gene or variant thereof packaged within a AAV4 capsid. |
| 2 | AAV5 | | HYAL1 | 3373 | Payload comprising a HYAL1 gene or variant thereof packaged within a AAV5 capsid. |
| 2 | AAV6 | | HYAL1 | 3373 | Payload comprising a HYAL1 gene or variant thereof packaged within a AAV6 capsid. |
| 2 | AAV7 | | HYAL1 | 3373 | Payload comprising a HYAL1 gene or variant thereof packaged within a AAV7 capsid. |
| 2 | AAV8 | 5075992 | HYAL1 | 3373 | Payload comprising a HYAL1 gene or variant thereof packaged within a AAV8 capsid. |
| 2 | AAV9 | | HYAL1 | 3373 | Payload comprising a HYAL1 gene or variant thereof packaged within a AAV9 capsid. |

Fig. 29 (Continued)

| | | | | | |
|---|---|---|---|---|---|
| 2 | AAV10 | | HYAL1 | 3373 | Payload comprising a HYAL1 gene or variant thereof packaged within a AAV10 capsid. |
| 2 | AAV11 | | HYAL1 | 3373 | Payload comprising a HYAL1 gene or variant thereof packaged within a AAV11 capsid. |
| 2 | AAVC11.01 | | HYAL1 | 3373 | Payload comprising a HYAL1 gene or variant thereof packaged within a AAVC11.01 capsid. |
| 2 | AAVC11.02 | | HYAL1 | 3373 | Payload comprising a HYAL1 gene or variant thereof packaged within a AAVC11.02 capsid. |
| 2 | AAVC11.03 | | HYAL1 | 3373 | Payload comprising a HYAL1 gene or variant thereof packaged within a AAVC11.03 capsid. |
| 2 | AAVC11.04 | | HYAL1 | 3373 | Payload comprising a HYAL1 gene or variant thereof packaged within a AAVC11.04 capsid. |
| 2 | AAVC11.05 | | HYAL1 | 3373 | Payload comprising a HYAL1 gene or variant thereof packaged within a AAVC11.05 capsid. |
| 2 | AAVC11.06 | | HYAL1 | 3373 | Payload comprising a HYAL1 gene or variant thereof packaged within a AAVC11.06 capsid. |
| 2 | AAVC11.07 | | HYAL1 | 3373 | Payload comprising a HYAL1 gene or variant thereof packaged within a AAVC11.07 capsid |
| 2 | AAVC11.08 | | HYAL1 | 3373 | Payload comprising a HYAL1 gene or variant thereof packaged within a AAVC11.08 capsid. |
| 2 | AAVC11.09 | | HYAL1 | 3373 | Payload comprising a HYAL1 gene or variant thereof packaged within a AAVC11.09 capsid. |
| 2 | AAVC11.10 | | HYAL1 | 3373 | Payload comprising a HYAL1 gene or variant thereof packaged within a AAVC11.10 capsid. |
| 2 | AAVC11.11 | | HYAL1 | 3373 | Payload comprising a HYAL1 gene or variant thereof packaged within a AAVC11.11 capsid. |
| 2 | AAVC11.12 | | HYAL1 | 3373 | Payload comprising a HYAL1 gene or variant thereof packaged within a AAVC11.12 capsid. |
| 2 | AAVC11.13 | | HYAL1 | 3373 | Payload comprising a HYAL1 gene or variant thereof packaged within a AAVC11.13 capsid. |
| 2 | AAVC11.14 | | HYAL1 | 3373 | Payload comprising a HYAL1 gene or variant thereof packaged within a AAVC11.14 capsid. |
| 2 | AAVC11.15 | | HYAL1 | 3373 | Payload comprising a HYAL1 gene or variant thereof packaged within a AAVC11.15 capsid. |

Fig. 29 (Continued)

| | | | | | |
|---|---|---|---|---|---|
| 2 | AAVC11.16 | | HYAL1 | 3373 | Payload comprising a HYAL1 gene or variant thereof packaged within a AAVC11.16 capsid. |
| 2 | AAVC11.17 | | HYAL1 | 3373 | Payload comprising a HYAL1 gene or variant thereof packaged within a AAVC11.17 capsid. |
| 2 | AAVC11.18 | | HYAL1 | 3373 | Payload comprising a HYAL1 gene or variant thereof packaged within a AAVC11.18 capsid |
| 2 | AAVC11.19 | | HYAL1 | 3373 | Payload comprising a HYAL1 gene or variant thereof packaged within a AAVC11.19 capsid. |
| 2 | AAV12 | | HYAL1 | 3373 | Payload comprising a HYAL1 gene or variant thereof packaged within a AAV12 capsid. |
| 2 | AAV13 | | HYAL1 | 3373 | Payload comprising a HYAL1 gene or variant thereof packaged within a AAV13 capsid. |
| 2 | AAV-DJ | | HYAL1 | 3373 | Payload comprising a HYAL1 gene or variant thereof packaged within a AAV-DJ capsid |
| 2 | AAV-LK03 | | HYAL1 | 3373 | Payload comprising a HYAL1 gene or variant thereof packaged within a AAV-LK03 capsid. |
| 2 | AAV-LK19 | | HYAL1 | 3373 | Payload comprising a HYAL1 gene or variant thereof packaged within a AAV-LK19 capsid. |
| 2 | AAVrh.74 | | HYAL1 | 3373 | Payload comprising a HYAL1 gene or variant thereof packaged within a AAVrh.74 capsid. |
| 2 | AAVrh.10 | | HYAL1 | 3373 | Payload comprising a HYAL1 gene or variant thereof packaged within a AAVrh.10 capsid. |
| 2 | AAVhu.37 | | HYAL1 | 3373 | Payload comprising a HYAL1 gene or variant thereof packaged within a AAVhu.37 capsid. |
| 2 | AAVrh.K | | HYAL1 | 3373 | Payload comprising a HYAL1 gene or variant thereof packaged within a AAVrh.K capsid. |
| 2 | AAVrh.39 | | HYAL1 | 3373 | Payload comprising a HYAL1 gene or variant thereof packaged within a AAVrh.39 capsid. |
| 2 | AAVrh.9 | | HYAL1 | 3373 | Payload comprising a HYAL1 gene or variant thereof packaged within a AAVrh.9 capsid. |
| 2 | avian AAV | | HYAL1 | 3373 | Payload comprising a HYAL1 gene or variant thereof packaged within a avian capsid. |

Fig. 29 (Continued)

| | | | | | |
|---|---|---|---|---|---|
| 2 | bovine AAV | | HYAL1 | 3373 | Payload comprising a HYAL1 gene or variant thereof packaged within a bovine capsid. |
| 2 | canine AAV | | HYAL1 | 3373 | Payload comprising a HYAL1 gene or variant thereof packaged within a canine capsid. |
| 2 | equine AAV | | HYAL1 | 3373 | Payload comprising a HYAL1 gene or variant thereof packaged within a equine capsid. |
| 2 | primate AAV | | HYAL1 | 3373 | Payload comprising a HYAL1 gene or variant thereof packaged within a primate capsid. |
| 2 | non-primate AAV | | HYAL1 | 3373 | Payload comprising a HYAL1 gene or variant thereof packaged within a non-primate capsid. |
| 2 | ovine AAV | | HYAL1 | 3373 | Payload comprising a HYAL1 gene or variant thereof packaged within a ovine capsid. |
| 2 | hybrid AAV | | HYAL1 | 3373 | Payload comprising a HYAL1 gene or variant thereof packaged within a hybrid capsid. |
| 2 | chimeric AAV | | HYAL1 | 3373 | Payload comprising a HYAL1 gene or variant thereof packaged within a chimeric capsid. |
| 1 | AAV1 | 1450374 | IDUA | 3425 | Payload comprising a IDUA gene or variant thereof packaged within a AAV1 capsid. |
| 1 | AAV2 | | IDUA | 3425 | Payload comprising a IDUA gene or variant thereof packaged within a AAV2 capsid. |
| 1 | AAV3 | | IDUA | 3425 | Payload comprising a IDUA gene or variant thereof packaged within a AAV3 capsid. |
| 1 | AAV4 | 1446389 | IDUA | 3425 | Payload comprising a IDUA gene or variant thereof packaged within a AAV4 capsid. |
| 1 | AAV5 | | IDUA | 3425 | Payload comprising a IDUA gene or variant thereof packaged within a AAV5 capsid. |
| 1 | AAV6 | | IDUA | 3425 | Payload comprising a IDUA gene or variant thereof packaged within a AAV6 capsid. |
| 1 | AAV7 | | IDUA | 3425 | Payload comprising a IDUA gene or variant thereof packaged within a AAV7 capsid. |
| 1 | AAV8 | 5075992 | IDUA | 3425 | Payload comprising a IDUA gene or variant thereof packaged within a AAV8 capsid. |
| 1 | AAV9 | | IDUA | 3425 | Payload comprising a IDUA gene or variant thereof packaged within a AAV9 capsid. |

Fig. 29 (Continued)

| | | | | | |
|---|---|---|---|---|---|
| 1 | AAV10 | | IDUA | 3425 | Payload comprising a IDUA gene or variant thereof packaged within a AAV10 capsid. |
| 1 | AAV11 | | IDUA | 3425 | Payload comprising a IDUA gene or variant thereof packaged within a AAV11 capsid. |
| 1 | AAVC11.01 | | IDUA | 3425 | Payload comprising a IDUA gene or variant thereof packaged within a AAVC11.01 capsid. |
| 1 | AAVC11.02 | | IDUA | 3425 | Payload comprising a IDUA gene or variant thereof packaged within a AAVC11.02 capsid. |
| 1 | AAVC11.03 | | IDUA | 3425 | Payload comprising a IDUA gene or variant thereof packaged within a AAVC11.03 capsid. |
| 1 | AAVC11.04 | | IDUA | 3425 | Payload comprising a IDUA gene or variant thereof packaged within a AAVC11.04 capsid. |
| 1 | AAVC11.05 | | IDUA | 3425 | Payload comprising a IDUA gene or variant thereof packaged within a AAVC11.05 capsid. |
| 1 | AAVC11.06 | | IDUA | 3425 | Payload comprising a IDUA gene or variant thereof packaged within a AAVC11.06 capsid. |
| 1 | AAVC11.07 | | IDUA | 3425 | Payload comprising a IDUA gene or variant thereof packaged within a AAVC11.07 capsid |
| 1 | AAVC11.08 | | IDUA | 3425 | Payload comprising a IDUA gene or variant thereof packaged within a AAVC11.08 capsid. |
| 1 | AAVC11.09 | | IDUA | 3425 | Payload comprising a IDUA gene or variant thereof packaged within a AAVC11.09 capsid. |
| 1 | AAVC11.10 | | IDUA | 3425 | Payload comprising a IDUA gene or variant thereof packaged within a AAVC11.10 capsid. |
| 1 | AAVC11.11 | | IDUA | 3425 | Payload comprising a IDUA gene or variant thereof packaged within a AAVC11.11 capsid. |
| 1 | AAVC11.12 | | IDUA | 3425 | Payload comprising a IDUA gene or variant thereof packaged within a AAVC11.12 capsid. |
| 1 | AAVC11.13 | | IDUA | 3425 | Payload comprising a IDUA gene or variant thereof packaged within a AAVC11.13 capsid. |
| 1 | AAVC11.14 | | IDUA | 3425 | Payload comprising a IDUA gene or variant thereof packaged within a AAVC11.14 capsid. |
| 1 | AAVC11.15 | | IDUA | 3425 | Payload comprising a IDUA gene or variant thereof packaged within a AAVC11.15 capsid. |

Fig. 29 (Continued)

| | | | | | |
|---|---|---|---|---|---|
| 1 | AAVC11.16 | | IDUA | 3425 | Payload comprising a IDUA gene or variant thereof packaged within a AAVC11.16 capsid. |
| 1 | AAVC11.17 | | IDUA | 3425 | Payload comprising a IDUA gene or variant thereof packaged within a AAVC11.17 capsid. |
| 1 | AAVC11.18 | | IDUA | 3425 | Payload comprising a IDUA gene or variant thereof packaged within a AAVC11.18 capsid |
| 1 | AAVC11.19 | | IDUA | 3425 | Payload comprising a IDUA gene or variant thereof packaged within a AAVC11.19 capsid. |
| 1 | AAV12 | | IDUA | 3425 | Payload comprising a IDUA gene or variant thereof packaged within a AAV12 capsid. |
| 1 | AAV13 | | IDUA | 3425 | Payload comprising a IDUA gene or variant thereof packaged within a AAV13 capsid. |
| 1 | AAV-DJ | | IDUA | 3425 | Payload comprising a IDUA gene or variant thereof packaged within a AAV-DJ capsid |
| 1 | AAV-LK03 | | IDUA | 3425 | Payload comprising a IDUA gene or variant thereof packaged within a AAV-LK03 capsid. |
| 1 | AAV-LK19 | | IDUA | 3425 | Payload comprising a IDUA gene or variant thereof packaged within a AAV-LK19 capsid. |
| 1 | AAVrh.74 | | IDUA | 3425 | Payload comprising a IDUA gene or variant thereof packaged within a AAVrh.74 capsid. |
| 1 | AAVrh.10 | | IDUA | 3425 | Payload comprising a IDUA gene or variant thereof packaged within a AAVrh.10 capsid. |
| 1 | AAVhu.37 | | IDUA | 3425 | Payload comprising a IDUA gene or variant thereof packaged within a AAVhu.37 capsid. |
| 1 | AAVrh.K | | IDUA | 3425 | Payload comprising a IDUA gene or variant thereof packaged within a AAVrh.K capsid. |
| 1 | AAVrh.39 | | IDUA | 3425 | Payload comprising a IDUA gene or variant thereof packaged within a AAVrh.39 capsid. |
| 1 | AAVrh.9 | | IDUA | 3425 | Payload comprising a IDUA gene or variant thereof packaged within a AAVrh.9 capsid. |
| 1 | avian AAV | | IDUA | 3425 | Payload comprising a IDUA gene or variant thereof packaged within a avian capsid. |

Fig. 29 (Continued)

| | | | | | |
|---|---|---|---|---|---|
| 1 | bovine AAV | | IDUA | 3425 | Payload comprising a IDUA gene or variant thereof packaged within a bovine capsid. |
| 1 | canine AAV | | IDUA | 3425 | Payload comprising a IDUA gene or variant thereof packaged within a canine capsid. |
| 1 | equine AAV | | IDUA | 3425 | Payload comprising a IDUA gene or variant thereof packaged within a equine capsid. |
| 1 | primate AAV | | IDUA | 3425 | Payload comprising a IDUA gene or variant thereof packaged within a primate capsid. |
| 1 | non-primate AAV | | IDUA | 3425 | Payload comprising a IDUA gene or variant thereof packaged within a non-primate capsid. |
| 1 | ovine AAV | | IDUA | 3425 | Payload comprising a IDUA gene or variant thereof packaged within a ovine capsid. |
| 1 | hybrid AAV | | IDUA | 3425 | Payload comprising a IDUA gene or variant thereof packaged within a hybrid capsid. |
| 1 | chimeric AAV | | IDUA | 3425 | Payload comprising a IDUA gene or variant thereof packaged within a chimeric capsid. |
| 2 | AAV1 | 1450374 | IDUA | 3425 | Payload comprising a IDUA gene or variant thereof packaged within a AAV1 capsid. |
| 2 | AAV2 | | IDUA | 3425 | Payload comprising a IDUA gene or variant thereof packaged within a AAV2 capsid. |
| 2 | AAV3 | | IDUA | 3425 | Payload comprising a IDUA gene or variant thereof packaged within a AAV3 capsid. |
| 2 | AAV4 | 1446389 | IDUA | 3425 | Payload comprising a IDUA gene or variant thereof packaged within a AAV4 capsid. |
| 2 | AAV5 | | IDUA | 3425 | Payload comprising a IDUA gene or variant thereof packaged within a AAV5 capsid. |
| 2 | AAV6 | | IDUA | 3425 | Payload comprising a IDUA gene or variant thereof packaged within a AAV6 capsid. |
| 2 | AAV7 | | IDUA | 3425 | Payload comprising a IDUA gene or variant thereof packaged within a AAV7 capsid. |
| 2 | AAV8 | 5075992 | IDUA | 3425 | Payload comprising a IDUA gene or variant thereof packaged within a AAV8 capsid. |
| 2 | AAV9 | | IDUA | 3425 | Payload comprising a IDUA gene or variant thereof packaged within a AAV9 capsid. |

Fig. 29 (Continued)

| | | | | | |
|---|---|---|---|---|---|
| 2 | AAV10 | | IDUA | 3425 | Payload comprising a IDUA gene or variant thereof packaged within a AAV10 capsid. |
| 2 | AAV11 | | IDUA | 3425 | Payload comprising a IDUA gene or variant thereof packaged within a AAV11 capsid. |
| 2 | AAVC11.01 | | IDUA | 3425 | Payload comprising a IDUA gene or variant thereof packaged within a AAVC11.01 capsid. |
| 2 | AAVC11.02 | | IDUA | 3425 | Payload comprising a IDUA gene or variant thereof packaged within a AAVC11.02 capsid. |
| 2 | AAVC11.03 | | IDUA | 3425 | Payload comprising a IDUA gene or variant thereof packaged within a AAVC11.03 capsid. |
| 2 | AAVC11.04 | | IDUA | 3425 | Payload comprising a IDUA gene or variant thereof packaged within a AAVC11.04 capsid. |
| 2 | AAVC11.05 | | IDUA | 3425 | Payload comprising a IDUA gene or variant thereof packaged within a AAVC11.05 capsid. |
| 2 | AAVC11.06 | | IDUA | 3425 | Payload comprising a IDUA gene or variant thereof packaged within a AAVC11.06 capsid. |
| 2 | AAVC11.07 | | IDUA | 3425 | Payload comprising a IDUA gene or variant thereof packaged within a AAVC11.07 capsid |
| 2 | AAVC11.08 | | IDUA | 3425 | Payload comprising a IDUA gene or variant thereof packaged within a AAVC11.08 capsid. |
| 2 | AAVC11.09 | | IDUA | 3425 | Payload comprising a IDUA gene or variant thereof packaged within a AAVC11.09 capsid. |
| 2 | AAVC11.10 | | IDUA | 3425 | Payload comprising a IDUA gene or variant thereof packaged within a AAVC11.10 capsid. |
| 2 | AAVC11.11 | | IDUA | 3425 | Payload comprising a IDUA gene or variant thereof packaged within a AAVC11.11 capsid. |
| 2 | AAVC11.12 | | IDUA | 3425 | Payload comprising a IDUA gene or variant thereof packaged within a AAVC11.12 capsid. |
| 2 | AAVC11.13 | | IDUA | 3425 | Payload comprising a IDUA gene or variant thereof packaged within a AAVC11.13 capsid. |
| 2 | AAVC11.14 | | IDUA | 3425 | Payload comprising a IDUA gene or variant thereof packaged within a AAVC11.14 capsid. |
| 2 | AAVC11.15 | | IDUA | 3425 | Payload comprising a IDUA gene or variant thereof packaged within a AAVC11.15 capsid. |

Fig. 29 (Continued)

| | | | | | |
|---|---|---|---|---|---|
| 2 | AAVC11.16 | | IDUA | 3425 | Payload comprising a IDUA gene or variant thereof packaged within a AAVC11.16 capsid. |
| 2 | AAVC11.17 | | IDUA | 3425 | Payload comprising a IDUA gene or variant thereof packaged within a AAVC11.17 capsid. |
| 2 | AAVC11.18 | | IDUA | 3425 | Payload comprising a IDUA gene or variant thereof packaged within a AAVC11.18 capsid |
| 2 | AAVC11.19 | | IDUA | 3425 | Payload comprising a IDUA gene or variant thereof packaged within a AAVC11.19 capsid. |
| 2 | AAV12 | | IDUA | 3425 | Payload comprising a IDUA gene or variant thereof packaged within a AAV12 capsid. |
| 2 | AAV13 | | IDUA | 3425 | Payload comprising a IDUA gene or variant thereof packaged within a AAV13 capsid. |
| 2 | AAV-DJ | | IDUA | 3425 | Payload comprising a IDUA gene or variant thereof packaged within a AAV-DJ capsid |
| 2 | AAV-LK03 | | IDUA | 3425 | Payload comprising a IDUA gene or variant thereof packaged within a AAV-LK03 capsid. |
| 2 | AAV-LK19 | | IDUA | 3425 | Payload comprising a IDUA gene or variant thereof packaged within a AAV-LK19 capsid. |
| 2 | AAVrh.74 | | IDUA | 3425 | Payload comprising a IDUA gene or variant thereof packaged within a AAVrh.74 capsid. |
| 2 | AAVrh.10 | | IDUA | 3425 | Payload comprising a IDUA gene or variant thereof packaged within a AAVrh.10 capsid. |
| 2 | AAVhu.37 | | IDUA | 3425 | Payload comprising a IDUA gene or variant thereof packaged within a AAVhu.37 capsid. |
| 2 | AAVrh.K | | IDUA | 3425 | Payload comprising a IDUA gene or variant thereof packaged within a AAVrh.K capsid. |
| 2 | AAVrh.39 | | IDUA | 3425 | Payload comprising a IDUA gene or variant thereof packaged within a AAVrh.39 capsid. |
| 2 | AAVrh.9 | | IDUA | 3425 | Payload comprising a IDUA gene or variant thereof packaged within a AAVrh.9 capsid. |
| 2 | avian AAV | | IDUA | 3425 | Payload comprising a IDUA gene or variant thereof packaged within a avian capsid. |

Fig. 29 (Continued)

| | | | | | |
|---|---|---|---|---|---|
| 2 | bovine AAV | | IDUA | 3425 | Payload comprising a IDUA gene or variant thereof packaged within a bovine capsid. |
| 2 | canine AAV | | IDUA | 3425 | Payload comprising a IDUA gene or variant thereof packaged within a canine capsid. |
| 2 | equine AAV | | IDUA | 3425 | Payload comprising a IDUA gene or variant thereof packaged within a equine capsid. |
| 2 | primate AAV | | IDUA | 3425 | Payload comprising a IDUA gene or variant thereof packaged within a primate capsid. |
| 2 | non-primate AAV | | IDUA | 3425 | Payload comprising a IDUA gene or variant thereof packaged within a non-primate capsid. |
| 2 | ovine AAV | | IDUA | 3425 | Payload comprising a IDUA gene or variant thereof packaged within a ovine capsid. |
| 2 | hybrid AAV | | IDUA | 3425 | Payload comprising a IDUA gene or variant thereof packaged within a hybrid capsid. |
| 2 | chimeric AAV | | IDUA | 3425 | Payload comprising a IDUA gene or variant thereof packaged within a chimeric capsid. |
| 1 | AAV1 | 1450374 | ITGB4 | 3691 | Payload comprising a ITGB4 gene or variant thereof packaged within a AAV1 capsid. |
| 1 | AAV2 | | ITGB4 | 3691 | Payload comprising a ITGB4 gene or variant thereof packaged within a AAV2 capsid. |
| 1 | AAV3 | | ITGB4 | 3691 | Payload comprising a ITGB4 gene or variant thereof packaged within a AAV3 capsid. |
| 1 | AAV4 | 1446389 | ITGB4 | 3691 | Payload comprising a ITGB4 gene or variant thereof packaged within a AAV4 capsid. |
| 1 | AAV5 | | ITGB4 | 3691 | Payload comprising a ITGB4 gene or variant thereof packaged within a AAV5 capsid. |
| 1 | AAV6 | | ITGB4 | 3691 | Payload comprising a ITGB4 gene or variant thereof packaged within a AAV6 capsid. |
| 1 | AAV7 | | ITGB4 | 3691 | Payload comprising a ITGB4 gene or variant thereof packaged within a AAV7 capsid. |
| 1 | AAV8 | 5075992 | ITGB4 | 3691 | Payload comprising a ITGB4 gene or variant thereof packaged within a AAV8 capsid. |
| 1 | AAV9 | | ITGB4 | 3691 | Payload comprising a ITGB4 gene or variant thereof packaged within a AAV9 capsid. |

Fig. 29 (Continued)

| | | | | | |
|---|---|---|---|---|---|
| 1 | AAV10 | | ITGB4 | 3691 | Payload comprising a ITGB4 gene or variant thereof packaged within a AAV10 capsid. |
| 1 | AAV11 | | ITGB4 | 3691 | Payload comprising a ITGB4 gene or variant thereof packaged within a AAV11 capsid. |
| 1 | AAVC11.01 | | ITGB4 | 3691 | Payload comprising a ITGB4 gene or variant thereof packaged within a AAVC11.01 capsid. |
| 1 | AAVC11.02 | | ITGB4 | 3691 | Payload comprising a ITGB4 gene or variant thereof packaged within a AAVC11.02 capsid. |
| 1 | AAVC11.03 | | ITGB4 | 3691 | Payload comprising a ITGB4 gene or variant thereof packaged within a AAVC11.03 capsid. |
| 1 | AAVC11.04 | | ITGB4 | 3691 | Payload comprising a ITGB4 gene or variant thereof packaged within a AAVC11.04 capsid. |
| 1 | AAVC11.05 | | ITGB4 | 3691 | Payload comprising a ITGB4 gene or variant thereof packaged within a AAVC11.05 capsid. |
| 1 | AAVC11.06 | | ITGB4 | 3691 | Payload comprising a ITGB4 gene or variant thereof packaged within a AAVC11.06 capsid. |
| 1 | AAVC11.07 | | ITGB4 | 3691 | Payload comprising a ITGB4 gene or variant thereof packaged within a AAVC11.07 capsid |
| 1 | AAVC11.08 | | ITGB4 | 3691 | Payload comprising a ITGB4 gene or variant thereof packaged within a AAVC11.08 capsid. |
| 1 | AAVC11.09 | | ITGB4 | 3691 | Payload comprising a ITGB4 gene or variant thereof packaged within a AAVC11.09 capsid. |
| 1 | AAVC11.10 | | ITGB4 | 3691 | Payload comprising a ITGB4 gene or variant thereof packaged within a AAVC11.10 capsid. |
| 1 | AAVC11.11 | | ITGB4 | 3691 | Payload comprising a ITGB4 gene or variant thereof packaged within a AAVC11.11 capsid. |
| 1 | AAVC11.12 | | ITGB4 | 3691 | Payload comprising a ITGB4 gene or variant thereof packaged within a AAVC11.12 capsid. |
| 1 | AAVC11.13 | | ITGB4 | 3691 | Payload comprising a ITGB4 gene or variant thereof packaged within a AAVC11.13 capsid. |
| 1 | AAVC11.14 | | ITGB4 | 3691 | Payload comprising a ITGB4 gene or variant thereof packaged within a AAVC11.14 capsid. |
| 1 | AAVC11.15 | | ITGB4 | 3691 | Payload comprising a ITGB4 gene or variant thereof packaged within a AAVC11.15 capsid. |

Fig. 29 (Continued)

| | | | | | |
|---|---|---|---|---|---|
| 1 | AAVC11.16 | | ITGB4 | 3691 | Payload comprising a ITGB4 gene or variant thereof packaged within a AAVC11.16 capsid. |
| 1 | AAVC11.17 | | ITGB4 | 3691 | Payload comprising a ITGB4 gene or variant thereof packaged within a AAVC11.17 capsid. |
| 1 | AAVC11.18 | | ITGB4 | 3691 | Payload comprising a ITGB4 gene or variant thereof packaged within a AAVC11.18 capsid |
| 1 | AAVC11.19 | | ITGB4 | 3691 | Payload comprising a ITGB4 gene or variant thereof packaged within a AAVC11.19 capsid. |
| 1 | AAV12 | | ITGB4 | 3691 | Payload comprising a ITGB4 gene or variant thereof packaged within a AAV12 capsid. |
| 1 | AAV13 | | ITGB4 | 3691 | Payload comprising a ITGB4 gene or variant thereof packaged within a AAV13 capsid. |
| 1 | AAV-DJ | | ITGB4 | 3691 | Payload comprising a ITGB4 gene or variant thereof packaged within a AAV-DJ capsid |
| 1 | AAV-LK03 | | ITGB4 | 3691 | Payload comprising a ITGB4 gene or variant thereof packaged within a AAV-LK03 capsid. |
| 1 | AAV-LK19 | | ITGB4 | 3691 | Payload comprising a ITGB4 gene or variant thereof packaged within a AAV-LK19 capsid. |
| 1 | AAVrh.74 | | ITGB4 | 3691 | Payload comprising a ITGB4 gene or variant thereof packaged within a AAVrh.74 capsid. |
| 1 | AAVrh.10 | | ITGB4 | 3691 | Payload comprising a ITGB4 gene or variant thereof packaged within a AAVrh.10 capsid. |
| 1 | AAVhu.37 | | ITGB4 | 3691 | Payload comprising a ITGB4 gene or variant thereof packaged within a AAVhu.37 capsid. |
| 1 | AAVrh.K | | ITGB4 | 3691 | Payload comprising a ITGB4 gene or variant thereof packaged within a AAVrh.K capsid. |
| 1 | AAVrh.39 | | ITGB4 | 3691 | Payload comprising a ITGB4 gene or variant thereof packaged within a AAVrh.39 capsid. |
| 1 | AAVrh.9 | | ITGB4 | 3691 | Payload comprising a ITGB4 gene or variant thereof packaged within a AAVrh.9 capsid. |
| 1 | avian AAV | | ITGB4 | 3691 | Payload comprising a ITGB4 gene or variant thereof packaged within a avian capsid. |

Fig. 29 (Continued)

| | | | | | |
|---|---|---|---|---|---|
| 1 | bovine AAV | | ITGB4 | 3691 | Payload comprising a ITGB4 gene or variant thereof packaged within a bovine capsid. |
| 1 | canine AAV | | ITGB4 | 3691 | Payload comprising a ITGB4 gene or variant thereof packaged within a canine capsid. |
| 1 | equine AAV | | ITGB4 | 3691 | Payload comprising a ITGB4 gene or variant thereof packaged within a equine capsid. |
| 1 | primate AAV | | ITGB4 | 3691 | Payload comprising a ITGB4 gene or variant thereof packaged within a primate capsid. |
| 1 | non-primate AAV | | ITGB4 | 3691 | Payload comprising a ITGB4 gene or variant thereof packaged within a non-primate capsid. |
| 1 | ovine AAV | | ITGB4 | 3691 | Payload comprising a ITGB4 gene or variant thereof packaged within a ovine capsid. |
| 1 | hybrid AAV | | ITGB4 | 3691 | Payload comprising a ITGB4 gene or variant thereof packaged within a hybrid capsid. |
| 1 | chimeric AAV | | ITGB4 | 3691 | Payload comprising a ITGB4 gene or variant thereof packaged within a chimeric capsid. |
| 2 | AAV1 | 1450374 | ITGB4 | 3691 | Payload comprising a ITGB4 gene or variant thereof packaged within a AAV1 capsid. |
| 2 | AAV2 | | ITGB4 | 3691 | Payload comprising a ITGB4 gene or variant thereof packaged within a AAV2 capsid. |
| 2 | AAV3 | | ITGB4 | 3691 | Payload comprising a ITGB4 gene or variant thereof packaged within a AAV3 capsid. |
| 2 | AAV4 | 1446389 | ITGB4 | 3691 | Payload comprising a ITGB4 gene or variant thereof packaged within a AAV4 capsid. |
| 2 | AAV5 | | ITGB4 | 3691 | Payload comprising a ITGB4 gene or variant thereof packaged within a AAV5 capsid. |
| 2 | AAV6 | | ITGB4 | 3691 | Payload comprising a ITGB4 gene or variant thereof packaged within a AAV6 capsid. |
| 2 | AAV7 | | ITGB4 | 3691 | Payload comprising a ITGB4 gene or variant thereof packaged within a AAV7 capsid. |
| 2 | AAV8 | 5075992 | ITGB4 | 3691 | Payload comprising a ITGB4 gene or variant thereof packaged within a AAV8 capsid. |
| 2 | AAV9 | | ITGB4 | 3691 | Payload comprising a ITGB4 gene or variant thereof packaged within a AAV9 capsid. |

Fig. 29 (Continued)

| | | | | | |
|---|---|---|---|---|---|
| 2 | AAV10 | | ITGB4 | 3691 | Payload comprising a ITGB4 gene or variant thereof packaged within a AAV10 capsid. |
| 2 | AAV11 | | ITGB4 | 3691 | Payload comprising a ITGB4 gene or variant thereof packaged within a AAV11 capsid. |
| 2 | AAVC11.01 | | ITGB4 | 3691 | Payload comprising a ITGB4 gene or variant thereof packaged within a AAVC11.01 capsid. |
| 2 | AAVC11.02 | | ITGB4 | 3691 | Payload comprising a ITGB4 gene or variant thereof packaged within a AAVC11.02 capsid. |
| 2 | AAVC11.03 | | ITGB4 | 3691 | Payload comprising a ITGB4 gene or variant thereof packaged within a AAVC11.03 capsid. |
| 2 | AAVC11.04 | | ITGB4 | 3691 | Payload comprising a ITGB4 gene or variant thereof packaged within a AAVC11.04 capsid. |
| 2 | AAVC11.05 | | ITGB4 | 3691 | Payload comprising a ITGB4 gene or variant thereof packaged within a AAVC11.05 capsid. |
| 2 | AAVC11.06 | | ITGB4 | 3691 | Payload comprising a ITGB4 gene or variant thereof packaged within a AAVC11.06 capsid. |
| 2 | AAVC11.07 | | ITGB4 | 3691 | Payload comprising a ITGB4 gene or variant thereof packaged within a AAVC11.07 capsid |
| 2 | AAVC11.08 | | ITGB4 | 3691 | Payload comprising a ITGB4 gene or variant thereof packaged within a AAVC11.08 capsid. |
| 2 | AAVC11.09 | | ITGB4 | 3691 | Payload comprising a ITGB4 gene or variant thereof packaged within a AAVC11.09 capsid. |
| 2 | AAVC11.10 | | ITGB4 | 3691 | Payload comprising a ITGB4 gene or variant thereof packaged within a AAVC11.10 capsid. |
| 2 | AAVC11.11 | | ITGB4 | 3691 | Payload comprising a ITGB4 gene or variant thereof packaged within a AAVC11.11 capsid. |
| 2 | AAVC11.12 | | ITGB4 | 3691 | Payload comprising a ITGB4 gene or variant thereof packaged within a AAVC11.12 capsid. |
| 2 | AAVC11.13 | | ITGB4 | 3691 | Payload comprising a ITGB4 gene or variant thereof packaged within a AAVC11.13 capsid. |
| 2 | AAVC11.14 | | ITGB4 | 3691 | Payload comprising a ITGB4 gene or variant thereof packaged within a AAVC11.14 capsid. |
| 2 | AAVC11.15 | | ITGB4 | 3691 | Payload comprising a ITGB4 gene or variant thereof packaged within a AAVC11.15 capsid. |

Fig. 29 (Continued)

| | | | | | |
|---|---|---|---|---|---|
| 2 | AAVC11.16 | | ITGB4 | 3691 | Payload comprising a ITGB4 gene or variant thereof packaged within a AAVC11.16 capsid. |
| 2 | AAVC11.17 | | ITGB4 | 3691 | Payload comprising a ITGB4 gene or variant thereof packaged within a AAVC11.17 capsid. |
| 2 | AAVC11.18 | | ITGB4 | 3691 | Payload comprising a ITGB4 gene or variant thereof packaged within a AAVC11.18 capsid |
| 2 | AAVC11.19 | | ITGB4 | 3691 | Payload comprising a ITGB4 gene or variant thereof packaged within a AAVC11.19 capsid. |
| 2 | AAV12 | | ITGB4 | 3691 | Payload comprising a ITGB4 gene or variant thereof packaged within a AAV12 capsid. |
| 2 | AAV13 | | ITGB4 | 3691 | Payload comprising a ITGB4 gene or variant thereof packaged within a AAV13 capsid. |
| 2 | AAV-DJ | | ITGB4 | 3691 | Payload comprising a ITGB4 gene or variant thereof packaged within a AAV-DJ capsid |
| 2 | AAV-LK03 | | ITGB4 | 3691 | Payload comprising a ITGB4 gene or variant thereof packaged within a AAV-LK03 capsid. |
| 2 | AAV-LK19 | | ITGB4 | 3691 | Payload comprising a ITGB4 gene or variant thereof packaged within a AAV-LK19 capsid. |
| 2 | AAVrh.74 | | ITGB4 | 3691 | Payload comprising a ITGB4 gene or variant thereof packaged within a AAVrh.74 capsid. |
| 2 | AAVrh.10 | | ITGB4 | 3691 | Payload comprising a ITGB4 gene or variant thereof packaged within a AAVrh.10 capsid. |
| 2 | AAVhu.37 | | ITGB4 | 3691 | Payload comprising a ITGB4 gene or variant thereof packaged within a AAVhu.37 capsid. |
| 2 | AAVrh.K | | ITGB4 | 3691 | Payload comprising a ITGB4 gene or variant thereof packaged within a AAVrh.K capsid. |
| 2 | AAVrh.39 | | ITGB4 | 3691 | Payload comprising a ITGB4 gene or variant thereof packaged within a AAVrh.39 capsid. |
| 2 | AAVrh.9 | | ITGB4 | 3691 | Payload comprising a ITGB4 gene or variant thereof packaged within a AAVrh.9 capsid. |
| 2 | avian AAV | | ITGB4 | 3691 | Payload comprising a ITGB4 gene or variant thereof packaged within a avian capsid. |

Fig. 29 (Continued)

| | | | | | |
|---|---|---|---|---|---|
| 2 | bovine AAV | | ITGB4 | 3691 | Payload comprising a ITGB4 gene or variant thereof packaged within a bovine capsid. |
| 2 | canine AAV | | ITGB4 | 3691 | Payload comprising a ITGB4 gene or variant thereof packaged within a canine capsid. |
| 2 | equine AAV | | ITGB4 | 3691 | Payload comprising a ITGB4 gene or variant thereof packaged within a equine capsid. |
| 2 | primate AAV | | ITGB4 | 3691 | Payload comprising a ITGB4 gene or variant thereof packaged within a primate capsid. |
| 2 | non-primate AAV | | ITGB4 | 3691 | Payload comprising a ITGB4 gene or variant thereof packaged within a non-primate capsid. |
| 2 | ovine AAV | | ITGB4 | 3691 | Payload comprising a ITGB4 gene or variant thereof packaged within a ovine capsid. |
| 2 | hybrid AAV | | ITGB4 | 3691 | Payload comprising a ITGB4 gene or variant thereof packaged within a hybrid capsid. |
| 2 | chimeric AAV | | ITGB4 | 3691 | Payload comprising a ITGB4 gene or variant thereof packaged within a chimeric capsid. |
| 1 | AAV1 | 1450374 | IVD | 3712 | Payload comprising a IVD gene or variant thereof packaged within a AAV1 capsid. |
| 1 | AAV2 | | IVD | 3712 | Payload comprising a IVD gene or variant thereof packaged within a AAV2 capsid. |
| 1 | AAV3 | | IVD | 3712 | Payload comprising a IVD gene or variant thereof packaged within a AAV3 capsid. |
| 1 | AAV4 | 1446389 | IVD | 3712 | Payload comprising a IVD gene or variant thereof packaged within a AAV4 capsid. |
| 1 | AAV5 | | IVD | 3712 | Payload comprising a IVD gene or variant thereof packaged within a AAV5 capsid. |
| 1 | AAV6 | | IVD | 3712 | Payload comprising a IVD gene or variant thereof packaged within a AAV6 capsid. |
| 1 | AAV7 | | IVD | 3712 | Payload comprising a IVD gene or variant thereof packaged within a AAV7 capsid. |
| 1 | AAV8 | 5075992 | IVD | 3712 | Payload comprising a IVD gene or variant thereof packaged within a AAV8 capsid. |
| 1 | AAV9 | | IVD | 3712 | Payload comprising a IVD gene or variant thereof packaged within a AAV9 capsid. |

Fig. 29 (Continued)

| | | | | | |
|---|---|---|---|---|---|
| 1 | AAV10 | | IVD | 3712 | Payload comprising a IVD gene or variant thereof packaged within a AAV10 capsid. |
| 1 | AAV11 | | IVD | 3712 | Payload comprising a IVD gene or variant thereof packaged within a AAV11 capsid. |
| 1 | AAVC11.01 | | IVD | 3712 | Payload comprising a IVD gene or variant thereof packaged within a AAVC11.01 capsid. |
| 1 | AAVC11.02 | | IVD | 3712 | Payload comprising a IVD gene or variant thereof packaged within a AAVC11.02 capsid. |
| 1 | AAVC11.03 | | IVD | 3712 | Payload comprising a IVD gene or variant thereof packaged within a AAVC11.03 capsid. |
| 1 | AAVC11.04 | | IVD | 3712 | Payload comprising a IVD gene or variant thereof packaged within a AAVC11.04 capsid. |
| 1 | AAVC11.05 | | IVD | 3712 | Payload comprising a IVD gene or variant thereof packaged within a AAVC11.05 capsid. |
| 1 | AAVC11.06 | | IVD | 3712 | Payload comprising a IVD gene or variant thereof packaged within a AAVC11.06 capsid. |
| 1 | AAVC11.07 | | IVD | 3712 | Payload comprising a IVD gene or variant thereof packaged within a AAVC11.07 capsid |
| 1 | AAVC11.08 | | IVD | 3712 | Payload comprising a IVD gene or variant thereof packaged within a AAVC11.08 capsid. |
| 1 | AAVC11.09 | | IVD | 3712 | Payload comprising a IVD gene or variant thereof packaged within a AAVC11.09 capsid. |
| 1 | AAVC11.10 | | IVD | 3712 | Payload comprising a IVD gene or variant thereof packaged within a AAVC11.10 capsid. |
| 1 | AAVC11.11 | | IVD | 3712 | Payload comprising a IVD gene or variant thereof packaged within a AAVC11.11 capsid. |
| 1 | AAVC11.12 | | IVD | 3712 | Payload comprising a IVD gene or variant thereof packaged within a AAVC11.12 capsid. |
| 1 | AAVC11.13 | | IVD | 3712 | Payload comprising a IVD gene or variant thereof packaged within a AAVC11.13 capsid. |
| 1 | AAVC11.14 | | IVD | 3712 | Payload comprising a IVD gene or variant thereof packaged within a AAVC11.14 capsid. |
| 1 | AAVC11.15 | | IVD | 3712 | Payload comprising a IVD gene or variant thereof packaged within a AAVC11.15 capsid. |

Fig. 29 (Continued)

| | | | | | |
|---|---|---|---|---|---|
| 1 | AAVC11.16 | | IVD | 3712 | Payload comprising a IVD gene or variant thereof packaged within a AAVC11.16 capsid. |
| 1 | AAVC11.17 | | IVD | 3712 | Payload comprising a IVD gene or variant thereof packaged within a AAVC11.17 capsid. |
| 1 | AAVC11.18 | | IVD | 3712 | Payload comprising a IVD gene or variant thereof packaged within a AAVC11.18 capsid |
| 1 | AAVC11.19 | | IVD | 3712 | Payload comprising a IVD gene or variant thereof packaged within a AAVC11.19 capsid. |
| 1 | AAV12 | | IVD | 3712 | Payload comprising a IVD gene or variant thereof packaged within a AAV12 capsid. |
| 1 | AAV13 | | IVD | 3712 | Payload comprising a IVD gene or variant thereof packaged within a AAV13 capsid. |
| 1 | AAV-DJ | | IVD | 3712 | Payload comprising a IVD gene or variant thereof packaged within a AAV-DJ capsid |
| 1 | AAV-LK03 | | IVD | 3712 | Payload comprising a IVD gene or variant thereof packaged within a AAV-LK03 capsid. |
| 1 | AAV-LK19 | | IVD | 3712 | Payload comprising a IVD gene or variant thereof packaged within a AAV-LK19 capsid. |
| 1 | AAVrh.74 | | IVD | 3712 | Payload comprising a IVD gene or variant thereof packaged within a AAVrh.74 capsid. |
| 1 | AAVrh.10 | | IVD | 3712 | Payload comprising a IVD gene or variant thereof packaged within a AAVrh.10 capsid. |
| 1 | AAVhu.37 | | IVD | 3712 | Payload comprising a IVD gene or variant thereof packaged within a AAVhu.37 capsid. |
| 1 | AAVrh.K | | IVD | 3712 | Payload comprising a IVD gene or variant thereof packaged within a AAVrh.K capsid. |
| 1 | AAVrh.39 | | IVD | 3712 | Payload comprising a IVD gene or variant thereof packaged within a AAVrh.39 capsid. |
| 1 | AAVrh.9 | | IVD | 3712 | Payload comprising a IVD gene or variant thereof packaged within a AAVrh.9 capsid. |
| 1 | avian AAV | | IVD | 3712 | Payload comprising a IVD gene or variant thereof packaged within a avian capsid. |

Fig. 29 (Continued)

| | | | | | |
|---|---|---|---|---|---|
| 1 | bovine AAV | | IVD | 3712 | Payload comprising a IVD gene or variant thereof packaged within a bovine capsid. |
| 1 | canine AAV | | IVD | 3712 | Payload comprising a IVD gene or variant thereof packaged within a canine capsid. |
| 1 | equine AAV | | IVD | 3712 | Payload comprising a IVD gene or variant thereof packaged within a equine capsid. |
| 1 | primate AAV | | IVD | 3712 | Payload comprising a IVD gene or variant thereof packaged within a primate capsid. |
| 1 | non-primate AAV | | IVD | 3712 | Payload comprising a IVD gene or variant thereof packaged within a non-primate capsid. |
| 1 | ovine AAV | | IVD | 3712 | Payload comprising a IVD gene or variant thereof packaged within a ovine capsid. |
| 1 | hybrid AAV | | IVD | 3712 | Payload comprising a IVD gene or variant thereof packaged within a hybrid capsid. |
| 1 | chimeric AAV | | IVD | 3712 | Payload comprising a IVD gene or variant thereof packaged within a chimeric capsid. |
| 2 | AAV1 | 1450374 | IVD | 3712 | Payload comprising a IVD gene or variant thereof packaged within a AAV1 capsid. |
| 2 | AAV2 | | IVD | 3712 | Payload comprising a IVD gene or variant thereof packaged within a AAV2 capsid. |
| 2 | AAV3 | | IVD | 3712 | Payload comprising a IVD gene or variant thereof packaged within a AAV3 capsid. |
| 2 | AAV4 | 1446389 | IVD | 3712 | Payload comprising a IVD gene or variant thereof packaged within a AAV4 capsid. |
| 2 | AAV5 | | IVD | 3712 | Payload comprising a IVD gene or variant thereof packaged within a AAV5 capsid. |
| 2 | AAV6 | | IVD | 3712 | Payload comprising a IVD gene or variant thereof packaged within a AAV6 capsid. |
| 2 | AAV7 | | IVD | 3712 | Payload comprising a IVD gene or variant thereof packaged within a AAV7 capsid. |
| 2 | AAV8 | 5075992 | IVD | 3712 | Payload comprising a IVD gene or variant thereof packaged within a AAV8 capsid. |
| 2 | AAV9 | | IVD | 3712 | Payload comprising a IVD gene or variant thereof packaged within a AAV9 capsid. |

Fig. 29 (Continued)

| | | | | | |
|---|---|---|---|---|---|
| 2 | AAV10 | | IVD | 3712 | Payload comprising a IVD gene or variant thereof packaged within a AAV10 capsid. |
| 2 | AAV11 | | IVD | 3712 | Payload comprising a IVD gene or variant thereof packaged within a AAV11 capsid. |
| 2 | AAVC11.01 | | IVD | 3712 | Payload comprising a IVD gene or variant thereof packaged within a AAVC11.01 capsid. |
| 2 | AAVC11.02 | | IVD | 3712 | Payload comprising a IVD gene or variant thereof packaged within a AAVC11.02 capsid. |
| 2 | AAVC11.03 | | IVD | 3712 | Payload comprising a IVD gene or variant thereof packaged within a AAVC11.03 capsid. |
| 2 | AAVC11.04 | | IVD | 3712 | Payload comprising a IVD gene or variant thereof packaged within a AAVC11.04 capsid. |
| 2 | AAVC11.05 | | IVD | 3712 | Payload comprising a IVD gene or variant thereof packaged within a AAVC11.05 capsid. |
| 2 | AAVC11.06 | | IVD | 3712 | Payload comprising a IVD gene or variant thereof packaged within a AAVC11.06 capsid. |
| 2 | AAVC11.07 | | IVD | 3712 | Payload comprising a IVD gene or variant thereof packaged within a AAVC11.07 capsid |
| 2 | AAVC11.08 | | IVD | 3712 | Payload comprising a IVD gene or variant thereof packaged within a AAVC11.08 capsid. |
| 2 | AAVC11.09 | | IVD | 3712 | Payload comprising a IVD gene or variant thereof packaged within a AAVC11.09 capsid. |
| 2 | AAVC11.10 | | IVD | 3712 | Payload comprising a IVD gene or variant thereof packaged within a AAVC11.10 capsid. |
| 2 | AAVC11.11 | | IVD | 3712 | Payload comprising a IVD gene or variant thereof packaged within a AAVC11.11 capsid. |
| 2 | AAVC11.12 | | IVD | 3712 | Payload comprising a IVD gene or variant thereof packaged within a AAVC11.12 capsid. |
| 2 | AAVC11.13 | | IVD | 3712 | Payload comprising a IVD gene or variant thereof packaged within a AAVC11.13 capsid. |
| 2 | AAVC11.14 | | IVD | 3712 | Payload comprising a IVD gene or variant thereof packaged within a AAVC11.14 capsid. |
| 2 | AAVC11.15 | | IVD | 3712 | Payload comprising a IVD gene or variant thereof packaged within a AAVC11.15 capsid. |

Fig. 29 (Continued)

| | | | | | |
|---|---|---|---|---|---|
| 2 | AAVC11.16 | | IVD | 3712 | Payload comprising a IVD gene or variant thereof packaged within a AAVC11.16 capsid. |
| 2 | AAVC11.17 | | IVD | 3712 | Payload comprising a IVD gene or variant thereof packaged within a AAVC11.17 capsid. |
| 2 | AAVC11.18 | | IVD | 3712 | Payload comprising a IVD gene or variant thereof packaged within a AAVC11.18 capsid |
| 2 | AAVC11.19 | | IVD | 3712 | Payload comprising a IVD gene or variant thereof packaged within a AAVC11.19 capsid. |
| 2 | AAV12 | | IVD | 3712 | Payload comprising a IVD gene or variant thereof packaged within a AAV12 capsid. |
| 2 | AAV13 | | IVD | 3712 | Payload comprising a IVD gene or variant thereof packaged within a AAV13 capsid. |
| 2 | AAV-DJ | | IVD | 3712 | Payload comprising a IVD gene or variant thereof packaged within a AAV-DJ capsid |
| 2 | AAV-LK03 | | IVD | 3712 | Payload comprising a IVD gene or variant thereof packaged within a AAV-LK03 capsid. |
| 2 | AAV-LK19 | | IVD | 3712 | Payload comprising a IVD gene or variant thereof packaged within a AAV-LK19 capsid. |
| 2 | AAVrh.74 | | IVD | 3712 | Payload comprising a IVD gene or variant thereof packaged within a AAVrh.74 capsid. |
| 2 | AAVrh.10 | | IVD | 3712 | Payload comprising a IVD gene or variant thereof packaged within a AAVrh.10 capsid. |
| 2 | AAVhu.37 | | IVD | 3712 | Payload comprising a IVD gene or variant thereof packaged within a AAVhu.37 capsid. |
| 2 | AAVrh.K | | IVD | 3712 | Payload comprising a IVD gene or variant thereof packaged within a AAVrh.K capsid. |
| 2 | AAVrh.39 | | IVD | 3712 | Payload comprising a IVD gene or variant thereof packaged within a AAVrh.39 capsid. |
| 2 | AAVrh.9 | | IVD | 3712 | Payload comprising a IVD gene or variant thereof packaged within a AAVrh.9 capsid. |
| 2 | avian AAV | | IVD | 3712 | Payload comprising a IVD gene or variant thereof packaged within a avian capsid. |

Fig. 29 (Continued)

| | | | | | |
|---|---|---|---|---|---|
| 2 | bovine AAV | | IVD | 3712 | Payload comprising a IVD gene or variant thereof packaged within a bovine capsid. |
| 2 | canine AAV | | IVD | 3712 | Payload comprising a IVD gene or variant thereof packaged within a canine capsid. |
| 2 | equine AAV | | IVD | 3712 | Payload comprising a IVD gene or variant thereof packaged within a equine capsid. |
| 2 | primate AAV | | IVD | 3712 | Payload comprising a IVD gene or variant thereof packaged within a primate capsid. |
| 2 | non-primate AAV | | IVD | 3712 | Payload comprising a IVD gene or variant thereof packaged within a non-primate capsid. |
| 2 | ovine AAV | | IVD | 3712 | Payload comprising a IVD gene or variant thereof packaged within a ovine capsid. |
| 2 | hybrid AAV | | IVD | 3712 | Payload comprising a IVD gene or variant thereof packaged within a hybrid capsid. |
| 2 | chimeric AAV | | IVD | 3712 | Payload comprising a IVD gene or variant thereof packaged within a chimeric capsid. |
| 1 | AAV1 | 1450374 | KRT5 | 3852 | Payload comprising a KRT5 gene or variant thereof packaged within a AAV1 capsid. |
| 1 | AAV2 | | KRT5 | 3852 | Payload comprising a KRT5 gene or variant thereof packaged within a AAV2 capsid. |
| 1 | AAV3 | | KRT5 | 3852 | Payload comprising a KRT5 gene or variant thereof packaged within a AAV3 capsid. |
| 1 | AAV4 | 1446389 | KRT5 | 3852 | Payload comprising a KRT5 gene or variant thereof packaged within a AAV4 capsid. |
| 1 | AAV5 | | KRT5 | 3852 | Payload comprising a KRT5 gene or variant thereof packaged within a AAV5 capsid. |
| 1 | AAV6 | | KRT5 | 3852 | Payload comprising a KRT5 gene or variant thereof packaged within a AAV6 capsid. |
| 1 | AAV7 | | KRT5 | 3852 | Payload comprising a KRT5 gene or variant thereof packaged within a AAV7 capsid. |
| 1 | AAV8 | 5075992 | KRT5 | 3852 | Payload comprising a KRT5 gene or variant thereof packaged within a AAV8 capsid. |
| 1 | AAV9 | | KRT5 | 3852 | Payload comprising a KRT5 gene or variant thereof packaged within a AAV9 capsid. |

Fig. 29 (Continued)

| | | | | | |
|---|---|---|---|---|---|
| 1 | AAV10 | | KRT5 | 3852 | Payload comprising a KRT5 gene or variant thereof packaged within a AAV10 capsid. |
| 1 | AAV11 | | KRT5 | 3852 | Payload comprising a KRT5 gene or variant thereof packaged within a AAV11 capsid. |
| 1 | AAVC11.01 | | KRT5 | 3852 | Payload comprising a KRT5 gene or variant thereof packaged within a AAVC11.01 capsid. |
| 1 | AAVC11.02 | | KRT5 | 3852 | Payload comprising a KRT5 gene or variant thereof packaged within a AAVC11.02 capsid. |
| 1 | AAVC11.03 | | KRT5 | 3852 | Payload comprising a KRT5 gene or variant thereof packaged within a AAVC11.03 capsid. |
| 1 | AAVC11.04 | | KRT5 | 3852 | Payload comprising a KRT5 gene or variant thereof packaged within a AAVC11.04 capsid. |
| 1 | AAVC11.05 | | KRT5 | 3852 | Payload comprising a KRT5 gene or variant thereof packaged within a AAVC11.05 capsid. |
| 1 | AAVC11.06 | | KRT5 | 3852 | Payload comprising a KRT5 gene or variant thereof packaged within a AAVC11.06 capsid. |
| 1 | AAVC11.07 | | KRT5 | 3852 | Payload comprising a KRT5 gene or variant thereof packaged within a AAVC11.07 capsid |
| 1 | AAVC11.08 | | KRT5 | 3852 | Payload comprising a KRT5 gene or variant thereof packaged within a AAVC11.08 capsid. |
| 1 | AAVC11.09 | | KRT5 | 3852 | Payload comprising a KRT5 gene or variant thereof packaged within a AAVC11.09 capsid. |
| 1 | AAVC11.10 | | KRT5 | 3852 | Payload comprising a KRT5 gene or variant thereof packaged within a AAVC11.10 capsid. |
| 1 | AAVC11.11 | | KRT5 | 3852 | Payload comprising a KRT5 gene or variant thereof packaged within a AAVC11.11 capsid. |
| 1 | AAVC11.12 | | KRT5 | 3852 | Payload comprising a KRT5 gene or variant thereof packaged within a AAVC11.12 capsid. |
| 1 | AAVC11.13 | | KRT5 | 3852 | Payload comprising a KRT5 gene or variant thereof packaged within a AAVC11.13 capsid. |
| 1 | AAVC11.14 | | KRT5 | 3852 | Payload comprising a KRT5 gene or variant thereof packaged within a AAVC11.14 capsid. |
| 1 | AAVC11.15 | | KRT5 | 3852 | Payload comprising a KRT5 gene or variant thereof packaged within a AAVC11.15 capsid. |

Fig. 29 (Continued)

| | | | | | |
|---|---|---|---|---|---|
| 1 | AAVC11.16 | | KRT5 | 3852 | Payload comprising a KRT5 gene or variant thereof packaged within a AAVC11.16 capsid. |
| 1 | AAVC11.17 | | KRT5 | 3852 | Payload comprising a KRT5 gene or variant thereof packaged within a AAVC11.17 capsid. |
| 1 | AAVC11.18 | | KRT5 | 3852 | Payload comprising a KRT5 gene or variant thereof packaged within a AAVC11.18 capsid |
| 1 | AAVC11.19 | | KRT5 | 3852 | Payload comprising a KRT5 gene or variant thereof packaged within a AAVC11.19 capsid. |
| 1 | AAV12 | | KRT5 | 3852 | Payload comprising a KRT5 gene or variant thereof packaged within a AAV12 capsid. |
| 1 | AAV13 | | KRT5 | 3852 | Payload comprising a KRT5 gene or variant thereof packaged within a AAV13 capsid. |
| 1 | AAV-DJ | | KRT5 | 3852 | Payload comprising a KRT5 gene or variant thereof packaged within a AAV-DJ capsid |
| 1 | AAV-LK03 | | KRT5 | 3852 | Payload comprising a KRT5 gene or variant thereof packaged within a AAV-LK03 capsid. |
| 1 | AAV-LK19 | | KRT5 | 3852 | Payload comprising a KRT5 gene or variant thereof packaged within a AAV-LK19 capsid. |
| 1 | AAVrh.74 | | KRT5 | 3852 | Payload comprising a KRT5 gene or variant thereof packaged within a AAVrh.74 capsid. |
| 1 | AAVrh.10 | | KRT5 | 3852 | Payload comprising a KRT5 gene or variant thereof packaged within a AAVrh.10 capsid. |
| 1 | AAVhu.37 | | KRT5 | 3852 | Payload comprising a KRT5 gene or variant thereof packaged within a AAVhu.37 capsid. |
| 1 | AAVrh.K | | KRT5 | 3852 | Payload comprising a KRT5 gene or variant thereof packaged within a AAVrh.K capsid. |
| 1 | AAVrh.39 | | KRT5 | 3852 | Payload comprising a KRT5 gene or variant thereof packaged within a AAVrh.39 capsid. |
| 1 | AAVrh.9 | | KRT5 | 3852 | Payload comprising a KRT5 gene or variant thereof packaged within a AAVrh.9 capsid. |
| 1 | avian AAV | | KRT5 | 3852 | Payload comprising a KRT5 gene or variant thereof packaged within a avian capsid. |

Fig. 29 (Continued)

| | | | | | |
|---|---|---|---|---|---|
| 1 | bovine AAV | | KRT5 | 3852 | Payload comprising a KRT5 gene or variant thereof packaged within a bovine capsid. |
| 1 | canine AAV | | KRT5 | 3852 | Payload comprising a KRT5 gene or variant thereof packaged within a canine capsid. |
| 1 | equine AAV | | KRT5 | 3852 | Payload comprising a KRT5 gene or variant thereof packaged within a equine capsid. |
| 1 | primate AAV | | KRT5 | 3852 | Payload comprising a KRT5 gene or variant thereof packaged within a primate capsid. |
| 1 | non-primate AAV | | KRT5 | 3852 | Payload comprising a KRT5 gene or variant thereof packaged within a non-primate capsid. |
| 1 | ovine AAV | | KRT5 | 3852 | Payload comprising a KRT5 gene or variant thereof packaged within a ovine capsid. |
| 1 | hybrid AAV | | KRT5 | 3852 | Payload comprising a KRT5 gene or variant thereof packaged within a hybrid capsid. |
| 1 | chimeric AAV | | KRT5 | 3852 | Payload comprising a KRT5 gene or variant thereof packaged within a chimeric capsid. |
| 2 | AAV1 | 1450374 | KRT5 | 3852 | Payload comprising a KRT5 gene or variant thereof packaged within a AAV1 capsid. |
| 2 | AAV2 | | KRT5 | 3852 | Payload comprising a KRT5 gene or variant thereof packaged within a AAV2 capsid. |
| 2 | AAV3 | | KRT5 | 3852 | Payload comprising a KRT5 gene or variant thereof packaged within a AAV3 capsid. |
| 2 | AAV4 | 1446389 | KRT5 | 3852 | Payload comprising a KRT5 gene or variant thereof packaged within a AAV4 capsid. |
| 2 | AAV5 | | KRT5 | 3852 | Payload comprising a KRT5 gene or variant thereof packaged within a AAV5 capsid. |
| 2 | AAV6 | | KRT5 | 3852 | Payload comprising a KRT5 gene or variant thereof packaged within a AAV6 capsid. |
| 2 | AAV7 | | KRT5 | 3852 | Payload comprising a KRT5 gene or variant thereof packaged within a AAV7 capsid. |
| 2 | AAV8 | 5075992 | KRT5 | 3852 | Payload comprising a KRT5 gene or variant thereof packaged within a AAV8 capsid. |
| 2 | AAV9 | | KRT5 | 3852 | Payload comprising a KRT5 gene or variant thereof packaged within a AAV9 capsid. |

Fig. 29 (Continued)

| | | | | | |
|---|---|---|---|---|---|
| 2 | AAV10 | | KRT5 | 3852 | Payload comprising a KRT5 gene or variant thereof packaged within a AAV10 capsid. |
| 2 | AAV11 | | KRT5 | 3852 | Payload comprising a KRT5 gene or variant thereof packaged within a AAV11 capsid. |
| 2 | AAVC11.01 | | KRT5 | 3852 | Payload comprising a KRT5 gene or variant thereof packaged within a AAVC11.01 capsid. |
| 2 | AAVC11.02 | | KRT5 | 3852 | Payload comprising a KRT5 gene or variant thereof packaged within a AAVC11.02 capsid. |
| 2 | AAVC11.03 | | KRT5 | 3852 | Payload comprising a KRT5 gene or variant thereof packaged within a AAVC11.03 capsid. |
| 2 | AAVC11.04 | | KRT5 | 3852 | Payload comprising a KRT5 gene or variant thereof packaged within a AAVC11.04 capsid. |
| 2 | AAVC11.05 | | KRT5 | 3852 | Payload comprising a KRT5 gene or variant thereof packaged within a AAVC11.05 capsid. |
| 2 | AAVC11.06 | | KRT5 | 3852 | Payload comprising a KRT5 gene or variant thereof packaged within a AAVC11.06 capsid. |
| 2 | AAVC11.07 | | KRT5 | 3852 | Payload comprising a KRT5 gene or variant thereof packaged within a AAVC11.07 capsid |
| 2 | AAVC11.08 | | KRT5 | 3852 | Payload comprising a KRT5 gene or variant thereof packaged within a AAVC11.08 capsid. |
| 2 | AAVC11.09 | | KRT5 | 3852 | Payload comprising a KRT5 gene or variant thereof packaged within a AAVC11.09 capsid. |
| 2 | AAVC11.10 | | KRT5 | 3852 | Payload comprising a KRT5 gene or variant thereof packaged within a AAVC11.10 capsid. |
| 2 | AAVC11.11 | | KRT5 | 3852 | Payload comprising a KRT5 gene or variant thereof packaged within a AAVC11.11 capsid. |
| 2 | AAVC11.12 | | KRT5 | 3852 | Payload comprising a KRT5 gene or variant thereof packaged within a AAVC11.12 capsid. |
| 2 | AAVC11.13 | | KRT5 | 3852 | Payload comprising a KRT5 gene or variant thereof packaged within a AAVC11.13 capsid. |
| 2 | AAVC11.14 | | KRT5 | 3852 | Payload comprising a KRT5 gene or variant thereof packaged within a AAVC11.14 capsid. |
| 2 | AAVC11.15 | | KRT5 | 3852 | Payload comprising a KRT5 gene or variant thereof packaged within a AAVC11.15 capsid. |

Fig. 29 (Continued)

| | | | | | |
|---|---|---|---|---|---|
| 2 | AAVC11.16 | | KRT5 | 3852 | Payload comprising a KRT5 gene or variant thereof packaged within a AAVC11.16 capsid. |
| 2 | AAVC11.17 | | KRT5 | 3852 | Payload comprising a KRT5 gene or variant thereof packaged within a AAVC11.17 capsid. |
| 2 | AAVC11.18 | | KRT5 | 3852 | Payload comprising a KRT5 gene or variant thereof packaged within a AAVC11.18 capsid |
| 2 | AAVC11.19 | | KRT5 | 3852 | Payload comprising a KRT5 gene or variant thereof packaged within a AAVC11.19 capsid. |
| 2 | AAV12 | | KRT5 | 3852 | Payload comprising a KRT5 gene or variant thereof packaged within a AAV12 capsid. |
| 2 | AAV13 | | KRT5 | 3852 | Payload comprising a KRT5 gene or variant thereof packaged within a AAV13 capsid. |
| 2 | AAV-DJ | | KRT5 | 3852 | Payload comprising a KRT5 gene or variant thereof packaged within a AAV-DJ capsid |
| 2 | AAV-LK03 | | KRT5 | 3852 | Payload comprising a KRT5 gene or variant thereof packaged within a AAV-LK03 capsid. |
| 2 | AAV-LK19 | | KRT5 | 3852 | Payload comprising a KRT5 gene or variant thereof packaged within a AAV-LK19 capsid. |
| 2 | AAVrh.74 | | KRT5 | 3852 | Payload comprising a KRT5 gene or variant thereof packaged within a AAVrh.74 capsid. |
| 2 | AAVrh.10 | | KRT5 | 3852 | Payload comprising a KRT5 gene or variant thereof packaged within a AAVrh.10 capsid. |
| 2 | AAVhu.37 | | KRT5 | 3852 | Payload comprising a KRT5 gene or variant thereof packaged within a AAVhu.37 capsid. |
| 2 | AAVrh.K | | KRT5 | 3852 | Payload comprising a KRT5 gene or variant thereof packaged within a AAVrh.K capsid. |
| 2 | AAVrh.39 | | KRT5 | 3852 | Payload comprising a KRT5 gene or variant thereof packaged within a AAVrh.39 capsid. |
| 2 | AAVrh.9 | | KRT5 | 3852 | Payload comprising a KRT5 gene or variant thereof packaged within a AAVrh.9 capsid. |
| 2 | avian AAV | | KRT5 | 3852 | Payload comprising a KRT5 gene or variant thereof packaged within a avian capsid. |

Fig. 29 (Continued)

| | | | | | |
|---|---|---|---|---|---|
| 2 | bovine AAV | | KRT5 | 3852 | Payload comprising a KRT5 gene or variant thereof packaged within a bovine capsid. |
| 2 | canine AAV | | KRT5 | 3852 | Payload comprising a KRT5 gene or variant thereof packaged within a canine capsid. |
| 2 | equine AAV | | KRT5 | 3852 | Payload comprising a KRT5 gene or variant thereof packaged within a equine capsid. |
| 2 | primate AAV | | KRT5 | 3852 | Payload comprising a KRT5 gene or variant thereof packaged within a primate capsid. |
| 2 | non-primate AAV | | KRT5 | 3852 | Payload comprising a KRT5 gene or variant thereof packaged within a non-primate capsid. |
| 2 | ovine AAV | | KRT5 | 3852 | Payload comprising a KRT5 gene or variant thereof packaged within a ovine capsid. |
| 2 | hybrid AAV | | KRT5 | 3852 | Payload comprising a KRT5 gene or variant thereof packaged within a hybrid capsid. |
| 2 | chimeric AAV | | KRT5 | 3852 | Payload comprising a KRT5 gene or variant thereof packaged within a chimeric capsid. |
| 1 | AAV1 | 1450374 | LAMA3 | 3909 | Payload comprising a LAMA3 gene or variant thereof packaged within a AAV1 capsid. |
| 1 | AAV2 | | LAMA3 | 3909 | Payload comprising a LAMA3 gene or variant thereof packaged within a AAV2 capsid. |
| 1 | AAV3 | | LAMA3 | 3909 | Payload comprising a LAMA3 gene or variant thereof packaged within a AAV3 capsid. |
| 1 | AAV4 | 1446389 | LAMA3 | 3909 | Payload comprising a LAMA3 gene or variant thereof packaged within a AAV4 capsid. |
| 1 | AAV5 | | LAMA3 | 3909 | Payload comprising a LAMA3 gene or variant thereof packaged within a AAV5 capsid. |
| 1 | AAV6 | | LAMA3 | 3909 | Payload comprising a LAMA3 gene or variant thereof packaged within a AAV6 capsid. |
| 1 | AAV7 | | LAMA3 | 3909 | Payload comprising a LAMA3 gene or variant thereof packaged within a AAV7 capsid. |
| 1 | AAV8 | 5075992 | LAMA3 | 3909 | Payload comprising a LAMA3 gene or variant thereof packaged within a AAV8 capsid. |
| 1 | AAV9 | | LAMA3 | 3909 | Payload comprising a LAMA3 gene or variant thereof packaged within a AAV9 capsid. |

Fig. 29 (Continued)

| | | | | | |
|---|---|---|---|---|---|
| 1 | AAV10 | | LAMA3 | 3909 | Payload comprising a LAMA3 gene or variant thereof packaged within a AAV10 capsid. |
| 1 | AAV11 | | LAMA3 | 3909 | Payload comprising a LAMA3 gene or variant thereof packaged within a AAV11 capsid. |
| 1 | AAVC11.01 | | LAMA3 | 3909 | Payload comprising a LAMA3 gene or variant thereof packaged within a AAVC11.01 capsid. |
| 1 | AAVC11.02 | | LAMA3 | 3909 | Payload comprising a LAMA3 gene or variant thereof packaged within a AAVC11.02 capsid. |
| 1 | AAVC11.03 | | LAMA3 | 3909 | Payload comprising a LAMA3 gene or variant thereof packaged within a AAVC11.03 capsid. |
| 1 | AAVC11.04 | | LAMA3 | 3909 | Payload comprising a LAMA3 gene or variant thereof packaged within a AAVC11.04 capsid. |
| 1 | AAVC11.05 | | LAMA3 | 3909 | Payload comprising a LAMA3 gene or variant thereof packaged within a AAVC11.05 capsid. |
| 1 | AAVC11.06 | | LAMA3 | 3909 | Payload comprising a LAMA3 gene or variant thereof packaged within a AAVC11.06 capsid. |
| 1 | AAVC11.07 | | LAMA3 | 3909 | Payload comprising a LAMA3 gene or variant thereof packaged within a AAVC11.07 capsid |
| 1 | AAVC11.08 | | LAMA3 | 3909 | Payload comprising a LAMA3 gene or variant thereof packaged within a AAVC11.08 capsid. |
| 1 | AAVC11.09 | | LAMA3 | 3909 | Payload comprising a LAMA3 gene or variant thereof packaged within a AAVC11.09 capsid. |
| 1 | AAVC11.10 | | LAMA3 | 3909 | Payload comprising a LAMA3 gene or variant thereof packaged within a AAVC11.10 capsid. |
| 1 | AAVC11.11 | | LAMA3 | 3909 | Payload comprising a LAMA3 gene or variant thereof packaged within a AAVC11.11 capsid. |
| 1 | AAVC11.12 | | LAMA3 | 3909 | Payload comprising a LAMA3 gene or variant thereof packaged within a AAVC11.12 capsid. |
| 1 | AAVC11.13 | | LAMA3 | 3909 | Payload comprising a LAMA3 gene or variant thereof packaged within a AAVC11.13 capsid. |
| 1 | AAVC11.14 | | LAMA3 | 3909 | Payload comprising a LAMA3 gene or variant thereof packaged within a AAVC11.14 capsid. |
| 1 | AAVC11.15 | | LAMA3 | 3909 | Payload comprising a LAMA3 gene or variant thereof packaged within a AAVC11.15 capsid. |

Fig. 29 (Continued)

| | | | | | |
|---|---|---|---|---|---|
| 1 | AAVC11.16 | | LAMA3 | 3909 | Payload comprising a LAMA3 gene or variant thereof packaged within a AAVC11.16 capsid. |
| 1 | AAVC11.17 | | LAMA3 | 3909 | Payload comprising a LAMA3 gene or variant thereof packaged within a AAVC11.17 capsid. |
| 1 | AAVC11.18 | | LAMA3 | 3909 | Payload comprising a LAMA3 gene or variant thereof packaged within a AAVC11.18 capsid |
| 1 | AAVC11.19 | | LAMA3 | 3909 | Payload comprising a LAMA3 gene or variant thereof packaged within a AAVC11.19 capsid. |
| 1 | AAV12 | | LAMA3 | 3909 | Payload comprising a LAMA3 gene or variant thereof packaged within a AAV12 capsid. |
| 1 | AAV13 | | LAMA3 | 3909 | Payload comprising a LAMA3 gene or variant thereof packaged within a AAV13 capsid. |
| 1 | AAV-DJ | | LAMA3 | 3909 | Payload comprising a LAMA3 gene or variant thereof packaged within a AAV-DJ capsid |
| 1 | AAV-LK03 | | LAMA3 | 3909 | Payload comprising a LAMA3 gene or variant thereof packaged within a AAV-LK03 capsid. |
| 1 | AAV-LK19 | | LAMA3 | 3909 | Payload comprising a LAMA3 gene or variant thereof packaged within a AAV-LK19 capsid. |
| 1 | AAVrh.74 | | LAMA3 | 3909 | Payload comprising a LAMA3 gene or variant thereof packaged within a AAVrh.74 capsid. |
| 1 | AAVrh.10 | | LAMA3 | 3909 | Payload comprising a LAMA3 gene or variant thereof packaged within a AAVrh.10 capsid. |
| 1 | AAVhu.37 | | LAMA3 | 3909 | Payload comprising a LAMA3 gene or variant thereof packaged within a AAVhu.37 capsid. |
| 1 | AAVrh.K | | LAMA3 | 3909 | Payload comprising a LAMA3 gene or variant thereof packaged within a AAVrh.K capsid. |
| 1 | AAVrh.39 | | LAMA3 | 3909 | Payload comprising a LAMA3 gene or variant thereof packaged within a AAVrh.39 capsid. |
| 1 | AAVrh.9 | | LAMA3 | 3909 | Payload comprising a LAMA3 gene or variant thereof packaged within a AAVrh.9 capsid. |
| 1 | avian AAV | | LAMA3 | 3909 | Payload comprising a LAMA3 gene or variant thereof packaged within a avian capsid. |

Fig. 29 (Continued)

| | | | | | |
|---|---|---|---|---|---|
| 1 | bovine AAV | | LAMA3 | 3909 | Payload comprising a LAMA3 gene or variant thereof packaged within a bovine capsid. |
| 1 | canine AAV | | LAMA3 | 3909 | Payload comprising a LAMA3 gene or variant thereof packaged within a canine capsid. |
| 1 | equine AAV | | LAMA3 | 3909 | Payload comprising a LAMA3 gene or variant thereof packaged within a equine capsid. |
| 1 | primate AAV | | LAMA3 | 3909 | Payload comprising a LAMA3 gene or variant thereof packaged within a primate capsid. |
| 1 | non-primate AAV | | LAMA3 | 3909 | Payload comprising a LAMA3 gene or variant thereof packaged within a non-primate capsid. |
| 1 | ovine AAV | | LAMA3 | 3909 | Payload comprising a LAMA3 gene or variant thereof packaged within a ovine capsid. |
| 1 | hybrid AAV | | LAMA3 | 3909 | Payload comprising a LAMA3 gene or variant thereof packaged within a hybrid capsid. |
| 1 | chimeric AAV | | LAMA3 | 3909 | Payload comprising a LAMA3 gene or variant thereof packaged within a chimeric capsid. |
| 2 | AAV1 | 1450374 | LAMA3 | 3909 | Payload comprising a LAMA3 gene or variant thereof packaged within a AAV1 capsid. |
| 2 | AAV2 | | LAMA3 | 3909 | Payload comprising a LAMA3 gene or variant thereof packaged within a AAV2 capsid. |
| 2 | AAV3 | | LAMA3 | 3909 | Payload comprising a LAMA3 gene or variant thereof packaged within a AAV3 capsid. |
| 2 | AAV4 | 1446389 | LAMA3 | 3909 | Payload comprising a LAMA3 gene or variant thereof packaged within a AAV4 capsid. |
| 2 | AAV5 | | LAMA3 | 3909 | Payload comprising a LAMA3 gene or variant thereof packaged within a AAV5 capsid. |
| 2 | AAV6 | | LAMA3 | 3909 | Payload comprising a LAMA3 gene or variant thereof packaged within a AAV6 capsid. |
| 2 | AAV7 | | LAMA3 | 3909 | Payload comprising a LAMA3 gene or variant thereof packaged within a AAV7 capsid. |
| 2 | AAV8 | 5075992 | LAMA3 | 3909 | Payload comprising a LAMA3 gene or variant thereof packaged within a AAV8 capsid. |
| 2 | AAV9 | | LAMA3 | 3909 | Payload comprising a LAMA3 gene or variant thereof packaged within a AAV9 capsid. |

Fig. 29 (Continued)

| | | | | | |
|---|---|---|---|---|---|
| 2 | AAV10 | | LAMA3 | 3909 | Payload comprising a LAMA3 gene or variant thereof packaged within a AAV10 capsid. |
| 2 | AAV11 | | LAMA3 | 3909 | Payload comprising a LAMA3 gene or variant thereof packaged within a AAV11 capsid. |
| 2 | AAVC11.01 | | LAMA3 | 3909 | Payload comprising a LAMA3 gene or variant thereof packaged within a AAVC11.01 capsid. |
| 2 | AAVC11.02 | | LAMA3 | 3909 | Payload comprising a LAMA3 gene or variant thereof packaged within a AAVC11.02 capsid. |
| 2 | AAVC11.03 | | LAMA3 | 3909 | Payload comprising a LAMA3 gene or variant thereof packaged within a AAVC11.03 capsid. |
| 2 | AAVC11.04 | | LAMA3 | 3909 | Payload comprising a LAMA3 gene or variant thereof packaged within a AAVC11.04 capsid. |
| 2 | AAVC11.05 | | LAMA3 | 3909 | Payload comprising a LAMA3 gene or variant thereof packaged within a AAVC11.05 capsid. |
| 2 | AAVC11.06 | | LAMA3 | 3909 | Payload comprising a LAMA3 gene or variant thereof packaged within a AAVC11.06 capsid. |
| 2 | AAVC11.07 | | LAMA3 | 3909 | Payload comprising a LAMA3 gene or variant thereof packaged within a AAVC11.07 capsid |
| 2 | AAVC11.08 | | LAMA3 | 3909 | Payload comprising a LAMA3 gene or variant thereof packaged within a AAVC11.08 capsid. |
| 2 | AAVC11.09 | | LAMA3 | 3909 | Payload comprising a LAMA3 gene or variant thereof packaged within a AAVC11.09 capsid. |
| 2 | AAVC11.10 | | LAMA3 | 3909 | Payload comprising a LAMA3 gene or variant thereof packaged within a AAVC11.10 capsid. |
| 2 | AAVC11.11 | | LAMA3 | 3909 | Payload comprising a LAMA3 gene or variant thereof packaged within a AAVC11.11 capsid. |
| 2 | AAVC11.12 | | LAMA3 | 3909 | Payload comprising a LAMA3 gene or variant thereof packaged within a AAVC11.12 capsid. |
| 2 | AAVC11.13 | | LAMA3 | 3909 | Payload comprising a LAMA3 gene or variant thereof packaged within a AAVC11.13 capsid. |
| 2 | AAVC11.14 | | LAMA3 | 3909 | Payload comprising a LAMA3 gene or variant thereof packaged within a AAVC11.14 capsid. |
| 2 | AAVC11.15 | | LAMA3 | 3909 | Payload comprising a LAMA3 gene or variant thereof packaged within a AAVC11.15 capsid. |

Fig. 29 (Continued)

| | | | | | |
|---|---|---|---|---|---|
| 2 | AAVC11.16 | | LAMA3 | 3909 | Payload comprising a LAMA3 gene or variant thereof packaged within a AAVC11.16 capsid. |
| 2 | AAVC11.17 | | LAMA3 | 3909 | Payload comprising a LAMA3 gene or variant thereof packaged within a AAVC11.17 capsid. |
| 2 | AAVC11.18 | | LAMA3 | 3909 | Payload comprising a LAMA3 gene or variant thereof packaged within a AAVC11.18 capsid |
| 2 | AAVC11.19 | | LAMA3 | 3909 | Payload comprising a LAMA3 gene or variant thereof packaged within a AAVC11.19 capsid. |
| 2 | AAV12 | | LAMA3 | 3909 | Payload comprising a LAMA3 gene or variant thereof packaged within a AAV12 capsid. |
| 2 | AAV13 | | LAMA3 | 3909 | Payload comprising a LAMA3 gene or variant thereof packaged within a AAV13 capsid. |
| 2 | AAV-DJ | | LAMA3 | 3909 | Payload comprising a LAMA3 gene or variant thereof packaged within a AAV-DJ capsid |
| 2 | AAV-LK03 | | LAMA3 | 3909 | Payload comprising a LAMA3 gene or variant thereof packaged within a AAV-LK03 capsid. |
| 2 | AAV-LK19 | | LAMA3 | 3909 | Payload comprising a LAMA3 gene or variant thereof packaged within a AAV-LK19 capsid. |
| 2 | AAVrh.74 | | LAMA3 | 3909 | Payload comprising a LAMA3 gene or variant thereof packaged within a AAVrh.74 capsid. |
| 2 | AAVrh.10 | | LAMA3 | 3909 | Payload comprising a LAMA3 gene or variant thereof packaged within a AAVrh.10 capsid. |
| 2 | AAVhu.37 | | LAMA3 | 3909 | Payload comprising a LAMA3 gene or variant thereof packaged within a AAVhu.37 capsid. |
| 2 | AAVrh.K | | LAMA3 | 3909 | Payload comprising a LAMA3 gene or variant thereof packaged within a AAVrh.K capsid. |
| 2 | AAVrh.39 | | LAMA3 | 3909 | Payload comprising a LAMA3 gene or variant thereof packaged within a AAVrh.39 capsid. |
| 2 | AAVrh.9 | | LAMA3 | 3909 | Payload comprising a LAMA3 gene or variant thereof packaged within a AAVrh.9 capsid. |
| 2 | avian AAV | | LAMA3 | 3909 | Payload comprising a LAMA3 gene or variant thereof packaged within a avian capsid. |

Fig. 29 (Continued)

| | | | | | |
|---|---|---|---|---|---|
| 2 | bovine AAV | | LAMA3 | 3909 | Payload comprising a LAMA3 gene or variant thereof packaged within a bovine capsid. |
| 2 | canine AAV | | LAMA3 | 3909 | Payload comprising a LAMA3 gene or variant thereof packaged within a canine capsid. |
| 2 | equine AAV | | LAMA3 | 3909 | Payload comprising a LAMA3 gene or variant thereof packaged within a equine capsid. |
| 2 | primate AAV | | LAMA3 | 3909 | Payload comprising a LAMA3 gene or variant thereof packaged within a primate capsid. |
| 2 | non-primate AAV | | LAMA3 | 3909 | Payload comprising a LAMA3 gene or variant thereof packaged within a non-primate capsid. |
| 2 | ovine AAV | | LAMA3 | 3909 | Payload comprising a LAMA3 gene or variant thereof packaged within a ovine capsid. |
| 2 | hybrid AAV | | LAMA3 | 3909 | Payload comprising a LAMA3 gene or variant thereof packaged within a hybrid capsid. |
| 2 | chimeric AAV | | LAMA3 | 3909 | Payload comprising a LAMA3 gene or variant thereof packaged within a chimeric capsid. |
| 1 | AAV1 | 1450374 | LAMB3 | 3914 | Payload comprising a LAMB3 gene or variant thereof packaged within a AAV1 capsid. |
| 1 | AAV2 | | LAMB3 | 3914 | Payload comprising a LAMB3 gene or variant thereof packaged within a AAV2 capsid. |
| 1 | AAV3 | | LAMB3 | 3914 | Payload comprising a LAMB3 gene or variant thereof packaged within a AAV3 capsid. |
| 1 | AAV4 | 1446389 | LAMB3 | 3914 | Payload comprising a LAMB3 gene or variant thereof packaged within a AAV4 capsid. |
| 1 | AAV5 | | LAMB3 | 3914 | Payload comprising a LAMB3 gene or variant thereof packaged within a AAV5 capsid. |
| 1 | AAV6 | | LAMB3 | 3914 | Payload comprising a LAMB3 gene or variant thereof packaged within a AAV6 capsid. |
| 1 | AAV7 | | LAMB3 | 3914 | Payload comprising a LAMB3 gene or variant thereof packaged within a AAV7 capsid. |
| 1 | AAV8 | 5075992 | LAMB3 | 3914 | Payload comprising a LAMB3 gene or variant thereof packaged within a AAV8 capsid. |
| 1 | AAV9 | | LAMB3 | 3914 | Payload comprising a LAMB3 gene or variant thereof packaged within a AAV9 capsid. |

Fig. 29 (Continued)

| | | | | | |
|---|---|---|---|---|---|
| 1 | AAV10 | | LAMB3 | 3914 | Payload comprising a LAMB3 gene or variant thereof packaged within a AAV10 capsid. |
| 1 | AAV11 | | LAMB3 | 3914 | Payload comprising a LAMB3 gene or variant thereof packaged within a AAV11 capsid. |
| 1 | AAVC11.01 | | LAMB3 | 3914 | Payload comprising a LAMB3 gene or variant thereof packaged within a AAVC11.01 capsid. |
| 1 | AAVC11.02 | | LAMB3 | 3914 | Payload comprising a LAMB3 gene or variant thereof packaged within a AAVC11.02 capsid. |
| 1 | AAVC11.03 | | LAMB3 | 3914 | Payload comprising a LAMB3 gene or variant thereof packaged within a AAVC11.03 capsid. |
| 1 | AAVC11.04 | | LAMB3 | 3914 | Payload comprising a LAMB3 gene or variant thereof packaged within a AAVC11.04 capsid. |
| 1 | AAVC11.05 | | LAMB3 | 3914 | Payload comprising a LAMB3 gene or variant thereof packaged within a AAVC11.05 capsid. |
| 1 | AAVC11.06 | | LAMB3 | 3914 | Payload comprising a LAMB3 gene or variant thereof packaged within a AAVC11.06 capsid. |
| 1 | AAVC11.07 | | LAMB3 | 3914 | Payload comprising a LAMB3 gene or variant thereof packaged within a AAVC11.07 capsid |
| 1 | AAVC11.08 | | LAMB3 | 3914 | Payload comprising a LAMB3 gene or variant thereof packaged within a AAVC11.08 capsid. |
| 1 | AAVC11.09 | | LAMB3 | 3914 | Payload comprising a LAMB3 gene or variant thereof packaged within a AAVC11.09 capsid. |
| 1 | AAVC11.10 | | LAMB3 | 3914 | Payload comprising a LAMB3 gene or variant thereof packaged within a AAVC11.10 capsid. |
| 1 | AAVC11.11 | | LAMB3 | 3914 | Payload comprising a LAMB3 gene or variant thereof packaged within a AAVC11.11 capsid. |
| 1 | AAVC11.12 | | LAMB3 | 3914 | Payload comprising a LAMB3 gene or variant thereof packaged within a AAVC11.12 capsid. |
| 1 | AAVC11.13 | | LAMB3 | 3914 | Payload comprising a LAMB3 gene or variant thereof packaged within a AAVC11.13 capsid. |
| 1 | AAVC11.14 | | LAMB3 | 3914 | Payload comprising a LAMB3 gene or variant thereof packaged within a AAVC11.14 capsid. |
| 1 | AAVC11.15 | | LAMB3 | 3914 | Payload comprising a LAMB3 gene or variant thereof packaged within a AAVC11.15 capsid. |

Fig. 29 (Continued)

| | | | | | |
|---|---|---|---|---|---|
| 1 | AAVC11.16 | | LAMB3 | 3914 | Payload comprising a LAMB3 gene or variant thereof packaged within a AAVC11.16 capsid. |
| 1 | AAVC11.17 | | LAMB3 | 3914 | Payload comprising a LAMB3 gene or variant thereof packaged within a AAVC11.17 capsid. |
| 1 | AAVC11.18 | | LAMB3 | 3914 | Payload comprising a LAMB3 gene or variant thereof packaged within a AAVC11.18 capsid |
| 1 | AAVC11.19 | | LAMB3 | 3914 | Payload comprising a LAMB3 gene or variant thereof packaged within a AAVC11.19 capsid. |
| 1 | AAV12 | | LAMB3 | 3914 | Payload comprising a LAMB3 gene or variant thereof packaged within a AAV12 capsid. |
| 1 | AAV13 | | LAMB3 | 3914 | Payload comprising a LAMB3 gene or variant thereof packaged within a AAV13 capsid. |
| 1 | AAV-DJ | | LAMB3 | 3914 | Payload comprising a LAMB3 gene or variant thereof packaged within a AAV-DJ capsid |
| 1 | AAV-LK03 | | LAMB3 | 3914 | Payload comprising a LAMB3 gene or variant thereof packaged within a AAV-LK03 capsid. |
| 1 | AAV-LK19 | | LAMB3 | 3914 | Payload comprising a LAMB3 gene or variant thereof packaged within a AAV-LK19 capsid. |
| 1 | AAVrh.74 | | LAMB3 | 3914 | Payload comprising a LAMB3 gene or variant thereof packaged within a AAVrh.74 capsid. |
| 1 | AAVrh.10 | | LAMB3 | 3914 | Payload comprising a LAMB3 gene or variant thereof packaged within a AAVrh.10 capsid. |
| 1 | AAVhu.37 | | LAMB3 | 3914 | Payload comprising a LAMB3 gene or variant thereof packaged within a AAVhu.37 capsid. |
| 1 | AAVrh.K | | LAMB3 | 3914 | Payload comprising a LAMB3 gene or variant thereof packaged within a AAVrh.K capsid. |
| 1 | AAVrh.39 | | LAMB3 | 3914 | Payload comprising a LAMB3 gene or variant thereof packaged within a AAVrh.39 capsid. |
| 1 | AAVrh.9 | | LAMB3 | 3914 | Payload comprising a LAMB3 gene or variant thereof packaged within a AAVrh.9 capsid. |
| 1 | avian AAV | | LAMB3 | 3914 | Payload comprising a LAMB3 gene or variant thereof packaged within a avian capsid. |

Fig. 29 (Continued)

| | | | | | |
|---|---|---|---|---|---|
| 1 | bovine AAV | | LAMB3 | 3914 | Payload comprising a LAMB3 gene or variant thereof packaged within a bovine capsid. |
| 1 | canine AAV | | LAMB3 | 3914 | Payload comprising a LAMB3 gene or variant thereof packaged within a canine capsid. |
| 1 | equine AAV | | LAMB3 | 3914 | Payload comprising a LAMB3 gene or variant thereof packaged within a equine capsid. |
| 1 | primate AAV | | LAMB3 | 3914 | Payload comprising a LAMB3 gene or variant thereof packaged within a primate capsid. |
| 1 | non-primate AAV | | LAMB3 | 3914 | Payload comprising a LAMB3 gene or variant thereof packaged within a non-primate capsid. |
| 1 | ovine AAV | | LAMB3 | 3914 | Payload comprising a LAMB3 gene or variant thereof packaged within a ovine capsid. |
| 1 | hybrid AAV | | LAMB3 | 3914 | Payload comprising a LAMB3 gene or variant thereof packaged within a hybrid capsid. |
| 1 | chimeric AAV | | LAMB3 | 3914 | Payload comprising a LAMB3 gene or variant thereof packaged within a chimeric capsid. |
| 2 | AAV1 | 1450374 | LAMB3 | 3914 | Payload comprising a LAMB3 gene or variant thereof packaged within a AAV1 capsid. |
| 2 | AAV2 | | LAMB3 | 3914 | Payload comprising a LAMB3 gene or variant thereof packaged within a AAV2 capsid. |
| 2 | AAV3 | | LAMB3 | 3914 | Payload comprising a LAMB3 gene or variant thereof packaged within a AAV3 capsid. |
| 2 | AAV4 | 1446389 | LAMB3 | 3914 | Payload comprising a LAMB3 gene or variant thereof packaged within a AAV4 capsid. |
| 2 | AAV5 | | LAMB3 | 3914 | Payload comprising a LAMB3 gene or variant thereof packaged within a AAV5 capsid. |
| 2 | AAV6 | | LAMB3 | 3914 | Payload comprising a LAMB3 gene or variant thereof packaged within a AAV6 capsid. |
| 2 | AAV7 | | LAMB3 | 3914 | Payload comprising a LAMB3 gene or variant thereof packaged within a AAV7 capsid. |
| 2 | AAV8 | 5075992 | LAMB3 | 3914 | Payload comprising a LAMB3 gene or variant thereof packaged within a AAV8 capsid. |
| 2 | AAV9 | | LAMB3 | 3914 | Payload comprising a LAMB3 gene or variant thereof packaged within a AAV9 capsid. |

Fig. 29 (Continued)

| | | | | | |
|---|---|---|---|---|---|
| 2 | AAV10 | | LAMB3 | 3914 | Payload comprising a LAMB3 gene or variant thereof packaged within a AAV10 capsid. |
| 2 | AAV11 | | LAMB3 | 3914 | Payload comprising a LAMB3 gene or variant thereof packaged within a AAV11 capsid. |
| 2 | AAVC11.01 | | LAMB3 | 3914 | Payload comprising a LAMB3 gene or variant thereof packaged within a AAVC11.01 capsid. |
| 2 | AAVC11.02 | | LAMB3 | 3914 | Payload comprising a LAMB3 gene or variant thereof packaged within a AAVC11.02 capsid. |
| 2 | AAVC11.03 | | LAMB3 | 3914 | Payload comprising a LAMB3 gene or variant thereof packaged within a AAVC11.03 capsid. |
| 2 | AAVC11.04 | | LAMB3 | 3914 | Payload comprising a LAMB3 gene or variant thereof packaged within a AAVC11.04 capsid. |
| 2 | AAVC11.05 | | LAMB3 | 3914 | Payload comprising a LAMB3 gene or variant thereof packaged within a AAVC11.05 capsid. |
| 2 | AAVC11.06 | | LAMB3 | 3914 | Payload comprising a LAMB3 gene or variant thereof packaged within a AAVC11.06 capsid. |
| 2 | AAVC11.07 | | LAMB3 | 3914 | Payload comprising a LAMB3 gene or variant thereof packaged within a AAVC11.07 capsid |
| 2 | AAVC11.08 | | LAMB3 | 3914 | Payload comprising a LAMB3 gene or variant thereof packaged within a AAVC11.08 capsid. |
| 2 | AAVC11.09 | | LAMB3 | 3914 | Payload comprising a LAMB3 gene or variant thereof packaged within a AAVC11.09 capsid. |
| 2 | AAVC11.10 | | LAMB3 | 3914 | Payload comprising a LAMB3 gene or variant thereof packaged within a AAVC11.10 capsid. |
| 2 | AAVC11.11 | | LAMB3 | 3914 | Payload comprising a LAMB3 gene or variant thereof packaged within a AAVC11.11 capsid. |
| 2 | AAVC11.12 | | LAMB3 | 3914 | Payload comprising a LAMB3 gene or variant thereof packaged within a AAVC11.12 capsid. |
| 2 | AAVC11.13 | | LAMB3 | 3914 | Payload comprising a LAMB3 gene or variant thereof packaged within a AAVC11.13 capsid. |
| 2 | AAVC11.14 | | LAMB3 | 3914 | Payload comprising a LAMB3 gene or variant thereof packaged within a AAVC11.14 capsid. |
| 2 | AAVC11.15 | | LAMB3 | 3914 | Payload comprising a LAMB3 gene or variant thereof packaged within a AAVC11.15 capsid. |

Fig. 29 (Continued)

| | | | | | |
|---|---|---|---|---|---|
| 2 | AAVC11.16 | | LAMB3 | 3914 | Payload comprising a LAMB3 gene or variant thereof packaged within a AAVC11.16 capsid. |
| 2 | AAVC11.17 | | LAMB3 | 3914 | Payload comprising a LAMB3 gene or variant thereof packaged within a AAVC11.17 capsid. |
| 2 | AAVC11.18 | | LAMB3 | 3914 | Payload comprising a LAMB3 gene or variant thereof packaged within a AAVC11.18 capsid |
| 2 | AAVC11.19 | | LAMB3 | 3914 | Payload comprising a LAMB3 gene or variant thereof packaged within a AAVC11.19 capsid. |
| 2 | AAV12 | | LAMB3 | 3914 | Payload comprising a LAMB3 gene or variant thereof packaged within a AAV12 capsid. |
| 2 | AAV13 | | LAMB3 | 3914 | Payload comprising a LAMB3 gene or variant thereof packaged within a AAV13 capsid. |
| 2 | AAV-DJ | | LAMB3 | 3914 | Payload comprising a LAMB3 gene or variant thereof packaged within a AAV-DJ capsid |
| 2 | AAV-LK03 | | LAMB3 | 3914 | Payload comprising a LAMB3 gene or variant thereof packaged within a AAV-LK03 capsid. |
| 2 | AAV-LK19 | | LAMB3 | 3914 | Payload comprising a LAMB3 gene or variant thereof packaged within a AAV-LK19 capsid. |
| 2 | AAVrh.74 | | LAMB3 | 3914 | Payload comprising a LAMB3 gene or variant thereof packaged within a AAVrh.74 capsid. |
| 2 | AAVrh.10 | | LAMB3 | 3914 | Payload comprising a LAMB3 gene or variant thereof packaged within a AAVrh.10 capsid. |
| 2 | AAVhu.37 | | LAMB3 | 3914 | Payload comprising a LAMB3 gene or variant thereof packaged within a AAVhu.37 capsid. |
| 2 | AAVrh.K | | LAMB3 | 3914 | Payload comprising a LAMB3 gene or variant thereof packaged within a AAVrh.K capsid. |
| 2 | AAVrh.39 | | LAMB3 | 3914 | Payload comprising a LAMB3 gene or variant thereof packaged within a AAVrh.39 capsid. |
| 2 | AAVrh.9 | | LAMB3 | 3914 | Payload comprising a LAMB3 gene or variant thereof packaged within a AAVrh.9 capsid. |
| 2 | avian AAV | | LAMB3 | 3914 | Payload comprising a LAMB3 gene or variant thereof packaged within a avian capsid. |

Fig. 29 (Continued)

| | | | | | |
|---|---|---|---|---|---|
| 2 | bovine AAV | | LAMB3 | 3914 | Payload comprising a LAMB3 gene or variant thereof packaged within a bovine capsid. |
| 2 | canine AAV | | LAMB3 | 3914 | Payload comprising a LAMB3 gene or variant thereof packaged within a canine capsid. |
| 2 | equine AAV | | LAMB3 | 3914 | Payload comprising a LAMB3 gene or variant thereof packaged within a equine capsid. |
| 2 | primate AAV | | LAMB3 | 3914 | Payload comprising a LAMB3 gene or variant thereof packaged within a primate capsid. |
| 2 | non-primate AAV | | LAMB3 | 3914 | Payload comprising a LAMB3 gene or variant thereof packaged within a non-primate capsid. |
| 2 | ovine AAV | | LAMB3 | 3914 | Payload comprising a LAMB3 gene or variant thereof packaged within a ovine capsid. |
| 2 | hybrid AAV | | LAMB3 | 3914 | Payload comprising a LAMB3 gene or variant thereof packaged within a hybrid capsid. |
| 2 | chimeric AAV | | LAMB3 | 3914 | Payload comprising a LAMB3 gene or variant thereof packaged within a chimeric capsid. |
| 1 | AAV1 | 1450374 | LAMC2 | 3918 | Payload comprising a LAMC2 gene or variant thereof packaged within a AAV1 capsid. |
| 1 | AAV2 | | LAMC2 | 3918 | Payload comprising a LAMC2 gene or variant thereof packaged within a AAV2 capsid. |
| 1 | AAV3 | | LAMC2 | 3918 | Payload comprising a LAMC2 gene or variant thereof packaged within a AAV3 capsid. |
| 1 | AAV4 | 1446389 | LAMC2 | 3918 | Payload comprising a LAMC2 gene or variant thereof packaged within a AAV4 capsid. |
| 1 | AAV5 | | LAMC2 | 3918 | Payload comprising a LAMC2 gene or variant thereof packaged within a AAV5 capsid. |
| 1 | AAV6 | | LAMC2 | 3918 | Payload comprising a LAMC2 gene or variant thereof packaged within a AAV6 capsid. |
| 1 | AAV7 | | LAMC2 | 3918 | Payload comprising a LAMC2 gene or variant thereof packaged within a AAV7 capsid. |
| 1 | AAV8 | 5075992 | LAMC2 | 3918 | Payload comprising a LAMC2 gene or variant thereof packaged within a AAV8 capsid. |
| 1 | AAV9 | | LAMC2 | 3918 | Payload comprising a LAMC2 gene or variant thereof packaged within a AAV9 capsid. |

Fig. 29 (Continued)

| | | | | | |
|---|---|---|---|---|---|
| 1 | AAV10 | | LAMC2 | 3918 | Payload comprising a LAMC2 gene or variant thereof packaged within a AAV10 capsid. |
| 1 | AAV11 | | LAMC2 | 3918 | Payload comprising a LAMC2 gene or variant thereof packaged within a AAV11 capsid. |
| 1 | AAVC11.01 | | LAMC2 | 3918 | Payload comprising a LAMC2 gene or variant thereof packaged within a AAVC11.01 capsid. |
| 1 | AAVC11.02 | | LAMC2 | 3918 | Payload comprising a LAMC2 gene or variant thereof packaged within a AAVC11.02 capsid. |
| 1 | AAVC11.03 | | LAMC2 | 3918 | Payload comprising a LAMC2 gene or variant thereof packaged within a AAVC11.03 capsid. |
| 1 | AAVC11.04 | | LAMC2 | 3918 | Payload comprising a LAMC2 gene or variant thereof packaged within a AAVC11.04 capsid. |
| 1 | AAVC11.05 | | LAMC2 | 3918 | Payload comprising a LAMC2 gene or variant thereof packaged within a AAVC11.05 capsid. |
| 1 | AAVC11.06 | | LAMC2 | 3918 | Payload comprising a LAMC2 gene or variant thereof packaged within a AAVC11.06 capsid. |
| 1 | AAVC11.07 | | LAMC2 | 3918 | Payload comprising a LAMC2 gene or variant thereof packaged within a AAVC11.07 capsid |
| 1 | AAVC11.08 | | LAMC2 | 3918 | Payload comprising a LAMC2 gene or variant thereof packaged within a AAVC11.08 capsid. |
| 1 | AAVC11.09 | | LAMC2 | 3918 | Payload comprising a LAMC2 gene or variant thereof packaged within a AAVC11.09 capsid. |
| 1 | AAVC11.10 | | LAMC2 | 3918 | Payload comprising a LAMC2 gene or variant thereof packaged within a AAVC11.10 capsid. |
| 1 | AAVC11.11 | | LAMC2 | 3918 | Payload comprising a LAMC2 gene or variant thereof packaged within a AAVC11.11 capsid. |
| 1 | AAVC11.12 | | LAMC2 | 3918 | Payload comprising a LAMC2 gene or variant thereof packaged within a AAVC11.12 capsid. |
| 1 | AAVC11.13 | | LAMC2 | 3918 | Payload comprising a LAMC2 gene or variant thereof packaged within a AAVC11.13 capsid. |
| 1 | AAVC11.14 | | LAMC2 | 3918 | Payload comprising a LAMC2 gene or variant thereof packaged within a AAVC11.14 capsid. |
| 1 | AAVC11.15 | | LAMC2 | 3918 | Payload comprising a LAMC2 gene or variant thereof packaged within a AAVC11.15 capsid. |

Fig. 29 (Continued)

| | | | | | |
|---|---|---|---|---|---|
| 1 | AAVC11.16 | | LAMC2 | 3918 | Payload comprising a LAMC2 gene or variant thereof packaged within a AAVC11.16 capsid. |
| 1 | AAVC11.17 | | LAMC2 | 3918 | Payload comprising a LAMC2 gene or variant thereof packaged within a AAVC11.17 capsid. |
| 1 | AAVC11.18 | | LAMC2 | 3918 | Payload comprising a LAMC2 gene or variant thereof packaged within a AAVC11.18 capsid |
| 1 | AAVC11.19 | | LAMC2 | 3918 | Payload comprising a LAMC2 gene or variant thereof packaged within a AAVC11.19 capsid. |
| 1 | AAV12 | | LAMC2 | 3918 | Payload comprising a LAMC2 gene or variant thereof packaged within a AAV12 capsid. |
| 1 | AAV13 | | LAMC2 | 3918 | Payload comprising a LAMC2 gene or variant thereof packaged within a AAV13 capsid. |
| 1 | AAV-DJ | | LAMC2 | 3918 | Payload comprising a LAMC2 gene or variant thereof packaged within a AAV-DJ capsid |
| 1 | AAV-LK03 | | LAMC2 | 3918 | Payload comprising a LAMC2 gene or variant thereof packaged within a AAV-LK03 capsid. |
| 1 | AAV-LK19 | | LAMC2 | 3918 | Payload comprising a LAMC2 gene or variant thereof packaged within a AAV-LK19 capsid. |
| 1 | AAVrh.74 | | LAMC2 | 3918 | Payload comprising a LAMC2 gene or variant thereof packaged within a AAVrh.74 capsid. |
| 1 | AAVrh.10 | | LAMC2 | 3918 | Payload comprising a LAMC2 gene or variant thereof packaged within a AAVrh.10 capsid. |
| 1 | AAVhu.37 | | LAMC2 | 3918 | Payload comprising a LAMC2 gene or variant thereof packaged within a AAVhu.37 capsid. |
| 1 | AAVrh.K | | LAMC2 | 3918 | Payload comprising a LAMC2 gene or variant thereof packaged within a AAVrh.K capsid. |
| 1 | AAVrh.39 | | LAMC2 | 3918 | Payload comprising a LAMC2 gene or variant thereof packaged within a AAVrh.39 capsid. |
| 1 | AAVrh.9 | | LAMC2 | 3918 | Payload comprising a LAMC2 gene or variant thereof packaged within a AAVrh.9 capsid. |
| 1 | avian AAV | | LAMC2 | 3918 | Payload comprising a LAMC2 gene or variant thereof packaged within a avian capsid. |

Fig. 29 (Continued)

| | | | | | |
|---|---|---|---|---|---|
| 1 | bovine AAV | | LAMC2 | 3918 | Payload comprising a LAMC2 gene or variant thereof packaged within a bovine capsid. |
| 1 | canine AAV | | LAMC2 | 3918 | Payload comprising a LAMC2 gene or variant thereof packaged within a canine capsid. |
| 1 | equine AAV | | LAMC2 | 3918 | Payload comprising a LAMC2 gene or variant thereof packaged within a equine capsid. |
| 1 | primate AAV | | LAMC2 | 3918 | Payload comprising a LAMC2 gene or variant thereof packaged within a primate capsid. |
| 1 | non-primate AAV | | LAMC2 | 3918 | Payload comprising a LAMC2 gene or variant thereof packaged within a non-primate capsid. |
| 1 | ovine AAV | | LAMC2 | 3918 | Payload comprising a LAMC2 gene or variant thereof packaged within a ovine capsid. |
| 1 | hybrid AAV | | LAMC2 | 3918 | Payload comprising a LAMC2 gene or variant thereof packaged within a hybrid capsid. |
| 1 | chimeric AAV | | LAMC2 | 3918 | Payload comprising a LAMC2 gene or variant thereof packaged within a chimeric capsid. |
| 2 | AAV1 | 1450374 | LAMC2 | 3918 | Payload comprising a LAMC2 gene or variant thereof packaged within a AAV1 capsid. |
| 2 | AAV2 | | LAMC2 | 3918 | Payload comprising a LAMC2 gene or variant thereof packaged within a AAV2 capsid. |
| 2 | AAV3 | | LAMC2 | 3918 | Payload comprising a LAMC2 gene or variant thereof packaged within a AAV3 capsid. |
| 2 | AAV4 | 1446389 | LAMC2 | 3918 | Payload comprising a LAMC2 gene or variant thereof packaged within a AAV4 capsid. |
| 2 | AAV5 | | LAMC2 | 3918 | Payload comprising a LAMC2 gene or variant thereof packaged within a AAV5 capsid. |
| 2 | AAV6 | | LAMC2 | 3918 | Payload comprising a LAMC2 gene or variant thereof packaged within a AAV6 capsid. |
| 2 | AAV7 | | LAMC2 | 3918 | Payload comprising a LAMC2 gene or variant thereof packaged within a AAV7 capsid. |
| 2 | AAV8 | 5075992 | LAMC2 | 3918 | Payload comprising a LAMC2 gene or variant thereof packaged within a AAV8 capsid. |
| 2 | AAV9 | | LAMC2 | 3918 | Payload comprising a LAMC2 gene or variant thereof packaged within a AAV9 capsid. |

Fig. 29 (Continued)

| | | | | | |
|---|---|---|---|---|---|
| 2 | AAV10 | | LAMC2 | 3918 | Payload comprising a LAMC2 gene or variant thereof packaged within a AAV10 capsid. |
| 2 | AAV11 | | LAMC2 | 3918 | Payload comprising a LAMC2 gene or variant thereof packaged within a AAV11 capsid. |
| 2 | AAVC11.01 | | LAMC2 | 3918 | Payload comprising a LAMC2 gene or variant thereof packaged within a AAVC11.01 capsid. |
| 2 | AAVC11.02 | | LAMC2 | 3918 | Payload comprising a LAMC2 gene or variant thereof packaged within a AAVC11.02 capsid. |
| 2 | AAVC11.03 | | LAMC2 | 3918 | Payload comprising a LAMC2 gene or variant thereof packaged within a AAVC11.03 capsid. |
| 2 | AAVC11.04 | | LAMC2 | 3918 | Payload comprising a LAMC2 gene or variant thereof packaged within a AAVC11.04 capsid. |
| 2 | AAVC11.05 | | LAMC2 | 3918 | Payload comprising a LAMC2 gene or variant thereof packaged within a AAVC11.05 capsid. |
| 2 | AAVC11.06 | | LAMC2 | 3918 | Payload comprising a LAMC2 gene or variant thereof packaged within a AAVC11.06 capsid. |
| 2 | AAVC11.07 | | LAMC2 | 3918 | Payload comprising a LAMC2 gene or variant thereof packaged within a AAVC11.07 capsid |
| 2 | AAVC11.08 | | LAMC2 | 3918 | Payload comprising a LAMC2 gene or variant thereof packaged within a AAVC11.08 capsid. |
| 2 | AAVC11.09 | | LAMC2 | 3918 | Payload comprising a LAMC2 gene or variant thereof packaged within a AAVC11.09 capsid. |
| 2 | AAVC11.10 | | LAMC2 | 3918 | Payload comprising a LAMC2 gene or variant thereof packaged within a AAVC11.10 capsid. |
| 2 | AAVC11.11 | | LAMC2 | 3918 | Payload comprising a LAMC2 gene or variant thereof packaged within a AAVC11.11 capsid. |
| 2 | AAVC11.12 | | LAMC2 | 3918 | Payload comprising a LAMC2 gene or variant thereof packaged within a AAVC11.12 capsid. |
| 2 | AAVC11.13 | | LAMC2 | 3918 | Payload comprising a LAMC2 gene or variant thereof packaged within a AAVC11.13 capsid. |
| 2 | AAVC11.14 | | LAMC2 | 3918 | Payload comprising a LAMC2 gene or variant thereof packaged within a AAVC11.14 capsid. |
| 2 | AAVC11.15 | | LAMC2 | 3918 | Payload comprising a LAMC2 gene or variant thereof packaged within a AAVC11.15 capsid. |

Fig. 29 (Continued)

| | | | | | |
|---|---|---|---|---|---|
| 2 | AAVC11.16 | | LAMC2 | 3918 | Payload comprising a LAMC2 gene or variant thereof packaged within a AAVC11.16 capsid. |
| 2 | AAVC11.17 | | LAMC2 | 3918 | Payload comprising a LAMC2 gene or variant thereof packaged within a AAVC11.17 capsid. |
| 2 | AAVC11.18 | | LAMC2 | 3918 | Payload comprising a LAMC2 gene or variant thereof packaged within a AAVC11.18 capsid |
| 2 | AAVC11.19 | | LAMC2 | 3918 | Payload comprising a LAMC2 gene or variant thereof packaged within a AAVC11.19 capsid. |
| 2 | AAV12 | | LAMC2 | 3918 | Payload comprising a LAMC2 gene or variant thereof packaged within a AAV12 capsid. |
| 2 | AAV13 | | LAMC2 | 3918 | Payload comprising a LAMC2 gene or variant thereof packaged within a AAV13 capsid. |
| 2 | AAV-DJ | | LAMC2 | 3918 | Payload comprising a LAMC2 gene or variant thereof packaged within a AAV-DJ capsid |
| 2 | AAV-LK03 | | LAMC2 | 3918 | Payload comprising a LAMC2 gene or variant thereof packaged within a AAV-LK03 capsid. |
| 2 | AAV-LK19 | | LAMC2 | 3918 | Payload comprising a LAMC2 gene or variant thereof packaged within a AAV-LK19 capsid. |
| 2 | AAVrh.74 | | LAMC2 | 3918 | Payload comprising a LAMC2 gene or variant thereof packaged within a AAVrh.74 capsid. |
| 2 | AAVrh.10 | | LAMC2 | 3918 | Payload comprising a LAMC2 gene or variant thereof packaged within a AAVrh.10 capsid. |
| 2 | AAVhu.37 | | LAMC2 | 3918 | Payload comprising a LAMC2 gene or variant thereof packaged within a AAVhu.37 capsid. |
| 2 | AAVrh.K | | LAMC2 | 3918 | Payload comprising a LAMC2 gene or variant thereof packaged within a AAVrh.K capsid. |
| 2 | AAVrh.39 | | LAMC2 | 3918 | Payload comprising a LAMC2 gene or variant thereof packaged within a AAVrh.39 capsid. |
| 2 | AAVrh.9 | | LAMC2 | 3918 | Payload comprising a LAMC2 gene or variant thereof packaged within a AAVrh.9 capsid. |
| 2 | avian AAV | | LAMC2 | 3918 | Payload comprising a LAMC2 gene or variant thereof packaged within a avian capsid. |

Fig. 29 (Continued)

| | | | | | |
|---|---|---|---|---|---|
| 2 | bovine AAV | | LAMC2 | 3918 | Payload comprising a LAMC2 gene or variant thereof packaged within a bovine capsid. |
| 2 | canine AAV | | LAMC2 | 3918 | Payload comprising a LAMC2 gene or variant thereof packaged within a canine capsid. |
| 2 | equine AAV | | LAMC2 | 3918 | Payload comprising a LAMC2 gene or variant thereof packaged within a equine capsid. |
| 2 | primate AAV | | LAMC2 | 3918 | Payload comprising a LAMC2 gene or variant thereof packaged within a primate capsid. |
| 2 | non-primate AAV | | LAMC2 | 3918 | Payload comprising a LAMC2 gene or variant thereof packaged within a non-primate capsid. |
| 2 | ovine AAV | | LAMC2 | 3918 | Payload comprising a LAMC2 gene or variant thereof packaged within a ovine capsid. |
| 2 | hybrid AAV | | LAMC2 | 3918 | Payload comprising a LAMC2 gene or variant thereof packaged within a hybrid capsid. |
| 2 | chimeric AAV | | LAMC2 | 3918 | Payload comprising a LAMC2 gene or variant thereof packaged within a chimeric capsid. |
| 1 | AAV1 | 1450374 | LCHAD | 3030 | Payload comprising a LCHAD gene or variant thereof packaged within a AAV1 capsid. |
| 1 | AAV2 | | LCHAD | 3030 | Payload comprising a LCHAD gene or variant thereof packaged within a AAV2 capsid. |
| 1 | AAV3 | | LCHAD | 3030 | Payload comprising a LCHAD gene or variant thereof packaged within a AAV3 capsid. |
| 1 | AAV4 | 1446389 | LCHAD | 3030 | Payload comprising a LCHAD gene or variant thereof packaged within a AAV4 capsid. |
| 1 | AAV5 | | LCHAD | 3030 | Payload comprising a LCHAD gene or variant thereof packaged within a AAV5 capsid. |
| 1 | AAV6 | | LCHAD | 3030 | Payload comprising a LCHAD gene or variant thereof packaged within a AAV6 capsid. |
| 1 | AAV7 | | LCHAD | 3030 | Payload comprising a LCHAD gene or variant thereof packaged within a AAV7 capsid. |
| 1 | AAV8 | 5075992 | LCHAD | 3030 | Payload comprising a LCHAD gene or variant thereof packaged within a AAV8 capsid. |
| 1 | AAV9 | | LCHAD | 3030 | Payload comprising a LCHAD gene or variant thereof packaged within a AAV9 capsid. |

Fig. 29 (Continued)

| | | | | | |
|---|---|---|---|---|---|
| 1 | AAV10 | | LCHAD | 3030 | Payload comprising a LCHAD gene or variant thereof packaged within a AAV10 capsid. |
| 1 | AAV11 | | LCHAD | 3030 | Payload comprising a LCHAD gene or variant thereof packaged within a AAV11 capsid. |
| 1 | AAVC11.01 | | LCHAD | 3030 | Payload comprising a LCHAD gene or variant thereof packaged within a AAVC11.01 capsid. |
| 1 | AAVC11.02 | | LCHAD | 3030 | Payload comprising a LCHAD gene or variant thereof packaged within a AAVC11.02 capsid. |
| 1 | AAVC11.03 | | LCHAD | 3030 | Payload comprising a LCHAD gene or variant thereof packaged within a AAVC11.03 capsid. |
| 1 | AAVC11.04 | | LCHAD | 3030 | Payload comprising a LCHAD gene or variant thereof packaged within a AAVC11.04 capsid. |
| 1 | AAVC11.05 | | LCHAD | 3030 | Payload comprising a LCHAD gene or variant thereof packaged within a AAVC11.05 capsid. |
| 1 | AAVC11.06 | | LCHAD | 3030 | Payload comprising a LCHAD gene or variant thereof packaged within a AAVC11.06 capsid. |
| 1 | AAVC11.07 | | LCHAD | 3030 | Payload comprising a LCHAD gene or variant thereof packaged within a AAVC11.07 capsid. |
| 1 | AAVC11.08 | | LCHAD | 3030 | Payload comprising a LCHAD gene or variant thereof packaged within a AAVC11.08 capsid. |
| 1 | AAVC11.09 | | LCHAD | 3030 | Payload comprising a LCHAD gene or variant thereof packaged within a AAVC11.09 capsid. |
| 1 | AAVC11.10 | | LCHAD | 3030 | Payload comprising a LCHAD gene or variant thereof packaged within a AAVC11.10 capsid. |
| 1 | AAVC11.11 | | LCHAD | 3030 | Payload comprising a LCHAD gene or variant thereof packaged within a AAVC11.11 capsid. |
| 1 | AAVC11.12 | | LCHAD | 3030 | Payload comprising a LCHAD gene or variant thereof packaged within a AAVC11.12 capsid. |
| 1 | AAVC11.13 | | LCHAD | 3030 | Payload comprising a LCHAD gene or variant thereof packaged within a AAVC11.13 capsid. |
| 1 | AAVC11.14 | | LCHAD | 3030 | Payload comprising a LCHAD gene or variant thereof packaged within a AAVC11.14 capsid. |
| 1 | AAVC11.15 | | LCHAD | 3030 | Payload comprising a LCHAD gene or variant thereof packaged within a AAVC11.15 capsid. |

Fig. 29 (Continued)

| | | | | | |
|---|---|---|---|---|---|
| 1 | AAVC11.16 | | LCHAD | 3030 | Payload comprising a LCHAD gene or variant thereof packaged within a AAVC11.16 capsid. |
| 1 | AAVC11.17 | | LCHAD | 3030 | Payload comprising a LCHAD gene or variant thereof packaged within a AAVC11.17 capsid. |
| 1 | AAVC11.18 | | LCHAD | 3030 | Payload comprising a LCHAD gene or variant thereof packaged within a AAVC11.18 capsid. |
| 1 | AAVC11.19 | | LCHAD | 3030 | Payload comprising a LCHAD gene or variant thereof packaged within a AAVC11.19 capsid. |
| 1 | AAV12 | | LCHAD | 3030 | Payload comprising a LCHAD gene or variant thereof packaged within a AAV12 capsid. |
| 1 | AAV13 | | LCHAD | 3030 | Payload comprising a LCHAD gene or variant thereof packaged within a AAV13 capsid. |
| 1 | AAV-DJ | | LCHAD | 3030 | Payload comprising a LCHAD gene or variant thereof packaged within a AAV-DJ capsid. |
| 1 | AAV-LK03 | | LCHAD | 3030 | Payload comprising a LCHAD gene or variant thereof packaged within a AAV-LK03 capsid. |
| 1 | AAV-LK19 | | LCHAD | 3030 | Payload comprising a LCHAD gene or variant thereof packaged within a AAV-LK19 capsid. |
| 1 | AAVrh.74 | | LCHAD | 3030 | Payload comprising a LCHAD gene or variant thereof packaged within a AAVrh.74 capsid. |
| 1 | AAVrh.10 | | LCHAD | 3030 | Payload comprising a LCHAD gene or variant thereof packaged within a AAVrh.10 capsid. |
| 1 | AAVhu.37 | | LCHAD | 3030 | Payload comprising a LCHAD gene or variant thereof packaged within a AAVhu.37 capsid. |
| 1 | AAVrh.K | | LCHAD | 3030 | Payload comprising a LCHAD gene or variant thereof packaged within a AAVrh.K capsid. |
| 1 | AAVrh.39 | | LCHAD | 3030 | Payload comprising a LCHAD gene or variant thereof packaged within a AAVrh.39 capsid. |
| 1 | AAVrh.9 | | LCHAD | 3030 | Payload comprising a LCHAD gene or variant thereof packaged within a AAVrh.9 capsid. |
| 1 | avian AAV | | LCHAD | 3030 | Payload comprising a LCHAD gene or variant thereof packaged within a avian capsid. |

Fig. 29 (Continued)

| | | | | | |
|---|---|---|---|---|---|
| 1 | bovine AAV | | LCHAD | 3030 | Payload comprising a LCHAD gene or variant thereof packaged within a bovine capsid. |
| 1 | canine AAV | | LCHAD | 3030 | Payload comprising a LCHAD gene or variant thereof packaged within a canine capsid. |
| 1 | equine AAV | | LCHAD | 3030 | Payload comprising a LCHAD gene or variant thereof packaged within a equine capsid. |
| 1 | primate AAV | | LCHAD | 3030 | Payload comprising a LCHAD gene or variant thereof packaged within a primate capsid. |
| 1 | non-primate AAV | | LCHAD | 3030 | Payload comprising a LCHAD gene or variant thereof packaged within a non-primate capsid. |
| 1 | ovine AAV | | LCHAD | 3030 | Payload comprising a LCHAD gene or variant thereof packaged within a ovine capsid. |
| 1 | hybrid AAV | | LCHAD | 3030 | Payload comprising a LCHAD gene or variant thereof packaged within a hybrid capsid. |
| 1 | chimeric AAV | | LCHAD | 3030 | Payload comprising a LCHAD gene or variant thereof packaged within a chimeric capsid. |
| 2 | AAV1 | 1450374 | LCHAD | 3030 | Payload comprising a LCHAD gene or variant thereof packaged within a AAV1 capsid. |
| 2 | AAV2 | | LCHAD | 3030 | Payload comprising a LCHAD gene or variant thereof packaged within a AAV2 capsid. |
| 2 | AAV3 | | LCHAD | 3030 | Payload comprising a LCHAD gene or variant thereof packaged within a AAV3 capsid. |
| 2 | AAV4 | 1446389 | LCHAD | 3030 | Payload comprising a LCHAD gene or variant thereof packaged within a AAV4 capsid. |
| 2 | AAV5 | | LCHAD | 3030 | Payload comprising a LCHAD gene or variant thereof packaged within a AAV5 capsid. |
| 2 | AAV6 | | LCHAD | 3030 | Payload comprising a LCHAD gene or variant thereof packaged within a AAV6 capsid. |
| 2 | AAV7 | | LCHAD | 3030 | Payload comprising a LCHAD gene or variant thereof packaged within a AAV7 capsid. |
| 2 | AAV8 | 5075992 | LCHAD | 3030 | Payload comprising a LCHAD gene or variant thereof packaged within a AAV8 capsid. |
| 2 | AAV9 | | LCHAD | 3030 | Payload comprising a LCHAD gene or variant thereof packaged within a AAV9 capsid. |

Fig. 29 (Continued)

| | | | | | |
|---|---|---|---|---|---|
| 2 | AAV10 | | LCHAD | 3030 | Payload comprising a LCHAD gene or variant thereof packaged within a AAV10 capsid. |
| 2 | AAV11 | | LCHAD | 3030 | Payload comprising a LCHAD gene or variant thereof packaged within a AAV11 capsid. |
| 2 | AAVC11.01 | | LCHAD | 3030 | Payload comprising a LCHAD gene or variant thereof packaged within a AAVC11.01 capsid. |
| 2 | AAVC11.02 | | LCHAD | 3030 | Payload comprising a LCHAD gene or variant thereof packaged within a AAVC11.02 capsid. |
| 2 | AAVC11.03 | | LCHAD | 3030 | Payload comprising a LCHAD gene or variant thereof packaged within a AAVC11.03 capsid. |
| 2 | AAVC11.04 | | LCHAD | 3030 | Payload comprising a LCHAD gene or variant thereof packaged within a AAVC11.04 capsid. |
| 2 | AAVC11.05 | | LCHAD | 3030 | Payload comprising a LCHAD gene or variant thereof packaged within a AAVC11.05 capsid. |
| 2 | AAVC11.06 | | LCHAD | 3030 | Payload comprising a LCHAD gene or variant thereof packaged within a AAVC11.06 capsid. |
| 2 | AAVC11.07 | | LCHAD | 3030 | Payload comprising a LCHAD gene or variant thereof packaged within a AAVC11.07 capsid. |
| 2 | AAVC11.08 | | LCHAD | 3030 | Payload comprising a LCHAD gene or variant thereof packaged within a AAVC11.08 capsid. |
| 2 | AAVC11.09 | | LCHAD | 3030 | Payload comprising a LCHAD gene or variant thereof packaged within a AAVC11.09 capsid. |
| 2 | AAVC11.10 | | LCHAD | 3030 | Payload comprising a LCHAD gene or variant thereof packaged within a AAVC11.10 capsid. |
| 2 | AAVC11.11 | | LCHAD | 3030 | Payload comprising a LCHAD gene or variant thereof packaged within a AAVC11.11 capsid. |
| 2 | AAVC11.12 | | LCHAD | 3030 | Payload comprising a LCHAD gene or variant thereof packaged within a AAVC11.12 capsid. |
| 2 | AAVC11.13 | | LCHAD | 3030 | Payload comprising a LCHAD gene or variant thereof packaged within a AAVC11.13 capsid. |
| 2 | AAVC11.14 | | LCHAD | 3030 | Payload comprising a LCHAD gene or variant thereof packaged within a AAVC11.14 capsid. |
| 2 | AAVC11.15 | | LCHAD | 3030 | Payload comprising a LCHAD gene or variant thereof packaged within a AAVC11.15 capsid. |

Fig. 29 (Continued)

| | | | | | |
|---|---|---|---|---|---|
| 2 | AAVC11.16 | | LCHAD | 3030 | Payload comprising a LCHAD gene or variant thereof packaged within a AAVC11.16 capsid. |
| 2 | AAVC11.17 | | LCHAD | 3030 | Payload comprising a LCHAD gene or variant thereof packaged within a AAVC11.17 capsid. |
| 2 | AAVC11.18 | | LCHAD | 3030 | Payload comprising a LCHAD gene or variant thereof packaged within a AAVC11.18 capsid. |
| 2 | AAVC11.19 | | LCHAD | 3030 | Payload comprising a LCHAD gene or variant thereof packaged within a AAVC11.19 capsid. |
| 2 | AAV12 | | LCHAD | 3030 | Payload comprising a LCHAD gene or variant thereof packaged within a AAV12 capsid. |
| 2 | AAV13 | | LCHAD | 3030 | Payload comprising a LCHAD gene or variant thereof packaged within a AAV13 capsid. |
| 2 | AAV-DJ | | LCHAD | 3030 | Payload comprising a LCHAD gene or variant thereof packaged within a AAV-DJ capsid. |
| 2 | AAV-LK03 | | LCHAD | 3030 | Payload comprising a LCHAD gene or variant thereof packaged within a AAV-LK03 capsid. |
| 2 | AAV-LK19 | | LCHAD | 3030 | Payload comprising a LCHAD gene or variant thereof packaged within a AAV-LK19 capsid. |
| 2 | AAVrh.74 | | LCHAD | 3030 | Payload comprising a LCHAD gene or variant thereof packaged within a AAVrh.74 capsid. |
| 2 | AAVrh.10 | | LCHAD | 3030 | Payload comprising a LCHAD gene or variant thereof packaged within a AAVrh.10 capsid. |
| 2 | AAVhu.37 | | LCHAD | 3030 | Payload comprising a LCHAD gene or variant thereof packaged within a AAVhu.37 capsid. |
| 2 | AAVrh.K | | LCHAD | 3030 | Payload comprising a LCHAD gene or variant thereof packaged within a AAVrh.K capsid. |
| 2 | AAVrh.39 | | LCHAD | 3030 | Payload comprising a LCHAD gene or variant thereof packaged within a AAVrh.39 capsid. |
| 2 | AAVrh.9 | | LCHAD | 3030 | Payload comprising a LCHAD gene or variant thereof packaged within a AAVrh.9 capsid. |
| 2 | avian AAV | | LCHAD | 3030 | Payload comprising a LCHAD gene or variant thereof packaged within a avian capsid. |

Fig. 29 (Continued)

| | | | | | |
|---|---|---|---|---|---|
| 2 | bovine AAV | | LCHAD | 3030 | Payload comprising a LCHAD gene or variant thereof packaged within a bovine capsid. |
| 2 | canine AAV | | LCHAD | 3030 | Payload comprising a LCHAD gene or variant thereof packaged within a canine capsid. |
| 2 | equine AAV | | LCHAD | 3030 | Payload comprising a LCHAD gene or variant thereof packaged within a equine capsid. |
| 2 | primate AAV | | LCHAD | 3030 | Payload comprising a LCHAD gene or variant thereof packaged within a primate capsid. |
| 2 | non-primate AAV | | LCHAD | 3030 | Payload comprising a LCHAD gene or variant thereof packaged within a non-primate capsid. |
| 2 | ovine AAV | | LCHAD | 3030 | Payload comprising a LCHAD gene or variant thereof packaged within a ovine capsid. |
| 2 | hybrid AAV | | LCHAD | 3030 | Payload comprising a LCHAD gene or variant thereof packaged within a hybrid capsid. |
| 2 | chimeric AAV | | LCHAD | 3030 | Payload comprising a LCHAD gene or variant thereof packaged within a chimeric capsid. |
| 1 | AAV1 | 1450374 | LMNA | 4000 | Payload comprising a LMNA gene or variant thereof packaged within a AAV1 capsid. |
| 1 | AAV2 | | LMNA | 4000 | Payload comprising a LMNA gene or variant thereof packaged within a AAV2 capsid. |
| 1 | AAV3 | | LMNA | 4000 | Payload comprising a LMNA gene or variant thereof packaged within a AAV3 capsid. |
| 1 | AAV4 | 1446389 | LMNA | 4000 | Payload comprising a LMNA gene or variant thereof packaged within a AAV4 capsid. |
| 1 | AAV5 | | LMNA | 4000 | Payload comprising a LMNA gene or variant thereof packaged within a AAV5 capsid. |
| 1 | AAV6 | | LMNA | 4000 | Payload comprising a LMNA gene or variant thereof packaged within a AAV6 capsid. |
| 1 | AAV7 | | LMNA | 4000 | Payload comprising a LMNA gene or variant thereof packaged within a AAV7 capsid. |
| 1 | AAV8 | 5075992 | LMNA | 4000 | Payload comprising a LMNA gene or variant thereof packaged within a AAV8 capsid. |
| 1 | AAV9 | | LMNA | 4000 | Payload comprising a LMNA gene or variant thereof packaged within a AAV9 capsid. |

Fig. 29 (Continued)

| | | | | | |
|---|---|---|---|---|---|
| 1 | AAV10 | | LMNA | 4000 | Payload comprising a LMNA gene or variant thereof packaged within a AAV10 capsid. |
| 1 | AAV11 | | LMNA | 4000 | Payload comprising a LMNA gene or variant thereof packaged within a AAV11 capsid. |
| 1 | AAVC11.01 | | LMNA | 4000 | Payload comprising a LMNA gene or variant thereof packaged within a AAVC11.01 capsid. |
| 1 | AAVC11.02 | | LMNA | 4000 | Payload comprising a LMNA gene or variant thereof packaged within a AAVC11.02 capsid. |
| 1 | AAVC11.03 | | LMNA | 4000 | Payload comprising a LMNA gene or variant thereof packaged within a AAVC11.03 capsid. |
| 1 | AAVC11.04 | | LMNA | 4000 | Payload comprising a LMNA gene or variant thereof packaged within a AAVC11.04 capsid. |
| 1 | AAVC11.05 | | LMNA | 4000 | Payload comprising a LMNA gene or variant thereof packaged within a AAVC11.05 capsid. |
| 1 | AAVC11.06 | | LMNA | 4000 | Payload comprising a LMNA gene or variant thereof packaged within a AAVC11.06 capsid. |
| 1 | AAVC11.07 | | LMNA | 4000 | Payload comprising a LMNA gene or variant thereof packaged within a AAVC11.07 capsid. |
| 1 | AAVC11.08 | | LMNA | 4000 | Payload comprising a LMNA gene or variant thereof packaged within a AAVC11.08 capsid. |
| 1 | AAVC11.09 | | LMNA | 4000 | Payload comprising a LMNA gene or variant thereof packaged within a AAVC11.09 capsid. |
| 1 | AAVC11.10 | | LMNA | 4000 | Payload comprising a LMNA gene or variant thereof packaged within a AAVC11.10 capsid. |
| 1 | AAVC11.11 | | LMNA | 4000 | Payload comprising a LMNA gene or variant thereof packaged within a AAVC11.11 capsid. |
| 1 | AAVC11.12 | | LMNA | 4000 | Payload comprising a LMNA gene or variant thereof packaged within a AAVC11.12 capsid. |
| 1 | AAVC11.13 | | LMNA | 4000 | Payload comprising a LMNA gene or variant thereof packaged within a AAVC11.13 capsid. |
| 1 | AAVC11.14 | | LMNA | 4000 | Payload comprising a LMNA gene or variant thereof packaged within a AAVC11.14 capsid. |
| 1 | AAVC11.15 | | LMNA | 4000 | Payload comprising a LMNA gene or variant thereof packaged within a AAVC11.15 capsid. |

Fig. 29 (Continued)

| | | | | | |
|---|---|---|---|---|---|
| 1 | AAVC11.16 | | LMNA | 4000 | Payload comprising a LMNA gene or variant thereof packaged within a AAVC11.16 capsid. |
| 1 | AAVC11.17 | | LMNA | 4000 | Payload comprising a LMNA gene or variant thereof packaged within a AAVC11.17 capsid. |
| 1 | AAVC11.18 | | LMNA | 4000 | Payload comprising a LMNA gene or variant thereof packaged within a AAVC11.18 capsid. |
| 1 | AAVC11.19 | | LMNA | 4000 | Payload comprising a LMNA gene or variant thereof packaged within a AAVC11.19 capsid. |
| 1 | AAV12 | | LMNA | 4000 | Payload comprising a LMNA gene or variant thereof packaged within a AAV12 capsid. |
| 1 | AAV13 | | LMNA | 4000 | Payload comprising a LMNA gene or variant thereof packaged within a AAV13 capsid. |
| 1 | AAV-DJ | | LMNA | 4000 | Payload comprising a LMNA gene or variant thereof packaged within a AAV-DJ capsid. |
| 1 | AAV-LK03 | | LMNA | 4000 | Payload comprising a LMNA gene or variant thereof packaged within a AAV-LK03 capsid. |
| 1 | AAV-LK19 | | LMNA | 4000 | Payload comprising a LMNA gene or variant thereof packaged within a AAV-LK19 capsid. |
| 1 | AAVrh.74 | | LMNA | 4000 | Payload comprising a LMNA gene or variant thereof packaged within a AAVrh.74 capsid. |
| 1 | AAVrh.10 | | LMNA | 4000 | Payload comprising a LMNA gene or variant thereof packaged within a AAVrh.10 capsid. |
| 1 | AAVhu.37 | | LMNA | 4000 | Payload comprising a LMNA gene or variant thereof packaged within a AAVhu.37 capsid. |
| 1 | AAVrh.K | | LMNA | 4000 | Payload comprising a LMNA gene or variant thereof packaged within a AAVrh.K capsid. |
| 1 | AAVrh.39 | | LMNA | 4000 | Payload comprising a LMNA gene or variant thereof packaged within a AAVrh.39 capsid. |
| 1 | AAVrh.9 | | LMNA | 4000 | Payload comprising a LMNA gene or variant thereof packaged within a AAVrh.9 capsid. |
| 1 | avian AAV | | LMNA | 4000 | Payload comprising a LMNA gene or variant thereof packaged within a avian capsid. |

Fig. 29 (Continued)

| | | | | | |
|---|---|---|---|---|---|
| 1 | bovine AAV | | LMNA | 4000 | Payload comprising a LMNA gene or variant thereof packaged within a bovine capsid. |
| 1 | canine AAV | | LMNA | 4000 | Payload comprising a LMNA gene or variant thereof packaged within a canine capsid. |
| 1 | equine AAV | | LMNA | 4000 | Payload comprising a LMNA gene or variant thereof packaged within a equine capsid. |
| 1 | primate AAV | | LMNA | 4000 | Payload comprising a LMNA gene or variant thereof packaged within a primate capsid. |
| 1 | non-primate AAV | | LMNA | 4000 | Payload comprising a LMNA gene or variant thereof packaged within a non-primate capsid. |
| 1 | ovine AAV | | LMNA | 4000 | Payload comprising a LMNA gene or variant thereof packaged within a ovine capsid. |
| 1 | hybrid AAV | | LMNA | 4000 | Payload comprising a LMNA gene or variant thereof packaged within a hybrid capsid. |
| 1 | chimeric AAV | | LMNA | 4000 | Payload comprising a LMNA gene or variant thereof packaged within a chimeric capsid. |
| 2 | AAV1 | 1450374 | LMNA | 4000 | Payload comprising a LMNA gene or variant thereof packaged within a AAV1 capsid. |
| 2 | AAV2 | | LMNA | 4000 | Payload comprising a LMNA gene or variant thereof packaged within a AAV2 capsid. |
| 2 | AAV3 | | LMNA | 4000 | Payload comprising a LMNA gene or variant thereof packaged within a AAV3 capsid. |
| 2 | AAV4 | 1446389 | LMNA | 4000 | Payload comprising a LMNA gene or variant thereof packaged within a AAV4 capsid. |
| 2 | AAV5 | | LMNA | 4000 | Payload comprising a LMNA gene or variant thereof packaged within a AAV5 capsid. |
| 2 | AAV6 | | LMNA | 4000 | Payload comprising a LMNA gene or variant thereof packaged within a AAV6 capsid. |
| 2 | AAV7 | | LMNA | 4000 | Payload comprising a LMNA gene or variant thereof packaged within a AAV7 capsid. |
| 2 | AAV8 | 5075992 | LMNA | 4000 | Payload comprising a LMNA gene or variant thereof packaged within a AAV8 capsid. |
| 2 | AAV9 | | LMNA | 4000 | Payload comprising a LMNA gene or variant thereof packaged within a AAV9 capsid. |

Fig. 29 (Continued)

| | | | | | |
|---|---|---|---|---|---|
| 2 | AAV10 | | LMNA | 4000 | Payload comprising a LMNA gene or variant thereof packaged within a AAV10 capsid. |
| 2 | AAV11 | | LMNA | 4000 | Payload comprising a LMNA gene or variant thereof packaged within a AAV11 capsid. |
| 2 | AAVC11.01 | | LMNA | 4000 | Payload comprising a LMNA gene or variant thereof packaged within a AAVC11.01 capsid. |
| 2 | AAVC11.02 | | LMNA | 4000 | Payload comprising a LMNA gene or variant thereof packaged within a AAVC11.02 capsid. |
| 2 | AAVC11.03 | | LMNA | 4000 | Payload comprising a LMNA gene or variant thereof packaged within a AAVC11.03 capsid. |
| 2 | AAVC11.04 | | LMNA | 4000 | Payload comprising a LMNA gene or variant thereof packaged within a AAVC11.04 capsid. |
| 2 | AAVC11.05 | | LMNA | 4000 | Payload comprising a LMNA gene or variant thereof packaged within a AAVC11.05 capsid. |
| 2 | AAVC11.06 | | LMNA | 4000 | Payload comprising a LMNA gene or variant thereof packaged within a AAVC11.06 capsid. |
| 2 | AAVC11.07 | | LMNA | 4000 | Payload comprising a LMNA gene or variant thereof packaged within a AAVC11.07 capsid. |
| 2 | AAVC11.08 | | LMNA | 4000 | Payload comprising a LMNA gene or variant thereof packaged within a AAVC11.08 capsid. |
| 2 | AAVC11.09 | | LMNA | 4000 | Payload comprising a LMNA gene or variant thereof packaged within a AAVC11.09 capsid. |
| 2 | AAVC11.10 | | LMNA | 4000 | Payload comprising a LMNA gene or variant thereof packaged within a AAVC11.10 capsid. |
| 2 | AAVC11.11 | | LMNA | 4000 | Payload comprising a LMNA gene or variant thereof packaged within a AAVC11.11 capsid. |
| 2 | AAVC11.12 | | LMNA | 4000 | Payload comprising a LMNA gene or variant thereof packaged within a AAVC11.12 capsid. |
| 2 | AAVC11.13 | | LMNA | 4000 | Payload comprising a LMNA gene or variant thereof packaged within a AAVC11.13 capsid. |
| 2 | AAVC11.14 | | LMNA | 4000 | Payload comprising a LMNA gene or variant thereof packaged within a AAVC11.14 capsid. |
| 2 | AAVC11.15 | | LMNA | 4000 | Payload comprising a LMNA gene or variant thereof packaged within a AAVC11.15 capsid. |

Fig. 29 (Continued)

| | | | | | |
|---|---|---|---|---|---|
| 2 | AAVC11.16 | | LMNA | 4000 | Payload comprising a LMNA gene or variant thereof packaged within a AAVC11.16 capsid. |
| 2 | AAVC11.17 | | LMNA | 4000 | Payload comprising a LMNA gene or variant thereof packaged within a AAVC11.17 capsid. |
| 2 | AAVC11.18 | | LMNA | 4000 | Payload comprising a LMNA gene or variant thereof packaged within a AAVC11.18 capsid. |
| 2 | AAVC11.19 | | LMNA | 4000 | Payload comprising a LMNA gene or variant thereof packaged within a AAVC11.19 capsid. |
| 2 | AAV12 | | LMNA | 4000 | Payload comprising a LMNA gene or variant thereof packaged within a AAV12 capsid. |
| 2 | AAV13 | | LMNA | 4000 | Payload comprising a LMNA gene or variant thereof packaged within a AAV13 capsid. |
| 2 | AAV-DJ | | LMNA | 4000 | Payload comprising a LMNA gene or variant thereof packaged within a AAV-DJ capsid. |
| 2 | AAV-LK03 | | LMNA | 4000 | Payload comprising a LMNA gene or variant thereof packaged within a AAV-LK03 capsid. |
| 2 | AAV-LK19 | | LMNA | 4000 | Payload comprising a LMNA gene or variant thereof packaged within a AAV-LK19 capsid. |
| 2 | AAVrh.74 | | LMNA | 4000 | Payload comprising a LMNA gene or variant thereof packaged within a AAVrh.74 capsid. |
| 2 | AAVrh.10 | | LMNA | 4000 | Payload comprising a LMNA gene or variant thereof packaged within a AAVrh.10 capsid. |
| 2 | AAVhu.37 | | LMNA | 4000 | Payload comprising a LMNA gene or variant thereof packaged within a AAVhu.37 capsid. |
| 2 | AAVrh.K | | LMNA | 4000 | Payload comprising a LMNA gene or variant thereof packaged within a AAVrh.K capsid. |
| 2 | AAVrh.39 | | LMNA | 4000 | Payload comprising a LMNA gene or variant thereof packaged within a AAVrh.39 capsid. |
| 2 | AAVrh.9 | | LMNA | 4000 | Payload comprising a LMNA gene or variant thereof packaged within a AAVrh.9 capsid. |
| 2 | avian AAV | | LMNA | 4000 | Payload comprising a LMNA gene or variant thereof packaged within a avian capsid. |

Fig. 29 (Continued)

| | | | | | |
|---|---|---|---|---|---|
| 2 | bovine AAV | | LMNA | 4000 | Payload comprising a LMNA gene or variant thereof packaged within a bovine capsid. |
| 2 | canine AAV | | LMNA | 4000 | Payload comprising a LMNA gene or variant thereof packaged within a canine capsid. |
| 2 | equine AAV | | LMNA | 4000 | Payload comprising a LMNA gene or variant thereof packaged within a equine capsid. |
| 2 | primate AAV | | LMNA | 4000 | Payload comprising a LMNA gene or variant thereof packaged within a primate capsid. |
| 2 | non-primate AAV | | LMNA | 4000 | Payload comprising a LMNA gene or variant thereof packaged within a non-primate capsid. |
| 2 | ovine AAV | | LMNA | 4000 | Payload comprising a LMNA gene or variant thereof packaged within a ovine capsid. |
| 2 | hybrid AAV | | LMNA | 4000 | Payload comprising a LMNA gene or variant thereof packaged within a hybrid capsid. |
| 2 | chimeric AAV | | LMNA | 4000 | Payload comprising a LMNA gene or variant thereof packaged within a chimeric capsid. |
| 1 | AAV1 | 1450374 | LRRK2 | 120892 | Payload comprising a LRRK2 gene or variant thereof packaged within a AAV1 capsid. |
| 1 | AAV2 | | LRRK2 | 120892 | Payload comprising a LRRK2 gene or variant thereof packaged within a AAV2 capsid. |
| 1 | AAV3 | | LRRK2 | 120892 | Payload comprising a LRRK2 gene or variant thereof packaged within a AAV3 capsid. |
| 1 | AAV4 | 1446389 | LRRK2 | 120892 | Payload comprising a LRRK2 gene or variant thereof packaged within a AAV4 capsid. |
| 1 | AAV5 | | LRRK2 | 120892 | Payload comprising a LRRK2 gene or variant thereof packaged within a AAV5 capsid. |
| 1 | AAV6 | | LRRK2 | 120892 | Payload comprising a LRRK2 gene or variant thereof packaged within a AAV6 capsid. |
| 1 | AAV7 | | LRRK2 | 120892 | Payload comprising a LRRK2 gene or variant thereof packaged within a AAV7 capsid. |
| 1 | AAV8 | 5075992 | LRRK2 | 120892 | Payload comprising a LRRK2 gene or variant thereof packaged within a AAV8 capsid. |
| 1 | AAV9 | | LRRK2 | 120892 | Payload comprising a LRRK2 gene or variant thereof packaged within a AAV9 capsid. |

Fig. 29 (Continued)

| | | | | | |
|---|---|---|---|---|---|
| 1 | AAV10 | | LRRK2 | 120892 | Payload comprising a LRRK2 gene or variant thereof packaged within a AAV10 capsid. |
| 1 | AAV11 | | LRRK2 | 120892 | Payload comprising a LRRK2 gene or variant thereof packaged within a AAV11 capsid. |
| 1 | AAVC11.01 | | LRRK2 | 120892 | Payload comprising a LRRK2 gene or variant thereof packaged within a AAVC11.01 capsid. |
| 1 | AAVC11.02 | | LRRK2 | 120892 | Payload comprising a LRRK2 gene or variant thereof packaged within a AAVC11.02 capsid. |
| 1 | AAVC11.03 | | LRRK2 | 120892 | Payload comprising a LRRK2 gene or variant thereof packaged within a AAVC11.03 capsid. |
| 1 | AAVC11.04 | | LRRK2 | 120892 | Payload comprising a LRRK2 gene or variant thereof packaged within a AAVC11.04 capsid. |
| 1 | AAVC11.05 | | LRRK2 | 120892 | Payload comprising a LRRK2 gene or variant thereof packaged within a AAVC11.05 capsid. |
| 1 | AAVC11.06 | | LRRK2 | 120892 | Payload comprising a LRRK2 gene or variant thereof packaged within a AAVC11.06 capsid. |
| 1 | AAVC11.07 | | LRRK2 | 120892 | Payload comprising a LRRK2 gene or variant thereof packaged within a AAVC11.07 capsid. |
| 1 | AAVC11.08 | | LRRK2 | 120892 | Payload comprising a LRRK2 gene or variant thereof packaged within a AAVC11.08 capsid. |
| 1 | AAVC11.09 | | LRRK2 | 120892 | Payload comprising a LRRK2 gene or variant thereof packaged within a AAVC11.09 capsid. |
| 1 | AAVC11.10 | | LRRK2 | 120892 | Payload comprising a LRRK2 gene or variant thereof packaged within a AAVC11.10 capsid. |
| 1 | AAVC11.11 | | LRRK2 | 120892 | Payload comprising a LRRK2 gene or variant thereof packaged within a AAVC11.11 capsid. |
| 1 | AAVC11.12 | | LRRK2 | 120892 | Payload comprising a LRRK2 gene or variant thereof packaged within a AAVC11.12 capsid. |
| 1 | AAVC11.13 | | LRRK2 | 120892 | Payload comprising a LRRK2 gene or variant thereof packaged within a AAVC11.13 capsid. |
| 1 | AAVC11.14 | | LRRK2 | 120892 | Payload comprising a LRRK2 gene or variant thereof packaged within a AAVC11.14 capsid. |
| 1 | AAVC11.15 | | LRRK2 | 120892 | Payload comprising a LRRK2 gene or variant thereof packaged within a AAVC11.15 capsid. |

Fig. 29 (Continued)

| | | | | | |
|---|---|---|---|---|---|
| 1 | AAVC11.16 | | LRRK2 | 120892 | Payload comprising a LRRK2 gene or variant thereof packaged within a AAVC11.16 capsid. |
| 1 | AAVC11.17 | | LRRK2 | 120892 | Payload comprising a LRRK2 gene or variant thereof packaged within a AAVC11.17 capsid. |
| 1 | AAVC11.18 | | LRRK2 | 120892 | Payload comprising a LRRK2 gene or variant thereof packaged within a AAVC11.18 capsid. |
| 1 | AAVC11.19 | | LRRK2 | 120892 | Payload comprising a LRRK2 gene or variant thereof packaged within a AAVC11.19 capsid. |
| 1 | AAV12 | | LRRK2 | 120892 | Payload comprising a LRRK2 gene or variant thereof packaged within a AAV12 capsid. |
| 1 | AAV13 | | LRRK2 | 120892 | Payload comprising a LRRK2 gene or variant thereof packaged within a AAV13 capsid. |
| 1 | AAV-DJ | | LRRK2 | 120892 | Payload comprising a LRRK2 gene or variant thereof packaged within a AAV-DJ capsid. |
| 1 | AAV-LK03 | | LRRK2 | 120892 | Payload comprising a LRRK2 gene or variant thereof packaged within a AAV-LK03 capsid. |
| 1 | AAV-LK19 | | LRRK2 | 120892 | Payload comprising a LRRK2 gene or variant thereof packaged within a AAV-LK19 capsid. |
| 1 | AAVrh.74 | | LRRK2 | 120892 | Payload comprising a LRRK2 gene or variant thereof packaged within a AAVrh.74 capsid. |
| 1 | AAVrh.10 | | LRRK2 | 120892 | Payload comprising a LRRK2 gene or variant thereof packaged within a AAVrh.10 capsid. |
| 1 | AAVhu.37 | | LRRK2 | 120892 | Payload comprising a LRRK2 gene or variant thereof packaged within a AAVhu.37 capsid. |
| 1 | AAVrh.K | | LRRK2 | 120892 | Payload comprising a LRRK2 gene or variant thereof packaged within a AAVrh.K capsid. |
| 1 | AAVrh.39 | | LRRK2 | 120892 | Payload comprising a LRRK2 gene or variant thereof packaged within a AAVrh.39 capsid. |
| 1 | AAVrh.9 | | LRRK2 | 120892 | Payload comprising a LRRK2 gene or variant thereof packaged within a AAVrh.9 capsid. |
| 1 | avian AAV | | LRRK2 | 120892 | Payload comprising a LRRK2 gene or variant thereof packaged within a avian capsid. |

Fig. 29 (Continued)

| | | | | | |
|---|---|---|---|---|---|
| 1 | bovine AAV | | LRRK2 | 120892 | Payload comprising a LRRK2 gene or variant thereof packaged within a bovine capsid. |
| 1 | canine AAV | | LRRK2 | 120892 | Payload comprising a LRRK2 gene or variant thereof packaged within a canine capsid. |
| 1 | equine AAV | | LRRK2 | 120892 | Payload comprising a LRRK2 gene or variant thereof packaged within a equine capsid. |
| 1 | primate AAV | | LRRK2 | 120892 | Payload comprising a LRRK2 gene or variant thereof packaged within a primate capsid. |
| 1 | non-primate AAV | | LRRK2 | 120892 | Payload comprising a LRRK2 gene or variant thereof packaged within a non-primate capsid. |
| 1 | ovine AAV | | LRRK2 | 120892 | Payload comprising a LRRK2 gene or variant thereof packaged within a ovine capsid. |
| 1 | hybrid AAV | | LRRK2 | 120892 | Payload comprising a LRRK2 gene or variant thereof packaged within a hybrid capsid. |
| 1 | chimeric AAV | | LRRK2 | 120892 | Payload comprising a LRRK2 gene or variant thereof packaged within a chimeric capsid. |
| 2 | AAV1 | 1450374 | LRRK2 | 120892 | Payload comprising a LRRK2 gene or variant thereof packaged within a AAV1 capsid. |
| 2 | AAV2 | | LRRK2 | 120892 | Payload comprising a LRRK2 gene or variant thereof packaged within a AAV2 capsid. |
| 2 | AAV3 | | LRRK2 | 120892 | Payload comprising a LRRK2 gene or variant thereof packaged within a AAV3 capsid. |
| 2 | AAV4 | 1446389 | LRRK2 | 120892 | Payload comprising a LRRK2 gene or variant thereof packaged within a AAV4 capsid. |
| 2 | AAV5 | | LRRK2 | 120892 | Payload comprising a LRRK2 gene or variant thereof packaged within a AAV5 capsid. |
| 2 | AAV6 | | LRRK2 | 120892 | Payload comprising a LRRK2 gene or variant thereof packaged within a AAV6 capsid. |
| 2 | AAV7 | | LRRK2 | 120892 | Payload comprising a LRRK2 gene or variant thereof packaged within a AAV7 capsid. |
| 2 | AAV8 | 5075992 | LRRK2 | 120892 | Payload comprising a LRRK2 gene or variant thereof packaged within a AAV8 capsid. |
| 2 | AAV9 | | LRRK2 | 120892 | Payload comprising a LRRK2 gene or variant thereof packaged within a AAV9 capsid. |

Fig. 29 (Continued)

| | | | | | |
|---|---|---|---|---|---|
| 2 | AAV10 | | LRRK2 | 120892 | Payload comprising a LRRK2 gene or variant thereof packaged within a AAV10 capsid. |
| 2 | AAV11 | | LRRK2 | 120892 | Payload comprising a LRRK2 gene or variant thereof packaged within a AAV11 capsid. |
| 2 | AAVC11.01 | | LRRK2 | 120892 | Payload comprising a LRRK2 gene or variant thereof packaged within a AAVC11.01 capsid. |
| 2 | AAVC11.02 | | LRRK2 | 120892 | Payload comprising a LRRK2 gene or variant thereof packaged within a AAVC11.02 capsid. |
| 2 | AAVC11.03 | | LRRK2 | 120892 | Payload comprising a LRRK2 gene or variant thereof packaged within a AAVC11.03 capsid. |
| 2 | AAVC11.04 | | LRRK2 | 120892 | Payload comprising a LRRK2 gene or variant thereof packaged within a AAVC11.04 capsid. |
| 2 | AAVC11.05 | | LRRK2 | 120892 | Payload comprising a LRRK2 gene or variant thereof packaged within a AAVC11.05 capsid. |
| 2 | AAVC11.06 | | LRRK2 | 120892 | Payload comprising a LRRK2 gene or variant thereof packaged within a AAVC11.06 capsid. |
| 2 | AAVC11.07 | | LRRK2 | 120892 | Payload comprising a LRRK2 gene or variant thereof packaged within a AAVC11.07 capsid. |
| 2 | AAVC11.08 | | LRRK2 | 120892 | Payload comprising a LRRK2 gene or variant thereof packaged within a AAVC11.08 capsid. |
| 2 | AAVC11.09 | | LRRK2 | 120892 | Payload comprising a LRRK2 gene or variant thereof packaged within a AAVC11.09 capsid. |
| 2 | AAVC11.10 | | LRRK2 | 120892 | Payload comprising a LRRK2 gene or variant thereof packaged within a AAVC11.10 capsid. |
| 2 | AAVC11.11 | | LRRK2 | 120892 | Payload comprising a LRRK2 gene or variant thereof packaged within a AAVC11.11 capsid. |
| 2 | AAVC11.12 | | LRRK2 | 120892 | Payload comprising a LRRK2 gene or variant thereof packaged within a AAVC11.12 capsid. |
| 2 | AAVC11.13 | | LRRK2 | 120892 | Payload comprising a LRRK2 gene or variant thereof packaged within a AAVC11.13 capsid. |
| 2 | AAVC11.14 | | LRRK2 | 120892 | Payload comprising a LRRK2 gene or variant thereof packaged within a AAVC11.14 capsid. |
| 2 | AAVC11.15 | | LRRK2 | 120892 | Payload comprising a LRRK2 gene or variant thereof packaged within a AAVC11.15 capsid. |

Fig. 29 (Continued)

| | | | | | |
|---|---|---|---|---|---|
| 2 | AAVC11.16 | | LRRK2 | 120892 | Payload comprising a LRRK2 gene or variant thereof packaged within a AAVC11.16 capsid. |
| 2 | AAVC11.17 | | LRRK2 | 120892 | Payload comprising a LRRK2 gene or variant thereof packaged within a AAVC11.17 capsid. |
| 2 | AAVC11.18 | | LRRK2 | 120892 | Payload comprising a LRRK2 gene or variant thereof packaged within a AAVC11.18 capsid. |
| 2 | AAVC11.19 | | LRRK2 | 120892 | Payload comprising a LRRK2 gene or variant thereof packaged within a AAVC11.19 capsid. |
| 2 | AAV12 | | LRRK2 | 120892 | Payload comprising a LRRK2 gene or variant thereof packaged within a AAV12 capsid. |
| 2 | AAV13 | | LRRK2 | 120892 | Payload comprising a LRRK2 gene or variant thereof packaged within a AAV13 capsid. |
| 2 | AAV-DJ | | LRRK2 | 120892 | Payload comprising a LRRK2 gene or variant thereof packaged within a AAV-DJ capsid. |
| 2 | AAV-LK03 | | LRRK2 | 120892 | Payload comprising a LRRK2 gene or variant thereof packaged within a AAV-LK03 capsid. |
| 2 | AAV-LK19 | | LRRK2 | 120892 | Payload comprising a LRRK2 gene or variant thereof packaged within a AAV-LK19 capsid. |
| 2 | AAVrh.74 | | LRRK2 | 120892 | Payload comprising a LRRK2 gene or variant thereof packaged within a AAVrh.74 capsid. |
| 2 | AAVrh.10 | | LRRK2 | 120892 | Payload comprising a LRRK2 gene or variant thereof packaged within a AAVrh.10 capsid. |
| 2 | AAVhu.37 | | LRRK2 | 120892 | Payload comprising a LRRK2 gene or variant thereof packaged within a AAVhu.37 capsid. |
| 2 | AAVrh.K | | LRRK2 | 120892 | Payload comprising a LRRK2 gene or variant thereof packaged within a AAVrh.K capsid. |
| 2 | AAVrh.39 | | LRRK2 | 120892 | Payload comprising a LRRK2 gene or variant thereof packaged within a AAVrh.39 capsid. |
| 2 | AAVrh.9 | | LRRK2 | 120892 | Payload comprising a LRRK2 gene or variant thereof packaged within a AAVrh.9 capsid. |
| 2 | avian AAV | | LRRK2 | 120892 | Payload comprising a LRRK2 gene or variant thereof packaged within a avian capsid. |

Fig. 29 (Continued)

| | | | | | |
|---|---|---|---|---|---|
| 2 | bovine AAV | | LRRK2 | 120892 | Payload comprising a LRRK2 gene or variant thereof packaged within a bovine capsid. |
| 2 | canine AAV | | LRRK2 | 120892 | Payload comprising a LRRK2 gene or variant thereof packaged within a canine capsid. |
| 2 | equine AAV | | LRRK2 | 120892 | Payload comprising a LRRK2 gene or variant thereof packaged within a equine capsid. |
| 2 | primate AAV | | LRRK2 | 120892 | Payload comprising a LRRK2 gene or variant thereof packaged within a primate capsid. |
| 2 | non-primate AAV | | LRRK2 | 120892 | Payload comprising a LRRK2 gene or variant thereof packaged within a non-primate capsid. |
| 2 | ovine AAV | | LRRK2 | 120892 | Payload comprising a LRRK2 gene or variant thereof packaged within a ovine capsid. |
| 2 | hybrid AAV | | LRRK2 | 120892 | Payload comprising a LRRK2 gene or variant thereof packaged within a hybrid capsid. |
| 2 | chimeric AAV | | LRRK2 | 120892 | Payload comprising a LRRK2 gene or variant thereof packaged within a chimeric capsid. |
| 1 | AAV1 | 1450374 | MMP1 | 4312 | Payload comprising a MMP1 gene or variant thereof packaged within a AAV1 capsid. |
| 1 | AAV2 | | MMP1 | 4312 | Payload comprising a MMP1 gene or variant thereof packaged within a AAV2 capsid. |
| 1 | AAV3 | | MMP1 | 4312 | Payload comprising a MMP1 gene or variant thereof packaged within a AAV3 capsid. |
| 1 | AAV4 | 1446389 | MMP1 | 4312 | Payload comprising a MMP1 gene or variant thereof packaged within a AAV4 capsid. |
| 1 | AAV5 | | MMP1 | 4312 | Payload comprising a MMP1 gene or variant thereof packaged within a AAV5 capsid. |
| 1 | AAV6 | | MMP1 | 4312 | Payload comprising a MMP1 gene or variant thereof packaged within a AAV6 capsid. |
| 1 | AAV7 | | MMP1 | 4312 | Payload comprising a MMP1 gene or variant thereof packaged within a AAV7 capsid. |
| 1 | AAV8 | 5075992 | MMP1 | 4312 | Payload comprising a MMP1 gene or variant thereof packaged within a AAV8 capsid. |
| 1 | AAV9 | | MMP1 | 4312 | Payload comprising a MMP1 gene or variant thereof packaged within a AAV9 capsid. |

Fig. 29 (Continued)

| | | | | | |
|---|---|---|---|---|---|
| 1 | AAV10 | | MMP1 | 4312 | Payload comprising a MMP1 gene or variant thereof packaged within a AAV10 capsid. |
| 1 | AAV11 | | MMP1 | 4312 | Payload comprising a MMP1 gene or variant thereof packaged within a AAV11 capsid. |
| 1 | AAVC11.01 | | MMP1 | 4312 | Payload comprising a MMP1 gene or variant thereof packaged within a AAVC11.01 capsid. |
| 1 | AAVC11.02 | | MMP1 | 4312 | Payload comprising a MMP1 gene or variant thereof packaged within a AAVC11.02 capsid. |
| 1 | AAVC11.03 | | MMP1 | 4312 | Payload comprising a MMP1 gene or variant thereof packaged within a AAVC11.03 capsid. |
| 1 | AAVC11.04 | | MMP1 | 4312 | Payload comprising a MMP1 gene or variant thereof packaged within a AAVC11.04 capsid. |
| 1 | AAVC11.05 | | MMP1 | 4312 | Payload comprising a MMP1 gene or variant thereof packaged within a AAVC11.05 capsid. |
| 1 | AAVC11.06 | | MMP1 | 4312 | Payload comprising a MMP1 gene or variant thereof packaged within a AAVC11.06 capsid. |
| 1 | AAVC11.07 | | MMP1 | 4312 | Payload comprising a MMP1 gene or variant thereof packaged within a AAVC11.07 capsid. |
| 1 | AAVC11.08 | | MMP1 | 4312 | Payload comprising a MMP1 gene or variant thereof packaged within a AAVC11.08 capsid. |
| 1 | AAVC11.09 | | MMP1 | 4312 | Payload comprising a MMP1 gene or variant thereof packaged within a AAVC11.09 capsid. |
| 1 | AAVC11.10 | | MMP1 | 4312 | Payload comprising a MMP1 gene or variant thereof packaged within a AAVC11.10 capsid. |
| 1 | AAVC11.11 | | MMP1 | 4312 | Payload comprising a MMP1 gene or variant thereof packaged within a AAVC11.11 capsid. |
| 1 | AAVC11.12 | | MMP1 | 4312 | Payload comprising a MMP1 gene or variant thereof packaged within a AAVC11.12 capsid. |
| 1 | AAVC11.13 | | MMP1 | 4312 | Payload comprising a MMP1 gene or variant thereof packaged within a AAVC11.13 capsid. |
| 1 | AAVC11.14 | | MMP1 | 4312 | Payload comprising a MMP1 gene or variant thereof packaged within a AAVC11.14 capsid. |
| 1 | AAVC11.15 | | MMP1 | 4312 | Payload comprising a MMP1 gene or variant thereof packaged within a AAVC11.15 capsid. |

Fig. 29 (Continued)

| | | | | | |
|---|---|---|---|---|---|
| 1 | AAVC11.16 | | MMP1 | 4312 | Payload comprising a MMP1 gene or variant thereof packaged within a AAVC11.16 capsid. |
| 1 | AAVC11.17 | | MMP1 | 4312 | Payload comprising a MMP1 gene or variant thereof packaged within a AAVC11.17 capsid. |
| 1 | AAVC11.18 | | MMP1 | 4312 | Payload comprising a MMP1 gene or variant thereof packaged within a AAVC11.18 capsid. |
| 1 | AAVC11.19 | | MMP1 | 4312 | Payload comprising a MMP1 gene or variant thereof packaged within a AAVC11.19 capsid. |
| 1 | AAV12 | | MMP1 | 4312 | Payload comprising a MMP1 gene or variant thereof packaged within a AAV12 capsid. |
| 1 | AAV13 | | MMP1 | 4312 | Payload comprising a MMP1 gene or variant thereof packaged within a AAV13 capsid. |
| 1 | AAV-DJ | | MMP1 | 4312 | Payload comprising a MMP1 gene or variant thereof packaged within a AAV-DJ capsid. |
| 1 | AAV-LK03 | | MMP1 | 4312 | Payload comprising a MMP1 gene or variant thereof packaged within a AAV-LK03 capsid. |
| 1 | AAV-LK19 | | MMP1 | 4312 | Payload comprising a MMP1 gene or variant thereof packaged within a AAV-LK19 capsid. |
| 1 | AAVrh.74 | | MMP1 | 4312 | Payload comprising a MMP1 gene or variant thereof packaged within a AAVrh.74 capsid. |
| 1 | AAVrh.10 | | MMP1 | 4312 | Payload comprising a MMP1 gene or variant thereof packaged within a AAVrh.10 capsid. |
| 1 | AAVhu.37 | | MMP1 | 4312 | Payload comprising a MMP1 gene or variant thereof packaged within a AAVhu.37 capsid. |
| 1 | AAVrh.K | | MMP1 | 4312 | Payload comprising a MMP1 gene or variant thereof packaged within a AAVrh.K capsid. |
| 1 | AAVrh.39 | | MMP1 | 4312 | Payload comprising a MMP1 gene or variant thereof packaged within a AAVrh.39 capsid. |
| 1 | AAVrh.9 | | MMP1 | 4312 | Payload comprising a MMP1 gene or variant thereof packaged within a AAVrh.9 capsid. |
| 1 | avian AAV | | MMP1 | 4312 | Payload comprising a MMP1 gene or variant thereof packaged within a avian capsid. |

Fig. 29 (Continued)

| | | | | | |
|---|---|---|---|---|---|
| 1 | bovine AAV | | MMP1 | 4312 | Payload comprising a MMP1 gene or variant thereof packaged within a bovine capsid. |
| 1 | canine AAV | | MMP1 | 4312 | Payload comprising a MMP1 gene or variant thereof packaged within a canine capsid. |
| 1 | equine AAV | | MMP1 | 4312 | Payload comprising a MMP1 gene or variant thereof packaged within a equine capsid. |
| 1 | primate AAV | | MMP1 | 4312 | Payload comprising a MMP1 gene or variant thereof packaged within a primate capsid. |
| 1 | non-primate AAV | | MMP1 | 4312 | Payload comprising a MMP1 gene or variant thereof packaged within a non-primate capsid. |
| 1 | ovine AAV | | MMP1 | 4312 | Payload comprising a MMP1 gene or variant thereof packaged within a ovine capsid. |
| 1 | hybrid AAV | | MMP1 | 4312 | Payload comprising a MMP1 gene or variant thereof packaged within a hybrid capsid. |
| 1 | chimeric AAV | | MMP1 | 4312 | Payload comprising a MMP1 gene or variant thereof packaged within a chimeric capsid. |
| 2 | AAV1 | 1450374 | MMP1 | 4312 | Payload comprising a MMP1 gene or variant thereof packaged within a AAV1 capsid. |
| 2 | AAV2 | | MMP1 | 4312 | Payload comprising a MMP1 gene or variant thereof packaged within a AAV2 capsid. |
| 2 | AAV3 | | MMP1 | 4312 | Payload comprising a MMP1 gene or variant thereof packaged within a AAV3 capsid. |
| 2 | AAV4 | 1446389 | MMP1 | 4312 | Payload comprising a MMP1 gene or variant thereof packaged within a AAV4 capsid. |
| 2 | AAV5 | | MMP1 | 4312 | Payload comprising a MMP1 gene or variant thereof packaged within a AAV5 capsid. |
| 2 | AAV6 | | MMP1 | 4312 | Payload comprising a MMP1 gene or variant thereof packaged within a AAV6 capsid. |
| 2 | AAV7 | | MMP1 | 4312 | Payload comprising a MMP1 gene or variant thereof packaged within a AAV7 capsid. |
| 2 | AAV8 | 5075992 | MMP1 | 4312 | Payload comprising a MMP1 gene or variant thereof packaged within a AAV8 capsid. |
| 2 | AAV9 | | MMP1 | 4312 | Payload comprising a MMP1 gene or variant thereof packaged within a AAV9 capsid. |

Fig. 29 (Continued)

| | | | | | |
|---|---|---|---|---|---|
| 2 | AAV10 | | MMP1 | 4312 | Payload comprising a MMP1 gene or variant thereof packaged within a AAV10 capsid. |
| 2 | AAV11 | | MMP1 | 4312 | Payload comprising a MMP1 gene or variant thereof packaged within a AAV11 capsid. |
| 2 | AAVC11.01 | | MMP1 | 4312 | Payload comprising a MMP1 gene or variant thereof packaged within a AAVC11.01 capsid. |
| 2 | AAVC11.02 | | MMP1 | 4312 | Payload comprising a MMP1 gene or variant thereof packaged within a AAVC11.02 capsid. |
| 2 | AAVC11.03 | | MMP1 | 4312 | Payload comprising a MMP1 gene or variant thereof packaged within a AAVC11.03 capsid. |
| 2 | AAVC11.04 | | MMP1 | 4312 | Payload comprising a MMP1 gene or variant thereof packaged within a AAVC11.04 capsid. |
| 2 | AAVC11.05 | | MMP1 | 4312 | Payload comprising a MMP1 gene or variant thereof packaged within a AAVC11.05 capsid. |
| 2 | AAVC11.06 | | MMP1 | 4312 | Payload comprising a MMP1 gene or variant thereof packaged within a AAVC11.06 capsid. |
| 2 | AAVC11.07 | | MMP1 | 4312 | Payload comprising a MMP1 gene or variant thereof packaged within a AAVC11.07 capsid. |
| 2 | AAVC11.08 | | MMP1 | 4312 | Payload comprising a MMP1 gene or variant thereof packaged within a AAVC11.08 capsid. |
| 2 | AAVC11.09 | | MMP1 | 4312 | Payload comprising a MMP1 gene or variant thereof packaged within a AAVC11.09 capsid. |
| 2 | AAVC11.10 | | MMP1 | 4312 | Payload comprising a MMP1 gene or variant thereof packaged within a AAVC11.10 capsid. |
| 2 | AAVC11.11 | | MMP1 | 4312 | Payload comprising a MMP1 gene or variant thereof packaged within a AAVC11.11 capsid. |
| 2 | AAVC11.12 | | MMP1 | 4312 | Payload comprising a MMP1 gene or variant thereof packaged within a AAVC11.12 capsid. |
| 2 | AAVC11.13 | | MMP1 | 4312 | Payload comprising a MMP1 gene or variant thereof packaged within a AAVC11.13 capsid. |
| 2 | AAVC11.14 | | MMP1 | 4312 | Payload comprising a MMP1 gene or variant thereof packaged within a AAVC11.14 capsid. |
| 2 | AAVC11.15 | | MMP1 | 4312 | Payload comprising a MMP1 gene or variant thereof packaged within a AAVC11.15 capsid. |

Fig. 29 (Continued)

| | | | | | |
|---|---|---|---|---|---|
| 2 | AAVC11.16 | | MMP1 | 4312 | Payload comprising a MMP1 gene or variant thereof packaged within a AAVC11.16 capsid. |
| 2 | AAVC11.17 | | MMP1 | 4312 | Payload comprising a MMP1 gene or variant thereof packaged within a AAVC11.17 capsid. |
| 2 | AAVC11.18 | | MMP1 | 4312 | Payload comprising a MMP1 gene or variant thereof packaged within a AAVC11.18 capsid. |
| 2 | AAVC11.19 | | MMP1 | 4312 | Payload comprising a MMP1 gene or variant thereof packaged within a AAVC11.19 capsid. |
| 2 | AAV12 | | MMP1 | 4312 | Payload comprising a MMP1 gene or variant thereof packaged within a AAV12 capsid. |
| 2 | AAV13 | | MMP1 | 4312 | Payload comprising a MMP1 gene or variant thereof packaged within a AAV13 capsid. |
| 2 | AAV-DJ | | MMP1 | 4312 | Payload comprising a MMP1 gene or variant thereof packaged within a AAV-DJ capsid. |
| 2 | AAV-LK03 | | MMP1 | 4312 | Payload comprising a MMP1 gene or variant thereof packaged within a AAV-LK03 capsid. |
| 2 | AAV-LK19 | | MMP1 | 4312 | Payload comprising a MMP1 gene or variant thereof packaged within a AAV-LK19 capsid. |
| 2 | AAVrh.74 | | MMP1 | 4312 | Payload comprising a MMP1 gene or variant thereof packaged within a AAVrh.74 capsid. |
| 2 | AAVrh.10 | | MMP1 | 4312 | Payload comprising a MMP1 gene or variant thereof packaged within a AAVrh.10 capsid. |
| 2 | AAVhu.37 | | MMP1 | 4312 | Payload comprising a MMP1 gene or variant thereof packaged within a AAVhu.37 capsid. |
| 2 | AAVrh.K | | MMP1 | 4312 | Payload comprising a MMP1 gene or variant thereof packaged within a AAVrh.K capsid. |
| 2 | AAVrh.39 | | MMP1 | 4312 | Payload comprising a MMP1 gene or variant thereof packaged within a AAVrh.39 capsid. |
| 2 | AAVrh.9 | | MMP1 | 4312 | Payload comprising a MMP1 gene or variant thereof packaged within a AAVrh.9 capsid. |
| 2 | avian AAV | | MMP1 | 4312 | Payload comprising a MMP1 gene or variant thereof packaged within a avian capsid. |

Fig. 29 (Continued)

| | | | | | |
|---|---|---|---|---|---|
| 2 | bovine AAV | | MMP1 | 4312 | Payload comprising a MMP1 gene or variant thereof packaged within a bovine capsid. |
| 2 | canine AAV | | MMP1 | 4312 | Payload comprising a MMP1 gene or variant thereof packaged within a canine capsid. |
| 2 | equine AAV | | MMP1 | 4312 | Payload comprising a MMP1 gene or variant thereof packaged within a equine capsid. |
| 2 | primate AAV | | MMP1 | 4312 | Payload comprising a MMP1 gene or variant thereof packaged within a primate capsid. |
| 2 | non-primate AAV | | MMP1 | 4312 | Payload comprising a MMP1 gene or variant thereof packaged within a non-primate capsid. |
| 2 | ovine AAV | | MMP1 | 4312 | Payload comprising a MMP1 gene or variant thereof packaged within a ovine capsid. |
| 2 | hybrid AAV | | MMP1 | 4312 | Payload comprising a MMP1 gene or variant thereof packaged within a hybrid capsid. |
| 2 | chimeric AAV | | MMP1 | 4312 | Payload comprising a MMP1 gene or variant thereof packaged within a chimeric capsid. |
| 1 | AAV1 | 1450374 | MMUT | 4594 | Payload comprising a MMUT gene or variant thereof packaged within a AAV1 capsid. |
| 1 | AAV2 | | MMUT | 4594 | Payload comprising a MMUT gene or variant thereof packaged within a AAV2 capsid. |
| 1 | AAV3 | | MMUT | 4594 | Payload comprising a MMUT gene or variant thereof packaged within a AAV3 capsid. |
| 1 | AAV4 | 1446389 | MMUT | 4594 | Payload comprising a MMUT gene or variant thereof packaged within a AAV4 capsid. |
| 1 | AAV5 | | MMUT | 4594 | Payload comprising a MMUT gene or variant thereof packaged within a AAV5 capsid. |
| 1 | AAV6 | | MMUT | 4594 | Payload comprising a MMUT gene or variant thereof packaged within a AAV6 capsid. |
| 1 | AAV7 | | MMUT | 4594 | Payload comprising a MMUT gene or variant thereof packaged within a AAV7 capsid. |
| 1 | AAV8 | 5075992 | MMUT | 4594 | Payload comprising a MMUT gene or variant thereof packaged within a AAV8 capsid. |
| 1 | AAV9 | | MMUT | 4594 | Payload comprising a MMUT gene or variant thereof packaged within a AAV9 capsid. |

Fig. 29 (Continued)

| | | | | | |
|---|---|---|---|---|---|
| 1 | AAV10 | | MMUT | 4594 | Payload comprising a MMUT gene or variant thereof packaged within a AAV10 capsid. |
| 1 | AAV11 | | MMUT | 4594 | Payload comprising a MMUT gene or variant thereof packaged within a AAV11 capsid. |
| 1 | AAVC11.01 | | MMUT | 4594 | Payload comprising a MMUT gene or variant thereof packaged within a AAVC11.01 capsid. |
| 1 | AAVC11.02 | | MMUT | 4594 | Payload comprising a MMUT gene or variant thereof packaged within a AAVC11.02 capsid. |
| 1 | AAVC11.03 | | MMUT | 4594 | Payload comprising a MMUT gene or variant thereof packaged within a AAVC11.03 capsid. |
| 1 | AAVC11.04 | | MMUT | 4594 | Payload comprising a MMUT gene or variant thereof packaged within a AAVC11.04 capsid. |
| 1 | AAVC11.05 | | MMUT | 4594 | Payload comprising a MMUT gene or variant thereof packaged within a AAVC11.05 capsid. |
| 1 | AAVC11.06 | | MMUT | 4594 | Payload comprising a MMUT gene or variant thereof packaged within a AAVC11.06 capsid. |
| 1 | AAVC11.07 | | MMUT | 4594 | Payload comprising a MMUT gene or variant thereof packaged within a AAVC11.07 capsid. |
| 1 | AAVC11.08 | | MMUT | 4594 | Payload comprising a MMUT gene or variant thereof packaged within a AAVC11.08 capsid. |
| 1 | AAVC11.09 | | MMUT | 4594 | Payload comprising a MMUT gene or variant thereof packaged within a AAVC11.09 capsid. |
| 1 | AAVC11.10 | | MMUT | 4594 | Payload comprising a MMUT gene or variant thereof packaged within a AAVC11.10 capsid. |
| 1 | AAVC11.11 | | MMUT | 4594 | Payload comprising a MMUT gene or variant thereof packaged within a AAVC11.11 capsid. |
| 1 | AAVC11.12 | | MMUT | 4594 | Payload comprising a MMUT gene or variant thereof packaged within a AAVC11.12 capsid. |
| 1 | AAVC11.13 | | MMUT | 4594 | Payload comprising a MMUT gene or variant thereof packaged within a AAVC11.13 capsid. |
| 1 | AAVC11.14 | | MMUT | 4594 | Payload comprising a MMUT gene or variant thereof packaged within a AAVC11.14 capsid. |
| 1 | AAVC11.15 | | MMUT | 4594 | Payload comprising a MMUT gene or variant thereof packaged within a AAVC11.15 capsid. |

Fig. 29 (Continued)

| | | | | | |
|---|---|---|---|---|---|
| 1 | AAVC11.16 | | MMUT | 4594 | Payload comprising a MMUT gene or variant thereof packaged within a AAVC11.16 capsid. |
| 1 | AAVC11.17 | | MMUT | 4594 | Payload comprising a MMUT gene or variant thereof packaged within a AAVC11.17 capsid. |
| 1 | AAVC11.18 | | MMUT | 4594 | Payload comprising a MMUT gene or variant thereof packaged within a AAVC11.18 capsid. |
| 1 | AAVC11.19 | | MMUT | 4594 | Payload comprising a MMUT gene or variant thereof packaged within a AAVC11.19 capsid. |
| 1 | AAV12 | | MMUT | 4594 | Payload comprising a MMUT gene or variant thereof packaged within a AAV12 capsid. |
| 1 | AAV13 | | MMUT | 4594 | Payload comprising a MMUT gene or variant thereof packaged within a AAV13 capsid. |
| 1 | AAV-DJ | | MMUT | 4594 | Payload comprising a MMUT gene or variant thereof packaged within a AAV-DJ capsid. |
| 1 | AAV-LK03 | | MMUT | 4594 | Payload comprising a MMUT gene or variant thereof packaged within a AAV-LK03 capsid. |
| 1 | AAV-LK19 | | MMUT | 4594 | Payload comprising a MMUT gene or variant thereof packaged within a AAV-LK19 capsid. |
| 1 | AAVrh.74 | | MMUT | 4594 | Payload comprising a MMUT gene or variant thereof packaged within a AAVrh.74 capsid. |
| 1 | AAVrh.10 | | MMUT | 4594 | Payload comprising a MMUT gene or variant thereof packaged within a AAVrh.10 capsid. |
| 1 | AAVhu.37 | | MMUT | 4594 | Payload comprising a MMUT gene or variant thereof packaged within a AAVhu.37 capsid. |
| 1 | AAVrh.K | | MMUT | 4594 | Payload comprising a MMUT gene or variant thereof packaged within a AAVrh.K capsid. |
| 1 | AAVrh.39 | | MMUT | 4594 | Payload comprising a MMUT gene or variant thereof packaged within a AAVrh.39 capsid. |
| 1 | AAVrh.9 | | MMUT | 4594 | Payload comprising a MMUT gene or variant thereof packaged within a AAVrh.9 capsid. |
| 1 | avian AAV | | MMUT | 4594 | Payload comprising a MMUT gene or variant thereof packaged within a avian capsid. |

Fig. 29 (Continued)

| | | | | | |
|---|---|---|---|---|---|
| 1 | bovine AAV | | MMUT | 4594 | Payload comprising a MMUT gene or variant thereof packaged within a bovine capsid. |
| 1 | canine AAV | | MMUT | 4594 | Payload comprising a MMUT gene or variant thereof packaged within a canine capsid. |
| 1 | equine AAV | | MMUT | 4594 | Payload comprising a MMUT gene or variant thereof packaged within a equine capsid. |
| 1 | primate AAV | | MMUT | 4594 | Payload comprising a MMUT gene or variant thereof packaged within a primate capsid. |
| 1 | non-primate AAV | | MMUT | 4594 | Payload comprising a MMUT gene or variant thereof packaged within a non-primate capsid. |
| 1 | ovine AAV | | MMUT | 4594 | Payload comprising a MMUT gene or variant thereof packaged within a ovine capsid. |
| 1 | hybrid AAV | | MMUT | 4594 | Payload comprising a MMUT gene or variant thereof packaged within a hybrid capsid. |
| 1 | chimeric AAV | | MMUT | 4594 | Payload comprising a MMUT gene or variant thereof packaged within a chimeric capsid. |
| 2 | AAV1 | 1450374 | MMUT | 4594 | Payload comprising a MMUT gene or variant thereof packaged within a AAV1 capsid. |
| 2 | AAV2 | | MMUT | 4594 | Payload comprising a MMUT gene or variant thereof packaged within a AAV2 capsid. |
| 2 | AAV3 | | MMUT | 4594 | Payload comprising a MMUT gene or variant thereof packaged within a AAV3 capsid. |
| 2 | AAV4 | 1446389 | MMUT | 4594 | Payload comprising a MMUT gene or variant thereof packaged within a AAV4 capsid. |
| 2 | AAV5 | | MMUT | 4594 | Payload comprising a MMUT gene or variant thereof packaged within a AAV5 capsid. |
| 2 | AAV6 | | MMUT | 4594 | Payload comprising a MMUT gene or variant thereof packaged within a AAV6 capsid. |
| 2 | AAV7 | | MMUT | 4594 | Payload comprising a MMUT gene or variant thereof packaged within a AAV7 capsid. |
| 2 | AAV8 | 5075992 | MMUT | 4594 | Payload comprising a MMUT gene or variant thereof packaged within a AAV8 capsid. |
| 2 | AAV9 | | MMUT | 4594 | Payload comprising a MMUT gene or variant thereof packaged within a AAV9 capsid. |

Fig. 29 (Continued)

| | | | | | |
|---|---|---|---|---|---|
| 2 | AAV10 | | MMUT | 4594 | Payload comprising a MMUT gene or variant thereof packaged within a AAV10 capsid. |
| 2 | AAV11 | | MMUT | 4594 | Payload comprising a MMUT gene or variant thereof packaged within a AAV11 capsid. |
| 2 | AAVC11.01 | | MMUT | 4594 | Payload comprising a MMUT gene or variant thereof packaged within a AAVC11.01 capsid. |
| 2 | AAVC11.02 | | MMUT | 4594 | Payload comprising a MMUT gene or variant thereof packaged within a AAVC11.02 capsid. |
| 2 | AAVC11.03 | | MMUT | 4594 | Payload comprising a MMUT gene or variant thereof packaged within a AAVC11.03 capsid. |
| 2 | AAVC11.04 | | MMUT | 4594 | Payload comprising a MMUT gene or variant thereof packaged within a AAVC11.04 capsid. |
| 2 | AAVC11.05 | | MMUT | 4594 | Payload comprising a MMUT gene or variant thereof packaged within a AAVC11.05 capsid. |
| 2 | AAVC11.06 | | MMUT | 4594 | Payload comprising a MMUT gene or variant thereof packaged within a AAVC11.06 capsid. |
| 2 | AAVC11.07 | | MMUT | 4594 | Payload comprising a MMUT gene or variant thereof packaged within a AAVC11.07 capsid. |
| 2 | AAVC11.08 | | MMUT | 4594 | Payload comprising a MMUT gene or variant thereof packaged within a AAVC11.08 capsid. |
| 2 | AAVC11.09 | | MMUT | 4594 | Payload comprising a MMUT gene or variant thereof packaged within a AAVC11.09 capsid. |
| 2 | AAVC11.10 | | MMUT | 4594 | Payload comprising a MMUT gene or variant thereof packaged within a AAVC11.10 capsid. |
| 2 | AAVC11.11 | | MMUT | 4594 | Payload comprising a MMUT gene or variant thereof packaged within a AAVC11.11 capsid. |
| 2 | AAVC11.12 | | MMUT | 4594 | Payload comprising a MMUT gene or variant thereof packaged within a AAVC11.12 capsid. |
| 2 | AAVC11.13 | | MMUT | 4594 | Payload comprising a MMUT gene or variant thereof packaged within a AAVC11.13 capsid. |
| 2 | AAVC11.14 | | MMUT | 4594 | Payload comprising a MMUT gene or variant thereof packaged within a AAVC11.14 capsid. |
| 2 | AAVC11.15 | | MMUT | 4594 | Payload comprising a MMUT gene or variant thereof packaged within a AAVC11.15 capsid. |

Fig. 29 (Continued)

| | | | | | |
|---|---|---|---|---|---|
| 2 | AAVC11.16 | | MMUT | 4594 | Payload comprising a MMUT gene or variant thereof packaged within a AAVC11.16 capsid. |
| 2 | AAVC11.17 | | MMUT | 4594 | Payload comprising a MMUT gene or variant thereof packaged within a AAVC11.17 capsid. |
| 2 | AAVC11.18 | | MMUT | 4594 | Payload comprising a MMUT gene or variant thereof packaged within a AAVC11.18 capsid. |
| 2 | AAVC11.19 | | MMUT | 4594 | Payload comprising a MMUT gene or variant thereof packaged within a AAVC11.19 capsid. |
| 2 | AAV12 | | MMUT | 4594 | Payload comprising a MMUT gene or variant thereof packaged within a AAV12 capsid. |
| 2 | AAV13 | | MMUT | 4594 | Payload comprising a MMUT gene or variant thereof packaged within a AAV13 capsid. |
| 2 | AAV-DJ | | MMUT | 4594 | Payload comprising a MMUT gene or variant thereof packaged within a AAV-DJ capsid. |
| 2 | AAV-LK03 | | MMUT | 4594 | Payload comprising a MMUT gene or variant thereof packaged within a AAV-LK03 capsid. |
| 2 | AAV-LK19 | | MMUT | 4594 | Payload comprising a MMUT gene or variant thereof packaged within a AAV-LK19 capsid. |
| 2 | AAVrh.74 | | MMUT | 4594 | Payload comprising a MMUT gene or variant thereof packaged within a AAVrh.74 capsid. |
| 2 | AAVrh.10 | | MMUT | 4594 | Payload comprising a MMUT gene or variant thereof packaged within a AAVrh.10 capsid. |
| 2 | AAVhu.37 | | MMUT | 4594 | Payload comprising a MMUT gene or variant thereof packaged within a AAVhu.37 capsid. |
| 2 | AAVrh.K | | MMUT | 4594 | Payload comprising a MMUT gene or variant thereof packaged within a AAVrh.K capsid. |
| 2 | AAVrh.39 | | MMUT | 4594 | Payload comprising a MMUT gene or variant thereof packaged within a AAVrh.39 capsid. |
| 2 | AAVrh.9 | | MMUT | 4594 | Payload comprising a MMUT gene or variant thereof packaged within a AAVrh.9 capsid. |
| 2 | avian AAV | | MMUT | 4594 | Payload comprising a MMUT gene or variant thereof packaged within a avian capsid. |

Fig. 29 (Continued)

| | | | | | |
|---|---|---|---|---|---|
| 2 | bovine AAV | | MMUT | 4594 | Payload comprising a MMUT gene or variant thereof packaged within a bovine capsid. |
| 2 | canine AAV | | MMUT | 4594 | Payload comprising a MMUT gene or variant thereof packaged within a canine capsid. |
| 2 | equine AAV | | MMUT | 4594 | Payload comprising a MMUT gene or variant thereof packaged within a equine capsid. |
| 2 | primate AAV | | MMUT | 4594 | Payload comprising a MMUT gene or variant thereof packaged within a primate capsid. |
| 2 | non-primate AAV | | MMUT | 4594 | Payload comprising a MMUT gene or variant thereof packaged within a non-primate capsid. |
| 2 | ovine AAV | | MMUT | 4594 | Payload comprising a MMUT gene or variant thereof packaged within a ovine capsid. |
| 2 | hybrid AAV | | MMUT | 4594 | Payload comprising a MMUT gene or variant thereof packaged within a hybrid capsid. |
| 2 | chimeric AAV | | MMUT | 4594 | Payload comprising a MMUT gene or variant thereof packaged within a chimeric capsid. |
| 1 | AAV1 | 1450374 | MTM1 | 4534 | Payload comprising a MTM1 gene or variant thereof packaged within a AAV1 capsid. |
| 1 | AAV2 | | MTM1 | 4534 | Payload comprising a MTM1 gene or variant thereof packaged within a AAV2 capsid. |
| 1 | AAV3 | | MTM1 | 4534 | Payload comprising a MTM1 gene or variant thereof packaged within a AAV3 capsid. |
| 1 | AAV4 | 1446389 | MTM1 | 4534 | Payload comprising a MTM1 gene or variant thereof packaged within a AAV4 capsid. |
| 1 | AAV5 | | MTM1 | 4534 | Payload comprising a MTM1 gene or variant thereof packaged within a AAV5 capsid. |
| 1 | AAV6 | | MTM1 | 4534 | Payload comprising a MTM1 gene or variant thereof packaged within a AAV6 capsid. |
| 1 | AAV7 | | MTM1 | 4534 | Payload comprising a MTM1 gene or variant thereof packaged within a AAV7 capsid. |
| 1 | AAV8 | 5075992 | MTM1 | 4534 | Payload comprising a MTM1 gene or variant thereof packaged within a AAV8 capsid. |
| 1 | AAV9 | | MTM1 | 4534 | Payload comprising a MTM1 gene or variant thereof packaged within a AAV9 capsid. |

Fig. 29 (Continued)

| | | | | | |
|---|---|---|---|---|---|
| 1 | AAV10 | | MTM1 | 4534 | Payload comprising a MTM1 gene or variant thereof packaged within a AAV10 capsid. |
| 1 | AAV11 | | MTM1 | 4534 | Payload comprising a MTM1 gene or variant thereof packaged within a AAV11 capsid. |
| 1 | AAVC11.01 | | MTM1 | 4534 | Payload comprising a MTM1 gene or variant thereof packaged within a AAVC11.01 capsid. |
| 1 | AAVC11.02 | | MTM1 | 4534 | Payload comprising a MTM1 gene or variant thereof packaged within a AAVC11.02 capsid. |
| 1 | AAVC11.03 | | MTM1 | 4534 | Payload comprising a MTM1 gene or variant thereof packaged within a AAVC11.03 capsid. |
| 1 | AAVC11.04 | | MTM1 | 4534 | Payload comprising a MTM1 gene or variant thereof packaged within a AAVC11.04 capsid. |
| 1 | AAVC11.05 | | MTM1 | 4534 | Payload comprising a MTM1 gene or variant thereof packaged within a AAVC11.05 capsid. |
| 1 | AAVC11.06 | | MTM1 | 4534 | Payload comprising a MTM1 gene or variant thereof packaged within a AAVC11.06 capsid. |
| 1 | AAVC11.07 | | MTM1 | 4534 | Payload comprising a MTM1 gene or variant thereof packaged within a AAVC11.07 capsid. |
| 1 | AAVC11.08 | | MTM1 | 4534 | Payload comprising a MTM1 gene or variant thereof packaged within a AAVC11.08 capsid. |
| 1 | AAVC11.09 | | MTM1 | 4534 | Payload comprising a MTM1 gene or variant thereof packaged within a AAVC11.09 capsid. |
| 1 | AAVC11.10 | | MTM1 | 4534 | Payload comprising a MTM1 gene or variant thereof packaged within a AAVC11.10 capsid. |
| 1 | AAVC11.11 | | MTM1 | 4534 | Payload comprising a MTM1 gene or variant thereof packaged within a AAVC11.11 capsid. |
| 1 | AAVC11.12 | | MTM1 | 4534 | Payload comprising a MTM1 gene or variant thereof packaged within a AAVC11.12 capsid. |
| 1 | AAVC11.13 | | MTM1 | 4534 | Payload comprising a MTM1 gene or variant thereof packaged within a AAVC11.13 capsid. |
| 1 | AAVC11.14 | | MTM1 | 4534 | Payload comprising a MTM1 gene or variant thereof packaged within a AAVC11.14 capsid. |
| 1 | AAVC11.15 | | MTM1 | 4534 | Payload comprising a MTM1 gene or variant thereof packaged within a AAVC11.15 capsid. |

Fig. 29 (Continued)

| | | | | | |
|---|---|---|---|---|---|
| 1 | AAVC11.16 | | MTM1 | 4534 | Payload comprising a MTM1 gene or variant thereof packaged within a AAVC11.16 capsid. |
| 1 | AAVC11.17 | | MTM1 | 4534 | Payload comprising a MTM1 gene or variant thereof packaged within a AAVC11.17 capsid. |
| 1 | AAVC11.18 | | MTM1 | 4534 | Payload comprising a MTM1 gene or variant thereof packaged within a AAVC11.18 capsid. |
| 1 | AAVC11.19 | | MTM1 | 4534 | Payload comprising a MTM1 gene or variant thereof packaged within a AAVC11.19 capsid. |
| 1 | AAV12 | | MTM1 | 4534 | Payload comprising a MTM1 gene or variant thereof packaged within a AAV12 capsid. |
| 1 | AAV13 | | MTM1 | 4534 | Payload comprising a MTM1 gene or variant thereof packaged within a AAV13 capsid. |
| 1 | AAV-DJ | | MTM1 | 4534 | Payload comprising a MTM1 gene or variant thereof packaged within a AAV-DJ capsid. |
| 1 | AAV-LK03 | | MTM1 | 4534 | Payload comprising a MTM1 gene or variant thereof packaged within a AAV-LK03 capsid. |
| 1 | AAV-LK19 | | MTM1 | 4534 | Payload comprising a MTM1 gene or variant thereof packaged within a AAV-LK19 capsid. |
| 1 | AAVrh.74 | | MTM1 | 4534 | Payload comprising a MTM1 gene or variant thereof packaged within a AAVrh.74 capsid. |
| 1 | AAVrh.10 | | MTM1 | 4534 | Payload comprising a MTM1 gene or variant thereof packaged within a AAVrh.10 capsid. |
| 1 | AAVhu.37 | | MTM1 | 4534 | Payload comprising a MTM1 gene or variant thereof packaged within a AAVhu.37 capsid. |
| 1 | AAVrh.K | | MTM1 | 4534 | Payload comprising a MTM1 gene or variant thereof packaged within a AAVrh.K capsid. |
| 1 | AAVrh.39 | | MTM1 | 4534 | Payload comprising a MTM1 gene or variant thereof packaged within a AAVrh.39 capsid. |
| 1 | AAVrh.9 | | MTM1 | 4534 | Payload comprising a MTM1 gene or variant thereof packaged within a AAVrh.9 capsid. |
| 1 | avian AAV | | MTM1 | 4534 | Payload comprising a MTM1 gene or variant thereof packaged within a avian capsid. |

Fig. 29 (Continued)

| | | | | | |
|---|---|---|---|---|---|
| 1 | bovine AAV | | MTM1 | 4534 | Payload comprising a MTM1 gene or variant thereof packaged within a bovine capsid. |
| 1 | canine AAV | | MTM1 | 4534 | Payload comprising a MTM1 gene or variant thereof packaged within a canine capsid. |
| 1 | equine AAV | | MTM1 | 4534 | Payload comprising a MTM1 gene or variant thereof packaged within a equine capsid. |
| 1 | primate AAV | | MTM1 | 4534 | Payload comprising a MTM1 gene or variant thereof packaged within a primate capsid. |
| 1 | non-primate AAV | | MTM1 | 4534 | Payload comprising a MTM1 gene or variant thereof packaged within a non-primate capsid. |
| 1 | ovine AAV | | MTM1 | 4534 | Payload comprising a MTM1 gene or variant thereof packaged within a ovine capsid. |
| 1 | hybrid AAV | | MTM1 | 4534 | Payload comprising a MTM1 gene or variant thereof packaged within a hybrid capsid. |
| 1 | chimeric AAV | | MTM1 | 4534 | Payload comprising a MTM1 gene or variant thereof packaged within a chimeric capsid. |
| 2 | AAV1 | 1450374 | MTM1 | 4534 | Payload comprising a MTM1 gene or variant thereof packaged within a AAV1 capsid. |
| 2 | AAV2 | | MTM1 | 4534 | Payload comprising a MTM1 gene or variant thereof packaged within a AAV2 capsid. |
| 2 | AAV3 | | MTM1 | 4534 | Payload comprising a MTM1 gene or variant thereof packaged within a AAV3 capsid. |
| 2 | AAV4 | 1446389 | MTM1 | 4534 | Payload comprising a MTM1 gene or variant thereof packaged within a AAV4 capsid. |
| 2 | AAV5 | | MTM1 | 4534 | Payload comprising a MTM1 gene or variant thereof packaged within a AAV5 capsid. |
| 2 | AAV6 | | MTM1 | 4534 | Payload comprising a MTM1 gene or variant thereof packaged within a AAV6 capsid. |
| 2 | AAV7 | | MTM1 | 4534 | Payload comprising a MTM1 gene or variant thereof packaged within a AAV7 capsid. |
| 2 | AAV8 | 5075992 | MTM1 | 4534 | Payload comprising a MTM1 gene or variant thereof packaged within a AAV8 capsid. |
| 2 | AAV9 | | MTM1 | 4534 | Payload comprising a MTM1 gene or variant thereof packaged within a AAV9 capsid. |

Fig. 29 (Continued)

| | | | | | |
|---|---|---|---|---|---|
| 2 | AAV10 | | MTM1 | 4534 | Payload comprising a MTM1 gene or variant thereof packaged within a AAV10 capsid. |
| 2 | AAV11 | | MTM1 | 4534 | Payload comprising a MTM1 gene or variant thereof packaged within a AAV11 capsid. |
| 2 | AAVC11.01 | | MTM1 | 4534 | Payload comprising a MTM1 gene or variant thereof packaged within a AAVC11.01 capsid. |
| 2 | AAVC11.02 | | MTM1 | 4534 | Payload comprising a MTM1 gene or variant thereof packaged within a AAVC11.02 capsid. |
| 2 | AAVC11.03 | | MTM1 | 4534 | Payload comprising a MTM1 gene or variant thereof packaged within a AAVC11.03 capsid. |
| 2 | AAVC11.04 | | MTM1 | 4534 | Payload comprising a MTM1 gene or variant thereof packaged within a AAVC11.04 capsid. |
| 2 | AAVC11.05 | | MTM1 | 4534 | Payload comprising a MTM1 gene or variant thereof packaged within a AAVC11.05 capsid. |
| 2 | AAVC11.06 | | MTM1 | 4534 | Payload comprising a MTM1 gene or variant thereof packaged within a AAVC11.06 capsid. |
| 2 | AAVC11.07 | | MTM1 | 4534 | Payload comprising a MTM1 gene or variant thereof packaged within a AAVC11.07 capsid. |
| 2 | AAVC11.08 | | MTM1 | 4534 | Payload comprising a MTM1 gene or variant thereof packaged within a AAVC11.08 capsid. |
| 2 | AAVC11.09 | | MTM1 | 4534 | Payload comprising a MTM1 gene or variant thereof packaged within a AAVC11.09 capsid. |
| 2 | AAVC11.10 | | MTM1 | 4534 | Payload comprising a MTM1 gene or variant thereof packaged within a AAVC11.10 capsid. |
| 2 | AAVC11.11 | | MTM1 | 4534 | Payload comprising a MTM1 gene or variant thereof packaged within a AAVC11.11 capsid. |
| 2 | AAVC11.12 | | MTM1 | 4534 | Payload comprising a MTM1 gene or variant thereof packaged within a AAVC11.12 capsid. |
| 2 | AAVC11.13 | | MTM1 | 4534 | Payload comprising a MTM1 gene or variant thereof packaged within a AAVC11.13 capsid. |
| 2 | AAVC11.14 | | MTM1 | 4534 | Payload comprising a MTM1 gene or variant thereof packaged within a AAVC11.14 capsid. |
| 2 | AAVC11.15 | | MTM1 | 4534 | Payload comprising a MTM1 gene or variant thereof packaged within a AAVC11.15 capsid. |

Fig. 29 (Continued)

| | | | | | |
|---|---|---|---|---|---|
| 2 | AAVC11.16 | | MTM1 | 4534 | Payload comprising a MTM1 gene or variant thereof packaged within a AAVC11.16 capsid. |
| 2 | AAVC11.17 | | MTM1 | 4534 | Payload comprising a MTM1 gene or variant thereof packaged within a AAVC11.17 capsid. |
| 2 | AAVC11.18 | | MTM1 | 4534 | Payload comprising a MTM1 gene or variant thereof packaged within a AAVC11.18 capsid. |
| 2 | AAVC11.19 | | MTM1 | 4534 | Payload comprising a MTM1 gene or variant thereof packaged within a AAVC11.19 capsid. |
| 2 | AAV12 | | MTM1 | 4534 | Payload comprising a MTM1 gene or variant thereof packaged within a AAV12 capsid. |
| 2 | AAV13 | | MTM1 | 4534 | Payload comprising a MTM1 gene or variant thereof packaged within a AAV13 capsid. |
| 2 | AAV-DJ | | MTM1 | 4534 | Payload comprising a MTM1 gene or variant thereof packaged within a AAV-DJ capsid. |
| 2 | AAV-LK03 | | MTM1 | 4534 | Payload comprising a MTM1 gene or variant thereof packaged within a AAV-LK03 capsid. |
| 2 | AAV-LK19 | | MTM1 | 4534 | Payload comprising a MTM1 gene or variant thereof packaged within a AAV-LK19 capsid. |
| 2 | AAVrh.74 | | MTM1 | 4534 | Payload comprising a MTM1 gene or variant thereof packaged within a AAVrh.74 capsid. |
| 2 | AAVrh.10 | | MTM1 | 4534 | Payload comprising a MTM1 gene or variant thereof packaged within a AAVrh.10 capsid. |
| 2 | AAVhu.37 | | MTM1 | 4534 | Payload comprising a MTM1 gene or variant thereof packaged within a AAVhu.37 capsid. |
| 2 | AAVrh.K | | MTM1 | 4534 | Payload comprising a MTM1 gene or variant thereof packaged within a AAVrh.K capsid. |
| 2 | AAVrh.39 | | MTM1 | 4534 | Payload comprising a MTM1 gene or variant thereof packaged within a AAVrh.39 capsid. |
| 2 | AAVrh.9 | | MTM1 | 4534 | Payload comprising a MTM1 gene or variant thereof packaged within a AAVrh.9 capsid. |
| 2 | avian AAV | | MTM1 | 4534 | Payload comprising a MTM1 gene or variant thereof packaged within a avian capsid. |

Fig. 29 (Continued)

| | | | | | |
|---|---|---|---|---|---|
| 2 | bovine AAV | | MTM1 | 4534 | Payload comprising a MTM1 gene or variant thereof packaged within a bovine capsid. |
| 2 | canine AAV | | MTM1 | 4534 | Payload comprising a MTM1 gene or variant thereof packaged within a canine capsid. |
| 2 | equine AAV | | MTM1 | 4534 | Payload comprising a MTM1 gene or variant thereof packaged within a equine capsid. |
| 2 | primate AAV | | MTM1 | 4534 | Payload comprising a MTM1 gene or variant thereof packaged within a primate capsid. |
| 2 | non-primate AAV | | MTM1 | 4534 | Payload comprising a MTM1 gene or variant thereof packaged within a non-primate capsid. |
| 2 | ovine AAV | | MTM1 | 4534 | Payload comprising a MTM1 gene or variant thereof packaged within a ovine capsid. |
| 2 | hybrid AAV | | MTM1 | 4534 | Payload comprising a MTM1 gene or variant thereof packaged within a hybrid capsid. |
| 2 | chimeric AAV | | MTM1 | 4534 | Payload comprising a MTM1 gene or variant thereof packaged within a chimeric capsid. |
| 1 | AAV1 | 1450374 | NAGLU | 4669 | Payload comprising a NAGLU gene or variant thereof packaged within a AAV1 capsid. |
| 1 | AAV2 | | NAGLU | 4669 | Payload comprising a NAGLU gene or variant thereof packaged within a AAV2 capsid. |
| 1 | AAV3 | | NAGLU | 4669 | Payload comprising a NAGLU gene or variant thereof packaged within a AAV3 capsid. |
| 1 | AAV4 | 1446389 | NAGLU | 4669 | Payload comprising a NAGLU gene or variant thereof packaged within a AAV4 capsid. |
| 1 | AAV5 | | NAGLU | 4669 | Payload comprising a NAGLU gene or variant thereof packaged within a AAV5 capsid. |
| 1 | AAV6 | | NAGLU | 4669 | Payload comprising a NAGLU gene or variant thereof packaged within a AAV6 capsid. |
| 1 | AAV7 | | NAGLU | 4669 | Payload comprising a NAGLU gene or variant thereof packaged within a AAV7 capsid. |
| 1 | AAV8 | 5075992 | NAGLU | 4669 | Payload comprising a NAGLU gene or variant thereof packaged within a AAV8 capsid. |
| 1 | AAV9 | | NAGLU | 4669 | Payload comprising a NAGLU gene or variant thereof packaged within a AAV9 capsid. |

Fig. 29 (Continued)

| | | | | | |
|---|---|---|---|---|---|
| 1 | AAV10 | | NAGLU | 4669 | Payload comprising a NAGLU gene or variant thereof packaged within a AAV10 capsid. |
| 1 | AAV11 | | NAGLU | 4669 | Payload comprising a NAGLU gene or variant thereof packaged within a AAV11 capsid. |
| 1 | AAVC11.01 | | NAGLU | 4669 | Payload comprising a NAGLU gene or variant thereof packaged within a AAVC11.01 capsid. |
| 1 | AAVC11.02 | | NAGLU | 4669 | Payload comprising a NAGLU gene or variant thereof packaged within a AAVC11.02 capsid. |
| 1 | AAVC11.03 | | NAGLU | 4669 | Payload comprising a NAGLU gene or variant thereof packaged within a AAVC11.03 capsid. |
| 1 | AAVC11.04 | | NAGLU | 4669 | Payload comprising a NAGLU gene or variant thereof packaged within a AAVC11.04 capsid. |
| 1 | AAVC11.05 | | NAGLU | 4669 | Payload comprising a NAGLU gene or variant thereof packaged within a AAVC11.05 capsid. |
| 1 | AAVC11.06 | | NAGLU | 4669 | Payload comprising a NAGLU gene or variant thereof packaged within a AAVC11.06 capsid. |
| 1 | AAVC11.07 | | NAGLU | 4669 | Payload comprising a NAGLU gene or variant thereof packaged within a AAVC11.07 capsid. |
| 1 | AAVC11.08 | | NAGLU | 4669 | Payload comprising a NAGLU gene or variant thereof packaged within a AAVC11.08 capsid. |
| 1 | AAVC11.09 | | NAGLU | 4669 | Payload comprising a NAGLU gene or variant thereof packaged within a AAVC11.09 capsid. |
| 1 | AAVC11.10 | | NAGLU | 4669 | Payload comprising a NAGLU gene or variant thereof packaged within a AAVC11.10 capsid. |
| 1 | AAVC11.11 | | NAGLU | 4669 | Payload comprising a NAGLU gene or variant thereof packaged within a AAVC11.11 capsid. |
| 1 | AAVC11.12 | | NAGLU | 4669 | Payload comprising a NAGLU gene or variant thereof packaged within a AAVC11.12 capsid. |
| 1 | AAVC11.13 | | NAGLU | 4669 | Payload comprising a NAGLU gene or variant thereof packaged within a AAVC11.13 capsid. |
| 1 | AAVC11.14 | | NAGLU | 4669 | Payload comprising a NAGLU gene or variant thereof packaged within a AAVC11.14 capsid. |
| 1 | AAVC11.15 | | NAGLU | 4669 | Payload comprising a NAGLU gene or variant thereof packaged within a AAVC11.15 capsid. |

Fig. 29 (Continued)

| | | | | | |
|---|---|---|---|---|---|
| 1 | AAVC11.16 | | NAGLU | 4669 | Payload comprising a NAGLU gene or variant thereof packaged within a AAVC11.16 capsid. |
| 1 | AAVC11.17 | | NAGLU | 4669 | Payload comprising a NAGLU gene or variant thereof packaged within a AAVC11.17 capsid. |
| 1 | AAVC11.18 | | NAGLU | 4669 | Payload comprising a NAGLU gene or variant thereof packaged within a AAVC11.18 capsid. |
| 1 | AAVC11.19 | | NAGLU | 4669 | Payload comprising a NAGLU gene or variant thereof packaged within a AAVC11.19 capsid. |
| 1 | AAV12 | | NAGLU | 4669 | Payload comprising a NAGLU gene or variant thereof packaged within a AAV12 capsid. |
| 1 | AAV13 | | NAGLU | 4669 | Payload comprising a NAGLU gene or variant thereof packaged within a AAV13 capsid. |
| 1 | AAV-DJ | | NAGLU | 4669 | Payload comprising a NAGLU gene or variant thereof packaged within a AAV-DJ capsid. |
| 1 | AAV-LK03 | | NAGLU | 4669 | Payload comprising a NAGLU gene or variant thereof packaged within a AAV-LK03 capsid. |
| 1 | AAV-LK19 | | NAGLU | 4669 | Payload comprising a NAGLU gene or variant thereof packaged within a AAV-LK19 capsid. |
| 1 | AAVrh.74 | | NAGLU | 4669 | Payload comprising a NAGLU gene or variant thereof packaged within a AAVrh.74 capsid. |
| 1 | AAVrh.10 | | NAGLU | 4669 | Payload comprising a NAGLU gene or variant thereof packaged within a AAVrh.10 capsid. |
| 1 | AAVhu.37 | | NAGLU | 4669 | Payload comprising a NAGLU gene or variant thereof packaged within a AAVhu.37 capsid. |
| 1 | AAVrh.K | | NAGLU | 4669 | Payload comprising a NAGLU gene or variant thereof packaged within a AAVrh.K capsid. |
| 1 | AAVrh.39 | | NAGLU | 4669 | Payload comprising a NAGLU gene or variant thereof packaged within a AAVrh.39 capsid. |
| 1 | AAVrh.9 | | NAGLU | 4669 | Payload comprising a NAGLU gene or variant thereof packaged within a AAVrh.9 capsid. |
| 1 | avian AAV | | NAGLU | 4669 | Payload comprising a NAGLU gene or variant thereof packaged within a avian capsid. |

Fig. 29 (Continued)

| | | | | | |
|---|---|---|---|---|---|
| 1 | bovine AAV | | NAGLU | 4669 | Payload comprising a NAGLU gene or variant thereof packaged within a bovine capsid. |
| 1 | canine AAV | | NAGLU | 4669 | Payload comprising a NAGLU gene or variant thereof packaged within a canine capsid. |
| 1 | equine AAV | | NAGLU | 4669 | Payload comprising a NAGLU gene or variant thereof packaged within a equine capsid. |
| 1 | primate AAV | | NAGLU | 4669 | Payload comprising a NAGLU gene or variant thereof packaged within a primate capsid. |
| 1 | non-primate AAV | | NAGLU | 4669 | Payload comprising a NAGLU gene or variant thereof packaged within a non-primate capsid. |
| 1 | ovine AAV | | NAGLU | 4669 | Payload comprising a NAGLU gene or variant thereof packaged within a ovine capsid. |
| 1 | hybrid AAV | | NAGLU | 4669 | Payload comprising a NAGLU gene or variant thereof packaged within a hybrid capsid. |
| 1 | chimeric AAV | | NAGLU | 4669 | Payload comprising a NAGLU gene or variant thereof packaged within a chimeric capsid. |
| 2 | AAV1 | 1450374 | NAGLU | 4669 | Payload comprising a NAGLU gene or variant thereof packaged within a AAV1 capsid. |
| 2 | AAV2 | | NAGLU | 4669 | Payload comprising a NAGLU gene or variant thereof packaged within a AAV2 capsid. |
| 2 | AAV3 | | NAGLU | 4669 | Payload comprising a NAGLU gene or variant thereof packaged within a AAV3 capsid. |
| 2 | AAV4 | 1446389 | NAGLU | 4669 | Payload comprising a NAGLU gene or variant thereof packaged within a AAV4 capsid. |
| 2 | AAV5 | | NAGLU | 4669 | Payload comprising a NAGLU gene or variant thereof packaged within a AAV5 capsid. |
| 2 | AAV6 | | NAGLU | 4669 | Payload comprising a NAGLU gene or variant thereof packaged within a AAV6 capsid. |
| 2 | AAV7 | | NAGLU | 4669 | Payload comprising a NAGLU gene or variant thereof packaged within a AAV7 capsid. |
| 2 | AAV8 | 5075992 | NAGLU | 4669 | Payload comprising a NAGLU gene or variant thereof packaged within a AAV8 capsid. |
| 2 | AAV9 | | NAGLU | 4669 | Payload comprising a NAGLU gene or variant thereof packaged within a AAV9 capsid. |

Fig. 29 (Continued)

| | | | | | |
|---|---|---|---|---|---|
| 2 | AAV10 | | NAGLU | 4669 | Payload comprising a NAGLU gene or variant thereof packaged within a AAV10 capsid. |
| 2 | AAV11 | | NAGLU | 4669 | Payload comprising a NAGLU gene or variant thereof packaged within a AAV11 capsid. |
| 2 | AAVC11.01 | | NAGLU | 4669 | Payload comprising a NAGLU gene or variant thereof packaged within a AAVC11.01 capsid. |
| 2 | AAVC11.02 | | NAGLU | 4669 | Payload comprising a NAGLU gene or variant thereof packaged within a AAVC11.02 capsid. |
| 2 | AAVC11.03 | | NAGLU | 4669 | Payload comprising a NAGLU gene or variant thereof packaged within a AAVC11.03 capsid. |
| 2 | AAVC11.04 | | NAGLU | 4669 | Payload comprising a NAGLU gene or variant thereof packaged within a AAVC11.04 capsid. |
| 2 | AAVC11.05 | | NAGLU | 4669 | Payload comprising a NAGLU gene or variant thereof packaged within a AAVC11.05 capsid. |
| 2 | AAVC11.06 | | NAGLU | 4669 | Payload comprising a NAGLU gene or variant thereof packaged within a AAVC11.06 capsid. |
| 2 | AAVC11.07 | | NAGLU | 4669 | Payload comprising a NAGLU gene or variant thereof packaged within a AAVC11.07 capsid. |
| 2 | AAVC11.08 | | NAGLU | 4669 | Payload comprising a NAGLU gene or variant thereof packaged within a AAVC11.08 capsid. |
| 2 | AAVC11.09 | | NAGLU | 4669 | Payload comprising a NAGLU gene or variant thereof packaged within a AAVC11.09 capsid. |
| 2 | AAVC11.10 | | NAGLU | 4669 | Payload comprising a NAGLU gene or variant thereof packaged within a AAVC11.10 capsid. |
| 2 | AAVC11.11 | | NAGLU | 4669 | Payload comprising a NAGLU gene or variant thereof packaged within a AAVC11.11 capsid. |
| 2 | AAVC11.12 | | NAGLU | 4669 | Payload comprising a NAGLU gene or variant thereof packaged within a AAVC11.12 capsid. |
| 2 | AAVC11.13 | | NAGLU | 4669 | Payload comprising a NAGLU gene or variant thereof packaged within a AAVC11.13 capsid. |
| 2 | AAVC11.14 | | NAGLU | 4669 | Payload comprising a NAGLU gene or variant thereof packaged within a AAVC11.14 capsid. |
| 2 | AAVC11.15 | | NAGLU | 4669 | Payload comprising a NAGLU gene or variant thereof packaged within a AAVC11.15 capsid. |

Fig. 29 (Continued)

| | | | | | |
|---|---|---|---|---|---|
| 2 | AAVC11.16 | | NAGLU | 4669 | Payload comprising a NAGLU gene or variant thereof packaged within a AAVC11.16 capsid. |
| 2 | AAVC11.17 | | NAGLU | 4669 | Payload comprising a NAGLU gene or variant thereof packaged within a AAVC11.17 capsid. |
| 2 | AAVC11.18 | | NAGLU | 4669 | Payload comprising a NAGLU gene or variant thereof packaged within a AAVC11.18 capsid. |
| 2 | AAVC11.19 | | NAGLU | 4669 | Payload comprising a NAGLU gene or variant thereof packaged within a AAVC11.19 capsid. |
| 2 | AAV12 | | NAGLU | 4669 | Payload comprising a NAGLU gene or variant thereof packaged within a AAV12 capsid. |
| 2 | AAV13 | | NAGLU | 4669 | Payload comprising a NAGLU gene or variant thereof packaged within a AAV13 capsid. |
| 2 | AAV-DJ | | NAGLU | 4669 | Payload comprising a NAGLU gene or variant thereof packaged within a AAV-DJ capsid. |
| 2 | AAV-LK03 | | NAGLU | 4669 | Payload comprising a NAGLU gene or variant thereof packaged within a AAV-LK03 capsid. |
| 2 | AAV-LK19 | | NAGLU | 4669 | Payload comprising a NAGLU gene or variant thereof packaged within a AAV-LK19 capsid. |
| 2 | AAVrh.74 | | NAGLU | 4669 | Payload comprising a NAGLU gene or variant thereof packaged within a AAVrh.74 capsid. |
| 2 | AAVrh.10 | | NAGLU | 4669 | Payload comprising a NAGLU gene or variant thereof packaged within a AAVrh.10 capsid. |
| 2 | AAVhu.37 | | NAGLU | 4669 | Payload comprising a NAGLU gene or variant thereof packaged within a AAVhu.37 capsid. |
| 2 | AAVrh.K | | NAGLU | 4669 | Payload comprising a NAGLU gene or variant thereof packaged within a AAVrh.K capsid. |
| 2 | AAVrh.39 | | NAGLU | 4669 | Payload comprising a NAGLU gene or variant thereof packaged within a AAVrh.39 capsid. |
| 2 | AAVrh.9 | | NAGLU | 4669 | Payload comprising a NAGLU gene or variant thereof packaged within a AAVrh.9 capsid. |
| 2 | avian AAV | | NAGLU | 4669 | Payload comprising a NAGLU gene or variant thereof packaged within a avian capsid. |

Fig. 29 (Continued)

| | | | | | |
|---|---|---|---|---|---|
| 2 | bovine AAV | | NAGLU | 4669 | Payload comprising a NAGLU gene or variant thereof packaged within a bovine capsid. |
| 2 | canine AAV | | NAGLU | 4669 | Payload comprising a NAGLU gene or variant thereof packaged within a canine capsid. |
| 2 | equine AAV | | NAGLU | 4669 | Payload comprising a NAGLU gene or variant thereof packaged within a equine capsid. |
| 2 | primate AAV | | NAGLU | 4669 | Payload comprising a NAGLU gene or variant thereof packaged within a primate capsid. |
| 2 | non-primate AAV | | NAGLU | 4669 | Payload comprising a NAGLU gene or variant thereof packaged within a non-primate capsid. |
| 2 | ovine AAV | | NAGLU | 4669 | Payload comprising a NAGLU gene or variant thereof packaged within a ovine capsid. |
| 2 | hybrid AAV | | NAGLU | 4669 | Payload comprising a NAGLU gene or variant thereof packaged within a hybrid capsid. |
| 2 | chimeric AAV | | NAGLU | 4669 | Payload comprising a NAGLU gene or variant thereof packaged within a chimeric capsid. |
| 1 | AAV1 | 1450374 | NPC1 | 4864 | Payload comprising a NPC1 gene or variant thereof packaged within a AAV1 capsid. |
| 1 | AAV2 | | NPC1 | 4864 | Payload comprising a NPC1 gene or variant thereof packaged within a AAV2 capsid. |
| 1 | AAV3 | | NPC1 | 4864 | Payload comprising a NPC1 gene or variant thereof packaged within a AAV3 capsid. |
| 1 | AAV4 | 1446389 | NPC1 | 4864 | Payload comprising a NPC1 gene or variant thereof packaged within a AAV4 capsid. |
| 1 | AAV5 | | NPC1 | 4864 | Payload comprising a NPC1 gene or variant thereof packaged within a AAV5 capsid. |
| 1 | AAV6 | | NPC1 | 4864 | Payload comprising a NPC1 gene or variant thereof packaged within a AAV6 capsid. |
| 1 | AAV7 | | NPC1 | 4864 | Payload comprising a NPC1 gene or variant thereof packaged within a AAV7 capsid. |
| 1 | AAV8 | 5075992 | NPC1 | 4864 | Payload comprising a NPC1 gene or variant thereof packaged within a AAV8 capsid. |
| 1 | AAV9 | | NPC1 | 4864 | Payload comprising a NPC1 gene or variant thereof packaged within a AAV9 capsid. |

Fig. 29 (Continued)

| | | | | | |
|---|---|---|---|---|---|
| 1 | AAV10 | | NPC1 | 4864 | Payload comprising a NPC1 gene or variant thereof packaged within a AAV10 capsid. |
| 1 | AAV11 | | NPC1 | 4864 | Payload comprising a NPC1 gene or variant thereof packaged within a AAV11 capsid. |
| 1 | AAVC11.01 | | NPC1 | 4864 | Payload comprising a NPC1 gene or variant thereof packaged within a AAVC11.01 capsid. |
| 1 | AAVC11.02 | | NPC1 | 4864 | Payload comprising a NPC1 gene or variant thereof packaged within a AAVC11.02 capsid. |
| 1 | AAVC11.03 | | NPC1 | 4864 | Payload comprising a NPC1 gene or variant thereof packaged within a AAVC11.03 capsid. |
| 1 | AAVC11.04 | | NPC1 | 4864 | Payload comprising a NPC1 gene or variant thereof packaged within a AAVC11.04 capsid. |
| 1 | AAVC11.05 | | NPC1 | 4864 | Payload comprising a NPC1 gene or variant thereof packaged within a AAVC11.05 capsid. |
| 1 | AAVC11.06 | | NPC1 | 4864 | Payload comprising a NPC1 gene or variant thereof packaged within a AAVC11.06 capsid. |
| 1 | AAVC11.07 | | NPC1 | 4864 | Payload comprising a NPC1 gene or variant thereof packaged within a AAVC11.07 capsid. |
| 1 | AAVC11.08 | | NPC1 | 4864 | Payload comprising a NPC1 gene or variant thereof packaged within a AAVC11.08 capsid. |
| 1 | AAVC11.09 | | NPC1 | 4864 | Payload comprising a NPC1 gene or variant thereof packaged within a AAVC11.09 capsid. |
| 1 | AAVC11.10 | | NPC1 | 4864 | Payload comprising a NPC1 gene or variant thereof packaged within a AAVC11.10 capsid. |
| 1 | AAVC11.11 | | NPC1 | 4864 | Payload comprising a NPC1 gene or variant thereof packaged within a AAVC11.11 capsid. |
| 1 | AAVC11.12 | | NPC1 | 4864 | Payload comprising a NPC1 gene or variant thereof packaged within a AAVC11.12 capsid. |
| 1 | AAVC11.13 | | NPC1 | 4864 | Payload comprising a NPC1 gene or variant thereof packaged within a AAVC11.13 capsid. |
| 1 | AAVC11.14 | | NPC1 | 4864 | Payload comprising a NPC1 gene or variant thereof packaged within a AAVC11.14 capsid. |
| 1 | AAVC11.15 | | NPC1 | 4864 | Payload comprising a NPC1 gene or variant thereof packaged within a AAVC11.15 capsid. |

Fig. 29 (Continued)

| | | | | | |
|---|---|---|---|---|---|
| 1 | AAVC11.16 | | NPC1 | 4864 | Payload comprising a NPC1 gene or variant thereof packaged within a AAVC11.16 capsid. |
| 1 | AAVC11.17 | | NPC1 | 4864 | Payload comprising a NPC1 gene or variant thereof packaged within a AAVC11.17 capsid. |
| 1 | AAVC11.18 | | NPC1 | 4864 | Payload comprising a NPC1 gene or variant thereof packaged within a AAVC11.18 capsid. |
| 1 | AAVC11.19 | | NPC1 | 4864 | Payload comprising a NPC1 gene or variant thereof packaged within a AAVC11.19 capsid. |
| 1 | AAV12 | | NPC1 | 4864 | Payload comprising a NPC1 gene or variant thereof packaged within a AAV12 capsid. |
| 1 | AAV13 | | NPC1 | 4864 | Payload comprising a NPC1 gene or variant thereof packaged within a AAV13 capsid. |
| 1 | AAV-DJ | | NPC1 | 4864 | Payload comprising a NPC1 gene or variant thereof packaged within a AAV-DJ capsid. |
| 1 | AAV-LK03 | | NPC1 | 4864 | Payload comprising a NPC1 gene or variant thereof packaged within a AAV-LK03 capsid. |
| 1 | AAV-LK19 | | NPC1 | 4864 | Payload comprising a NPC1 gene or variant thereof packaged within a AAV-LK19 capsid. |
| 1 | AAVrh.74 | | NPC1 | 4864 | Payload comprising a NPC1 gene or variant thereof packaged within a AAVrh.74 capsid. |
| 1 | AAVrh.10 | | NPC1 | 4864 | Payload comprising a NPC1 gene or variant thereof packaged within a AAVrh.10 capsid. |
| 1 | AAVhu.37 | | NPC1 | 4864 | Payload comprising a NPC1 gene or variant thereof packaged within a AAVhu.37 capsid. |
| 1 | AAVrh.K | | NPC1 | 4864 | Payload comprising a NPC1 gene or variant thereof packaged within a AAVrh.K capsid. |
| 1 | AAVrh.39 | | NPC1 | 4864 | Payload comprising a NPC1 gene or variant thereof packaged within a AAVrh.39 capsid. |
| 1 | AAVrh.9 | | NPC1 | 4864 | Payload comprising a NPC1 gene or variant thereof packaged within a AAVrh.9 capsid. |
| 1 | avian AAV | | NPC1 | 4864 | Payload comprising a NPC1 gene or variant thereof packaged within a avian capsid. |

Fig. 29 (Continued)

| | | | | | |
|---|---|---|---|---|---|
| 1 | bovine AAV | | NPC1 | 4864 | Payload comprising a NPC1 gene or variant thereof packaged within a bovine capsid. |
| 1 | canine AAV | | NPC1 | 4864 | Payload comprising a NPC1 gene or variant thereof packaged within a canine capsid. |
| 1 | equine AAV | | NPC1 | 4864 | Payload comprising a NPC1 gene or variant thereof packaged within a equine capsid. |
| 1 | primate AAV | | NPC1 | 4864 | Payload comprising a NPC1 gene or variant thereof packaged within a primate capsid. |
| 1 | non-primate AAV | | NPC1 | 4864 | Payload comprising a NPC1 gene or variant thereof packaged within a non-primate capsid. |
| 1 | ovine AAV | | NPC1 | 4864 | Payload comprising a NPC1 gene or variant thereof packaged within a ovine capsid. |
| 1 | hybrid AAV | | NPC1 | 4864 | Payload comprising a NPC1 gene or variant thereof packaged within a hybrid capsid. |
| 1 | chimeric AAV | | NPC1 | 4864 | Payload comprising a NPC1 gene or variant thereof packaged within a chimeric capsid. |
| 2 | AAV1 | 1450374 | NPC1 | 4864 | Payload comprising a NPC1 gene or variant thereof packaged within a AAV1 capsid. |
| 2 | AAV2 | | NPC1 | 4864 | Payload comprising a NPC1 gene or variant thereof packaged within a AAV2 capsid. |
| 2 | AAV3 | | NPC1 | 4864 | Payload comprising a NPC1 gene or variant thereof packaged within a AAV3 capsid. |
| 2 | AAV4 | 1446389 | NPC1 | 4864 | Payload comprising a NPC1 gene or variant thereof packaged within a AAV4 capsid. |
| 2 | AAV5 | | NPC1 | 4864 | Payload comprising a NPC1 gene or variant thereof packaged within a AAV5 capsid. |
| 2 | AAV6 | | NPC1 | 4864 | Payload comprising a NPC1 gene or variant thereof packaged within a AAV6 capsid. |
| 2 | AAV7 | | NPC1 | 4864 | Payload comprising a NPC1 gene or variant thereof packaged within a AAV7 capsid. |
| 2 | AAV8 | 5075992 | NPC1 | 4864 | Payload comprising a NPC1 gene or variant thereof packaged within a AAV8 capsid. |
| 2 | AAV9 | | NPC1 | 4864 | Payload comprising a NPC1 gene or variant thereof packaged within a AAV9 capsid. |

Fig. 29 (Continued)

| | | | | | |
|---|---|---|---|---|---|
| 2 | AAV10 | | NPC1 | 4864 | Payload comprising a NPC1 gene or variant thereof packaged within a AAV10 capsid. |
| 2 | AAV11 | | NPC1 | 4864 | Payload comprising a NPC1 gene or variant thereof packaged within a AAV11 capsid. |
| 2 | AAVC11.01 | | NPC1 | 4864 | Payload comprising a NPC1 gene or variant thereof packaged within a AAVC11.01 capsid. |
| 2 | AAVC11.02 | | NPC1 | 4864 | Payload comprising a NPC1 gene or variant thereof packaged within a AAVC11.02 capsid. |
| 2 | AAVC11.03 | | NPC1 | 4864 | Payload comprising a NPC1 gene or variant thereof packaged within a AAVC11.03 capsid. |
| 2 | AAVC11.04 | | NPC1 | 4864 | Payload comprising a NPC1 gene or variant thereof packaged within a AAVC11.04 capsid. |
| 2 | AAVC11.05 | | NPC1 | 4864 | Payload comprising a NPC1 gene or variant thereof packaged within a AAVC11.05 capsid. |
| 2 | AAVC11.06 | | NPC1 | 4864 | Payload comprising a NPC1 gene or variant thereof packaged within a AAVC11.06 capsid. |
| 2 | AAVC11.07 | | NPC1 | 4864 | Payload comprising a NPC1 gene or variant thereof packaged within a AAVC11.07 capsid. |
| 2 | AAVC11.08 | | NPC1 | 4864 | Payload comprising a NPC1 gene or variant thereof packaged within a AAVC11.08 capsid. |
| 2 | AAVC11.09 | | NPC1 | 4864 | Payload comprising a NPC1 gene or variant thereof packaged within a AAVC11.09 capsid. |
| 2 | AAVC11.10 | | NPC1 | 4864 | Payload comprising a NPC1 gene or variant thereof packaged within a AAVC11.10 capsid. |
| 2 | AAVC11.11 | | NPC1 | 4864 | Payload comprising a NPC1 gene or variant thereof packaged within a AAVC11.11 capsid. |
| 2 | AAVC11.12 | | NPC1 | 4864 | Payload comprising a NPC1 gene or variant thereof packaged within a AAVC11.12 capsid. |
| 2 | AAVC11.13 | | NPC1 | 4864 | Payload comprising a NPC1 gene or variant thereof packaged within a AAVC11.13 capsid. |
| 2 | AAVC11.14 | | NPC1 | 4864 | Payload comprising a NPC1 gene or variant thereof packaged within a AAVC11.14 capsid. |
| 2 | AAVC11.15 | | NPC1 | 4864 | Payload comprising a NPC1 gene or variant thereof packaged within a AAVC11.15 capsid. |

Fig. 29 (Continued)

| | | | | | |
|---|---|---|---|---|---|
| 2 | AAVC11.16 | | NPC1 | 4864 | Payload comprising a NPC1 gene or variant thereof packaged within a AAVC11.16 capsid. |
| 2 | AAVC11.17 | | NPC1 | 4864 | Payload comprising a NPC1 gene or variant thereof packaged within a AAVC11.17 capsid. |
| 2 | AAVC11.18 | | NPC1 | 4864 | Payload comprising a NPC1 gene or variant thereof packaged within a AAVC11.18 capsid. |
| 2 | AAVC11.19 | | NPC1 | 4864 | Payload comprising a NPC1 gene or variant thereof packaged within a AAVC11.19 capsid. |
| 2 | AAV12 | | NPC1 | 4864 | Payload comprising a NPC1 gene or variant thereof packaged within a AAV12 capsid. |
| 2 | AAV13 | | NPC1 | 4864 | Payload comprising a NPC1 gene or variant thereof packaged within a AAV13 capsid. |
| 2 | AAV-DJ | | NPC1 | 4864 | Payload comprising a NPC1 gene or variant thereof packaged within a AAV-DJ capsid. |
| 2 | AAV-LK03 | | NPC1 | 4864 | Payload comprising a NPC1 gene or variant thereof packaged within a AAV-LK03 capsid. |
| 2 | AAV-LK19 | | NPC1 | 4864 | Payload comprising a NPC1 gene or variant thereof packaged within a AAV-LK19 capsid. |
| 2 | AAVrh.74 | | NPC1 | 4864 | Payload comprising a NPC1 gene or variant thereof packaged within a AAVrh.74 capsid. |
| 2 | AAVrh.10 | | NPC1 | 4864 | Payload comprising a NPC1 gene or variant thereof packaged within a AAVrh.10 capsid. |
| 2 | AAVhu.37 | | NPC1 | 4864 | Payload comprising a NPC1 gene or variant thereof packaged within a AAVhu.37 capsid. |
| 2 | AAVrh.K | | NPC1 | 4864 | Payload comprising a NPC1 gene or variant thereof packaged within a AAVrh.K capsid. |
| 2 | AAVrh.39 | | NPC1 | 4864 | Payload comprising a NPC1 gene or variant thereof packaged within a AAVrh.39 capsid. |
| 2 | AAVrh.9 | | NPC1 | 4864 | Payload comprising a NPC1 gene or variant thereof packaged within a AAVrh.9 capsid. |
| 2 | avian AAV | | NPC1 | 4864 | Payload comprising a NPC1 gene or variant thereof packaged within a avian capsid. |

Fig. 29 (Continued)

| | | | | | |
|---|---|---|---|---|---|
| 2 | bovine AAV | | NPC1 | 4864 | Payload comprising a NPC1 gene or variant thereof packaged within a bovine capsid. |
| 2 | canine AAV | | NPC1 | 4864 | Payload comprising a NPC1 gene or variant thereof packaged within a canine capsid. |
| 2 | equine AAV | | NPC1 | 4864 | Payload comprising a NPC1 gene or variant thereof packaged within a equine capsid. |
| 2 | primate AAV | | NPC1 | 4864 | Payload comprising a NPC1 gene or variant thereof packaged within a primate capsid. |
| 2 | non-primate AAV | | NPC1 | 4864 | Payload comprising a NPC1 gene or variant thereof packaged within a non-primate capsid. |
| 2 | ovine AAV | | NPC1 | 4864 | Payload comprising a NPC1 gene or variant thereof packaged within a ovine capsid. |
| 2 | hybrid AAV | | NPC1 | 4864 | Payload comprising a NPC1 gene or variant thereof packaged within a hybrid capsid. |
| 2 | chimeric AAV | | NPC1 | 4864 | Payload comprising a NPC1 gene or variant thereof packaged within a chimeric capsid. |
| 1 | AAV1 | 1450374 | NPC2 | 10577 | Payload comprising a NPC2 gene or variant thereof packaged within a AAV1 capsid. |
| 1 | AAV2 | | NPC2 | 10577 | Payload comprising a NPC2 gene or variant thereof packaged within a AAV2 capsid. |
| 1 | AAV3 | | NPC2 | 10577 | Payload comprising a NPC2 gene or variant thereof packaged within a AAV3 capsid. |
| 1 | AAV4 | 1446389 | NPC2 | 10577 | Payload comprising a NPC2 gene or variant thereof packaged within a AAV4 capsid. |
| 1 | AAV5 | | NPC2 | 10577 | Payload comprising a NPC2 gene or variant thereof packaged within a AAV5 capsid. |
| 1 | AAV6 | | NPC2 | 10577 | Payload comprising a NPC2 gene or variant thereof packaged within a AAV6 capsid. |
| 1 | AAV7 | | NPC2 | 10577 | Payload comprising a NPC2 gene or variant thereof packaged within a AAV7 capsid. |
| 1 | AAV8 | 5075992 | NPC2 | 10577 | Payload comprising a NPC2 gene or variant thereof packaged within a AAV8 capsid. |
| 1 | AAV9 | | NPC2 | 10577 | Payload comprising a NPC2 gene or variant thereof packaged within a AAV9 capsid. |

Fig. 29 (Continued)

| | | | | | |
|---|---|---|---|---|---|
| 1 | AAV10 | | NPC2 | 10577 | Payload comprising a NPC2 gene or variant thereof packaged within a AAV10 capsid. |
| 1 | AAV11 | | NPC2 | 10577 | Payload comprising a NPC2 gene or variant thereof packaged within a AAV11 capsid. |
| 1 | AAVC11.01 | | NPC2 | 10577 | Payload comprising a NPC2 gene or variant thereof packaged within a AAVC11.01 capsid. |
| 1 | AAVC11.02 | | NPC2 | 10577 | Payload comprising a NPC2 gene or variant thereof packaged within a AAVC11.02 capsid. |
| 1 | AAVC11.03 | | NPC2 | 10577 | Payload comprising a NPC2 gene or variant thereof packaged within a AAVC11.03 capsid. |
| 1 | AAVC11.04 | | NPC2 | 10577 | Payload comprising a NPC2 gene or variant thereof packaged within a AAVC11.04 capsid. |
| 1 | AAVC11.05 | | NPC2 | 10577 | Payload comprising a NPC2 gene or variant thereof packaged within a AAVC11.05 capsid. |
| 1 | AAVC11.06 | | NPC2 | 10577 | Payload comprising a NPC2 gene or variant thereof packaged within a AAVC11.06 capsid. |
| 1 | AAVC11.07 | | NPC2 | 10577 | Payload comprising a NPC2 gene or variant thereof packaged within a AAVC11.07 capsid. |
| 1 | AAVC11.08 | | NPC2 | 10577 | Payload comprising a NPC2 gene or variant thereof packaged within a AAVC11.08 capsid. |
| 1 | AAVC11.09 | | NPC2 | 10577 | Payload comprising a NPC2 gene or variant thereof packaged within a AAVC11.09 capsid. |
| 1 | AAVC11.10 | | NPC2 | 10577 | Payload comprising a NPC2 gene or variant thereof packaged within a AAVC11.10 capsid. |
| 1 | AAVC11.11 | | NPC2 | 10577 | Payload comprising a NPC2 gene or variant thereof packaged within a AAVC11.11 capsid. |
| 1 | AAVC11.12 | | NPC2 | 10577 | Payload comprising a NPC2 gene or variant thereof packaged within a AAVC11.12 capsid. |
| 1 | AAVC11.13 | | NPC2 | 10577 | Payload comprising a NPC2 gene or variant thereof packaged within a AAVC11.13 capsid. |
| 1 | AAVC11.14 | | NPC2 | 10577 | Payload comprising a NPC2 gene or variant thereof packaged within a AAVC11.14 capsid. |
| 1 | AAVC11.15 | | NPC2 | 10577 | Payload comprising a NPC2 gene or variant thereof packaged within a AAVC11.15 capsid. |

Fig. 29 (Continued)

| | | | | | |
|---|---|---|---|---|---|
| 1 | AAVC11.16 | | NPC2 | 10577 | Payload comprising a NPC2 gene or variant thereof packaged within a AAVC11.16 capsid. |
| 1 | AAVC11.17 | | NPC2 | 10577 | Payload comprising a NPC2 gene or variant thereof packaged within a AAVC11.17 capsid. |
| 1 | AAVC11.18 | | NPC2 | 10577 | Payload comprising a NPC2 gene or variant thereof packaged within a AAVC11.18 capsid. |
| 1 | AAVC11.19 | | NPC2 | 10577 | Payload comprising a NPC2 gene or variant thereof packaged within a AAVC11.19 capsid. |
| 1 | AAV12 | | NPC2 | 10577 | Payload comprising a NPC2 gene or variant thereof packaged within a AAV12 capsid. |
| 1 | AAV13 | | NPC2 | 10577 | Payload comprising a NPC2 gene or variant thereof packaged within a AAV13 capsid. |
| 1 | AAV-DJ | | NPC2 | 10577 | Payload comprising a NPC2 gene or variant thereof packaged within a AAV-DJ capsid. |
| 1 | AAV-LK03 | | NPC2 | 10577 | Payload comprising a NPC2 gene or variant thereof packaged within a AAV-LK03 capsid. |
| 1 | AAV-LK19 | | NPC2 | 10577 | Payload comprising a NPC2 gene or variant thereof packaged within a AAV-LK19 capsid. |
| 1 | AAVrh.74 | | NPC2 | 10577 | Payload comprising a NPC2 gene or variant thereof packaged within a AAVrh.74 capsid. |
| 1 | AAVrh.10 | | NPC2 | 10577 | Payload comprising a NPC2 gene or variant thereof packaged within a AAVrh.10 capsid. |
| 1 | AAVhu.37 | | NPC2 | 10577 | Payload comprising a NPC2 gene or variant thereof packaged within a AAVhu.37 capsid. |
| 1 | AAVrh.K | | NPC2 | 10577 | Payload comprising a NPC2 gene or variant thereof packaged within a AAVrh.K capsid. |
| 1 | AAVrh.39 | | NPC2 | 10577 | Payload comprising a NPC2 gene or variant thereof packaged within a AAVrh.39 capsid. |
| 1 | AAVrh.9 | | NPC2 | 10577 | Payload comprising a NPC2 gene or variant thereof packaged within a AAVrh.9 capsid. |
| 1 | avian AAV | | NPC2 | 10577 | Payload comprising a NPC2 gene or variant thereof packaged within a avian capsid. |

Fig. 29 (Continued)

| | | | | | |
|---|---|---|---|---|---|
| 1 | bovine AAV | | NPC2 | 10577 | Payload comprising a NPC2 gene or variant thereof packaged within a bovine capsid. |
| 1 | canine AAV | | NPC2 | 10577 | Payload comprising a NPC2 gene or variant thereof packaged within a canine capsid. |
| 1 | equine AAV | | NPC2 | 10577 | Payload comprising a NPC2 gene or variant thereof packaged within a equine capsid. |
| 1 | primate AAV | | NPC2 | 10577 | Payload comprising a NPC2 gene or variant thereof packaged within a primate capsid. |
| 1 | non-primate AAV | | NPC2 | 10577 | Payload comprising a NPC2 gene or variant thereof packaged within a non-primate capsid. |
| 1 | ovine AAV | | NPC2 | 10577 | Payload comprising a NPC2 gene or variant thereof packaged within a ovine capsid. |
| 1 | hybrid AAV | | NPC2 | 10577 | Payload comprising a NPC2 gene or variant thereof packaged within a hybrid capsid. |
| 1 | chimeric AAV | | NPC2 | 10577 | Payload comprising a NPC2 gene or variant thereof packaged within a chimeric capsid. |
| 2 | AAV1 | 1450374 | NPC2 | 10577 | Payload comprising a NPC2 gene or variant thereof packaged within a AAV1 capsid. |
| 2 | AAV2 | | NPC2 | 10577 | Payload comprising a NPC2 gene or variant thereof packaged within a AAV2 capsid. |
| 2 | AAV3 | | NPC2 | 10577 | Payload comprising a NPC2 gene or variant thereof packaged within a AAV3 capsid. |
| 2 | AAV4 | 1446389 | NPC2 | 10577 | Payload comprising a NPC2 gene or variant thereof packaged within a AAV4 capsid. |
| 2 | AAV5 | | NPC2 | 10577 | Payload comprising a NPC2 gene or variant thereof packaged within a AAV5 capsid. |
| 2 | AAV6 | | NPC2 | 10577 | Payload comprising a NPC2 gene or variant thereof packaged within a AAV6 capsid. |
| 2 | AAV7 | | NPC2 | 10577 | Payload comprising a NPC2 gene or variant thereof packaged within a AAV7 capsid. |
| 2 | AAV8 | 5075992 | NPC2 | 10577 | Payload comprising a NPC2 gene or variant thereof packaged within a AAV8 capsid. |
| 2 | AAV9 | | NPC2 | 10577 | Payload comprising a NPC2 gene or variant thereof packaged within a AAV9 capsid. |

Fig. 29 (Continued)

| | | | | | |
|---|---|---|---|---|---|
| 2 | AAV10 | | NPC2 | 10577 | Payload comprising a NPC2 gene or variant thereof packaged within a AAV10 capsid. |
| 2 | AAV11 | | NPC2 | 10577 | Payload comprising a NPC2 gene or variant thereof packaged within a AAV11 capsid. |
| 2 | AAVC11.01 | | NPC2 | 10577 | Payload comprising a NPC2 gene or variant thereof packaged within a AAVC11.01 capsid. |
| 2 | AAVC11.02 | | NPC2 | 10577 | Payload comprising a NPC2 gene or variant thereof packaged within a AAVC11.02 capsid. |
| 2 | AAVC11.03 | | NPC2 | 10577 | Payload comprising a NPC2 gene or variant thereof packaged within a AAVC11.03 capsid. |
| 2 | AAVC11.04 | | NPC2 | 10577 | Payload comprising a NPC2 gene or variant thereof packaged within a AAVC11.04 capsid. |
| 2 | AAVC11.05 | | NPC2 | 10577 | Payload comprising a NPC2 gene or variant thereof packaged within a AAVC11.05 capsid. |
| 2 | AAVC11.06 | | NPC2 | 10577 | Payload comprising a NPC2 gene or variant thereof packaged within a AAVC11.06 capsid. |
| 2 | AAVC11.07 | | NPC2 | 10577 | Payload comprising a NPC2 gene or variant thereof packaged within a AAVC11.07 capsid. |
| 2 | AAVC11.08 | | NPC2 | 10577 | Payload comprising a NPC2 gene or variant thereof packaged within a AAVC11.08 capsid. |
| 2 | AAVC11.09 | | NPC2 | 10577 | Payload comprising a NPC2 gene or variant thereof packaged within a AAVC11.09 capsid. |
| 2 | AAVC11.10 | | NPC2 | 10577 | Payload comprising a NPC2 gene or variant thereof packaged within a AAVC11.10 capsid. |
| 2 | AAVC11.11 | | NPC2 | 10577 | Payload comprising a NPC2 gene or variant thereof packaged within a AAVC11.11 capsid. |
| 2 | AAVC11.12 | | NPC2 | 10577 | Payload comprising a NPC2 gene or variant thereof packaged within a AAVC11.12 capsid. |
| 2 | AAVC11.13 | | NPC2 | 10577 | Payload comprising a NPC2 gene or variant thereof packaged within a AAVC11.13 capsid. |
| 2 | AAVC11.14 | | NPC2 | 10577 | Payload comprising a NPC2 gene or variant thereof packaged within a AAVC11.14 capsid. |
| 2 | AAVC11.15 | | NPC2 | 10577 | Payload comprising a NPC2 gene or variant thereof packaged within a AAVC11.15 capsid. |

Fig. 29 (Continued)

| | | | | | |
|---|---|---|---|---|---|
| 2 | AAVC11.16 | | NPC2 | 10577 | Payload comprising a NPC2 gene or variant thereof packaged within a AAVC11.16 capsid. |
| 2 | AAVC11.17 | | NPC2 | 10577 | Payload comprising a NPC2 gene or variant thereof packaged within a AAVC11.17 capsid. |
| 2 | AAVC11.18 | | NPC2 | 10577 | Payload comprising a NPC2 gene or variant thereof packaged within a AAVC11.18 capsid. |
| 2 | AAVC11.19 | | NPC2 | 10577 | Payload comprising a NPC2 gene or variant thereof packaged within a AAVC11.19 capsid. |
| 2 | AAV12 | | NPC2 | 10577 | Payload comprising a NPC2 gene or variant thereof packaged within a AAV12 capsid. |
| 2 | AAV13 | | NPC2 | 10577 | Payload comprising a NPC2 gene or variant thereof packaged within a AAV13 capsid. |
| 2 | AAV-DJ | | NPC2 | 10577 | Payload comprising a NPC2 gene or variant thereof packaged within a AAV-DJ capsid. |
| 2 | AAV-LK03 | | NPC2 | 10577 | Payload comprising a NPC2 gene or variant thereof packaged within a AAV-LK03 capsid. |
| 2 | AAV-LK19 | | NPC2 | 10577 | Payload comprising a NPC2 gene or variant thereof packaged within a AAV-LK19 capsid. |
| 2 | AAVrh.74 | | NPC2 | 10577 | Payload comprising a NPC2 gene or variant thereof packaged within a AAVrh.74 capsid. |
| 2 | AAVrh.10 | | NPC2 | 10577 | Payload comprising a NPC2 gene or variant thereof packaged within a AAVrh.10 capsid. |
| 2 | AAVhu.37 | | NPC2 | 10577 | Payload comprising a NPC2 gene or variant thereof packaged within a AAVhu.37 capsid. |
| 2 | AAVrh.K | | NPC2 | 10577 | Payload comprising a NPC2 gene or variant thereof packaged within a AAVrh.K capsid. |
| 2 | AAVrh.39 | | NPC2 | 10577 | Payload comprising a NPC2 gene or variant thereof packaged within a AAVrh.39 capsid. |
| 2 | AAVrh.9 | | NPC2 | 10577 | Payload comprising a NPC2 gene or variant thereof packaged within a AAVrh.9 capsid. |
| 2 | avian AAV | | NPC2 | 10577 | Payload comprising a NPC2 gene or variant thereof packaged within a avian capsid. |

Fig. 29 (Continued)

| | | | | | |
|---|---|---|---|---|---|
| 2 | bovine AAV | | NPC2 | 10577 | Payload comprising a NPC2 gene or variant thereof packaged within a bovine capsid. |
| 2 | canine AAV | | NPC2 | 10577 | Payload comprising a NPC2 gene or variant thereof packaged within a canine capsid. |
| 2 | equine AAV | | NPC2 | 10577 | Payload comprising a NPC2 gene or variant thereof packaged within a equine capsid. |
| 2 | primate AAV | | NPC2 | 10577 | Payload comprising a NPC2 gene or variant thereof packaged within a primate capsid. |
| 2 | non-primate AAV | | NPC2 | 10577 | Payload comprising a NPC2 gene or variant thereof packaged within a non-primate capsid. |
| 2 | ovine AAV | | NPC2 | 10577 | Payload comprising a NPC2 gene or variant thereof packaged within a ovine capsid. |
| 2 | hybrid AAV | | NPC2 | 10577 | Payload comprising a NPC2 gene or variant thereof packaged within a hybrid capsid. |
| 2 | chimeric AAV | | NPC2 | 10577 | Payload comprising a NPC2 gene or variant thereof packaged within a chimeric capsid. |
| 1 | AAV1 | 1450374 | NTF3 | 4908 | Payload comprising a NTF3 gene or variant thereof packaged within a AAV1 capsid. |
| 1 | AAV2 | | NTF3 | 4908 | Payload comprising a NTF3 gene or variant thereof packaged within a AAV2 capsid. |
| 1 | AAV3 | | NTF3 | 4908 | Payload comprising a NTF3 gene or variant thereof packaged within a AAV3 capsid. |
| 1 | AAV4 | 1446389 | NTF3 | 4908 | Payload comprising a NTF3 gene or variant thereof packaged within a AAV4 capsid. |
| 1 | AAV5 | | NTF3 | 4908 | Payload comprising a NTF3 gene or variant thereof packaged within a AAV5 capsid. |
| 1 | AAV6 | | NTF3 | 4908 | Payload comprising a NTF3 gene or variant thereof packaged within a AAV6 capsid. |
| 1 | AAV7 | | NTF3 | 4908 | Payload comprising a NTF3 gene or variant thereof packaged within a AAV7 capsid. |
| 1 | AAV8 | 5075992 | NTF3 | 4908 | Payload comprising a NTF3 gene or variant thereof packaged within a AAV8 capsid. |
| 1 | AAV9 | | NTF3 | 4908 | Payload comprising a NTF3 gene or variant thereof packaged within a AAV9 capsid. |

Fig. 29 (Continued)

| | | | | | |
|---|---|---|---|---|---|
| 1 | AAV10 | | NTF3 | 4908 | Payload comprising a NTF3 gene or variant thereof packaged within a AAV10 capsid. |
| 1 | AAV11 | | NTF3 | 4908 | Payload comprising a NTF3 gene or variant thereof packaged within a AAV11 capsid. |
| 1 | AAVC11.01 | | NTF3 | 4908 | Payload comprising a NTF3 gene or variant thereof packaged within a AAVC11.01 capsid. |
| 1 | AAVC11.02 | | NTF3 | 4908 | Payload comprising a NTF3 gene or variant thereof packaged within a AAVC11.02 capsid. |
| 1 | AAVC11.03 | | NTF3 | 4908 | Payload comprising a NTF3 gene or variant thereof packaged within a AAVC11.03 capsid. |
| 1 | AAVC11.04 | | NTF3 | 4908 | Payload comprising a NTF3 gene or variant thereof packaged within a AAVC11.04 capsid. |
| 1 | AAVC11.05 | | NTF3 | 4908 | Payload comprising a NTF3 gene or variant thereof packaged within a AAVC11.05 capsid. |
| 1 | AAVC11.06 | | NTF3 | 4908 | Payload comprising a NTF3 gene or variant thereof packaged within a AAVC11.06 capsid. |
| 1 | AAVC11.07 | | NTF3 | 4908 | Payload comprising a NTF3 gene or variant thereof packaged within a AAVC11.07 capsid. |
| 1 | AAVC11.08 | | NTF3 | 4908 | Payload comprising a NTF3 gene or variant thereof packaged within a AAVC11.08 capsid. |
| 1 | AAVC11.09 | | NTF3 | 4908 | Payload comprising a NTF3 gene or variant thereof packaged within a AAVC11.09 capsid. |
| 1 | AAVC11.10 | | NTF3 | 4908 | Payload comprising a NTF3 gene or variant thereof packaged within a AAVC11.10 capsid. |
| 1 | AAVC11.11 | | NTF3 | 4908 | Payload comprising a NTF3 gene or variant thereof packaged within a AAVC11.11 capsid. |
| 1 | AAVC11.12 | | NTF3 | 4908 | Payload comprising a NTF3 gene or variant thereof packaged within a AAVC11.12 capsid. |
| 1 | AAVC11.13 | | NTF3 | 4908 | Payload comprising a NTF3 gene or variant thereof packaged within a AAVC11.13 capsid. |
| 1 | AAVC11.14 | | NTF3 | 4908 | Payload comprising a NTF3 gene or variant thereof packaged within a AAVC11.14 capsid. |
| 1 | AAVC11.15 | | NTF3 | 4908 | Payload comprising a NTF3 gene or variant thereof packaged within a AAVC11.15 capsid. |

Fig. 29 (Continued)

| | | | | | |
|---|---|---|---|---|---|
| 1 | AAVC11.16 | | NTF3 | 4908 | Payload comprising a NTF3 gene or variant thereof packaged within a AAVC11.16 capsid. |
| 1 | AAVC11.17 | | NTF3 | 4908 | Payload comprising a NTF3 gene or variant thereof packaged within a AAVC11.17 capsid. |
| 1 | AAVC11.18 | | NTF3 | 4908 | Payload comprising a NTF3 gene or variant thereof packaged within a AAVC11.18 capsid. |
| 1 | AAVC11.19 | | NTF3 | 4908 | Payload comprising a NTF3 gene or variant thereof packaged within a AAVC11.19 capsid. |
| 1 | AAV12 | | NTF3 | 4908 | Payload comprising a NTF3 gene or variant thereof packaged within a AAV12 capsid. |
| 1 | AAV13 | | NTF3 | 4908 | Payload comprising a NTF3 gene or variant thereof packaged within a AAV13 capsid. |
| 1 | AAV-DJ | | NTF3 | 4908 | Payload comprising a NTF3 gene or variant thereof packaged within a AAV-DJ capsid. |
| 1 | AAV-LK03 | | NTF3 | 4908 | Payload comprising a NTF3 gene or variant thereof packaged within a AAV-LK03 capsid. |
| 1 | AAV-LK19 | | NTF3 | 4908 | Payload comprising a NTF3 gene or variant thereof packaged within a AAV-LK19 capsid. |
| 1 | AAVrh.74 | | NTF3 | 4908 | Payload comprising a NTF3 gene or variant thereof packaged within a AAVrh.74 capsid. |
| 1 | AAVrh.10 | | NTF3 | 4908 | Payload comprising a NTF3 gene or variant thereof packaged within a AAVrh.10 capsid. |
| 1 | AAVhu.37 | | NTF3 | 4908 | Payload comprising a NTF3 gene or variant thereof packaged within a AAVhu.37 capsid. |
| 1 | AAVrh.K | | NTF3 | 4908 | Payload comprising a NTF3 gene or variant thereof packaged within a AAVrh.K capsid. |
| 1 | AAVrh.39 | | NTF3 | 4908 | Payload comprising a NTF3 gene or variant thereof packaged within a AAVrh.39 capsid. |
| 1 | AAVrh.9 | | NTF3 | 4908 | Payload comprising a NTF3 gene or variant thereof packaged within a AAVrh.9 capsid. |
| 1 | avian AAV | | NTF3 | 4908 | Payload comprising a NTF3 gene or variant thereof packaged within a avian capsid. |

Fig. 29 (Continued)

| | | | | | |
|---|---|---|---|---|---|
| 1 | bovine AAV | | NTF3 | 4908 | Payload comprising a NTF3 gene or variant thereof packaged within a bovine capsid. |
| 1 | canine AAV | | NTF3 | 4908 | Payload comprising a NTF3 gene or variant thereof packaged within a canine capsid. |
| 1 | equine AAV | | NTF3 | 4908 | Payload comprising a NTF3 gene or variant thereof packaged within a equine capsid. |
| 1 | primate AAV | | NTF3 | 4908 | Payload comprising a NTF3 gene or variant thereof packaged within a primate capsid. |
| 1 | non-primate AAV | | NTF3 | 4908 | Payload comprising a NTF3 gene or variant thereof packaged within a non-primate capsid. |
| 1 | ovine AAV | | NTF3 | 4908 | Payload comprising a NTF3 gene or variant thereof packaged within a ovine capsid. |
| 1 | hybrid AAV | | NTF3 | 4908 | Payload comprising a NTF3 gene or variant thereof packaged within a hybrid capsid. |
| 1 | chimeric AAV | | NTF3 | 4908 | Payload comprising a NTF3 gene or variant thereof packaged within a chimeric capsid. |
| 2 | AAV1 | 1450374 | NTF3 | 4908 | Payload comprising a NTF3 gene or variant thereof packaged within a AAV1 capsid. |
| 2 | AAV2 | | NTF3 | 4908 | Payload comprising a NTF3 gene or variant thereof packaged within a AAV2 capsid. |
| 2 | AAV3 | | NTF3 | 4908 | Payload comprising a NTF3 gene or variant thereof packaged within a AAV3 capsid. |
| 2 | AAV4 | 1446389 | NTF3 | 4908 | Payload comprising a NTF3 gene or variant thereof packaged within a AAV4 capsid. |
| 2 | AAV5 | | NTF3 | 4908 | Payload comprising a NTF3 gene or variant thereof packaged within a AAV5 capsid. |
| 2 | AAV6 | | NTF3 | 4908 | Payload comprising a NTF3 gene or variant thereof packaged within a AAV6 capsid. |
| 2 | AAV7 | | NTF3 | 4908 | Payload comprising a NTF3 gene or variant thereof packaged within a AAV7 capsid. |
| 2 | AAV8 | 5075992 | NTF3 | 4908 | Payload comprising a NTF3 gene or variant thereof packaged within a AAV8 capsid. |
| 2 | AAV9 | | NTF3 | 4908 | Payload comprising a NTF3 gene or variant thereof packaged within a AAV9 capsid. |

Fig. 29 (Continued)

| | | | | | |
|---|---|---|---|---|---|
| 2 | AAV10 | | NTF3 | 4908 | Payload comprising a NTF3 gene or variant thereof packaged within a AAV10 capsid. |
| 2 | AAV11 | | NTF3 | 4908 | Payload comprising a NTF3 gene or variant thereof packaged within a AAV11 capsid. |
| 2 | AAVC11.01 | | NTF3 | 4908 | Payload comprising a NTF3 gene or variant thereof packaged within a AAVC11.01 capsid. |
| 2 | AAVC11.02 | | NTF3 | 4908 | Payload comprising a NTF3 gene or variant thereof packaged within a AAVC11.02 capsid. |
| 2 | AAVC11.03 | | NTF3 | 4908 | Payload comprising a NTF3 gene or variant thereof packaged within a AAVC11.03 capsid. |
| 2 | AAVC11.04 | | NTF3 | 4908 | Payload comprising a NTF3 gene or variant thereof packaged within a AAVC11.04 capsid. |
| 2 | AAVC11.05 | | NTF3 | 4908 | Payload comprising a NTF3 gene or variant thereof packaged within a AAVC11.05 capsid. |
| 2 | AAVC11.06 | | NTF3 | 4908 | Payload comprising a NTF3 gene or variant thereof packaged within a AAVC11.06 capsid. |
| 2 | AAVC11.07 | | NTF3 | 4908 | Payload comprising a NTF3 gene or variant thereof packaged within a AAVC11.07 capsid. |
| 2 | AAVC11.08 | | NTF3 | 4908 | Payload comprising a NTF3 gene or variant thereof packaged within a AAVC11.08 capsid. |
| 2 | AAVC11.09 | | NTF3 | 4908 | Payload comprising a NTF3 gene or variant thereof packaged within a AAVC11.09 capsid. |
| 2 | AAVC11.10 | | NTF3 | 4908 | Payload comprising a NTF3 gene or variant thereof packaged within a AAVC11.10 capsid. |
| 2 | AAVC11.11 | | NTF3 | 4908 | Payload comprising a NTF3 gene or variant thereof packaged within a AAVC11.11 capsid. |
| 2 | AAVC11.12 | | NTF3 | 4908 | Payload comprising a NTF3 gene or variant thereof packaged within a AAVC11.12 capsid. |
| 2 | AAVC11.13 | | NTF3 | 4908 | Payload comprising a NTF3 gene or variant thereof packaged within a AAVC11.13 capsid. |
| 2 | AAVC11.14 | | NTF3 | 4908 | Payload comprising a NTF3 gene or variant thereof packaged within a AAVC11.14 capsid. |
| 2 | AAVC11.15 | | NTF3 | 4908 | Payload comprising a NTF3 gene or variant thereof packaged within a AAVC11.15 capsid. |

Fig. 29 (Continued)

| | | | | | |
|---|---|---|---|---|---|
| 2 | AAVC11.16 | | NTF3 | 4908 | Payload comprising a NTF3 gene or variant thereof packaged within a AAVC11.16 capsid. |
| 2 | AAVC11.17 | | NTF3 | 4908 | Payload comprising a NTF3 gene or variant thereof packaged within a AAVC11.17 capsid. |
| 2 | AAVC11.18 | | NTF3 | 4908 | Payload comprising a NTF3 gene or variant thereof packaged within a AAVC11.18 capsid. |
| 2 | AAVC11.19 | | NTF3 | 4908 | Payload comprising a NTF3 gene or variant thereof packaged within a AAVC11.19 capsid. |
| 2 | AAV12 | | NTF3 | 4908 | Payload comprising a NTF3 gene or variant thereof packaged within a AAV12 capsid. |
| 2 | AAV13 | | NTF3 | 4908 | Payload comprising a NTF3 gene or variant thereof packaged within a AAV13 capsid. |
| 2 | AAV-DJ | | NTF3 | 4908 | Payload comprising a NTF3 gene or variant thereof packaged within a AAV-DJ capsid. |
| 2 | AAV-LK03 | | NTF3 | 4908 | Payload comprising a NTF3 gene or variant thereof packaged within a AAV-LK03 capsid. |
| 2 | AAV-LK19 | | NTF3 | 4908 | Payload comprising a NTF3 gene or variant thereof packaged within a AAV-LK19 capsid. |
| 2 | AAVrh.74 | | NTF3 | 4908 | Payload comprising a NTF3 gene or variant thereof packaged within a AAVrh.74 capsid. |
| 2 | AAVrh.10 | | NTF3 | 4908 | Payload comprising a NTF3 gene or variant thereof packaged within a AAVrh.10 capsid. |
| 2 | AAVhu.37 | | NTF3 | 4908 | Payload comprising a NTF3 gene or variant thereof packaged within a AAVhu.37 capsid. |
| 2 | AAVrh.K | | NTF3 | 4908 | Payload comprising a NTF3 gene or variant thereof packaged within a AAVrh.K capsid. |
| 2 | AAVrh.39 | | NTF3 | 4908 | Payload comprising a NTF3 gene or variant thereof packaged within a AAVrh.39 capsid. |
| 2 | AAVrh.9 | | NTF3 | 4908 | Payload comprising a NTF3 gene or variant thereof packaged within a AAVrh.9 capsid. |
| 2 | avian AAV | | NTF3 | 4908 | Payload comprising a NTF3 gene or variant thereof packaged within a avian capsid. |

Fig. 29 (Continued)

| | | | | | |
|---|---|---|---|---|---|
| 2 | bovine AAV | | NTF3 | 4908 | Payload comprising a NTF3 gene or variant thereof packaged within a bovine capsid. |
| 2 | canine AAV | | NTF3 | 4908 | Payload comprising a NTF3 gene or variant thereof packaged within a canine capsid. |
| 2 | equine AAV | | NTF3 | 4908 | Payload comprising a NTF3 gene or variant thereof packaged within a equine capsid. |
| 2 | primate AAV | | NTF3 | 4908 | Payload comprising a NTF3 gene or variant thereof packaged within a primate capsid. |
| 2 | non-primate AAV | | NTF3 | 4908 | Payload comprising a NTF3 gene or variant thereof packaged within a non-primate capsid. |
| 2 | ovine AAV | | NTF3 | 4908 | Payload comprising a NTF3 gene or variant thereof packaged within a ovine capsid. |
| 2 | hybrid AAV | | NTF3 | 4908 | Payload comprising a NTF3 gene or variant thereof packaged within a hybrid capsid. |
| 2 | chimeric AAV | | NTF3 | 4908 | Payload comprising a NTF3 gene or variant thereof packaged within a chimeric capsid. |
| 1 | AAV1 | 1450374 | OCTN2 | 6584 | Payload comprising a OCTN2 gene or variant thereof packaged within a AAV1 capsid. |
| 1 | AAV2 | | OCTN2 | 6584 | Payload comprising a OCTN2 gene or variant thereof packaged within a AAV2 capsid. |
| 1 | AAV3 | | OCTN2 | 6584 | Payload comprising a OCTN2 gene or variant thereof packaged within a AAV3 capsid. |
| 1 | AAV4 | 1446389 | OCTN2 | 6584 | Payload comprising a OCTN2 gene or variant thereof packaged within a AAV4 capsid. |
| 1 | AAV5 | | OCTN2 | 6584 | Payload comprising a OCTN2 gene or variant thereof packaged within a AAV5 capsid. |
| 1 | AAV6 | | OCTN2 | 6584 | Payload comprising a OCTN2 gene or variant thereof packaged within a AAV6 capsid. |
| 1 | AAV7 | | OCTN2 | 6584 | Payload comprising a OCTN2 gene or variant thereof packaged within a AAV7 capsid. |
| 1 | AAV8 | 5075992 | OCTN2 | 6584 | Payload comprising a OCTN2 gene or variant thereof packaged within a AAV8 capsid. |
| 1 | AAV9 | | OCTN2 | 6584 | Payload comprising a OCTN2 gene or variant thereof packaged within a AAV9 capsid. |

Fig. 29 (Continued)

| | | | | | |
|---|---|---|---|---|---|
| 1 | AAV10 | | OCTN2 | 6584 | Payload comprising a OCTN2 gene or variant thereof packaged within a AAV10 capsid. |
| 1 | AAV11 | | OCTN2 | 6584 | Payload comprising a OCTN2 gene or variant thereof packaged within a AAV11 capsid. |
| 1 | AAVC11.01 | | OCTN2 | 6584 | Payload comprising a OCTN2 gene or variant thereof packaged within a AAVC11.01 capsid. |
| 1 | AAVC11.02 | | OCTN2 | 6584 | Payload comprising a OCTN2 gene or variant thereof packaged within a AAVC11.02 capsid. |
| 1 | AAVC11.03 | | OCTN2 | 6584 | Payload comprising a OCTN2 gene or variant thereof packaged within a AAVC11.03 capsid. |
| 1 | AAVC11.04 | | OCTN2 | 6584 | Payload comprising a OCTN2 gene or variant thereof packaged within a AAVC11.04 capsid. |
| 1 | AAVC11.05 | | OCTN2 | 6584 | Payload comprising a OCTN2 gene or variant thereof packaged within a AAVC11.05 capsid. |
| 1 | AAVC11.06 | | OCTN2 | 6584 | Payload comprising a OCTN2 gene or variant thereof packaged within a AAVC11.06 capsid. |
| 1 | AAVC11.07 | | OCTN2 | 6584 | Payload comprising a OCTN2 gene or variant thereof packaged within a AAVC11.07 capsid. |
| 1 | AAVC11.08 | | OCTN2 | 6584 | Payload comprising a OCTN2 gene or variant thereof packaged within a AAVC11.08 capsid. |
| 1 | AAVC11.09 | | OCTN2 | 6584 | Payload comprising a OCTN2 gene or variant thereof packaged within a AAVC11.09 capsid. |
| 1 | AAVC11.10 | | OCTN2 | 6584 | Payload comprising a OCTN2 gene or variant thereof packaged within a AAVC11.10 capsid. |
| 1 | AAVC11.11 | | OCTN2 | 6584 | Payload comprising a OCTN2 gene or variant thereof packaged within a AAVC11.11 capsid. |
| 1 | AAVC11.12 | | OCTN2 | 6584 | Payload comprising a OCTN2 gene or variant thereof packaged within a AAVC11.12 capsid. |
| 1 | AAVC11.13 | | OCTN2 | 6584 | Payload comprising a OCTN2 gene or variant thereof packaged within a AAVC11.13 capsid. |
| 1 | AAVC11.14 | | OCTN2 | 6584 | Payload comprising a OCTN2 gene or variant thereof packaged within a AAVC11.14 capsid. |
| 1 | AAVC11.15 | | OCTN2 | 6584 | Payload comprising a OCTN2 gene or variant thereof packaged within a AAVC11.15 capsid. |

Fig. 29 (Continued)

| | | | | | |
|---|---|---|---|---|---|
| 1 | AAVC11.16 | | OCTN2 | 6584 | Payload comprising a OCTN2 gene or variant thereof packaged within a AAVC11.16 capsid. |
| 1 | AAVC11.17 | | OCTN2 | 6584 | Payload comprising a OCTN2 gene or variant thereof packaged within a AAVC11.17 capsid. |
| 1 | AAVC11.18 | | OCTN2 | 6584 | Payload comprising a OCTN2 gene or variant thereof packaged within a AAVC11.18 capsid. |
| 1 | AAVC11.19 | | OCTN2 | 6584 | Payload comprising a OCTN2 gene or variant thereof packaged within a AAVC11.19 capsid. |
| 1 | AAV12 | | OCTN2 | 6584 | Payload comprising a OCTN2 gene or variant thereof packaged within a AAV12 capsid. |
| 1 | AAV13 | | OCTN2 | 6584 | Payload comprising a OCTN2 gene or variant thereof packaged within a AAV13 capsid. |
| 1 | AAV-DJ | | OCTN2 | 6584 | Payload comprising a OCTN2 gene or variant thereof packaged within a AAV-DJ capsid. |
| 1 | AAV-LK03 | | OCTN2 | 6584 | Payload comprising a OCTN2 gene or variant thereof packaged within a AAV-LK03 capsid. |
| 1 | AAV-LK19 | | OCTN2 | 6584 | Payload comprising a OCTN2 gene or variant thereof packaged within a AAV-LK19 capsid. |
| 1 | AAVrh.74 | | OCTN2 | 6584 | Payload comprising a OCTN2 gene or variant thereof packaged within a AAVrh.74 capsid. |
| 1 | AAVrh.10 | | OCTN2 | 6584 | Payload comprising a OCTN2 gene or variant thereof packaged within a AAVrh.10 capsid. |
| 1 | AAVhu.37 | | OCTN2 | 6584 | Payload comprising a OCTN2 gene or variant thereof packaged within a AAVhu.37 capsid. |
| 1 | AAVrh.K | | OCTN2 | 6584 | Payload comprising a OCTN2 gene or variant thereof packaged within a AAVrh.K capsid. |
| 1 | AAVrh.39 | | OCTN2 | 6584 | Payload comprising a OCTN2 gene or variant thereof packaged within a AAVrh.39 capsid. |
| 1 | AAVrh.9 | | OCTN2 | 6584 | Payload comprising a OCTN2 gene or variant thereof packaged within a AAVrh.9 capsid. |
| 1 | avian AAV | | OCTN2 | 6584 | Payload comprising a OCTN2 gene or variant thereof packaged within a avian capsid. |

Fig. 29 (Continued)

| | | | | | |
|---|---|---|---|---|---|
| 1 | bovine AAV | | OCTN2 | 6584 | Payload comprising a OCTN2 gene or variant thereof packaged within a bovine capsid. |
| 1 | canine AAV | | OCTN2 | 6584 | Payload comprising a OCTN2 gene or variant thereof packaged within a canine capsid. |
| 1 | equine AAV | | OCTN2 | 6584 | Payload comprising a OCTN2 gene or variant thereof packaged within a equine capsid. |
| 1 | primate AAV | | OCTN2 | 6584 | Payload comprising a OCTN2 gene or variant thereof packaged within a primate capsid. |
| 1 | non-primate AAV | | OCTN2 | 6584 | Payload comprising a OCTN2 gene or variant thereof packaged within a non-primate capsid. |
| 1 | ovine AAV | | OCTN2 | 6584 | Payload comprising a OCTN2 gene or variant thereof packaged within a ovine capsid. |
| 1 | hybrid AAV | | OCTN2 | 6584 | Payload comprising a OCTN2 gene or variant thereof packaged within a hybrid capsid. |
| 1 | chimeric AAV | | OCTN2 | 6584 | Payload comprising a OCTN2 gene or variant thereof packaged within a chimeric capsid. |
| 2 | AAV1 | 1450374 | OCTN2 | 6584 | Payload comprising a OCTN2 gene or variant thereof packaged within a AAV1 capsid. |
| 2 | AAV2 | | OCTN2 | 6584 | Payload comprising a OCTN2 gene or variant thereof packaged within a AAV2 capsid. |
| 2 | AAV3 | | OCTN2 | 6584 | Payload comprising a OCTN2 gene or variant thereof packaged within a AAV3 capsid. |
| 2 | AAV4 | 1446389 | OCTN2 | 6584 | Payload comprising a OCTN2 gene or variant thereof packaged within a AAV4 capsid. |
| 2 | AAV5 | | OCTN2 | 6584 | Payload comprising a OCTN2 gene or variant thereof packaged within a AAV5 capsid. |
| 2 | AAV6 | | OCTN2 | 6584 | Payload comprising a OCTN2 gene or variant thereof packaged within a AAV6 capsid. |
| 2 | AAV7 | | OCTN2 | 6584 | Payload comprising a OCTN2 gene or variant thereof packaged within a AAV7 capsid. |
| 2 | AAV8 | 5075992 | OCTN2 | 6584 | Payload comprising a OCTN2 gene or variant thereof packaged within a AAV8 capsid. |
| 2 | AAV9 | | OCTN2 | 6584 | Payload comprising a OCTN2 gene or variant thereof packaged within a AAV9 capsid. |

Fig. 29 (Continued)

| | | | | | |
|---|---|---|---|---|---|
| 2 | AAV10 | | OCTN2 | 6584 | Payload comprising a OCTN2 gene or variant thereof packaged within a AAV10 capsid. |
| 2 | AAV11 | | OCTN2 | 6584 | Payload comprising a OCTN2 gene or variant thereof packaged within a AAV11 capsid. |
| 2 | AAVC11.01 | | OCTN2 | 6584 | Payload comprising a OCTN2 gene or variant thereof packaged within a AAVC11.01 capsid. |
| 2 | AAVC11.02 | | OCTN2 | 6584 | Payload comprising a OCTN2 gene or variant thereof packaged within a AAVC11.02 capsid. |
| 2 | AAVC11.03 | | OCTN2 | 6584 | Payload comprising a OCTN2 gene or variant thereof packaged within a AAVC11.03 capsid. |
| 2 | AAVC11.04 | | OCTN2 | 6584 | Payload comprising a OCTN2 gene or variant thereof packaged within a AAVC11.04 capsid. |
| 2 | AAVC11.05 | | OCTN2 | 6584 | Payload comprising a OCTN2 gene or variant thereof packaged within a AAVC11.05 capsid. |
| 2 | AAVC11.06 | | OCTN2 | 6584 | Payload comprising a OCTN2 gene or variant thereof packaged within a AAVC11.06 capsid. |
| 2 | AAVC11.07 | | OCTN2 | 6584 | Payload comprising a OCTN2 gene or variant thereof packaged within a AAVC11.07 capsid. |
| 2 | AAVC11.08 | | OCTN2 | 6584 | Payload comprising a OCTN2 gene or variant thereof packaged within a AAVC11.08 capsid. |
| 2 | AAVC11.09 | | OCTN2 | 6584 | Payload comprising a OCTN2 gene or variant thereof packaged within a AAVC11.09 capsid. |
| 2 | AAVC11.10 | | OCTN2 | 6584 | Payload comprising a OCTN2 gene or variant thereof packaged within a AAVC11.10 capsid. |
| 2 | AAVC11.11 | | OCTN2 | 6584 | Payload comprising a OCTN2 gene or variant thereof packaged within a AAVC11.11 capsid. |
| 2 | AAVC11.12 | | OCTN2 | 6584 | Payload comprising a OCTN2 gene or variant thereof packaged within a AAVC11.12 capsid. |
| 2 | AAVC11.13 | | OCTN2 | 6584 | Payload comprising a OCTN2 gene or variant thereof packaged within a AAVC11.13 capsid. |
| 2 | AAVC11.14 | | OCTN2 | 6584 | Payload comprising a OCTN2 gene or variant thereof packaged within a AAVC11.14 capsid. |
| 2 | AAVC11.15 | | OCTN2 | 6584 | Payload comprising a OCTN2 gene or variant thereof packaged within a AAVC11.15 capsid. |

Fig. 29 (Continued)

| | | | | | |
|---|---|---|---|---|---|
| 2 | AAVC11.16 | | OCTN2 | 6584 | Payload comprising a OCTN2 gene or variant thereof packaged within a AAVC11.16 capsid. |
| 2 | AAVC11.17 | | OCTN2 | 6584 | Payload comprising a OCTN2 gene or variant thereof packaged within a AAVC11.17 capsid. |
| 2 | AAVC11.18 | | OCTN2 | 6584 | Payload comprising a OCTN2 gene or variant thereof packaged within a AAVC11.18 capsid. |
| 2 | AAVC11.19 | | OCTN2 | 6584 | Payload comprising a OCTN2 gene or variant thereof packaged within a AAVC11.19 capsid. |
| 2 | AAV12 | | OCTN2 | 6584 | Payload comprising a OCTN2 gene or variant thereof packaged within a AAV12 capsid. |
| 2 | AAV13 | | OCTN2 | 6584 | Payload comprising a OCTN2 gene or variant thereof packaged within a AAV13 capsid. |
| 2 | AAV-DJ | | OCTN2 | 6584 | Payload comprising a OCTN2 gene or variant thereof packaged within a AAV-DJ capsid. |
| 2 | AAV-LK03 | | OCTN2 | 6584 | Payload comprising a OCTN2 gene or variant thereof packaged within a AAV-LK03 capsid. |
| 2 | AAV-LK19 | | OCTN2 | 6584 | Payload comprising a OCTN2 gene or variant thereof packaged within a AAV-LK19 capsid. |
| 2 | AAVrh.74 | | OCTN2 | 6584 | Payload comprising a OCTN2 gene or variant thereof packaged within a AAVrh.74 capsid. |
| 2 | AAVrh.10 | | OCTN2 | 6584 | Payload comprising a OCTN2 gene or variant thereof packaged within a AAVrh.10 capsid. |
| 2 | AAVhu.37 | | OCTN2 | 6584 | Payload comprising a OCTN2 gene or variant thereof packaged within a AAVhu.37 capsid. |
| 2 | AAVrh.K | | OCTN2 | 6584 | Payload comprising a OCTN2 gene or variant thereof packaged within a AAVrh.K capsid. |
| 2 | AAVrh.39 | | OCTN2 | 6584 | Payload comprising a OCTN2 gene or variant thereof packaged within a AAVrh.39 capsid. |
| 2 | AAVrh.9 | | OCTN2 | 6584 | Payload comprising a OCTN2 gene or variant thereof packaged within a AAVrh.9 capsid. |
| 2 | avian AAV | | OCTN2 | 6584 | Payload comprising a OCTN2 gene or variant thereof packaged within a avian capsid. |

Fig. 29 (Continued)

| | | | | | |
|---|---|---|---|---|---|
| 2 | bovine AAV | | OCTN2 | 6584 | Payload comprising a OCTN2 gene or variant thereof packaged within a bovine capsid. |
| 2 | canine AAV | | OCTN2 | 6584 | Payload comprising a OCTN2 gene or variant thereof packaged within a canine capsid. |
| 2 | equine AAV | | OCTN2 | 6584 | Payload comprising a OCTN2 gene or variant thereof packaged within a equine capsid. |
| 2 | primate AAV | | OCTN2 | 6584 | Payload comprising a OCTN2 gene or variant thereof packaged within a primate capsid. |
| 2 | non-primate AAV | | OCTN2 | 6584 | Payload comprising a OCTN2 gene or variant thereof packaged within a non-primate capsid. |
| 2 | ovine AAV | | OCTN2 | 6584 | Payload comprising a OCTN2 gene or variant thereof packaged within a ovine capsid. |
| 2 | hybrid AAV | | OCTN2 | 6584 | Payload comprising a OCTN2 gene or variant thereof packaged within a hybrid capsid. |
| 2 | chimeric AAV | | OCTN2 | 6584 | Payload comprising a OCTN2 gene or variant thereof packaged within a chimeric capsid. |
| 1 | AAV1 | 1450374 | OTC | 5009 | Payload comprising a OTC gene or variant thereof packaged within a AAV1 capsid. |
| 1 | AAV2 | | OTC | 5009 | Payload comprising a OTC gene or variant thereof packaged within a AAV2 capsid. |
| 1 | AAV3 | | OTC | 5009 | Payload comprising a OTC gene or variant thereof packaged within a AAV3 capsid. |
| 1 | AAV4 | 1446389 | OTC | 5009 | Payload comprising a OTC gene or variant thereof packaged within a AAV4 capsid. |
| 1 | AAV5 | | OTC | 5009 | Payload comprising a OTC gene or variant thereof packaged within a AAV5 capsid. |
| 1 | AAV6 | | OTC | 5009 | Payload comprising a OTC gene or variant thereof packaged within a AAV6 capsid. |
| 1 | AAV7 | | OTC | 5009 | Payload comprising a OTC gene or variant thereof packaged within a AAV7 capsid. |
| 1 | AAV8 | 5075992 | OTC | 5009 | Payload comprising a OTC gene or variant thereof packaged within a AAV8 capsid. |
| 1 | AAV9 | | OTC | 5009 | Payload comprising a OTC gene or variant thereof packaged within a AAV9 capsid. |

Fig. 29 (Continued)

| | | | | | |
|---|---|---|---|---|---|
| 1 | AAV10 | | OTC | 5009 | Payload comprising a OTC gene or variant thereof packaged within a AAV10 capsid. |
| 1 | AAV11 | | OTC | 5009 | Payload comprising a OTC gene or variant thereof packaged within a AAV11 capsid. |
| 1 | AAVC11.01 | | OTC | 5009 | Payload comprising a OTC gene or variant thereof packaged within a AAVC11.01 capsid. |
| 1 | AAVC11.02 | | OTC | 5009 | Payload comprising a OTC gene or variant thereof packaged within a AAVC11.02 capsid. |
| 1 | AAVC11.03 | | OTC | 5009 | Payload comprising a OTC gene or variant thereof packaged within a AAVC11.03 capsid. |
| 1 | AAVC11.04 | | OTC | 5009 | Payload comprising a OTC gene or variant thereof packaged within a AAVC11.04 capsid. |
| 1 | AAVC11.05 | | OTC | 5009 | Payload comprising a OTC gene or variant thereof packaged within a AAVC11.05 capsid. |
| 1 | AAVC11.06 | | OTC | 5009 | Payload comprising a OTC gene or variant thereof packaged within a AAVC11.06 capsid. |
| 1 | AAVC11.07 | | OTC | 5009 | Payload comprising a OTC gene or variant thereof packaged within a AAVC11.07 capsid. |
| 1 | AAVC11.08 | | OTC | 5009 | Payload comprising a OTC gene or variant thereof packaged within a AAVC11.08 capsid. |
| 1 | AAVC11.09 | | OTC | 5009 | Payload comprising a OTC gene or variant thereof packaged within a AAVC11.09 capsid. |
| 1 | AAVC11.10 | | OTC | 5009 | Payload comprising a OTC gene or variant thereof packaged within a AAVC11.10 capsid. |
| 1 | AAVC11.11 | | OTC | 5009 | Payload comprising a OTC gene or variant thereof packaged within a AAVC11.11 capsid. |
| 1 | AAVC11.12 | | OTC | 5009 | Payload comprising a OTC gene or variant thereof packaged within a AAVC11.12 capsid. |
| 1 | AAVC11.13 | | OTC | 5009 | Payload comprising a OTC gene or variant thereof packaged within a AAVC11.13 capsid. |
| 1 | AAVC11.14 | | OTC | 5009 | Payload comprising a OTC gene or variant thereof packaged within a AAVC11.14 capsid. |
| 1 | AAVC11.15 | | OTC | 5009 | Payload comprising a OTC gene or variant thereof packaged within a AAVC11.15 capsid. |

Fig. 29 (Continued)

| | | | | | |
|---|---|---|---|---|---|
| 1 | AAVC11.16 | | OTC | 5009 | Payload comprising a OTC gene or variant thereof packaged within a AAVC11.16 capsid. |
| 1 | AAVC11.17 | | OTC | 5009 | Payload comprising a OTC gene or variant thereof packaged within a AAVC11.17 capsid. |
| 1 | AAVC11.18 | | OTC | 5009 | Payload comprising a OTC gene or variant thereof packaged within a AAVC11.18 capsid. |
| 1 | AAVC11.19 | | OTC | 5009 | Payload comprising a OTC gene or variant thereof packaged within a AAVC11.19 capsid. |
| 1 | AAV12 | | OTC | 5009 | Payload comprising a OTC gene or variant thereof packaged within a AAV12 capsid. |
| 1 | AAV13 | | OTC | 5009 | Payload comprising a OTC gene or variant thereof packaged within a AAV13 capsid. |
| 1 | AAV-DJ | | OTC | 5009 | Payload comprising a OTC gene or variant thereof packaged within a AAV-DJ capsid. |
| 1 | AAV-LK03 | | OTC | 5009 | Payload comprising a OTC gene or variant thereof packaged within a AAV-LK03 capsid. |
| 1 | AAV-LK19 | | OTC | 5009 | Payload comprising a OTC gene or variant thereof packaged within a AAV-LK19 capsid. |
| 1 | AAVrh.74 | | OTC | 5009 | Payload comprising a OTC gene or variant thereof packaged within a AAVrh.74 capsid. |
| 1 | AAVrh.10 | | OTC | 5009 | Payload comprising a OTC gene or variant thereof packaged within a AAVrh.10 capsid. |
| 1 | AAVhu.37 | | OTC | 5009 | Payload comprising a OTC gene or variant thereof packaged within a AAVhu.37 capsid. |
| 1 | AAVrh.K | | OTC | 5009 | Payload comprising a OTC gene or variant thereof packaged within a AAVrh.K capsid. |
| 1 | AAVrh.39 | | OTC | 5009 | Payload comprising a OTC gene or variant thereof packaged within a AAVrh.39 capsid. |
| 1 | AAVrh.9 | | OTC | 5009 | Payload comprising a OTC gene or variant thereof packaged within a AAVrh.9 capsid. |
| 1 | avian AAV | | OTC | 5009 | Payload comprising a OTC gene or variant thereof packaged within a avian AAV capsid. |

Fig. 29 (Continued)

| | | | | | |
|---|---|---|---|---|---|
| 1 | bovine AAV | | OTC | 5009 | Payload comprising a OTC gene or variant thereof packaged within a bovine capsid. |
| 1 | canine AAV | | OTC | 5009 | Payload comprising a OTC gene or variant thereof packaged within a canine capsid. |
| 1 | equine AAV | | OTC | 5009 | Payload comprising a OTC gene or variant thereof packaged within a equine capsid. |
| 1 | primate AAV | | OTC | 5009 | Payload comprising a OTC gene or variant thereof packaged within a primate capsid. |
| 1 | non-primate AAV | | OTC | 5009 | Payload comprising a OTC gene or variant thereof packaged within a non-primate capsid. |
| 1 | ovine AAV | | OTC | 5009 | Payload comprising a OTC gene or variant thereof packaged within a ovine capsid. |
| 1 | hybrid AAV | | OTC | 5009 | Payload comprising a OTC gene or variant thereof packaged within a hybrid capsid. |
| 1 | chimeric AAV | | OTC | 5009 | Payload comprising a OTC gene or variant thereof packaged within a chimeric capsid. |
| 2 | AAV1 | 1450374 | OTC | 5009 | Payload comprising a OTC gene or variant thereof packaged within a AAV1 capsid. |
| 2 | AAV2 | | OTC | 5009 | Payload comprising a OTC gene or variant thereof packaged within a AAV2 capsid. |
| 2 | AAV3 | | OTC | 5009 | Payload comprising a OTC gene or variant thereof packaged within a AAV3 capsid. |
| 2 | AAV4 | 1446389 | OTC | 5009 | Payload comprising a OTC gene or variant thereof packaged within a AAV4 capsid. |
| 2 | AAV5 | | OTC | 5009 | Payload comprising a OTC gene or variant thereof packaged within a AAV5 capsid. |
| 2 | AAV6 | | OTC | 5009 | Payload comprising a OTC gene or variant thereof packaged within a AAV6 capsid. |
| 2 | AAV7 | | OTC | 5009 | Payload comprising a OTC gene or variant thereof packaged within a AAV7 capsid. |
| 2 | AAV8 | 5075992 | OTC | 5009 | Payload comprising a OTC gene or variant thereof packaged within a AAV8 capsid. |
| 2 | AAV9 | | OTC | 5009 | Payload comprising a OTC gene or variant thereof packaged within a AAV9 capsid. |

Fig. 29 (Continued)

| | | | | | |
|---|---|---|---|---|---|
| 2 | AAV10 | | OTC | 5009 | Payload comprising a OTC gene or variant thereof packaged within a AAV10 capsid. |
| 2 | AAV11 | | OTC | 5009 | Payload comprising a OTC gene or variant thereof packaged within a AAV11 capsid. |
| 2 | AAVC11.01 | | OTC | 5009 | Payload comprising a OTC gene or variant thereof packaged within a AAVC11.01 capsid. |
| 2 | AAVC11.02 | | OTC | 5009 | Payload comprising a OTC gene or variant thereof packaged within a AAVC11.02 capsid. |
| 2 | AAVC11.03 | | OTC | 5009 | Payload comprising a OTC gene or variant thereof packaged within a AAVC11.03 capsid. |
| 2 | AAVC11.04 | | OTC | 5009 | Payload comprising a OTC gene or variant thereof packaged within a AAVC11.04 capsid. |
| 2 | AAVC11.05 | | OTC | 5009 | Payload comprising a OTC gene or variant thereof packaged within a AAVC11.05 capsid. |
| 2 | AAVC11.06 | | OTC | 5009 | Payload comprising a OTC gene or variant thereof packaged within a AAVC11.06 capsid. |
| 2 | AAVC11.07 | | OTC | 5009 | Payload comprising a OTC gene or variant thereof packaged within a AAVC11.07 capsid. |
| 2 | AAVC11.08 | | OTC | 5009 | Payload comprising a OTC gene or variant thereof packaged within a AAVC11.08 capsid. |
| 2 | AAVC11.09 | | OTC | 5009 | Payload comprising a OTC gene or variant thereof packaged within a AAVC11.09 capsid. |
| 2 | AAVC11.10 | | OTC | 5009 | Payload comprising a OTC gene or variant thereof packaged within a AAVC11.10 capsid. |
| 2 | AAVC11.11 | | OTC | 5009 | Payload comprising a OTC gene or variant thereof packaged within a AAVC11.11 capsid. |
| 2 | AAVC11.12 | | OTC | 5009 | Payload comprising a OTC gene or variant thereof packaged within a AAVC11.12 capsid. |
| 2 | AAVC11.13 | | OTC | 5009 | Payload comprising a OTC gene or variant thereof packaged within a AAVC11.13 capsid. |
| 2 | AAVC11.14 | | OTC | 5009 | Payload comprising a OTC gene or variant thereof packaged within a AAVC11.14 capsid. |
| 2 | AAVC11.15 | | OTC | 5009 | Payload comprising a OTC gene or variant thereof packaged within a AAVC11.15 capsid. |

Fig. 29 (Continued)

| | | | | | |
|---|---|---|---|---|---|
| 2 | AAVC11.16 | | OTC | 5009 | Payload comprising a OTC gene or variant thereof packaged within a AAVC11.16 capsid. |
| 2 | AAVC11.17 | | OTC | 5009 | Payload comprising a OTC gene or variant thereof packaged within a AAVC11.17 capsid. |
| 2 | AAVC11.18 | | OTC | 5009 | Payload comprising a OTC gene or variant thereof packaged within a AAVC11.18 capsid. |
| 2 | AAVC11.19 | | OTC | 5009 | Payload comprising a OTC gene or variant thereof packaged within a AAVC11.19 capsid. |
| 2 | AAV12 | | OTC | 5009 | Payload comprising a OTC gene or variant thereof packaged within a AAV12 capsid. |
| 2 | AAV13 | | OTC | 5009 | Payload comprising a OTC gene or variant thereof packaged within a AAV13 capsid. |
| 2 | AAV-DJ | | OTC | 5009 | Payload comprising a OTC gene or variant thereof packaged within a AAV-DJ capsid. |
| 2 | AAV-LK03 | | OTC | 5009 | Payload comprising a OTC gene or variant thereof packaged within a AAV-LK03 capsid. |
| 2 | AAV-LK19 | | OTC | 5009 | Payload comprising a OTC gene or variant thereof packaged within a AAV-LK19 capsid. |
| 2 | AAVrh.74 | | OTC | 5009 | Payload comprising a OTC gene or variant thereof packaged within a AAVrh.74 capsid. |
| 2 | AAVrh.10 | | OTC | 5009 | Payload comprising a OTC gene or variant thereof packaged within a AAVrh.10 capsid. |
| 2 | AAVhu.37 | | OTC | 5009 | Payload comprising a OTC gene or variant thereof packaged within a AAVhu.37 capsid. |
| 2 | AAVrh.K | | OTC | 5009 | Payload comprising a OTC gene or variant thereof packaged within a AAVrh.K capsid. |
| 2 | AAVrh.39 | | OTC | 5009 | Payload comprising a OTC gene or variant thereof packaged within a AAVrh.39 capsid. |
| 2 | AAVrh.9 | | OTC | 5009 | Payload comprising a OTC gene or variant thereof packaged within a AAVrh.9 capsid. |
| 2 | avian AAV | | OTC | 5009 | Payload comprising a OTC gene or variant thereof packaged within a avian capsid. |

Fig. 29 (Continued)

| | | | | | |
|---|---|---|---|---|---|
| 2 | bovine AAV | | OTC | 5009 | Payload comprising a OTC gene or variant thereof packaged within a bovine capsid. |
| 2 | canine AAV | | OTC | 5009 | Payload comprising a OTC gene or variant thereof packaged within a canine capsid. |
| 2 | equine AAV | | OTC | 5009 | Payload comprising a OTC gene or variant thereof packaged within a equine capsid. |
| 2 | primate AAV | | OTC | 5009 | Payload comprising a OTC gene or variant thereof packaged within a primate capsid. |
| 2 | non-primate AAV | | OTC | 5009 | Payload comprising a OTC gene or variant thereof packaged within a non-primate capsid. |
| 2 | ovine AAV | | OTC | 5009 | Payload comprising a OTC gene or variant thereof packaged within a ovine capsid. |
| 2 | hybrid AAV | | OTC | 5009 | Payload comprising a OTC gene or variant thereof packaged within a hybrid capsid. |
| 2 | chimeric AAV | | OTC | 5009 | Payload comprising a OTC gene or variant thereof packaged within a chimeric capsid. |
| 1 | AAV1 | 1450374 | PCCA | 5095 | Payload comprising a PCCA gene or variant thereof packaged within a AAV1 capsid. |
| 1 | AAV2 | | PCCA | 5095 | Payload comprising a PCCA gene or variant thereof packaged within a AAV2 capsid. |
| 1 | AAV3 | | PCCA | 5095 | Payload comprising a PCCA gene or variant thereof packaged within a AAV3 capsid. |
| 1 | AAV4 | 1446389 | PCCA | 5095 | Payload comprising a PCCA gene or variant thereof packaged within a AAV4 capsid. |
| 1 | AAV5 | | PCCA | 5095 | Payload comprising a PCCA gene or variant thereof packaged within a AAV5 capsid. |
| 1 | AAV6 | | PCCA | 5095 | Payload comprising a PCCA gene or variant thereof packaged within a AAV6 capsid. |
| 1 | AAV7 | | PCCA | 5095 | Payload comprising a PCCA gene or variant thereof packaged within a AAV7 capsid. |
| 1 | AAV8 | 5075992 | PCCA | 5095 | Payload comprising a PCCA gene or variant thereof packaged within a AAV8 capsid. |
| 1 | AAV9 | | PCCA | 5095 | Payload comprising a PCCA gene or variant thereof packaged within a AAV9 capsid. |

Fig. 29 (Continued)

| | | | | | |
|---|---|---|---|---|---|
| 1 | AAV10 | | PCCA | 5095 | Payload comprising a PCCA gene or variant thereof packaged within a AAV10 capsid. |
| 1 | AAV11 | | PCCA | 5095 | Payload comprising a PCCA gene or variant thereof packaged within a AAV11 capsid. |
| 1 | AAVC11.01 | | PCCA | 5095 | Payload comprising a PCCA gene or variant thereof packaged within a AAVC11.01 capsid. |
| 1 | AAVC11.02 | | PCCA | 5095 | Payload comprising a PCCA gene or variant thereof packaged within a AAVC11.02 capsid. |
| 1 | AAVC11.03 | | PCCA | 5095 | Payload comprising a PCCA gene or variant thereof packaged within a AAVC11.03 capsid. |
| 1 | AAVC11.04 | | PCCA | 5095 | Payload comprising a PCCA gene or variant thereof packaged within a AAVC11.04 capsid. |
| 1 | AAVC11.05 | | PCCA | 5095 | Payload comprising a PCCA gene or variant thereof packaged within a AAVC11.05 capsid. |
| 1 | AAVC11.06 | | PCCA | 5095 | Payload comprising a PCCA gene or variant thereof packaged within a AAVC11.06 capsid. |
| 1 | AAVC11.07 | | PCCA | 5095 | Payload comprising a PCCA gene or variant thereof packaged within a AAVC11.07 capsid. |
| 1 | AAVC11.08 | | PCCA | 5095 | Payload comprising a PCCA gene or variant thereof packaged within a AAVC11.08 capsid. |
| 1 | AAVC11.09 | | PCCA | 5095 | Payload comprising a PCCA gene or variant thereof packaged within a AAVC11.09 capsid. |
| 1 | AAVC11.10 | | PCCA | 5095 | Payload comprising a PCCA gene or variant thereof packaged within a AAVC11.10 capsid. |
| 1 | AAVC11.11 | | PCCA | 5095 | Payload comprising a PCCA gene or variant thereof packaged within a AAVC11.11 capsid. |
| 1 | AAVC11.12 | | PCCA | 5095 | Payload comprising a PCCA gene or variant thereof packaged within a AAVC11.12 capsid. |
| 1 | AAVC11.13 | | PCCA | 5095 | Payload comprising a PCCA gene or variant thereof packaged within a AAVC11.13 capsid. |
| 1 | AAVC11.14 | | PCCA | 5095 | Payload comprising a PCCA gene or variant thereof packaged within a AAVC11.14 capsid. |
| 1 | AAVC11.15 | | PCCA | 5095 | Payload comprising a PCCA gene or variant thereof packaged within a AAVC11.15 capsid. |

Fig. 29 (Continued)

| | | | | | |
|---|---|---|---|---|---|
| 1 | AAVC11.16 | | PCCA | 5095 | Payload comprising a PCCA gene or variant thereof packaged within a AAVC11.16 capsid. |
| 1 | AAVC11.17 | | PCCA | 5095 | Payload comprising a PCCA gene or variant thereof packaged within a AAVC11.17 capsid. |
| 1 | AAVC11.18 | | PCCA | 5095 | Payload comprising a PCCA gene or variant thereof packaged within a AAVC11.18 capsid. |
| 1 | AAVC11.19 | | PCCA | 5095 | Payload comprising a PCCA gene or variant thereof packaged within a AAVC11.19 capsid. |
| 1 | AAV12 | | PCCA | 5095 | Payload comprising a PCCA gene or variant thereof packaged within a AAV12 capsid. |
| 1 | AAV13 | | PCCA | 5095 | Payload comprising a PCCA gene or variant thereof packaged within a AAV13 capsid. |
| 1 | AAV-DJ | | PCCA | 5095 | Payload comprising a PCCA gene or variant thereof packaged within a AAV-DJ capsid. |
| 1 | AAV-LK03 | | PCCA | 5095 | Payload comprising a PCCA gene or variant thereof packaged within a AAV-LK03 capsid. |
| 1 | AAV-LK19 | | PCCA | 5095 | Payload comprising a PCCA gene or variant thereof packaged within a AAV-LK19 capsid. |
| 1 | AAVrh.74 | | PCCA | 5095 | Payload comprising a PCCA gene or variant thereof packaged within a AAVrh.74 capsid. |
| 1 | AAVrh.10 | | PCCA | 5095 | Payload comprising a PCCA gene or variant thereof packaged within a AAVrh.10 capsid. |
| 1 | AAVhu.37 | | PCCA | 5095 | Payload comprising a PCCA gene or variant thereof packaged within a AAVhu.37 capsid. |
| 1 | AAVrh.K | | PCCA | 5095 | Payload comprising a PCCA gene or variant thereof packaged within a AAVrh.K capsid. |
| 1 | AAVrh.39 | | PCCA | 5095 | Payload comprising a PCCA gene or variant thereof packaged within a AAVrh.39 capsid. |
| 1 | AAVrh.9 | | PCCA | 5095 | Payload comprising a PCCA gene or variant thereof packaged within a AAVrh.9 capsid. |
| 1 | avian AAV | | PCCA | 5095 | Payload comprising a PCCA gene or variant thereof packaged within a avian capsid. |

Fig. 29 (Continued)

| | | | | | |
|---|---|---|---|---|---|
| 1 | bovine AAV | | PCCA | 5095 | Payload comprising a PCCA gene or variant thereof packaged within a bovine capsid. |
| 1 | canine AAV | | PCCA | 5095 | Payload comprising a PCCA gene or variant thereof packaged within a canine capsid. |
| 1 | equine AAV | | PCCA | 5095 | Payload comprising a PCCA gene or variant thereof packaged within a equine capsid. |
| 1 | primate AAV | | PCCA | 5095 | Payload comprising a PCCA gene or variant thereof packaged within a primate capsid. |
| 1 | non-primate AAV | | PCCA | 5095 | Payload comprising a PCCA gene or variant thereof packaged within a non-primate capsid. |
| 1 | ovine AAV | | PCCA | 5095 | Payload comprising a PCCA gene or variant thereof packaged within a ovine capsid. |
| 1 | hybrid AAV | | PCCA | 5095 | Payload comprising a PCCA gene or variant thereof packaged within a hybrid capsid. |
| 1 | chimeric AAV | | PCCA | 5095 | Payload comprising a PCCA gene or variant thereof packaged within a chimeric capsid. |
| 2 | AAV1 | 1450374 | PCCA | 5095 | Payload comprising a PCCA gene or variant thereof packaged within a AAV1 capsid. |
| 2 | AAV2 | | PCCA | 5095 | Payload comprising a PCCA gene or variant thereof packaged within a AAV2 capsid. |
| 2 | AAV3 | | PCCA | 5095 | Payload comprising a PCCA gene or variant thereof packaged within a AAV3 capsid. |
| 2 | AAV4 | 1446389 | PCCA | 5095 | Payload comprising a PCCA gene or variant thereof packaged within a AAV4 capsid. |
| 2 | AAV5 | | PCCA | 5095 | Payload comprising a PCCA gene or variant thereof packaged within a AAV5 capsid. |
| 2 | AAV6 | | PCCA | 5095 | Payload comprising a PCCA gene or variant thereof packaged within a AAV6 capsid. |
| 2 | AAV7 | | PCCA | 5095 | Payload comprising a PCCA gene or variant thereof packaged within a AAV7 capsid. |
| 2 | AAV8 | 5075992 | PCCA | 5095 | Payload comprising a PCCA gene or variant thereof packaged within a AAV8 capsid. |
| 2 | AAV9 | | PCCA | 5095 | Payload comprising a PCCA gene or variant thereof packaged within a AAV9 capsid. |

Fig. 29 (Continued)

| | | | | | |
|---|---|---|---|---|---|
| 2 | AAV10 | | PCCA | 5095 | Payload comprising a PCCA gene or variant thereof packaged within a AAV10 capsid. |
| 2 | AAV11 | | PCCA | 5095 | Payload comprising a PCCA gene or variant thereof packaged within a AAV11 capsid. |
| 2 | AAVC11.01 | | PCCA | 5095 | Payload comprising a PCCA gene or variant thereof packaged within a AAVC11.01 capsid. |
| 2 | AAVC11.02 | | PCCA | 5095 | Payload comprising a PCCA gene or variant thereof packaged within a AAVC11.02 capsid. |
| 2 | AAVC11.03 | | PCCA | 5095 | Payload comprising a PCCA gene or variant thereof packaged within a AAVC11.03 capsid. |
| 2 | AAVC11.04 | | PCCA | 5095 | Payload comprising a PCCA gene or variant thereof packaged within a AAVC11.04 capsid. |
| 2 | AAVC11.05 | | PCCA | 5095 | Payload comprising a PCCA gene or variant thereof packaged within a AAVC11.05 capsid. |
| 2 | AAVC11.06 | | PCCA | 5095 | Payload comprising a PCCA gene or variant thereof packaged within a AAVC11.06 capsid. |
| 2 | AAVC11.07 | | PCCA | 5095 | Payload comprising a PCCA gene or variant thereof packaged within a AAVC11.07 capsid. |
| 2 | AAVC11.08 | | PCCA | 5095 | Payload comprising a PCCA gene or variant thereof packaged within a AAVC11.08 capsid. |
| 2 | AAVC11.09 | | PCCA | 5095 | Payload comprising a PCCA gene or variant thereof packaged within a AAVC11.09 capsid. |
| 2 | AAVC11.10 | | PCCA | 5095 | Payload comprising a PCCA gene or variant thereof packaged within a AAVC11.10 capsid. |
| 2 | AAVC11.11 | | PCCA | 5095 | Payload comprising a PCCA gene or variant thereof packaged within a AAVC11.11 capsid. |
| 2 | AAVC11.12 | | PCCA | 5095 | Payload comprising a PCCA gene or variant thereof packaged within a AAVC11.12 capsid. |
| 2 | AAVC11.13 | | PCCA | 5095 | Payload comprising a PCCA gene or variant thereof packaged within a AAVC11.13 capsid. |
| 2 | AAVC11.14 | | PCCA | 5095 | Payload comprising a PCCA gene or variant thereof packaged within a AAVC11.14 capsid. |
| 2 | AAVC11.15 | | PCCA | 5095 | Payload comprising a PCCA gene or variant thereof packaged within a AAVC11.15 capsid. |

Fig. 29 (Continued)

| | | | | | |
|---|---|---|---|---|---|
| 2 | AAVC11.16 | | PCCA | 5095 | Payload comprising a PCCA gene or variant thereof packaged within a AAVC11.16 capsid. |
| 2 | AAVC11.17 | | PCCA | 5095 | Payload comprising a PCCA gene or variant thereof packaged within a AAVC11.17 capsid. |
| 2 | AAVC11.18 | | PCCA | 5095 | Payload comprising a PCCA gene or variant thereof packaged within a AAVC11.18 capsid. |
| 2 | AAVC11.19 | | PCCA | 5095 | Payload comprising a PCCA gene or variant thereof packaged within a AAVC11.19 capsid. |
| 2 | AAV12 | | PCCA | 5095 | Payload comprising a PCCA gene or variant thereof packaged within a AAV12 capsid. |
| 2 | AAV13 | | PCCA | 5095 | Payload comprising a PCCA gene or variant thereof packaged within a AAV13 capsid. |
| 2 | AAV-DJ | | PCCA | 5095 | Payload comprising a PCCA gene or variant thereof packaged within a AAV-DJ capsid. |
| 2 | AAV-LK03 | | PCCA | 5095 | Payload comprising a PCCA gene or variant thereof packaged within a AAV-LK03 capsid. |
| 2 | AAV-LK19 | | PCCA | 5095 | Payload comprising a PCCA gene or variant thereof packaged within a AAV-LK19 capsid. |
| 2 | AAVrh.74 | | PCCA | 5095 | Payload comprising a PCCA gene or variant thereof packaged within a AAVrh.74 capsid. |
| 2 | AAVrh.10 | | PCCA | 5095 | Payload comprising a PCCA gene or variant thereof packaged within a AAVrh.10 capsid. |
| 2 | AAVhu.37 | | PCCA | 5095 | Payload comprising a PCCA gene or variant thereof packaged within a AAVhu.37 capsid. |
| 2 | AAVrh.K | | PCCA | 5095 | Payload comprising a PCCA gene or variant thereof packaged within a AAVrh.K capsid. |
| 2 | AAVrh.39 | | PCCA | 5095 | Payload comprising a PCCA gene or variant thereof packaged within a AAVrh.39 capsid. |
| 2 | AAVrh.9 | | PCCA | 5095 | Payload comprising a PCCA gene or variant thereof packaged within a AAVrh.9 capsid. |
| 2 | avian AAV | | PCCA | 5095 | Payload comprising a PCCA gene or variant thereof packaged within a avian capsid. |

Fig. 29 (Continued)

| | | | | | |
|---|---|---|---|---|---|
| 2 | bovine AAV | | PCCA | 5095 | Payload comprising a PCCA gene or variant thereof packaged within a bovine capsid. |
| 2 | canine AAV | | PCCA | 5095 | Payload comprising a PCCA gene or variant thereof packaged within a canine capsid. |
| 2 | equine AAV | | PCCA | 5095 | Payload comprising a PCCA gene or variant thereof packaged within a equine capsid. |
| 2 | primate AAV | | PCCA | 5095 | Payload comprising a PCCA gene or variant thereof packaged within a primate capsid. |
| 2 | non-primate AAV | | PCCA | 5095 | Payload comprising a PCCA gene or variant thereof packaged within a non-primate capsid. |
| 2 | ovine AAV | | PCCA | 5095 | Payload comprising a PCCA gene or variant thereof packaged within a ovine capsid. |
| 2 | hybrid AAV | | PCCA | 5095 | Payload comprising a PCCA gene or variant thereof packaged within a hybrid capsid. |
| 2 | chimeric AAV | | PCCA | 5095 | Payload comprising a PCCA gene or variant thereof packaged within a chimeric capsid. |
| 1 | AAV1 | 1450374 | PCCB | 5096 | Payload comprising a PCCB gene or variant thereof packaged within a AAV1 capsid. |
| 1 | AAV2 | | PCCB | 5096 | Payload comprising a PCCB gene or variant thereof packaged within a AAV2 capsid. |
| 1 | AAV3 | | PCCB | 5096 | Payload comprising a PCCB gene or variant thereof packaged within a AAV3 capsid. |
| 1 | AAV4 | 1446389 | PCCB | 5096 | Payload comprising a PCCB gene or variant thereof packaged within a AAV4 capsid. |
| 1 | AAV5 | | PCCB | 5096 | Payload comprising a PCCB gene or variant thereof packaged within a AAV5 capsid. |
| 1 | AAV6 | | PCCB | 5096 | Payload comprising a PCCB gene or variant thereof packaged within a AAV6 capsid. |
| 1 | AAV7 | | PCCB | 5096 | Payload comprising a PCCB gene or variant thereof packaged within a AAV7 capsid. |
| 1 | AAV8 | 5075992 | PCCB | 5096 | Payload comprising a PCCB gene or variant thereof packaged within a AAV8 capsid. |
| 1 | AAV9 | | PCCB | 5096 | Payload comprising a PCCB gene or variant thereof packaged within a AAV9 capsid. |

Fig. 29 (Continued)

| | | | | | |
|---|---|---|---|---|---|
| 1 | AAV10 | | PCCB | 5096 | Payload comprising a PCCB gene or variant thereof packaged within a AAV10 capsid. |
| 1 | AAV11 | | PCCB | 5096 | Payload comprising a PCCB gene or variant thereof packaged within a AAV11 capsid. |
| 1 | AAVC11.01 | | PCCB | 5096 | Payload comprising a PCCB gene or variant thereof packaged within a AAVC11.01 capsid. |
| 1 | AAVC11.02 | | PCCB | 5096 | Payload comprising a PCCB gene or variant thereof packaged within a AAVC11.02 capsid. |
| 1 | AAVC11.03 | | PCCB | 5096 | Payload comprising a PCCB gene or variant thereof packaged within a AAVC11.03 capsid. |
| 1 | AAVC11.04 | | PCCB | 5096 | Payload comprising a PCCB gene or variant thereof packaged within a AAVC11.04 capsid. |
| 1 | AAVC11.05 | | PCCB | 5096 | Payload comprising a PCCB gene or variant thereof packaged within a AAVC11.05 capsid. |
| 1 | AAVC11.06 | | PCCB | 5096 | Payload comprising a PCCB gene or variant thereof packaged within a AAVC11.06 capsid. |
| 1 | AAVC11.07 | | PCCB | 5096 | Payload comprising a PCCB gene or variant thereof packaged within a AAVC11.07 capsid. |
| 1 | AAVC11.08 | | PCCB | 5096 | Payload comprising a PCCB gene or variant thereof packaged within a AAVC11.08 capsid. |
| 1 | AAVC11.09 | | PCCB | 5096 | Payload comprising a PCCB gene or variant thereof packaged within a AAVC11.09 capsid. |
| 1 | AAVC11.10 | | PCCB | 5096 | Payload comprising a PCCB gene or variant thereof packaged within a AAVC11.10 capsid. |
| 1 | AAVC11.11 | | PCCB | 5096 | Payload comprising a PCCB gene or variant thereof packaged within a AAVC11.11 capsid. |
| 1 | AAVC11.12 | | PCCB | 5096 | Payload comprising a PCCB gene or variant thereof packaged within a AAVC11.12 capsid. |
| 1 | AAVC11.13 | | PCCB | 5096 | Payload comprising a PCCB gene or variant thereof packaged within a AAVC11.13 capsid. |
| 1 | AAVC11.14 | | PCCB | 5096 | Payload comprising a PCCB gene or variant thereof packaged within a AAVC11.14 capsid. |
| 1 | AAVC11.15 | | PCCB | 5096 | Payload comprising a PCCB gene or variant thereof packaged within a AAVC11.15 capsid. |

Fig. 29 (Continued)

| | | | | | |
|---|---|---|---|---|---|
| 1 | AAVC11.16 | | PCCB | 5096 | Payload comprising a PCCB gene or variant thereof packaged within a AAVC11.16 capsid. |
| 1 | AAVC11.17 | | PCCB | 5096 | Payload comprising a PCCB gene or variant thereof packaged within a AAVC11.17 capsid. |
| 1 | AAVC11.18 | | PCCB | 5096 | Payload comprising a PCCB gene or variant thereof packaged within a AAVC11.18 capsid. |
| 1 | AAVC11.19 | | PCCB | 5096 | Payload comprising a PCCB gene or variant thereof packaged within a AAVC11.19 capsid. |
| 1 | AAV12 | | PCCB | 5096 | Payload comprising a PCCB gene or variant thereof packaged within a AAV12 capsid. |
| 1 | AAV13 | | PCCB | 5096 | Payload comprising a PCCB gene or variant thereof packaged within a AAV13 capsid. |
| 1 | AAV-DJ | | PCCB | 5096 | Payload comprising a PCCB gene or variant thereof packaged within a AAV-DJ capsid. |
| 1 | AAV-LK03 | | PCCB | 5096 | Payload comprising a PCCB gene or variant thereof packaged within a AAV-LK03 capsid. |
| 1 | AAV-LK19 | | PCCB | 5096 | Payload comprising a PCCB gene or variant thereof packaged within a AAV-LK19 capsid. |
| 1 | AAVrh.74 | | PCCB | 5096 | Payload comprising a PCCB gene or variant thereof packaged within a AAVrh.74 capsid. |
| 1 | AAVrh.10 | | PCCB | 5096 | Payload comprising a PCCB gene or variant thereof packaged within a AAVrh.10 capsid. |
| 1 | AAVhu.37 | | PCCB | 5096 | Payload comprising a PCCB gene or variant thereof packaged within a AAVhu.37 capsid. |
| 1 | AAVrh.K | | PCCB | 5096 | Payload comprising a PCCB gene or variant thereof packaged within a AAVrh.K capsid. |
| 1 | AAVrh.39 | | PCCB | 5096 | Payload comprising a PCCB gene or variant thereof packaged within a AAVrh.39 capsid. |
| 1 | AAVrh.9 | | PCCB | 5096 | Payload comprising a PCCB gene or variant thereof packaged within a AAVrh.9 capsid. |
| 1 | avian AAV | | PCCB | 5096 | Payload comprising a PCCB gene or variant thereof packaged within a avian capsid. |

Fig. 29 (Continued)

| | | | | | |
|---|---|---|---|---|---|
| 1 | bovine AAV | | PCCB | 5096 | Payload comprising a PCCB gene or variant thereof packaged within a bovine capsid. |
| 1 | canine AAV | | PCCB | 5096 | Payload comprising a PCCB gene or variant thereof packaged within a canine capsid. |
| 1 | equine AAV | | PCCB | 5096 | Payload comprising a PCCB gene or variant thereof packaged within a equine capsid. |
| 1 | primate AAV | | PCCB | 5096 | Payload comprising a PCCB gene or variant thereof packaged within a primate capsid. |
| 1 | non-primate AAV | | PCCB | 5096 | Payload comprising a PCCB gene or variant thereof packaged within a non-primate capsid. |
| 1 | ovine AAV | | PCCB | 5096 | Payload comprising a PCCB gene or variant thereof packaged within a ovine capsid. |
| 1 | hybrid AAV | | PCCB | 5096 | Payload comprising a PCCB gene or variant thereof packaged within a hybrid capsid. |
| 1 | chimeric AAV | | PCCB | 5096 | Payload comprising a PCCB gene or variant thereof packaged within a chimeric capsid. |
| 2 | AAV1 | 1450374 | PCCB | 5096 | Payload comprising a PCCB gene or variant thereof packaged within a AAV1 capsid. |
| 2 | AAV2 | | PCCB | 5096 | Payload comprising a PCCB gene or variant thereof packaged within a AAV2 capsid. |
| 2 | AAV3 | | PCCB | 5096 | Payload comprising a PCCB gene or variant thereof packaged within a AAV3 capsid. |
| 2 | AAV4 | 1446389 | PCCB | 5096 | Payload comprising a PCCB gene or variant thereof packaged within a AAV4 capsid. |
| 2 | AAV5 | | PCCB | 5096 | Payload comprising a PCCB gene or variant thereof packaged within a AAV5 capsid. |
| 2 | AAV6 | | PCCB | 5096 | Payload comprising a PCCB gene or variant thereof packaged within a AAV6 capsid. |
| 2 | AAV7 | | PCCB | 5096 | Payload comprising a PCCB gene or variant thereof packaged within a AAV7 capsid. |
| 2 | AAV8 | 5075992 | PCCB | 5096 | Payload comprising a PCCB gene or variant thereof packaged within a AAV8 capsid. |
| 2 | AAV9 | | PCCB | 5096 | Payload comprising a PCCB gene or variant thereof packaged within a AAV9 capsid. |

Fig. 29 (Continued)

| | | | | | |
|---|---|---|---|---|---|
| 2 | AAV10 | | PCCB | 5096 | Payload comprising a PCCB gene or variant thereof packaged within a AAV10 capsid. |
| 2 | AAV11 | | PCCB | 5096 | Payload comprising a PCCB gene or variant thereof packaged within a AAV11 capsid. |
| 2 | AAVC11.01 | | PCCB | 5096 | Payload comprising a PCCB gene or variant thereof packaged within a AAVC11.01 capsid. |
| 2 | AAVC11.02 | | PCCB | 5096 | Payload comprising a PCCB gene or variant thereof packaged within a AAVC11.02 capsid. |
| 2 | AAVC11.03 | | PCCB | 5096 | Payload comprising a PCCB gene or variant thereof packaged within a AAVC11.03 capsid. |
| 2 | AAVC11.04 | | PCCB | 5096 | Payload comprising a PCCB gene or variant thereof packaged within a AAVC11.04 capsid. |
| 2 | AAVC11.05 | | PCCB | 5096 | Payload comprising a PCCB gene or variant thereof packaged within a AAVC11.05 capsid. |
| 2 | AAVC11.06 | | PCCB | 5096 | Payload comprising a PCCB gene or variant thereof packaged within a AAVC11.06 capsid. |
| 2 | AAVC11.07 | | PCCB | 5096 | Payload comprising a PCCB gene or variant thereof packaged within a AAVC11.07 capsid. |
| 2 | AAVC11.08 | | PCCB | 5096 | Payload comprising a PCCB gene or variant thereof packaged within a AAVC11.08 capsid. |
| 2 | AAVC11.09 | | PCCB | 5096 | Payload comprising a PCCB gene or variant thereof packaged within a AAVC11.09 capsid. |
| 2 | AAVC11.10 | | PCCB | 5096 | Payload comprising a PCCB gene or variant thereof packaged within a AAVC11.10 capsid. |
| 2 | AAVC11.11 | | PCCB | 5096 | Payload comprising a PCCB gene or variant thereof packaged within a AAVC11.11 capsid. |
| 2 | AAVC11.12 | | PCCB | 5096 | Payload comprising a PCCB gene or variant thereof packaged within a AAVC11.12 capsid. |
| 2 | AAVC11.13 | | PCCB | 5096 | Payload comprising a PCCB gene or variant thereof packaged within a AAVC11.13 capsid. |
| 2 | AAVC11.14 | | PCCB | 5096 | Payload comprising a PCCB gene or variant thereof packaged within a AAVC11.14 capsid. |
| 2 | AAVC11.15 | | PCCB | 5096 | Payload comprising a PCCB gene or variant thereof packaged within a AAVC11.15 capsid. |

Fig. 29 (Continued)

| | | | | | |
|---|---|---|---|---|---|
| 2 | AAVC11.16 | | PCCB | 5095 | Payload comprising a PCCB gene or variant thereof packaged within a AAVC11.16 capsid. |
| 2 | AAVC11.17 | | PCCB | 5095 | Payload comprising a PCCB gene or variant thereof packaged within a AAVC11.17 capsid. |
| 2 | AAVC11.18 | | PCCB | 5095 | Payload comprising a PCCB gene or variant thereof packaged within a AAVC11.18 capsid. |
| 2 | AAVC11.19 | | PCCB | 5095 | Payload comprising a PCCB gene or variant thereof packaged within a AAVC11.19 capsid. |
| 2 | AAV12 | | PCCB | 5095 | Payload comprising a PCCB gene or variant thereof packaged within a AAV12 capsid. |
| 2 | AAV13 | | PCCB | 5095 | Payload comprising a PCCB gene or variant thereof packaged within a AAV13 capsid. |
| 2 | AAV-DJ | | PCCB | 5095 | Payload comprising a PCCB gene or variant thereof packaged within a AAV-DJ capsid. |
| 2 | AAV-LK03 | | PCCB | 5095 | Payload comprising a PCCB gene or variant thereof packaged within a AAV-LK03 capsid. |
| 2 | AAV-LK19 | | PCCB | 5095 | Payload comprising a PCCB gene or variant thereof packaged within a AAV-LK19 capsid. |
| 2 | AAVrh.74 | | PCCB | 5095 | Payload comprising a PCCB gene or variant thereof packaged within a AAVrh.74 capsid. |
| 2 | AAVrh.10 | | PCCB | 5095 | Payload comprising a PCCB gene or variant thereof packaged within a AAVrh.10 capsid. |
| 2 | AAVhu.37 | | PCCB | 5095 | Payload comprising a PCCB gene or variant thereof packaged within a AAVhu.37 capsid. |
| 2 | AAVrh.K | | PCCB | 5095 | Payload comprising a PCCB gene or variant thereof packaged within a AAVrh.K capsid. |
| 2 | AAVrh.39 | | PCCB | 5095 | Payload comprising a PCCB gene or variant thereof packaged within a AAVrh.39 capsid. |
| 2 | AAVrh.9 | | PCCB | 5095 | Payload comprising a PCCB gene or variant thereof packaged within a AAVrh.9 capsid. |
| 2 | avian AAV | | PCCB | 5095 | Payload comprising a PCCB gene or variant thereof packaged within a avian capsid. |

Fig. 29 (Continued)

| | | | | | |
|---|---|---|---|---|---|
| 2 | bovine AAV | | PCCB | 5096 | Payload comprising a PCCB gene or variant thereof packaged within a bovine capsid. |
| 2 | canine AAV | | PCCB | 5096 | Payload comprising a PCCB gene or variant thereof packaged within a canine capsid. |
| 2 | equine AAV | | PCCB | 5096 | Payload comprising a PCCB gene or variant thereof packaged within a equine capsid. |
| 2 | primate AAV | | PCCB | 5096 | Payload comprising a PCCB gene or variant thereof packaged within a primate capsid. |
| 2 | non-primate AAV | | PCCB | 5096 | Payload comprising a PCCB gene or variant thereof packaged within a non-primate capsid. |
| 2 | ovine AAV | | PCCB | 5096 | Payload comprising a PCCB gene or variant thereof packaged within a ovine capsid. |
| 2 | hybrid AAV | | PCCB | 5096 | Payload comprising a PCCB gene or variant thereof packaged within a hybrid capsid. |
| 2 | chimeric AAV | | PCCB | 5096 | Payload comprising a PCCB gene or variant thereof packaged within a chimeric capsid. |
| 1 | AAV1 | 1450374 | PRKN | 5071 | Payload comprising a PRKN gene or variant thereof packaged within a AAV1 capsid. |
| 1 | AAV2 | | PRKN | 5071 | Payload comprising a PRKN gene or variant thereof packaged within a AAV2 capsid. |
| 1 | AAV3 | | PRKN | 5071 | Payload comprising a PRKN gene or variant thereof packaged within a AAV3 capsid. |
| 1 | AAV4 | 1446389 | PRKN | 5071 | Payload comprising a PRKN gene or variant thereof packaged within a AAV4 capsid. |
| 1 | AAV5 | | PRKN | 5071 | Payload comprising a PRKN gene or variant thereof packaged within a AAV5 capsid. |
| 1 | AAV6 | | PRKN | 5071 | Payload comprising a PRKN gene or variant thereof packaged within a AAV6 capsid. |
| 1 | AAV7 | | PRKN | 5071 | Payload comprising a PRKN gene or variant thereof packaged within a AAV7 capsid. |
| 1 | AAV8 | 5075992 | PRKN | 5071 | Payload comprising a PRKN gene or variant thereof packaged within a AAV8 capsid. |
| 1 | AAV9 | | PRKN | 5071 | Payload comprising a PRKN gene or variant thereof packaged within a AAV9 capsid. |

Fig. 29 (Continued)

| | | | | | |
|---|---|---|---|---|---|
| 1 | AAV10 | | PRKN | 5071 | Payload comprising a PRKN gene or variant thereof packaged within a AAV10 capsid. |
| 1 | AAV11 | | PRKN | 5071 | Payload comprising a PRKN gene or variant thereof packaged within a AAV11 capsid. |
| 1 | AAVC11.01 | | PRKN | 5071 | Payload comprising a PRKN gene or variant thereof packaged within a AAVC11.01 capsid. |
| 1 | AAVC11.02 | | PRKN | 5071 | Payload comprising a PRKN gene or variant thereof packaged within a AAVC11.02 capsid. |
| 1 | AAVC11.03 | | PRKN | 5071 | Payload comprising a PRKN gene or variant thereof packaged within a AAVC11.03 capsid. |
| 1 | AAVC11.04 | | PRKN | 5071 | Payload comprising a PRKN gene or variant thereof packaged within a AAVC11.04 capsid. |
| 1 | AAVC11.05 | | PRKN | 5071 | Payload comprising a PRKN gene or variant thereof packaged within a AAVC11.05 capsid. |
| 1 | AAVC11.06 | | PRKN | 5071 | Payload comprising a PRKN gene or variant thereof packaged within a AAVC11.06 capsid. |
| 1 | AAVC11.07 | | PRKN | 5071 | Payload comprising a PRKN gene or variant thereof packaged within a AAVC11.07 capsid. |
| 1 | AAVC11.08 | | PRKN | 5071 | Payload comprising a PRKN gene or variant thereof packaged within a AAVC11.08 capsid. |
| 1 | AAVC11.09 | | PRKN | 5071 | Payload comprising a PRKN gene or variant thereof packaged within a AAVC11.09 capsid. |
| 1 | AAVC11.10 | | PRKN | 5071 | Payload comprising a PRKN gene or variant thereof packaged within a AAVC11.10 capsid. |
| 1 | AAVC11.11 | | PRKN | 5071 | Payload comprising a PRKN gene or variant thereof packaged within a AAVC11.11 capsid. |
| 1 | AAVC11.12 | | PRKN | 5071 | Payload comprising a PRKN gene or variant thereof packaged within a AAVC11.12 capsid. |
| 1 | AAVC11.13 | | PRKN | 5071 | Payload comprising a PRKN gene or variant thereof packaged within a AAVC11.13 capsid. |
| 1 | AAVC11.14 | | PRKN | 5071 | Payload comprising a PRKN gene or variant thereof packaged within a AAVC11.14 capsid. |
| 1 | AAVC11.15 | | PRKN | 5071 | Payload comprising a PRKN gene or variant thereof packaged within a AAVC11.15 capsid. |

Fig. 29 (Continued)

| | | | | | |
|---|---|---|---|---|---|
| 1 | AAVC11.16 | | PRKN | 5071 | Payload comprising a PRKN gene or variant thereof packaged within a AAVC11.16 capsid. |
| 1 | AAVC11.17 | | PRKN | 5071 | Payload comprising a PRKN gene or variant thereof packaged within a AAVC11.17 capsid. |
| 1 | AAVC11.18 | | PRKN | 5071 | Payload comprising a PRKN gene or variant thereof packaged within a AAVC11.18 capsid. |
| 1 | AAVC11.19 | | PRKN | 5071 | Payload comprising a PRKN gene or variant thereof packaged within a AAVC11.19 capsid. |
| 1 | AAV12 | | PRKN | 5071 | Payload comprising a PRKN gene or variant thereof packaged within a AAV12 capsid. |
| 1 | AAV13 | | PRKN | 5071 | Payload comprising a PRKN gene or variant thereof packaged within a AAV13 capsid. |
| 1 | AAV-DJ | | PRKN | 5071 | Payload comprising a PRKN gene or variant thereof packaged within a AAV-DJ capsid. |
| 1 | AAV-LK03 | | PRKN | 5071 | Payload comprising a PRKN gene or variant thereof packaged within a AAV-LK03 capsid. |
| 1 | AAV-LK19 | | PRKN | 5071 | Payload comprising a PRKN gene or variant thereof packaged within a AAV-LK19 capsid. |
| 1 | AAVrh.74 | | PRKN | 5071 | Payload comprising a PRKN gene or variant thereof packaged within a AAVrh.74 capsid. |
| 1 | AAVrh.10 | | PRKN | 5071 | Payload comprising a PRKN gene or variant thereof packaged within a AAVrh.10 capsid. |
| 1 | AAVhu.37 | | PRKN | 5071 | Payload comprising a PRKN gene or variant thereof packaged within a AAVhu.37 capsid. |
| 1 | AAVrh.K | | PRKN | 5071 | Payload comprising a PRKN gene or variant thereof packaged within a AAVrh.K capsid. |
| 1 | AAVrh.39 | | PRKN | 5071 | Payload comprising a PRKN gene or variant thereof packaged within a AAVrh.39 capsid. |
| 1 | AAVrh.9 | | PRKN | 5071 | Payload comprising a PRKN gene or variant thereof packaged within a AAVrh.9 capsid. |
| 1 | avian AAV | | PRKN | 5071 | Payload comprising a PRKN gene or variant thereof packaged within a avian capsid. |

Fig. 29 (Continued)

| | | | | | |
|---|---|---|---|---|---|
| 1 | bovine AAV | | PRKN | 5071 | Payload comprising a PRKN gene or variant thereof packaged within a bovine capsid. |
| 1 | canine AAV | | PRKN | 5071 | Payload comprising a PRKN gene or variant thereof packaged within a canine capsid. |
| 1 | equine AAV | | PRKN | 5071 | Payload comprising a PRKN gene or variant thereof packaged within a equine capsid. |
| 1 | primate AAV | | PRKN | 5071 | Payload comprising a PRKN gene or variant thereof packaged within a primate capsid. |
| 1 | non-primate AAV | | PRKN | 5071 | Payload comprising a PRKN gene or variant thereof packaged within a non-primate capsid. |
| 1 | ovine AAV | | PRKN | 5071 | Payload comprising a PRKN gene or variant thereof packaged within a ovine capsid. |
| 1 | hybrid AAV | | PRKN | 5071 | Payload comprising a PRKN gene or variant thereof packaged within a hybrid capsid. |
| 1 | chimeric AAV | | PRKN | 5071 | Payload comprising a PRKN gene or variant thereof packaged within a chimeric capsid. |
| 2 | AAV1 | 1450374 | PRKN | 5071 | Payload comprising a PRKN gene or variant thereof packaged within a AAV1 capsid. |
| 2 | AAV2 | | PRKN | 5071 | Payload comprising a PRKN gene or variant thereof packaged within a AAV2 capsid. |
| 2 | AAV3 | | PRKN | 5071 | Payload comprising a PRKN gene or variant thereof packaged within a AAV3 capsid. |
| 2 | AAV4 | 1446389 | PRKN | 5071 | Payload comprising a PRKN gene or variant thereof packaged within a AAV4 capsid. |
| 2 | AAV5 | | PRKN | 5071 | Payload comprising a PRKN gene or variant thereof packaged within a AAV5 capsid. |
| 2 | AAV6 | | PRKN | 5071 | Payload comprising a PRKN gene or variant thereof packaged within a AAV6 capsid. |
| 2 | AAV7 | | PRKN | 5071 | Payload comprising a PRKN gene or variant thereof packaged within a AAV7 capsid. |
| 2 | AAV8 | 5075992 | PRKN | 5071 | Payload comprising a PRKN gene or variant thereof packaged within a AAV8 capsid. |
| 2 | AAV9 | | PRKN | 5071 | Payload comprising a PRKN gene or variant thereof packaged within a AAV9 capsid. |

Fig. 29 (Continued)

| | | | | | |
|---|---|---|---|---|---|
| 2 | AAV10 | | PRKN | 5071 | Payload comprising a PRKN gene or variant thereof packaged within a AAV10 capsid. |
| 2 | AAV11 | | PRKN | 5071 | Payload comprising a PRKN gene or variant thereof packaged within a AAV11 capsid. |
| 2 | AAVC11.01 | | PRKN | 5071 | Payload comprising a PRKN gene or variant thereof packaged within a AAVC11.01 capsid. |
| 2 | AAVC11.02 | | PRKN | 5071 | Payload comprising a PRKN gene or variant thereof packaged within a AAVC11.02 capsid. |
| 2 | AAVC11.03 | | PRKN | 5071 | Payload comprising a PRKN gene or variant thereof packaged within a AAVC11.03 capsid. |
| 2 | AAVC11.04 | | PRKN | 5071 | Payload comprising a PRKN gene or variant thereof packaged within a AAVC11.04 capsid. |
| 2 | AAVC11.05 | | PRKN | 5071 | Payload comprising a PRKN gene or variant thereof packaged within a AAVC11.05 capsid. |
| 2 | AAVC11.06 | | PRKN | 5071 | Payload comprising a PRKN gene or variant thereof packaged within a AAVC11.06 capsid. |
| 2 | AAVC11.07 | | PRKN | 5071 | Payload comprising a PRKN gene or variant thereof packaged within a AAVC11.07 capsid. |
| 2 | AAVC11.08 | | PRKN | 5071 | Payload comprising a PRKN gene or variant thereof packaged within a AAVC11.08 capsid. |
| 2 | AAVC11.09 | | PRKN | 5071 | Payload comprising a PRKN gene or variant thereof packaged within a AAVC11.09 capsid. |
| 2 | AAVC11.10 | | PRKN | 5071 | Payload comprising a PRKN gene or variant thereof packaged within a AAVC11.10 capsid. |
| 2 | AAVC11.11 | | PRKN | 5071 | Payload comprising a PRKN gene or variant thereof packaged within a AAVC11.11 capsid. |
| 2 | AAVC11.12 | | PRKN | 5071 | Payload comprising a PRKN gene or variant thereof packaged within a AAVC11.12 capsid. |
| 2 | AAVC11.13 | | PRKN | 5071 | Payload comprising a PRKN gene or variant thereof packaged within a AAVC11.13 capsid. |
| 2 | AAVC11.14 | | PRKN | 5071 | Payload comprising a PRKN gene or variant thereof packaged within a AAVC11.14 capsid. |
| 2 | AAVC11.15 | | PRKN | 5071 | Payload comprising a PRKN gene or variant thereof packaged within a AAVC11.15 capsid. |

Fig. 29 (Continued)

| | | | | | |
|---|---|---|---|---|---|
| 2 | AAVC11.16 | | PRKN | 5071 | Payload comprising a PRKN gene or variant thereof packaged within a AAVC11.16 capsid. |
| 2 | AAVC11.17 | | PRKN | 5071 | Payload comprising a PRKN gene or variant thereof packaged within a AAVC11.17 capsid. |
| 2 | AAVC11.18 | | PRKN | 5071 | Payload comprising a PRKN gene or variant thereof packaged within a AAVC11.18 capsid. |
| 2 | AAVC11.19 | | PRKN | 5071 | Payload comprising a PRKN gene or variant thereof packaged within a AAVC11.19 capsid. |
| 2 | AAV12 | | PRKN | 5071 | Payload comprising a PRKN gene or variant thereof packaged within a AAV12 capsid. |
| 2 | AAV13 | | PRKN | 5071 | Payload comprising a PRKN gene or variant thereof packaged within a AAV13 capsid. |
| 2 | AAV-DJ | | PRKN | 5071 | Payload comprising a PRKN gene or variant thereof packaged within a AAV-DJ capsid. |
| 2 | AAV-LK03 | | PRKN | 5071 | Payload comprising a PRKN gene or variant thereof packaged within a AAV-LK03 capsid. |
| 2 | AAV-LK19 | | PRKN | 5071 | Payload comprising a PRKN gene or variant thereof packaged within a AAV-LK19 capsid. |
| 2 | AAVrh.74 | | PRKN | 5071 | Payload comprising a PRKN gene or variant thereof packaged within a AAVrh.74 capsid. |
| 2 | AAVrh.10 | | PRKN | 5071 | Payload comprising a PRKN gene or variant thereof packaged within a AAVrh.10 capsid. |
| 2 | AAVhu.37 | | PRKN | 5071 | Payload comprising a PRKN gene or variant thereof packaged within a AAVhu.37 capsid. |
| 2 | AAVrh.K | | PRKN | 5071 | Payload comprising a PRKN gene or variant thereof packaged within a AAVrh.K capsid. |
| 2 | AAVrh.39 | | PRKN | 5071 | Payload comprising a PRKN gene or variant thereof packaged within a AAVrh.39 capsid. |
| 2 | AAVrh.9 | | PRKN | 5071 | Payload comprising a PRKN gene or variant thereof packaged within a AAVrh.9 capsid. |
| 2 | avian AAV | | PRKN | 5071 | Payload comprising a PRKN gene or variant thereof packaged within a avian capsid. |

Fig. 29 (Continued)

| | | | | | |
|---|---|---|---|---|---|
| 2 | bovine AAV | | PRKN | 5071 | Payload comprising a PRKN gene or variant thereof packaged within a bovine capsid. |
| 2 | canine AAV | | PRKN | 5071 | Payload comprising a PRKN gene or variant thereof packaged within a canine capsid. |
| 2 | equine AAV | | PRKN | 5071 | Payload comprising a PRKN gene or variant thereof packaged within a equine capsid. |
| 2 | primate AAV | | PRKN | 5071 | Payload comprising a PRKN gene or variant thereof packaged within a primate capsid. |
| 2 | non-primate AAV | | PRKN | 5071 | Payload comprising a PRKN gene or variant thereof packaged within a non-primate capsid. |
| 2 | ovine AAV | | PRKN | 5071 | Payload comprising a PRKN gene or variant thereof packaged within a ovine capsid. |
| 2 | hybrid AAV | | PRKN | 5071 | Payload comprising a PRKN gene or variant thereof packaged within a hybrid capsid. |
| 2 | chimeric AAV | | PRKN | 5071 | Payload comprising a PRKN gene or variant thereof packaged within a chimeric capsid. |
| 1 | AAV1 | 1450374 | SCN1A | 6323 | Payload comprising a SCN1A gene or variant thereof packaged within a AAV1 capsid. |
| 1 | AAV2 | | SCN1A | 6323 | Payload comprising a SCN1A gene or variant thereof packaged within a AAV2 capsid. |
| 1 | AAV3 | | SCN1A | 6323 | Payload comprising a SCN1A gene or variant thereof packaged within a AAV3 capsid. |
| 1 | AAV4 | 1446389 | SCN1A | 6323 | Payload comprising a SCN1A gene or variant thereof packaged within a AAV4 capsid. |
| 1 | AAV5 | | SCN1A | 6323 | Payload comprising a SCN1A gene or variant thereof packaged within a AAV5 capsid. |
| 1 | AAV6 | | SCN1A | 6323 | Payload comprising a SCN1A gene or variant thereof packaged within a AAV6 capsid. |
| 1 | AAV7 | | SCN1A | 6323 | Payload comprising a SCN1A gene or variant thereof packaged within a AAV7 capsid. |
| 1 | AAV8 | 5075992 | SCN1A | 6323 | Payload comprising a SCN1A gene or variant thereof packaged within a AAV8 capsid. |
| 1 | AAV9 | | SCN1A | 6323 | Payload comprising a SCN1A gene or variant thereof packaged within a AAV9 capsid. |

Fig. 29 (Continued)

| | | | | | |
|---|---|---|---|---|---|
| 1 | AAV10 | | SCN1A | 6323 | Payload comprising a SCN1A gene or variant thereof packaged within a AAV10 capsid. |
| 1 | AAV11 | | SCN1A | 6323 | Payload comprising a SCN1A gene or variant thereof packaged within a AAV11 capsid. |
| 1 | AAVC11.01 | | SCN1A | 6323 | Payload comprising a SCN1A gene or variant thereof packaged within a AAVC11.01 capsid. |
| 1 | AAVC11.02 | | SCN1A | 6323 | Payload comprising a SCN1A gene or variant thereof packaged within a AAVC11.02 capsid. |
| 1 | AAVC11.03 | | SCN1A | 6323 | Payload comprising a SCN1A gene or variant thereof packaged within a AAVC11.03 capsid. |
| 1 | AAVC11.04 | | SCN1A | 6323 | Payload comprising a SCN1A gene or variant thereof packaged within a AAVC11.04 capsid. |
| 1 | AAVC11.05 | | SCN1A | 6323 | Payload comprising a SCN1A gene or variant thereof packaged within a AAVC11.05 capsid. |
| 1 | AAVC11.06 | | SCN1A | 6323 | Payload comprising a SCN1A gene or variant thereof packaged within a AAVC11.06 capsid. |
| 1 | AAVC11.07 | | SCN1A | 6323 | Payload comprising a SCN1A gene or variant thereof packaged within a AAVC11.07 capsid. |
| 1 | AAVC11.08 | | SCN1A | 6323 | Payload comprising a SCN1A gene or variant thereof packaged within a AAVC11.08 capsid. |
| 1 | AAVC11.09 | | SCN1A | 6323 | Payload comprising a SCN1A gene or variant thereof packaged within a AAVC11.09 capsid. |
| 1 | AAVC11.10 | | SCN1A | 6323 | Payload comprising a SCN1A gene or variant thereof packaged within a AAVC11.10 capsid. |
| 1 | AAVC11.11 | | SCN1A | 6323 | Payload comprising a SCN1A gene or variant thereof packaged within a AAVC11.11 capsid. |
| 1 | AAVC11.12 | | SCN1A | 6323 | Payload comprising a SCN1A gene or variant thereof packaged within a AAVC11.12 capsid. |
| 1 | AAVC11.13 | | SCN1A | 6323 | Payload comprising a SCN1A gene or variant thereof packaged within a AAVC11.13 capsid. |
| 1 | AAVC11.14 | | SCN1A | 6323 | Payload comprising a SCN1A gene or variant thereof packaged within a AAVC11.14 capsid. |
| 1 | AAVC11.15 | | SCN1A | 6323 | Payload comprising a SCN1A gene or variant thereof packaged within a AAVC11.15 capsid. |

Fig. 29 (Continued)

| | | | | | |
|---|---|---|---|---|---|
| 1 | AAVC11.16 | | SCN1A | 6323 | Payload comprising a SCN1A gene or variant thereof packaged within a AAVC11.16 capsid. |
| 1 | AAVC11.17 | | SCN1A | 6323 | Payload comprising a SCN1A gene or variant thereof packaged within a AAVC11.17 capsid. |
| 1 | AAVC11.18 | | SCN1A | 6323 | Payload comprising a SCN1A gene or variant thereof packaged within a AAVC11.18 capsid. |
| 1 | AAVC11.19 | | SCN1A | 6323 | Payload comprising a SCN1A gene or variant thereof packaged within a AAVC11.19 capsid. |
| 1 | AAV12 | | SCN1A | 6323 | Payload comprising a SCN1A gene or variant thereof packaged within a AAV12 capsid. |
| 1 | AAV13 | | SCN1A | 6323 | Payload comprising a SCN1A gene or variant thereof packaged within a AAV13 capsid. |
| 1 | AAV-DJ | | SCN1A | 6323 | Payload comprising a SCN1A gene or variant thereof packaged within a AAV-DJ capsid. |
| 1 | AAV-LK03 | | SCN1A | 6323 | Payload comprising a SCN1A gene or variant thereof packaged within a AAV-LK03 capsid. |
| 1 | AAV-LK19 | | SCN1A | 6323 | Payload comprising a SCN1A gene or variant thereof packaged within a AAV-LK19 capsid. |
| 1 | AAVrh.74 | | SCN1A | 6323 | Payload comprising a SCN1A gene or variant thereof packaged within a AAVrh.74 capsid. |
| 1 | AAVrh.10 | | SCN1A | 6323 | Payload comprising a SCN1A gene or variant thereof packaged within a AAVrh.10 capsid. |
| 1 | AAVhu.37 | | SCN1A | 6323 | Payload comprising a SCN1A gene or variant thereof packaged within a AAVhu.37 capsid. |
| 1 | AAVrh.K | | SCN1A | 6323 | Payload comprising a SCN1A gene or variant thereof packaged within a AAVrh.K capsid. |
| 1 | AAVrh.39 | | SCN1A | 6323 | Payload comprising a SCN1A gene or variant thereof packaged within a AAVrh.39 capsid. |
| 1 | AAVrh.9 | | SCN1A | 6323 | Payload comprising a SCN1A gene or variant thereof packaged within a AAVrh.9 capsid. |
| 1 | avian AAV | | SCN1A | 6323 | Payload comprising a SCN1A gene or variant thereof packaged within a avian capsid. |

Fig. 29 (Continued)

| | | | | | |
|---|---|---|---|---|---|
| 1 | bovine AAV | | SCN1A | 6323 | Payload comprising a SCN1A gene or variant thereof packaged within a bovine capsid. |
| 1 | canine AAV | | SCN1A | 6323 | Payload comprising a SCN1A gene or variant thereof packaged within a canine capsid. |
| 1 | equine AAV | | SCN1A | 6323 | Payload comprising a SCN1A gene or variant thereof packaged within a equine capsid. |
| 1 | primate AAV | | SCN1A | 6323 | Payload comprising a SCN1A gene or variant thereof packaged within a primate capsid. |
| 1 | non-primate AAV | | SCN1A | 6323 | Payload comprising a SCN1A gene or variant thereof packaged within a non-primate capsid. |
| 1 | ovine AAV | | SCN1A | 6323 | Payload comprising a SCN1A gene or variant thereof packaged within a ovine capsid. |
| 1 | hybrid AAV | | SCN1A | 6323 | Payload comprising a SCN1A gene or variant thereof packaged within a hybrid capsid. |
| 1 | chimeric AAV | | SCN1A | 6323 | Payload comprising a SCN1A gene or variant thereof packaged within a chimeric capsid. |
| 2 | AAV1 | 1450374 | SCN1A | 6323 | Payload comprising a SCN1A gene or variant thereof packaged within a AAV1 capsid. |
| 2 | AAV2 | | SCN1A | 6323 | Payload comprising a SCN1A gene or variant thereof packaged within a AAV2 capsid. |
| 2 | AAV3 | | SCN1A | 6323 | Payload comprising a SCN1A gene or variant thereof packaged within a AAV3 capsid. |
| 2 | AAV4 | 1446389 | SCN1A | 6323 | Payload comprising a SCN1A gene or variant thereof packaged within a AAV4 capsid. |
| 2 | AAV5 | | SCN1A | 6323 | Payload comprising a SCN1A gene or variant thereof packaged within a AAV5 capsid. |
| 2 | AAV6 | | SCN1A | 6323 | Payload comprising a SCN1A gene or variant thereof packaged within a AAV6 capsid. |
| 2 | AAV7 | | SCN1A | 6323 | Payload comprising a SCN1A gene or variant thereof packaged within a AAV7 capsid. |
| 2 | AAV8 | 5075992 | SCN1A | 6323 | Payload comprising a SCN1A gene or variant thereof packaged within a AAV8 capsid. |
| 2 | AAV9 | | SCN1A | 6323 | Payload comprising a SCN1A gene or variant thereof packaged within a AAV9 capsid. |

Fig. 29 (Continued)

| | | | | | |
|---|---|---|---|---|---|
| 2 | AAV10 | | SCN1A | 6323 | Payload comprising a SCN1A gene or variant thereof packaged within a AAV10 capsid. |
| 2 | AAV11 | | SCN1A | 6323 | Payload comprising a SCN1A gene or variant thereof packaged within a AAV11 capsid. |
| 2 | AAVC11.01 | | SCN1A | 6323 | Payload comprising a SCN1A gene or variant thereof packaged within a AAVC11.01 capsid. |
| 2 | AAVC11.02 | | SCN1A | 6323 | Payload comprising a SCN1A gene or variant thereof packaged within a AAVC11.02 capsid. |
| 2 | AAVC11.03 | | SCN1A | 6323 | Payload comprising a SCN1A gene or variant thereof packaged within a AAVC11.03 capsid. |
| 2 | AAVC11.04 | | SCN1A | 6323 | Payload comprising a SCN1A gene or variant thereof packaged within a AAVC11.04 capsid. |
| 2 | AAVC11.05 | | SCN1A | 6323 | Payload comprising a SCN1A gene or variant thereof packaged within a AAVC11.05 capsid. |
| 2 | AAVC11.06 | | SCN1A | 6323 | Payload comprising a SCN1A gene or variant thereof packaged within a AAVC11.06 capsid. |
| 2 | AAVC11.07 | | SCN1A | 6323 | Payload comprising a SCN1A gene or variant thereof packaged within a AAVC11.07 capsid. |
| 2 | AAVC11.08 | | SCN1A | 6323 | Payload comprising a SCN1A gene or variant thereof packaged within a AAVC11.08 capsid. |
| 2 | AAVC11.09 | | SCN1A | 6323 | Payload comprising a SCN1A gene or variant thereof packaged within a AAVC11.09 capsid. |
| 2 | AAVC11.10 | | SCN1A | 6323 | Payload comprising a SCN1A gene or variant thereof packaged within a AAVC11.10 capsid. |
| 2 | AAVC11.11 | | SCN1A | 6323 | Payload comprising a SCN1A gene or variant thereof packaged within a AAVC11.11 capsid. |
| 2 | AAVC11.12 | | SCN1A | 6323 | Payload comprising a SCN1A gene or variant thereof packaged within a AAVC11.12 capsid. |
| 2 | AAVC11.13 | | SCN1A | 6323 | Payload comprising a SCN1A gene or variant thereof packaged within a AAVC11.13 capsid. |
| 2 | AAVC11.14 | | SCN1A | 6323 | Payload comprising a SCN1A gene or variant thereof packaged within a AAVC11.14 capsid. |
| 2 | AAVC11.15 | | SCN1A | 6323 | Payload comprising a SCN1A gene or variant thereof packaged within a AAVC11.15 capsid. |

Fig. 29 (Continued)

| | | | | | |
|---|---|---|---|---|---|
| 2 | AAVC11.16 | | SCN1A | 6323 | Payload comprising a SCN1A gene or variant thereof packaged within a AAVC11.16 capsid. |
| 2 | AAVC11.17 | | SCN1A | 6323 | Payload comprising a SCN1A gene or variant thereof packaged within a AAVC11.17 capsid. |
| 2 | AAVC11.18 | | SCN1A | 6323 | Payload comprising a SCN1A gene or variant thereof packaged within a AAVC11.18 capsid. |
| 2 | AAVC11.19 | | SCN1A | 6323 | Payload comprising a SCN1A gene or variant thereof packaged within a AAVC11.19 capsid. |
| 2 | AAV12 | | SCN1A | 6323 | Payload comprising a SCN1A gene or variant thereof packaged within a AAV12 capsid. |
| 2 | AAV13 | | SCN1A | 6323 | Payload comprising a SCN1A gene or variant thereof packaged within a AAV13 capsid. |
| 2 | AAV-DJ | | SCN1A | 6323 | Payload comprising a SCN1A gene or variant thereof packaged within a AAV-DJ capsid. |
| 2 | AAV-LK03 | | SCN1A | 6323 | Payload comprising a SCN1A gene or variant thereof packaged within a AAV-LK03 capsid. |
| 2 | AAV-LK19 | | SCN1A | 6323 | Payload comprising a SCN1A gene or variant thereof packaged within a AAV-LK19 capsid. |
| 2 | AAVrh.74 | | SCN1A | 6323 | Payload comprising a SCN1A gene or variant thereof packaged within a AAVrh.74 capsid. |
| 2 | AAVrh.10 | | SCN1A | 6323 | Payload comprising a SCN1A gene or variant thereof packaged within a AAVrh.10 capsid. |
| 2 | AAVhu.37 | | SCN1A | 6323 | Payload comprising a SCN1A gene or variant thereof packaged within a AAVhu.37 capsid. |
| 2 | AAVrh.K | | SCN1A | 6323 | Payload comprising a SCN1A gene or variant thereof packaged within a AAVrh.K capsid. |
| 2 | AAVrh.39 | | SCN1A | 6323 | Payload comprising a SCN1A gene or variant thereof packaged within a AAVrh.39 capsid. |
| 2 | AAVrh.9 | | SCN1A | 6323 | Payload comprising a SCN1A gene or variant thereof packaged within a AAVrh.9 capsid. |
| 2 | avian AAV | | SCN1A | 6323 | Payload comprising a SCN1A gene or variant thereof packaged within a avian capsid. |

Fig. 29 (Continued)

| | | | | | |
|---|---|---|---|---|---|
| 2 | bovine AAV | | SCN1A | 6323 | Payload comprising a SCN1A gene or variant thereof packaged within a bovine capsid. |
| 2 | canine AAV | | SCN1A | 6323 | Payload comprising a SCN1A gene or variant thereof packaged within a canine capsid. |
| 2 | equine AAV | | SCN1A | 6323 | Payload comprising a SCN1A gene or variant thereof packaged within a equine capsid. |
| 2 | primate AAV | | SCN1A | 6323 | Payload comprising a SCN1A gene or variant thereof packaged within a primate capsid. |
| 2 | non-primate AAV | | SCN1A | 6323 | Payload comprising a SCN1A gene or variant thereof packaged within a non-primate capsid. |
| 2 | ovine AAV | | SCN1A | 6323 | Payload comprising a SCN1A gene or variant thereof packaged within a ovine capsid. |
| 2 | hybrid AAV | | SCN1A | 6323 | Payload comprising a SCN1A gene or variant thereof packaged within a hybrid capsid. |
| 2 | chimeric AAV | | SCN1A | 6323 | Payload comprising a SCN1A gene or variant thereof packaged within a chimeric capsid. |
| 1 | AAV1 | 1450374 | SCN1B | 6324 | Payload comprising a SCN1B gene or variant thereof packaged within a AAV1 capsid. |
| 1 | AAV2 | | SCN1B | 6324 | Payload comprising a SCN1B gene or variant thereof packaged within a AAV2 capsid. |
| 1 | AAV3 | | SCN1B | 6324 | Payload comprising a SCN1B gene or variant thereof packaged within a AAV3 capsid. |
| 1 | AAV4 | 1446389 | SCN1B | 6324 | Payload comprising a SCN1B gene or variant thereof packaged within a AAV4 capsid. |
| 1 | AAV5 | | SCN1B | 6324 | Payload comprising a SCN1B gene or variant thereof packaged within a AAV5 capsid. |
| 1 | AAV6 | | SCN1B | 6324 | Payload comprising a SCN1B gene or variant thereof packaged within a AAV6 capsid. |
| 1 | AAV7 | | SCN1B | 6324 | Payload comprising a SCN1B gene or variant thereof packaged within a AAV7 capsid. |
| 1 | AAV8 | 5075992 | SCN1B | 6324 | Payload comprising a SCN1B gene or variant thereof packaged within a AAV8 capsid. |
| 1 | AAV9 | | SCN1B | 6324 | Payload comprising a SCN1B gene or variant thereof packaged within a AAV9 capsid. |

Fig. 29 (Continued)

| | | | | | |
|---|---|---|---|---|---|
| 1 | AAV10 | | SCN1B | 6324 | Payload comprising a SCN1B gene or variant thereof packaged within a AAV10 capsid. |
| 1 | AAV11 | | SCN1B | 6324 | Payload comprising a SCN1B gene or variant thereof packaged within a AAV11 capsid. |
| 1 | AAVC11.01 | | SCN1B | 6324 | Payload comprising a SCN1B gene or variant thereof packaged within a AAVC11.01 capsid. |
| 1 | AAVC11.02 | | SCN1B | 6324 | Payload comprising a SCN1B gene or variant thereof packaged within a AAVC11.02 capsid. |
| 1 | AAVC11.03 | | SCN1B | 6324 | Payload comprising a SCN1B gene or variant thereof packaged within a AAVC11.03 capsid. |
| 1 | AAVC11.04 | | SCN1B | 6324 | Payload comprising a SCN1B gene or variant thereof packaged within a AAVC11.04 capsid. |
| 1 | AAVC11.05 | | SCN1B | 6324 | Payload comprising a SCN1B gene or variant thereof packaged within a AAVC11.05 capsid. |
| 1 | AAVC11.06 | | SCN1B | 6324 | Payload comprising a SCN1B gene or variant thereof packaged within a AAVC11.06 capsid. |
| 1 | AAVC11.07 | | SCN1B | 6324 | Payload comprising a SCN1B gene or variant thereof packaged within a AAVC11.07 capsid. |
| 1 | AAVC11.08 | | SCN1B | 6324 | Payload comprising a SCN1B gene or variant thereof packaged within a AAVC11.08 capsid. |
| 1 | AAVC11.09 | | SCN1B | 6324 | Payload comprising a SCN1B gene or variant thereof packaged within a AAVC11.09 capsid. |
| 1 | AAVC11.10 | | SCN1B | 6324 | Payload comprising a SCN1B gene or variant thereof packaged within a AAVC11.10 capsid. |
| 1 | AAVC11.11 | | SCN1B | 6324 | Payload comprising a SCN1B gene or variant thereof packaged within a AAVC11.11 capsid. |
| 1 | AAVC11.12 | | SCN1B | 6324 | Payload comprising a SCN1B gene or variant thereof packaged within a AAVC11.12 capsid. |
| 1 | AAVC11.13 | | SCN1B | 6324 | Payload comprising a SCN1B gene or variant thereof packaged within a AAVC11.13 capsid. |
| 1 | AAVC11.14 | | SCN1B | 6324 | Payload comprising a SCN1B gene or variant thereof packaged within a AAVC11.14 capsid. |
| 1 | AAVC11.15 | | SCN1B | 6324 | Payload comprising a SCN1B gene or variant thereof packaged within a AAVC11.15 capsid. |

Fig. 29 (Continued)

| | | | | | |
|---|---|---|---|---|---|
| 1 | AAVC11.16 | | SCN1B | 6324 | Payload comprising a SCN1B gene or variant thereof packaged within a AAVC11.16 capsid. |
| 1 | AAVC11.17 | | SCN1B | 6324 | Payload comprising a SCN1B gene or variant thereof packaged within a AAVC11.17 capsid. |
| 1 | AAVC11.18 | | SCN1B | 6324 | Payload comprising a SCN1B gene or variant thereof packaged within a AAVC11.18 capsid. |
| 1 | AAVC11.19 | | SCN1B | 6324 | Payload comprising a SCN1B gene or variant thereof packaged within a AAVC11.19 capsid. |
| 1 | AAV12 | | SCN1B | 6324 | Payload comprising a SCN1B gene or variant thereof packaged within a AAV12 capsid. |
| 1 | AAV13 | | SCN1B | 6324 | Payload comprising a SCN1B gene or variant thereof packaged within a AAV13 capsid. |
| 1 | AAV-DJ | | SCN1B | 6324 | Payload comprising a SCN1B gene or variant thereof packaged within a AAV-DJ capsid. |
| 1 | AAV-LK03 | | SCN1B | 6324 | Payload comprising a SCN1B gene or variant thereof packaged within a AAV-LK03 capsid. |
| 1 | AAV-LK19 | | SCN1B | 6324 | Payload comprising a SCN1B gene or variant thereof packaged within a AAV-LK19 capsid. |
| 1 | AAVrh.74 | | SCN1B | 6324 | Payload comprising a SCN1B gene or variant thereof packaged within a AAVrh.74 capsid. |
| 1 | AAVrh.10 | | SCN1B | 6324 | Payload comprising a SCN1B gene or variant thereof packaged within a AAVrh.10 capsid. |
| 1 | AAVhu.37 | | SCN1B | 6324 | Payload comprising a SCN1B gene or variant thereof packaged within a AAVhu.37 capsid. |
| 1 | AAVrh.K | | SCN1B | 6324 | Payload comprising a SCN1B gene or variant thereof packaged within a AAVrh.K capsid. |
| 1 | AAVrh.39 | | SCN1B | 6324 | Payload comprising a SCN1B gene or variant thereof packaged within a AAVrh.39 capsid. |
| 1 | AAVrh.9 | | SCN1B | 6324 | Payload comprising a SCN1B gene or variant thereof packaged within a AAVrh.9 capsid. |
| 1 | avian AAV | | SCN1B | 6324 | Payload comprising a SCN1B gene or variant thereof packaged within a avian capsid. |

Fig. 29 (Continued)

| | | | | | |
|---|---|---|---|---|---|
| 1 | bovine AAV | | SCN1B | 6324 | Payload comprising a SCN1B gene or variant thereof packaged within a bovine capsid. |
| 1 | canine AAV | | SCN1B | 6324 | Payload comprising a SCN1B gene or variant thereof packaged within a canine capsid. |
| 1 | equine AAV | | SCN1B | 6324 | Payload comprising a SCN1B gene or variant thereof packaged within a equine capsid. |
| 1 | primate AAV | | SCN1B | 6324 | Payload comprising a SCN1B gene or variant thereof packaged within a primate capsid. |
| 1 | non-primate AAV | | SCN1B | 6324 | Payload comprising a SCN1B gene or variant thereof packaged within a non-primate capsid. |
| 1 | ovine AAV | | SCN1B | 6324 | Payload comprising a SCN1B gene or variant thereof packaged within a ovine capsid. |
| 1 | hybrid AAV | | SCN1B | 6324 | Payload comprising a SCN1B gene or variant thereof packaged within a hybrid capsid. |
| 1 | chimeric AAV | | SCN1B | 6324 | Payload comprising a SCN1B gene or variant thereof packaged within a chimeric capsid. |
| 2 | AAV1 | 1450374 | SCN1B | 6324 | Payload comprising a SCN1B gene or variant thereof packaged within a AAV1 capsid. |
| 2 | AAV2 | | SCN1B | 6324 | Payload comprising a SCN1B gene or variant thereof packaged within a AAV2 capsid. |
| 2 | AAV3 | | SCN1B | 6324 | Payload comprising a SCN1B gene or variant thereof packaged within a AAV3 capsid. |
| 2 | AAV4 | 1446389 | SCN1B | 6324 | Payload comprising a SCN1B gene or variant thereof packaged within a AAV4 capsid. |
| 2 | AAV5 | | SCN1B | 6324 | Payload comprising a SCN1B gene or variant thereof packaged within a AAV5 capsid. |
| 2 | AAV6 | | SCN1B | 6324 | Payload comprising a SCN1B gene or variant thereof packaged within a AAV6 capsid. |
| 2 | AAV7 | | SCN1B | 6324 | Payload comprising a SCN1B gene or variant thereof packaged within a AAV7 capsid. |
| 2 | AAV8 | 5075992 | SCN1B | 6324 | Payload comprising a SCN1B gene or variant thereof packaged within a AAV8 capsid. |
| 2 | AAV9 | | SCN1B | 6324 | Payload comprising a SCN1B gene or variant thereof packaged within a AAV9 capsid. |

Fig. 29 (Continued)

| | | | | | |
|---|---|---|---|---|---|
| 2 | AAV10 | | SCN1B | 6324 | Payload comprising a SCN1B gene or variant thereof packaged within a AAV10 capsid. |
| 2 | AAV11 | | SCN1B | 6324 | Payload comprising a SCN1B gene or variant thereof packaged within a AAV11 capsid. |
| 2 | AAVC11.01 | | SCN1B | 6324 | Payload comprising a SCN1B gene or variant thereof packaged within a AAVC11.01 capsid. |
| 2 | AAVC11.02 | | SCN1B | 6324 | Payload comprising a SCN1B gene or variant thereof packaged within a AAVC11.02 capsid. |
| 2 | AAVC11.03 | | SCN1B | 6324 | Payload comprising a SCN1B gene or variant thereof packaged within a AAVC11.03 capsid. |
| 2 | AAVC11.04 | | SCN1B | 6324 | Payload comprising a SCN1B gene or variant thereof packaged within a AAVC11.04 capsid. |
| 2 | AAVC11.05 | | SCN1B | 6324 | Payload comprising a SCN1B gene or variant thereof packaged within a AAVC11.05 capsid. |
| 2 | AAVC11.06 | | SCN1B | 6324 | Payload comprising a SCN1B gene or variant thereof packaged within a AAVC11.06 capsid. |
| 2 | AAVC11.07 | | SCN1B | 6324 | Payload comprising a SCN1B gene or variant thereof packaged within a AAVC11.07 capsid. |
| 2 | AAVC11.08 | | SCN1B | 6324 | Payload comprising a SCN1B gene or variant thereof packaged within a AAVC11.08 capsid. |
| 2 | AAVC11.09 | | SCN1B | 6324 | Payload comprising a SCN1B gene or variant thereof packaged within a AAVC11.09 capsid. |
| 2 | AAVC11.10 | | SCN1B | 6324 | Payload comprising a SCN1B gene or variant thereof packaged within a AAVC11.10 capsid. |
| 2 | AAVC11.11 | | SCN1B | 6324 | Payload comprising a SCN1B gene or variant thereof packaged within a AAVC11.11 capsid. |
| 2 | AAVC11.12 | | SCN1B | 6324 | Payload comprising a SCN1B gene or variant thereof packaged within a AAVC11.12 capsid. |
| 2 | AAVC11.13 | | SCN1B | 6324 | Payload comprising a SCN1B gene or variant thereof packaged within a AAVC11.13 capsid. |
| 2 | AAVC11.14 | | SCN1B | 6324 | Payload comprising a SCN1B gene or variant thereof packaged within a AAVC11.14 capsid. |
| 2 | AAVC11.15 | | SCN1B | 6324 | Payload comprising a SCN1B gene or variant thereof packaged within a AAVC11.15 capsid. |

Fig. 29 (Continued)

| | | | | | |
|---|---|---|---|---|---|
| 2 | AAVC11.16 | | SCN1B | 6324 | Payload comprising a SCN1B gene or variant thereof packaged within a AAVC11.16 capsid. |
| 2 | AAVC11.17 | | SCN1B | 6324 | Payload comprising a SCN1B gene or variant thereof packaged within a AAVC11.17 capsid. |
| 2 | AAVC11.18 | | SCN1B | 6324 | Payload comprising a SCN1B gene or variant thereof packaged within a AAVC11.18 capsid. |
| 2 | AAVC11.19 | | SCN1B | 6324 | Payload comprising a SCN1B gene or variant thereof packaged within a AAVC11.19 capsid. |
| 2 | AAV12 | | SCN1B | 6324 | Payload comprising a SCN1B gene or variant thereof packaged within a AAV12 capsid. |
| 2 | AAV13 | | SCN1B | 6324 | Payload comprising a SCN1B gene or variant thereof packaged within a AAV13 capsid. |
| 2 | AAV-DJ | | SCN1B | 6324 | Payload comprising a SCN1B gene or variant thereof packaged within a AAV-DJ capsid. |
| 2 | AAV-LK03 | | SCN1B | 6324 | Payload comprising a SCN1B gene or variant thereof packaged within a AAV-LK03 capsid. |
| 2 | AAV-LK19 | | SCN1B | 6324 | Payload comprising a SCN1B gene or variant thereof packaged within a AAV-LK19 capsid. |
| 2 | AAVrh.74 | | SCN1B | 6324 | Payload comprising a SCN1B gene or variant thereof packaged within a AAVrh.74 capsid. |
| 2 | AAVrh.10 | | SCN1B | 6324 | Payload comprising a SCN1B gene or variant thereof packaged within a AAVrh.10 capsid. |
| 2 | AAVhu.37 | | SCN1B | 6324 | Payload comprising a SCN1B gene or variant thereof packaged within a AAVhu.37 capsid. |
| 2 | AAVrh.K | | SCN1B | 6324 | Payload comprising a SCN1B gene or variant thereof packaged within a AAVrh.K capsid. |
| 2 | AAVrh.39 | | SCN1B | 6324 | Payload comprising a SCN1B gene or variant thereof packaged within a AAVrh.39 capsid. |
| 2 | AAVrh.9 | | SCN1B | 6324 | Payload comprising a SCN1B gene or variant thereof packaged within a AAVrh.9 capsid. |
| 2 | avian AAV | | SCN1B | 6324 | Payload comprising a SCN1B gene or variant thereof packaged within a avian capsid. |

Fig. 29 (Continued)

| | | | | | |
|---|---|---|---|---|---|
| 2 | bovine AAV | | SCN1B | 6324 | Payload comprising a SCN1B gene or variant thereof packaged within a bovine capsid. |
| 2 | canine AAV | | SCN1B | 6324 | Payload comprising a SCN1B gene or variant thereof packaged within a canine capsid. |
| 2 | equine AAV | | SCN1B | 6324 | Payload comprising a SCN1B gene or variant thereof packaged within a equine capsid. |
| 2 | primate AAV | | SCN1B | 6324 | Payload comprising a SCN1B gene or variant thereof packaged within a primate capsid. |
| 2 | non-primate AAV | | SCN1B | 6324 | Payload comprising a SCN1B gene or variant thereof packaged within a non-primate capsid. |
| 2 | ovine AAV | | SCN1B | 6324 | Payload comprising a SCN1B gene or variant thereof packaged within a ovine capsid. |
| 2 | hybrid AAV | | SCN1B | 6324 | Payload comprising a SCN1B gene or variant thereof packaged within a hybrid capsid. |
| 2 | chimeric AAV | | SCN1B | 6324 | Payload comprising a SCN1B gene or variant thereof packaged within a chimeric capsid. |
| 1 | AAV1 | 1450374 | SCN2A | 6326 | Payload comprising a SCN2A gene or variant thereof packaged within a AAV1 capsid. |
| 1 | AAV2 | | SCN2A | 6326 | Payload comprising a SCN2A gene or variant thereof packaged within a AAV2 capsid. |
| 1 | AAV3 | | SCN2A | 6326 | Payload comprising a SCN2A gene or variant thereof packaged within a AAV3 capsid. |
| 1 | AAV4 | 1446389 | SCN2A | 6326 | Payload comprising a SCN2A gene or variant thereof packaged within a AAV4 capsid. |
| 1 | AAV5 | | SCN2A | 6326 | Payload comprising a SCN2A gene or variant thereof packaged within a AAV5 capsid. |
| 1 | AAV6 | | SCN2A | 6326 | Payload comprising a SCN2A gene or variant thereof packaged within a AAV6 capsid. |
| 1 | AAV7 | | SCN2A | 6326 | Payload comprising a SCN2A gene or variant thereof packaged within a AAV7 capsid. |
| 1 | AAV8 | 5075992 | SCN2A | 6326 | Payload comprising a SCN2A gene or variant thereof packaged within a AAV8 capsid. |
| 1 | AAV9 | | SCN2A | 6326 | Payload comprising a SCN2A gene or variant thereof packaged within a AAV9 capsid. |

Fig. 29 (Continued)

| | | | | | |
|---|---|---|---|---|---|
| 1 | AAV10 | | SCN2A | 6326 | Payload comprising a SCN2A gene or variant thereof packaged within a AAV10 capsid. |
| 1 | AAV11 | | SCN2A | 6326 | Payload comprising a SCN2A gene or variant thereof packaged within a AAV11 capsid. |
| 1 | AAVC11.01 | | SCN2A | 6326 | Payload comprising a SCN2A gene or variant thereof packaged within a AAVC11.01 capsid. |
| 1 | AAVC11.02 | | SCN2A | 6326 | Payload comprising a SCN2A gene or variant thereof packaged within a AAVC11.02 capsid. |
| 1 | AAVC11.03 | | SCN2A | 6326 | Payload comprising a SCN2A gene or variant thereof packaged within a AAVC11.03 capsid. |
| 1 | AAVC11.04 | | SCN2A | 6326 | Payload comprising a SCN2A gene or variant thereof packaged within a AAVC11.04 capsid. |
| 1 | AAVC11.05 | | SCN2A | 6326 | Payload comprising a SCN2A gene or variant thereof packaged within a AAVC11.05 capsid. |
| 1 | AAVC11.06 | | SCN2A | 6326 | Payload comprising a SCN2A gene or variant thereof packaged within a AAVC11.06 capsid. |
| 1 | AAVC11.07 | | SCN2A | 6326 | Payload comprising a SCN2A gene or variant thereof packaged within a AAVC11.07 capsid. |
| 1 | AAVC11.08 | | SCN2A | 6326 | Payload comprising a SCN2A gene or variant thereof packaged within a AAVC11.08 capsid. |
| 1 | AAVC11.09 | | SCN2A | 6326 | Payload comprising a SCN2A gene or variant thereof packaged within a AAVC11.09 capsid. |
| 1 | AAVC11.10 | | SCN2A | 6326 | Payload comprising a SCN2A gene or variant thereof packaged within a AAVC11.10 capsid. |
| 1 | AAVC11.11 | | SCN2A | 6326 | Payload comprising a SCN2A gene or variant thereof packaged within a AAVC11.11 capsid. |
| 1 | AAVC11.12 | | SCN2A | 6326 | Payload comprising a SCN2A gene or variant thereof packaged within a AAVC11.12 capsid. |
| 1 | AAVC11.13 | | SCN2A | 6326 | Payload comprising a SCN2A gene or variant thereof packaged within a AAVC11.13 capsid. |
| 1 | AAVC11.14 | | SCN2A | 6326 | Payload comprising a SCN2A gene or variant thereof packaged within a AAVC11.14 capsid. |
| 1 | AAVC11.15 | | SCN2A | 6326 | Payload comprising a SCN2A gene or variant thereof packaged within a AAVC11.15 capsid. |

Fig. 29 (Continued)

| | | | | | |
|---|---|---|---|---|---|
| 1 | AAVC11.16 | | SCN2A | 6326 | Payload comprising a SCN2A gene or variant thereof packaged within a AAVC11.16 capsid. |
| 1 | AAVC11.17 | | SCN2A | 6326 | Payload comprising a SCN2A gene or variant thereof packaged within a AAVC11.17 capsid. |
| 1 | AAVC11.18 | | SCN2A | 6326 | Payload comprising a SCN2A gene or variant thereof packaged within a AAVC11.18 capsid. |
| 1 | AAVC11.19 | | SCN2A | 6326 | Payload comprising a SCN2A gene or variant thereof packaged within a AAVC11.19 capsid. |
| 1 | AAV12 | | SCN2A | 6326 | Payload comprising a SCN2A gene or variant thereof packaged within a AAV12 capsid. |
| 1 | AAV13 | | SCN2A | 6326 | Payload comprising a SCN2A gene or variant thereof packaged within a AAV13 capsid. |
| 1 | AAV-DJ | | SCN2A | 6326 | Payload comprising a SCN2A gene or variant thereof packaged within a AAV-DJ capsid. |
| 1 | AAV-LK03 | | SCN2A | 6326 | Payload comprising a SCN2A gene or variant thereof packaged within a AAV-LK03 capsid. |
| 1 | AAV-LK19 | | SCN2A | 6326 | Payload comprising a SCN2A gene or variant thereof packaged within a AAV-LK19 capsid. |
| 1 | AAVrh.74 | | SCN2A | 6326 | Payload comprising a SCN2A gene or variant thereof packaged within a AAVrh.74 capsid. |
| 1 | AAVrh.10 | | SCN2A | 6326 | Payload comprising a SCN2A gene or variant thereof packaged within a AAVrh.10 capsid. |
| 1 | AAVhu.37 | | SCN2A | 6326 | Payload comprising a SCN2A gene or variant thereof packaged within a AAVhu.37 capsid. |
| 1 | AAVrh.K | | SCN2A | 6326 | Payload comprising a SCN2A gene or variant thereof packaged within a AAVrh.K capsid. |
| 1 | AAVrh.39 | | SCN2A | 6326 | Payload comprising a SCN2A gene or variant thereof packaged within a AAVrh.39 capsid. |
| 1 | AAVrh.9 | | SCN2A | 6326 | Payload comprising a SCN2A gene or variant thereof packaged within a AAVrh.9 capsid. |
| 1 | avian AAV | | SCN2A | 6326 | Payload comprising a SCN2A gene or variant thereof packaged within a avian capsid. |

Fig. 29 (Continued)

| | | | | | |
|---|---|---|---|---|---|
| 1 | bovine AAV | | SCN2A | 6326 | Payload comprising a SCN2A gene or variant thereof packaged within a bovine capsid. |
| 1 | canine AAV | | SCN2A | 6326 | Payload comprising a SCN2A gene or variant thereof packaged within a canine capsid. |
| 1 | equine AAV | | SCN2A | 6326 | Payload comprising a SCN2A gene or variant thereof packaged within a equine capsid. |
| 1 | primate AAV | | SCN2A | 6326 | Payload comprising a SCN2A gene or variant thereof packaged within a primate capsid. |
| 1 | non-primate AAV | | SCN2A | 6326 | Payload comprising a SCN2A gene or variant thereof packaged within a non-primate capsid. |
| 1 | ovine AAV | | SCN2A | 6326 | Payload comprising a SCN2A gene or variant thereof packaged within a ovine capsid. |
| 1 | hybrid AAV | | SCN2A | 6326 | Payload comprising a SCN2A gene or variant thereof packaged within a hybrid capsid. |
| 1 | chimeric AAV | | SCN2A | 6326 | Payload comprising a SCN2A gene or variant thereof packaged within a chimeric capsid. |
| 2 | AAV1 | 1450374 | SCN2A | 6326 | Payload comprising a SCN2A gene or variant thereof packaged within a AAV1 capsid. |
| 2 | AAV2 | | SCN2A | 6326 | Payload comprising a SCN2A gene or variant thereof packaged within a AAV2 capsid. |
| 2 | AAV3 | | SCN2A | 6326 | Payload comprising a SCN2A gene or variant thereof packaged within a AAV3 capsid. |
| 2 | AAV4 | 1446389 | SCN2A | 6326 | Payload comprising a SCN2A gene or variant thereof packaged within a AAV4 capsid. |
| 2 | AAV5 | | SCN2A | 6326 | Payload comprising a SCN2A gene or variant thereof packaged within a AAV5 capsid. |
| 2 | AAV6 | | SCN2A | 6326 | Payload comprising a SCN2A gene or variant thereof packaged within a AAV6 capsid. |
| 2 | AAV7 | | SCN2A | 6326 | Payload comprising a SCN2A gene or variant thereof packaged within a AAV7 capsid. |
| 2 | AAV8 | 5075992 | SCN2A | 6326 | Payload comprising a SCN2A gene or variant thereof packaged within a AAV8 capsid. |
| 2 | AAV9 | | SCN2A | 6326 | Payload comprising a SCN2A gene or variant thereof packaged within a AAV9 capsid. |

Fig. 29 (Continued)

| | | | | | |
|---|---|---|---|---|---|
| 2 | AAV10 | | SCN2A | 6326 | Payload comprising a SCN2A gene or variant thereof packaged within a AAV10 capsid. |
| 2 | AAV11 | | SCN2A | 6326 | Payload comprising a SCN2A gene or variant thereof packaged within a AAV11 capsid. |
| 2 | AAVC11.01 | | SCN2A | 6326 | Payload comprising a SCN2A gene or variant thereof packaged within a AAVC11.01 capsid. |
| 2 | AAVC11.02 | | SCN2A | 6326 | Payload comprising a SCN2A gene or variant thereof packaged within a AAVC11.02 capsid. |
| 2 | AAVC11.03 | | SCN2A | 6326 | Payload comprising a SCN2A gene or variant thereof packaged within a AAVC11.03 capsid. |
| 2 | AAVC11.04 | | SCN2A | 6326 | Payload comprising a SCN2A gene or variant thereof packaged within a AAVC11.04 capsid. |
| 2 | AAVC11.05 | | SCN2A | 6326 | Payload comprising a SCN2A gene or variant thereof packaged within a AAVC11.05 capsid. |
| 2 | AAVC11.06 | | SCN2A | 6326 | Payload comprising a SCN2A gene or variant thereof packaged within a AAVC11.06 capsid. |
| 2 | AAVC11.07 | | SCN2A | 6326 | Payload comprising a SCN2A gene or variant thereof packaged within a AAVC11.07 capsid. |
| 2 | AAVC11.08 | | SCN2A | 6326 | Payload comprising a SCN2A gene or variant thereof packaged within a AAVC11.08 capsid. |
| 2 | AAVC11.09 | | SCN2A | 6326 | Payload comprising a SCN2A gene or variant thereof packaged within a AAVC11.09 capsid. |
| 2 | AAVC11.10 | | SCN2A | 6326 | Payload comprising a SCN2A gene or variant thereof packaged within a AAVC11.10 capsid. |
| 2 | AAVC11.11 | | SCN2A | 6326 | Payload comprising a SCN2A gene or variant thereof packaged within a AAVC11.11 capsid. |
| 2 | AAVC11.12 | | SCN2A | 6326 | Payload comprising a SCN2A gene or variant thereof packaged within a AAVC11.12 capsid. |
| 2 | AAVC11.13 | | SCN2A | 6326 | Payload comprising a SCN2A gene or variant thereof packaged within a AAVC11.13 capsid. |
| 2 | AAVC11.14 | | SCN2A | 6326 | Payload comprising a SCN2A gene or variant thereof packaged within a AAVC11.14 capsid. |
| 2 | AAVC11.15 | | SCN2A | 6326 | Payload comprising a SCN2A gene or variant thereof packaged within a AAVC11.15 capsid. |

Fig. 29 (Continued)

| | | | | | |
|---|---|---|---|---|---|
| 2 | AAVC11.16 | | SCN2A | 6326 | Payload comprising a SCN2A gene or variant thereof packaged within a AAVC11.16 capsid. |
| 2 | AAVC11.17 | | SCN2A | 6326 | Payload comprising a SCN2A gene or variant thereof packaged within a AAVC11.17 capsid. |
| 2 | AAVC11.18 | | SCN2A | 6326 | Payload comprising a SCN2A gene or variant thereof packaged within a AAVC11.18 capsid. |
| 2 | AAVC11.19 | | SCN2A | 6326 | Payload comprising a SCN2A gene or variant thereof packaged within a AAVC11.19 capsid. |
| 2 | AAV12 | | SCN2A | 6326 | Payload comprising a SCN2A gene or variant thereof packaged within a AAV12 capsid. |
| 2 | AAV13 | | SCN2A | 6326 | Payload comprising a SCN2A gene or variant thereof packaged within a AAV13 capsid. |
| 2 | AAV-DJ | | SCN2A | 6326 | Payload comprising a SCN2A gene or variant thereof packaged within a AAV-DJ capsid. |
| 2 | AAV-LK03 | | SCN2A | 6326 | Payload comprising a SCN2A gene or variant thereof packaged within a AAV-LK03 capsid. |
| 2 | AAV-LK19 | | SCN2A | 6326 | Payload comprising a SCN2A gene or variant thereof packaged within a AAV-LK19 capsid. |
| 2 | AAVrh.74 | | SCN2A | 6326 | Payload comprising a SCN2A gene or variant thereof packaged within a AAVrh.74 capsid. |
| 2 | AAVrh.10 | | SCN2A | 6326 | Payload comprising a SCN2A gene or variant thereof packaged within a AAVrh.10 capsid. |
| 2 | AAVhu.37 | | SCN2A | 6326 | Payload comprising a SCN2A gene or variant thereof packaged within a AAVhu.37 capsid. |
| 2 | AAVrh.K | | SCN2A | 6326 | Payload comprising a SCN2A gene or variant thereof packaged within a AAVrh.K capsid. |
| 2 | AAVrh.39 | | SCN2A | 6326 | Payload comprising a SCN2A gene or variant thereof packaged within a AAVrh.39 capsid. |
| 2 | AAVrh.9 | | SCN2A | 6326 | Payload comprising a SCN2A gene or variant thereof packaged within a AAVrh.9 capsid. |
| 2 | avian AAV | | SCN2A | 6326 | Payload comprising a SCN2A gene or variant thereof packaged within a avian capsid. |

Fig. 29 (Continued)

| | | | | | |
|---|---|---|---|---|---|
| 2 | bovine AAV | | SCN2A | 6326 | Payload comprising a SCN2A gene or variant thereof packaged within a bovine capsid. |
| 2 | canine AAV | | SCN2A | 6326 | Payload comprising a SCN2A gene or variant thereof packaged within a canine capsid. |
| 2 | equine AAV | | SCN2A | 6326 | Payload comprising a SCN2A gene or variant thereof packaged within a equine capsid. |
| 2 | primate AAV | | SCN2A | 6326 | Payload comprising a SCN2A gene or variant thereof packaged within a primate capsid. |
| 2 | non-primate AAV | | SCN2A | 6326 | Payload comprising a SCN2A gene or variant thereof packaged within a non-primate capsid. |
| 2 | ovine AAV | | SCN2A | 6326 | Payload comprising a SCN2A gene or variant thereof packaged within a ovine capsid. |
| 2 | hybrid AAV | | SCN2A | 6326 | Payload comprising a SCN2A gene or variant thereof packaged within a hybrid capsid. |
| 2 | chimeric AAV | | SCN2A | 6326 | Payload comprising a SCN2A gene or variant thereof packaged within a chimeric capsid. |
| 1 | AAV1 | 1450374 | SCN8A | 6334 | Payload comprising a SCN8A gene or variant thereof packaged within a AAV1 capsid. |
| 1 | AAV2 | | SCN8A | 6334 | Payload comprising a SCN8A gene or variant thereof packaged within a AAV2 capsid. |
| 1 | AAV3 | | SCN8A | 6334 | Payload comprising a SCN8A gene or variant thereof packaged within a AAV3 capsid. |
| 1 | AAV4 | 1446389 | SCN8A | 6334 | Payload comprising a SCN8A gene or variant thereof packaged within a AAV4 capsid. |
| 1 | AAV5 | | SCN8A | 6334 | Payload comprising a SCN8A gene or variant thereof packaged within a AAV5 capsid. |
| 1 | AAV6 | | SCN8A | 6334 | Payload comprising a SCN8A gene or variant thereof packaged within a AAV6 capsid. |
| 1 | AAV7 | | SCN8A | 6334 | Payload comprising a SCN8A gene or variant thereof packaged within a AAV7 capsid. |
| 1 | AAV8 | 5075992 | SCN8A | 6334 | Payload comprising a SCN8A gene or variant thereof packaged within a AAV8 capsid. |
| 1 | AAV9 | | SCN8A | 6334 | Payload comprising a SCN8A gene or variant thereof packaged within a AAV9 capsid. |

Fig. 29 (Continued)

| | | | | | |
|---|---|---|---|---|---|
| 1 | AAV10 | | SCN8A | 6334 | Payload comprising a SCN8A gene or variant thereof packaged within a AAV10 capsid. |
| 1 | AAV11 | | SCN8A | 6334 | Payload comprising a SCN8A gene or variant thereof packaged within a AAV11 capsid. |
| 1 | AAVC11.01 | | SCN8A | 6334 | Payload comprising a SCN8A gene or variant thereof packaged within a AAVC11.01 capsid. |
| 1 | AAVC11.02 | | SCN8A | 6334 | Payload comprising a SCN8A gene or variant thereof packaged within a AAVC11.02 capsid. |
| 1 | AAVC11.03 | | SCN8A | 6334 | Payload comprising a SCN8A gene or variant thereof packaged within a AAVC11.03 capsid. |
| 1 | AAVC11.04 | | SCN8A | 6334 | Payload comprising a SCN8A gene or variant thereof packaged within a AAVC11.04 capsid. |
| 1 | AAVC11.05 | | SCN8A | 6334 | Payload comprising a SCN8A gene or variant thereof packaged within a AAVC11.05 capsid. |
| 1 | AAVC11.06 | | SCN8A | 6334 | Payload comprising a SCN8A gene or variant thereof packaged within a AAVC11.06 capsid. |
| 1 | AAVC11.07 | | SCN8A | 6334 | Payload comprising a SCN8A gene or variant thereof packaged within a AAVC11.07 capsid. |
| 1 | AAVC11.08 | | SCN8A | 6334 | Payload comprising a SCN8A gene or variant thereof packaged within a AAVC11.08 capsid. |
| 1 | AAVC11.09 | | SCN8A | 6334 | Payload comprising a SCN8A gene or variant thereof packaged within a AAVC11.09 capsid. |
| 1 | AAVC11.10 | | SCN8A | 6334 | Payload comprising a SCN8A gene or variant thereof packaged within a AAVC11.10 capsid. |
| 1 | AAVC11.11 | | SCN8A | 6334 | Payload comprising a SCN8A gene or variant thereof packaged within a AAVC11.11 capsid. |
| 1 | AAVC11.12 | | SCN8A | 6334 | Payload comprising a SCN8A gene or variant thereof packaged within a AAVC11.12 capsid. |
| 1 | AAVC11.13 | | SCN8A | 6334 | Payload comprising a SCN8A gene or variant thereof packaged within a AAVC11.13 capsid. |
| 1 | AAVC11.14 | | SCN8A | 6334 | Payload comprising a SCN8A gene or variant thereof packaged within a AAVC11.14 capsid. |
| 1 | AAVC11.15 | | SCN8A | 6334 | Payload comprising a SCN8A gene or variant thereof packaged within a AAVC11.15 capsid. |

Fig. 29 (Continued)

| | | | | | |
|---|---|---|---|---|---|
| 1 | AAVC11.16 | | SCN8A | 6334 | Payload comprising a SCN8A gene or variant thereof packaged within a AAVC11.16 capsid. |
| 1 | AAVC11.17 | | SCN8A | 6334 | Payload comprising a SCN8A gene or variant thereof packaged within a AAVC11.17 capsid. |
| 1 | AAVC11.18 | | SCN8A | 6334 | Payload comprising a SCN8A gene or variant thereof packaged within a AAVC11.18 capsid. |
| 1 | AAVC11.19 | | SCN8A | 6334 | Payload comprising a SCN8A gene or variant thereof packaged within a AAVC11.19 capsid. |
| 1 | AAV12 | | SCN8A | 6334 | Payload comprising a SCN8A gene or variant thereof packaged within a AAV12 capsid. |
| 1 | AAV13 | | SCN8A | 6334 | Payload comprising a SCN8A gene or variant thereof packaged within a AAV13 capsid. |
| 1 | AAV-DJ | | SCN8A | 6334 | Payload comprising a SCN8A gene or variant thereof packaged within a AAV-DJ capsid. |
| 1 | AAV-LK03 | | SCN8A | 6334 | Payload comprising a SCN8A gene or variant thereof packaged within a AAV-LK03 capsid. |
| 1 | AAV-LK19 | | SCN8A | 6334 | Payload comprising a SCN8A gene or variant thereof packaged within a AAV-LK19 capsid. |
| 1 | AAVrh.74 | | SCN8A | 6334 | Payload comprising a SCN8A gene or variant thereof packaged within a AAVrh.74 capsid. |
| 1 | AAVrh.10 | | SCN8A | 6334 | Payload comprising a SCN8A gene or variant thereof packaged within a AAVrh.10 capsid. |
| 1 | AAVhu.37 | | SCN8A | 6334 | Payload comprising a SCN8A gene or variant thereof packaged within a AAVhu.37 capsid. |
| 1 | AAVrh.K | | SCN8A | 6334 | Payload comprising a SCN8A gene or variant thereof packaged within a AAVrh.K capsid. |
| 1 | AAVrh.39 | | SCN8A | 6334 | Payload comprising a SCN8A gene or variant thereof packaged within a AAVrh.39 capsid. |
| 1 | AAVrh.9 | | SCN8A | 6334 | Payload comprising a SCN8A gene or variant thereof packaged within a AAVrh.9 capsid. |
| 1 | avian AAV | | SCN8A | 6334 | Payload comprising a SCN8A gene or variant thereof packaged within a avian capsid. |

Fig. 29 (Continued)

| | | | | | |
|---|---|---|---|---|---|
| 1 | bovine AAV | | SCN8A | 6334 | Payload comprising a SCN8A gene or variant thereof packaged within a bovine capsid. |
| 1 | canine AAV | | SCN8A | 6334 | Payload comprising a SCN8A gene or variant thereof packaged within a canine capsid. |
| 1 | equine AAV | | SCN8A | 6334 | Payload comprising a SCN8A gene or variant thereof packaged within a equine capsid. |
| 1 | primate AAV | | SCN8A | 6334 | Payload comprising a SCN8A gene or variant thereof packaged within a primate capsid. |
| 1 | non-primate AAV | | SCN8A | 6334 | Payload comprising a SCN8A gene or variant thereof packaged within a non-primate capsid. |
| 1 | ovine AAV | | SCN8A | 6334 | Payload comprising a SCN8A gene or variant thereof packaged within a ovine capsid. |
| 1 | hybrid AAV | | SCN8A | 6334 | Payload comprising a SCN8A gene or variant thereof packaged within a hybrid capsid. |
| 1 | chimeric AAV | | SCN8A | 6334 | Payload comprising a SCN8A gene or variant thereof packaged within a chimeric capsid. |
| 2 | AAV1 | 1450374 | SCN8A | 6334 | Payload comprising a SCN8A gene or variant thereof packaged within a AAV1 capsid. |
| 2 | AAV2 | | SCN8A | 6334 | Payload comprising a SCN8A gene or variant thereof packaged within a AAV2 capsid. |
| 2 | AAV3 | | SCN8A | 6334 | Payload comprising a SCN8A gene or variant thereof packaged within a AAV3 capsid. |
| 2 | AAV4 | 1446389 | SCN8A | 6334 | Payload comprising a SCN8A gene or variant thereof packaged within a AAV4 capsid. |
| 2 | AAV5 | | SCN8A | 6334 | Payload comprising a SCN8A gene or variant thereof packaged within a AAV5 capsid. |
| 2 | AAV6 | | SCN8A | 6334 | Payload comprising a SCN8A gene or variant thereof packaged within a AAV6 capsid. |
| 2 | AAV7 | | SCN8A | 6334 | Payload comprising a SCN8A gene or variant thereof packaged within a AAV7 capsid. |
| 2 | AAV8 | 5075992 | SCN8A | 6334 | Payload comprising a SCN8A gene or variant thereof packaged within a AAV8 capsid. |
| 2 | AAV9 | | SCN8A | 6334 | Payload comprising a SCN8A gene or variant thereof packaged within a AAV9 capsid. |

Fig. 29 (Continued)

| | | | | | |
|---|---|---|---|---|---|
| 2 | AAV10 | | SCN8A | 6334 | Payload comprising a SCN8A gene or variant thereof packaged within a AAV10 capsid. |
| 2 | AAV11 | | SCN8A | 6334 | Payload comprising a SCN8A gene or variant thereof packaged within a AAV11 capsid. |
| 2 | AAVC11.01 | | SCN8A | 6334 | Payload comprising a SCN8A gene or variant thereof packaged within a AAVC11.01 capsid. |
| 2 | AAVC11.02 | | SCN8A | 6334 | Payload comprising a SCN8A gene or variant thereof packaged within a AAVC11.02 capsid. |
| 2 | AAVC11.03 | | SCN8A | 6334 | Payload comprising a SCN8A gene or variant thereof packaged within a AAVC11.03 capsid. |
| 2 | AAVC11.04 | | SCN8A | 6334 | Payload comprising a SCN8A gene or variant thereof packaged within a AAVC11.04 capsid. |
| 2 | AAVC11.05 | | SCN8A | 6334 | Payload comprising a SCN8A gene or variant thereof packaged within a AAVC11.05 capsid. |
| 2 | AAVC11.06 | | SCN8A | 6334 | Payload comprising a SCN8A gene or variant thereof packaged within a AAVC11.06 capsid. |
| 2 | AAVC11.07 | | SCN8A | 6334 | Payload comprising a SCN8A gene or variant thereof packaged within a AAVC11.07 capsid. |
| 2 | AAVC11.08 | | SCN8A | 6334 | Payload comprising a SCN8A gene or variant thereof packaged within a AAVC11.08 capsid. |
| 2 | AAVC11.09 | | SCN8A | 6334 | Payload comprising a SCN8A gene or variant thereof packaged within a AAVC11.09 capsid. |
| 2 | AAVC11.10 | | SCN8A | 6334 | Payload comprising a SCN8A gene or variant thereof packaged within a AAVC11.10 capsid. |
| 2 | AAVC11.11 | | SCN8A | 6334 | Payload comprising a SCN8A gene or variant thereof packaged within a AAVC11.11 capsid. |
| 2 | AAVC11.12 | | SCN8A | 6334 | Payload comprising a SCN8A gene or variant thereof packaged within a AAVC11.12 capsid. |
| 2 | AAVC11.13 | | SCN8A | 6334 | Payload comprising a SCN8A gene or variant thereof packaged within a AAVC11.13 capsid. |
| 2 | AAVC11.14 | | SCN8A | 6334 | Payload comprising a SCN8A gene or variant thereof packaged within a AAVC11.14 capsid. |
| 2 | AAVC11.15 | | SCN8A | 6334 | Payload comprising a SCN8A gene or variant thereof packaged within a AAVC11.15 capsid. |

Fig. 29 (Continued)

| | | | | | |
|---|---|---|---|---|---|
| 2 | AAVC11.16 | | SCN8A | 6334 | Payload comprising a SCN8A gene or variant thereof packaged within a AAVC11.16 capsid. |
| 2 | AAVC11.17 | | SCN8A | 6334 | Payload comprising a SCN8A gene or variant thereof packaged within a AAVC11.17 capsid. |
| 2 | AAVC11.18 | | SCN8A | 6334 | Payload comprising a SCN8A gene or variant thereof packaged within a AAVC11.18 capsid. |
| 2 | AAVC11.19 | | SCN8A | 6334 | Payload comprising a SCN8A gene or variant thereof packaged within a AAVC11.19 capsid. |
| 2 | AAV12 | | SCN8A | 6334 | Payload comprising a SCN8A gene or variant thereof packaged within a AAV12 capsid. |
| 2 | AAV13 | | SCN8A | 6334 | Payload comprising a SCN8A gene or variant thereof packaged within a AAV13 capsid. |
| 2 | AAV-DJ | | SCN8A | 6334 | Payload comprising a SCN8A gene or variant thereof packaged within a AAV-DJ capsid. |
| 2 | AAV-LK03 | | SCN8A | 6334 | Payload comprising a SCN8A gene or variant thereof packaged within a AAV-LK03 capsid. |
| 2 | AAV-LK19 | | SCN8A | 6334 | Payload comprising a SCN8A gene or variant thereof packaged within a AAV-LK19 capsid. |
| 2 | AAVrh.74 | | SCN8A | 6334 | Payload comprising a SCN8A gene or variant thereof packaged within a AAVrh.74 capsid. |
| 2 | AAVrh.10 | | SCN8A | 6334 | Payload comprising a SCN8A gene or variant thereof packaged within a AAVrh.10 capsid. |
| 2 | AAVhu.37 | | SCN8A | 6334 | Payload comprising a SCN8A gene or variant thereof packaged within a AAVhu.37 capsid. |
| 2 | AAVrh.K | | SCN8A | 6334 | Payload comprising a SCN8A gene or variant thereof packaged within a AAVrh.K capsid. |
| 2 | AAVrh.39 | | SCN8A | 6334 | Payload comprising a SCN8A gene or variant thereof packaged within a AAVrh.39 capsid. |
| 2 | AAVrh.9 | | SCN8A | 6334 | Payload comprising a SCN8A gene or variant thereof packaged within a AAVrh.9 capsid. |
| 2 | avian AAV | | SCN8A | 6334 | Payload comprising a SCN8A gene or variant thereof packaged within a avian capsid. |

Fig. 29 (Continued)

| | | | | | |
|---|---|---|---|---|---|
| 2 | bovine AAV | | SCN8A | 6334 | Payload comprising a SCN8A gene or variant thereof packaged within a bovine capsid. |
| 2 | canine AAV | | SCN8A | 6334 | Payload comprising a SCN8A gene or variant thereof packaged within a canine capsid. |
| 2 | equine AAV | | SCN8A | 6334 | Payload comprising a SCN8A gene or variant thereof packaged within a equine capsid. |
| 2 | primate AAV | | SCN8A | 6334 | Payload comprising a SCN8A gene or variant thereof packaged within a primate capsid. |
| 2 | non-primate AAV | | SCN8A | 6334 | Payload comprising a SCN8A gene or variant thereof packaged within a non-primate capsid. |
| 2 | ovine AAV | | SCN8A | 6334 | Payload comprising a SCN8A gene or variant thereof packaged within a ovine capsid. |
| 2 | hybrid AAV | | SCN8A | 6334 | Payload comprising a SCN8A gene or variant thereof packaged within a hybrid capsid. |
| 2 | chimeric AAV | | SCN8A | 6334 | Payload comprising a SCN8A gene or variant thereof packaged within a chimeric capsid. |
| 1 | AAV1 | 1450374 | SCNA | 6622 | Payload comprising a SCNA gene or variant thereof packaged within a AAV1 capsid. |
| 1 | AAV2 | | SCNA | 6622 | Payload comprising a SCNA gene or variant thereof packaged within a AAV2 capsid. |
| 1 | AAV3 | | SCNA | 6622 | Payload comprising a SCNA gene or variant thereof packaged within a AAV3 capsid. |
| 1 | AAV4 | 1446389 | SCNA | 6622 | Payload comprising a SCNA gene or variant thereof packaged within a AAV4 capsid. |
| 1 | AAV5 | | SCNA | 6622 | Payload comprising a SCNA gene or variant thereof packaged within a AAV5 capsid. |
| 1 | AAV6 | | SCNA | 6622 | Payload comprising a SCNA gene or variant thereof packaged within a AAV6 capsid. |
| 1 | AAV7 | | SCNA | 6622 | Payload comprising a SCNA gene or variant thereof packaged within a AAV7 capsid. |
| 1 | AAV8 | 5075992 | SCNA | 6622 | Payload comprising a SCNA gene or variant thereof packaged within a AAV8 capsid. |
| 1 | AAV9 | | SCNA | 6622 | Payload comprising a SCNA gene or variant thereof packaged within a AAV9 capsid. |

Fig. 29 (Continued)

| | | | | | |
|---|---|---|---|---|---|
| 1 | AAV10 | | SCNA | 6622 | Payload comprising a SCNA gene or variant thereof packaged within a AAV10 capsid. |
| 1 | AAV11 | | SCNA | 6622 | Payload comprising a SCNA gene or variant thereof packaged within a AAV11 capsid. |
| 1 | AAVC11.01 | | SCNA | 6622 | Payload comprising a SCNA gene or variant thereof packaged within a AAVC11.01 capsid. |
| 1 | AAVC11.02 | | SCNA | 6622 | Payload comprising a SCNA gene or variant thereof packaged within a AAVC11.02 capsid. |
| 1 | AAVC11.03 | | SCNA | 6622 | Payload comprising a SCNA gene or variant thereof packaged within a AAVC11.03 capsid. |
| 1 | AAVC11.04 | | SCNA | 6622 | Payload comprising a SCNA gene or variant thereof packaged within a AAVC11.04 capsid. |
| 1 | AAVC11.05 | | SCNA | 6622 | Payload comprising a SCNA gene or variant thereof packaged within a AAVC11.05 capsid. |
| 1 | AAVC11.06 | | SCNA | 6622 | Payload comprising a SCNA gene or variant thereof packaged within a AAVC11.06 capsid. |
| 1 | AAVC11.07 | | SCNA | 6622 | Payload comprising a SCNA gene or variant thereof packaged within a AAVC11.07 capsid. |
| 1 | AAVC11.08 | | SCNA | 6622 | Payload comprising a SCNA gene or variant thereof packaged within a AAVC11.08 capsid. |
| 1 | AAVC11.09 | | SCNA | 6622 | Payload comprising a SCNA gene or variant thereof packaged within a AAVC11.09 capsid. |
| 1 | AAVC11.10 | | SCNA | 6622 | Payload comprising a SCNA gene or variant thereof packaged within a AAVC11.10 capsid. |
| 1 | AAVC11.11 | | SCNA | 6622 | Payload comprising a SCNA gene or variant thereof packaged within a AAVC11.11 capsid. |
| 1 | AAVC11.12 | | SCNA | 6622 | Payload comprising a SCNA gene or variant thereof packaged within a AAVC11.12 capsid. |
| 1 | AAVC11.13 | | SCNA | 6622 | Payload comprising a SCNA gene or variant thereof packaged within a AAVC11.13 capsid. |
| 1 | AAVC11.14 | | SCNA | 6622 | Payload comprising a SCNA gene or variant thereof packaged within a AAVC11.14 capsid. |
| 1 | AAVC11.15 | | SCNA | 6622 | Payload comprising a SCNA gene or variant thereof packaged within a AAVC11.15 capsid. |

Fig. 29 (Continued)

| | | | | | |
|---|---|---|---|---|---|
| 1 | AAVC11.16 | | SCNA | 6622 | Payload comprising a SCNA gene or variant thereof packaged within a AAVC11.16 capsid. |
| 1 | AAVC11.17 | | SCNA | 6622 | Payload comprising a SCNA gene or variant thereof packaged within a AAVC11.17 capsid. |
| 1 | AAVC11.18 | | SCNA | 6622 | Payload comprising a SCNA gene or variant thereof packaged within a AAVC11.18 capsid. |
| 1 | AAVC11.19 | | SCNA | 6622 | Payload comprising a SCNA gene or variant thereof packaged within a AAVC11.19 capsid. |
| 1 | AAV12 | | SCNA | 6622 | Payload comprising a SCNA gene or variant thereof packaged within a AAV12 capsid. |
| 1 | AAV13 | | SCNA | 6622 | Payload comprising a SCNA gene or variant thereof packaged within a AAV13 capsid. |
| 1 | AAV-DJ | | SCNA | 6622 | Payload comprising a SCNA gene or variant thereof packaged within a AAV-DJ capsid. |
| 1 | AAV-LK03 | | SCNA | 6622 | Payload comprising a SCNA gene or variant thereof packaged within a AAV-LK03 capsid. |
| 1 | AAV-LK19 | | SCNA | 6622 | Payload comprising a SCNA gene or variant thereof packaged within a AAV-LK19 capsid. |
| 1 | AAVrh.74 | | SCNA | 6622 | Payload comprising a SCNA gene or variant thereof packaged within a AAVrh.74 capsid. |
| 1 | AAVrh.10 | | SCNA | 6622 | Payload comprising a SCNA gene or variant thereof packaged within a AAVrh.10 capsid. |
| 1 | AAVhu.37 | | SCNA | 6622 | Payload comprising a SCNA gene or variant thereof packaged within a AAVhu.37 capsid. |
| 1 | AAVrh.K | | SCNA | 6622 | Payload comprising a SCNA gene or variant thereof packaged within a AAVrh.K capsid. |
| 1 | AAVrh.39 | | SCNA | 6622 | Payload comprising a SCNA gene or variant thereof packaged within a AAVrh.39 capsid. |
| 1 | AAVrh.9 | | SCNA | 6622 | Payload comprising a SCNA gene or variant thereof packaged within a AAVrh.9 capsid. |
| 1 | avian AAV | | SCNA | 6622 | Payload comprising a SCNA gene or variant thereof packaged within a avian capsid. |

Fig. 29 (Continued)

| | | | | | |
|---|---|---|---|---|---|
| 1 | bovine AAV | | SCNA | 6622 | Payload comprising a SCNA gene or variant thereof packaged within a bovine capsid. |
| 1 | canine AAV | | SCNA | 6622 | Payload comprising a SCNA gene or variant thereof packaged within a canine capsid. |
| 1 | equine AAV | | SCNA | 6622 | Payload comprising a SCNA gene or variant thereof packaged within a equine capsid. |
| 1 | primate AAV | | SCNA | 6622 | Payload comprising a SCNA gene or variant thereof packaged within a primate capsid. |
| 1 | non-primate AAV | | SCNA | 6622 | Payload comprising a SCNA gene or variant thereof packaged within a non-primate capsid. |
| 1 | ovine AAV | | SCNA | 6622 | Payload comprising a SCNA gene or variant thereof packaged within a ovine capsid. |
| 1 | hybrid AAV | | SCNA | 6622 | Payload comprising a SCNA gene or variant thereof packaged within a hybrid capsid. |
| 1 | chimeric AAV | | SCNA | 6622 | Payload comprising a SCNA gene or variant thereof packaged within a chimeric capsid. |
| 2 | AAV1 | 1450374 | SCNA | 6622 | Payload comprising a SCNA gene or variant thereof packaged within a AAV1 capsid. |
| 2 | AAV2 | | SCNA | 6622 | Payload comprising a SCNA gene or variant thereof packaged within a AAV2 capsid. |
| 2 | AAV3 | | SCNA | 6622 | Payload comprising a SCNA gene or variant thereof packaged within a AAV3 capsid. |
| 2 | AAV4 | 1446389 | SCNA | 6622 | Payload comprising a SCNA gene or variant thereof packaged within a AAV4 capsid. |
| 2 | AAV5 | | SCNA | 6622 | Payload comprising a SCNA gene or variant thereof packaged within a AAV5 capsid. |
| 2 | AAV6 | | SCNA | 6622 | Payload comprising a SCNA gene or variant thereof packaged within a AAV6 capsid. |
| 2 | AAV7 | | SCNA | 6622 | Payload comprising a SCNA gene or variant thereof packaged within a AAV7 capsid. |
| 2 | AAV8 | 5075992 | SCNA | 6622 | Payload comprising a SCNA gene or variant thereof packaged within a AAV8 capsid. |
| 2 | AAV9 | | SCNA | 6622 | Payload comprising a SCNA gene or variant thereof packaged within a AAV9 capsid. |

Fig. 29 (Continued)

| | | | | | |
|---|---|---|---|---|---|
| 2 | AAV10 | | SCNA | 6622 | Payload comprising a SCNA gene or variant thereof packaged within a AAV10 capsid. |
| 2 | AAV11 | | SCNA | 6622 | Payload comprising a SCNA gene or variant thereof packaged within a AAV11 capsid. |
| 2 | AAVC11.01 | | SCNA | 6622 | Payload comprising a SCNA gene or variant thereof packaged within a AAVC11.01 capsid. |
| 2 | AAVC11.02 | | SCNA | 6622 | Payload comprising a SCNA gene or variant thereof packaged within a AAVC11.02 capsid. |
| 2 | AAVC11.03 | | SCNA | 6622 | Payload comprising a SCNA gene or variant thereof packaged within a AAVC11.03 capsid. |
| 2 | AAVC11.04 | | SCNA | 6622 | Payload comprising a SCNA gene or variant thereof packaged within a AAVC11.04 capsid. |
| 2 | AAVC11.05 | | SCNA | 6622 | Payload comprising a SCNA gene or variant thereof packaged within a AAVC11.05 capsid. |
| 2 | AAVC11.06 | | SCNA | 6622 | Payload comprising a SCNA gene or variant thereof packaged within a AAVC11.06 capsid. |
| 2 | AAVC11.07 | | SCNA | 6622 | Payload comprising a SCNA gene or variant thereof packaged within a AAVC11.07 capsid. |
| 2 | AAVC11.08 | | SCNA | 6622 | Payload comprising a SCNA gene or variant thereof packaged within a AAVC11.08 capsid. |
| 2 | AAVC11.09 | | SCNA | 6622 | Payload comprising a SCNA gene or variant thereof packaged within a AAVC11.09 capsid. |
| 2 | AAVC11.10 | | SCNA | 6622 | Payload comprising a SCNA gene or variant thereof packaged within a AAVC11.10 capsid. |
| 2 | AAVC11.11 | | SCNA | 6622 | Payload comprising a SCNA gene or variant thereof packaged within a AAVC11.11 capsid. |
| 2 | AAVC11.12 | | SCNA | 6622 | Payload comprising a SCNA gene or variant thereof packaged within a AAVC11.12 capsid. |
| 2 | AAVC11.13 | | SCNA | 6622 | Payload comprising a SCNA gene or variant thereof packaged within a AAVC11.13 capsid. |
| 2 | AAVC11.14 | | SCNA | 6622 | Payload comprising a SCNA gene or variant thereof packaged within a AAVC11.14 capsid. |
| 2 | AAVC11.15 | | SCNA | 6622 | Payload comprising a SCNA gene or variant thereof packaged within a AAVC11.15 capsid. |

Fig. 29 (Continued)

| | | | | | |
|---|---|---|---|---|---|
| 2 | AAVC11.16 | | SCNA | 6622 | Payload comprising a SCNA gene or variant thereof packaged within a AAVC11.16 capsid. |
| 2 | AAVC11.17 | | SCNA | 6622 | Payload comprising a SCNA gene or variant thereof packaged within a AAVC11.17 capsid. |
| 2 | AAVC11.18 | | SCNA | 6622 | Payload comprising a SCNA gene or variant thereof packaged within a AAVC11.18 capsid. |
| 2 | AAVC11.19 | | SCNA | 6622 | Payload comprising a SCNA gene or variant thereof packaged within a AAVC11.19 capsid. |
| 2 | AAV12 | | SCNA | 6622 | Payload comprising a SCNA gene or variant thereof packaged within a AAV12 capsid. |
| 2 | AAV13 | | SCNA | 6622 | Payload comprising a SCNA gene or variant thereof packaged within a AAV13 capsid. |
| 2 | AAV-DJ | | SCNA | 6622 | Payload comprising a SCNA gene or variant thereof packaged within a AAV-DJ capsid. |
| 2 | AAV-LK03 | | SCNA | 6622 | Payload comprising a SCNA gene or variant thereof packaged within a AAV-LK03 capsid. |
| 2 | AAV-LK19 | | SCNA | 6622 | Payload comprising a SCNA gene or variant thereof packaged within a AAV-LK19 capsid. |
| 2 | AAVrh.74 | | SCNA | 6622 | Payload comprising a SCNA gene or variant thereof packaged within a AAVrh.74 capsid. |
| 2 | AAVrh.10 | | SCNA | 6622 | Payload comprising a SCNA gene or variant thereof packaged within a AAVrh.10 capsid. |
| 2 | AAVhu.37 | | SCNA | 6622 | Payload comprising a SCNA gene or variant thereof packaged within a AAVhu.37 capsid. |
| 2 | AAVrh.K | | SCNA | 6622 | Payload comprising a SCNA gene or variant thereof packaged within a AAVrh.K capsid. |
| 2 | AAVrh.39 | | SCNA | 6622 | Payload comprising a SCNA gene or variant thereof packaged within a AAVrh.39 capsid. |
| 2 | AAVrh.9 | | SCNA | 6622 | Payload comprising a SCNA gene or variant thereof packaged within a AAVrh.9 capsid. |
| 2 | avian AAV | | SCNA | 6622 | Payload comprising a SCNA gene or variant thereof packaged within a avian capsid. |

Fig. 29 (Continued)

| | | | | | |
|---|---|---|---|---|---|
| 2 | bovine AAV | | SCNA | 6622 | Payload comprising a SCNA gene or variant thereof packaged within a bovine capsid. |
| 2 | canine AAV | | SCNA | 6622 | Payload comprising a SCNA gene or variant thereof packaged within a canine capsid. |
| 2 | equine AAV | | SCNA | 6622 | Payload comprising a SCNA gene or variant thereof packaged within a equine capsid. |
| 2 | primate AAV | | SCNA | 6622 | Payload comprising a SCNA gene or variant thereof packaged within a primate capsid. |
| 2 | non-primate AAV | | SCNA | 6622 | Payload comprising a SCNA gene or variant thereof packaged within a non-primate capsid. |
| 2 | ovine AAV | | SCNA | 6622 | Payload comprising a SCNA gene or variant thereof packaged within a ovine capsid. |
| 2 | hybrid AAV | | SCNA | 6622 | Payload comprising a SCNA gene or variant thereof packaged within a hybrid capsid. |
| 2 | chimeric AAV | | SCNA | 6622 | Payload comprising a SCNA gene or variant thereof packaged within a chimeric capsid. |
| 1 | AAV1 | 1450374 | SERPINA1 | 5265 | Payload comprising a SERPINA1 gene or variant thereof packaged within a AAV1 capsid. |
| 1 | AAV2 | | SERPINA1 | 5265 | Payload comprising a SERPINA1 gene or variant thereof packaged within a AAV2 capsid. |
| 1 | AAV3 | | SERPINA1 | 5265 | Payload comprising a SERPINA1 gene or variant thereof packaged within a AAV3 capsid. |
| 1 | AAV4 | 1446389 | SERPINA1 | 5265 | Payload comprising a SERPINA1 gene or variant thereof packaged within a AAV4 capsid. |
| 1 | AAV5 | | SERPINA1 | 5265 | Payload comprising a SERPINA1 gene or variant thereof packaged within a AAV5 capsid. |
| 1 | AAV6 | | SERPINA1 | 5265 | Payload comprising a SERPINA1 gene or variant thereof packaged within a AAV6 capsid. |
| 1 | AAV7 | | SERPINA1 | 5265 | Payload comprising a SERPINA1 gene or variant thereof packaged within a AAV7 capsid. |
| 1 | AAV8 | 5075992 | SERPINA1 | 5265 | Payload comprising a SERPINA1 gene or variant thereof packaged within a AAV8 capsid. |
| 1 | AAV9 | | SERPINA1 | 5265 | Payload comprising a SERPINA1 gene or variant thereof packaged within a AAV9 capsid. |

Fig. 29 (Continued)

| | | | | | |
|---|---|---|---|---|---|
| 1 | AAV10 | | SERPINA1 | 5265 | Payload comprising a SERPINA1 gene or variant thereof packaged within a AAV10 capsid. |
| 1 | AAV11 | | SERPINA1 | 5265 | Payload comprising a SERPINA1 gene or variant thereof packaged within a AAV11 capsid. |
| 1 | AAVC11.01 | | SERPINA1 | 5265 | Payload comprising a SERPINA1 gene or variant thereof packaged within a AAVC11.01 capsid. |
| 1 | AAVC11.02 | | SERPINA1 | 5265 | Payload comprising a SERPINA1 gene or variant thereof packaged within a AAVC11.02 capsid. |
| 1 | AAVC11.03 | | SERPINA1 | 5265 | Payload comprising a SERPINA1 gene or variant thereof packaged within a AAVC11.03 capsid. |
| 1 | AAVC11.04 | | SERPINA1 | 5265 | Payload comprising a SERPINA1 gene or variant thereof packaged within a AAVC11.04 capsid. |
| 1 | AAVC11.05 | | SERPINA1 | 5265 | Payload comprising a SERPINA1 gene or variant thereof packaged within a AAVC11.05 capsid. |
| 1 | AAVC11.06 | | SERPINA1 | 5265 | Payload comprising a SERPINA1 gene or variant thereof packaged within a AAVC11.06 capsid. |
| 1 | AAVC11.07 | | SERPINA1 | 5265 | Payload comprising a SERPINA1 gene or variant thereof packaged within a AAVC11.07 capsid. |
| 1 | AAVC11.08 | | SERPINA1 | 5265 | Payload comprising a SERPINA1 gene or variant thereof packaged within a AAVC11.08 capsid. |
| 1 | AAVC11.09 | | SERPINA1 | 5265 | Payload comprising a SERPINA1 gene or variant thereof packaged within a AAVC11.09 capsid. |
| 1 | AAVC11.10 | | SERPINA1 | 5265 | Payload comprising a SERPINA1 gene or variant thereof packaged within a AAVC11.10 capsid. |
| 1 | AAVC11.11 | | SERPINA1 | 5265 | Payload comprising a SERPINA1 gene or variant thereof packaged within a AAVC11.11 capsid. |
| 1 | AAVC11.12 | | SERPINA1 | 5265 | Payload comprising a SERPINA1 gene or variant thereof packaged within a AAVC11.12 capsid. |
| 1 | AAVC11.13 | | SERPINA1 | 5265 | Payload comprising a SERPINA1 gene or variant thereof packaged within a AAVC11.13 capsid. |
| 1 | AAVC11.14 | | SERPINA1 | 5265 | Payload comprising a SERPINA1 gene or variant thereof packaged within a AAVC11.14 capsid. |
| 1 | AAVC11.15 | | SERPINA1 | 5265 | Payload comprising a SERPINA1 gene or variant thereof packaged within a AAVC11.15 capsid. |

Fig. 29 (Continued)

| | | | | | |
|---|---|---|---|---|---|
| 1 | AAVC11.16 | | SERPINA1 | 5265 | Payload comprising a SERPINA1 gene or variant thereof packaged within a AAVC11.16 capsid. |
| 1 | AAVC11.17 | | SERPINA1 | 5265 | Payload comprising a SERPINA1 gene or variant thereof packaged within a AAVC11.17 capsid. |
| 1 | AAVC11.18 | | SERPINA1 | 5265 | Payload comprising a SERPINA1 gene or variant thereof packaged within a AAVC11.18 capsid. |
| 1 | AAVC11.19 | | SERPINA1 | 5265 | Payload comprising a SERPINA1 gene or variant thereof packaged within a AAVC11.19 capsid. |
| 1 | AAV12 | | SERPINA1 | 5265 | Payload comprising a SERPINA1 gene or variant thereof packaged within a AAV12 capsid. |
| 1 | AAV13 | | SERPINA1 | 5265 | Payload comprising a SERPINA1 gene or variant thereof packaged within a AAV13 capsid. |
| 1 | AAV-DJ | | SERPINA1 | 5265 | Payload comprising a SERPINA1 gene or variant thereof packaged within a AAV-DJ capsid. |
| 1 | AAV-LK03 | | SERPINA1 | 5265 | Payload comprising a SERPINA1 gene or variant thereof packaged within a AAV-LK03 capsid. |
| 1 | AAV-LK19 | | SERPINA1 | 5265 | Payload comprising a SERPINA1 gene or variant thereof packaged within a AAV-LK19 capsid. |
| 1 | AAVrh.74 | | SERPINA1 | 5265 | Payload comprising a SERPINA1 gene or variant thereof packaged within a AAVrh.74 capsid. |
| 1 | AAVrh.10 | | SERPINA1 | 5265 | Payload comprising a SERPINA1 gene or variant thereof packaged within a AAVrh.10 capsid. |
| 1 | AAVhu.37 | | SERPINA1 | 5265 | Payload comprising a SERPINA1 gene or variant thereof packaged within a AAVhu.37 capsid. |
| 1 | AAVrh.K | | SERPINA1 | 5265 | Payload comprising a SERPINA1 gene or variant thereof packaged within a AAVrh.K capsid. |
| 1 | AAVrh.39 | | SERPINA1 | 5265 | Payload comprising a SERPINA1 gene or variant thereof packaged within a AAVrh.39 capsid. |
| 1 | AAVrh.9 | | SERPINA1 | 5265 | Payload comprising a SERPINA1 gene or variant thereof packaged within a AAVrh.9 capsid. |
| 1 | avian AAV | | SERPINA1 | 5265 | Payload comprising a SERPINA1 gene or variant thereof packaged within a avian capsid. |

Fig. 29 (Continued)

| | | | | | |
|---|---|---|---|---|---|
| 1 | bovine AAV | | SERPINA1 | 5265 | Payload comprising a SERPINA1 gene or variant thereof packaged within a bovine capsid. |
| 1 | canine AAV | | SERPINA1 | 5265 | Payload comprising a SERPINA1 gene or variant thereof packaged within a canine capsid. |
| 1 | equine AAV | | SERPINA1 | 5265 | Payload comprising a SERPINA1 gene or variant thereof packaged within a equine capsid. |
| 1 | primate AAV | | SERPINA1 | 5265 | Payload comprising a SERPINA1 gene or variant thereof packaged within a primate capsid. |
| 1 | non-primate AAV | | SERPINA1 | 5265 | Payload comprising a SERPINA1 gene or variant thereof packaged within a non-primate capsid. |
| 1 | ovine AAV | | SERPINA1 | 5265 | Payload comprising a SERPINA1 gene or variant thereof packaged within a ovine capsid. |
| 1 | hybrid AAV | | SERPINA1 | 5265 | Payload comprising a SERPINA1 gene or variant thereof packaged within a hybrid capsid. |
| 1 | chimeric AAV | | SERPINA1 | 5265 | Payload comprising a SERPINA1 gene or variant thereof packaged within a chimeric capsid. |
| 2 | AAV1 | 1450374 | SERPINA1 | 5265 | Payload comprising a SERPINA1 gene or variant thereof packaged within a AAV1 capsid. |
| 2 | AAV2 | | SERPINA1 | 5265 | Payload comprising a SERPINA1 gene or variant thereof packaged within a AAV2 capsid. |
| 2 | AAV3 | | SERPINA1 | 5265 | Payload comprising a SERPINA1 gene or variant thereof packaged within a AAV3 capsid. |
| 2 | AAV4 | 1446389 | SERPINA1 | 5265 | Payload comprising a SERPINA1 gene or variant thereof packaged within a AAV4 capsid. |
| 2 | AAV5 | | SERPINA1 | 5265 | Payload comprising a SERPINA1 gene or variant thereof packaged within a AAV5 capsid. |
| 2 | AAV6 | | SERPINA1 | 5265 | Payload comprising a SERPINA1 gene or variant thereof packaged within a AAV6 capsid. |
| 2 | AAV7 | | SERPINA1 | 5265 | Payload comprising a SERPINA1 gene or variant thereof packaged within a AAV7 capsid. |
| 2 | AAV8 | 5075992 | SERPINA1 | 5265 | Payload comprising a SERPINA1 gene or variant thereof packaged within a AAV8 capsid. |
| 2 | AAV9 | | SERPINA1 | 5265 | Payload comprising a SERPINA1 gene or variant thereof packaged within a AAV9 capsid. |

Fig. 29 (Continued)

| | | | | | |
|---|---|---|---|---|---|
| 2 | AAV10 | | SERPINA1 | 5265 | Payload comprising a SERPINA1 gene or variant thereof packaged within a AAV10 capsid. |
| 2 | AAV11 | | SERPINA1 | 5265 | Payload comprising a SERPINA1 gene or variant thereof packaged within a AAV11 capsid. |
| 2 | AAVC11.01 | | SERPINA1 | 5265 | Payload comprising a SERPINA1 gene or variant thereof packaged within a AAVC11.01 capsid. |
| 2 | AAVC11.02 | | SERPINA1 | 5265 | Payload comprising a SERPINA1 gene or variant thereof packaged within a AAVC11.02 capsid. |
| 2 | AAVC11.03 | | SERPINA1 | 5265 | Payload comprising a SERPINA1 gene or variant thereof packaged within a AAVC11.03 capsid. |
| 2 | AAVC11.04 | | SERPINA1 | 5265 | Payload comprising a SERPINA1 gene or variant thereof packaged within a AAVC11.04 capsid. |
| 2 | AAVC11.05 | | SERPINA1 | 5265 | Payload comprising a SERPINA1 gene or variant thereof packaged within a AAVC11.05 capsid. |
| 2 | AAVC11.06 | | SERPINA1 | 5265 | Payload comprising a SERPINA1 gene or variant thereof packaged within a AAVC11.06 capsid. |
| 2 | AAVC11.07 | | SERPINA1 | 5265 | Payload comprising a SERPINA1 gene or variant thereof packaged within a AAVC11.07 capsid. |
| 2 | AAVC11.08 | | SERPINA1 | 5265 | Payload comprising a SERPINA1 gene or variant thereof packaged within a AAVC11.08 capsid. |
| 2 | AAVC11.09 | | SERPINA1 | 5265 | Payload comprising a SERPINA1 gene or variant thereof packaged within a AAVC11.09 capsid. |
| 2 | AAVC11.10 | | SERPINA1 | 5265 | Payload comprising a SERPINA1 gene or variant thereof packaged within a AAVC11.10 capsid. |
| 2 | AAVC11.11 | | SERPINA1 | 5265 | Payload comprising a SERPINA1 gene or variant thereof packaged within a AAVC11.11 capsid. |
| 2 | AAVC11.12 | | SERPINA1 | 5265 | Payload comprising a SERPINA1 gene or variant thereof packaged within a AAVC11.12 capsid. |
| 2 | AAVC11.13 | | SERPINA1 | 5265 | Payload comprising a SERPINA1 gene or variant thereof packaged within a AAVC11.13 capsid. |
| 2 | AAVC11.14 | | SERPINA1 | 5265 | Payload comprising a SERPINA1 gene or variant thereof packaged within a AAVC11.14 capsid. |
| 2 | AAVC11.15 | | SERPINA1 | 5265 | Payload comprising a SERPINA1 gene or variant thereof packaged within a AAVC11.15 capsid. |

Fig. 29 (Continued)

| | | | | | |
|---|---|---|---|---|---|
| 2 | AAVC11.16 | | SERPINA1 | 5265 | Payload comprising a SERPINA1 gene or variant thereof packaged within a AAVC11.16 capsid. |
| 2 | AAVC11.17 | | SERPINA1 | 5265 | Payload comprising a SERPINA1 gene or variant thereof packaged within a AAVC11.17 capsid. |
| 2 | AAVC11.18 | | SERPINA1 | 5265 | Payload comprising a SERPINA1 gene or variant thereof packaged within a AAVC11.18 capsid. |
| 2 | AAVC11.19 | | SERPINA1 | 5265 | Payload comprising a SERPINA1 gene or variant thereof packaged within a AAVC11.19 capsid. |
| 2 | AAV12 | | SERPINA1 | 5265 | Payload comprising a SERPINA1 gene or variant thereof packaged within a AAV12 capsid. |
| 2 | AAV13 | | SERPINA1 | 5265 | Payload comprising a SERPINA1 gene or variant thereof packaged within a AAV13 capsid. |
| 2 | AAV-DJ | | SERPINA1 | 5265 | Payload comprising a SERPINA1 gene or variant thereof packaged within a AAV-DJ capsid. |
| 2 | AAV-LK03 | | SERPINA1 | 5265 | Payload comprising a SERPINA1 gene or variant thereof packaged within a AAV-LK03 capsid. |
| 2 | AAV-LK19 | | SERPINA1 | 5265 | Payload comprising a SERPINA1 gene or variant thereof packaged within a AAV-LK19 capsid. |
| 2 | AAVrh.74 | | SERPINA1 | 5265 | Payload comprising a SERPINA1 gene or variant thereof packaged within a AAVrh.74 capsid. |
| 2 | AAVrh.10 | | SERPINA1 | 5265 | Payload comprising a SERPINA1 gene or variant thereof packaged within a AAVrh.10 capsid. |
| 2 | AAVhu.37 | | SERPINA1 | 5265 | Payload comprising a SERPINA1 gene or variant thereof packaged within a AAVhu.37 capsid. |
| 2 | AAVrh.K | | SERPINA1 | 5265 | Payload comprising a SERPINA1 gene or variant thereof packaged within a AAVrh.K capsid. |
| 2 | AAVrh.39 | | SERPINA1 | 5265 | Payload comprising a SERPINA1 gene or variant thereof packaged within a AAVrh.39 capsid. |
| 2 | AAVrh.9 | | SERPINA1 | 5265 | Payload comprising a SERPINA1 gene or variant thereof packaged within a AAVrh.9 capsid. |
| 2 | avian AAV | | SERPINA1 | 5265 | Payload comprising a SERPINA1 gene or variant thereof packaged within a avian capsid. |

Fig. 29 (Continued)

| | | | | | |
|---|---|---|---|---|---|
| 2 | bovine AAV | | SERPINA1 | 5265 | Payload comprising a SERPINA1 gene or variant thereof packaged within a bovine capsid. |
| 2 | canine AAV | | SERPINA1 | 5265 | Payload comprising a SERPINA1 gene or variant thereof packaged within a canine capsid. |
| 2 | equine AAV | | SERPINA1 | 5265 | Payload comprising a SERPINA1 gene or variant thereof packaged within a equine capsid. |
| 2 | primate AAV | | SERPINA1 | 5265 | Payload comprising a SERPINA1 gene or variant thereof packaged within a primate capsid. |
| 2 | non-primate AAV | | SERPINA1 | 5265 | Payload comprising a SERPINA1 gene or variant thereof packaged within a non-primate capsid. |
| 2 | ovine AAV | | SERPINA1 | 5265 | Payload comprising a SERPINA1 gene or variant thereof packaged within a ovine capsid. |
| 2 | hybrid AAV | | SERPINA1 | 5265 | Payload comprising a SERPINA1 gene or variant thereof packaged within a hybrid capsid. |
| 2 | chimeric AAV | | SERPINA1 | 5265 | Payload comprising a SERPINA1 gene or variant thereof packaged within a chimeric capsid. |
| 1 | AAV1 | 1450374 | SGCA | 6442 | Payload comprising a SGCA gene or variant thereof packaged within a AAV1 capsid. |
| 1 | AAV2 | | SGCA | 6442 | Payload comprising a SGCA gene or variant thereof packaged within a AAV2 capsid. |
| 1 | AAV3 | | SGCA | 6442 | Payload comprising a SGCA gene or variant thereof packaged within a AAV3 capsid. |
| 1 | AAV4 | 1446389 | SGCA | 6442 | Payload comprising a SGCA gene or variant thereof packaged within a AAV4 capsid. |
| 1 | AAV5 | | SGCA | 6442 | Payload comprising a SGCA gene or variant thereof packaged within a AAV5 capsid. |
| 1 | AAV6 | | SGCA | 6442 | Payload comprising a SGCA gene or variant thereof packaged within a AAV6 capsid. |
| 1 | AAV7 | | SGCA | 6442 | Payload comprising a SGCA gene or variant thereof packaged within a AAV7 capsid. |
| 1 | AAV8 | 5075992 | SGCA | 6442 | Payload comprising a SGCA gene or variant thereof packaged within a AAV8 capsid. |
| 1 | AAV9 | | SGCA | 6442 | Payload comprising a SGCA gene or variant thereof packaged within a AAV9 capsid. |

Fig. 29 (Continued)

| | | | | | |
|---|---|---|---|---|---|
| 1 | AAV10 | | SGCA | 6442 | Payload comprising a SGCA gene or variant thereof packaged within a AAV10 capsid. |
| 1 | AAV11 | | SGCA | 6442 | Payload comprising a SGCA gene or variant thereof packaged within a AAV11 capsid. |
| 1 | AAVC11.01 | | SGCA | 6442 | Payload comprising a SGCA gene or variant thereof packaged within a AAVC11.01 capsid. |
| 1 | AAVC11.02 | | SGCA | 6442 | Payload comprising a SGCA gene or variant thereof packaged within a AAVC11.02 capsid. |
| 1 | AAVC11.03 | | SGCA | 6442 | Payload comprising a SGCA gene or variant thereof packaged within a AAVC11.03 capsid. |
| 1 | AAVC11.04 | | SGCA | 6442 | Payload comprising a SGCA gene or variant thereof packaged within a AAVC11.04 capsid. |
| 1 | AAVC11.05 | | SGCA | 6442 | Payload comprising a SGCA gene or variant thereof packaged within a AAVC11.05 capsid. |
| 1 | AAVC11.06 | | SGCA | 6442 | Payload comprising a SGCA gene or variant thereof packaged within a AAVC11.06 capsid. |
| 1 | AAVC11.07 | | SGCA | 6442 | Payload comprising a SGCA gene or variant thereof packaged within a AAVC11.07 capsid. |
| 1 | AAVC11.08 | | SGCA | 6442 | Payload comprising a SGCA gene or variant thereof packaged within a AAVC11.08 capsid. |
| 1 | AAVC11.09 | | SGCA | 6442 | Payload comprising a SGCA gene or variant thereof packaged within a AAVC11.09 capsid. |
| 1 | AAVC11.10 | | SGCA | 6442 | Payload comprising a SGCA gene or variant thereof packaged within a AAVC11.10 capsid. |
| 1 | AAVC11.11 | | SGCA | 6442 | Payload comprising a SGCA gene or variant thereof packaged within a AAVC11.11 capsid. |
| 1 | AAVC11.12 | | SGCA | 6442 | Payload comprising a SGCA gene or variant thereof packaged within a AAVC11.12 capsid. |
| 1 | AAVC11.13 | | SGCA | 6442 | Payload comprising a SGCA gene or variant thereof packaged within a AAVC11.13 capsid. |
| 1 | AAVC11.14 | | SGCA | 6442 | Payload comprising a SGCA gene or variant thereof packaged within a AAVC11.14 capsid. |
| 1 | AAVC11.15 | | SGCA | 6442 | Payload comprising a SGCA gene or variant thereof packaged within a AAVC11.15 capsid. |

Fig. 29 (Continued)

| | | | | | |
|---|---|---|---|---|---|
| 1 | AAVC11.16 | | SGCA | 6442 | Payload comprising a SGCA gene or variant thereof packaged within a AAVC11.16 capsid. |
| 1 | AAVC11.17 | | SGCA | 6442 | Payload comprising a SGCA gene or variant thereof packaged within a AAVC11.17 capsid. |
| 1 | AAVC11.18 | | SGCA | 6442 | Payload comprising a SGCA gene or variant thereof packaged within a AAVC11.18 capsid. |
| 1 | AAVC11.19 | | SGCA | 6442 | Payload comprising a SGCA gene or variant thereof packaged within a AAVC11.19 capsid. |
| 1 | AAV12 | | SGCA | 6442 | Payload comprising a SGCA gene or variant thereof packaged within a AAV12 capsid. |
| 1 | AAV13 | | SGCA | 6442 | Payload comprising a SGCA gene or variant thereof packaged within a AAV13 capsid. |
| 1 | AAV-DJ | | SGCA | 6442 | Payload comprising a SGCA gene or variant thereof packaged within a AAV-DJ capsid. |
| 1 | AAV-LK03 | | SGCA | 6442 | Payload comprising a SGCA gene or variant thereof packaged within a AAV-LK03 capsid. |
| 1 | AAV-LK19 | | SGCA | 6442 | Payload comprising a SGCA gene or variant thereof packaged within a AAV-LK19 capsid. |
| 1 | AAVrh.74 | | SGCA | 6442 | Payload comprising a SGCA gene or variant thereof packaged within a AAVrh.74 capsid. |
| 1 | AAVrh.10 | | SGCA | 6442 | Payload comprising a SGCA gene or variant thereof packaged within a AAVrh.10 capsid. |
| 1 | AAVhu.37 | | SGCA | 6442 | Payload comprising a SGCA gene or variant thereof packaged within a AAVhu.37 capsid. |
| 1 | AAVrh.K | | SGCA | 6442 | Payload comprising a SGCA gene or variant thereof packaged within a AAVrh.K capsid. |
| 1 | AAVrh.39 | | SGCA | 6442 | Payload comprising a SGCA gene or variant thereof packaged within a AAVrh.39 capsid. |
| 1 | AAVrh.9 | | SGCA | 6442 | Payload comprising a SGCA gene or variant thereof packaged within a AAVrh.9 capsid. |
| 1 | avian AAV | | SGCA | 6442 | Payload comprising a SGCA gene or variant thereof packaged within a avian capsid. |

Fig. 29 (Continued)

| | | | | | |
|---|---|---|---|---|---|
| 1 | bovine AAV | | SGCA | 6442 | Payload comprising a SGCA gene or variant thereof packaged within a bovine capsid. |
| 1 | canine AAV | | SGCA | 6442 | Payload comprising a SGCA gene or variant thereof packaged within a canine capsid. |
| 1 | equine AAV | | SGCA | 6442 | Payload comprising a SGCA gene or variant thereof packaged within a equine capsid. |
| 1 | primate AAV | | SGCA | 6442 | Payload comprising a SGCA gene or variant thereof packaged within a primate capsid. |
| 1 | non-primate AAV | | SGCA | 6442 | Payload comprising a SGCA gene or variant thereof packaged within a non-primate capsid. |
| 1 | ovine AAV | | SGCA | 6442 | Payload comprising a SGCA gene or variant thereof packaged within a ovine capsid. |
| 1 | hybrid AAV | | SGCA | 6442 | Payload comprising a SGCA gene or variant thereof packaged within a hybrid capsid. |
| 1 | chimeric AAV | | SGCA | 6442 | Payload comprising a SGCA gene or variant thereof packaged within a chimeric capsid. |
| 2 | AAV1 | 1450374 | SGCA | 6442 | Payload comprising a SGCA gene or variant thereof packaged within a AAV1 capsid. |
| 2 | AAV2 | | SGCA | 6442 | Payload comprising a SGCA gene or variant thereof packaged within a AAV2 capsid. |
| 2 | AAV3 | | SGCA | 6442 | Payload comprising a SGCA gene or variant thereof packaged within a AAV3 capsid. |
| 2 | AAV4 | 1446389 | SGCA | 6442 | Payload comprising a SGCA gene or variant thereof packaged within a AAV4 capsid. |
| 2 | AAV5 | | SGCA | 6442 | Payload comprising a SGCA gene or variant thereof packaged within a AAV5 capsid. |
| 2 | AAV6 | | SGCA | 6442 | Payload comprising a SGCA gene or variant thereof packaged within a AAV6 capsid. |
| 2 | AAV7 | | SGCA | 6442 | Payload comprising a SGCA gene or variant thereof packaged within a AAV7 capsid. |
| 2 | AAV8 | 5075992 | SGCA | 6442 | Payload comprising a SGCA gene or variant thereof packaged within a AAV8 capsid. |
| 2 | AAV9 | | SGCA | 6442 | Payload comprising a SGCA gene or variant thereof packaged within a AAV9 capsid. |

Fig. 29 (Continued)

| | | | | | |
|---|---|---|---|---|---|
| 2 | AAV10 | | SGCA | 6442 | Payload comprising a SGCA gene or variant thereof packaged within a AAV10 capsid. |
| 2 | AAV11 | | SGCA | 6442 | Payload comprising a SGCA gene or variant thereof packaged within a AAV11 capsid. |
| 2 | AAVC11.01 | | SGCA | 6442 | Payload comprising a SGCA gene or variant thereof packaged within a AAVC11.01 capsid. |
| 2 | AAVC11.02 | | SGCA | 6442 | Payload comprising a SGCA gene or variant thereof packaged within a AAVC11.02 capsid. |
| 2 | AAVC11.03 | | SGCA | 6442 | Payload comprising a SGCA gene or variant thereof packaged within a AAVC11.03 capsid. |
| 2 | AAVC11.04 | | SGCA | 6442 | Payload comprising a SGCA gene or variant thereof packaged within a AAVC11.04 capsid. |
| 2 | AAVC11.05 | | SGCA | 6442 | Payload comprising a SGCA gene or variant thereof packaged within a AAVC11.05 capsid. |
| 2 | AAVC11.06 | | SGCA | 6442 | Payload comprising a SGCA gene or variant thereof packaged within a AAVC11.06 capsid. |
| 2 | AAVC11.07 | | SGCA | 6442 | Payload comprising a SGCA gene or variant thereof packaged within a AAVC11.07 capsid. |
| 2 | AAVC11.08 | | SGCA | 6442 | Payload comprising a SGCA gene or variant thereof packaged within a AAVC11.08 capsid. |
| 2 | AAVC11.09 | | SGCA | 6442 | Payload comprising a SGCA gene or variant thereof packaged within a AAVC11.09 capsid. |
| 2 | AAVC11.10 | | SGCA | 6442 | Payload comprising a SGCA gene or variant thereof packaged within a AAVC11.10 capsid. |
| 2 | AAVC11.11 | | SGCA | 6442 | Payload comprising a SGCA gene or variant thereof packaged within a AAVC11.11 capsid. |
| 2 | AAVC11.12 | | SGCA | 6442 | Payload comprising a SGCA gene or variant thereof packaged within a AAVC11.12 capsid. |
| 2 | AAVC11.13 | | SGCA | 6442 | Payload comprising a SGCA gene or variant thereof packaged within a AAVC11.13 capsid. |
| 2 | AAVC11.14 | | SGCA | 6442 | Payload comprising a SGCA gene or variant thereof packaged within a AAVC11.14 capsid. |
| 2 | AAVC11.15 | | SGCA | 6442 | Payload comprising a SGCA gene or variant thereof packaged within a AAVC11.15 capsid. |

Fig. 29 (Continued)

| | | | | | |
|---|---|---|---|---|---|
| 2 | AAVC11.16 | | SGCA | 6442 | Payload comprising a SGCA gene or variant thereof packaged within a AAVC11.16 capsid. |
| 2 | AAVC11.17 | | SGCA | 6442 | Payload comprising a SGCA gene or variant thereof packaged within a AAVC11.17 capsid. |
| 2 | AAVC11.18 | | SGCA | 6442 | Payload comprising a SGCA gene or variant thereof packaged within a AAVC11.18 capsid. |
| 2 | AAVC11.19 | | SGCA | 6442 | Payload comprising a SGCA gene or variant thereof packaged within a AAVC11.19 capsid. |
| 2 | AAV12 | | SGCA | 6442 | Payload comprising a SGCA gene or variant thereof packaged within a AAV12 capsid. |
| 2 | AAV13 | | SGCA | 6442 | Payload comprising a SGCA gene or variant thereof packaged within a AAV13 capsid. |
| 2 | AAV-DJ | | SGCA | 6442 | Payload comprising a SGCA gene or variant thereof packaged within a AAV-DJ capsid. |
| 2 | AAV-LK03 | | SGCA | 6442 | Payload comprising a SGCA gene or variant thereof packaged within a AAV-LK03 capsid. |
| 2 | AAV-LK19 | | SGCA | 6442 | Payload comprising a SGCA gene or variant thereof packaged within a AAV-LK19 capsid. |
| 2 | AAVrh.74 | | SGCA | 6442 | Payload comprising a SGCA gene or variant thereof packaged within a AAVrh.74 capsid. |
| 2 | AAVrh.10 | | SGCA | 6442 | Payload comprising a SGCA gene or variant thereof packaged within a AAVrh.10 capsid. |
| 2 | AAVhu.37 | | SGCA | 6442 | Payload comprising a SGCA gene or variant thereof packaged within a AAVhu.37 capsid. |
| 2 | AAVrh.K | | SGCA | 6442 | Payload comprising a SGCA gene or variant thereof packaged within a AAVrh.K capsid. |
| 2 | AAVrh.39 | | SGCA | 6442 | Payload comprising a SGCA gene or variant thereof packaged within a AAVrh.39 capsid. |
| 2 | AAVrh.9 | | SGCA | 6442 | Payload comprising a SGCA gene or variant thereof packaged within a AAVrh.9 capsid. |
| 2 | avian AAV | | SGCA | 6442 | Payload comprising a SGCA gene or variant thereof packaged within a avian capsid. |

Fig. 29 (Continued)

| | | | | | |
|---|---|---|---|---|---|
| 2 | bovine AAV | | SGCA | 6442 | Payload comprising a SGCA gene or variant thereof packaged within a bovine capsid. |
| 2 | canine AAV | | SGCA | 6442 | Payload comprising a SGCA gene or variant thereof packaged within a canine capsid. |
| 2 | equine AAV | | SGCA | 6442 | Payload comprising a SGCA gene or variant thereof packaged within a equine capsid. |
| 2 | primate AAV | | SGCA | 6442 | Payload comprising a SGCA gene or variant thereof packaged within a primate capsid. |
| 2 | non-primate AAV | | SGCA | 6442 | Payload comprising a SGCA gene or variant thereof packaged within a non-primate capsid. |
| 2 | ovine AAV | | SGCA | 6442 | Payload comprising a SGCA gene or variant thereof packaged within a ovine capsid. |
| 2 | hybrid AAV | | SGCA | 6442 | Payload comprising a SGCA gene or variant thereof packaged within a hybrid capsid. |
| 2 | chimeric AAV | | SGCA | 6442 | Payload comprising a SGCA gene or variant thereof packaged within a chimeric capsid. |

FIG. 29 (Continued)

SEQUENCE LISTING

```
<160> NUMBER OF SEQ ID NOS: 18

<210> SEQ ID NO 1
<211> LENGTH: 20985
<212> TYPE: DNA
<213> ORGANISM: Artificial Sequence
<220> FEATURE:
<223> OTHER INFORMATION: Synthetic: Rep/Helper Plasmid
```

<400> SEQUENCE: 1
tcttccgctt cctcgctcac tgactcgctg cgctcggtcg ttcggctgcg gcgagcggta 60
tcagctcact caaaggcggt aatacggtta tccacagaat caggggataa cgcaggaaag 120
aacatgtgag caaaaggcca gcaaaaggcc aggaaccgta aaaaggccgc gttgctggcg 180
tttttccata ggctccgccc ccctgacgag catcacaaaa atcgacgctc aagtcagagg 240
tggcgaaacc cgacaggact ataaagatac caggcgtttc cccctggaag ctccctcgtg 300
cgctctcctg ttccgaccct gccgcttacc ggatacctgt ccgcctttct cccttcggga 360
agcgtggcgc tttctcatag ctcacgctgt aggtatctca gttcggtgta ggtcgttcgc 420
tccaagctgg gctgtgtgca cgaacccccc gttcagcccg accgctgcgc cttatccggt 480
aactatcgtc ttgagtccaa cccggtaaga cacgacttat cgccactggc agcagccact 540
ggtaacagga ttagcagagc gaggtatgta ggcggtgcta cagagttctt gaagtggtgg 600
cctaactacg gctacactag aagaacagta tttggtatct gcgctctgct gaagccagtt 660
accttcggaa aaagagttgg tagctcttga tccggcaaac aaaccaccgc tggtagcggt 720
ggtttttttg tttgcaagca gcagattacg cgcagaaaaa aaggatctca agaagatcct 780
ttgatctttt ctacggggtc tgacgctcag tggaacgaaa actcacgtta agggattttg 840
gtcatgagat tatcaaaaag gatcttcacc tagatccttt taaattaaaa atgaagtttt 900
aaatcaatct aaagtatata tgagtaaact tggtctgaca gttattagaa aaactcatcg 960
agcatcaaat gaaactgcaa tttattcata tcaggattat caataccata tttttgaaaa 1020
agccgtttct gtaatgaagg agaaaactca ccgaggcagt tccataggat ggcaagatcc 1080
tggtatcggt ctgcgattcc gactcgtcca acatcaatac aacctattaa tttcccctcg 1140
tcaaaaataa ggttatcaag tgagaaatca ccatgagtga cgactgaatc cggtgagaat 1200
ggcaaaagtt tatgcatttc tttccagact tgttcaacag gccagccatt acgctcgtca 1260
tcaaaatcac tcgcatcaac caaaccgtta ttcattcgtg attgcgcctg agcgagacga 1320
aatacgcgat cgctgttaaa aggacaatta caaacaggaa tcgaatgcaa ccggcgcagg 1380
aacactgcca gcgcatcaac aatattttca cctgaatcag gatattcttc taatacctgg 1440
aatgctgttt ttccggggat cgcagtggtg agtaaccatg catcatcagg agtacggata 1500
aaatgcttga tggtcggaag aggcataaat tccgtcagcc agtttagtct gaccatctca 1560
tctgtaacat cattggcaac gctacctttg ccatgtttca gaaacaactc tggcgcatcg 1620
ggcttcccat acaagcgata gattgtcgca cctgattgcc cgacattatc gcgagcccat 1680
ttatacccat ataaatcagc atccatgttg gaatttaatc gcggcctcga cgtttcccgt 1740
tgaatatggc tcatactctt cctttttcaa tattattgaa gcatttatca gggttattgt 1800
ctcatgagcg gatacatatt tgaatgtatt tagaaaaata aacaaatagg ggttccgcgc 1860
acatttcccc gaaaagtgcc acctgacgtc taagaaacca ttattatcat gacattaacc 1920
tataaaaata ggcgtatcac gaggcccttt cgtctcgcgc gtttcggtga tgacggtgaa 1980
aacctctgac acatgcagct cccggagacg gtcacagctt gtctgtaagc ggatgccggg 2040
agcagacaag cccgtcaggg cgcgtcagcg ggtgttggcg ggtgtcgggg ctggcttaac 2100
tatgcggcat cagagcagat tgtactgaga gtgcaccata aaattgtaaa cgttacgtca 2160
tagggttagg gaggtcctgt attagaggtc acgtgagtgt tttgcgacat tttgcgacac 2220
catgtggtca cgctgggtat ttaagcccga gtgagcacgc agggtctcca ttttgaagcg 2280

-continued

```
ggaggtttga acgcgcagcc gccatgccgg ggttttacga gattgtgatt aaggtcccca   2340
gcgaccttga cgagcatctg cccggcattt ctgacagctt tgtgaactgg gtggccgaga   2400
aggaatggga gttgccgcca gattctgaca tggatctgaa tctgattgag caggcacccc   2460
tgaccgtggc cgagaagctg cagcgcgact ttctgacgga atggcgccgt gtgagtaagg   2520
ccccggaggc ccttttcttt gtgcaatttg agaagggaga gagctacttc cacatgcacg   2580
tgctcgtgga aaccaccggg gtgaaatcca tggttttggg acgtttcctg agtcagattc   2640
gcgaaaaact gattcagaga atttaccgcg ggatcgagcc gactttgcca aactggttcg   2700
cggtcacaaa gaccagaaat ggcgccggag gcgggaacaa ggtggtggat gagtgctaca   2760
tccccaatta cttgctcccc aaaacccagc ctgagctcca gtgggcgtgg actaatatgg   2820
aacagtattt aagcgcctgt ttgaatctca cggagcgtaa acggttggtg gcgcagcatc   2880
tgacgcacgt gtcgcagacg caggagcaga acaaagagaa tcagaatccc aattctgatg   2940
cgccggtgat cagatcaaaa acttcagcca ggtacatgga gctggtcggg tggctcgtgg   3000
acaaggggat tacctcggag aagcagtgga tccaggagga ccaggcctca tacatctcct   3060
tcaatgcggc ctccaactcg cggtcccaaa tcaaggctgc cttggacaat gcgggaaaga   3120
ttatgagcct gactaaaacc gcccccgact acctggtggg ccagcagccc gtggaggaca   3180
tttccagcaa tcggatttat aaaattttgg aactaaacgg gtacgatccc caatatgcgg   3240
cttccgtctt tctgggatgg gccacgaaaa agttcggcaa gaggaacacc atctggctgt   3300
ttgggcctgc aactaccggg aagaccaaca tcgcggaggc catagcccac actgtgccct   3360
tctacgggtg cgtaaactgg accaatgaga actttccctt caacgactgt gtcgacaaga   3420
tggtgatctg gtgggaggag gggaagatga ccgccaaggt cgtggagtcg gccaaagcca   3480
ttctcggagg aagcaaggtg cgcgtggacc agaaatgcaa gtcctcggcc cagatagacc   3540
cgactcccgt gatcgtcacc tccaacacca acatgtgcgc cgtgattgac gggaactcaa   3600
cgaccttcga acaccagcag ccgttgcaag accggatgtt caaatttgaa ctcacccgcc   3660
gtctggatca tgactttggg aaggtcacca agcaggaagt caaagacttt ttccggtggg   3720
caaaggatca cgtggttgag gtggagcatg aattctacgt caaaaagggt ggagccaaga   3780
aaagacccgc ccccagtgac gcagatataa gtgagcccaa acgggtgcgc gagtcagttg   3840
cgcagccatc gacgtcagac gcggaagctt cgatcaacta cgcagacagg taccaaaaca   3900
aatgttctcg tcacgtgggc atgaatctga tgctgtttcc ctgcagacaa tgcgagagaa   3960
tgaatcagaa ttcaaatatc tgcttcactc acggacagaa agactgttta gagtgctttc   4020
ccgtgtcaga atctcaaccc gtttctgtcg tcaaaaaggc gtatcagaaa ctgtgctaca   4080
ttcatcatat catgggaaag gtgccagacg cttgcactgc ctgcgatctg gtcaatgtgg   4140
atttggatga ctgcatcttt gaacaataaa tgatttaaat caggtatggc tgccgatggt   4200
tatcttccag attggctcga ggacactctc tctgatcgac gtttaaacca tatgaacgtt   4260
aatattttgt taaaattcgc gttaaatttt tgttaaatca gctcattttt taaccaatag   4320
gccgaaatcg gcaaaatccc ttataaatca aaagaatagc ccgagatagg gttgagtgtt   4380
gttccagttt ggaacaagag tccactatta aagaacgtgg actccaacgt caaagggcga   4440
aaaaccgtct atcagggcga tggcccacta cgtgaaccat cacccaaatc aagttttttg   4500
gggtcgaggt gccgtaaagc actaaatcgg aaccctaaag ggagcccccg atttagagct   4560
tgacggggaa agccggcgaa cgtggcgaga aaggaaggga agaaagcgaa aggagcgggc   4620
gctagggcgc tggcaagtgt agcggtcacg ctgcgcgtaa ccaccacacc cgccgcgctt   4680
```

```
aatgcgccgc tacagggcgc gtactatggt tgctttgacg tatgcggtgt gaaataccgc   4740
acagatgcgt aaggagaaaa taccgcatca ggcgccattc gccattcagg ctgcgcaact   4800
gttgggaagg gcgatcggtg cgggcctctt cgctattacg ccagctggcg aaagggggat   4860
gtgctgcaag gcgattaagt tgggtaacgc cagggttttc ccagtcacga cgttgtaaaa   4920
cgacggccag tgccaagctt aaggtgcacg gcccacgtgg ccactagtac ttctcgacag   4980
aagcaccatg tccttgggtc cggcctgctg aatgcgcagg cggtcggcca tgccccaggc   5040
ttcgttttga catcggcgca ggtctttgta gtagtcttgc atgagccttt ctaccggcac   5100
ttcttcttct ccttcctctt gtcctgcatc tcttgcatct atcgctgcgg cggcggcgga   5160
gtttggccgt aggtggcgcc ctcttcctcc catgcgtgtg accccgaagc ccctcatcgg   5220
ctgaagcagg gctaggtcgg cgacaacgcg ctcggctaat atggcctgct gcacctgcgt   5280
gagggtagac tggaagtcat ccatgtccac aaagcggtgg tatgcgcccg tgttgatggt   5340
gtaagtgcag ttggccataa cggaccagtt aacggtctgg tgacccggct gcgagagctc   5400
ggtgtacctg agacgcgagt aagccctcga gtcaaatacg tagtcgttgc aagtccgcac   5460
caggtactgg tatcccacca aaaagtgcgg cggcggctgg cggtagaggg gccagcgtag   5520
ggtggccggg gctccggggg cgagatcttc caacataagg cgatgatatc cgtagatgta   5580
cctggacatc caggtgatgc cggcggcggt ggtggaggcg cgcggaaagt cgcggacgcg   5640
gttccagatg ttgcgcagcg gcaaaaagtg ctccatggtc gggacgctct ggccggtcag   5700
gcgcgcgcaa tcgttgacgc tctaccgtgc aaaaggagag cctgtaagcg ggcactcttc   5760
cgtggtctgg tggataaatt cgcaagggta tcatggcgga cgaccggggt tcgagccccg   5820
tatccggccg tccgccgtga tccatgcggt taccgcccgc gtgtcgaacc caggtgtgcg   5880
acgtcagaca acgggggagt gctccttttg gcttccttcc aggcgcggcg gctgctgcgc   5940
tagctttttt ggccactggc cgcgcgcagc gtaagcggtt aggctggaaa gcgaaagcat   6000
taagtggctc gctccctgta gccggagggt tattttccaa gggttgagtc gcgggacccc   6060
cggttcgagt ctcggaccgg ccggactgcg gcgaacgggg gtttgcctcc ccgtcatgca   6120
agaccccgct tgcaaattcc tccggaaaca gggacgagcc ccttttttgc ttttcccaga   6180
tgcatccggt gctgcggcag atgcgccccc ctcctcagca gcggcaagag caagagcagc   6240
ggcagacatg cagggcaccc tcccctcctc ctaccgcgtc aggaggggcg acatccgcgg   6300
ttgacgcggc agcagatggt gattacgaac cccgcggcg ccgggcccgg cactacctgg   6360
acttggagga gggcgagggc ctggcgcggc taggagcgcc ctctcctgag cggtacccaa   6420
gggtgcagct gaagcgtgat acgcgtgagg cgtacgtgcc gcggcagaac ctgtttcgcg   6480
accgcgaggg agaggagccc gaggagatgc gggatcgaaa gttccacgca gggcgcgagc   6540
tgcggcatgg cctgaatcgc gagcggttgc tgcgcgagga ggactttgag cccgacgcgc   6600
gaaccgggat tagtcccgcg cgcgcacacg tggcggccgc cgacctggta accgcatacg   6660
agcagacggt gaaccaggag attaactttc aaaaaagctt taacaaccac gtgcgtacgc   6720
ttgtggcgcg cgaggaggtg gctataggac tgatgcatct gtgggacttt gtaagcgcgc   6780
tggagcaaaa cccaaatagc aagccgctca tggcgcagct gttccttata gtgcagcaca   6840
gcagggacaa cgaggcattc agggatgcgc tgctaaacat agtagagccc gagggccgct   6900
ggctgctcga tttgataaac atcctgcaga gcatagtggt gcaggagcgc agcttgagcc   6960
tggctgacaa ggtggccgcc atcaactatt ccatgcttag cctgggcaag ttttacgccc   7020
```

-continued

```
gcaagatata ccatacccct tacgttccca tagacaagga ggtaaagatc gaggggttct   7080
acatgcgcat ggcgctgaag gtgcttacct tgagcgacga cctgggcgtt tatcgcaacg   7140
agcgcatcca caaggccgtg agcgtgagcc ggcggcgcga gctcagcgac cgcgagctga   7200
tgcacagcct gcaaagggcc ctggctggca cgggcagcgg cgatagagag gccgagtcct   7260
actttgacgc gggcgctgac ctgcgctggg ccccaagccg acgcgccctg gaggcagctg   7320
gggccggacc tgggctggcg gtggcacccg cgcgcgctgg caacgtcggc ggcgtggagg   7380
aatatgacga ggacgatgag tacgagccag aggacggcga gtactaagcg gtgatgtttc   7440
tgatcagatg atgcaagacg caacggaccc ggcggtgcgg gcggcgctgc agagccagcc   7500
gtccggcctt aactccacgg acgactggcg ccaggtcatg gaccgcatca tgtcgctgac   7560
tgcgcgcaat cctgacgcgt tccggcagca gccgcaggcc aaccggctct ccgcaattct   7620
ggaagcggtg gtcccggcgc gcgcaaaccc cacgcacgag aaggtgctgg cgatcgtaaa   7680
cgcgctggcc gaaaacaggg ccatccggcc cgacgaggcc ggcctggtct acgacgcgct   7740
gcttcagcgc gtggctcgtt acaacagcgg caacgtgcag accaacctgg accggctggt   7800
gggggatgtg cgcgaggccg tggcgcagcg tgagcgcgcg cagcagcagg gcaacctggg   7860
ctccatggtt gcactaaacg ccttcctgag tacacagccc gccaacgtgc cgcggggaca   7920
ggaggactac accaactttg tgagcgcact gcggctaatg gtgactgaga caccgcaaag   7980
tgaggtgtac cagtctgggc cagactattt tttccagacc agtagacaag gcctgcagac   8040
cgtaaacctg agccaggctt tcaaaaactt gcaggggctg tggggggtgc gggctcccac   8100
aggcgaccgc gcgaccgtgt ctagcttgct gacgcccaac tcgcgcctgt tgctgctgct   8160
aatagcgccc ttcacggaca gtggcagcgt gtcccgggac acatacctag gtcacttgct   8220
gacactgtac cgcgaggcca taggtcaggc gcatgtggac gagcatactt tccaggagat   8280
tacaagtgtc agccgcgcgc tggggcagga ggacacgggc agcctggagg caaccctaaa   8340
ctacctgctg accaaccggc ggcagaagat cccctcgttg cacagtttcg cacccttgg   8400
cgcatcccat tctccagtaa ctttatgtcc atgggcgcac tcacagacct gggccaaaac   8460
cttctctacg ccaactccgc ccacgcgcta gacatgactt ttgaggtgga tcccatggac   8520
gagcccaccc ttctttatgt tttgtttgaa gtctttgacg tggtccgtgt gcaccggccg   8580
caccgcggcg tcatcgaaac cgtgtacctg cgcacgccct tctcggccgg caacgccaca   8640
acataaagaa gcaagcaaca tcaacaacag ctgccgccat gggctccagt gagcaggaac   8700
tgaaagccat tgtcaaagat cttggttgtg ggccatattt tttgggcacc tatgacaagc   8760
gctttccagg ctttgtttct ccacacaagc tcgcctgcgc catagtcaat acggccggtc   8820
gcgagactgg gggcgtacac tggatggcct ttgcctggaa cccgcactca aaaacatgct   8880
acctctttga gccctttggc ttttctgacc agcgactcaa gcaggtttac cagtttgagt   8940
acgagtcact cctgcgccgt agcgccattg cttcttcccc cgaccgctgt ataacgctgg   9000
aaaagtccac ccaaagcgta caggggccca actcggccgc ctgtggacta ttctgctgca   9060
tgtttctcca cgcctttgcc aactggcccc aaactcccat ggatcacaac cccaccatga   9120
accttattac cggggtaccc aactccatgc tcaacagtcc ccaggtacag cccaccctgc   9180
gtcgcaacca ggaacagctc tacagcttcc tggagcgcca ctcgccctac ttccgcagcc   9240
acagtgcgca gattaggagc gccacttctt tttgtcactt gaaaaacatg taaaaataat   9300
gtactagaga cactttcaat aaaggcaaat gcttttattt gtacactctc gggtgattat   9360
ttacccccac ccttgccgtc tgcgccgttt aaaaatcaaa ggggttctgc cgcgcatcgc   9420
```

-continued

```
tatgcgccac tggcagggac acgttgcgat actggtgttt agtgctccac ttaaactcag   9480
gcacaaccat ccgcggcagc tcggtgaagt tttcactcca caggctgcgc accatcacca   9540
acgcgtttag caggtcgggc gccgatatct tgaagtcgca gttggggcct ccgccctgcg   9600
cgcgcgagtt gcgatacaca gggttgcagc actggaacac tatcagcgcc gggtggtgca   9660
cgctggccag cacgctcttg tcggagatca gatccgcgtc caggtcctcc gcgttgctca   9720
gggcgaacgg agtcaacttt ggtagctgcc ttcccaaaaa gggcgcgtgc ccaggctttg   9780
agttgcactc gcaccgtagt ggcatcaaaa ggtgaccgtg cccggtctgg gcgttaggat   9840
acagcgcctg cataaaagcc ttgatctgct taaaagccac ctgagccttt gcgccttcag   9900
agaagaacat gccgcaagac ttgccggaaa actgattggc cggacaggcc gcgtcgtgca   9960
cgcagcacct tgcgtcggtg ttggagatct gcaccacatt tcggccccac cggttcttca  10020
cgatcttggc cttgctagac tgctccttca gcgcgcgctg cccgttttcg ctcgtcacat  10080
ccatttcaat cacgtgctcc ttatttatca taatgcttcc gtgtagacac ttaagctcgc  10140
cttcgatctc agcgcagcgg tgcagccaca acgcgcagcc cgtgggctcg tgatgcttgt  10200
aggtcacctc tgcaaacgac tgcaggtacg cctgcaggaa tcgccccatc atcgtcacaa  10260
aggtcttgtt gctggtgaag gtcagctgca acccgcggtg ctcctcgttc agccaggtct  10320
tgcatacggc cgccagagct tccacttggt caggcagtag tttgaagttc gcctttagat  10380
cgttatccac gtggtacttg tccatcagcg cgcgcgcagc ctccatgccc ttctcccacg  10440
cagacacgat cggcacactc agcgggttca tcaccgtaat ttcactttcc gcttcgctgg  10500
gctcttcctc ttcctcttgc gtccgcatac cacgcgccac tggtcgtct tcattcagcc  10560
gccgcactgt gcgcttacct cctttgccat gcttgattag caccggtggg ttgctgaaac  10620
ccaccatttg tagcgccaca tcttctcttt cttcctcgct gtccacgatt acctctggtg  10680
atggcgggcg ctcgggcttg ggagaagggc gcttcttttt cttcttgggc gcaatggcca  10740
aatccgccgc cgaggtcgat ggccgcgggc tgggtgtgcg cggcaccagc gcgtcttgtg  10800
atgagtcttc ctcgtcctcg gactcgatac gccgcctcat ccgctttttt gggggcgccc  10860
ggggaggcgg cggcgacggg gacggggacg acacgtcctc catggttggg ggacgtcgcg  10920
ccgcaccgcg tccgcgctcg ggggtggttt cgcgctgctc ctcttcccga ctggccattt  10980
ccttctccta taggcagaaa aagatcatgg agtcagtcga gaagaaggac agcctaaccg  11040
ccccctctga gttcgccacc accgcctcca ccgatgccgc caacgcgcct accaccttcc  11100
ccgtcgaggc acccccgctt gaggaggagg aagtgattat cgagcaggac ccaggttttg  11160
taagcgaaga cgacgaggac cgctcagtac caacagagga taaaaagcaa gaccaggaca  11220
acgcagaggc aaacgaggaa caagtcgggc ggggggacga aaggcatggc gactacctag  11280
atgtgggaga cgacgtgctg ttgaagcatc tgcagcgcca gtgcgccatt atctgcgacg  11340
cgttgcaaga gcgcagcgat gtgcccctcg ccatagcgga tgtcagcctt gcctacgaac  11400
gccacctatt ctcaccgcgc gtaccccca aacgccaaga aaacggcaca tgcgagccca  11460
acccgcgcct caacttctac cccgtatttg ccgtgccaga ggtgcttgcc acctatcaca  11520
tctttttcca aaactgcaag atacccctat cctgccgtgc caaccgcagc cgagcggaca  11580
agcagctggc cttgcggcag ggcgctgtca tacctgatat cgcctcgctc aacgaagtgc  11640
caaaaatctt tgagggtctt ggacgcgacg agaagcgcgc ggcaaacgct ctgcaacagg  11700
aaaacagcga aaatgaaagt cactctggag tgttggtgga actcgagggt gacaacgcgc  11760
```

-continued

```
gcctagccgt actaaaacgc agcatcgagg tcacccactt tgcctacccg gcacttaacc  11820
taccccccaa ggtcatgagc acagtcatga gtgagctgat cgtgcgccgt gcgcagcccc  11880
tggagaggga tgcaaatttg caagaacaaa cagaggaggg cctacccgca gttggcgacg  11940
agcagctagc gcgctggctt caaacgcgcg agcctgccga cttggaggag cgacgcaaac  12000
taatgatggc cgcagtgctc gttaccgtgg agcttgagtg catgcagcgg ttctttgctg  12060
acccggagat gcagcgcaag ctagaggaaa cattgcacta cacctttcga cagggctacg  12120
tacgccaggc ctgcaagatc tccaacgtgg agctctgcaa cctggtctcc taccttggaa  12180
ttttgcacga aaaccgcctt gggcaaaacg tgcttcattc cacgctcaag ggcgaggcgc  12240
gccgcgacta cgtccgcgac tgcgtttact tatttctatg ctacacctgg cagacggcca  12300
tgggcgtttg gcagcagtgc ttggaggagt gcaacctcaa ggagctgcag aaactgctaa  12360
agcaaaactt gaaggaccta tggacggcct tcaacgagcg ctccgtggcc gcgcacctgg  12420
cggacatcat tttccccgaa cgcctgctta aaaccctgca acagggtctg ccagacttca  12480
ccagtcaaag catgttgcag aactttagga actttatcct agagcgctca ggaatcttgc  12540
ccgccacctg ctgtgcactt cctagcgact ttgtgcccat taagtaccgc gaatgccctc  12600
cgccgctttg gggccactgc taccttctgc agctagccaa ctaccttgcc taccactctg  12660
acataatgga agacgtgagc ggtgacggtc tactggagtg tcactgtcgc tgcaacctat  12720
gcaccccgca ccgctccctg gtttgcaatt cgcagctgct taacgaaagt caaattatcg  12780
gtacctttga gctgcagggt ccctcgcctg acgaaaagtc cgcggctccg gggttgaaac  12840
tcactccggg gctgtggacg tcggcttacc ttcgcaaatt tgtacctgag gactaccacg  12900
cccacgagat taggttctac gaagaccaat cccgcccgcc atatgcggag cttaccgcct  12960
gcgtcattac ccagggccac attcttggcc aattgcaagc catcaacaaa gcccgccaag  13020
agtttctgct acgaaaggga cggggggttt acttggaccc ccagtccggc gaggagctca  13080
acccaatccc cccgccgccg cagccctatc agcagcagcc gcgggccctt gcttcccagg  13140
atggcaccca aaaagaagct gcagctgccg ccgccaccca cggacgagga ggaatactgg  13200
gacagtcagg cagaggaggt tttggacgag gaggaggagg acatgatgga agactgggag  13260
agcctagacg aggaagcttc cgaggtcgaa gaggtgtcag acgaaacacc gtcaccctcg  13320
gtcgcattcc cctcgccggc gccccagaaa tcggcaaccg gttccagcat ggctacaacc  13380
tccgctcctc aggcgccgcc ggcactgccc gttcgccgac ccaaccgtag atgggacacc  13440
actggaacca gggccggtaa gtccaagcag ccgccgccgt tagcccaaga gcaacaacag  13500
cgccaaggct accgctcatg gcgcgggcac aagaacgcca tagttgcttg cttgcaagac  13560
tgtgggggca acatctcctt cgcccgccgc tttcttctct accatcacgg cgtggccttc  13620
ccccgtaaca tcctgcatta ctaccgtcat ctctacagcc catactgcac cggcggcagc  13680
ggcagcaaca gcagcggcca cacagaagca aaggcgaccg gatagcaaga ctctgacaaa  13740
gcccaagaaa tccacagcgg cggcagcagc aggaggagga gcgctgcgtc tggcgcccaa  13800
cgaacccgta tcgacccgcg agcttagaaa caggattttt cccactctgt atgctatatt  13860
tcaacagagc aggggccaag aacaagagct gaaaataaaa aacaggtctc tgcgatccct  13920
cacccgcagc tgcctgtatc acaaaagcga agatcagctt cggcgcacgc tggaagacgc  13980
ggaggctctc ttcagtaaat actgcgcgct gactcttaag gactagtttc gcgccctttc  14040
tcaaatttaa gcgcgaaaac tacgtcatct ccagcggcca cacccggcgc cagcacctgt  14100
tgtcagcgcc attatgagca aggaaattcc cacgccctac atgtggagtt accagccaca  14160
```

-continued aatgggactt gcggctggag ctgcccaaga ctactcaacc cgaataaact acatgagcgc 14220
gggaccccac atgatatccc gggtcaacgg aatacgcgcc caccgaaacc gaattctctc 14280
ggaacaggcg gctattacca ccacacctcg taataacctt aatccccgta gttggcccgc 14340
tgccctggtg taccaggaaa gtcccgctcc caccactgtg gtacttccca gagacgccca 14400
ggccgaagtt cagatgacta actcaggggc gcagcttgcg ggcggctttc gtcacagggt 14460
gcggtcgccc gggcagggta taactcacct gacaatcaga gggcgaggta ttcagctcaa 14520
cgacgagtcg gtgagctcct cgcttggtct ccgtccggac gggacatttc agatcggcgg 14580
cgccggccgc tcttcattca cgcctcgtca ggcaatccta actctgcaga cctcgtcctc 14640
tgagccgcgc tctggaggca ttggaactct gcaatttatt gaggagtttg tgccatcggt 14700
ctactttaac cccttctcgg gacctcccgg ccactatccg gatcaattta ttcctaactt 14760
tgacgcggta aaggactcgg cggacggcta cgactgaatg ttaagtggag aggcagagca 14820
actgcgcctg aaacacctgg tccactgtcg ccgccacaag tgctttgccc gcgactccgg 14880
tgagttttgc tactttgaat tgcccgagga tcatatcgag ggcccggcgc acggcgtccg 14940
gcttaccgcc cagggagagc ttgcccgtag cctgattcgg gagtttaccc agcgcccccct 15000
gctagttgag cgggacaggg gaccctgtgt tctcactgtg atttgcaact gtcctaaccc 15060
tggattacat caagatcctc tagttaatta actagagtac ccggggatct tattcccttt 15120
aactaataaa aaaaaataat aaagcatcac ttacttaaaa tcagttagca aatttctgtc 15180
cagtttattc agcagcacct ccttgccctc ctcccagctc tggtattgca gcttcctcct 15240
ggctgcaaac tttctccaca atctaaatgg aatgtcagtt tcctcctgtt cctgtccatc 15300
cgcacccact atcttcatgt tgttgcagat gaagcgcgca agaccgtctg aagatacctt 15360
caaccccgtg tatccatatg acacggaaac cggtcctcca actgtgcctt ttcttactcc 15420
tccctttgta tcccccaatg ggtttcaaga gagtcccccct ggggtactct ctttgcgcct 15480
atccgaacct ctagttacct ccaatggcat gcttgcgctc aaaatgggca acggcctctc 15540
tctggacgag gccggcaacc ttacctccca aaatgtaacc actgtgagcc cacctctcaa 15600
aaaaaccaag tcaaacataa acctggaaat atctgcaccc ctcacagtta cctcagaagc 15660
cctaactgtg gctgccgccg cacctctaat ggtcgcgggc aacacactca ccatgcaatc 15720
acaggccccg ctaaccgtgc acgactccaa acttagcatt gccacccaag gacccctcac 15780
agtgtcagaa ggaaagctag ccctgcaaac atcaggcccc ctcaccacca ccgatagcag 15840
taccccttact atcactgcct caccccctct aactactgcc actggtagct tgggcattga 15900
cttgaaagag cccatttata cacaaaatgg aaaactagga ctaaagtacg gggctccttt 15960
gcatgtaaca gacgacctaa acactttgac cgtagcaact ggtccaggtg tgactattaa 16020
taatacttcc ttgcaaacta aagttactgg agccttgggt tttgattcac aaggcaatat 16080
gcaacttaat gtagcaggag gactaaggat tgattctcaa aacagacgcc ttatacttga 16140
tgttagttat ccgtttgatg ctcaaaacca actaaatcta agactaggac agggccctct 16200
ttttataaac tcagcccaca acttggatat taactacaac aaaggccttt acttgtttac 16260
agcttcaaac aattccaaaa agcttgaggt taacctaagc actgccaagg ggttgatgtt 16320
tgacgctaca gccatagcca ttaatgcagg agatgggctt gaatttggtt cacctaatgc 16380
accaaacaca aatcccctca aaacaaaaat tggccatggc ctagaatttg attcaaacaa 16440
ggctatggtt cctaaactag gaactggcct tagttttgac agcacaggtg ccattacagt 16500

-continued

```
aggaaacaaa aataatgata agctaacttt gtggaccaca ccagctccat ctcctaactg  16560
tagactaaat gcagagaaag atgctaaact cactttggtc ttaacaaaat gtggcagtca  16620
aatacttgct acagtttcag ttttggctgt taaaggcagt ttggctccaa tatctggaac  16680
agttcaaagt gctcatctta ttataagatt tgacgaaaat ggagtgctac taaacaattc  16740
cttcctggac ccagaatatt ggaactttag aaatggagat cttactgaag gcacagccta  16800
tacaaacgct gttggattta tgcctaacct atcagcttat ccaaaatctc acggtaaaac  16860
tgccaaaagt aacattgtca gtcaagttta cttaaacgga gacaaaacta aacctgtaac  16920
actaaccatt acactaaacg gtacacagga aacaggagac acaactccaa gtgcatactc  16980
tatgtcattt tcatgggact ggtctggcca caactacatt aatgaaatat ttgccacatc  17040
ctcttacact ttttcataca ttgcccaaga ataaagaatc gtttgtgtta tgtttcaacg  17100
tgtttatttt tcaattgcag aaaatttcaa gtcatttttc attcagtagt atagccccac  17160
caccacatag cttatacaga tcaccgtacc ttaatcaaac tcacagaacc ctagtattca  17220
acctgccacc tccctcccaa cacacagagt acacagtcct ttctccccgg ctggccttaa  17280
aaagcatcat atcatgggta acagacatat tcttaggtgt tatattccac acggtttcct  17340
gtcgagccaa acgctcatca gtgatattaa taaactcccc gggcagctca cttaagttca  17400
tgtcgctgtc cagctgctga gccacaggct gctgtccaac ttgcggttgc ttaacgggcg  17460
gcgaaggaga agtccacgcc tacatggggg tagagtcata atcgtgcatc aggatagggc  17520
ggtggtgctg cagcagcgcg cgaataaact gctgccgccg ccgctccgtc ctgcaggaat  17580
acaacatggc agtggtctcc tcagcgatga ttcgcaccgc ccgcagcata aggcgccttg  17640
tcctccgggc acagcagcgc accctgatct cacttaaatc agcacagtaa ctgcagcaca  17700
gcaccacaat attgttcaaa atcccacagt gcaaggcgct gtatccaaag ctcatggcgg  17760
ggaccacaga acccacgtgg ccatcatacc acaagcgcag gtagattaag tggcgacccc  17820
tcataaacac gctggacata aacattacct cttttggcat gttgtaattc accacctccc  17880
ggtaccatat aaacctctga ttaaacatgg cgccatccac caccatccta aaccagctgg  17940
ccaaaacctg cccgccggct atacactgca gggaaccggg actggaacaa tgacagtgga  18000
gagcccagga ctcgtaacca tggatcatca tgctcgtcat gatatcaatg ttggcacaac  18060
acaggcacac gtgcatacac ttcctcagga ttacaagctc ctcccgcgtt agaaccatat  18120
cccagggaac aacccattcc tgaatcagcg taaatcccac actgcaggga agacctcgca  18180
cgtaactcac gttgtgcatt gtcaaagtgt tacattcggg cagcagcgga tgatcctcca  18240
gtatggtagc gcgggtttct gtctcaaaag gaggtagacg atccctactg tacggagtgc  18300
gccgagacaa ccgagatcgt gttggtcgta gtgtcatgcc aaatggaacg ccggacgtag  18360
tcatatttcc tgaagcaaaa ccaggtgcgg gcgtgacaaa cagatctgcg tctccggtct  18420
cgccgcttag atcgctctgt gtagtagttg tagtatatcc actctctcaa agcatccagg  18480
cgccccctgg cttcgggttc tatgtaaact ccttcatgcg ccgctgccct gataacatcc  18540
accaccgcag aataagccac acccagccaa cctacacatt cgttctgcga gtcacacacg  18600
ggaggagcgg gaagagctgg aagaaccatg tttttttttt tattccaaaa gattatccaa  18660
aacctcaaaa tgaagatcta ttaagtgaac gcgctcccct ccggtggcgt ggtcaaactc  18720
tacagccaaa gaacagataa tggcatttgt aagatgttgc acaatggctt ccaaaaggca  18780
aacggccctc acgtccaagt ggacgtaaag gctaaaccct tcagggtgaa tctcctctat  18840
aaacattcca gcaccttcaa ccatgcccaa ataattctca tctcgccacc ttctcaatat  18900
```

-continued

```
atctctaagc aaatcccgaa tattaagtcc ggccattgta aaaatctgct ccagagcgcc  18960
ctccaccttc agcctcaagc agcgaatcat gattgcaaaa attcaggttc ctcacagacc  19020
tgtataagat tcaaaagcgg aacattaaca aaaataccgc gatcccgtag gtcccttcgc  19080
agggccagct gaacataatc gtgcaggtct gcacggacca gcgcggccac ttccccgcca  19140
ggaaccatga caaaagaacc cacactgatt atgacacgca tactcggagc tatgctaacc  19200
agcgtagccc cgatgtaagc ttgttgcatg ggcggcgata taaaatgcaa ggtgctgctc  19260
aaaaaatcag gcaaagcctc gcgcaaaaaa gaaagcacat cgtagtcatg ctcatgcaga  19320
taaaggcagg taagctccgg aaccaccaca gaaaaagaca ccatttttct ctcaaacatg  19380
tctgcgggtt tctgcataaa cacaaaataa aataacaaaa aaacatttaa acattagaag  19440
cctgtcttac aacaggaaaa acaaccctta taagcataag acggactacg gccatgccgg  19500
cgtgaccgta aaaaaactgg tcaccgtgat taaaaagcac caccgacagc tcctcggtca  19560
tgtccggagt cataatgtaa gactcggtaa acacatcagg ttgattcaca tcggtcagtg  19620
ctaaaaagcg accgaaatag cccgggggaa tacatacccg caggcgtaga gacaacatta  19680
cagccccat aggaggtata acaaaattaa taggagagaa aaacacataa acacctgaaa  19740
aaccctcctg cctaggcaaa atagcaccct cccgctccag aacaacatac agcgcttcca  19800
cagcggcagc cataacagtc agccttacca gtaaaaaaga aaacctatta aaaaaacacc  19860
actcgacacg gcaccagctc aatcagtcac agtgtaaaaa agggccaagt gcagagcgag  19920
tatatatagg actaaaaaat gacgtaacgg ttaaagtcca caaaaaacac ccagaaaacc  19980
gcacgcgaac ctacgcccag aaacgaaagc caaaaaaccc acaacttcct caaatcgtca  20040
cttccgtttt cccacgttac gtaacttccc attttaagaa aactacaatt cccaacacat  20100
acaagttact ccgccctaaa acctacgtca cccgccccgt tcccacgccc cgcgccacgt  20160
cacaaactcc accccctcat tatcatattg gcttcaatcc aaaataaggt atattattga  20220
tgatttattt tggattgaag ccaatatgat aatgaggggg tggagtttgt gacgtggcgc  20280
ggggcgtggg aacggggcgg gtgacgtagt agtgtggcgg aagtgtgatg ttgcaagtgt  20340
ggcggaacac atgtaagcga cggatgtggc aaaagtgacg tttttggtgt gcgccggatc  20400
cacaggacgg gtgtggtcgc catgatcgcg tagtcgatag tggctccaag tagcgaagcg  20460
agcaggactg ggcggcggcc aaagcggtcg gacagtgctc cgagaacggg tgcgcataga  20520
aattgcatca acgcatatag cgctagcagc acgccatagt gactggcgat gctgtcggaa  20580
tggacgatat cccgcaagag gcccggcagt accggcataa ccaagcctat gcctacagca  20640
tccagggtga cggtgccgag gatgacgatg agcgcattgt tagatttcat acacggtgcc  20700
tgactgcgtt agcaatttaa ctgtgataaa ctaccgcatt aaagcttatc gaattcgtaa  20760
tcatggtcat agctgtttcc tgtgtgaaat tgttatccgc tcacaattcc acacaacata  20820
cgagccggaa gcataaagtg taaagcctgg ggtgcctaat gagtgagcta actcacatta  20880
attgcgttgc gctcactgcc cgctttccag tcgggaaacc tgtcgtgcca gctgcattaa  20940
tgaatcggcc aacgcgcggg gagaggcggt ttgcgtattg ggcgc                  20985
```

<210> SEQ ID NO 2
<211> LENGTH: 22423
<212> TYPE: DNA
<213> ORGANISM: Artificial Sequence
<220> FEATURE:
<223> OTHER INFORMATION: Synthetic: Rep/Helper Plasmid with intron

<400> SEQUENCE: 2

```
tcttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aagaacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttattagaa aaactcatcg    960
agcatcaaat gaaactgcaa tttattcata tcaggattat caataccata tttttgaaaa   1020
agccgtttct gtaatgaagg agaaaactca ccgaggcagt tccataggat ggcaagatcc   1080
tggtatcggt ctgcgattcc gactcgtcca acatcaatac aacctattaa tttcccctcg   1140
tcaaaaataa ggttatcaag tgagaaatca ccatgagtga cgactgaatc cggtgagaat   1200
ggcaaaagtt tatgcatttc tttccagact tgttcaacag gccagccatt acgctcgtca   1260
tcaaaatcac tcgcatcaac caaaccgtta ttcattcgtg attgcgcctg agcgagacga   1320
aatacgcgat cgctgttaaa aggacaatta caaacaggaa tcgaatgcaa ccggcgcagg   1380
aacactgcca gcgcatcaac aatattttca cctgaatcag gatattcttc taatacctgg   1440
aatgctgttt ttccggggat cgcagtggtg agtaaccatg catcatcagg agtacggata   1500
aaatgcttga tggtcggaag aggcataaat tccgtcagcc agtttagtct gaccatctca   1560
tctgtaacat cattggcaac gctacctttg ccatgtttca gaaacaactc tggcgcatcg   1620
ggcttcccat acaagcgata gattgtcgca cctgattgcc cgacattatc gcgagcccat   1680
ttatacccat ataaatcagc atccatgttg gaatttaatc gcggcctcga cgtttcccgt   1740
tgaatatggc tcatactctt cctttttcaa tattattgaa gcatttatca gggttattgt   1800
ctcatgagcg gatacatatt tgaatgtatt tagaaaaata aacaaatagg ggttccgcgc   1860
acatttcccc gaaaagtgcc acctgacgtc taagaaacca ttattatcat gacattaacc   1920
tataaaaata ggcgtatcac gaggcccttt cgtctcgcgc gtttcggtga tgacggtgaa   1980
aacctctgac acatgcagct cccggagacg gtcacagctt gtctgtaagc ggatgccggg   2040
agcagacaag cccgtcaggg cgcgtcagcg ggtgttggcg ggtgtcgggg ctggcttaac   2100
tatgcggcat cagagcagat tgtactgaga gtgcaccata aaattgtaaa cgttcatatg   2160
gtttaaacgt cgatcagaga gagtgtcctc gagccaatct ggaagataac catcggcagc   2220
catacctgat ttaaatcatt tattgttcaa agatgcagtc atccaaatcc acattgacca   2280
gatcgcaggc agtgcaagcg tctggcacct ttcccatgat atgatgaatg tagcacagtt   2340
```

```
tctgatacgc ctttttgacg acagaaacgg gttgagattc tgacacggga aagcactcta   2400
aacagtcttt ctgtccgtga gtgaagcaga tatttgaatt ctgattcatt ctctcgcatt   2460
gtctgcaggg aaacagcatc agattcatgc ccacgtgacg agaacatttg ttttggtacc   2520
tgtctgcgta gttgatcgaa gcttccgcgt ctgacgtcga tggctgcgca actgactcgc   2580
gcacccgttt gggctcactt atatctgcgt cactgggggc gggtcttttc ttggctccac   2640
ccttttgac gtagaattca tgctccacct caaccacgtg atcctttgcc caccggaaaa   2700
agtctttgac ttcctgcttg gtgaccttcc caaagtcatg atccagacgg cgggtgagtt   2760
caaatttgaa catccggtct tgcaacggct gctggtgttc gaaggtcgtt gagttcccgt   2820
caatcacggc gcacatgttg gtgttggagg tgacgatcac gggagtcggg tctatctggg   2880
ccgaggactt gcatttctgg tccacgcgca ccttgcttcc tccgagaatg gctttggccg   2940
actccacgac cttggcggtc atcttcccct cctcccacca gatcaccatc ttgtcgacac   3000
agtcgttgaa gggaaagttc tcattggtcc agtttacgca cccgtagaag ggcacagtgt   3060
gggctatggc ctccgcgatg ttggtcttcc cggtagttgc aggcccaaac agccagatgg   3120
tgttcctctt gccgaacttt ttcgtggccc atcccagaaa gacggaagcc gcatattggg   3180
gatcgtaccc gtttagttcc aaaattttat aaatccgatt gctggaaatg tcctccacgg   3240
gctgctggcc caccaggtag tcgggggcgg ttttagtcag gctcataatc tttcccgcat   3300
tgtccaaggc agccttgatt tgggaccgcg agttggaggc cgcattgaag gagatgtatg   3360
aggcctggtc ctcctggatc cactgcttct ccgaggtaat ccccttgtcc acgagccacc   3420
cgaccagctc catgtacctg gctgaagttt ttgatctgat caccggcgca tcagaattgg   3480
gattctgatt ctctttgttc tgctcctgcg tctgcgacac gtgcgtcaga tgctgcgcca   3540
ccaaccgttt acgctccgtg agattcaaac aggcgcttaa atactgttcc atattagtcc   3600
acgcccactg gagctcaggc tgggttttgg ggagcaagta attggggatg tagcactcat   3660
ccaccacctt gttcccgcct ccggcgccat ttctggtctt tgtgaccgcg aaccagtttg   3720
gcaaagtcgg ctcgatcccg cggtaaattc tctgaatcag tttttcgcga atctgactca   3780
ggaaacgtcc caaaaccatg gatttcaccc cggtggtttc cacgagcacg tgcatgtgga   3840
agtagctctc tcccttctca aattgcacaa agaaaagggc ctccggggcc ttactcacac   3900
ggcgccattc cgtcagaaag tcgcgctgca gcttctcggc cacggtcagg ggtgcctgct   3960
caatcagatt cagatccatg tcagaatctg gcggcaactc ccattccttc tcggccaccc   4020
agttcacaaa gctgtcagaa atgccgggca gatgctcgtc aaggtcgctg gggaccttaa   4080
tcacaatctc gtaaaacccc ggcatctgaa atgtaaaaga ataattcttt agttttagca   4140
aaaaagaaaa catcatgaaa attttacatc tcttaagaaa gtctttgttt ttaatccaaa   4200
taatctgaaa gccaatttct ctttagggca tggagccaaa atctgtgatg ttcccacagt   4260
actgtataca catggagatt taggaattaa aattcaattt tacttttagt caagagaatt   4320
ccagtaataa aaggtcagat ttctaatcat atttgaattt actttggatg aaaaagaaag   4380
ttctcaaatg agcggttaac ttcacacttt gtcatcactt gaaaatagct cattgaggat   4440
ctttgcaaag tgatccatca ccctggctgg gctgttttca gaatatggtt gcccaaatga   4500
ctttgaacaa atgtctcctg aagaacagaa gcctaattat ggtccagcga cgtcgatttc   4560
acagctgaca tcatgtctgg agtgggaacc acagggccag tcagctttct gggggtgctt   4620
agggttggca cccctgatcc tggtactgtc agctactaga tttgattcta gaaagttgac   4680
```

-continued aagtaagtgt gataaatgct tcctgtgaga acatgctgtt tgtccaaatg ggataatttc 4740
ttccctgtat gccttcctct gggaaataca taaagtcact gtagttgtga aaaaacaaag 4800
tgatatatgt tgcattagct aacttcctac tctttatgtc aattcttaag cttgcttttc 4860
tcccctaggg aactcaactg agtattgtgt ttccccaaat atcaactcca agatgtttga 4920
catagagaca aaatgatttt ttcctaatcc atgaaaagct ttggtgataa ctaacagctt 4980
gctaatgaaa ggttaatctt tatgttttaa ctaaaacttt aaattgaaga tatataattt 5040
aaaaaattag agacacacct cattacatac ttctgaaacc ttgaaatgtc atatatctta 5100
aaatcagact ttttgtgtaa ataaggccat tgtttgtgct tttgtttccc attttgattt 5160
caaagtggta agtccaaaca aaaataatgt ggttattttt tttcactata ttctgctatt 5220
tctttgtttt cccactttta attttttaa accaaggaga tgaatgtttt ctaacaggaa 5280
ttacatgacc aaatcatgaa ctgaacagtg tttattaaac ataaatgcat cataagcatt 5340
gtcgatctat ttagttttaa aaatgaagaa gaagaaaacc tagctaacaa agaaccagta 5400
cttaccaacc tgcgtgctgg ctgttagact cttcaatatt gctgtcaaat catgtaatca 5460
aaatttagtg aagaagacag catcagatat ttctatatct aaaaggcaag catactcaat 5520
gtattttaaa aaaggaaaca aacggcggct gcgcgttcaa acctcccgct tcaaaatgga 5580
gaccctgcgt gctcactcgg gcttaaatac ccagcgtgac cacatggtgt cgcaaaatgt 5640
cgcaaaacac tcacgtgacc tctaatacag gacctcccta accctatgac gtaacgttaa 5700
tattttgtta aaattcgcgt taaatttttg ttaaatcagc tcattttta accaataggc 5760
cgaaatcggc aaaatccctt ataaatcaaa agaatagccc gagatagggt tgagtgttgt 5820
tccagtttgg aacaagagtc cactattaaa gaacgtggac tccaacgtca aagggcgaaa 5880
aaccgtctat cagggcgatg gcccactacg tgaaccatca cccaaatcaa gtttttggg 5940
gtcgaggtgc cgtaaagcac taaatcggaa ccctaaaggg agcccccgat ttagagcttg 6000
acggggaaag ccggcgaacg tggcgagaaa ggaagggaag aaagcgaaag gagcgggcgc 6060
tagggcgctg gcaagtgtag cggtcacgct gcgcgtaacc accacacccg ccgcgcttaa 6120
tgcgccgcta cagggcgcgt actatggttg ctttgacgta tgcggtgtga aataccgcac 6180
agatgcgtaa ggagaaaata ccgcatcagg cgccattcgc cattcaggct gcgcaactgt 6240
tgggaagggc gatcggtgcg ggcctcttcg ctattacgcc agctggcgaa agggggatgt 6300
gctgcaaggc gattaagttg ggtaacgcca gggttttccc agtcacgacg ttgtaaaacg 6360
acggccagtg ccaagcttaa ggtgcacggc ccacgtggcc actagtactt ctcgacagaa 6420
gcaccatgtc cttgggtccg gcctgctgaa tgcgcaggcg gtcggccatg ccccaggctt 6480
cgttttgaca tcggcgcagg tctttgtagt agtcttgcat gagcctttct accggcactt 6540
cttcttctcc ttcctcttgt cctgcatctc ttgcatctat cgctgcggcg gcggcggagt 6600
ttggccgtag gtggcgccct cttcctccca tgcgtgtgac cccgaagccc ctcatcggct 6660
gaagcagggc taggtcggcg acaacgcgct cggctaatat ggcctgctgc acctgcgtga 6720
gggtagactg gaagtcatcc atgtccacaa agcggtggta tgcgcccgtg ttgatggtgt 6780
aagtgcagtt ggccataacg gaccagttaa cggtctggtg acccggctgc gagagctcgg 6840
tgtacctgag acgcgagtaa gccctcgagt caaatacgta gtcgttgcaa gtccgcacca 6900
ggtactggta tcccaccaaa aagtgcggcg gcggctggcg gtagaggggc cagcgtaggg 6960
tggccggggc tccgggggcg agatcttcca acataaggcg atgatatccg tagatgtacc 7020
tggacatcca ggtgatgccg gcggcggtgg tggaggcgcg cggaaagtcg cggacgcggt 7080

-continued

```
tccagatgtt gcgcagcggc aaaaagtgct ccatggtcgg gacgctctgg ccggtcaggc   7140
gcgcgcaatc gttgacgctc taccgtgcaa aaggagagcc tgtaagcggg cactcttccg   7200
tggtctggtg gataaattcg caagggtatc atggcggacg accggggttc gagccccgta   7260
tccggccgtc cgccgtgatc catgcggtta ccgcccgcgt gtcgaaccca ggtgtgcgac   7320
gtcagacaac gggggagtgc tccttttggc ttccttccag gcgcggcggc tgctgcgcta   7380
gcttttttgg ccactggccg cgcgcagcgt aagcggttag gctggaaagc gaaagcatta   7440
agtggctcgc tccctgtagc cggagggtta ttttccaagg gttgagtcgc gggacccccg   7500
gttcgagtct cggaccggcc ggactgcggc gaacgggggt ttgcctcccc gtcatgcaag   7560
accccgcttg caaattcctc cggaaacagg gacgagcccc ttttttgctt ttcccagatg   7620
catccggtgc tgcggcagat gcgccccct cctcagcagc ggcaagagca agagcagcgg   7680
cagacatgca gggcaccctc ccctcctcct accgcgtcag gaggggcgac atccgcggtt   7740
gacgcggcag cagatggtga ttacgaaccc ccgcggcgcc gggcccggca ctacctggac   7800
ttggaggagg gcgagggcct ggcgcggcta ggagcgccct ctcctgagcg gtacccaagg   7860
gtgcagctga agcgtgatac gcgtgaggcg tacgtgccgc ggcagaacct gtttcgcgac   7920
cgcgagggag aggagcccga ggagatgcgg gatcgaaagt tccacgcagg gcgcgagctg   7980
cggcatggcc tgaatcgcga gcggttgctg cgcgaggagg actttgagcc cgacgcgcga   8040
accgggatta gtcccgcgcg cgcacacgtg gcggccgccg acctggtaac cgcatacgag   8100
cagacggtga accaggagat taactttcaa aaaagcttta acaaccacgt gcgtacgctt   8160
gtggcgcgcg aggaggtggc tataggactg atgcatctgt gggactttgt aagcgcgctg   8220
gagcaaaacc caaatagcaa gccgctcatg gcgcagctgt tccttatagt gcagcacagc   8280
agggacaacg aggcattcag ggatgcgctg ctaaacatag tagagcccga gggccgctgg   8340
ctgctcgatt tgataaacat cctgcagagc atagtggtgc aggagcgcag cttgagcctg   8400
gctgacaagg tggccgccat caactattcc atgcttagcc tgggcaagtt ttacgcccgc   8460
aagatatacc atacccctta cgttcccata gacaaggagg taaagatcga ggggttctac   8520
atgcgcatgg cgctgaaggt gcttaccttg agcgacgacc tgggcgttta tcgcaacgag   8580
cgcatccaca aggccgtgag cgtgagccgg cggcgcgagc tcagcgaccg cgagctgatg   8640
cacagcctgc aaagggccct ggctggcacg ggcagcggcg atagagaggc cgagtcctac   8700
tttgacgcgg gcgctgacct gcgctgggcc ccaagccgac gcgccctgga ggcagctggg   8760
gccggacctg ggctggcggt ggcacccgcg cgcgctggca acgtcggcgg cgtggaggaa   8820
tatgacgagg acgatgagta cgagccagag gacggcgagt actaagcggt gatgtttctg   8880
atcagatgat gcaagacgca acggacccgg cggtgcgggc ggcgctgcag agccagccgt   8940
ccggccttaa ctccacggac gactggcgcc aggtcatgga ccgcatcatg tcgctgactg   9000
cgcgcaatcc tgacgcgttc cggcagcagc cgcaggccaa ccggctctcc gcaattctgg   9060
aagcggtggt cccggcgcgc gcaaacccca cgcacgagaa ggtgctggcg atcgtaaacg   9120
cgctggccga aaacagggcc atccggcccg acgaggccgg cctggtctac gacgcgctgc   9180
ttcagcgcgt ggctcgttac aacagcggca acgtgcagac caacctggac cggctggtgg   9240
gggatgtgcg cgaggccgtg gcgcagcgtg agcgcgcgca gcagcagggc aacctgggct   9300
ccatggttgc actaaacgcc ttcctgagta cacagcccgc caacgtgccg cggggacagg   9360
aggactacac caactttgtg agcgcactgc ggctaatggt gactgagaca ccgcaaagtg   9420
```

-continued

```
aggtgtacca gtctgggcca gactattttt tccagaccag tagacaaggc ctgcagaccg   9480
taaacctgag ccaggctttc aaaaacttgc aggggctgtg gggggtgcgg gctcccacag   9540
gcgaccgcgc gaccgtgtct agcttgctga cgcccaactc gcgcctgttg ctgctgctaa   9600
tagcgccctt cacggacagt ggcagcgtgt cccgggacac atacctaggt cacttgctga   9660
cactgtaccg cgaggccata ggtcaggcgc atgtggacga gcatactttc caggagatta   9720
caagtgtcag ccgcgcgctg gggcaggagg acacgggcag cctggaggca accctaaact   9780
acctgctgac caaccggcgg cagaagatcc cctcgttgca cagtttcgca ccctttggcg   9840
catcccattc tccagtaact ttatgtccat gggcgcactc acagacctgg gccaaaacct   9900
tctctacgcc aactccgccc acgcgctaga catgactttt gaggtggatc ccatggacga   9960
gcccaccctt ctttatgttt tgtttgaagt ctttgacgtg gtccgtgtgc accggccgca  10020
ccgcggcgtc atcgaaaccg tgtacctgcg cacgcccttc tcggccggca acgccacaac  10080
ataaagaagc aagcaacatc aacaacagct gccgccatgg gctccagtga gcaggaactg  10140
aaagccattg tcaaagatct tggttgtggg ccatattttt tgggcaccta tgacaagcgc  10200
tttccaggct ttgtttctcc acacaagctc gcctgcgcca tagtcaatac ggccggtcgc  10260
gagactgggg gcgtacactg gatggccttt gcctggaacc cgcactcaaa aacatgctac  10320
ctctttgagc cctttggctt ttctgaccag cgactcaagc aggtttacca gtttgagtac  10380
gagtcactcc tgcgccgtag cgccattgct tcttccccg accgctgtat aacgctggaa   10440
aagtccaccc aaagcgtaca ggggcccaac tcggccgcct gtggactatt ctgctgcatg  10500
tttctccacg cctttgccaa ctggccccaa actcccatgg atcacaaccc caccatgaac  10560
cttattaccg gggtacccaa ctccatgctc aacagtcccc aggtacagcc caccctgcgt  10620
cgcaaccagg aacagctcta cagcttcctg gagcgccact cgccctactt ccgcagccac  10680
agtgcgcaga ttaggagcgc cacttctttt tgtcacttga aaaacatgta aaaataatgt  10740
actagagaca ctttcaataa aggcaaatgc ttttatttgt acactctcgg gtgattattt  10800
acccccaccc ttgccgtctg cgccgtttaa aaatcaaagg ggttctgccg cgcatcgcta  10860
tgcgccactg gcagggacac gttgcgatac tggtgtttag tgctccactt aaactcaggc  10920
acaaccatcc gcggcagctc ggtgaagttt tcactccaca ggctgcgcac catcaccaac  10980
gcgtttagca ggtcgggcgc cgatatcttg aagtcgcagt tggggcctcc gccctgcgcg  11040
cgcgagttgc gatacacagg gttgcagcac tggaacacta tcagcgccgg gtggtgcacg  11100
ctggccagca cgctcttgtc ggagatcaga tccgcgtcca ggtcctccgc gttgctcagg  11160
gcgaacggag tcaactttgg tagctgcctt cccaaaaagg gcgcgtgccc aggctttgag  11220
ttgcactcgc accgtagtgg catcaaaagg tgaccgtgcc cggtctgggc gttaggatac  11280
agcgcctgca taaaagcctt gatctgctta aaagccacct gagcctttgc gccttcagag  11340
aagaacatgc cgcaagactt gccggaaaac tgattggccg gacaggccgc gtcgtgcacg  11400
cagcaccttg cgtcggtgtt ggagatctgc accacatttc ggccccaccg gttcttcacg  11460
atcttggcct tgctagactg ctccttcagc gcgcgctgcc cgttttcgct cgtcacatcc  11520
atttcaatca cgtgctcctt atttatcata atgcttccgt gtagacactt aagctcgcct  11580
tcgatctcag cgcagcggtg cagccacaac gcgcagcccg tgggctcgtg atgcttgtag  11640
gtcacctctg caaacgactg caggtacgcc tgcaggaatc gccccatcat cgtcacaaag  11700
gtcttgttgc tggtgaaggt cagctgcaac ccgcggtgct cctcgttcag ccaggtcttg  11760
catacggccg ccagagcttc cacttggtca ggcagtagtt tgaagttcgc ctttagatcg  11820
```

-continued

```
ttatccacgt ggtacttgtc catcagcgcg cgcgcagcct ccatgccctt ctcccacgca  11880
gacacgatcg gcacactcag cgggttcatc accgtaattt cactttccgc ttcgctgggc  11940
tcttcctctt cctcttgcgt ccgcatacca cgcgccactg ggtcgtcttc attcagccgc  12000
cgcactgtgc gcttacctcc tttgccatgc ttgattagca ccggtgggtt gctgaaaccc  12060
accatttgta gcgccacatc ttctctttct tcctcgctgt ccacgattac ctctggtgat  12120
ggcgggcgct cgggcttggg agaagggcgc ttcttttttct tcttgggcgc aatggccaaa  12180
tccgccgccg aggtcgatgg ccgcgggctg ggtgtgcgcg gcaccagcgc gtcttgtgat  12240
gagtcttcct cgtcctcgga ctcgatacgc cgcctcatcc gcttttttgg gggcgcccgg  12300
ggaggcggcg gcgacgggga cggggacgac acgtcctcca tggttggggg acgtcgcgcc  12360
gcaccgcgtc cgcgctcggg ggtggtttcg cgctgctcct cttcccgact ggccatttcc  12420
ttctcctata ggcagaaaaa gatcatggag tcagtcgaga agaaggacag cctaaccgcc  12480
ccctctgagt tcgccaccac cgcctccacc gatgccgcca acgcgcctac caccttcccc  12540
gtcgaggcac ccccgcttga ggaggaggaa gtgattatcg agcaggaccc aggttttgta  12600
agcgaagacg acgaggaccg ctcagtacca acagaggata aaaagcaaga ccaggacaac  12660
gcagaggcaa acgaggaaca agtcgggcgg ggggacgaaa ggcatggcga ctacctagat  12720
gtgggagacg acgtgctgtt gaagcatctg cagcgccagt gcgccattat ctgcgacgcg  12780
ttgcaagagc gcagcgatgt gcccctcgcc atagcggatg tcagccttgc ctacgaacgc  12840
cacctattct caccgcgcgt accccccaaa cgccaagaaa acggcacatg cgagcccaac  12900
ccgcgcctca acttctaccc cgtatttgcc gtgccagagg tgcttgccac ctatcacatc  12960
tttttccaaa actgcaagat acccctatcc tgccgtgcca accgcagccg agcggacaag  13020
cagctggcct tgcggcaggg cgctgtcata cctgatatcg cctcgctcaa cgaagtgcca  13080
aaaatctttg agggtcttgg acgcgacgag aagcgcgcgg caaacgctct gcaacaggaa  13140
aacagcgaaa atgaaagtca ctctggagtg ttggtggaac tcgagggtga caacgcgcgc  13200
ctagccgtac taaaacgcag catcgaggtc acccactttg cctacccggc acttaaccta  13260
ccccccaagg tcatgagcac agtcatgagt gagctgatcg tgcgccgtgc gcagcccctg  13320
gagagggatg caaatttgca agaacaaaca gaggagggcc tacccgcagt tggcgacgag  13380
cagctagcgc gctggcttca aacgcgcgag cctgccgact tggaggagcg acgcaaacta  13440
atgatggccg cagtgctcgt taccgtggag cttgagtgca tgcagcggtt ctttgctgac  13500
ccggagatgc agcgcaagct agaggaaaca ttgcactaca cctttcgaca gggctacgta  13560
cgccaggcct gcaagatctc caacgtggag ctctgcaacc tggtctccta ccttggaatt  13620
ttgcacgaaa accgccttgg gcaaaacgtg cttcattcca cgctcaaggg cgaggcgcgc  13680
cgcgactacg tccgcgactg cgtttactta tttctatgct acacctggca gacggccatg  13740
ggcgtttggc agcagtgctt ggaggagtgc aacctcaagg agctgcagaa actgctaaag  13800
caaaacttga aggacctatg gacggccttc aacgagcgct ccgtggccgc gcacctggcg  13860
gacatcattt tccccgaacg cctgcttaaa accctgcaac agggtctgcc agacttcacc  13920
agtcaaagca tgttgcagaa ctttaggaac tttatcctag agcgctcagg aatcttgccc  13980
gccacctgct gtgcacttcc tagcgacttt gtgcccatta agtaccgcga atgccctccg  14040
ccgctttggg gccactgcta ccttctgcag ctagccaact accttgccta ccactctgac  14100
ataatggaag acgtgagcgg tgacggtcta ctggagtgtc actgtcgctg caacctatgc  14160
```

-continued

```
accccgcacc gctccctggt ttgcaattcg cagctgctta acgaaagtca aattatcggt  14220
acctttgagc tgcagggtcc ctcgcctgac gaaaagtccg cggctccggg gttgaaactc  14280
actccggggc tgtggacgtc ggcttacctt cgcaaatttg tacctgagga ctaccacgcc  14340
cacgagatta ggttctacga agaccaatcc cgcccgccat atgcggagct taccgcctgc  14400
gtcattaccc agggccacat tcttggccaa ttgcaagcca tcaacaaagc ccgccaagag  14460
tttctgctac gaaagggacg gggggtttac ttggaccccc agtccggcga ggagctcaac  14520
ccaatccccc cgccgccgca gccctatcag cagcagccgc gggcccttgc ttcccaggat  14580
ggcacccaaa aagaagctgc agctgccgcc gccacccacg gacgaggagg aatactggga  14640
cagtcaggca gaggaggttt tggacgagga ggaggaggac atgatggaag actgggagag  14700
cctagacgag gaagcttccg aggtcgaaga ggtgtcagac gaaacaccgt caccctcggt  14760
cgcattcccc tcgccggcgc cccagaaatc ggcaaccggt tccagcatgg ctacaacctc  14820
cgctcctcag gcgccgccgg cactgcccgt tcgccgaccc aaccgtagat gggacaccac  14880
tggaaccagg gccggtaagt ccaagcagcc gccgccgtta gcccaagagc aacaacagcg  14940
ccaaggctac cgctcatggc gcgggcacaa gaacgccata gttgcttgct tgcaagactg  15000
tgggggcaac atctccttcg cccgccgctt tcttctctac catcacggcg tggccttccc  15060
ccgtaacatc ctgcattact accgtcatct ctacagccca tactgcaccg gcggcagcgg  15120
cagcaacagc agcggccaca cagaagcaaa ggcgaccgga tagcaagact ctgacaaagc  15180
ccaagaaatc cacagcggcg gcagcagcag gaggaggagc gctgcgtctg gcgcccaacg  15240
aacccgtatc gacccgcgag cttagaaaca ggatttttcc cactctgtat gctatatttc  15300
aacagagcag gggccaagaa caagagctga aaataaaaaa caggtctctg cgatccctca  15360
cccgcagctg cctgtatcac aaaagcgaag atcagcttcg gcgcacgctg gaagacgcgg  15420
aggctctctt cagtaaatac tgcgcgctga ctcttaagga ctagtttcgc gccctttctc  15480
aaatttaagc gcgaaaacta cgtcatctcc agcggccaca cccggcgcca gcacctgttg  15540
tcagcgccat tatgagcaag gaaattccca cgccctacat gtggagttac cagccacaaa  15600
tgggacttgc ggctggagct gcccaagact actcaacccg aataaactac atgagcgcgg  15660
gaccccacat gatatcccgg gtcaacggaa tacgcgccca ccgaaaccga attctctcgg  15720
aacaggcggc tattaccacc acacctcgta ataaccttaa tccccgtagt tggcccgctg  15780
ccctggtgta ccaggaaagt cccgctccca ccactgtggt acttcccaga gacgcccagg  15840
ccgaagttca gatgactaac tcaggggcgc agcttgcggg cggctttcgt cacagggtgc  15900
ggtcgcccgg gcagggtata actcacctga caatcagagg gcgaggtatt cagctcaacg  15960
acgagtcggt gagctcctcg cttggtctcc gtccggacgg gacatttcag atcggcggcg  16020
ccggccgctc ttcattcacg cctcgtcagg caatcctaac tctgcagacc tcgtcctctg  16080
agccgcgctc tggaggcatt ggaactctgc aatttattga ggagtttgtg ccatcggtct  16140
actttaaccc cttctcggga cctcccggcc actatccgga tcaatttatt cctaactttg  16200
acgcggtaaa ggactcggcg gacggctacg actgaatgtt aagtggagag gcagagcaac  16260
tgcgcctgaa acacctggtc cactgtcgcc gccacaagtg ctttgcccgc gactccggtg  16320
agttttgcta ctttgaattg cccgaggatc atatcgaggg cccggcgcac ggcgtccggc  16380
ttaccgccca gggagagctt gcccgtagcc tgattcggga gtttacccag cgcccccctgc  16440
tagttgagcg ggacagggga ccctgtgttc tcactgtgat ttgcaactgt cctaaccctg  16500
gattacatca agatcctcta gttaattaac tagagtaccc ggggatctta ttccctttaa  16560
```

ctaataaaaa aaaataataa agcatcactt acttaaaatc agttagcaaa tttctgtcca 16620
gtttattcag cagcacctcc ttgccctcct cccagctctg gtattgcagc ttcctcctgg 16680
ctgcaaactt tctccacaat ctaaatggaa tgtcagtttc ctcctgttcc tgtccatccg 16740
cacccactat cttcatgttg ttgcagatga agcgcgcaag accgtctgaa gataccttca 16800
accccgtgta tccatatgac acggaaaccg gtcctccaac tgtgcctttt cttactcctc 16860
cctttgtatc ccccaatggg tttcaagaga gtccccctgg ggtactctct ttgcgcctat 16920
ccgaacctct agttacctcc aatggcatgc ttgcgctcaa aatgggcaac ggcctctctc 16980
tggacgaggc cggcaacctt acctcccaaa atgtaaccac tgtgagccca cctctcaaaa 17040
aaaccaagtc aaacataaac ctggaaatat ctgcacccct cacagttacc tcagaagccc 17100
taactgtggc tgccgccgca cctctaatgg tcgcgggcaa cacactcacc atgcaatcac 17160
aggccccgct aaccgtgcac gactccaaac ttagcattgc cacccaagga cccctcacag 17220
tgtcagaagg aaagctagcc ctgcaaacat caggcccccct caccaccacc gatagcagta 17280
cccttactat cactgcctca ccccctctaa ctactgccac tggtagcttg ggcattgact 17340
tgaaagagcc catttataca caaaatggaa aactaggact aaagtacggg gctcctttgc 17400
atgtaacaga cgacctaaac actttgaccg tagcaactgg tccaggtgtg actattaata 17460
atacttcctt gcaaactaaa gttactggag ccttgggttt tgattcacaa ggcaatatgc 17520
aacttaatgt agcaggagga ctaaggattg attctcaaaa cagacgcctt atacttgatg 17580
ttagttatcc gtttgatgct caaaaccaac taaatctaag actaggacag ggccctcttt 17640
ttataaactc agcccacaac ttggatatta actacaacaa aggcctttac ttgtttacag 17700
cttcaaacaa ttccaaaaag cttgaggtta acctaagcac tgccaagggg ttgatgtttg 17760
acgctacagc catagccatt aatgcaggag atgggcttga atttggttca cctaatgcac 17820
caaacacaaa tcccctcaaa acaaaaattg gccatggcct agaatttgat tcaaacaagg 17880
ctatggttcc taaactagga actggcctta gttttgacag cacaggtgcc attacagtag 17940
gaaacaaaaa taatgataag ctaactttgt ggaccacacc agctccatct cctaactgta 18000
gactaaatgc agagaaagat gctaaactca ctttggtctt aacaaaatgt ggcagtcaaa 18060
tacttgctac agtttcagtt ttggctgtta aaggcagttt ggctccaata tctggaacag 18120
ttcaaagtgc tcatcttatt ataagatttg acgaaaatgg agtgctacta aacaattcct 18180
tcctggaccc agaatattgg aactttagaa atggagatct tactgaaggc acagcctata 18240
caaacgctgt tggatttatg cctaacctat cagcttatcc aaaatctcac ggtaaaactg 18300
ccaaaagtaa cattgtcagt caagtttact taaacggaga caaaactaaa cctgtaacac 18360
taaccattac actaaacggt acacaggaaa caggagacac aactccaagt gcatactcta 18420
tgtcattttc atgggactgg tctggccaca actacattaa tgaaatattt gccacatcct 18480
cttacacttt ttcatacatt gcccaagaat aaagaatcgt ttgtgttatg tttcaacgtg 18540
tttatttttc aattgcagaa aatttcaagt catttttcat tcagtagtat agccccacca 18600
ccacatagct tatacagatc accgtacctt aatcaaactc acagaaccct agtattcaac 18660
ctgccacctc cctcccaaca cacagagtac acagtccttt ctccccggct ggccttaaaa 18720
agcatcatat catgggtaac agacatattc ttaggtgtta tattccacac ggtttcctgt 18780
cgagccaaac gctcatcagt gatattaata aactccccgg gcagctcact taagttcatg 18840
tcgctgtcca gctgctgagc cacaggctgc tgtccaactt gcggttgctt aacgggcggc 18900

-continued

```
gaaggagaag tccacgccta catgggggta gagtcataat cgtgcatcag gatagggcgg  18960
tggtgctgca gcagcgcgcg aataaactgc tgccgccgcc gctccgtcct gcaggaatac  19020
aacatggcag tggtctcctc agcgatgatt cgcaccgccc gcagcataag gcgccttgtc  19080
ctccgggcac agcagcgcac cctgatctca cttaaatcag cacagtaact gcagcacagc  19140
accacaatat tgttcaaaat cccacagtgc aaggcgctgt atccaaagct catggcgggg  19200
accacagaac ccacgtggcc atcataccac aagcgcaggt agattaagtg gcgacccctc  19260
ataaacacgc tggacataaa cattacctct tttggcatgt tgtaattcac cacctcccgg  19320
taccatataa acctctgatt aaacatggcg ccatccacca ccatcctaaa ccagctggcc  19380
aaaacctgcc cgccggctat acactgcagg gaaccgggac tggaacaatg acagtggaga  19440
gcccaggact cgtaaccatg gatcatcatg ctcgtcatga tatcaatgtt ggcacaacac  19500
aggcacacgt gcatacactt cctcaggatt acaagctcct cccgcgttag aaccatatcc  19560
cagggaacaa cccattcctg aatcagcgta aatcccacac tgcagggaag acctcgcacg  19620
taactcacgt tgtgcattgt caaagtgtta cattcgggca gcagcggatg atcctccagt  19680
atggtagcgc gggtttctgt ctcaaaagga ggtagacgat ccctactgta cggagtgcgc  19740
cgagacaacc gagatcgtgt tggtcgtagt gtcatgccaa atggaacgcc ggacgtagtc  19800
atatttcctg aagcaaaacc aggtgcgggc gtgacaaaca gatctgcgtc tccggtctcg  19860
ccgcttagat cgctctgtgt agtagttgta gtatatccac tctctcaaag catccaggcg  19920
ccccctggct tcgggttcta tgtaaactcc ttcatgcgcc gctgccctga taacatccac  19980
caccgcagaa taagccacac ccagccaacc tacacattcg ttctgcgagt cacacacggg  20040
aggagcggga agagctggaa gaaccatgtt ttttttttta ttccaaaaga ttatccaaaa  20100
cctcaaaatg aagatctatt aagtgaacgc gctcccctcc ggtggcgtgg tcaaactcta  20160
cagccaaaga acagataatg gcatttgtaa gatgttgcac aatggcttcc aaaaggcaaa  20220
cggccctcac gtccaagtgg acgtaaaggc taaacccttc agggtgaatc tcctctataa  20280
acattccagc accttcaacc atgcccaaat aattctcatc tcgccacctt ctcaatatat  20340
ctctaagcaa atcccgaata ttaagtccgg ccattgtaaa aatctgctcc agagcgccct  20400
ccaccttcag cctcaagcag cgaatcatga ttgcaaaaat tcaggttcct cacagacctg  20460
tataagattc aaaagcggaa cattaacaaa aataccgcga tcccgtaggt cccttcgcag  20520
ggccagctga acataatcgt gcaggtctgc acggaccagc gcggccactt ccccgccagg  20580
aaccatgaca aaagaaccca cactgattat gacacgcata ctcggagcta tgctaaccag  20640
cgtagccccg atgtaagctt gttgcatggg cggcgatata aaatgcaagg tgctgctcaa  20700
aaaatcaggc aaagcctcgc gcaaaaaaga aagcacatcg tagtcatgct catgcagata  20760
aaggcaggta agctccggaa ccaccacaga aaaagacacc atttttctct caaacatgtc  20820
tgcgggtttc tgcataaaca caaaataaaa taacaaaaaa acatttaaac attagaagcc  20880
tgtcttacaa caggaaaaac aacccttata agcataagac ggactacggc catgccggcg  20940
tgaccgtaaa aaaactggtc accgtgatta aaaagcacca ccgacagctc ctcggtcatg  21000
tccggagtca taatgtaaga ctcggtaaac acatcaggtt gattcacatc ggtcagtgct  21060
aaaaagcgac cgaaatagcc cgggggaata catacccgca ggcgtagaga caacattaca  21120
gcccccatag gaggtataac aaaattaata ggagagaaaa acacataaac acctgaaaaa  21180
ccctcctgcc taggcaaaat agcaccctcc cgctccagaa caacatacag cgcttccaca  21240
gcggcagcca taacagtcag ccttaccagt aaaaaagaaa acctattaaa aaaacaccac  21300
```

```
tcgacacggc accagctcaa tcagtcacag tgtaaaaaag ggccaagtgc agagcgagta  21360

tatataggac taaaaaatga cgtaacggtt aaagtccaca aaaaacaccc agaaaaccgc  21420

acgcgaacct acgcccagaa acgaaagcca aaaaacccac aacttcctca aatcgtcact  21480

tccgttttcc cacgttacgt aacttcccat tttaagaaaa ctacaattcc caacacatac  21540

aagttactcc gccctaaaac ctacgtcacc cgccccgttc ccacgccccg cgccacgtca  21600

caaactccac cccctcatta tcatattggc ttcaatccaa aataaggtat attattgatg  21660

atttattttg gattgaagcc aatatgataa tgagggggtg gagtttgtga cgtggcgcgg  21720

ggcgtgggaa cggggcgggt gacgtagtag tgtggcggaa gtgtgatgtt gcaagtgtgg  21780

cggaacacat gtaagcgacg gatgtggcaa aagtgacgtt tttggtgtgc gccggatcca  21840

caggacgggt gtggtcgcca tgatcgcgta gtcgatagtg gctccaagta gcgaagcgag  21900

caggactggg cggcggccaa agcggtcgga cagtgctccg agaacgggtg cgcatagaaa  21960

ttgcatcaac gcatatagcg ctagcagcac gccatagtga ctggcgatgc tgtcggaatg  22020

gacgatatcc cgcaagaggc ccggcagtac cggcataacc aagcctatgc ctacagcatc  22080

cagggtgacg gtgccgagga tgacgatgag cgcattgtta gatttcatac acggtgcctg  22140

actgcgttag caatttaact gtgataaact accgcattaa agcttatcga attcgtaatc  22200

atggtcatag ctgtttcctg tgtgaaattg ttatccgctc acaattccac acaacatacg  22260

agccggaagc ataaagtgta aagcctgggg tgcctaatga gtgagctaac tcacattaat  22320

tgcgttgcgc tcactgcccg ctttccagtc gggaaacctg tcgtgccagc tgcattaatg  22380

aatcggccaa cgcgcgggga gaggcggttt gcgtattggg cgc                    22423
```

<210> SEQ ID NO 3
<211> LENGTH: 10365
<212> TYPE: DNA
<213> ORGANISM: Artificial Sequence
<220> FEATURE:
<223> OTHER INFORMATION: Synthetic: Payload/Cap Plasmid Factor IX / AAV2

<400> SEQUENCE: 3

```
gtatatatga gtaaacttgg tctgacagtt accaatgctt aatcagtgag gcacctatct     60

cagcgatctg tctatttcgt tcatccatag ttgcctgact ccccgtcgtg tagataacta    120

cgatacggga gggcttacca tctggcccca gtgctgcaat gataccgcga gacccacgct    180

caccggctcc agatttatca gcaataaacc agccagccgg aagggccgag cgcagaagtg    240

gtcctgcaac tttatccgcc tccatccagt ctattaattg ttgccgggaa gctagagtaa    300

gtagttcgcc agttaatagt ttgcgcaacg ttgttgccat tgctacaggc atcgtggtgt    360

cacgctcgtc gtttggtatg gcttcattca gctccggttc ccaacgatca aggcgagtta    420

catgatcccc catgttgtgc aaaaaagcgg ttagctcctt cggtcctccg atcgttgtca    480

gaagtaagtt ggccgcagtg ttatcactca tggttatggc agcactgcat aattctctta    540

ctgtcatgcc atccgtaaga tgcttttctg tgactggtga gtactcaacc aagtcattct    600

gagaatagtg tatgcggcga ccgagttgct cttgcccggc gtcaatacgg gataataccg    660

cgccacatag cagaacttta aaagtgctca tcattggaaa acgttcttcg gggcgaaaac    720

tctcaaggat cttaccgctg ttgagatcca gttcgatgta acccactcgt gcacccaact    780

gatcttcagc atcttttact ttcaccagcg tttctgggtg agcaaaaaca ggaaggcaaa    840

atgccgcaaa aaagggaata agggcgacac ggaaatgttg aatactcata ctcttccttt    900
```

-continued

```
ttcaatatta ttgaagcatt tatcagggtt attgtctcat gagcggatac atatttgaat    960
gtatttagaa aaataaacaa ataggggttc cgcgcacatt tccccgaaaa gtgccacctg   1020
acgtctaaga aaccattatt atcatgacat taacctataa aaataggcgt atcacgaggc   1080
cctttcgtct cgcgcgtttc ggtgatgacg gtgaaaacct ctgacacatg cagctcccgg   1140
agacggtcac agcttgtctg taagcggatg ccgggagcag acaagcccgt cagggcgcgt   1200
cagcgggtgt tggcgggtgt cggggctggc ttaactatgc ggcatcagag cagattgtac   1260
tgagagtgca ccattcgacg ctctccctta tgcgactcct gcattaggaa gcagcccagt   1320
agtaggttga ggccgttgag caccgccgcc gcaaggaatg gtgcatgcaa ggagatggcg   1380
cccaacagtc ccccggccac ggggcctgcc accataccca cgccgaaaca agcgctcatg   1440
agcccgaagt ggcgagcccg atcttcccca tcggtgatgt cggcgatata ggcgccagca   1500
accgcacctg tggcgccggt gggtcaccaa gcaggaagtc aaagactttt tccggtgggc   1560
aaaggatcac gtggttgagg tggagcatga attctacgtc aaaaagggtg gagccaagaa   1620
aagacccgcc cccagtgacg cagatataag tgagcccaaa cgggtgcgcg agtcagttgc   1680
gcagccatcg acgtcagacg cggaagcttc gatcaactac gcagacaggt accaaaacaa   1740
atgttctcgt cacgtgggca tgaatctgat gctgtttccc tgcagacaat gcgagagaat   1800
gaatcagaat tcaaatatct gcttcactca cggacagaaa gactgtttag agtgctttcc   1860
cgtgtcagaa tctcaacccg tttctgtcgt caaaaaggcg tatcagaaac tgtgctacat   1920
tcatcatatc atgggaaagg tgccagacgc ttgcactgcc tgcgatctgg tcaatgtgga   1980
tttggatgac tgcatctttg aacaataaat gatttaaatc aggtatggct gccgatggtt   2040
atcttccaga ttggctcgag gacactctct ctgaaggaat aagacagtgg tggaagctca   2100
aacctggccc accaccacca aagcccgcag agcggcataa ggacgacagc aggggtcttg   2160
tgcttcctgg gtacaagtac ctcggaccct tcaacggact cgacaaggga gagccggtca   2220
acgaggcaga cgccgcggcc ctcgagcacg acaaagccta cgaccggcag ctcgacagcg   2280
gagacaaccc gtacctcaag tacaaccacg ccgacgcgga gtttcaggag cgccttaaag   2340
aagatacgtc ttttgggggc aacctcggac gagcagtctt ccaggcgaaa aagagggttc   2400
ttgaacctct gggcctggtt gaggaacctg ttaagacggc tccgggaaaa aagaggccgg   2460
tagagcactc tcctgtggag ccagactcct cctcgggaac cggaaaggcg ggccagcagc   2520
ctgcaagaaa aagattgaat tttggtcaga ctggagacgc agactcagta cctgaccccc   2580
agcctctcgg acagccacca gcagccccct ctggtctggg aactaatacg atggctacag   2640
gcagtggcgc accaatggca gacaataacg agggcgccga cggagtgggt aattcctcgg   2700
gaaattggca ttgcgattcc acatggatgg gcgacagagt catcaccacc agcacccgaa   2760
cctgggccct gcccacctac aacaaccacc tctacaaaca aatttccagc caatcaggag   2820
cctcgaacga caatcactac tttggctaca gcaccccttg ggggtatttt gacttcaaca   2880
gattccactg ccacttttca ccacgtgact ggcaaagact catcaacaac aactggggat   2940
tccgacccaa gagactcaac ttcaagctct ttaacattca agtcaaagag gtcacgcaga   3000
atgacggtac gacgacgatt gccaataacc ttaccagcac ggttcaggtg tttactgact   3060
cggagtacca gctcccgtac gtcctcggct cggcgcatca aggatgcctc ccgccgttcc   3120
cagcagacgt cttcatggtg ccacagtatg gatacctcac cctgaacaac gggagtcagg   3180
cagtaggacg ctcttcattt tactgcctgg agtactttcc ttctcagatg ctgcgtaccg   3240
gaaacaactt taccttcagc tacactttg aggacgttcc tttccacagc agctacgctc    3300
```

-continued acagccagag tctggaccgt ctcatgaatc ctctcatcga ccagtacctg tattacttga 3360
gcagaacaaa cactccaagt ggaaccacca cgcagtcaag gcttcagttt tctcaggccg 3420
gagcgagtga cattcgggac cagtctagga actggcttcc tggaccctgt taccgccagc 3480
agcgagtatc aaagacatct gcggataaca acaacagtga atactcgtgg actggagcta 3540
ccaagtacca cctcaatggc agagactctc tggtgaatcc gggcccggcc atggcaagcc 3600
acaaggacga tgaagaaaag tttttttcctc agagcggggt tctcatcttt gggaagcaag 3660
gctcagagaa aacaaatgtg gacattgaaa aggtcatgat tacagacgaa gaggaaatca 3720
ggacaaccaa tcccgtggct acggagcagt atggttctgt atctaccaac ctccagagag 3780
gcaacagaca agcagctacc gcagatgtca acacacaagg cgttcttcca ggcatggtct 3840
ggcaggacag agatgtgtac cttcaggggc ccatctgggc aaagattcca cacacggacg 3900
gacattttca cccctctccc ctcatgggtg gattcggact taaacaccct cctccacaga 3960
ttctcatcaa gaacaccccg gtacctgcga atccttcgac caccttcagt gcggcaaagt 4020
ttgcttcctt catcacacag tactccacgg gacaggtcag cgtggagatc gagtgggagc 4080
tgcagaagga aaacagcaaa cgctggaatc ccgaaattca gtacacttcc aactacaaca 4140
agtctgttaa tgtggacttt actgtggaca ctaatggcgt gtattcagag cctcgcccca 4200
ttggcaccag atacctgact cgtaatctgt aattgcttgt taatcaataa accgtttaat 4260
tcgtttcagt tgaactttgg tctctgcgta tttctttctt atctagtttc catatgcatg 4320
tagataagta gcatggcggg ttaatcatta actaaccggt acctctagaa ctatagctag 4380
cgatgaccct gctgattggt tcgctgacca tttccgggtg cgggacggcg ttaccagaaa 4440
ctcagaaggt tcgtccaacc aaaccgactc tgacggcagt ttacgagaga gatgataggg 4500
tctgcttcag taagccagat gctacacaat taggcttgta catattgtcg ttagaacgcg 4560
gctacaatta atacataacc ttatgtatca tacacatacg atttaggtga cactatagaa 4620
tacacggaat taattcttgg ccactccctc tctgcgcgct cgctcgctca ctgaggccgc 4680
ccgggcaaag cccgggcgtc gggcgacctt tggtcgcccg gcctcagtga gcgagcgagc 4740
gcgcagagag ggagtggcca actccatcac taggggttcc ttacgtagga cgtcccctgc 4800
aggcagggag gggtggagtc gtgacgtaaa gatctgatat catcgatcgc gatgcattaa 4860
ttaagcggcc gaggctcaga ggcacacagg agtttctggg ctcaccctgc ccccttccaa 4920
cccctcagtt cccatcctcc agcagctgtt tgtgtgctgc ctctgaagtc cacactgaac 4980
aaacttcagc ctactcatgt ccctaaaatg ggcaaacatt gcaagcagca aacagcaaac 5040
acacagccct ccctgcctgc tgaccttgga gctggggcag aggtcagaga cctctctggg 5100
cccatgccac ctccaacatc cactcgaccc cttggaattt cggtggagag gagcagaggt 5160
tgtcctggcg tggtttaggt agtgtgagag gggtacccgg ggatcttgct accagtggaa 5220
cagccactaa ggattctgca gtgagagcag agggccagct aagtggtact ctcccagaga 5280
ctgtctgact cacgccaccc cctccacctt ggacacagga cgctgtggtt tctgagccag 5340
gtacaatgac tcctttcggt aagtgcagtg gaagctgtac actgcccagg caaagcgtcc 5400
gggcagcgta ggcgggcgac tcagatccca gccagtggac ttagcccctg tttgctcctc 5460
cgataactgg ggtgaccttg gttaatattc accagcagcc tcccccgttg cccctctgga 5520
tccactgctt aaatacggac gaggacaggg ccctgtctcc tcagcttcag gcaccaccac 5580
tgacctggga cagtgaatga tccccctgat ctgcggcctc gacggtatcg ataagcttga 5640

```
tatcgaattc tagtcgtcga ccactttcac aatctgctag caaaggttgc caccatgcag   5700
cgcgtgaaca tgattatggc cgagagccct ggcctgatca ccatctgcct gctgggctac   5760
ctgctgagcg ccgagtgtac aggtttgttt cctttttaa aatacattga gtatgcttgc   5820
cttttagata tagaaatatc tgatgctgtc ttcttcacta aattttgatt acatgatttg   5880
acagcaatat tgaagagtct aacagccagc acgcaggttg gtaagtactg gttctttgtt   5940
agctaggttt tcttcttctt catttttaaa actaaataga tcgacaatgc ttatgatgca   6000
tttatgttta ataaacactg ttcagttcat gatttggtca tgtaattcct gttagaaaac   6060
attcatctcc ttggtttaaa aaaattaaaa gtgggaaaac aaagaaatag cagaatatag   6120
tgaaaaaaaa taaccacatt atttttgttt ggacttacca ctttgaaatc aaaatgggaa   6180
acaaaagcac aaacaatggc cttatttaca caaaaagtct gattttaaga tatatgacat   6240
ttcaaggttt cagaagtatg taatgaggtg tgtctctaat tttttaaatt atatatcttc   6300
aatttaaagt tttagttaaa acataaagat taacctttca ttagcaagct gttagttatc   6360
accaaagctt ttcatggatt aggaaaaaat catttttgtct ctatgtcaaa catcttggag   6420
ttgatatttg gggaaacaca atactcagtt gagttcccta ggggagaaaa gcaagcttaa   6480
gaattgacat aaagagtagg aagttagcta atgcaacata tatcactttg tttttttcaca   6540
actacagtga ctttatgtat ttcccagagg aaggcataca gggaagaaat tatcccattt   6600
ggacaaacag catgttctca caggaagcat ttatcacact tacttgtcaa ctttctagaa   6660
tcaaatctag tagctgacag taccaggatc aggggtgcca accctaagca cccccagaaa   6720
gctgactggc cctgtggttc ccactccaga catgatgtca gctgtgaaat cgacgtcgct   6780
ggaccataat taggcttctg ttcttcagga gacatttgtt caaagtcatt tgggcaacca   6840
tattctgaaa acagcccagc cagggtgatg gatcactttg caaagatcct caatgagcta   6900
ttttcaagtg atgacaaagt gtgaagttaa ccgctcattt gagaactttc tttttcatcc   6960
aaagtaaatt caaatatgat tagaaatctg accttttatt actggaattc tcttgactaa   7020
aagtaaaatt gaattttaat tcctaaatct ccatgtgtat acagtactgt gggaacatca   7080
cagattttgg ctccatgccc taaagagaaa ttggctttca gattatttgg attaaaaaca   7140
aagactttct taagagatgt aaaattttca tgatgttttc tttttgcta aaactaaaga   7200
attattcttt tacatttcag tgttcctgga ccacgagaac gccaacaaga tcctgaacag   7260
acccaagaga tacaacagcg gcaagctgga agagttcgtg cagggcaacc tggaacgcga   7320
gtgcatggaa gagaagtgca gcttcgaaga ggccagagag gtgttcgaga acaccgagag   7380
aaccaccgag ttctggaagc agtacgtgga cggcgaccag tgcgagagca acccttgtct   7440
gaacggcggc agctgcaagg acgacatcaa cagctacgag tgctggtgcc ccttcggctt   7500
cgagggcaag aactgcgagc tggacgtgac ctgcaacatc aagaacggca gatgcgagca   7560
gttctgcaag aacagcgccg acaacaaggt cgtgtgctcc tgcaccgagg gctacagact   7620
ggccgagaac cagaagtcct gcgagcccgc tgtgcctttc ccatgcggaa gagtgtccgt   7680
gtcccagacc agcaagctga ccagagccga gacagtgttc cccgacgtgg actacgtgaa   7740
cagcaccgag gccgagacaa tcctggacaa catcacccag agcacccagt ccttcaacga   7800
cttcaccaga gtcgtgggcg gcgaggatgc taagcctggc cagttcccgt ggcaggtggt   7860
gctgaacgga aaggtggacg ccttctgcgg cggctccatc gtgaacgaga agtggatcgt   7920
gacagccgcc cactgcgtgg aaaccggcgt gaagatcaca gtggtggccg gcgagcacaa   7980
catcgaggaa accgagcaca cagagcagaa aagaaacgtg atcaggatca tcccccacca   8040
```

-continued

```
caactacaac gccgccatca acaagtacaa ccacgatatc gccctgctgg aactggacga   8100
gcccctggtg ctgaatagct acgtgacccc catctgtatc gccgacaaag agtacaccaa   8160
catctttctg aagttcggca gcggctacgt gtccggctgg ggcagagtgt ttcacaaggg   8220
cagatccgct ctggtgctgc agtacctgag agtgcctctg gtggacagag ccacctgtct   8280
gagaagcacc aagttcacca tctacaacaa catgttctgc gctggcttcc acgagggcgg   8340
cagagactct tgtcagggcg attctggcgg ccctcacgtg acagaggtgg aaggcaccag   8400
ctttctgacc ggcatcatca gctggggcga ggaatgcgcc atgaagggga agtacggcat   8460
ctacaccaag gtgtccagat acgtgaactg gatcaaagaa aagaccaagc tgacataatg   8520
aaagatggat ttccaaggtt aattcattgg aattgaaaat taacagcccc cccccccccc   8580
ccctgcagat ctcgagccga attcctgcag cccgggggat cagcctcgac tgtgccttct   8640
agttgccagc catctgttgt ttgcccctcc cccgtgcctt ccttgaccct ggaaggtgcc   8700
actcccactg tcctttccta ataaaatgag gaaattgcat cgcattgtct gagtaggtgt   8760
cattctattc tggggggtgg ggtggggcag gacagcaagg gggaggattg ggaagacaat   8820
agcaggcatg ctggggatgc ggtgggctct atggcttctg aggcggaaag aaccagctgg   8880
ggctcgagat ccactagact agtgtacacg cgtgatatca gatctgttac gtaaggaacc   8940
cctagtgatg gagttggcca ctccctctct gcgcgctcgc tcgctcactg aggccgcccg   9000
ggcaaagccc gggcggcctc agtgagcgag cgagcgcgca gagagggagt ggccaacttt   9060
ttgcaaaagc ctaggcctcc aaaaaagcct cctcactact tctggaatag ctcagaggcc   9120
gaggcggcct cggcctctgc ataaataaaa aaaattagtc agccatgggg cggagaatgg   9180
gcggaactgg gcggagttag gggcgggatg ggcggagtta ggggcgggac tatggttgct   9240
gactaattga gatgcatgct ttgcatactt ctgcctgctg gggagcctgg ggactttcca   9300
cacctggttg ctgactaatt gagatgcatg ctttgcatac ttctgcctgc tggggagcct   9360
ggggactttc cacaccctaa ctgacacaca ttccacagct gcattaatga atcggccaac   9420
gcgcggggag aggcggtttg cgtattgggc gctcttccgc ttcctcgctc actgactcgc   9480
tgcgctcggt cgttcggctg cggcgagcgg tatcagctca ctcaaaggcg gtaatacggt   9540
tatccacaga atcaggggat aacgcaggaa agaacatgtg agcaaaaggc cagcaaaagg   9600
ccaggaaccg taaaaaggcc gcgttgctgg cgtttttcca taggctccgc ccccctgacg   9660
agcatcacaa aaatcgacgc tcaagtcaga ggtggcgaaa cccgacagga ctataaagat   9720
accaggcgtt tccccctgga agctccctcg tgcgctctcc tgttccgacc ctgccgctta   9780
ccggatacct gtccgccttt ctcccttcgg gaagcgtggc gctttctcat agctcacgct   9840
gtaggtatct cagttcggtg taggtcgttc gctccaagct gggctgtgtg cacgaacccc   9900
ccgttcagcc cgaccgctgc gccttatccg gtaactatcg tcttgagtcc aacccggtaa   9960
gacacgactt atcgccactg gcagcagcca ctggtaacag gattagcaga gcgaggtatg  10020
taggcggtgc tacagagttc ttgaagtggt ggcctaacta cggctacact agaagaacag  10080
tatttggtat ctgcgctctg ctgaagccag ttaccttcgg aaaaagagtt ggtagctctt  10140
gatccggcaa acaaaccacc gctggtagcg gtggtttttt tgtttgcaag cagcagatta  10200
cgcgcagaaa aaaaggatct caagaagatc ctttgatctt ttctacgggg tctgacgctc  10260
agtggaacga aaactcacgt taagggattt tggtcatgag attatcaaaa aggatcttca  10320
cctagatcct tttaaattaa aaatgaagtt ttaaatcaat ctaaa                  10365
```

<210> SEQ ID NO 4
<211> LENGTH: 10332
<212> TYPE: DNA
<213> ORGANISM: Artificial Sequence
<220> FEATURE:
<223> OTHER INFORMATION: Synthetic: Payload/Cap Plasmid Factor IX / AAV5

<400> SEQUENCE: 4
agttttaaat caatctaaag tatatatgag taaacttggt ctgacagtta ccaatgctta 60
atcagtgagg cacctatctc agcgatctgt ctatttcgtt catccatagt tgcctgactc 120
cccgtcgtgt agataactac gatacgggag ggcttaccat ctggccccag tgctgcaatg 180
ataccgcgag acccacgctc accggctcca gatttatcag caataaacca gccagccgga 240
agggccgagc gcagaagtgg tcctgcaact ttatccgcct ccatccagtc tattaattgt 300
tgccgggaag ctagagtaag tagttcgcca gttaatagtt tgcgcaacgt tgttgccatt 360
gctacaggca tcgtggtgtc acgctcgtcg tttggtatgg cttcattcag ctccggttcc 420
caacgatcaa ggcgagttac atgatccccc atgttgtgca aaaaagcggt tagctccttc 480
ggtcctccga tcgttgtcag aagtaagttg gccgcagtgt tatcactcat ggttatggca 540
gcactgcata attctcttac tgtcatgcca tccgtaagat gcttttctgt gactggtgag 600
tactcaacca agtcattctg agaatagtgt atgcggcgac cgagttgctc ttgcccggcg 660
tcaatacggg ataataccgc gccacatagc agaactttaa aagtgctcat cattggaaaa 720
cgttcttcgg ggcgaaaact ctcaaggatc ttaccgctgt tgagatccag ttcgatgtaa 780
cccactcgtg cacccaactg atcttcagca tcttttactt tcaccagcgt ttctgggtga 840
gcaaaaacag gaaggcaaaa tgccgcaaaa aagggaataa gggcgacacg gaaatgttga 900
atactcatac tcttcctttt tcaatattat tgaagcattt atcagggtta ttgtctcatg 960
agcggataca tatttgaatg tatttagaaa aataaacaaa taggggttcc gcgcacattt 1020
ccccgaaaag tgccacctga cgtctaagaa accattatta tcatgacatt aacctataaa 1080
aataggcgta tcacgaggcc ctttcgtctc gcgcgtttcg gtgatgacgg tgaaaacctc 1140
tgacacatgc agctcccgga gacggtcaca gcttgtctgt aagcggatgc cgggagcaga 1200
caagcccgtc agggcgcgtc agcgggtgtt ggcgggtgtc ggggctggct taactatgcg 1260
gcatcagagc agattgtact gagagtgcac cattcgacgc tctcccttat gcgactcctg 1320
cattaggaag cagcccagta gtaggttgag gccgttgagc accgccgccg caaggaatgg 1380
tgcatgcaag gagatggcgc ccaacagtcc cccggccacg gggcctgcca ccatacccac 1440
gccgaaacaa gcgctcatga gcccgaagtg gcgagcccga tcttccccat cggtgatgtc 1500
ggcgatatag gcgccagcaa ccgcacctgt ggcgccggtg ggtcaccaag caggaagtca 1560
aagacttttt ccggtgggca aaggatcacg tggttgaggt ggagcatgaa ttctacgtca 1620
aaaagggtgg agccaagaaa agacccgccc ccagtgacgc agatataagt gagcccaaac 1680
gggtgcgcga gtcagttgcg cagccatcga cgtcagacgc ggaagcttcg atcaactacg 1740
cagacaggta ccaaaacaaa tgttctcgtc acgtgggcat gaatctgatg ctgtttccct 1800
gcagacaatg cgagagaatg aatcagaatt caaatatctg cttcactcac ggacagaaag 1860
actgtttaga gtgctttccc gtgtcagaat ctcaacccgt ttctgtcgtc aaaaaggcgt 1920
atcagaaact gtgctacatt catcatatca tgggaaaggt gccagacgct tgcactgcct 1980
gcgatctggt caatgtggat ttggatgact gcatctttga acaataaatg atttaaatca 2040
ggtatgtctt ttgttgatca ccctccagat tggttggaag aagttggtga aggtcttcgc 2100

-continued

```
gagtttttgg gccttgaagc gggcccaccg aaaccaaaac ccaatcagca gcatcaagat   2160
caagcccgtg gtcttgtgct gcctggttat aactatctcg gacccggaaa cggtctcgat   2220
cgaggagagc ctgtcaacag ggcagacgag gtcgcgcgag agcacgacat ctcgtacaac   2280
gagcagcttg aggcgggaga caacccctac ctcaagtaca accacgcgga cgccgagttt   2340
caggagaagc tcgccgacga cacatccttc gggggaaacc tcggaaaggc agtctttcag   2400
gccaagaaaa gggttctcga accttttggc ctggttgaag agggtgctaa gacggcccct   2460
accggaaagc ggatagacga ccactttcca aaaagaaaga aggctcggac cgaagaggac   2520
tccaagcctt ccacctcgtc agacgccgaa gctggaccca gcggatccca gcagctgcaa   2580
atcccagccc aaccagcctc aagtttggga gctgatacaa tgtctgcggg aggtggcggc   2640
ccattgggcg acaataacca aggtgccgat ggagtgggca atgcctcggg agattggcat   2700
tgcgattcca cgtggatggg ggacagagtc gtcaccaagt ccacccgaac ctgggtgctg   2760
cccagctaca acaaccacca gtaccgagag atcaaaagcg gctccgtcga cggaagcaac   2820
gccaacgcct actttggata cagcaccccc tgggggtact ttgactttaa ccgcttccac   2880
agccactgga gcccccgaga ctggcaaaga ctcatcaaca actactgggg cttcagaccc   2940
cggtccctca gagtcaaaat cttcaacatt caagtcaaag aggtcacggt gcaggactcc   3000
accaccacca tcgccaacaa cctcacctcc accgtccaag tgtttacgga cgacgactac   3060
cagctgccct acgtcgtcgg caacgggacc gagggatgcc tgccggcctt ccctccgcag   3120
gtctttacgc tgccgcagta cggttacgcg acgctgaacc gcgacaacac agaaaatccc   3180
accgagagga gcagcttctt ctgcctagag tactttccca gcaagatgct gagaacgggc   3240
aacaactttg agtttaccta caactttgag gaggtgccct tccactccag cttcgctccc   3300
agtcagaacc tgttcaagct ggccaacccg ctggtggacc agtacttgta ccgcttcgtg   3360
agcacaaata acactggcgg agtccagttc aacaagaacc tggccgggag atacgccaac   3420
acctacaaaa actggttccc ggggcccatg ggccgaaccc agggctggaa cctgggctcc   3480
ggggtcaacc gcgccagtgt cagcgccttc gccacgacca ataggatgga gctcgagggc   3540
gcgagttacc aggtgccccc gcagccgaac ggcatgacca acaacctcca gggcagcaac   3600
acctatgccc tggagaacac tatgatcttc aacagccagc cggcgaaccc gggcaccacc   3660
gccacgtacc tcgagggcaa catgctcatc accagcgaga gcgagacgca gccggtgaac   3720
cgcgtggcgt acaacgtcgg cggcagatg  gccaccaaca accagagctc caccactgcc   3780
cccgcgaccg gcacgtacaa cctccaggaa atcgtgcccg gcagcgtgtg gatggagagg   3840
gacgtgtacc tccaaggacc catctgggcc aagatcccag agacgggggc gcactttcac   3900
ccctctccgg ccatgggcgg attcggactc aaacacccac cgcccatgat gctcatcaag   3960
aacacgcctg tgcccggaaa tatcaccagc ttctcggacg tgcccgtcag cagcttcatc   4020
acccagtaca gcaccgggca ggtcaccgtg gagatggagt gggagctcaa gaaggaaaac   4080
tccaagaggt ggaacccaga gatccagtac acaaacaact acaacgaccc ccagtttgtg   4140
gactttgccc cggacagcac cggggaatac agaaccacca gacctatcgg aacccgatac   4200
cttacccgac ccctttaatt gcttgttaat caataaaccg tttaattcgt ttcagttgaa   4260
ctttggtctc tgcgtatttc tttcttatct agtttccata tgcatgtaga taagtagcat   4320
ggcgggttaa tcattaacta accggtacct ctagaactat agctagcgat gaccctgctg   4380
attggttcgc tgaccatttc cgggtgcggg acggcgttac cagaaactca gaaggttcgt   4440
```

-continued ccaaccaaac cgactctgac ggcagtttac gagagagatg atagggtctg cttcagtaag 4500
ccagatgcta cacaattagg cttgtacata ttgtcgttag aacgcggcta caattaatac 4560
ataaccttat gtatcataca catacgattt aggtgacact atagaataca cggaattaat 4620
tcttggccac tccctctctg cgcgctcgct cgctcactga ggccgcccgg gcaaagcccg 4680
ggcgtcgggc gacctttggt cgcccggcct cagtgagcga gcgagcgcgc agagagggag 4740
tggccaactc catcactagg ggttccttac gtaggacgtc ccctgcaggc agggaggggt 4800
ggagtcgtga cgtaaagatc tgatatcatc gatcgcgatg cattaattaa gcggccgagg 4860
ctcagaggca cacaggagtt tctgggctca ccctgccccc ttccaacccc tcagttccca 4920
tcctccagca gctgtttgtg tgctgcctct gaagtccaca ctgaacaaac ttcagcctac 4980
tcatgtccct aaaatgggca aacattgcaa gcagcaaaca gcaaacacac agccctccct 5040
gcctgctgac cttggagctg gggcagaggt cagagacctc tctgggccca tgccacctcc 5100
aacatccact cgaccccttg gaatttcggt ggagaggagc agaggttgtc ctggcgtggt 5160
ttaggtagtg tgagaggggt acccggggat cttgctacca gtggaacagc cactaaggat 5220
tctgcagtga gagcagaggg ccagctaagt ggtactctcc cagagactgt ctgactcacg 5280
ccacccccctc caccttggac acaggacgct gtggtttctg agccaggtac aatgactcct 5340
ttcggtaagt gcagtggaag ctgtacactg cccaggcaaa gcgtccgggc agcgtaggcg 5400
ggcgactcag atcccagcca gtggacttag cccctgtttg ctcctccgat aactggggtg 5460
accttggtta atattcacca gcagcctccc ccgttgcccc tctggatcca ctgcttaaat 5520
acggacgagg acagggccct gtctcctcag cttcaggcac caccactgac ctgggacagt 5580
gaatgatccc cctgatctgc ggcctcgacg gtatcgataa gcttgatatc gaattctagt 5640
cgtcgaccac tttcacaatc tgctagcaaa ggttgccacc atgcagcgcg tgaacatgat 5700
tatggccgag agccctggcc tgatcaccat ctgcctgctg ggctacctgc tgagcgccga 5760
gtgtacaggt ttgtttcctt ttttaaaata cattgagtat gcttgccttt tagatataga 5820
aatatctgat gctgtcttct tcactaaatt ttgattacat gatttgacag caatattgaa 5880
gagtctaaca gccagcacgc aggttggtaa gtactggttc tttgttagct aggttttctt 5940
cttcttcatt tttaaaacta aatagatcga caatgcttat gatgcattta tgtttaataa 6000
acactgttca gttcatgatt tggtcatgta attcctgtta gaaaacattc atctccttgg 6060
tttaaaaaaa ttaaaagtgg gaaaacaaag aaatagcaga atatagtgaa aaaaaataac 6120
cacattattt ttgtttggac ttaccacttt gaaatcaaaa tgggaaacaa aagcacaaac 6180
aatggcctta tttacacaaa aagtctgatt ttaagatata tgacatttca aggtttcaga 6240
agtatgtaat gaggtgtgtc tctaattttt taaattatat atcttcaatt taaagtttta 6300
gttaaaacat aaagattaac ctttcattag caagctgtta gttatcacca aagcttttca 6360
tggattagga aaaaatcatt ttgtctctat gtcaaacatc ttggagttga tatttgggga 6420
aacacaatac tcagttgagt tccctagggg agaaaagcaa gcttaagaat tgacataaag 6480
agtaggaagt tagctaatgc aacatatatc actttgtttt ttcacaacta cagtgacttt 6540
atgtatttcc cagaggaagg catacaggga agaaattatc ccatttggac aaacagcatg 6600
ttctcacagg aagcatttat cacacttact tgtcaacttt ctagaatcaa atctagtagc 6660
tgacagtacc aggatcaggg gtgccaaccc taagcacccc cagaaagctg actggccctg 6720
tggttcccac tccagacatg atgtcagctg tgaaatcgac gtcgctggac cataattagg 6780
cttctgttct tcaggagaca tttgttcaaa gtcatttggg caaccatatt ctgaaaacag 6840

-continued cccagccagg gtgatggatc actttgcaaa gatcctcaat gagctatttt caagtgatga 6900
caaagtgtga agttaaccgc tcatttgaga actttctttt tcatccaaag taaattcaaa 6960
tatgattaga aatctgacct tttattactg gaattctctt gactaaaagt aaaattgaat 7020
tttaattcct aaatctccat gtgtatacag tactgtggga acatcacaga ttttggctcc 7080
atgccctaaa gagaaattgg ctttcagatt atttggatta aaaacaaaga ctttcttaag 7140
agatgtaaaa ttttcatgat gttttctttt ttgctaaaac taaagaatta ttcttttaca 7200
tttcagtgtt cctggaccac gagaacgcca acaagatcct gaacagaccc aagagataca 7260
acagcggcaa gctggaagag ttcgtgcagg gcaacctgga acgcgagtgc atggaagaga 7320
agtgcagctt cgaagaggcc agagaggtgt tcgagaacac cgagagaacc accgagttct 7380
ggaagcagta cgtggacggc gaccagtgcg agagcaaccc ttgtctgaac ggcggcagct 7440
gcaaggacga catcaacagc tacgagtgct ggtgcccctt cggcttcgag ggcaagaact 7500
gcgagctgga cgtgacctgc aacatcaaga acggcagatg cgagcagttc tgcaagaaca 7560
gcgccgacaa caaggtcgtg tgctcctgca ccgagggcta cagactggcc gagaaccaga 7620
agtcctgcga gcccgctgtg cctttcccat gcggaagagt gtccgtgtcc cagaccagca 7680
agctgaccag agccgagaca gtgttccccg acgtggacta cgtgaacagc accgaggccg 7740
agacaatcct ggacaacatc acccagagca cccagtcctt caacgacttc accagagtcg 7800
tgggcggcga ggatgctaag cctggccagt tcccgtggca ggtggtgctg aacggaaagg 7860
tggacgcctt ctgcggcggc tccatcgtga acgagaagtg gatcgtgaca gccgcccact 7920
gcgtggaaac cggcgtgaag atcacagtgg tggccggcga gcacaacatc gaggaaaccg 7980
agcacacaga gcagaaaaga aacgtgatca ggatcatccc ccaccacaac tacaacgccg 8040
ccatcaacaa gtacaaccac gatatcgccc tgctggaact ggacgagccc ctggtgctga 8100
atagctacgt gacccccatc tgtatcgccg acaaagagta caccaacatc tttctgaagt 8160
tcggcagcgg ctacgtgtcc ggctggggca gagtgtttca caagggcaga tccgctctgg 8220
tgctgcagta cctgagagtg cctctggtgg acagagccac ctgtctgaga agcaccaagt 8280
tcaccatcta caacaacatg ttctgcgctg gcttccacga gggcggcaga gactcttgtc 8340
agggcgattc tggcggccct cacgtgacag aggtggaagg caccagcttt ctgaccggca 8400
tcatcagctg gggcgaggaa tgcgccatga aggggaagta cggcatctac accaaggtgt 8460
ccagatacgt gaactggatc aaagaaaaga ccaagctgac ataatgaaag atggatttcc 8520
aaggttaatt cattggaatt gaaaattaac agcccccccc cccccccct gcagatctcg 8580 agccgaattc ctgcagcccg ggggatcagc ctcgactgtg ccttctagtt gccagccatc 8640
tgttgtttgc ccctcccccg tgccttcctt gaccctggaa ggtgccactc ccactgtcct 8700
ttcctaataa aatgaggaaa ttgcatcgca ttgtctgagt aggtgtcatt ctattctggg 8760
gggtggggtg gggcaggaca gcaaggggga ggattgggaa gacaatagca ggcatgctgg 8820
ggatgcggtg ggctctatgg cttctgaggc ggaaagaacc agctggggct cgagatccac 8880
tagactagtg tacacgcgtg atatcagatc tgttacgtaa ggaaccccta gtgatggagt 8940
tggccactcc ctctctgcgc gctcgctcgc tcactgaggc cgcccgggca aagcccgggc 9000
ggcctcagtg agcgagcgag cgcgcagaga gggagtggcc aactttttgc aaaagcctag 9060
gcctccaaaa aagcctcctc actacttctg gaatagctca gaggccgagg cggcctcggc 9120
ctctgcataa ataaaaaaaa ttagtcagcc atggggcgga gaatgggcgg aactgggcgg 9180
agttaggggc gggatgggcg gagttagggg cgggactatg gttgctgact aattgagatg 9240
catgctttgc atacttctgc ctgctgggga gcctggggac tttccacacc tggttgctga 9300
ctaattgaga tgcatgcttt gcatacttct gcctgctggg gagcctgggg actttccaca 9360
ccctaactga cacacattcc acagctgcat taatgaatcg gccaacgcgc ggggagaggc 9420
ggtttgcgta ttgggcgctc ttccgcttcc tcgctcactg actcgctgcg ctcggtcgtt 9480
cggctgcggc gagcggtatc agctcactca aaggcggtaa tacggttatc cacagaatca 9540
ggggataacg caggaaagaa catgtgagca aaaggccagc aaaaggccag gaaccgtaaa 9600
aaggccgcgt tgctggcgtt tttccatagg ctccgccccc ctgacgagca tcacaaaaat 9660
cgacgctcaa gtcagaggtg gcgaaacccg acaggactat aaagatacca ggcgtttccc 9720
cctggaagct ccctcgtgcg ctctcctgtt ccgaccctgc cgcttaccgg atacctgtcc 9780
gcctttctcc cttcgggaag cgtggcgctt tctcatagct cacgctgtag gtatctcagt 9840
tcggtgtagg tcgttcgctc caagctgggc tgtgtgcacg aaccccccgt tcagcccgac 9900
cgctgcgcct tatccggtaa ctatcgtctt gagtccaacc cggtaagaca cgacttatcg 9960
ccactggcag cagccactgg taacaggatt agcagagcga ggtatgtagg cggtgctaca 10020
gagttcttga agtggtggcc taactacggc tacactagaa gaacagtatt tggtatctgc 10080
gctctgctga agccagttac cttcggaaaa agagttggta gctcttgatc cggcaaacaa 10140
accaccgctg gtagcggtgg tttttttgtt tgcaagcagc agattacgcg cagaaaaaaa 10200
ggatctcaag aagatccttt gatcttttct acggggtctg acgctcagtg gaacgaaaac 10260
tcacgttaag ggattttggt catgagatta tcaaaaagga tcttcaccta gatcctttta 10320
aattaaaaat ga 10332

<210> SEQ ID NO 5
<211> LENGTH: 10368
<212> TYPE: DNA
<213> ORGANISM: Artificial Sequence
<220> FEATURE:
<223> OTHER INFORMATION: Synthetic: Payload/Cap Plasmid Factor IX / AAV6

<400> SEQUENCE: 5
gataccgcga gacccacgct caccggctcc agatttatca gcaataaacc agccagccgg 60
aagggccgag cgcagaagtg gtcctgcaac tttatccgcc tccatccagt ctattaattg 120
ttgccgggaa gctagagtaa gtagttcgcc agttaatagt ttgcgcaacg ttgttgccat 180
tgctacaggc atcgtggtgt cacgctcgtc gtttggtatg gcttcattca gctccggttc 240
ccaacgatca aggcgagtta catgatcccc catgttgtgc aaaaaagcgg ttagctcctt 300
cggtcctccg atcgttgtca gaagtaagtt ggccgcagtg ttatcactca tggttatggc 360
agcactgcat aattctctta ctgtcatgcc atccgtaaga tgcttttctg tgactggtga 420
gtactcaacc aagtcattct gagaatagtg tatgcggcga ccgagttgct cttgcccggc 480
gtcaatacgg gataataccg cgccacatag cagaacttta aaagtgctca tcattggaaa 540
acgttcttcg gggcgaaaac tctcaaggat cttaccgctg ttgagatcca gttcgatgta 600
acccactcgt gcacccaact gatcttcagc atcttttact ttcaccagcg tttctgggtg 660
agcaaaaaca ggaaggcaaa atgccgcaaa aaagggaata agggcgacac ggaaatgttg 720
aatactcata ctcttccttt ttcaatatta ttgaagcatt tatcagggtt attgtctcat 780
gagcggatac atatttgaat gtatttagaa aaataaacaa ataggggttc cgcgcacatt 840
tccccgaaaa gtgccacctg acgtctaaga aaccattatt atcatgacat taacctataa 900

-continued

```
aaataggcgt atcacgaggc cctttcgtct cgcgcgtttc ggtgatgacg gtgaaaacct    960
ctgacacatg cagctcccgg agacggtcac agcttgtctg taagcggatg ccgggagcag   1020
acaagcccgt cagggcgcgt cagcgggtgt tggcgggtgt cggggctggc ttaactatgc   1080
ggcatcagag cagattgtac tgagagtgca ccattcgacg ctctccctta tgcgactcct   1140
gcattaggaa gcagcccagt agtaggttga ggccgttgag caccgccgcc gcaaggaatg   1200
gtgcatgcaa ggagatggcg cccaacagtc ccccggccac ggggcctgcc accataccca   1260
cgccgaaaca agcgctcatg agcccgaagt ggcgagcccg atcttcccca tcggtgatgt   1320
cggcgatata ggcgccagca accgcacctg tggcgccggt gggtcaccaa gcaggaagtc   1380
aaagactttt tccggtgggc aaaggatcac gtggttgagg tggagcatga attctacgtc   1440
aaaaagggtg gagccaagaa aagacccgcc cccagtgacg cagatataag tgagcccaaa   1500
cgggtgcgcg agtcagttgc gcagccatcg acgtcagacg cggaagcttc gatcaactac   1560
gcagacaggt accaaaaacaa atgttctcgt cacgtgggca tgaatctgat gctgtttccc   1620
tgcagacaat gcgagagaat gaatcagaat tcaaatatct gcttcactca cggacagaaa   1680
gactgtttag agtgctttcc cgtgtcagaa tctcaacccg tttctgtcgt caaaaaggcg   1740
tatcagaaac tgtgctacat tcatcatatc atgggaaagg tgccagacgc ttgcactgcc   1800
tgcgatctgg tcaatgtgga tttggatgac tgcatctttg aacaataaat gatttaaatc   1860
aggtatggct gccgatggtt atcttccaga ttggctcgag gacaacctct ctgagggcat   1920
tcgcgagtgg tgggacttga aacctggagc cccgaaaccc aaagccaacc agcaaaagca   1980
ggacgacggc cggggtctgg tgcttcctgg ctacaagtac ctcggaccct tcaacggact   2040
cgacaagggg gagcccgtca acgcggcgga tgcagcggcc ctcgagcacg acaaggccta   2100
cgaccagcag ctcaaagcgg gtgacaatcc gtacctgcgg tataaccacg ccgacgccga   2160
gtttcaggag cgtctgcaag aagatacgtc ttttgggggc aacctcgggc gagcagtctt   2220
ccaggccaag aagagggttc tcgaaccttt tggtctggtt gaggaaggtg ctaagacggc   2280
tcctggaaag aaacgtccgg tagagcagtc gccacaagag ccagactcct cctcgggcat   2340
tggcaagaca ggccagcagc ccgctaaaaa gagactcaat tttggtcaga ctggcgactc   2400
agagtcagtc cccgacccac aacctctcgg agaacctcca gcaacccccg ctgctgtggg   2460
acctactaca atggcttcag gcggtggcgc accaatggca gacaataacg aaggcgccga   2520
cggagtgggt aatgcctcag gaaattggca ttgcgattcc acatggctgg gcgacagagt   2580
catcaccacc agcacccgaa catgggcctt gcccacctat aacaaccacc tctacaagca   2640
aatctccagt gcttcaacgg gggccagcaa cgacaaccac tacttcggct acagcacccc   2700
ctgggggtat tttgatttca acagattcca ctgccatttc tcaccacgtg actggcagcg   2760
actcatcaac aacaattggg gattccggcc caagagactc aacttcaagc tcttcaacat   2820
ccaagtcaag gaggtcacga cgaatgatgg cgtcacgacc atcgctaata accttaccag   2880
cacggttcaa gtcttctcgg actcggagta ccagttgccg tacgtcctcg gctctgcgca   2940
ccagggctgc ctccctccgt tcccggcgga cgtgttcatg attccgcagt acggctacct   3000
aacgctcaac aatggcagcc aggcagtggg acggtcatcc ttttactgcc tggaatattt   3060
cccatcgcag atgctgagaa cgggcaataa ctttaccttc agctacacct tcgaggacgt   3120
gcctttccac agcagctacg cgcacagcca gagcctggac cggctgatga atcctctcat   3180
cgaccagtac ctgtattacc tgaacagaac tcagaatcag tccggaagtg cccaaaacaa   3240
```

-continued

```
ggacttgctg tttagccggg ggtctccagc tggcatgtct gttcagccca aaaactggct   3300
acctggaccc tgttaccggc agcagcgcgt ttctaaaaca aaaacagaca acaacaacag   3360
caactttacc tggactggtg cttcaaaata taaccttaat gggcgtgaat ctataatcaa   3420
ccctggcact gctatggcct cacacaaaga cgacgaagac aagttctttc ccatgagcgg   3480
tgtcatgatt tttggaaagg agagcgccgg agcttcaaac actgcattgg acaatgtcat   3540
gatcacagac gaagaggaaa tcaaagccac taaccccgtg gccaccgaaa gatttgggac   3600
tgtggcagtc aatctccaga gcagcagcac agaccctgcg accggagatg tgcatgttat   3660
gggagcctta cctggaatgg tgtggcaaga cagagacgta tacctgcagg gtcctatttg   3720
ggccaaaatt cctcacacgg atggacactt tcacccgtct cctctcatgg gcggctttgg   3780
acttaagcac ccgcctcctc agatcctcat caaaaacacg cctgttcctg cgaatcctcc   3840
ggcagagttt tcggctacaa agtttgcttc attcatcacc cagtattcca caggacaagt   3900
gagcgtggag attgaatggg agctgcagaa agaaaacagc aaacgctgga atcccgaagt   3960
gcagtataca tctaactatg caaaatctgc caacgttgat ttcactgtgg acaacaatgg   4020
actttatact gagcctcgcc ccattggcac ccgttacctc acccgtcccc tgtaattgct   4080
tgttaatcaa taaaccgttt aattcgtttc agttgaactt tggtctctgc gtatttcttt   4140
cttatctagt ttccatatgc atgtagataa gtagcatggc gggttaatca ttaactaacc   4200
ggtacctcta gaactatagc tagcgatgac cctgctgatt ggttcgctga ccatttccgg   4260
gtgcgggacg gcgttaccag aaactcagaa ggttcgtcca accaaaccga ctctgacggc   4320
agtttacgag agagatgata gggtctgctt cagtaagcca gatgctacac aattaggctt   4380
gtacatattg tcgttagaac gcggctacaa ttaatacata accttatgta tcatacacat   4440
acgatttagg tgacactata gaatacacgg aattaattct tggccactcc ctctctgcgc   4500
gctcgctcgc tcactgaggc cgcccgggca aagcccgggc gtcgggcgac ctttggtcgc   4560
ccggcctcag tgagcgagcg agcgcgcaga gagggagtgg ccaactccat cactaggggt   4620
tccttacgta ggacgtcccc tgcaggcagg gaggggtgga gtcgtgacgt aaagatctga   4680
tatcatcgat cgcgatgcat taattaagcg gccgaggctc agaggcacac aggagtttct   4740
gggctcaccc tgccccttc caacccctca gttcccatcc tccagcagct gtttgtgtgc   4800
tgcctctgaa gtccacactg aacaaacttc agcctactca tgtccctaaa atgggcaaac   4860
attgcaagca gcaaacagca aacacacagc cctccctgcc tgctgacctt ggagctgggg   4920
cagaggtcag agacctctct gggcccatgc cacctccaac atccactcga ccccttggaa   4980
tttcggtgga gaggagcaga ggttgtcctg gcgtggttta ggtagtgtga gaggggtacc   5040
cggggatctt gctaccagtg gaacagccac taaggattct gcagtgagag cagagggcca   5100
gctaagtggt actctcccag agactgtctg actcacgcca ccccctccac cttggacaca   5160
ggacgctgtg gtttctgagc caggtacaat gactcctttc ggtaagtgca gtggaagctg   5220
tacactgccc aggcaaagcg tccgggcagc gtaggcgggc gactcagatc ccagccagtg   5280
gacttagccc ctgtttgctc ctccgataac tggggtgacc ttggttaata ttcaccagca   5340
gcctcccccg ttgcccctct ggatccactg cttaaatacg gacgaggaca gggccctgtc   5400
tcctcagctt caggcaccac cactgacctg ggacagtgaa tgatccccct gatctgcggc   5460
ctcgacggta tcgataagct tgatatcgaa ttctagtcgt cgaccacttt cacaatctgc   5520
tagcaaaggt tgccaccatg cagcgcgtga acatgattat ggccgagagc cctggcctga   5580
tcaccatctg cctgctgggc tacctgctga gcgccgagtg tacaggtttg tttcctttt    5640
```

-continued

```
taaaatacat tgagtatgct tgccttttag atatagaaat atctgatgct gtcttcttca   5700
ctaaattttg attacatgat ttgacagcaa tattgaagag tctaacagcc agcacgcagg   5760
ttggtaagta ctggttcttt gttagctagg ttttcttctt cttcattttt aaaactaaat   5820
agatcgacaa tgcttatgat gcatttatgt ttaataaaca ctgttcagtt catgatttgg   5880
tcatgtaatt cctgttagaa aacattcatc tccttggttt aaaaaaatta aaagtgggaa   5940
aacaaagaaa tagcagaata tagtgaaaaa aaataaccac attatttttg tttggactta   6000
ccactttgaa atcaaaatgg gaaacaaaag cacaaacaat ggccttattt acacaaaaag   6060
tctgatttta agatatatga catttcaagg tttcagaagt atgtaatgag gtgtgtctct   6120
aatttttaa attatatatc ttcaatttaa agttttagtt aaaacataaa gattaacctt   6180
tcattagcaa gctgttagtt atcaccaaag cttttcatgg attaggaaaa aatcattttg   6240
tctctatgtc aaacatcttg gagttgatat ttggggaaac acaatactca gttgagttcc   6300
ctaggggaga aaagcaagct taagaattga cataaagagt aggaagttag ctaatgcaac   6360
atatatcact ttgtttttc acaactacag tgactttatg tatttcccag aggaaggcat   6420
acagggaaga aattatccca tttggacaaa cagcatgttc tcacaggaag catttatcac   6480
acttacttgt caactttcta gaatcaaatc tagtagctga cagtaccagg atcaggggtg   6540
ccaaccctaa gcacccccag aaagctgact ggccctgtgg ttcccactcc agacatgatg   6600
tcagctgtga aatcgacgtc gctggaccat aattaggctt ctgttcttca ggagacattt   6660
gttcaaagtc atttgggcaa ccatattctg aaaacagccc agccagggtg atggatcact   6720
ttgcaaagat cctcaatgag ctattttcaa gtgatgacaa agtgtgaagt taaccgctca   6780
tttgagaact ttctttttca tccaaagtaa attcaaatat gattagaaat ctgacctttt   6840
attactggaa ttctcttgac taaaagtaaa attgaatttt aattcctaaa tctccatgtg   6900
tatacagtac tgtgggaaca tcacagattt tggctccatg ccctaaagag aaattggctt   6960
tcagattatt tggattaaaa acaaagactt tcttaagaga tgtaaaattt tcatgatgtt   7020
ttcttttttg ctaaaactaa agaattattc ttttacattt cagtgttcct ggaccacgag   7080
aacgccaaca agatcctgaa cagacccaag agatacaaca gcggcaagct ggaagagttc   7140
gtgcagggca acctggaacg cgagtgcatg gaagagaagt gcagcttcga agaggccaga   7200
gaggtgttcg agaacaccga gagaaccacc gagttctgga agcagtacgt ggacggcgac   7260
cagtgcgaga gcaacccttg tctgaacggc ggcagctgca aggacgacat caacagctac   7320
gagtgctggt gccccttcgg cttcgagggc aagaactgcg agctggacgt gacctgcaac   7380
atcaagaacg gcagatgcga gcagttctgc aagaacagcg ccgacaacaa ggtcgtgtgc   7440
tcctgcaccg agggctacag actggccgag aaccagaagt cctgcgagcc cgctgtgcct   7500
ttcccatgcg gaagagtgtc cgtgtcccag accagcaagc tgaccagagc cgagacagtg   7560
ttccccgacg tggactacgt gaacagcacc gaggccgaga caatcctgga caacatcacc   7620
cagagcaccc agtccttcaa cgacttcacc agagtcgtgg gcggcgagga tgctaagcct   7680
ggccagttcc cgtggcaggt ggtgctgaac ggaaaggtgg acgccttctg cggcggctcc   7740
atcgtgaacg agaagtggat cgtgacagcc gcccactgcg tggaaaccgg cgtgaagatc   7800
acagtggtgg ccggcgagca caacatcgag gaaaccgagc acacagagca gaaaagaaac   7860
gtgatcagga tcatccccca ccacaactac aacgccgcca tcaacaagta caaccacgat   7920
atcgccctgc tggaactgga cgagcccctg gtgctgaata gctacgtgac ccccatctgt   7980
```

```
atcgccgaca aagagtacac caacatcttt ctgaagttcg gcagcggcta cgtgtccggc   8040
tggggcagag tgtttcacaa gggcagatcc gctctggtgc tgcagtacct gagagtgcct   8100
ctggtggaca gagccacctg tctgagaagc accaagttca ccatctacaa caacatgttc   8160
tgcgctggct tccacgaggg cggcagagac tcttgtcagg gcgattctgg cggccctcac   8220
gtgacagagg tggaaggcac cagctttctg accggcatca tcagctgggg cgaggaatgc   8280
gccatgaagg ggaagtacgg catctacacc aaggtgtcca gatacgtgaa ctggatcaaa   8340
gaaaagacca agctgacata atgaaagatg gatttccaag gttaattcat tggaattgaa   8400
aattaacagc cccccccccc ccccccctgca gatctcgagc cgaattcctg cagcccgggg   8460
gatcagcctc gactgtgcct tctagttgcc agccatctgt tgtttgcccc tcccccgtgc   8520
cttccttgac cctggaaggt gccactccca ctgtcctttc ctaataaaat gaggaaattg   8580
catcgcattg tctgagtagg tgtcattcta ttctgggggg tggggtgggg caggacagca   8640
agggggagga ttgggaagac aatagcaggc atgctgggga tgcggtgggc tctatggctt   8700
ctgaggcgga aagaaccagc tggggctcga gatccactag actagtgtac acgcgtgata   8760
tcagatctgt tacgtaagga acccctagtg atggagttgg ccactccctc tctgcgcgct   8820
cgctcgctca ctgaggccgc ccgggcaaag cccgggcggc ctcagtgagc gagcgagcgc   8880
gcagagaggg agtggccaac tttttgcaaa agcctaggcc tccaaaaaag cctcctcact   8940
acttctggaa tagctcagag gccgaggcgg cctcggcctc tgcataaata aaaaaaatta   9000
gtcagccatg gggcggagaa tgggcggaac tgggcggagt taggggcggg atgggcggag   9060
ttaggggcgg gactatggtt gctgactaat tgagatgcat gctttgcata cttctgcctg   9120
ctggggagcc tggggacttt ccacacctgg ttgctgacta attgagatgc atgctttgca   9180
tacttctgcc tgctggggag cctggggact ttccacaccc taactgacac acattccaca   9240
gctgcattaa tgaatcggcc aacgcgcggg gagaggcggt ttgcgtattg ggcgctcttc   9300
cgcttcctcg ctcactgact cgctgcgctc ggtcgttcgg ctgcggcgag cggtatcagc   9360
tcactcaaag gcggtaatac ggttatccac agaatcaggg gataacgcag gaaagaacat   9420
gtgagcaaaa ggccagcaaa aggccaggaa ccgtaaaaag gccgcgttgc tggcgttttt   9480
ccataggctc cgcccccctg acgagcatca caaaaatcga cgctcaagtc agaggtggcg   9540
aaacccgaca ggactataaa gataccaggc gtttccccct ggaagctccc tcgtgcgctc   9600
tcctgttccg accctgccgc ttaccggata cctgtccgcc tttctccctt cgggaagcgt   9660
ggcgctttct catagctcac gctgtaggta tctcagttcg gtgtaggtcg ttcgctccaa   9720
gctgggctgt gtgcacgaac cccccgttca gcccgaccgc tgcgccttat ccggtaacta   9780
tcgtcttgag tccaacccgg taagacacga cttatcgcca ctggcagcag ccactggtaa   9840
caggattagc agagcgaggt atgtaggcgg tgctacagag ttcttgaagt ggtggcctaa   9900
ctacggctac actagaagaa cagtatttgg tatctgcgct ctgctgaagc cagttacctt   9960
cggaaaaaga gttggtagct cttgatccgg caaacaaacc accgctggta gcggtggttt   10020
ttttgtttgc aagcagcaga ttacgcgcag aaaaaaagga tctcaagaag atcctttgat   10080
cttttctacg gggtctgacg ctcagtggaa cgaaaactca cgttaaggga ttttggtcat   10140
gagattatca aaaaggatct tcacctagat ccttttaaat taaaaatgaa gttttaaatc   10200
aatctaaagt atatatgagt aaacttggtc tgacagttac caatgcttaa tcagtgaggc   10260
acctatctca gcgatctgtc tatttcgttc atccatagtt gcctgactcc ccgtcgtgta   10320
gataactacg atacgggagg gcttaccatc tggccccagt gctgcaat                10368
```

<210> SEQ ID NO 6
<211> LENGTH: 10374
<212> TYPE: DNA
<213> ORGANISM: Artificial Sequence
<220> FEATURE:
<223> OTHER INFORMATION: Synthetic: Payload/Cap Plasmid Factor IX / AAV8

<400> SEQUENCE: 6

```
gtatatatga gtaaacttgg tctgacagtt accaatgctt aatcagtgag gcacctatct     60
cagcgatctg tctatttcgt tcatccatag ttgcctgact ccccgtcgtg tagataacta    120
cgatacggga gggcttacca tctggcccca gtgctgcaat gataccgcga gacccacgct    180
caccggctcc agatttatca gcaataaacc agccagccgg aagggccgag cgcagaagtg    240
gtcctgcaac tttatccgcc tccatccagt ctattaattg ttgccgggaa gctagagtaa    300
gtagttcgcc agttaatagt ttgcgcaacg ttgttgccat tgctacaggc atcgtggtgt    360
cacgctcgtc gtttggtatg gcttcattca gctccggttc ccaacgatca aggcgagtta    420
catgatcccc catgttgtgc aaaaaagcgg ttagctcctt cggtcctccg atcgttgtca    480
gaagtaagtt ggccgcagtg ttatcactca tggttatggc agcactgcat aattctctta    540
ctgtcatgcc atccgtaaga tgcttttctg tgactggtga gtactcaacc aagtcattct    600
gagaatagtg tatgcggcga ccgagttgct cttgcccggc gtcaatacgg gataataccg    660
cgccacatag cagaacttta aaagtgctca tcattggaaa acgttcttcg gggcgaaaac    720
tctcaaggat cttaccgctg ttgagatcca gttcgatgta acccactcgt gcacccaact    780
gatcttcagc atcttttact ttcaccagcg tttctgggtg agcaaaaaca ggaaggcaaa    840
atgccgcaaa aaagggaata agggcgacac ggaaatgttg aatactcata ctcttccttt    900
ttcaatatta ttgaagcatt tatcagggtt attgtctcat gagcggatac atatttgaat    960
gtatttagaa aaataaacaa ataggggttc cgcgcacatt tccccgaaaa gtgccacctg   1020
acgtctaaga aaccattatt atcatgacat taacctataa aaataggcgt atcacgaggc   1080
cctttcgtct cgcgcgtttc ggtgatgacg gtgaaaacct ctgacacatg cagctcccgg   1140
agacggtcac agcttgtctg taagcggatg ccgggagcag acaagcccgt cagggcgcgt   1200
cagcgggtgt tggcgggtgt cggggctggc ttaactatgc ggcatcagag cagattgtac   1260
tgagagtgca ccattcgacg ctctccctta tgcgactcct gcattaggaa gcagcccagt   1320
agtaggttga ggccgttgag caccgccgcc gcaaggaatg gtgcatgcaa ggagatggcg   1380
cccaacagtc ccccggccac ggggcctgcc accataccca cgccgaaaca agcgctcatg   1440
agcccgaagt ggcgagcccg atcttcccca tcggtgatgt cggcgatata ggcgccagca   1500
accgcacctg tggcgccggt gggtcaccaa gcaggaagtc aaagactttt tccggtgggc   1560
aaaggatcac gtggttgagg tggagcatga attctacgtc aaaaagggtg gagccaagaa   1620
aagacccgcc cccagtgacg cagatataag tgagcccaaa cgggtgcgcg agtcagttgc   1680
gcagccatcg acgtcagacg cggaagcttc gatcaactac gcagacaggt accaaaacaa   1740
atgttctcgt cacgtgggca tgaatctgat gctgtttccc tgcagacaat gcgagagaat   1800
gaatcagaat tcaaatatct gcttcactca cggacagaaa gactgtttag agtgctttcc   1860
cgtgtcagaa tctcaacccg tttctgtcgt caaaaaggcg tatcagaaac tgtgctacat   1920
tcatcatatc atgggaaagg tgccagacgc ttgcactgcc tgcgatctgg tcaatgtgga   1980
tttggatgac tgcatctttg aacaataaat gatttaaatc aggtatggct gccgatggtt   2040
```

-continued

```
atcttccaga ttggctcgag gacaacctct ctgagggcat tcgcgagtgg tgggcgctga   2100
aacctggagc cccgaagccc aaagccaacc agcaaaagca ggacgacggc cggggtctgg   2160
tgcttcctgg ctacaagtac ctcggaccct tcaacggact cgacaagggg gagcccgtca   2220
acgcggcgga cgcagcggcc ctcgagcacg acaaggccta cgaccagcag ctgcaggcgg   2280
gtgacaatcc gtacctgcgg tataaccacg ccgacgccga gtttcaggag cgtctgcaag   2340
aagatacgtc ttttgggggc aacctcgggc gagcagtctt ccaggccaag aagcgggttc   2400
tcgaacctct cggtctggtt gaggaaggcg ctaagacggc tcctggaaag aagagaccgg   2460
tagagccatc accccagcgt tctccagact cctctacggg catcggcaag aaaggccaac   2520
agcccgccag aaaaagactc aattttggtc agactggcga ctcagagtca gttccagacc   2580
ctcaacctct cggagaacct ccagcagcgc cctctggtgt gggacctaat acaatggctg   2640
caggcggtgg cgcaccaatg gcagacaata acgaaggcgc cgacggagtg ggtagttcct   2700
cgggaaattg gcattgcgat tccacatggc tgggcgacag agtcatcacc accagcaccc   2760
gaacctgggc cctgcccacc tacaacaacc acctctacaa gcaaatctcc aacgggacat   2820
cgggaggagc caccaacgac aacacctact tcggctacag caccccctgg gggtattttg   2880
actttaacag attccactgc cacttttcac cacgtgactg gcagcgactc atcaacaaca   2940
actggggatt ccggcccaag agactcagct tcaagctctt caacatccag gtcaaggagg   3000
tcacgcagaa tgaaggcacc aagaccatcg ccaataacct caccagcacc atccaggtgt   3060
ttacggactc ggagtaccag ctgccgtacg ttctcggctc tgcccaccag ggctgcctgc   3120
ctccgttccc ggcggacgtg ttcatgattc cccagtacgg ctacctaaca ctcaacaacg   3180
gtagtcaggc cgtgggacgc tcctccttct actgcctgga atactttcct tcgcagatgc   3240
tgagaaccgg caacaacttc cagtttactt acaccttcga ggacgtgcct ttccacagca   3300
gctacgccca cagccagagc ttggaccggc tgatgaatcc tctgattgac cagtacctgt   3360
actacttgtc tcggactcaa acaacaggag gcacggcaaa tacgcagact ctgggcttca   3420
gccaaggtgg gcctaataca atggccaatc aggcaaagaa ctggctgcca ggaccctgtt   3480
accgccaaca acgcgtctca acgacaaccg ggcaaaacaa caatagcaac tttgcctgga   3540
ctgctgggac caaataccat ctgaatggaa gaaattcatt ggctaatcct ggcatcgcta   3600
tggcaacaca caaagacgac gaggagcgtt tttttcccag taacgggatc ctgatttttg   3660
gcaaacaaaa tgctgccaga gacaatgcgg attacagcga tgtcatgctc accagcgagg   3720
aagaaatcaa aaccactaac cctgtggcta cagaggaata cggtatcgtg gcagataact   3780
tgcagcagca aaacacggct cctcaaattg gaactgtcaa cagccagggg gccttacccg   3840
gtatggtctg gcagaaccgg gacgtgtacc tgcagggtcc catctgggcc aagattcctc   3900
acacggacgg caacttccac ccgtctccgc tgatgggcgg ctttggcctg aaacatcctc   3960
cgcctcagat cctgatcaag aacacgcctg tacctgcgga tcctccgacc accttcaacc   4020
agtcaaagct gaactctttc atcacgcaat acagcaccgg acaggtcagc gtggaaattg   4080
aatgggagct gcagaaggaa aacagcaagc gctggaaccc cgagatccag tacacctcca   4140
actactacaa atctacaagt gtggactttg ctgttaatac agaaggcgtg tactctgaac   4200
cccgccccat tggcacccgt tacctcaccc gtaatctgta attgcttgtt aatcaataaa   4260
ccgtttaatt cgtttcagtt gaactttggt ctctgcgtat ttctttctta tctagtttcc   4320
atatgcatgt agataagtag catggcgggt taatcattaa ctaaccggta cctctagaac   4380
tatagctagc gatgaccctg ctgattggtt cgctgaccat ttccgggtgc gggacggcgt   4440
```

```
taccagaaac tcagaaggtt cgtccaacca aaccgactct gacggcagtt tacgagagag   4500
atgatagggt ctgcttcagt aagccagatg ctacacaatt aggcttgtac atattgtcgt   4560
tagaacgcgg ctacaattaa tacataacct tatgtatcat acacatacga tttaggtgac   4620
actatagaat acacggaatt aattcttggc cactccctct ctgcgcgctc gctcgctcac   4680
tgaggccgcc cgggcaaagc ccgggcgtcg ggcgaccttt ggtcgcccgg cctcagtgag   4740
cgagcgagcg cgcagagagg gagtggccaa ctccatcact aggggttcct tacgtaggac   4800
gtcccctgca ggcagggagg ggtggagtcg tgacgtaaag atctgatatc atcgatcgcg   4860
atgcattaat taagcggccg aggctcagag gcacacagga gtttctgggc tcaccctgcc   4920
cccttccaac ccctcagttc ccatcctcca gcagctgttt gtgtgctgcc tctgaagtcc   4980
acactgaaca aacttcagcc tactcatgtc cctaaaatgg gcaaacattg caagcagcaa   5040
acagcaaaca cacagccctc cctgcctgct gaccttggag ctggggcaga ggtcagagac   5100
ctctctgggc ccatgccacc tccaacatcc actcgacccc ttggaatttc ggtggagagg   5160
agcagaggtt gtcctggcgt ggtttaggta gtgtgagagg ggtacccggg gatcttgcta   5220
ccagtggaac agccactaag gattctgcag tgagagcaga gggccagcta agtggtactc   5280
tcccagagac tgtctgactc acgccacccc ctccaccttg gacacaggac gctgtggttt   5340
ctgagccagg tacaatgact cctttcggta agtgcagtgg aagctgtaca ctgcccaggc   5400
aaagcgtccg ggcagcgtag gcgggcgact cagatcccag ccagtggact tagcccctgt   5460
ttgctcctcc gataactggg gtgaccttgg ttaatattca ccagcagcct cccccgttgc   5520
ccctctggat ccactgctta aatacggacg aggacagggc cctgtctcct cagcttcagg   5580
caccaccact gacctgggac agtgaatgat ccccctgatc tgcggcctcg acggtatcga   5640
taagcttgat atcgaattct agtcgtcgac cactttcaca atctgctagc aaaggttgcc   5700
accatgcagc gcgtgaacat gattatggcc gagagccctg gcctgatcac catctgcctg   5760
ctgggctacc tgctgagcgc cgagtgtaca ggtttgtttc ctttttttaaa atacattgag   5820
tatgcttgcc ttttagatat agaaatatct gatgctgtct tcttcactaa attttgatta   5880
catgatttga cagcaatatt gaagagtcta acagccagca cgcaggttgg taagtactgg   5940
ttctttgtta gctaggtttt cttcttcttc atttttaaaa ctaaatagat cgacaatgct   6000
tatgatgcat ttatgtttaa taaacactgt tcagttcatg atttggtcat gtaattcctg   6060
ttagaaaaca ttcatctcct tggtttaaaa aaattaaaag tgggaaaaca aagaaatagc   6120
agaatatagt gaaaaaaaat aaccacatta tttttgtttg gacttaccac tttgaaatca   6180
aaatgggaaa caaaagcaca aacaatggcc ttatttacac aaaaagtctg attttaagat   6240
atatgacatt tcaaggtttc agaagtatgt aatgaggtgt gtctctaatt ttttaaatta   6300
tatatcttca atttaaagtt ttagttaaaa cataaagatt aacctttcat tagcaagctg   6360
ttagttatca ccaaagcttt tcatggatta ggaaaaaatc attttgtctc tatgtcaaac   6420
atcttggagt tgatatttgg ggaaacacaa tactcagttg agttccctag gggagaaaag   6480
caagcttaag aattgacata aagagtagga agttagctaa tgcaacatat atcactttgt   6540
tttttcacaa ctacagtgac tttatgtatt tcccagagga aggcatacag ggaagaaatt   6600
atcccatttg gacaaacagc atgttctcac aggaagcatt tatcacactt acttgtcaac   6660
tttctagaat caaatctagt agctgacagt accaggatca ggggtgccaa ccctaagcac   6720
ccccagaaag ctgactggcc ctgtggttcc cactccagac atgatgtcag ctgtgaaatc   6780
```

-continued

```
gacgtcgctg gaccataatt aggcttctgt tcttcaggag acatttgttc aaagtcattt   6840
gggcaaccat attctgaaaa cagcccagcc agggtgatgg atcactttgc aaagatcctc   6900
aatgagctat tttcaagtga tgacaaagtg tgaagttaac cgctcatttg agaactttct   6960
ttttcatcca aagtaaattc aaatatgatt agaaatctga ccttttatta ctggaattct   7020
cttgactaaa agtaaaattg aattttaatt cctaaatctc catgtgtata cagtactgtg   7080
ggaacatcac agattttggc tccatgccct aaagagaaat tggctttcag attatttgga   7140
ttaaaaacaa agactttctt aagagatgta aaattttcat gatgttttct tttttgctaa   7200
aactaaagaa ttattctttt acatttcagt gttcctggac cacgagaacg ccaacaagat   7260
cctgaacaga cccaagagat acaacagcgg caagctggaa gagttcgtgc agggcaacct   7320
ggaacgcgag tgcatggaag agaagtgcag cttcgaagag gccagagagg tgttcgagaa   7380
caccgagaga accaccgagt tctggaagca gtacgtggac ggcgaccagt gcgagagcaa   7440
cccttgtctg aacggcggca gctgcaagga cgacatcaac agctacgagt gctggtgccc   7500
cttcggcttc gagggcaaga actgcgagct ggacgtgacc tgcaacatca agaacggcag   7560
atgcgagcag ttctgcaaga acagcgccga caacaaggtc gtgtgctcct gcaccgaggg   7620
ctacagactg gccgagaacc agaagtcctg cgagcccgct gtgcctttcc catgcggaag   7680
agtgtccgtg tcccagacca gcaagctgac cagagccgag acagtgttcc ccgacgtgga   7740
ctacgtgaac agcaccgagg ccgagacaat cctggacaac atcacccaga gcacccagtc   7800
cttcaacgac ttcaccagag tcgtgggcgg cgaggatgct aagcctggcc agttcccgtg   7860
gcaggtggtg ctgaacggaa aggtggacgc cttctgcggc ggctccatcg tgaacgagaa   7920
gtggatcgtg acagccgccc actgcgtgga aaccggcgtg aagatcacag tggtggccgg   7980
cgagcacaac atcgaggaaa ccgagcacac agagcagaaa agaaacgtga tcaggatcat   8040
cccccaccac aactacaacg ccgccatcaa caagtacaac cacgatatcg ccctgctgga   8100
actggacgag cccctggtgc tgaatagcta cgtgaccccc atctgtatcg ccgacaaaga   8160
gtacaccaac atctttctga agttcggcag cggctacgtg tccggctggg gcagagtgtt   8220
tcacaagggc agatccgctc tggtgctgca gtacctgaga gtgcctctgg tggacagagc   8280
cacctgtctg agaagcacca agttcaccat ctacaacaac atgttctgcg ctggcttcca   8340
cgagggcggc agagactctt gtcagggcga ttctggcggc cctcacgtga cagaggtgga   8400
aggcaccagc tttctgaccg gcatcatcag ctggggcgag gaatgcgcca tgaaggggaa   8460
gtacggcatc tacaccaagg tgtccagata cgtgaactgg atcaaagaaa agaccaagct   8520
gacataatga aagatggatt tccaaggtta attcattgga attgaaaatt aacagccccc   8580
cccccccccc cctgcagatc tcgagccgaa ttcctgcagc ccgggggatc agcctcgact   8640
gtgccttcta gttgccagcc atctgttgtt tgcccctccc ccgtgccttc cttgaccctg   8700
gaaggtgcca ctcccactgt cctttcctaa taaaatgagg aaattgcatc gcattgtctg   8760
agtaggtgtc attctattct ggggggtggg gtggggcagg acagcaaggg ggaggattgg   8820
gaagacaata gcaggcatgc tggggatgcg gtgggctcta tggcttctga ggcggaaaga   8880
accagctggg gctcgagatc cactagacta gtgtacacgc gtgatatcag atctgttacg   8940
taaggaaccc ctagtgatgg agttggccac tccctctctg cgcgctcgct cgctcactga   9000
ggccgcccgg gcaaagcccg ggcggcctca gtgagcgagc gagcgcgcag agagggagtg   9060
gccaactttt tgcaaaagcc taggcctcca aaaaagcctc ctcactactt ctggaatagc   9120
tcagaggccg aggcggcctc ggcctctgca taaataaaaa aaattagtca gccatggggc   9180
```

-continued ggagaatggg cggaactggg cggagttagg ggcgggatgg gcggagttag gggcgggact 9240
atggttgctg actaattgag atgcatgctt tgcatacttc tgcctgctgg ggagcctggg 9300
gactttccac acctggttgc tgactaattg agatgcatgc tttgcatact tctgcctgct 9360
ggggagcctg gggactttcc acaccctaac tgacacacat tccacagctg cattaatgaa 9420
tcggccaacg cgcggggaga ggcggtttgc gtattgggcg ctcttccgct tcctcgctca 9480
ctgactcgct gcgctcggtc gttcggctgc ggcgagcggt atcagctcac tcaaaggcgg 9540
taatacggtt atccacagaa tcaggggata acgcaggaaa gaacatgtga gcaaaaggcc 9600
agcaaaaggc caggaaccgt aaaaaggccg cgttgctggc gtttttccat aggctccgcc 9660
cccctgacga gcatcacaaa aatcgacgct caagtcagag gtggcgaaac ccgacaggac 9720
tataaagata ccaggcgttt ccccctggaa gctccctcgt gcgctctcct gttccgaccc 9780
tgccgcttac cggatacctg tccgcctttc tcccttcggg aagcgtggcg ctttctcata 9840
gctcacgctg taggtatctc agttcggtgt aggtcgttcg ctccaagctg ggctgtgtgc 9900
acgaaccccc cgttcagccc gaccgctgcg ccttatccgg taactatcgt cttgagtcca 9960
acccggtaag acacgactta tcgccactgg cagcagccac tggtaacagg attagcagag 10020
cgaggtatgt aggcggtgct acagagttct tgaagtggtg gcctaactac ggctacacta 10080
gaagaacagt atttggtatc tgcgctctgc tgaagccagt taccttcgga aaaagagttg 10140
gtagctcttg atccggcaaa caaaccaccg ctggtagcgg tggttttttt gtttgcaagc 10200
agcagattac gcgcagaaaa aaaggatctc aagaagatcc tttgatcttt tctacggggt 10260
ctgacgctca gtggaacgaa aactcacgtt aagggatttt ggtcatgaga ttatcaaaaa 10320
ggatcttcac ctagatcctt ttaaattaaa aatgaagttt taaatcaatc taaa 10374

<210> SEQ ID NO 7
<211> LENGTH: 10332
<212> TYPE: DNA
<213> ORGANISM: Artificial Sequence
<220> FEATURE:
<223> OTHER INFORMATION: Synthetic: Payload/Cap Plasmid Factor IX / AAV9

<400> SEQUENCE: 7
gtatatatga gtaaacttgg tctgacagtt accaatgctt aatcagtgag gcacctatct 60
cagcgatctg tctatttcgt tcatccatag ttgcctgact ccccgtcgtg tagataacta 120
cgatacggga gggcttacca tctggcccca gtgctgcaat gataccgcga gacccacgct 180
caccggctcc agatttatca gcaataaacc agccagccgg aagggccgag cgcagaagtg 240
gtcctgcaac tttatccgcc tccatccagt ctattaattg ttgccgggaa gctagagtaa 300
gtagttcgcc agttaatagt ttgcgcaacg ttgttgccat tgctacaggc atcgtggtgt 360
cacgctcgtc gtttggtatg gcttcattca gctccggttc ccaacgatca aggcgagtta 420
catgatcccc catgttgtgc aaaaaagcgg ttagctcctt cggtcctccg atcgttgtca 480
gaagtaagtt ggccgcagtg ttatcactca tggttatggc agcactgcat aattctctta 540
ctgtcatgcc atccgtaaga tgcttttctg tgactggtga gtactcaacc aagtcattct 600
gagaatagtg tatgcggcga ccgagttgct cttgcccggc gtcaatacgg gataataccg 660
cgccacatag cagaacttta aaagtgctca tcattggaaa acgttcttcg gggcgaaaac 720
tctcaaggat cttaccgctg ttgagatcca gttcgatgta acccactcgt gcacccaact 780
gatcttcagc atcttttact ttcaccagcg tttctgggtg agcaaaaaca ggaaggcaaa 840

-continued

```
atgccgcaaa aaagggaata agggcgacac ggaaatgttg aatactcata ctcttccttt    900
ttcaatatta ttgaagcatt tatcagggtt attgtctcat gagcggatac atatttgaat    960
gtatttagaa aaataaacaa ataggggttc cgcgcacatt tccccgaaaa gtgccacctg   1020
acgtctaaga aaccattatt atcatgacat taacctataa aaataggcgt atcacgaggc   1080
cctttcgtct cgcgcgtttc ggtgatgacg gtgaaaacct ctgacacatg cagctcccgg   1140
agacggtcac agcttgtctg taagcggatg ccgggagcag acaagcccgt cagggcgcgt   1200
cagcgggtgt tggcgggtgt cggggctggc ttaactatgc ggcatcagag cagattgtac   1260
tgagagtgca ccattcgacg ctctccctta tgcgactcct gcattaggaa gcagcccagt   1320
agtaggttga ggccgttgag caccgccgcc gcaaggaatg gtgcatgcaa ggagatggcg   1380
cccaacagtc ccccggccac ggggcctgcc accataccca cgccgaaaca agcgctcatg   1440
agcccgaagt ggcgagcccg atcttcccca tcggtgatgt cggcgatata ggcgccagca   1500
accgcacctg tggcgccggt gggtcaccaa gcaggaagtc aaagactttt tccggtgggc   1560
aaaggatcac gtggttgagg tggagcatga attctacgtc aaaaagggtg gagccaagaa   1620
aagacccgcc cccagtgacg cagatataag tgagcccaaa cgggtgcgcg agtcagttgc   1680
gcagccatcg acgtcagacg cggaagcttc gatcaactac gcagacaggt accaaaacaa   1740
atgttctcgt cacgtgggca tgaatctgat gctgtttccc tgcagacaat gcgagagaat   1800
gaatcagaat tcaaatatct gcttcactca cggacagaaa gactgtttag agtgctttcc   1860
cgtgtcagaa tctcaacccg tttctgtcgt caaaaaggcg tatcagaaac tgtgctacat   1920
tcatcatatc atgggaaagg tgccagtaac gcttgcactg cctgcgatct ggtcaatgtg   1980
gatttggatg actgcatctt tgaacaataa atgatttaaa tcaggtatgg ctgccgatgg   2040
ttatcttcca gattggctcg aggacaacct tagtgaagga attcgcgagt ggtgggcttt   2100
gaaacctgga gcccctcaac ccaaggcaaa tcaacaacat caagacaacg ctcgaggtct   2160
tgtgcttccg ggttacaaat accttggacc cggcaacgga ctcgacaagg gggagccggt   2220
caacgcagca gacgcggcgg ccctcgagca cgacaaggcc tacgaccagc agctcaaggc   2280
cggagacaac ccgtacctca agtacaacca cgccgacgcc gagttccagg agcggctcaa   2340
agaagatacg tcttttgggg gcaacctcgg gcgagcagtc ttccaggcca aaaagaggct   2400
tcttgaacct cttggtctgg ttgaggaagc ggctaagacg gctcctggaa agaagaggcc   2460
tgtagagcag tctcctcagg aaccggactc ctccgcgggt attggcaaat cgggtgcaca   2520
gcccgctaaa aagagactca atttcggtca gactggcgac acagagtcag tcccagaccc   2580
tcaaccaatc ggagaacctc ccgcagcccc ctcaggtgtg ggatctctta caatggcttc   2640
aggtggtggc gcaccagtgg cagacaataa cgaaggtgcc gatggagtgg gtagttcctc   2700
gggaaattgg cattgcgatt cccaatggct gggggacaga gtcatcacca ccagcacccg   2760
aacctgggcc ctgcccacct acaacaatca cctctacaag caaatctcca acagcacatc   2820
tggaggatct tcaaatgaca acgcctactt cggctacagc accccctggg ggtattttga   2880
cttcaacaga ttccactgcc acttctcacc acgtgactgg cagcgactca tcaacaacaa   2940
ctggggattc cggcctaagc gactcaactt caagctcttc aacattcagg tcaaagaggt   3000
tacggacaac aatggagtca agaccatcgc caataacctt accagcacgg tccaggtctt   3060
cacggactca gactatcagc tcccgtacgt gctcgggtcg gctcacgagg gctgcctccc   3120
gccgttccca gcggacgttt tcatgattcc tcagtacggg tatctgacgc ttaatgatgg   3180
aagccaggcc gtgggtcgtt cgtcctttta ctgcctggaa tatttcccgt cgcaaatgct   3240
```

aagaacgggt aacaacttcc agttcagcta cgagtttgag aacgtacctt tccatagcag 3300
ctacgctcac agccaaagcc tggaccgact aatgaatcca ctcatcgacc aatacttgta 3360
ctatctctca aagactatta acggttctgg acagaatcaa caaacgctaa aattcagtgt 3420
ggccggaccc agcaacatgg ctgtccaggg aagaaactac atacctggac ccagctaccg 3480
acaacaacgt gtctcaacca ctgtgactca aaacaacaac agcgaatttg cttggcctgg 3540
agcttcttct tgggctctca atggacgtaa tagcttgatg aatcctggac ctgctatggc 3600
cagccacaaa gaaggagagg accgtttctt tcctttgtct ggatctttaa tttttggcaa 3660
acaaggaact ggaagagaca acgtggatgc ggacaaagtc atgataacca acgaagaaga 3720
aattaaaact actaacccgg tagcaacgga gtcctatgga caagtggcca caaaccacca 3780
gagtgcccaa gcacaggcgc agaccggctg ggttcaaaac caaggaatac ttccgggtat 3840
ggtttggcag gacagagatg tgtacctgca aggacccatt tgggccaaaa ttcctcacac 3900
ggacggcaac tttcaccctt ctccgctgat gggagggttt ggaatgaagc acccgcctcc 3960
tcagatcctc atcaaaaaca cacctgtacc tgcggatcct ccaacggcct tcaacaagga 4020
caagctgaac tctttcatca cccagtattc tactggccaa gtcagcgtgg agatcgagtg 4080
ggagctgcag aaggaaaaca gcaagcgctg gaacccggag atccagtaca cttccaacta 4140
ttacaagtct aataatgttg aatttgctgt taatactggt gtatatagtg aaccccgccc 4200
cattggcacc agatacctga ctcgtaatct gtaattgcct gttaatcaat aaaccggttg 4260
attcgtttca gttgaacttt ggtctctgcg aagggcgaat tcgtttaaac ctgcaggact 4320
aaccggtacc tctagaacta tagctagcga tgaccctgct gattggttcg ctgaccattt 4380
ccgggtgcgg gacggcgtta ccagaaactc agaaggttcg tccaaccaaa ccgactctga 4440
cggcagttta cgagagagat gatagggtct gcttcagtaa gccagatgct acacaattag 4500
gcttgtacat attgtcgtta gaacgcggct acaattaata cataacctta tgtatcatac 4560
acatacgatt taggtgacac tatagaatac acggaattaa ttcttggcca ctccctctct 4620
gcgcgctcgc tcgctcactg aggccgcccg ggcaaagccc gggcgtcggg cgacctttgg 4680
tcgcccggcc tcagtgagcg agcgagcgcg cagagaggga gtggccaact ccatcactag 4740
gggttcctta cgtaggacgt cccctgcagg cagggagggg tggagtcgtg acgtaaagat 4800
ctgatatcat cgatcgcgat gcattaatta agcggccgag gctcagaggc acacaggagt 4860
ttctgggctc accctgcccc cttccaaccc ctcagttccc atcctccagc agctgtttgt 4920
gtgctgcctc tgaagtccac actgaacaaa cttcagccta ctcatgtccc taaaatgggc 4980
aaacattgca agcagcaaac agcaaacaca cagccctccc tgcctgctga ccttggagct 5040
ggggcagagg tcagagacct ctctgggccc atgccacctc caacatccac tcgacccctt 5100
ggaatttcgg tggagaggag cagaggttgt cctggcgtgg tttaggtagt gtgagagggg 5160
tacccgggga tcttgctacc agtggaacag ccactaagga ttctgcagtg agagcagagg 5220
gccagctaag tggtactctc ccagagactg tctgactcac gccaccccct ccaccttgga 5280
cacaggacgc tgtggtttct gagccaggta caatgactcc tttcggtaag tgcagtggaa 5340
gctgtacact gcccaggcaa agcgtccggg cagcgtaggc gggcgactca gatcccagcc 5400
agtggactta gcccctgttt gctcctccga taactggggt gaccttggtt aatattcacc 5460
agcagcctcc cccgttgccc ctctggatcc actgcttaaa tacggacgag gacagggccc 5520
tgtctcctca gcttcaggca ccaccactga cctgggacag tgaatgatcc ccctgatctg 5580

-continued

```
cggcctcgac ggtatcgata agcttgatat cgaattctag tcgtcgacca ctttcacaat   5640
ctgctagcaa aggttgccac catgcagcgc gtgaacatga ttatggccga gagccctggc   5700
ctgatcacca tctgcctgct gggctacctg ctgagcgccg agtgtacagg tttgtttcct   5760
tttttaaaat acattgagta tgcttgcctt ttagatatag aaatatctga tgctgtcttc   5820
ttcactaaat tttgattaca tgatttgaca gcaatattga agagtctaac agccagcacg   5880
caggttggta agtactggtt ctttgttagc taggttttct tcttcttcat ttttaaaact   5940
aaatagatcg acaatgctta tgatgcattt atgtttaata aacactgttc agttcatgat   6000
ttggtcatgt aattcctgtt agaaaacatt catctccttg gtttaaaaaa attaaaagtg   6060
ggaaaacaaa gaaatagcag aatatagtga aaaaaaataa ccacattatt tttgtttgga   6120
cttaccactt tgaaatcaaa atgggaaaca aaagcacaaa caatggcctt atttacacaa   6180
aaagtctgat tttaagatat atgacatttc aaggtttcag aagtatgtaa tgaggtgtgt   6240
ctctaatttt ttaaattata tatcttcaat ttaaagtttt agttaaaaca taaagattaa   6300
cctttcatta gcaagctgtt agttatcacc aaagcttttc atggattagg aaaaaatcat   6360
tttgtctcta tgtcaaacat cttggagttg atatttgggg aaacacaata ctcagttgag   6420
ttccctaggg gagaaaagca agcttaagaa ttgacataaa gagtaggaag ttagctaatg   6480
caacatatat cactttgttt tttcacaact acagtgactt tatgtatttc ccagaggaag   6540
gcatacaggg aagaaattat cccatttgga caaacagcat gttctcacag gaagcattta   6600
tcacacttac ttgtcaactt tctagaatca aatctagtag ctgacagtac caggatcagg   6660
ggtgccaacc ctaagcaccc ccagaaagct gactggccct gtggttccca ctccagacat   6720
gatgtcagct gtgaaatcga cgtcgctgga ccataattag gcttctgttc ttcaggagac   6780
atttgttcaa agtcatttgg gcaaccatat tctgaaaaca gcccagccag ggtgatggat   6840
cactttgcaa agatcctcaa tgagctattt tcaagtgatg acaaagtgtg aagttaaccg   6900
ctcatttgag aactttcttt ttcatccaaa gtaaattcaa atatgattag aaatctgacc   6960
ttttattact ggaattctct tgactaaaag taaaattgaa ttttaattcc taaatctcca   7020
tgtgtataca gtactgtggg aacatcacag attttggctc catgccctaa agagaaattg   7080
gctttcagat tatttggatt aaaaacaaag actttcttaa gagatgtaaa attttcatga   7140
tgttttcttt tttgctaaaa ctaaagaatt attcttttac atttcagtgt tcctggacca   7200
cgagaacgcc aacaagatcc tgaacagacc caagagatac aacagcggca agctggaaga   7260
gttcgtgcag ggcaacctgg aacgcgagtg catggaagag aagtgcagct tcgaagaggc   7320
cagagaggtg ttcgagaaca ccgagagaac caccgagttc tggaagcagt acgtggacgg   7380
cgaccagtgc gagagcaacc cttgtctgaa cggcggcagc tgcaaggacg acatcaacag   7440
ctacgagtgc tggtgcccct tcggcttcga gggcaagaac tgcgagctgg acgtgacctg   7500
caacatcaag aacggcagat gcgagcagtt ctgcaagaac agcgccgaca acaaggtcgt   7560
gtgctcctgc accgagggct acagactggc cgagaaccag aagtcctgcg agcccgctgt   7620
gcctttccca tgcggaagag tgtccgtgtc ccagaccagc aagctgacca gagccgagac   7680
agtgttcccc gacgtggact acgtgaacag caccgaggcc gagacaatcc tggacaacat   7740
cacccagagc acccagtcct tcaacgactt caccagagtc gtgggcggcg aggatgctaa   7800
gcctggccag ttcccgtggc aggtggtgct gaacggaaag gtggacgcct tctgcggcgg   7860
ctccatcgtg aacgagaagt ggatcgtgac agccgcccac tgcgtggaaa ccggcgtgaa   7920
gatcacagtg gtggccggcg agcacaacat cgaggaaacc gagcacacag agcagaaaag   7980
```

```
aaacgtgatc aggatcatcc cccaccacaa ctacaacgcc gccatcaaca agtacaacca   8040
cgatatcgcc ctgctggaac tggacgagcc cctggtgctg aatagctacg tgacccccat   8100
ctgtatcgcc gacaaagagt acaccaacat ctttctgaag ttcggcagcg gctacgtgtc   8160
cggctggggc agagtgtttc acaagggcag atccgctctg gtgctgcagt acctgagagt   8220
gcctctggtg gacagagcca cctgtctgag aagcaccaag ttcaccatct acaacaacat   8280
gttctgcgct ggcttccacg agggcggcag agactcttgt cagggcgatt ctggcggccc   8340
tcacgtgaca gaggtggaag gcaccagctt tctgaccggc atcatcagct ggggcgagga   8400
atgcgccatg aaggggaagt acggcatcta caccaaggtg tccagatacg tgaactggat   8460
caaagaaaag accaagctga cataatgaaa gatggatttc caaggttaat tcattggaat   8520
tgaaaattaa cagccccccc cccccccccc tgcagatctc gagccgaatt cctgcagccc   8580
gggggatcag cctcgactgt gccttctagt tgccagccat ctgttgtttg cccctccccc   8640
gtgccttcct tgaccctgga aggtgccact cccactgtcc tttcctaata aaatgaggaa   8700
attgcatcgc attgtctgag taggtgtcat tctattctgg ggggtggggt ggggcaggac   8760
agcaaggggg aggattggga agacaatagc aggcatgctg gggatgcggt gggctctatg   8820
gcttctgagg cggaaagaac cagctggggc tcgagatcca ctagactagt gtacacgcgt   8880
gatatcagat ctgttacgta aggaacccct agtgatggag ttggccactc cctctctgcg   8940
cgctcgctcg ctcactgagg ccgcccgggc aaagcccggg cggcctcagt gagcgagcga   9000
gcgcgcagag agggagtggc caactttttg caaaagccta ggcctccaaa aaagcctcct   9060
cactacttct ggaatagctc agaggccgag gcggcctcgg cctctgcata aataaaaaaa   9120
attagtcagc catggggcgg agaatgggcg gaactgggcg gagttagggg cgggatgggc   9180
ggagttaggg gcgggactat ggttgctgac taattgagat gcatgctttg catacttctg   9240
cctgctgggg agcctgggga ctttccacac ctggttgctg actaattgag atgcatgctt   9300
tgcatacttc tgcctgctgg ggagcctggg gactttccac accctaactg acacacattc   9360
cacagctgca ttaatgaatc ggccaacgcg cggggagagg cggtttgcgt attgggcgct   9420
cttccgcttc ctcgctcact gactcgctgc gctcggtcgt tcggctgcgg cgagcggtat   9480
cagctcactc aaaggcggta atacggttat ccacagaatc aggggataac gcaggaaaga   9540
acatgtgagc aaaaggccag caaaaggcca ggaaccgtaa aaaggccgcg ttgctggcgt   9600
ttttccatag gctccgcccc cctgacgagc atcacaaaaa tcgacgctca agtcagaggt   9660
ggcgaaaccc gacaggacta taaagatacc aggcgtttcc ccctggaagc tccctcgtgc   9720
gctctcctgt tccgaccctg ccgcttaccg gatacctgtc cgcctttctc ccttcgggaa   9780
gcgtggcgct ttctcatagc tcacgctgta ggtatctcag ttcggtgtag gtcgttcgct   9840
ccaagctggg ctgtgtgcac gaaccccccg ttcagcccga ccgctgcgcc ttatccggta   9900
actatcgtct tgagtccaac ccggtaagac acgacttatc gccactggca gcagccactg   9960
gtaacaggat tagcagagcg aggtatgtag gcggtgctac agagttcttg aagtggtggc  10020
ctaactacgg ctacactaga agaacagtat ttggtatctg cgctctgctg aagccagtta  10080
ccttcggaaa aagagttggt agctcttgat ccggcaaaca aaccaccgct ggtagcggtg  10140
gtttttttgt ttgcaagcag cagattacgc gcagaaaaaa aggatctcaa gaagatcctt  10200
tgatcttttc tacggggtct gacgctcagt ggaacgaaaa ctcacgttaa gggattttgg  10260
tcatgagatt atcaaaaagg atcttcacct agatcctttt aaattaaaaa tgaagtttta  10320
```

aatcaatcta aa 10332

<210> SEQ ID NO 8
<211> LENGTH: 10371
<212> TYPE: DNA
<213> ORGANISM: Artificial Sequence
<220> FEATURE:
<223> OTHER INFORMATION: Synthetic: Payload/Cap Plasmid Factor IX /
AAV-DJ

<400> SEQUENCE: 8
gtatatatga gtaaacttgg tctgacagtt accaatgctt aatcagtgag gcacctatct 60
cagcgatctg tctatttcgt tcatccatag ttgcctgact ccccgtcgtg tagataacta 120
cgatacggga gggcttacca tctggcccca gtgctgcaat gataccgcga gacccacgct 180
caccggctcc agatttatca gcaataaacc agccagccgg aagggccgag cgcagaagtg 240
gtcctgcaac tttatccgcc tccatccagt ctattaattg ttgccgggaa gctagagtaa 300
gtagttcgcc agttaatagt ttgcgcaacg ttgttgccat tgctacaggc atcgtggtgt 360
cacgctcgtc gtttggtatg gcttcattca gctccggttc ccaacgatca aggcgagtta 420
catgatcccc catgttgtgc aaaaaagcgg ttagctcctt cggtcctccg atcgttgtca 480
gaagtaagtt ggccgcagtg ttatcactca tggttatggc agcactgcat aattctctta 540
ctgtcatgcc atccgtaaga tgcttttctg tgactggtga gtactcaacc aagtcattct 600
gagaatagtg tatgcggcga ccgagttgct cttgcccggc gtcaatacgg gataataccg 660
cgccacatag cagaacttta aaagtgctca tcattggaaa acgttcttcg gggcgaaaac 720
tctcaaggat cttaccgctg ttgagatcca gttcgatgta acccactcgt gcacccaact 780
gatcttcagc atcttttact ttcaccagcg tttctgggtg agcaaaaaca ggaaggcaaa 840
atgccgcaaa aaagggaata agggcgacac ggaaatgttg aatactcata ctcttccttt 900
ttcaatatta ttgaagcatt tatcagggtt attgtctcat gagcggatac atatttgaat 960
gtatttagaa aaataaacaa ataggggttc cgcgcacatt tccccgaaaa gtgccacctg 1020
acgtctaaga aaccattatt atcatgacat taacctataa aaataggcgt atcacgaggc 1080
cctttcgtct cgcgcgtttc ggtgatgacg gtgaaaacct ctgacacatg cagctcccgg 1140
agacggtcac agcttgtctg taagcggatg ccgggagcag acaagcccgt cagggcgcgt 1200
cagcgggtgt tggcgggtgt cggggctggc ttaactatgc ggcatcagag cagattgtac 1260
tgagagtgca ccattcgacg ctctccctta tgcgactcct gcattaggaa gcagcccagt 1320
agtaggttga ggccgttgag caccgccgcc gcaaggaatg gtgcatgcaa ggagatggcg 1380
cccaacagtc ccccggccac ggggcctgcc accataccca cgccgaaaca agcgctcatg 1440
agcccgaagt ggcgagcccg atcttcccca tcggtgatgt cggcgatata ggcgccagca 1500
accgcacctg tggcgccggt gggtcaccaa gcaggaagtc aaagactttt tccggtgggc 1560
aaaggatcac gtggttgagg tggagcatga attctacgtc aaaaagggtg gagccaagaa 1620
aagacccgcc cccagtgacg cagatataag tgagcccaaa cgggtgcgcg agtcagttgc 1680
gcagccatcg acgtcagacg cggaagcttc gatcaactac gcagacaggt accaaaacaa 1740
atgttctcgt cacgtgggca tgaatctgat gctgtttccc tgcagacaat gcgagagaat 1800
gaatcagaat tcaaatatct gcttcactca cggacagaaa gactgtttag agtgctttcc 1860
cgtgtcagaa tctcaacccg tttctgtcgt caaaaaggcg tatcagaaac tgtgctacat 1920
tcatcatatc atgggaaagg tgccagacgc ttgcactgcc tgcgatctgg tcaatgtgga 1980

-continued

```
tttggatgac tgcatctttg aacaataaat gatttaaatc aggtatggct gccgatggtt   2040
atcttccaga ttggctcgag gacactctct ctgaaggaat aagacagtgg tggaagctca   2100
aacctggccc accaccacca aagcccgcag agcggcataa ggacgacagc aggggtcttg   2160
tgcttcctgg gtacaagtac ctcggaccct tcaacggact cgacaaggga gagccggtca   2220
acgaggcaga cgccgcggcc ctcgagcacg acaaagccta cgaccggcag ctcgacagcg   2280
gagacaaccc gtacctcaag tacaaccacg ccgacgccga gttccaggag cggctcaaag   2340
aagatacgtc ttttgggggc aacctcgggc gagcagtctt ccaggccaaa aagaggcttc   2400
ttgaacctct tggtctggtt gaggaagcgg ctaagacggc tcctggaaag aagaggcctg   2460
tagagcactc tcctgtggag ccagactcct cctcgggaac cggaaaggcg ggccagcagc   2520
ctgcaagaaa aagattgaat tttggtcaga ctggagacgc agactcagtc ccagaccctc   2580
aaccaatcgg agaacctccc gcagccccct caggtgtggg atctcttaca atggctgcag   2640
gcggtggcgc accaatggca gacaataacg agggcgccga cggagtgggt aattcctcgg   2700
gaaattggca ttgcgattcc acatggatgg gcgacagagt catcaccacc agcacccgaa   2760
cctgggccct gcccacctac aacaaccacc tctacaagca aatctccaac agcacatctg   2820
gaggatcttc aaatgacaac gcctacttcg gctacagcac cccctggggg tattttgact   2880
ttaacagatt ccactgccac ttttcaccac gtgactggca gcgactcatc aacaacaact   2940
ggggattccg gcccaagaga ctcagcttca agctcttcaa catccaggtc aaggaggtca   3000
cgcagaatga aggcaccaag accatcgcca ataacctcac cagcaccatc caggtgttta   3060
cggactcgga gtaccagctg ccgtacgttc tcggctctgc ccaccagggc tgcctgcctc   3120
cgttcccggc ggacgtgttc atgattcccc agtacggcta cctaacactc aacaacggta   3180
gtcaggccgt gggacgctcc tccttctact gcctggaata ctttccttcg cagatgctga   3240
gaaccggcaa caacttccag tttacttaca ccttcgagga cgtgcctttc cacagcagct   3300
acgcccacag ccagagcttg gaccggctga tgaatcctct gattgaccag tacctgtact   3360
acttgtctcg gactcaaaca acaggaggca cgacaaatac gcagactctg ggcttcagcc   3420
aaggtgggcc taatacaatg gccaatcagg caaagaactg gctgccagga ccctgttacc   3480
gccagcagcg agtatcaaag acatctgcgg ataacaacaa cagtgaatac tcgtggactg   3540
gagctaccaa gtaccacctc aatggcagag actctctggt gaatccgggc ccggccatgg   3600
caagccacaa ggacgatgaa gaaaagtttt ttcctcagag cggggttctc atctttggga   3660
agcaaggctc agagaaaaca aatgtggaca ttgaaaaggt catgattaca gacgaagagg   3720
aaatcaggac aaccaatccc gtggctacgg agcagtatgg ttctgtatct accaacctcc   3780
agagaggcaa cagacaagca gctaccgcag atgtcaacac acaaggcgtt cttccaggca   3840
tggtctggca ggacagagat gtgtaccttc aggggcccat ctgggcaaag attccacaca   3900
cggacggaca ttttcacccc tctcccctca tgggtggatt cggacttaaa caccctccgc   3960
ctcagatcct gatcaagaac acgcctgtac ctgcggatcc tccgaccacc ttcaaccagt   4020
caaagctgaa ctctttcatc acccagtatt ctactggcca agtcagcgtg gagatcgagt   4080
gggagctgca gaaggaaaac agcaagcgct ggaaccccga gatccagtac acctccaact   4140
actacaaatc tacaagtgtg gactttgctg ttaatacaga aggcgtgtac tctgaacccc   4200
gccccattgg cacccgttac ctcacccgta atctgtaatt gcttgttaat caataaaccg   4260
tttaattcgt ttcagttgaa ctttggtctc tgcgtatttc tttcttatct agtttccata   4320
tgcatgtaga taagtagcat ggcgggttaa tcattaacta accggtacct ctagaactat   4380
```

agctagcgat gaccctgctg attggttcgc tgaccatttc cgggtgcggg acggcgttac 4440
cagaaactca gaaggttcgt ccaaccaaac cgactctgac ggcagtttac gagagagatg 4500
atagggtctg cttcagtaag ccagatgcta cacaattagg cttgtacata ttgtcgttag 4560
aacgcggcta caattaatac ataaccttat gtatcataca catacgattt aggtgacact 4620
atagaataca cggaattaat tcttggccac tccctctctg cgcgctcgct cgctcactga 4680
ggccgcccgg gcaaagcccg ggcgtcgggc gacctttggt cgcccggcct cagtgagcga 4740
gcgagcgcgc agagagggag tggccaactc catcactagg ggttccttac gtaggacgtc 4800
ccctgcaggc agggaggggt ggagtcgtga cgtaaagatc tgatatcatc gatcgcgatg 4860
cattaattaa gcggccgagg ctcagaggca cacaggagtt tctgggctca ccctgccccc 4920
ttccaacccc tcagttccca tcctccagca gctgtttgtg tgctgcctct gaagtccaca 4980
ctgaacaaac ttcagcctac tcatgtccct aaaatgggca aacattgcaa gcagcaaaca 5040
gcaaacacac agccctccct gcctgctgac cttggagctg gggcagaggt cagagacctc 5100
tctgggccca tgccacctcc aacatccact cgaccccttg gaatttcggt ggagaggagc 5160
agaggttgtc ctggcgtggt ttaggtagtg tgagaggggt acccggggat cttgctacca 5220
gtggaacagc cactaaggat tctgcagtga gagcagaggg ccagctaagt ggtactctcc 5280
cagagactgt ctgactcacg ccaccccctc caccttggac acaggacgct gtggtttctg 5340
agccaggtac aatgactcct ttcggtaagt gcagtggaag ctgtacactg cccaggcaaa 5400
gcgtccgggc agcgtaggcg ggcgactcag atcccagcca gtggacttag cccctgtttg 5460
ctcctccgat aactggggtg accttggtta atattcacca gcagcctccc ccgttgcccc 5520
tctggatcca ctgcttaaat acggacgagg acagggccct gtctcctcag cttcaggcac 5580
caccactgac ctgggacagt gaatgatccc cctgatctgc ggcctcgacg gtatcgataa 5640
gcttgatatc gaattctagt cgtcgaccac tttcacaatc tgctagcaaa ggttgccacc 5700
atgcagcgcg tgaacatgat tatggccgag agccctggcc tgatcaccat ctgcctgctg 5760
ggctacctgc tgagcgccga gtgtacaggt ttgtttcctt ttttaaaata cattgagtat 5820
gcttgccttt tagatataga aatatctgat gctgtcttct tcactaaatt ttgattacat 5880
gatttgacag caatattgaa gagtctaaca gccagcacgc aggttggtaa gtactggttc 5940
tttgttagct aggttttctt cttcttcatt tttaaaacta aatagatcga caatgcttat 6000
gatgcattta tgtttaataa acactgttca gttcatgatt tggtcatgta attcctgtta 6060
gaaaacattc atctccttgg tttaaaaaaa ttaaaagtgg gaaaacaaag aaatagcaga 6120
atatagtgaa aaaaaataac cacattattt ttgtttggac ttaccacttt gaaatcaaaa 6180
tgggaaacaa aagcacaaac aatggcctta tttacacaaa aagtctgatt ttaagatata 6240
tgacatttca aggtttcaga agtatgtaat gaggtgtgtc tctaattttt taaattatat 6300
atcttcaatt taaagtttta gttaaaacat aaagattaac ctttcattag caagctgtta 6360
gttatcacca aagcttttca tggattagga aaaaatcatt ttgtctctat gtcaaacatc 6420
ttggagttga tatttgggga aacacaatac tcagttgagt tccctagggg agaaaagcaa 6480
gcttaagaat tgacataaag agtaggaagt tagctaatgc aacatatatc actttgtttt 6540
ttcacaacta cagtgacttt atgtatttcc cagaggaagg catacaggga agaaattatc 6600
ccatttggac aaacagcatg ttctcacagg aagcatttat cacacttact tgtcaacttt 6660
ctagaatcaa atctagtagc tgacagtacc aggatcaggg gtgccaaccc taagcacccc 6720

-continued cagaaagctg actggccctg tggttcccac tccagacatg atgtcagctg tgaaatcgac 6780
gtcgctggac cataattagg cttctgttct tcaggagaca tttgttcaaa gtcatttggg 6840
caaccatatt ctgaaaacag cccagccagg gtgatggatc actttgcaaa gatcctcaat 6900
gagctatttt caagtgatga caaagtgtga agttaaccgc tcatttgaga actttctttt 6960
tcatccaaag taaattcaaa tatgattaga aatctgacct tttattactg gaattctctt 7020
gactaaaagt aaaattgaat tttaattcct aaatctccat gtgtatacag tactgtggga 7080
acatcacaga ttttggctcc atgccctaaa gagaaattgg ctttcagatt atttggatta 7140
aaaacaaaga ctttcttaag agatgtaaaa ttttcatgat gttttctttt ttgctaaaac 7200
taaagaatta ttcttttaca tttcagtgtt cctggaccac gagaacgcca acaagatcct 7260
gaacagaccc aagagataca acagcggcaa gctggaagag ttcgtgcagg gcaacctgga 7320
acgcgagtgc atggaagaga agtgcagctt cgaagaggcc agagaggtgt tcgagaacac 7380
cgagagaacc accgagttct ggaagcagta cgtggacggc gaccagtgcg agagcaaccc 7440
ttgtctgaac ggcggcagct gcaaggacga catcaacagc tacgagtgct ggtgcccctt 7500
cggcttcgag ggcaagaact gcgagctgga cgtgacctgc aacatcaaga acggcagatg 7560
cgagcagttc tgcaagaaca gcgccgacaa caaggtcgtg tgctcctgca ccgagggcta 7620
cagactggcc gagaaccaga agtcctgcga gcccgctgtg cctttcccat gcggaagagt 7680
gtccgtgtcc cagaccagca agctgaccag agccgagaca gtgttccccg acgtggacta 7740
cgtgaacagc accgaggccg agacaatcct ggacaacatc acccagagca cccagtcctt 7800
caacgacttc accagagtcg tgggcggcga ggatgctaag cctggccagt tcccgtggca 7860
ggtggtgctg aacggaaagg tggacgcctt ctgcggcggc tccatcgtga acgagaagtg 7920
gatcgtgaca gccgcccact gcgtggaaac cggcgtgaag atcacagtgg tggccggcga 7980
gcacaacatc gaggaaaccg agcacacaga gcagaaaaga aacgtgatca ggatcatccc 8040
ccaccacaac tacaacgccg ccatcaacaa gtacaaccac gatatcgccc tgctggaact 8100
ggacgagccc ctggtgctga atagctacgt gacccccatc tgtatcgccg acaaagagta 8160
caccaacatc tttctgaagt tcggcagcgg ctacgtgtcc ggctggggca gagtgtttca 8220
caagggcaga tccgctctgg tgctgcagta cctgagagtg cctctggtgg acagagccac 8280
ctgtctgaga agcaccaagt tcaccatcta caacaacatg ttctgcgctg gcttccacga 8340
gggcggcaga gactcttgtc agggcgattc tggcggccct cacgtgacag aggtggaagg 8400
caccagcttt ctgaccggca tcatcagctg gggcgaggaa tgcgccatga aggggaagta 8460
cggcatctac accaaggtgt ccagatacgt gaactggatc aaagaaaaga ccaagctgac 8520
ataatgaaag atggatttcc aaggttaatt cattggaatt gaaaattaac agcccccccc 8580 cccccccccct gcagatctcg agccgaattc ctgcagcccg ggggatcagc ctcgactgtg 8640
ccttctagtt gccagccatc tgttgtttgc ccctcccccg tgccttcctt gaccctggaa 8700
ggtgccactc ccactgtcct ttcctaataa aatgaggaaa ttgcatcgca ttgtctgagt 8760
aggtgtcatt ctattctggg gggtggggtg gggcaggaca gcaaggggga ggattgggaa 8820
gacaatagca ggcatgctgg ggatgcggtg ggctctatgg cttctgaggc ggaaagaacc 8880
agctggggct cgagatccac tagactagtg tacacgcgtg atatcagatc tgttacgtaa 8940
ggaaccccta gtgatggagt tggccactcc ctctctgcgc gctcgctcgc tcactgaggc 9000
cgcccgggca aagcccgggc ggcctcagtg agcgagcgag cgcgcagaga gggagtggcc 9060
aactttttgc aaaagcctag gcctccaaaa aagcctcctc actacttctg gaatagctca 9120
gaggccgagg cggcctcggc ctctgcataa ataaaaaaaa ttagtcagcc atggggcgga 9180
gaatgggcgg aactgggcgg agttaggggc gggatgggcg gagttagggg cgggactatg 9240
gttgctgact aattgagatg catgctttgc atacttctgc ctgctgggga gcctggggac 9300
tttccacacc tggttgctga ctaattgaga tgcatgcttt gcatacttct gcctgctggg 9360
gagcctgggg actttccaca ccctaactga cacacattcc acagctgcat taatgaatcg 9420
gccaacgcgc ggggagaggc ggtttgcgta ttgggcgctc ttccgcttcc tcgctcactg 9480
actcgctgcg ctcggtcgtt cggctgcggc gagcggtatc agctcactca aaggcggtaa 9540
tacggttatc cacagaatca ggggataacg caggaaagaa catgtgagca aaaggccagc 9600
aaaaggccag gaaccgtaaa aaggccgcgt tgctggcgtt tttccatagg ctccgccccc 9660
ctgacgagca tcacaaaaat cgacgctcaa gtcagaggtg gcgaaacccg acaggactat 9720
aaagatacca ggcgtttccc cctggaagct ccctcgtgcg ctctcctgtt ccgaccctgc 9780
cgcttaccgg atacctgtcc gcctttctcc cttcgggaag cgtggcgctt tctcatagct 9840
cacgctgtag gtatctcagt tcggtgtagg tcgttcgctc caagctgggc tgtgtgcacg 9900
aaccccccgt tcagcccgac cgctgcgcct tatccggtaa ctatcgtctt gagtccaacc 9960
cggtaagaca cgacttatcg ccactggcag cagccactgg taacaggatt agcagagcga 10020
ggtatgtagg cggtgctaca gagttcttga agtggtggcc taactacggc tacactagaa 10080
gaacagtatt tggtatctgc gctctgctga agccagttac cttcggaaaa agagttggta 10140
gctcttgatc cggcaaacaa accaccgctg gtagcggtgg tttttttgtt tgcaagcagc 10200
agattacgcg cagaaaaaaa ggatctcaag aagatccttt gatcttttct acggggtctg 10260
acgctcagtg gaacgaaaac tcacgttaag ggattttggt catgagatta tcaaaaagga 10320
tcttcaccta gatcctttta aattaaaaat gaagttttaa atcaatctaa a 10371

<210> SEQ ID NO 9
<211> LENGTH: 10368
<212> TYPE: DNA
<213> ORGANISM: Artificial Sequence
<220> FEATURE:
<223> OTHER INFORMATION: Synthetic: Payload/Cap Plasmid Factor IX / AAV-LK03

<400> SEQUENCE: 9
atggctgctg acggttatct tccagattgg ctcgaggaca acctttctga aggcattcga 60
gagtggtggg cgctgcaacc tggagcccct aaacccaagg caaatcaaca acatcaggac 120
aacgctcggg gtcttgtgct tccgggttac aaatacctcg gacccggcaa cggactcgac 180
aagggggaac ccgtcaacgc agcggacgcg gcagccctcg agcacgacaa ggcctacgac 240
cagcagctca aggccggtga caacccctac ctcaagtaca accacgccga cgccgagttc 300
caggagcggc tcaaagaaga tacgtctttt gggggcaacc tcgggcgagc agtcttccag 360
gccaaaaaga ggcttcttga acctcttggt ctggttgagg aagcggctaa gacggctcct 420
ggaaagaaga ggcctgtaga tcagtctcct caggaaccgg actcatcatc tggtgttggc 480
aaatcgggca aacagcctgc cagaaaaaga ctaaatttcg gtcagactgg cgactcagag 540
tcagtcccag accctcaacc tctcggagaa ccaccagcag cccccacaag tttgggatct 600
aatacaatgg cttcaggcgg tggcgcacca atggcagaca ataacgaggg tgccgatgga 660
gtgggtaatt cctcaggaaa ttggcattgc gattcccaat ggctgggcga cagagtcatc 720
accaccagca ccagaacctg ggccctgccc acttacaaca accatctcta caagcaaatc 780

```
tccagccaat caggagcttc aaacgacaac cactactttg gctacagcac cccttggggg    840
tattttgact ttaacagatt ccactgccac ttctcaccac gtgactggca gcgactcatt    900
aacaacaact ggggattccg gcccaagaaa ctcagcttca agctcttcaa catccaagtt    960
aaagaggtca cgcagaacga tggcacgacg actattgcca ataaccttac cagcacggtt   1020
caagtgttta cggactcgga gtatcagctc ccgtacgtgc tcgggtcggc gcaccaaggc   1080
tgtctcccgc cgtttccagc ggacgtcttc atggtccctc agtatggata cctcaccctg   1140
aacaacggaa gtcaagcggt gggacgctca tccttttact gcctggagta cttcccttcg   1200
cagatgctaa ggactggaaa taacttccaa ttcagctata ccttcgagga tgtacctttt   1260
cacagcagct acgctcacag ccagagtttg gatcgcttga tgaatcctct tattgatcag   1320
tatctgtact acctgaacag aacgcaagga acaacctctg gaacaaccaa ccaatcacgg   1380
ctgcttttta gccaggctgg gcctcagtct atgtctttgc aggccagaaa ttggctacct   1440
gggccctgct accggcaaca gagactttca aagactgcta acgacaacaa caacagtaac   1500
tttccttgga cagcggccag caaatatcat ctcaatggcc gcgactcgct ggtgaatcca   1560
ggaccagcta tggccagtca caaggacgat gaagaaaaat tttccctat gcacggcaat   1620
ctaatatttg gcaaagaagg gacaacggca agtaacgcag aattagataa tgtaatgatt   1680
acggatgaag aagagattcg taccaccaat cctgtggcaa cagagcagta tggaactgtg   1740
gcaaataact tgcagagctc aaatacagct cccacgacta gaactgtcaa tgatcagggg   1800
gccttacctg gcatggtgtg gcaagatcgt gacgtgtacc ttcaaggacc tatctgggca   1860
aagattcctc acacggatgg acactttcat ccttctcctc tgatgggagg ctttggactg   1920
aaacatccgc ctcctcaaat catgatcaaa aatactccgg taccggcaaa tcctccgacg   1980
actttcagcc cggccaagtt tgcttcattt atcactcagt actccactgg acaggtcagc   2040
gtggaaattg agtgggagct acagaaagaa aacagcaaac gttggaatcc agagattcag   2100
tacacttcca actacaacaa gtctgttaat gtggacttta ctgtagacac taatggtgtt   2160
tatagtgaac ctcgccccat tggcacccgt taccttaccc gtcccctgta attgcttgtt   2220
aatcaataaa ccgtttaatt cgtttcagtt gaactttggt ctctgcgtat ttctttctta   2280
tctagtttcc atatgcatgt agataagtag catggcgggt taatcattaa ctaaccggta   2340
cctctagaac tatagctagc gatgaccctg ctgattggtt cgctgaccat ttccgggtgc   2400
gggacggcgt taccagaaac tcagaaggtt cgtccaacca aaccgactct gacggcagtt   2460
tacgagagag atgatagggt ctgcttcagt aagccagatg ctacacaatt aggcttgtac   2520
atattgtcgt tagaacgcgg ctacaattaa tacataacct tatgtatcat acacatacga   2580
tttaggtgac actatagaat acacggaatt aattcttggc cactccctct ctgcgcgctc   2640
gctcgctcac tgaggccgcc cgggcaaagc ccgggcgtcg ggcgaccttt ggtcgcccgg   2700
cctcagtgag cgagcgagcg cgcagagagg gagtggccaa ctccatcact aggggttcct   2760
tacgtaggac gtcccctgca ggcagggagg ggtggagtcg tgacgtaaag atctgatatc   2820
atcgatcgcg atgcattaat taagcggccg aggctcagag gcacacagga gtttctgggc   2880
tcaccctgcc cccttccaac ccctcagttc ccatcctcca gcagctgttt gtgtgctgcc   2940
tctgaagtcc acactgaaca aacttcagcc tactcatgtc cctaaaatgg gcaaacattg   3000
caagcagcaa acagcaaaca cacagccctc cctgcctgct gaccttggag ctggggcaga   3060
ggtcagagac ctctctgggc ccatgccacc tccaacatcc actcgacccc ttggaatttc   3120
```

-continued

```
ggtggagagg agcagaggtt gtcctggcgt ggtttaggta gtgtgagagg ggtacccggg   3180
gatcttgcta ccagtggaac agccactaag gattctgcag tgagagcaga gggccagcta   3240
agtggtactc tcccagagac tgtctgactc acgccacccc ctccaccttg gacacaggac   3300
gctgtggttt ctgagccagg tacaatgact cctttcggta agtgcagtgg aagctgtaca   3360
ctgcccaggc aaagcgtccg ggcagcgtag gcgggcgact cagatcccag ccagtggact   3420
tagcccctgt ttgctcctcc gataactggg gtgaccttgg ttaatattca ccagcagcct   3480
cccccgttgc ccctctggat ccactgctta aatacggacg aggacagggc cctgtctcct   3540
cagcttcagg caccaccact gacctgggac agtgaatgat ccccctgatc tgcggcctcg   3600
acggtatcga taagcttgat atcgaattct agtcgtcgac cactttcaca atctgctagc   3660
aaaggttgcc accatgcagc gcgtgaacat gattatggcc gagagccctg gcctgatcac   3720
catctgcctg ctgggctacc tgctgagcgc cgagtgtaca ggtttgtttc ctttttttaaa   3780
atacattgag tatgcttgcc ttttagatat agaaatatct gatgctgtct tcttcactaa   3840
attttgatta catgatttga cagcaatatt gaagagtcta acagccagca cgcaggttgg   3900
taagtactgg ttctttgtta gctaggtttt cttcttcttc atttttaaaa ctaaatagat   3960
cgacaatgct tatgatgcat ttatgtttaa taaacactgt tcagttcatg atttggtcat   4020
gtaattcctg ttagaaaaca ttcatctcct tggtttaaaa aaattaaaag tgggaaaaca   4080
aagaaatagc agaatatagt gaaaaaaaat aaccacatta tttttgtttg gacttaccac   4140
tttgaaatca aaatgggaaa caaaagcaca aacaatggcc ttatttacac aaaaagtctg   4200
attttaagat atatgacatt tcaaggtttc agaagtatgt aatgaggtgt gtctctaatt   4260
ttttaaatta tatatcttca atttaaagtt ttagttaaaa cataaagatt aacctttcat   4320
tagcaagctg ttagttatca ccaaagcttt tcatggatta ggaaaaaatc attttgtctc   4380
tatgtcaaac atcttggagt tgatatttgg ggaaacacaa tactcagttg agttccctag   4440
gggagaaaag caagcttaag aattgacata aagagtagga agttagctaa tgcaacatat   4500
atcactttgt tttttcacaa ctacagtgac tttatgtatt tcccagagga aggcatacag   4560
ggaagaaatt atcccatttg gacaaacagc atgttctcac aggaagcatt tatcacactt   4620
acttgtcaac tttctagaat caaatctagt agctgacagt accaggatca ggggtgccaa   4680
ccctaagcac ccccagaaag ctgactggcc ctgtggttcc cactccagac atgatgtcag   4740
ctgtgaaatc gacgtcgctg gaccataatt aggcttctgt tcttcaggag acatttgttc   4800
aaagtcattt gggcaaccat attctgaaaa cagcccagcc agggtgatgg atcactttgc   4860
aaagatcctc aatgagctat tttcaagtga tgacaaagtg tgaagttaac cgctcatttg   4920
agaactttct ttttcatcca aagtaaattc aaatatgatt agaaatctga ccttttatta   4980
ctggaattct cttgactaaa agtaaaattg aattttaatt cctaaatctc catgtgtata   5040
cagtactgtg ggaacatcac agattttggc tccatgccct aaagagaaat tggctttcag   5100
attatttgga ttaaaaacaa agactttctt aagagatgta aaattttcat gatgttttct   5160
tttttgctaa aactaaagaa ttattctttt acatttcagt gttcctggac cacgagaacg   5220
ccaacaagat cctgaacaga cccaagagat acaacagcgg caagctggaa gagttcgtgc   5280
agggcaacct ggaacgcgag tgcatggaag agaagtgcag cttcgaagag gccagagagg   5340
tgttcgagaa caccgagaga accaccgagt tctggaagca gtacgtggac ggcgaccagt   5400
gcgagagcaa cccttgtctg aacggcggca gctgcaagga cgacatcaac agctacgagt   5460
gctggtgccc cttcggcttc gagggcaaga actgcgagct ggacgtgacc tgcaacatca   5520
```

```
agaacggcag atgcgagcag ttctgcaaga acagcgccga caacaaggtc gtgtgctcct   5580
gcaccgaggg ctacagactg gccgagaacc agaagtcctg cgagcccgct gtgcctttcc   5640
catgcggaag agtgtccgtg tcccagacca gcaagctgac cagagccgag acagtgttcc   5700
ccgacgtgga ctacgtgaac agcaccgagg ccgagacaat cctggacaac atcacccaga   5760
gcacccagtc cttcaacgac ttcaccagag tcgtgggcgg cgaggatgct aagcctggcc   5820
agttcccgtg gcaggtggtg ctgaacggaa aggtggacgc cttctgcggc ggctccatcg   5880
tgaacgagaa gtggatcgtg acagccgccc actgcgtgga aaccggcgtg aagatcacag   5940
tggtggccgg cgagcacaac atcgaggaaa ccgagcacac agagcagaaa agaaacgtga   6000
tcaggatcat cccccaccac aactacaacg ccgccatcaa caagtacaac cacgatatcg   6060
ccctgctgga actggacgag cccctggtgc tgaatagcta cgtgaccccc atctgtatcg   6120
ccgacaaaga gtacaccaac atctttctga agttcggcag cggctacgtg tccggctggg   6180
gcagagtgtt tcacaagggc agatccgctc tggtgctgca gtacctgaga gtgcctctgg   6240
tggacagagc cacctgtctg agaagcacca agttcaccat ctacaacaac atgttctgcg   6300
ctggcttcca cgagggcggc agagactctt gtcagggcga ttctggcggc cctcacgtga   6360
cagaggtgga aggcaccagc tttctgaccg gcatcatcag ctggggcgag gaatgcgcca   6420
tgaaggggaa gtacggcatc tacaccaagg tgtccagata cgtgaactgg atcaaagaaa   6480
agaccaagct gacataatga aagatggatt tccaaggtta attcattgga attgaaaatt   6540
aacagccccc cccccccccc cctgcagatc tcgagccgaa ttcctgcagc ccgggggatc   6600
agcctcgact gtgccttcta gttgccagcc atctgttgtt tgcccctccc ccgtgccttc   6660
cttgaccctg gaaggtgcca ctcccactgt cctttcctaa taaaatgagg aaattgcatc   6720
gcattgtctg agtaggtgtc attctattct ggggggtggg gtggggcagg acagcaaggg   6780
ggaggattgg gaagacaata gcaggcatgc tggggatgcg gtgggctcta tggcttctga   6840
ggcggaaaga accagctggg gctcgagatc cactagacta gtgtacacgc gtgatatcag   6900
atctgttacg taaggaaccc ctagtgatgg agttggccac tccctctctg cgcgctcgct   6960
cgctcactga ggccgcccgg gcaaagcccg ggcggcctca gtgagcgagc gagcgcgcag   7020
agagggagtg gccaactttt tgcaaaagcc taggcctcca aaaaagcctc ctcactactt   7080
ctggaatagc tcagaggccg aggcggcctc ggcctctgca taaataaaaa aaattagtca   7140
gccatggggc ggagaatggg cggaactggg cggagttagg ggcgggatgg gcggagttag   7200
gggcgggact atggttgctg actaattgag atgcatgctt tgcatacttc tgcctgctgg   7260
ggagcctggg gactttccac acctggttgc tgactaattg agatgcatgc tttgcatact   7320
tctgcctgct ggggagcctg gggactttcc acaccctaac tgacacacat tccacagctg   7380
cattaatgaa tcggccaacg cgcggggaga ggcggtttgc gtattgggcg ctcttccgct   7440
tcctcgctca ctgactcgct gcgctcggtc gttcggctgc ggcgagcggt atcagctcac   7500
tcaaaggcgg taatacggtt atccacagaa tcaggggata acgcaggaaa gaacatgtga   7560
gcaaaaggcc agcaaaaggc caggaaccgt aaaaaggccg cgttgctggc gtttttccat   7620
aggctccgcc cccctgacga gcatcacaaa aatcgacgct caagtcagag gtggcgaaac   7680
ccgacaggac tataaagata ccaggcgttt ccccctggaa gctccctcgt gcgctctcct   7740
gttccgaccc tgccgcttac cggatacctg tccgcctttc tcccttcggg aagcgtggcg   7800
ctttctcata gctcacgctg taggtatctc agttcggtgt aggtcgttcg ctccaagctg   7860
```

-continued

```
ggctgtgtgc acgaaccccc cgttcagccc gaccgctgcg ccttatccgg taactatcgt   7920
cttgagtcca acccggtaag acacgactta tcgccactgg cagcagccac tggtaacagg   7980
attagcagag cgaggtatgt aggcggtgct acagagttct tgaagtggtg gcctaactac   8040
ggctacacta gaagaacagt atttggtatc tgcgctctgc tgaagccagt taccttcgga   8100
aaaagagttg gtagctcttg atccggcaaa caaaccaccg ctggtagcgg tggttttttt   8160
gtttgcaagc agcagattac gcgcagaaaa aaaggatctc aagaagatcc tttgatcttt   8220
tctacggggt ctgacgctca gtggaacgaa aactcacgtt aagggatttt ggtcatgaga   8280
ttatcaaaaa ggatcttcac ctagatcctt ttaaattaaa aatgaagttt taaatcaatc   8340
taaagtatat atgagtaaac ttggtctgac agttaccaat gcttaatcag tgaggcacct   8400
atctcagcga tctgtctatt tcgttcatcc atagttgcct gactccccgt cgtgtagata   8460
actacgatac gggagggctt accatctggc cccagtgctg caatgatacc gcgagaccca   8520
cgctcaccgg ctccagattt atcagcaata aaccagccag ccggaagggc cgagcgcaga   8580
agtggtcctg caactttatc cgcctccatc cagtctatta attgttgccg ggaagctaga   8640
gtaagtagtt cgccagttaa tagtttgcgc aacgttgttg ccattgctac aggcatcgtg   8700
gtgtcacgct cgtcgtttgg tatggcttca ttcagctccg gttcccaacg atcaaggcga   8760
gttacatgat cccccatgtt gtgcaaaaaa gcggttagct ccttcggtcc tccgatcgtt   8820
gtcagaagta agttggccgc agtgttatca ctcatggtta tggcagcact gcataattct   8880
cttactgtca tgccatccgt aagatgcttt tctgtgactg gtgagtactc aaccaagtca   8940
ttctgagaat agtgtatgcg gcgaccgagt tgctcttgcc cggcgtcaat acgggataat   9000
accgcgccac atagcagaac tttaaaagtg ctcatcattg gaaaacgttc ttcggggcga   9060
aaactctcaa ggatcttacc gctgttgaga tccagttcga tgtaacccac tcgtgcaccc   9120
aactgatctt cagcatcttt tactttcacc agcgtttctg ggtgagcaaa aacaggaagg   9180
caaaatgccg caaaaaaggg aataagggcg acacggaaat gttgaatact catactcttc   9240
ctttttcaat attattgaag catttatcag ggttattgtc tcatgagcgg atacatattt   9300
gaatgtattt agaaaaataa acaaataggg gttccgcgca catttccccg aaaagtgcca   9360
cctgacgtct aagaaaccat tattatcatg acattaacct ataaaaatag gcgtatcacg   9420
aggccctttc gtctcgcgcg tttcggtgat gacggtgaaa acctctgaca catgcagctc   9480
ccggagacgg tcacagcttg tctgtaagcg gatgccggga gcagacaagc ccgtcagggc   9540
gcgtcagcgg gtgttggcgg gtgtcggggc tggcttaact atgcggcatc agagcagatt   9600
gtactgagag tgcaccattc gacgctctcc cttatgcgac tcctgcatta ggaagcagcc   9660
cagtagtagg ttgaggccgt tgagcaccgc cgccgcaagg aatggtgcat gcaaggagat   9720
ggcgcccaac agtcccccgg ccacggggcc tgccaccata cccacgccga aacaagcgct   9780
catgagcccg aagtggcgag cccgatcttc cccatcggtg atgtcggcga tataggcgcc   9840
agcaaccgca cctgtggcgc cggtgggtca ccaagcagga agtcaaagac tttttccggt   9900
gggcaaagga tcacgtggtt gaggtggagc atgaattcta cgtcaaaaag ggtggagcca   9960
agaaaagacc cgcccccagt gacgcagata taagtgagcc caaacgggtg cgcgagtcag  10020
ttgcgcagcc atcgacgtca gacgcggaag cttcgatcaa ctacgcagac aggtaccaaa  10080
acaaatgttc tcgtcacgtg ggcatgaatc tgatgctgtt tccctgcaga caatgcgaga  10140
gaatgaatca gaattcaaat atctgcttca ctcacggaca gaaagactgt ttagagtgct  10200
ttcccgtgtc agaatctcaa cccgtttctg tcgtcaaaaa ggcgtatcag aaactgtgct  10260
```

acattcatca tatcatggga aaggtgccag acgcttgcac tgcctgcgat ctggtcaatg 10320
tggatttgga tgactgcatc tttgaacaat aaatgattta aatcaggt 10368

<210> SEQ ID NO 10
<211> LENGTH: 10365
<212> TYPE: DNA
<213> ORGANISM: Artificial Sequence
<220> FEATURE:
<223> OTHER INFORMATION: Synthetic: Payload/Cap Plasmid Factor IX / AAV-sL65

<400> SEQUENCE: 10
cccctgtaat tgcttgttaa tcaataaacc gtttaattcg tttcagttga actttggtct 60
ctgcgtattt ctttcttatc tagtttccat atgcatgtag ataagtagca tggcgggtta 120
atcattaact aaccggtacc tctagaacta tagctagcga tgaccctgct gattggttcg 180
ctgaccattt ccgggtgcgg gacggcgtta ccagaaactc agaaggttcg tccaaccaaa 240
ccgactctga cggcagttta cgagagagat gatagggtct gcttcagtaa gccagatgct 300
acacaattag gcttgtacat attgtcgtta gaacgcggct acaattaata cataacctta 360
tgtatcatac acatacgatt taggtgacac tatagaatac acggaattaa ttcttggcca 420
ctccctctct gcgcgctcgc tcgctcactg aggccgcccg ggcaaagccc gggcgtcggg 480
cgacctttgg tcgcccggcc tcagtgagcg agcgagcgcg cagagaggga gtggccaact 540
ccatcactag gggttcctta cgtaggacgt cccctgcagg cagggagggg tggagtcgtg 600
acgtaaagat ctgatatcat cgatcgcgat gcgagagtta agcggccgag gctcagaggc 660
acacaggagt ttctgggctc accctgcccc cttccaaccc ctcagttccc atcctccagc 720
agctgtttgt gtgctgcctc tgaagtccac actgaacaaa cttcagccta ctcatgtccc 780
taaaatgggc aaacattgca agcagcaaac agcaaacaca cagccctccc tgcctgctga 840
ccttggagct ggggcagagg tcagagacct ctctgggccc atgccacctc caacatccac 900
tcgacccctt ggaatttcgg tggagaggag cagaggttgt cctggcgtgg tttaggtagt 960
gtgagagggg tacccgggga tcttgctacc agtggaacag ccactaagga ttctgcagtg 1020
agagcagagg gccagctaag tggtactctc ccagagactg tctgactcac gccacccct 1080 ccaccttgga cacaggacgc tgtggtttct gagccaggta caatgactcc tttcggtaag 1140
tgcagtggaa gctgtacact gcccaggcaa agcgtccggg cagcgtaggc gggcgactca 1200
gatcccagcc agtggactta gcccctgttt gctcctccga taactggggt gaccttggtt 1260
aatattcacc agcagcctcc cccgttgccc ctctggatcc actgcttaaa tacggacgag 1320
gacagggccc tgtctcctca gcttcaggca ccaccactga cctgggacag tgaatgatcc 1380
ccctgatctg cggcctcgac ggtatcgata agcttgatat cgaattctag tcgtcgacca 1440
ctttcacaat ctgctagcaa aggttgccac catgcagcgc gtgaacatga ttatggccga 1500
gagccctggc ctgatcacca tctgcctgct gggctacctg ctgagcgccg agtgtacagg 1560
tttgtttcct tttttaaaat acattgagta tgcttgcctt ttagatatag aaatatctga 1620
tgctgtcttc ttcactaaat tttgattaca tgatttgaca gcaatattga agagtctaac 1680
agccagcacg caggttggta agtactggtt ctttgttagc taggttttct tcttcttcat 1740
ttttaaaact aaatagatcg acaatgctta tgatgcattt atgtttaata aacactgttc 1800
agttcatgat ttggtcatgt aattcctgtt agaaaacatt catctccttg gtttaaaaaa 1860
attaaaagtg ggaaaacaaa gaaatagcag aatatagtga aaaaaaataa ccacattatt 1920

```
tttgtttgga cttaccactt tgaaatcaaa atgggaaaca aaagcacaaa caatggcctt   1980
atttacacaa aaagtctgat tttaagatat atgacatttc aaggtttcag aagtatgtaa   2040
tgaggtgtgt ctctaatttt ttaaattata tatcttcaat ttaaagtttt agttaaaaca   2100
taaagattaa cctttcatta gcaagctgtt agttatcacc aaagcttttc atggattagg   2160
aaaaaatcat tttgtctcta tgtcaaacat cttggagttg atatttgggg aaacacaata   2220
ctcagttgag ttccctaggg gagaaaagca agcttaagaa ttgacataaa gagtaggaag   2280
ttagctaatg caacatatat cactttgttt tttcacaact acagtgactt tatgtatttc   2340
ccagaggaag gcatacaggg aagaaattat cccatttgga caaacagcat gttctcacag   2400
gaagcattta tcacacttac ttgtcaactt tctagaatca aatctagtag ctgacagtac   2460
caggatcagg ggtgccaacc ctaagcaccc ccagaaagct gactggccct gtggttccca   2520
ctccagacat gatgtcagct gtgaaatcga cgtcgctgga ccataattag gcttctgttc   2580
ttcaggagac atttgttcaa agtcatttgg gcaaccatat tctgaaaaca gcccagccag   2640
ggtgatggat cactttgcaa agatcctcaa tgagctattt tcaagtgatg acaaagtgtg   2700
aagttaaccg ctcatttgag aactttcttt ttcatccaaa gtaaattcaa atatgattag   2760
aaatctgacc ttttattact ggaattctct tgactaaaag taaaattgaa ttttaattcc   2820
taaatctcca tgtgtataca gtactgtggg aacatcacag attttggctc catgccctaa   2880
agagaaattg gctttcagat tatttggatt aaaaacaaag actttcttaa gagatgtaaa   2940
attttcatga tgttttcttt tttgctaaaa ctaaagaatt attcttttac atttcagtgt   3000
tcctggacca cgagaacgcc aacaagatcc tgaacagacc caagagatac aacagcggca   3060
agctggaaga gttcgtgcag ggcaacctgg aacgcgagtg catggaagag aagtgcagct   3120
tcgaagaggc cagagaggtg ttcgagaaca ccgagagaac caccgagttc tggaagcagt   3180
acgtggacgg cgaccagtgc gagagcaacc cttgtctgaa cggcggcagc tgcaaggacg   3240
acatcaacag ctacgagtgc tggtgcccct tcggcttcga gggcaagaac tgcgagctgg   3300
acgtgacctg caacatcaag aacggcagat gcgagcagtt ctgcaagaac agcgccgaca   3360
acaaggtcgt gtgctcctgc accgagggct acagactggc cgagaaccag aagtcctgcg   3420
agcccgctgt gcctttccca tgcggaagag tgtccgtgtc ccagaccagc aagctgacca   3480
gagccgagac agtgttcccc gacgtggact acgtgaacag caccgaggcc gagacaatcc   3540
tggacaacat cacccagagc acccagtcct tcaacgactt caccagagtc gtgggcggcg   3600
aggatgctaa gcctggccag ttcccgtggc aggtggtgct gaacggaaag gtggacgcct   3660
tctgcggcgg ctccatcgtg aacgagaagt ggatcgtgac agccgcccac tgcgtggaaa   3720
ccggcgtgaa gatcacagtg gtggccggcg agcacaacat cgaggaaacc gagcacacag   3780
agcagaaaag aaacgtgatc aggatcatcc cccaccacaa ctacaacgcc gccatcaaca   3840
agtacaacca cgatatcgcc ctgctggaac tggacgagcc cctggtgctg aatagctacg   3900
tgacccccat ctgtatcgcc gacaaagagt acaccaacat ctttctgaag ttcggcagcg   3960
gctacgtgtc cggctggggc agagtgtttc acaagggcag atccgctctg gtgctgcagt   4020
acctgagagt gcctctggtg gacagagcca cctgtctgag aagcaccaag ttcaccatct   4080
acaacaacat gttctgcgct ggcttccacg agggcggcag agactcttgt cagggcgatt   4140
ctggcggccc tcacgtgaca gaggtggaag gcaccagctt tctgaccggc atcatcagct   4200
ggggcgagga atgcgccatg aaggggaagt acggcatcta caccaaggtg tccagatacg   4260
```

-continued

```
tgaactggat caaagaaaag accaagctga cataatgaaa gatggatttc caaggttaat   4320
tcattggaat tgaaaattaa cagccccccc cccccccccc tgcagatctc gagccgaatt   4380
cctgcagccc gggggatcag cctcgactgt gccttctagt tgccagccat ctgttgtttg   4440
cccctccccc gtgccttcct tgaccctgga aggtgccact cccactgtcc tttcctaata   4500
aaatgaggaa attgcatcgc attgtctgag taggtgtcat tctattctgg ggggtggggt   4560
ggggcaggac agcaaggggg aggattggga agacaatagc aggcatgctg gggatgcggt   4620
gggctctatg gcttctgagg cggaaagaac cagctggggc tcgagatcca ctagactagt   4680
gtacacgcgt gatatcagat ctgttacgta aggaacccct agtgatggag ttggccactc   4740
cctctctgcg cgctcgctcg ctcactgagg ccgcccgggc aaagcccggg cggcctcagt   4800
gagcgagcga gcgcgcagag agggagtggc caactttttg caaaagccta ggcctccaaa   4860
aaagcctcct cactacttct ggaatagctc agaggccgag gcggcctcgg cctctgcata   4920
aataaaaaaa attagtcagc catggggcgg agaatgggcg gaactgggcg gagttagggg   4980
cgggatgggc ggagttaggg gcgggactat ggttgctgac taattgagat gcatgctttg   5040
catacttctg cctgctgggg agcctgggga ctttccacac ctggttgctg actaattgag   5100
atgcatgctt tgcatacttc tgcctgctgg ggagcctggg gactttccac accctaactg   5160
acacacattc cacagctgca ttaatgaatc ggccaacgcg cggggagagg cggtttgcgt   5220
attgggcgct cttccgcttc ctcgctcact gactcgctgc gctcggtcgt tcggctgcgg   5280
cgagcggtat cagctcactc aaaggcggta atacggttat ccacagaatc aggggataac   5340
gcaggaaaga acatgtgagc aaaaggccag caaaaggcca ggaaccgtaa aaaggccgcg   5400
ttgctggcgt ttttccatag gctccgcccc cctgacgagc atcacaaaaa tcgacgctca   5460
agtcagaggt ggcgaaaccc gacaggacta taaagatacc aggcgtttcc ccctggaagc   5520
tccctcgtgc gctctcctgt tccgaccctg ccgcttaccg gatacctgtc cgcctttctc   5580
ccttcgggaa gcgtggcgct ttctcatagc tcacgctgta ggtatctcag ttcggtgtag   5640
gtcgttcgct ccaagctggg ctgtgtgcac gaaccccccg ttcagcccga ccgctgcgcc   5700
ttatccggta actatcgtct tgagtccaac ccggtaagac acgacttatc gccactggca   5760
gcagccactg gtaacaggat tagcagagcg aggtatgtag gcggtgctac agagttcttg   5820
aagtggtggc ctaactacgg ctacactaga agaacagtat ttggtatctg cgctctgctg   5880
aagccagtta ccttcggaaa aagagttggt agctcttgat ccggcaaaca aaccaccgct   5940
ggtagcggtg gtttttttgt ttgcaagcag cagattacgc gcagaaaaaa aggatctcaa   6000
gaagatcctt tgatcttttc tacggggtct gacgctcagt ggaacgaaaa ctcacgttaa   6060
gggattttgg tcatgagatt atcaaaaagg atcttcacct agatcctttt aaattaaaaa   6120
tgaagtttta aatcaatcta aagtatatat gagtaaactt ggtctgacag ttaccaatgc   6180
ttaatcagtg aggcacctat ctcagcgatc tgtctatttc gttcatccat agttgcctga   6240
ctccccgtcg tgtagataac tacgatacgg gagggcttac catctggccc cagtgctgca   6300
atgataccgc gagacccacg ctcaccggct ccagatttat cagcaataaa ccagccagcc   6360
ggaagggccg agcgcagaag tggtcctgca actttatccg cctccatcca gtctattaat   6420
tgttgccggg aagctagagt aagtagttcg ccagttaata gtttgcgcaa cgttgttgcc   6480
attgctacag gcatcgtggt gtcacgctcg tcgtttggta tggcttcatt cagctccggt   6540
tcccaacgat caaggcgagt tacatgatcc cccatgttgt gcaaaaaagc ggttagctcc   6600
ttcggtcctc cgatcgttgt cagaagtaag ttggccgcag tgttatcact catggttatg   6660
```

gcagcactgc ataattctct tactgtcatg ccatccgtaa gatgcttttc tgtgactggt 6720
gagtactcaa ccaagtcatt ctgagaatag tgtatgcggc gaccgagttg ctcttgcccg 6780
gcgtcaatac gggataatac cgcgccacat agcagaactt taaaagtgct catcattgga 6840
aaacgttctt cggggcgaaa actctcaagg atcttaccgc tgttgagatc cagttcgatg 6900
taacccactc gtgcacccaa ctgatcttca gcatctttta ctttcaccag cgtttctggg 6960
tgagcaaaaa caggaaggca aaatgccgca aaaaagggaa taagggcgac acggaaatgt 7020
tgaatactca tactcttcct ttttcaatat tattgaagca tttatcaggg ttattgtctc 7080
atgagcggat acatatttga atgtatttag aaaaataaac aaataggggt tccgcgcaca 7140
tttccccgaa aagtgccacc tgacgtctaa gaaaccatta ttatcatgac attaacctat 7200
aaaaataggc gtatcacgag gccctttcgt ctcgcgcgtt tcggtgatga cggtgaaaac 7260
ctctgacaca tgcagctccc ggagacggtc acagcttgtc tgtaagcgga tgccgggagc 7320
agacaagccc gtcagggcgc gtcagcgggt gttggcgggt gtcggggctg gcttaactat 7380
gcggcatcag agcagattgt actgagagtg caccattcga cgctctccct tatgcgactc 7440
ctgcattagg aagcagccca gtagtaggtt gaggccgttg agcaccgccg ccgcaaggaa 7500
tggtgcatgc aaggagatgg cgcccaacag tcccccggcc acggggcctg ccaccatacc 7560
cacgccgaaa caagcgctca tgagcccgaa gtggcgagcc cgatcttccc catcggtgat 7620
gtcggcgata taggcgccag caaccgcacc tgtggcgccg gtgggtcacc aagcaggaag 7680
tcaaagactt tttccggtgg gcaaaggatc acgtggttga ggtggagcat gaattctacg 7740
tcaaaaaggg tggagccaag aaaagacccg cccccagtga cgcagatata agtgagccca 7800
aacgggtgcg cgagtcagtt gcgcagccat cgacgtcaga cgcggaagct tcgatcaact 7860
acgcagacag gtaccaaaac aaatgttctc gtcacgtggg catgaatctg atgctgtttc 7920
cctgcagaca atgcgagaga atgaatcaga attcaaatat ctgcttcact cacggacaga 7980
aagactgttt agagtgcttt cccgtgtcag aatctcaacc cgtttctgtc gtcaaaaagg 8040
cgtatcagaa actgtgctac attcatcata tcatgggaaa ggtgccagac gcttgcactg 8100
cctgcgatct ggtcaatgtg gatttggatg actgcatctt tgaacaataa atgatttaaa 8160
tcaggtatgg ctgctgacgg ttatcttcca gattggctcg aggacactct ctctgaaggc 8220
attcgcgagt ggtgggcgct gaaacctgga gctccacaac ccaaggccaa ccaacagcat 8280
caggacaacg gcaggggtct tgtgcttcct gggtacaagt acctcggacc cttcaacgga 8340
ctcgacaagg gagagccggt caacgaggca gacgccgcgg ccctcgagca cgacaaggcc 8400
tacgacaagc agctcgagca gggggacaac ccgtacctca agtacaacca cgccgacgcc 8460
gagtttcagg agcgtctgca agaagatacg tcttttgggg gcaacctcgg gcgagcagtc 8520
ttccaggcca agaagcgggt tctcgaacct ctcggtctgg ttgaggaagg cgctaagacg 8580
gctcctggaa agaagagacc ggtagagccg tcacctcagc gttcccccga ctcctccacg 8640
ggcatcggca agaaaggcca gcagcccgcc agaaagagac tcaatttcgg tcagactggc 8700
gactcagagt cagtccccga ccctcaacct ctcggagaac ctccagcagc gccctctagt 8760
gtgggatctg gtacagtggc tgcaggcggt ggcgcaccaa tggcagacaa taacgaaggt 8820
gccgacggag tgggtaatgc ctcaggaaat tggcattgcg attccacatg gctgggcgac 8880
agagtcatta ccaccagcac ccgaacctgg gccctgccca cctacaacaa ccacctctac 8940
aagcaaatct ccagccaatc aggagcttca aacgacaacc actactttgg ctacagcacc 9000

-continued ccttgggggt attttgactt taacagattc cactgccact tctcaccacg tgactggcag 9060
cgactcatta acaacaactg ggattccgg cccaagagac tcaacttcaa gctcttcaac 9120
atccaagtca aggaggtcac gacgaatgat ggcgtcacga ccatcgctaa taaccttacc 9180
agcacggttc aagtcttctc ggactcggag taccagttgc cgtacgtcct cggctctgcg 9240
caccagggct gcctccctcc gttcccggcg gacgtgttca tgattcccca gtacggctac 9300
ctaacactca acaacggtag tcaggccgtg ggacgctcct ccttttactg cctggaatat 9360
ttcccatcgc agatgctgag aacgggcaat aactttgagt tcagctacag cttcgaggac 9420
gtgcctttcc acagcagcta cgcacacagc cagagcttgg accgactgat gaatcctctc 9480
attgaccagt acctgtacta cttatccaga actcagtcca caggaggaac tcaaggtacc 9540
cagcaattgt tattttctca agctgggcct gcaaacatgt cggctcaggc caagaactgg 9600
ctgcctggac cttgctaccg gcagcagcga gtctccacga cactgtcgca aaacaacaac 9660
agcaactttg cttggactgg tgccaccaaa tatcacctga acggcagaaa ctcgttggtt 9720
aatcccggcg tcgccatggc aactcacaag gacgacgagg accgcttttt cccatccagc 9780
ggagtcctga tttttggaaa aactggagca actaacaaaa ctacattgga aaatgtgtta 9840
atgacaaatg aagaagaaat tcgtcctact aatcctgtag ccacggaaga atacgggata 9900
gtcagcagca acttacaagc ggctaatact gcagcccaga cacaagttgt caacaaccag 9960
ggagccttac ctggcatggt ctggcagaac cgggacgtgt acctgcaggg tcccatttgg 10020
gccaaaattc ctcacacaga tggacacttt cacccgtctc ctcttatggg cggctttgga 10080
ctcaagaacc cgcctcctca gatcctcatc aaaaacacgc ctgttcctgc gaatcctccg 10140
gcggagtttt cagctacaaa gtttgcttca ttcatcaccc agtattccac aggacaagtg 10200
agcgtggaga ttgaatggga gctgcagaaa gaaaacagca aacgctggaa tcccgaagtg 10260
cagtatacat ctaactatgc aaaatctgcc aacgttgatt tcactgtgga caacaatgga 10320
ctttatactg agcctcgccc cattggcacc cgttacctta cccgt 10365

<210> SEQ ID NO 11
<211> LENGTH: 4174
<212> TYPE: DNA
<213> ORGANISM: Artificial Sequence
<220> FEATURE:
<223> OTHER INFORMATION: Synthetic: Plasmid Backbone 1 for insertion of
Payload / Cap

<400> SEQUENCE: 11
gtatatatga gtaaacttgg tctgacagtt accaatgctt aatcagtgag gcacctatct 60
cagcgatctg tctatttcgt tcatccatag ttgcctgact ccccgtcgtg tagataacta 120
cgatacggga gggcttacca tctggcccca gtgctgcaat gataccgcga gacccacgct 180
caccggctcc agatttatca gcaataaacc agccagccgg aagggccgag cgcagaagtg 240
gtcctgcaac tttatccgcc tccatccagt ctattaattg ttgccgggaa gctagagtaa 300
gtagttcgcc agttaatagt ttgcgcaacg ttgttgccat tgctacaggc atcgtggtgt 360
cacgctcgtc gtttggtatg gcttcattca gctccggttc ccaacgatca aggcgagtta 420
catgatcccc catgttgtgc aaaaaagcgg ttagctcctt cggtcctccg atcgttgtca 480
gaagtaagtt ggccgcagtg ttatcactca tggttatggc agcactgcat aattctctta 540
ctgtcatgcc atccgtaaga tgcttttctg tgactggtga gtactcaacc aagtcattct 600
gagaatagtg tatgcggcga ccgagttgct cttgcccggc gtcaatacgg gataataccg 660

-continued cgccacatag cagaacttta aaagtgctca tcattggaaa acgttcttcg gggcgaaaac 720
tctcaaggat cttaccgctg ttgagatcca gttcgatgta acccactcgt gcacccaact 780
gatcttcagc atcttttact ttcaccagcg tttctgggtg agcaaaaaca ggaaggcaaa 840
atgccgcaaa aaagggaata agggcgacac ggaaatgttg aatactcata ctcttccttt 900
ttcaatatta ttgaagcatt tatcagggtt attgtctcat gagcggatac atatttgaat 960
gtatttagaa aaataaacaa ataggggttc cgcgcacatt tccccgaaaa gtgccacctg 1020
acgtctaaga aaccattatt atcatgacat taacctataa aaataggcgt atcacgaggc 1080
cctttcgtct cgcgcgtttc ggtgatgacg gtgaaaacct ctgacacatg cagctcccgg 1140
agacggtcac agcttgtctg taagcggatg ccgggagcag acaagcccgt cagggcgcgt 1200
cagcgggtgt tggcgggtgt cggggctggc ttaactatgc ggcatcagag cagattgtac 1260
tgagagtgca ccattcgacg ctctccctta tgcgactcct gcattaggaa gcagcccagt 1320
agtaggttga ggccgttgag caccgccgcc gcaaggaatg gtgcatgcaa ggagatggcg 1380
cccaacagtc ccccggccac ggggcctgcc accataccca cgccgaaaca agcgctcatg 1440
agcccgaagt ggcgagcccg atcttcccca tcggtgatgt cggcgatata ggcgccagca 1500
accgcacctg tggcgccggt gggtcaccaa gcaggaagtc aaagactttt tccggtgggc 1560
aaaggatcac gtggttgagg tggagcatga attctacgtc aaaaagggtg gagccaagaa 1620
aagacccgcc cccagtgacg cagatataag tgagcccaaa cgggtgcgcg agtcagttgc 1680
gcagccatcg acgtcagacg cggaagcttc gatcaactac gcagacaggt accaaaacaa 1740
atgttctcgt cacgtgggca tgaatctgat gctgtttccc tgcagacaat gcgagagaat 1800
gaatcagaat tcaaatatct gcttcactca cggacagaaa gactgtttag agtgctttcc 1860
cgtgtcagaa tctcaacccg tttctgtcgt caaaaaggcg tatcagaaac tgtgctacat 1920
tcatcatatc atgggaaagg tgccagacgc ttgcactgcc tgcgatctgg tcaatgtgga 1980
tttggatgac tgcatctttg aacaataaat gatttaaatc aggtttgctt gttaatcaat 2040
aaaccgttta attcgtttca gttgaacttt ggtctctgcg tatttctttc ttatctagtt 2100
tccatatgca tgtagataag tagcatggcg ggttaatcat taactaaccg gtacctctag 2160
aactatagct agcgatgacc ctgctgattg gttcgctgac catttccggg tgcgggacgg 2220
cgttaccaga aactcagaag gttcgtccaa ccaaaccgac tctgacggca gtttacgaga 2280
gagatgatag ggtctgcttc agtaagccag atgctacaca attaggcttg tacatattgt 2340
cgttagaacg cggctacaat taatacataa ccttatgtat catacacata cgatttaggt 2400
gacactatag aatacacgga attaattctt ggccactccc tctctgcgcg ctcgctcgct 2460
cactgaggcc gcccgggcaa agcccgggcg tcgggcgacc tttggtcgcc cggcctcagt 2520
gagcgagcga gcgcgcagag agggagtggc caactccatc actaggggtt ccttacgtag 2580
gacgtcccct gcaggcaggg aggggtggag tcgtgacgta aagatctgat atcatcgatc 2640
gcgatgcatt aattaagcgg ccgcttctga ggcggaaaga accagctggg gctcgagatc 2700
cactagacta gtgtacacgc gtgatatcag atctgttacg taaggaaccc ctagtgatgg 2760
agttggccac tccctctctg cgcgctcgct cgctcactga ggccgcccgg gcaaagcccg 2820
ggcggcctca gtgagcgagc gagcgcgcag agagggagtg gccaactttt tgcaaaagcc 2880
taggcctcca aaaaagcctc ctcactactt ctggaatagc tcagaggccg aggcggcctc 2940
ggcctctgca taaataaaaa aaattagtca gccatggggc ggagaatggg cggaactggg 3000
cggagttagg ggcgggatgg gcggagttag gggcgggact atggttgctg actaattgag 3060
atgcatgctt tgcatacttc tgcctgctgg ggagcctggg gactttccac acctggttgc 3120
tgactaattg agatgcatgc tttgcatact tctgcctgct ggggagcctg gggactttcc 3180
acaccctaac tgacacacat tccacagctg cattaatgaa tcggccaacg cgcggggaga 3240
ggcggtttgc gtattgggcg ctcttccgct tcctcgctca ctgactcgct gcgctcggtc 3300
gttcggctgc ggcgagcggt atcagctcac tcaaaggcgg taatacggtt atccacagaa 3360
tcaggggata acgcaggaaa gaacatgtga gcaaaaggcc agcaaaaggc caggaaccgt 3420
aaaaaggccg cgttgctggc gtttttccat aggctccgcc cccctgacga gcatcacaaa 3480
aatcgacgct caagtcagag gtggcgaaac ccgacaggac tataaagata ccaggcgttt 3540
ccccctggaa gctccctcgt gcgctctcct gttccgaccc tgccgcttac cggatacctg 3600
tccgcctttc tcccttcggg aagcgtggcg ctttctcata gctcacgctg taggtatctc 3660
agttcggtgt aggtcgttcg ctccaagctg ggctgtgtgc acgaaccccc cgttcagccc 3720
gaccgctgcg ccttatccgg taactatcgt cttgagtcca acccggtaag acacgactta 3780
tcgccactgg cagcagccac tggtaacagg attagcagag cgaggtatgt aggcggtgct 3840
acagagttct tgaagtggtg gcctaactac ggctacacta gaagaacagt atttggtatc 3900
tgcgctctgc tgaagccagt taccttcgga aaaagagttg gtagctcttg atccggcaaa 3960
caaaccaccg ctggtagcgg tggttttttt gtttgcaagc agcagattac gcgcagaaaa 4020
aaaggatctc aagaagatcc tttgatcttt tctacggggt ctgacgctca gtggaacgaa 4080
aactcacgtt aagggatttt ggtcatgaga ttatcaaaaa ggatcttcac ctagatcctt 4140
ttaaattaaa aatgaagttt taaatcaatc taaa 4174

<210> SEQ ID NO 12
<211> LENGTH: 3884
<212> TYPE: DNA
<213> ORGANISM: Artificial Sequence
<220> FEATURE:
<223> OTHER INFORMATION: Synthetic: Plasmid Backbone 2 for insertion of Payload / Cap

<400> SEQUENCE: 12
gtatatatga gtaaacttgg tctgacagtt accaatgctt aatcagtgag gcacctatct 60
cagcgatctg tctatttcgt tcatccatag ttgcctgact ccccgtcgtg tagataacta 120
cgatacggga gggcttacca tctggcccca gtgctgcaat gataccgcga gacccacgct 180
caccggctcc agatttatca gcaataaacc agccagccgg aagggccgag cgcagaagtg 240
gtcctgcaac tttatccgcc tccatccagt ctattaattg ttgccgggaa gctagagtaa 300
gtagttcgcc agttaatagt ttgcgcaacg ttgttgccat tgctacaggc atcgtggtgt 360
cacgctcgtc gtttggtatg gcttcattca gctccggttc ccaacgatca aggcgagtta 420
catgatcccc catgttgtgc aaaaaagcgg ttagctcctt cggtcctccg atcgttgtca 480
gaagtaagtt ggccgcagtg ttatcactca tggttatggc agcactgcat aattctctta 540
ctgtcatgcc atccgtaaga tgcttttctg tgactggtga gtactcaacc aagtcattct 600
gagaatagtg tatgcggcga ccgagttgct cttgcccggc gtcaatacgg gataataccg 660
cgccacatag cagaacttta aaagtgctca tcattggaaa acgttcttcg gggcgaaaac 720
tctcaaggat cttaccgctg ttgagatcca gttcgatgta acccactcgt gcacccaact 780
gatcttcagc atcttttact ttcaccagcg tttctgggtg agcaaaaaca ggaaggcaaa 840
atgccgcaaa aaagggaata agggcgacac ggaaatgttg aatactcata ctcttccttt 900

-continued

```
ttcaatatta ttgaagcatt tatcagggtt attgtctcat gagcggatac atatttgaat    960
gtatttagaa aaataaacaa ataggggttc cgcgcacatt tccccgaaaa gtgccacctg   1020
acgtctaaga aaccattatt atcatgacat taacctataa aaataggcgt atcacgaggc   1080
cctttcgtct cgcgcgtttc ggtgatgacg gtgaaaacct ctgacacatg cagctcccgg   1140
agacggtcac agcttgtctg taagcggatg ccgggagcag acaagcccgt cagggcgcgt   1200
cagcgggtgt tggcgggtgt cggggctggc ttaactatgc ggcatcagag cagattgtac   1260
tgagagtgca ccattcgacg ctctccctta tgcgactcct gcattaggaa gcagcccagt   1320
agtaggttga ggccgttgag caccgccgcc gcaaggaatg gtgcatgcaa ggagatggcg   1380
cccaacagtc ccccggccac ggggcctgcc accataccca cgccgaaaca agcgctcatg   1440
agcccgaagt ggcgagcccg atcttcccca tcggtgatgt cggcgatata ggcgccagca   1500
accgcacctg tggcgccggt gggtcaccaa gcaggaagtc aaagactttt tccggtgggc   1560
aaaggatcac gtggttgagg tggagcatga attctacgtc aaaaagggtg gagccaagaa   1620
aagacccgcc cccagtgacg cagatataag tgagcccaaa cgggtgcgcg agtcagttgc   1680
gcagccatcg acgtcagacg cggaagcttc gatcaactac gcagacaggt accaaaacaa   1740
atgttctcgt cacgtgggca tgaatctgat gctgtttccc tgcagacaat gcgagagaat   1800
gaatcagaat tcaaatatct gcttcactca cggacagaaa gactgtttag agtgctttcc   1860
cgtgtcagaa tctcaacccg tttctgtcgt caaaaaggcg tatcagaaac tgtgctacat   1920
tcatcatatc atgggaaagg tgccagacgc ttgcactgcc tgcgatctgg tcaatgtgga   1980
tttggatgac tgcatctttg aacaataaat gatttaaata ccggtacctc tagaactata   2040
gctagcgatg accctgctga ttggttcgct gaccatttcc gggtgcggga cggcgttacc   2100
agaaactcag aaggttcgtc caaccaaacc gactctgacg gcagtttacg agagagatga   2160
tagggtctgc ttcagtaagc cagatgctac acaattaggc ttgtacatat tgtcgttaga   2220
acgcggctac aattaataca taaccttatg tatcatacac atacgattta ggtgacacta   2280
tagaatacac ggaattaatt cttggccact ccctctctgc gcgctcgctc gctcactgag   2340
gccgcccggg caaagcccgg gcgtcgggcg acctttggtc gcccggcctc agtgagcgag   2400
cgagcgcgca gagagggagt ggccaactcc atcactaggg gttccttacg taaggaaccc   2460
ctagtgatgg agttggccac tccctctctg cgcgctcgct cgctcactga ggccgcccgg   2520
gcaaagcccg ggcggcctca gtgagcgagc gagcgcgcag agagggagtg gccaactttt   2580
tgcaaaagcc taggcctcca aaaaagcctc ctcactactt ctggaatagc tcagaggccg   2640
aggcggcctc ggcctctgca taaataaaaa aaattagtca gccatggggc ggagaatggg   2700
cggaactggg cggagttagg ggcgggatgg gcggagttag gggcgggact atggttgctg   2760
actaattgag atgcatgctt tgcatacttc tgcctgctgg ggagcctggg gactttccac   2820
acctggttgc tgactaattg agatgcatgc tttgcatact tctgcctgct ggggagcctg   2880
gggactttcc acaccctaac tgacacacat tccacagctg cattaatgaa tcggccaacg   2940
cgcggggaga ggcggtttgc gtattgggcg ctcttccgct tcctcgctca ctgactcgct   3000
gcgctcggtc gttcggctgc ggcgagcggt atcagctcac tcaaaggcgg taatacggtt   3060
atccacagaa tcaggggata acgcaggaaa gaacatgtga gcaaaaggcc agcaaaaggc   3120
caggaaccgt aaaaaggccg cgttgctggc gtttttccat aggctccgcc cccctgacga   3180
gcatcacaaa aatcgacgct caagtcagag gtggcgaaac ccgacaggac tataaagata   3240
```

-continued ccaggcgttt ccccctggaa gctccctcgt gcgctctcct gttccgaccc tgccgcttac 3300
cggatacctg tccgcctttc tcccttcggg aagcgtggcg ctttctcata gctcacgctg 3360
taggtatctc agttcggtgt aggtcgttcg ctccaagctg ggctgtgtgc acgaaccccc 3420
cgttcagccc gaccgctgcg ccttatccgg taactatcgt cttgagtcca acccggtaag 3480
acacgactta tcgccactgg cagcagccac tggtaacagg attagcagag cgaggtatgt 3540
aggcggtgct acagagttct tgaagtggtg gcctaactac ggctacacta gaagaacagt 3600
atttggtatc tgcgctctgc tgaagccagt taccttcgga aaaagagttg gtagctcttg 3660
atccggcaaa caaaccaccg ctggtagcgg tggttttttt gtttgcaagc agcagattac 3720
gcgcagaaaa aaaggatctc aagaagatcc tttgatcttt tctacggggt ctgacgctca 3780
gtggaacgaa aactcacgtt aagggatttt ggtcatgaga ttatcaaaaa ggatcttcac 3840
ctagatcctt ttaaattaaa aatgaagttt taaatcaatc taaa 3884

<210> SEQ ID NO 13
<211> LENGTH: 145
<212> TYPE: DNA
<213> ORGANISM: Artificial Sequence
<220> FEATURE:
<223> OTHER INFORMATION: Synthetic: Wild type ITR, flip orientation

<400> SEQUENCE: 13
aggaacccct agtgatggag ttggccactc cctctctgcg cgctcgctcg ctcactgagg 60
ccgcccgggc aaagcccggg cgtcgggcga cctttggtcg cccggcctca gtgagcgagc 120
gagcgcgcag agagggagtg gccaa 145

<210> SEQ ID NO 14
<211> LENGTH: 145
<212> TYPE: DNA
<213> ORGANISM: Artificial Sequence
<220> FEATURE:
<223> OTHER INFORMATION: Synthetic: Wild type ITR, flop orientation

<400> SEQUENCE: 14
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag agagggagtg gccaa 145

<210> SEQ ID NO 15
<211> LENGTH: 123
<212> TYPE: DNA
<213> ORGANISM: Artificial Sequence
<220> FEATURE:
<223> OTHER INFORMATION: Synthetic: B loop deleted ITR

<400> SEQUENCE: 15
aggaacccct agtgatggag ttggccactc cctctctgcg cgctcgctcg ctcactgagg 60
ccgcccgggc tttgcccggg cggcctcagt gagcgagcga gcgcgcagag agggagtggc 120
caa 123

<210> SEQ ID NO 16
<211> LENGTH: 123
<212> TYPE: DNA
<213> ORGANISM: Artificial Sequence
<220> FEATURE:
<223> OTHER INFORMATION: Synthetic: C loop deleted ITR

<400> SEQUENCE: 16

-continued

```
aggaacccct agtgatggag ttggccactc cctctctgcg cgctcgctcg ctcactgagg     60

ccgggcgacc aaaggtcgcc cggcctcagt gagcgagcga gcgcgcagag agggagtggc    120

caa                                                                  123


<210> SEQ ID NO 17
<211> LENGTH: 130
<212> TYPE: DNA
<213> ORGANISM: Artificial Sequence
<220> FEATURE:
<223> OTHER INFORMATION: Synthetic: A region deleted ITR

<400> SEQUENCE: 17

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag                                                           130


<210> SEQ ID NO 18
<211> LENGTH: 105
<212> TYPE: DNA
<213> ORGANISM: Artificial Sequence
<220> FEATURE:
<223> OTHER INFORMATION: Synthetic: D region deleted ITR

<400> SEQUENCE: 18

ctgcgcgctc gctcgctcac tgaggccgcc cgggcaaagc ccgggcgtcg ggcgaccttt     60

ggtcgcccgg cctcagtgag cgagcgagcg cgcagagagg gagtg                    105
```

MANUFACTURING AND USE OF RECOMBINANT AAV VECTORS

CROSS-REFERENCE TO RELATED APPLICATIONS

This application is a continuation of PCT Application No. PCT/US22/17901, filed Feb. 25, 2022, which claims priority to United States Provisional Application Nos. 63/154,474, filed Feb. 26, 2021, 63/234,610, filed Aug. 18, 2021, and 63/257,036, filed Oct. 18, 2021, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Oct. 25, 2022, is named SequenceListing.txt and is 179,182 bytes in size.

BACKGROUND

Genetic diseases caused by dysfunctional genes account for a large fraction of diseases worldwide. Gene therapy is emerging as a promising form of treatment aiming to mitigate the effects of genetic diseases.

SUMMARY

The present disclosure provides methods and technologies for improving the design and/or production of viral vectors, including AAV vectors. In accordance with various embodiments, the present disclosure provides an insight that certain design elements of expression constructs (e.g., plasmids) and/or transfection conditions may significantly impact one or more properties and/or characteristics of viral (e.g., AAV) production (including, e.g., one or more of viral vector yield, packaging efficiency, and/or replication-competent AAV levels).

The present disclosure demonstrates, among other things, that two-plasmid transfection systems with particular combinations of sequence elements (e.g., rep genes or gene variants, cap genes or gene variants, one or more helper virus genes or gene variants, and/or one or more genes of interest) can be effective in enhancing downstream production of, inter alia, viral vectors for use in gene therapy. For example, in some embodiments, the present disclosure provides an insight that two-plasmid transfection systems with particular combinations of wild-type sequence elements (e.g., rep genes or gene variants, one or more helper virus genes or gene variants, one or more viral promoters) can be effective in enhancing production of viral vectors.

In some embodiments, the present disclosure demonstrates that two-plasmid transfection systems with particular combinations of sequence elements may be combined with various transfections reagents (e.g., chemical transfection reagents, including lipids, polymers, and cationic molecules [e.g., one or more cationic lipids]) can be effective in enhancing production of viral vectors.

In some embodiments, the present disclosure provides an insight that optimization of plasmid ratios in a two-plasmid system can provide still further improved production of one or more aspects of viral vectors, for example, AAV vectors (including, e.g., one or more of viral vector yield, packaging efficiency, and/or replication-competent AAV levels). Without wishing to be bound by any particular theory, the present disclosure demonstrates that transfection with a two-plasmid system comprising a first plasmid with viral helper genes (e.g., Adenovirus genes or Herpesvirus genes) and either AAV rep gene or AAV cap gene, and a second plasmid with a payload and either AAV rep gene or AAV cap gene can produce improved viral vector yield relative to a reference. In some embodiments, the present disclosure demonstrates that a particular transfection ratio comprising great amounts of a first plasmid with helper virus genes as compared to a second plasmid with a payload can produce improved viral vector yield and packaging efficiency relative to a reference.

In some embodiments, the present disclosure provides plasmids, including at least one of a polynucleotide sequence encoding an AAV cap gene, a polynucleotide sequence encoding an AAV rep gene, a polynucleotide sequence encoding a payload and flanking ITRs, and/or a polynucleotide sequence encoding one or more viral helper genes. In some embodiments, provided plasmids further include a polynucleotide sequence encoding a promoter, for example, a native p5 promoter, a native p40 promoter, a CMV promoter, and/or one or more wild-type promoters. In some embodiments, provided plasmids further include a polyA sequence. In some embodiments, provided plasmids further include an intron, for example, an intron between a promoter and an AAV rep gene. In some embodiments, provided plasmids further comprise polynucleotide sequences encoding wild-type viral helper genes. In some embodiments, provided plasmids further comprise a transgene, for example, one or more of Propionyl-CoA Carboxylase, ATP7B, Factor IX, methylmalonyl CoA mutase (MUT), α1-antitrypsin (A1AT), UGT1A1, or variants thereof. In some embodiments, provided plasmids do not include a polynucleotide sequence encoding a nuclease.

In some embodiments, a first and second provided plasmid are present in a composition, wherein each plasmid includes different sequence elements (e.g., a polynucleotide sequence encoding an AAV cap gene, a polynucleotide sequence encoding an AAV rep gene, a polynucleotide sequence encoding a payload and flanking ITRs, and/or a polynucleotide sequence encoding one or more viral helper genes). In some embodiments, provided compositions include a first plasmid comprising a polynucleotide sequence encoding an AAV cap gene and a second plasmid comprising a polynucleotide sequence encoding an AAV rep gene. In some embodiments, provided compositions include a first plasmid comprising a polynucleotide sequence encoding a payload and flanking ITRs and a second plasmid comprising a polynucleotide sequence encoding one or more viral helper genes. In some embodiments, provided compositions include a first plasmid comprising a polynucleotide sequence encoding one or more viral helper genes and a second plasmid comprising a polynucleotide sequence encoding a payload and flanking ITRs. In some embodiments, provided compositions are formulated for co-delivery of a first and second plasmid to a cell. In some embodiments, provided compositions include a particular ratio of a first and second plasmid to achieve a particular ratio between the two plasmids. In some embodiments, provided compositions include a greater amount of a first plasmid relative to a second plasmid. In some embodiments, provided compositions include a first and second plasmid, wherein the ratio of the first plasmid to the second plasmid is greater than or equal to 1.5:1 up to 10:1. In some embodiments, provided compositions include a first plasmid comprising a polynucleotide sequence encoding one or more viral helper genes and a second plasmid comprising a polynucleotide sequence encoding a payload and flanking ITRs. In some embodiments, provided compositions include a first plasmid comprising a polynucleotide sequence encoding one or more viral helper genes and a rep gene and a second plasmid comprising a polynucleotide sequence encoding a payload and flanking ITRs and a cap gene. In some embodiments, provided compositions include a first plasmid comprising a polynucleotide sequence encoding one or more viral helper genes and a cap gene and a second plasmid comprising a polynucleotide sequence encoding a payload and flanking ITRs and a rep gene.

In some embodiments, provided compositions include one or more of a polynucleotide sequence encoding one or more enhancer sequences, a polynucleotide sequence encoding one or more promoter sequences, a polynucleotide sequence encoding one or more intron sequences, a polynucleotide sequence encoding a gene, and a polynucleotide sequence comprising a polyA sequence. In some embodiments, provided polynucleotide sequences encoding a payload include a polynucleotide sequence comprising a first nucleic acid sequence and a second nucleic acid sequence, wherein the first nucleic acid sequence comprises at least one gene and the second nucleic acid sequence is positioned 5' or 3' to the first nucleic acid sequence and promotes the production of two independent gene products upon integration into a target integration site, a third nucleic acid sequence positioned 5' to the polynucleotide and comprising a sequence that is homologous to a genomic sequence 5' of the target integration site, and a fourth nucleic acid sequence positioned 3' to the polynucleotide and comprising a sequence that is homologous to a genomic sequence 3' of the target integration site. In some embodiments, provided target integration sites comprise the 3' end of an endogenous gene. In some embodiments, provided third nucleic acid sequences are homologous to DNA sequences upstream of a stop codon in an endogenous gene. In some embodiments, provided fourth nucleic acid sequences are homologous to DNA downstream of a stop codon in an endogenous gene. In some embodiments, provided target integration sites are in the genome of a cell. In some embodiments, provided target integration sites are in the genome of a liver, muscle, or CNS cell.

In some embodiments, provided compositions include compositions for use in packaging an AAV vector. In some embodiments, provided compositions are used in a method of manufacturing a packaged AAV vector. In some embodiments, provided compositions are delivered to a cell, including a mammalian cell, a liver cell, a muscle cell, a CNS cell, or a cell isolated from a subject. In some embodiments, provided compositions are delivered to a cell by means of a chemical transfection reagent, including a cationic molecule and/or a cationic lipid. In some embodiments, provided compositions include a packaged AAV vector composition. In some embodiments, provided compositions may be administered in a method of treatment to a subject in need thereof, including a subject having or suspected of having one or more of propionic acidemia, Wilson's Disease, hemophilia, Crigler-Najjar syndrome, methylmalonic acidemia (MMA), alpha-1 anti-trypsin deficiency (A1ATD), a glycogen storage disease (GSD), Duchenne's muscular dystrophy, limb girdle muscular dystrophy, X-linked myotubular myopathy, Parkinson's Disease, Mucopolysaccharidosis, hemophilia A, hemophilia B, or hereditary angioedema (HAE). In some embodiments, provided compositions do not comprise a nuclease.

BRIEF DESCRIPTION OF THE DRAWING

FIG. 29 provides exemplary expression constructs comprising certain sequence features and combinations thereof. Exemplary viral vector products that may be produced with such expression construct combinations are also provided.

DEFINITIONS

Figure 1:
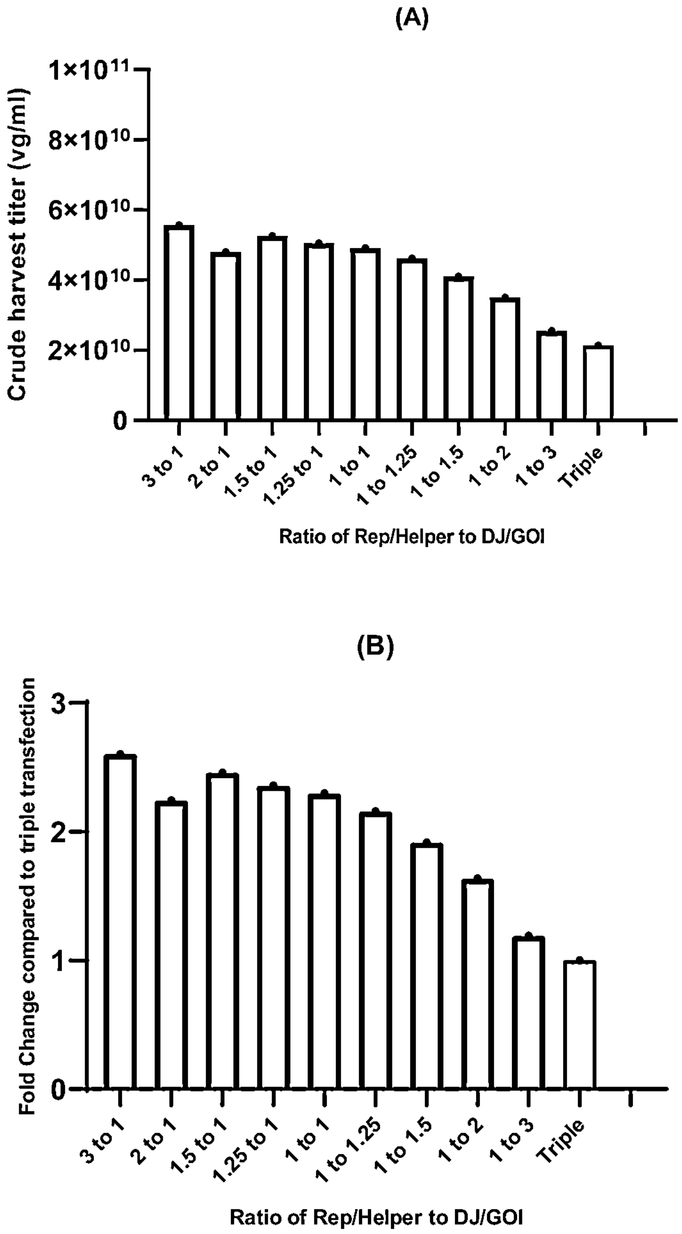
FIG. 1 compares two-plasmid and three-plasmid systems for cell transfection. (A) depicts the viral vector yields (vg/mL) produced for different two-plasmid ratios as compared to a three-plasmid system. (B) depicts relative fold-change in viral vector yields relative to a three-plasmid system. The cap gene encodes for AAV-DJ and the gene of interest (GOI) is human Factor IX flanked by murine albumin homology arms (mHA-hFIX).

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

The articles "a" and "an" are used herein to refer to one or to more than one (i.e., to at least one) of the grammatical object of the article. By way of example, "an element" means one element or more than one element.

About: The term "about" or "approximately", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Codon optimization: As used herein, the term "codon optimization" refers to a process of changing codons of a given gene in such a manner that the polypeptide sequence encoded by the gene remains the same while the changed codons improve the process of expression of the polypeptide sequence. For example, if the polypeptide is of a human protein sequence and expressed in *E. coli*, expression will often be improved if codon optimization is performed on the DNA sequence to change the human codons to codons that are more effective for expression in *E. coli.*

Combination Therapy: As used herein, the term "combination therapy" refers to a clinical intervention in which a subject is simultaneously exposed to two or more therapeutic regimens (e.g. two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Corresponding to: As used herein, the term "corresponding to" may be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Excipient: As used herein, refers to a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Gene: As used herein, the term "gene" refers to a DNA sequence in a chromosome that encodes a gene product (e.g., an RNA product and/or a polypeptide product). In some embodiments, a gene includes a coding sequence (e.g., a sequence that encodes a particular gene product); in some embodiments, a gene includes a non-coding sequence. In some particular embodiments, a gene may include both coding (e.g., exonic) and non-coding (e.g., intronic) sequences. In some embodiments, a gene may include one or more regulatory elements (e.g. promoters, enhancers, silencers, termination signals) that, for example, may control or impact one or more aspects of gene expression (e.g., cell-type-specific expression, inducible expression).

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to the overall relatedness between polymeric molecules, e.g., between polypeptide molecules. In some embodiments, polymeric molecules such as antibodies are considered to be "homologous" to one another if their sequences are at least 80%, 85%, 90%, 95%, or 99% identical. In some embodiments, polymeric molecules are considered to be "homologous" to one another if their sequences are at least 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

"Improved," "increased" or "reduced": As used herein, these terms, or grammatically comparable comparative terms, indicate values that are relative to a comparable reference measurement. For example, in some embodiments, an assessed value achieved with an agent of interest (e.g., a therapeutic agent) may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Marker: A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide. In some embodiments, a nucleic acid has enzymatic activity.

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Prevent or prevention: as used herein when used in connection with the occurrence of a disease, disorder, and/or condition, refers to reducing the risk of developing the disease, disorder and/or condition and/or to delaying onset of one or more characteristics, signs, or symptoms of the disease, disorder or condition. Prevention may be considered complete when onset of a disease, disorder or condition has been delayed for a predefined period of time.

Risk: as will be understood from context, "risk" of a disease, disorder, and/or condition refers to a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the phrase "therapeutic agent" refers to an agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Treatment: As used herein, the term "treatment" (also "treat" or "treating") refers to administration of a therapy that partially or completely alleviates, ameliorates, relives, inhibits, delays onset of, reduces severity of, and/or reduces incidence of one or more signs, symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition. Thus, in some embodiments, treatment may be prophylactic; in some embodiments, treatment may be therapeutic.

Variant: As used herein, the term "variant" refers to an entity that shows significant structural identity with a reference entity but differs structurally from the reference entity in the presence or absence or in the level of one or more chemical moieties as compared with the reference entity. In some embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence and/or one or more differences in chemical moieties (e.g., carbohydrates, lipids, phosphate groups) that are covalently components of the polypeptide or nucleic acid (e.g., that are attached to the polypeptide or nucleic acid backbone). In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%.). In some embodiments, a variant polypeptide or nucleic acid shows an overall sequence identity with a portion of a reference polypeptide or nucleic acid that is at least 85%, 86%, 87%, 88%, 89%, 90%, 91%, 92%, 93%, 94%, 95%, 96%, 97%, or 99%. Alternatively or additionally, in some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid. For example, in some embodiments, a variant polypeptide or nucleic acid shares one or more of the biological activities of the reference polypeptide or nucleic acid and further comprises one or more sequence variations (e.g., deletion, insertion, truncation, codon optimization, etc.). In some embodiments, a variant polypeptide or nucleic acid lacks one or more of the biological activities of the reference polypeptide or nucleic acid. In some embodiments, a variant polypeptide or nucleic acid shows a reduced level of one or more biological activities as compared to the reference polypeptide or nucleic acid. In some embodiments, a polypeptide or nucleic acid of interest is considered to be a "variant" of a parent or reference polypeptide or nucleic acid if it has an amino acid or nucleotide sequence that is identical to that of the reference but for a small number of sequence alterations at particular positions. Typically, fewer than about 20%, about 15%, about 10%, about 9%, about 8%, about 7%, about 6%, about 5%, about 4%, about 3%, or about 2% of the residues in a variant are substituted, inserted, or deleted, as compared to the reference. In some embodiments, a variant polypeptide or nucleic acid comprises about 10, about 9, about 8, about 7, about 6, about 5, about 4, about 3, about 2, or about 1 substituted residue(s) as compared with a reference. Often, a variant polypeptide or nucleic acid comprises a very small number (e.g., fewer than about 5, about 4, about 3, about 2, or about 1) number of substituted, inserted, or deleted, functional residues (i.e., residues that participate in a particular biological activity) relative to the reference. In some embodiments, a variant polypeptide or nucleic acid comprises not more than about 5, about 4, about 3, about 2, or about 1 addition(s) or deletion(s), and, in some embodiments, comprises no additions or deletions, as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 additions or deletions as compared to the reference. In some embodiments, a reference polypeptide or nucleic acid is one found in nature. In some embodiments, a reference polypeptide or nucleic acid is a human polypeptide or nucleic acid.

Detailed Description of Certain Embodiments

Gene Therapy

Genetic diseases caused by dysfunctional genes have been reported to account for nearly 80% of approximately 7,136 diseases reported as of 2019 (See, Genetic and rare Diseases Information Center and Global Genes). More than 330 million people worldwide are affected by a genetic disease, and almost half of these cases are estimated to be children. However, only about 500 human diseases are estimated to be treatable with available drugs, indicating that new therapies and options for treatment are necessary to address a substantial proportion of these genetic disorders. Gene therapy is an emerging form of treatment that aims to mediate the effects of genetic disorders through transmission of genetic material into a subject. In some embodiments, gene therapy may comprise transcription and/or translation of transferred genetic material, and/or by integration of transferred genetic material into a host genome through administration of nucleic acids, viruses, or genetically engineered microorganisms (See, FDA Guidelines). Gene therapy can allow delivery of therapeutic genetic material to any specific cell, tissue, and/or organ of a subject for treatment. In some embodiments, gene therapy involves transfer of a therapeutic gene, or transgene, to a host cell.

Viral Gene Therapy

Viruses have emerged as an appealing vehicle for gene therapy due to their ability to express high levels of a payload (e.g., a transgene) and, in some embodiments, their ability to stably express a payload (e.g., transgene) within a hosts genome. Recombinant AAVs are popular viral vectors for gene therapy, as they often produce high viral yields, mild immune response, and are able to infect different cell types.

In conventional AAV gene therapy, rAAVs can be engineered to deliver therapeutic payloads (e.g., transgenes) to target cells without integrating into chromosomal DNA. One or more payloads (e.g., transgenes) may be expressed from a non-integrated genetic element called an episome that exists within the cell nucleus. Although conventional gene therapy may be effective in initially transduced cells, episomal expression is transient and gradually decreases over time, inter alia, with cell turnover. For cells with a longer lifespan (e.g., cells that exist for a significant portion of a subject's lifetime), episomal expression can be effective. However, conventional gene therapy can have drawbacks when applied to a subject early in life (e.g., during childhood), as rapid tissue growth during development can result in dilution and eventual loss of therapeutic benefit of a payload (e.g., transgene).

A second type of AAV gene therapy, GENERIDE™, harnesses homologous recombination (HR), a naturally occurring DNA repair process that maintains the fidelity of a cell genome. GENERIDE™ uses HR to insert one or more payloads (e.g., transgenes) into specific target loci within a genomic sequence. In some embodiments, GENERIDE™ makes use of endogenous promoters at one or more target loci to drive high levels of tissue-specific expression. GENERIDE™ does not require use of exogenous nucleases or promoters, thereby reducing detrimental effects often associated with these elements. Furthermore, GENERIDE™ platform technology has potential to overcome some of the key limitations of both traditional gene therapy and conventional gene editing approaches in a way that is well positioned to treat genetic diseases, particularly in pediatric subjects. GENERIDE™ uses an AAV vector to deliver a gene into the nucleus of the cell. It then uses HR to stably integrate a corrective gene into the genome of a subject at a location where it is regulated by an endogenous promoter, allowing lifelong protein production, even as the body grows and changes over time, which is not feasible with conventional AAV gene therapy.

Previous work on non-disruptive gene targeting is described in WO 2013/158309, incorporated herein by reference. Previous work on genome editing without nucleases is described in WO 2015/143177, incorporated herein by reference. Previous work on non-disruptive gene therapy for the treatment of MMA is described in WO 2020/032986, incorporated herein by reference. Previous work on monitoring of gene therapy is described in WO/2020/214582, incorporated herein by reference.

Viral Structure and Function

Viral Vectors

Viral vectors comprise virus or viral chromosomal material, within which a heterologous nucleic acid sequence can be inserted for transfer into a target sequence of interest (e.g., for transfer into genomic DNA within a cell). Various viruses can be used as viral vectors, including, e.g., single-stranded DNA (ssDNA), double-stranded DNA (dsDNA) viruses, and/or RNA viruses with a DNA stage in their lifecycle. In some embodiments, a viral vector is or comprises an adeno-associated virus (AAV) or AAV variant.

In some embodiments, a vector particle is a single unit of virus comprising a capsid encapsidating a virus-based polynucleotide (e.g., a wild-type viral genome or a recombinant viral vector). In some embodiments, a vector particle is or comprises an AAV vector particle. In some embodiments, an AAV vector particle refers to a vector particle comprised of at least one AAV capsid protein and an encapsidated AAV vector. In some embodiments, a vector particle (also referred to as a viral vector) comprises at least one AAV capsid protein and an encapsidated AAV vector, wherein the vector further comprises one or more heterologous polynucleotide sequences.

Capsid Proteins

In some embodiments, an expression construct comprises polynucleotide sequences encoding capsid proteins from one or more AAV subtypes, including naturally occurring and recombinant AAVs. In some embodiments, an expression construct comprises polynucleotide sequences encoding capsid proteins from AAV1, AAV2, AAV3, AAV4, AAV5, AAV6, AAV7, AAV8, AAV9, AAV10, AAV11, AAVC11.01, AAVC11.02, AAVC11.03, AAVC11.04, AAVC11.05, AAVC11.06, AAVC11.07, AAVC11.08, AAVC11.09, AAVC11.10, AAVC11.11 (referred to interchangeably herein as sL65), AAVC11.12, AAVC11.13, AAVC11.14, AAVC11.15, AAVC11.16, AAVC11.17, AAVC11.18, AAVC11.19, AAV-DJ, AAV-LK03, AAV-LK19, AAVrh.74, AAVrh.10, AAVhu.37, AAVrh.K, AAVrh.39, AAV12, AAV 13, AAVrh.8, avian AAV, bovine AAV, canine AAV, equine AAV, primate AAV, non-primate AAV, ovine AAV, a hybrid AAV (e.g., an AAV comprising one more sequences of one AAV subtype and one or more sequences of a second subtype), and/or an AAV comprising a mutant AAV capsid protein or a chimeric AAV capsid (e.g., a capsid with polynucleotide sequences derived from two or more different serotypes of AAV), or variants thereof.

In some embodiments, viral vectors are packaged within capsid proteins (e.g., capsid proteins from one or more AAV subtypes). In some embodiments, capsid proteins provide increased or enhanced transduction of cells (e.g., human or murine cells) relative to a reference capsid protein. In some embodiments, capsid proteins provide increased or enhanced transduction of certain cells or tissue types (e.g., liver tropism, muscle tropism, CNS tropism) relative to a reference capsid protein. In some embodiments, capsid proteins increase or enhance transduction of cells or tissues (e.g., liver, muscle, and/or CNS) by at least about 10%, 20%, 30%, 40%, 50%, 60%, 70%, 80%, 90%, 100%, 200%, 300%, 400%, 500%, 600%, 700%, 800%, 900%, 1000%, or more relative to a reference capsid protein. In some embodiments, capsid proteins increase or enhance transduction of cells or tissues (e.g., liver, muscle, and/or CNS) by at least about 1.2×, 1.5×, 2×, 3×, 4×, 5×, 6×, 7×, 8×, 9×, 10×, 11×, 12×, 13×, 14×, 15×, 16×, 17×, 18×, 19×, 20×, 30×, 40×, 50×, 60×, 70×, 80×, 90×, 100×, or more relative to a reference capsid protein.

AAV Structure and Function

Adeno-associated virus (AAV) is a parvovirus composed of an icosahedral protein capsid and a single-stranded DNA genome. The AAV viral capsid comprises three subunits, VP1, VP2, and VP3 and two inverted terminal repeat (ITR) regions, which are at the ends of the genomic sequence. The ITRs serve as origins of replication and play a role in viral packaging. The viral genome also comprises rep and cap genes, which are associated with replication and capsid packaging, respectively. In most wild-type AAV, the rep gene encodes four proteins required for viral replication, Rep 78, Rep68, Rep52, and Rep40. The cap gene encodes the capsid subunits as well as the assembly activating protein (AAP), which promotes assembly of viral particles. AAVs are generally replication-deficient, requiring the presence of a helper virus or helper virus functions (e.g., herpes simplex virus (HSV) and/or adenovirus (AdV)) in order to replicate within an infected cell. For example, in some embodiments AAVs require adenoviral E1A, E2A, E4, and VA RNA genes in order to replicate within a host cell.

Recombinant AAV

In general, recombinant AAV (rAAV) vectors can comprise many of the same elements found in wild-type AAVs, including similar capsid sequences and structures, as well as polynucleotide sequences that are not of AAV origin (e.g., a polynucleotide heterologous to AAV). In some embodiments, rAAVs will replace native, wild-type AAV sequences with polynucleotide sequences encoding a payload. For example, in some embodiments an rAAV will comprise polynucleotide sequences encoding one or more genes intended for therapeutic purposes (e.g., for gene therapy). rAAVs may be modified to remove one or more wild-type viral coding sequences. For example, rAAVs may be engineered to comprise only one ITR, and/or one or more fewer genes necessary for packaging (e.g., rep and cap genes) than would be found in a wild type AAV. Gene expression with rAAVs is generally limited to one or more genes that total 5 kb or less, as larger sequences are not efficiently packaged within the viral capsid. In some embodiments, two or more rAAVs can be used to provide portions of a larger payload, for example, in order to provide an entire coding sequence for a gene that would normally be too large to fit in a single AAV.

Among other things, the present disclosure provides viral vectors comprising one or more polypeptides described herein. In some embodiments, rAAVs may comprise one or more capsid proteins (e.g., one or more capsid proteins from AAV1, AAV2, AAV3, AAV4, AAV5, AAV6, AAV7, AAV8, AAV9, AAV10, AAV11, AAVC11.01, AAVC11.02, AAVC11.03, AAVC11.04, AAVC11.05, AAVC11.06, AAVC11.07, AAVC11.08, AAVC11.09, AAVC11.10, AAVC11.11 (referred to interchangeably herein as sL65), AAVC11.12, AAVC11.13, AAVC11.14, AAVC11.15, AAVC11.16, AAVC11.17, AAVC11.18, AAVC11.19, AAV-DJ, AAV-LK03, AAV-LK19, AAVrh.74, AAVrh.10, AAVhu.37, AAVrh.K, AAVrh.39, AAV12, AAV 13, AAVrh.8, avian AAV, bovine AAV, canine AAV, equine AAV, primate AAV, non-primate AAV, ovine AAV, a hybrid AAV (e.g., an AAV comprising one more sequences of one AAV subtype and one or more sequences of a second subtype), and/or an AAV comprising a mutant AAV capsid protein or a chimeric AAV capsid (e.g., a capsid with polynucleotide sequences derived from two or more different serotypes of AAV). In some embodiments, rAAVs may comprise one or more polynucleotide sequences encoding a gene or nucleic acid of interest (e.g., a gene for treatment of a genetic disease/disorder and/or a inhibitory nucleic acid sequence).

AAV vectors may be capable of being replicated in an infected host cell (replication competent) or incapable of being replicated in an infected host cell (replication incompetent). A replication competent AAV (rcAAV) requires the presence of one or more functional AAV packaging genes. Recombinant AAV vectors are generally designed to be replication-incompetent in mammalian cells, in order to reduce the possibility that rcAAV are generated through recombination with sequences encoding AAV packaging genes. In some embodiments, rAAV vector preparations as described herein are designed to comprise few, if any, rcAAV vectors. In some embodiments, rAAV vector preparations comprise less than about 1 rcAAV per $10^2$ rAAV vectors. In some embodiments, rAAV vector preparations comprise less than about 1 rcAAV per $10^4$ rAAV vectors. In some embodiments, rAAV vector preparations comprise less than about 1 rcAAV per $10^8$ rAAV vectors. In some embodiments, rAAV vector preparations comprise less than about 1 rcAAV per $10^{12}$ rAAV vectors. In some embodiments, rAAV vector preparations comprise no rcAAV vectors.

Heterologous Nucleic Acids

Payloads

In some embodiments, one or more vectors or constructs described herein may comprise a polynucleotide sequence encoding one or more payloads. In accordance with various aspects, any of a variety of payloads may be used (e.g., those with a diagnostic and/or therapeutic purpose), alone or in combination. In some embodiments, a payload may be or comprise a polynucleotide sequence encoding a peptide or polypeptide. In some embodiments, a payload is a peptide that has cell-intrinsic or cell-extrinsic activity that promotes a biological process to treat a medical condition. In some embodiments, a payload may be or comprise a transgene (also referred to herein as a gene of interest (GOI)). In some embodiments, a payload may be or comprise one or more inverted terminal repeat (ITR) sequences (e.g., one or more AAV ITRs). In some embodiments, a payload may be or comprise one or more transgenes with flanking ITR sequences. In some embodiments, a payload may be or comprise one or more transgenes with flanking homology arm sequences. In some embodiments, a payload may be or comprise one or more transgenes with flanking homology arm sequences and flanking ITRs. In some embodiments, a payload may be or comprise one or more heterologous nucleic acid sequences encoding a reporter gene (e.g., a fluorescent or luminescent reporter). In some embodiments, a payload may be or comprise one or more biomarkers (e.g., proxy for payload expression). In some embodiments, expression constructs comprise one or more transcription termination sequences (e.g., a polyA sequence). In some embodiments, expression constructs comprise one or more promoter sequences. In some embodiments, expression constructs comprise one or more enhancer sequences. In some embodiments, expression constructs comprise one or more intron sequences. In some embodiments, a payload may comprise a sequence for polycistronic expression (including, e.g., a 2A peptide, or intronic sequence, internal ribosomal entry site). In some embodiments, 2A peptides are small (e.g., approximately 18-22 amino acids) peptide sequences enabling co-expression of two or more discrete protein products within a single coding sequence. In some embodiments, 2A peptides allows co-expression of two or more discrete protein products regardless of arrangement of protein coding sequences. In some embodiments, 2A peptides are or comprise a consensus motif (e.g., DVEXNPGP). In some embodiments, 2A peptides promote protein cleavage. In some embodiments, 2A peptides are or comprise viral sequences (e.g., foot-and-mouth diseases virus (F2A), equine Rhinitis A virus, porcine teschovirus-1 (P2A), or Thosea asigna virus (T2A)).

In some embodiments, biomarkers are or comprise a 2A peptide (e.g., P2A, T2A, E2A, and/or F2A). In some embodiments, biomarkers are or comprise a Furin cleavage motif (See, Tian et al., FurinDB: A Database of 20-Residue Furin Cleavage Site Motifs, Substrates and Their Associated Drugs, (2011), Int. J. Mol. Sci., vol. 12: 1060-1065). In some embodiments, biomarkers are or comprise a tag (e.g., an immunological tag). In some embodiments, a payload may comprise one or more functional nucleic acids (e.g., one or more siRNA or miRNA). In some embodiments, a payload may comprise one or more inhibitory nucleic acids (including, e.g., ribozyme, miRNA, siRNA, or shRNA, among other things). In some embodiments, a payload may comprise one or more nucleases (e.g., Cas proteins, endonucleases, TALENs, ZFNs).

Transgenes

In some embodiments, a transgene is a corrective gene chosen to improve one or more signs and/or symptoms of a disease, disorder, or condition. In some embodiments, a transgene may integrate into a host cell genome through use of vector(s) encompassed by the present disclosure. In some embodiments, transgenes are functional versions of disease associated genes (i.e., gene isoform(s) which are associated with the manifestation or worsening of a disease, disorder or condition) found in a host cell. In some embodiments, transgenes are an optimized version of disease-associated genes found in a host cell (e.g., codon optimized or expression-optimized variants). In some embodiments, transgenes are variants of disease-associated genes found in a host cell (e.g., functional gene fragment or variant thereof). In some embodiments, a transgene is a gene that causes expression of a peptide that is normally expressed in one or more healthy tissues. In some embodiments, a transgene is a gene that causes expression of a peptide that is normally expressed in liver cells. In some embodiments, a transgene is a gene that causes expression of a peptide that is normally expressed in muscle cells. In some embodiments, a transgene is a gene that causes expression of a peptide that is normally expressed in central nervous system cells.

In some embodiments, a transgene may be or comprise a gene that causes expression of a peptide that is not normally expressed in one or more healthy tissues (e.g., peptide expressed ectopically). In some embodiments, a transgene is a gene that causes expression of a peptide that is ectopically expressed in one or more healthy tissues (e.g., liver, muscle, central nervous system (CNS)). In some embodiments, a transgene is a gene that causes expression of a peptide that is ectopically expressed in one or more healthy tissues and normally expressed in one or more healthy tissues (e.g., liver, muscle, central nervous system (CNS)).

In some embodiments, a transgene may be or comprise a gene encoding a functional nucleic acid. In some embodiments, a therapeutic agent is or comprises an agent that has a therapeutic effect upon a host cell or subject (including, e.g., a ribozyme, guide RNA (gRNA), antisense oligonucleotide (ASO), miRNA, siRNA, and/or shRNA). For example, in some embodiments, a therapeutic agent promotes a biological process to treat a medical condition, e.g., at least one symptom of a disease, disorder, or condition.

In some embodiments, transgene expression in a subject results substantially from integration at a target locus. In some embodiments, 75% or more (e.g., 80% or more, 85% or more, 90% or more, 95% or more, 99% or more, 99.5% or more) of total transgene expression in a subject is from transgene integration at a target locus. In some embodiments, 25% or less (e.g., 20% or less, 15% or less, 10% or less, 5% or less, 1% or less, 0.5% or less, 0.1% or less) of total transgene expression in a subject is from a source other than transgene integration at a target locus (e.g., episomal expression, integration at a non-target locus).

In some embodiments, transgenes are transiently expressed in a subject (e.g., episomal expression from plasmids, minicircle DNAs, viruses, etc.). In some embodiments, 75% or more (e.g., 80% or more, 85% or more, 90% or more, 95% or more, 99% or more, 99.5% or more) of total transgene expression in a subject is from transient expression. In some embodiments, 25% or less (e.g., 20% or less, 15% or less, 10% or less, 5% or less, 1% or less, 0.5% or less, 0.1% or less) of total transgene expression in a subject is from a source other than transient expression (e.g., integration at a non-target locus). In some embodiments, transgenes are transiently expressed in a subject (e.g., episomal expression from plasmids, minicircle DNAs, viruses, etc.) for one or more weeks after treatment. In some embodiments, transgenes are transiently expressed in a subject (e.g., episomal expression from plasmids, minicircle DNAs, viruses, etc.) for one or more months after treatment.

In some embodiments, transgenes are transiently expressed in a subject (e.g., episomal expression from plasmids, minicircle DNAs, viruses, etc.) one or more weeks after treatment at a level comparable to that observed within one or more days after treatment. In some embodiments, transgenes are transiently expressed in a subject (e.g., episomal expression from plasmids, minicircle DNAs, viruses, etc.) one or more months after treatment at a level comparable to that observed within one or more days after treatment.

In some embodiments, transgenes are transiently expressed in a subject (e.g., episomal expression from plasmids, minicircle DNAs, viruses, etc.) one or more weeks after treatment at a level that is reduced relative to that observed within one or more days after treatment. In some embodiments, transgenes are transiently expressed in a subject (e.g., episomal expression from plasmids, minicircle DNAs, viruses, etc.) one or more months after treatment at a level that is reduced relative to that observed within one or more days after treatment.

In some embodiments, transgenes are transiently expressed in a subject (e.g., episomal expression from plasmids, minicircle DNAs, viruses, etc.) for no more than one month after treatment. In some embodiments, transgenes are transiently expressed in a subject (e.g., episomal expression from plasmids, minicircle DNAs, viruses, etc.) for no more than two months after treatment. In some embodiments, transgenes are transiently expressed in a subject (e.g., episomal expression from plasmids, minicircle DNAs, viruses, etc.) for no more than three months after treatment. In some embodiments, transgenes are transiently expressed in a subject (e.g., episomal expression from plasmids, minicircle DNAs, viruses, etc.) for no more than four months after treatment. In some embodiments, transgenes are transiently expressed in a subject (e.g., episomal expression from plasmids, minicircle DNAs, viruses, etc.) for no more than five months after treatment. In some embodiments, transgenes are transiently expressed in a subject (e.g., episomal expression from plasmids, minicircle DNAs, viruses, etc.) for no more than six months after treatment.

In some embodiments, a transgene is selected may be or comprise a polynucleotide sequence encoding C1NH, fumarylacetoacetate hydrolase (FAH), ATP7B, UGT1A1, G6PC, G6PT1, SLC17A3, SLCA4, GAA, DDC, Factor IX, Factor VIII, COL7A1, COL17A1, MMP1, KRT5, LAMA3, LAMB3, LAMC2, ITGB4, CBS, CPS1, ARG1, ASL, OTC, IDUA, SGSH, NAGLU, HGSNAT, GNS, GALNS, GLB1, ARSB, GUSB, HYAL1, OCTN2, CPT1, CACT, CPT2, HADHA, HADHB, LCHAD, ACADM, ACADVL, BCKDH complex (Ela, Elb, and E2 subunits), methylmalonyl-CoA mutase (MUT), propionyl-CoA carboxylase, isovaleryl CoA dehydrogenase, argininosuccinate lysase (ASL), CAPN3, ANO5, DYSF, SGCG, SGCA, SGCB, Calpain 3, Neutrophin-3, SCN1a, SCN8a, SCN1b, SCN2a, NPC1, NPC2, LMNA, SYNE1, SYNE2, FHL1, TTR, Factor XII, SERPINA1, AGL, microdystrophin, minidystrophin, AADC, alpha SARC, gamma SARC, beta SARC, FKRP, MTM1, SMN1, SMN2, or variants thereof.

Homology Arms

In some embodiments, viral vectors described herein comprise one or more flanking polynucleotide sequences with significant sequence homology to a target locus (e.g., homology arms). In some embodiments, homology arms flank a polynucleotide sequence encoding a payload (e.g., transgene). In some embodiments, homology arms flank a polynucleotide sequence encoding a transgene. In some embodiments, homology arms direct site-specific integration of a payload (e.g., transgene). In some embodiments, a payload may comprise homology arms and a transgene, wherein the homology arms direct site-specific integration of the transgene.

In some embodiments, homology arms are of the same length (also referred to herein as balanced homology arms or even homology arms). In some embodiments, viral vectors comprising homology arms of the same length, wherein the homology arms are at least a certain length, provide improved effects (e.g., improved rate of target integration). In some embodiments, homology arms are between 50 nt and 500 nt in length. In some embodiments, homology arms are between 50 nt and 100 nt in length. In some embodiments, homology arms are between 100 nt and 1000 nt in length. In some embodiments, homology arms are between 200 nt and 1000 nt in length. In some embodiments, homology arms are between 500 nt and 1500 nt in length. In some embodiments, homology arms are between 1000 nt and 2000 nt in length. In some embodiments, homology arms are greater than 2000 nt in length. In some embodiments, each homology arm is at least 750 nt in length. In some embodiments, each homology arm is at least 1000 nt in length. In some embodiments, each homology arm is at least 1250 nt in length. In some embodiments, homology arms are less than 1000 nt in length.

In some embodiments, homology arms are of different lengths (also referred to herein as unbalanced homology arms or uneven homology arms). In some embodiments, viral vectors comprising unbalanced homology arms of different lengths provide improved effects (e.g., increased rate of target site integration) as compared to a reference sequence. In some embodiments, viral vectors comprising homology arms of different lengths, wherein each homology arm is at least a certain length, provide improved effects (e.g., increased rate of target site integration) as compared to a reference sequence (e.g., a viral vector comprising homology arms of the same length or a viral vector comprising one or more homology arms less than 1000 nt in length).

In some embodiments, each homology arm is greater than 50 nt in length. In some embodiments, each homology arm is greater than 100 nt in length. In some embodiments, each homology arm is greater than 200 nt in length. In some embodiments, each homology arm is greater than 500 nt in length. In some embodiments, each homology arm is at least 750 nt length. In some embodiments, each homology arm is at least 1000 nt in length. In some embodiments, one homology arm is at least 750 nt in length and another homology arm is at least 1000 nt in length. In some embodiments, one homology arm is at least 750 nt in length and another homology arm is at least 1100 nt in length. In some embodiments, one homology arm is at least 750 nt in length and another homology arm is at least 1200 nt in length. In some embodiments, one homology arm is at least 750 nt in length and another homology arm is at least 1300 nt in length. In some embodiments, one homology arm is at least 750 nt in length and another homology arm is at least 1400 nt in length. In some embodiments, one homology arm is at least 750 nt in length and another homology arm is at least 1500 nt in length. In some embodiments, one homology arm is at least 750 nt in length and another homology arm is at least 1600 nt in length. In some embodiments, one homology arm is at least 750 nt in length and another homology arm is at least 1700 nt in length. In some embodiments, one homology arm is at least 750 nt in length and another homology arm is at least 1800 nt in length. In some embodiments, one homology arm is at least 750 nt in length and another homology arm is at least 1900 nt in length. In some embodiments, one homology arm is at least 750 nt in length and another homology arm is at least 2000 nt in length. In some embodiments, one homology arm is at least 1000 nt in length and another homology arm is at least 1100 nt in length. In some embodiments, one homology arm is at least 1000 nt in length and another homology arm is at least 1200 nt in length. In some embodiments, one homology arm is at least 1000 nt in length and another homology arm is at least 1300 nt in length. In some embodiments, one homology arm is at least 1000 nt in length and another homology arm is at least 1400 nt in length. In some embodiments, one homology arm is at least 1000 nt in length and another homology arm is at least 1500 nt in length. In some embodiments, one homology arm is at least 1000 nt in length and another homology arm is at least 1600 nt in length. In some embodiments, one homology arm is at least 1000 nt in length and another homology arm is at least 1700 nt in length. In some embodiments, one homology arm is at least 1000 nt in length and another homology arm is at least 1800 nt in length. In some embodiments, one homology arm is at least 1000 nt in length and another homology arm is at least 1900 nt in length. In some embodiments, one homology arm is at least 1000 nt in length and another homology arm is at least 2000 nt in length. In some embodiments, one homology arm is at least 1300 nt in length and another homology arm is at least 1400 nt in lengthIn some embodiments, a 5' homology arm is longer than a 3' homology arm. In some embodiments, a 3' homology arm is longer than a 5' homology arm.

In some embodiments, homology arms contain at least 70% homology to a target locus. In some embodiments, homology arms contain at least 80% homology to a target locus. In some embodiments, homology arms contain at least 90% homology to a target locus. In some embodiments, homology arms contain at least 95% homology to a target locus. In some embodiments, homology arms contain at least 99% homology to a target locus. In some embodiments, homology arms contain 100% homology to a target locus.

In some embodiments, viral vectors comprising homology arms provide an increased rate of target site integration as compared to a reference sequence (e.g., viral vectors lacking homology arms). In some embodiments, viral vectors comprising homology arms provide rates of target site integration of 0.01% or more (e.g., 0.05% or more, 0.1% or more, 0.2% or more, 0.3% or more, 0.4% or more, 0.5% or more, 0.6% or more, 0.7% or more, 0.8% or more, 0.9% or more, 1% or more, 1.5% or more, 2% or more, 5% or more, 10% or more, 20% or more, 30% or more). In some embodiments, viral vectors comprising homology arms provide increasing rates of target site integration over time. In some embodiments, rates of target site integration increase over time relative to an initial measurement of target site integration. In some embodiments, rates of target site integration over time are at least 1.5× higher than an initial measurement of target site integration (e.g., 1.5×, 2×, 3×, 4×, 5×, 10×, 20×, 30×, 40×, 50×, 60×, 70×, 80×, 90×, 100×, 200×). In some embodiments, rates of target site integration are measured after one or more days. In some embodiments, rates of target site integration are measured after one or more weeks. In some embodiments, rates of target site integration are measured after one or more months. In some embodiments, rates of target site integration are measured after one or more years. In some embodiments, rates of target site integration are measured through assessment of one or more biomarkers (e.g., biomarkers comprising a 2A peptide). In some embodiments, rates of target site integration are measured through assessment of one or more isolated nucleic acids (e.g., mRNA, gDNA). In some embodiments, rates of target site integration are measured through assessment of gene expression (e.g., through immunohistochemical staining).

TABLE 1

Exemplary methods for assessment of target site integration

| | | | |
|---|---|---|---|
| Genomic DNA integration rate (gDNA Int %) | Liver (frozen) | qPCR | Liver biopsy subjected to genomic DNA extraction. qPCR method run to detect percentage of allele (e.g. albumin) containing on-target insertion. |
| Fused mRNA | Liver (frozen) | ddPCR | Liver biopsy subjected to RNA extraction. ddPCR method run to quantify the copy number of fused mRNA (unique chimeric mRNA transcribed from edited allele). This assay measures the transcriptional activity after target insertion. |

TABLE 1-continued

| Exemplary methods for assessment of target site integration | | | |
|---|---|---|---|
| ALB-2A | Plasma | ELISA | Blood collected and processed for plasma. Proprietary ELISA used to measure 2A-tagged albumin (universal circulating biomarker for targeted integration) This assy measures total protein expression after target insertion. |
| Hepatocyte editing % | Fixed liver section | IHC | Fixed liver sectioned and stained against transgene. Transgene-positive cells counted and used to calculate percentage of hepatocyte editing. For targeted integration into the albumin locus, transgene expression should be hepatocyte-specific. This assay focuses on per-cell target integration and is orthogonal to gDNA Int %, which focuses on per allele target integration. |

In some embodiments, viral vectors comprising homology arms of different lengths may provide improved gene editing in a species or a model system for a species (e.g., mouse, human, or models thereof). In some embodiments, viral vectors may comprise different combinations of homology arm lengths when optimized for expression in a particular species or a model system for a particular species (e.g., mouse, human, or models thereof). In some embodiments, viral vectors comprising specific combinations of homology arm lengths may provide improved gene editing in one species or a model system of one species (e.g., human, humanized mouse model) as compared to a second species or a model system of a second species (e.g., mouse, pure mouse model). In some embodiments, viral vectors comprising specific combinations of homology arm lengths may be optimized for high levels of gene editing in one species or a model of one species (e.g., human, humanized mouse model) as compared to a second species or a model system of a second species (e.g., mouse, pure mouse model).

In some embodiments, homology arms direct integration of a transgene immediately behind a highly expressed endogenous gene. In some embodiments, homology arms direct integration of a transgene without disrupting endogenous gene expression (non-disruptive integration).

Methods of Treatment

Compositions and constructs disclosed herein may be used in any in vitro or in vivo application wherein expression of a payload (e.g. transgene) from a particular target locus in a cell while maintaining expression of endogenous genes at and surrounding the target locus. For example, compositions and constructs disclosed herein may be used to treat a disorder, disease, or medical condition in a subject (e.g., through gene therapy).

In some embodiments, treatment comprises obtaining or maintaining a desired pharmacologic and/or physiologic effect. In some embodiments, a desired pharmacologic and/or physiologic effect may comprise completely or partially preventing a disease (e.g., preventing symptoms of disease). In some embodiments, a desired pharmacologic and/or physiologic effect may comprise completely or partially curing a disease (e.g., curing adverse effects associated with a disease). In some embodiments, a desired pharmacologic and/or physiologic effect may comprise preventing recurrence of a disease. In some embodiments, a desired pharmacologic and/or physiologic effect may comprise slowing progression of a disease. In some embodiments, a desired pharmacologic and/or physiologic effect may comprise relieving symptoms of a disease. In some embodiments, a desired pharmacologic and/or physiologic effect may comprise preventing regression of a disease. In some embodiments, a desired pharmacologic and/or physiologic effect may comprise stabilizing and/or reducing symptoms associated with a disease.

In some embodiments, treatment comprises administering a composition before, during, or after onset of a disease (e.g., before, during, or after appearance of symptoms associated with a disease). In some embodiments, treatment comprises combination therapy (e.g., with one or more therapies, including different types of therapies).

Diseases of Interest

In some embodiments, compositions and constructs disclosed herein may be used to treat any disease of interest that includes a genetic deficiency or abnormality as a component of the disease.

By way of specific example, in some embodiments, compositions and constructs such as those disclosed herein may be used to treat branched-chain organic acidurias (e.g., Maple Syrup Urine Disease (MSUD), methylmalonic acidemia (MMA), propionic acidemia (PA), isovaleric acidemia (IVA)). In some embodiments, treatment comprises introduction of a polynucleotide sequence encoding one or more transgenes of interest (e.g., BCKDH complex (E1a, E1b, and E2 subunits), methylmalonyl-CoA mutase, propionyl-CoA carboxylase (alpha and beta subunits), isovaleryl CoA dehydrogenase, and/or variants thereof). In some embodiments, treatment comprises reduction of aberrant proteins (e.g., non-functional proteins) associated with branched chain organic acidurias. In some embodiments, treatment comprises reduction of signs and/or symptoms associated with branched chain organic acidurias (e.g., hypotonia, developmental delay, seizures, optic atrophy, acute encephalopathy, hyperventilation, respiratory distress, temperature instability, recurrent vomiting, ketoacidosis, pancreatitis, constipation, neutropenia, pancytopenia, secondary hemophagocytosis, cardiac arrhythmia, cardiomyopathy, chronic renal failure, dermatitis, hearing loss).

In some embodiments, compositions and constructs disclosed herein may be used to treat fatty acid oxidation disorders (e.g., trifunctional protein deficiency, Long-chain L-3 hydroxyacyl-CoA dehydrogenase (LCAD) deficiency, Medium-chain acyl-CoA dehydrogenase (MCHAD) deficiency, Very long-chain acyl-CoA dehydrogenase (VLCHAD) deficiency). In some embodiments, treatment comprises introduction of a polynucleotide sequence encoding one or more transgenes of interest (e.g., HADHA, HADHB, LCHAD, ACADM, ACADVL, and/or variants thereof). In some embodiments, treatment comprises reduction of aberrant proteins (e.g., non-functional proteins) associated with fatty acid oxidation disorders. In some embodiments, treatment comprises reduction of signs and/or symptoms associated with fatty acid oxidation disorders (e.g., enlarged liver, delayed mental and physical development, cardiac muscle weakness, cardiac arrhythmia, nerve damage, abnormal liver function, rhabdomyolysis, myoglobinuria, hypoglycemia, metabolic acidosis, respiratory distress, hepatomegaly, hypotonia, cardiomyopathy).

In some embodiments, compositions and constructs disclosed herein may be used to treat glycogen storage diseases (e.g., glycogen storage disease type 1 (GSD1), glycogen storage disease type 2 (Pompe disease, GSD2), glycogen storage disease type 3 (GSD3)). In some embodiments, treatment comprises introduction of a polynucleotide sequence encoding one or more transgenes of interest (e.g., G6PC (GSD1a), G6PT1 (GSD1b), SLC17A3, SLC37A4 (GSD1c), AGL, acid alpha-glucosidase, and/or variants thereof). In some embodiments, treatment comprises reduction of aberrant proteins (e.g., non-functional proteins) associated with glycogen storage diseases. In some embodiments, treatment comprises reduction of signs and/or symptoms associated with glycogen storage diseases (e.g., enlarged liver, hypoglycemia, muscle weakness, muscle cramps, fatigue, delayed development, obesity, bleeding disorders, abnormal liver function, abnormal kidney function, abnormal respiratory function, abnormal cardiac function, mouth sores, gout, cirrhosis, fibrosis, liver tumors).

In some embodiments, compositions and constructs disclosed herein may be used to treat carnitine cycle disorders. In some embodiments, treatment comprises introduction of a polynucleotide sequence encoding one or more transgenes of interest (e.g., OCTN2, CPT1, CACT, CPT2, and/or variants thereof). In some embodiments, treatment comprises reduction of aberrant proteins (e.g., non-functional proteins) associated with carnitine cycle disorders. In some embodiments, treatment comprises reduction of signs and/or symptoms associated with carnitine cycle disorders (e.g., hypoketotic hypoglycemia, cardiomyopathy, muscle weakness, fatigue, delayed motor development, edema).

In some embodiments, compositions and constructs disclosed herein may be used to treat urea cycle disorders. In some embodiments, treatment comprises introduction of a polynucleotide sequence encoding one or more transgenes of interest (e.g., CPS1, ARG1, ASL, OTC, and/or variants thereof). In some embodiments, treatment comprises reduction of aberrant proteins (e.g., non-functional proteins) associated with urea cycle disorders. In some embodiments, treatment comprises reduction of signs and/or symptoms associated with urea cycle disorders (e.g., vomiting, nausea, behavior abnormalities, fatigue, coma, psychosis, lethargy, cyclical vomiting, myopia, hyperammonemia, elevated ornithine levels).

In some embodiments, compositions and constructs disclosed herein may be used to treat homocystinuria (HCU). In some embodiments, treatment comprises introduction of a polynucleotide sequence encoding one or more transgenes of interest (e.g., cystathionine beta synthase (CBS), and/or variants thereof). In some embodiments, treatment comprises reduction of aberrant proteins (e.g., non-functional proteins) associated with HCU. In some embodiments, treatment comprises reduction of signs and/or symptoms associated with HCU (e.g., ectopia lentis, myopia, iridodenesis, cataracts, optic atrophy, glaucoma, retinal detachment, retinal damage, delayed developmental milestones, intellectual disability, depression, anxiety, obsessive-compulsive disorder, dolichostenomelia, genu valgum, pes cavus, scoliosis, pectus carinatum, pectus excavatum, osteoporosis, increased clot development, thromboembolism, pulmonary embolism, fragile skin, hypopigmentation, malar flushing, inguinal hernia, pancreatitis, kyphosis, spontaneous pneumothorax).

In some embodiments, compositions and constructs disclosed herein may be used to treat Crigler-Najjar syndrome. In some embodiments, treatment comprises introduction of a polynucleotide sequence encoding one or more transgenes of interest (e.g., UGT1A1, and/or variants thereof). In some embodiments, treatment comprises reduction of aberrant proteins (e.g., non-functional proteins) associated with Crigler-Najjar syndrome. In some embodiments, treatment comprises reduction of signs and/or symptoms associated with Crigler-Najjar syndrome (e.g., jaundice, kernicterus, lethargy, vomiting, fever, abnormal reflexes, muscle spasms, opisthotonus, spasticity, hypotonia, athetosis, elevated bilirubin levels, diarrhea, slurred speech, confusion, difficulty swallowing, seizures).

In some embodiments, compositions and constructs disclosed herein may be used to treat hereditary tyrosinemia. In some embodiments, treatment comprises introduction of a polynucleotide sequence encoding one or more transgenes of interest (e.g., fumarylacetoacetate hydrolase (FAH), and/or variants thereof). In some embodiments, treatment comprises reduction of aberrant proteins (e.g., non-functional proteins) associated with hereditary tyrosinemia. In some embodiments, treatment comprises reduction of signs and/or symptoms associated with hereditary tyrosinemia (e.g., hepatomegaly, jaundice, liver disease, cirrhosis, hepatocarcinoma, fever, diarrhea, melena, vomiting, splenomegaly, edema, coagulopathy, abnormal kidney function, rickets, weakness, hypertonia, ileus, tachycardia, hypertension, neurological crises, respiratory failure, cardiomyopathy).

In some embodiments, compositions and constructs disclosed herein may be used to treat epidermolysis bullosa. In some embodiments, treatment comprises introduction of a polynucleotide sequence encoding one or more transgenes of interest (e.g., COL7A1, COL17A1, MMP1, KRT5, LAMA3, LAMB3, LAMC2, ITGB4, and/or variants thereof). In some embodiments, treatment comprises reduction of aberrant proteins (e.g., non-functional proteins) associated with epidermolysis bullosa. In some embodiments, treatment comprises reduction of signs and/or symptoms associated with epidermolysis bullosa (e.g., fragile skin, abnormal nail growth, blisters, thickened skin, scarring alopecia, atrophic scarring, milia, dental problems, dysphagia, skin itching and pain).

In some embodiments, compositions and constructs disclosed herein may be used to treat alpha-1 antitrypsin deficiency (A1ATD). In some embodiments, treatment comprises introduction of a polynucleotide sequence encoding one or more transgenes of interest (e.g., alpha-1 antitrypsin (A1AT), and/or variants thereof). In some embodiments, treatment comprises reduction of aberrant proteins (e.g., non-functional proteins) associated with alpha-1 antitrypsin deficiency. In some embodiments, treatment comprises reduction of signs and/or symptoms associated with A1ATD (e.g., emphysema, chronic cough, phlegm production, wheezing, chronic respiratory infections, jaundice, enlarged liver, bleeding, abnormal fluid accumulation, elevated liver enzymes, liver dysfunction, portal hypertension, fatigue, edema, chronic active hepatitis, cirrhosis, hepatocarcinoma, panniculitis).

In some embodiments, compositions and constructs disclosed herein may be used to treat Wilson's disease. In some embodiments, treatment comprises introduction of a polynucleotide sequence encoding one or more transgenes of interest (e.g., ATP7B, and/or variants thereof). In some embodiments, treatment comprises reduction of aberrant proteins (e.g., non-functional proteins) associated with Wilson's disease. In some embodiments, treatment comprises reduction of signs and/or symptoms associated with Wilson's disease (e.g., fatigue, lack of appetite, abdominal pain, jaundice, Kayser-Fleischer rings, edema, speech problems, problems swallowing, loss of physical coordination, uncontrolled movements, muscle stiffness, liver disease, anemia, depression, schizophrenia, ammenorrhea, infertility, kidney stones, renal tubular damage, arthritis, osteoporosis, osteophytes)

In some embodiments, compositions and constructs disclosed herein may be used to treat hematologic diseases (e.g., hemophilia A, hemophilia B). In some embodiments, treatment comprises introduction of a polynucleotide sequence encoding one or more transgenes of interest (e.g., Factor IX (FIX), Factor VIII (FVIII), and/or variants thereof). In some embodiments, treatment comprises reduction of aberrant proteins (e.g., non-functional proteins) associated with hematologic diseases. In some embodiments, treatment comprises reduction of signs and/or symptoms associated with hematologic diseases (e.g., excessive bleeding, abnormal bruising, joint pain and swelling, bloody urine, bloody stool, abnormal nosebleeds, headache, lethargy, vomiting, double vision, weakness, convulsions, seizures).

In some embodiments, compositions and constructs disclosed herein may be used to treat hereditary angioedema. In some embodiments, treatment comprises introduction of a polynucleotide sequence encoding one or more transgenes of interest (e.g., C1 esterase inhibitor (C1-inh)). In some embodiments, treatment comprises reduction of aberrant proteins (e.g., non-functional proteins) associated with hereditary angioedema. In some embodiments, treatment comprises reduction of signs and/or symptoms associated with hereditary angioedema (e.g., edema, pruritus, urticaria, nausea, vomiting, acute abdominal pain, dysphagia, dysphonia, stridor).

In some embodiments, compositions and constructs disclosed herein may be used to treat Parkinson's disease. In some embodiments, treatment comprises introduction of a polynucleotide sequence encoding one or more transgenes of interest (e.g., dopamine decarboxylase (DDC)). In some embodiments, treatment comprises reduction of aberrant proteins (e.g., non-functional proteins) associated with Parkinson's disease. In some embodiments, treatment comprises reduction of signs and/or symptoms associated with Parkinson's disease (e.g., tremors, bradykinesia, muscle stiffness, impaired posture and balance, loss of automatic movements, speech changes, writing changes).

In some embodiments, compositions and constructs disclosed herein may be used to treat muscular diseases. In some embodiments, treatment comprises introduction of a polynucleotide sequence encoding one or more transgenes of interest (e.g., muscular dystrophies, Duchenne's muscular dystrophy (DMD), limb girdle muscular dystrophies). X-linked myotubular myopathy). In some embodiments, treatment comprises reduction of aberrant proteins (e.g., non-functional proteins) associated with muscular diseases. In some embodiments, treatment comprises reduction of signs and/or symptoms associated with muscular diseases (e.g., difficult movement, enlarged calf muscles, muscle pain and stiffness, delayed development, learning disabilities, unusual gait, scoliosis, breathing problems, difficulty swallowing, arrhythmia, cardiomyopathy, abnormal joint function, hypotonia, respiratory distress, absence of reflexes).

In some embodiments, compositions and constructs disclosed herein may be used to treat mucopolysaccharidosis (MPS) (e.g., MPS IH, MPS IH/S, MPS IS, MPS II, MPS IIIA, MPS IIIB, MPS IIIC, MPS IIID, MPS IVA, MPS IVB, MPS V, MPS VI, MPS VII, MPS IX). In some embodiments, treatment comprises introduction of a polynucleotide sequence encoding one or more transgenes of interest (e.g., IDUA, IDS, SGSH, NAGLU, HGSNAT, GNS, GALNS, GLB1, ARSB, GUSB, HYAL1). In some embodiments, treatment comprises reduction of aberrant proteins (e.g., non-functional proteins) associated with mucopolysaccharidosis. In some embodiments, treatment comprises reduction of signs and/or symptoms associated with MPS (e.g., heart abnormalities, breathing irregularities, enlarged liver, enlarged spleen, neurological abnormalities, developmental delays, recurring infections, persistent nasal discharge, noisy breathing, clouding of the cornea, enlarged tongue, spine deformities, joint stiffness, carpal tunnel, aortic regurgitation, progressive hearing loss, seizures, unsteady gait, accumulation of heparan sulfate, enzyme deficiencies, abnormal skeleton and musculature, heart disease, cysts, soft-tissue masses).

In some embodiments, compositions and constructs disclosed herein may be used to treat aromatic 1-amino acid decarboxylase (AADC) deficiency. In some embodiments, treatment comprises introduction of a polynucleotide sequence encoding one or more transgenes of interest (e.g., DDC, AADC). In some embodiments, treatment comprises reduction of aberrant proteins (e.g., non-functional proteins) associated with AADC deficiency. In some embodiments, treatment comprises reduction of signs and/or symptoms associated with AADC deficiency (e.g., hypotonia, oculogyric crises, hypokinesia, hypertonia, dystonia, athetosis, chorea, termors, excessive sweating, hypersalivation, ptosis, nasal congestion, temperature instability, hypotension, behavioral problems, insomnia, hypersomnia, hyporeflexia, hyperreflexia, gastrointestinal problems).

In some embodiments, compositions and constructs disclosed herein may be used to treat Duchenne Muscular Dystrophy (DMD). In some embodiments, treatment comprises introduction of a polynucleotide sequence encoding one or more transgenes of interest (e.g., dystrophin, microdystrophin, minidystrophin). In some embodiments, treatment comprises reduction of aberrant proteins (e.g., non-functional proteins) associated with DMD. In some embodiments, treatment comprises reduction of signs and/or symptoms associated with DMD (e.g., delayed motor development, pseudohypertrophy, muscle weakness, gait changes, Gower's maneuver, cardiomyopathy, breathing problems, scoliosis, contractures, cognitive impairment).

In some embodiments, compositions and constructs disclosed herein may be used to treat X-linked myotubular myopathy (XLMTM). In some embodiments, treatment comprises introduction of a polynucleotide sequence encoding one or more transgenes of interest (e.g., MTM1). In some embodiments, treatment comprises reduction of aberrant proteins (e.g., non-functional proteins) associated with XLMTM. In some embodiments, treatment comprises reduction of signs and/or symptoms associated with XLMTM (e.g., muscle weakness, hypotonia, repiratory distress, poor muscle development, midface hypoplasia, dolichocephaly, malocclusion, ophthalmoparesis, myopia, macrocephaly, areflexia, cryptorchidism, contractures, scoliosis, hip dysplasia, premature adrenarche, pyloric stenosis, gallstones, kidney stones, anima, spherocytosis, bleeding abnormalities, liver dysfunction).

In some embodiments, compositions and constructs disclosed herein may be used to treat one or more limb girdle muscular dystrophies (LGMDs). In some embodiments, treatment comprises introduction of a polynucleotide sequence encoding one or more transgenes of interest (e.g., sarcoglycan genes, alpha sarcoglycan (SGCA), beta sarcoglycan (SGCB), gamma sarcoglycan (SGCG), Dysferlin, Calpain 3, Anoctamin 5, Fukutin-related protein (FKRP), etc.). In some embodiments, treatment comprises reduction of aberrant proteins (e.g., non-functional proteins) associated with one or more LGMDs. In some embodiments, treatment comprises reduction of signs and/or symptoms associated with one or more LGMDs (e.g., muscle weakness, atrophy, scoliosis, lordosis, contractures, hypertrophy, cardiomyopathy, fagitue, heart block, arrhythmias, heart failure, dysphagia, dysarthria).

In some embodiments, compositions and constructs disclosed herein may be used to treat spinal muscular atrophy (SMA). In some embodiments, treatment comprises introduction of a polynucleotide sequence encoding one or more transgenes of interest (e.g., SMN1). In some embodiments, treatment comprises reduction of aberrant proteins (e.g., non-functional proteins) associated with SMA. In some embodiments, treatment comprises reduction of signs and/or symptoms associated with SMA (e.g., muscle weakness, atrophy, hypotonia, hyporeflexia, areflexia, fasciculations, congenital heart defects, dysphagia, tremor, scoliosis, heart issues).

In some embodiments, compositions and constructs disclosed herein may be used to treat Parkinson's Disease (PD). In some embodiments, treatment comprises introduction of a polynucleotide sequence encoding one or more transgenes of interest (e.g., PRKN, SNCA, PARK3, UCHL1, LRRK2, GIGYF2, HTRA2, EIF4G1, TMEM230, CHCHD2, RIC3, VPS35, etc.). In some embodiments, treatment comprises reduction of aberrant proteins (e.g., non-functional proteins) associated with Parkinson's Disease. In some embodiments, treatment comprises reduction of signs and/or symptoms associated with Parkinson's Disease (e.g., tremor, rigidity, bradykinesia, akinesia, postural instability, gait disturbances, posture disturbances, speech and swallowing disturbances, cognitive abnormalities).

In some embodiments, compositions and constructs disclosed herein may be used to treat a disease associated with a genetic deficiency. In some embodiments, treatment comprises introduction of a polynucleotide sequence encoding one or more transgenes of interest disclosed herein. In some embodiments, treatment comprises reduction of aberrant proteins (e.g., non-functional proteins) associated with a disease. In some embodiments, treatment comprises reduction of signs and/or symptoms associated with a disease.

Targeted Integration

In some embodiments, compositions and constructs provided herein direct integration of a payload (e.g., a transgene and/or functional nucleic acid) at a target locus (e.g., an endogenous gene). In some embodiments, compositions and constructs provided herein direct integration of a payload at a target locus in a specific cell type (e.g., tissue-specific loci). In some embodiments, integration of a payload occurs in a specific tissue (e.g., liver, central nervous system (CNS), muscle, kidney, vascular). In some embodiments, integration of a payload occurs in multiple tissues (e.g., liver, central nervous system (CNS), muscle, kidney, vascular).

In some embodiments, compositions and constructs provided herein direct integration of a payload at a target locus that is considered a safe-harbor site (e.g., albumin, Apolipoprotein A2 (ApoA2), haptaglobin). In some embodiments, a target locus may be selected from any genomic site appropriate for use with methods and compositions provided herein. In some embodiments, a target locus encodes a polypeptide. In some embodiments, a target locus encodes a polypeptide that is highly expressed in a subject (e.g., a subject not suffering from a disease, disorder, or condition, or a subject suffering from a disease, disorder, or condition). In some embodiments, integration of a payload occurs at a 5' or 3' end of one or more endogenous genes (e.g., genes encoding polypeptides). In some embodiments, integration of a payload occurs between a 5' or 3' end of one or more endogenous genes (e.g., genes encoding polypeptides).

In some embodiments, compositions and constructs provided herein direct integration of a payload at a target locus with minimal or no off-target integration (e.g., integration at a non-target locus). In some embodiments, compositions and constructs provided herein direct integration of a payload at a target locus with reduced off-target integration compared to a reference composition or construct (e.g., relative to a composition or construct without flanking homology sequences).

In some embodiments, integration of a transgene at a target locus allows expression of a payload without disrupting endogenous gene expression. In some embodiments, integration of a transgene at a target locus allows expression of a payload from an endogenous promoter. In some embodiments, integration of a transgene at a target locus disrupts endogenous gene expression. In some embodiments, integration of a transgene at a target locus disrupts endogenous gene expression without adversely affecting a target cell and/or subject (e.g., by targeting a safe-harbor site). In some embodiments, integration of a transgene at a target locus does not require use of a nuclease (e.g., Cas proteins, endonucleases, TALENs, ZFNs). In some embodiments, integration of a transgene at a target locus is assisted by use of a nuclease (e.g., Cas proteins, endonucleases, TALENs, ZFNs).

In some embodiments, integration of a transgene at a target locus confers a selective advantage (e.g., increased survival rate in a plurality of cells relative to other cells in a tissue). In some embodiments, a selective advantage may produce an increased percentage of cells in one or more tissues expressing a transgene.

Compositions

In some embodiments, compositions can be produced using methods and constructs provided herein (e.g., viral vectors). In some embodiments, compositions include liquid, solid, and gaseous compositions. In some embodiments, compositions comprise additional ingredients (e.g., diluents, stabilizer, excipients, adjuvants). In some embodiments, additional ingredients can comprise buffers (e.g., phosphate, citrate, organic acid buffers), antioxidants (e.g., ascorbic acid), low molecular weight polypeptides (e.g., less than 10 residues), various proteins (e.g., serum albumin, gelatin, immunoglobulins), hydrophilic polymers (e.g., polyvinylpyrrolidone), amino acids (e.g., glycine, glutamine, asparagine, arginine, lysine), carbohydrates (e.g., monosaccharides, disaccharides, glucose, mannose, dextrins), chelating agents (e.g., EDTA), sugar alcohols (e.g., mannitol, sorbitol), salt-forming counterions (e.g., sodium, potassium), and/or nonionic surfactants (e.g. Tween™, Pluronics™, polyethylene glycol (PEG)), among other things. In some embodiments, an aqueous carrier is an aqueous pH buffered solution.

In some embodiments, compositions provided herein may be provided in a range of dosages. In some embodiments, compositions provided herein may be provided in a single dose. In some embodiments, compositions provided herein may be provided in multiple dosages. In some embodiments, compositions are provided over a period of time. In some embodiments, compositions are provided at specific intervals (e.g., varying intervals, set intervals). In some embodiments, dosages may vary depending upon dosage form and route of administration. In some embodiments, compositions provided herein may be provided in dosages between Tell and 1e14 vg/kg. In some embodiments, compositions provided herein may be provided in dosages between 1e12 and 1e13 vg/kg. In some embodiments, compositions provided herein may be provided in dosages between 1e12 and 1e14 vg/kg. In some embodiments, compositions provided herein may be provided in dosages between 1e14 and 1e15 vg/kg. In some embodiments, compositions provided herein may be provided in dosages of no more than 1e14 vg/kg. In some embodiments, compositions provided herein may be provided in dosages of no more than 1e15 vg/kg.

Routes of Administration

In some embodiments, compositions provided herein may be administered to a subject via any one (or more) of a variety of routes known in the art (e.g., parenteral, subcutaneous, intravenous, intracranial, intraspinal, intraocular, intramuscular, intravaginal, intraperitoneal, epicutaneous, intradermal, rectal, pulmonary, intraosseous, oral, buccal, intraportal, intra-arterial, intratracheal, or nasal). In some embodiments, compositions provided herein may be introduced into cells, which are then introduced into a subject (e.g., liver, muscle, central nervous system (CNS), hematologic cells). In some embodiments, compositions provided herein may be introduced via delivery methods known in the art (e.g., injection, catheter).

Methods of Producing Viral Vectors

Production of Viral Vectors

Prior to the present disclosure, production of viral vectors typically involves the use of three separate expression constructs (e.g., plasmids), one comprising a viral rep gene or gene variant (e.g., AAV rep gene) and a viral cap gene or gene variant (e.g., AAV cap gene), one comprising one or more viral helper genes or gene variants (e.g., adenovirus helper genes), and one comprising a payload (e.g., transgene with flanking ITRs). As used herein, upstream production processes refer to steps involved in generation of viral vectors and downstream production processes refer to steps involved in subsequent processing of viral vectors once generated (i.e., once the desired payload and other components have been integrated into the vector). Among other things, the present disclosure recognizes limitation in previous three-plasmid systems for production or viral vectors. In some embodiments, constructs and methods described in the present disclosure are designed to overcome limitations in previous three-plasmid systems for production of viral vectors through use of the two plasmid systems described herein.

In some embodiments, production of viral vectors (e.g., AAV viral vectors) may include both upstream steps to generate viral vectors (e.g. cell-based culturing) and downstream steps to process viral vectors (e.g., purification, formulation, etc.). In some embodiments, upstream steps may comprise one or more of cell expansion, cell culture, cell transfection, cell lysis, viral vector production, and/or viral vector harvest.

In some embodiments, downstream steps may comprise one or more of separation, filtration, concentration, clarification, purification, chromatography (e.g., affinity, ion exchange, hydrophobic, mixed-mode), centrifugation (e.g., ultracentrifugation), and/or formulation.

In some embodiments, constructs and methods described herein are designed to increase viral vector yields (e.g., AAV vector yields), reduce levels of replication-competent viral vectors (e.g., replication competent AAV (rcAAV)), improve viral vectors packaging efficiency (e.g., AAV vector capsid packaging), and/or any combinations thereof, relative to a reference construct or method, for example those in Xiao et al. 1998 and Grieger et al. 2015, each of which is incorporated herein by reference in its entirety.

Cell Lines and Transfection Reagents

In some embodiments, production of viral vectors comprises use of cells (e.g., cell culture). In some embodiments, production of viral vectors comprises use cell culture of one or more cell lines (e.g., mammalian cell lines). In some embodiments, production of viral vectors comprises use of HEK293 cell lines or variants thereof (e.g., HEK293T, HEK293F cell lines). In some embodiments, cells are capable of being grown in suspension. In some embodiments, cells are comprised of adherent cells. In some embodiments, cells are capable of being grown in media that does not comprise animal components (e.g. animal serum). In some embodiments, cells are capable of being grown in serum-free media (e.g., F17 media, Expi293 media). In some embodiments, production of viral vectors comprises transfection of cells with expression constructs (e.g., plasmids). In some embodiments, cells are selected for high expression of viral vectors (e.g. AAV vectors). In some embodiments, cells are selected for high packaging efficiency of viral vectors (e.g., capsid packaging of AAV vectors). In some embodiments, cells are selected for improved transfection efficiency (e.g., with chemical transfection reagents, including cationic molecules). In some embodiments, cells are engineered for high expression of viral vectors (e.g. AAV vectors). In some embodiments, cells are engineered for high packaging efficiency of viral vectors (e.g., capsid packaging of AAV vectors). In some embodiments, cells are engineered for improved transfection efficiency (e.g., with chemical transfection reagents, including cationic molecules). In some embodiments, cells may be engineered or selected for two or more of the above attributes. In some embodiments, cells are contacted with one or more expression constructs (e.g. plasmids). In some embodiments, cells are contacted with one or more transfection reagents (e.g., chemical transfection reagents, including lipids, polymers, and cationic molecules) and one or more expression constructs. In some embodiments, cells are contacted with one or more cationic molecules (e.g., cationic lipid, PEI reagent) and one or more expression constructs. In some embodiments, cells are contacted with a PEIMAX reagent and one or more expression constructs. In some embodiments, cells are contacted with a FectoVir-AAV reagent and one or more expression constructs. In some embodiments, cells are contacted with one or more transfection reagents and one or more expression constructs at particular ratios. In some embodiments, ratios of transfection reagents to expression constructs improves production of viral vectors (e.g., improved vector yield, improved packaging efficiency, and/or improved transfection efficiency).

Expression Constructs

In some embodiments, expression constructs are or comprise one or more polynucleotide sequences (e.g., plasmids). In some embodiments, expression constructs comprise particular polynucleotide sequence elements (e.g., payloads, promoters, viral genes, etc.). In some embodiments, expression constructs comprise polynucleotide sequences encoding viral genes (e.g., a rep or cap gene or gene variant, one or more helper virus genes or gene variants). In some embodiments, expression constructs of a particular type comprise specific combinations of polynucleotide sequence elements. In some embodiments, expression constructs of a particular type do not comprise specific combinations of polynucleotide sequence elements. In some embodiments, a particular expression construct does not comprise polynucleotide sequence elements encoding both rep and cap genes and/or gene variants.

In some embodiments, expression constructs comprise polynucleotide sequences encoding wild-type viral genes (e.g., wild-type rep genes, cap genes, viral helper genes, or combinations thereof). In some embodiments, expression constructs comprise polynucleotide sequences encoding viral helper genes or gene variants (e.g., herpesvirus genes or gene variants, adenovirus genes or gene variants). In some embodiments, expression constructs comprise polynucleotide sequences encoding one or more gene copies that express one or more wild-type Rep proteins (e.g., 1 copy, 2 copies, 3 copies, 4 copies, 5 copies, etc.). In some embodiments, expression constructs comprise polynucleotide sequences encoding a single gene copy that expresses one or more wild-type Rep proteins (e.g., Rep68, Rep40, Rep52, Rep78, or combinations thereof). In some embodiments, expression constructs comprise polynucleotide sequences encoding one or more wild-type Rep proteins (e.g., Rep68, Rep40, Rep52, Rep78, or combinations thereof). In some embodiments, expression constructs comprise polynucleotide sequences encoding at least four wild-type Rep proteins (e.g., Rep68, Rep40, Rep52, Rep78). In some embodiments, expression constructs comprise polynucleotide sequences encoding each of Rep68, Rep40, Rep52, and Rep78. In some embodiments, expression constructs comprise polynucleotide sequences encoding one or more wild-type adenoviral helper proteins (e.g., E2 and E4).

In some embodiments, expression constructs comprise wild-type polynucleotide sequences encoding wild-type viral genes (e.g., rep genes, cap genes, helper genes). In some embodiments, expression constructs comprise modified polynucleotide sequences (e.g., codon-optimized) encoding wild-type viral genes (e.g., rep genes, cap genes, helper genes). In some embodiments, expression constructs comprise modified polynucleotide sequences encoding modified viral genes (e.g., rep genes, cap genes, helper genes). In some embodiments, modified viral genes are designed and/or engineered for certain improvements (e.g., improved transduction, tissue specificity, reduced size, reduced immune response, improved packaging, reduced rcAAV levels, etc.).

In accordance with various embodiments, expression constructs disclosed herein may offer increased flexibility and modularity as compared to previous technologies. In some embodiments, expression constructs disclosed herein may allow swapping of various polynucleotide sequences (e.g., different rep genes, cap genes, payloads, helper genes, promoters, etc.) while providing certain improvements (e.g., increased viral vector yield, increased packaging, reduced rcAAV levels, etc.). In some embodiments, expression constructs disclosed herein are compatible with various upstream production processes (e.g., different cell culture conditions, different transfection reagents, etc.) while providing certain improvements (e.g., increased viral vector yield, increased packaging, reduced rcAAV levels, etc.)

In some embodiments, expression constructs of different types comprise different combinations of polynucleotide sequences. In some embodiments, an expression construct of one type comprises one or more polynucleotide sequence elements (e.g., payloads, promoters, viral genes, etc.) that is not present in an expression construct of a different type. In some embodiments, an expression construct of one type comprises polynucleotide sequence elements encoding a viral gene (e.g., a rep or cap gene or gene variant) and polynucleotide sequence elements encoding a payload (e.g., a transgene and/or functional nucleic acid). In some embodiments, an expression construct of one type comprises polynucleotide sequence elements encoding one or more viral genes (e.g., a rep or cap gene or gene variant and/or one or more helper virus genes). In some embodiments, an expression construct of one type comprises polynucleotide sequence elements encoding one or more viral genes, wherein the viral genes are from one or more virus types (e.g., genes or gene variants from AAV and adenovirus). In some embodiments, viral genes from adenovirus are genes and/or gene variants. In some embodiments, viral genes from adenovirus are one or more of E2A (e.g., E2A DNA Binding Protein (DBP), E4 (e.g., E4 Open Reading Frame (ORF) 2, ORF3, ORF4, ORF6/7), VA, and/or variants thereof. In some embodiments, expression constructs are used for production of viral vectors (e.g. through cell culture). In some embodiments, expression constructs are contacted with cells in combination with one or more transfection reagents (e.g., chemical transfection reagents). In some embodiments, expression constructs are contacted with cells at particular ratios in combination with one or more transfection reagents. In some embodiments, expression constructs of different types are contacted with cells at particular ratios (e.g., weight ratios) in combination with one or more transfection reagents. In some embodiments, expression constructs of different types are contacted with cells at about a 10:1, 9:1, 8:1, 7:1, 6:1, 5:1, 4:1, 3:1, 2:1, 1.5:1, 1:1, 1:1.5, 1:2, 1:3, 1:4, 1:5, 1:6, 1:7, 1:8, 1:9, or 1:10 ratio (e.g., weight ratio). In some embodiments, a first expression construct comprising one or more viral helper genes and a second expression construct comprising one or more payloads are contacted with cells at about a 10:1, 9:1, 8:1, 7:1, 6:1, 5:1, 4:1, 3:1, 2:1, 1.5:1, 1:1, 1:1.5, 1:2, 1:3, 1:4, 1:5, 1:6, 1:7, 1:8, 1:9, or 1:10 ratio (e.g., weight ratio) of the first expression construct to the second expression construct. In some embodiments, a first expression construct comprising one or more payloads and a second expression construct comprising one or more viral helper genes are contacted with cells at about a 10:1, 9:1, 8:1, 7:1, 6:1, 5:1, 4:1, 3:1, 2:1, 1.5:1, 1:1, 1:1.5, 1:2, 1:3, 1:4, 1:5, 1:6, 1:7, 1:8, 1:9, or 1:10 ratio (e.g., weight ratio) of the first expression construct to the second expression construct. In some embodiments, particular ratios of expression constructs improve production of AAV (e.g., increased viral vector yields, increased packaging efficiency, and/or increased transfection efficiency. In some embodiments, cells are contacted with two or more expression constructs (e.g., sequentially or substantially simultaneously). In some embodiments, three or more expression constructs are contacted with cells. In some embodiments, expression constructs comprise one or more promoters (e.g., one or more exogenous promoters). In some embodiments, promoters are or comprise CMV, RSV, CAG, EF1alpha, PGK, A1AT, C5-12, MCK, desmin, p5, p40, or combinations thereof. In some embodiments, expression constructs comprise one or more promoters upstream of a particular polynucleotide sequence element (e.g., a rep or cap gene or gene variant). In some embodiments, expression constructs comprise one or more promoters downstream of a particular polynucleotide sequence element (e.g., a rep or cap gene or gene variant).

In some embodiments, a first expression construct comprising one or more viral helper genes and a second expression construct comprising one or more payloads are contacted with cells at a ratio greater than or equal to 1:1 up to 3:1, wherein viral titer yields are at at least 1.5× greater than those obtained through administration of a reference system (e.g., a three-plasmid comprising separate plasmids, each encoding one of: 1) an AAV rep and AAV cap sequence, 2) relevant sequence from a helper virus, and 3) a payload). In some embodiments, a first expression construct comprising one or more viral helper genes and a second expression construct comprising one or more payloads are contacted with cells at a ratio greater than or equal to 1:1 up to 5:1, wherein viral titer yields are at at least 1.5× greater than those obtained through administration of a reference system (e.g., a three-plasmid comprising separate plasmids, each encoding one of: 1) an AAV rep and AAV cap sequence, 2) relevant sequence from a helper virus, and 3) a payload). In some embodiments, a first expression construct comprising one or more viral helper genes and a second expression construct comprising one or more payloads are contacted with cells at a ratio greater than or equal to 1:1 up to 6:1, wherein viral titer yields are at at least 1.5× greater than those obtained through administration of a reference system (e.g., a three-plasmid comprising separate plasmids, each encoding one of: 1) an AAV rep and AAV cap sequence, 2) relevant sequence from a helper virus, and 3) a payload). In some embodiments, a first expression construct comprising one or more viral helper genes and a second expression construct comprising one or more payloads are contacted with cells at a ratio greater than or equal to 1:1 up to 8:1, wherein viral titer yields are at at least 1.5× greater than those obtained through administration of a reference system (e.g., a three-plasmid comprising separate plasmids, each encoding one of: 1) an AAV rep and AAV cap sequence, 2) relevant sequence from a helper virus, and 3) a payload). In some embodiments, a first expression construct comprising one or more viral helper genes and a second expression construct comprising one or more payloads are contacted with cells at a ratio greater than or equal to 1:1 up to 10:1, wherein viral titer yields are at at least 1.5× greater than those obtained through administration of a reference system (e.g., a three-plasmid comprising separate plasmids, each encoding one of: 1) an AAV rep and AAV cap sequence, 2) relevant sequence from a helper virus, and 3) a payload).

In some embodiments, a first expression construct comprising one or more viral helper genes and a second expression construct comprising one or more payloads are contacted with cells at a ratio between 10:1 and 1:1. In some embodiments, a first expression construct comprising one or more viral helper genes and a second expression construct comprising one or more payloads are contacted with cells at a ratio between 9:1 and 1:1. In some embodiments, a first expression construct comprising one or more viral helper genes and a second expression construct comprising one or more payloads are contacted with cells at a ratio between 8:1 and 1:1. In some embodiments, a first expression construct comprising one or more viral helper genes and a second expression construct comprising one or more payloads are contacted with cells at a ratio between 7:1 and 1:1. In some embodiments, a first expression construct comprising one or more viral helper genes and a second expression construct comprising one or more payloads are contacted with cells at a ratio between 6:1 and 1:1. In some embodiments, a first expression construct comprising one or more viral helper genes and a second expression construct comprising one or more payloads are contacted with cells at a ratio between 5:1 and 1:1. In some embodiments, a first expression construct comprising one or more viral helper genes and a second expression construct comprising one or more payloads are contacted with cells at a ratio between 4:1 and 1:1. In some embodiments, a first expression construct comprising one or more viral helper genes and a second expression construct comprising one or more payloads are contacted with cells at a ratio between 3:1 and 1:1. In some embodiments, a first expression construct comprising one or more viral helper genes and a second expression construct comprising one or more payloads are contacted with cells at a ratio between 2:1 and 1:1.

In some embodiments, a first expression construct comprising one or more viral helper genes and a second expression construct comprising one or more payloads are contacted with cells at a ratio between 1:1 and 2:1. In some embodiments, a first expression construct comprising one or more viral helper genes and a second expression construct comprising one or more payloads are contacted with cells at a ratio between 1:1 and 3:1. In some embodiments, a first expression construct comprising one or more viral helper genes and a second expression construct comprising one or more payloads are contacted with cells at a ratio between 1:1 and 4:1. In some embodiments, a first expression construct comprising one or more viral helper genes and a second expression construct comprising one or more payloads are contacted with cells at a ratio between 1:1 and 5:1. In some embodiments, a first expression construct comprising one or more viral helper genes and a second expression construct comprising one or more payloads are contacted with cells at a ratio between 1:1 and 6:1. In some embodiments, a first expression construct comprising one or more viral helper genes and a second expression construct comprising one or more payloads are contacted with cells at a ratio between 1:1 and 7:1. In some embodiments, a first expression construct comprising one or more viral helper genes and a second expression construct comprising one or more payloads are contacted with cells at a ratio between 1:1 and 8:1. In some embodiments, a first expression construct comprising one or more viral helper genes and a second expression construct comprising one or more payloads are contacted with cells at a ratio between 1:1 and 9:1. In some embodiments, a first expression construct comprising one or more viral helper genes and a second expression construct comprising one or more payloads are contacted with cells at a ratio between 1:1 and 10:1. In some embodiments, a first expression construct comprising one or more viral helper genes and a second expression construct comprising one or more payloads are contacted with cells at a ratio of 1.5:1.

In some embodiments, expression constructs comprise one or more polynucleotide sequences encoding elements (e.g., selection markers, origins of replication) necessary for cell culture (e.g., bacterial cell culture, mammalian cell culture). In some embodiments, expression constructs comprise one or more polynucleotide sequences encoding antibiotic resistance genes (e.g., kanamycin resistance genes, ampicillin resistance genes). In some embodiments, expression constructs comprise one or more polynucleotide sequences encoding a bacterial original of replication (e.g., colE1 origin of replication).

In some embodiments, expression constructs comprise one or more transcription termination sequences (e.g., a polyA sequence). In some embodiments, expression constructs comprise one or more of BGH polyA, FIX polyA, SV40 polyA, synthetic polyA, or combinations thereof. In some embodiments, expression constructs comprise one or more transcription termination sequences downstream of a particular sequence element (e.g., a rep or cap gene or gene variant). In some embodiments, expression constructs comprise one or more transcription termination sequences upstream of a particular sequence element (e.g., a rep or cap gene or gene variant).

In some embodiments, expression constructs comprise one or more intron sequences. In some embodiments, expression constructs comprise one or more of introns of different origins (e.g., known genes), including but not limited to FIX intron, Albumin intron, or combinations thereof. In some embodiments, expression constructs comprise one or more introns of different lengths (e.g., 133 bp to 4 kb). In some embodiments, expression constructs comprise one or more intron sequences upstream of a particular sequence element (e.g., a rep or cap gene or gene variant). In some embodiments, expression constructs comprise one or more intron sequences within a particular sequence element (e.g., a rep or cap gene or gene variant). In some embodiments, expression constructs comprise one or more intron sequences downstream of particular sequence element (e.g., a rep or cap gene or gene variant). In some embodiments, expression constructs comprise one or more intron sequences after a promoter (e.g., a p5 promoter). In some embodiments, expression constructs comprise one or more intron sequences before a rep gene or gene variant. In some embodiments, expression constructs comprise one or more intron sequences between a promoter and a rep gene or gene variant. In some embodiments, compositions provided herein comprise expression constructs. In some embodiments, compositions comprise: (i) a first expression construct comprising a polynucleotide sequence encoding one or more rep genes and a polynucleotide sequence encoding one or more wild-type adenoviral helper proteins; and (ii) a second expression construct comprising a polynucleotide sequence encoding one or more cap genes and one or more payloads.

In some embodiments, compositions comprise a first expression construct that comprises a sequence that has at least 70%, at least 75%, at least 80%, at least 85%, at least 90%, at least 95%, at least 99%, or 100% sequence identity with a sequence in Table 1C below or a variant thereof. In some embodiments, compositions comprise a first expression construct that comprises a sequence that has at least 70%, at least 75%, at least 80%, at least 85%, at least 90%, at least 95%, at least 99%, or 100% sequence identity with a portion of a sequence in Table 1C below or a variant thereof. In some embodiments, compositions comprise a first expression construct that consists of a sequence in Table 1C below. In some embodiments, compositions comprise a first expression construct that consists of a sequence in Table 1C below. In some embodiments, compositions comprise a first expression construct that consists of a portion of a sequence in Table 1C below.

TABLE 1C

Exemplary expression construct sequences comprising one or more helper genes and a rep gene.

| Description | Sequence | SEQ ID NO |
|---|---|---|
| Rep/Helper Plasmid | TCTTCCGCTTCCTCGCTCACTGACTCGCTGCGCTCGGTCGTTCGGCTGCGGCGAGCGGTATCAGCTCACTCAAAGGCG<br>GTAATACGGTTATCCACAGAATCAGGGGATAACGCAGGAAAGAACATGTGAGCAAAAGGCCAGCAAAAGGCCAGGA<br>ACCGTAAAAAGGCCGCGTTGCTGGCGTTTTTCCATAGGCTCCGCCCCCCTGACGAGCATCACAAAAATCGACGCTCAA<br>GTCAGAGGTGGCGAAACCCGACAGGACTATAAAGATACCAGGCGTTTCCCCCTGGAAGCTCCCTCGTGCGCTCTCCTG<br>TTCCGACCCTGCCGCTTACCGGATACCTGTCCGCCTTTCTCCCTTCGGGAAGCGTGGCGCTTTCTCATAGCTCACGCTG<br>TAGGTATCTCAGTTCGGTGTAGGTCGTTCGCTCCAAGCTGGGCTGTGTGCACGAACCCCCCGTTCAGCCCGACCGCTG<br>CGCCTTATCCGGTAACTATCGTCTTGAGTCCAACCCGGTAAGACACGACTTATCGCCACTGGCAGCAGCCACTGGTAA<br>CAGGATTAGCAGAGCGAGGTATGTAGGCGGTGCTACAGAGTTCTTGAAGTGGTGGCCTAACTACGGCTACACTAGAA<br>GAACAGTATTTGGTATCTGCGCTCTGCTGAAGCCAGTTACCTTCGGAAAAAGAGTTGGTAGCTCTTGATCCGGCAAAC<br>AAACCACCGCTGGTAGCGGTGGTTTTTTTGTTTGCAAGCAGCAGATTACGCGCAGAAAAAAAGGATCTCAAGAAGAT<br>CCTTTGATCTTTTCTACGGGGTCTGACGCTCAGTGGAACGAAAACTCACGTTAAGGGATTTTGGTCATGAGATTATCA<br>AAAAGGATCTTCACCTAGATCCTTTTAAATTAAAAATGAAGTTTTAAATCAATCTAAAGTATATATGAGTAAACTTGG<br>TCTGACAGTTATTAGAAAAACTCATCGAGCATCAAATGAAACTGCAATTTATTCATATCAGGATTATCAATACCATAT<br>TTTTGAAAAAGCCGTTTCTGTAATGAAGGAGAAAACTCACCGAGGCAGTTCCATAGGATGGCAAGATCCTGGTATCG<br>GTCTGCGATTCCGACTCGTCCAACATCAATACAACCTATTAATTTCCCCTCGTCAAAAATAAGGTTATCAAGTGAGAA<br>ATCACCATGAGTGACGACTGAATCCGGTGAGAATGGCAAAAGTTTATGCATTTCTTTCCAGACTTGTTCAACAGGCCA<br>GCCATTACGCTCGTCATCAAAATCACTCGCATCAACCAAACCGTTATTCATTCGTGATTGCGCCTGAGCGAGACGAAA<br>TACGCGATCGCTGTTAAAAGGACAATTACAAACAGGAATCGAATGCAACCGGCGCAGGAACACTGCCAGCGCATCAA<br>CAATATTTTCACCTGAATCAGGATATTCTTCTAATACCTGGAATGCTGTTTTTCCGGGGATCGCAGTGGTGAGTAACCA<br>TGCATCATCAGGAGTACGGATAAAATGCTTGATGGTCGGAAGAGGCATAAATTCCGTCAGCCAGTTTAGTCTGACCAT<br>CTCATCTGTAACATCATTGGCAACGCTACCTTTGCCATGTTTCAGAAACAACTCTGGCGCATCGGGCTTCCCATACAA<br>GCGATAGATTGTCGCACCTGATTGCCCGACATTATCGCGAGCCCATTTATACCCATATAAATCAGCATCCATGTTGGA<br>ATTTAATCGCGGCCTCGACGTTTCCCGTTGAATATGGCTCATACTCTTCCTTTTTCAATATTATTGAAGCATTTATCAGG<br>GTTATTGTCTCATGAGCGGATACATATTTGAATGTATTTAGAAAAATAAACAAATAGGGGTTCCGCGCACATTTCCCC<br>GAAAAGTGCCACCTGACGTCTAAGAAACCATTATTATCATGACATTAACCTATAAAAATAGGCGTATCACGAGGCCCT<br>TTCGTCTCGCGCGTTTCGGTGATGACGGTGAAAACCTCTGACACATGCAGCTCCCGGAGACGGTCACAGCTTGTCTGT<br>AAGCGGATGCCGGGAGCAGACAAGCCCGTCAGGGCGCGTCAGCGGGTGTTGGCGGGTGTCGGGGCTGGCTTAACTAT<br>GCGGCATCAGAGCAGATTGTACTGAGAGTGCACCATAAAATTGTAAACGTTACGTCATAGGGTTAGGGAGGTCCTGT<br>ATTAGAGGTCACGTGAGTGTTTTGCGACATTTTGCGACACCATGTGGTCACGCTGGGTATTTAAGCCCGAGTGAGCAC<br>GCAGGGTCTCCATTTTGAAGCGGGAGGTTTGAACGCGCAGCCGCCATGCCGGGGTTTTACGAGATTGTGATTAAGGTC<br>CCCAGCGACCTTGACGAGCATCTGCCCGGCATTTCTGACAGCTTTGTGAACTGGGTGGCCGAGAAGGAATGGGAGTT<br>GCCGCCAGATTCTGACATGGATCTGAATCTGATTGAGCAGGCACCCCTGACCGTGGCCGAGAAGCTGCAGCGCGACT<br>TTCTGACGGAATGGCGCCGTGTGAGTAAGGCCCCGGAGGCCCTTTTCTTTGTGCAATTTGAGAAGGGAGAGAGCTACT<br>TCCACATGCACGTGCTCGTGGAAACCACCGGGGTGAAATCCATGGTTTTGGGACGTTTCCTGAGTCAGATTCGCGAAA<br>AACTGATTCAGAGAATTTACCGCGGGATCGAGCCGACTTTGCCAAACTGGTTCGCGGTCACAAAGACCAGAAATGGC<br>GCCGGAGGCGGGAACAAGGTGGTGGATGAGTGCTACATCCCCAATTACTTGCTCCCCAAAACCCAGCCTGAGCTCCA<br>GTGGGCGTGGACTAATATGGAACAGTATTTAAGCGCCTGTTTGAATCTCACGGAGCGTAAACGGTTGGTGGCGCAGC<br>ATCTGACGCACGTGTCGCAGACGCAGGAGCAGAACAAAGAGAATCAGAATCCCAATTCTGATGCGCCGGTGATCAGA<br>TCAAAAACTTCAGCCAGGTACATGGAGCTGGTCGGGTGGCTCGTGGACAAGGGGATTACCTCGGAGAAGCAGTGGAT<br>CCAGGAGGACCAGGCCTCATACATCTCCTTCAATGCGGCCTCCAACTCGCGGTCCCAAATCAAGGCTGCCTTGGACAA<br>TGCGGGAAAGATTATGAGCCTGACTAAAACCGCCCCCGACTACCTGGTGGGCCAGCAGCCCGTGGAGGACATTTCCA | 1 |

TABLE 1C-continued

Exemplary expression construct sequences comprising one or more helper genes and a rep gene.

| Description | Sequence | SEQ ID NO |
|---|---|---|
| | GCAATCGGATTTATAAAATTTTGGAACTAAACGGGTACGATCCCCAATATGCGGCTTCCGTCTTTCTGGGATGGGCCA | |
| | CGAAAAAGTTCGGCAAGAGGAACACCATCTGGCTGTTTGGGCCTGCAACTACCGGGAAGACCAACATCGCGGAGGCC | |
| | ATAGCCCACACTGTGCCCTTCTACGGGTGCGTAAACTGGACCAATGAGAACTTTCCCTTCAACGACTGTGTCGACAAG | |
| | ATGGTGATCTGGTGGGAGGAGGGGAAGATGACCGCCAAGGTCGTGGAGTCGGCCAAAGCCATTCTCGGAGGAAGCA | |
| | AGGTGCGCGTGGACCAGAAATGCAAGTCCTCGGCCCAGATAGACCCGACTCCCGTGATCGTCACCTCCAACACCAAC | |
| | ATGTGCGCCGTGATTGACGGGAACTCAACGACCTTCGAACACCAGCAGCCGTTGCAAGACCGGATGTTCAAATTTGA | |
| | ACTCACCCGCCGTCTGGATCATGACTTTGGGAAGGTCACCAAGCAGGAAGTCAAAGACTTTTTCCGGTGGGCAAAGG | |
| | ATCACGTGGTTGAGGTGGAGCATGAATTCTACGTCAAAAAGGGTGGAGCCAAGAAAAGACCCGCCCCCAGTGACGCA | |
| | GATATAAGTGAGCCCAAACGGGTGCGCGAGTCAGTTGCGCAGCCATCGACGTCAGACGCGGAAGCTTCGATCAACTA | |
| | CGCAGACAGGTACCAAAACAAATGTTCTCGTCACGTGGGCATGAATCTGATGCTGTTTCCCTGCAGACAATGCGAGA | |
| | GAATGAATCAGAATTCAAATATCTGCTTCACTCACGGACAGAAAGACTGTTTAGAGTGCTTTCCCGTGTCAGAATCTC | |
| | AACCCGTTTCTGTCGTCAAAAAGGCGTATCAGAAACTGTGCTACATTCATCATATCATGGGAAAGGTGCCAGACGCTT | |
| | GCACTGCCTGCGATCTGGTCAATGTGGATTTGGATGACTGCATCTTTGAACAATAAATGATTTAAATCAGGTATGGCT | |
| | GCCGATGGTTATCTTCCAGATTGGCTCGAGGACACTCTCTCTGATCGACGTTTAAACCATATGAACGTTAATATTTTGT | |
| | TAAAATTCGCGTTAAATTTTTGTTAAATCAGCTCATTTTTTAACCAATAGGCCGAAATCGGCAAAATCCCTTATAAATC | |
| | AAAAGAATAGCCCGAGATAGGGTTGAGTGTTGTTCCAGTTTGGAACAAGAGTCCACTATTAAAGAACGTGGACTCCA | |
| | ACGTCAAAGGGCGAAAAACCGTCTATCAGGGCGATGGCCCACTACGTGAACCATCACCCAAATCAAGTTTTTTGGGG | |
| | TCGAGGTGCCGTAAAGCACTAAATCGGAACCCTAAAGGGAGCCCCCGATTTAGAGCTTGACGGGGAAAGCCGGCGAA | |
| | CGTGGCGAGAAAGGAAGGGAAGAAAGCGAAAGGAGCGGGCGCTAGGGCGCTGGCAAGTGTAGCGGTCACGCTGCGC | |
| | GTAACCACCACACCCGCCGCGCTTAATGCGCCGCTACAGGGCGCGTACTATGGTTGCTTTGACGTATGCGGTGTGAAA | |
| | TACCGCACAGATGCGTAAGGAGAAAATACCGCATCAGGCGCCATTCGCCATTCAGGCTGCGCAACTGTTGGGAAGGG | |
| | CGATCGGTGCGGGCCTCTTCGCTATTACGCCAGCTGGCGAAAGGGGGATGTGCTGCAAGGCGATTAAGTTGGGTAAC | |
| | GCCAGGGTTTTCCCAGTCACGACGTTGTAAAACGACGGCCAGTGCCAAGCTTAAGGTGCACGGCCCACGTGGCCACT | |
| | AGTACTTCTCGACAGAAGCACCATGTCCTTGGGTCCGGCCTGCTGAATGCGCAGGCGGTCGGCCATGCCCCAGGCTTC | |
| | GTTTTGACATCGGCGCAGGTCTTTGTAGTAGTCTTGCATGAGCCTTTCTACCGGCACTTCTTCTTCTCCTTCCTCTTGTC | |
| | CTGCATCTCTTGCATCTATCGCTGCGGCGGCGGCGGAGTTTGGCCGTAGGTGGCGCCCTCTTCCTCCCATGCGTGTGAC | |
| | CCCGAAGCCCCTCATCGGCTGAAGCAGGGCTAGGTCGGCGACAACGCGCTCGGCTAATATGGCCTGCTGCACCTGCG | |
| | TGAGGGTAGACTGGAAGTCATCCATGTCCACAAAGCGGTGGTATGCGCCCGTGTTGATGGTGTAAGTGCAGTTGGCC | |
| | ATAACGGACCAGTTAACGGTCTGGTGACCCGGCTGCGAGAGCTCGGTGTACCTGAGACGCGAGTAAGCCCTCGAGTC | |
| | AAATACGTAGTCGTTGCAAGTCCGCACCAGGTACTGGTATCCCACCAAAAAGTGCGGCGGCGGCTGGCGGTAGAGGG | |
| | GCCAGCGTAGGGTGGCCGGGGCTCCGGGGGCGAGATCTTCCAACATAAGGCGATGATATCCGTAGATGTACCTGGAC | |
| | ATCCAGGTGATGCCGGCGGCGGTGGTGGAGGCGCGCGGAAAGTCGCGGACGCGGTTCCAGATGTTGCGCAGCGGCAA | |
| | AAAGTGCTCCATGGTCGGGACGCTCTGGCCGGTCAGGCGCGCGCAATCGTTGACGCTCTACCGTGCAAAAGGAGAGC | |
| | CTGTAAGCGGGCACTCTTCCGTGGTCTGGTGGATAAATTCGCAAGGGTATCATGGCGGACGACCGGGGTTCGAGCCCC | |
| | GTATCCGGCCGTCCGCCGTGATCCATGCGGTTACCGCCCGCGTGTCGAACCCAGGTGTGCGACGTCAGACAACGGGG | |
| | GAGTGCTCCTTTTGGCTTCCTTCCAGGCGCGGCGGCTGCTGCGCTAGCTTTTTTGGCCACTGGCCGCGCGCAGCGTAAG | |
| | CGGTTAGGCTGGAAAGCGAAAGCATTAAGTGGCTCGCTCCCTGTAGCCGGAGGGTTATTTTCCAAGGGTTGAGTCGCG | |
| | GGACCCCCGGTTCGAGTCTCGGACCGGCCGGACTGCGGCGAACGGGGGTTTGCCTCCCCGTCATGCAAGACCCCGCTT | |
| | GCAAATTCCTCCGGAAACAGGGACGAGCCCCTTTTTTGCTTTTCCCAGATGCATCCGGTGCTGCGGCAGATGCGCCCC | |
| | CCTCCTCAGCAGCGGCAAGAGCAAGAGCAGCGGCAGACATGCAGGGCACCCTCCCCTCCTCCTACCGCGTCAGGAGG | |
| | GGCGACATCCGCGGTTGACGCGGCAGCAGATGGTGATTACGAACCCCCGCGGCGCCGGGCCCGGCACTACCTGGACT | |
| | TGGAGGAGGGCGAGGGCCTGGCGCGGCTAGGAGCGCCCTCTCCTGAGCGGTACCCAAGGGTGCAGCTGAAGCGTGAT | |
| | ACGCGTGAGGCGTACGTGCCGCGGCAGAACCTGTTTCGCGACCGCGAGGGAGAGGAGCCCGAGGAGATGCGGGATC | |
| | GAAAGTTCCACGCAGGGCGCGAGCTGCGGCATGGCCTGAATCGCGAGCGGTTGCTGCGCGAGGAGGACTTTGAGCCC | |
| | GACGCGCGAACCGGGATTAGTCCCGCGCGCGCACACGTGGCGGCCGCCGACCTGGTAACCGCATACGAGCAGACGGT | |
| | GAACCAGGAGATTAACTTTCAAAAAAGCTTTAACAACCACGTGCGTACGCTTGTGGCGCGCGAGGAGGTGGCTATAG | |
| | GACTGATGCATCTGTGGGACTTTGTAAGCGCGCTGGAGCAAAACCCAAATAGCAAGCCGCTCATGGCGCAGCTGTTC | |
| | CTTATAGTGCAGCACAGCAGGGACAACGAGGCATTCAGGGATGCGCTGCTAAACATAGTAGAGCCCGAGGGCCGCTG | |
| | GCTGCTCGATTTGATAAACATCCTGCAGAGCATAGTGGTGCAGGAGCGCAGCTTGAGCCTGGCTGACAAGGTGGCCG | |
| | CCATCAACTATTCCATGCTTAGCCTGGGCAAGTTTTACGCCCGCAAGATATACCATACCCCTTACGTTCCCATAGACA | |
| | AGGAGGTAAAGATCGAGGGGTTCTACATGCGCATGGCGCTGAAGGTGCTTACCTTGAGCGACGACCTGGGCGTTTAT | |
| | CGCAACGAGCGCATCCACAAGGCCGTGAGCGTGAGCCGGCGGCGCGAGCTCAGCGACCGCGAGCTGATGCACAGCCT | |
| | GCAAAGGGCCCTGGCTGGCACGGGCAGCGGCGATAGAGAGGCCGAGTCCTACTTTGACGCGGGCGCTGACCTGCGCT | |
| | GGGCCCCAAGCCGACGCGCCCTGGAGGCAGCTGGGGCCGGACCTGGGCTGGCGGTGGCACCCGCGCGCGCTGGCAAC | |
| | GTCGGCGGCGTGGAGGAATATGACGAGGACGATGAGTACGAGCCAGAGGACGGCGAGTACTAAGCGGTGATGTTTCT | |
| | GATCAGATGATGCAAGACGCAACGGACCCGGCGGTGCGGGCGGCGCTGCAGAGCCAGCCGTCCGGCCTTAACTCCAC | |
| | GGACGACTGGCGCCAGGTCATGGACCGCATCATGTCGCTGACTGCGCGCAATCCTGACGCGTTCCGGCAGCAGCCGC | |
| | AGGCCAACCGGCTCTCCGCAATTCTGGAAGCGGTGGTCCCGGCGCGCGCAAACCCCACGCACGAGAAGGTGCTGGCG | |
| | ATCGTAAACGCGCTGGCCGAAAACAGGGCCATCCGGCCCGACGAGGCCGGCCTGGTCTACGACGCGCTGCTTCAGCG | |
| | CGTGGCTCGTTACAACAGCGGCAACGTGCAGACCAACCTGGACCGGCTGGTGGGGGATGTGCGCGAGGCCGTGGCGC | |
| | AGCGTGAGCGCGCGCAGCAGCAGGGCAACCTGGGCTCCATGGTTGCACTAAACGCCTTCCTGAGTACACAGCCCGCC | |
| | AACGTGCCGCGGGGACAGGAGGACTACACCAACTTTGTGAGCGCACTGCGGCTAATGGTGACTGAGACACCGCAAAG | |
| | TGAGGTGTACCAGTCTGGGCCAGACTATTTTTTCCAGACCAGTAGACAAGGCCTGCAGACCGTAAACCTGAGCCAGG | |
| | CTTTCAAAAACTTGCAGGGGCTGTGGGGGGTGCGGGCTCCCACAGGCGACCGCGCGACCGTGTCTAGCTTGCTGACG | |
| | CCCAACTCGCGCCTGTTGCTGCTGCTAATAGCGCCCTTCACGGACAGTGGCAGCGTGTCCCGGGACACATACCTAGGT | |
| | CACTTGCTGACACTGTACCGCGAGGCCATAGGTCAGGCGCATGTGGACGAGCATACTTTCCAGGAGATTACAAGTGTC | |
| | AGCCGCGCGCTGGGGCAGGAGGACACGGGCAGCCTGGAGGCAACCCTAAACTACCTGCTGACCAACCGGCGGCAGA | |
| | AGATCCCCTCGTTGCACAGTTTCGCACCCTTTGGCGCATCCCATTCTCCAGTAACTTTATGTCCATGGGCGCACTCACA | |
| | GACCTGGGCCAAAACCTTCTCTACGCCAACTCCGCCCACGCGCTAGACATGACTTTTGAGGTGGATCCCATGGACGAG | |
| | CCCACCCTTCTTTATGTTTGTTTGAAGTCTTTGACGTGGTCCGTGTGCACCGGCCGCACCGCGGCGTCATCGAAACCG | |
| | TGTACCTGCGCACGCCCTTCTCGGCCGGCAACGCCACAACATAAAGAAGCAAGCAACATCAACAACAGCTGCCGCCA | |
| | TGGGCTCCAGTGAGCAGGAACTGAAAGCCATTGTCAAAGATCTTGGTTGTGGGCCATATTTTTTGGGCACCTATGACA | |
| | AGCGCTTTCCAGGCTTTGTTTCTCCACACAAGCTCGCCTGCGCCATAGTCAATACGGCCGGTCGCGAGACTGGGGGCG | |
| | TACACTGGATGGCCTTTGCCTGGAACCCGCACTCAAAAACATGCTACCTCTTTGAGCCCTTTGGCTTTTCTGACCAGCG | |

TABLE 1C-continued

Exemplary expression construct sequences comprising one or more helper genes and a rep gene.

| Description | Sequence | SEQ ID NO |
|---|---|---|
| | ACTCAAGCAGGTTTACCAGTTTGAGTACGAGTCACTCCTGCGCCGTAGCGCCATTGCTTCTTCCCCCGACCGCTGTATA<br>ACGCTGGAAAAGTCCACCCAAAGCGTACAGGGGCCCAACTCGGCCGCCTGTGGACTATTCTGCTGCATGTTTCTCCAC<br>GCCTTTGCCAACTGGCCCCAAACTCCCATGGATCACAACCCCACCATGAACCTTATTACCGGGGTACCCAACTCCATG<br>CTCAACAGTCCCCAGGTACAGCCCACCCTGCGTCGCAACCAGGAACAGCTCTACAGCTTCCTGGAGCGCCACTCGCCC<br>TACTTCCGCAGCCACAGTGCGCAGATTAGGAGCGCCACTTCTTTTTGTCACTTGAAAAACATGTAAAAATAATGTACT<br>AGAGACACTTTCAATAAAGGCAAATGCTTTTATTTGTACACTCTCGGGTGATTATTTACCCCCACCCTTGCCGTCTGCG<br>CCGTTTAAAAATCAAAGGGGTTCTGCCGCGCATCGCTATGCGCCACTGGCAGGGACACGTTGCGATACTGGTGTTTAG<br>TGCTCCACTTAAACTCAGGCACAACCATCCGCGGCAGCTCGGTGAAGTTTTCACTCCACAGGCTGCGCACCATCACCA<br>ACGCGTTTAGCAGGTCGGGCGCCGATATCTTGAAGTCGCAGTTGGGGCCTCCGCCCTGCGCGCGCGAGTTGCGATACA<br>CAGGGTTGCAGCACTGGAACACTATCAGCGCCGGGTGGTGCACGCTGGCCAGCACGCTCTTGTCGGAGATCAGATCC<br>GCGTCCAGGTCCTCCGCGTTGCTCAGGGCGAACGGAGTCAACTTTGGTAGCTGCCTTCCCAAAAAGGGCGCGTGCCCA<br>GGCTTTGAGTTGCACTCGCACCGTAGTGGCATCAAAAGGTGACCGTGCCCGGTCTGGGCGTTAGGATACAGCGCCTGC<br>ATAAAAGCCTTGATCTGCTTAAAAGCCACCTGAGCCTTTGCGCCTTCAGAGAAGAACATGCCGCAAGACTTGCCGGA<br>AAACTGATTGGCCGGACAGGCCGCGTCGTGCACGCAGCACCTTGCGTCGGTGTTGGAGATCTGCACCACATTTCGGCC<br>CCACCGGTTCTTCACGATCTTGGCCTTGCTAGACTGCTCCTTCAGCGCGCGCTGCCCGTTTTCGCTCGTCACATCCATTT<br>CAATCACGTGCTCCTTATTTATCATAATGCTTCCGTGTAGACACTTAAGCTCGCCTTCGATCTCAGCGCAGCGGTGCAG<br>CCACAACGCGCAGCCCGTGGGCTCGTGATGCTTGTAGGTCACCTCTGCAAACGACTGCAGGTACGCCTGCAGGAATC<br>GCCCCATCATCGTCACAAAGGTCTTGTTGCTGGTGAAGGTCAGCTGCAACCCGCGGTGCTCCTCGTTCAGCCAGGTCT<br>TGCATACGGCCGCCAGAGCTTCCACTTGGTCAGGCAGTAGTTTGAAGTTCGCCTTTAGATCGTTATCCACGTGGTACTT<br>GTCCATCAGCGCGCGCGCAGCCTCCATGCCCTTCTCCCACGCAGACACGATCGGCACACTCAGCGGGTTCATCACCGT<br>AATTTCACTTTCCGCTTCGCTGGGCTCTTCCTCTTCCTCTTGCGTCCGCATACCACGCGCCACTGGGTCGTCTTCATTCA<br>GCCGCCGCACTGTGCGCTTACCTCCTTTGCCATGCTTGATTAGCACCGGTGGGTTGCTGAAACCCACCATTTGTAGCGC<br>CACATCTTCTCTTTCTTCCTCGCTGTCCACGATTACCTCTGGTGATGGCGGGCGCTCGGGCTTGGGAGAAGGGCGCTTC<br>TTTTTCTTCTTGGGCGCAATGGCCAAATCCGCCGCCGAGGTCGATGGCCGCGGGCTGGGTGTGCGCGGCACCAGCGCG<br>TCTTGTGATGAGTCTTCCTCGTCCTCGGACTCGATACGCCGCCTCATCCGCTTTTTTGGGGGCGCCCGGGGAGGCGGCG<br>GCGACGGGGACGGGGACGACACGTCCTCCATGGTTGGGGGACGTCGCGCCGCACCGCGTCCGCGCTCGGGGGTGGTT<br>TCGCGCTGCTCCTCTTCCCGACTGGCCATTTCCTTCTCCTATAGGCAGAAAAAGATCATGGAGTCAGTCGAGAAGAAG<br>GACAGCCTAACCGCCCCCTCTGAGTTCGCCACCACCGCCTCCACCGATGCCGCCAACGCGCCTACCACCTTCCCCGTC<br>GAGGCACCCCCGCTTGAGGAGGAGGAAGTGATTATCGAGCAGGACCCAGGTTTTGTAAGCGAAGACGACGAGGACC<br>GCTCAGTACCAACAGAGGATAAAAAGCAAGACCAGGACAACGCAGAGGCAAACGAGGAACAAGTCGGGCGGGGGG<br>ACGAAAGGCATGGCGACTACCTAGATGTGGGAGACGACGTGCTGTTGAAGCATCTGCAGCGCCAGTGCGCCATTATC<br>TGCGACGCGTTGCAAGAGCGCAGCGATGTGCCCCTCGCCATAGCGGATGTCAGCCTTGCCTACGAACGCCACCTATTC<br>TCACCGCGCGTACCCCCCAAACGCCAAGAAAACGGCACATGCGAGCCCAACCCGCGCCTCAACTTCTACCCCGTATTT<br>GCCGTGCCAGAGGTGCTTGCCACCTATCACATCTTTTTCCAAAACTGCAAGATACCCCTATCCTGCCGTGCCAACCGC<br>AGCCGAGCGGACAAGCAGCTGGCCTTGCGGCAGGGCGCTGTCATACCTGATATCGCCTCGCTCAACGAAGTGCCAAA<br>AATCTTTGAGGGTCTTGGACGCGACGAGAAGCGCGCGGCAAACGCTCTGCAACAGGAAAACAGCGAAAATGAAAGT<br>CACTCTGGAGTGTTGGTGGAACTCGAGGGTGACAACGCGCGCCTAGCCGTACTAAAACGCAGCATCGAGGTCACCCA<br>CTTTGCCTACCCGGCACTTAACCTACCCCCCAAGGTCATGAGCACAGTCATGAGTGAGCTGATCGTGCGCCGTGCGCA<br>GCCCCTGGAGAGGGATGCAAATTTGCAAGAACAAACAGAGGAGGGCCTACCCGCAGTTGGCGACGAGCAGCTAGCG<br>CGCTGGCTTCAAACGCGCGAGCCTGCCGACTTGGAGGAGCGACGCAAACTAATGATGGCCGCAGTGCTCGTTACCGT<br>GGAGCTTGAGTGCATGCAGCGGTTCTTTGCTGACCCGGAGATGCAGCGCAAGCTAGAGGAAACATTGCACTACACCT<br>TTCGACAGGGCTACGTACGCCAGGCCTGCAAGATCTCCAACGTGGAGCTCTGCAACCTGGTCTCCTACCTTGGAATTT<br>TGCACGAAAACCGCCTTGGGCAAAACGTGCTTCATTCCACGCTCAAGGGCGAGGCGCGCCGCGACTACGTCCGCGAC<br>TGCGTTTACTTATTTCTATGCTACACCTGGCAGACGGCCATGGGCGTTTGGCAGCAGTGCTTGGAGGAGTGCAACCTC<br>AAGGAGCTGCAGAAACTGCTAAAGCAAAACTTGAAGGACCTATGGACGGCCTTCAACGAGCGCTCCGTGGCCGCGCA<br>CCTGGCGGACATCATTTTCCCCGAACGCCTGCTTAAAACCCTGCAACAGGGTCTGCCAGACTTCACCAGTCAAAGCAT<br>GTTGCAGAACTTTAGGAACTTTATCCTAGAGCGCTCAGGAATCTTGCCCGCCACCTGCTGTGCACTTCCTAGCGACTTT<br>GTGCCCATTAAGTACCGCGAATGCCCTCCGCCGCTTTGGGGCCACTGCTACCTTCTGCAGCTAGCCAACTACCTTGCCT<br>ACCACTCTGACATAATGGAAGACGTGAGCGGTGACGGTCTACTGGAGTGTCACTGTCGCTGCAACCTATGCACCCCGC<br>ACCGCTCCCTGGTTTGCAATTCGCAGCTGCTTAACGAAAGTCAAATTATCGGTACCTTTGAGCTGCAGGGTCCCTCGC<br>CTGACGAAAAGTCCGCGGCTCCGGGGTTGAAACTCACTCCGGGGCTGTGGACGTCGGCTTACCTTCGCAAATTTGTAC<br>CTGAGGACTACCACGCCCACGAGATTAGGTTCTACGAAGACCAATCCCGCCCGCCATATGCGGAGCTTACCGCCTGCG<br>TCATTACCCAGGGCCACATTCTTGGCCAATTGCAAGCCATCAACAAAGCCCGCCAAGAGTTTCTGCTACGAAAGGGAC<br>GGGGGGTTTACTTGGACCCCCAGTCCGGCGAGGAGCTCAACCCAATCCCCCCGCCGCCGCAGCCCTATCAGCAGCAG<br>CCGCGGGCCCTTGCTTCCCAGGATGGCACCCAAAAAGAAGCTGCAGCTGCCGCCGCCACCCACGGACGAGGAGGAAT<br>ACTGGGACAGTCAGGCAGAGGAGGTTTTGGACGAGGAGGAGGAGGACATGATGGAAGACTGGGAGAGCCTAGACGA<br>GGAAGCTTCCGAGGTCGAAGAGGTGTCAGACGAAACACCGTCACCCTCGGTCGCATTCCCCTCGCCGGCGCCCCAGA<br>AATCGGCAACCGGTTCCAGCATGGCTACAACCTCCGCTCCTCAGGCGCCGCCGGCACTGCCCGTTCGCCGACCCAACC<br>GTAGATGGGACACCACTGGAACCAGGGCCGGTAAGTCCAAGCAGCCGCCGCCGTTAGCCCAAGAGCAACAACAGCG<br>CCAAGGCTACCGCTCATGGCGCGGGCACAAGAACGCCATAGTTGCTTGCTTGCAAGACTGTGGGGGCAACATCTCCTT<br>CGCCCGCCGCTTTCTTCTCTACCATCACGGCGTGGCCTTCCCCCGTAACATCCTGCATTACTACCGTCATCTCTACAGC<br>CCATACTGCACCGGCGGCAGCGGCAGCAACAGCAGCGGCCACACAGAAGCAAAGGCGACCGGATAGCAAGACTCTG<br>ACAAAGCCCAAGAAATCCACAGCGGCGGCAGCAGCAGGAGGAGGAGCGCTGCGTCTGGCGCCCAACGAACCCGTAT<br>CGACCCGCGAGCTTAGAAACAGGATTTTTCCCACTCTGTATGCTATATTTCAACAGAGCAGGGGCCAAGAACAAGAG<br>CTGAAAATAAAAAACAGGTCTCTGCGATCCCTCACCCGCAGCTGCCTGTATCACAAAAGCGAAGATCAGCTTCGGCG<br>CACGCTGGAAGACGCGGAGGCTCTCTTCAGTAAATACTGCGCGCTGACTCTTAAGGACTAGTTTCGCGCCCTTTCTCA<br>AATTTAAGCGCGAAAACTACGTCATCTCCAGCGGCCACACCCGGCGCCAGCACCTGTTGTCAGCGCCATTATGAGCAA<br>GGAAATTCCCACGCCCTACATGTGGAGTTACCAGCCACAAATGGGACTTGCGGCTGGAGCTGCCCAAGACTACTCAA<br>CCCGAATAAACTACATGAGCGCGGACCCCACATGATATCCCGGGTCAACGGAATACGCGCCCACCGAAACCGAATT<br>CTCTCGGAACAGGCGGCTATTACCACCACACCTCGTAATAACCTTAATCCCCGTAGTTGGCCCGCTGCCCTGGTGTAC<br>CAGGAAAGTCCCGCTCCCACCACTGTGGTACTTCCCAGAGACGCCCAGGCCGAAGTTCAGATGACTAACTCAGGGGC<br>GCAGCTTGCGGGCGGCTTTCGTCACAGGGTGCGGTCGCCCGGGCAGGGTATAACTCACCTGACAATCAGAGGGCGAG<br>GTATTCAGCTCAACGACGAGTCGGTGAGCTCCTCGCTTGGTCTCCGTCCGGACGGACATTTCAGATCGGCGGCGCCG<br>GCCGCTCTTCATTCACGCCTCGTCAGGCAATCCTAACTCTGCAGACCTCGTCCTCTGAGCCGCGCTCTGGAGGCATTGG | |

TABLE 1C-continued

Exemplary expression construct sequences comprising one or more helper genes and a rep gene.

| Description | Sequence | SEQ ID NO |
|---|---|---|
| | AACTCTGCAATTTATTGAGGAGTTTGTGCCATCGGTCTACTTTAACCCCTTCTCGGGACCTCCCGGCCACTATCCGGAT | |
| | CAATTTATTCCTAACTTTGACGCGGTAAAGGACTCGGCGGACGGCTACGACTGAATGTTAAGTGGAGAGGCAGAGCA | |
| | ACTGCGCCTGAAACACCTGGTCCACTGTCGCCGCCACAAGTGCTTTGCCCGCGACTCCGGTGAGTTTTGCTACTTTGA | |
| | ATTGCCCGAGGATCATATCGAGGGCCCGGCGCACGGCGTCCGGCTTACCGCCCAGGGAGAGCTTGCCCGTAGCCTGA | |
| | TTCGGGAGTTTACCCAGCGCCCCCTGCTAGTTGAGCGGGACAGGGGACCCTGTGTTCTCACTGTGATTTGCAACTGTC | |
| | CTAACCCTGGATTACATCAAGATCCTCTAGTTAATTAACTAGAGTACCCGGGGATCTTATTCCCTTTAACTAATAAAA | |
| | AAAAATAATAAAGCATCACTTACTTAAAATCAGTTAGCAAATTTCTGTCCAGTTTATTCAGCAGCACCTCCTTGCCCTC | |
| | CTCCCAGCTCTGGTATTGCAGCTTCCTCCTGGCTGCAAACTTTCTCCACAATCTAAATGGAATGTCAGTTTCCTCCTGT | |
| | TCCTGTCCATCCGCACCCACTATCTTCATGTTGTTGCAGATGAAGCGCGCAAGACCGTCTGAAGATACCTTCAACCCC | |
| | GTGTATCCATATGACACGGAAACCGGTCCTCCAACTGTGCCTTTTCTTACTCCTCCCTTTGTATCCCCCAATGGGTTTC | |
| | AAGAGAGTCCCCCTGGGGTACTCTCTTTGCGCCTATCCGAACCTCTAGTTACCTCCAATGGCATGCTTGCGCTCAAAAT | |
| | GGGCAACGGCCTCTCTCTGGACGAGGCCGGCAACCTTACCTCCCAAAATGTAACCACTGTGAGCCCACCTCTCAAAAA | |
| | AACCAAGTCAAACATAAACCTGGAAATATCTGCACCCCTCACAGTTACCTCAGAAGCCCTAACTGTGGCTGCCGCCGC | |
| | ACCTCTAATGGTCGCGGGCAACACACTCACCATGCAATCACAGGCCCCGCTAACCGTGCACGACTCCAAACTTAGCAT | |
| | TGCCACCCAAGGACCCCTCACAGTGTCAGAAGGAAAGCTAGCCCTGCAAACATCAGGCCCCCTCACCACCACCGATA | |
| | GCAGTACCCTTACTATCACTGCCTCACCCCCTCTAACTACTGCCACTGGTAGCTTGGGCATTGACTTGAAAGAGCCCAT | |
| | TTATACACAAAATGGAAAACTAGGACTAAAGTACGGGGCTCCTTTGCATGTAACAGACGACCTAAACACTTTGACCG | |
| | TAGCAACTGGTCCAGGTGTGACTATTAATAATACTTCCTTGCAAACTAAAGTTACTGGAGCCTTGGGTTTTGATTCACA | |
| | AGGCAATATGCAACTTAATGTAGCAGGAGGACTAAGGATTGATTCTCAAAACAGACGCCTTATACTTGATGTTAGTTA | |
| | TCCGTTTGATGCTCAAAACCAACTAAATCTAAGACTAGGACAGGGCCCTCTTTTTATAAACTCAGCCCACAACTTGGA | |
| | TATTAACTACAACAAAGGCCTTTACTTGTTTACAGCTTCAAACAATTCCAAAAAGCTTGAGGTTAACCTAAGCACTGC | |
| | CAAGGGGTTGATGTTTGACGCTACAGCCATAGCCATTAATGCAGGAGATGGGCTTGAATTTGGTTCACCTAATGCACC | |
| | AAACACAAATCCCCTCAAAACAAAAATTGGCCATGGCCTAGAATTTGATTCAAACAAGGCTATGGTTCCTAAACTAG | |
| | GAACTGGCCTTAGTTTTGACAGCACAGGTGCCATTACAGTAGGAAACAAAAATAATGATAAGCTAACTTTGTGGACC | |
| | ACACCAGCTCCATCTCCTAACTGTAGACTAAATGCAGAGAAAGATGCTAAACTCACTTTGGTCTTAACAAAATGTGGC | |
| | AGTCAAATACTTGCTACAGTTTCAGTTTTGGCTGTTAAAGGCAGTTTGGCTCCAATATCTGGAACAGTTCAAAGTGCTC | |
| | ATCTTATTATAAGATTTGACGAAAATGGAGTGCTACTAAACAATTCCTTCCTGGACCCAGAATATTGGAACTTTAGAA | |
| | ATGGAGATCTTACTGAAGGCACAGCCTATACAAACGCTGTTGGATTTATGCCTAACCTATCAGCTTATCCAAAATCTC | |
| | ACGGTAAAACTGCCAAAAGTAACATTGTCAGTCAAGTTTACTTAAACGGAGACAAAACTAAACCTGTAACACTAACC | |
| | ATTACACTAAACGGTACACAGGAAACAGGAGACACAACTCCAAGTGCATACTCTATGTCATTTTCATGGGACTGGTCT | |
| | GGCCACAACTACATTAATGAAATATTTGCCACATCCTCTTACACTTTTTCATACATTGCCCAAGAATAAAGAATCGTTT | |
| | GTGTTATGTTTCAACGTGTTTATTTTTCAATTGCAGAAAATTTCAAGTCATTTTTCATTCAGTAGTATAGCCCCACCACC | |
| | ACATAGCTTATACAGATCACCGTACCTTAATCAAACTCACAGAACCCTAGTATTCAACCTGCCACCTCCCTCCCAACA | |
| | CACAGAGTACACAGTCCTTTCTCCCCGGCTGGCCTTAAAAAGCATCATATCATGGGTAACAGACATATTCTTAGGTGT | |
| | TATATTCCACACGGTTTCCTGTCGAGCCAAACGCTCATCAGTGATATTAATAAACTCCCCGGGCAGCTCACTTAAGTTC | |
| | ATGTCGCTGTCCAGCTGCTGAGCCACAGGCTGCTGTCCAACTTGCGGTTGCTTAACGGGCGGCGAAGGAGAAGTCCAC | |
| | GCCTACATGGGGGTAGAGTCATAATCGTGCATCAGGATAGGGCGGTGGTGCTGCAGCAGCGCGCGAATAAACTGCTG | |
| | CCGCCGCCGCTCCGTCCTGCAGGAATACAACATGGCAGTGGTCTCCTCAGCGATGATTCGCACCGCCCGCAGCATAAG | |
| | GCGCCTTGTCCTCCGGGCACAGCAGCGCACCCTGATCTCACTTAAATCAGCACAGTAACTGCAGCACAGCACCACAAT | |
| | ATTGTTCAAAATCCCACAGTGCAAGGCGCTGTATCCAAAGCTCATGGCGGGGACCACAGAACCCACGTGGCCATCAT | |
| | ACCACAAGCGCAGGTAGATTAAGTGGCGACCCCTCATAAACACGCTGGACATAAACATTACCTCTTTTGGCATGTTGT | |
| | AATTCACCACCTCCCGGTACCATATAAACCTCTGATTAAACATGGCGCCATCCACCACCATCCTAAACCAGCTGGCCA | |
| | AAACCTGCCCGCCGGCTATACACTGCAGGGAACCGGGACTGGAACAATGACAGTGGAGAGCCCAGGACTCGTAACCA | |
| | TGGATCATCATGCTCGTCATGATATCAATGTTGGCACAACACAGGCACACGTGCATACACTTCCTCAGGATTACAAGC | |
| | TCCTCCCGCGTTAGAACCATATCCCAGGGAACAACCCATTCCTGAATCAGCGTAAATCCCACACTGCAGGGAAGACCT | |
| | CGCACGTAACTCACGTTGTGCATTGTCAAAGTGTTACATTCGGGCAGCAGCGGATGATCCTCCAGTATGGTAGCGCGG | |
| | GTTTCTGTCTCAAAAGGAGGTAGACGATCCCTACTGTACGGAGTGCGCCGAGACAACCGAGATCGTGTTGGTCGTAGT | |
| | GTCATGCCAAATGGAACGCCGGACGTAGTCATATTTCCTGAAGCAAAACCAGGTGCGGGCGTGACAAACAGATCTGC | |
| | GTCTCCGGTCTCGCCGCTTAGATCGCTCTGTGTAGTAGTTGTAGTATATCCACTCTCTCAAAGCATCCAGGCGCCCCCT | |
| | GGCTTCGGGTTCTATGTAAACTCCTTCATGCGCCGCTGCCCTGATAACATCCACCACCGCAGAATAAGCCACACCCAG | |
| | CCAACCTACACATTCGTTCTGCGAGTCACACACGGGAGGAGCGGGAAGAGCTGGAAGAACCATGTTTTTTTTTTTATT | |
| | CCAAAAGATTATCCAAAACCTCAAAATGAAGATCTATTAAGTGAACGCGCTCCCCTCCGGTGGCGTGGTCAAACTCTA | |
| | CAGCCAAAGAACAGATAATGGCATTTGTAAGATGTTGCACAATGGCTTCCAAAAGGCAAACGGCCCTCACGTCCAAG | |
| | TGGACGTAAAGGCTAAACCCTTCAGGGTGAATCTCCTCTATAAACATTCCAGCACCTTCAACCATGCCCAAATAATTC | |
| | TCATCTCGCCACCTTCTCAATATATCTCTAAGCAAATCCCGAATATTAAGTCCGGCCATTGTAAAAATCTGCTCCAGAG | |
| | CGCCCTCCACCTTCAGCCTCAAGCAGCGAATCATGATTGCAAAAATTCAGGTTCCTCACAGACCTGTATAAGATTCAA | |
| | AAGCGGAACATTAACAAAAATACCGCGATCCCGTAGGTCCCTTCGCAGGGCCAGCTGAACATAATCGTGCAGGTCTG | |
| | CACGGACCAGCGCGGCCACTTCCCCGCCAGGAACCATGACAAAAGAACCCACACTGATTATGACACGCATACTCGGA | |
| | GCTATGCTAACCAGCGTAGCCCCGATGTAAGCTTGTTGCATGGGCGGCGATATAAAATGCAAGGTGCTGCTCAAAAA | |
| | ATCAGGCAAAGCCTCGCGCAAAAAAGAAAGCACATCGTAGTCATGCTCATGCAGATAAAGGCAGGTAAGCTCCGGA | |
| | ACCACCACAGAAAAAGACACCATTTTTCTCTCAAACATGTCTGCGGGTTTCTGCATAAACACAAAATAAAATAACAA | |
| | AAAAACATTTAAACATTAGAAGCCTGTCTTACAACAGGAAAAACAACCCTTATAAGCATAAGACGGACTACGGCCAT | |
| | GCCGGCGTGACCGTAAAAAAACTGGTCACCGTGATTAAAAAGCACCACCGACAGCTCCTCGGTCATGTCCGGAGTCA | |
| | TAATGTAAGACTCGGTAAACACATCAGGTTGATTCACATCGGTCAGTGCTAAAAAGCGACCGAAATAGCCCGGGGGA | |
| | ATACATACCCGCAGGCGTAGAGACAACATTACAGCCCCCATAGGAGGTATAACAAAATTAATAGGAGAGAAAAACA | |
| | CATAAACACCTGAAAAACCCTCCTGCCTAGGCAAAATAGCACCCTCCCGCTCCAGAACAACATACAGCGCTTCCACA | |
| | GCGGCAGCCATAACAGTCAGCCTTACCAGTAAAAAAGAAAACCTATTAAAAAAACACCACTCGACACGGCACCAGCT | |
| | CAATCAGTCACAGTGTAAAAAAGGGCCAAGTGCAGAGCGAGTATATATAGGACTAAAAAATGACGTAACGGTTAAA | |
| | GTCCACAAAAAACACCCAGAAAACCGCACGCGAACCTACGCCCAGAAACGAAAGCCAAAAAACCCACAACTTCCTC | |
| | AAATCGTCACTTCCGTTTTCCCACGTTACGTAACTTCCCATTTTAAGAAAACTACAATTCCCAACACATACAAGTTACT | |
| | CCGCCCTAAAACCTACGTCACCCGCCCCGTTCCCACGCCCCGCGCCACGTCACAAACTCCACCCCCTCATTATCATATT | |
| | GGCTTCAATCCAAAATAAGGTATATTATTGATGATTTATTTTGGATTGAAGCCAATATGATAATGAGGGGGTGGAGTT | |
| | TGTGACGTGGCGCGGGGCGTGGGAACGGGGCGGGTGACGTAGTAGTGTGGCGGAAGTGTGATGTTGCAAGTGTGGCG | |
| | GAACACATGTAAGCGACGGATGTGGCAAAAGTGACGTTTTTGGTGTGCGCCGGATCCACAGGACGGGTGTGGTCGCC | |

TABLE 1C-continued

Exemplary expression construct sequences comprising one or more helper genes and a rep gene.

| Description | Sequence | SEQ ID NO |
|---|---|---|
| | ATGATCGCGTAGTCGATAGTGGCTCCAAGTAGCGAAGCGAGCAGGACTGGGCGGCGGCCAAAGCGGTCGGACAGTG<br>CTCCGAGAACGGGTGCGCATAGAAATTGCATCAACGCATATAGCGCTAGCAGCACGCCATAGTGACTGGCGATGCTG<br>TCGGAATGGACGATATCCCGCAAGAGGCCCGGCAGTACCGGCATAACCAAGCCTATGCCTACAGCATCCAGGGTGAC<br>GGTGCCGAGGATGACGATGAGCGCATTGTTAGATTTCATACACGGTGCCTGACTGCGTTAGCAATTTAACTGTGATAA<br>ACTACCGCATTAAAGCTTATCGAATTCGTAATCATGGTCATAGCTGTTTCCTGTGTGAAATTGTTATCCGCTCACAATT<br>CCACACAACATACGAGCCGGAAGCATAAAGTGTAAAGCCTGGGGTGCCTAATGAGTGAGCTAACTCACATTAATTGC<br>GTTGCGCTCACTGCCCGCTTTCCAGTCGGGAAACCTGTCGTGCCAGCTGCATTAATGAATCGGCCAACGCGCGGGGAG<br>AGGCGGTTTGCGTATTGGGCGC | |
| Rep/Helper Plasmid with intron | TCTTCCGCTTCCTCGCTCACTGACTCGCTGCGCTCGGTCGTTCGGCTGCGGCGAGCGGTATCAGCTCACTCAAAGGCG<br>GTAATACGGTTATCCACAGAATCAGGGGATAACGCAGGAAAGAACATGTGAGCAAAAGGCCAGCAAAAGGCCAGGA<br>ACCGTAAAAAGGCCGCGTTGCTGGCGTTTTTCCATAGGCTCCGCCCCCCTGACGAGCATCACAAAAATCGACGCTCAA<br>GTCAGAGGTGGCGAAACCCGACAGGACTATAAAGATACCAGGCGTTTCCCCCTGGAAGCTCCCTCGTGCGCTCTCCTG<br>TTCCGACCCTGCCGCTTACCGGATACCTGTCCGCCTTTCTCCCTTCGGGAAGCGTGGCGCTTTCTCATAGCTCACGCTG<br>TAGGTATCTCAGTTCGGTGTAGGTCGTTCGCTCCAAGCTGGGCTGTGTGCACGAACCCCCCGTTCAGCCCGACCGCTG<br>CGCCTTATCCGGTAACTATCGTCTTGAGTCCAACCCGGTAAGACACGACTTATCGCCACTGGCAGCAGCCACTGGTAA<br>CAGGATTAGCAGAGCGAGGTATGTAGGCGGTGCTACAGAGTTCTTGAAGTGGTGGCCTAACTACGGCTACACTAGAA<br>GAACAGTATTTGGTATCTGCGCTCTGCTGAAGCCAGTTACCTTCGGAAAAAGAGTTGGTAGCTCTTGATCCGGCAAAC<br>AAACCACCGCTGGTAGCGGTGGTTTTTTTGTTTGCAAGCAGCAGATTACGCGCAGAAAAAAAGGATCTCAAGAAGAT<br>CCTTTGATCTTTTCTACGGGGTCTGACGCTCAGTGGAACGAAAACTCACGTTAAGGGATTTTGGTCATGAGATTATCA<br>AAAAGGATCTTCACCTAGATCCTTTTAAATTAAAAATGAAGTTTTAAATCAATCTAAAGTATATATGAGTAAACTTGG<br>TCTGACAGTTATTAGAAAAACTCATCGAGCATCAAATGAAACTGCAATTTATTCATATCAGGATTATCAATACCATAT<br>TTTTGAAAAAGCCGTTTCTGTAATGAAGGAGAAAACTCACCGAGGCAGTTCCATAGGATGGCAAGATCCTGGTATCG<br>GTCTGCGATTCCGACTCGTCCAACATCAATACAACCTATTAATTTCCCCTCGTCAAAAATAAGGTTATCAAGTGAGAA<br>ATCACCATGAGTGACGACTGAATCCGGTGAGAATGGCAAAAGTTTATGCATTTCTTTCCAGACTTGTTCAACAGGCCA<br>GCCATTACGCTCGTCATCAAAATCACTCGCATCAACCAAACCGTTATTCATTCGTGATTGCGCCTGAGCGAGACGAAA<br>TACGCGATCGCTGTTAAAAGGACAATTACAAACAGGAATCGAATGCAACCGGCGCAGGAACACTGCCAGCGCATCAA<br>CAATATTTTCACCTGAATCAGGATATTCTTCTAATACCTGGAATGCTGTTTTCCGGGGATCGCAGTGGTGAGTAACCA<br>TGCATCATCAGGAGTACGGATAAAATGCTTGATGGTCGGAAGAGGCATAAATTCCGTCAGCCAGTTTAGTCTGACCAT<br>CTCATCTGTAACATCATTGGCAACGCTACCTTTGCCATGTTTCAGAAACAACTCTGGCGCATCGGGCTTCCCATACAA<br>GCGATAGATTGTCGCACCTGATTGCCCGACATTATCGCGAGCCCATTTATACCCATATAAATCAGCATCCATGTTGGA<br>ATTTAATCGCGGCCTCGACGTTTCCCGTTGAATATGGCTCATACTCTTCCTTTTTCAATATTATTGAAGCATTTATCAGG<br>GTTATTGTCTCATGAGCGGATACATATTTGAATGTATTTAGAAAAATAAACAAATAGGGGTTCCGCGCACATTTCCCC<br>GAAAAGTGCCACCTGACGTCTAAGAAACCATTATTATCATGACATTAACCTATAAAAATAGGCGTATCACGAGGCCCT<br>TTCGTCTCGCGCGTTTCGGTGATGACGGTGAAAACCTCTGACACATGCAGCTCCCGGAGACGGTCACAGCTTGTCTGT<br>AAGCGGATGCCGGGAGCAGACAAGCCCGTCAGGGCGCGTCAGCGGGTGTTGGCGGGTGTCGGGGCTGGCTTAACTAT<br>GCGGCATCAGAGCAGATTGTACTGAGAGTGCACCATAAAATTGTAAACGTTCATATGGTTTAAACGTCGATCAGAGA<br>GAGTGTCCTCGAGCCAATCTGGAAGATAACCATCGGCAGCCATACCTGATTTAAATCATTTATTGTTCAAAGATGCAG<br>TCATCCAAATCCACATTGACCAGATCGCAGGCAGTGCAAGCGTCTGGCACCTTTCCCATGATATGATGAATGTAGCAC<br>AGTTTCTGATACGCCTTTTTGACGACAGAAACGGGTTGAGATTCTGACACGGGAAAGCACTCTAAACAGTCTTTCTGT<br>CCGTGAGTGAAGCAGATATTTGAATTCTGATTCATTCTCTCGCATTGTCTGCAGGGAAACAGCATCAGATTCATGCCC<br>ACGTGACGAGAACATTTGTTTTGGTACCTGTCTGCGTAGTTGATCGAAGCTTCCGCGTCTGACGTCGATGGCTGCGCA<br>ACTGACTCGCGCACCCGTTTGGGCTCACTTATATCTGCGTCACTGGGGGCGGGTCTTTTCTTGGCTCCACCCTTTTTGA<br>CGTAGAATTCATGCTCCACCTCAACCACGTGATCCTTTGCCCACCGGAAAAAGTCTTTGACTTCCTGCTTGGTGACCTT<br>CCCAAAGTCATGATCCAGACGGCGGGTGAGTTCAAATTTGAACATCCGGTCTTGCAACGGCTGCTGGTGTTCGAAGGT<br>CGTTGAGTTCCCGTCAATCACGGCGCACATGTTGGTGTTGGAGGTGACGATCACGGGAGTCGGGTCTATCTGGGCCGA<br>GGACTTGCATTTCTGGTCCACGCGCACCTTGCTTCCTCCGAGAATGGCTTTGGCCGACTCCACGACCTTGGCGGTCATC<br>TTCCCCTCCTCCCACCAGATCACCATCTTGTCGACACAGTCGTTGAAGGGAAAGTTCTCATTGGTCCAGTTTACGCACC<br>CGTAGAAGGGCACAGTGTGGGCTATGGCCTCCGCGATGTTGGTCTTCCCGGTAGTTGCAGGCCCAAACAGCCAGATG<br>GTGTTCCTCTTGCCGAACTTTTTCGTGGCCCATCCCAGAAAGACGGAAGCCGCATATTGGGGATCGTACCCGTTTAGTT<br>CCAAAATTTTATAAATCCGATTGCTGGAAATGTCCTCCACGGGCTGCTGGCCCACCAGGTAGTCGGGGGCGGTTTTAG<br>TCAGGCTCATAATCTTTCCCGCATTGTCCAAGGCAGCCTTGATTTGGGACCGCGAGTTGGAGGCCGCATTGAAGGAGA<br>TGTATGAGGCCTGGTCCTCCTGGATCCACTGCTTCTCCGAGGTAATCCCCTTGTCCACGAGCCACCCGACCAGCTCCAT<br>GTACCTGGCTGAAGTTTTTGATCTGATCACCGGCGCATCAGAATTGGGATTCTGATTCTCTTTGTTCTGCTCCTGCGTC<br>TGCGACACGTGCGTCAGATGCTGCGCCACCAACCGTTTACGCTCCGTGAGATTCAAACAGGCGCTTAAATACTGTTCC<br>ATATTAGTCCACGCCCACTGGAGCTCAGGCTGGGTTTTGGGGAGCAAGTAATTGGGGATGTAGCACTCATCCACCACC<br>TTGTTCCCGCCTCCGGCGCCATTTCTGGTCTTTGTGACCGCGAACCAGTTTGGCAAAGTCGGCTCGATCCCGCGGTAAA<br>TTCTCTGAATCAGTTTTTCGCGAATCTGACTCAGGAAACGTCCCAAAACCATGGATTTCACCCCGGTGGTTTCCACGA<br>GCACGTGCATGTGGAAGTAGCTCTCTCCCTTCTCAAATTGCACAAAGAAAAGGGCCTCCGGGGCCTTACTCACACGGC<br>GCCATTCCGTCAGAAAGTCGCGCTGCAGCTTCTCGGCCACGGTCAGGGGTGCCTGCTCAATCAGATTCAGATCCATGT<br>CAGAATCTGGCGGCAACTCCCATTCCTTCTCGGCCACCCAGTTCACAAAGCTGTCAGAAATGCCGGGCAGATGCTCGT<br>CAAGGTCGCTGGGGACCTTAATCACAATCTCGTAAAACCCCGGCATCTGAAATGTAAAAGAATAATTCTTTAGTTTTA<br>GCAAAAAAGAAAACATCATGAAAATTTTACATCTCTTAAGAAAGTCTTTGTTTTTAATCCAAATAATCTGAAAGCCAA<br>TTTCTCTTTAGGGCATGGAGCCAAAATCTGTGATGTTCCCACAGTACTGTATACACATGGAGATTTAGGAATTAAAAT<br>TCAATTTTACTTTTAGTCAAGAGAATTCCAGTAATAAAAGGTCAGATTTCTAATCATATTTGAATTTACTTTGGATGAA<br>AAAGAAAGTTCTCAAATGAGCGGTTAACTTCACACTTTGTCATCACTTGAAAATAGCTCATTGAGGATCTTTGCAAAG<br>TGATCCATCACCCTGGCTGGGCTGTTTTCAGAATATGGTTGCCCAAATGACTTTGAACAAATGTCTCCTGAAGAACAG<br>AAGCCTAATTATGGTCCAGCGACGTCGATTTCACAGCTGACATCATGTCTGGAGTGGGAACCACAGGGCCAGTCAGCT<br>TTCTGGGGGTGCTTAGGGTTGGCACCCCTGATCCTGGTACTGTCAGCTACTAGATTTGATTCTAGAAAGTTGACAAGT<br>AAGTGTGATAAATGCTTCCTGTGAGAACATGCTGTTTGTCCAAATGGGATAATTTCTTCCCTGTATGCCTTCCTCTGGG<br>AAATACATAAAGTCACTGTAGTTGTGAAAAAACAAAGTGATATATGTTGCATTAGCTAACTTCCTACTCTTTATGTCA<br>ATTCTTAAGCTTGCTTTTCTCCCCTAGGGAACTCAACTGAGTATTGTGTTTCCCCAAATATCAACTCCAAGATGTTTGA<br>CATAGAGACAAAATGATTTTTTCCTAATCCATGAAAAGCTTTGGTGATAACTAACAGCTTGCTAATGAAAGGTTAATC<br>TTTATGTTTTAACTAAAACTTTAAATTGAAGATATATAATTTAAAAAATTAGAGACACACCTCATTACATACTTCTGAA | 2 |

TABLE 1C-continued

Exemplary expression construct sequences comprising one or more helper genes and a rep gene.

| Description | Sequence | SEQ ID NO |
|---|---|---|
| | ACCTTGAAATGTCATATATCTTAAAATCAGACTTTTTGTGTAAATAAGGCCATTGTTTGTGCTTTTGTTTCCCATTTTGA<br>TTTCAAAGTGGTAAGTCCAAACAAAAATAATGTGGTTATTTTTTTTCACTATATTCTGCTATTTCTTTGTTTTCCCACTT<br>TTAATTTTTTTAAACCAAGGAGATGAATGTTTTCTAACAGGAATTACATGACCAAATCATGAACTGAACAGTGTTTAT<br>TAAACATAAATGCATCATAAGCATTGTCGATCTATTTAGTTTTAAAAATGAAGAAGAAGAAAACCTAGCTAACAAAG<br>AACCAGTACTTACCAACCTGCGTGCTGGCTGTTAGACTCTTCAATATTGCTGTCAAATCATGTAATCAAAATTTAGTGA<br>AGAAGACAGCATCAGATATTTCTATATCTAAAAGGCAAGCATACTCAATGTATTTTAAAAAAGGAAACAAACGGCGG<br>CTGCGCGTTCAAACCTCCCGCTTCAAAATGGAGACCCTGCGTGCTCACTCGGGCTTAAATACCCAGCGTGACCACATG<br>GTGTCGCAAAATGTCGCAAAACACTCACGTGACCTCTAATACAGGACCTCCCTAACCCTATGACGTAACGTTAATATT<br>TTGTTAAAATTCGCGTTAAATTTTTGTTAAATCAGCTCATTTTTTAACCAATAGGCCGAAATCGGCAAAATCCCTTATA<br>AATCAAAAGAATAGCCCGAGATAGGGTTGAGTGTTGTTCCAGTTTGGAACAAGAGTCCACTATTAAAGAACGTGGAC<br>TCCAACGTCAAAGGGCGAAAAACCGTCTATCAGGGCGATGGCCCACTACGTGAACCATCACCCAAATCAAGTTTTTTG<br>GGGTCGAGGTGCCGTAAAGCACTAAATCGGAACCCTAAAGGGAGCCCCCGATTTAGAGCTTGACGGGGAAAGCCGGC<br>GAACGTGGCGAGAAAGGAAGGGAAGAAAGCGAAAGGAGCGGGCGCTAGGGCGCTGGCAAGTGTAGCGGTCACGCT<br>GCGCGTAACCACCACACCCGCCGCGCTTAATGCGCCGCTACAGGGCGCGTACTATGGTTGCTTTGACGTATGCGGTGT<br>GAAATACCGCACAGATGCGTAAGGAGAAAATACCGCATCAGGCGCCATTCGCCATTCAGGCTGCGCAACTGTTGGGA<br>AGGGCGATCGGTGCGGGCCTCTTCGCTATTACGCCAGCTGGCGAAAGGGGGATGTGCTGCAAGGCGATTAAGTTGGG<br>TAACGCCAGGGTTTTCCCAGTCACGACGTTGTAAAACGACGGCCAGTGCCAAGCTTAAGGTGCACGGCCCACGTGGC<br>CACTAGTACTTCTCGACAGAAGCACCATGTCCTTGGGTCCGGCCTGCTGAATGCGCAGGCGGTCGGCCATGCCCCAGG<br>CTTCGTTTTGACATCGGCGCAGGTCTTTGTAGTAGTCTTGCATGAGCCTTTCTACCGGCACTTCTTCTTCTCCTTCCTCT<br>TGTCCTGCATCTCTTGCATCTATCGCTGCGGCGGCGGCGGAGTTTGGCCGTAGGTGGCGCCCTCTTCCTCCCATGCGTG<br>TGACCCCGAAGCCCCTCATCGGCTGAAGCAGGGCTAGGTCGGCGACAACGCGCTCGGCTAATATGGCCTGCTGCACC<br>TGCGTGAGGGTAGACTGGAAGTCATCCATGTCCACAAAGCGGTGGTATGCGCCCGTGTTGATGGTGTAAGTGCAGTTG<br>GCCATAACGGACCAGTTAACGGTCTGGTGACCCGGCTGCGAGAGCTCGGTGTACCTGAGACGCGAGTAAGCCCTCGA<br>GTCAAATACGTAGTCGTTGCAAGTCCGCACCAGGTACTGGTATCCCACCAAAAAGTGCGGCGGCGGCTGGCGGTAGA<br>GGGGCCAGCGTAGGGTGGCCGGGGCTCCGGGGGCGAGATCTTCCAACATAAGGCGATGATATCCGTAGATGTACCTG<br>GACATCCAGGTGATGCCGGCGGCGGTGGTGGAGGCGCGCGGAAAGTCGCGGACGCGGTTCCAGATGTTGCGCAGCGG<br>CAAAAAGTGCTCCATGGTCGGGACGCTCTGGCCGGTCAGGCGCGCGCAATCGTTGACGCTCTACCGTGCAAAAGGAG<br>AGCCTGTAAGCGGGCACTCTTCCGTGGTCTGGTGGATAAATTCGCAAGGGTATCATGGCGGACGACCGGGGTTCGAG<br>CCCCGTATCCGGCCGTCCGCCGTGATCCATGCGGTTACCGCCCGCGTGTCGAACCCAGGTGTGCGACGTCAGACAACG<br>GGGGAGTGCTCCTTTTGGCTTCCTTCCAGGCGCGGCGGCTGCTGCGCTAGCTTTTTTGGCCACTGGCCGCGCGCAGCGT<br>AAGCGGTTAGGCTGGAAAGCGAAAGCATTAAGTGGCTCGCTCCCTGTAGCCGGAGGGTTATTTTCCAAGGGTTGAGT<br>CGCGGGACCCCCGGTTCGAGTCTCGGACCGGCCGGACTGCGGCGAACGGGGGTTTGCCTCCCCGTCATGCAAGACCC<br>CGCTTGCAAATTCCTCCGGAAACAGGGACGAGCCCCTTTTTTGCTTTTCCCAGATGCATCCGGTGCTGCGGCAGATGC<br>GCCCCCCTCCTCAGCAGCGGCAAGAGCAAGAGCAGCGGCAGACATGCAGGGCACCCTCCCCTCCTCCTACCGCGTCA<br>GGAGGGGCGACATCCGCGGTTGACGCGGCAGCAGATGGTGATTACGAACCCCCGCGGCGCCGGGCCCGGCACTACCT<br>GGACTTGGAGGAGGGCGAGGGCCTGGCGCGGCTAGGAGCGCCCTCTCCTGAGCGGTACCCAAGGGTGCAGCTGAAGC<br>GTGATACGCGTGAGGCGTACGTGCCGCGGCAGAACCTGTTTCGCGACCGCGAGGGAGAGGAGCCCGAGGAGATGCG<br>GGATCGAAAGTTCCACGCAGGGCGCGAGCTGCGGCATGGCCTGAATCGCGAGCGGTTGCTGCGCGAGGAGGACTTTG<br>AGCCCGACGCGCGAACCGGGATTAGTCCCGCGCGCGCACACGTGGCGGCCGCCGACCTGGTAACCGCATACGAGCAG<br>ACGGTGAACCAGGAGATTAACTTTCAAAAAAGCTTTAACAACCACGTGCGTACGCTTGTGGCGCGCGAGGAGGTGGC<br>TATAGGACTGATGCATCTGTGGGACTTTGTAAGCGCGCTGGAGCAAAACCCAAATAGCAAGCCGCTCATGGCGCAGC<br>TGTTCCTTATAGTGCAGCACAGCAGGGACAACGAGGCATTCAGGGATGCGCTGCTAAACATAGTAGAGCCCGAGGGC<br>CGCTGGCTGCTCGATTTGATAAACATCCTGCAGAGCATAGTGGTGCAGGAGCGCAGCTTGAGCCTGGCTGACAAGGT<br>GGCCGCCATCAACTATTCCATGCTTAGCCTGGGCAAGTTTTACGCCCGCAAGATATACCATACCCCTTACGTTCCCATA<br>GACAAGGAGGTAAAGATCGAGGGGTTCTACATGCGCATGGCGCTGAAGGTGCTTACCTTGAGCGACGACCTGGGCGT<br>TTATCGCAACGAGCGCATCCACAAGGCCGTGAGCGTGAGCCGGCGGCGCGAGCTCAGCGACCGCGAGCTGATGCACA<br>GCCTGCAAAGGGCCCTGGCTGGCACGGGCAGCGGCGATAGAGAGGCCGAGTCCTACTTTGACGCGGGCGCTGACCTG<br>CGCTGGGCCCCAAGCCGACGCGCCCTGGAGGCAGCTGGGGCCGGACCTGGGCTGGCGGTGGCACCCGCGCGCGCTGG<br>CAACGTCGGCGGCGTGGAGGAATATGACGAGGACGATGAGTACGAGCCAGAGGACGGCGAGTACTAAGCGGTGATG<br>TTTCTGATCAGATGATGCAAGACGCAACGGACCCGGCGGTGCGGGCGGCGCTGCAGAGCCAGCCGTCCGGCCTTAAC<br>TCCACGGACGACTGGCGCCAGGTCATGGACCGCATCATGTCGCTGACTGCGCGCAATCCTGACGCGTTCCGGCAGCA<br>GCCGCAGGCCAACCGGCTCTCCGCAATTCTGGAAGCGGTGGTCCCGGCGCGCGCAAACCCCACGCACGAGAAGGTGC<br>TGGCGATCGTAAACGCGCTGGCCGAAAACAGGGCCATCCGGCCCGACGAGGCCGGCCTGGTCTACGACGCGCTGCTT<br>CAGCGCGTGGCTCGTTACAACAGCGGCAACGTGCAGACCAACCTGGACCGGCTGGTGGGGGATGTGCGCGAGGCCGT<br>GGCGCAGCGTGAGCGCGCGCAGCAGCAGGGCAACCTGGGCTCCATGGTTGCACTAAACGCCTTCCTGAGTACACAGC<br>CCGCCAACGTGCCGCGGGGACAGGAGGACTACACCAACTTTGTGAGCGCACTGCGGCTAATGGTGACTGAGACACCG<br>CAAAGTGAGGTGTACCAGTCTGGGCCAGACTATTTTTTCCAGACCAGTAGACAAGGCCTGCAGACCGTAAACCTGAG<br>CCAGGCTTTCAAAAACTTGCAGGGGCTGTGGGGGGTGCGGGCTCCCACAGGCGACCGCGCGACCGTGTCTAGCTTGC<br>TGACGCCCAACTCGCGCCTGTTGCTGCTGCTAATAGCGCCCTTCACGGACAGTGGCAGCGTGTCCCGGGACACATACC<br>TAGGTCACTTGCTGACACTGTACCGCGAGGCCATAGGTCAGGCGCATGTGGACGAGCATACTTTCCAGGAGATTACA<br>AGTGTCAGCCGCGCGCTGGGGCAGGAGGACACGGGCAGCCTGGAGGCAACCCTAAACTACCTGCTGACCAACCGGCG<br>GCAGAAGATCCCCTCGTTGCACAGTTTCGCACCCTTTGGCGCATCCCATTCTCCAGTAACTTTATGTCCATGGGCGCAC<br>TCACAGACCTGGGCCAAAACCTTCTCTACGCCAACTCCGCCCACGCGCTAGACATGACTTTTGAGGTGGATCCCATGG<br>ACGAGCCCACCCTTCTTTATGTTTTGTTTGAAGTCTTTGACGTGGTCCGTGTGCACCGGCCGCACCGCGGCGTCATCGA<br>AACCGTGTACCTGCGCACGCCCTTCTCGGCCGGCAACGCCACAACATAAAGAAGCAAGCAACATCAACAACAGCTGC<br>CGCCATGGGCTCCAGTGAGCAGGAACTGAAAGCCATTGTCAAAGATCTTGGTTGTGGGCCATATTTTTTGGGCACCTA<br>TGACAAGCGCTTTCCAGGCTTTGTTTCTCCACACAAGCTCGCCTGCGCCATAGTCAATACGGCCGGTCGCGAGACTGG<br>GGGCGTACACTGGATGGCCTTTGCCTGGAACCCGCACTCAAAAACATGCTACCTCTTTGAGCCCTTTGGCTTTTCTGAC<br>CAGCGACTCAAGCAGGTTTACCAGTTTGAGTACGAGTCACTCCTGCGCCGTAGCGCCATTGCTTCTTCCCCCGACCGC<br>TGTATAACGCTGGAAAAGTCCACCCAAAGCGTACAGGGGCCCAACTCGGCCGCCTGTGGACTATTCTGCTGCATGTTT<br>CTCCACGCCTTTGCCAACTGGCCCCAAACTCCCATGGATCACAACCCCACCATGAACCTTATTACCGGGGTACCCAAC<br>TCCATGCTCAACAGTCCCCAGGTACAGCCCACCCTGCGTCGCAACCAGGAACAGCTCTACAGCTTCCTGGAGCGCCAC<br>TCGCCCTACTTCCGCAGCCACAGTGCGCAGATTAGGAGCGCCACTTCTTTTTGTCACTTGAAAAACATGTAAAAATAA<br>TGTACTAGAGACACTTTCAATAAAGGCAAATGCTTTTATTTGTACACTCTCGGGTGATTATTTACCCCCACCCTTGCCG | |

TABLE 1C-continued

Exemplary expression construct sequences comprising one or more helper genes and a rep gene.

| Description | Sequence | SEQ ID NO |
|---|---|---|
| | TCTGCGCCGTTTAAAAATCAAAGGGGTTCTGCCGCGCATCGCTATGCGCCACTGGCAGGGACACGTTGCGATACTGGT<br>GTTTAGTGCTCCACTTAAACTCAGGCACAACCATCCGCGGCAGCTCGGTGAAGTTTTCACTCCACAGGCTGCGCACCA<br>TCACCAACGCGTTTAGCAGGTCGGGCGCCGATATCTTGAAGTCGCAGTTGGGGCCTCCGCCCTGCGCGCGCGAGTTGC<br>GATACACAGGGTTGCAGCACTGGAACACTATCAGCGCCGGGTGGTGCACGCTGGCCAGCACGCTCTTGTCGGAGATC<br>AGATCCGCGTCCAGGTCCTCCGCGTTGCTCAGGGCGAACGGAGTCAACTTTGGTAGCTGCCTTCCCAAAAAGGGCGCG<br>TGCCCAGGCTTTGAGTTGCACTCGCACCGTAGTGGCATCAAAAGGTGACCGTGCCCGGTCTGGGCGTTAGGATACAGC<br>GCCTGCATAAAAGCCTTGATCTGCTTAAAAGCCACCTGAGCCTTTGCGCCTTCAGAGAAGAACATGCCGCAAGACTTG<br>CCGGAAAACTGATTGGCCGGACAGGCCGCGTCGTGCACGCAGCACCTTGCGTCGGTGTTGGAGATCTGCACCACATTT<br>CGGCCCCACCGGTTCTTCACGATCTTGGCCTTGCTAGACTGCTCCTTCAGCGCGCGCTGCCCGTTTTCGCTCGTCACAT<br>CCATTTCAATCACGTGCTCCTTATTTATCATAATGCTTCCGTGTAGACACTTAAGCTCGCCTTCGATCTCAGCGCAGCG<br>GTGCAGCCACAACGCGCAGCCCGTGGGCTCGTGATGCTTGTAGGTCACCTCTGCAAACGACTGCAGGTACGCCTGCA<br>GGAATCGCCCCATCATCGTCACAAAGGTCTTGTTGCTGGTGAAGGTCAGCTGCAACCCGCGGTGCTCCTCGTTCAGCC<br>AGGTCTTGCATACGGCCGCCAGAGCTTCCACTTGGTCAGGCAGTAGTTTGAAGTTCGCCTTTAGATCGTTATCCACGT<br>GGTACTTGTCCATCAGCGCGCGCGCAGCCTCCATGCCCTTCTCCCACGCAGACACGATCGGCACACTCAGCGGGTTCA<br>TCACCGTAATTTCACTTTCCGCTTCGCTGGGCTCTTCCTCTTCCTCTTGCGTCCGCATACCACGCGCCACTGGGTCGTCT<br>TCATTCAGCCGCCGCACTGTGCGCTTACCTCCTTTGCCATGCTTGATTAGCACCGGTGGGTTGCTGAAACCCACCATTT<br>GTAGCGCCACATCTTCTCTTTCTTCCTCGCTGTCCACGATTACCTCTGGTGATGGCGGGCGCTCGGGCTTGGGAGAAGG<br>GCGCTTCTTTTTCTTCTTGGGCGCAATGGCCAAATCCGCCGCCGAGGTCGATGGCCGCGGGCTGGGTGTGCGCGGCAC<br>CAGCGCGTCTTGTGATGAGTCTTCCTCGTCCTCGGACTCGATACGCCGCCTCATCCGCTTTTTTGGGGGCGCCCGGGGA<br>GGCGGCGGCGACGGGGACGGGGACGACACGTCCTCCATGGTTGGGGGACGTCGCGCCGCACCGCGTCCGCGCTCGGG<br>GGTGGTTTCGCGCTGCTCCTCTTCCCGACTGGCCATTTCCTTCTCCTATAGGCAGAAAAAGATCATGGAGTCAGTCGA<br>GAAGAAGGACAGCCTAACCGCCCCCTCTGAGTTCGCCACCACCGCCTCCACCGATGCCGCCAACGCGCCTACCACCTT<br>CCCCGTCGAGGCACCCCCGCTTGAGGAGGAGGAAGTGATTATCGAGCAGGACCCAGGTTTTGTAAGCGAAGACGACG<br>AGGACCGCTCAGTACCAACAGAGGATAAAAAGCAAGACCAGGACAACGCAGAGGCAAACGAGGAACAAGTCGGGC<br>GGGGGGACGAAAGGCATGGCGACTACCTAGATGTGGGAGACGACGTGCTGTTGAAGCATCTGCAGCGCCAGTGCGCC<br>ATTATCTGCGACGCGTTGCAAGAGCGCAGCGATGTGCCCCTCGCCATAGCGGATGTCAGCCTTGCCTACGAACGCCAC<br>CTATTCTCACCGCGCGTACCCCCCAAACGCCAAGAAAACGGCACATGCGAGCCCAACCCGCGCCTCAACTTCTACCCC<br>GTATTTGCCGTGCCAGAGGTGCTTGCCACCTATCACATCTTTTTCCAAAACTGCAAGATACCCCTATCCTGCCGTGCCA<br>ACCGCAGCCGAGCGGACAAGCAGCTGGCCTTGCGGCAGGGCGCTGTCATACCTGATATCGCCTCGCTCAACGAAGTG<br>CCAAAAATCTTTGAGGGTCTTGGACGCGACGAGAAGCGCGCGGCAAACGCTCTGCAACAGGAAAACAGCGAAAATG<br>AAAGTCACTCTGGAGTGTTGGTGGAACTCGAGGGTGACAACGCGCGCCTAGCCGTACTAAAACGCAGCATCGAGGTC<br>ACCCACTTTGCCTACCCGGCACTTAACCTACCCCCCAAGGTCATGAGCACAGTCATGAGTGAGCTGATCGTGCGCCGT<br>GCGCAGCCCCTGGAGAGGGATGCAAATTTGCAAGAACAAACAGAGGAGGGCCTACCCGCAGTTGGCGACGAGCAGC<br>TAGCGCGCTGGCTTCAAACGCGCGAGCCTGCCGACTTGGAGGAGCGACGCAAACTAATGATGGCCGCAGTGCTCGTT<br>ACCGTGGAGCTTGAGTGCATGCAGCGGTTCTTTGCTGACCCGGAGATGCAGCGCAAGCTAGAGGAAACATTGCACTA<br>CACCTTTCGACAGGGCTACGTACGCCAGGCCTGCAAGATCTCCAACGTGGAGCTCTGCAACCTGGTCTCCTACCTTGG<br>AATTTTGCACGAAAACCGCCTTGGGCAAAACGTGCTTCATTCCACGCTCAAGGGCGAGGCGCGCCGCGACTACGTCC<br>GCGACTGCGTTTACTTATTTCTATGCTACACCTGGCAGACGGCCATGGGCGTTTGGCAGCAGTGCTTGGAGGAGTGCA<br>ACCTCAAGGAGCTGCAGAAACTGCTAAAGCAAAACTTGAAGGACCTATGGACGGCCTTCAACGAGCGCTCCGTGGCC<br>GCGCACCTGGCGGACATCATTTTCCCCGAACGCCTGCTTAAAACCCTGCAACAGGGTCTGCCAGACTTCACCAGTCAA<br>AGCATGTTGCAGAACTTTAGGAACTTTATCCTAGAGCGCTCAGGAATCTTGCCCGCCACCTGCTGTGCACTTCCTAGC<br>GACTTTGTGCCCATTAAGTACCGCGAATGCCCTCCGCCGCTTTGGGGCCACTGCTACCTTCTGCAGCTAGCCAACTACC<br>TTGCCTACCACTCTGACATAATGGAAGACGTGAGCGGTGACGGTCTACTGGAGTGTCACTGTCGCTGCAACCTATGCA<br>CCCCGCACCGCTCCCTGGTTTGCAATTCGCAGCTGCTTAACGAAAGTCAAATTATCGGTACCTTTGAGCTGCAGGGTC<br>CCTCGCCTGACGAAAAGTCCGCGGCTCCGGGGTTGAAACTCACTCCGGGGCTGTGGACGTCGGCTTACCTTCGCAAAT<br>TTGTACCTGAGGACTACCACGCCCACGAGATTAGGTTCTACGAAGACCAATCCCGCCCGCCATATGCGGAGCTTACCG<br>CCTGCGTCATTACCCAGGGCCACATTCTTGGCCAATTGCAAGCCATCAACAAAGCCCGCCAAGAGTTTCTGCTACGAA<br>AGGGACGGGGGGTTTACTTGGACCCCCAGTCCGGCGAGGAGCTCAACCCAATCCCCCCGCCGCCGCAGCCCTATCAG<br>CAGCAGCCGCGGGCCCTTGCTTCCCAGGATGGCACCCAAAAAGAAGCTGCAGCTGCCGCCGCCACCCACGGACGAGG<br>AGGAATACTGGGACAGTCAGGCAGAGGAGGTTTTGGACGAGGAGGAGGAGGACATGATGGAAGACTGGGAGAGCCT<br>AGACGAGGAAGCTTCCGAGGTCGAAGAGGTGTCAGACGAAACACCGTCACCCTCGGTCGCATTCCCCTCGCCGGCGC<br>CCCAGAAATCGGCAACCGGTTCCAGCATGGCTACAACCTCCGCTCCTCAGGCGCCGCCGGCACTGCCCGTTCGCCGAC<br>CCAACCGTAGATGGGACACCACTGGAACCAGGGCCGGTAAGTCCAAGCAGCCGCCGCCGTTAGCCCAAGAGCAACA<br>ACAGCGCCAAGGCTACCGCTCATGGCGCGGGCACAAGAACGCCATAGTTGCTTGCTTGCAAGACTGTGGGGGCAACA<br>TCTCCTTCGCCCGCCGCTTTCTTCTCTACCATCACGGCGTGGCCTTCCCCCGTAACATCCTGCATTACTACCGTCATCTC<br>TACAGCCCATACTGCACCGGCGGCAGCGGCAGCAACAGCAGCGGCCACACAGAAGCAAAGGCGACCGGATAGCAAG<br>ACTCTGACAAAGCCCAAGAAATCCACAGCGGCGGCAGCAGCAGGAGGAGGAGCGCTGCGTCTGGCGCCCAACGAAC<br>CCGTATCGACCCGCGAGCTTAGAAACAGGATTTTTCCCACTCTGTATGCTATATTTCAACAGAGCAGGGGCCAAGAAC<br>AAGAGCTGAAAATAAAAAACAGGTCTCTGCGATCCCTCACCCGCAGCTGCCTGTATCACAAAAGCGAAGATCAGCTT<br>CGGCGCACGCTGGAAGACGCGGAGGCTCTCTTCAGTAAATACTGCGCGCTGACTCTTAAGGACTAGTTTCGCGCCCTT<br>TCTCAAATTTAAGCGCGAAAACTACGTCATCTCCAGCGGCCACACCCGGCGCCAGCACCTGTTGTCAGCGCCATTATG<br>AGCAAGGAAATTCCCACGCCCTACATGTGGAGTTACCAGCCACAAATGGGACTTGCGGCTGGAGCTGCCCAAGACTA<br>CTCAACCCGAATAAACTACATGAGCGCGGACCCCACATGATATCCCGGGTCAACGGAATACGCGCCCACCGAAACC<br>GAATTCTCTCGGAACAGGCGGCTATTACCACCACACCTCGTAATAACCTTAATCCCCGTAGTTGGCCCGCTGCCCTGG<br>TGTACCAGGAAAGTCCCGCTCCCACCACTGTGGTACTTCCCAGAGACGCCCAGGCCGAAGTTCAGATGACTAACTCAG<br>GGGCGCAGCTTGCGGGCGGCTTTCGTCACAGGGTGCGGTCGCCCGGGCAGGGTATAACTCACCTGACAATCAGAGGG<br>CGAGGTATTCAGCTCAACGACGAGTCGGTGAGCTCCTCGCTTGGTCTCCGTCCGGACGGGACATTTCAGATCGGCGGC<br>GCCGGCCGCTCTTCATTCACGCCTCGTCAGGCAATCCTAACTCTGCAGACCTCGTCCTCTGAGCCGCGCTCTGGAGGC<br>ATTGGAACTCTGCAATTTATTGAGGAGTTTGTGCCATCGGTCTACTTTAACCCCTTCTCGGGACCTCCCGGCCACTATC<br>CGGATCAATTTATTCCTAACTTTGACGCGGTAAAGGACTCGGCGGACGGCTACGACTGAATGTTAAGTGGAGAGGCA<br>GAGCAACTGCGCCTGAAACACCTGGTCCACTGTCGCCGCCACAAGTGCTTTGCCCGCGACTCCGGTGAGTTTTGCTAC<br>TTTGAATTGCCCGAGGATCATATCGAGGGCCCGGCGCACGGCGTCCGGCTTACCGCCCAGGGAGAGCTTGCCCGTAG<br>CCTGATTCGGGAGTTTACCCAGCGCCCCCTGCTAGTTGAGCGGGACAGGGGACCCTGTGTTCTCACTGTGATTTGCAA<br>CTGTCCTAACCCTGGATTACATCAAGATCCTCTAGTTAATTAACTAGAGTACCCGGGGATCTTATTCCCTTTAACTAAT | |

TABLE 1C-continued

Exemplary expression construct sequences comprising one or more helper genes and a rep gene.

| Description | Sequence | SEQ ID NO |
|---|---|---|
| | AAAAAAAAATAATAAAGCATCACTTACTTAAAATCAGTTAGCAAATTTCTGTCCAGTTTATTCAGCAGCACCTCCTTG<br>CCCTCCTCCCAGCTCTGGTATTGCAGCTTCCTCCTGGCTGCAAACTTTCTCCACAATCTAAATGGAATGTCAGTTTCCT<br>CCTGTTCCTGTCCATCCGCACCCACTATCTTCATGTTGTTGCAGATGAAGCGCGCAAGACCGTCTGAAGATACCTTCAA<br>CCCCGTGTATCCATATGACACGGAAACCGGTCCTCCAACTGTGCCTTTTCTTACTCCTCCCTTTGTATCCCCCAATGGG<br>TTTCAAGAGAGTCCCCCTGGGGTACTCTCTTTGCGCCTATCCGAACCTCTAGTTACCTCCAATGGCATGCTTGCGCTCA<br>AAATGGGCAACGGCCTCTCTCTGGACGAGGCCGGCAACCTTACCTCCCAAAATGTAACCACTGTGAGCCCACCTCTCA<br>AAAAAACCAAGTCAAACATAAACCTGGAAATATCTGCACCCCTCACAGTTACCTCAGAAGCCCTAACTGTGGCTGCC<br>GCCGCACCTCTAATGGTCGCGGGCAACACACTCACCATGCAATCACAGGCCCCGCTAACCGTGCACGACTCCAAACTT<br>AGCATTGCCACCCAAGGACCCCTCACAGTGTCAGAAGGAAAGCTAGCCCTGCAAACATCAGGCCCCCTCACCACCAC<br>CGATAGCAGTACCCTTACTATCACTGCCTCACCCCCTCTAACTACTGCCACTGGTAGCTTGGGCATTGACTTGAAAGA<br>GCCCATTTATACACAAAATGGAAAACTAGGACTAAAGTACGGGGCTCCTTTGCATGTAACAGACGACCTAAACACTTT<br>GACCGTAGCAACTGGTCCAGGTGTGACTATTAATAATACTTCCTTGCAAACTAAAGTTACTGGAGCCTTGGGTTTTGA<br>TTCACAAGGCAATATGCAACTTAATGTAGCAGGAGGACTAAGGATTGATTCTCAAAACAGACGCCTTATACTTGATGT<br>TAGTTATCCGTTTGATGCTCAAAACCAACTAAATCTAAGACTAGGACAGGGCCCTCTTTTTATAAACTCAGCCCACAA<br>CTTGGATATTAACTACAACAAAGGCCTTTACTTGTTTACAGCTTCAAACAATTCCAAAAAGCTTGAGGTTAACCTAAG<br>CACTGCCAAGGGGTTGATGTTTGACGCTACAGCCATAGCCATTAATGCAGGAGATGGGCTTGAATTTGGTTCACCTAA<br>TGCACCAAACACAAATCCCCTCAAAACAAAAATTGGCCATGGCCTAGAATTTGATTCAAACAAGGCTATGGTTCCTAA<br>ACTAGGAACTGGCCTTAGTTTTGACAGCACAGGTGCCATTACAGTAGGAAACAAAAATAATGATAAGCTAACTTTGT<br>GGACCACACCAGCTCCATCTCCTAACTGTAGACTAAATGCAGAGAAAGATGCTAAACTCACTTTGGTCTTAACAAAAT<br>GTGGCAGTCAAATACTTGCTACAGTTTCAGTTTTGGCTGTTAAAGGCAGTTTGGCTCCAATATCTGGAACAGTTCAAA<br>GTGCTCATCTTATTATAAGATTTGACGAAAATGGAGTGCTACTAAACAATTCCTTCCTGGACCCAGAATATTGGAACT<br>TTAGAAATGGAGATCTTACTGAAGGCACAGCCTATACAAACGCTGTTGGATTTATGCCTAACCTATCAGCTTATCCAA<br>AATCTCACGGTAAAACTGCCAAAAGTAACATTGTCAGTCAAGTTTACTTAAACGGAGACAAAACTAAACCTGTAACA<br>CTAACCATTACACTAAACGGTACACAGGAAACAGGAGACACAACTCCAAGTGCATACTCTATGTCATTTTCATGGGAC<br>TGGTCTGGCCACAACTACATTAATGAAATATTTGCCACATCCTCTTACACTTTTTCATACATTGCCCAAGAATAAAGAA<br>TCGTTTGTGTTATGTTTCAACGTGTTTATTTTTCAATTGCAGAAAATTTCAAGTCATTTTTCATTCAGTAGTATAGCCCC<br>ACCACCACATAGCTTATACAGATCACCGTACCTTAATCAAACTCACAGAACCCTAGTATTCAACCTGCCACCTCCCTC<br>CCAACACACAGAGTACACAGTCCTTTCTCCCCGGCTGGCCTTAAAAAGCATCATATCATGGGTAACAGACATATTCTT<br>AGGTGTTATATTCCACACGGTTTCCTGTCGAGCCAAACGCTCATCAGTGATATTAATAAACTCCCCGGGCAGCTCACT<br>TAAGTTCATGTCGCTGTCCAGCTGCTGAGCCACAGGCTGCTGTCCAACTTGCGGTTGCTTAACGGGCGGCGAAGGAGA<br>AGTCCACGCCTACATGGGGGTAGAGTCATAATCGTGCATCAGGATAGGGCGGTGGTGCTGCAGCAGCGCGCGAATAA<br>ACTGCTGCCGCCGCCGCTCCGTCCTGCAGGAATACAACATGGCAGTGGTCTCCTCAGCGATGATTCGCACCGCCCGCA<br>GCATAAGGCGCCTTGTCCTCCGGGCACAGCAGCGCACCCTGATCTCACTTAAATCAGCACAGTAACTGCAGCACAGC<br>ACCACAATATTGTTCAAAATCCCACAGTGCAAGGCGCTGTATCCAAAGCTCATGGCGGGGACCACAGAACCCACGTG<br>GCCATCATACCACAAGCGCAGGTAGATTAAGTGGCGACCCCTCATAAACACGCTGGACATAAACATTACCTCTTTTGG<br>CATGTTGTAATTCACCACCTCCCGGTACCATATAAACCTCTGATTAAACATGGCGCCATCCACCACCATCCTAAACCA<br>GCTGGCCAAAACCTGCCCGCCGGCTATACACTGCAGGGAACCGGGACTGGAACAATGACAGTGGAGAGCCCAGGACT<br>CGTAACCATGGATCATCATGCTCGTCATGATATCAATGTTGGCACAACACAGGCACACGTGCATACACTTCCTCAGGA<br>TTACAAGCTCCTCCCGCGTTAGAACCATATCCCAGGGAACAACCCATTCCTGAATCAGCGTAAATCCCACACTGCAGG<br>GAAGACCTCGCACGTAACTCACGTTGTGCATTGTCAAAGTGTTACATTCGGGCAGCAGCGGATGATCCTCCAGTATGG<br>TAGCGCGGGTTTCTGTCTCAAAAGGAGGTAGACGATCCCTACTGTACGGAGTGCGCCGAGACAACCGAGATCGTGTT<br>GGTCGTAGTGTCATGCCAAATGGAACGCCGGACGTAGTCATATTTCCTGAAGCAAAACCAGGTGCGGGCGTGACAAA<br>CAGATCTGCGTCTCCGGTCTCGCCGCTTAGATCGCTCTGTGTAGTAGTTGTAGTATATCCACTCTCTCAAAGCATCCAG<br>GCGCCCCCTGGCTTCGGGTTCTATGTAAACTCCTTCATGCGCCGCTGCCCTGATAACATCCACCACCGCAGAATAAGC<br>CACACCCAGCCAACCTACACATTCGTTCTGCGAGTCACACACGGGAGGAGCGGGAAGAGCTGGAAGAACCATGTTTT<br>TTTTTTTATTCCAAAAGATTATCCAAAACCTCAAAATGAAGATCTATTAAGTGAACGCGCTCCCCTCCGGTGGCGTGG<br>TCAAACTCTACAGCCAAAGAACAGATAATGGCATTTGTAAGATGTTGCACAATGGCTTCCAAAAGGCAAACGGCCCT<br>CACGTCCAAGTGGACGTAAAGGCTAAACCCTTCAGGGTGAATCTCCTCTATAAACATTCCAGCACCTTCAACCATGCC<br>CAAATAATTCTCATCTCGCCACCTTCTCAATATATCTCTAAGCAAATCCCGAATATTAAGTCCGGCCATTGTAAAAATC<br>TGCTCCAGAGCGCCCTCCACCTTCAGCCTCAAGCAGCGAATCATGATTGCAAAAATTCAGGTTCCTCACAGACCTGTA<br>TAAGATTCAAAAGCGGAACATTAACAAAAATACCGCGATCCCGTAGGTCCCTTCGCAGGGCCAGCTGAACATAATCG<br>TGCAGGTCTGCACGGACCAGCGCGGCCACTTCCCCGCCAGGAACCATGACAAAAGAACCCACACTGATTATGACACG<br>CATACTCGGAGCTATGCTAACCAGCGTAGCCCCGATGTAAGCTTGTTGCATGGGCGGCGATATAAAATGCAAGGTGCT<br>GCTCAAAAAATCAGGCAAAGCCTCGCGCAAAAAAGAAAGCACATCGTAGTCATGCTCATGCAGATAAAGGCAGGTA<br>AGCTCCGGAACCACCACAGAAAAAGACACCATTTTTCTCTCAAACATGTCTGCGGGTTTCTGCATAAACACAAAATAA<br>AATAACAAAAAAACATTTAAACATTAGAAGCCTGTCTTACAACAGGAAAAACAACCCTTATAAGCATAAGACGGACT<br>ACGGCCATGCCGGCGTGACCGTAAAAAAACTGGTCACCGTGATTAAAAAGCACCACCGACAGCTCCTCGGTCATGTC<br>CGGAGTCATAATGTAAGACTCGGTAAACACATCAGGTTGATTCACATCGGTCAGTGCTAAAAAGCGACCGAAATAGC<br>CCGGGGGAATACATACCCGCAGGCGTAGAGACAACATTACAGCCCCCATAGGAGGTATAACAAAATTAATAGGAGA<br>GAAAAACACATAAACACCTGAAAAACCCTCCTGCCTAGGCAAAATAGCACCCTCCCGCTCCAGAACAACATACAGCG<br>CTTCCACAGCGGCAGCCATAACAGTCAGCCTTACCAGTAAAAAAGAAAACCTATTAAAAAAACACCACTCGACACGG<br>CACCAGCTCAATCAGTCACAGTGTAAAAAAGGGCCAAGTGCAGAGCGAGTATATATAGGACTAAAAAATGACGTAAC<br>GGTTAAAGTCCACAAAAAACACCCAGAAAACCGCACGCGAACCTACGCCCAGAAACGAAAGCCAAAAAACCCACAA<br>CTTCCTCAAATCGTCACTTCCGTTTTCCCACGTTACGTAACTTCCCATTTTAAGAAAACTACAATTCCCAACACATACA<br>AGTTACTCCGCCCTAAAACCTACGTCACCCGCCCCGTTCCCACGCCCCGCGCCACGTCACAAACTCCACCCCCTCATT<br>ATCATATTGGCTTCAATCCAAAATAAGGTATATTATTGATGATTTATTTTGGATTGAAGCCAATATGATAATGAGGGG<br>GTGGAGTTTGTGACGTGGCGCGGGGCGTGGGAACGGGGCGGGTGACGTAGTAGTGTGGCGGAAGTGTGATGTTGCAA<br>GTGTGGCGGAACACATGTAAGCGACGGATGTGGCAAAAGTGACGTTTTTGGTGTGCGCCGGATCCACAGGACGGGTG<br>TGGTCGCCATGATCGCGTAGTCGATAGTGGCTCCAAGTAGCGAAGCGAGCAGGACTGGGCGGCGGCCAAAGCGGTCG<br>GACAGTGCTCCGAGAACGGGTGCGCATAGAAATTGCATCAACGCATATAGCGCTAGCAGCACGCCATAGTGACTGGC<br>GATGCTGTCGGAATGGACGATATCCCGCAAGAGGCCCGGCAGTACCGGCATAACCAAGCCTATGCCTACAGCATCCA<br>GGGTGACGGTGCCGAGGATGACGATGAGCGCATTGTTAGATTTCATACACGGTGCCTGACTGCGTTAGCAATTTAACT<br>GTGATAAACTACCGCATTAAAGCTTATCGAATTCGTAATCATGGTCATAGCTGTTTCCTGTGTGAAATTGTTATCCGCT<br>CACAATTCCACACAACATACGAGCCGGAAGCATAAAGTGTAAAGCCTGGGGTGCCTAATGAGTGAGCTAACTCACAT | |

TABLE 1C-continued

Exemplary expression construct sequences comprising one or more helper genes and a rep gene.

| Description | Sequence | SEQ ID NO |
|---|---|---|
| | TAATTGCGTTGCGCTCACTGCCCGCTTTCCAGTCGGGAAACCTGTCGTGCCAGCTGCATTAATGAATCGGCCAACGCG<br>CGGGGAGAGGCGGTTTGCGTATTGGGCGC | |

In some embodiments, compositions provided herein comprise expression constructs. In some embodiments, compositions comprise: (i) a first expression construct comprising a polynucleotide sequence encoding one or more rep genes and a polynucleotide sequence encoding one or more wild-type adenoviral helper proteins; and (ii) a second expression construct comprising a polynucleotide sequence encoding one or more cap genes and one or more payloads.

In some embodiments, compositions comprise a second expression construct comprising a sequence that has at least 70%, at least 75%, at least 80%, at least 85%, at least 90%, at least 95%, at least 99%, or 100% sequence identity with a sequence in Table 1D below or a variant thereof. In some embodiments, compositions comprise a second expression construct comprising a sequence that has at least 70%, at least 75%, at least 80%, at least 85%, at least 90%, at least 95%, at least 99%, or 100% sequence identity with a portion of a sequence in Table 1D below or a variant thereof. In some embodiments, compositions comprise a second expression construct that consists of a sequence in Table 1D below. In some embodiments, compositions comprise a second expression construct that consists of a portion of a sequence in Table 1D below.

In some embodiments, compositions comprise a second expression construct comprising a sequence that has at least 70%, at least 75%, at least 80%, at least 85%, at least 90%, at least 95%, at least 99%, or 100% sequence identity with SEQ ID NO: 11. In some embodiments, compositions comprise a second expression construct that consists of: (i) SEQ ID NO: 11; (ii) a polynucleotide sequence encoding a cap gene; and (iii) a polynucleotide sequence encoding a payload (e.g., a transgene, ITR, 2A peptide, homology arms, or combinations thereof). In some embodiments, compositions comprise a second expression construct that comprises SEQ ID NO: 11, wherein a polynucleotide sequence comprising a sequence encoding a cap gene is inserted before position 2025 and a polynucleotide sequence encoding a payload comprising a polynucleotide sequence encoding a transgene is inserted after position 2663. In some embodiments, compositions comprise a second expression construct that consists of SEQ ID NO: 11, wherein a polynucleotide sequence encoding a cap gene is inserted before position 2025 and a polynucleotide sequence encoding a payload comprising a polynucleotide sequence encoding a transgene is inserted after position 2663.

TABLE 1D

Exemplary expression construct sequences, optionally comprising a payload and a cap gene.

| Description | Sequence | SEQ ID NO |
|---|---|---|
| Payload/Cap Plasmid Factor IX/ AAV2 | GTATATATGAGTAAACTTGGTCTGACAGTTACCAATGCTTAATCAGTGAGGCACCTATCTCAGCGATCTGTCTATTTCGT<br>TCATCCATAGTTGCCTGACTCCCCGTCGTGTAGATAACTACGATACGGGAGGGCTTACCATCTGGCCCCAGTGCTGCAAT<br>GATACCGCGAGACCCACGCTCACCGGCTCCAGATTTATCAGCAATAAACCAGCCAGCCGGAAGGGCCGAGCGCAGAAG<br>TGGTCCTGCAACTTTATCCGCCTCCATCCAGTCTATTAATTGTTGCCGGGAAGCTAGAGTAAGTAGTTCGCCAGTTAATA<br>GTTTGCGCAACGTTGTTGCCATTGCTACAGGCATCGTGGTGTCACGCTCGTCGTTTGGTATGGCTTCATTCAGCTCCGGT<br>TCCCAACGATCAAGGCGAGTTACATGATCCCCCATGTTGTGCAAAAAAGCGGTTAGCTCCTTCGGTCCTCCGATCGTTGT<br>CAGAAGTAAGTTGGCCGCAGTGTTATCACTCATGGTTATGGCAGCACTGCATAATTCTCTTACTGTCATGCCATCCGTAA<br>GATGCTTTTCTGTGACTGGTGAGTACTCAACCAAGTCATTCTGAGAATAGTGTATGCGGCGACCGAGTTGCTCTTGCCCG<br>GCGTCAATACGGGATAATACCGCGCCACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTGCACCCAACTGATCTTCAGCATCTTTT<br>ACTTTCACCAGCGTTTCTGGGTGAGCAAAAACAGGAAGGCAAAATGCCGCAAAAAAGGGAATAAGGGCGACACGGAA<br>ATGTTGAATACTCATACTCTTCCTTTTTCAATATTATTGAAGCATTTATCAGGGTTATTGTCTCATGAGCGGATACATATT<br>TGAATGTATTTAGAAAAATAAACAAATAGGGGTTCCGCGCACATTTCCCCGAAAAGTGCCACCTGACGTCTAAGAAACC<br>ATTATTATCATGACATTAACCTATAAAAATAGGCGTATCACGAGGCCCTTTCGTCTCGCGCGTTTCGGTGATGACGGTGA<br>AAACCTCTGACACATGCAGCTCCCGGAGACGGTCACAGCTTGTCTGTAAGCGGATGCCGGGAGCAGACAAGCCCGTCA<br>GGGCGCGTCAGCGGGTGTTGGCGGGTGTCGGGGCTGGCTTAACTATGCGGCATCAGAGCAGATTGTACTGAGAGTGCA<br>CCATTCGACGCTCTCCCTTATGCGACTCCTGCATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGGCCACGGGGCCTGCCACCATACCCACGCCGAA<br>ACAAGCGCTCATGAGCCCGAAGTGGCGAGCCCGATCTTCCCCATCGGTGATGTCGGCGATATAGGCGCCAGCAACCGC<br>ACCTGTGGCGCCGGTGGGTCACCAAGCAGGAAGTCAAAGACTTTTTCCGGTGGGCAAAGGATCACGTGGTTGAGGTGG<br>AGCATGAATTCTACGTCAAAAAGGGTGGAGCCAAGAAAAGACCCGCCCCCAGTGACGCAGATATAAGTGAGCCCAAAC<br>GGGTGCGCGAGTCAGTTGCGCAGCCATCGACGTCAGACGCGGAAGCTTCGATCAACTACGCAGACAGGTACCAAAACA<br>AATGTTCTCGTCACGTGGGCATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACCCGTTTCTGTCGTCAAAAAGG<br>CGTATCAGAAACTGTGCTACATTCATCATATCATGGGAAAGGTGCCAGACGCTTGCACTGCCTGCGATCTGGTCAATGT<br>GGATTTGGATGACTGCATCTTTGAACAATAAATGATTTAAATCAGGTATGGCTGCCGATGGTTATCTTCCAGATTGGCTC<br>GAGGACACTCTCTCTGAAGGAATAAGACAGTGGTGGAAGCTCAAACCTGGCCCACCACCACCAAAGCCCGCAGAGCGG<br>CATAAGGACGACAGCAGGGGTCTTGTGCTTCCTGGGTACAAGTACCTCGGACCCTTCAACGGACTCGACAAGGGAGAG<br>CCGGTCAACGAGGCAGACGCCGCGGCCCTCGAGCACGACAAAGCCTACGACCGGCAGCTCGACAGCGGAGACAACCCG<br>TACCTCAAGTACAACCACGCCGACGCGGAGTTTCAGGAGCGCCTTAAAGAAGATACGTCTTTTGGGGGCAACCTCGGAC<br>GAGCAGTCTTCCAGGCGAAAAAGAGGGTTCTTGAACCTCTGGGCCTGGTTGAGGAACCTGTTAAGACGGCTCCGGGAA | 3 |

TABLE 1D-continued

Exemplary expression construct sequences, optionally comprising a payload and a cap gene.

| Description | Sequence | SEQ ID NO |
|---|---|---|
| | AAAAGAGGCCGGTAGAGCACTCTCCTGTGGAGCCAGACTCCTCCTCGGGAACCGGAAAGGCGGGCCAGCAGCCTGCAA<br>GAAAAAGATTGAATTTTGGTCAGACTGGAGACGCAGACTCAGTACCTGACCCCCAGCCTCTCGGACAGCCACCAGCAG<br>CCCCCTCTGGTCTGGGAACTAATACGATGGCTACAGGCAGTGGCGCACCAATGGCAGACAATAACGAGGGCGCCGACG<br>GAGTGGGTAATTCCTCGGGAAATTGGCATTGCGATTCCACATGGATGGGCGACAGAGTCATCACCACCAGCACCCGAAC<br>CTGGGCCCTGCCCACCTACAACAACCACCTCTACAAACAAATTTCCAGCCAATCAGGAGCCTCGAACGACAATCACTAC<br>TTTGGCTACAGCACCCCTTGGGGGTATTTTGACTTCAACAGATTCCACTGCCACTTTTCACCACGTGACTGGCAAAGACT<br>CATCAACAACAACTGGGGATTCCGACCCAAGAGACTCAACTTCAAGCTCTTTAACATTCAAGTCAAAGAGGTCACGCAG<br>AATGACGGTACGACGACGATTGCCAATAACCTTACCAGCACGGTTCAGGTGTTTACTGACTCGGAGTACCAGCTCCCGT<br>ACGTCCTCGGCTCGGCGCATCAAGGATGCCTCCCGCCGTTCCCAGCAGACGTCTTCATGGTGCCACAGTATGGATACCT<br>CACCCTGAACAACGGGAGTCAGGCAGTAGGACGCTCTTCATTTTACTGCCTGGAGTACTTTCCTTCTCAGATGCTGCGTA<br>CCGGAAACAACTTTACCTTCAGCTACACTTTTGAGGACGTTCCTTTCCACAGCAGCTACGCTCACAGCCAGAGTCTGGAC<br>CGTCTCATGAATCCTCTCATCGACCAGTACCTGTATTACTTGAGCAGAACAAACACTCCAAGTGGAACCACCACGCAGT<br>CAAGGCTTCAGTTTTCTCAGGCCGGAGCGAGTGACATTCGGGACCAGTCTAGGAACTGGCTTCCTGGACCCTGTTACCG<br>CCAGCAGCGAGTATCAAAGACATCTGCGGATAACAACAACAGTGAATACTCGTGGACTGGAGCTACCAAGTACCACCT<br>CAATGGCAGAGACTCTCTGGTGAATCCGGGCCCGGCCATGGCAAGCCACAAGGACGATGAAGAAAAGTTTTTTCCTCA<br>GAGCGGGGTTCTCATCTTTGGGAAGCAAGGCTCAGAGAAAACAAATGTGGACATTGAAAAGGTCATGATTACAGACGA<br>AGAGGAAATCAGGACAACCAATCCCGTGGCTACGGAGCAGTATGGTTCTGTATCTACCAACCTCCAGAGAGGCAACAG<br>ACAAGCAGCTACCGCAGATGTCAACACACAAGGCGTTCTTCCAGGCATGGTCTGGCAGGACAGAGATGTGTACCTTCAG<br>GGGCCCATCTGGGCAAAGATTCCACACACGGACGGACATTTTCACCCCTCTCCCCTCATGGGTGGATTCGGACTTAAAC<br>ACCCTCCTCCACAGATTCTCATCAAGAACACCCCGGTACCTGCGAATCCTTCGACCACCTTCAGTGCGGCAAAGTTTGCT<br>TCCTTCATCACACAGTACTCCACGGGACAGGTCAGCGTGGAGATCGAGTGGGAGCTGCAGAAGGAAAACAGCAAACGC<br>TGGAATCCCGAAATTCAGTACACTTCCAACTACAACAAGTCTGTTAATGTGGACTTTACTGTGGACACTAATGGCGTGT<br>ATTCAGAGCCTCGCCCCATTGGCACCAGATACCTGACTCGTAATCTGTAATTGCTTGTTAATCAATAAACCGTTTAATTC<br>GTTTCAGTTGAACTTTGGTCTCTGCGTATTTCTTTCTTATCTAGTTTCCATATGCATGTAGATAAGTAGCATGGCGGGTTA<br>ATCATTAACTAACCGGTACCTCTAGAACTATAGCTAGCGATGACCCTGCTGATTGGTTCGCTGACCATTTCCGGGTGCGG<br>GACGGCGTTACCAGAAACTCAGAAGGTTCGTCCAACCAAACCGACTCTGACGGCAGTTTACGAGAGAGATGATAGGGT<br>CTGCTTCAGTAAGCCAGATGCTACACAATTAGGCTTGTACATATTGTCGTTAGAACGCGGCTACAATTAATACATAACCT<br>TATGTATCATACACATACGATTTAGGTGACACTATAGAATACACGGAATTAATTCTTGGCCACTCCCTCTCTGCGCGCTC<br>GCTCGCTCACTGAGGCCGCCCGGGCAAAGCCCGGGCGTCGGGCGACCTTTGGTCGCCCGGCCTCAGTGAGCGAGCGAG<br>CGCGCAGAGAGGGAGTGGCCAACTCCATCACTAGGGGTTCCTTACGTAGGACGTCCCCTGCAGGCAGGGAGGGGTGGA<br>GTCGTGACGTAAAGATCTGATATCATCGATCGCGATGCATTAATTAAGCGGCCGAGGCTCAGAGGCACACAGGAGTTTC<br>TGGGCTCACCCTGCCCCCTTCCAACCCCTCAGTTCCCATCCTCCAGCAGCTGTTTGTGTGCTGCCTCTGAAGTCCACACT<br>GAACAAACTTCAGCCTACTCATGTCCCTAAAATGGGCAAACATTGCAAGCAGCAAACAGCAAACACACAGCCCTCCCT<br>GCCTGCTGACCTTGGAGCTGGGGCAGAGGTCAGAGACCTCTCTGGGCCCATGCCACCTCCAACATCCACTCGACCCCTT<br>GGAATTTCGGTGGAGAGGAGCAGAGGTTGTCCTGGCGTGGTTTAGGTAGTGTGAGAGGGGTACCCGGGGATCTTGCTAC<br>CAGTGGAACAGCCACTAAGGATTCTGCAGTGAGAGCAGAGGGCCAGCTAAGTGGTACTCTCCCAGAGACTGTCTGACT<br>CACGCCACCCCCTCCACCTTGGACACAGGACGCTGTGGTTTCTGAGCCAGGTACAATGACTCCTTTCGGTAAGTGCAGT<br>GGAAGCTGTACACTGCCCAGGCAAAGCGTCCGGGCAGCGTAGGCGGGCGACTCAGATCCCAGCCAGTGGACTTAGCCC<br>CTGTTTGCTCCTCCGATAACTGGGGTGACCTTGGTTAATATTCACCAGCAGCCTCCCCCGTTGCCCCTCTGGATCCACTG<br>CTTAAATACGGACGAGGACAGGGCCCTGTCTCCTCAGCTTCAGGCACCACCACTGACCTGGGACAGTGAATGATCCCCC<br>TGATCTGCGGCCTCGACGGTATCGATAAGCTTGATATCGAATTCTAGTCGTCGACCACTTTCACAATCTGCTAGCAAAGG<br>TTGCCACCATGCAGCGCGTGAACATGATTATGGCCGAGAGCCCTGGCCTGATCACCATCTGCCTGCTGGGCTACCTGCT<br>GAGCGCCGAGTGTACAGGTTTGTTTCCTTTTTTAAAATACATTGAGTATGCTTGCCTTTTAGATATAGAAATATCTGATG<br>CTGTCTTCTTCACTAAATTTTGATTACATGATTTGACAGCAATATTGAAGAGTCTAACAGCCAGCACGCAGGTTGGTAAG<br>TACTGGTTCTTTGTTAGCTAGGTTTTCTTCTTCTTCATTTTTAAAACTAAATAGATCGACAATGCTTATGATGCATTTATG<br>TTTAATAAACACTGTTCAGTTCATGATTTGGTCATGTAATTCCTGTTAGAAAACATTCATCTCCTTGGTTTAAAAAAATT<br>AAAAGTGGGAAAACAAAGAAATAGCAGAATATAGTGAAAAAAAATAACCACATTATTTTTGTTTGGACTTACCACTTTG<br>AAATCAAAATGGGAAACAAAAGCACAAACAATGGCCTTATTTACACAAAAAGTCTGATTTTAAGATATATGACATTTCA<br>AGGTTTCAGAAGTATGTAATGAGGTGTGTCTCTAATTTTTTAAATTATATATCTTCAATTTAAAGTTTTAGTTAAAACATA<br>AAGATTAACCTTTCATTAGCAAGCTGTTAGTTATCACCAAAGCTTTTCATGGATTAGGAAAAAATCATTTTGTCTCTATG<br>TCAAACATCTTGGAGTTGATATTTGGGGAAACACAATACTCAGTTGAGTTCCCTAGGGGAGAAAAGCAAGCTTAAGAAT<br>TGACATAAAGAGTAGGAAGTTAGCTAATGCAACATATATCACTTTGTTTTTTCACAACTACAGTGACTTTATGTATTTCC<br>CAGAGGAAGGCATACAGGGAAGAAATTATCCCATTTGGACAAACAGCATGTTCTCACAGGAAGCATTTATCACACTTAC<br>TTGTCAACTTTCTAGAATCAAATCTAGTAGCTGACAGTACCAGGATCAGGGGTGCCAACCCTAAGCACCCCCAGAAAGC<br>TGACTGGCCCTGTGGTTCCCACTCCAGACATGATGTCAGCTGTGAAATCGACGTCGCTGGACCATAATTAGGCTTCTGTT<br>CTTCAGGAGACATTTGTTCAAAGTCATTTGGGCAACCATATTCTGAAAACAGCCCAGCCAGGGTGATGGATCACTTTGC<br>AAAGATCCTCAATGAGCTATTTTCAAGTGATGACAAAGTGTGAAGTTAACCGCTCATTTGAGAACTTTCTTTTTCATCCA<br>AAGTAAATTCAAATATGATTAGAAATCTGACCTTTTATTACTGGAATTCTCTTGACTAAAAGTAAAATTGAATTTTAATT<br>CCTAAATCTCCATGTGTATACAGTACTGTGGGAACATCACAGATTTTGGCTCCATGCCCTAAAGAGAAATTGGCTTTCAG<br>ATTATTTGGATTAAAAACAAAGACTTTCTTAAGAGATGTAAAATTTTCATGATGTTTTCTTTTTTGCTAAAACTAAAGAA<br>TTATTCTTTTACATTTCAGTGTTCCTGGACCACGAGAACGCCAACAAGATCCTGAACAGACCCAAGAGATACAACAGCG<br>GCAAGCTGGAAGAGTTCGTGCAGGGCAACCTGGAACGCGAGTGCATGGAAGAGAAGTGCAGCTTCGAAGAGGCCAGA<br>GAGGTGTTCGAGAACACCGAGAGAACCACCGAGTTCTGGAAGCAGTACGTGGACGGCGACCAGTGCGAGAGCAACCCT<br>TGTCTGAACGGCGGCAGCTGCAAGGACGACATCAACAGCTACGAGTGCTGGTGCCCCTTCGGCTTCGAGGGCAAGAAC<br>TGCGAGCTGGACGTGACCTGCAACATCAAGAACGGCAGATGCGAGCAGTTCTGCAAGAACAGCGCCGACAACAAGGTC<br>GTGTGCTCCTGCACCGAGGGCTACAGACTGGCCGAGAACCAGAAGTCCTGCGAGCCCGCTGTGCCTTTCCCATGCGGAA<br>GAGTGTCCGTGTCCCAGACCAGCAAGCTGACCAGAGCCGAGACAGTGTTCCCCGACGTGGACTACGTGAACAGCACCG<br>AGGCCGAGACAATCCTGGACAACATCACCCAGAGCACCCAGTCCTTCAACGACTTCACCAGAGTCGTGGGCGGCGAGG<br>ATGCTAAGCCTGGCCAGTTCCCGTGGCAGGTGGTGCTGAACGGAAAGGTGGACGCCTTCTGCGGCGGCTCCATCGTGAA<br>CGAGAAGTGGATCGTGACAGCCGCCCACTGCGTGGAAACCGGCGTGAAGATCACAGTGGTGGCCGGCGAGCACAACAT<br>CGAGGAAACCGAGCACACAGAGCAGAAAAGAAACGTGATCAGGATCATCCCCCACCACAACTACAACGCCGCCATCAA<br>CAAGTACAACCACGATATCGCCCTGCTGGAACTGGACGAGCCCCTGGTGCTGAATAGCTACGTGACCCCCATCTGTATC<br>GCCGACAAAGAGTACACCAACATCTTTCTGAAGTTCGGCAGCGGCTACGTGTCCGGCTGGGGCAGAGTGTTTCACAAGG<br>GCAGATCCGCTCTGGTGCTGCAGTACCTGAGAGTGCCTCTGGTGGACAGAGCCACCTGTCTGAGAAGCACCAAGTTCAC | |

TABLE 1D-continued

Exemplary expression construct sequences, optionally comprising a payload and a cap gene.

| Description | Sequence | SEQ ID NO |
|---|---|---|
| | CATCTACAACAACATGTTCTGCGCTGGCTTCCACGAGGGCGGCAGAGACTCTTGTCAGGGCGATTCTGGCGGCCCTCAC<br>GTGACAGAGGTGGAAGGCACCAGCTTTCTGACCGGCATCATCAGCTGGGGCGAGGAATGCGCCATGAAGGGGAAGTAC<br>GGCATCTACACCAAGGTGTCCAGATACGTGAACTGGATCAAAGAAAAGACCAAGCTGACATAATGAAAGATGGATTTC<br>CAAGGTTAATTCATTGGAATTGAAAATTAACAGCCCCCCCCCCCCCCCCCTGCAGATCTCGAGCCGAATTCCTGCAGCC<br>CGGGGGATCAGCCTCGACTGTGCCTTCTAGTTGCCAGCCATCTGTTGTTTGCCCCTCCCCCGTGCCTTCCTTGACCCTGG<br>AAGGTGCCACTCCCACTGTCCTTTCCTAATAAAATGAGGAAATTGCATCGCATTGTCTGAGTAGGTGTCATTCTATTCTG<br>GGGGGTGGGGTGGGGCAGGACAGCAAGGGGGAGGATTGGGAAGACAATAGCAGGCATGCTGGGGATGCGGTGGGCTC<br>TATGGCTTCTGAGGCGGAAAGAACCAGCTGGGGCTCGAGATCCACTAGACTAGTGTACACGCGTGATATCAGATCTGTT<br>ACGTAAGGAACCCCTAGTGATGGAGTTGGCCACTCCCTCTCTGCGCGCTCGCTCGCTCACTGAGGCCGCCCGGGCAAAG<br>CCCGGGCGGCCTCAGTGAGCGAGCGAGCGCGCAGAGAGGGAGTGGCCAACTTTTTGCAAAAGCCTAGGCCTCCAAAAA<br>AGCCTCCTCACTACTTCTGGAATAGCTCAGAGGCCGAGGCGGCCTCGGCCTCTGCATAAATAAAAAAAATTAGTCAGCC<br>ATGGGGCGGAGAATGGGCGGAACTGGGCGGAGTTAGGGGCGGGATGGGCGGAGTTAGGGGCGGGACTATGGTTGCTG<br>ACTAATTGAGATGCATGCTTTGCATACTTCTGCCTGCTGGGGAGCCTGGGGACTTTCCACACCTGGTTGCTGACTAATTG<br>AGATGCATGCTTTGCATACTTCTGCCTGCTGGGGAGCCTGGGGACTTTCCACACCCTAACTGACACACATTCCACAGCTG<br>CATTAATGAATCGGCCAACGCGCGGGGAGAGGCGGTTTGCGTATTGGGCGCTCTTCCGCTTCCTCGCTCACTGACTCGCT<br>GCGCTCGGTCGTTCGGCTGCGGCGAGCGGTATCAGCTCACTCAAAGGCGGTAATACGGTTATCCACAGAATCAGGGGAT<br>AACGCAGGAAAGAACATGTGAGCAAAAGGCCAGCAAAAGGCCAGGAACCGTAAAAAGGCCGCGTTGCTGGCGTTTTTC<br>CATAGGCTCCGCCCCCCTGACGAGCATCACAAAAATCGACGCTCAAGTCAGAGGTGGCGAAACCCGACAGGACTATAA<br>AGATACCAGGCGTTTCCCCCTGGAAGCTCCCTCGTGCGCTCTCCTGTTCCGACCCTGCCGCTTACCGGATACCTGTCCGC<br>CTTTCTCCCTTCGGGAAGCGTGGCGCTTTCTCATAGCTCACGCTGTAGGTATCTCAGTTCGGTGTAGGTCGTTCGCTCCA<br>AGCTGGGCTGTGTGCACGAACCCCCCGTTCAGCCCGACCGCTGCGCCTTATCCGGTAACTATCGTCTTGAGTCCAACCCG<br>GTAAGACACGACTTATCGCCACTGGCAGCAGCCACTGGTAACAGGATTAGCAGAGCGAGGTATGTAGGCGGTGCTACA<br>GAGTTCTTGAAGTGGTGGCCTAACTACGGCTACACTAGAAGAACAGTATTTGGTATCTGCGCTCTGCTGAAGCCAGTTA<br>CCTTCGGAAAAAGAGTTGGTAGCTCTTGATCCGGCAAACAAACCACCGCTGGTAGCGGTGGTTTTTTTGTTTGCAAGCA<br>GCAGATTACGCGCAGAAAAAAAGGATCTCAAGAAGATCCTTTGATCTTTTCTACGGGGTCTGACGCTCAGTGGAACGAA<br>AACTCACGTTAAGGGATTTTGGTCATGAGATTATCAAAAAGGATCTTCACCTAGATCCTTTTAAATTAAAAATGAAGTTT<br>TAAATCAATCTAAA | |
| Payload/Cap Plasmid Factor IX/ AAV5 | AGTTTTAAATCAATCTAAAGTATATATGAGTAAACTTGGTCTGACAGTTACCAATGCTTAATCAGTGAGGCACCTATCTC<br>AGCGATCTGTCTATTTCGTTCATCCATAGTTGCCTGACTCCCCGTCGTGTAGATAACTACGATACGGGAGGGCTTACCAT<br>CTGGCCCCAGTGCTGCAATGATACCGCGAGACCCACGCTCACCGGCTCCAGATTTATCAGCAATAAACCAGCCAGCCGG<br>AAGGGCCGAGCGCAGAAGTGGTCCTGCAACTTTATCCGCCTCCATCCAGTCTATTAATTGTTGCCGGGAAGCTAGAGTA<br>AGTAGTTCGCCAGTTAATAGTTTGCGCAACGTTGTTGCCATTGCTACAGGCATCGTGGTGTCACGCTCGTCGTTTGGTAT<br>GGCTTCATTCAGCTCCGGTTCCCAACGATCAAGGCGAGTTACATGATCCCCCATGTTGTGCAAAAAAGCGGTTAGCTCC<br>TTCGGTCCTCCGATCGTTGTCAGAAGTAAGTTGGCCGCAGTGTTATCACTCATGGTTATGGCAGCACTGCATAATTCTCT<br>TACTGTCATGCCATCCGTAAGATGCTTTTCTGTGACTGGTGAGTACTCAACCAAGTCATTCTGAGAATAGTGTATGCGGC<br>GACCGAGTTGCTCTTGCCCGGCGTCAATACGGGATAATACCGCGCCACATAGCAGAACTTTAAAAGTGCTCATCATTGG<br>AAAACGTTCTTCGGGGCGAAAACTCTCAAGGATCTTACCGCTGTTGAGATCCAGTTCGATGTAACCCACTCGTGCACCC<br>AACTGATCTTCAGCATCTTTTACTTTCACCAGCGTTTCTGGGTGAGCAAAAACAGGAAGGCAAAATGCCGCAAAAAAGG<br>GAATAAGGGCGACACGGAAATGTTGAATACTCATACTCTTCCTTTTTCAATATTATTGAAGCATTTATCAGGGTTATTGT<br>CTCATGAGCGGATACATATTTGAATGTATTTAGAAAAATAAACAAATAGGGGTTCCGCGCACATTTCCCCGAAAAGTGC<br>CACCTGACGTCTAAGAAACCATTATTATCATGACATTAACCTATAAAAATAGGCGTATCACGAGGCCCTTTCGTCTCGC<br>GCGTTTCGGTGATGACGGTGAAAACCTCTGACACATGCAGCTCCCGGAGACGGTCACAGCTTGTCTGTAAGCGGATGCC<br>GGGAGCAGACAAGCCCGTCAGGGCGCGTCAGCGGGTGTTGGCGGGTGTCGGGGCTGGCTTAACTATGCGGCATCAGAG<br>CAGATTGTACTGAGAGTGCACCATTCGACGCTCTCCCTTATGCGACTCCTGCATTAGGAAGCAGCCCAGTAGTAGGTTG<br>AGGCCGTTGAGCACCGCCGCCGCAAGGAATGGTGCATGCAAGGAGATGGCGCCCAACAGTCCCCCGGCCACGGGGCCT<br>GCCACCATACCCACGCCGAAACAAGCGCTCATGAGCCCGAAGTGGCGAGCCCGATCTTCCCCATCGGTGATGTCGGCGA<br>TATAGGCGCCAGCAACCGCACCTGTGGCGCCGGTGGGTCACCAAGCAGGAAGTCAAAGACTTTTTCCGGTGGGCAAAG<br>GATCACGTGGTTGAGGTGGAGCATGAATTCTACGTCAAAAAGGGTGGAGCCAAGAAAAGACCCGCCCCCAGTGACGCA<br>GATATAAGTGAGCCCAAACGGGTGCGCGAGTCAGTTGCGCAGCCATCGACGTCAGACGCGGAAGCTTCGATCAACTAC<br>GCAGACAGGTACCAAAACAAATGTTCTCGTCACGTGGGCATGAATCTGATGCTGTTTCCCTGCAGACAATGCGAGAGAA<br>TGAATCAGAATTCAAATATCTGCTTCACTCACGGACAGAAAGACTGTTTAGAGTGCTTTCCCGTGTCAGAATCTCAACCC<br>GTTTCTGTCGTCAAAAAGGCGTATCAGAAACTGTGCTACATTCATCATATCATGGGAAAGGTGCCAGACGCTTGCACTG<br>CCTGCGATCTGGTCAATGTGGATTTGGATGACTGCATCTTTGAACAATAAATGATTTAAATCAGGTATGTCTTTTGTTGA<br>TCACCCTCCAGATTGGTTGGAAGAAGTTGGTGAAGGTCTTCGCGAGTTTTTGGGCCTTGAAGCGGGCCCACCGAAACCA<br>AAACCCAATCAGCAGCATCAAGATCAAGCCCGTGGTCTTGTGCTGCCTGGTTATAACTATCTCGGACCCGGAAACGGTC<br>TCGATCGAGGAGAGCCTGTCAACAGGGCAGACGAGGTCGCGCGAGAGCACGACATCTCGTACAACGAGCAGCTTGAGG<br>CGGGAGACAACCCCTACCTCAAGTACAACCACGCGGACGCCGAGTTTCAGGAGAAGCTCGCCGACGACACATCCTTCG<br>GGGGAAACCTCGGAAAGGCAGTCTTTCAGGCCAAGAAAAGGGTTCTCGAACCTTTTGGCCTGGTTGAAGAGGGTGCTA<br>AGACGGCCCCTACCGGAAAGCGGATAGACGACCACTTTCCAAAAAGAAAGAAGGCTCGGACCGAAGAGGACTCCAAG<br>CCTTCCACCTCGTCAGACGCCGAAGCTGGACCCAGCGGATCCCAGCAGCTGCAAATCCCAGCCCAACCAGCCTCAAGTT<br>TGGGAGCTGATACAATGTCTGCGGGAGGTGGCGGCCCATTGGGCGACAATAACCAAGGTGCCGATGGAGTGGGCAATG<br>CCTCGGGAGATTGGCATTGCGATTCCACGTGGATGGGGGACAGAGTCGTCACCAAGTCCACCCGAACCTGGGTGCTGCC<br>CAGCTACAACAACCACCAGTACCGAGAGATCAAAAGCGGCTCCGTCGACGGAAGCAACGCCAACGCCTACTTTGGATA<br>CAGCACCCCCTGGGGGTACTTTGACTTTAACCGCTTCCACAGCCACTGGAGCCCCCGAGACTGGCAAAGACTCATCAAC<br>AACTACTGGGGCTTCAGACCCCGGTCCCTCAGAGTCAAAATCTTCAACATTCAAGTCAAAGAGGTCACGGTGCAGGACT<br>CCACCACCACCATCGCCAACAACCTCACCTCCACCGTCCAAGTGTTTACGGACGACGACTACCAGCTGCCCTACGTCGT<br>CGGCAACGGGACCGAGGGATGCCTGCCGGCCTTCCCTCCGCAGGTCTTTACGCTGCCGCAGTACGGTTACGCGACGCTG<br>AACCGCGACAACACAGAAAATCCCACCGAGAGGAGCAGCTTCTTCTGCCTAGAGTACTTTCCCAGCAAGATGCTGAGA<br>ACGGGCAACAACTTTGAGTTTACCTACAACTTTGAGGAGGTGCCCTTCCACTCCAGCTTCGCTCCCAGTCAGAACCTGTT<br>CAAGCTGGCCAACCCGCTGGTGGACCAGTACTTGTACCGCTTCGTGAGCACAAATAACACTGGCGGAGTCCAGTTCAAC<br>AAGAACCTGGCCGGGAGATACGCCAACACCTACAAAAACTGGTTCCCGGGGCCCATGGGCCGAACCCAGGGCTGGAAC<br>CTGGGCTCCGGGGTCAACCGCGCCAGTGTCAGCGCCTTCGCCACGACCAATAGGATGGAGCTCGAGGGCGCGAGTTAC<br>CAGGTGCCCCCGCAGCCGAACGGCATGACCAACAACCTCCAGGGCAGCAACACCTATGCCCTGGAGAACACTATGATC | 4 |

TABLE 1D-continued

Exemplary expression construct sequences, optionally comprising a payload and a cap gene.

| Description | Sequence | SEQ ID NO |
|---|---|---|
| | TTCAACAGCCAGCCGGCGAACCCGGGCACCACCGCCACGTACCTCGAGGGCAACATGCTCATCACCAGCGAGAGCGAG | |
| | ACGCAGCCGGTGAACCGCGTGGCGTACAACGTCGGCGGGCAGATGGCCACCAACAACCAGAGCTCCACCACTGCCCCC | |
| | GCGACCGGCACGTACAACCTCCAGGAAATCGTGCCCGGCAGCGTGTGGATGGAGAGGGACGTGTACCTCCAAGGACCC | |
| | ATCTGGGCCAAGATCCCAGAGACGGGGGCGCACTTTCACCCCTCTCCGGCCATGGGCGGATTCGGACTCAAACACCCAC | |
| | CGCCCATGATGCTCATCAAGAACACGCCTGTGCCCGGAAATATCACCAGCTTCTCGGACGTGCCCGTCAGCAGCTTCAT | |
| | CACCCAGTACAGCACCGGGCAGGTCACCGTGGAGATGGAGTGGGAGCTCAAGAAGGAAAACTCCAAGAGGTGGAACC | |
| | CAGAGATCCAGTACACAAACAACTACAACGACCCCCAGTTTGTGGACTTTGCCCCGGACAGCACCGGGGAATACAGAA | |
| | CCACCAGACCTATCGGAACCCGATACCTTACCCGACCCCTTTAATTGCTTGTTAATCAATAAACCGTTTAATTCGTTTCA | |
| | GTTGAACTTTGGTCTCTGCGTATTTCTTTCTTATCTAGTTTCCATATGCATGTAGATAAGTAGCATGGCGGGTTAATCATT | |
| | AACTAACCGGTACCTCTAGAACTATAGCTAGCGATGACCCTGCTGATTGGTTCGCTGACCATTTCCGGGTGCGGGACGG | |
| | CGTTACCAGAAACTCAGAAGGTTCGTCCAACCAAACCGACTCTGACGGCAGTTTACGAGAGAGATGATAGGGTCTGCTT | |
| | CAGTAAGCCAGATGCTACACAATTAGGCTTGTACATATTGTCGTTAGAACGCGGCTACAATTAATACATAACCTTATGT | |
| | ATCATACACATACGATTTAGGTGACACTATAGAATACACGGAATTAATTCTTGGCCACTCCCTCTCTGCGCGCTCGCTCG | |
| | CTCACTGAGGCCGCCCGGGCAAAGCCCGGGCGTCGGGCGACCTTTGGTCGCCCGGCCTCAGTGAGCGAGCGAGCGCGC | |
| | AGAGAGGGAGTGGCCAACTCCATCACTAGGGGTTCCTTACGTAGGACGTCCCCTGCAGGCAGGGAGGGGTGGAGTCGT | |
| | GACGTAAAGATCTGATATCATCGATCGCGATGCATTAATTAAGCGGCCGAGGCTCAGAGGCACACAGGAGTTTCTGGGC | |
| | TCACCCTGCCCCCTTCCAACCCCTCAGTTCCCATCCTCCAGCAGCTGTTTGTGTGCTGCCTCTGAAGTCCACACTGAACA | |
| | AACTTCAGCCTACTCATGTCCCTAAAATGGGCAAACATTGCAAGCAGCAAACAGCAAACACACAGCCCTCCCTGCCTGC | |
| | TGACCTTGGAGCTGGGGCAGAGGTCAGAGACCTCTCTGGGCCCATGCCACCTCCAACATCCACTCGACCCCTTGGAATT | |
| | TCGGTGGAGAGGAGCAGAGGTTGTCCTGGCGTGGTTTAGGTAGTGTGAGAGGGGTACCCGGGGATCTTGCTACCAGTG | |
| | GAACAGCCACTAAGGATTCTGCAGTGAGAGCAGAGGGCCAGCTAAGTGGTACTCTCCCAGAGACTGTCTGACTCACGC | |
| | CACCCCCTCCACCTTGGACACAGGACGCTGTGGTTTCTGAGCCAGGTACAATGACTCCTTTCGGTAAGTGCAGTGGAAG | |
| | CTGTACACTGCCCAGGCAAAGCGTCCGGGCAGCGTAGGCGGGCGACTCAGATCCCAGCCAGTGGACTTAGCCCCTGTTT | |
| | GCTCCTCCGATAACTGGGGTGACCTTGGTTAATATTCACCAGCAGCCTCCCCCGTTGCCCCTCTGGATCCACTGCTTAAA | |
| | TACGGACGAGGACAGGGCCCTGTCTCCTCAGCTTCAGGCACCACCACTGACCTGGGACAGTGAATGATCCCCCTGATCT | |
| | GCGGCCTCGACGGTATCGATAAGCTTGATATCGAATTCTAGTCGTCGACCACTTTCACAATCTGCTAGCAAAGGTTGCC | |
| | ACCATGCAGCGCGTGAACATGATTATGGCCGAGAGCCCTGGCCTGATCACCATCTGCCTGCTGGGCTACCTGCTGAGCG | |
| | CCGAGTGTACAGGTTTGTTTCCTTTTTTAAAATACATTGAGTATGCTTGCCTTTTAGATATAGAAATATCTGATGCTGTCT | |
| | TCTTCACTAAATTTTGATTACATGATTTGACAGCAATATTGAAGAGTCTAACAGCCAGCACGCAGGTTGGTAAGTACTG | |
| | GTrCTTTGTTAGCTAGGTTTTCTTCTTCTTCATTTTTAAAACTAAATAGATCGACAATGCTTATGATGCATTTATGTTTAAT | |
| | AAACACTGTTCAGTTCATGATTTGGTCATGTAATTCCTGTTAGAAAACATTCATCTCCTTGGTTTAAAAAAATTAAAAGT | |
| | GGGAAAACAAAGAAATAGCAGAATATAGTGAAAAAAAATAACCACATTATTTTTGTTTGGACTTACCACTTTGAAATCA | |
| | AAATGGGAAACAAAAGCACAAACAATGGCCTTATTTACACAAAAAGTCTGATTTTAAGATATATGACATTTCAAGGTTT | |
| | CAGAAGTATGTAATGAGGTGTGTCTCTAATTTTTTAAATTATATATCTTCAATTTAAAGTTTTAGTTAAAACATAAAGAT | |
| | TAACCTTTCATTAGCAAGCTGTTAGTTATCACCAAAGCTTTTCATGGATTAGGAAAAAATCATTTTGTCTCTATGTCAAA | |
| | CATCTTGGAGTTGATATTTGGGGAAACACAATACTCAGTTGAGTTCCCTAGGGGAGAAAAGCAAGCTTAAGAATTGACA | |
| | TAAAGAGTAGGAAGTTAGCTAATGCAACATATATCACTTTGTTTTTTCACAACTACAGTGACTTTATGTATTTCCCAGAG | |
| | GAAGGCATACAGGGAAGAAATTATCCCATTTGGACAAACAGCATGTTCTCACAGGAAGCATTTATCACACTTACTTGTC | |
| | AACTTTCTAGAATCAAATCTAGTAGCTGACAGTACCAGGATCAGGGGTGCCAACCCTAAGCACCCCCAGAAAGCTGACT | |
| | GGCCCTGTGGTTCCCACTCCAGACATGATGTCAGCTGTGAAATCGACGTCGCTGGACCATAATTAGGCTTCTGTTCTTCA | |
| | GGAGACATTTGTTCAAAGTCATTTGGGCAACCATATTCTGAAAACAGCCCAGCCAGGGTGATGGATCACTTTGCAAAGA | |
| | TCCTCAATGAGCTATTTTCAAGTGATGACAAAGTGTGAAGTTAACCGCTCATTTGAGAACTTTCTTTTTCATCCAAAGTA | |
| | AATTCAAATATGATTAGAAATCTGACCTTTTATTACTGGAATTCTCTTGACTAAAAGTAAAATTGAATTTTAATTCCTAA | |
| | ATCTCCATGTGTATACAGTACTGTGGGAACATCACAGATTTTGGCTCCATGCCCTAAAGAGAAATTGGCTTTCAGATTAT | |
| | TTGGATTAAAAACAAAGACTTTCTTAAGAGATGTAAAATTTTCATGATGTTTTCTTTTTTGCTAAAACTAAAGAATTATT | |
| | CTTTTACATTTCAGTGTTCCTGGACCACGAGAACGCCAACAAGATCCTGAACAGACCCAAGAGATACAACAGCGGCAA | |
| | GCTGGAAGAGTTCGTGCAGGGCAACCTGGAACGCGAGTGCATGGAAGAGAAGTGCAGCTTCGAAGAGGCCAGAGAGG | |
| | TGTTCGAGAACACCGAGAGAACCACCGAGTTCTGGAAGCAGTACGTGGACGGCGACCAGTGCGAGAGCAACCCTTGTC | |
| | TGAACGGCGGCAGCTGCAAGGACGACATCAACAGCTACGAGTGCTGGTGCCCCTTCGGCTTCGAGGGCAAGAACTGCG | |
| | AGCTGGACGTGACCTGCAACATCAAGAACGGCAGATGCGAGCAGTTCTGCAAGAACAGCGCCGACAACAAGGTCGTGT | |
| | GCTCCTGCACCGAGGGCTACAGACTGGCCGAGAACCAGAAGTCCTGCGAGCCCGCTGTGCCTTTCCCATGCGGAAGAGT | |
| | GTCCGTGTCCCAGACCAGCAAGCTGACCAGAGCCGAGACAGTGTTCCCCGACGTGGACTACGTGAACAGCACCGAGGC | |
| | CGAGACAATCCTGGACAACATCACCCAGAGCACCCAGTCCTTCAACGACTTCACCAGAGTCGTGGGCGGCGAGGATGC | |
| | TAAGCCTGGCCAGTTCCCGTGGCAGGTGGTGCTGAACGGAAAGGTGGACGCCTTCTGCGGCGGCTCCATCGTGAACGAG | |
| | AAGTGGATCGTGACAGCCGCCCACTGCGTGGAAACCGGCGTGAAGATCACAGTGGTGGCCGGCGAGCACAACATCGAG | |
| | GAAACCGAGCACACAGAGCAGAAAAGAAACGTGATCAGGATCATCCCCCACCACAACTACAACGCCGCCATCAACAAG | |
| | TACAACCACGATATCGCCCTGCTGGAACTGGACGAGCCCCTGGTGCTGAATAGCTACGTGACCCCCATCTGTATCGCCG | |
| | ACAAAGAGTACACCAACATCTTTCTGAAGTTCGGCAGCGGCTACGTGTCCGGCTGGGGCAGAGTGTTTCACAAGGGCAG | |
| | ATCCGCTCTGGTGCTGCAGTACCTGAGAGTGCCTCTGGTGGACAGAGCCACCTGTCTGAGAAGCACCAAGTTCACCATC | |
| | TACAACAACATGTTCTGCGCTGGCTTCCACGAGGGCGGCAGAGACTCTTGTCAGGGCGATTCTGGCGGCCCTCACGTGA | |
| | CAGAGGTGGAAGGCACCAGCTTTCTGACCGGCATCATCAGCTGGGGCGAGGAATGCGCCATGAAGGGGAAGTACGGCA | |
| | TCTACACCAAGGTGTCCAGATACGTGAACTGGATCAAAGAAAAGACCAAGCTGACATAATGAAAGATGGATTTCCAAG | |
| | GTTAATTCATTGGAATTGAAAATTAACAGCCCCCCCCCCCCCCCCCTGCAGATCTCGAGCCGAATTCCTGCAGCCCGGG | |
| | GGATCAGCCTCGACTGTGCCTTCTAGTTGCCAGCCATCTGTTGTTTGCCCCTCCCCCGTGCCTTCCTTGACCCTGGAAGGT | |
| | GCCACTCCCACTGTCCTTTCCTAATAAAATGAGGAAATTGCATCGCATTGTCTGAGTAGGTGTCATTCTATTCTGGGGGG | |
| | TGGGGTGGGGCAGGACAGCAAGGGGGAGGATTGGGAAGACAATAGCAGGCATGCTGGGGATGCGGTGGGCTCTATGG | |
| | CTTCTGAGGCGGAAAGAACCAGCTGGGGCTCGAGATCCACTAGACTAGTGTACACGCGTGATATCAGATCTGTTACGTA | |
| | AGGAACCCCTAGTGATGGAGTTGGCCACTCCCTCTCTGCGCGCTCGCTCGCTCACTGAGGCCGCCCGGGCAAAGCCCGG | |
| | GCGGCCTCAGTGAGCGAGCGAGCGCGCAGAGAGGGAGTGGCCAACTTTTTGCAAAAGCCTAGGCCTCCAAAAAAGCCT | |
| | CCTCACTACTTCTGGAATAGCTCAGAGGCCGAGGCGGCCTCGGCCTCTGCATAAATAAAAAAAATTAGTCAGCCATGGG | |
| | GCGGAGAATGGGCGGAACTGGGCGGAGTTAGGGGCGGGATGGGCGGAGTTAGGGGCGGGACTATGGTTGCTGACTAAT | |
| | TGAGATGCATGCTTTGCATACTTCTGCCTGCTGGGGAGCCTGGGGACTTTCCACACCTGGTTGCTGACTAATTGAGATGC | |
| | ATGCTTTGCATACTTCTGCCTGCTGGGGAGCCTGGGGACTTTCCACACCCTAACTGACACACATTCCACAGCTGCATTAA | |
| | TGAATCGGCCAACGCGCGGGGAGAGGCGGTTTGCGTATTGGGCGCTCTTCCGCTTCCTCGCTCACTGACTCGCTGCGCTC | |

TABLE 1D-continued

| Exemplary expression construct sequences, optionally comprising a payload and a cap gene. | | |
|---|---|---|
| Description | Sequence | SEQ ID NO |
| | GGTCGTTCGGCTGCGGCGAGCGGTATCAGCTCACTCAAAGGCGGTAATACGGTTATCCACAGAATCAGGGGATAACGC<br>AGGAAAGAACATGTGAGCAAAAGGCCAGCAAAAGGCCAGGAACCGTAAAAAGGCCGCGTTGCTGGCGTTTTTCCATAG<br>GCTCCGCCCCCCTGACGAGCATCACAAAAATCGACGCTCAAGTCAGAGGTGGCGAAACCCGACAGGACTATAAAGATA<br>CCAGGCGTTTCCCCCTGGAAGCTCCCTCGTGCGCTCTCCTGTTCCGACCCTGCCGCTTACCGGATACCTGTCCGCCTTTCT<br>CCCTTCGGGAAGCGTGGCGCTTTCTCATAGCTCACGCTGTAGGTATCTCAGTTCGGTGTAGGTCGTTCGCTCCAAGCTGG<br>GCTGTGTGCACGAACCCCCCGTTCAGCCCGACCGCTGCGCCTTATCCGGTAACTATCGTCTTGAGTCCAACCCGGTAAG<br>ACACGACTTATCGCCACTGGCAGCAGCCACTGGTAACAGGATTAGCAGAGCGAGGTATGTAGGCGGTGCTACAGAGTT<br>CTTGAAGTGGTGGCCTAACTACGGCTACACTAGAAGAACAGTATTTGGTATCTGCGCTCTGCTGAAGCCAGTTACCTTC<br>GGAAAAAGAGTTGGTAGCTCTTGATCCGGCAAACAAACCACCGCTGGTAGCGGTGGTTTTTTTGTTTGCAAGCAGCAGA<br>TTACGCGCAGAAAAAAAGGATCTCAAGAAGATCCTTTGATCTTTTCTACGGGGTCTGACGCTCAGTGGAACGAAAACTC<br>ACGTTAAGGGATTTTGGTCATGAGATTATCAAAAAGGATCTTCACCTAGATCCTTTTAAATTAAAAATGA | |
| Payload/Cap Plasmid Factor IX/ AAV6 | GATACCGCGAGACCCACGCTCACCGGCTCCAGATTTATCAGCAATAAACCAGCCAGCCGGAAGGGCCGAGCGCAGAAG<br>TGGTCCTGCAACTTTATCCGCCTCCATCCAGTCTATTAATTGTTGCCGGGAAGCTAGAGTAAGTAGTTCGCCAGTTAATA<br>GTTTGCGCAACGTTGTTGCCATTGCTACAGGCATCGTGGTGTCACGCTCGTCGTTTGGTATGGCTTCATTCAGCTCCGGT<br>TCCCAACGATCAAGGCGAGTTACATGATCCCCCATGTTGTGCAAAAAAGCGGTTAGCTCCTTCGGTCCTCCGATCGTTGT<br>CAGAAGTAAGTTGGCCGCAGTGTTATCACTCATGGTTATGGCAGCACTGCATAATTCTCTTACTGTCATGCCATCCGTAA<br>GATGCTTTTCTGTGACTGGTGAGTACTCAACCAAGTCATTCTGAGAATAGTGTATGCGGCGACCGAGTTGCTCTTGCCCG<br>GCGTCAATACGGGATAATACCGCGCCACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTGCACCCAACTGATCTTCAGCATCTTTT<br>ACTTTCACCAGCGTTTCTGGGTGAGCAAAAACAGGAAGGCAAAATGCCGCAAAAAAGGGAATAAGGGCGACACGGAA<br>ATGTTGAATACTCATACTCTTCCTTTTTCAATATTATTGAAGCATTTATCAGGGTTATTGTCTCATGAGCGGATACATATT<br>TGAATGTATTTAGAAAAATAAACAAATAGGGGTTCCGCGCACATTTCCCCGAAAAGTGCCACCTGACGTCTAAGAAACC<br>ATTATTATCATGACATTAACCTATAAAAATAGGCGTATCACGAGGCCCTTTCGTCTCGCGCGTTTCGGTGATGACGGTGA<br>AAACCTCTGACACATGCAGCTCCCGGAGACGGTCACAGCTTGTCTGTAAGCGGATGCCGGGAGCAGACAAGCCCGTCA<br>GGGCGCGTCAGCGGGTGTTGGCGGGTGTCGGGGCTGGCTTAACTATGCGGCATCAGAGCAGATTGTACTGAGAGTGCA<br>CCATTCGACGCTCTCCCTTATGCGACTCCTGCATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGGCCACGGGGCCTGCCACCATACCCACGCCGAA<br>ACAAGCGCTCATGAGCCCGAAGTGGCGAGCCCGATCTTCCCCATCGGTGATGTCGGCGATATAGGCGCCAGCAACCGC<br>ACCTGTGGCGCCGGTGGGTCACCAAGCAGGAAGTCAAAGACTTTTTCCGGTGGGCAAAGGATCACGTGGTTGAGGTGG<br>AGCATGAATTCTACGTCAAAAAGGGTGGAGCCAAGAAAAGACCCGCCCCCAGTGACGCAGATATAAGTGAGCCCAAAC<br>GGGTGCGCGAGTCAGTTGCGCAGCCATCGACGTCAGACGCGGAAGCTTCGATCAACTACGCAGACAGGTACCAAAACA<br>AATGTTCTCGTCACGTGGGCATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACCCGTTTCTGTCGTCAAAAAGG<br>CGTATCAGAAACTGTGCTACATTCATCATATCATGGGAAAGGTGCCAGACGCTTGCACTGCCTGCGATCTGGTCAATGT<br>GGATTTGGATGACTGCATCTTTGAACAATAAATGATTTAAATCAGGTATGGCTGCCGATGGTTATCTTCCAGATTGGCTC<br>GAGGACAACCTCTCTGAGGGCATTCGCGAGTGGTGGGACTTGAAACCTGGAGCCCCGAAACCCAAAGCCAACCAGCAA<br>AAGCAGGACGACGGCCGGGGTCTGGTGCTTCCTGGCTACAAGTACCTCGGACCCTTCAACGGACTCGACAAGGGGGAG<br>CCCGTCAACGCGGCGGATGCAGCGGCCCTCGAGCACGACAAGGCCTACGACCAGCAGCTCAAAGCGGGTGACAATCCG<br>TACCTGCGGTATAACCACGCCGACGCCGAGTTTCAGGAGCGTCTGCAAGAAGATACGTCTTTTGGGGGCAACCTCGGGC<br>GAGCAGTCTTCCAGGCCAAGAAGAGGGTTCTCGAACCTTTTGGTCTGGTTGAGGAAGGTGCTAAGACGGCTCCTGGAAA<br>GAAACGTCCGGTAGAGCAGTCGCCACAAGAGCCAGACTCCTCCTCGGGCATTGGCAAGACAGGCCAGCAGCCCGCTAA<br>AAAGAGACTCAATTTTGGTCAGACTGGCGACTCAGAGTCAGTCCCCGACCCACAACCTCTCGGAGAACCTCCAGCAACC<br>CCCGCTGCTGTGGGACCTACTACAATGGCTTCAGGCGGTGGCGCACCAATGGCAGACAATAACGAAGGCGCCGACGGA<br>GTGGGTAATGCCTCAGGAAATTGGCATTGCGATTCCACATGGCTGGGCGACAGAGTCATCACCACCAGCACCCGAACAT<br>GGGCCTTGCCCACCTATAACAACCACCTCTACAAGCAAATCTCCAGTGCTTCAACGGGGGCCAGCAACGACAACCACTA<br>CTTCGGCTACAGCACCCCCTGGGGGTATTTTGATTTCAACAGATTCCACTGCCATTTCTCACCACGTGACTGGCAGCGAC<br>TCATCAACAACAATTGGGGATTCCGGCCCAAGAGACTCAACTTCAAGCTCTTCAACATCCAAGTCAAGGAGGTCACGAC<br>GAATGATGGCGTCACGACCATCGCTAATAACCTTACCAGCACGGTTCAAGTCTTCTCGGACTCGGAGTACCAGTTGCCG<br>TACGTCCTCGGCTCTGCGCACCAGGGCTGCCTCCCTCCGTTCCCGGCGGACGTGTTCATGATTCCGCAGTACGGCTACCT<br>AACGCTCAACAATGGCAGCCAGGCAGTGGGACGGTCATCCTTTTACTGCCTGGAATATTTCCCATCGCAGATGCTGAGA<br>ACGGGCAATAACTTTACCTTCAGCTACACCTTCGAGGACGTGCCTTTCCACAGCAGCTACGCGCACAGCCAGAGCCTGG<br>ACCGGCTGATGAATCCTCTCATCGACCAGTACCTGTATTACCTGAACAGAACTCAGAATCAGTCCGGAAGTGCCCAAAA<br>CAAGGACTTGCTGTTTAGCCGGGGGTCTCCAGCTGGCATGTCTGTTCAGCCCAAAAACTGGCTACCTGGACCCTGTTACC<br>GGCAGCAGCGCGTTTCTAAAACAAAAACAGACAACAACAACAGCAACTTTACCTGGACTGGTGCTTCAAAATATAACC<br>TTAATGGGCGTGAATCTATAATCAACCCTGGCACTGCTATGGCCTCACACAAAGACGACGAAGACAAGTTCTTTCCCAT<br>GAGCGGTGTCATGATTTTTGGAAAGGAGAGCGCCGGAGCTTCAAACACTGCATTGGACAATGTCATGATCACAGACGA<br>AGAGGAAATCAAAGCCACTAACCCCGTGGCCACCGAAAGATTTGGGACTGTGGCAGTCAATCTCCAGAGCAGCAGCAC<br>AGACCCTGCGACCGGAGATGTGCATGTTATGGGAGCCTTACCTGGAATGGTGTGGCAAGACAGAGACGTATACCTGCA<br>GGGTCCTATTTGGGCCAAAATTCCTCACACGGATGGACACTTTCACCCGTCTCCTCTCATGGGCGGCTTTGGACTTAAGC<br>ACCCGCCTCCTCAGATCCTCATCAAAAACACGCCTGTTCCTGCGAATCCTCCGGCAGAGTTTTCGGCTACAAAGTTTGCT<br>TCATTCATCACCCAGTATTCCACAGGACAAGTGAGCGTGGAGATTGAATGGGAGCTGCAGAAAGAAAACAGCAAACGC<br>TGGAATCCCGAAGTGCAGTATACATCTAACTATGCAAAATCTGCCAACGTTGATTTCACTGTGGACAACAATGGACTTT<br>ATACTGAGCCTCGCCCCATTGGCACCCGTTACCTCACCCGTCCCCTGTAATTGCTTGTTAATCAATAAACCGTTTAATTC<br>GTTTCAGTTGAACTTTGGTCTCTGCGTATTTCTTTCTTATCTAGTTTCCATATGCATGTAGATAAGTAGCATGGCGGGTTA<br>ATCATTAACTAACCGGTACCTCTAGAACTATAGCTAGCGATGACCCTGCTGATTGGTTCGCTGACCATTTCCGGGTGCGG<br>GACGGCGTTACCAGAAACTCAGAAGGTTCGTCCAACCAAACCGACTCTGACGGCAGTTTACGAGAGAGATGATAGGGT<br>CTGCTTCAGTAAGCCAGATGCTACACAATTAGGCTTGTACATATTGTCGTTAGAACGCGGCTACAATTAATACATAACCT<br>TATGTATCATACACATACGATTTAGGTGACACTATAGAATACACGGAATTAATTCTTGGCCACTCCCTCTCTGCGCGCTC<br>GCTCGCTCACTGAGGCCGCCCGGGCAAAGCCCGGGCGTCGGGCGACCTTTGGTCGCCCGGCCTCAGTGAGCGAGCGAG<br>CGCGCAGAGAGGGAGTGGCCAACTCCATCACTAGGGGTTCCTTACGTAGGACGTCCCCTGCAGGCAGGGAGGGGTGGA<br>GTCGTGACGTAAAGATCTGATATCATCGATCGCGATGCATTAATTAAGCGGCCGAGGCTCAGAGGCACACAGGAGTTTC<br>TGGGCTCACCCTGCCCCCTTCCAACCCCTCAGTTCCCATCCTCCAGCAGCTGTTTGTGTGCTGCCTCTGAAGTCCACACT<br>GAACAAACTTCAGCCTACTCATGTCCCTAAAATGGGCAAACATTGCAAGCAGCAAACAGCAAACACACAGCCCTCCCT | 5 |

TABLE 1D-continued

Exemplary expression construct sequences, optionally comprising a payload and a cap gene.

| Description | Sequence | SEQ ID NO |
|---|---|---|
| | GCCTGCTGACCTTGGAGCTGGGGCAGAGGTCAGAGACCTCTCTGGGCCCATGCCACCTCCAACATCCACTCGACCCCTT<br>GGAATTTCGGTGGAGAGGAGCAGAGGTTGTCCTGGCGTGGTTTAGGTAGTGTGAGAGGGGTACCCGGGGATCTTGCTAC<br>CAGTGGAACAGCCACTAAGGATTCTGCAGTGAGAGCAGAGGGCCAGCTAAGTGGTACTCTCCCAGAGACTGTCTGACT<br>CACGCCACCCCCTCCACCTTGGACACAGGACGCTGTGGTTTCTGAGCCAGGTACAATGACTCCTTTCGGTAAGTGCAGT<br>GGAAGCTGTACACTGCCCAGGCAAAGCGTCCGGGCAGCGTAGGCGGGCGACTCAGATCCCAGCCAGTGGACTTAGCCC<br>CTGTTTGCTCCTCCGATAACTGGGGTGACCTTGGTTAATATTCACCAGCAGCCTCCCCCGTTGCCCCTCTGGATCCACTG<br>CTTAAATACGGACGAGGACAGGGCCCTGTCTCCTCAGCTTCAGGCACCACCACTGACCTGGGACAGTGAATGATCCCCC<br>TGATCTGCGGCCTCGACGGTATCGATAAGCTTGATATCGAATTCTAGTCGTCGACCACTTTCACAATCTGCTAGCAAAGG<br>TTGCCACCATGCAGCGCGTGAACATGATTATGGCCGAGAGCCCTGGCCTGATCACCATCTGCCTGCTGGGCTACCTGCT<br>GAGCGCCGAGTGTACAGGTTTGTTTCCTTTTTTAAAATACATTGAGTATGCTTGCCTTTTAGATATAGAAATATCTGATG<br>CTGTCTTCTTCACTAAATTTTGATTACATGATTTGACAGCAATATTGAAGAGTCTAACAGCCAGCACGCAGGTTGGTAAG<br>TACTGGTTCTTTGTTAGCTAGGTTTTCTTCTTCTTCATTTTTAAAACTAAATAGATCGACAATGCTTATGATGCATTTATG<br>TTTAATAAACACTGTTCAGTTCATGATTTGGTCATGTAATTCCTGTTAGAAAACATTCATCTCCTTGGTTTAAAAAAATT<br>AAAAGTGGGAAAACAAAGAAATAGCAGAATATAGTGAAAAAAAATAACCACATTATTTTTGTTTGGACTTACCACTTTG<br>AAATCAAAATGGGAAACAAAAGCACAAACAATGGCCTTATTTACACAAAAAGTCTGATTTTAAGATATATGACATTTCA<br>AGGTTTCAGAAGTATGTAATGAGGTGTGTCTCTAATTTTTTAAATTATATATCTTCAATTTAAAGTTTTAGTTAAAACATA<br>AAGATTAACCTTTCATTAGCAAGCTGTTAGTTATCACCAAAGCTTTTCATGGATTAGGAAAAAATCATTTTGTCTCTATG<br>TCAAACATCTTGGAGTTGATATTTGGGGAAACACAATACTCAGTTGAGTTCCCTAGGGGAGAAAAGCAAGCTTAAGAAT<br>TGACATAAAGAGTAGGAAGTTAGCTAATGCAACATATATCACTTTGTTTTTTCACAACTACAGTGACTTTATGTATTTCC<br>CAGAGGAAGGCATACAGGGAAGAAATTATCCCATTTGGACAAACAGCATGTTCTCACAGGAAGCATTTATCACACTTAC<br>TTGTCAACTTTCTAGAATCAAATCTAGTAGCTGACAGTACCAGGATCAGGGGTGCCAACCCTAAGCACCCCCAGAAAGC<br>TGACTGGCCCTGTGGTTCCCACTCCAGACATGATGTCAGCTGTGAAATCGACGTCGCTGGACCATAATTAGGCTTCTGTT<br>CTTCAGGAGACATTTGTTCAAAGTCATTTGGGCAACCATATTCTGAAAACAGCCCAGCCAGGGTGATGGATCACTTTGC<br>AAAGATCCTCAATGAGCTATTTTCAAGTGATGACAAAGTGTGAAGTTAACCGCTCATTTGAGAACTTTCTTTTTCATCCA<br>AAGTAAATTCAAATATGATTAGAAATCTGACCTTTTATTACTGGAATTCTCTTGACTAAAAGTAAAATTGAATTTTAATT<br>CCTAAATCTCCATGTGTATACAGTACTGTGGGAACATCACAGATTTTGGCTCCATGCCCTAAAGAGAAATTGGCTTTCAG<br>ATTATTTGGATTAAAAACAAAGACTTTCTTAAGAGATGTAAAATTTTCATGATGTTTTCTTTTTTGCTAAAACTAAAGAA<br>TTATTCTTTTACATTTCAGTGTTCCTGGACCACGAGAACGCCAACAAGATCCTGAACAGACCCAAGAGATACAACAGCG<br>GCAAGCTGGAAGAGTTCGTGCAGGGCAACCTGGAACGCGAGTGCATGGAAGAGAAGTGCAGCTTCGAAGAGGCCAGA<br>GAGGTGTTCGAGAACACCGAGAGAACCACCGAGTTCTGGAAGCAGTACGTGGACGGCGACCAGTGCGAGAGCAACCCT<br>TGTCTGAACGGCGGCAGCTGCAAGGACGACATCAACAGCTACGAGTGCTGGTGCCCCTTCGGCTTCGAGGGCAAGAAC<br>TGCGAGCTGGACGTGACCTGCAACATCAAGAACGGCAGATGCGAGCAGTTCTGCAAGAACAGCGCCGACAACAAGGTC<br>GTGTGCTCCTGCACCGAGGGCTACAGACTGGCCGAGAACCAGAAGTCCTGCGAGCCCGCTGTGCCTTTCCCATGCGGAA<br>GAGTGTCCGTGTCCCAGACCAGCAAGCTGACCAGAGCCGAGACAGTGTTCCCCGACGTGGACTACGTGAACAGCACCG<br>AGGCCGAGACAATCCTGGACAACATCACCCAGAGCACCCAGTCCTTCAACGACTTCACCAGAGTCGTGGGCGGCGAGG<br>ATGCTAAGCCTGGCCAGTTCCCGTGGCAGGTGGTGCTGAACGGAAAGGTGGACGCCTTCTGCGGCGGCTCCATCGTGAA<br>CGAGAAGTGGATCGTGACAGCCGCCCACTGCGTGGAAACCGGCGTGAAGATCACAGTGGTGGCCGGCGAGCACAACAT<br>CGAGGAAACCGAGCACACAGAGCAGAAAAGAAACGTGATCAGGATCATCCCCCACCACAACTACAACGCCGCCATCAA<br>CAAGTACAACCACGATATCGCCCTGCTGGAACTGGACGAGCCCCTGGTGCTGAATAGCTACGTGACCCCCATCTGTATC<br>GCCGACAAAGAGTACACCAACATCTTTCTGAAGTTCGGCAGCGGCTACGTGTCCGGCTGGGGCAGAGTGTTTCACAAGG<br>GCAGATCCGCTCTGGTGCTGCAGTACCTGAGAGTGCCTCTGGTGGACAGAGCCACCTGTCTGAGAAGCACCAAGTTCAC<br>CATCTACAACAACATGTTCTGCGCTGGCTTCCACGAGGGCGGCAGAGACTCTTGTCAGGGCGATTCTGGCGGCCCTCAC<br>GTGACAGAGGTGGAAGGCACCAGCTTTCTGACCGGCATCATCAGCTGGGGCGAGGAATGCGCCATGAAGGGGAAGTAC<br>GGCATCTACACCAAGGTGTCCAGATACGTGAACTGGATCAAAGAAAAGACCAAGCTGACATAATGAAAGATGGATTTC<br>CAAGGTTAATTCATTGGAATTGAAAATTAACAGCCCCCCCCCCCCCCCCCTGCAGATCTCGAGCCGAATTCCTGCAGCC<br>CGGGGGATCAGCCTCGACTGTGCCTTCTAGTTGCCAGCCATCTGTTGTTTGCCCCTCCCCCGTGCCTTCCTTGACCCTGG<br>AAGGTGCCACTCCCACTGTCCTTTCCTAATAAAATGAGGAAATTGCATCGCATTGTCTGAGTAGGTGTCATTCTATTCTG<br>GGGGGTGGGGTGGGGCAGGACAGCAAGGGGGAGGATTGGGAAGACAATAGCAGGCATGCTGGGGATGCGGTGGGCTC<br>TATGGCTTCTGAGGCGGAAAGAACCAGCTGGGGCTCGAGATCCACTAGACTAGTGTACACGCGTGATATCAGATCTGTT<br>ACGTAAGGAACCCCTAGTGATGGAGTTGGCCACTCCCTCTCTGCGCGCTCGCTCGCTCACTGAGGCCGCCCGGGCAAAG<br>CCCGGGCGGCCTCAGTGAGCGAGCGAGCGCGCAGAGAGGGAGTGGCCAACTTTTTGCAAAAGCCTAGGCCTCCAAAAA<br>AGCCTCCTCACTACTTCTGGAATAGCTCAGAGGCCGAGGCGGCCTCGGCCTCTGCATAAATAAAAAAAATTAGTCAGCC<br>ATGGGGCGGAGAATGGGCGGAACTGGGCGGAGTTAGGGGCGGGATGGGCGGAGTTAGGGGCGGGACTATGGTTGCTG<br>ACTAATTGAGATGCATGCTTTGCATACTTCTGCCTGCTGGGGAGCCTGGGGACTTTCCACACCTGGTTGCTGACTAATTG<br>AGATGCATGCTTTGCATACTTCTGCCTGCTGGGGAGCCTGGGGACTTTCCACACCCTAACTGACACACATTCCACAGCTG<br>CATTAATGAATCGGCCAACGCGCGGGGAGAGGCGGTTTGCGTATTGGGCGCTCTTCCGCTTCCTCGCTCACTGACTCGCT<br>GCGCTCGGTCGTTCGGCTGCGGCGAGCGGTATCAGCTCACTCAAAGGCGGTAATACGGTTATCCACAGAATCAGGGGAT<br>AACGCAGGAAAGAACATGTGAGCAAAAGGCCAGCAAAAGGCCAGGAACCGTAAAAAGGCCGCGTTGCTGGCGTTTTTC<br>CATAGGCTCCGCCCCCCTGACGAGCATCACAAAAATCGACGCTCAAGTCAGAGGTGGCGAAACCCGACAGGACTATAA<br>AGATACCAGGCGTTTCCCCCTGGAAGCTCCCTCGTGCGCTCTCCTGTTCCGACCCTGCCGCTTACCGGATACCTGTCCGC<br>CTTTCTCCCTTCGGGAAGCGTGGCGCTTTCTCATAGCTCACGCTGTAGGTATCTCAGTTCGGTGTAGGTCGTTCGCTCCA<br>AGCTGGGCTGTGTGCACGAACCCCCCGTTCAGCCCGACCGCTGCGCCTTATCCGGTAACTATCGTCTTGAGTCCAACCCG<br>GTAAGACACGACTTATCGCCACTGGCAGCAGCCACTGGTAACAGGATTAGCAGAGCGAGGTATGTAGGCGGTGCTACA<br>GAGTTCTTGAAGTGGTGGCCTAACTACGGCTACACTAGAAGAACAGTATTTGGTATCTGCGCTCTGCTGAAGCCAGTTA<br>CCTTCGGAAAAAGAGTTGGTAGCTCTTGATCCGGCAAACAAACCACCGCTGGTAGCGGTGGTTTTTTTGTTTGCAAGCA<br>GCAGATTACGCGCAGAAAAAAAGGATCTCAAGAAGATCCTTTGATCTTTTCTACGGGGTCTGACGCTCAGTGGAACGAA<br>AACTCACGTTAAGGGATTTTGGTCATGAGATTATCAAAAAGGATCTTCACCTAGATCCTTTTAAATTAAAAATGAAGTTT<br>TAAATCAATCTAAAGTATATATGAGTAAACTTGGTCTGACAGTTACCAATGCTTAATCAGTGAGGCACCTATCTCAGCG<br>ATCTGTCTATTTCGTTCATCCATAGTTGCCTGACTCCCCGTCGTGTAGATAACTACGATACGGGAGGGCTTACCATCTGG<br>CCCCAGTGCTGCAAT | |

TABLE 1D-continued

| Exemplary expression construct sequences, optionally comprising a payload and a cap gene. | | |
|---|---|---|
| Description | Sequence | SEQ ID NO |
| Payload/Cap Plasmid Factor IX/ AAV8 | GTATATATGAGTAAACTTGGTCTGACAGTTACCAATGCTTAATCAGTGAGGCACCTATCTCAGCGATCTGTCTATTTCGT<br>TCATCCATAGTTGCCTGACTCCCCGTCGTGTAGATAACTACGATACGGGAGGGCTTACCATCTGGCCCCAGTGCTGCAAT<br>GATACCGCGAGACCCACGCTCACCGGCTCCAGATTTATCAGCAATAAACCAGCCAGCCGGAAGGGCCGAGCGCAGAAG<br>TGGTCCTGCAACTTTATCCGCCTCCATCCAGTCTATTAATTGTTGCCGGGAAGCTAGAGTAAGTAGTTCGCCAGTTAATA<br>GTTTGCGCAACGTTGTTGCCATTGCTACAGGCATCGTGGTGTCACGCTCGTCGTTTGGTATGGCTTCATTCAGCTCCGGT<br>TCCCAACGATCAAGGCGAGTTACATGATCCCCCATGTTGTGCAAAAAAGCGGTTAGCTCCTTCGGTCCTCCGATCGTTGT<br>CAGAAGTAAGTTGGCCGCAGTGTTATCACTCATGGTTATGGCAGCACTGCATAATTCTCTTACTGTCATGCCATCCGTAA<br>GATGCTTTTCTGTGACTGGTGAGTACTCAACCAAGTCATTCTGAGAATAGTGTATGCGGCGACCGAGTTGCTCTTGCCCG<br>GCGTCAATACGGGATAATACCGCGCCACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTGCACCCAACTGATCTTCAGCATCTTTT<br>ACTTTCACCAGCGTTTCTGGGTGAGCAAAAACAGGAAGGCAAAATGCCGCAAAAAAGGGAATAAGGGCGACACGGAA<br>ATGTTGAATACTCATACTCTTCCTTTTTCAATATTATTGAAGCATTTATCAGGGTTATTGTCTCATGAGCGGATACATATT<br>TGAATGTATTTAGAAAAATAAACAAATAGGGGTTCCGCGCACATTTCCCCGAAAAGTGCCACCTGACGTCTAAGAAACC<br>ATTATTATCATGACATTAACCTATAAAAATAGGCGTATCACGAGGCCCTTTCGTCTCGCGCGTTTCGGTGATGACGGTGA<br>AAACCTCTGACACATGCAGCTCCCGGAGACGGTCACAGCTTGTCTGTAAGCGGATGCCGGGAGCAGACAAGCCCGTCA<br>GGGCGCGTCAGCGGGTGTTGGCGGGTGTCGGGGCTGGCTTAACTATGCGGCATCAGAGCAGATTGTACTGAGAGTGCA<br>CCATTCGACGCTCTCCCTTATGCGACTCCTGCATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGGCCACGGGGCCTGCCACCATACCCACGCCGAA<br>ACAAGCGCTCATGAGCCCGAAGTGGCGAGCCCGATCTTCCCCATCGGTGATGTCGGCGATATAGGCGCCAGCAACCGC<br>ACCTGTGGCGCCGGTGGGTCACCAAGCAGGAAGTCAAAGACTTTTTCCGGTGGGCAAAGGATCACGTGGTTGAGGTGG<br>AGCATGAATTCTACGTCAAAAAGGGTGGAGCCAAGAAAAGACCCGCCCCCAGTGACGCAGATATAAGTGAGCCCAAAC<br>GGGTGCGCGAGTCAGTTGCGCAGCCATCGACGTCAGACGCGGAAGCTTCGATCAACTACGCAGACAGGTACCAAAACA<br>AATGTTCTCGTCACGTGGGCATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACCCGTTTCTGTCGTCAAAAAGG<br>CGTATCAGAAACTGTGCTACATTCATCATATCATGGGAAAGGTGCCAGACGCTTGCACTGCCTGCGATCTGGTCAATGT<br>GGATTTGGATGACTGCATCTTTGAACAATAAATGATTTAAATCAGGTATGGCTGCCGATGGTTATCTTCCAGATTGGCTC<br>GAGGACAACCTCTCTGAGGGCATTCGCGAGTGGTGGGCGCTGAAACCTGGAGCCCCGAAGCCCAAAGCCAACCAGCAA<br>AAGCAGGACGACGGCCGGGGTCTGGTGCTTCCTGGCTACAAGTACCTCGGACCCTTCAACGGACTCGACAAGGGGGAG<br>CCCGTCAACGCGGCGGACGCAGCGGCCCTCGAGCACGACAAGGCCTACGACCAGCAGCTGCAGGCGGGTGACAATCCG<br>TACCTGCGGTATAACCACGCCGACGCCGAGTTTCAGGAGCGTCTGCAAGAAGATACGTCTTTTGGGGGCAACCTCGGGC<br>GAGCAGTCTTCCAGGCCAAGAAGCGGGTTCTCGAACCTCTCGGTCTGGTTGAGGAAGGCGCTAAGACGGCTCCTGGAA<br>AGAAGAGACCGGTAGAGCCATCACCCCAGCGTTCTCCAGACTCCTCTACGGGCATCGGCAAGAAAGGCCAACAGCCCG<br>CCAGAAAAAGACTCAATTTTGGTCAGACTGGCGACTCAGAGTCAGTTCCAGACCCTCAACCTCTCGGAGAACCTCCAGC<br>AGCGCCCTCTGGTGTGGGACCTAATACAATGGCTGCAGGCGGTGGCGCACCAATGGCAGACAATAACGAAGGCGCCGA<br>CGGAGTGGGTAGTTCCTCGGGAAATTGGCATTGCGATTCCACATGGCTGGGCGACAGAGTCATCACCACCAGCACCCGA<br>ACCTGGGCCCTGCCCACCTACAACAACCACCTCTACAAGCAAATCTCCAACGGGACATCGGGAGGAGCCACCAACGAC<br>AACACCTACTTCGGCTACAGCACCCCCTGGGGGTATTTTGACTTTAACAGATTCCACTGCCACTTTTCACCACGTGACTG<br>GCAGCGACTCATCAACAACAACTGGGGATTCCGGCCCAAGAGACTCAGCTTCAAGCTCTTCAACATCCAGGTCAAGGA<br>GGTCACGCAGAATGAAGGCACCAAGACCATCGCCAATAACCTCACCAGCACCATCCAGGTGTTTACGGACTCGGAGTA<br>CCAGCTGCCGTACGTTCTCGGCTCTGCCCACCAGGGCTGCCTGCCTCCGTTCCCGGCGGACGTGTTCATGATTCCCCAGT<br>ACGGCTACCTAACACTCAACAACGGTAGTCAGGCCGTGGGACGCTCCTCCTTCTACTGCCTGGAATACTTTCCTTCGCAG<br>ATGCTGAGAACCGGCAACAACTTCCAGTTTACTTACACCTTCGAGGACGTGCCTTTCCACAGCAGCTACGCCCACAGCC<br>AGAGCTTGGACCGGCTGATGAATCCTCTGATTGACCAGTACCTGTACTACTTGTCTCGGACTCAAACAACAGGAGGCAC<br>GGCAAATACGCAGACTCTGGGCTTCAGCCAAGGTGGGCCTAATACAATGGCCAATCAGGCAAAGAACTGGCTGCCAGG<br>ACCCTGTTACCGCCAACAACGCGTCTCAACGACAACCGGGCAAAACAACAATAGCAACTTTGCCTGGACTGCTGGGACC<br>AAATACCATCTGAATGGAAGAAATTCATTGGCTAATCCTGGCATCGCTATGGCAACACACAAAGACGACGAGGAGCGT<br>TTTTTTCCCAGTAACGGGATCCTGATTTTTGGCAAACAAAATGCTGCCAGAGACAATGCGGATTACAGCGATGTCATGC<br>TCACCAGCGAGGAAGAAATCAAAACCACTAACCCTGTGGCTACAGAGGAATACGGTATCGTGGCAGATAACTTGCAGC<br>AGCAAAACACGGCTCCTCAAATTGGAACTGTCAACAGCCAGGGGGCCTTACCCGGTATGGTCTGGCAGAACCGGGACG<br>TGTACCTGCAGGGTCCCATCTGGGCCAAGATTCCTCACACGGACGGCAACTTCCACCCGTCTCCGCTGATGGGCGGCTTT<br>GGCCTGAAACATCCTCCGCCTCAGATCCTGATCAAGAACACGCCTGTACCTGCGGATCCTCCGACCACCTTCAACCAGT<br>CAAAGCTGAACTCTTTCATCACGCAATACAGCACCGGACAGGTCAGCGTGGAAATTGAATGGGAGCTGCAGAAGGAAA<br>ACAGCAAGCGCTGGAACCCCGAGATCCAGTACACCTCCAACTACTACAAATCTACAAGTGTGGACTTTGCTGTTAATAC<br>AGAAGGCGTGTACTCTGAACCCCGCCCCATTGGCACCCGTTACCTCACCCGTAATCTGTAATTGCTTGTTAATCAATAAA<br>CCGTTTAATTCGTTTCAGTTGAACTTTGGTCTCTGCGTATTTCTTTCTTATCTAGTTTCCATATGCATGTAGATAAGTAGC<br>ATGGCGGGTTAATCATTAACTAACCGGTACCTCTAGAACTATAGCTAGCGATGACCCTGCTGATTGGTTCGCTGACCATT<br>TCCGGGTGCGGGACGGCGTTACCAGAAACTCAGAAGGTTCGTCCAACCAAACCGACTCTGACGGCAGTTTACGAGAGA<br>GATGATAGGGTCTGCTTCAGTAAGCCAGATGCTACACAATTAGGCTTGTACATATTGTCGTTAGAACGCGGCTACAATT<br>AATACATAACCTTATGTATCATACACATACGATTTAGGTGACACTATAGAATACACGGAATTAATTCTTGGCCACTCCCT<br>CTCTGCGCGCTCGCTCGCTCACTGAGGCCGCCCGGGCAAAGCCCGGGCGTCGGGCGACCTTTGGTCGCCCGGCCTCAGT<br>GAGCGAGCGAGCGCGCAGAGAGGGAGTGGCCAACTCCATCACTAGGGGTTCCTTACGTAGGACGTCCCCTGCAGGCAG<br>GGAGGGGTGGAGTCGTGACGTAAAGATCTGATATCATCGATCGCGATGCATTAATTAAGCGGCCGAGGCTCAGAGGCA<br>CACAGGAGTTTCTGGGCTCACCCTGCCCCCTTCCAACCCCTCAGTTCCCATCCTCCAGCAGCTGTTTGTGTGCTGCCTCTG<br>AAGTCCACACTGAACAAACTTCAGCCTACTCATGTCCCTAAAATGGGCAAACATTGCAAGCAGCAAACAGCAAACACA<br>CAGCCCTCCCTGCCTGCTGACCTTGGAGCTGGGGCAGAGGTCAGAGACCTCTCTGGGCCCATGCCACCTCCAACATCCA<br>CTCGACCCCTTGGAATTTCGGTGGAGAGGAGCAGAGGTTGTCCTGGCGTGGTTTAGGTAGTGTGAGAGGGGTACCCGGG<br>GATCTTGCTACCAGTGGAACAGCCACTAAGGATTCTGCAGTGAGAGCAGAGGGCCAGCTAAGTGGTACTCTCCCAGAG<br>ACTGTCTGACTCACGCCACCCCCTCCACCTTGGACACAGGACGCTGTGGTTTCTGAGCCAGGTACAATGACTCCTTTCGG<br>TAAGTGCAGTGGAAGCTGTACACTGCCCAGGCAAAGCGTCCGGGCAGCGTAGGCGGGCGACTCAGATCCCAGCCAGTG<br>GACTTAGCCCCTGTTTGCTCCTCCGATAACTGGGGTGACCTTGGTTAATATTCACCAGCAGCCTCCCCCGTTGCCCCTCT<br>GGATCCACTGCTTAAATACGGACGAGGACAGGGCCCTGTCTCCTCAGCTTCAGGCACCACCACTGACCTGGGACAGTGA<br>ATGATCCCCCTGATCTGCGGCCTCGACGGTATCGATAAGCTTGATATCGAATTCTAGTCGTCGACCACTTTCACAATCTG<br>CTAGCAAAGGTTGCCACCATGCAGCGCGTGAACATGATTATGGCCGAGAGCCCTGGCCTGATCACCATCTGCCTGCTGG | 6 |

TABLE 1D-continued

Exemplary expression construct sequences, optionally comprising a payload and a cap gene.

| Description | Sequence | SEQ ID NO |
|---|---|---|
| | GCTACCTGCTGAGCGCCGAGTGTACAGGTTTGTTTCCTTTTTAAAATACATTGAGTATGCTTGCCTTTTAGATATAGAA<br>ATATCTGATGCTGTCTTCTTCACTAAATTTTGATTACATGATTTGACAGCAATATTGAAGAGTCTAACAGCCAGCACGCA<br>GGTTGGTAAGTACTGGTTCTTTGTTAGCTAGGTTTTCTTCTTCTTCATTTTTAAAACTAAATAGATCGACAATGCTTATGA<br>TGCATTTATGTTTAATAAACACTGTTCAGTTCATGATTTGGTCATGTAATTCCTGTTAGAAAACATTCATCTCCTTGGTTT<br>AAAAAAATTAAAAGTGGGAAAACAAAGAAATAGCAGAATATAGTGAAAAAAAATAACCACATTATTTTTGTTTGGACT<br>TACCACTTTGAAATCAAAATGGGAAACAAAAGCACAAACAATGGCCTTATTTACACAAAAAGTCTGATTTTAAGATATA<br>TGACATTTCAAGGTTTCAGAAGTATGTAATGAGGTGTGTCTCTAATTTTTTAAATTATATATCTTCAATTTAAAGTTTTAG<br>TTAAAACATAAAGATTAACCTTTCATTAGCAAGCTGTTAGTTATCACCAAAGCTTTTCATGGATTAGGAAAAAATCATTT<br>TGTCTCTATGTCAAACATCTTGGAGTTGATATTTGGGGAAACACAATACTCAGTTGAGTTCCCTAGGGGAGAAAAGCAA<br>GCTTAAGAATTGACATAAAGAGTAGGAAGTTAGCTAATGCAACATATATCACTTTGTTTTTTCACAACTACAGTGACTTT<br>ATGTATTTCCCAGAGGAAGGCATACAGGGAAGAAATTATCCCATTTGGACAAACAGCATGTTCTCACAGGAAGCATTTA<br>TCACACTTACTTGTCAACTTTCTAGAATCAAATCTAGTAGCTGACAGTACCAGGATCAGGGGTGCCAACCCTAAGCACC<br>CCCAGAAAGCTGACTGGCCCTGTGGTTCCCACTCCAGACATGATGTCAGCTGTGAAATCGACGTCGCTGGACCATAATT<br>AGGCTTCTGTTCTTCAGGAGACATTTGTTCAAAGTCATTTGGGCAACCATATTCTGAAAACAGCCCAGCCAGGGTGATG<br>GATCACTTTGCAAAGATCCTCAATGAGCTATTTTCAAGTGATGACAAAGTGTGAAGTTAACCGCTCATTTGAGAACTTTC<br>TTTTTCATCCAAAGTAAATTCAAATATGATTAGAAATCTGACCTTTTATTACTGGAATTCTCTTGACTAAAAGTAAAATT<br>GAATTTTAATTCCTAAATCTCCATGTGTATACAGTACTGTGGGAACATCACAGATTTTGGCTCCATGCCCTAAAGAGAAA<br>TTGGCTTTCAGATTATTTGGATTAAAAACAAAGACTTTCTTAAGAGATGTAAAATTTTCATGATGTTTTCTTTTTTGCTAA<br>AACTAAAGAATTATTCTTTTACATTTCAGTGTTCCTGGACCACGAGAACGCCAACAAGATCCTGAACAGACCCAAGAGA<br>TACAACAGCGGCAAGCTGGAAGAGTTCGTGCAGGGCAACCTGGAACGCGAGTGCATGGAAGAGAAGTGCAGCTTCGAA<br>GAGGCCAGAGAGGTGTTCGAGAACACCGAGAGAACCACCGAGTTCTGGAAGCAGTACGTGGACGGCGACCAGTGCGA<br>GAGCAACCCTTGTCTGAACGGCGGCAGCTGCAAGGACGACATCAACAGCTACGAGTGCTGGTGCCCCTTCGGCTTCGAG<br>GGCAAGAACTGCGAGCTGGACGTGACCTGCAACATCAAGAACGGCAGATGCGAGCAGTTCTGCAAGAACAGCGCCGAC<br>AACAAGGTCGTGTGCTCCTGCACCGAGGGCTACAGACTGGCCGAGAACCAGAAGTCCTGCGAGCCCGCTGTGCCTTTCC<br>CATGCGGAAGAGTGTCCGTGTCCCAGACCAGCAAGCTGACCAGAGCCGAGACAGTGTTCCCCGACGTGGACTACGTGA<br>ACAGCACCGAGGCCGAGACAATCCTGGACAACATCACCCAGAGCACCCAGTCCTTCAACGACTTCACCAGAGTCGTGG<br>GCGGCGAGGATGCTAAGCCTGGCCAGTTCCCGTGGCAGGTGGTGCTGAACGGAAAGGTGGACGCCTTCTGCGGCGGCT<br>CCATCGTGAACGAGAAGTGGATCGTGACAGCCGCCCACTGCGTGGAAACCGGCGTGAAGATCACAGTGGTGGCCGGCG<br>AGCACAACATCGAGGAAACCGAGCACACAGAGCAGAAAAGAAACGTGATCAGGATCATCCCCCACCACAACTACAAC<br>GCCGCCATCAACAAGTACAACCACGATATCGCCCTGCTGGAACTGGACGAGCCCCTGGTGCTGAATAGCTACGTGACCC<br>CCATCTGTATCGCCGACAAAGAGTACACCAACATCTTTCTGAAGTTCGGCAGCGGCTACGTGTCCGGCTGGGGCAGAGT<br>GTTTCACAAGGGCAGATCCGCTCTGGTGCTGCAGTACCTGAGAGTGCCTCTGGTGGACAGAGCCACCTGTCTGAGAAGC<br>ACCAAGTTCACCATCTACAACAACATGTTCTGCGCTGGCTTCCACGAGGGCGGCAGAGACTCTTGTCAGGGCGATTCTG<br>GCGGCCCTCACGTGACAGAGGTGGAAGGCACCAGCTTTCTGACCGGCATCATCAGCTGGGGCGAGGAATGCGCCATGA<br>AGGGGAAGTACGGCATCTACACCAAGGTGTCCAGATACGTGAACTGGATCAAAGAAAAGACCAAGCTGACATAATGAA<br>AGATGGATTTCCAAGGTTAATTCATTGGAATTGAAAATTAACAGCCCCCCCCCCCCCCCCCTGCAGATCTCGAGCCGAA<br>TTCCTGCAGCCCGGGGGATCAGCCTCGACTGTGCCTTCTAGTTGCCAGCCATCTGTTGTTTGCCCCTCCCCCGTGCCTTCC<br>TTGACCCTGGAAGGTGCCACTCCCACTGTCCTTTCCTAATAAAATGAGGAAATTGCATCGCATTGTCTGAGTAGGTGTCA<br>TTCTATTCTGGGGGGTGGGGTGGGGCAGGACAGCAAGGGGGAGGATTGGGAAGACAATAGCAGGCATGCTGGGGATGC<br>GGTGGGCTCTATGGCTTCTGAGGCGGAAAGAACCAGCTGGGGCTCGAGATCCACTAGACTAGTGTACACGCGTGATATC<br>AGATCTGTTACGTAAGGAACCCCTAGTGATGGAGTTGGCCACTCCCTCTCTGCGCGCTCGCTCGCTCACTGAGGCCGCCC<br>GGGCAAAGCCCGGGCGGCCTCAGTGAGCGAGCGAGCGCGCAGAGAGGGAGTGGCCAACTTTTTGCAAAAGCCTAGGCC<br>TCCAAAAAAGCCTCCTCACTACTTCTGGAATAGCTCAGAGGCCGAGGCGGCCTCGGCCTCTGCATAAATAAAAAAAATT<br>AGTCAGCCATGGGGCGGAGAATGGGCGGAACTGGGCGGAGTTAGGGGCGGGATGGGCGGAGTTAGGGGCGGGACTAT<br>GGTTGCTGACTAATTGAGATGCATGCTTTGCATACTTCTGCCTGCTGGGGAGCCTGGGGACTTTCCACACCTGGTTGCTG<br>ACTAATTGAGATGCATGCTTTGCATACTTCTGCCTGCTGGGGAGCCTGGGGACTTTCCACACCCTAACTGACACACATTC<br>CACAGCTGCATTAATGAATCGGCCAACGCGCGGGGAGAGGCGGTTTGCGTATTGGGCGCTCTTCCGCTTCCTCGCTCAC<br>TGACTCGCTGCGCTCGGTCGTTCGGCTGCGGCGAGCGGTATCAGCTCACTCAAAGGCGGTAATACGGTTATCCACAGAA<br>TCAGGGGATAACGCAGGAAAGAACATGTGAGCAAAAGGCCAGCAAAAGGCCAGGAACCGTAAAAAGGCCGCGTTGCT<br>GGCGTTTTTCCATAGGCTCCGCCCCCCTGACGAGCATCACAAAAATCGACGCTCAAGTCAGAGGTGGCGAAACCCGACA<br>GGACTATAAAGATACCAGGCGTTTCCCCCTGGAAGCTCCCTCGTGCGCTCTCCTGTTCCGACCCTGCCGCTTACCGGATA<br>CCTGTCCGCCTTTCTCCCTTCGGGAAGCGTGGCGCTTTCTCATAGCTCACGCTGTAGGTATCTCAGTTCGGTGTAGGTCG<br>TTCGCTCCAAGCTGGGCTGTGTGCACGAACCCCCCGTTCAGCCCGACCGCTGCGCCTTATCCGGTAACTATCGTCTTGAG<br>TCCAACCCGGTAAGACACGACTTATCGCCACTGGCAGCAGCCACTGGTAACAGGATTAGCAGAGCGAGGTATGTAGGC<br>GGTGCTACAGAGTTCTTGAAGTGGTGGCCTAACTACGGCTACACTAGAAGAACAGTATTTGGTATCTGCGCTCTGCTGA<br>AGCCAGTTACCTTCGGAAAAAGAGTTGGTAGCTCTTGATCCGGCAAACAAACCACCGCTGGTAGCGGTGGTTTTTTTGT<br>TTGCAAGCAGCAGATTACGCGCAGAAAAAAAGGATCTCAAGAAGATCCTTTGATCTTTTCTACGGGGTCTGACGCTCAG<br>TGGAACGAAAACTCACGTTAAGGGATTTTGGTCATGAGATTATCAAAAAGGATCTTCACCTAGATCCTTTTAAATTAAA<br>AATGAAGTTTTAAATCAATCTAAA | |
| Payload/Cap Plasmid Factor IX/ AAV9 | GTATATATGAGTAAACTTGGTCTGACAGTTACCAATGCTTAATCAGTGAGGCACCTATCTCAGCGATCTGTCTATTTCGT<br>TCATCCATAGTTGCCTGACTCCCCGTCGTGTAGATAACTACGATACGGGAGGGCTTACCATCTGGCCCCAGTGCTGCAAT<br>GATACCGCGAGACCCACGCTCACCGGCTCCAGATTTATCAGCAATAAACCAGCCAGCCGGAAGGGCCGAGCGCAGAAG<br>TGGTCCTGCAACTTTATCCGCCTCCATCCAGTCTATTAATTGTTGCCGGGAAGCTAGAGTAAGTAGTTCGCCAGTTAATA<br>GTTTGCGCAACGTTGTTGCCATTGCTACAGGCATCGTGGTGTCACGCTCGTCGTTTGGTATGGCTTCATTCAGCTCCGGT<br>TCCCAACGATCAAGGCGAGTTACATGATCCCCCATGTTGTGCAAAAAAGCGGTTAGCTCCTTCGGTCCTCCGATCGTTGT<br>CAGAAGTAAGTTGGCCGCAGTGTTATCACTCATGGTTATGGCAGCACTGCATAATTCTCTTACTGTCATGCCATCCGTAA<br>GATGCTTTTCTGTGACTGGTGAGTACTCAACCAAGTCATTCTGAGAATAGTGTATGCGGCGACCGAGTTGCTCTTGCCCG<br>GCGTCAATACGGGATAATACCGCGCCACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTGCACCCAACTGATCTTCAGCATCTTTT<br>ACTTTCACCAGCGTTTCTGGGTGAGCAAAAACAGGAAGGCAAAATGCCGCAAAAAAGGGAATAAGGGCGACACGGAA<br>ATGTTGAATACTCATACTCTTCCTTTTTCAATATTATTGAAGCATTTATCAGGGTTATTGTCTCATGAGCGGATACATATT<br>TGAATGTATTTAGAAAAATAAACAAATAGGGGTTCCGCGCACATTTCCCCGAAAAGTGCCACCTGACGTCTAAGAAACC<br>ATTATTATCATGACATTAACCTATAAAAATAGGCGTATCACGAGGCCCTTTCGTCTCGCGCGTTTCGGTGATGACGGTGA | 7 |

TABLE 1D-continued

Exemplary expression construct sequences, optionally comprising a payload and a cap gene.

| Description | Sequence | SEQ ID NO |
|---|---|---|
| | AAACCTCTGACACATGCAGCTCCCGGAGACGGTCACAGCTTGTCTGTAAGCGGATGCCGGGAGCAGACAAGCCCGTCA<br>GGGCGCGTCAGCGGGTGTTGGCGGGTGTCGGGGCTGGCTTAACTATGCGGCATCAGAGCAGATTGTACTGAGAGTGCA<br>CCATTCGACGCTCTCCCTTATGCGACTCCTGCATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGGCCACGGGGCCTGCCACCATACCCACGCCGAA<br>ACAAGCGCTCATGAGCCCGAAGTGGCGAGCCCGATCTTCCCCATCGGTGATGTCGGCGATATAGGCGCCAGCAACCGC<br>ACCTGTGGCGCCGGTGGGTCACCAAGCAGGAAGTCAAAGACTTTTTCCGGTGGGCAAAGGATCACGTGGTTGAGGTGG<br>AGCATGAATTCTACGTCAAAAAGGGTGGAGCCAAGAAAAGACCCGCCCCCAGTGACGCAGATATAAGTGAGCCCAAAC<br>GGGTGCGCGAGTCAGTTGCGCAGCCATCGACGTCAGACGCGGAAGCTTCGATCAACTACGCAGACAGGTACCAAAACA<br>AATGTTCTCGTCACGTGGGCATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACCCGTTTCTGTCGTCAAAAAGG<br>CGTATCAGAAACTGTGCTACATTCATCATATCATGGGAAAGGTGCCAGTAACGCTTGCACTGCCTGCGATCTGGTCAAT<br>GTGGATTTGGATGACTGCATCTTTGAACAATAAATGATTTAAATCAGGTATGGCTGCCGATGGTTATCTTCCAGATTGGC<br>TCGAGGACAACCTTAGTGAAGGAATTCGCGAGTGGTGGGCTTTGAAACCTGGAGCCCCTCAACCCAAGGCAAATCAAC<br>AACATCAAGACAACGCTCGAGGTCTTGTGCTTCCGGGTTACAAATACCTTGGACCCGGCAACGGACTCGACAAGGGGG<br>AGCCGGTCAACGCAGCAGACGCGGCGGCCCTCGAGCACGACAAGGCCTACGACCAGCAGCTCAAGGCCGGAGACAAC<br>CCGTACCTCAAGTACAACCACGCCGACGCCGAGTTCCAGGAGCGGCTCAAAGAAGATACGTCTTTTGGGGGCAACCTCG<br>GGCGAGCAGTCTTCCAGGCCAAAAAGAGGCTTCTTGAACCTCTTGGTCTGGTTGAGGAAGCGGCTAAGACGGCTCCTGG<br>AAAGAAGAGGCCTGTAGAGCAGTCTCCTCAGGAACCGGACTCCTCCGCGGGTATTGGCAAATCGGGTGCACAGCCCGC<br>TAAAAAGAGACTCAATTTCGGTCAGACTGGCGACACAGAGTCAGTCCCAGACCCTCAACCAATCGGAGAACCTCCCGC<br>AGCCCCCTCAGGTGTGGGATCTCTTACAATGGCTTCAGGTGGTGGCGCACCAGTGGCAGACAATAACGAAGGTGCCGAT<br>GGAGTGGGTAGTTCCTCGGGAAATTGGCATTGCGATTCCCAATGGCTGGGGGACAGAGTCATCACCACCAGCACCCGA<br>ACCTGGGCCCTGCCCACCTACAACAATCACCTCTACAAGCAAATCTCCAACAGCACATCTGGAGGATCTTCAAATGACA<br>ACGCCTACTTCGGCTACAGCACCCCCTGGGGGTATTTTGACTTCAACAGATTCCACTGCCACTTCTCACCACGTGACTGG<br>CAGCGACTCATCAACAACAACTGGGGATTCCGGCCTAAGCGACTCAACTTCAAGCTCTTCAACATTCAGGTCAAAGAGG<br>TTACGGACAACAATGGAGTCAAGACCATCGCCAATAACCTTACCAGCACGGTCCAGGTCTTCACGGACTCAGACTATCA<br>GCTCCCGTACGTGCTCGGGTCGGCTCACGAGGGCTGCCTCCCGCCGTTCCCAGCGGACGTTTTCATGATTCCTCAGTACG<br>GGTATCTGACGCTTAATGATGGAAGCCAGGCCGTGGGTCGTTCGTCCTTTTACTGCCTGGAATATTTCCCGTCGCAAATG<br>CTAAGAACGGGTAACAACTTCCAGTTCAGCTACGAGTTTGAGAACGTACCTTTCCATAGCAGCTACGCTCACAGCCAAA<br>GCCTGGACCGACTAATGAATCCACTCATCGACCAATACTTGTACTATCTCTCAAAGACTATTAACGGTTCTGGACAGAA<br>TCAACAAACGCTAAAATTCAGTGTGGCCGGACCCAGCAACATGGCTGTCCAGGGAAGAAACTACATACCTGGACCCAG<br>CTACCGACAACAACGTGTCTCAACCACTGTGACTCAAAACAACAACAGCGAATTTGCTTGGCCTGGAGCTTCTTCTTGG<br>GCTCTCAATGGACGTAATAGCTTGATGAATCCTGGACCTGCTATGGCCAGCCACAAAGAAGGAGAGGACCGTTTCTTTC<br>CTTTGTCTGGATCTTTAATTTTTGGCAAACAAGGAACTGGAAGAGACAACGTGGATGCGGACAAAGTCATGATAACCAA<br>CGAAGAAGAAATTAAAACTACTAACCCGGTAGCAACGGAGTCCTATGGACAAGTGGCCACAAACCACCAGAGTGCCCA<br>AGCACAGGCGCAGACCGGCTGGGTTCAAAACCAAGGAATACTTCCGGGTATGGTTTGGCAGGACAGAGATGTGTACCT<br>GCAAGGACCCATTTGGGCCAAAATTCCTCACACGGACGGCAACTTTCACCCTTCTCCGCTGATGGGAGGGTTTGGAATG<br>AAGCACCCGCCTCCTCAGATCCTCATCAAAAACACACCTGTACCTGCGGATCCTCCAACGGCCTTCAACAAGGACAAGC<br>TGAACTCTTTCATCACCCAGTATTCTACTGGCCAAGTCAGCGTGGAGATCGAGTGGGAGCTGCAGAAGGAAAACAGCA<br>AGCGCTGGAACCCGGAGATCCAGTACACTTCCAACTATTACAAGTCTAATAATGTTGAATTTGCTGTTAATACTGGTGTA<br>TATAGTGAACCCCGCCCCATTGGCACCAGATACCTGACTCGTAATCTGTAATTGCCTGTTAATCAATAAACCGGTTGATT<br>CGTTTCAGTTGAACTTTGGTCTCTGCGAAGGGCGAATTCGTTTAAACCTGCAGGACTAACCGGTACCTCTAGAACTATAG<br>CTAGCGATGACCCTGCTGATTGGTTCGCTGACCATTTCCGGGTGCGGGACGGCGTTACCAGAAACTCAGAAGGTTCGTC<br>CAACCAAACCGACTCTGACGGCAGTTTACGAGAGAGATGATAGGGTCTGCTTCAGTAAGCCAGATGCTACACAATTAG<br>GCTTGTACATATTGTCGTTAGAACGCGGCTACAATTAATACATAACCTTATGTATCATACACATACGATTTAGGTGACAC<br>TATAGAATACACGGAATTAATTCTTGGCCACTCCCTCTCTGCGCGCTCGCTCGCTCACTGAGGCCGCCCGGGCAAAGCC<br>CGGGCGTCGGGCGACCTTTGGTCGCCCGGCCTCAGTGAGCGAGCGAGCGCGCAGAGAGGGAGTGGCCAACTCCATCAC<br>TAGGGGTTCCTTACGTAGGACGTCCCCTGCAGGCAGGGAGGGGTGGAGTCGTGACGTAAAGATCTGATATCATCGATCG<br>CGATGCATTAATTAAGCGGCCGAGGCTCAGAGGCACACAGGAGTTTCTGGGCTCACCCTGCCCCCTTCCAACCCCTCAG<br>TTCCCATCCTCCAGCAGCTGTTTGTGTGCTGCCTCTGAAGTCCACACTGAACAAACTTCAGCCTACTCATGTCCCTAAAA<br>TGGGCAAACATTGCAAGCAGCAAACAGCAAACACACAGCCCTCCCTGCCTGCTGACCTTGGAGCTGGGGCAGAGGTCA<br>GAGACCTCTCTGGGCCCATGCCACCTCCAACATCCACTCGACCCCTTGGAATTTCGGTGGAGAGGAGCAGAGGTTGTCC<br>TGGCGTGGTTTAGGTAGTGTGAGAGGGGTACCCGGGGATCTTGCTACCAGTGGAACAGCCACTAAGGATTCTGCAGTGA<br>GAGCAGAGGGCCAGCTAAGTGGTACTCTCCCAGAGACTGTCTGACTCACGCCACCCCCTCCACCTTGGACACAGGACGC<br>TGTGGTTTCTGAGCCAGGTACAATGACTCCTTTCGGTAAGTGCAGTGGAAGCTGTACACTGCCCAGGCAAAGCGTCCGG<br>GCAGCGTAGGCGGGCGACTCAGATCCCAGCCAGTGGACTTAGCCCCTGTTTGCTCCTCCGATAACTGGGGTGACCTTGG<br>TTAATATTCACCAGCAGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATGATCCCCCTGATCTGCGGCCTCGACGGTATCGATAAGCTTGA<br>TATCGAATTCTAGTCGTCGACCACTTTCACAATCTGCTAGCAAAGGTTGCCACCATGCAGCGCGTGAACATGATTATGG<br>CCGAGAGCCCTGGCCTGATCACCATCTGCCTGCTGGGCTACCTGCTGAGCGCCGAGTGTACAGGTTTGTTTCCTTTTTTA<br>AAATACATTGAGTATGCTTGCCTTTTAGATATAGAAATATCTGATGCTGTCTTCTTCACTAAATTTTGATTACATGATTTG<br>ACAGCAATATTGAAGAGTCTAACAGCCAGCACGCAGGTTGGTAAGTACTGGTTCTTTGTTAGCTAGGTTTTCTTCTTCTT<br>CATTTTTAAAACTAAATAGATCGACAATGCTTATGATGCATTTATGTTTAATAAACACTGTTCAGTTCATGATTTGGTCA<br>TGTAATTCCTGTTAGAAAACATTCATCTCCTTGGTTTAAAAAAATTAAAAGTGGAAAACAAAGAAATAGCAGAATATA<br>GTGAAAAAAAATAACCACATTATTTTTGTTTGGACTTACCACTTTGAAATCAAAATGGGAAACAAAAGCACAAACAATG<br>GCCTTATTTACACAAAAAGTCTGATTTTAAGATATATGACATTTCAAGGTTTCAGAAGTATGTAATGAGGTGTGTCTCTA<br>ATTTTTTAAATTATATATCTTCAATTTAAAGTTTTAGTTAAAACATAAAGATTAACCTTTCATTAGCAAGCTGTTAGTTAT<br>CACCAAAGCTTTTCATGGATTAGGAAAAAATCATTTTGTCTCTATGTCAAACATCTTGGAGTTGATATTTGGGGAAACAC<br>AATACTCAGTTGAGTTCCCTAGGGGAGAAAAGCAAGCTTAAGAATTGACATAAAGAGTAGGAAGTTAGCTAATGCAAC<br>ATATATCACTTTGTTTTTTCACAACTACAGTGACTTTATGTATTTCCCAGAGGAAGGCATACAGGGAAGAAATTATCCCA<br>TTTGGACAAACAGCATGTTCTCACAGGAAGCATTTATCACACTTACTTGTCAACTTTCTAGAATCAAATCTAGTAGCTGA<br>CAGTACCAGGATCAGGGGTGCCAACCCTAAGCACCCCCAGAAAGCTGACTGGCCCTGTGGTTCCCACTCCAGACATGAT<br>GTCAGCTGTGAAATCGACGTCGCTGGACCATAATTAGGCTTCTGTTCTTCAGGAGACATTTGTTCAAAGTCATTTGGGCA<br>ACCATATTCTGAAAACAGCCCAGCCAGGGTGATGGATCACTTTGCAAAGATCCTCAATGAGCTATTTTCAAGTGATGAC<br>AAAGTGTGAAGTTAACCGCTCATTTGAGAACTTTCTTTTTCATCCAAAGTAAATTCAAATATGATTAGAAATCTGACCTT | |

TABLE 1D-continued

Exemplary expression construct sequences, optionally comprising a payload and a cap gene.

| Description | Sequence | SEQ ID NO |
|---|---|---|
| | TTATTACTGGAATTCTCTTGACTAAAAGTAAAATTGAATTTTAATTCCTAAATCTCCATGTGTATACAGTACTGTGGAA<br>CATCACAGATTTTGGCTCCATGCCCTAAAGAGAAATTGGCTTTCAGATTATTTGGATTAAAAACAAAGACTTTCTTAAGA<br>GATGTAAAATTTTCATGATGTTTTCTTTTTTGCTAAAACTAAAGAATTATTCTTTTACATTTCAGTGTTCCTGGACCACGA<br>GAACGCCAACAAGATCCTGAACAGACCCAAGAGATACAACAGCGGCAAGCTGGAAGAGTTCGTGCAGGGCAACCTGG<br>AACGCGAGTGCATGGAAGAGAAGTGCAGCTTCGAAGAGGCCAGAGAGGTGTTCGAGAACACCGAGAGAACCACCGAG<br>TTCTGGAAGCAGTACGTGGACGGCGACCAGTGCGAGAGCAACCCTTGTCTGAACGGCGGCAGCTGCAAGGACGACATC<br>AACAGCTACGAGTGCTGGTGCCCCTTCGGCTTCGAGGGCAAGAACTGCGAGCTGGACGTGACCTGCAACATCAAGAAC<br>GGCAGATGCGAGCAGTTCTGCAAGAACAGCGCCGACAACAAGGTCGTGTGCTCCTGCACCGAGGGCTACAGACTGGCC<br>GAGAACCAGAAGTCCTGCGAGCCCGCTGTGCCTTTCCCATGCGGAAGAGTGTCCGTGTCCCAGACCAGCAAGCTGACCA<br>GAGCCGAGACAGTGTTCCCCGACGTGGACTACGTGAACAGCACCGAGGCCGAGACAATCCTGGACAACATCACCCAGA<br>GCACCCAGTCCTTCAACGACTTCACCAGAGTCGTGGGCGGCGAGGATGCTAAGCCTGGCCAGTTCCCGTGGCAGGTGGT<br>GCTGAACGGAAAGGTGGACGCCTTCTGCGGCGGCTCCATCGTGAACGAGAAGTGGATCGTGACAGCCGCCCACTGCGT<br>GGAAACCGGCGTGAAGATCACAGTGGTGGCCGGCGAGCACAACATCGAGGAAACCGAGCACACAGAGCAGAAAAGAA<br>ACGTGATCAGGATCATCCCCCACCACAACTACAACGCCGCCATCAACAAGTACAACCACGATATCGCCCTGCTGGAACT<br>GGACGAGCCCCTGGTGCTGAATAGCTACGTGACCCCCATCTGTATCGCCGACAAAGAGTACACCAACATCTTTCTGAAG<br>TTCGGCAGCGGCTACGTGTCCGGCTGGGGCAGAGTGTTTCACAAGGGCAGATCCGCTCTGGTGCTGCAGTACCTGAGAG<br>TGCCTCTGGTGGACAGAGCCACCTGTCTGAGAAGCACCAAGTTCACCATCTACAACAACATGTTCTGCGCTGGCTTCCA<br>CGAGGGCGGCAGAGACTCTTGTCAGGGCGATTCTGGCGGCCCTCACGTGACAGAGGTGGAAGGCACCAGCTTTCTGAC<br>CGGCATCATCAGCTGGGGCGAGGAATGCGCCATGAAGGGGAAGTACGGCATCTACACCAAGGTGTCCAGATACGTGAA<br>CTGGATCAAAGAAAAGACCAAGCTGACATAATGAAAGATGGATTTCCAAGGTTAATTCATTGGAATTGAAAATTAACA<br>GCCCCCCCCCCCCCCCCCTGCAGATCTCGAGCCGAATTCCTGCAGCCCGGGGGATCAGCCTCGACTGTGCCTTCTAGTTG<br>CCAGCCATCTGTTGTTTGCCCCTCCCCCGTGCCTTCCTTGACCCTGGAAGGTGCCACTCCCACTGTCCTTTCCTAATAAAA<br>TGAGGAAATTGCATCGCATTGTCTGAGTAGGTGTCATTCTATTCTGGGGGGTGGGGTGGGGCAGGACAGCAAGGGGGA<br>GGATTGGGAAGACAATAGCAGGCATGCTGGGGATGCGGTGGGCTCTATGGCTTCTGAGGCGGAAAGAACCAGCTGGGG<br>CTCGAGATCCACTAGACTAGTGTACACGCGTGATATCAGATCTGTTACGTAAGGAACCCCTAGTGATGGAGTTGGCCAC<br>TCCCTCTCTGCGCGCTCGCTCGCTCACTGAGGCCGCCCGGGCAAAGCCCGGGCGGCCTCAGTGAGCGAGCGAGCGCGCA<br>GAGAGGGAGTGGCCAACTTTTTGCAAAAGCCTAGGCCTCCAAAAAAGCCTCCTCACTACTTCTGGAATAGCTCAGAGGC<br>CGAGGCGGCCTCGGCCTCTGCATAAATAAAAAAAATTAGTCAGCCATGGGGCGGAGAATGGGCGGAACTGGGCGGAGT<br>TAGGGGCGGGATGGGCGGAGTTAGGGGCGGGACTATGGTTGCTGACTAATTGAGATGCATGCTTTGCATACTTCTGCCT<br>GCTGGGGAGCCTGGGGACTTTCCACACCTGGTTGCTGACTAATTGAGATGCATGCTTTGCATACTTCTGCCTGCTGGGGA<br>GCCTGGGGACTTTCCACACCCTAACTGACACACATTCCACAGCTGCATTAATGAATCGGCCAACGCGCGGGGAGAGGCG<br>GTTTGCGTATTGGGCGCTCTTCCGCTTCCTCGCTCACTGACTCGCTGCGCTCGGTCGTTCGGCTGCGGCGAGCGGTATCA<br>GCTCACTCAAAGGCGGTAATACGGTTATCCACAGAATCAGGGGATAACGCAGGAAAGAACATGTGAGCAAAAGGCCAG<br>CAAAAGGCCAGGAACCGTAAAAAGGCCGCGTTGCTGGCGTTTTTCCATAGGCTCCGCCCCCCTGACGAGCATCACAAAA<br>ATCGACGCTCAAGTCAGAGGTGGCGAAACCCGACAGGACTATAAAGATACCAGGCGTTTCCCCCTGGAAGCTCCCTCGT<br>GCGCTCTCCTGTTCCGACCCTGCCGCTTACCGGATACCTGTCCGCCTTTCTCCCTTCGGGAAGCGTGGCGCTTTCTCATAG<br>CTCACGCTGTAGGTATCTCAGTTCGGTGTAGGTCGTTCGCTCCAAGCTGGGCTGTGTGCACGAACCCCCCGTTCAGCCCG<br>ACCGCTGCGCCTTATCCGGTAACTATCGTCTTGAGTCCAACCCGGTAAGACACGACTTATCGCCACTGGCAGCAGCCAC<br>TGGTAACAGGATTAGCAGAGCGAGGTATGTAGGCGGTGCTACAGAGTTCTTGAAGTGGTGGCCTAACTACGGCTACACT<br>AGAAGAACAGTATTTGGTATCTGCGCTCTGCTGAAGCCAGTTACCTTCGGAAAAAGAGTTGGTAGCTCTTGATCCGGCA<br>AACAAACCACCGCTGGTAGCGGTGGTTTTTTTGTTTGCAAGCAGCAGATTACGCGCAGAAAAAAAGGATCTCAAGAAG<br>ATCCTTTGATCTTTTCTACGGGGTCTGACGCTCAGTGGAACGAAAACTCACGTTAAGGGATTTTGGTCATGAGATTATCA<br>AAAAGGATCTTCACCTAGATCCTTTTAAATTAAAAATGAAGTTTTAAATCAATCTAAA | |
| Payload/Cap Plasmid Factor IX/ AAV-DJ | GTATATATGAGTAAACTTGGTCTGACAGTTACCAATGCTTAATCAGTGAGGCACCTATCTCAGCGATCTGTCTATTTCGT<br>TCATCCATAGTTGCCTGACTCCCCGTCGTGTAGATAACTACGATACGGGAGGGCTTACCATCTGGCCCCAGTGCTGCAAT<br>GATACCGCGAGACCCACGCTCACCGGCTCCAGATTTATCAGCAATAAACCAGCCAGCCGGAAGGGCCGAGCGCAGAAG<br>TGGTCCTGCAACTTTATCCGCCTCCATCCAGTCTATTAATTGTTGCCGGGAAGCTAGAGTAAGTAGTTCGCCAGTTAATA<br>GTTTGCGCAACGTTGTTGCCATTGCTACAGGCATCGTGGTGTCACGCTCGTCGTTTGGTATGGCTTCATTCAGCTCCGGT<br>TCCCAACGATCAAGGCGAGTTACATGATCCCCCATGTTGTGCAAAAAAGCGGTTAGCTCCTTCGGTCCTCCGATCGTTGT<br>CAGAAGTAAGTTGGCCGCAGTGTTATCACTCATGGTTATGGCAGCACTGCATAATTCTCTTACTGTCATGCCATCCGTAA<br>GATGCTTTTCTGTGACTGGTGAGTACTCAACCAAGTCATTCTGAGAATAGTGTATGCGGCGACCGAGTTGCTCTTGCCCG<br>GCGTCAATACGGGATAATACCGCGCCACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTGCACCCAACTGATCTTCAGCATCTTTT<br>ACTTTCACCAGCGTTTCTGGGTGAGCAAAAACAGGAAGGCAAAATGCCGCAAAAAAGGGAATAAGGGCGACACGGAA<br>ATGTTGAATACTCATACTCTTCCTTTTTCAATATTATTGAAGCATTTATCAGGGTTATTGTCTCATGAGCGGATACATATT<br>TGAATGTATTTAGAAAAATAAACAAATAGGGGTTCCGCGCACATTTCCCCGAAAAGTGCCACCTGACGTCTAAGAAACC<br>ATTATTATCATGACATTAACCTATAAAAATAGGCGTATCACGAGGCCCTTTCGTCTCGCGCGTTTCGGTGATGACGGTGA<br>AAACCTCTGACACATGCAGCTCCCGGAGACGGTCACAGCTTGTCTGTAAGCGGATGCCGGGAGCAGACAAGCCCGTCA<br>GGGCGCGTCAGCGGGTGTTGGCGGGTGTCGGGGCTGGCTTAACTATGCGGCATCAGAGCAGATTGTACTGAGAGTGCA<br>CCATTCGACGCTCTCCCTTATGCGACTCCTGCATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGGCCACGGGGCCTGCCACCATACCCACGCCGAA<br>ACAAGCGCTCATGAGCCCGAAGTGGCGAGCCCGATCTTCCCCATCGGTGATGTCGGCGATATAGGCGCCAGCAACCGC<br>ACCTGTGGCGCCGGTGGGTCACCAAGCAGGAAGTCAAAGACTTTTTCCGGTGGGCAAAGGATCACGTGGTTGAGGTGG<br>AGCATGAATTCTACGTCAAAAAGGGTGGAGCCAAGAAAAGACCCGCCCCCAGTGACGCAGATATAAGTGAGCCCAAAC<br>GGGTGCGCGAGTCAGTTGCGCAGCCATCGACGTCAGACGCGGAAGCTTCGATCAACTACGCAGACAGGTACCAAAACA<br>AATGTTCTCGTCACGTGGGCATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACCCGTTTCTGTCGTCAAAAAGG<br>CGTATCAGAAACTGTGCTACATTCATCATATCATGGGAAAGGTGCCAGACGCTTGCACTGCCTGCGATCTGGTCAATGT<br>GGATTTGGATGACTGCATCTTTGAACAATAAATGATTTAAATCAGGTATGGCTGCCGATGGTTATCTTCCAGATTGGCTC<br>GAGGACACTCTCTCTGAAGGAATAAGACAGTGGTGGAAGCTCAAACCTGGCCCACCACCACCAAAGCCCGCAGAGCGG<br>CATAAGGACGACAGCAGGGGTCTTGTGCTTCCTGGGTACAAGTACCTCGGACCCTTCAACGGACTCGACAAGGGAGAG<br>CCGGTCAACGAGGCAGACGCCGCGGCCCTCGAGCACGACAAAGCCTACGACCGGCAGCTCGACAGCGGAGACAACCCG<br>TACCTCAAGTACAACCACGCCGACGCCGAGTTCCAGGAGCGGCTCAAAGAAGATACGTCTTTTGGGGGCAACCTCGGG | 8 |

TABLE 1D-continued

Exemplary expression construct sequences, optionally comprising a payload and a cap gene.

| Description | Sequence | SEQ ID NO |
|---|---|---|
| | CGAGCAGTCTTCCAGGCCAAAAAGAGGCTTCTTGAACCTCTTGGTCTGGTTGAGGAAGCGGCTAAGACGGCTCCTGGAA<br>AGAAGAGGCCTGTAGAGCACTCTCCTGTGGAGCCAGACTCCTCCTCGGGAACCGGAAAGGCGGGCCAGCAGCCTGCAA<br>GAAAAAGATTGAATTTTGGTCAGACTGGAGACGCAGACTCAGTCCCAGACCCTCAACCAATCGGAGAACCTCCCGCAG<br>CCCCCTCAGGTGTGGGATCTCTTACAATGGCTGCAGGCGGTGGCGCACCAATGGCAGACAATAACGAGGGCGCCGACG<br>GAGTGGGTAATTCCTCGGGAAATTGGCATTGCGATTCCACATGGATGGGCGACAGAGTCATCACCACCAGCACCCGAAC<br>CTGGGCCCTGCCCACCTACAACAACCACCTCTACAAGCAAATCTCCAACAGCACATCTGGAGGATCTTCAAATGACAAC<br>GCCTACTTCGGCTACAGCACCCCCTGGGGGTATTTTGACTTTAACAGATTCCACTGCCACTTTTCACCACGTGACTGGCA<br>GCGACTCATCAACAACAACTGGGGATTCCGGCCCAAGAGACTCAGCTTCAAGCTCTTCAACATCCAGGTCAAGGAGGTC<br>ACGCAGAATGAAGGCACCAAGACCATCGCCAATAACCTCACCAGCACCATCCAGGTGTTTACGGACTCGGAGTACCAG<br>CTGCCGTACGTTCTCGGCTCTGCCCACCAGGGCTGCCTGCCTCCGTTCCCGGCGGACGTGTTCATGATTCCCCAGTACGG<br>CTACCTAACACTCAACAACGGTAGTCAGGCCGTGGGACGCTCCTCCTTCTACTGCCTGGAATACTTTCCTTCGCAGATGC<br>TGAGAACCGGCAACAACTTCCAGTTTACTTACACCTTCGAGGACGTGCCTTTCCACAGCAGCTACGCCCACAGCCAGAG<br>CTTGGACCGGCTGATGAATCCTCTGATTGACCAGTACCTGTACTACTTGTCTCGGACTCAAACAACAGGAGGCACGACA<br>AATACGCAGACTCTGGGCTTCAGCCAAGGTGGGCCTAATACAATGGCCAATCAGGCAAAGAACTGGCTGCCAGGACCC<br>TGTTACCGCCAGCAGCGAGTATCAAAGACATCTGCGGATAACAACAACAGTGAATACTCGTGGACTGGAGCTACCAAG<br>TACCACCTCAATGGCAGAGACTCTCTGGTGAATCCGGGCCCGGCCATGGCAAGCCACAAGGACGATGAAGAAAAGTTT<br>TTTCCTCAGAGCGGGGTTCTCATCTTTGGGAAGCAAGGCTCAGAGAAAACAAATGTGGACATTGAAAAGGTCATGATTA<br>CAGACGAAGAGGAAATCAGGACAACCAATCCCGTGGCTACGGAGCAGTATGGTTCTGTATCTACCAACCTCCAGAGAG<br>GCAACAGACAAGCAGCTACCGCAGATGTCAACACACAAGGCGTTCTTCCAGGCATGGTCTGGCAGGACAGAGATGTGT<br>ACCTTCAGGGGCCCATCTGGGCAAAGATTCCACACACGGACGGACATTTTCACCCCTCTCCCCTCATGGGTGGATTCGG<br>ACTTAAACACCCTCCGCCTCAGATCCTGATCAAGAACACGCCTGTACCTGCGGATCCTCCGACCACCTTCAACCAGTCA<br>AAGCTGAACTCTTTCATCACCCAGTATTCTACTGGCCAAGTCAGCGTGGAGATCGAGTGGGAGCTGCAGAAGGAAAAC<br>AGCAAGCGCTGGAACCCCGAGATCCAGTACACCTCCAACTACTACAAATCTACAAGTGTGGACTTTGCTGTTAATACAG<br>AAGGCGTGTACTCTGAACCCCGCCCCATTGGCACCCGTTACCTCACCCGTAATCTGTAATTGCTTGTTAATCAATAAACC<br>GTTTAATTCGTTTCAGTTGAACTTTGGTCTCTGCGTATTTCTTTCTTATCTAGTTTCCATATGCATGTAGATAAGTAGCAT<br>GGCGGGTTAATCATTAACTAACCGGTACCTCTAGAACTATAGCTAGCGATGACCCTGCTGATTGGTTCGCTGACCATTTC<br>CGGGTGCGGGACGGCGTTACCAGAAACTCAGAAGGTTCGTCCAACCAAACCGACTCTGACGGCAGTTTACGAGAGAGA<br>TGATAGGGTCTGCTTCAGTAAGCCAGATGCTACACAATTAGGCTTGTACATATTGTCGTTAGAACGCGGCTACAATTAA<br>TACATAACCTTATGTATCATACACATACGATTTAGGTGACACTATAGAATACACGGAATTAATTCTTGGCCACTCCCTCT<br>CTGCGCGCTCGCTCGCTCACTGAGGCCGCCCGGGCAAAGCCCGGGCGTCGGGCGACCTTTGGTCGCCCGGCCTCAGTGA<br>GCGAGCGAGCGCGCAGAGAGGGAGTGGCCAACTCCATCACTAGGGGTTCCTTACGTAGGACGTCCCCTGCAGGCAGGG<br>AGGGGTGGAGTCGTGACGTAAAGATCTGATATCATCGATCGCGATGCATTAATTAAGCGGCCGAGGCTCAGAGGCACA<br>CAGGAGTTTCTGGGCTCACCCTGCCCCCTTCCAACCCCTCAGTTCCCATCCTCCAGCAGCTGTTTGTGTGCTGCCTCTGA<br>AGTCCACACTGAACAAACTTCAGCCTACTCATGTCCCTAAAATGGGCAAACATTGCAAGCAGCAAACAGCAAACACAC<br>AGCCCTCCCTGCCTGCTGACCTTGGAGCTGGGGCAGAGGTCAGAGACCTCTCTGGGCCCATGCCACCTCCAACATCCAC<br>TCGACCCCTTGGAATTTCGGTGGAGAGGAGCAGAGGTTGTCCTGGCGTGGTTTAGGTAGTGTGAGAGGGGTACCCGGGG<br>ATCTTGCTACCAGTGGAACAGCCACTAAGGATTCTGCAGTGAGAGCAGAGGGCCAGCTAAGTGGTACTCTCCCAGAGA<br>CTGTCTGACTCACGCCACCCCCTCCACCTTGGACACAGGACGCTGTGGTTTCTGAGCCAGGTACAATGACTCCTTTCGGT<br>AAGTGCAGTGGAAGCTGTACACTGCCCAGGCAAAGCGTCCGGGCAGCGTAGGCGGGCGACTCAGATCCCAGCCAGTGG<br>ACTTAGCCCCTGTTTGCTCCTCCGATAACTGGGGTGACCTTGGTTAATATTCACCAGCAGCCTCCCCCGTTGCCCCTCTG<br>GATCCACTGCTTAAATACGGACGAGGACAGGGCCCTGTCTCCTCAGCTTCAGGCACCACCACTGACCTGGGACAGTGAA<br>TGATCCCCCTGATCTGCGGCCTCGACGGTATCGATAAGCTTGATATCGAATTCTAGTCGTCGACCACTTTCACAATCTGC<br>TAGCAAAGGTTGCCACCATGCAGCGCGTGAACATGATTATGGCCGAGAGCCCTGGCCTGATCACCATCTGCCTGCTGGG<br>CTACCTGCTGAGCGCCGAGTGTACAGGTTTGTTTCCTTTTTTAAAATACATTGAGTATGCTTGCCTTTTAGATATAGAAA<br>TATCTGATGCTGTCTTCTTCACTAAATTTTGATTACATGATTTGACAGCAATATTGAAGAGTCTAACAGCCAGCACGCAG<br>GTTGGTAAGTACTGGTTCTTTGTTAGCTAGGTTTTCTTCTTCTTCATTTTTAAAACTAAATAGATCGACAATGCTTATGAT<br>GCATTTATGTTTAATAAACACTGTTCAGTTCATGATTTGGTCATGTAATTCCTGTTAGAAAACATTCATCTCCTTGGTTTA<br>AAAAAATTAAAAGTGGAAAACAAAGAAATAGCAGAATATAGTGAAAAAAAATAACCACATTATTTTTGTTTGGACTT<br>ACCACTTTGAAATCAAAATGGGAAACAAAAGCACAAACAATGGCCTTATTTACACAAAAAGTCTGATTTTAAGATATAT<br>GACATTTCAAGGTTTCAGAAGTATGTAATGAGGTGTGTCTCTAATTTTTTAAATTATATATCTTCAATTTAAAGTTTTAGT<br>TAAAACATAAAGATTAACCTTTCATTAGCAAGCTGTTAGTTATCACCAAAGCTTTTCATGGATTAGGAAAAAATCATTTT<br>GTCTCTATGTCAAACATCTTGGAGTTGATATTTGGGGAAACACAATACTCAGTTGAGTTCCCTAGGGGAGAAAAGCAAG<br>CTTAAGAATTGACATAAAGAGTAGGAAGTTAGCTAATGCAACATATATCACTTTGTTTTTTCACAACTACAGTGACTTTA<br>TGTATTTCCCAGAGGAAGGCATACAGGGAAGAAATTATCCCATTTGGACAAACAGCATGTTCTCACAGGAAGCATTTAT<br>CACACTTACTTGTCAACTTTCTAGAATCAAATCTAGTAGCTGACAGTACCAGGATCAGGGGTGCCAACCCTAAGCACCC<br>CCAGAAAGCTGACTGGCCCTGTGGTTCCCACTCCAGACATGATGTCAGCTGTGAAATCGACGTCGCTGGACCATAATTA<br>GGCTTCTGTTCTTCAGGAGACATTTGTTCAAAGTCATTTGGGCAACCATATTCTGAAAACAGCCCAGCCAGGGTGATGG<br>ATCACTTTGCAAAGATCCTCAATGAGCTATTTTCAAGTGATGACAAAGTGTGAAGTTAACCGCTCATTTGAGAACTTTCT<br>TTTTCATCCAAAGTAAATTCAAATATGATTAGAAATCTGACCTTTTATTACTGGAATTCTCTTGACTAAAAGTAAAATTG<br>AATTTTAATTCCTAAATCTCCATGTGTATACAGTACTGTGGGAACATCACAGATTTTGGCTCCATGCCCTAAAGAGAAAT<br>TGGCTTTCAGATTATTTGGATTAAAAACAAAGACTTTCTTAAGAGATGTAAAATTTTCATGATGTTTTCTTTTTTGCTAAA<br>ACTAAAGAATTATTCTTTTACATTTCAGTGTTCCTGGACCACGAGAACGCCAACAAGATCCTGAACAGACCCAAGAGAT<br>ACAACAGCGGCAAGCTGGAAGAGTTCGTGCAGGGCAACCTGGAACGCGAGTGCATGGAAGAGAAGTGCAGCTTCGAA<br>GAGGCCAGAGAGGTGTTCGAGAACACCGAGAGAACCACCGAGTTCTGGAAGCAGTACGTGGACGGCGACCAGTGCGA<br>GAGCAACCCTTGTCTGAACGGCGGCAGCTGCAAGGACGACATCAACAGCTACGAGTGCTGGTGCCCCTTCGGCTTCGAG<br>GGCAAGAACTGCGAGCTGGACGTGACCTGCAACATCAAGAACGGCAGATGCGAGCAGTTCTGCAAGAACAGCGCCGAC<br>AACAAGGTCGTGTGCTCCTGCACCGAGGGCTACAGACTGGCCGAGAACCAGAAGTCCTGCGAGCCCGCTGTGCCTTTCC<br>CATGCGGAAGAGTGTCCGTGTCCCAGACCAGCAAGCTGACCAGAGCCGAGACAGTGTTCCCCGACGTGGACTACGTGA<br>ACAGCACCGAGGCCGAGACAATCCTGGACAACATCACCCAGAGCACCCAGTCCTTCAACGACTTCACCAGAGTCGTGG<br>GCGGCGAGGATGCTAAGCCTGGCCAGTTCCCGTGGCAGGTGGTGCTGAACGGAAAGGTGGACGCCTTCTGCGGCGGCT<br>CCATCGTGAACGAGAAGTGGATCGTGACAGCCGCCCACTGCGTGGAAACCGGCGTGAAGATCACAGTGGTGGCCGGCG<br>AGCACAACATCGAGGAAACCGAGCACACAGAGCAGAAAAGAAACGTGATCAGGATCATCCCCCACCACAACTACAAC<br>GCCGCCATCAACAAGTACAACCACGATATCGCCCTGCTGGAACTGGACGAGCCCCTGGTGCTGAATAGCTACGTGACCC<br>CCATCTGTATCGCCGACAAAGAGTACACCAACATCTTTCTGAAGTTCGGCAGCGGCTACGTGTCCGGCTGGGGCAGAGT | |

TABLE 1D-continued

Exemplary expression construct sequences, optionally comprising a payload and a cap gene.

| Description | Sequence | SEQ ID NO |
| --- | --- | --- |
| | GTTTCACAAGGGCAGATCCGCTCTGGTGCTGCAGTACCTGAGAGTGCCTCTGGTGGACAGAGCCACCTGTCTGAGAAGC<br>ACCAAGTTCACCATCTACAACAACATGTTCTGCGCTGGCTTCCACGAGGGCGGCAGAGACTCTTGTCAGGGCGATTCTG<br>GCGGCCCTCACGTGACAGAGGTGGAAGGCACCAGCTTTCTGACCGGCATCATCAGCTGGGGCGAGGAATGCGCCATGA<br>AGGGGAAGTACGGCATCTACACCAAGGTGTCCAGATACGTGAACTGGATCAAAGAAAAGACCAAGCTGACATAATGAA<br>AGATGGATTTCCAAGGTTAATTCATTGGAATTGAAAATTAACAGCCCCCCCCCCCCCCCCCTGCAGATCTCGAGCCGAA<br>TTCCTGCAGCCCGGGGGATCAGCCTCGACTGTGCCTTCTAGTTGCCAGCCATCTGTTGTTTGCCCCTCCCCCGTGCCTTCC<br>TTGACCCTGGAAGGTGCCACTCCCACTGTCCTTTCCTAATAAAATGAGGAAATTGCATCGCATTGTCTGAGTAGGTGTCA<br>TTCTATTCTGGGGGGTGGGGTGGGGCAGGACAGCAAGGGGGAGGATTGGGAAGACAATAGCAGGCATGCTGGGGATGC<br>GGTGGGCTCTATGGCTTCTGAGGCGGAAAGAACCAGCTGGGGCTCGAGATCCACTAGACTAGTGTACACGCGTGATATC<br>AGATCTGTTACGTAAGGAACCCCTAGTGATGGAGTTGGCCACTCCCTCTCTGCGCGCTCGCTCGCTCACTGAGGCCGCCC<br>GGGCAAAGCCCGGGCGGCCTCAGTGAGCGAGCGAGCGCGCAGAGAGGGAGTGGCCAACTTTTTGCAAAAGCCTAGGCC<br>TCCAAAAAAGCCTCCTCACTACTTCTGGAATAGCTCAGAGGCCGAGGCGGCCTCGGCCTCTGCATAAATAAAAAAAATT<br>AGTCAGCCATGGGGCGGAGAATGGGCGGAACTGGGCGGAGTTAGGGGCGGGATGGGCGGAGTTAGGGGCGGGACTAT<br>GGTTGCTGACTAATTGAGATGCATGCTTTGCATACTTCTGCCTGCTGGGGAGCCTGGGGACTTTCCACACCTGGTTGCTG<br>ACTAATTGAGATGCATGCTTTGCATACTTCTGCCTGCTGGGGAGCCTGGGGACTTTCCACACCCTAACTGACACACATTC<br>CACAGCTGCATTAATGAATCGGCCAACGCGCGGGGAGAGGCGGTTTGCGTATTGGGCGCTCTTCCGCTTCCTCGCTCAC<br>TGACTCGCTGCGCTCGGTCGTTCGGCTGCGGCGAGCGGTATCAGCTCACTCAAAGGCGGTAATACGGTTATCCACAGAA<br>TCAGGGGATAACGCAGGAAAGAACATGTGAGCAAAAGGCCAGCAAAAGGCCAGGAACCGTAAAAAGGCCGCGTTGCT<br>GGCGTTTTTCCATAGGCTCCGCCCCCCTGACGAGCATCACAAAAATCGACGCTCAAGTCAGAGGTGGCGAAACCCGACA<br>GGACTATAAAGATACCAGGCGTTTCCCCCTGGAAGCTCCCTCGTGCGCTCTCCTGTTCCGACCCTGCCGCTTACCGGATA<br>CCTGTCCGCCTTTCTCCCTTCGGGAAGCGTGGCGCTTTCTCATAGCTCACGCTGTAGGTATCTCAGTTCGGTGTAGGTCG<br>TTCGCTCCAAGCTGGGCTGTGTGCACGAACCCCCCGTTCAGCCCGACCGCTGCGCCTTATCCGGTAACTATCGTCTTGAG<br>TCCAACCCGGTAAGACACGACTTATCGCCACTGGCAGCAGCCACTGGTAACAGGATTAGCAGAGCGAGGTATGTAGGC<br>GGTGCTACAGAGTTCTTGAAGTGGTGGCCTAACTACGGCTACACTAGAAGAACAGTATTTGGTATCTGCGCTCTGCTGA<br>AGCCAGTTACCTTCGGAAAAAGAGTTGGTAGCTCTTGATCCGGCAAACAAACCACCGCTGGTAGCGGTGGTTTTTTTGT<br>TTGCAAGCAGCAGATTACGCGCAGAAAAAAAGGATCTCAAGAAGATCCTTTGATCTTTTCTACGGGGTCTGACGCTCAG<br>TGGAACGAAAACTCACGTTAAGGGATTTTGGTCATGAGATTATCAAAAAGGATCTTCACCTAGATCCTTTTAAATTAAA<br>AATGAAGTTTTAAATCAATCTAAA | |
| Payload/Cap Plasmid Factor IX/ AAV-LK03 | ATGGCTGCTGACGGTTATCTTCCAGATTGGCTCGAGGACAACCTTTCTGAAGGCATTCGAGAGTGGTGGGCGCTGCAAC<br>CTGGAGCCCCTAAACCCAAGGCAAATCAACAACATCAGGACAACGCTCGGGGTCTTGTGCTTCCGGGTTACAAATACCT<br>CGGACCCGGCAACGGACTCGACAAGGGGGAACCCGTCAACGCAGCGGACGCGGCAGCCCTCGAGCACGACAAGGCCT<br>ACGACCAGCAGCTCAAGGCCGGTGACAACCCCTACCTCAAGTACAACCACGCCGACGCCGAGTTCCAGGAGCGGCTCA<br>AAGAAGATACGTCTTTTGGGGGCAACCTCGGGCGAGCAGTCTTCCAGGCCAAAAAGAGGCTTCTTGAACCTCTTGGTCT<br>GGTTGAGGAAGCGGCTAAGACGGCTCCTGGAAAGAAGAGGCCTGTAGATCAGTCTCCTCAGGAACCGGACTCATCATC<br>TGGTGTTGGCAAATCGGGCAAACAGCCTGCCAGAAAAAGACTAAATTTCGGTCAGACTGGCGACTCAGAGTCAGTCCC<br>AGACCCTCAACCTCTCGGAGAACCACCAGCAGCCCCCACAAGTTTGGGATCTAATACAATGGCTTCAGGCGGTGGCGCA<br>CCAATGGCAGACAATAACGAGGGTGCCGATGGAGTGGGTAATTCCTCAGGAAATTGGCATTGCGATTCCCAATGGCTG<br>GGCGACAGAGTCATCACCACCAGCACCAGAACCTGGGCCCTGCCCACTTACAACAACCATCTCTACAAGCAAATCTCCA<br>GCCAATCAGGAGCTTCAAACGACAACCACTACTTTGGCTACAGCACCCCTTGGGGGTATTTTGACTTTAACAGATTCCA<br>CTGCCACTTCTCACCACGTGACTGGCAGCGACTCATTAACAACAACTGGGGATTCCGGCCCAAGAAACTCAGCTTCAAG<br>CTCTTCAACATCCAAGTTAAAGAGGTCACGCAGAACGATGGCACGACGACTATTGCCAATAACCTTACCAGCACGGTTC<br>AAGTGTTTACGGACTCGGAGTATCAGCTCCCGTACGTGCTCGGGTCGGCGCACCAAGGCTGTCTCCCGCCGTTTCCAGC<br>GGACGTCTTCATGGTCCCTCAGTATGGATACCTCACCCTGAACAACGGAAGTCAAGCGGTGGGACGCTCATCCTTTTAC<br>TGCCTGGAGTACTTCCCTTCGCAGATGCTAAGGACTGGAAATAACTTCCAATTCAGCTATACCTTCGAGGATGTACCTTT<br>TCACAGCAGCTACGCTCACAGCCAGAGTTTGGATCGCTTGATGAATCCTCTTATTGATCAGTATCTGTACTACCTGAACA<br>GAACGCAAGGAACAACCTCTGGAACAACCAACCAATCACGGCTGCTTTTTAGCCAGGCTGGGCCTCAGTCTATGTCTTT<br>GCAGGCCAGAAATTGGCTACCTGGGCCCTGCTACCGGCAACAGAGACTTTCAAAGACTGCTAACGACAACAACAACAG<br>TAACTTTCCTTGGACAGCGGCCAGCAAATATCATCTCAATGGCCGCGACTCGCTGGTGAATCCAGGACCAGCTATGGCC<br>AGTCACAAGGACGATGAAGAAAAATTTTTCCCTATGCACGGCAATCTAATATTTGGCAAAGAAGGGACAACGGCAAGT<br>AACGCAGAATTAGATAATGTAATGATTACGGATGAAGAAGAGATTCGTACCACCAATCCTGTGGCAACAGAGCAGTAT<br>GGAACTGTGGCAAATAACTTGCAGAGCTCAAATACAGCTCCCACGACTAGAACTGTCAATGATCAGGGGGCCTTACCTG<br>GCATGGTGTGGCAAGATCGTGACGTGTACCTTCAAGGACCTATCTGGGCAAAGATTCCTCACACGGATGGACACTTTCA<br>TCCTTCTCCTCTGATGGGAGGCTTTGGACTGAAACATCCGCCTCCTCAAATCATGATCAAAAATACTCCGGTACCGGCAA<br>ATCCTCCGACGACTTTCAGCCCGGCCAAGTTTGCTTCATTTATCACTCAGTACTCCACTGGACAGGTCAGCGTGGAAATT<br>GAGTGGGAGCTACAGAAAGAAAACAGCAAACGTTGGAATCCAGAGATTCAGTACACTTCCAACTACAACAAGTCTGTT<br>AATGTGGACTTTACTGTAGACACTAATGGTGTTTATAGTGAACCTCGCCCCATTGGCACCCGTTACCTTACCCGTCCCCT<br>GTAATTGCTTGTTAATCAATAAACCGTTTAATTCGTTTCAGTTGAACTTTGGTCTCTGCGTATTTCTTTCTTATCTAGTTTC<br>CATATGCATGTAGATAAGTAGCATGGCGGGTTAATCATTAACTAACCGGTACCTCTAGAACTATAGCTAGCGATGACCC<br>TGCTGATTGGTTCGCTGACCATTTCCGGGTGCGGGACGGCGTTACCAGAAACTCAGAAGGTTCGTCCAACCAAACCGAC<br>TCTGACGGCAGTTTACGAGAGAGATGATAGGGTCTGCTTCAGTAAGCCAGATGCTACACAATTAGGCTTGTACATATTG<br>TCGTTAGAACGCGGCTACAATTAATACATAACCTTATGTATCATACACATACGATTTAGGTGACACTATAGAATACACG<br>GAATTAATTCTTGGCCACTCCCTCTCTGCGCGCTCGCTCGCTCACTGAGGCCGCCCGGGCAAAGCCCGGGCGTCGGGCG<br>ACCTTTGGTCGCCCGGCCTCAGTGAGCGAGCGAGCGCGCAGAGAGGGAGTGGCCAACTCCATCACTAGGGGTTCCTTAC<br>GTAGGACGTCCCCTGCAGGCAGGGAGGGGTGGAGTCGTGACGTAAAGATCTGATATCATCGATCGCGATGCATTAATTA<br>AGCGGCCGAGGCTCAGAGGCACACAGGAGTTTCTGGGCTCACCCTGCCCCCTTCCAACCCCTCAGTTCCCATCCTCCAG<br>CAGCTGTTTGTGTGCTGCCTCTGAAGTCCACACTGAACAAACTTCAGCCTACTCATGTCCCTAAAATGGGCAAACATTGC<br>AAGCAGCAAACAGCAAACACACAGCCCTCCCTGCCTGCTGACCTTGGAGCTGGGGCAGAGGTCAGAGACCTCTCTGGG<br>CCCATGCCACCTCCAACATCCACTCGACCCCTTGGAATTTCGGTGGAGAGGAGCAGAGGTTGTCCTGGCGTGGTTTAGG<br>TAGTGTGAGAGGGGTACCCGGGGATCTTGCTACCAGTGGAACAGCCACTAAGGATTCTGCAGTGAGAGCAGAGGGCCA<br>GCTAAGTGGTACTCTCCCAGAGACTGTCTGACTCACGCCACCCCCTCCACCTTGGACACAGGACGCTGTGGTTTCTGAGC<br>CAGGTACAATGACTCCTTTCGGTAAGTGCAGTGGAAGCTGTACACTGCCCAGGCAAAGCGTCCGGGCAGCGTAGGCGG<br>GCGACTCAGATCCCAGCCAGTGGACTTAGCCCCTGTTTGCTCCTCCGATAACTGGGGTGACCTTGGTTAATATTCACCAG<br>CAGCCTCCCCCGTTGCCCCTCTGGATCCACTGCTTAAATACGGACGAGGACAGGGCCCTGTCTCCTCAGCTTCAGGCACC | 9 |

TABLE 1D-continued

Exemplary expression construct sequences, optionally comprising a payload and a cap gene.

| Description | Sequence | SEQ ID NO |
|---|---|---|
| | ACCACTGACCTGGGACAGTGAATGATCCCCCTGATCTGCGGCCTCGACGGTATCGATAAGCTTGATATCGAATTCTAGT<br>CGTCGACCACTTTCACAATCTGCTAGCAAAGGTTGCCACCATGCAGCGCGTGAACATGATTATGGCCGAGAGCCCTGGC<br>CTGATCACCATCTGCCTGCTGGGCTACCTGCTGAGCGCCGAGTGTACAGGTTTGTTTCCTTTTTTAAAATACATTGAGTA<br>TGCTTGCCTTTTAGATATAGAAATATCTGATGCTGTCTTCTTCACTAAATTTTGATTACATGATTTGACAGCAATATTGAA<br>GAGTCTAACAGCCAGCACGCAGGTTGGTAAGTACTGGTTCTTTGTTAGCTAGGTTTTCTTCTTCTTCATTTTTAAAACTAA<br>ATAGATCGACAATGCTTATGATGCATTTATGTTTAATAAACACTGTTCAGTTCATGATTTGGTCATGTAATTCCTGTTAG<br>AAAACATTCATCTCCTTGGTTTAAAAAAATTAAAAGTGGGAAAACAAAGAAATAGCAGAATATAGTGAAAAAAAATAA<br>CCACATTATTTTTGTTTGGACTTACCACTTTGAAATCAAAATGGGAAACAAAAGCACAAACAATGGCCTTATTTACACA<br>AAAAGTCTGATTTTAAGATATATGACATTTCAAGGTTTCAGAAGTATGTAATGAGGTGTGTCTCTAATTTTTTAAATTAT<br>ATATCTTCAATTTAAAGTTTTAGTTAAAACATAAAGATTAACCTTTCATTAGCAAGCTGTTAGTTATCACCAAAGCTTTT<br>CATGGATTAGGAAAAAATCATTTTGTCTCTATGTCAAACATCTTGGAGTTGATATTTGGGGAAACACAATACTCAGTTG<br>AGTTCCCTAGGGGAGAAAAGCAAGCTTAAGAATTGACATAAAGAGTAGGAAGTTAGCTAATGCAACATATATCACTTT<br>GTTTTTTCACAACTACAGTGACTTTATGTATTTCCCAGAGGAAGGCATACAGGGAAGAAATTATCCCATTTGGACAAAC<br>AGCATGTTCTCACAGGAAGCATTTATCACACTTACTTGTCAACTTTCTAGAATCAAATCTAGTAGCTGACAGTACCAGGA<br>TCAGGGGTGCCAACCCTAAGCACCCCCAGAAAGCTGACTGGCCCTGTGGTTCCCACTCCAGACATGATGTCAGCTGTGA<br>AATCGACGTCGCTGGACCATAATTAGGCTTCTGTTCTTCAGGAGACATTTGTTCAAAGTCATTTGGGCAACCATATTCTG<br>AAAACAGCCCAGCCAGGGTGATGGATCACTTTGCAAAGATCCTCAATGAGCTATTTTCAAGTGATGACAAAGTGTGAAG<br>TTAACCGCTCATTTGAGAACTTTCTTTTTCATCCAAAGTAAATTCAAATATGATTAGAAATCTGACCTTTTATTACTGGA<br>ATTCTCTTGACTAAAAGTAAAATTGAATTTTAATTCCTAAATCTCCATGTGTATACAGTACTGTGGGAACATCACAGATT<br>TTGGCTCCATGCCCTAAAGAGAAATTGGCTTTCAGATTATTTGGATTAAAAACAAAGACTTTCTTAAGAGATGTAAAAT<br>TTTCATGATGTTTTCTTTTTTGCTAAAACTAAAGAATTATTCTTTTACATTTCAGTGTTCCTGGACCACGAGAACGCCAAC<br>AAGATCCTGAACAGACCCAAGAGATACAACAGCGGCAAGCTGGAAGAGTTCGTGCAGGGCAACCTGGAACGCGAGTG<br>CATGGAAGAGAAGTGCAGCTTCGAAGAGGCCAGAGAGGTGTTCGAGAACACCGAGAGAACCACCGAGTTCTGGAAGC<br>AGTACGTGGACGGCGACCAGTGCGAGAGCAACCCTTGTCTGAACGGCGGCAGCTGCAAGGACGACATCAACAGCTACG<br>AGTGCTGGTGCCCCTTCGGCTTCGAGGGCAAGAACTGCGAGCTGGACGTGACCTGCAACATCAAGAACGGCAGATGCG<br>AGCAGTTCTGCAAGAACAGCGCCGACAACAAGGTCGTGTGCTCCTGCACCGAGGGCTACAGACTGGCCGAGAACCAGA<br>AGTCCTGCGAGCCCGCTGTGCCTTTCCCATGCGGAAGAGTGTCCGTGTCCCAGACCAGCAAGCTGACCAGAGCCGAGAC<br>AGTGTTCCCCGACGTGGACTACGTGAACAGCACCGAGGCCGAGACAATCCTGGACAACATCACCCAGAGCACCCAGTC<br>CTTCAACGACTTCACCAGAGTCGTGGGCGGCGAGGATGCTAAGCCTGGCCAGTTCCCGTGGCAGGTGGTGCTGAACGGA<br>AAGGTGGACGCCTTCTGCGGCGGCTCCATCGTGAACGAGAAGTGGATCGTGACAGCCGCCCACTGCGTGGAAACCGGC<br>GTGAAGATCACAGTGGTGGCCGGCGAGCACAACATCGAGGAAACCGAGCACACAGAGCAGAAAAGAAACGTGATCAG<br>GATCATCCCCCACCACAACTACAACGCCGCCATCAACAAGTACAACCACGATATCGCCCTGCTGGAACTGGACGAGCCC<br>CTGGTGCTGAATAGCTACGTGACCCCCATCTGTATCGCCGACAAAGAGTACACCAACATCTTTCTGAAGTTCGGCAGCG<br>GCTACGTGTCCGGCTGGGGCAGAGTGTTTCACAAGGGCAGATCCGCTCTGGTGCTGCAGTACCTGAGAGTGCCTCTGGT<br>GGACAGAGCCACCTGTCTGAGAAGCACCAAGTTCACCATCTACAACAACATGTTCTGCGCTGGCTTCCACGAGGGCGGC<br>AGAGACTCTTGTCAGGGCGATTCTGGCGGCCCTCACGTGACAGAGGTGGAAGGCACCAGCTTTCTGACCGGCATCATCA<br>GCTGGGGCGAGGAATGCGCCATGAAGGGGAAGTACGGCATCTACACCAAGGTGTCCAGATACGTGAACTGGATCAAAG<br>AAAAGACCAAGCTGACATAATGAAAGATGGATTTCCAAGGTTAATTCATTGGAATTGAAAATTAACAGCCCCCCCCCC<br>CCCCCCTGCAGATCTCGAGCCGAATTCCTGCAGCCCGGGGGATCAGCCTCGACTGTGCCTTCTAGTTGCCAGCCATCTGT<br>TGTTTGCCCCTCCCCCGTGCCTTCCTTGACCCTGGAAGGTGCCACTCCCACTGTCCTTTCCTAATAAAATGAGGAAATTG<br>CATCGCATTGTCTGAGTAGGTGTCATTCTATTCTGGGGGGTGGGGTGGGGCAGGACAGCAAGGGGGAGGATTGGGAAG<br>ACAATAGCAGGCATGCTGGGGATGCGGTGGGCTCTATGGCTTCTGAGGCGGAAAGAACCAGCTGGGGCTCGAGATCCA<br>CTAGACTAGTGTACACGCGTGATATCAGATCTGTTACGTAAGGAACCCCTAGTGATGGAGTTGGCCACTCCCTCTCTGC<br>GCGCTCGCTCGCTCACTGAGGCCGCCCGGGCAAAGCCCGGGCGGCCTCAGTGAGCGAGCGAGCGCGCAGAGAGGGAGT<br>GGCCAACTTTTTGCAAAAGCCTAGGCCTCCAAAAAAGCCTCCTCACTACTTCTGGAATAGCTCAGAGGCCGAGGCGGCC<br>TCGGCCTCTGCATAAATAAAAAAAATTAGTCAGCCATGGGGCGGAGAATGGGCGGAACTGGGCGGAGTTAGGGGCGGG<br>ATGGGCGGAGTTAGGGGCGGGACTATGGTTGCTGACTAATTGAGATGCATGCTTTGCATACTTCTGCCTGCTGGGGAGC<br>CTGGGGACTTTCCACACCTGGTTGCTGACTAATTGAGATGCATGCTTTGCATACTTCTGCCTGCTGGGGAGCCTGGGGAC<br>TTTCCACACCCTAACTGACACACATTCCACAGCTGCATTAATGAATCGGCCAACGCGCGGGGAGAGGCGGTTTGCGTAT<br>TGGGCGCTCTTCCGCTTCCTCGCTCACTGACTCGCTGCGCTCGGTCGTTCGGCTGCGGCGAGCGGTATCAGCTCACTCAA<br>AGGCGGTAATACGGTTATCCACAGAATCAGGGGATAACGCAGGAAAGAACATGTGAGCAAAAGGCCAGCAAAAGGCC<br>AGGAACCGTAAAAAGGCCGCGTTGCTGGCGTTTTTCCATAGGCTCCGCCCCCCTGACGAGCATCACAAAAATCGACGCT<br>CAAGTCAGAGGTGGCGAAACCCGACAGGACTATAAAGATACCAGGCGTTTCCCCCTGGAAGCTCCCTCGTGCGCTCTCC<br>TGTTCCGACCCTGCCGCTTACCGGATACCTGTCCGCCTTTCTCCCTTCGGGAAGCGTGGCGCTTTCTCATAGCTCACGCT<br>GTAGGTATCTCAGTTCGGTGTAGGTCGTTCGCTCCAAGCTGGGCTGTGTGCACGAACCCCCCGTTCAGCCCGACCGCTGC<br>GCCTTATCCGGTAACTATCGTCTTGAGTCCAACCCGGTAAGACACGACTTATCGCCACTGGCAGCAGCCACTGGTAACA<br>GGATTAGCAGAGCGAGGTATGTAGGCGGTGCTACAGAGTTCTTGAAGTGGTGGCCTAACTACGGCTACACTAGAAGAA<br>CAGTATTTGGTATCTGCGCTCTGCTGAAGCCAGTTACCTTCGGAAAAAGAGTTGGTAGCTCTTGATCCGGCAAACAAAC<br>CACCGCTGGTAGCGGTGGTTTTTTTGTTTGCAAGCAGCAGATTACGCGCAGAAAAAAAGGATCTCAAGAAGATCCTTTG<br>ATCTTTTCTACGGGGTCTGACGCTCAGTGGAACGAAAACTCACGTTAAGGGATTTTGGTCATGAGATTATCAAAAAGGA<br>TCTTCACCTAGATCCTTTTAAATTAAAAATGAAGTTTTAAATCAATCTAAAGTATATATGAGTAAACTTGGTCTGACAGT<br>TACCAATGCTTAATCAGTGAGGCACCTATCTCAGCGATCTGTCTATTTCGTTCATCCATAGTTGCCTGACTCCCCGTCGT<br>GTAGATAACTACGATACGGGAGGGCTTACCATCTGGCCCCAGTGCTGCAATGATACCGCGAGACCCACGCTCACCGGCT<br>CCAGATTTATCAGCAATAAACCAGCCAGCCGGAAGGGCCGAGCGCAGAAGTGGTCCTGCAACTTTATCCGCCTCCATCC<br>AGTCTATTAATTGTTGCCGGGAAGCTAGAGTAAGTAGTTCGCCAGTTAATAGTTTGCGCAACGTTGTTGCCATTGCTACA<br>GGCATCGTGGTGTCACGCTCGTCGTTTGGTATGGCTTCATTCAGCTCCGGTTCCCAACGATCAAGGCGAGTTACATGATC<br>CCCCATGTTGTGCAAAAAAGCGGTTAGCTCCTTCGGTCCTCCGATCGTTGTCAGAAGTAAGTTGGCCGCAGTGTTATCAC<br>TCATGGTTATGGCAGCACTGCATAATTCTCTTACTGTCATGCCATCCGTAAGATGCTTTTCTGTGACTGGTGAGTACTCA<br>ACCAAGTCATTCTGAGAATAGTGTATGCGGCGACCGAGTTGCTCTTGCCCGGCGTCAATACGGGATAATACCGCGCCAC<br>ATAGCAGAACTTTAAAAGTGCTCATCATTGGAAAACGTTCTTCGGGGCGAAAACTCTCAAGGATCTTACCGCTGTTGAG<br>ATCCAGTTCGATGTAACCCACTCGTGCACCCAACTGATCTTCAGCATCTTTTACTTTCACCAGCGTTTCTGGGTGAGCAA<br>AAACAGGAAGGCAAAATGCCGCAAAAAAGGGAATAAGGGCGACACGGAAATGTTGAATACTCATACTCTTCCTTTTTC<br>AATATTATTGAAGCATTTATCAGGGTTATTGTCTCATGAGCGGATACATATTTGAATGTATTTAGAAAAATAAACAAAT<br>AGGGGTTCCGCGCACATTTCCCCGAAAAGTGCCACCTGACGTCTAAGAAACCATTATTATCATGACATTAACCTATAAA | |

TABLE 1D-continued

Exemplary expression construct sequences, optionally comprising a payload and a cap gene.

| Description | Sequence | SEQ ID NO |
|---|---|---|
| | AATAGGCGTATCACGAGGCCCTTTCGTCTCGCGCGTTTCGGTGATGACGGTGAAAACCTCTGACACATGCAGCTCCCGG<br>AGACGGTCACAGCTTGTCTGTAAGCGGATGCCGGGAGCAGACAAGCCCGTCAGGGCGCGTCAGCGGGTGTTGGCGGGT<br>GTCGGGGCTGGCTTAACTATGCGGCATCAGAGCAGATTGTACTGAGAGTGCACCATTCGACGCTCTCCCTTATGCGACT<br>CCTGCATTAGGAAGCAGCCCAGTAGTAGGTTGAGGCCGTTGAGCACCGCCGCCGCAAGGAATGGTGCATGCAAGGAGA<br>TGGCGCCCAACAGTCCCCCGGCCACGGGGCCTGCCACCATACCCACGCCGAAACAAGCGCTCATGAGCCCGAAGTGGC<br>GAGCCCGATCTTCCCCATCGGTGATGTCGGCGATATAGGCGCCAGCAACCGCACCTGTGGCGCCGGTGGGTCACCAAGC<br>AGGAAGTCAAAGACTTTTTCCGGTGGGCAAAGGATCACGTGGTTGAGGTGGAGCATGAATTCTACGTCAAAAAGGGTG<br>GAGCCAAGAAAAGACCCGCCCCCAGTGACGCAGATATAAGTGAGCCCAAACGGGTGCGCGAGTCAGTTGCGCAGCCAT<br>CGACGTCAGACGCGGAAGCTTCGATCAACTACGCAGACAGGTACCAAAACAAATGTTCTCGTCACGTGGGCATGAATCT<br>GATGCTGTTTCCCTGCAGACAATGCGAGAGAATGAATCAGAATTCAAATATCTGCTTCACTCACGGACAGAAAGACTGT<br>TTAGAGTGCTTTCCCGTGTCAGAATCTCAACCCGTTTCTGTCGTCAAAAAGGCGTATCAGAAACTGTGCTACATTCATCA<br>TATCATGGGAAAGGTGCCAGACGCTTGCACTGCCTGCGATCTGGTCAATGTGGATTTGGATGACTGCATCTTTGAACAA<br>TAAATGATTTAAATCAGGT | |
| Payload/Cap Plasmid Factor IX/ AAV-sL65 | CCCCTGTAATTGCTTGTTAATCAATAAACCGTTTAATTCGTTTCAGTTGAACTTTGGTCTCTGCGTATTTCTTTCTTATCT<br>AGTTTCCATATGCATGTAGATAAGTAGCATGGCGGGTTAATCATTAACTAACCGGTACCTCTAGAACTATAGCTAGCGAT<br>GACCCTGCTGATTGGTTCGCTGACCATTTCCGGGTGCGGGACGGCGTTACCAGAAACTCAGAAGGTTCGTCCAACCAAA<br>CCGACTCTGACGGCAGTTTACGAGAGAGATGATAGGGTCTGCTTCAGTAAGCCAGATGCTACACAATTAGGCTTGTACA<br>TATTGTCGTTAGAACGCGGCTACAATTAATACATAACCTTATGTATCATACACATACGATTTAGGTGACACTATAGAATA<br>CACGGAATTAATTCTTGGCCACTCCCTCTCTGCGCGCTCGCTCGCTCACTGAGGCCGCCCGGGCAAAGCCCGGGCGTCG<br>GGCGACCTTTGGTCGCCCGGCCTCAGTGAGCGAGCGAGCGCGCAGAGAGGGAGTGGCCAACTCCATCACTAGGGGTTC<br>CTTACGTAGGACGTCCCCTGCAGGCAGGGAGGGGTGGAGTCGTGACGTAAAGATCTGATATCATCGATCGCGATGCGA<br>GAGTTAAGCGGCCGAGGCTCAGAGGCACACAGGAGTTTCTGGGCTCACCCTGCCCCCTTCCAACCCCTCAGTTCCCATC<br>CTCCAGCAGCTGTTTGTGTGCTGCCTCTGAAGTCCACACTGAACAAACTTCAGCCTACTCATGTCCCTAAAATGGGCAAA<br>CATTGCAAGCAGCAAACAGCAAACACACAGCCCTCCCTGCCTGCTGACCTTGGAGCTGGGGCAGAGGTCAGAGACCTC<br>TCTGGGCCCATGCCACCTCCAACATCCACTCGACCCCTTGGAATTTCGGTGGAGAGGAGCAGAGGTTGTCCTGGCGTGG<br>TTTAGGTAGTGTGAGAGGGGTACCCGGGGATCTTGCTACCAGTGGAACAGCCACTAAGGATTCTGCAGTGAGAGCAGA<br>GGGCCAGCTAAGTGGTACTCTCCCAGAGACTGTCTGACTCACGCCACCCCCTCCACCTTGGACACAGGACGCTGTGGTT<br>TCTGAGCCAGGTACAATGACTCCTTTCGGTAAGTGCAGTGGAAGCTGTACACTGCCCAGGCAAAGCGTCCGGGCAGCGT<br>AGGCGGGCGACTCAGATCCCAGCCAGTGGACTTAGCCCCTGTTTGCTCCTCCGATAACTGGGGTGACCTTGGTTAATATT<br>CACCAGCAGCCTCCCCCGTTGCCCCTCTGGATCCACTGCTTAAATACGGACGAGGACAGGGCCCTGTCTCCTCAGCTTCA<br>GGCACCACCACTGACCTGGGACAGTGAATGATCCCCCTGATCTGCGGCCTCGACGGTATCGATAAGCTTGATATCGAAT<br>TCTAGTCGTCGACCACTTTCACAATCTGCTAGCAAAGGTTGCCACCATGCAGCGCGTGAACATGATTATGGCCGAGAGC<br>CCTGGCCTGATCACCATCTGCCTGCTGGGCTACCTGCTGAGCGCCGAGTGTACAGGTTTGTTTCCTTTTTTAAAATACAT<br>TGAGTATGCTTGCCTTTTAGATATAGAAATATCTGATGCTGTCTTCTTCACTAAATTTTGATTACATGATTTGACAGCAAT<br>ATTGAAGAGTCTAACAGCCAGCACGCAGGTTGGTAAGTACTGGTTCTTTGTTAGCTAGGTTTTCTTCTTCTTCATTTTTAA<br>AACTAAATAGATCGACAATGCTTATGATGCATTTATGTTTAATAAACACTGTTCAGTTCATGATTTGGTCATGTAATTCC<br>TGTTAGAAAACATTCATCTCCTTGGTTTAAAAAAATTAAAAGTGGGAAAACAAAGAAATAGCAGAATATAGTGAAAAA<br>AAATAACCACATTATTTTTGTTTGGACTTACCACTTTGAAATCAAAATGGGAAACAAAAGCACAAACAATGGCCTTATT<br>TACACAAAAAGTCTGATTTTAAGATATATGACATTTCAAGGTTTCAGAAGTATGTAATGAGGTGTGTCTCTAATTTTTTA<br>AATTATATATCTTCAATTTAAAGTTTTAGTTAAAACATAAAGATTAACCTTTCATTAGCAAGCTGTTAGTTATCACCAAA<br>GCTTTTCATGGATTAGGAAAAAATCATTTTGTCTCTATGTCAAACATCTTGGAGTTGATATTTGGGGAAACACAATACTC<br>AGTTGAGTTCCCTAGGGGAGAAAAGCAAGCTTAAGAATTGACATAAAGAGTAGGAAGTTAGCTAATGCAACATATATC<br>ACTTTGTTTTTTCACAACTACAGTGACTTTATGTATTTCCCAGAGGAAGGCATACAGGGAAGAAATTATCCCATTTGGAC<br>AAACAGCATGTTCTCACAGGAAGCATTTATCACACTTACTTGTCAACTTTCTAGAATCAAATCTAGTAGCTGACAGTACC<br>AGGATCAGGGGTGCCAACCCTAAGCACCCCCAGAAAGCTGACTGGCCCTGTGGTTCCCACTCCAGACATGATGTCAGCT<br>GTGAAATCGACGTCGCTGGACCATAATTAGGCTTCTGTTCTTCAGGAGACATTTGTTCAAAGTCATTTGGGCAACCATAT<br>TCTGAAAACAGCCCAGCCAGGGTGATGGATCACTTTGCAAAGATCCTCAATGAGCTATTTTCAAGTGATGACAAAGTGT<br>GAAGTTAACCGCTCATTTGAGAACTTTCTTTTTCATCCAAAGTAAATTCAAATATGATTAGAAATCTGACCTTTTATTAC<br>TGGAATTCTCTTGACTAAAAGTAAAATTGAATTTTAATTCCTAAATCTCCATGTGTATACAGTACTGTGGGAACATCACA<br>GATTTTGGCTCCATGCCCTAAAGAGAAATTGGCTTTCAGATTATTTGGATTAAAAACAAAGACTTTCTTAAGAGATGTA<br>AAATTTTCATGATGTTTTCTTTTTTGCTAAAACTAAAGAATTATTCTTTTACATTTCAGTGTTCCTGGACCACGAGAACGC<br>CAACAAGATCCTGAACAGACCCAAGAGATACAACAGCGGCAAGCTGGAAGAGTTCGTGCAGGGCAACCTGGAACGCG<br>AGTGCATGGAAGAGAAGTGCAGCTTCGAAGAGGCCAGAGAGGTGTTCGAGAACACCGAGAGAACCACCGAGTTCTGG<br>AAGCAGTACGTGGACGGCGACCAGTGCGAGAGCAACCCTTGTCTGAACGGCGGCAGCTGCAAGGACGACATCAACAGC<br>TACGAGTGCTGGTGCCCCTTCGGCTTCGAGGGCAAGAACTGCGAGCTGGACGTGACCTGCAACATCAAGAACGGCAGA<br>TGCGAGCAGTTCTGCAAGAACAGCGCCGACAACAAGGTCGTGTGCTCCTGCACCGAGGGCTACAGACTGGCCGAGAAC<br>CAGAAGTCCTGCGAGCCCGCTGTGCCTTTCCCATGCGGAAGAGTGTCCGTGTCCCAGACCAGCAAGCTGACCAGAGCCG<br>AGACAGTGTTCCCCGACGTGGACTACGTGAACAGCACCGAGGCCGAGACAATCCTGGACAACATCACCCAGAGCACCC<br>AGTCCTTCAACGACTTCACCAGAGTCGTGGGCGGCGAGGATGCTAAGCCTGGCCAGTTCCCGTGGCAGGTGGTGCTGAA<br>CGGAAAGGTGGACGCCTTCTGCGGCGGCTCCATCGTGAACGAGAAGTGGATCGTGACAGCCGCCCACTGCGTGGAAAC<br>CGGCGTGAAGATCACAGTGGTGGCCGGCGAGCACAACATCGAGGAAACCGAGCACACAGAGCAGAAAAGAAACGTGA<br>TCAGGATCATCCCCCACCACAACTACAACGCCGCCATCAACAAGTACAACCACGATATCGCCCTGCTGGAACTGGACGA<br>GCCCCTGGTGCTGAATAGCTACGTGACCCCCATCTGTATCGCCGACAAAGAGTACACCAACATCTTTCTGAAGTTCGGC<br>AGCGGCTACGTGTCCGGCTGGGGCAGAGTGTTTCACAAGGGCAGATCCGCTCTGGTGCTGCAGTACCTGAGAGTGCCTC<br>TGGTGGACAGAGCCACCTGTCTGAGAAGCACCAAGTTCACCATCTACAACAACATGTTCTGCGCTGGCTTCCACGAGGG<br>CGGCAGAGACTCTTGTCAGGGCGATTCTGGCGGCCCTCACGTGACAGAGGTGGAAGGCACCAGCTTTCTGACCGGCATC<br>ATCAGCTGGGGCGAGGAATGCGCCATGAAGGGGAAGTACGGCATCTACACCAAGGTGTCCAGATACGTGAACTGGATC<br>AAAGAAAAGACCAAGCTGACATAATGAAAGATGGATTTCCAAGGTTAATTCATTGGAATTGAAAATTAACAGCCCCCC<br>CCCCCCCCCCCTGCAGATCTCGAGCCGAATTCCTGCAGCCCGGGGGATCAGCCTCGACTGTGCCTTCTAGTTGCCAGCCA<br>TCTGTTGTTTGCCCCTCCCCCGTGCCTTCCTTGACCCTGGAAGGTGCCACTCCCACTGTCCTTTCCTAATAAAATGAGGA<br>AATTGCATCGCATTGTCTGAGTAGGTGTCATTCTATTCTGGGGGGTGGGGTGGGGCAGGACAGCAAGGGGGAGGATTG<br>GGAAGACAATAGCAGGCATGCTGGGGATGCGGTGGGCTCTATGGCTTCTGAGGCGGAAAGAACCAGCTGGGGCTCGAG<br>ATCCACTAGACTAGTGTACACGCGTGATATCAGATCTGTTACGTAAGGAACCCCTAGTGATGGAGTTGGCCACTCCCTC | 10 |

TABLE 1D-continued

Exemplary expression construct sequences, optionally comprising a payload and a cap gene.

| Description | Sequence | SEQ ID NO |
|---|---|---|
| | TCTGCGCGCTCGCTCGCTCACTGAGGCCGCCCGGGCAAAGCCCGGGCGGCCTCAGTGAGCGAGCGAGCGCGCAGAGAG<br>GGAGTGGCCAACTTTTTGCAAAAGCCTAGGCCTCCAAAAAAGCCTCCTCACTACTTCTGGAATAGCTCAGAGGCCGAGG<br>CGGCCTCGGCCTCTGCATAAATAAAAAAAATTAGTCAGCCATGGGGCGGAGAATGGGCGGAACTGGGCGGAGTTAGGG<br>GCGGGATGGGCGGAGTTAGGGGCGGGACTATGGTTGCTGACTAATTGAGATGCATGCTTTGCATACTTCTGCCTGCTGG<br>GGAGCCTGGGGACTTTCCACACCTGGTTGCTGACTAATTGAGATGCATGCTTTGCATACTTCTGCCTGCTGGGGAGCCTG<br>GGGACTTTCCACACCCTAACTGACACACATTCCACAGCTGCATTAATGAATCGGCCAACGCGCGGGGAGAGGCGGTTTG<br>CGTATTGGGCGCTCTTCCGCTTCCTCGCTCACTGACTCGCTGCGCTCGGTCGTTCGGCTGCGGCGAGCGGTATCAGCTCA<br>CTCAAAGGCGGTAATACGGTTATCCACAGAATCAGGGGATAACGCAGGAAAGAACATGTGAGCAAAAGGCCAGCAAA<br>AGGCCAGGAACCGTAAAAAGGCCGCGTTGCTGGCGTTTTTCCATAGGCTCCGCCCCCCTGACGAGCATCACAAAAATCG<br>ACGCTCAAGTCAGAGGTGGCGAAACCCGACAGGACTATAAAGATACCAGGCGTTTCCCCCTGGAAGCTCCCTCGTGCGC<br>TCTCCTGTTCCGACCCTGCCGCTTACCGGATACCTGTCCGCCTTTCTCCCTTCGGGAAGCGTGGCGCTTTCTCATAGCTCA<br>CGCTGTAGGTATCTCAGTTCGGTGTAGGTCGTTCGCTCCAAGCTGGGCTGTGTGCACGAACCCCCCGTTCAGCCCGACCG<br>CTGCGCCTTATCCGGTAACTATCGTCTTGAGTCCAACCCGGTAAGACACGACTTATCGCCACTGGCAGCAGCCACTGGT<br>AACAGGATTAGCAGAGCGAGGTATGTAGGCGGTGCTACAGAGTTCTTGAAGTGGTGGCCTAACTACGGCTACACTAGA<br>AGAACAGTATTTGGTATCTGCGCTCTGCTGAAGCCAGTTACCTTCGGAAAAAGAGTTGGTAGCTCTTGATCCGGCAAAC<br>AAACCACCGCTGGTAGCGGTGGTTTTTTTGTTTGCAAGCAGCAGATTACGCGCAGAAAAAAAGGATCTCAAGAAGATCC<br>TTTGATCTTTTCTACGGGGTCTGACGCTCAGTGGAACGAAAACTCACGTTAAGGGATTTTGGTCATGAGATTATCAAAA<br>AGGATCTTCACCTAGATCCTTTTAAATTAAAAATGAAGTTTTAAATCAATCTAAAGTATATATGAGTAAACTTGGTCTGA<br>CAGTTACCAATGCTTAATCAGTGAGGCACCTATCTCAGCGATCTGTCTATTTCGTTCATCCATAGTTGCCTGACTCCCCG<br>TCGTGTAGATAACTACGATACGGGAGGGCTTACCATCTGGCCCCAGTGCTGCAATGATACCGCGAGACCCACGCTCACC<br>GGCTCCAGATTTATCAGCAATAAACCAGCCAGCCGGAAGGGCCGAGCGCAGAAGTGGTCCTGCAACTTTATCCGCCTCC<br>ATCCAGTCTATTAATTGTTGCCGGGAAGCTAGAGTAAGTAGTTCGCCAGTTAATAGTTTGCGCAACGTTGTTGCCATTGC<br>TACAGGCATCGTGGTGTCACGCTCGTCGTTTGGTATGGCTTCATTCAGCTCCGGTTCCCAACGATCAAGGCGAGTTACAT<br>GATCCCCCATGTTGTGCAAAAAAGCGGTTAGCTCCTTCGGTCCTCCGATCGTTGTCAGAAGTAAGTTGGCCGCAGTGTTA<br>TCACTCATGGTTATGGCAGCACTGCATAATTCTCTTACTGTCATGCCATCCGTAAGATGCTTTTCTGTGACTGGTGAGTA<br>CTCAACCAAGTCATTCTGAGAATAGTGTATGCGGCGACCGAGTTGCTCTTGCCCGGCGTCAATACGGGATAATACCGCG<br>CCACATAGCAGAACTTTAAAAGTGCTCATCATTGGAAAACGTTCTTCGGGGCGAAAACTCTCAAGGATCTTACCGCTGT<br>TGAGATCCAGTTCGATGTAACCCACTCGTGCACCCAACTGATCTTCAGCATCTTTTACTTTCACCAGCGTTTCTGGGTGA<br>GCAAAAACAGGAAGGCAAAATGCCGCAAAAAAGGGAATAAGGGCGACACGGAAATGTTGAATACTCATACTCTTCCTT<br>TTTCAATATTATTGAAGCATTTATCAGGGTTATTGTCTCATGAGCGGATACATATTTGAATGTATTTAGAAAAATAAACA<br>AATAGGGGTTCCGCGCACATTTCCCCGAAAAGTGCCACCTGACGTCTAAGAAACCATTATTATCATGACATTAACCTAT<br>AAAAATAGGCGTATCACGAGGCCCTTTCGTCTCGCGCGTTTCGGTGATGACGGTGAAAACCTCTGACACATGCAGCTCC<br>CGGAGACGGTCACAGCTTGTCTGTAAGCGGATGCCGGGAGCAGACAAGCCCGTCAGGGCGCGTCAGCGGGTGTTGGCG<br>GGTGTCGGGGCTGGCTTAACTATGCGGCATCAGAGCAGATTGTACTGAGAGTGCACCATTCGACGCTCTCCCTTATGCG<br>ACTCCTGCATTAGGAAGCAGCCCAGTAGTAGGTTGAGGCCGTTGAGCACCGCCGCCGCAAGGAATGGTGCATGCAAGG<br>AGATGGCGCCCAACAGTCCCCCGGCCACGGGGCCTGCCACCATACCCACGCCGAAACAAGCGCTCATGAGCCCGAAGT<br>GGCGAGCCCGATCTTCCCCATCGGTGATGTCGGCGATATAGGCGCCAGCAACCGCACCTGTGGCGCCGGTGGGTCACCA<br>AGCAGGAAGTCAAAGACTTTTTCCGGTGGGCAAAGGATCACGTGGTTGAGGTGGAGCATGAATTCTACGTCAAAAAGG<br>GTGGAGCCAAGAAAAGACCCGCCCCCAGTGACGCAGATATAAGTGAGCCCAAACGGGTGCGCGAGTCAGTTGCGCAGC<br>CATCGACGTCAGACGCGGAAGCTTCGATCAACTACGCAGACAGGTACCAAAACAAATGTTCTCGTCACGTGGGCATGA<br>ATCTGATGCTGTTTCCCTGCAGACAATGCGAGAGAATGAATCAGAATTCAAATATCTGCTTCACTCACGGACAGAAAGA<br>CTGTTTAGAGTGCTTTCCCGTGTCAGAATCTCAACCCGTTTCTGTCGTCAAAAAGGCGTATCAGAAACTGTGCTACATTC<br>ATCATATCATGGGAAAGGTGCCAGACGCTTGCACTGCCTGCGATCTGGTCAATGTGGATTTGGATGACTGCATCTTTGA<br>ACAATAAATGATTTAAATCAGGTATGGCTGCTGACGGTTATCTTCCAGATTGGCTCGAGGACACTCTCTCTGAAGGCATT<br>CGCGAGTGGTGGGCGCTGAAACCTGGAGCTCCACAACCCAAGGCCAACCAACAGCATCAGGACAACGGCAGGGGTCTT<br>GTGCTTCCTGGGTACAAGTACCTCGGACCCTTCAACGGACTCGACAAGGGAGAGCCGGTCAACGAGGCAGACGCCGCG<br>GCCCTCGAGCACGACAAGGCCTACGACAAGCAGCTCGAGCAGGGGGACAACCCGTACCTCAAGTACAACCACGCCGAC<br>GCCGAGTTTCAGGAGCGTCTGCAAGAAGATACGTCTTTTGGGGGCAACCTCGGGCGAGCAGTCTTCCAGGCCAAGAAG<br>CGGGTTCTCGAACCTCTCGGTCTGGTTGAGGAAGGCGCTAAGACGGCTCCTGGAAAGAAGAGACCGGTAGAGCCGTCA<br>CCTCAGCGTTCCCCCGACTCCTCCACGGGCATCGGCAAGAAAGGCCAGCAGCCCGCCAGAAAGAGACTCAATTTCGGTC<br>AGACTGGCGACTCAGAGTCAGTCCCCGACCCTCAACCTCTCGGAGAACCTCCAGCAGCGCCCTCTAGTGTGGGATCTGG<br>TACAGTGGCTGCAGGCGGTGGCGCACCAATGGCAGACAATAACGAAGGTGCCGACGGAGTGGGTAATGCCTCAGGAAA<br>TTGGCATTGCGATTCCACATGGCTGGGCGACAGAGTCATTACCACCAGCACCCGAACCTGGGCCCTGCCCACCTACAAC<br>AACCACCTCTACAAGCAAATCTCCAGCCAATCAGGAGCTTCAAACGACAACCACTACTTTGGCTACAGCACCCCTTGGG<br>GGTATTTTGACTTTAACAGATTCCACTGCCACTTCTCACCACGTGACTGGCAGCGACTCATTAACAACAACTGGGGATTC<br>CGGCCCAAGAGACTCAACTTCAAGCTCTTCAACATCCAAGTCAAGGAGGTCACGACGAATGATGGCGTCACGACCATC<br>GCTAATAACCTTACCAGCACGGTTCAAGTCTTCTCGGACTCGGAGTACCAGTTGCCGTACGTCCTCGGCTCTGCGCACCA<br>GGGCTGCCTCCCTCCGTTCCCGGCGGACGTGTTCATGATTCCCCAGTACGGCTACCTAACACTCAACAACGGTAGTCAG<br>GCCGTGGGACGCTCCTCCTTTTACTGCCTGGAATATTTCCCATCGCAGATGCTGAGAACGGGCAATAACTTTGAGTTCAG<br>CTACAGCTTCGAGGACGTGCCTTTCCACAGCAGCTACGCACACAGCCAGAGCTTGGACCGACTGATGAATCCTCTCATT<br>GACCAGTACCTGTACTACTTATCCAGAACTCAGTCCACAGGAGGAACTCAAGGTACCCAGCAATTGTTATTTTCTCAAG<br>CTGGGCCTGCAAACATGTCGGCTCAGGCCAAGAACTGGCTGCCTGGACCTTGCTACCGGCAGCAGCGAGTCTCCACGAC<br>ACTGTCGCAAAACAACAACAGCAACTTTGCTTGGACTGGTGCCACCAAATATCACCTGAACGGCAGAAACTCGTTGGTT<br>AATCCCGGCGTCGCCATGGCAACTCACAAGGACGACGAGGACCGCTTTTTCCCATCCAGCGGAGTCCTGATTTTTGGAA<br>AAACTGGAGCAACTAACAAAACTACATTGGAAAATGTGTTAATGACAAATGAAGAAGAAATTCGTCCTACTAATCCTGT<br>AGCCACGGAAGAATACGGGATAGTCAGCAGCAACTTACAAGCGGCTAATACTGCAGCCCAGACACAAGTTGTCAACAA<br>CCAGGGAGCCTTACCTGGCATGGTCTGGCAGAACCGGGACGTGTACCTGCAGGGTCCCATTTGGGCCAAAATTCCTCAC<br>ACAGATGGACACTTTCACCCGTCTCCTCTTATGGGCGGCTTTGGACTCAAGAACCCGCCTCCTCAGATCCTCATCAAAAA<br>CACGCCTGTTCCTGCGAATCCTCCGGCGGAGTTTTCAGCTACAAAGTTTGCTTCATTCATCACCCAGTATTCCACAGGAC<br>AAGTGAGCGTGGAGATTGAATGGGAGCTGCAGAAAGAAAACAGCAAACGCTGGAATCCCGAAGTGCAGTATACATCTA<br>ACTATGCAAAATCTGCCAACGTTGATTTCACTGTGGACAACAATGGACTTTATACTGAGCCTCGCCCCATTGGCACCCGT<br>TACCTTACCCGT | |

TABLE 1D-continued

Exemplary expression construct sequences, optionally comprising a payload and a cap gene.

| Description | Sequence | SEQ ID NO |
| --- | --- | --- |
| Plasmid Backbone 1 for of insertion Payload/Cap | GTATATATGAGTAAACTTGGTCTGACAGTTACCAATGCTTAATCAGTGAGGCACCTATCTCAGCGATCTGTCTATTTCGT<br>TCATCCATAGTTGCCTGACTCCCCGTCGTGTAGATAACTACGATACGGGAGGGCTTACCATCTGGCCCCAGTGCTGCAAT<br>GATACCGCGAGACCCACGCTCACCGGCTCCAGATTTATCAGCAATAAACCAGCCAGCCGGAAGGGCCGAGCGCAGAAG<br>TGGTCCTGCAACTTTATCCGCCTCCATCCAGTCTATTAATTGTTGCCGGGAAGCTAGAGTAAGTAGTTCGCCAGTTAATA<br>GTTTGCGCAACGTTGTTGCCATTGCTACAGGCATCGTGGTGTCACGCTCGTCGTTTGGTATGGCTTCATTCAGCTCCGGT<br>TCCCAACGATCAAGGCGAGTTACATGATCCCCCATGTTGTGCAAAAAAGCGGTTAGCTCCTTCGGTCCTCCGATCGTTGT<br>CAGAAGTAAGTTGGCCGCAGTGTTATCACTCATGGTTATGGCAGCACTGCATAATTCTCTTACTGTCATGCCATCCGTAA<br>GATGCTTTTCTGTGACTGGTGAGTACTCAACCAAGTCATTCTGAGAATAGTGTATGCGGCGACCGAGTTGCTCTTGCCCG<br>GCGTCAATACGGGATAATACCGCGCCACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTGCACCCAACTGATCTTCAGCATCTTTT<br>ACTTTCACCAGCGTTTCTGGGTGAGCAAAAACAGGAAGGCAAAATGCCGCAAAAAAGGGAATAAGGGCGACACGGAA<br>ATGTTGAATACTCATACTCTTCCTTTTTCAATATTATTGAAGCATTTATCAGGGTTATTGTCTCATGAGCGGATACATATT<br>TGAATGTATTTAGAAAAATAAACAAATAGGGGTTCCGCGCACATTTCCCCGAAAAGTGCCACCTGACGTCTAAGAAACC<br>ATTATTATCATGACATTAACCTATAAAAATAGGCGTATCACGAGGCCCTTTCGTCTCGCGCGTTTCGGTGATGACGGTGA<br>AAACCTCTGACACATGCAGCTCCCGGAGACGGTCACAGCTTGTCTGTAAGCGGATGCCGGGAGCAGACAAGCCCGTCA<br>GGGCGCGTCAGCGGGTGTTGGCGGGTGTCGGGGCTGGCTTAACTATGCGGCATCAGAGCAGATTGTACTGAGAGTGCA<br>CCATTCGACGCTCTCCCTTATGCGACTCCTGCATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGGCCACGGGGCCTGCCACCATACCCACGCCGAA<br>ACAAGCGCTCATGAGCCCGAAGTGGCGAGCCCGATCTTCCCCATCGGTGATGTCGGCGATATAGGCGCCAGCAACCGC<br>ACCTGTGGCGCCGGTGGGTCACCAAGCAGGAAGTCAAAGACTTTTTCCGGTGGGCAAAGGATCACGTGGTTGAGGTGG<br>AGCATGAATTCTACGTCAAAAAGGGTGGAGCCAAGAAAAGACCCGCCCCCAGTGACGCAGATATAAGTGAGCCCAAAC<br>GGGTGCGCGAGTCAGTTGCGCAGCCATCGACGTCAGACGCGGAAGCTTCGATCAACTACGCAGACAGGTACCAAAACA<br>AATGTTCTCGTCACGTGGGCATGAATCTGATGCTGTTTCCCTGCAGACAATGCGAGAGAATGAATCAGAATTCAAATAT<br>CTGCTTCACTCACGGACAGAAAGACTGTTTAGAGTGCTTTCCCGTGTCAGAATCTCAACCCGTTTCTGTCGTCAAAAAGG<br>CGTATCAGAAACTGTGCTACATTCATCATATCATGGGAAAGGTGCCAGACGCTTGCACTGCCTGCGATCTGGTCAATGT<br>GGATTTGGATGACTGCATCTTTGAACAATAAATGATTTAAATCAGGTTTGCTTGTTAATCAATAAACCGTTTAATTCGTT<br>TCAGTTGAACTTTGGTCTCTGCGTATTTCTTTCTTATCTAGTTTCCATATGCATGTAGATAAGTAGCATGGCGGGTTAATC<br>ATTAACTAACCGGTACCTCTAGAACTATAGCTAGCGATGACCCTGCTGATTGGTTCGCTGACCATTTCCGGGTGCGGGA<br>CGGCGTTACCAGAAACTCAGAAGGTTCGTCCAACCAAACCGACTCTGACGGCAGTTTACGAGAGAGATGATAGGGTCT<br>GCTTCAGTAAGCCAGATGCTACACAATTAGGCTTGTACATATTGTCGTTAGAACGCGGCTACAATTAATACATAACCTT<br>ATGTATCATACACATACGATTTAGGTGACACTATAGAATACACGGAATTAATTCTTGGCCACTCCCTCTCTGCGCGCTCG<br>CTCGCTCACTGAGGCCGCCCGGGCAAAGCCCGGGCGTCGGGCGACCTTTGGTCGCCCGGCCTCAGTGAGCGAGCGAGC<br>GCGCAGAGAGGGAGTGGCCAACTCCATCACTAGGGGTTCCTTACGTAGGACGTCCCCTGCAGGCAGGGAGGGGTGGAG<br>TCGTGACGTAAAGATCTGATATCATCGATCGCGATGCATTAATTAAGCGGCCGCTTCTGAGGCGGAAAGAACCAGCTGG<br>GGCTCGAGATCCACTAGACTAGTGTACACGCGTGATATCAGATCTGTTACGTAAGGAACCCCTAGTGATGGAGTTGGCC<br>ACTCCCTCTCTGCGCGCTCGCTCGCTCACTGAGGCCGCCCGGGCAAAGCCCGGGCGGCCTCAGTGAGCGAGCGAGCGCG<br>CAGAGAGGGAGTGGCCAACTTTTTGCAAAAGCCTAGGCCTCCAAAAAAGCCTCCTCACTACTTCTGGAATAGCTCAGAG<br>GCCGAGGCGGCCTCGGCCTCTGCATAAATAAAAAAAATTAGTCAGCCATGGGGCGGAGAATGGGCGGAACTGGGCGGA<br>GTTAGGGGCGGGATGGGCGGAGTTAGGGGCGGGACTATGGTTGCTGACTAATTGAGATGCATGCTTTGCATACTTCTGC<br>CTGCTGGGGAGCCTGGGGACTTTCCACACCTGGTTGCTGACTAATTGAGATGCATGCTTTGCATACTTCTGCCTGCTGGG<br>GAGCCTGGGGACTTTCCACACCCTAACTGACACACATTCCACAGCTGCATTAATGAATCGGCCAACGCGCGGGGAGAG<br>GCGGTTTGCGTATTGGGCGCTCTTCCGCTTCCTCGCTCACTGACTCGCTGCGCTCGGTCGTTCGGCTGCGGCGAGCGGTA<br>TCAGCTCACTCAAAGGCGGTAATACGGTTATCCACAGAATCAGGGGATAACGCAGGAAAGAACATGTGAGCAAAAGGC<br>CAGCAAAAGGCCAGGAACCGTAAAAAGGCCGCGTTGCTGGCGTTTTTCCATAGGCTCCGCCCCCCTGACGAGCATCACA<br>AAAATCGACGCTCAAGTCAGAGGTGGCGAAACCCGACAGGACTATAAAGATACCAGGCGTTTCCCCCTGGAAGCTCCC<br>TCGTGCGCTCTCCTGTTCCGACCCTGCCGCTTACCGGATACCTGTCCGCCTTTCTCCCTTCGGGAAGCGTGGCGCTTTCTC<br>ATAGCTCACGCTGTAGGTATCTCAGTTCGGTGTAGGTCGTTCGCTCCAAGCTGGGCTGTGTGCACGAACCCCCCGTTCAG<br>CCCGACCGCTGCGCCTTATCCGGTAACTATCGTCTTGAGTCCAACCCGGTAAGACACGACTTATCGCCACTGGCAGCAG<br>CCACTGGTAACAGGATTAGCAGAGCGAGGTATGTAGGCGGTGCTACAGAGTTCTTGAAGTGGTGGCCTAACTACGGCTA<br>CACTAGAAGAACAGTATTTGGTATCTGCGCTCTGCTGAAGCCAGTTACCTTCGGAAAAAGAGTTGGTAGCTCTTGATCC<br>GGCAAACAAACCACCGCTGGTAGCGGTGGTTTTTTTGTTTGCAAGCAGCAGATTACGCGCAGAAAAAAAGGATCTCAA<br>GAAGATCCTTTGATCTTTTCTACGGGGTCTGACGCTCAGTGGAACGAAAACTCACGTTAAGGGATTTTGGTCATGAGATT<br>ATCAAAAAGGATCTTCACCTAGATCCTTTTAAATTAAAAATGAAGTTTTAAATCAATCTAAA | 11 |
| Plasmid Backbone 2 for of insertion Payload/Cap | GTATATATGAGTAAACTTGGTCTGACAGTTACCAATGCTTAATCAGTGAGGCACCTATCTCAGCGATCTGTCTATTTCGT<br>TCATCCATAGTTGCCTGACTCCCCGTCGTGTAGATAACTACGATACGGGAGGGCTTACCATCTGGCCCCAGTGCTGCAAT<br>GATACCGCGAGACCCACGCTCACCGGCTCCAGATTTATCAGCAATAAACCAGCCAGCCGGAAGGGCCGAGCGCAGAAG<br>TGGTCCTGCAACTTTATCCGCCTCCATCCAGTCTATTAATTGTTGCCGGGAAGCTAGAGTAAGTAGTTCGCCAGTTAATA<br>GTTTGCGCAACGTTGTTGCCATTGCTACAGGCATCGTGGTGTCACGCTCGTCGTTTGGTATGGCTTCATTCAGCTCCGGT<br>TCCCAACGATCAAGGCGAGTTACATGATCCCCCATGTTGTGCAAAAAAGCGGTTAGCTCCTTCGGTCCTCCGATCGTTGT<br>CAGAAGTAAGTTGGCCGCAGTGTTATCACTCATGGTTATGGCAGCACTGCATAATTCTCTTACTGTCATGCCATCCGTAA<br>GATGCTTTTCTGTGACTGGTGAGTACTCAACCAAGTCATTCTGAGAATAGTGTATGCGGCGACCGAGTTGCTCTTGCCCG<br>GCGTCAATACGGGATAATACCGCGCCACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTGCACCCAACTGATCTTCAGCATCTTTT<br>ACTTTCACCAGCGTTTCTGGGTGAGCAAAAACAGGAAGGCAAAATGCCGCAAAAAAGGGAATAAGGGCGACACGGAA<br>ATGTTGAATACTCATACTCTTCCTTTTTCAATATTATTGAAGCATTTATCAGGGTTATTGTCTCATGAGCGGATACATATT<br>TGAATGTATTTAGAAAAATAAACAAATAGGGGTTCCGCGCACATTTCCCCGAAAAGTGCCACCTGACGTCTAAGAAACC<br>ATTATTATCATGACATTAACCTATAAAAATAGGCGTATCACGAGGCCCTTTCGTCTCGCGCGTTTCGGTGATGACGGTGA<br>AAACCTCTGACACATGCAGCTCCCGGAGACGGTCACAGCTTGTCTGTAAGCGGATGCCGGGAGCAGACAAGCCCGTCA<br>GGGCGCGTCAGCGGGTGTTGGCGGGTGTCGGGGCTGGCTTAACTATGCGGCATCAGAGCAGATTGTACTGAGAGTGCA<br>CCATTCGACGCTCTCCCTTATGCGACTCCTGCATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGGCCACGGGGCCTGCCACCATACCCACGCCGAA<br>ACAAGCGCTCATGAGCCCGAAGTGGCGAGCCCGATCTTCCCCATCGGTGATGTCGGCGATATAGGCGCCAGCAACCGC | 12 |

TABLE 1D-continued

Exemplary expression construct sequences, optionally comprising a payload and a cap gene.

| Description | Sequence | SEQ ID NO |
|---|---|---|
| | ACCTGTGGCGCCGGTGGGTCACCAAGCAGGAAGTCAAAGACTTTTTCCGGTGGGCAAAGGATCACGTGGTTGAGGTGG AGCATGAATTCTACGTCAAAAAGGGTGGAGCCAAGAAAAGACCCGCCCCCAGTGACGCAGATATAAGTGAGCCCAAAC GGGTGCGCGAGTCAGTTGCGCAGCCATCGACGTCAGACGCGGAAGCTTCGATCAACTACGCAGACAGGTACCAAAACA AATGTTCTCGTCACGTGGGCATGAATCTGATGCTGTTTCCCTGCAGACAATGCGAGAGAATGAATCAGAATTCAAATAT CTGCTTCACTCACGGACAGAAAGACTGTTTAGAGTGCTTTCCCGTGTCAGAATCTCAACCCGTTTCTGTCGTCAAAAAGG CGTATCAGAAACTGTGCTACATTCATCATATCATGGGAAAGGTGCCAGACGCTTGCACTGCCTGCGATCTGGTCAATGT GGATTTGGATGACTGCATCTTTGAACAATAAATGATTTAAATACCGGTACCTCTAGAACTATAGCTAGCGATGACCCTG CTGATTGGTTCGCTGACCATTTCCGGGTGCGGGACGGCGTTACCAGAAACTCAGAAGGTTCGTCCAACCAAACCGACTC TGACGGCAGTTTACGAGAGAGATGATAGGGTCTGCTTCAGTAAGCCAGATGCTACACAATTAGGCTTGTACATATTGTC GTTAGAACGCGGCTACAATTAATACATAACCTTATGTATCATACACATACGATTTAGGTGACACTATAGAATACACGGA ATTAATTCTTGGCCACTCCCTCTCTGCGCGCTCGCTCGCTCACTGAGGCCGCCCGGGCAAAGCCCGGGCGTCGGGCGAC CTTTGGTCGCCCGGCCTCAGTGAGCGAGCGAGCGCGCAGAGAGGGAGTGGCCAACTCCATCACTAGGGGTTCCTTACGT AAGGAACCCCTAGTGATGGAGTTGGCCACTCCCTCTCTGCGCGCTCGCTCGCTCACTGAGGCCGCCCGGGCAAAGCCCG GGCGGCCTCAGTGAGCGAGCGAGCGCGCAGAGAGGGAGTGGCCAACTTTTTGCAAAAGCCTAGGCCTCCAAAAAAGCC TCCTCACTACTTCTGGAATAGCTCAGAGGCCGAGGCGGCCTCGGCCTCTGCATAAATAAAAAAAATTAGTCAGCCATGG GGCGGAGAATGGGCGGAACTGGGCGGAGTTAGGGGCGGGATGGGCGGAGTTAGGGGCGGGACTATGGTTGCTGACTA ATTGAGATGCATGCTTTGCATACTTCTGCCTGCTGGGGAGCCTGGGGACTTTCCACACCTGGTTGCTGACTAATTGAGAT GCATGCTTTGCATACTTCTGCCTGCTGGGGAGCCTGGGGACTTTCCACACCCTAACTGACACACATTCCACAGCTGCATT AATGAATCGGCCAACGCGCGGGGAGAGGCGGTTTGCGTATTGGGCGCTCTTCCGCTTCCTCGCTCACTGACTCGCTGCG CTCGGTCGTTCGGCTGCGGCGAGCGGTATCAGCTCACTCAAAGGCGGTAATACGGTTATCCACAGAATCAGGGGATAAC GCAGGAAAGAACATGTGAGCAAAAGGCCAGCAAAAGGCCAGGAACCGTAAAAAGGCCGCGTTGCTGGCGTTTTTCCAT AGGCTCCGCCCCCCTGACGAGCATCACAAAAATCGACGCTCAAGTCAGAGGTGGCGAAACCCGACAGGACTATAAAGA TACCAGGCGTTTCCCCCTGGAAGCTCCCTCGTGCGCTCTCCTGTTCCGACCCTGCCGCTTACCGGATACCTGTCCGCCTTT CTCCCTTCGGGAAGCGTGGCGCTTTCTCATAGCTCACGCTGTAGGTATCTCAGTTCGGTGTAGGTCGTTCGCTCCAAGCT GGGCTGTGTGCACGAACCCCCCGTTCAGCCCGACCGCTGCGCCTTATCCGGTAACTATCGTCTTGAGTCCAACCCGGTA AGACACGACTTATCGCCACTGGCAGCAGCCACTGGTAACAGGATTAGCAGAGCGAGGTATGTAGGCGGTGCTACAGAG TTCTTGAAGTGGTGGCCTAACTACGGCTACACTAGAAGAACAGTATTTGGTATCTGCGCTCTGCTGAAGCCAGTTACCTT CGGAAAAAGAGTTGGTAGCTCTTGATCCGGCAAACAAACCACCGCTGGTAGCGGTGGTTTTTTTGTTTGCAAGCAGCAG ATTACGCGCAGAAAAAAAGGATCTCAAGAAGATCCTTTGATCTTTTCTACGGGGTCTGACGCTCAGTGGAACGAAAACT CACGTTAAGGGATTTTGGTCATGAGATTATCAAAAAGGATCTTCACCTAGATCCTTTTAAATTAAAAATGAAGTTTTAAA TCAATCTAAA | |

In some embodiments, compositions comprise: (i) a first expression construct comprising a polynucleotide sequence encoding one or more rep genes and a polynucleotide sequence encoding one or more wild-type adenoviral helper proteins; and (ii) a second expression construct comprising a polynucleotide sequence encoding a capsid protein and a polynucleotide sequence encoding a payload comprising a polynucleotide sequence encoding a gene (or variant thereof). In some embodiments, compositions comprise: (i) a first expression construct comprising a sequence outlined in FIG. 29; and (ii) a second expression construct comprising a polynucleotide sequence encoding a capsid outlined in FIG. 29 and a polynucleotide sequence encoding a payload comprising a polynucleotide sequence encoding a gene (or variant thereof) outlined in FIG. 29. In some embodiments, compositions comprise: (i) a first expression construct comprising a sequence outlined in FIG. 29; and (ii) a second expression construct comprising a polynucleotide sequence encoding a capsid outlined in FIG. 29 and a polynucleotide sequence encoding a payload comprising a polynucleotide sequence encoding a gene (or variant thereof) outlined in FIG. 29, wherein the first and second expression construct are present in a combination as outlined in a single row of FIG. 29. In some embodiments, compositions comprise: (i) a first expression construct comprising a sequence outlined in FIG. 29; and (ii) a second expression construct comprising a polynucleotide sequence encoding a capsid outlined in FIG. 29 and a polynucleotide sequence encoding a payload comprising a polynucleotide sequence encoding a gene (or variant thereof) outlined in FIG. 29, wherein the first and second expression construct are present in a combination as outlined in a single row of FIG. 29, and wherein compositions comprising such a combination of a first expression construct and second expression construct may be administered to one or more cells to produce an exemplary viral vector product, as outlined in FIG. 29.

In some embodiments, compositions comprise: (i) a first expression construct consisting of a sequence outlined in FIG. 29; and (ii) a second expression construct consisting of a sequence of SEQ ID NO: 11, wherein a polynucleotide sequence encoding a payload comprising a polynucleotide sequence encoding a gene (or variant thereof) outlined in FIG. 29 is inserted after position 2663 of SEQ ID NO: 11 and a polynucleotide sequence encoding a capsid outlined in FIG. 29 is inserted before position 2025 of SEQ ID NO: 11. In some embodiments, compositions comprise: (i) a first expression construct consisting of a sequence in FIG. 29; and (ii) a second expression construct consisting of a sequence of SEQ ID NO: 11, wherein a polynucleotide sequence encoding a payload comprising a polynucleotide sequence encoding a gene (or variant thereof) outlined in FIG. 29 is inserted after position 2663 of SEQ ID NO: 11 and a polynucleotide sequence encoding a capsid outlined in FIG. 29 is inserted before position 2025 of SEQ ID NO: 11, wherein the first and second expression construct are present in a combination as outlined in a single row in FIG. 29. In some embodiments, compositions comprise: (i) a first expression construct consisting of a sequence in FIG. 29; and (ii) a second expression construct consisting of a sequence of SEQ ID NO: 11, wherein a polynucleotide sequence encoding a payload comprising a polynucleotide sequence encoding a payload comprising a polynucleotide sequence encoding a payload comprising a polynucleotide sequence encoding a gene (or variant thereof) outlined in FIG. 29 is inserted after position 2663 of SEQ ID NO: 11 and a polynucleotide sequence encoding a capsid outlined in FIG. 29 is inserted before position 2025 of SEQ ID NO: 11, wherein the first and second expression construct are present in a combination as outlined in a single row in FIG. 29 and wherein compositions comprising such a combination of a first expression construct and second expression construct may be administered to one or more cells to produce an exemplary viral vector product, as outlined in FIG. 29.

In some embodiments, compositions comprise: (i) a first expression construct consisting of a sequence outlined in FIG. 29; and (ii) a second expression construct consisting of a sequence of SEQ ID NO: 12, wherein a polynucleotide sequence encoding a payload comprising a polynucleotide sequence encoding a gene (or variant thereof) outlined in FIG. 29 is inserted between positions 2011-2026 of SEQ ID NO: 12 and a polynucleotide sequence encoding a capsid outlined in FIG. 29 is inserted between positions 2446-2453 of SEQ ID NO: 12. In some embodiments, compositions comprise: (i) a first expression construct consisting of a sequence in FIG. 29; and (ii) a second expression construct consisting of a sequence of SEQ ID NO: 12, wherein a polynucleotide sequence encoding a payload comprising a polynucleotide sequence encoding a gene (or variant thereof) outlined in FIG. 29 is inserted between positions 2011-2026 of SEQ ID NO: 12 and a polynucleotide sequence encoding a capsid outlined in FIG. 29 is inserted between positions 2446-2453 of SEQ ID NO: 12, wherein the first and second expression construct are present in a combination as outlined in a single row in FIG. 29. In some embodiments, compositions comprise: (i) a first expression construct consisting of a sequence in FIG. 29; and (ii) a second expression construct consisting of a sequence of SEQ ID NO: 12, wherein a polynucleotide sequence encoding a payload comprising a polynucleotide sequence encoding a gene (or variant thereof) outlined in FIG. 29 is inserted between positions 2011-2026 of SEQ ID NO: 12 and a polynucleotide sequence encoding a capsid outlined in FIG. 29 is inserted between positions 2446-2453 of SEQ ID NO: 12, wherein the first and second expression construct are present in a combination as outlined in a single row in FIG. 29 and wherein compositions comprising such a combination of a first expression construct and second expression construct may be administered to one or more cells to produce an exemplary viral vector product, as outlined in FIG. 29. In some embodiments insertion of a polynucleotide sequence into SEQ ID NO: 12 results in removal, replacement, and/or deletion of intervening portions of the polynucleotide sequence (e.g., insertion between positions 2011-2026 results in deletion of former nucleotides at positions 2012-2025 and insertion of a polynucleotide sequence).

In some embodiments, compositions comprise a first expression construct (e.g. plasmid) that comprises a sequence that has at least 70%, at least 75%, at least 80%, at least 85%, at least 90%, at least 95%, at least 99%, or 100% sequence identity with a sequence in Table 1C or a variant thereof and a second expression construct (e.g. plasmid) that comprises a sequence that has at least 70%, at least 75%, at least 80%, at least 85%, at least 90%, at least 95%, at least 99%, or 100% sequence identity with a sequence in Table 1D or a variant thereof. In some embodiments, compositions comprise a first plasmid (e.g. Rep/Helper Plasmid) that comprises a sequence that has at least 70%, at least 75%, at least 80%, at least 85%, at least 90%, at least 95%, at least 99%, or 100% sequence identity with a sequence in Table 1C or a variant thereof and a second plasmid (e.g. Payload/Cap Plasmid) that comprises a sequence that has at least 70%, at least 75%, at least 80%, at least 85%, at least 90%, at least 95%, at least 99%, or 100% sequence identity with a sequence in Table 1D or a variant thereof.

Methods of Characterizing AAV Viral Vectors

In accordance with various embodiments, viral vectors may be characterized through assessment of various characteristics and/or features. In some embodiments, assessment of viral vectors can be conducted at various points in a production process. In some embodiments, assessment of viral vectors can be conducted after completion of upstream production steps. In some embodiments, assessment of viral vectors can be conducted after completion of downstream production steps.

Viral Yields

In some embodiments, characterization of viral vectors comprises assessment of viral yields (e.g., viral titer). In some embodiments, characterization of viral vectors comprises assessment of viral yields prior to purification and/or filtration. In some embodiments, characterization of viral vectors comprises assessment of viral yields after purification and/or filtration. In some embodiments, characterization of viral vectors comprises assessing whether viral yield is greater than or equal to 1e10 vg/mL.

In some embodiments, characterization of viral vectors comprises assessing whether viral yield in crude cell lysates is greater than or equal to 1e11 vg/mL. In some embodiments, characterization of viral vectors comprises assessing whether viral yield in crude cell lysates is greater than or equal to 5e11 vg/mL. In some embodiments, characterization of viral vectors comprises assessing whether viral yield in crude cell lysates is greater than or equal to 1e12 vg/mL. In some embodiments, characterization of viral vectors comprises assessing whether viral yield in crude lysates is between 5e9 vg/mL and 5e11 vg/mL. In some embodiments, characterization of viral vectors comprises assessing whether viral yield in crude lysates is between 5e9 vg/mL and 1e10 vg/mL. In some embodiments, characterization of viral vectors comprises assessing whether viral yield in crude lysates is between 1e10 vg/mL and 1e11 vg/mL. In some embodiments, characterization of viral vectors comprises assessing whether viral yield in crude lysates is between 1e11 vg/mL and 1e12 vg/mL. In some embodiments, characterization of viral vectors comprises assessing whether viral yield in crude lysates is between 1e12 vg/mL and 1e13 vg/mL.

In some embodiments, characterization of viral vectors comprises assessing whether viral yield in purified drug product is greater than or equal to 1e11 vg/mL. In some embodiments, characterization of viral vectors comprises assessing whether viral yield in purified drug product is greater than or equal to 1e12 vg/mL. In some embodiments, characterization of viral vectors comprises assessing whether viral yield in purified drug product is between 1e10 vg/mL and 1e15 vg/mL. In some embodiments, characterization of viral vectors comprises assessing whether viral yield in purified drug product is between 1e11 vg/mL and 1e15 vg/mL. In some embodiments, characterization of viral vectors comprises assessing whether viral yield in purified drug product is between 1e12 vg/mL and 1e14 vg/mL. In some embodiments, characterization of viral vectors comprises assessing whether viral yield in purified drug product is between 1e13 and 1e14 vg/mL.

In some embodiments, methods and compositions provided herein can provide comparable or increased viral vector yields as compared to previous methods known in the art. For example, in some embodiments, provided methods for producing and/or manufacturing viral vectors comprising use of a two-plasmid transfection system provide comparable or increased viral vector yields as compared to a three-plasmid system. In some embodiments, provided methods for producing and/or manufacturing viral vectors comprising use of a two-plasmid transfection system with particular combinations of sequence elements provide comparable or increased viral vector yields as compared to a two-plasmid system with a different combination of sequence elements. In some embodiments, provided methods for producing and/or manufacturing viral vectors comprising use of a two-plasmid transfection system with particular plasmid ratios provide comparable or increased viral vector yields as compared to a two-plasmid system with different plasmid ratios. In some embodiments, provided methods for producing and/or manufacturing viral vectors comprising use of a two-plasmid transfection system with particular plasmid ratios provide comparable or increased viral vector yields as compared to a reference (e.g., two-plasmid system with different plasmid ratios, three-plasmid system) under particular culture conditions. In some embodiments, provided methods for producing and/or manufacturing viral vectors comprising use of a two-plasmid transfection system with particular plasmid ratios provide comparable or increased viral vector yields as compared to a reference (e.g., two-plasmid system with different plasmid ratios, three-plasmid system) under large-scale culture conditions (e.g., greater than 100 mL, greater than 250 mL, greater than 1 L, greater than 10 L, greater than 20 L, greater than 30 L, greater than 40 L, greater than 50 L, etc.).

Viral Packaging

In some embodiments, characterization of viral vectors comprises assessment of viral packaging efficiency (e.g., percent of full versus empty capsids). In some embodiments, characterization of viral vectors comprises assessment of viral packaging efficiency prior to purification and/or full capsid enrichment (e.g., cesium chloride-based density gradient, iodixanol-based density gradient or ion exchange chromatography). In some embodiments, characterization of viral vectors comprises assessing whether viral packaging efficiency is greater than or equal to 20% prior to purification and/or filtration (e.g., 20%, 25%, 30%, 35%, 40%, 45%, 50%, 55%, 60%, 65%, 70%, 75%, 80%, 85%, 90%, 95%, 99%, 100%). In some embodiments, characterization of viral vectors comprises assessment of viral packaging efficiency after purification and/or full capsid enrichment. In some embodiments, characterization of viral vectors comprises assessing whether viral packaging efficiency is greater than or equal to 50% after purification and/or filtration (e.g., 50%, 55%, 60%, 65%, 70%, 75%, 80%, 85%, 90%, 95%, 99%, 100%).

In some embodiments, methods and compositions provided herein can provide comparable or increased packaging efficiency as compared to previous methods known in the art. For example, in some embodiments, provided methods for producing and/or manufacturing viral vectors comprising use of a two-plasmid transfection system provide comparable or increased packaging efficiency as compared to a three-plasmid system. In some embodiments, provided methods for producing and/or manufacturing viral vectors comprising use of a two-plasmid transfection system with particular combinations of sequence elements provide comparable or increased packaging efficiency as compared to a two-plasmid system with a different combination of sequence elements. In some embodiments, provided methods for producing and/or manufacturing viral vectors comprising use of a two-plasmid transfection system with particular plasmid ratios provide comparable or increased packaging efficiency as compared to a two-plasmid system with different plasmid ratios.

Replication Competent Vector Levels

In some embodiments, characterization of viral vectors comprises assessment of levels of replication competent vectors. In some embodiments, characterization of viral vectors comprises assessment of levels of replication competent vectors prior to purification and/or filtration. In some embodiments, characterization of viral vectors comprises assessment of levels of replication competent vectors after purification and/or filtration. In some embodiments, characterization of viral vectors comprises assessing whether replication competent vector levels are less than or equal to 1 rcAAV in 1E10 vg.

In some embodiments, methods and compositions provided herein can provide comparable or reduced replication competent vector levels as compared to previous methods known in the art. For example, in some embodiments, provided methods for producing viral vectors comprising use of a two-plasmid transfection system provide comparable or reduced replication competent vector levels as compared to a three-plasmid system. In some embodiments, provided methods for producing viral vectors comprising use of a two-plasmid transfection system with particular combinations of sequence elements provide comparable or reduced replication competent vector levels as compared to a two-plasmid system with a different combination of sequence elements. In some embodiments, provided methods for producing viral vectors comprise use of a two-plasmid transfection system with one or more intronic sequences inserted in the rep gene provide comparable or reduced replication competent vector levels as compared to a two-plasmid system without said intronic sequence(s).

Exemplification

Example 1: Two-Plasmid System can Increase Volumetric Yield

The present example demonstrates that, among other things, a two-plasmid system can produce increased viral yields as compared to a three-plasmid system at particular plasmid ratios.

HEK293F cells were expanded for use in vector production. Cells were split to 2e6 cells/mL in 100 mL of Expi293 media in a 500 mL flask. Plasmid mixes for various transfection conditions outlined in Tables 1 and 1A below were made and filtered through a 0.22 μm filter unit. A transfection reagent mix (e.g., PEI) was prepared according to manufacturer's protocol. Plasmid and transfection reagent mixes were combined to produce a single transfection mix. 20 mL of transfection mix was added to 100 mL of HEK293F cells in a 500 mL flask and allowed to incubate at 37° C. for 72 hours.

In some embodiments, plasmids tested in a two-plasmid system comprise an AAV rep sequence and relevant sequences from a helper virus ("Rep/Helper Plasmid") or an AAV cap sequence and a payload ("Payload/Cap Plasmid"). In some embodiments, plasmids tested in a three-plasmid system comprise separate plasmids, each encoding one of: 1) an AAV rep and AAV cap sequence, 2) relevant sequence from a helper virus, and 3) a payload. A human Factor IX gene sequence with flanking homology arms for mouse albumin ("mHA-FIX") was tested as the payload and AAV-DJ was tested as the viral capsid in experiments outlined below.

TABLE 1

Transfection conditions for two-plasmid system. Relative amounts are shown, normalized so that Rep/Helper and payload/Cap amounts sum to 1.

| Capsid | Payload | Rep/Helper Plasmid | Payload/Cap Plasmid |
|---|---|---|---|
| AAV-DJ | mHA- hFIX | 0.75 | 0.25 |
| AAV-DJ | mHA- hFIX | 0.667 | 0.333 |
| AAV-DJ | mHA- hFIX | 0.6 | 0.4 |
| AAV-DJ | mHA- hFIX | 0.556 | 0.444 |
| AAV-DJ | mHA- hFIX | 0.5 | 0.5 |
| AAV-DJ | mHA- hFIX | 0.444 | 0.556 |
| AAV-DJ | mHA- hFIX | 0.4 | 0.6 |
| AAV-DJ | mHA- hFIX | 0.333 | 0.667 |
| AAV-DJ | mHA- hFIX | 0.25 | 0.75 |

TABLE 1A

Transfection condition for three-plasmid system.

| Capsid | Payload | Helper Plasmid | Rep/Cap Plasmid | Payload Plasmid |
|---|---|---|---|---|
| AAV-DJ | mHA- hFIX | 0.43 | 0.35 | 0.22 |

Benzonase was added to a 10× lysis buffer (10% v/v Tween 20, 500 mM Trix-HCl pH8.0, 20 mM $MgCl_2$ pH 8.0, Milli-Q water) at 100 U of benzonase per mL of lysis buffer. 22 mL of the lysis and benzonase mixture was added to each cell culture flask and placed in an incubator to shake at 37° C. for 90 minutes at 120 or 130 rpm. Next, 24.2 mL of sterile-filtered 5M NaCl was added to each flask (to reach a target concentration of 0.5 M NaCl) and incubated at 37° C. for 30 minutes while shaking at 130 rpm. Entire lysed culture or 40 mL aliquot was taken to next step. Lysed cultures were then spun at 4° C. for 10 minutes at 5000 rpm. Supernatants were reserved for analysis of vector titers by ddPCR and pellets were discarded.

Figure 2:
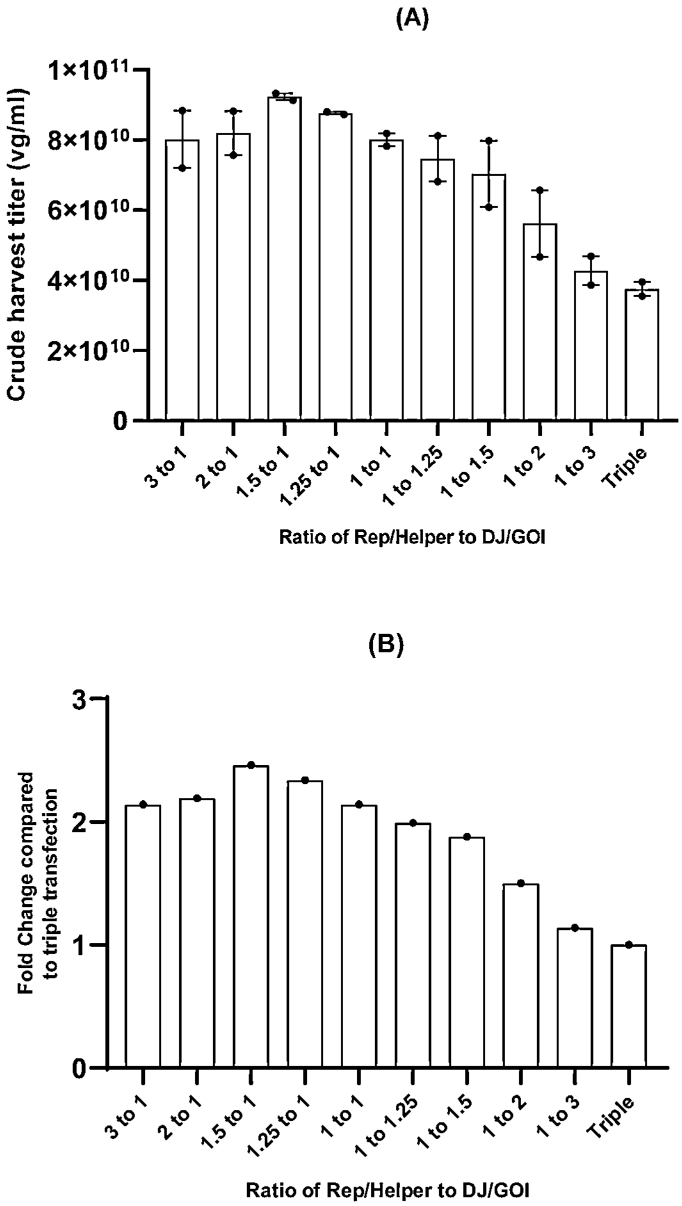
FIG. 2 compares two-plasmid and three-plasmid systems for cell transfection. (A) depicts the viral vector yields (vg/mL) produced for different two-plasmid ratios as compared to a three-plasmid system. (B) depicts relative fold-change in viral vector yields relative to a three-plasmid system. The cap gene encodes for AAV-DJ and the gene of interest (GOI) is human Factor IX flanked by murine albumin homology arms (mHA-hFIX).

Among other things, the present disclosure demonstrates that a two-plasmid transfection system with particular sequence features can improve volumetric yields. In some embodiments, as demonstrated in FIGS. 1 and 2, transfection of a two-plasmid system at certain relative plasmid ratios can further improve yields, e.g., as compared to a three-plasmid "triple transfection" system.

Example 2: Two-Plasmid System can Increase Volumetric Yield at Certain Plasmid Ratios The present example demonstrates that, among other things, a two-plasmid system can produce increased viral yields as compared to a three-plasmid system at particular plasmid ratios.

HEK293F cells were expanded for use in vector production. Cells were split to 2e6 cells/mL in 200 mL of Expi293 media in a 500 mL flask. Plasmid mixes for various transfection conditions outlined in Tables 2 and 2A below were made and filtered through a 0.22 μM filter unit. A transfection reagent mix (e.g., PEI) was prepared according to manufacturer's protocol. Plasmid and transfection reagent mixes were combined to produce a single transfection mix. 20 mL of transfection mix was added to 100 mL of HEK293F cells in a 500 mL flask and allowed to incubate at 37° C. for 72 hours.

In some embodiments, plasmids tested in a two-plasmid system comprise an AAV rep sequence and relevant sequences from a helper virus ("Rep/Helper Plasmid") or an AAV cap sequence and a payload ("Payload/Cap Plasmid"). In some embodiments, plasmids tested in a three-plasmid system comprise separate plasmids, each encoding one of: 1) an AAV rep and AAV cap sequence, 2) relevant sequence from a helper virus, and 3) a payload. A human Factor IX gene sequence with flanking homology arms for mouse albumin ("mHA-FIX") was tested as the payload and AAV-DJ was tested as the viral capsid in experiments outlined below.

TABLE 2

Transfection conditions for two-plasmid system. Relative amounts are shown, normalized so that Rep/Helper and Payload/Cap amounts sum to 1.

| Capsid | Payload | Rep/Helper Plasmid | Payload/Cap Plasmid |
|---|---|---|---|
| AAV-DJ | mHA- hFIX | 0.909 | 0.091 |
| AAV-DJ | mHA- hFIX | 0.888 | 0.111 |
| AAV-DJ | mHA- hFIX | 0.857 | 0.143 |
| AAV-DJ | mHA- hFIX | 0.8 | 0.2 |
| AAV-DJ | mHA- hFIX | 0.667 | 0.333 |
| AAV-DJ | mHA- hFIX | 0.5 | 0.5 |
| AAV-DJ | mHA- hFIX | 0.333 | 0.667 |
| AAV-DJ | mHA- hFIX | 0.2 | 0.8 |
| AAV-DJ | mHA- hFIX | 0.143 | 0.857 |
| AAV-DJ | mHA- hFIX | 0.111 | 0.888 |
| AAV-DJ | mHA- hFIX | 0.091 | 0.909 |

TABLE 2A

Transfection condition for three-plasmid system.

| Capsid | Payload | Helper Plasmid | Rep/Cap Plasmid | PayloadPlasmid |
|---|---|---|---|---|
| AAV-DJ | mHA- hFIX | 0.43 | 0.35 | 0.22 |

Benzonase was added to a 10× lysis buffer (10% v/v Tween 20, 500 mM Trix-HCl pH8.0, 20 mM $MgCl_2$ pH 8.0, Milli-Q water) at 100 U of benzonase per mL of lysis buffer. 22 mL of the lysis and benzonase mixture was added to each cell culture flask and placed in an incubator to shake at 37° C. for 90 minutes at 120 rpm. Next, 24.2 mL of sterile-filtered 5M NaCl was added to each flask (to reach a target concentration of 0.5 M NaCl) and incubated at 37° C. for 30 minutes while shaking at 120 rpm. 40 mL aliquot was taken to next step. Lysed cultures were then spun at 4° C. for 10 minutes at 5000 rpm. Supernatants were reserved for analysis of vector titers by ddPCR and pellets were discarded.

Figure 3:
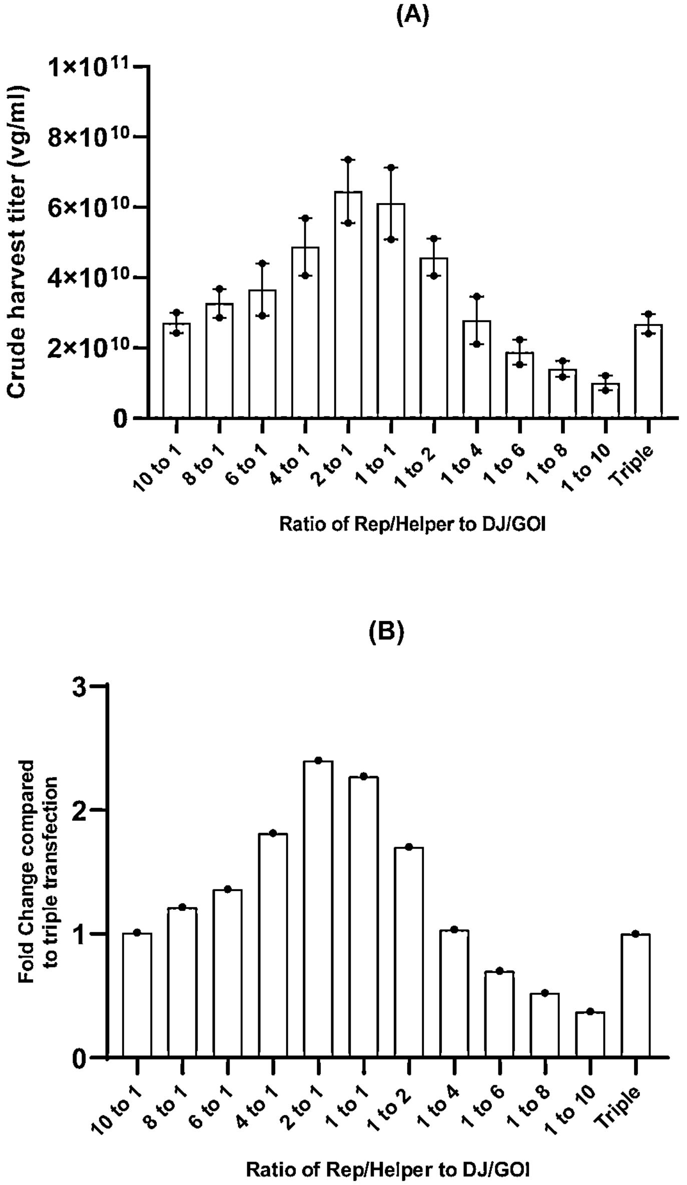
FIG. 3 compares two-plasmid and three-plasmid systems for cell transfection. (A) depicts the viral vector yields (vg/mL) produced for different two-plasmid ratios as compared to a three-plasmid system. (B) depicts relative fold-change in viral vector yields relative to a three-plasmid system. The cap gene encodes for AAV-DJ and the gene of interest (GOI) is human Factor IX flanked by murine albumin homology arms (mHA-hFIX).

Among other things, the present disclosure demonstrates that certain transfection conditions for a two-plasmid transfection system can produce surprising and unexpected improvements in volumetric yields (e.g., as compared to a three-plasmid, "triple transfection" system). As demonstrated in FIG. 3, relatively small changes in the ratio between two plasmids can produce significant changes in viral yield.

Example 3: Two-Plasmid System can Increase Volumetric Yield for a Variety of AAV Capsids The present example demonstrates that, among other things, various AAV capsids can be employed in a two-plasmid system to produce high viral yields.

HEK293F cells were expanded for use in vector production. Cells were split to 2e6 cells/mL in 200 mL of Expi293 media in a 500 mL flask. Plasmid mixes for various transfection conditions outlined in Tables 3 and 3A below were made and filtered through a 0.22 μM filter unit. A transfection reagent mix (e.g., PEI) was prepared according to manufacturer's protocol. Plasmid and transfection reagent mixes were combined to produce a single transfection mix. 20 mL of transfection mix was added to 100 mL of HEK293F cells in a 500 mL flask and allowed to incubate at 37° C. for 72 hours.

In some embodiments, plasmids tested in a two-plasmid system comprise an AAV rep sequence and relevant sequences from a helper viruses ("Rep/Helper Plasmid") or an AAV cap sequence and a payload ("Payload/Cap Plasmid"). In some embodiments, plasmids tested in a three-plasmid system comprise separate plasmids, each encoding one of: 1) an AAV rep and AAV cap sequence, 2) relevant sequence from a helper virus, and 3) a payload. A human Factor IX gene sequence with flanking homology arms for mouse albumin ("mHA-FIX"), which is compatible with a GeneRide system, was tested as the payload in experiments outlined below. A variety of AAV cap genes encoding different chimeric capsids were assessed within the Payload/Cap plasmid, using different plasmid ratios as described in Table 3.

TABLE 3

Transfection conditions for two-plasmid system with various AAV capsids. Plasmid ratio (w/w) is shown for Rep/Helper plasmid to Payload/Cap plasmid.

| Capsid | Payload | Rep/Helper Plasmid:Payload/Cap Plasmid Ratio |
|---|---|---|
| AAV-DJ | mHA- hFIX | 6:1 |
| | | 1.5:1 |
| | | 1:6 |
| LK03 | mHA- hFIX | 6:1 |
| | | 1.5:1 |
| | | 1:6 |
| AAVC11.04 | mHA- hFIX | 6:1 |
| | | 1.5:1 |
| | | 1:6 |
| AAVC11.11 | mHA- hFIX | 6:1 |
| | | 1.5:1 |
| | | 1:6 |
| AAVC11.12 | mHA- hFIX | 6:1 |
| | | 1.5:1 |
| | | 1:6 |

TABLE 3A

Transfection condition for three-plasmid system.

| Capsid | Payload | Helper Plasmid | Rep/Cap Plasmid | Payload Plasmid |
|---|---|---|---|---|
| AAV-DJ | mHA- hFIX | 0.43 | 0.35 | 0.22 |
| LK03 | mHA- hFIX | 0.43 | 0.35 | 0.22 |
| AAVC11.04 | mHA- hFIX | 0.43 | 0.35 | 0.22 |
| AAVC11.11 | mHA- hFIX | 0.43 | 0.35 | 0.22 |
| AAVC11.12 | mHA- hFIX | 0.43 | 0.35 | 0.22 |

Samples of 5 mL were collected for every 500 mL culture flask. Benzonase was mixed with Expi293 media, using 2 uL benzonase (approximately 250 U/uL) and 50 uL media. Master mix made for 30 samples (60 uL benzonase and 1500 uL media). 50 uL master mix added to each sample for 100 U of benzonase per 1 mL of culture volume. Samples incubated at 37° C. for 15 minutes with shaking. A 10× lysis buffer (10% v/v Tween 20, 500 mM Trix-HCl pH8.0, 20 mM $MgCl_2$ pH 8.0, Milli-Q water) was made and 500 uL (10% culture volume) was added to each sample, followed by incubation at 37° C. for 90 minutes with shaking. Next, 500 uL of sterile-filtered 5M NaCl was added to each flask (to reach a target concentration of 0.5 M NaCl) and incubated at 37° C. for 30 minutes while shaking. Lysed cultures were then spun for 10 minutes at 3900 rpm. Supernatants were reserved for analysis of vector titers by ddPCR and pellets were discarded.

Figure 4:
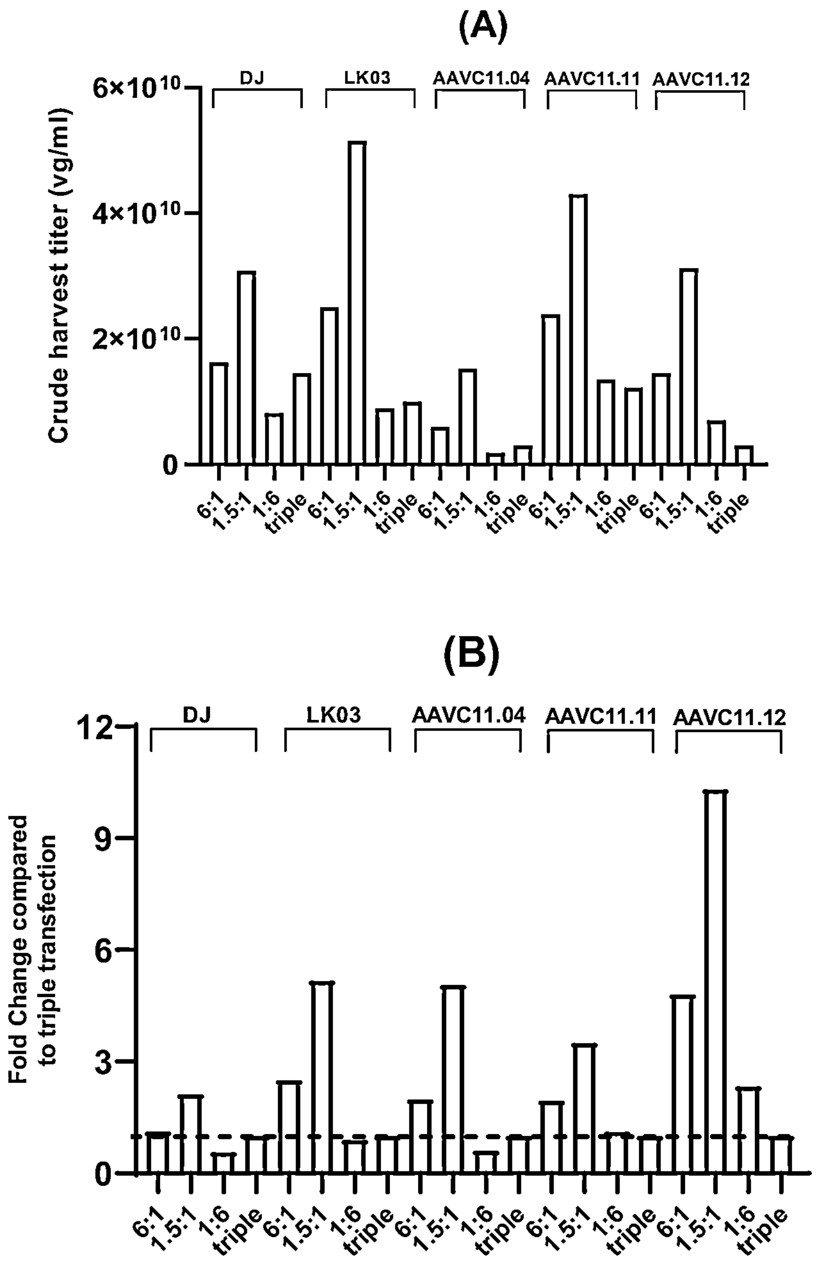
FIG. 4 compares two-plasmid and three-plasmid systems for cell transfection. (A) depicts the viral vector yields (vg/mL) produced for different two-plasmid ratios as compared to a three-plasmid system. (B) depicts relative fold-change in viral vector yields relative to a three-plasmid system. The cap gene encodes a variety of chimeric AAV serotypes (DJ, LK03, AAVC11.04, AAVC11.11, AAVC11.12) and the gene of interest (GOI) is human Factor IX flanked by murine albumin homology arms (mHA-hFIX).

Among other things, the present disclosure demonstrates that a two-plasmid transfection system can produce surprising and unexpected improvements in volumetric yields (e.g., as compared to a three-plasmid, "triple transfection" system) for a variety of different capsids. As demonstrated in FIG. 4, AAV-DJ, LK03, AAVC11.04, AAVC11.11, and AAVC11.12 all appeared to produce similar trends in viral yield for the three different plasmid ratios tested. A 1.5:1 ratio of Rep/Helper plasmid to Payload/Cap plasmid consistently produced the highest yields for each capsid. These data suggest that, in some embodiments, a two-plasmid system with particular ratios between a Rep/Helper plasmid and Payload/Cap plasmid may be widely applicable to different capsids of interest in order to increase volumetric yield.

Example 4: Two-Plasmid System can Increase Volumetric Yield for a Variety of AAV Capsids Using Alternative Payloads The present example demonstrates that, among other things, various AAV capsids and payloads can be employed in a two-plasmid system to produce high viral yields.

HEK293F cells were expanded for use in vector production. Cells were split to 2e6 cells/mL in 200 mL of Expi293 media in a 500 mL flask. Plasmid mixes for various transfection conditions outlined in Tables 4 and 4A below were made and filtered through a 0.22 μm filter unit. A transfection reagent mix (e.g., PEI) was prepared according to manufacturer's protocol. Plasmid and transfection reagent mixes were combined to produce a single transfection mix. 20 mL of transfection mix was added to 100 mL of HEK293F cells in a 500 mL flask and allowed to incubate at 37° C. for 72 hours.

In some embodiments, plasmids tested in a two-plasmid system comprise an AAV rep sequence and relevant sequences from a helper viruses ("Rep/Helper Plasmid") or an AAV cap sequence and a payload ("Payload/CAP Plasmid"). In some embodiments, plasmids tested in a three-plasmid system comprise separate plasmids, each encoding one of: 1) an AAV rep and AAV cap sequence, 2) relevant sequence from a helper virus, and 3) a payload. A human Factor IX gene sequence under the control of a liver specific promoter (LSP) was tested as the payload in experiments outlined below. A variety of AAV cap genes encoding different chimeric capsids were assessed within the Payload/Cap plasmid, using different plasmid ratios as described in table 4.

TABLE 4

Transfection conditions for two-plasmid system with various AAV capsids. Plasmid ratio (w/w) is shown for Rep/Helper plasmid to Payload/Cap plasmid.

| Capsid | Payload | Rep/Helper Plasmid:Payload/Cap Plasmid Ratio |
|---|---|---|
| AAV-DJ | LSP-hFIX | 6:1 |
| | | 1.5:1 |
| | | 1:6 |

TABLE 4-continued

Transfection conditions for two-plasmid system with various AAV capsids. Plasmid ratio (w/w) is shown for Rep/Helper plasmid to Payload/Cap plasmid.

| Capsid | Payload | Rep/Helper Plasmid:Payload/Cap Plasmid Ratio |
|---|---|---|
| LK03 | LSP-hFIX | 6:1 |
| | | 1.5:1 |
| | | 1:6 |
| AAVC11.01 | LSP-hFIX | 6:1 |
| | | 1.5:1 |
| | | 1:6 |
| AAVC11.04 | LSP-hFIX | 6:1 |
| | | 1.5:1 |
| | | 1:6 |
| AAVC11.06 | LSP-hFIX | 6:1 |
| | | 1.5:1 |
| | | 1:6 |
| AAVC11.09 | LSP-hFIX | 6:1 |
| | | 1.5:1 |
| | | 1:6 |
| AAVC11.11 | LSP-hFIX | 6:1 |
| | | 1.5:1 |
| | | 1:6 |
| AAVC11.12 | LSP-hFIX | 6:1 |
| | | 1.5:1 |
| | | 1:6 |
| AAVC11.13 | LSP-hFIX | 6:1 |
| | | 1.5:1 |
| | | 1:6 |
| AAVC11.15 | LSP-hFIX | 6:1 |
| | | 1.5:1 |
| | | 1:6 |

TABLE 4A

Transfection condition for three-plasmid system.

| Capsid | Payload | Helper Plasmid | Rep/Cap Plasmid | Payload Plasmid |
|---|---|---|---|---|
| AAV-DJ | LSP-hFIX | 0.43 | 0.35 | 0.22 |
| LK03 | LSP-hFIX | 0.43 | 0.35 | 0.22 |
| AAVC11.01 | LSP-hFIX | 0.43 | 0.35 | 0.22 |
| AAVC11.04 | LSP-hFIX | 0.43 | 0.35 | 0.22 |
| AAVC11.06 | LSP-hFIX | 0.43 | 0.35 | 0.22 |
| AAVC11.09 | LSP-hFIX | 0.43 | 0.35 | 0.22 |
| AAVC11.11 | LSP-hFIX | 0.43 | 0.35 | 0.22 |
| AAVC11.12 | LSP-hFIX | 0.43 | 0.35 | 0.22 |
| AAVC11.13 | LSP-hFIX | 0.43 | 0.35 | 0.22 |
| AAVC11.15 | LSP-hFIX | 0.43 | 0.35 | 0.22 |

Samples of 5 mL were collected for every 500 mL culture flask. Benzonase was mixed with Expi293 media, using 2 uL benzonase (approximately 250 U/uL) and 50 uL media. Master mix made for 30 samples (60 uL benzonase and 1500 uL media). 50 uL master mix added to each sample for 100 U of benzonase per 1 mL of culture volume. Samples incubated at 37° C. for 15 minutes with shaking. A 10× lysis buffer (10% v/v Tween 20, 500 mM Trix-HCl pH8.0, 20 mM $MgCl_2$ pH 8.0, Milli-Q water) was made and 500 uL (10% culture volume) was added to each sample, followed by incubation at 37° C. for 90 minutes with shaking. Next, 500 uL of sterile-filtered 5M NaCl was added to each flask (to reach a target concentration of 0.5 M NaCl) and incubated at 37° C. for 30 minutes while shaking. Lysed cultures were then spun at room temperature for 10 minutes at 3900 rpm. Supernatants were reserved for analysis of vector titers by ddPCR and pellets were discarded.

Figure 5:
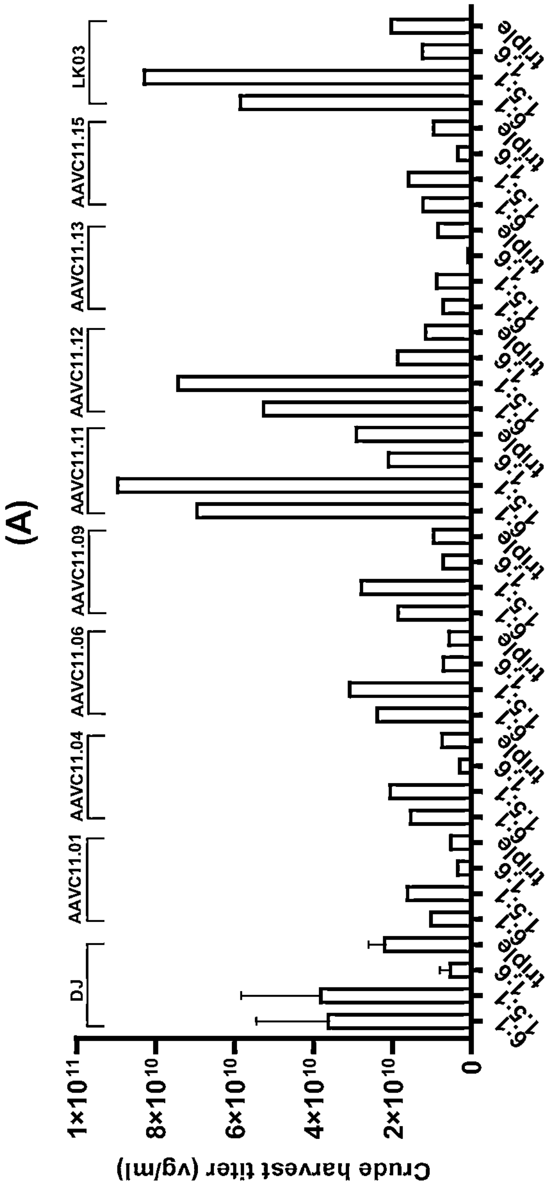
FIG. 5 compares two-plasmid and three-plasmid systems for cell transfection. (A) depicts the viral vector yields (vg/mL) produced for different two-plasmid ratios as compared to a three-plasmid system. (B) depicts relative fold-change in viral vector yields relative to a three-plasmid system. The cap gene encodes a variety of chimeric AAV serotypes (DJ, AAVC11.01, AAVC11.04, AAVC11.06, AAVC11.09, AAVC11.11, AAVC11.12, AAVC11.13, AAVC11.15, LK03) and the gene of interest (GOI) is human Factor IX under the control of a liver-specific promoter (LSP-hFIX).
Figure 5:
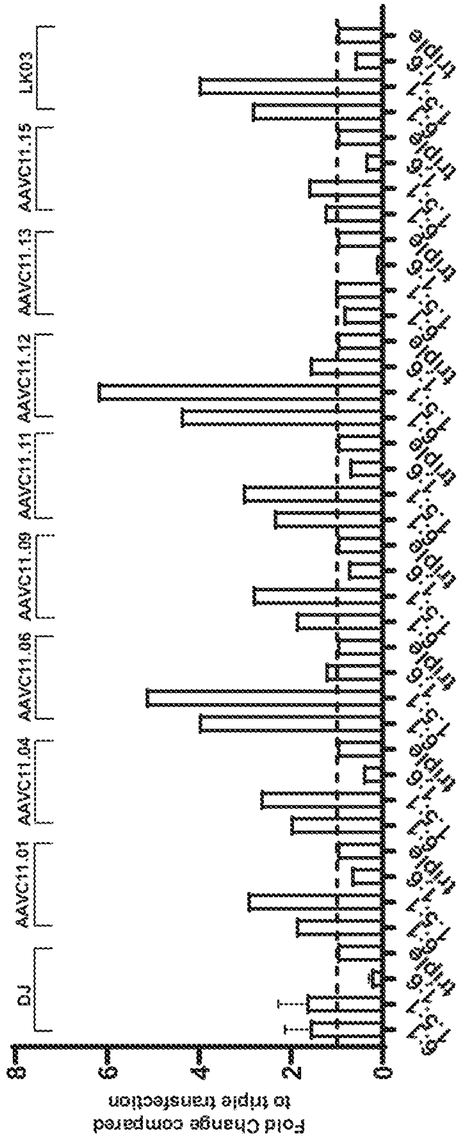

Among other things, the present disclosure demonstrates that a two-plasmid transfection system can produce surprising and unexpected improvements in volumetric yields (e.g., as compared to a three-plasmid, “triple transfection” system) for different capsids with a payload that is useful in conventional gene therapy (e.g., human Factor IX). As demonstrated in FIG. 5, AAV-DJ, LK03, AAVC11.01, AAVC11.04, AAVC11.06, AAVC11.09, AAVC11.11, AAVC11.12, AAVC11.13, and AAVC11.15 all appeared to produce similar trends in viral yield for the three different plasmid ratios tested. A 1.5:1 ratio of Rep/Helper plasmid to payload/Cap plasmid consistently produced the highest yields for each capsid, similar to what was observed for the mHA-hFIX payload, with the exception of AAVC13, where the 1.5:1 ratio produced similar yields to that seen with the three-plasmid system These data suggest that, in some embodiments, a two-plasmid system with particular ratios between a Rep/Helper plasmid and payload/Cap plasmid can be successfully employed with different capsids and different genes of interest (e.g., for both conventional gene therapy and GeneRide methods) in order to increase volumetric yield.

Example 5: Two-Plasmid System can be Combined with Various Transfection Reagents, Various Culture Media and in Different Culture Vessels (Shake Flasks and Stirred-Tank Bioreactors)

The present example demonstrates that a two-plasmid system can be combined with various transfection reagents (PEIMAX and FectoVIR-AAV), various culture media (Expi293 and F17) and different culture systems (shake flasks and stirred-tank bioreactors, AmBr250 system) to further improve viral genome yields.

HEK293F cells were expanded in 500-mL shake flasks for use in vector production. Cell counts were first recorded on the ViCell XR Cell Counter to ensure VCDs were between 2.0e6-2.6e6 cells/mL and Viabilities were above 95% at the time of transfection. Transfection mixes were then prepared by first pre-weighing Expi293 media in two separate vessels, “DNA media” and “transfection reagent media”, each containing equal volume requirements from transfection mix calculations. Transfection reagent was then added to the bottle labeled “transfection reagent media” and set aside. The mass fractions of the pHelper, pRep/Cap, and pGOI were 0.43, 0.35, and 0.22, respectively for the 3-plasmid transfection system. The mass fractions of the Rep/Helper plasmid and Payload/Cap plasmid were 0.60 and 0.40, respectively (1.5:1 plasmid ratio) for the 2-plasmid transfection system. Plasmids were sterile-filtered through a Corning 0.22 um PES bottle-top filter by first wetting the membrane with media from the bottle labeled “DNA media”, adding appropriate amount of pDNA to the bottle-top, turning on the vacuum for the filter, and finally flushing the residual DNA on the filter with the remaining media from the “DNA media” bottle. Once the transfection reagent/media and DNA/media solutions were prepared, at a 1:1 volumetric ratio, both mixes were combined into a separate vessel and inverted 10 times to begin the complexation process. The transfection mix was then transferred to an incubator at 37° C. shaking at 95 RPM for 15 min when using PEIMAX, and 30 min when using FectoVIR-AAV. Once the time elapsed, the transfection mix was added to the culture medium at a 10% culture volume fraction (e.g. 20 mL transfection mix added to 200 mL culture) and grown at 37° C. for 72 hr, unless otherwise stated.

Figure 6:
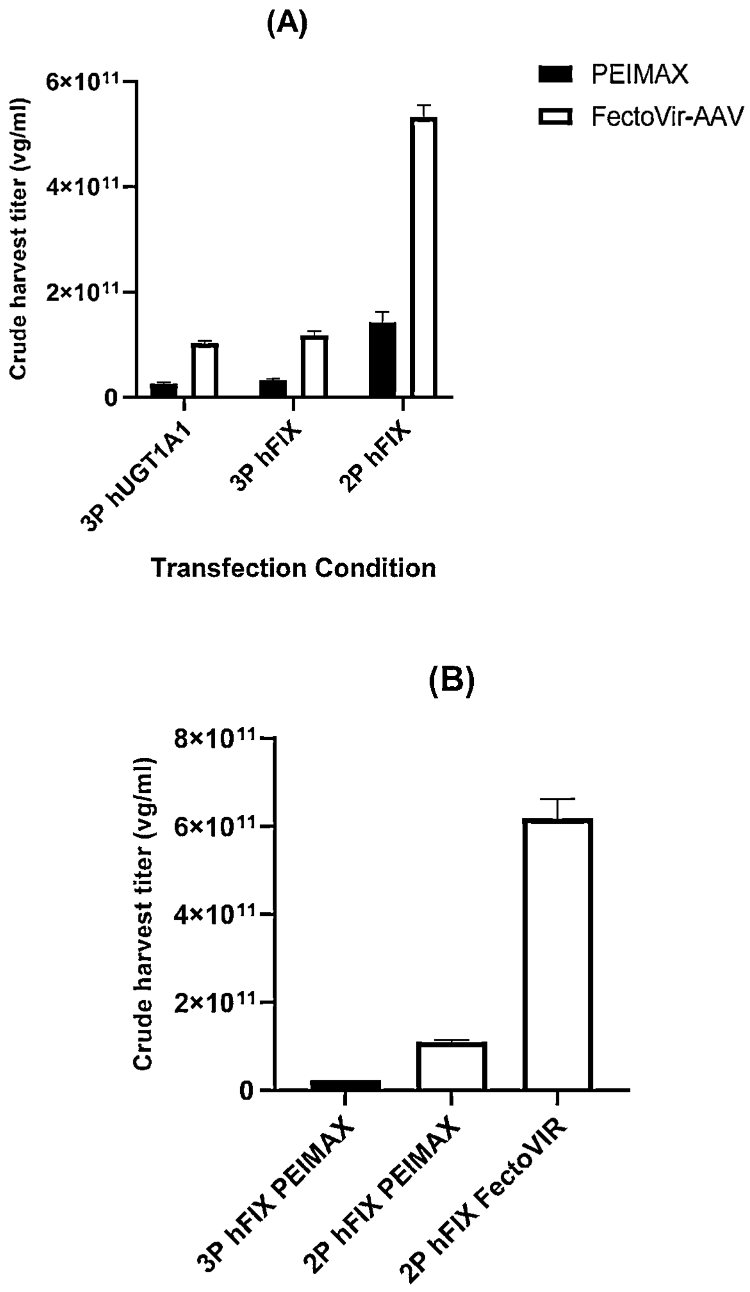
FIG. 6 depicts viral vector yields (vg/mL) for two-plasmid (2P) and three-plasmid (3P) systems for cell transfection with different transfection reagents (PEIMAX and FectoVIR AAV) in different culture vessels (shake flasks and bioreactors). (A) Viral vector yield for two-plasmid and three-plasmid systems in shake flasks with a human UGT1A1 or human Factor IX (hFIX) payload are depicted. (B) Viral vector yields for two-plasmid and three-plasmid systems in AmBr250 bioreactors using PEIMAX reagent as compared to two-plasmid system using FectoVir-AAV reagent.

Cells were harvested 72 hr after transfection of cultures. 5 mL of culture was transferred to a 15 mL centrifuge tube and 50 uL of a 10 units/uL benzonase in Expi293 media solution was added to the tube and shaken in the incubator horizontally at 37° C. and 145 RPM for 15 min. 500 uL of lysis buffer (500 mM Tris pH 8, 20 mM MgCl2, 10% polysorbate-20) was then added to the tube and incubated under the same conditions for 90 min. Finally, 500 uL of 5M NaCl was added to the tubes and incubated for 30 min under the same conditions. After the NaCl incubation, cell lysate was spun down in a centrifuge at 3200 g to clarify the harvested culture media. 1 mL of the supernatant, which contained the AAV particles, was collected in 1.5 mL Eppendorf tubes and stored at −80° C. until preparation for sample analysis. The results of volumetric titer yield are presented in FIG. 6.

TABLE 5

Conditions to evaluate transfection systems and transfection reagents.

| Condition | Vector Description | Transfection System | Transfection Reagent |
|---|---|---|---|
| 1 | LK03/hHA-hUGT1A1 | 3-plasmid | PEIMAX |
| 2 | LK03/hHA-hUGT1A1 | 3-plasmid | FectoVIR-AAV |
| 3 | LK03/LSP-hFIX | 3-plasmid | PEIMAX |
| 4 | LK03/LSP-hFIX | 3-plasmid | FectoVIR-AAV |
| 5 | LK03/LSP-hFIX | 2-plasmid | PEIMAX |
| 6 | LK03/LSP-hFIX | 2-plasmid | FectoVIR-AAV |

TABLE 5A

Transfection parameters for different transfection reagents.

| Parameter | PEIMAX | FectoVIR-AAV |
|---|---|---|
| Total DNA per 1e6 cells (ug) | 0.75 | 0.75 |
| TR:DNA w/w ratio | 1.5 | 1.5 |
| Transfection Mix Percent of Culture Volume (%) | 10 | 10 |
| Complexation Time (min) | 15 | 30 |

The same transfection conditions were then tested in AmBr250 bioreactors to determine if similar trends in viral yields could be obtained in bench-scale stirred tank bioreactors modelling larger-scale manufacturing conditions.

TABLE 5B

Conditions for bioreactor verification study.

| Condition | Vector Description | Transfection System | Transfection Reagent |
|---|---|---|---|
| 1 | LK03/LSP-hFIX | 3-plasmid | PEIMAX |
| 2 | LK03/LSP-hFIX | 2-plasmid | PEIMAX |
| 3 | LK03/LSP-hFIX | 2-plasmid | FectoVIR-AAV |

TABLE 5C

Titers and fold-changes between conditions from bioreactor study.

| Condition | Titer (vg/mL) | Fold Increase |
|---|---|---|
| 3-plasmid PEIMAX | 2.31e10 | 1 |
| 2-plasmid PEIMAX | 1.10e11 | 4.8 |
| 2-plasmid FectoVIR | 6.18e11 | 26.8 |

In another experiment, the 2-plasmid system was tested in HEK293F that were expanded in different culture media: Expi293 and F17. Cells were split to 2e6 cells/mL in 200 mL of Expi293 media or F17 media in a 500 mL flask. Plasmid mixes for various transfection conditions outlined in Table 5D below were made and filtered through a 0.22 μm filter unit. A transfection reagent mix (e.g., PEI) was prepared according to manufacturer's protocol. Plasmid and transfection reagent mixes were combined to produce a single transfection mix. 20 mL of transfection mix was added to 100 mL of HEK293 cells in a 500 mL flask and allowed to incubate at 37° C. for 72 hours.

In some embodiments, plasmids tested in a two-plasmid system comprise an AAV rep sequence and relevant sequences from a helper virus ("Rep/Helper Plasmid") or an AAV cap sequence and a payload ("Payload/Cap Plasmid"). In some embodiments, plasmids tested in a three-plasmid system comprise separate plasmids, each encoding one of: 1) an AAV rep and AAV cap sequence, 2) relevant sequence from a helper virus, and 3) a payload. A human Factor IX gene (hFIX) flanked by mouse albumin homology arm sequences (mHA) was tested as the payload in experiments outlined below. The plasmid ratio was Rep/Helper:Payload/Cap=1.5:1 for the 2-plasmid system and Helper:Repcap:Payload=0.43:0.35:0.22 for the 3-plasmid system.

The results in table 5D show comparable trends in different culture media with the 2-plasmid system giving higher titers than the 3-plasmid system.

TABLE 5D

Transfection parameters for different culture media.

| Vector Description | System | Culture Media | Crude volumetric yield (vg/mL transfected) |
|---|---|---|---|
| DJ-mHA-hFIX | 3-plasmid | Expi293 | 2.30E+10 |
| DJ-mHA-hFIX | 2-plasmid | Expi293 | 4.61E+10 |
| DJ-mHA-hFIX | 3-plasmid | F17 | 2.90E+10 |
| DJ-mHA-hFIX | 2-plasmid | F17 | 4.13E+10 |

Among other things, the present disclosure demonstrates that a two-plasmid system can be combined with various transfection reagents to produce high viral yields in both a small-scale and manufacturing setup. As demonstrated in FIG. 6, the FectoVir-AAV transfection system provided improved yields for both plasmid systems, with an approximately 4-fold increase in vector genome titer compared to PEIMAX. When combined with the two-plasmid system at an optimized plasmid ratio (1.5:1 Rep/Helper to Payload/Cap), FectoVir-AAV led to a more than 16-fold increase in vector genome titer in small-scale, shake flask conditions and an almost 27-fold increase in vector genome titer in bench-scale bioreactor conditions (Table 5C). Furthermore, as shown in Table 5D above, improvements in viral yield are consistent between different types of cell culture media. The present disclosure demonstrates that optimization of transfection conditions through combination of a two-plasmid system (e.g., at a particular plasmid ratio) and a particular transfection reagent (e.g., FectoVir-AAV) can produce large increases in viral vector yields in mammalian cells, which can be consistent between different cell culture conditions (e.g., different culture media and different culture vessels).

Example 6: Two-Plasmid System can Increase Volumetric Yield in Different Cell Line Grown in Adherent Culture The previous examples 1 to 5 showed production of AAV vectors using a two-plasmid system in suspension HEK293F. The present example shows that a two-plasmid system can also increase AAV yields in adherent 293T cells.

Experiments were conducted on 293T cells in 12-well plates. The cells were plated at 8E5 cells/well in DMEM+ 10% FCS. One day later, the cells were transfected with a mix of plasmid in OptiMEM which was combined with a lipid-based transfection reagent (Fugene HD). To quantify AAV vector, benzonase was added to each culture at 100 U/mL. After 15 minutes at 37° C., the cells were lysed by adding 200 μL of lysis buffer (10% Tween20, 500 mM Tris, 20 mM MgCl2, pH8) and incubated for 90 minutes at 37° C. Then, NaCl was added to a final concentration of 0.5M and the samples were centrifuged at 3900 rpm for 10 minutes at room temperature. The supernatant was collected for vector genome titration using ddPCR.

A two-plasmid system comprising a plasmid comprising an AAV rep sequence and relevant sequences from a helper viruses ("Rep/Helper Plasmid") and a plasmid comprising an AAV cap sequence and a payload ("Payload/Cap Plasmid") was tested in the present example. A three-plasmid system comprising separate plasmids, each encoding one of: 1) an AAV rep and AAV cap sequence, 2) relevant sequence from a helper virus, and 3) a payload was also included for comparison. A human Factor IX gene sequence with flanking homology arms for mouse albumin ("mHA-FIX") was tested as the payload in experiments outlined below.

TABLE 6

Transfection conditions for two-plasmid system. Relative amounts of Rep/Helper and Payload/Cap plasmids are shown.

| Capsid | Payload | Rep/Helper Plasmid | Payload/Cap Plasmid |
|---|---|---|---|
| AAV-DJ | mHA- hFIX | 10 | 1 |
| AAV-DJ | mHA- hFIX | 6 | 1 |
| AAV-DJ | mHA- hFIX | 1 | 1 |
| AAV-DJ | mHA- hFIX | 1 | 6 |
| AAV-DJ | mHA- hFIX | 1 | 10 |

TABLE 6A

Transfection condition for three-plasmid system.

| Capsid | Payload | Helper Plasmid | Rep/Cap Plasmid | Payload Plasmid |
|---|---|---|---|---|
| AAV-DJ | mHA- hFIX | 0.43 | 0.35 | 0.22 |

Figure 7:
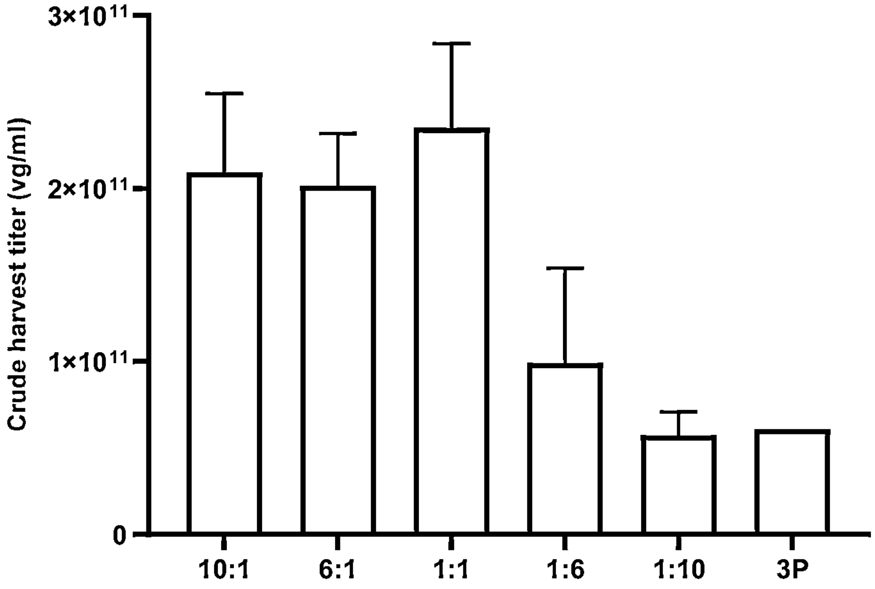
FIG. 7 depicts viral vector yields (vg/mL) for a two-plasmid system at various plasmid ratios as compared to a three-plasmid system (3P) in adherent 293T cells grown in 12-well plates and transfected using a lipidic transfection agent (Fugene HD). The cap gene encodes for AAV-DJ and the gene of interest (GOI) is human Factor IX flanked by murine albumin homology arms (mHA-hFIX).

Among other things, the present disclosure demonstrates that a two-plasmid system at various ratios can produce AAV vector yield comparable to or higher than a three-plasmid system in 293T cells grown in adherent culture conditions. As demonstrated in FIG. 7, a two-plasmid system can produce up to 4-fold more vector than the three-plasmid system (3P) when the plasmid ratio of rep/helper to payload/cap is greater than or equal to 1. The present disclosure also demonstrates that a two-plasmid system can produce high AAV vector yield using a lipid-based transfection agent (e.g., Fugene HD).

Example 7: Two-Plasmid System can Increase Volumetric Yield and Alter Packaging Efficiency of AAV Vectors The Present Example Demonstrates that a Two-Plasmid System can be employed with larger-scale cell culture conditions (above 1 L of culture) to provide increased volumetric yields following similar trends to those observed for smaller-scale conditions. Furthermore, the present example demonstrates that particular plasmid ratios can affect capsid packaging efficiency.

Experiments were conducted on HEK293F cells in 2.8 L culture flasks. HEK293F cells were expanded and were split to 2e6 cells/mL in 1.4 L of Expi293 media in a 2.8 L flask. Plasmid mixes for various transfection conditions outlined in Tables 6 below were made and filtered through a 0.22 μm filter unit. A transfection reagent mix (e.g., PEI) was prepared according to manufacturer's protocol. Plasmid and transfection reagent mixes were combined to produce a single transfection mix. 140 mL of transfection mix was added to 1.4 L of HEK293F cells in a 2.8 L flask and allowed to incubate at 37° C. for 72 hours. To harvest the vector, the cell cultures were distributed in 1 L bottles and centrifuged at 3500 rpm for 5 min. The supernatants were discarded and each cell pellet was lysed by addition of 130 mL of lysis buffer (PBS, 1 mM MgCl2, 0.5% Triton-X 100) and 7800 U of benzonase. Then the lysates underwent 3 freeze-thaw cycles (−80° C. and 37° C.). After elimination of the cell debris by centrifugation at 3900 rpm for 5 min, the lysates were assayed via ddPCR to determine volumetric yields of viral vectors. A portion of the lysates were purified by affinity chromatography on POROS AAVX resin. After elution at pH 2.5, the purified vectors were dialyzed against PBS using Amicon cartridges. The dialyzed vectors were then tested for capsid packaging efficiency (percent packaged (full) versus unpackaged (empty) capsids) through SDS-PAGE and sedimentation velocity analytical ultracentrifugation (SV-AUC).

In some embodiments, plasmids tested in a two-plasmid system comprise an AAV rep sequence and relevant sequences from a helper viruses ("Rep/Helper Plasmid") or an AAV cap sequence and a payload ("Payload/Cap Plasmid"). In some embodiments, plasmids tested in a three-plasmid system comprise separate plasmids, each encoding one of: 1) an AAV rep and AAV cap sequence, 2) relevant sequence from a helper virus, and 3) a payload. A human Factor IX gene sequence with flanking homology arms for mouse albumin ("mHA-FIX") was tested as the payload in experiments outlined below.

TABLE 7

Conditions to evaluate transfection systems and transfection reagents.

| Capsid | Payload | Rep/Helper Plasmid:Payload/Cap Plasmid Ratio |
|---|---|---|
| AAV-DJ | mHA-hFIX | 10:1 |
| AAV-DJ | mHA-hFIX | 8:1 |
| AAV-DJ | mHA-hFIX | 6:1 |
| AAV-DJ | mHA-hFIX | 4:1 |
| AAV-DJ | mHA-hFIX | 3:1 |
| AAV-DJ | mHA-hFIX | 2:1 |
| AAV-DJ | mHA-hFIX | 1.5:1 |
| AAV-DJ | mHA-hFIX | 1.25:1 |
| AAV-DJ | mHA-hFIX | 1:1 |
| AAV-DJ | mHA-hFIX | 1:1.25 |
| AAV-DJ | mHA-hFIX | 1:1.5 |
| AAV-DJ | mHA-hFIX | 1:2 |
| AAV-DJ | mHA-hFIX | 1:3 |
| AAV-DJ | mHA-hFIX | 1:4 |
| AAV-DJ | mHA-hFIX | 1:6 |
| AAV-DJ | mHA-hFIX | 1:8 |
| AAV-DJ | mHA-hFIX | 1:10 |

TABLE 7A

Packaging efficiency for selected ratios with two-plasmid system as compared to three-plasmid system.

| Rep/Helper Plasmid:Payload/ Cap Plasmid Ratio | Full Capsids (%) | Partially Full Capsids (%) | Empty Capsids (%) |
|---|---|---|---|
| 10:1 | 27.18 | 11.54 | 57.60 |
| 4:1 | 26.24 | 7.18 | 63.87 |
| 1.5:1 | 17.46 | 8.59 | 71.46 |
| 1:1.25 | 15.21 | 5.10 | 77.64 |
| 1:3 | 6.53 | 10.95 | 82.52 |
| 1:10 | 0.99 | 7.57 | 89.97 |
| Three-plasmid system | 25.74 | 11.83 | 59.90 |

Figure 8:
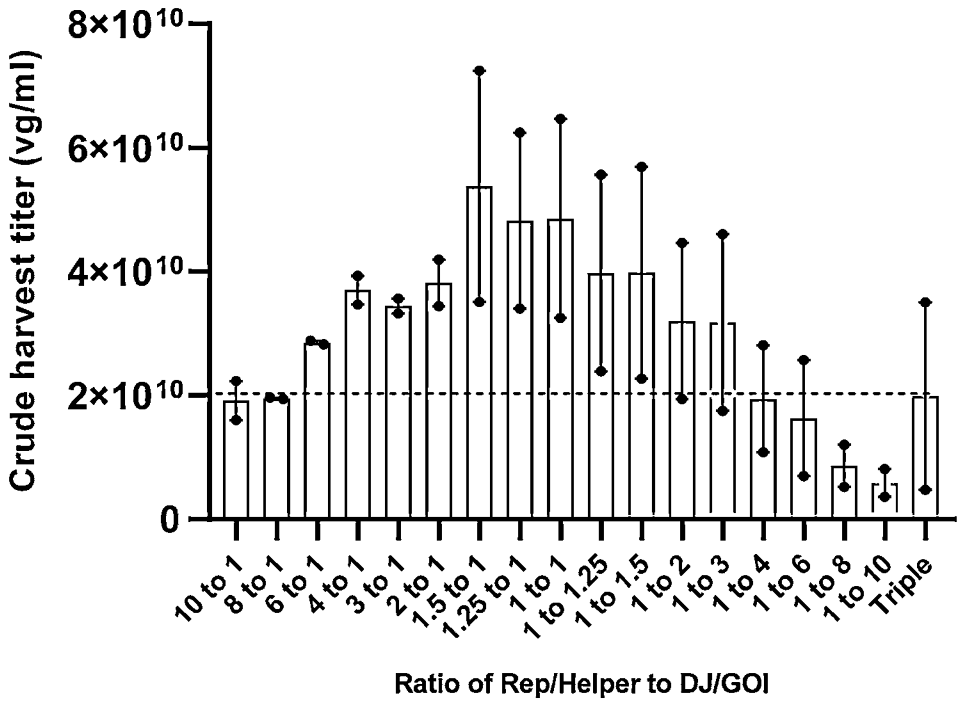
FIG. 8 depicts viral vector yields (vg/mL) for a two-plasmid system at various plasmid ratios as compared to a three-plasmid system, for larger cell culture volumes (>1 L). The cap gene encodes for AAV-DJ serotype and the gene of interest (GOI) is human Factor IX flanked by murine albumin homology arms (mHA-hFIX).

Among other things, the present disclosure demonstrates that a two-plasmid transfection system can produce improved volumetric vector yields as compared to a three-plasmid transfection system. As shown in FIG. 8, similar trends in volumetric yields were observed for a two-plasmid system at different plasmid ratios with larger-scale culture conditions.

Furthermore, as shown in Table 7A, a two-plasmid transfection system can also produce different packaging efficiencies depending on the ratio between Rep/Helper and Payload/Cap plasmids. Certain plasmid ratios produced a higher percentage of full capsids compared to a three-plasmid system, while others showed similar or lower percentages.

Example 8: Viral Vectors Generated with Two-Plasmid System are Functional In Vivo The present example demonstrates that viral vectors generated using a two-plasmid system are functional in vivo.

Figure 9:
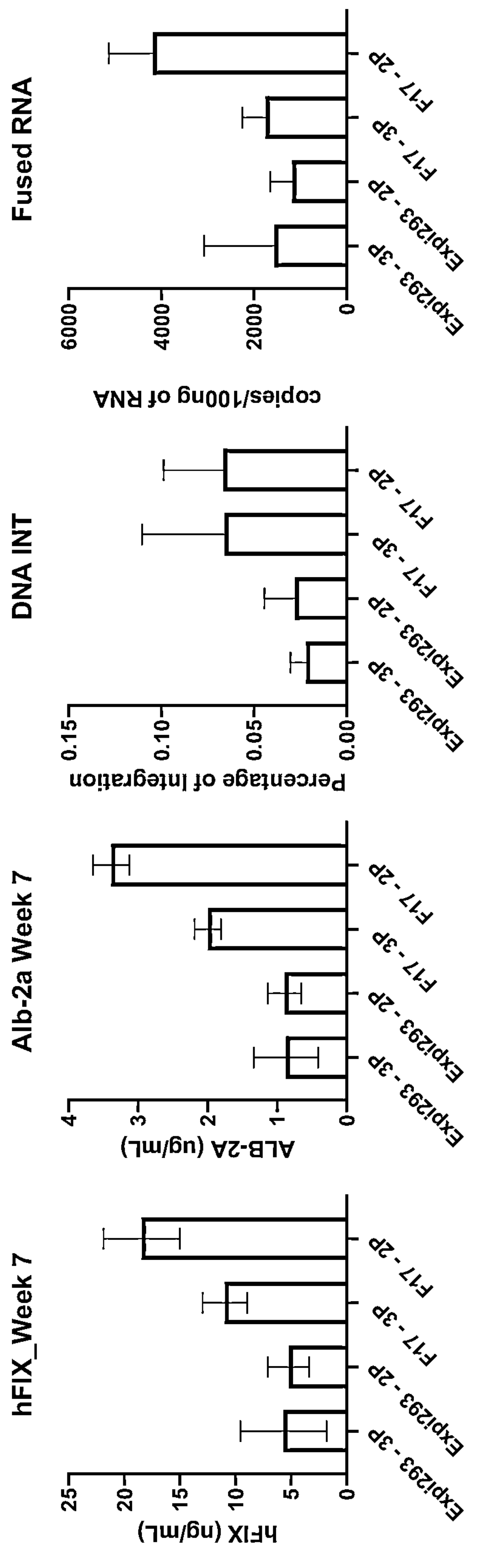
FIG. 9 depicts in vivo efficacy of AAV vectors in wild type mice. The AAV vectors were manufactured using three-plasmid system (3P) or two-plasmid system (2P) in different culture media (Expi293 and F17). The cap gene encodes for AAV-DJ and the gene of interest (GOI) is human Factor IX flanked by murine albumin homology arms (mHA-hFIX). Viral vectors were inoculated intravenously at a dose of 1E13 vg/kg. In vivo expression levels of payloads (FIX) and integration marker (ALB-2A) are quantified in the mouse plasma seven weeks post dosing. The protein expression levels are correlated to the percentage of FIX gene integrated into the albumin locus (DNA INT) and to the level of fused RNA consisting of albumin mRNA followed by FIX mRNA.

The vectors produced in Table 5D were purified by affinity chromatography using POROS AAVX and dialysed against PBS. Mice (FVB/NJ) were injected at a dosage of 1e13 vg/kg with compositions comprising packaged viral vectors produced using two- and three-plasmid transfection conditions in both types of culture media (Table 5D). The payload contains murine homology arms (mHA) allowing recombination into the albumin locus and a 2A peptide sequence followed by human Factor IX (hFIX). The vector efficacy in vivo was demonstrated by measuring in the mouse plasma the 2 expression products resulting from the inserted hFIX: albumin bearing the 2A peptide at the C terminus (ALB-2A) and human factor IX (hFIX). Additionally, liver samples were extracted to measure the copy number of hFIX gene integrated into the albumin locus and to measure the albumin-hFIX fused mRNA. As shown in FIG. 9, vectors produced via two and three-plasmid systems exhibited similar expression of Factor IX and ALB-2A and similar DNA integration and mRNA expression in the liver.

The present disclosure demonstrates that viral vectors generated through cell transfection with a two-plasmid system exhibit comparable performance in vivo relative to vectors produced through cell transfection with a three-plasmid system.

Example 9: Two-Plasmid System Sequence Elements are Interchangeable

The present example demonstrates that a two-plasmid system for cell transfection may provide improved vector yield for several combinations of certain sequence elements.

HEK293F cells were expanded for use in vector production. Cells were split to 2e6 cells/mL in 200 mL of Expi293 media in a 500 mL flask. Plasmid mixes for various transfection conditions outlined in Table 7 below were made and filtered through a 0.22 μM filter unit. A transfection reagent mix (e.g., PEI) was prepared according to manufacturer's protocol. Plasmid and transfection reagent mixes were combined to produce a single transfection mix. 20 mL of transfection mix was added to 100 mL of HEK293F cells in a 500 mL flask and allowed to incubate at 37° C. for 72 hours. In some embodiments, plasmids tested in a two-plasmid system comprise an AAV rep sequence and relevant sequences from a helper viruses ("Rep/Helper Plasmid") or an AAV cap sequence and a payload ("Payload/Cap Plasmid"). In some embodiments, plasmids tested in a two-plasmid system comprise an AAV cap sequence and relevant sequences from a helper viruses ("Cap/Helper Plasmid") or an AAV rep sequence and a payload ("Payload/Rep Plasmid"). In some embodiments, plasmids tested in a three-plasmid system comprise separate plasmids, each encoding one of: 1) an AAV rep and AAV cap sequence, 2) relevant sequence from a helper virus, and 3) a payload. A human Factor IX gene sequence under the control of a liver-specific promoter (LSP) was tested as the payload in experiments outlined below.

Figure 10:
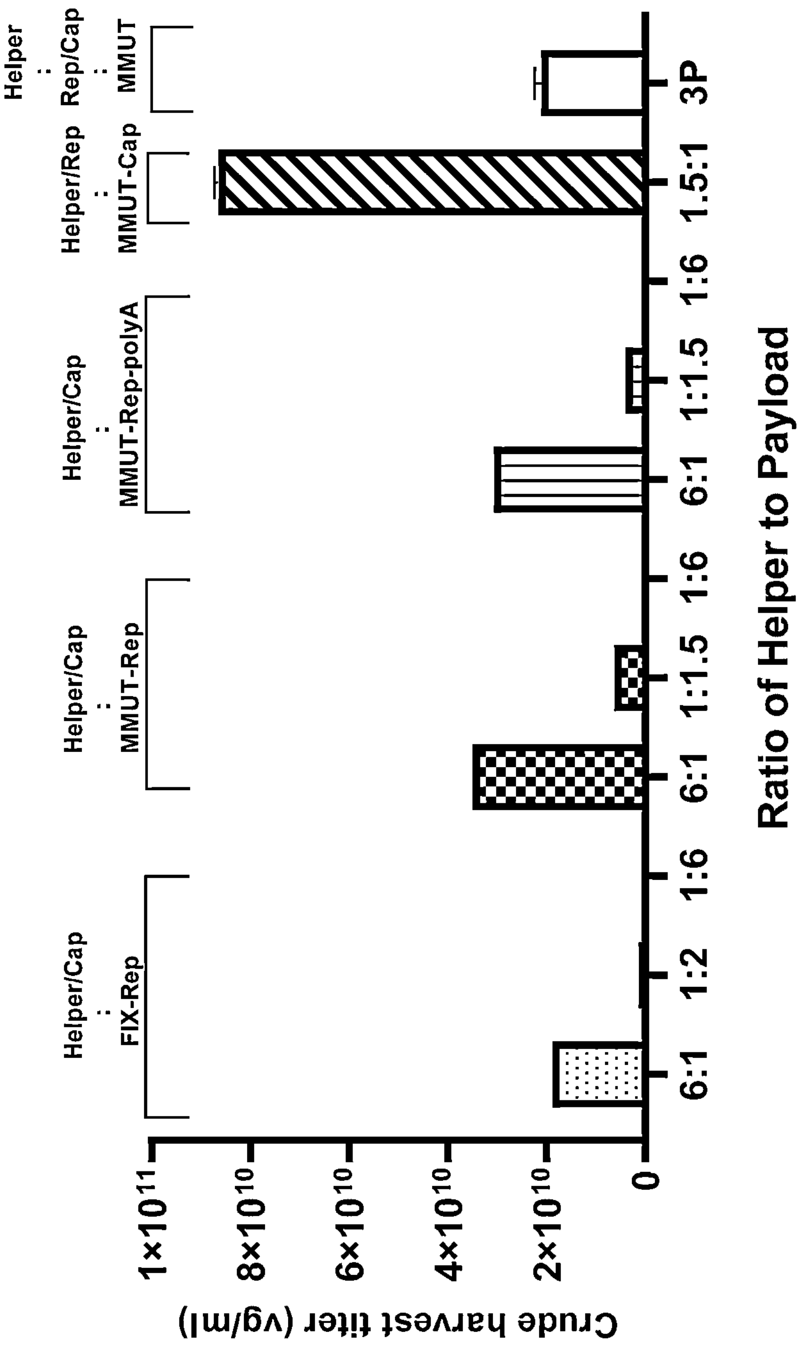
FIG. 10 depicts viral vector yields (vg/mL) for different combinations of genetic elements in a two-plasmid system as compared to a three-plasmid system. The different combinations include a plasmid comprising helper virus genes with cap (Helper/Cap) as compared to a plasmid containing helper virus genes with rep (Helper/Rep). Additionally, the different combinations include a plasmid containing the payload with rep (Payload/Rep) or rep followed by a polyA (Payload/Rep-polyA) as compared to plasmid containing the payload with cap (Payload/Cap). In this example, the cap gene is LKO3 serotype and two different payloads were tested (FIX and MMUT). Different ratios of the helper plasmid to the payload plasmid are presented.

The results presented in FIG. 10 show that a two plasmid system comprising a rep/helper plasmid and a payload/cap plasmid at a ratio of 1.5:1 produced high viral yields. Swapped two plasmid system combinations comprising cap/helper and payload/rep plasmids produced yields similar to or higher than a 3-plasmid system when a ratio of 6:1 was used.

The present disclosure demonstrates, among other things, that several combinations of the genetic elements in a two-plasmid system can produce comparable or higher yields than a 3-plasmid system. Noticeably, higher AAV yields can be achieved when the ratio between the two plasmids is unbalanced to increase the amount of helper virus sequences relative to the payload (from 1.5:1 to 6:1 or beyond).

Example 10: Two-Plasmid System Combined with Intron Insertion can Reduce Levels of Replication Competent AAV (rcAAV)

The present example demonstrates that a two-plasmid system for cell transfection may reduce levels of replication competent AAV (rcAAV) produced in vivo or in vitro. Particularly, when an intron is inserted between the p5 promoter and the start codon of the rep gene, the levels of rcAAV may be particularly reduced.

In some embodiments, the present example includes expansion of HEK293F cells for use in vector production. Cells were split to 2e6 cells/mL in 200 mL of Expi293 media in a 500 mL flask. Plasmid mixes for various transfection conditions outlined in Table 8 below were made and filtered through a 0.22 μM filter unit. A transfection reagent mix (e.g., PEI) was prepared according to manufacturer's protocol. Plasmid and transfection reagent mixes were combined to produce a single transfection mix. 20 mL of transfection mix was added to 100 mL of HEK293F cells in a 500 mL flask and was allowed to incubate at 37° C. for 72 hours.

In some embodiments, plasmids in a two-plasmid system comprise an AAV rep sequence and relevant sequences from a helper viruses ("Rep/Helper Plasmid") or an AAV cap sequence and a payload ("Payload/Cap Plasmid"). In some embodiments, plasmids in a three-plasmid system comprise separate plasmids, each encoding one of: 1) an AAV rep and AAV cap sequence, 2) relevant sequence from a helper virus, and 3) a payload. A human Factor IX gene sequence under the control of a liver-specific promoter (LSP) or a human mutase (MMUT) were tested as the payload in experiments outlined below. In some embodiments, an intron sequence was inserted between the p5 promoter and the rep gene. In some embodiments, an intron sequence can present several lengths (133 bp, 1.43 kb or 3.3 kb)

In this experiment, a two-plasmid system comprising various intron combinations was tested at different ratios of Rep/Helper plasmid to Payload/Cap plasmid as presented in Table 10.

TABLE 10

Transfection conditions for a two-plasmid system comprising various introns between p5 promoter and rep gene.

| Capsid | Payload | Intron between p5 and rep | Rep/Helper Plasmid | Payload/Cap Plasmid |
|---|---|---|---|---|
| LK03 | hFIX | No intron | 6 | 1 |
| LK03 | hFIX | No intron | 1.5 | 1 |
| LK03 | hFIX | No intron | 1 | 6 |
| LK03 | hFIX | 1.43 kb | 6 | 1 |
| LK03 | hFIX | 1.43 kb | 1.5 | 1 |
| LK03 | hFIX | 1.43 kb | 1 | 6 |
| LK03 | hFIX | 133 bp | 6 | 1 |
| LK03 | hFIX | 133 bp | 1.5 | 1 |
| LK03 | hFIX | 133 bp | 1 | 6 |

TABLE 10A

Transfection condition for three-plasmid (3P) system.

| Capsid | Payload | Intron between p5 and rep | Helper Plasmid | Rep/Cap Plasmid | Payload Plasmid |
|---|---|---|---|---|---|
| LK03 | hFIX | No intron | 0.43 | 0.35 | 0.22 |

In a second experiment, a longer intron (3.3 kb) was tested in comparison to the 1.43 kb intron as shown in table 10B

TABLE 10B

Transfection conditions for two-plasmid system containing two different introns between p5 promoter and rep gene.

| Capsid | Payload | Intron between p5 and rep | Rep/Helper Plasmid | Payload/Cap Plasmid |
|---|---|---|---|---|
| LK03 | MMUT | 1.43 kb intron | 1.5 | 1 |
| LK03 | MMUT | 3.3 kb intron | 1.5 | 1 |

To assess reduction of rcAAV occurrence during AAV manufacturing using embodiments of a two-plasmid system, the vectors described in Table 10B were tested in an rcAAV assay. A similar vector (LKO3 capsid and MMUT payload), which was produced using a three-plasmid system (with no intron inserted in the rep gene), was tested side by side in the same assay for comparison.

HeLa cells were transduced with 1e6, 1e8, and 1e10 vector genomes (vgs) of the test sample in the presence of wild-type adenovirus (Ad5). In order to demonstrate the limit of detection of the assay, cells were also inoculated with test samples (1e6, 1e8, and 1e10 vgs) spiked with 10 infectious particles of wild-type AAV2 (wtAAV2). Following the first amplification cycle, cells were harvested and a sample was collected for qPCR quantification; remaining cells were frozen. Cell lysates were prepared by three successive freeze-thaw cycles, and these samples were used to transduce a second batch of HeLa cells. This procedure was repeated for a total of three rounds of amplification of samples.

DNA was extracted from cell harvest samples using the DNeasy Blood and Tissue Kit (Qiagen, Cat #69506). Isolated DNA samples were subjected to real-time qPCR with amplification of two sequences: AAV Rep2 and human albumin (hAlb). AAV Rep2 sequences were amplified if rcAAVs were present in the test sample, while human albumin served as a housekeeping gene. The copy number of each sequence was determined by comparing Ct values to that of the assay plasmid standard curve (ranging from 1e2 to 1e8 copies/reaction). Relative copy number of Rep2 per cell was determined by calculating the ratio of Rep2 copies to human albumin copies, multiplied by 2. Replication was confirmed if the relative copy number of Rep2 was >10 in at least one of the three rounds of amplification. If it was observed that the relative copy number of Rep2 increases with each successive round of amplification, this indicated the presence of replication competent AAV in a test sample. Results of rcAAV testing are presented in Table 10C.

TABLE 10C rcAAV detection in AAV vector batches manufactured using three-plasmid system without intron or using two-plasmid system with an intron in the rep gene sequence.

| Vector | Production system | Intron in rep sequence | rcAAV detection in 1E6 vg | rcAAV detection in 1E8 vg | rcAAV detection in 1E10 vg |
|---|---|---|---|---|---|
| LK03-MMUT | 3 plasmids | None | Not detected | Not detected | Positive |
| LK03-MMUT | 2 plasmids | 1.43 kb | Not detected | Not detected | Not detected |
| LK03-MMUT | 2 plasmids | 3.3 kb | Not detected | Not detected | Not detected |

Viral vectors manufactured using the two-plasmid system were found to be negative for rcAAV replication. In contrast, viral vectors produced using the traditional three plasmid system demonstrated replication of rcAAV (rcAAV positive) at the highest dose of 1E+10 vgs.

Figure 11:
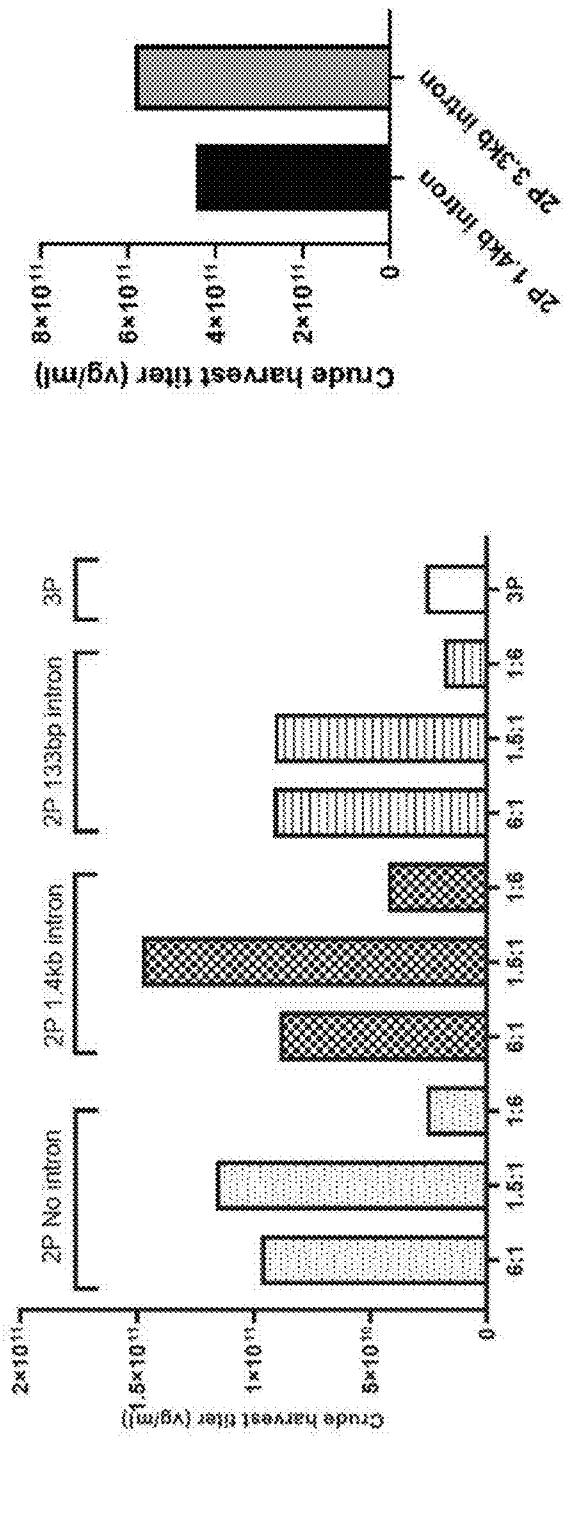
FIG. 11 depicts viral vector yields (vg/mL) for a two-plasmid system containing an additional intron between AAV p5 promoter and rep gene at various plasmid ratios as compared to a two-plasmid system and three-plasmid system with no intron. (A) an intron of 1.4 kb and an intron of 133 bp were tested, the cap gene was LKO3 and the payload was hFIX. (B) an intron of 1.4 kb and an intron of 3.3 kb were tested, the cap gene was LKO3 and the payload was MMUT.
Figure 12:
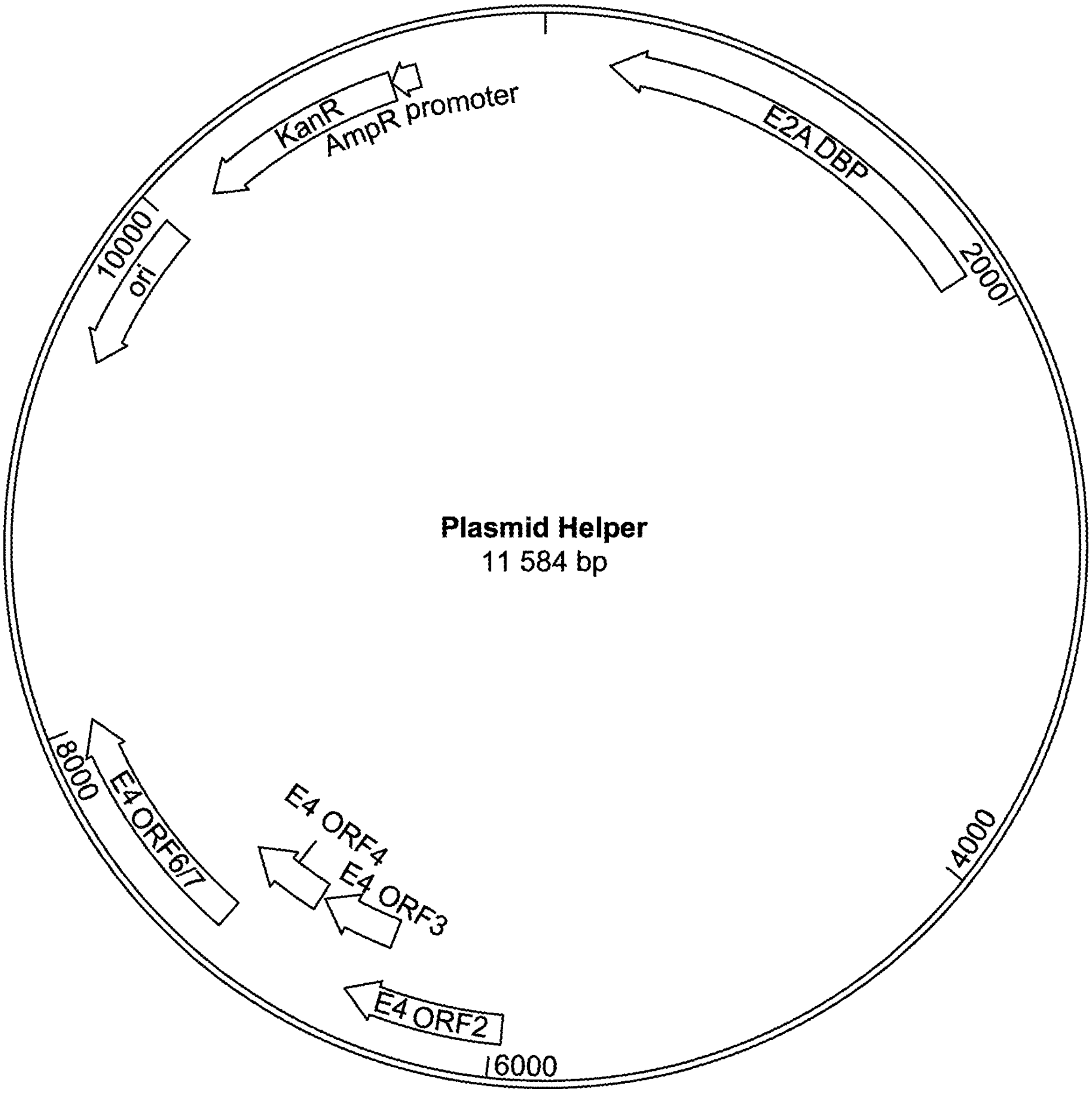
FIG. 12 depicts a schematic map of a helper plasmid for AAV production using a 3-plasmid system. A helper plasmid may contain several Adenovirus genes, such as, e.g., E2A DNA Binding Protein (DBP) gene, E4 Open Reading Frame (ORF) 2, ORF3, ORF4 and ORF6/7. Plasmids may also contain elements necessary for bacterial culture like the colE1 origin of replication (ori), and antibiotic resistance gene (e.g. kanamycin).
Figure 13:
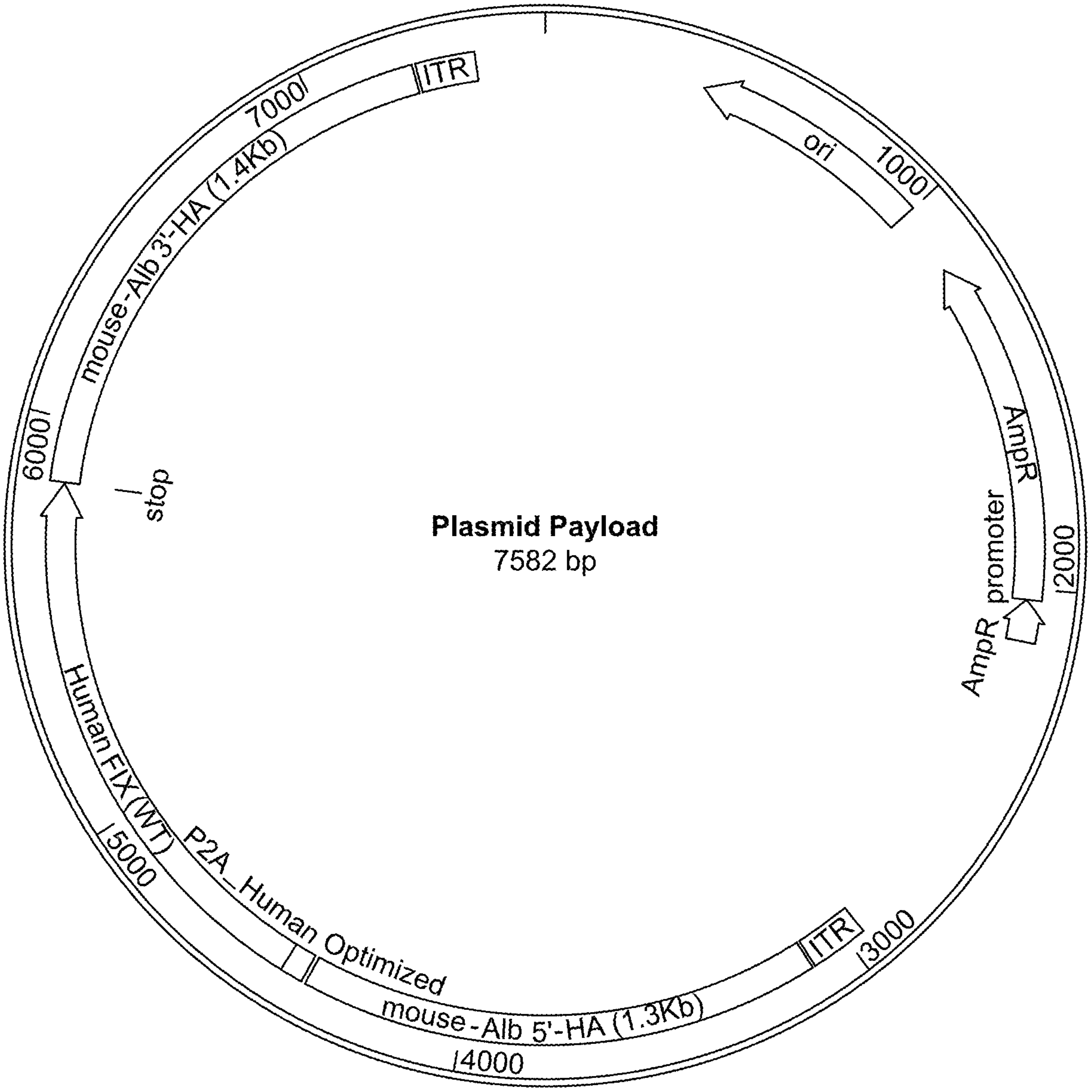
FIG. 13 depicts a schematic map of a payload plasmid for AAV production using a 3-plasmid system. Payload plasmids may contain AAV Inverted Terminal Repeats (ITRs) flanking the payload. As shown in the schematic, a payload may contain human Factor IX gene (human FIX) as the gene of interest, and mouse albumin gene sequences used as homology arms (mouse HA) located in 5' and 3' position of the gene of interest. A peptide 2A is located between the 5' homology arm and the gene of interest to allow independent translation of the gene of interest. Plasmids may also contain elements necessary for bacterial culture like the colE1 origin of replication (ori), and antibiotic resistance gene (e.g. ampicillin).
Figure 14:
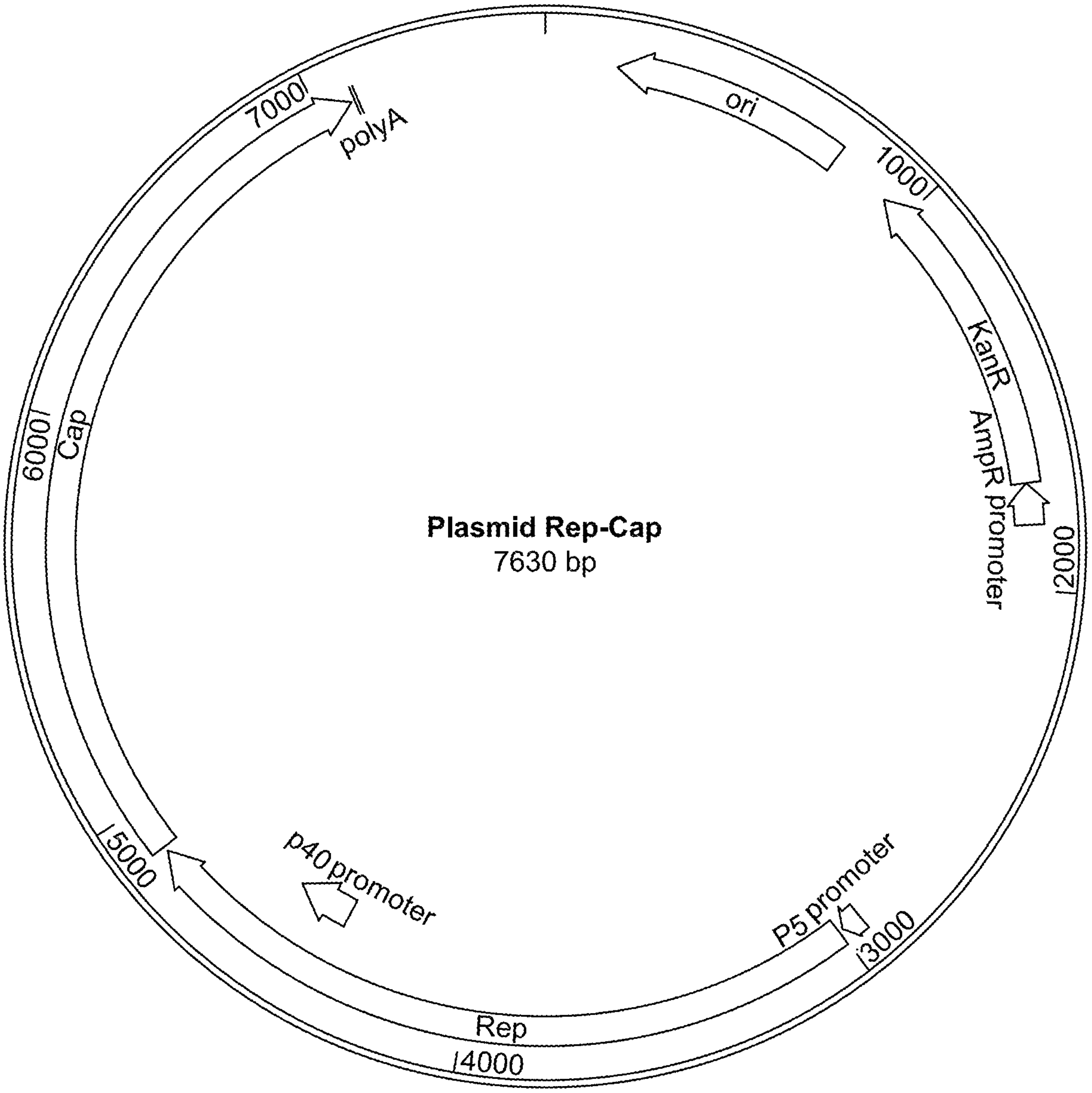
FIG. 14 depicts a schematic map of a rep-cap plasmid for AAV production using a 3-plasmid system. Helper plasmids may contain a rep gene and a cap gene in their native genomic organization, e.g., with a p5 promoter upstream of the rep gene and a p40 promoter located upstream of the cap gene and in the coding sequence of the rep gene. A cap gene can encode for a variety of AAV serotypes and synthetic variants. Plasmids may also contain elements necessary for bacterial culture like the colE1 origin of replication (ori), and antibiotic resistance gene (e.g. kanamycin).
Figure 15:
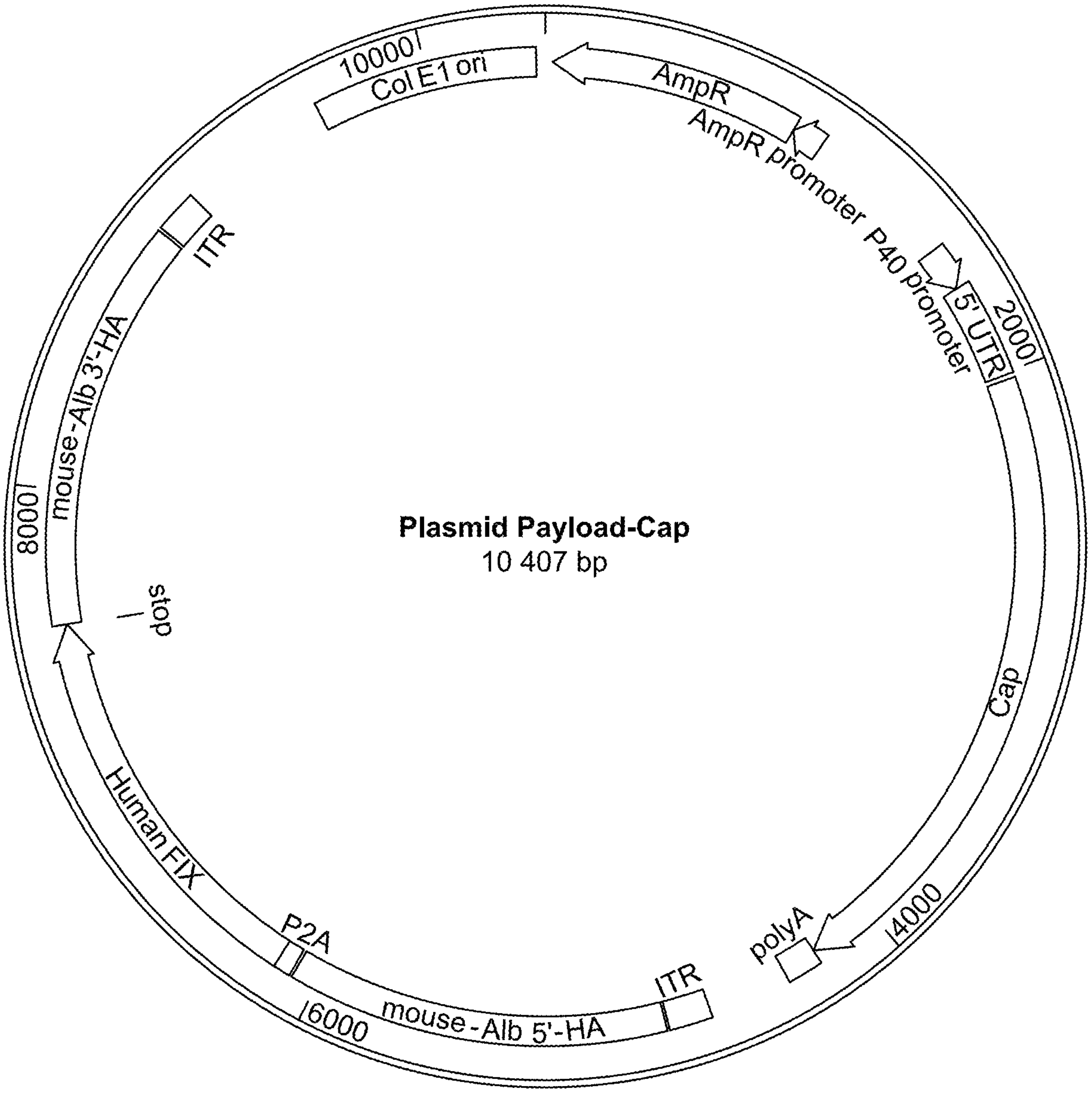
FIG. 15 depicts a schematic map of a Payload-Cap plasmid for AAV production using a 2-plasmid system. Plasmids may contain AAV Inverted Terminal Repeats (ITRs) flanking a payload. Payloads may contain human Factor IX gene (human FIX) as a gene of interest, and mouse albumin gene sequences used as homology arms (mouse HA) located in 5' and 3' position of the gene of interest. A peptide 2A is located between the 5' homology arm and the gene of interest to allow independent translation of the gene of interest. In addition, plasmids may contain an AAV cap gene downstream of a p40 promoter and upstream of a polyA. A cap gene can encode for a variety of AAV serotypes and synthetic variants. Plasmids may also contain elements necessary for bacterial culture like the colE1 origin of replication (ori), and antibiotic resistance gene (e.g. ampicillin).
Figure 16:
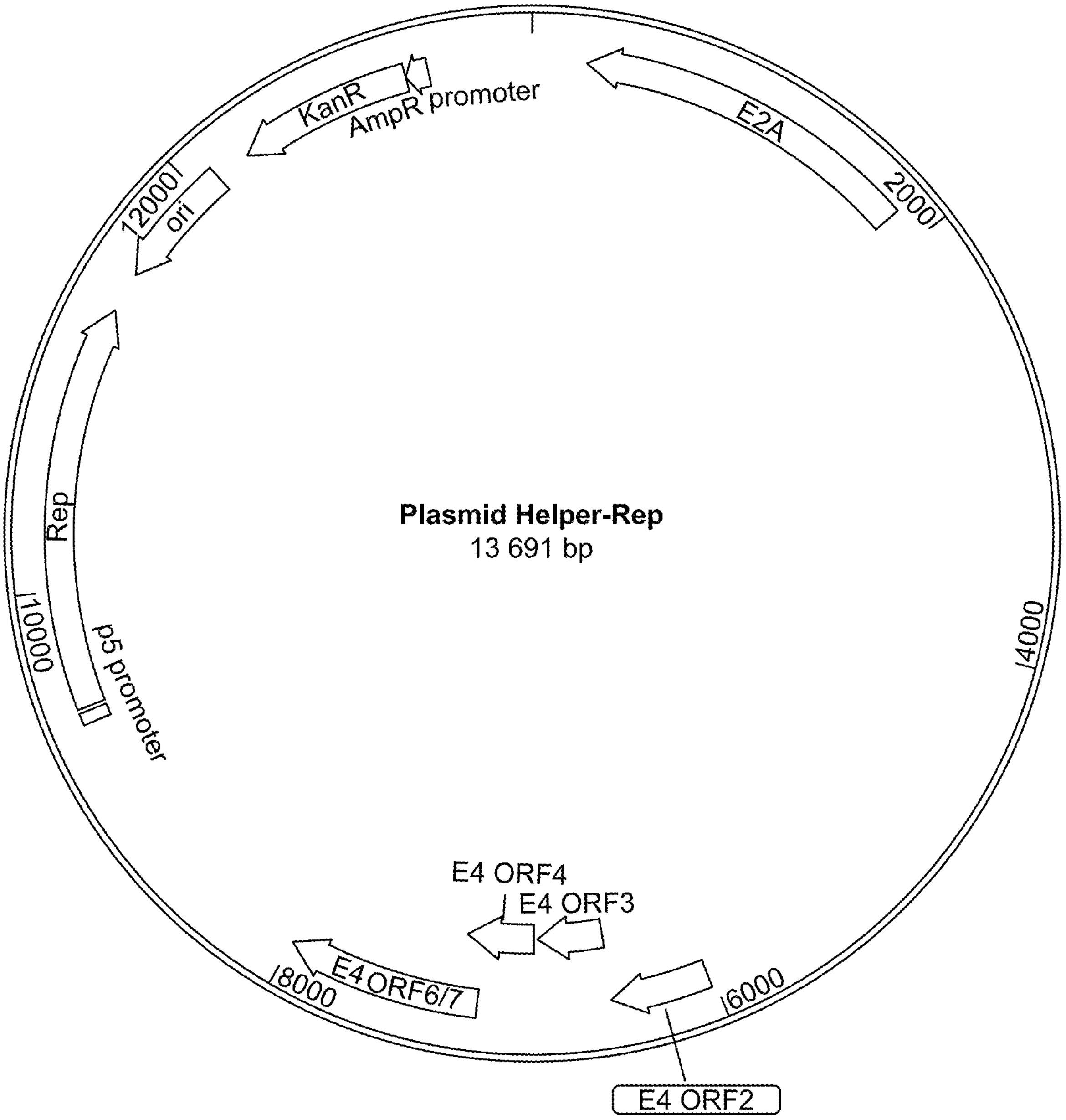
FIG. 16 depicts a schematic map of a Helper-Rep plasmid for AAV production using a 2-plasmid system. Plasmids may contain several Adenovirus genes, like E2A DNA Binding Protein (DBP) gene, E4 Open Reading Frame (ORF) 2, ORF3, ORF4 and ORF6/7. In addition, plasmids may contain an AAV rep gene downstream of a p5 promoter. Plasmids may also contain elements necessary for bacterial culture like the colE1 origin of replication (ori), and antibiotic resistance gene (e.g. kanamycin).
Figure 17:
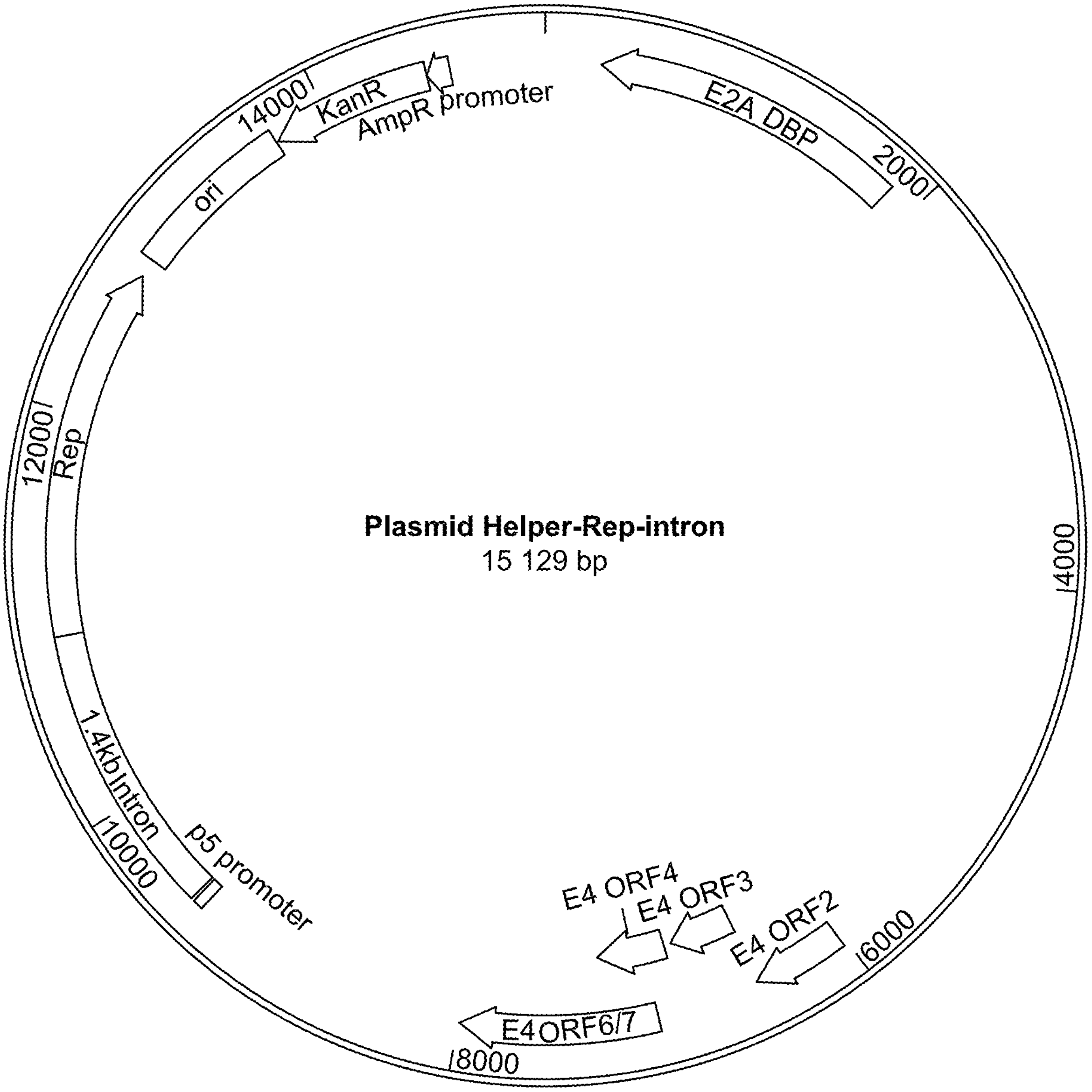
FIG. 17 depicts a schematic map of a Helper-Rep-intron plasmid for AAV production using a 2-plasmid system. Plasmids may contain several Adenovirus genes, like E2A DNA Binding Protein (DBP) gene, E4 Open Reading Frame (ORF) 2, ORF3, ORF4 and ORF6/7. In addition, plasmids may contain an AAV rep gene downstream of a p5 promoter and an intron. An intron can be selected from a variety of sizes, e.g., 1.4 kb in the schematic. Plasmids may also contain elements necessary for bacterial culture like the colE1 origin of replication (ori), and antibiotic resistance gene (e.g. kanamycin).
Figure 18:
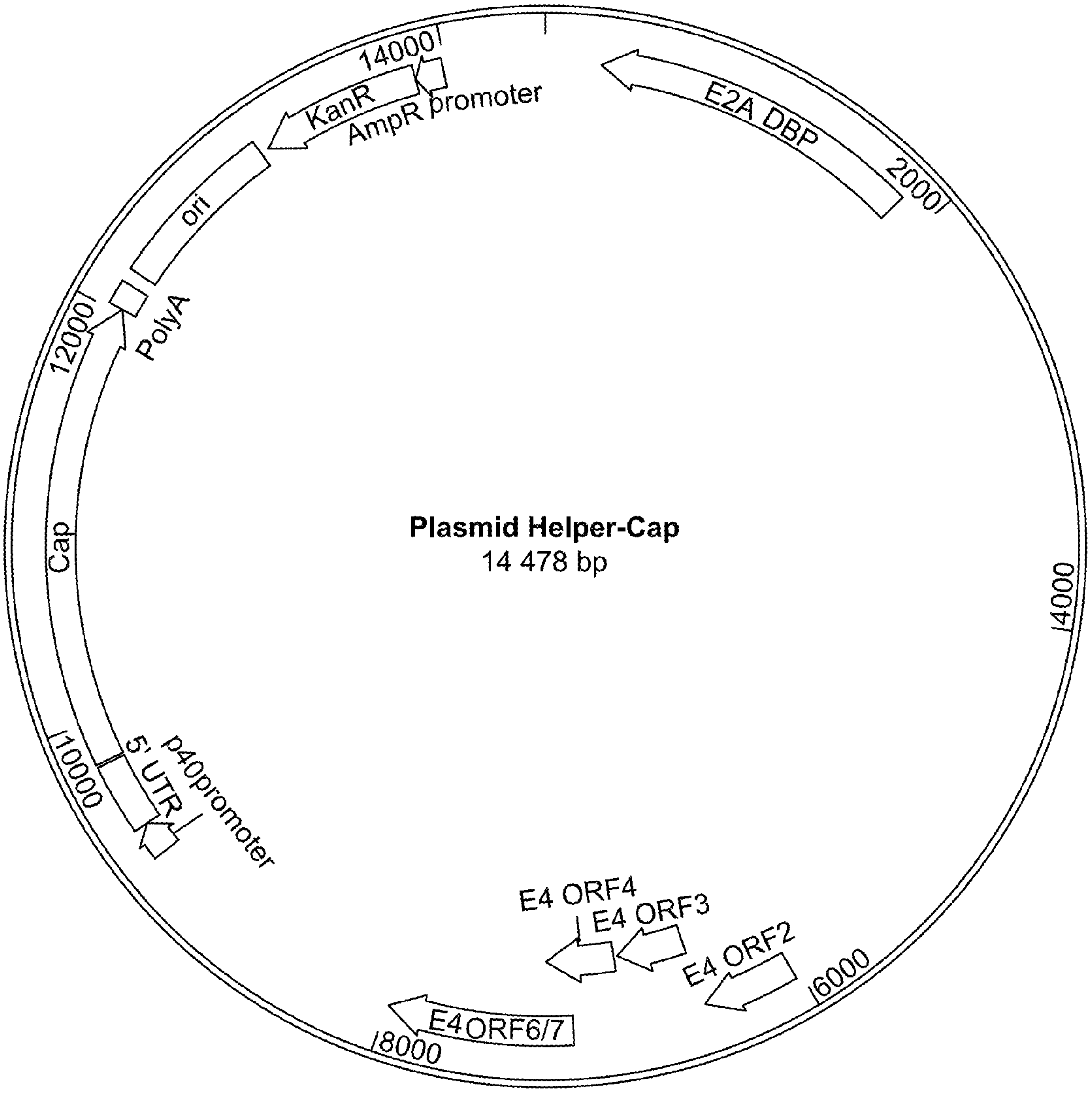
FIG. 18 depicts a schematic map of a Helper-Cap plasmid for AAV production using a 2-plasmid system. Plasmids may contain several Adenovirus genes, like E2A DNA Binding Protein (DBP) gene, E4 Open Reading Frame (ORF) 2, ORF3, ORF4 and ORF6/7. In addition, plasmids may contain an AAV cap gene downstream of a p40 promoter and upstream of a polyA. A cap gene can encode for a variety of AAV serotypes and synthetic variants. Plasmids may also contain elements necessary for bacterial culture like the colE1 origin of replication (ori), and antibiotic resistance gene (e.g. kanamycin).
Figure 19:
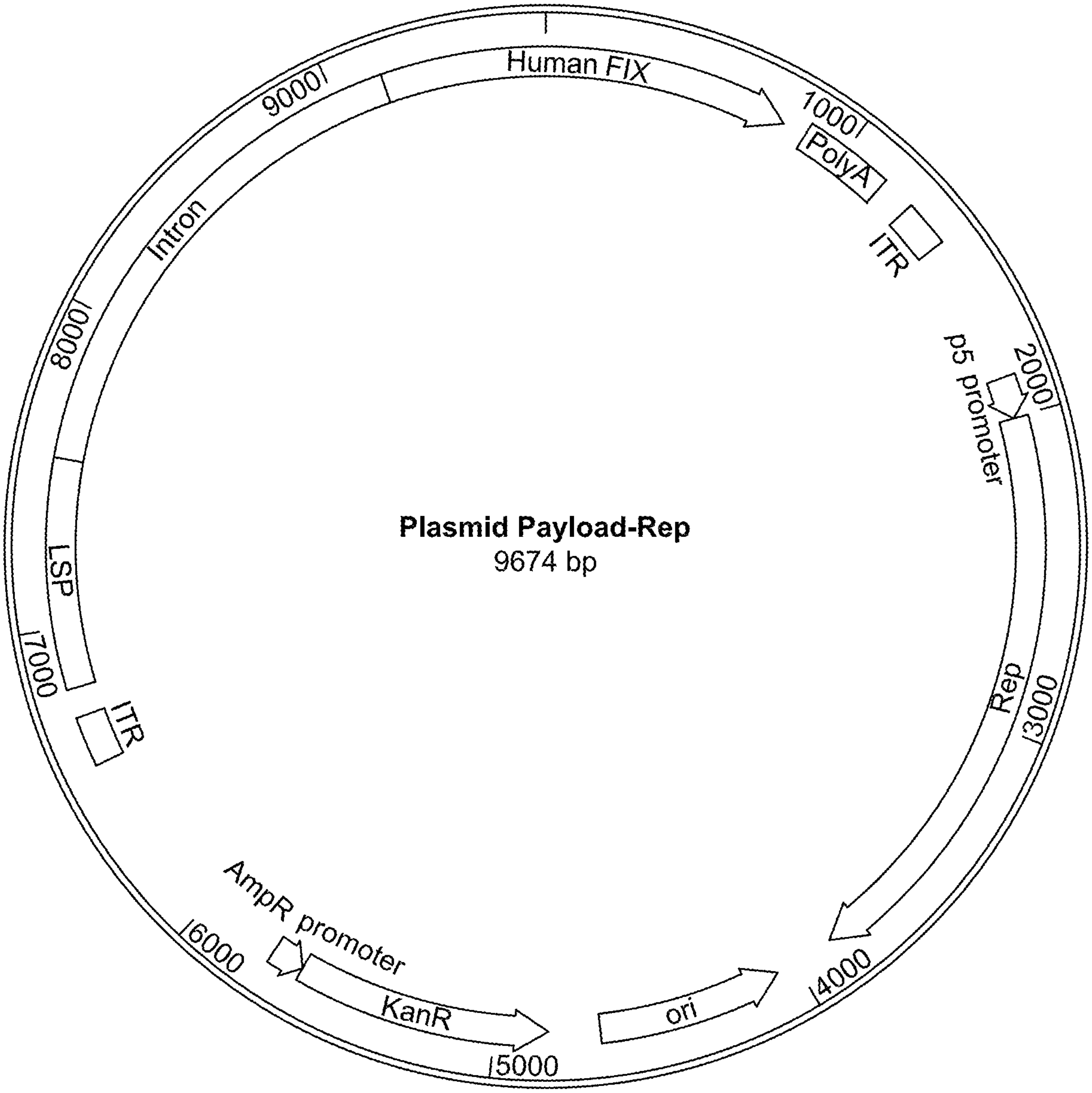
FIG. 19 depicts a schematic map of a Payload-Rep plasmid for AAV production using a 2-plasmid system. Plasmids may contain AAV Inverted Terminal Repeats (ITRs) flanking the payload. A payload may contain human Factor IX gene (human FIX) as the gene of interest, which is located downstream of a liver-specific promoter (LSP) and an intron, and upstream of a polyA. In addition, plasmids may contain an AAV rep gene downstream of a p5 promoter. Plasmids may also contain elements necessary for bacterial culture like the colE1 origin of replication (ori), and antibiotic resistance gene (e.g. kanamycin).

Among other things, the present disclosure demonstrates that the insertion of an intron between an AAV p5 promoter and a rep gene in a two-plasmid system generates vector yields comparable to or higher than the 2-plasmid system without intron, and the 3-plasmid system (FIG. 11). In some embodiments, insertion of an intron between an AAV p5 promoter and a rep gene in a two-plasmid system may reduce occurrence of replication competent AAV (rcAAV) as compared to a traditional three-plasmid system.

Example 11: Two-Plasmid System Provides Similar Capsid Viral Protein (VP) Ratios and Purity as Compared to Three-Plasmid System The present example demonstrates that a two-plasmid system for cell transfection may provide similar protein purity and observed ratios between the VP1, VP2, and VP3 capsid proteins as compared to a three-plasmid system.

In this Example, HEK293F cells were expanded for use in vector production. HEK293F cells were expanded using Expi293 basal media for cell growth. Cell counts were first recorded to ensure viable cell densities were between 2.0e6-2.6e6 cells/mL and viabilities were above 95% at the time of transfection. Transfection mixes were prepared by pre-weighing Expi293 media (two-plasmid system) or OptiPRO SFM media (three-plasmid system) in two separate vessels, labeled "DNA media" and "TR media", each containing equal volume requirements from transfection mix calculations. PEIMAX was added to plasmid DNA (pDNA) (three-plasmid system) and FectoVIR-AAV was added to pDNA (two-plasmid system). Each mixture was added to separate bottles labeled "TR media" and set aside. The mass fractions of the Helper plasmid, Rep/Cap plasmid, and Payload plasmid were 0.43, 0.35, and 0.22, respectively for the three-plasmid transfection system. The mass fractions of the Rep/Helper plasmid and Payload/Cap plasmid were 0.60 and 0.40, respectively (1.5:1 w/w plasmid ratio) for the two-plasmid transfection system. Plasmids were sterile-filtered through a Corning 0.22 um PES bottle-top filter by first wetting the membrane with media from the bottle labeled "DNA media", adding appropriate amount of pDNA to the bottle-top, turning on the vacuum for the filter, and finally flushing residual DNA on the filter with the remaining media from the "DNA media" bottle. Once the "TR media" and "DNA media" solutions were prepared, both mixes were combined into a separate vessel and inverted to begin the complexation process. The transfection mix was then left to incubate for 20 minutes at room temperature when using PEIMAX (three-plasmid system), and left to incubate for 30 min at room temperature when using FectoVIR-AAV (two-plasmid system). Once the time elapsed, the transfection mix was added to the culture medium at a 10% final culture volume fraction (e.g., 25 mL transfection mix added to 225 mL culture) and grown at 37° C. for 72 hr.

At time of harvest, Benzonase was mixed with Expi293 media, using 100 uL Benzonase (approximately 250 U/uL) and 2.5 mL media per reactor for 100 U of Benzonase per 1 mL of culture volume. Bioreactor culture was incubated at 37° C. for 15 minutes. A 10× lysis buffer (10% v/v Tween 20, 500 mM Tris-HCl pH 8.0, 20 mM $MgCl_2$, Milli-Q water) was made and 25 mL (10% culture volume) was added to each bioreactor, followed by incubation at 37° C. for 90 minutes. Next, 25 mL of sterile-filtered 5M NaCl was added to each flask (to reach a target concentration of 0.5 M NaCl) and incubated at 37° C. for 30 minutes. Lysed cultures were then spun for 10 minutes at 3500×g. Supernatants were filtered through a 0.22 um Corning sterile filter and sampled for crude lysate analysis. After sterile filtration, samples were loaded on a 5 mL POROS GoPure AAVX Pre-packed Column. Eluate was neutralized to between pH 7.0-7.5, using 20% v/v Tris-HCl pH 8.5 before sampling and subsequent analysis.

Sodium dodecyl sulfate polyacrylamide gel electrophoresis (SDS-PAGE) was used to determine the purity of the three AAV structural proteins (VP1, VP2, and VP3) that were present in the samples. Samples and the LKO3 capsid manufactured using the three-plasmid system were mixed with lithium dodecyl sulfate (LDS) sample buffer and dithiothreitol (DTT), and then were subjected to heat denaturation. Denatured samples and molecular weight marker were loaded onto a Bis-Tris gel and subsequent application of an electrical field separated protein species based on relative size. Following electrophoresis, the gel was stained with Imperial Protein Stain, washed, and imaged on the LI-COR CLx. ImageJ software was used to quantify the protein intensity of each band present in every test sample. Viral protein purity was determined by the percentage of the ratio of the sum of VP1, VP2, and VP3 product peak areas to the total sum of all peak areas. Any peak that was not a product (VP1, VP2, VP3) peak was considered an impurity.

Figure 20:
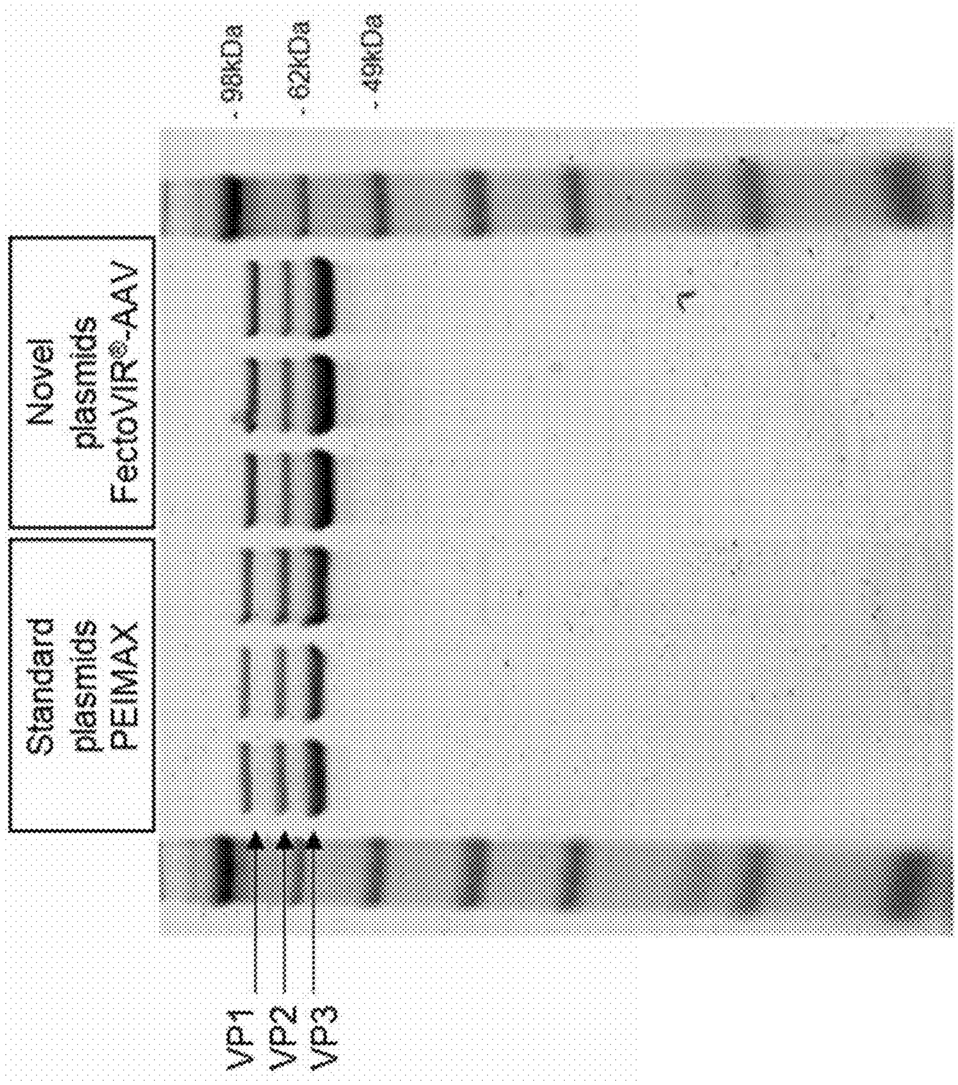
FIG. 20 depicts a SDS-PAGE gel measuring purity of AAV LKO3 capsid viral proteins (VPs) produced through a three-plasmid system ("Standard plasmids PEIMAX") and two-plasmid system ("Novel plasmids FectoVIR-AAV").

Among other things, the present disclosure demonstrates that a two-plasmid system may produce capsid proteins with comparable purity and capsid protein ratios to those obtained through a three-plasmid system (FIG. 20).

Example 12: Two-Plasmid System can be Employed for Large-Scale Production of AAV Capsid The present example demonstrates that a two-plasmid system for cell transfection may be employed in a larger-scale system (e.g., 50 L bioreactor) to produce high levels of viral genome titers. This example also illustrates that a two-plasmid system may reduce the amount of plasmid DNA (e.g., comprising a kanamycin resistance gene) that is non-specifically packaged in AAV capsids during a manufacturing process.

Figure 21:
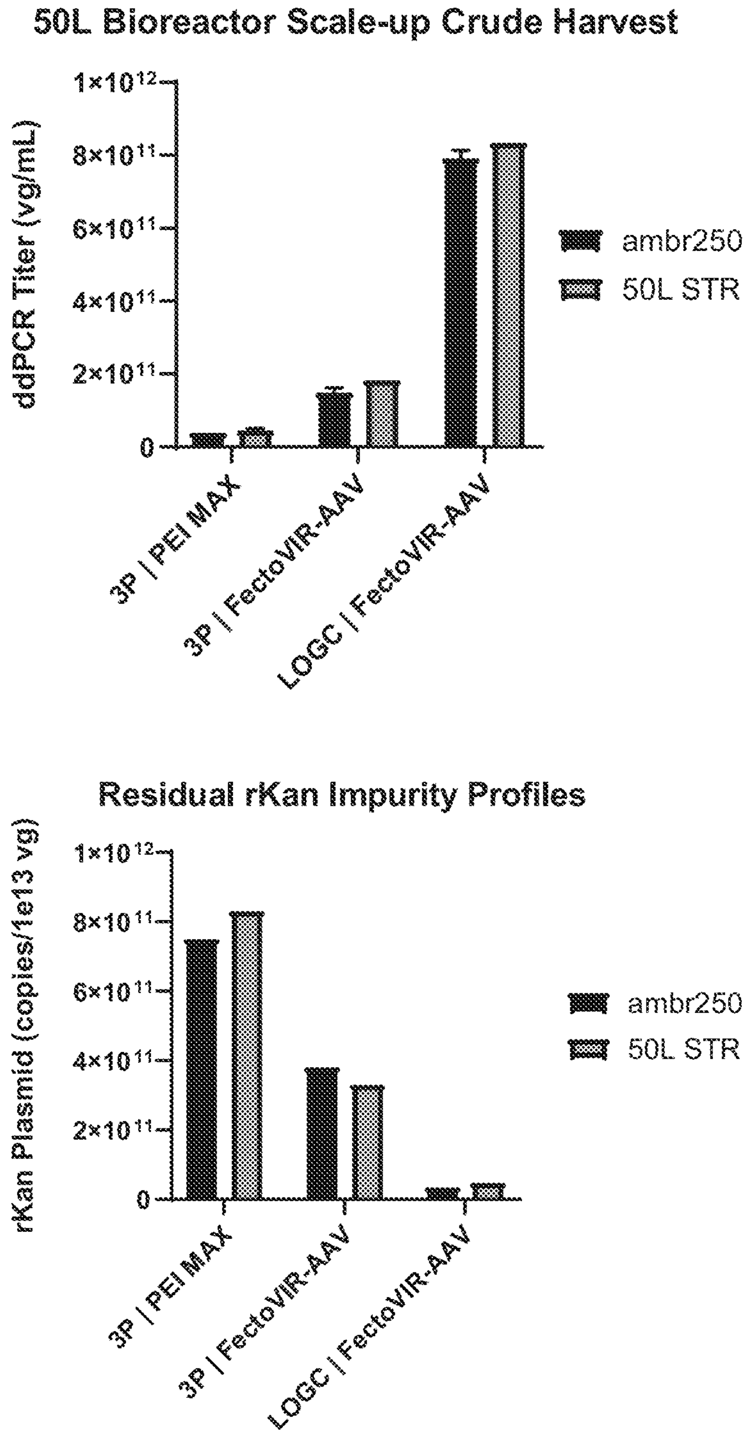
FIG. 21 depicts viral titer levels (vg/mL) in crude lysate produced by HEK293F cells transfected with a three-plasmid system and PEIMAX (3P PEI MAX), a three-plasmid system and FectoVir-AAV (3P|FectoVir-AAV), and a two-plasmid system with FectoVIR-AAV (LOGC|FectoVIR- AAV). Residual levels of plasmid DNA (rKan) were measured for each transfection condition. Cells were cultured in an ambr250 bioreactor or 50 L bioreactor setup.

In this Example, HEK293F cells were expanded as previously described herein for culturing in an ambr250 bioreactor as well as a 50 L Sartorius BioSTAT STR bioreactor. Crude viral titer (vg/mL) and residual levels of transfection-derived plasmid DNA in the AAVX purified pool were measured for both reactor setups (FIG. 21).

HEK293F cells were expanded for use in vector production. HEK293F cells were expanded using Expi293 basal media for cell growth. Cell counts were first recorded to ensure viable cell densities were between 2.0e6-2.6e6 cells/mL and viabilities were above 95% at time of transfection. Transfection mixes were prepared by pre-weighing Expi293 media (two-plasmid system) or OptiPRO SFM media (three-plasmid system) in two separate vessels, labeled "DNA media" and "TR media", each containing equal volume requirements from transfection mix calculations. PEIMAX was added to plasmid DNA (pDNA) (three-plasmid system) and FectoVIR-AAV was added to pDNA (two-plasmid system). Each mixture was added to separate bottles labeled "TR media" and set aside. Mass fractions of Helper plasmid, Rep/Cap plasmid, and Payload plasmid were 0.43, 0.35, and 0.22, respectively for three-plasmid transfection system (1.5:1 w/w TR:plasmid ratio). Mass fractions of Rep/Helper plasmid and Payload/Cap plasmid were 0.60 and 0.40, respectively (1:1 w/w TR:plasmid ratio) for two-plasmid transfection system. Plasmids were sterile-filtered through a 0.22 um filter and finally flushed with remaining media from the "DNA media" bottle. Once "TR media" and "DNA media" solutions were prepared, both mixes were combined into a separate vessel and inverted for 1 minute to begin complexation process. Transfection mix was then left to incubate for 20 minutes at room temperature when using PEIMAX (three-plasmid system), and left to incubate for 30 min at room temperature when using FectoVIR-AAV (two-plasmid system). Once time had elapsed, transfection mix was added to the culture medium at a 10% final culture volume fraction (e.g., 25 mL transfection mix added to 225 mL culture for ambr250; 5 L transfection mix added to 45 L culture for SOL) and grown at 37° C. for 72 hr.

At time of harvest, Benzonase was mixed with Expi293 media, using Benzonase (approximately 250 U/uL) at 10 U of Benzonase per 1 mL of culture volume and 1% culture volume media per reactor. Bioreactor culture was incubated at 37° C. for 15 minutes. A 10× lysis buffer (10% v/v Tween 20, 500 mM Tris-HCl pH 8.0, 20 mM $MgCl_2$, Milli-Q water) was made and 10% culture volume was added to each bioreactor, followed by incubation at 37° C. for 90 minutes.

Next, 10% of culture volume of sterile-filtered 5M NaCl was added to each flask (to reach a target concentration of 0.5 M NaCl) and incubated at 37° C. for 30 minutes. Lysed cultures were then spun for 10 minutes at 3500×g. Supernatants were filtered through a 0.22 um sterile filter and sampled for crude lysate analysis. After sterile filtration, samples for additional analytics were loaded through AAVX chromatography resin. Eluate was neutralized to between pH 7.0-7.5, using 20% v/v Tris-HCl pH 8.5 before sampling and subsequent analysis.

Vector genome titers were quantified by ddPCR in lysed crude harvest samples. Packaged residual plasmid DNA was quantified from purified vector using ddPCR and primers/probe set targeting the kanamycin resistance gene located in the backbone of each plasmid used in this example. In this assay, test samples were treated with and without salt active nuclease to confirm that residual plasmid DNA was packaged in AAV capsids (and thus nuclease resistant). Samples were then subjected to treatment with proteinase K to extract DNA from capsids. Samples were diluted and mixed with ddPCR master mix containing a primers/probe set that binds specifically to Kanamycin gene. A Bio-Rad Automated Droplet Generator was used to generate droplets for each sample, which were then thermocycled to amplify DNA of interest using standard PCR. Positive and negative droplets were quantified using Bio Rad QX200 Droplet Reader and analyzed using Poisson distribution analysis. The number of copies of Kanamycin amplicon was corrected by sample preparation to yield concentration of residual Kan plasmid DNA in units of copies/mL.

Among other things, the present disclosure demonstrates that a two-plasmid system may produce high levels of viral capsids at larger-scale volumes (e.g., 50 L or greater) as compared to those obtained with a three plasmid system. In some embodiments, a two-plasmid system may also provide significantly reduced levels of transfection-derived plasmid DNA in AAVX purified pool as compared to a three plasmid system.

Example 13: Various Factors May Impact Viral Vector Yields in a Two-Plasmid System The present example demonstrates that, among other things, a two-plasmid system can produce increased viral yields when particular transfection conditions are optimized. In some embodiments, specific combinations of different levels of transfection reagent (e.g., FectoVir), cell density (e.g., HEK293F cells), and/or plasmid DNA (e.g., total plasmid DNA) can produce increased viral yields while minimizing cost.

In this Example, HEK293F cells were expanded for use in vector production. HEK293F cells were expanded using Expi293 basal media for cell growth. Cell counts were first recorded to ensure viable cell densities were between 2.0e6-2.6e6 cells/mL and viabilities were above 95% at the time of transfection. Transfection mixes were prepared by pre-weighing Expi293 media in two separate vessels, labeled “DNA media” and “TR media”, each containing equal volume requirements from transfection mix calculations. FectoVIR-AAV was added to vessel labeled “TR media” and set aside. Mass fractions of Rep/Helper plasmid and Payload/Cap plasmid were 0.60 and 0.40, respectively (1.5:1 w/w plasmid ratio) for two-plasmid transfection system. Plasmids were sterile-filtered through a Corning 0.22 um PES bottle-top filter by first wetting membrane with media from the bottle labeled “DNA media”, adding appropriate amount of pDNA to bottle-top, turning on vacuum for the filter, and finally flushing residual DNA on filter with remaining media from the “DNA media” bottle. Once “TR media” and “DNA media” solutions were prepared, mixes were combined into a separate vessel and inverted to begin the complexation process. Transfection mix was then left to incubate for 30 min at room temperature when using FectoVIR-AAV. Once time had elapsed, transfection mix was added to culture medium at a 10% final culture volume fraction (e.g., 25 mL transfection mix added to 225 mL culture) and grown at 37° C. for 72 hr.

At time of harvest, Benzonase was mixed with Expi293 media, using 100 uL Benzonase (approximately 250 U/uL) and 2.5 mL media per reactor for 100 U of Benzonase per 1 mL of culture volume. Bioreactor culture was incubated at 37° C. for 15 minutes. A 10× lysis buffer (10% v/v Tween 20, 500 mM Tris-HCl pH 8.0, 20 mM MgCl2, Milli-Q water) was made and 25 mL (10% culture volume) was added to each bioreactor, followed by incubation at 37° C. for 90 minutes. Next, 25 mL of sterile-filtered 5M NaCl was added to each flask (to reach a target concentration of 0.5 M NaCl) and incubated at 37° C. for 30 minutes. Lysed cultures were then spun for 10 minutes at 3500×g. Supernatants were filtered through a 0.22 um Corning sterile filter and sampled for crude lysate analysis.

Figure 22:
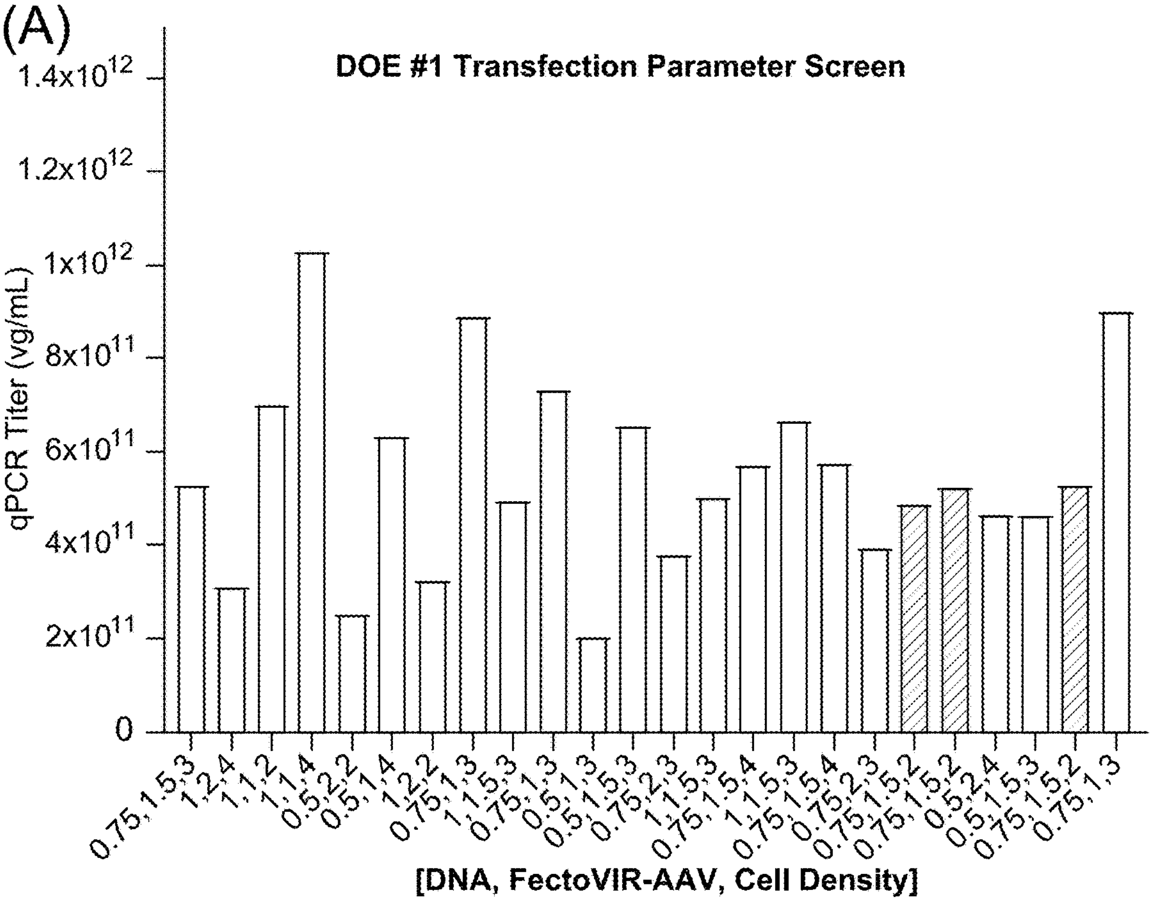
FIG. 22 depicts a first round screening DOE analysis of various transfection conditions to determine which combination could produce maximal viral titer at minimal cost. Conditions tested were plasmid DNA amount, FectoVir-AAV amount, and HEK293F cell density. (A) Measurement of viral titer for indicated conditions using qPCR. (B) Analysis of viral titer as a predictive model from DOE results. (C) Comparison of predictions for viral titer and cost for various conditions. (D) Graphical representation of optimization of indicated conditions.
Figure 22:
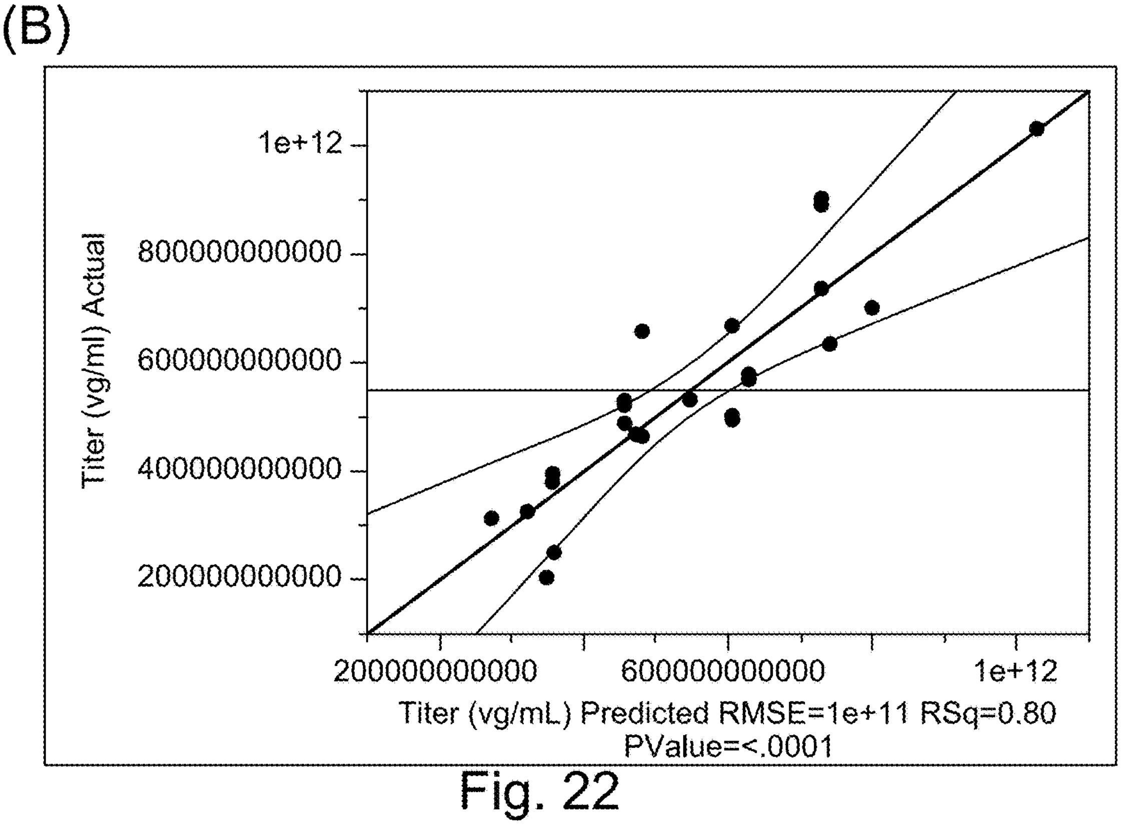
Figure 22:
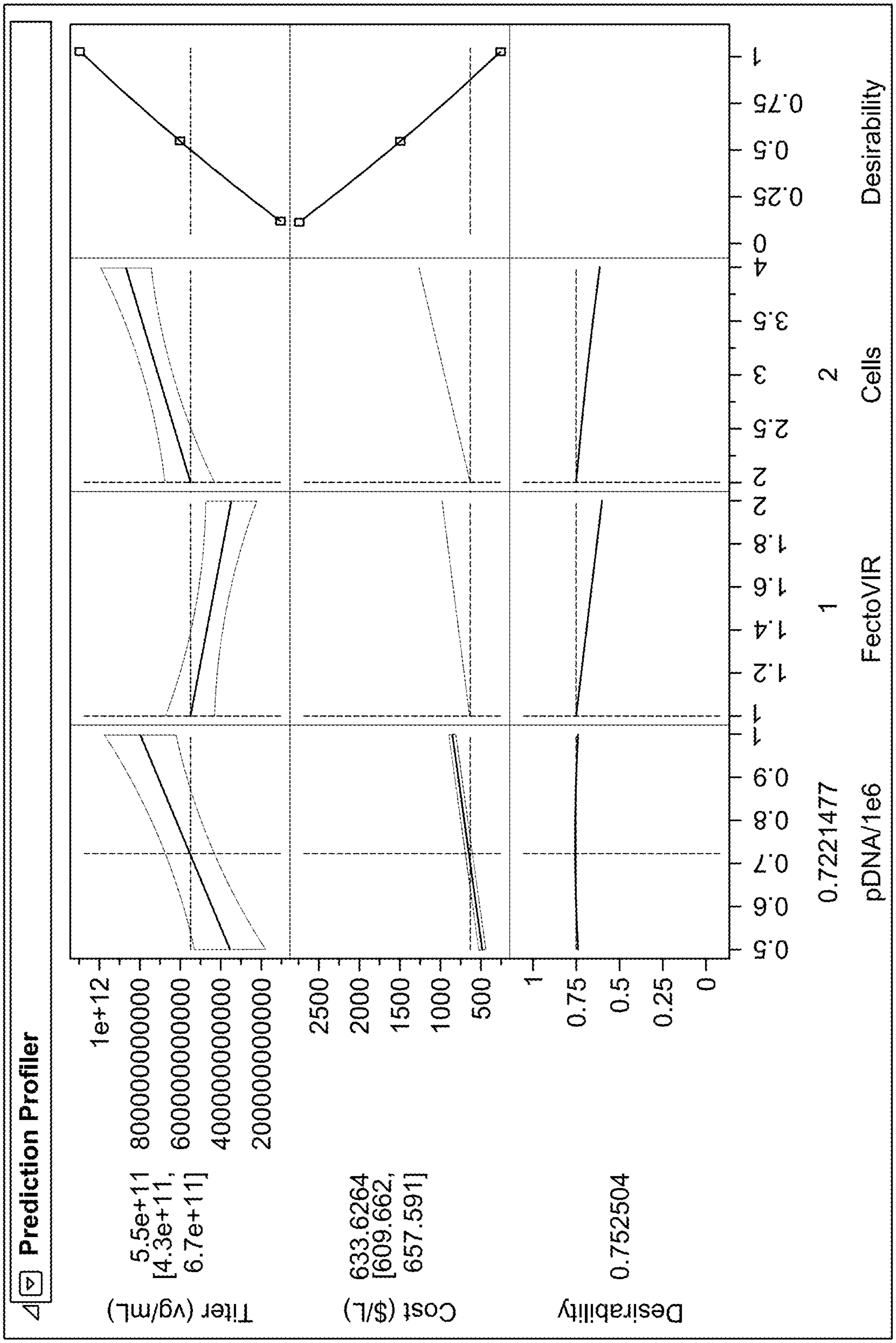
Figure 22:
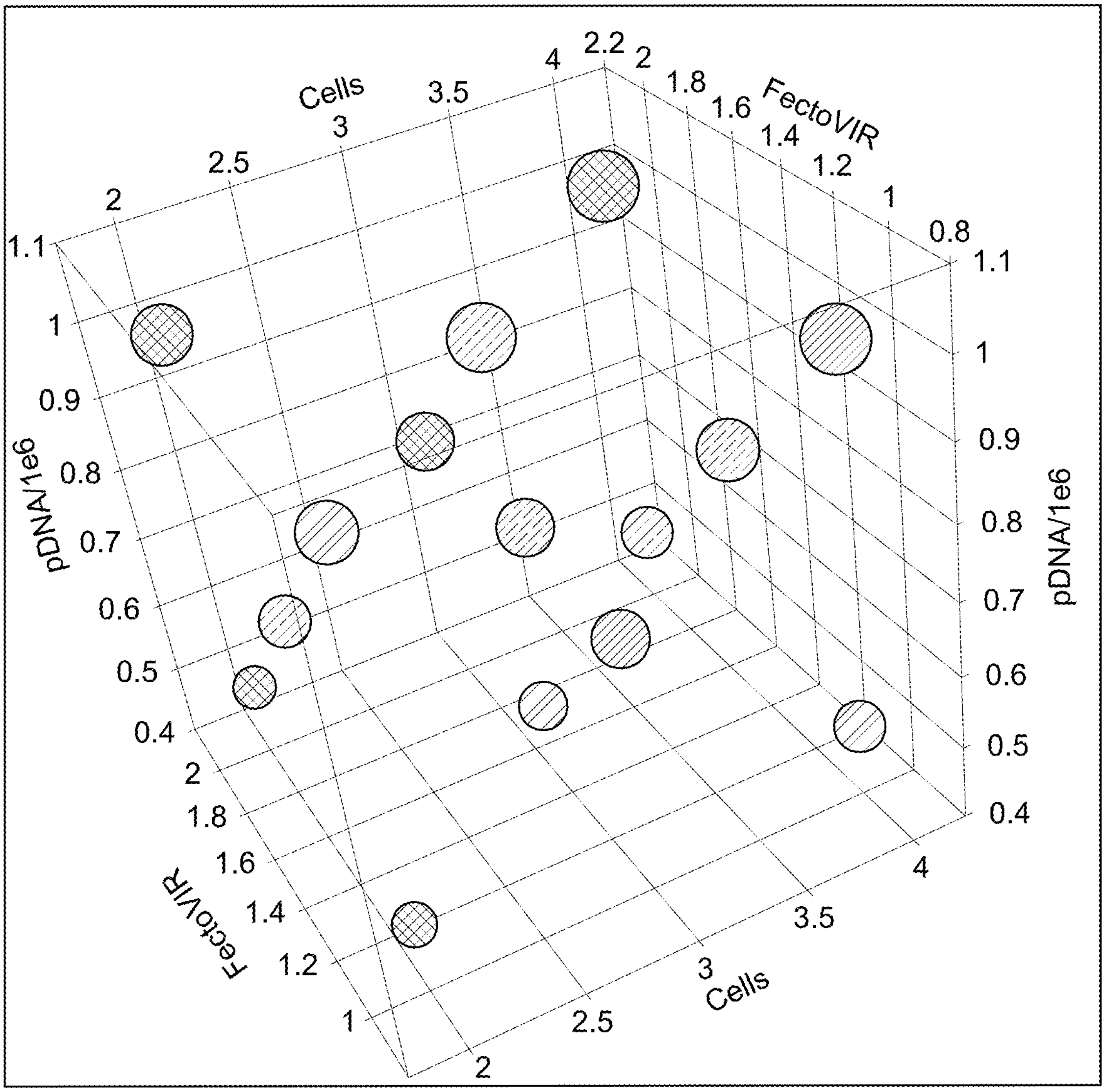
Figure 23:
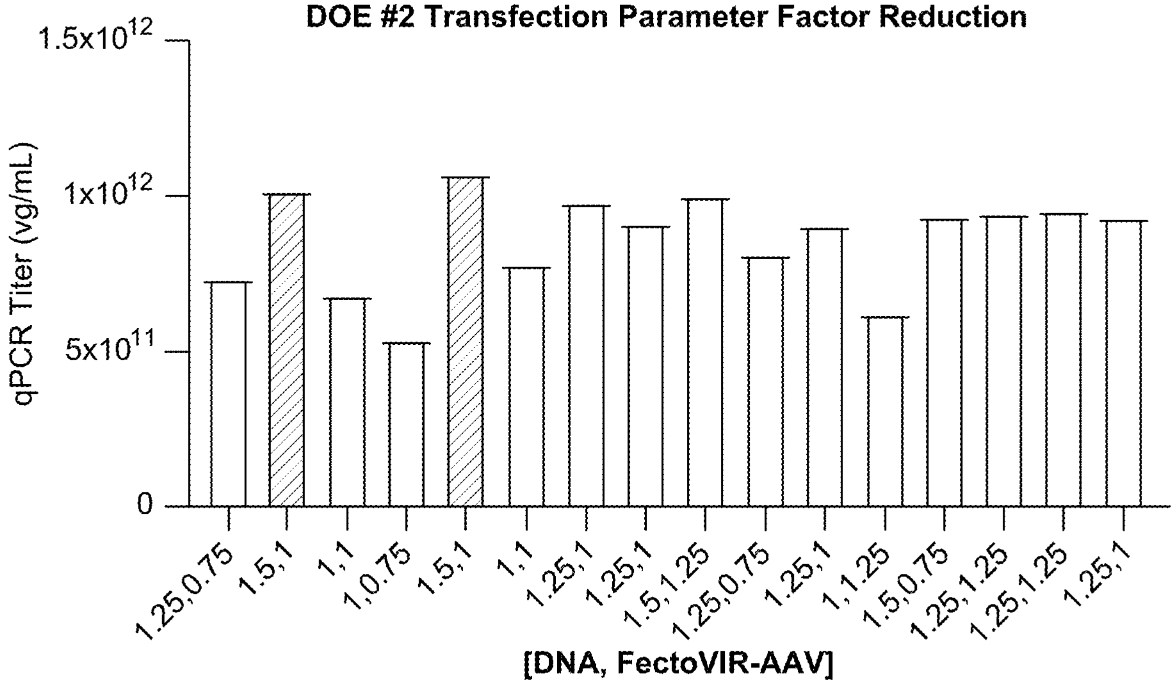
FIG. 23 depicts a secondary optimization DOE analysis of various transfection conditions to determine which combination could produce maximal viral titer at minimal cost. Conditions tested were plasmid DNA amount and FectoVir-AAV amount. (A) Measurement of viral titer for indicated conditions using qPCR. (B) Analysis of viral titer as a predictive model from second DOE. (C) Comparison of predictions for viral titer for various conditions. (D) Graphical representation of optimization of indicated conditions.
Figure 23:
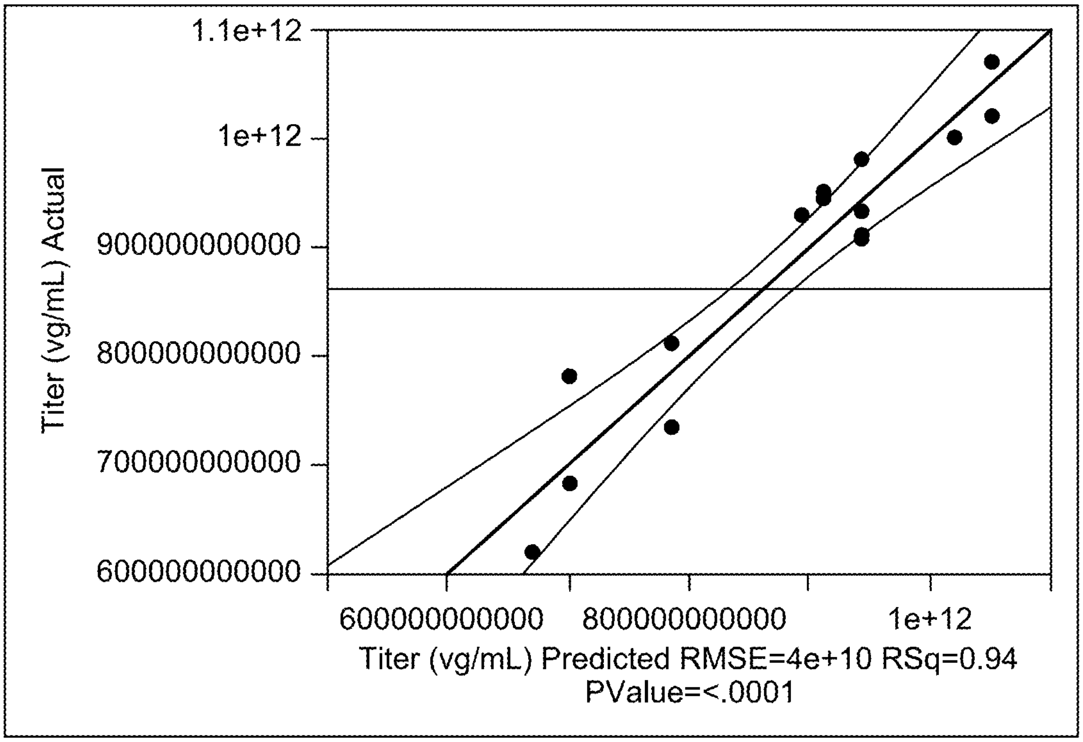
Figure 23:
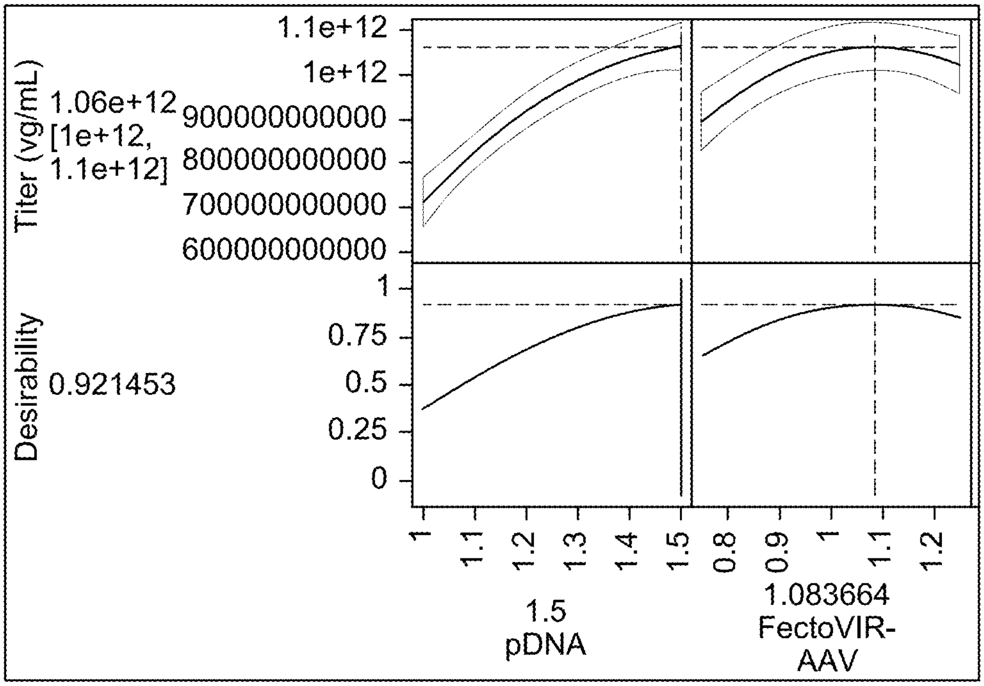
Figure 23:
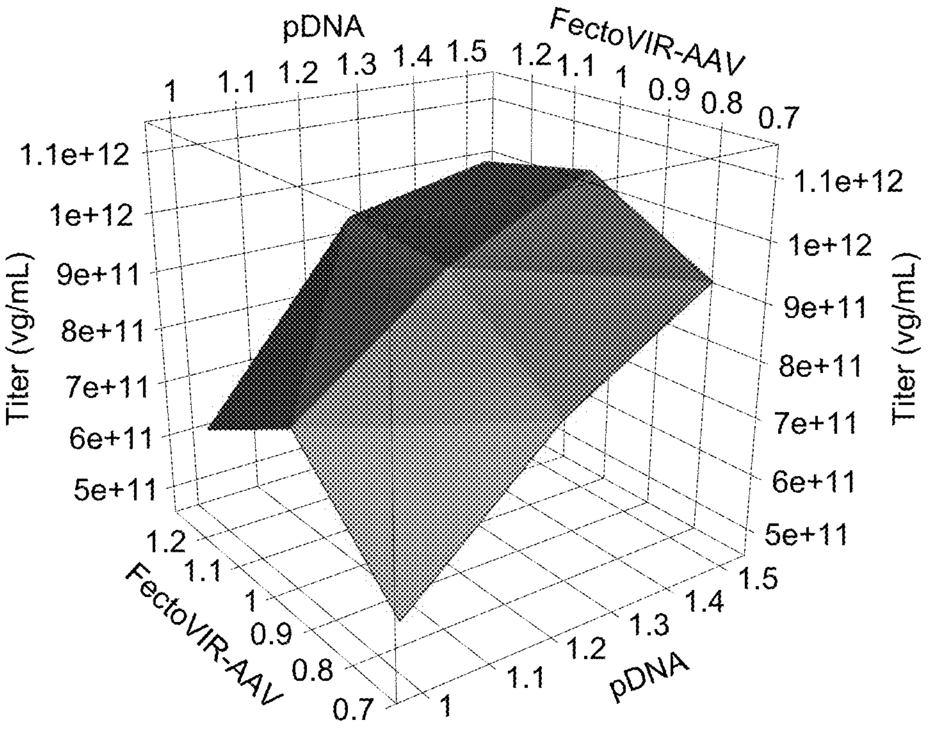

Various combinations of transfection conditions (e.g., total plasmid DNA amount, transfection reagent amount, cell density) were tested to determine which conditions could produce improved viral titer yields. A first round of testing was conducted through analysis of all three of total plasmid DNA amount, FectoVir-AAV amount, and cell density in the levels outlined in Table 11A. Analysis was conducted to determine optimal conditions to maximize viral titer while minimizing total cost (FIG. 22). Further testing optimized combinations of total plasmid DNA amount and FectoVir-AAV amount, as outlined in Table 11B. Second round analysis again focused on maximizing viral titer while not exceeding cost threshold established in first-round analysis (FIG. 23).

Among other things, the present example demonstrates that transfection conditions may be optimized in a two-plasmid system to provide increased viral titer yields as compared to a reference (e.g., alternative transfection conditions, three-plasmid system) while minimizing cost.

TABLE 11A

Transfection conditions tested in first round of analysis (FIG. 22)

| Plasmid DNA (mg/1E6 cells/mL) | FectoVir-AAV (w/w transfection reagent:plasmid DNA) | Cell Density ($10^6$ cells/mL) |
|---|---|---|
| 0.75 | 1.5 | 3 |
| 1 | 2 | 4 |
| 1 | 1 | 2 |
| 1 | 1 | 4 |
| 0.5 | 2 | 2 |
| 0.5 | 1 | 4 |
| 1 | 2 | 2 |
| 0.75 | 1 | 3 |
| 1 | 1.5 | 3 |
| 0.75 | 1 | 3 |
| 0.5 | 1 | 2 |
| 0.5 | 1.5 | 3 |
| 0.75 | 2 | 3 |
| 1 | 1.5 | 3 |
| 0.75 | 1.5 | 4 |
| 1 | 1.5 | 3 |
| 0.75 | 1.5 | 4 |
| 0.75 | 2 | 3 |
| 0.75 | 1.5 | 2 |

TABLE 11A-continued

| Transfection conditions tested in first round of analysis (FIG. 22) | | |
|---|---|---|
| Plasmid DNA (mg/1E6 cells/mL) | FectoVir-AAV (w/w transfection reagent:plasmid DNA) | Cell Density ($10^6$ cells/mL) |
| 0.75 | 1.5 | 2 |
| 0.5 | 2 | 4 |
| 0.5 | 1.5 | 3 |
| 0.75 | 1.5 | 2 |
| 0.75 | 1 | 3 |

TABLE 11B

| Transfection conditions tested in second round of analysis (FIG. 23) | |
|---|---|
| Plasmid DNA (mg/L) | FectoVir-AAV (w/w transfection reagent:plasmid DNA) |
| 1.25 | 0.75 |
| 1.5 | 1 |
| 1 | 1 |
| 1 | 0.75 |
| 1.5 | 1 |
| 1 | 1 |
| 1.25 | 1 |
| 1.25 | 1 |
| 1.5 | 1.25 |
| 1.25 | 0.75 |
| 1.25 | 1 |
| 1 | 1.25 |
| 1.5 | 0.75 |
| 1.25 | 1.25 |
| 1.25 | 1.25 |
| 1.25 | 1 |
| 1.5 | 1.5 |
| 1.5 | 1.5 |

Example 14: Two-Plasmid System with FectoVIR-AAV can Increase Volumetric Yield for a Variety AAV Serotypes The present example demonstrates that, among other things, various AAV serotypes may be employed in two-plasmid systems with FectoVIR-AAV to produce surprisingly high viral yields.

HEK293F cells were expanded in 500-mL shake flasks for use in vector production. Cell counts were first recorded on the ViCell XR Cell Counter to ensure VCDs were between 2.0e6-2.6e6 cells/mL and Viabilities were above 95% at the time of transfection. Transfection mixes were then prepared by first pre-weighing Expi293 media in two separate vessels, "DNA media" and "transfection reagent media", each containing equal volume requirements from transfection mix calculations. Transfection reagent was then added to the bottle labeled "transfection reagent media" and set aside. The mass fractions of the pHelper, pRep/Cap, and pGOI were 0.43, 0.35, and 0.22, respectively for the 3-plasmid transfection system. The mass fractions of the Rep/Helper plasmid and Payload/Cap plasmid were 0.60 and 0.40, respectively (1.5:1 plasmid ratio) for the 2-plasmid transfection system. Plasmids were sterile-filtered through a Corning 0.22 um PES bottle-top filter by first wetting the membrane with media from the bottle labeled "DNA media", adding appropriate amount of pDNA to the bottle-top, turning on the vacuum for the filter, and finally flushing the residual DNA on the filter with the remaining media from the "DNA media" bottle. Once the transfection reagent/media and DNA/media solutions were prepared, at a 1:1 volumetric ratio, both mixes were combined into a separate vessel and inverted 10 times to begin the complexation process. The transfection mix was then kept still in room temperature for 15 min when using PEIMAX, and 30 min when using FectoVIR-AAV. Once the time elapsed, the transfection mix was added to the culture medium at a 10% culture volume fraction (e.g. 20 mL transfection mix added to 200 mL culture) and grown at 37° C. for 72 hr, unless otherwise stated.

TABLE 12A

| Conditions to evaluate transfection systems and transfection reagents for different serotypes. | | | |
|---|---|---|---|
| Condition | Vector Description | Transfection System | Transfection Reagent |
| 1 | Capsid/LSP-hFIX | 3-plasmid | PEIMAX |
| 2 | Capsid/LSP-hFIX | 2-plasmid | PEIMAX |
| 3 | Capsid/LSP-hFIX | 3-plasmid | FectoVIR-AAV |
| 4 | Capsid/LSP-hFIX | 2-plasmid | FectoVIR-AAV |

TABLE 12B

| Transfection parameters for different transfection reagents. | | |
|---|---|---|
| Parameter | PEIMAX | FectoVIR-AAV |
| Total DNA per 1e6 cells (ug) | 0.75 | 0.75 |
| TR:DNA w/w ratio | 1.5 | 1.0 |
| Transfection Mix Percent of Culture Volume (%) | 10 | 10 |
| Complexation Time (min) | 15 | 30 |

Cells were harvested 72 hr after transfection of cultures. 5 mL of culture was transferred to a 15 mL centrifuge tube and 50 uL of a 10 units/uL benzonase in Expi293 media solution was added to the tube and shaken in the incubator horizontally at 37° C. and 145 RPM for 15 min. 500 uL of lysis buffer (500 mM Tris pH 8, 20 mM $MgCl_2$, 10% polysorbate-20) was then added to the tube and incubated under the same conditions for 90 min. Finally, 500 uL of 5M NaCl was added to the tubes and incubated for 30 min under the same conditions. After the NaCl incubation, cell lysate was spun down in a centrifuge at 3200 g to clarify the harvested culture media. 1 mL of the supernatant, which contained the AAV particles, was collected in 1.5 mL Eppendorf tubes and stored at −80° C. until preparation for sample analysis.

In some embodiments, plasmids tested in a two-plasmid system comprise an AAV rep sequence and relevant sequences from a helper virus ("Rep/Helper Plasmid") or an AAV cap sequence and a payload ("Payload/Cap Plasmid"). In some embodiments, plasmids tested in a 3-plasmid system comprise separate plasmids, each encoding one of: 1) an AAV rep and AAV cap sequence, 2) relevant sequence from a helper virus, and 3) a payload. A human Factor IX gene (hFIX) flanked by albumin homology arm sequences was tested as the payload in experiments outlined herein. The plasmid ratio was Rep/Helper:Payload/Cap=1.5:1 for the 2-plasmid system and Helper:Repcap:Payload=0.43:0.35:0.22 for the 3-plasmid system.

Figure 24:
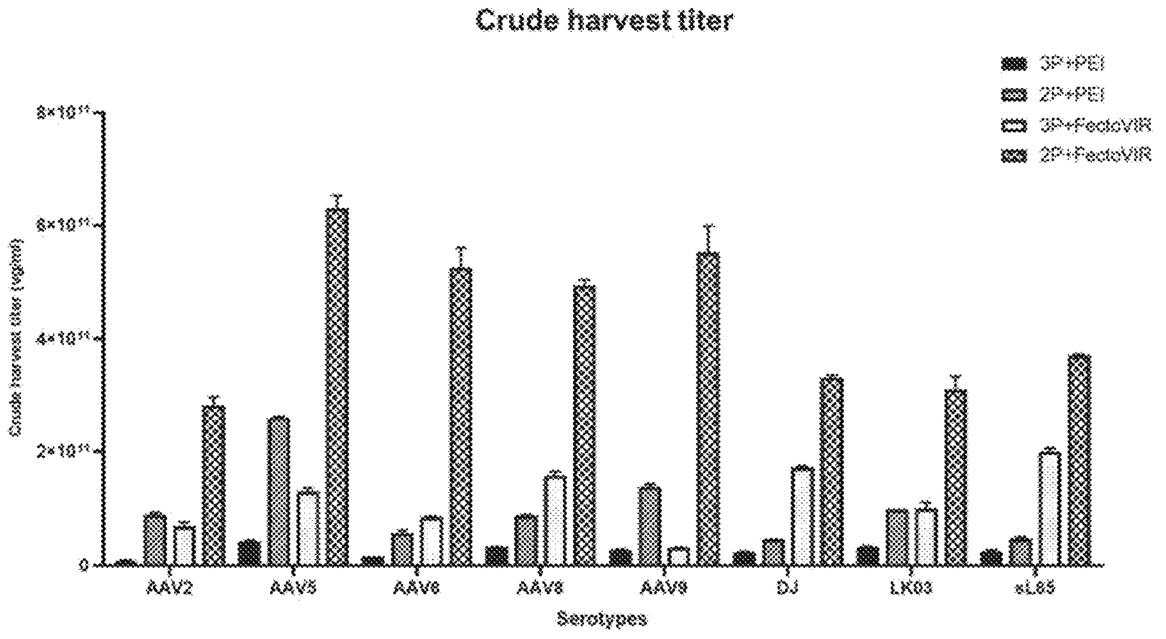
FIG. 24 depicts viral titer levels (vg/mL) in crude lysate produced by HEK293F cells transfected with a three-plasmid system and PEIMAX (3P+PEI MAX), a two-plasmid system with PEIMAX (2P+PEI MAX), a three-plasmid system and FectoVir-AAV (3P+FectoVir-AAV), and a two-plasmid system with FectoVIR-AAV (2P+FectoVIR-AAV). (B) depicts relative fold-change in viral vector yields relative to a three-plasmid system and PEIMAX (3P+PEI MAX). The cap gene encodes a variety of natural and chimeric AAV serotypes (AAV2, AAV5, AAV6, AAV8, AAV9, DJ, LK03, and sL65) and the gene of interest (GOI) is human Factor IX under the control of a liver-specific promoter (LSP-hFIX).
Figure 24:
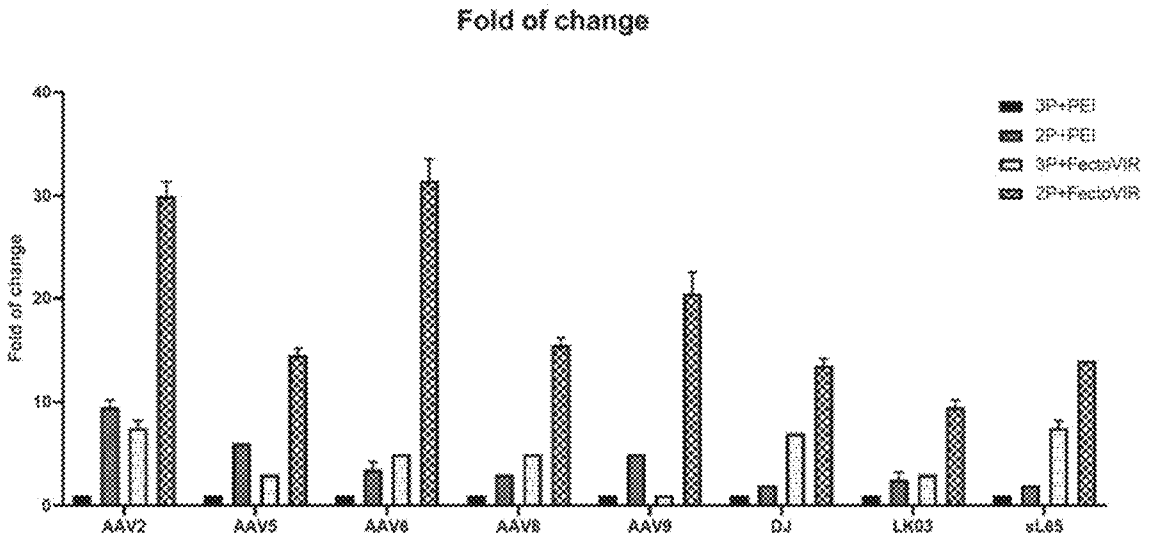

Among other things, the present disclosure demonstrates that certain transfection reagents for a two-plasmid transfection system can produce surprising and unexpected improvements in volumetric yields (e.g., as compared to a three-plasmid, "triple transfection" system) for natural serotypes. As demonstrated in FIG. 24, the FectoVir-AAV transfection system combined with the two-plasmid system provides improved yields (e.g., as compared to a three-plasmid, "triple transfection" system combined with FectoVir).

Example 15: Two-Plasmid System can Provide High Titers Independently of the Adenovirus Helper Plasmid Design The present example demonstrates that, among other things, several combinations of the genetic elements in a two-plasmid system may produce comparable or higher yields than a 3-plasmid system.

HEK293F cells were expanded in 125-mL shake flasks for use in vector production. Cell counts were first recorded on the ViCell XR Cell Counter to ensure VCDs were between 2.0e6-2.6e6 cells/mL and viabilities were above 95% at the time of transfection. Transfection mixes were then prepared by first pre-weighing Expi293 media in two separate vessels, "DNA media" and "transfection reagent media", each containing equal volume requirements from transfection mix calculations. Transfection reagent was then added to the bottle labeled "transfection reagent media" and set aside. The mass fractions of the pHelper, pRep/Cap, and pGOI were 0.43, 0.35, and 0.22, respectively for the 3-plasmid transfection system. The mass fractions of the Rep/Helper plasmid and Payload/Cap plasmid were 0.60 and 0.40, respectively (1.5:1 plasmid ratio) for the 2-plasmid transfection system. Plasmids were sterile-filtered through a Corning 0.22 um PES bottle-top filter by first wetting the membrane with media from the bottle labeled "DNA media", adding appropriate amount of pDNA to the bottle-top, turning on the vacuum for the filter, and finally flushing the residual DNA on the filter with the remaining media from the "DNA media" bottle. Once the transfection reagent/media and DNA/media solutions were prepared, at a 1:1 volumetric ratio, both mixes were combined into a separate vessel and inverted 10 times to begin the complexation process. The transfection mix was then kept still in room temperature for 30 min using FectoVIR-AAV. Once the time elapsed, the transfection mix was added to the culture medium at a 10% culture volume fraction (e.g. 20 mL transfection mix added to 200 mL culture) and grown at 37° C. for 72 hr, unless otherwise stated.

Cells were harvested 72 hr after transfection of cultures. 5 mL of culture was transferred to a 15 mL centrifuge tube and 50 uL of a 10 units/uL benzonase in Expi293 media solution was added to the tube and shaken in the incubator horizontally at 37° C. and 145 RPM for 15 min. 500 uL of lysis buffer (500 mM Tris pH 8, 20 mM MgCl2, 10% polysorbate-20) was then added to the tube and incubated under the same conditions for 90 min. Finally, 500 uL of 5M NaCl was added to the tubes and incubated for 30 min under the same conditions. After the NaCl incubation, cell lysate was spun down in a centrifuge at 3200 g to clarify the harvested culture media. 1 mL of the supernatant, which contained the AAV particles, was collected in 1.5 mL Eppendorf tubes and stored at −80° C. until preparation for sample analysis. Samples were analyzed by ddPCR to determine vector genome titers.

TABLE 13A

Conditions to evaluate transfection systems with different helper genes.

| Condition | Helper plasmid | Vector Description | Transfection System | Transfection Reagent |
|---|---|---|---|---|
| 1 | Helper | LK03/LSP-hFIX | 3-plasmid | FectoVIR-AAV |
| 2 | XX6 | LK03/LSP-hFIX | 3-plasmid | FectoVIR-AAV |
| 3 | Helper-Rep | LK03/LSP-hFIX | 2-plasmid without intron | FectoVIR-AAV |
| 4 | XX6-Rep | LK03/LSP-hFIX | 2-plasmid without intron | FectoVIR-AAV |
| 5 | Helper-Rep-intron | LK03/LSP-hFIX | 2-plasmid with intron | FectoVIR-AAV |
| 6 | XX6-Rep-intron | LK03/LSP-hFIX | 2-plasmid with intron | FectoVIR-AAV |

TABLE 13B

Transfection parameters for transfection reagent.

| Parameter | FectoVIR-AAV |
|---|---|
| Total DNA per 1e6 cells (ug) | 0.75 |
| TR:DNA w/w ratio | 1.0 |
| Transfection Mix Percent of Culture Volume (%) | 10 |
| Complexation Time (min) | 30 |

In some embodiments, plasmids tested in a two-plasmid system comprise an AAV rep sequence and relevant sequences from a helper virus ("Rep/Helper Plasmid") or an AAV cap sequence and a payload ("Payload/Cap Plasmid"). In some embodiments, plasmids tested in a 3-plasmid system comprise separate plasmids, each encoding one of: 1) an AAV rep and AAV cap sequence, 2) relevant sequence from a helper virus, and 3) a payload. A human Factor IX gene (hFIX) flanked by albumin homology arm sequences was tested as the payload in experiments outlined herein. The plasmid ratio was Rep/Helper: Payload/Cap=1.5:1 for the 2-plasmid system and Helper:Repcap:Payload=0.43:0.35:0.22 for the 3-plasmid system.

Figure 25:
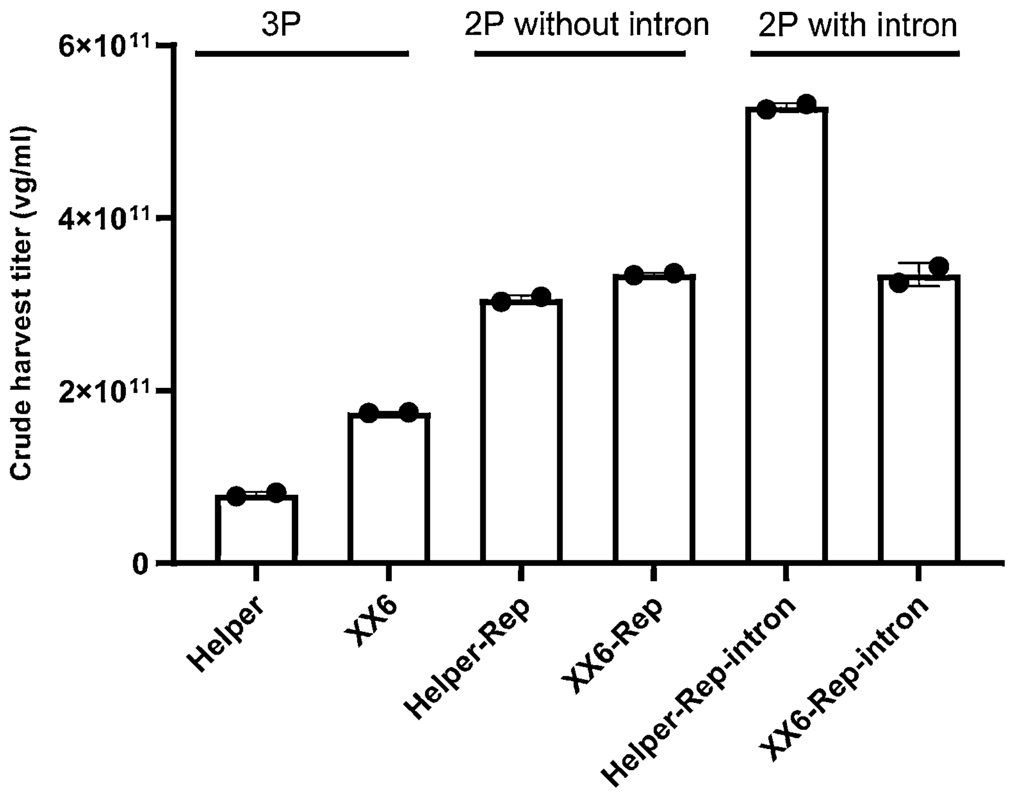
FIG. 25 depicts viral vector yields (vg/mL) for three-plasmid (3P) and two-plasmid (2P) systems for cell transfection with different plasmid design and number of adenovirus genes.
Figure 26:
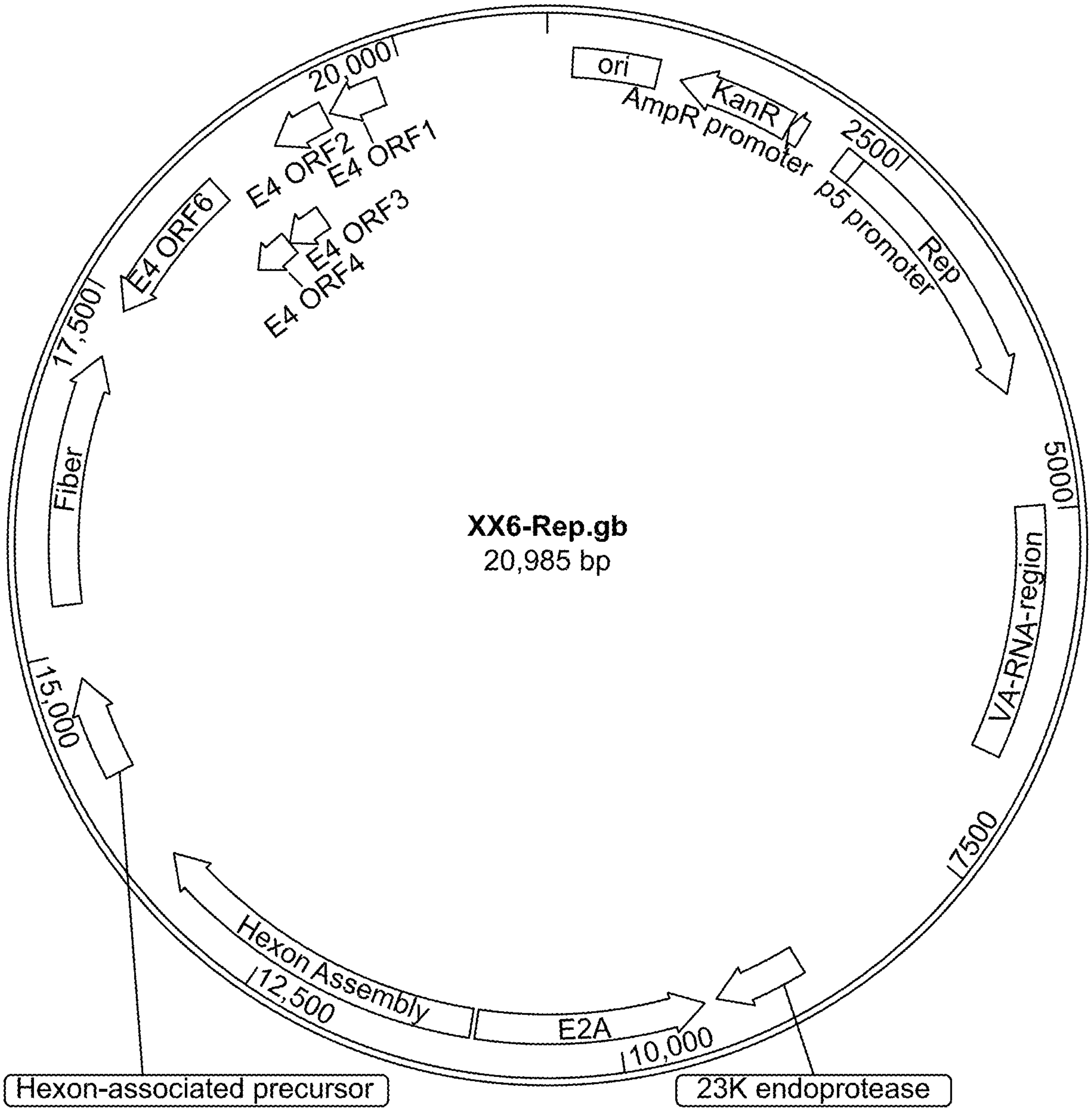
FIG. 26 depicts a schematic map of a Helper (pXX6)-Rep plasmid for AAV production using a 2-plasmid system. Plasmids may contain several Adenovirus genes, like E2A DNA Binding Protein (DBP) gene, E4 Open Reading Frame (ORF) 2, ORF3, ORF4 and ORF6/7. In addition, plasmids may contain an AAV rep gene downstream of a p5 promoter. Plasmids may also contain elements necessary for bacterial culture like the colE1 origin of replication (ori), and antibiotic resistance gene (e.g. kanamycin).
Figure 27:
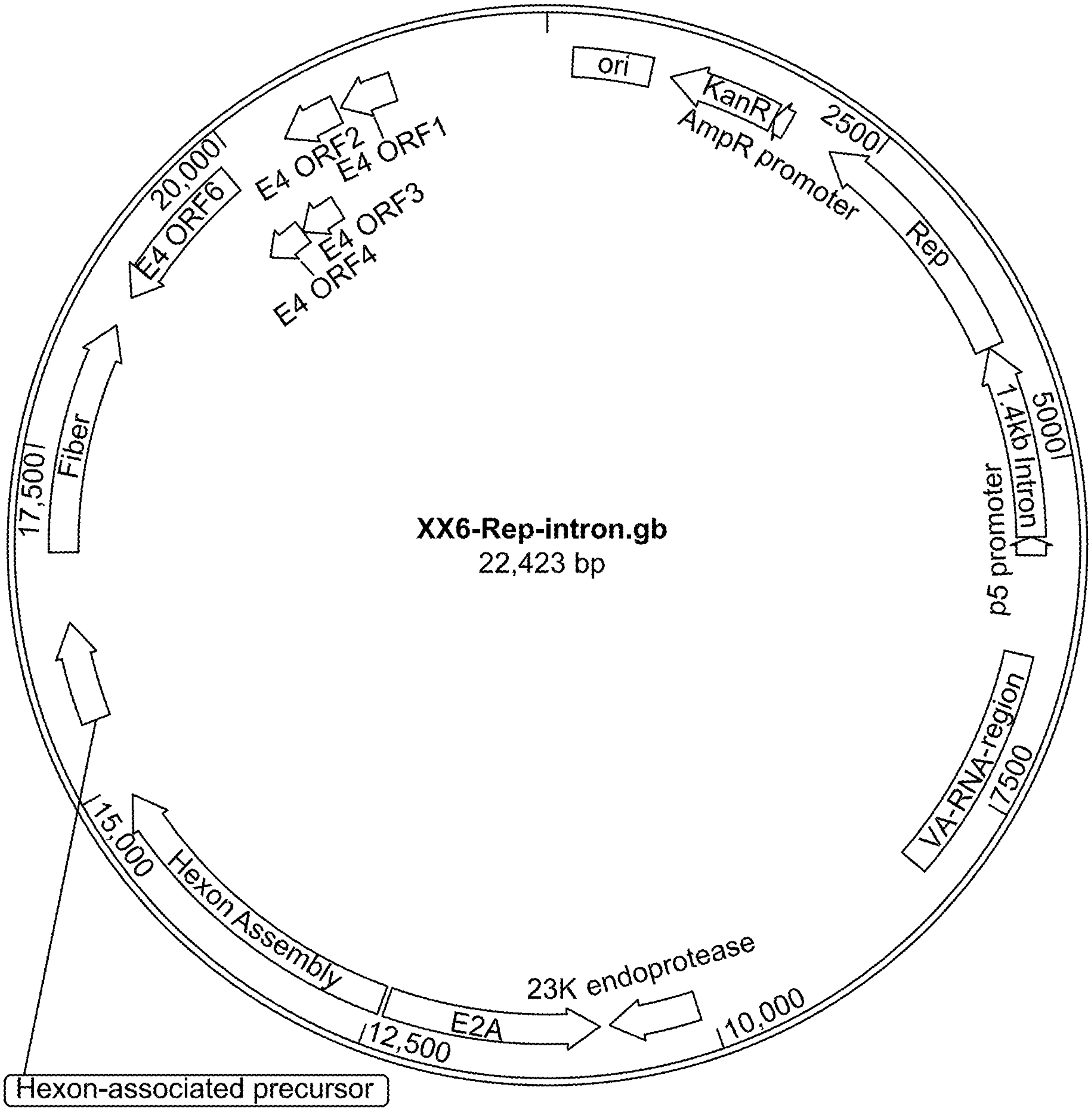
FIG. 27 depicts a schematic map of a Helper (pXX6)-Rep-intron plasmid for AAV production using a 2-plasmid system. Plasmids may contain several Adenovirus genes, like E2A DNA Binding Protein (DBP) gene, E4 Open Reading Frame (ORF) 2, ORF3, ORF4 and ORF6/7. In addition, plasmids may contain an AAV rep gene downstream of a p5 promoter and an intron. An intron can be selected from a variety of sizes, e.g., 1.4 kb in the schematic. Plasmids may also contain elements necessary for bacterial culture like the colE1 origin of replication (ori), and antibiotic resistance gene (e.g. kanamycin).
Figure 28:
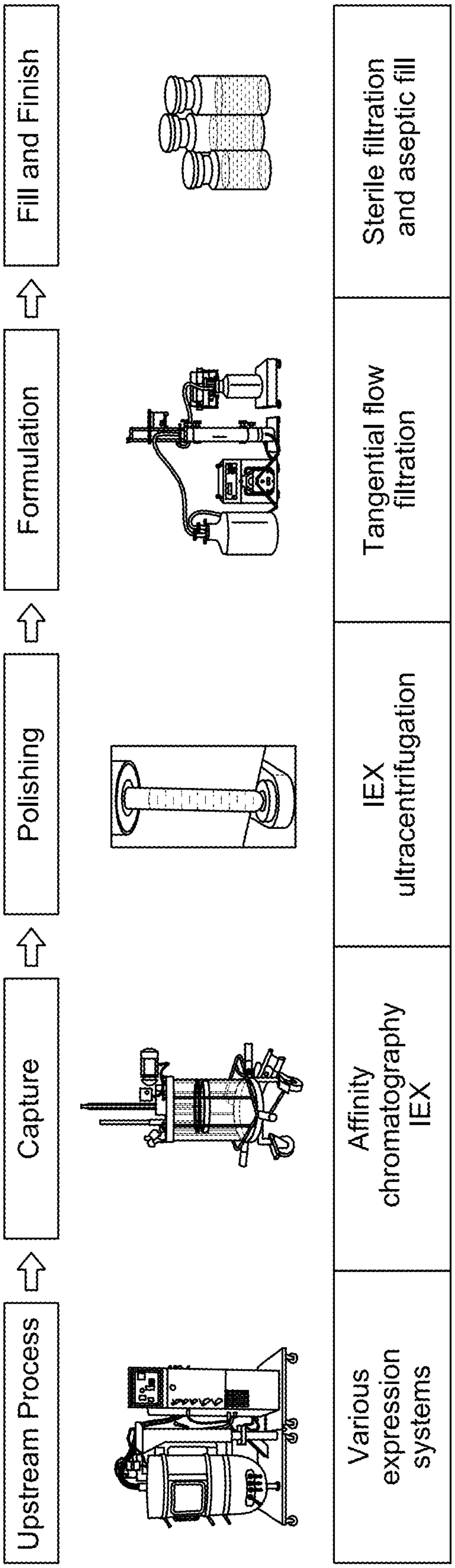
FIG. 28 depicts an exemplary set of steps for production of viral vectors, including upstream processes (e.g., use of various expression systems), capture steps (e.g., affinity chromatography, IEX), polishing steps (e.g., IEX, ultracentrifugation), formulation steps (e.g., tangential flow filtration), and/or fill and finish steps (e.g., sterile filtration and aseptic fill). In some embodiments, compositions and methods disclosed herein are intended to improve one or more properties and/or characteristics of viral (e.g., AAV) production (including, e.g., one or more of viral vector yield, packaging efficiency, and/or replication-competent AAV levels) through modification of one or more upstream processing steps.

Among other things, the present disclosure demonstrates that the AAV titers at culture harvest are higher when cells are transfected with a two-plasmid system compared to a 3-plasmid system. As demonstrated in FIG. 25, the titers are increased independently of the design of the plasmid bearing the adenovirus helper genes and the AAV rep gene.

Example 17: Two-Plasmid System Allows Production of AAV Vectors with Various ITRs The present example demonstrates that, among other things, both single stranded AAV vectors and double stranded AAV vectors may be produced at high levels using a two-plasmid system. In some embodiments, various ITR sequences may be used to flank a payload in a Payload/Cap plasmid in a two-plasmid system.

Inverted terminal repeats (ITRs) are AAV sequence elements required in cis in the vector genome sequence to allow vector genome replication and packaging in AAV capsids (Samulski et al., 1987; McLaughlin et al. 1988). As part of the natural replication process of AAV, ITR sequences and their reverse complementary sequences are alternatively associated to the positive strand and negative strand of the AAV genome, a feature which is named flip and flop orientation (reviewed in Wilmott et al., 2019). The wild type ITR sequence of AAV2, which is commonly used in AAV vectors, is shown in Table 14A in both flip and flop orientations.

As ITR sequences are generally GC rich and display hairpin-like secondary structure, they can be difficult to maintain in plasmids in the process of cloning and generating AAV vectors. ITRs may generate instability and may recombine and/or suffer from partial deletions during plasmid production in *E. coli*. As a result, several different ITR variants may be observed experimentally. For example, a 22 base pair deletion in the B loop, a 22 base pair deletion in the C loop, a 15 base pair deletion in the A region, and a 40 base pair deletion in the D region of AAV2 ITRs are shown in Table 14A. The B and C loop deletion and A region deletion ITR variants may retain full functionality to replicate and package a vector genome within a capsid. However, the D region deletion ITR variant results in loss of packaging signal and terminal resolution site (trs). The D region deletion ITR variant has been described as a method to generate self-complementary AAV (scAAV), also known as double-stranded AAV (dsAAV) (Wang et al, 2003).

HEK293F cells are expanded in 125-mL shake flasks. Cell counts are first recorded on the ViCell XR Cell Counter to ensure VCDs were between 2.0e6-2.6e6 cells/mL and Viabilities were above 95% at the time of transfection. Transfection mixes are then prepared by first pre-weighing Expi293 media in two separate vessels, "DNA media" and "transfection reagent media", each containing equal volume requirements from transfection mix calculations. Transfection reagent is added to the bottle labeled "transfection reagent media" and set aside. The mass fractions of the Rep/Helper plasmid and Payload/Cap plasmid are 0.60 and 0.40, respectively (1.5:1 plasmid ratio). Plasmids are sterile-filtered through a Corning 0.22 um PES bottle-top filter by first wetting the membrane with media from the bottle labeled "DNA media", adding appropriate amount of pDNA to the bottle-top, turning on the vacuum for the filter, and finally flushing the residual DNA on the filter with the remaining media from the "DNA media" bottle. Transfection reagent/media and DNA/media solutions are prepared, both mixes are combined at a 1:1 volumetric ratio into a separate vessel and are inverted 10 times to begin the complexation process. The transfection mix is then kept still in room temperature for 30 min using FectoVIR-AAV. Once the time elapsed, the transfection mix is added to the culture medium at a 10% culture volume fraction (e.g. 20 mL transfection mix added to 200 mL culture) and grown at 37° C. for 72 hr.

Cells are harvested 72 hr after transfection of cultures. 5 mL of culture are transferred to a 15 mL centrifuge tube and 50 uL of a 10 units/uL benzonase in Expi293 media solution are added to the tube and shaken in the incubator horizontally at 37° C. and 145 RPM for 15 min. 500 uL of lysis buffer (500 mM Tris pH 8, 20 mM MgCl2, 10% polysorbate-20) are then added to the tube and incubated under the same conditions for 90 min. Finally, 500 uL of 5M NaCl are added to the tubes and incubated for 30 min under the same conditions. After the NaCl incubation, cell lysate is spun down in a centrifuge at 3200 g to clarify the harvested culture media. 1 mL of the supernatant, which contains the AAV particles, is collected in 1.5 mL Eppendorf tubes and stored at −80° C. until preparation for sample analysis. Samples are analyzed by ddPCR to determine vector genome titers. Vector genomes can be analyzed on an alkaline agarose gel to confirm the single stranded and double stranded vector genome feature.

Example 16: Two-Plasmid System May Provide High Titers of Natural and Chimeric AAV Serotype The present example demonstrates that, among other things, a two-plasmid system may produce increased AAV viral yields as compared to a three-plasmid system independent of the AAV serotype.

HEK293F cells are expanded for use in vector production. Cells are split to 2e6 cells/mL in 200 mL of Expi293 media in a 500 mL flask. Plasmid mixes for various transfection conditions are made and filtered through a 0.22 μM filter unit. A transfection reagent mix (e.g., PEI or FectoVIR-AAV) is prepared according to manufacturer's protocol. Plasmid and transfection reagent mixes are combined to produce a single transfection mix. 20 mL of transfection mix is added to 100 mL of HEK293F cells in a 500 mL flask and allowed to incubate at 37° C. for 72 hours.

In some embodiments, plasmids tested in a two-plasmid system comprise an AAV rep sequence and relevant sequences from a helper viruses ("Rep/Helper Plasmid") or an AAV cap sequence and a payload ("Payload/Cap Plasmid"). In some embodiments, plasmids tested in a three-plasmid system comprise separate plasmids, each encoding one of: 1) an AAV rep and AAV cap sequence, 2) relevant sequence from a helper virus, and 3) a payload. A human gene of interest sequence with flanking homology arms for mouse albumin ("mHA-FIX"), which is compatible with a GeneRide system, is tested as the payload in experiments. A variety of AAV cap genes encoding different AAV capsids are assessed within the Payload/Cap plasmid. In some embodiments, the AAV cap gene may encode a AAV1, AAV2, AAV3, AAV4, AAV5, AAV6, AAV7, AAV8, AAV9, AAV10, AAV11, AAVC11.01, AAVC11.02, AAVC11.03, AAVC11.04, AAVC11.05, AAVC11.06, AAVC11.07, AAVC11.08, AAVC11.09, AAVC11.10, AAVC11.11, AAVC11.12, AAVC11.13, AAVC11.14, AAVC11.15, AAVC11.16, AAVC11.17, AAVC11.18, AAVC11.19, AAV-DJ, AAV-LK03, AAV-LK19, AAVrh.74, AAVrh.10, AAVhu.37, AAVrh.K, AAVrh.39, AAV12, AAV 13, AAVrh.8, avian AAV, bovine AAV, canine AAV, equine AAV, primate AAV, non-primate AAV, ovine AAV, a hybrid AAV (e.g., an AAV comprising one more sequences of one AAV subtype and one or more sequences of a second subtype).

Among other things, the present disclosure demonstrates that a two-plasmid transfection system with FectoVIR-AAV may produce improvements in volumetric yields (e.g., as compared to a three-plasmid, "triple transfection" system) for different capsids with a payload that is useful in conventional gene therapy (e.g., human Factor IX).

TABLE 14A

Inverted terminal repeat (ITR) variants and their sequences (left end ITR in 5' to 3' orientation)

| Name | Sequence (5' to 3') | Size (bp) | SEQ ID NO |
|---|---|---|---|
| Wild type ITR, flip orientation | AGGAACCCCTAGTGATGGAGTTGGCCACTCCC TCTCTGCGCGCTCGCTCGCTCACTGAGGCCGC CCGGGCAAAGCCCGGGCGTCGGGCGACCTTT GGTCGCCCGGCCTCAGTGAGCGAGCGAGCGC GCAGAGAGGGAGTGGCCAA | 145 | 13 |
| Wild type ITR, flop orientation | AGGAACCCCTAGTGATGGAGTTGGCCACTCCC TCTCTGCGCGCTCGCTCGCTCACTGAGGCCGG GCGACCAAAGGTCGCCCGACGCCCGGGCTTT GCCCGGGCGGCCTCAGTGAGCGAGCGAGCGC GCAGAGAGGGAGTGGCCAA | 145 | 14 |
| B loop deleted ITR | AGGAACCCCTAGTGATGGAGTTGGCCACTCCC TCTCTGCGCGCTCGCTCGCTCACTGAGGCCGC CCGGGCTTTGCCCGGGCGGCCTCAGTGAGCG AGCGAGCGCGCAGAGAGGGAGTGGCCAA | 123 | 15 |
| C loop deleted ITR | AGGAACCCCTAGTGATGGAGTTGGCCACTCCC TCTCTGCGCGCTCGCTCGCTCACTGAGGCCGG GCGACCAAAGGTCGCCCGGCCTCAGTGAGCG AGCGAGCGCGCAGAGAGGGAGTGGCCAA | 123 | 16 |
| A region deleted ITR | AGGAACCCCTAGTGATGGAGTTGGCCACTCCC TCTCTGCGCGCTCGCTCGCTCACTGAGGCCGG GCGACCAAAGGTCGCCCGACGCCCGGGCTTT GCCCGGGCGGCCTCAGTGAGCGAGCGAGCGC GCAG | 130 | 17 |
| D region deleted ITR | CTGCGCGCTCGCTCGCTCACTGAGGCCGCCCG GGCAAAGCCCGGGCGTCGGGCGACCTTTGGT CGCCCGGCCTCAGTGAGCGAGCGAGCGCGCA GAGAGGGAGTG | 105 | 18 |

TABLE 14B

Exemplary ITR combinations in a Payload/Cap plasmid and the expected AAV vector features

| Left end ITR | Transgene | Right end ITR | Capsid | AAV Vector Description |
|---|---|---|---|---|
| Wild type | Factor IX | Wild type | AAV8 | Single stranded |
| Wild type | Factor IX | B loop deletion | AAV8 | Single stranded |
| Wild type | Factor IX | C loop deletion | AAV8 | Single stranded |
| Wild type | Factor IX | A region deletion | AAV8 | Single stranded |
| A region deletion | Factor IX | A region deletion | AAV8 | Single stranded |
| Wild type | Factor IX | D region deletion | AAV8 | Double stranded |

Among other things, the present disclosure demonstrates that a two-plasmid system may produce high levels of double stranded AAV vectors (e.g., self-complementary AAV (scAAV) vectors). In some embodiments, double stranded AAV vectors comprise a deletion in the D region in at least one ITR flanking a payload. In some embodiments, a two-plasmid system may produce high levels of double-stranded vectors outlined in Table 14B above. In some embodiments, a two-plasmid transfection system may produce comparable or higher yields of double-stranded AAV vectors (e.g., scAAV) as compared to a three-plasmid system.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

Exemplary Embodiments

Exemplary embodiments as described below are also within the scope of the present disclosure:

1. A plasmid comprising at least one of:
   (i) a polynucleotide sequence encoding an AAV cap gene;
   (ii) a polynucleotide sequence encoding an AAV rep gene;
   (iii) a polynucleotide sequence encoding a payload and flanking ITRs; and/or
   (iv) a polynucleotide sequence encoding one or more viral helper genes.
2. The plasmid of embodiment 1, further comprising a polynucleotide sequence encoding a promoter.
3. The plasmid of embodiment 1 or embodiment 2, wherein the promoter is or comprises a native p5 promoter, native p40 promoter, or a CMV promoter.
4. The plasmid of embodiment 1, further comprising a polyA sequence.
5. The plasmid of embodiment 1, further comprising an intron.
6. The plasmid of embodiment 5, wherein the intron is between a promoter and an AAV rep gene.
7. A composition comprising two of the plasmids of any of embodiments 1-6, a first plasmid and a second plasmid, wherein the first and second plasmids each include different elements (i)-(iv).

8. The composition of embodiment 7, wherein:
   (i) the first plasmid comprises a polynucleotide sequence encoding an AAV cap gene; and
   (ii) the second plasmid comprises a polynucleotide sequence encoding an AAV rep gene.
9. The composition of embodiment 7, wherein:
   (i) the first plasmid comprises a polynucleotide sequence encoding a payload and flanking ITRs; and
   (ii) the second plasmid comprises a polynucleotide sequence encoding one or more viral helper genes.
10. The composition of embodiment 8, wherein:
   (i) the first plasmid further comprises a polynucleotide sequence encoding a payload and flanking ITRs; and
   (ii) the second plasmid further comprises a polynucleotide sequence encoding one or more viral helper genes.
11. The composition of embodiment 8, wherein:
   (i) the first plasmid further comprises a polynucleotide sequence encoding one or more viral helper genes; and
   (ii) the second plasmid further comprises a polynucleotide sequence encoding a payload and flanking ITRs.
12. The composition of any one of embodiments 7-11, wherein the polynucleotide sequence encoding a payload comprises one or more of:
   (i) a polynucleotide encoding one or more enhancer sequences;
   (ii) a polynucleotide encoding one or more promoter sequences;
   (iii) a polynucleotide encoding one or more intron sequences;
   (iv) a polynucleotide encoding a gene; and
   (v) a polynucleotide comprising a polyA sequence.
13. The composition of any one of embodiments 7-11, wherein the polynucleotide sequence encoding a payload comprises:
   (i) a polynucleotide comprising a first nucleic acid sequence and a second nucleic acid sequence, wherein the first nucleic acid sequence comprises at least one gene and the second nucleic acid sequence is positioned 5' or 3' to the first nucleic acid sequence and promotes the production of two independent gene products upon integration into a target integration site;
   (ii) a third nucleic acid sequence positioned 5' to the polynucleotide and comprising a sequence that is homologous to a genomic sequence 5' of the target integration site; and
   (iii) a fourth nucleic acid sequence positioned 3' to the polynucleotide and comprising a sequence that is homologous to a genomic sequence 3' of the target integration site.
14. The composition of embodiment 13, wherein the target integration site is in the genome of a cell.
15. The composition of embodiment 13 or 14, wherein:
   the target integration site comprises the 3' end of an endogenous gene;
   the sequence of the third nucleic acid sequence is homologous to the DNA sequence upstream of the stop codon of the endogenous gene; and
   the sequence of the fourth nucleic acid sequence is homologous to the DNA sequence downstream of the stop codon of the endogenous gene.
16. The composition of any one of embodiments 13-15, wherein the cell is a liver, muscle, or CNS cell.
17. The composition of any one of embodiments 7-16, for use in packaging an AAV vector.
18. The composition of any one of embodiments 7-16, wherein the composition is formulated for co-delivery of the first and second plasmid to a cell.
19. The composition of any one of embodiments 7-18, wherein the composition comprises certain amounts of the first and second plasmid to achieve a particular ratio between the two plasmids.
20. The composition of any one of the above embodiments, wherein the composition comprises a greater amount of the first plasmid relative to the second plasmid.
21. The composition of embodiment 19, wherein the plasmid ratio of the first plasmid to the second plasmid is greater than or equal to 1.5:1.
22. The composition of embodiment 20 or 21, wherein the first plasmid comprises a polynucleotide sequence encoding one or more viral helper genes and the second plasmid comprises a polynucleotide sequence encoding a payload and flanking ITRs.
23. The composition of embodiment 22, wherein the first plasmid further comprises a rep gene and the second plasmid further comprises a cap gene.
24. The composition of embodiment 22, wherein the first plasmid further comprises a cap gene and the second plasmid further comprises a rep gene.
25. The composition of any one of the above embodiments, wherein the rep gene is a wild-type gene.
26. The composition of any one of the above embodiments, wherein the one or more viral helper genes are wild-type genes.
27. The composition of any one of the above embodiments, wherein the rep and cap genes are regulated by one or more wild-type promoters.
28. A method of manufacturing a packaged AAV vector, comprising delivering to a cell a composition of any one of embodiments 7-27.
29. The method of embodiment 28, wherein the cell is a mammalian cell.
30. A method of manufacturing according to embodiment 28, additional comprising use of a chemical transfection reagent
31. The method of embodiment 30, wherein the chemical transfection reagent is or comprises a cationic molecule.
32. The method of embodiment 30, wherein the chemical transfection reagent is or comprises a cationic lipid.
33. A packaged AAV vector composition prepared by delivering the composition of any one of embodiments 7-27 to a cell.
34. The composition of any one of the above embodiments, wherein the payload comprises a transgene that is or comprises one or more of Propionyl-CoA Carboxylase, ATP7B, Factor IX, methylmalonyl-CoA mutase (MUT), α1-antitrypsin (A1AT), UGT1A1, or variants thereof.
35. A method of treatment comprising administering a composition comprising a packaged AAV vector produced by the method of embodiment 28 or 30 to a subject in need thereof.
36. The method of embodiment 35, wherein the subject has or is suspected to have a genetic disorder affecting the metabolism, liver, skeletal muscle, cardiac muscle, central nervous system, and/or blood.
37. The method of embodiment 36, wherein the subject has or is suspected to have one or more of propionic acidemia, Wilson's Disease, hemophilia, Crigler-Najjar syndrome, methylmalonic acidemia (MMA), alpha-1 anti-trypsin deficiency (A1ATD), a glycogen storage disease (GSD), Duchenne's muscular dystrophy, limb girdle muscular dystrophy, X-linked myotubular myopathy, Parkinson's Disease, Mucopolysaccharidosis, hemophilia A, hemophilia B, or hereditary angioedema (HAE).

38. The method of embodiment 35 or 37 wherein the composition is delivered to a cell.

39. The method of embodiment 38, wherein the cell is a liver, muscle, or CNS cell.

40. The method of embodiment 38 or 39, wherein the cell is isolated from a subject.

41. The method of any one of embodiments 35-40, wherein the composition does not comprise a nuclease or a nucleic acid encoding a nuclease.

42. A Rep/Helper Plasmid having a polynucleotide sequence comprising the polynucleotide sequence of SEQ ID NO:1 that does not comprise a polynucleotide sequence encoding an AAV cap gene.

43. A Payload/Cap Plasmid comprising a polynucleotide sequence comprising SEQ ID NO:11, a polynucleotide sequence encoding an AAV cap gene, and a polynucleotide sequence comprising a payload, wherein the plasmid does not comprise a polynucleotide sequence encoding an AAV rep gene.

44. A method comprising the step of combining a cell population for production of AAV in a transfection reagent mixture for AAV vector production with a Rep/Helper Plasmid and a Payload/Cap Plasmid, under conditions effective to produce the AAV vector in the transfection reagent mixture in the absence of any plasmid comprising a polynucleotide sequence encoding both an AAV rep and an AAV cap.

45. The method of embodiment 44, wherein the Rep/Helper Plasmid is the Rep/Helper Plasmid of embodiment 42.

46. The method of any one of embodiments 44 or 45, wherein the Payload/Cap Plasmid is the Payload/Cap Plasmid of embodiment 43.

47. The method of any one of embodiments 44-46, wherein the Rep/Helper Plasmid and the Payload/Cap Plasmid are combined with the cell population in a relative w/w plasmid ratio of between 1:10 and 10:1.

48. The method of any one of embodiments 44-47, wherein the Rep/Helper Plasmid and the Payload/Cap Plasmid are combined with the cell population in a relative w/w plasmid ratio of between 1:3 and 3:1.

49. The method of any one of embodiments 44-48, wherein the Rep/Helper Plasmid and the Payload/Cap Plasmid are combined with the cell population in a relative w/w plasmid ratio of about 1.5:1.

50. A composition comprising two plasmids, wherein:
  the first plasmid comprises a sequence of SEQ ID NO: 1; and
  the second plasmid comprises a sequence of SEQ ID NO: 11;
wherein the second plasmid further comprises:
  a polynucleotide sequence comprising a sequence encoding a cap gene; and
  a polynucleotide sequence encoding a payload;
wherein the second plasmid does not comprise a polynucleotide sequence encoding a rep gene.

51. A composition comprising two plasmids, wherein:
  the first plasmid comprises a sequence of SEQ ID NO: 2; and
  the second plasmid comprises a sequence of SEQ ID NO: 11;
wherein the second plasmid further comprises:
  a polynucleotide sequence comprising a sequence encoding a cap gene; and
  a polynucleotide sequence encoding a payload;
wherein the second plasmid does not comprise a polynucleotide sequence encoding a rep gene.

52. A composition comprising two plasmids, wherein:
  the first plasmid consists of a sequence of SEQ ID NO: 1; and
  the second plasmid consists of:
    a sequence of SEQ ID NO: 11;
    a polynucleotide sequence comprising a sequence encoding a cap gene; and
    a polynucleotide sequence encoding a payload;
wherein the second plasmid does not comprise a polynucleotide sequence encoding a rep gene.

53. A composition comprising two plasmids, wherein:
  the first plasmid consists of a sequence of SEQ ID NO: 2; and
  the second plasmid consists of:
    a sequence of SEQ ID NO: 11;
    a polynucleotide sequence comprising a sequence encoding a cap gene; and
    a polynucleotide sequence encoding a payload;
wherein the second plasmid does not comprise a polynucleotide sequence encoding a rep gene.

54. The composition of any one of the above embodiments, wherein the cap gene is selected from AAV1, AAV2, AAV3, AAV4, AAV5, AAV6, AAV7, AAV8, AAV9, AAV10, AAV11, AAVC11.01, AAVC11.02, AAVC11.03, AAVC11.04, AAVC11.05, AAVC11.06, AAVC11.07, AAVC11.08, AAVC11.09, AAVC11.10, AAVC11.11, AAVC11.12, AAVC11.13, AAVC11.14, AAVC11.15, AAVC11.16, AAVC11.17, AAVC11.18, AAVC11.19, AAV-DJ, AAV-LK03, AAV-LK19, AAVrh.74, AAVrh.10, AAVhu.37, AAVrh.K, AAVrh.39, AAV12, AAV 13, AAVrh.8, avian AAV, bovine AAV, canine AAV, equine AAV, primate AAV, non-primate AAV, ovine AAV, or a hybrid AAV.

55. The composition of any one of the above embodiments, wherein the polynucleotide sequence comprising a sequence encoding a cap gene is inserted before position 2025 of SEQ ID NO: 11.

56. The composition of any one of the above embodiments, wherein the polynucleotide sequence encoding a payload comprises a polynucleotide sequence encoding a transgene.

57. The composition of any one of the above embodiments, wherein the polynucleotide sequence encoding a payload is inserted after position 2663 of SEQ ID NO: 11.

58. The composition of any one of embodiments 56 or 57, wherein the transgene is or comprises a gene listed in FIG. 29, or a variant thereof.

59. The composition of any one of embodiments 56 or 57, wherein the transgene is or comprises one or more of Propionyl-CoA Carboxylase, ATP7B, Factor IX, methylmalonyl-CoA mutase (MUT), al-antitrypsin (A1AT), UGT1A1, fumarylacetoacetate hydrolase (FAH), cystathionine beta synthase (CBS), or variants thereof.

60. The composition of any one of the above embodiments, wherein the composition comprises no more than two distinct plasmids.

61. The composition of any one of the above embodiments, wherein the composition comprises no fewer than three distinct plasmids.
62. A composition comprising two plasmids, wherein:
    the first plasmid comprises a sequence of SEQ ID NO: 1; and
    the second plasmid comprises a sequence of SEQ ID NO: 9;
wherein the second plasmid does not comprise a polynucleotide sequence encoding a rep gene.
63. A composition comprising two plasmids, wherein:
    the first plasmid comprises a sequence of SEQ ID NO: 1; and
    the second plasmid comprises a sequence of SEQ ID NO: 10;
wherein the second plasmid does not comprise a polynucleotide sequence encoding a rep gene.
64. A composition comprising two plasmids, wherein:
    the first plasmid comprises a sequence of SEQ ID NO: 2; and
    the second plasmid comprises a sequence of SEQ ID NO: 9;
wherein the second plasmid does not comprise a polynucleotide sequence encoding a rep gene.
65. A composition comprising two plasmids, wherein:
    the first plasmid comprises a sequence of SEQ ID NO: 2; and
    the second plasmid comprises a sequence of SEQ ID NO: 10;
wherein the second plasmid does not comprise a polynucleotide sequence encoding a rep gene.
66. A composition comprising two plasmids, wherein:
    the first plasmid consists of a sequence of SEQ ID NO: 1; and
    the second plasmid consists of a sequence of SEQ ID NO: 9.
67. A composition comprising two plasmids, wherein:
    the first plasmid consists of a sequence of SEQ ID NO: 1; and
    the second plasmid consists of a sequence of SEQ ID NO: 10.
68. A composition comprising two plasmids, wherein:
    the first plasmid consists of a sequence of SEQ ID NO: 2; and
    the second plasmid consists of a sequence of SEQ ID NO: 9.
69. A composition comprising two plasmids, wherein:
    the first plasmid consists of a sequence of SEQ ID NO: 2; and
    the second plasmid consists of a sequence of SEQ ID NO: 10.
70. The composition of any one of embodiments 62-69, wherein the composition comprises no more than two distinct plasmids.
71. The composition of any one of embodiments 62-70, wherein the composition comprises no fewer than three distinct plasmids.
72. The composition of any one of the above embodiments, wherein the plasmid ratio of the first plasmid to the second plasmid is greater than or equal to 1.5:1 up to 10:1.
73. The composition of any one of the above embodiments, for use in packaging an AAV vector.
74. The composition of any one of the above embodiments, wherein the composition is formulated for co-delivery of the first and second plasmid to a cell.
75. A method of manufacturing a packaged AAV vector, comprising delivering to a cell a composition of any one of the above embodiments.
76. The method of embodiment 75, wherein the cell is a mammalian cell.
77. The method of any one of embodiments 75 or 76, additionally comprising use of a chemical transfection reagent.
78. The method of embodiment 77, wherein the chemical transfection reagent is or comprises a cationic lipid.
79. The method of embodiment 78, wherein the chemical transfection reagent is or comprises a cationic molecule.
80. A packaged AAV vector composition prepared by delivering the composition of any one of embodiments 50-74 to a cell.
81. A method of treatment comprising administering a composition comprising a packaged AAV vector produced by the method of any one of embodiments 75-79 to a subject in need thereof.
82. The method of embodiment 81, wherein the subject has or is suspected to have a genetic disorder affecting the metabolism, liver, skeletal muscle, cardiac muscle, central nervous system, and/or blood.
83. The method of embodiment 82, wherein the subject has or is suspected to have one or more of propionic acidemia, Wilson's Disease, hemophilia, Crigler-Najjar syndrome, methylmalonic acidemia (MMA), alpha-1 anti-trypsin deficiency (A1ATD), a glycogen storage disease (GSD), Duchenne's muscular dystrophy, limb girdle muscular dystrophy, X-linked myotubular myopathy, Parkinson's Disease, Mucopolysaccharidosis, hemophilia A, hemophilia B, homocystinuria, a urea cycle disorder, hereditary tyrosinemia (HT1) or hereditary angioedema (HAE).
84. The method of any one of embodiments 82 or 83 wherein the composition is delivered to a cell.
85. The method of any one of embodiments 84, wherein the cell is a liver, muscle, or CNS cell.
86. The method of any one of embodiments 84 or 85 wherein the cell is isolated from a subject.
87. The method of any one of embodiments 81-86, wherein the composition does not comprise a nuclease or a nucleic acid encoding a nuclease.

We claim:

1. A transfection system for the production of AAV vectors, the system comprising;

a closed, circular DNA plasmid consisting of a polynucleotide sequence of SEQ ID NO:2 as a Rep/Helper plasmid; and a Payload/Cap plasmid consisting of a polynucleotide sequence of SEQ ID NO: 11, a polynucleotide sequence encoding a Cap gene and a polynucleotide sequence encoding a transgene, wherein the polynucleotide sequence encoding the Cap gene is inserted before position 2025 of SEQ ID NO:11, and wherein the polynucleotide sequence encoding the transgene is inserted after position 2663 of SEQ ID NO: 11.

2. The transfection system of claim 1, wherein the plasmid ratio of the Rep/Helper plasmid to the Payload/Cap plasmid is 1.5:1 up to 10:1.

3. The transfection system of claim 2, wherein the transfection system comprises no plasmid other than the Rep/Helper plasmid and the Payload/Cap plasmid.

4. The transfection system of claim 1, wherein the transfection system comprises no plasmid other than the Rep/Helper plasmid and the Payload/Cap plasmid.

5. A method of producing an AAV vector in a cell line, the method comprising the step of transfecting the cell line with only two unique plasmids in the presence of a transfection reagent, the two plasmids consisting of:

(a) a closed, circular DNA plasmid consisting of a polynucleotide sequence of SEQ ID NO:2 as a first plasmid, and (b) a second Payload/Cap plasmid consisting of a polynucleotide sequence of SEQ ID NO:11, a polynucleotide sequence encoding a Cap gene, and a polynucleotide sequence encoding a transgene, wherein the polynucleotide sequence encoding the Cap gene is inserted before positions 2025 of SEQ ID NO:11, and wherein the polynucleotide sequence encoding the transgene is inserted after position 2663 of SEQ ID NO:11 wherein the transfected cell line expresses the plasmids to produce the AAV vector.

6. The method of claim 5, wherein the cell line is a HEK293 cell line.

7. The method of claim 5, wherein the transfection reagent is a cationic polymer reagent.

8. The method of claim 5, wherein the method comprises transfecting the cell line with the first plasmid and the second plasmid with a plasmid ratio of about 1.5:1 to 10:1.

9. The method of claim 8, wherein the method comprises transfecting the cell line with the first plasmid and the second plasmid with a plasmid ratio of about 1.5:1.

10. The method of claim 8, wherein (a) the cell line is a HEK293 cell line; and (b) the Transfection Reagent is a cationic polymer reagent.

11. The method of claim 10, wherein the method comprises transfecting the cell line with the first plasmid and the second plasmid with a plasmid ratio of about 1.5:1.

12. The method of claim 10, wherein the cell line is HEK293F.

13. A method of expressing producing an AAV vector in a HEK293 cell line, the method comprising the step of transfecting the cell line with only two unique plasmids in the presence of a transfection reagent, the two plasmids consisting of:

(a) a closed, circular DNA plasmid consisting of a polynucleotide sequence of SEQ ID NO:2 as a Rep/Helper plasmid, and (b) a Payload/Cap plasmid consisting of a polynucleotide sequence of SEQ ID NO:11, a polynucleotide sequence encoding a Cap gene, and a polynucleotide sequence encoding a transgene, wherein the polynucleotide sequence encoding the Cap gene is inserted before position 2025 of SEQ ID NO:11, and wherein the polynucleotide sequence encoding the transgene is inserted after position 2663 of SEQ ID NO:11; and wherein the HEK293 cell line is transfected with the Rep/Helper plasmid and the Payload/Cap plasmid with a plasmid ratio of about 1.5:1 to 10:1 and in the absence of any other Rep/helper or Payload/Cap Plasmid, wherein the transfected HEK293 cell line expresses the plasmids to produce the AAV vector.

* * * * *

UNITED STATES PATENT AND TRADEMARK OFFICE
CERTIFICATE OF CORRECTION

| | |
|---|---|
| PATENT NO. | : 11,814,642 B2 |
| APPLICATION NO. | : 17/848307 |
| DATED | : November 14, 2023 |
| INVENTOR(S) | : Matthias Charles Jerome Hebben et al. |

It is certified that error appears in the above-identified patent and that said Letters Patent is hereby corrected as shown below:

In the Claims

Column 246, Claim 13, Line 63, replace "of expressing producing" with --of producing--.

Signed and Sealed this
Fifteenth Day of October, 2024

Katherine Kelly Vidal
*Director of the United States Patent and Trademark Office*